US008871756B2

(12) United States Patent
Chen et al.

(10) Patent No.: US 8,871,756 B2
(45) Date of Patent: Oct. 28, 2014

(54) COMPOUNDS FOR THE TREATMENT AND PROPHYLAXIS OF RESPIRATORY SYNCYTIAL VIRUS DISEASE

(75) Inventors: Li Chen, Shanghai (CN); Lichun Feng, Shanghai (CN); Song Feng, Shanghai (CN); Lu Gao, Shanghai (CN); Tao Guo, Shanghai (CN); Mengwei Huang, Shanghai (CN); Chungen Liang, Shanghai (CN); Yongfu Liu, Shanghai (CN); Lisha Wang, Shanghai (CN); Jason Christopher Wong, Shanghai (CN); Jim Zhen Wu, Shanghai (CN); Xihan Wu, Nanjing (CN); Hongying Yun, Shanghai (CN); Xiufang Zheng, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 150 days.

(21) Appl. No.: 13/561,366

(22) Filed: Jul. 30, 2012

(65) Prior Publication Data

US 2013/0196974 A1 Aug. 1, 2013

(30) Foreign Application Priority Data

Aug. 11, 2011 (WO) ................ PCT/CN2011/078258
Jul. 10, 2012 (WO) ................ PCT/CN2012/078439

(51) Int. Cl.

| | |
|---|---|
| *C07D 493/10* | (2006.01) |
| *C07D 487/04* | (2006.01) |
| *C07D 413/04* | (2006.01) |
| *C07D 407/14* | (2006.01) |
| *C07D 401/04* | (2006.01) |
| *C07D 417/14* | (2006.01) |
| *C07D 417/04* | (2006.01) |
| *C07D 409/14* | (2006.01) |
| *C07D 491/107* | (2006.01) |
| *C07D 413/14* | (2006.01) |
| *C07D 405/14* | (2006.01) |
| *C07D 401/14* | (2006.01) |

(52) U.S. Cl.

CPC ............ *C07D 493/10* (2013.01); *C07D 409/14* (2013.01); *C07D 491/107* (2013.01); *C07D 487/04* (2013.01); *C07D 413/14* (2013.01); *C07D 417/04* (2013.01); *C07D 401/04* (2013.01); *C07D 405/14* (2013.01); *C07D 401/14* (2013.01); *C07D 417/14* (2013.01); *C07D 413/04* (2013.01); *C07D 407/14* (2013.01)

USPC ............ 514/210.21; 514/211.09; 514/213.01; 514/221; 540/504; 540/552; 540/593

(58) Field of Classification Search

None

See application file for complete search history.

(56) References Cited

U.S. PATENT DOCUMENTS 4,044,136 A * 8/1977 Danilewicz et al. ..... 514/266.21
2002/0099208 A1 7/2002 Yu et al.

FOREIGN PATENT DOCUMENTS

WO 2005/061513 7/2005

OTHER PUBLICATIONS (International Search Report for PCT/EP2012/065499 Sep. 28, 2012).

* cited by examiner

*Primary Examiner* — Michael Barker
*Assistant Examiner* — Po-Chih Chen

(57) ABSTRACT

A compound of formula (I)

(I)

as well as pharmaceutically acceptable salt thereof, wherein $R^1$ to $R^{10}$, A, Q, X and Y are as defined in the specification and claims, and their use as a pharmaceutical for the treatment or prophylaxis of respiratory syncytial virus disease.

56 Claims, No Drawings

COMPOUNDS FOR THE TREATMENT AND PROPHYLAXIS OF RESPIRATORY SYNCYTIAL VIRUS DISEASE

PRIORITY TO RELATED APPLICATION(S)

This application claims the benefit of International Patent Application Nos. PCT/CN2012/078439, filed Jul. 10, 2012 and PCT/CN2011/078258, filed Aug. 11, 2011, which are hereby incorporated by reference in their entirety.

FIELD OF THE INVENTION

The invention relates to compounds which are respiratory syncytial virus (RSV) inhibitors and which are useful in the treatment or prophylaxis of RSV disease.

BACKGROUND OF THE INVENTION

Respiratory Syncytial Virus (RSV) belongs to the family of Paramyxoviridae, subfamily of Pneumovirinae. The human RSV is a major cause of acute upper and lower respiratory tract infection in infants and children. Almost all children are infected by RSV at least once by age of three. Natural human immunity against RSV is incomplete. In normal adults and older children, RSV infection is mainly associated with upper respiratory tract symptoms. Severe cases of RSV infection often lead to bronchiolitis and pneumonia, which requires hospitalization. High-risk factors for lower respiratory track infections include premature birth, congenital heart disease, chronic pulmonary disease, and immuno-compromised conditions. A severe infection at young age may lead to recurrent wheezing and asthma. For the elderly, RSV-related mortality rate becomes higher with advancing age.

There is no RSV vaccine available for human use, despite of many attempts in subunit vaccine and live-attenuated vaccine approaches. Virazole®, the aerosol form of ribavirin, is the only approved antiviral drug for treatment of RSV infection. However, it is rarely used clinically, due to limited efficacy and potential side effects. Two marketed prophalyxis antibodies were developed by MedImmune (CA, USA).

RSV-IGIV (brand name RespiGam) is polyclonal-concentrated RSV neutralizing antibody administered through monthly infusion of 750 mg/kg in hospital (Wandstrat T L, Ann Pharmacother. 1997 January; 31(1):83-8). Subsequently, the usage of RSV-IGIV was largely replaced by palivizumab (brand name Synagis®), a humanized monoclonal antibody against RSV fusion (F) protein approved for prophylaxis in high-risk infants in 1998. When administered intramuscularly at 15 mg/kg once a month for the duration of RSV season, palivizumab demonstrated 45-55% reduction of hospitalization rate caused by RSV infection in selected infants (Pediatrics. 1998 September; 102(3):531-7; Feltes T F et al, J Pediatr. 2003 October; 143(4):532-40). Unfortunately, palivizumab is not effective in the treatment of established RSV infection. A newer version monoclonal antibody, motavizumab, was designed as potential replacement of palivizumab but failed to show additional benefit over palivizumab in recent Phase III clinical trials (Feltes T F et al, Pediatr Res. 2011 April 25, Epub ahead of print).

A number of small molecule RSV inhibitors have been discovered. Among them, only a few reached Phase I or II clinical trials. Arrow Therapeutics (now a group in AstraZeneca, UK) completed a five-year Phase II trial of nucleocapsid (N) protein inhibitor RSV-604 in stem cell transplantation patients by February 2010 (www.clinicaltrials.gov), but has not released the final results. Most of other small molecules were put on hold for various reasons.

RNAi therapeutics against RSV have also been thoroughly studied. ALN-RSV01 (Alnylam Pharmaceuticals, MA, USA) is a siRNA targeting on RSV gene. A nasal spay administered for two days before and for three days after RSV inoculation decreased infection rate among adult volunteers (DeVincenzo J. et al, Proc Natl Acad Sci USA. 2010 May 11; 107 (19):8800-5). In another Phase II trial using naturally infected lung transplantation patients, results were not sufficient for conclusion of antiviral efficacy, though certain health benefits have been observed (Zamora M R et al, Am J Respir Crit Care Med. 2011 Feb. 15; 183(4):531-8). Additional Phase IIb clinical trials in similar patient population for ALN-RSV01 are on-going (www.clinicaltrials.gov).

Nevertheless, safe and effective treatment for RSV disease is needed urgently.

SUMMARY OF THE INVENTION

The invention relates to compounds of formula (I)

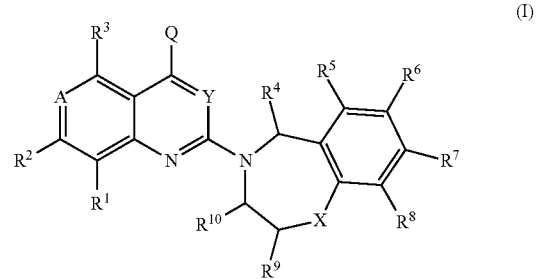

and their use in pharmaceuticals for the treatment and prophylaxis of RSV disease.

DETAILED DESCRIPTION OF THE INVENTION

The invention relates in particular to compounds of formula (I)

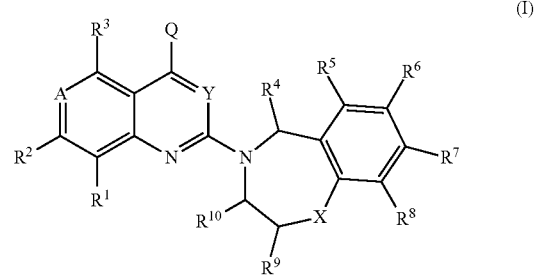

Wherein
  $R^1$ is hydrogen, halogen, or $C_{1-6}$alkyl;
  $R^2$ is hydrogen, halogen, or $C_{1-6}$alkyl;
  $R^3$ is hydrogen, halogen, or $C_{1-6}$alkyl;
  $R^4$ is hydrogen, or $C_{1-6}$alkyl;
  $R^5$ is hydrogen, or halogen;
  $R^6$ is hydrogen, halogen, hydroxy, $C_{1-6}$alkoxy, carboxy, morpholinyl, or 4-$C_{0-6}$alkylpiperazin-1-yl;
  $R^7$ is hydrogen, halogen, $C_{1-6}$alkyl, $C_{1-6}$alkoxy, $C_{1-6}$alkylaminocarbonyl, di$C_{1-6}$alkylaminocarbonyl, $C_{1-6}$alkylsulfonyl, phenoxy, or hydroxy$(CH_2)_{2-6}$—O—;

R[8] is hydrogen, halogen, or $C_{1-6}$alkoxy;
R[9] is hydrogen, $C_{1-6}$alkyl, or =O;
R[10] is hydrogen, or =O, provided that R[9] and R[10] are not =O simultaneously;
A is nitrogen, or —C—R[11], wherein R[11] is hydrogen, halogen, $C_{1-6}$alkyl, cycloalkyl, $C_{1-6}$alkoxy, trifluoromethyl, trifluoromethoxy, pyridinyloxy, $C_{1-6}$alkoxy(CH$_2$)$_{1-6}$—O—, difluoromethoxy, cyano, nitro, amino, vinyl, acetylenyl, aminocarbonyl, hydroxy(CH$_2$)$_{2-6}$—O—, $C_{1-6}$alkylsulfinyl, $C_{1-6}$alkylsulfonyl, hydroxy(CH$_2$)$_{1-6}$, deuterated $C_{1-6}$alkyl, carboxyl, $C_{1-6}$alkoxycarbonyl, hydroxy, difluoromethyl, —CH(hydroxy) $C_{1-6}$alkyl, or $C_{1-6}$alkylsulfanyl;
X is —CH$_2$—, —O—, —NH—, —CF$_2$—, —C($C_{1-6}$alkyl)(OH)—, —S—, —C(=O)—, —C(=NOC$_{0-6}$alkyl)-, —S(=O)—, —S(O$_2$)— or —S(=O)(NH)—;
Y is —CH—, or nitrogen;
Q is hydrogen; halogen; $C_{1-6}$alkyl, unsubstituted or once or twice substituted by amino or hydroxy, provided that di-substitution is not on the same carbon; amino(CH$_2$)$_{2-6}$aminosulfonyl; 2-amino-4,5-dihydro-1,3-oxazol-4-yl(CH$_2$)$_{1-6}$; carboxy(CH$_2$)$_{1-6}$; phenylsulfonyl; piperidin-4-yl-carbonyl; 1H-pyrazol-3-yl; pyrrolidin-3-yloxy; piperidin-4-yloxy; amino(CH$_2$)$_{2-6}$—O—; or NR[12]R[13], wherein one of R[12] and R[13] is hydrogen, $C_{1-6}$alkyl, or hydroxy(CH$_2$)$_{2-6}$;
and the other one is
{1-[amino(CH$_2$)$_{0-6}$]-3,3-difluorocyclobutyl}(CH$_2$)$_{1-6}$; guanidino(CH$_2$)$_{2-6}$; (S—$C_{1-6}$alkylsulfonimidoyl)(CH$_2$)$_{2-6}$; 2-oxa-6-aza-spiro[3.4]oct-8-yl; {3-[amino(CH$_2$)$_{0-6}$]tetrahydrofuran-3-yl}(CH$_2$)$_{1-6}$; 3-aminomethyl-1,1-dioxidothietan-3-ylmethyl; 3-amino-1,1-dioxidothietan-3-ylmethyl; 3-(aminomethyl)thietan-3-ylmethyl; (1,1-dioxidothiomorpholin-4-yl)ethyl; $C_{0-6}$alkyl(oxetanyl)N(CH$_2$)$_{2-6}$; 4,5-dihydro-1H-imidazol-2-yl; amino(CH$_2$)$_{2-6}$—O—(CH$_2$)$_{2-6}$; amino(CH$_2$)$_{2-10}$; amino(CH$_2$)$_{1-6}$difluoromethyl(CH$_2$)$_{1-6}$; amino(CH$_2$)$_{1-6}$difluoromethyldifluoromethyl(CH$_2$)$_{1-6}$; amino(CH$_2$)$_{1-6}$fluoromethyl(CH$_2$)$_{1-6}$; amino(CH$_2$)$_{1-6}$oxetanyl(CH$_2$)$_{0-6}$; amino(CH$_2$)$_{0-6}$oxetanyl(CH$_2$)$_{1-6}$; amino(CH$_2$)$_{2-6}$sulfanyl(CH$_2$)$_{2-6}$; amino(CH$_2$)$_{2-6}$sulfonyl(CH$_2$)$_{2-6}$; amino(CH$_2$)$_{0-6}$carbonyl(CH$_2$)$_{0-6}$; aminocycloalkyl(CH$_2$)$_{0-6}$; 2-aminodihydrooxazol-4-yl(CH$_2$)$_{1-6}$; 2-aminodihydrooxazol-5-yl(CH$_2$)$_{1-6}$; (2-amino-5-methyl-4,5-dihydro-1,3-oxazol-5-yl)methyl; aminophenyl; 4-aminotetrahydropyran-4-yl(CH$_2$)$_{1-6}$; azetidin-2-yl(CH$_2$)$_{1-6}$; azetidin-3-yl(CH$_2$)$_{0-6}$; azetidinylcarbonyl; $C_{1-6}$alkoxy(CH$_2$)$_{2-6}$; $C_{1-6}$alkoxy(CH$_2$)$_{2-6}$amino(CH$_2$)$_{2-6}$; $C_{1-6}$alkyl; $C_{1-6}$alkylamino(CH$_2$)$_{2-6}$; $C_{1-6}$alkylaminocarbonyl(CH$_2$)$_{0-6}$; $C_{1-6}$alkylaminooxetanyl(CH$_2$)$_{1-6}$; $C_{1-6}$alkylcarbonyl; $C_{1-6}$alkylcarbonylamino(CH$_2$)$_{2-6}$; $C_{1-6}$alkylcarbonylamino(CH$_2$)$_{1-6}$oxetanyl(CH$_2$)$_{0-6}$; $C_{1-6}$alkylsulfinyl(CH$_2$)$_{2-6}$; $C_{1-6}$alkylsulfonyl; carboxy(CH$_2$)$_{1-6}$; cyano(CH$_2$)$_{1-6}$; diC$_{1-6}$alkylamino(CH$_2$)$_{2-6}$; diC$_{1-6}$alkylaminocarbonyl; difluoromethyl(CH$_2$)$_{1-6}$amino(CH$_2$)$_{2-6}$; hydrogen; hydroxy(CH$_2$)$_{2-10}$; hydroxy(CH$_2$)$_{2-6}$amino(CH$_2$)$_{2-6}$; hydroxy(CH$_2$)$_{1-6}$carbonyl; hydroxy(CH$_2$)$_{0-6}$oxetanyl(CH$_2$)$_{1-6}$; hydroxy(CH$_2$)$_{1-6}$oxetanyl(CH$_2$)$_{0-6}$; hydroxycycloalkyl; isoxazolyl; morpholin-2-yl(CH$_2$)$_{1-6}$; morpholin-4-yl(CH$_2$)$_{2-6}$; oxetanyl(CH$_2$)$_{0-6}$; N-oxetanylpyrrolidin-3-yl; oxo-pyrrolidinylcarbonyl; phenylaminocarbonyl; phenyl(CH$_2$)$_{0-6}$aminooxetanyl(CH$_2$)$_{1-6}$; phenylcarbonyl; piperazinyl(CH$_2$)$_{2-6}$; piperidin-1-yl(CH$_2$)$_{2-6}$; piperidin-2-yl(CH$_2$)$_{1-6}$; piperidin-3-yl(CH$_2$)$_{0-6}$; piperidin-4-yl(CH$_2$)$_{0-6}$; piperidinylcarbonyl; pyrazinylcarbonyl; pyrazol-3-yl; pyridazinylcarbonyl; pyridinyl(CH$_2$)$_{0-6}$carbonyl; pyridinylamino(CH$_2$)$_{2-6}$; pyrrolidin-3-yl, unsubstituted or 4-substituted by halogen; pyrrolidin-4-yl, unsubstituted or 3-substituted by hydroxy or $C_{1-6}$alkoxy; pyrrolidin-2-yl(CH$_2$)$_{1-6}$; pyrrolidinylcarbonyl; tetrahydrofuran-3-yl; tetrahydropyran-4-yl; tetrazolyl(CH$_2$)$_{2-6}$; trifluoromethylcarbonylamino(CH$_2$)$_{1-6}$ oxetanyl; trifluoromethylsulfonyl;

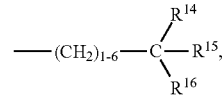

wherein R[14] is hydrogen, $C_{1-6}$alkyl or hydroxy(CH$_2$)$_{1-6}$; R[15] is hydroxy, $C_{1-6}$alkyl, hydroxy(CH$_2$)$_{1-6}$ or amino; and R[16] is $C_{1-6}$alkyl, trifluoromethyl, hydroxy(CH$_2$)$_{1-6}$, amino(CH$_2$)$_{1-6}$, aminocarboxy or carboxy(CH$_2$)$_{1-6}$;

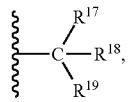

wherein R[17] is hydrogen, $C_{1-6}$alkyl or hydroxy(CH$_2$)$_{1-6}$; R[18] is hydroxy(CH$_2$)$_{1-6}$ or $C_{1-6}$alkyl; R[19] is hydroxy(CH$_2$)$_{1-6}$, amino(CH$_2$)$_{1-6}$, carboxy or aminocarboxy(CH$_2$)$_{0-6}$; or

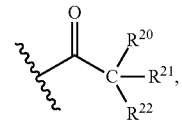

wherein R[20] is hydrogen or $C_{1-6}$alkyl; R[21] is $C_{1-6}$alkyl; R[22] is $C_{1-6}$alkoxy or amino;
R[12] and R[13], with the nitrogen atom to which they are attached, may form a pyrrolidinyl, piperazinyl, piperidinyl, morpholinyl, azetidinyl, diazepanyl or oxopyrrolidinyl ring; which may be unsubstituted, once or twice substituted by a group selected from halogen, $C_{1-6}$alkyl, $C_{1-6}$alkoxy, gemdimethyl, amino, aminocarbonyl, hydroxy, oxetanylamino, $C_{1-6}$alkylpiperazinyl, and amino(CH$_2$)$_{1-6}$;
R[12] and R[13], with the nitrogen atom to which they are attached may form a bridge ring or a spiral ring selected from 2-oxa-6-aza-spiro[3.4]octan-6-yl, 2-oxa-5,7-diazaspiro[3.4]octan-6-one-5-yl, (4aS,7aR)-hexahydropyrrolo[3,4-b][1,4]oxazin-6(2H)-yl, 4,5,6,6a-tetrahydro-3aH-pyrrolo[3,4-d][1,3]oxazol-5-yl, 2-aza-bicyclo[2.1.1]hexan-2-yl, and 3-aza-bicyclo[3.1.0]hexan-3-yl; which may be unsubstituted or further substituted by amino;
and pharmaceutically acceptable salt and stereoisomers thereof.

It has been found that the compounds of the present invention belong to a new chemical class of RSV inhibitors for the treatment or prophylaxis of RSV infection. The compounds of the invention are therefore useful in the treatment or prophylaxis of RSV disease.

As used herein, the term "$C_{0-6}$alkyl" alone or in combination signifies a chemical bond, or hydrogen, or saturated, linear- or branched chain alkyl group containing 1 to 6, preferably 1 to 4 carbon atoms, for example methyl, ethyl, propyl, isopropyl, 1-butyl, 2-butyl, tert-butyl and the like. Preferred "$C_{0-6}$alkyl" groups are chemical bond, hydrogen, methyl, ethyl, isopropyl, tert-butyl.

As used herein, the term "$C_{1-6}$alkyl" alone or in combination signifies a saturated, linear- or branched chain alkyl group containing 1 to 6, preferably 1 to 4 carbon atoms, for example methyl, ethyl, propyl, isopropyl, 1-butyl, 2-butyl, tert-butyl and the like. Preferred "$C_{1-6}$alkyl" groups are methyl, ethyl, isopropyl, tert-butyl.

As used herein, the term "$C_{2-6}$alkyl" alone or in combination signifies a saturated, linear- or branched chain alkyl group containing 2 to 6, preferably 2 to 4 carbon atoms, for example ethyl, propyl, isopropyl, 1-butyl, 2-butyl, tert-butyl and the like. Preferred "$C_{2-6}$alkyl" groups are ethyl, isopropyl, tert-butyl.

As used herein, the term "—$(CH_2)_{0-6}$—" signifies a chemical link, hydrogen, or a saturated, linear alkyl chain containing from 1 to 6 carbon atoms, preferably, the term signifies hydrogen or —$(CH_2)_{1-4}$—.

As used herein, the term "—$(CH_2)_{1-6}$—" signifies a saturated, linear alkyl chain containing from 1 to 6 carbon atoms, preferably from 1 to 4 carbon atoms.

As used herein, the term "—$(CH_2)_{2-6}$—" signifies a saturated, linear alkyl chain containing from 2 to 6 carbon atoms, preferably from 2 to 4 carbon atoms.

As used herein, the term "—$(CH_2)_{2-10}$—" signifies a saturated, linear alkyl chain containing from 2 to 10 carbon atoms, preferably from 2 to 4 carbon atoms.

The term "cycloalkyl", alone or in combination, refers to a saturated carbon ring containing from 3 to 7 carbon atoms, preferably from 3 to 6 carbon atoms, for example, cyclopropyl, cyclobutyl, cyclopentyl, cyclohexyl, cycloheptyl and the like. Preferred cycloalkyl groups are cyclopropyl, cyclopentyl and cyclohexyl.

The term "$C_{1-6}$alkoxy" alone or in combination signifies a group $C_{1-6}$alkyl-O—, wherein the "$C_{1-6}$alkyl" is as defined above; for example methoxy, ethoxy, propoxy, isopropoxy, n-butoxy, i-butoxy, 2-butoxy, t-butoxy and the like. Preferred $C_{1-6}$alkoxy groups are methoxy and ethoxy and more preferably methoxy.

The term "$C_{2-6}$alkoxy" alone or in combination signifies a group $C_{2-6}$alkyl-O—, wherein the "$C_{2-6}$alkyl" is as defined above; for example ethoxy, propoxy, isopropoxy, n-butoxy, i-butoxy, 2-butoxy, t-butoxy and the like. Preferred $C_{1-6}$alkoxy groups is ethoxy.

The term "halogen" means fluorine, chlorine, bromine or iodine. Halogen is preferably fluorine or chlorine.

The term "hydroxy" alone or in combination refers to the group —OH.

The term "carbonyl" alone or in combination refers to the group —C(O)—.

The term "carboxy" alone or in combination refers to the group —COOH.

The term "amino", alone or in combination, refers to primary (—$NH_2$), secondary (—NH—) or tertiary amino

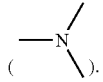

The term "sulfonyl" alone or in combination refers to the group —$S(O)_2$—.

The term "$C_{1-6}$alkylsulfanyl" alone or in combination refers to the group —S—$C_{1-6}$alkyl.

The term "$C_{1-6}$alkylsulfinyl" alone or in combination refers to the group —S(O)—$C_{1-6}$alkyl.

The term "oxetanyl" alone or in combination refers to the group

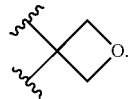

The compounds according to formula I does not include those in which the sp³ hybrid carbon atom is disubstituted by two nitrogen atoms, or one nitrogen atom and one oxygen atom simultaneously. The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula (I) and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et. al., Organic Process Research & Development 2000, 4, 427-435; or in Ansel, H., et. al., In: Pharmaceutical Dosage Forms and Drug Delivery Systems, 6th ed. (1995), pp. 196 and 1456-1457. Preferred are the sodium salts of the compounds of formula (I).

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as acetate, propionate and isobutyrate. Additionally, any physiologically acceptable equivalents of the compounds of general formula (I), similar to the metabolically labile esters, which are capable of producing the parent compounds of general formula (I) in vivo, are within the scope of this invention. Preferred are the methyl and ethyl esters of the compounds of formula (I).

Compounds of the general formula (I) which contain one or several chiral centers can either be present as racemates, diastereomeric mixtures, or optically active single isomers. The racemates can be separated according to known methods into the enantiomers. Preferably, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Another embodiment of present invention is (ii) a compound of formula (I) or a pharmaceutically acceptable salt thereof, wherein
$R^1$ is hydrogen, halogen or $C_{1-6}$alkyl;
$R^2$ is hydrogen, halogen or $C_{1-6}$alkyl;

$R^3$ is hydrogen, halogen or $C_{1-6}$alkyl;

$R^4$ is hydrogen or $C_{1-6}$alkyl;

$R^5$ is hydrogen;

$R^6$ is hydrogen, halogen, hydroxy, $C_{1-6}$ alkoxy, morpholinyl or 4-$C_{0-6}$alkylpiperazin-1-yl;

$R^7$ is hydrogen, halogen, $C_{1-6}$alkyl, $C_{1-6}$alkoxy, phenoxy or hydroxy$(CH_2)_{2-6}$—O—;

$R^8$ is hydrogen, halogen or $C_{1-6}$alkoxy;

$R^9$ is hydrogen or $C_{1-6}$alkyl;

$R^{10}$ is hydrogen;

A is nitrogen or —C—$R^{11}$, wherein $R^{11}$ is hydrogen, halogen, $C_{1-6}$ alkyl, cycloalkyl, $C_{1-6}$alkoxy, trifluoromethyl, trifluoromethoxy, pyridinyloxy, $C_{1-6}$alkoxy$(CH_2)_{1-6}$—O—, difluoromethoxy, cyano, nitro, amino, vinyl, acetylenyl, aminocarbonyl, hydroxy$(CH_2)_{2-6}$—O—, $C_{1-6}$alkylsulfinyl, hydroxy$(CH_2)_{1-6}$, deuterated$C_{1-6}$alkyl, carboxyl, alkoxycarbonyl, hydroxy, difluoromethyl, —CH(hydroxy)$C_{1-6}$alkyl or $C_{1-6}$alkylsulfanyl;

X is S, S=O, $SO_2$ or S(O)NH;

Y is —CH— or nitrogen;

Q is $C_{1-6}$alkyl, unsubstituted or once substituted by amino; amino$(CH_2)_{2-6}$aminosulfonyl; 2-amino-4,5-dihydro-1,3-oxazol-4-ylethyl; carboxy$(CH_2)_{1-6}$; phenylsulfonyl; piperidin-4-yl-carbonyl; 1H-pyrazol-3-yl; pyrrolidin-3-yloxy; piperidin-4-yloxy; amino$(CH_2)_{2-6}$—O—;

or $NR^{12}R^{13}$, wherein one of $R^{12}$ and $R^{13}$ is hydrogen, $C_{1-6}$alkyl or hydroxy$(CH_2)_{2-6}$;

and the other one is

{1-[amino$(CH_2)_{0-6}$]-3,3-difluorocyclobutyl}$(CH_2)_{1-6}$; (S—$C_{1-6}$ alkylsulfonimidoyl)$(CH_2)_{2-6}$; {3-[amino$(CH_2)_{0-6}$]tetrahydrofuran-3-yl}$(CH_2)_{1-6}$; (2-amino-5-methyl-4,5-dihydro-1,3-oxazol-5-yl)methyl; 3-aminomethyl-1,1-dioxidothietan-3-ylmethyl; 3-(aminomethyl)thietan-3-ylmethyl; (1,1-dioxidothiomorpholin-4-yl)ethyl; $C_{0-6}$alkyl(oxetanyl)N$(CH_2)_{2-6}$; 4,5-dihydro-1H-imidazol-2-yl; amino$(CH_2)_{2-6}$—O—$(CH_2)_{2-6}$; amino$(CH_2)_{2-10}$; amino$(CH_2)_{0-6}$carbonyl$(CH_2)_{0-6}$; amino$(CH_2)_{1-6}$ difluoromethyl$(CH_2)_{1-6}$; amino$(CH_2)_{1-6}$ difluoromethyldifluoromethyl$(CH_2)_{1-6}$; amino$(CH_2)_{1-6}$fluoromethyl$(CH_2)_{1-6}$; amino$(CH_2)_{1-6}$ oxetanyl$(CH_2)_{0-6}$; amino$(CH_2)_{0-6}$oxetanyl$(CH_2)_{1-6}$; amino$(CH_2)_{2-6}$sulfanyl$(CH_2)_{2-6}$; amino$(CH_2)_{2-6}$sulfonyl$(CH_2)_{2-6}$; 1-aminocyclobutylmethyl; 2-aminocyclohexyl; 3-aminocyclohexyl; 4-aminocyclohexyl; 1-aminocyclohexylmethyl; 2-aminocyclopentyl; 1-aminocyclopropylethyl; 1-aminocyclopropylmethyl; (2-amino-4,5-dihydro-oxazol-5-yl)$(CH_2)_{1-6}$; (2-amino-4,5-dihydro-oxazol-4-yl)$(CH_2)_{1-6}$; aminophenyl; 4-aminotetrahydropyran-4-yl$(CH_2)_{1-6}$; azetidin-2-yl$(CH_2)_{1-6}$; azetidin-3-yl$(CH_2)_{0-6}$; azetidin-3-ylcarbonyl; $C_{1-6}$alkoxy$(CH_2)_{2-6}$; $C_{1-6}$alkoxy$(CH_2)_{2-6}$amino$(CH_2)_{2-6}$; $C_{1-6}$alkyl; $C_{1-6}$alkylamino$(CH_2)_{2-6}$; $C_{1-6}$ alkylaminooxetanyl$(CH_2)_{1-6}$; $C_{1-6}$ alkylcarbonyl; $C_{1-6}$alkylaminocarbonyl$(CH_2)_{0-6}$; $C_{1-6}$ alkylcarbonylamino$(CH_2)_{2-6}$; $C_{1-6}$alkylcarbonylamino$(CH_2)_{1-6}$oxetanyl$(CH_2)_{0-6}$; $C_{1-6}$ alkylsulfinyl$(CH_2)_{2-6}$; $C_{1-6}$alkylsulfonyl; carboxy$(CH_2)_{1-6}$; cyano$(CH_2)_{1-6}$; di$C_{1-6}$ alkylamino$(CH_2)_{2-6}$; di$C_{1-6}$ alkylaminocarbonyl; difluoromethyl$(CH_2)_{1-6}$ amino$(CH_2)_{2-6}$; hydrogen; hydroxy$(CH_2)_{2-10}$; hydroxy$(CH_2)_{2-6}$amino$(CH_2)_{2-6}$; hydroxy$(CH_2)_{1-6}$carbonyl; hydroxy$(CH_2)_{1-6}$oxetanyl$(CH_2)_{0-6}$; hydroxy$(CH_2)_{0-6}$oxetanyl$(CH_2)_{1-6}$; 4-hydroxycyclohexyl; isoxazol-3-yl; morpholin-2-yl$(CH_2)_{1-6}$; morpholin-4-yl$(CH_2)_{2-6}$; 2-oxa-6-aza-spiro[3.4]oct-8-yl; oxetanyl$(CH_2)_{0-6}$; N-oxetanylpyrrolidin-3-yl; oxopyrrolidinylcarbonyl; phenylaminocarbonyl; phenyl$(CH_2)_{0-6}$aminooxetanyl$(CH_2)_{1-6}$, phenylcarbonyl; piperazinyl$(CH_2)_{2-6}$; piperidin-1-yl$(CH_2)_{2-6}$; piperidin-2-yl$(CH_2)_{1-6}$; piperidin-3-yl$(CH_2)_{0-6}$; piperidin-4-yl$(CH_2)_{0-6}$; piperidinylcarbonyl; pyrazinylcarbonyl; pyrazol-3-yl; pyridazinylcarbonyl; pyridinyl$(CH_2)_{0-6}$ carbonyl; pyridinylamino$(CH_2)_{2-6}$; pyrrolidin-3-yl, unsubstituted or 4-substituted by halogen; pyrrolidin-4-yl, unsubstituted or 3-substituted by hydroxy or $C_{1-6}$alkoxy; pyrrolidin-2-yl$(CH_2)_{1-6}$; pyrrolidinylcarbonyl; tetrahydrofuran-3-yl; tetrahydropyran-4-yl; tetrazolyl$(CH_2)_{2-6}$; trifluoromethylcarbonylamino$(CH_2)_{1-6}$ oxetanyl; trifluoromethylsulfonyl;

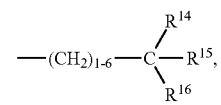

wherein $R^{14}$ is hydrogen or $C_{1-6}$alkyl; $R^{15}$ is hydroxy, $C_{1-6}$alkyl or amino; and $R^{16}$ is $C_{1-6}$alkyl, trifluoromethyl, hydroxy$(CH_2)_{1-6}$, amino$(CH_2)_{1-6}$, aminocarbonyl or carboxy$(CH_2)_{1-6}$;

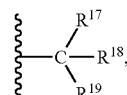

wherein $R^{17}$ is hydrogen, $C_{1-6}$alkyl or hydroxy$(CH_2)_{1-6}$; $R^{18}$ is hydroxy$(CH_2)_{1-6}$ or $C_{1-6}$alkyl; $R^{19}$ is hydroxy$(CH_2)_{1-6}$, amino$(CH_2)_{1-6}$, carboxy or aminocarbonyl$(CH_2)_{0-6}$; or

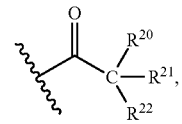

wherein $R^{20}$ is hydrogen or $C_{1-6}$alkyl; $R^{21}$ is $C_{1-6}$alkyl; $R^{22}$ is $C_{1-6}$alkoxy or amino;

$R^{12}$ and $R^{13}$, with the nitrogen atom to which they are attached, may form a pyrrolidinyl, piperazinyl, piperidinyl, morpholinyl, azetidinyl, diazepanyl or oxopyrrolidinyl ring; which may be unsubstituted, once or twice substituted by a group selected from halogen, $C_{1-6}$alkyl, $C_{1-6}$alkoxy, gemdimethyl, amino, aminocarbonyl, hydroxy, oxetanylamino, $C_{1-6}$alkylpiperazinyl, and amino$(CH_2)_{1-6}$;

$R^{12}$ and $R^{13}$, with the nitrogen atom to which they are may form a bridge ring or a spiral ring selected from 2-oxa-6-aza-spiro[3.4]octan-6-yl, 2-oxa-5,7-diazaspiro[3.4]octan-6-one-5-yl, (4aS,7aR)-hexahydropyrrolo[3,4-b][1,4]oxazin-6(2H)-yl, 4,5,6,6a-tetrahydro-3aH-pyrrolo[3,4-d][1,3]oxazol-5-yl, 2-aza-bicyclo[2.1.1]hexan-2-yl and 3-aza-bicyclo[3.1.0]hexan-3-yl; which may be unsubstituted or further substituted by amino.

Further embodiment of present invention is (iii) a compound of formula (I) or a pharmaceutically acceptable salt thereof, wherein $R^1$, $R^2$ or $R^3$ are hydrogen, fluoro, chloro or methyl;

$R^4$ is hydrogen or methyl;

$R^5$ is hydrogen;

R⁶ is hydrogen, fluoro, hydroxy, methoxy, morpholinyl or 4-(propan-2-yl)piperazin-1-yl;

R⁷ is hydrogen, fluoro, chloro, methyl, methoxy, ethoxy, hydroxyethoxy or phenoxy;

R⁸ is hydrogen, fluoro or methoxy;

R⁹ is hydrogen or methyl;

R¹⁰ is hydrogen;

A is nitrogen or —C—R¹¹, wherein R¹¹ is hydrogen, fluoro, chloro, bromo, methyl, ethyl, cyclopropyl, methoxy, trifluoromethyl, trifluoromethoxy, pyridinyloxy, methoxyethoxy, difluoromethoxy, cyano, nitro, amino, vinyl, acetylenyl, aminocarbonyl, hydroxyethoxy, methylsulfanyl, methylsulfinyl, hydroxymethyl, deuteratedmethyl, carboxyl, methoxycarbonyl, hydroxy, difluoromethyl, methylCH(hydroxy)- or methylsulfonyl;

X is S, S=O, SO₂ or S(O)NH;

Y is —CH— or nitrogen;

Q is 2-amino-4,5-dihydro-1,3-oxazol-4-ylethyl; aminoethoxy; aminoethylaminosulfonyl; aminopropyl; carboxyethyl; methyl; phenylsulfonyl; piperidin-4-yl-carbonyl; piperidin-4-yloxy; 1H-pyrazol-3-yl; pyrrolidin-3-yloxy; or NR¹²R¹³, wherein one of R¹² and R¹³ is hydrogen, methyl or hydroxyethyl; and the other one is aminobutyl; aminocarbonylethyl; aminocarbonylmethyl; 1-aminocyclobutylmethyl; 2-aminocyclohexyl; 3-aminocyclohexyl; 4-aminocyclohexyl; 1-aminocyclohexylmethyl; 2-aminocyclopentyl; 1-aminocyclopropylethyl; 1-aminocyclopropylmethyl; aminodecyl; (2-amino-4,5-dihydro-oxazol-5-yl)methyl; (2-amino-4,5-dihydro-oxazol-4-yl)methyl; aminoethoxyethyl; aminoethyl; aminoethylcarbonyl; amino ethylfluoromethylmethyl; amino ethylsulfanylethyl; aminoethylsulfonylethyl; aminoheptyl; aminohexyl; aminomethylcarbonyl; (1-aminomethyl-3,3-difluorocyclobutyl)methyl; aminomethyldifluoromethyldifluoromethylmethyl; aminomethyldifluoromethylmethyl; (2-amino-5-methyl-4,5-dihydro-1,3-oxazol-5-yl)methyl; 3-aminomethyl-1,1-dioxidothietan-3-ylmethyl; aminomethylfluoromethylethyl; aminomethylfluoromethylmethyl; aminomethyloxetanyl; aminomethyloxetanylmethyl; 3-(aminomethyl)thietan-3-ylmethyl; aminononyl; aminooctyl; aminooxetanylethyl; aminooxetanylmethyl; aminopentyl; aminophenyl; aminopropyl; 4-aminotetrahydropyran-4-ylmethyl; 3-aminotetrahydrofuran-3-ylmethyl; azetidin-3-yl; azetidin-3-ylcarbonyl; azetidin-2-ylmethyl; azetidin-3-ylmethyl; carboxyethyl; carboxymethyl; cyanoethyl; difluoromethylmethylaminoethyl; 4,5-dihydro-1H-imidazol-2-yl; dimethylaminocarbonyl; dimethylaminoethyl; (1,1-dioxidothiomorpholin-4-yl)ethyl; ethyl; ethylaminocarbonyl; ethylaminoethyl; ethylaminooxetanylmethyl; ethyl(oxetanyl)aminoethyl; hydrogen; 4-hydroxycyclohexyl; hydroxyethyl; hydroxyethylaminoethyl; hydroxyethyloxetanyl; hydroxymethylcarbonyl; hydroxymethyloxetanylmethyl; hydroxynonyl; hydroxypropyl; isoxazol-3-yl; methoxyethyl; methoxyethylaminoethyl; methyl; methylaminocarbonylmethyl; methylaminoethyl; methylcarbonyl; methylcarbonylaminoethyl; methylcarbonylaminomethyloxetanylmethyl; methylcarbonylaminopropyl; methylsulfinylethyl; 2-(S-methylsulfonimidoyl)ethyl; methylsulfonyl; morpholin-4-ylethyl; morpholin-2-ylmethyl; 2-oxa-6-aza-spiro[3.4]oct-8-yl; oxetanyl; oxetanylaminoethyl; oxetanylaminopropyl; oxetanylmethyl; N-oxetanylpyrrolidin-3-yl; oxo-pyrrolidin-4-ylcarbonyl; phenylaminoethyl; phenylcarbonyl; phenylmethylaminooxetanylmethyl; piperazin-1-ylethyl; piperidin-2-ylcarbonyl; piperidin-3-ylcarbonyl; piperidin-4-ylcarbonyl; piperidin-3-yl; piperidin-4-yl; piperidin-1-ylethyl; piperidin-2-ylmethyl; pyrazin-2-ylcarbonyl; pyrazol-3-yl; pyridazin-3-ylcarbonyl; pyridine-2-ylmethylcarbonyl; pyridine-2-ylaminoethyl; pyridine-2-ylcarbonyl; pyridine-3-ylcarbonyl; pyrrolidin-3-yl, unsubstituted or 4-substituted by fluoro; pyrrolidin-4-yl, unsubstituted or 3-substituted by hydroxy or methoxy; pyrrolidin-2-ylmethyl; pyrrolidin-2-ylcarbonyl; tetrahydrofuran-3-yl; tetrahydropyran-4-yl; tetrazolylethyl; trifluoromethylsulfonyl; trifluoromethylcarbonylaminomethyloxetanyl;

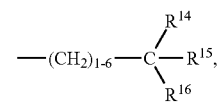

wherein R¹⁴ is hydrogen or methyl; R¹⁵ is hydroxy, methyl or amino; and R¹⁶ is methyl, trifluoromethyl, hydroxymethyl, hydroxyethyl, aminomethyl, aminocarbonyl or carboxymethyl;

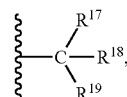

wherein R¹⁷ is hydrogen, methyl or hydroxymethyl; R¹⁸ is hydroxymethyl or methyl; R¹⁹ is hydroxymethyl, aminomethyl, carboxy, aminocarbonyl or aminocarbonylmethyl;

or

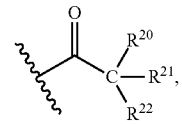

wherein R²⁰ is hydrogen or methyl; R²¹ is methyl or ethyl; R²² is methoxy or amino;

R¹² and R¹³, with the nitrogen atom to which they are attached, may form a pyrrolidinyl, piperazinyl, piperidinyl, morpholinyl, azetidinyl, diazepanyl or oxopyrrolidinyl ring; which may be unsubstituted, once or twice substituted by a group selected from fluoro, methyl, methoxy, gemdimethyl, amino, aminocarbonyl, hydroxy, oxetanylamino, methylpiperazinyl and aminomethyl;

R¹² and R¹³, with the nitrogen atom to which they are attached may form a bridge ring or a spiral ring selected from 2-oxa-6-aza-spiro[3.4]octan-6-yl, 2-oxa-5,7-diazaspiro[3.4]octan-6-one-5-yl, (4aS,7aR)-hexahydropyrrolo[3,4-b][1,4]oxazin-6(2H)-yl, 4,5,6,6a-tetrahydro-3aH-pyrrolo[3,4-d][1,3]oxazol-5-yl, 2-aza-bicyclo[2.1.1]hexan-2-yl or 3-aza-bicyclo[3.1.0]hexan-3-yl; which may be unsubstituted or further substituted by amino; and all the remaining substituents are as defined above in embodiment (i) or (ii).

Another embodiment of present invention is (iv) a compound of formula (I) or a pharmaceutically acceptable salt thereof, wherein $R^1$, $R^2$, $R^3$, $R^4$, $R^5$, $R^6$, $R^7$, $R^8$, $R^9$ and $R^{10}$ are hydrogen;

A is —C—$R^{11}$, wherein $R^{11}$ is hydrogen, halogen or $C_{1-6}$alkyl;

X is S;

Y is —CH— or nitrogen;

Q is $NR^{12}R^{13}$, wherein one of $R^{12}$ and $R^{13}$ is hydrogen; and the other one is amino$(CH_2)_{2-6}$, amino$(CH_2)_{1-6}$difluoromethyl$(CH_2)_{1-6}$, amino$(CH_2)_{0-6}$oxetanyl$(CH_2)_{1-6}$ or hydrogen;

$R^{12}$ and $R^{13}$, with the nitrogen atom to which they are attached, may form a pyrrolidinyl ring, which may be once substituted by amino; and all the remaining substituents are as defined above in embodiment (i) to (iii).

Further embodiment of present invention is (v) a compound of formula (I) or a pharmaceutically acceptable salt thereof, wherein $R^1$, $R^2$, $R^3$, $R^4$, $R^5$, $R^6$, $R^7$, $R^8$, $R^9$ and $R^{10}$ are hydrogen;

A is —C—$R^{11}$, wherein $R^{11}$ is hydrogen, chloro or methyl;

Q is $NR^{12}R^{13}$, wherein one of $R^{12}$ and $R^{13}$ is hydrogen; and the other one is aminoethyl, aminomethyldifluoromethyl, aminomethyloxetanylmethyl, aminooxetanylmethyl or hydrogen;

$R^{12}$ and $R^{13}$, with the nitrogen atom to which they are attached, may form a pyrrolidinyl ring, which may be once substituted by amino; and all the remaining substituents are as defined above in embodiment (iv).

Another further embodiment of present invention is (vi) a compound of formula (I) or a pharmaceutically acceptable salt thereof, wherein $R^1$, $R^2$, $R^3$, $R^4$, $R^5$, $R^6$, $R^7$, $R^8$, $R^9$ and $R^{10}$ are hydrogen;

A is —C—$R^{11}$, wherein $R^{11}$ is hydrogen, halogen, $C_{1-6}$alkyl, hydroxy$(CH_2)_{1-6}$, deuteratedmethyl or carboxyl;

X is S=O;

Y is —CH— or nitrogen;

Q is $NR^{12}R^{13}$, wherein one of $R^{12}$ and $R^{13}$ is hydrogen; and the other one is amino$(CH_2)_{2-6}$; amino$(CH_2)_{1-6}$difluoromethyl$(CH_2)_{1-6}$; amino$(CH_2)_{1-6}$fluoromethyl$(CH_2)_{1-6}$; amino$(CH_2)_{1-6}$oxetanyl; amino$(CH_2)_{1-6}$oxetanyl$(CH_2)_{1-6}$; aminooxetanyl$(CH_2)_{1-6}$; hydroxy$(CH_2)_{2-10}$; phenyl$(CH_2)_{1-6}$aminooxetanyl$(CH_2)_{1-6}$; pyrrolidin-3-yl, 4-substituted by halogen;

or

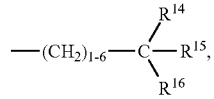

wherein $R^{14}$ is hydrogen, $R^{15}$ is hydroxy, and $R^{16}$ is hydroxy$(CH_2)_{1-6}$;

$R^{12}$ and $R^{13}$, with the nitrogen atom to which they are attached, may form a pyrrolidinyl ring, which may be once or twice substituted by a group selected from halogen, amino and hydroxyl; and all the remaining substituents are as defined above in embodiment (i) to (v).

More further embodiment of present invention is (vii) a compound of formula (I) or a pharmaceutically acceptable salt thereof, wherein $R^1$, $R^2$, $R^3$, $R^4$, $R^5$, $R^6$, $R^7$, $R^8$, $R^9$ and $R^{10}$ are hydrogen;

A is —C—$R^{11}$, wherein $R^{11}$ is hydrogen, chloro, methyl, hydroxymethyl, deuteratedmethyl or carboxyl;

Q is $NR^{12}R^{13}$, wherein one of $R^{12}$ and $R^{13}$ is hydrogen; and the other one is aminoethyl; aminomethyldifluoromethyl; aminomethylfluoromethylmethyl; aminomethyloxetanyl; aminomethyloxetanylmethyl; aminooxetanylmethyl; aminopropyl; hydroxyethyl; phenylmethylaminooxetanylmethyl; pyrrolidin-3-yl, 4-substituted by fluoro;

or

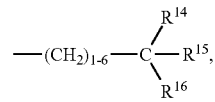

wherein $R^{14}$ is hydrogen, $R^{15}$ is hydroxy, and $R^{16}$ is hydroxymethyl;

$R^{12}$ and $R^{13}$, with the nitrogen atom to which they are attached, may form a pyrrolidinyl ring, which may be once or twice substituted by a group selected from fluoro, amino and hydroxyl; and all the remaining substituents are as defined above in embodiment (vi). Still further embodiment of present invention is (viii) a compound of formula (I) or a pharmaceutically acceptable salt thereof, wherein $R^1$, $R^2$, and $R^3$ are hydrogen, halogen or $C_{1-6}$alkyl;

$R^4$ is hydrogen or $C_{1-6}$alkyl;

$R^5$ is hydrogen;

$R^6$ is hydrogen, halogen, hydroxy, $C_{1-6}$alkoxy, morpholinyl or 4-(propan-2-yl)piperazin-1-yl;

$R^7$ is hydrogen, halogen, $C_{1-6}$alkyl, $C_{1-6}$alkoxy, hydroxy$(CH_2)_{2-6}$—O—, or phenoxy;

$R^8$ is hydrogen, halogen or $C_{1-6}$alkoxy;

$R^9$ is hydrogen or $C_{1-6}$alkyl;

$R^{10}$ is hydrogen;

A is nitrogen or —C—$R^{11}$, wherein $R^{11}$ is hydrogen, halogen, $C_{1-6}$alkyl, $C_{1-6}$alkoxy, trifluoromethyl, trifluoromethoxy, pyridinyloxy, $C_{1-6}$alkoxy$(CH_2)_{1-6}$—O—, difluoromethoxy, nitro, cycloalkyl, cyano, amino, vinyl, acetylenyl, aminocarbonyl, hydroxy$(CH_2)_{2-6}$—O—, $C_{1-6}$alkylsulfanyl, $C_{1-6}$alkylsulfinyl, hydroxy$(CH_2)_{1-6}$, deuteratedmethyl, carboxyl, $C_{1-6}$alkoxycarbonyl, hydroxy, difluoromethyl or methylCH(hydroxy)-;

X is $SO_2$;

Y is —CH— or nitrogen;

Q is 2-amino-4,5-dihydro-1,3-oxazol-4-ylethyl; amino$(CH_2)_{2-6}$—O—; amino$(CH_2)_{2-6}$aminosulfonyl; $C_{1-6}$alkyl, unsubstituted or once substituted by amino; carboxy$(CH_2)_{1-6}$; phenylsulfonyl; piperidin-4-yl-carbonyl; piperidin-4-yloxy; 1H-pyrazol-3-yl; pyrrolidin-3-yloxy; or $NR^{12}R^{13}$, wherein one of $R^{12}$ and $R^{13}$ is hydrogen, $C_{1-6}$alkyl or hydroxy$(CH_2)_{2-6}$; and the other one is {1-[amino$(CH_2)_{0-6}$]-3,3-difluorocyclobutyl}$(CH_2)_{1-6}$; (S—$C_{1-6}$alkylsulfonimidoyl)$(CH_2)_{2-6}$; 3-aminotetrahydrofuran-3-yl$(CH_2)_{1-6}$; (2-amino-5-methyl-4,5-dihydro-1,3-oxazol-5-yl)methyl; 3-aminomethyl-1,1-dioxidothietan-3-ylmethyl; 3-(aminomethyl)thietan-3-ylmethyl; (1,1-dioxidothiomorpholin-4-yl)ethyl; $C_{0-6}$alkyl(oxetanyl)N$(CH_2)_{2-6}$; 4,5-dihydro-1H-imidazol-2-yl; amino$(CH_2)_{2-6}$—O—$(CH_2)_{2-6}$; amino$(CH_2)_{2-10}$; amino$(CH_2)_{1-6}$ carbonyl; aminocarbonyl$(CH_2)_{1-6}$; amino$(CH_2)_{1-6}$difluoromethyl$(CH_2)_{1-6}$; amino$(CH_2)_{1-6}$ difluoromethyldifluoromethyl$(CH_2)_{1-6}$; amino$(CH_2)_{1-6}$fluoromethyl$(CH_2)_{1-6}$; amino$(CH_2)_{1-6}$oxetanyl$(CH_2)_{0-6}$; amino$(CH_2)_{0-6}$oxetanyl$(CH_2)_{1-6}$; amino$(CH_2)_{2-6}$sulfanyl$(CH_2)_{2-6}$; amino$(CH_2)_{2-6}$sulfonyl$(CH_2)_{2-6}$; 1-aminocyclobutylmethyl; 2-aminocyclohexyl; 3-aminocyclohexyl; 4-aminocyclohexyl; 1-aminocyclohexylmethyl; 2-aminocyclopentyl;

1-aminocyclopropylethyl; 1-aminocyclopropylmethyl; (2-amino-4,5-dihydro-oxazol-5-yl)($CH_2$)$_{1-6}$; (2-amino-4,5-dihydro-oxazol-4-yl)($CH_2$)$_{1-6}$; aminophenyl; 4-aminotetrahydropyran-4-yl($CH_2$)$_{1-6}$; azetidin-2-yl($CH_2$)$_{1-6}$; azetidin-3-yl($CH_2$)$_{0-6}$; azetidin-3-ylcarbonyl; $C_{1-6}$alkoxy($CH_2$)$_{2-6}$; $C_{1-6}$alkoxy($CH_2$)$_{2-6}$amino($CH_2$)$_{2-6}$; $C_{1-6}$alkyl; $C_{1-6}$alkylamino($CH_2$)$_{2-6}$; $C_{1-6}$alkylaminooxetanyl($CH_2$)$_{1-6}$; $C_{1-6}$alkylcarbonyl; $C_{1-6}$alkylcarbonylamino($CH_2$)$_{2-6}$; $C_{1-6}$alkylcarbonylamino($CH_2$)$_{1-6}$oxetanyl($CH_2$)$_{0-6}$; $C_{1-6}$ alkylsulfinyl($CH_2$)$_{2-6}$; $C_{1-6}$ alkylsulfonyl; carboxy($CH_2$)$_{1-6}$; cyano($CH_2$)$_{1-6}$; $C_{1-6}$alkylaminocarbonyl($CH_2$)$_{0-6}$; di$C_{1-6}$alkylamino($CH_2$)$_{2-6}$; di$C_{1-6}$alkylaminocarbonyl; difluoromethyl($CH_2$)$_{1-6}$ amino($CH_2$)$_{2-6}$; hydrogen; hydroxy($CH_2$)$_{2-10}$; hydroxy($CH_2$)$_{2-6}$amino($CH_2$)$_{2-6}$; hydroxy($CH_2$)$_{1-6}$carbonyl; hydroxy($CH_2$)$_{1-6}$oxetanyl($CH_2$)$_{0-6}$; 4-hydroxycyclohexyl; isoxazol-3-yl; morpholin-2-yl($CH_2$)$_{1-6}$; morpholin-4-yl($CH_2$)$_{2-6}$; 2-oxa-6-aza-spiro[3.4]oct-8-yl; oxetanyl($CH_2$)$_{0-6}$; N-oxetanylpyrrolidin-3-yl; oxopyrrolidin-4-ylcarbonyl; phenylaminocarbonyl; phenyl($CH_2$)$_{1-6}$aminooxetanyl($CH_2$)$_{1-6}$, phenylcarbonyl; piperazinyl($CH_2$)$_{2-6}$; piperidin-1-yl($CH_2$)$_{2-6}$; piperidin-2-yl($CH_2$)$_{1-6}$; piperidin-3-yl($CH_2$)$_{0-6}$; piperidin-4-yl($CH_2$)$_{0-6}$; piperidin-2-ylcarbonyl; piperidin-3-ylcarbonyl; piperidin-4-ylcarbonyl; pyrazin-2-ylcarbonyl; pyrazol-3-yl; pyridazin-3-ylcarbonyl; pyridine-2-yl($CH_2$)$_{0-6}$carbonyl; pyridine-3-yl($CH_2$)$_{0-6}$carbonyl; pyridine-2-ylamino($CH_2$)$_{2-6}$; pyrrolidin-3-yl, unsubstituted or 4-substituted by halogen; pyrrolidin-4-yl, unsubstituted or 3-substituted by hydroxy or $C_{1-6}$alkoxy; pyrrolidin-2-yl($CH_2$)$_{1-6}$; pyrrolidin-2-ylcarbonyl; tetrahydrofuran-3-yl; tetrahydropyran-4-yl; tetrazolyl($CH_2$)$_{2-6}$; trifluoromethylcarbonylamino($CH_2$)$_{1-6}$oxetanyl; trifluoromethylsulfonyl;

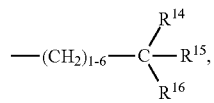

wherein $R^{14}$ is hydrogen or $C_{1-6}$alkyl; $R^{15}$ is hydroxy, $C_{1-6}$alkyl or amino; and $R^{16}$ is $C_{1-6}$alkyl, trifluoromethyl, hydroxy($CH_2$)$_{1-6}$, amino($CH_2$)$_{1-6}$, aminocarbonyl or carboxy($CH_2$)$_{1-6}$;

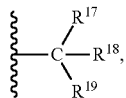

wherein $R^{17}$ is hydrogen, $C_{1-6}$alkyl or hydroxy($CH_2$)$_{1-6}$; $R^{18}$ is hydroxy($CH_2$)$_{1-6}$ or $C_{1-6}$alkyl; $R^{19}$ is hydroxy($CH_2$)$_{1-6}$, amino($CH_2$)$_{1-6}$, carboxy or aminocarbonyl($CH_2$)$_{0-6}$;
or

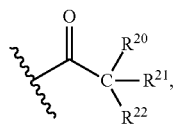

wherein $R^{20}$ is hydrogen or $C_{1-6}$alkyl; $R^{21}$ is $C_{1-6}$alkyl; $R^{22}$ is $C_{1-6}$alkoxy or amino;

$R^{12}$ and $R^{13}$, with the nitrogen atom to which they are attached, may form a pyrrolidinyl, piperazinyl, piperidinyl, morpholinyl, azetidinyl, diazepanyl or oxopyrrolidinyl ring; which may be unsubstituted, once or twice substituted by a group selected from halogen, $C_{1-6}$alkyl, $C_{1-6}$alkoxy, gemdimethyl, amino, aminocarbonyl, hydroxy, oxetanylamino, $C_{1-6}$alkylpiperazinyl and amino($CH_2$)$_{1-6}$;

$R^{12}$ and $R^{13}$, with the nitrogen atom to which they are attached may form a bridge ring or a spiral ring selected from 2-oxa-6-aza-spiro[3.4]octan-6-yl, 2-oxa-5,7-diazaspiro[3.4]octan-6-one-5-yl, (4aS,7aR)-hexahydropyrrolo[3,4-b][1,4]oxazin-6(2H)-yl, 4,5,6,6a-tetrahydro-3aH-pyrrolo[3,4-d][1,3]oxazol-5-yl, 2-aza-bicyclo[2.1.1]hexan-2-yl or 3-aza-bicyclo[3.1.0]hexan-3-yl; which may be unsubstituted or further substituted by amino; and all the remaining substituents are as defined above in embodiment (i) to (vii).

Particular embodiment of present invention is (ix) a compound of formula (I) or a pharmaceutically acceptable salt thereof, wherein $R^1$, $R^2$, and $R^3$ are hydrogen, fluoro, chloro or methyl;

$R^4$ is hydrogen or methyl;

$R^5$ is hydrogen;

$R^6$ is hydrogen, fluoro, hydroxy, methoxy, morpholinyl or 4-(propan-2-yl)piperazin-1-yl;

$R^7$ is hydrogen, fluoro, chloro, methyl, methoxy, hydroxyethoxy, or phenoxy;

$R^8$ is hydrogen, fluoro or methoxy;

$R^9$ is hydrogen or methyl;

$R^{10}$ is hydrogen;

A is nitrogen or —C—$R^{11}$, wherein $R^{11}$ is hydrogen, fluoro, chloro, bromo, methyl, ethyl, methoxy, trifluoromethyl, trifluoromethoxy, pyridinyloxy, methoxyethoxy, difluoromethoxy, nitro, cyclopropyl, cyano, amino, vinyl, acetylenyl, aminocarbonyl, hydroxyethoxy, methylsulfanyl, methylsulfinyl, hydroxymethyl, deuteratedmethyl, carboxyl, methoxycarbonyl, hydroxy, difluoromethyl or methylCH(hydroxy)-;

Y is —CH— or nitrogen;

Q is 2-amino-4,5-dihydro-1,3-oxazol-4-ylethyl; aminoethoxy; aminoethylaminosulfonyl; aminopropyl; carboxyethyl; methyl; phenylsulfonyl; piperidin-4-yl-carbonyl; piperidin-4-yloxy; 1H-pyrazol-3-yl; pyrrolidin-3-yloxy; or $NR^{12}R^{13}$, wherein one of $R^{12}$ and $R^{13}$ is hydrogen, methyl or hydroxyethyl, and the other one is aminobutyl; aminocarbonylethyl; aminocarbonylmethyl; 1-aminocyclobutylmethyl; 2-aminocyclohexyl; 3-aminocyclohexyl; 4-aminocyclohexyl; 1-aminocyclohexylmethyl; 2-aminocyclopentyl; 1-aminocyclopropylethyl; 1-aminocyclopropylmethyl; aminodecyl; (2-amino-4,5-dihydro-oxazol-5-yl)methyl; (2-amino-4,5-dihydro-oxazol-4-yl)methyl; aminoethoxyethyl; aminoethyl; aminoethylcarbonyl; aminoethylfluoromethylmethyl; aminoethylsulfanylethyl; aminoethylsulfonylethyl; aminoheptyl; aminohexyl; aminomethylcarbonyl; (1-aminomethyl-3,3-difluorocyclobutyl)methyl; aminomethyldifluoromethyldifluoromethylmethyl; aminomethyldifluoromethylmethyl; (2-amino-5-methyl-4,5-dihydro-1,3-oxazol-5-yl)methyl; 3-aminomethyl-1,1-dioxidothietan-3-ylmethyl; aminomethylfluoromethylethyl; aminomethylfluoromethylmethyl; aminomethyloxetanyl; aminomethyloxetanylmethyl; 3-(aminomethyl)thietan-3-ylmethyl; aminononyl; aminooctyl; aminooxetanylethyl; aminooxetanylmethyl; aminopentyl; aminophenyl; aminopropyl; 4-aminotetrahydropyran-4-ylmethyl; 3-aminotetrahydrofuran-3-ylmethyl; azetidin-3-yl; azetidin-3-ylcarbonyl; azetidin-2-ylmethyl; azetidin-3-ylmethyl; carboxyethyl; carboxymethyl; cyanoethyl; difluoromethylmethylaminoethyl; 4,5-dihydro-1H-imidazol-2-yl; dimethylaminocarbonyl; dimethylaminoethyl; (1,1-dioxidothiomorpholin-4-yl)ethyl; ethyl; ethylaminocarbonyl; ethylaminoethyl; ethylaminooxetanylmethyl; ethyl(oxetanyl)aminoethyl; hydrogen; 4-hydroxycyclohexyl; hydroxyethyl; hydroxyethylaminoethyl; hydroxyethyloxetanyl; hydroxymethylcarbonyl; hydroxymethyloxetanylmethyl; hydroxynonyl; hydroxypropyl; isoxazol-3-yl; methoxyethyl; methoxyethylaminoethyl; methyl; methylaminocarbonylmethyl; methylaminoethyl; methylcarbonyl; methylcarbonylaminoethyl; methylcarbonylaminomethyloxetanylmethyl; methylcarbonylaminopropyl; methylsulfinylethyl; 2-(S-methylsulfonimidoyl)ethyl; methylsulfonyl; morpholin-4-ylethyl; morpholin-2-ylmethyl; 2-oxa-6-aza-spiro[3.4]oct-8-yl; oxetanyl; oxetanylaminoethyl; oxetanylaminopropyl; oxetanylmethyl; N-oxetanylpyrrolidin-3-yl; oxo-pyrrolidin-4-ylcarbonyl; phenylaminocarbonyl; phenylcarbonyl; phenylmethylaminooxetanylmethyl; piperazin-1-ylethyl; piperidin-2-ylcarbonyl; piperidin-3-ylcarbonyl; piperidin-4-ylcarbonyl; piperidine-3-yl; piperidine-4-yl; piperidin-1-ylethyl; piperidin-2-ylmethyl; pyrazin-2-ylcarbonyl; pyrazol-3-yl; pyridazin-3-ylcarbonyl; pyridine-2-ylmethylcarbonyl; pyridine-2-ylaminoethyl; pyridine-2-ylcarbonyl; pyridine-3-ylcarbonyl; pyrrolidin-3-yl, unsubstituted or 4-substituted by fluoro; pyrrolidin-4-yl, unsubstituted or 3-substituted by hydroxy or methoxy; pyrrolidin-2-ylmethyl; pyrrolidin-2-ylcarbonyl; tetrahydrofuran-3-yl; tetrahydropyran-4-yl; tetrazolylethyl; trifluoromethylsulfonyl; trifluoromethylcarbonylaminomethyloxetanyl;

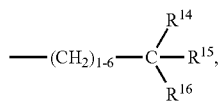

wherein $R^{14}$ is hydrogen or methyl; $R^{15}$ is hydroxy, methyl or amino; and $R^{16}$ is methyl, trifluoromethyl, hydroxymethyl, hydroxyethyl, aminomethyl, aminocarbonyl or carboxymethyl;

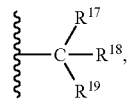

wherein $R^{17}$ is hydrogen, methyl or hydroxymethyl; $R^{18}$ is hydroxymethyl or methyl; $R^{19}$ is hydroxymethyl, aminomethyl, carboxy, aminocarbonyl or aminocarbonylmethyl; or

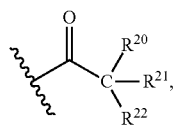

wherein $R^{20}$ is hydrogen or methyl; $R^{21}$ is methyl or ethyl; $R^{22}$ is methoxy or amino;

$R^{12}$ and $R^{13}$, with the nitrogen atom to which they are attached, may form a pyrrolidinyl, piperazinyl, piperidinyl, morpholinyl, azetidinyl, diazepanyl or oxopyrrolidinyl ring; which may be unsubstituted, once or twice substituted by a group selected from fluoro, methyl, methoxy, gemdimethyl, amino, aminocarbonyl, hydroxy, oxetanylamino, methylpiperazinyl and aminomethyl;

$R^{12}$ and $R^{13}$, with the nitrogen atom to which they are attached may form a bridge ring or a spiral ring selected from 2-oxa-6-aza-spiro[3.4]octan-6-yl, 2-oxa-5,7-diazaspiro[3.4]octan-6-one-5-yl, (4aS,7aR)-hexahydropyrrolo[3,4-b][1,4]oxazin-6(2H)-yl, 4,5,6,6a-tetrahydro-3aH-pyrrolo[3,4-d][1,3]oxazol-5-yl, 2-aza-bicyclo[2.1.1]hexan-2-yl or 3-aza-bicyclo[3.1.0]hexan-3-yl; which may be unsubstituted or further substituted by amino; and all the remaining substituents are as defined above in embodiment (viii).

Another particular embodiment of present invention is (x) a compound of formula (I) or a pharmaceutically acceptable salt thereof, wherein $R^1, R^2, R^3, R^4, R^5, R^6, R^7, R^8, R^9$, and $R^{10}$ are hydrogen;
A is —C—$R^{11}$, wherein $R^{11}$ is $C_{1-6}$alkyl;
X is S(O)NH;
Y is —CH—;
Q is $NR^{12}R^{13}$, wherein one of $R^{12}$ and $R^{13}$ is hydrogen; and the other one is amino$(CH_2)_{2-6}$;
$R^{12}$ and $R^{13}$, with the nitrogen atom to which they are attached, may form a pyrrolidinyl ring, which may be twice substituted by a group selected from amino and hydroxyl; and all the remaining substituents are as defined above in embodiment (i) to (ix).

Still another particular embodiment of invention is (xi) a compound of formula (I) or a pharmaceutically acceptable salt thereof, wherein $R^1, R^2, R^3, R^4, R^5, R^6, R^7, R^8, R^9$, and $R^{10}$ are hydrogen;
A is —C—$R^{11}$, wherein $R^{11}$ is methyl;
Q is $NR^{12}R^{13}$, wherein one of $R^{12}$ and $R^{13}$ is hydrogen; and the other one is aminoethyl;
$R^{12}$ and $R^{13}$, with the nitrogen atom to which they are attached, may form a pyrrolidinyl ring, which may be twice substituted by a group selected from amino and hydroxyl; and all the remaining substituents are as defined above in embodiment (x).

Particular embodiment of present invention is a compound of formula (I) or a pharmaceutically acceptable salt thereof, selected from: N-[(3-aminooxetan-3-yl)methyl]-2-(8-methoxy-1,1-dioxido-2,3-dihydro-1,4-benzothiazepin-4(5H)-yl)-6-methylquinolin-4-amine; N-[(3-aminooxetan-3-yl)methyl]-2-(8-fluoro-1,1-dioxido-2,3-dihydro-1,4-benzothiazepin-4(5H)-yl)-6-methylquinolin-4-amine; N-[(3-aminooxetan-3-yl)methyl]-2-(7-fluoro-1,1-dioxido-2,3-dihydro-1,4-benzothiazepin-4(5H)-yl)-6-methylquinolin-4-amine; N-[(3-aminooxetan-3-yl)methyl]-2-(9-fluoro-1,1-dioxido-2,3-dihydro-1,4-benzothiazepin-4(5H)-yl)-6-methylquinolin-4-amine; N-[(3-aminooxetan-3-yl)methyl]-2-(7-methoxy-1,1-dioxido-2,3-dihydro-1,4-benzothiazepin-4(5H)-yl)-6-methylquinolin-4-amine; N-[(3-aminooxetan-3-yl)methyl]-2-(8-chloro-1,1-dioxido-2,3-dihydro-1,4-benzothiazepin-4(5H)-yl)-6-methylquinolin-4-amine; N-[(3-aminooxetan-3-yl)methyl]-2-(7-methoxy-1,1-dioxido-2,3-dihydro-1,4-benzothiazepin-4(5H)-yl)quinolin-4-amine; N-[(3-aminotetrahydrofuran-3-yl)methyl]-2-(1,1-dioxido-2,3-dihydro-1,4-benzothiazepin-4(5H)-yl)-6-methylquinolin-4-amine; N-[(3-aminooxetan-3-yl)methyl]-2-(1,1-dioxido-2,3-dihydro-1,4-benzothiazepin-4(5H)-yl)-6-methylquinolin-4-amine; N-[(4-aminotetrahydro-2H- pyran-4-yl)methyl]-2-(1,1-dioxido-2,3-dihydro-1,4-benzothiazepin-4(5H)-yl)-6-methylquinolin-4-amine; N-[(3-aminooxetan-3-yl)methyl]-2-(8-methyl-1,1-dioxido-2,3-dihydro-1,4-benzothiazepin-4(5H)-yl)quinolin-4-amine; N-[(3-aminooxetan-3-yl)methyl]-6-methyl-2-(8-methyl-1,1-dioxido-2,3-dihydro-1,4-benzothiazepin-4(5H)-yl)quinolin-4-amine; 2-(1,1-dioxido-2,3-dihydro-1,4-benzothiazepin-4(5H)-yl)-6-methyl-N-(2-oxa-6-azaspiro[3.4]oct-8-yl)quinolin-4-amine; N-[2-(3-aminooxetan-3-yl)ethyl]-2-(1,1-dioxido-2,3-dihydro-1,4-benzothiazepin-4(5H)-yl)-6-methylquinolin-4-amine; N-[(3-aminooxetan-3-yl)methyl]-6-methyl-2-(5-methyl-1,1-dioxido-2,3-dihydro-1,4-benzothiazepin-4(5H)-yl)quinolin-4-amine; N-[(3-aminooxetan-3-yl)methyl]-2-(8-methoxy-1,1-dioxido-2,3-dihydro-1,4-benzothiazepin-4(5H)-yl)quinolin-4-amine; N-[(3-aminooxetan-3-yl)methyl]-2-(1,1-dioxido-2,3-dihydro-1,4-benzothiazepin-4(5H)-yl)-1,6-naphthyridin-4-amine; N-[(1-aminocyclohexyl)methyl]-2-(1,1-dioxido-2,3-dihydro-1,4-benzothiazepin-4(5H)-yl)-6-methylquinolin-4-amine; N-{[3-(aminomethyl)oxetan-3-yl]methyl}-2-(8-fluoro-1,1-dioxido-2,3-dihydro-1,4-benzothiazepin-4(5H)-yl)-6-methylquinolin-4-amine; N-{[3-(benzylamino)oxetan-3-yl]methyl}-6-chloro-2-(7-fluoro-1,1-dioxido-2,3-dihydro-1,4-benzothiazepin-4(5H)-yl)quinolin-4-amine; N-[(3-aminooxetan-3-yl)methyl]-6-chloro-2-(7-fluoro-1,1-dioxido-2,3-dihydro-1,4-benzothiazepin-4(5H)-yl)quinolin-4-amine; N-{[3-(aminomethyl)oxetan-3-yl]methyl}-2-(7-methoxy-1,1-dioxido-2,3-dihydro-1,4-benzothiazepin-4(5H)-yl)quinolin-4-amine; N-{[3-(aminomethyl)oxetan-3-yl]methyl}-2-(7-methoxy-1,1-dioxido-2,3-dihydro-1,4-benzothiazepin-4(5H)-yl)-6-methylquinolin-4-amine; N-{[3-({[2-(7-methoxy-1,1-dioxido-2,3-dihydro-1,4-benzothiazepin-4(5H)-yl)-6-methylquinolin-4-yl]amino}methyl)oxetan-3-yl]methyl}acetamide; N-{[3-(aminomethyl)oxetan-3-yl]methyl}-2-(8-methyl-1,1-dioxido-2,3-dihydro-1,4-benzothiazepin-4(5H)-yl)quinolin-4-amine; N-{[3-(aminomethyl)oxetan-3-yl]methyl}-6-methyl-2-(8-methyl-1,1-dioxido-2,3-dihydro-1,4-benzothiazepin-4(5H)-yl)quinolin-4-amine; [3-({[2-(1,1-dioxido-2,3-dihydro-1,4-benzothiazepin-4(5H)-yl)-6-methylquinolin-4-yl]amino}methyl)oxetan-3-yl]methanol; (2S)-3-{[2-(1,1-dioxido-2,3-dihydro-1,4-benzothiazepin-4(5H)-yl)-6-methylquinolin-4-yl]amino}propane-1,2-diol; (2R)-3-{[2-(1,1-dioxido-2,3-dihydro-1,4-benzothiazepin-4(5H)-yl)-6-methylquinolin-4-yl]amino}propane-1,2-diol; N-{[1-(aminomethyl)-3,3-difluorocyclobutyl]methyl}-2-(1,1-dioxido-2,3-dihydro-1,4-benzothiazepin-4(5H)-yl)-6-methylquinolin-4-amine; N-[(3-aminooxetan-3-yl)methyl]-6-chloro-2-(8-methoxy-1,1-dioxido-2,3-dihydro-1,4-benzothiazepin-4(5H)-yl)quinolin-4-amine; N-{[3-(aminomethyl)oxetan-3-yl]methyl}-6-chloro-2-(8-methoxy-1,1-dioxido-2,3-dihydro-1,4-benzothiazepin-4(5H)-yl)quinolin-4-amine; trans-N-[2-(1,1-dioxido-2,3-dihydro-1,4-benzothiazepin-4(5H)-yl)-6-methylquinolin-4-yl]cyclohexane-1,2-diamine; N-[2-(1,1-dioxido-2,3-dihydro-1,4-benzothiazepin-4(5H)-yl)-6-methylquinolin-4-yl]cyclohexane-1,3-diamine; (3R)-1-[2-(1,1-dioxido-2,3-dihydro-1,4-benzothiazepin-4(5H)-yl)-6-methylquinolin-4-yl]-4,4-dimethylpyrrolidin-3-ol; cis-N-[2-(1,1-dioxido-2,3-dihydro-1,4-benzothiazepin-4(5H)-yl)-6-methylquinolin-4-yl]cyclohexane-1,4-diamine; N-[2-(1,1-dioxido-2,3-dihydro-1,4-benzothiazepin-4(5H)-yl)-6-methylquinolin-4-yl]-2,2-difluoropropane-1,3-diamine; N-[6-chloro-2-(1,1-dioxido-2,3-dihydro-1,4-benzothiazepin-4(5H)-yl)quinolin-4-yl]-2,2-difluoropropane-1,3-diamine; N-[2-(1,1-dioxido-2,3-dihydro-1,4-benzothiazepin-4(5H)-yl)-6-methylquinolin-4-yl]-2-fluoropropane-1,3-diamine; N-[(3-aminooxetan-3-yl)methyl]-6-chloro-2-(1,1-dioxido-2,3-dihydro-1,4-benzothiazepin-4(5H)-yl)quinolin-4-amine; [4-{[(3-aminooxetan-3-yl)methyl]amino}-2-(1,1-dioxido-2,3-dihydro-1,4-benzothiazepin-4(5H)-yl)quinolin-6-yl]methanol; N-[(3-aminooxetan-3-yl)methyl]-2-(1,1-dioxido-2,3-dihydro-1,4-benzothiazepin-4(5H)-yl)-7-fluoro-6-methylquinolin-4-amine; N-[(3-aminooxetan-3-yl)methyl]-2-(1,1-dioxido-2,3-dihydro-1,4-benzothiazepin-4(5H)-yl)-5-fluoro-6-methylquinolin-4-amine; N~1~-[6-chloro-2-(1,1-dioxido-2,3-dihydro-1,4-benzothiazepin-4(5H)-yl)quinolin-4-yl]-2-methylpropane-1,2-diamine; 2-(1,1-dioxido-2,3-dihydro-1,4-benzothiazepin-4(5H)-yl)-6-methyl-N-(tetrahydro-2H-pyran-4-yl)quinolin-4-amine; 2-(1,1-dioxido-2,3-dihydro-1,4-benzothiazepin-4(5H)-yl)-6-methyl-N-[2-(piperazin-1-yl)ethyl]quinolin-4-amine; 2-(1,1-dioxido-2,3-dihydro-1,4-benzothiazepin-4(5H)-yl)-6-methyl-N-(piperidin-4-ylmethyl)quinolin-4-amine; N-[2-(1,1-dioxido-2,3-dihydro-1,4-benzothiazepin-4(5H)-yl)-6-methylquinolin-4-yl]heptane-1,7-diamine; N-[2-(1,1-dioxido-2,3-dihydro-1,4-benzothiazepin-4(5H)-yl)-6-methylquinolin-4-yl]-N'-methylethane-1,2-diamine; N'-[2-(1,1-dioxido-2,3-dihydro-1,4-benzothiazepin-4(5H)-yl)-6-methylquinolin-4-yl]-N,N-dimethylethane-1,2-diamine; 2-(1,1-dioxido-2,3-dihydro-1,4-benzothiazepin-4(5H)-yl)-N,6-dimethylquinolin-4-amine trifluoroacetate; (3S,4S)-1-[2-(1,1-dioxido-2,3-dihydro-1,4-benzothiazepin-4(5H)-yl)-6-methylquinolin-4-yl]pyrrolidine-3,4-diol; 2-(1,1-dioxido-2,3-dihydro-1,4-benzothiazepin-4(5H)-yl)-6-methyl-N-(pyrrolidin-2-ylmethyl)quinolin-4-amine; 4-[4-(1,4-diazepan-1-yl)-6-methylquinolin-2-yl]-2,3,4,5-tetrahydro-1,4-benzothiazepine 1,1-dioxide; N-[2-(1,1-dioxido-2,3-dihydro-1,4-benzothiazepin-4(5H)-yl)-6-methylquinolin-4-yl]-N'-ethylethane-1,2-diamine; 2-{[2-(1,1-dioxido-2,3-dihydro-1,4-benzothiazepin-4(5H)-yl)-6-methylquinolin-4-yl]amino}ethanol; 2-(1,1-dioxido-2,3-dihydro-1,4-benzothiazepin-4(5H)-yl)-6-methyl-N-(piperidin-4-yl)quinolin-4-amine; 2-(1,1-dioxido-2,3-dihydro-1,4-benzothiazepin-4(5H)-yl)-6-methyl-N-(piperidin-3-yl)quinolin-4-amine; 2-(1,1-dioxido-2,3-dihydro-1,4-benzothiazepin-4(5H)-yl)-6-methyl-N-(piperidin-2-ylmethyl)quinolin-4-amine; 2-[(2-{[2-(1,1-dioxido-2,3-dihydro-1,4-benzothiazepin-4(5H)-yl)-6-methylquinolin-4-yl]amino}ethyl)amino]ethanol; N-[2-(1,1-dioxido-2,3-dihydro-1,4-benzothiazepin-4(5H)-yl)-6-methylquinolin-4-yl]-2,2,3,3-tetrafluorobutane-1,4-diamine; N-[2-(1,1-dioxido-2,3-dihydro-1,4-benzothiazepin-4(5H)-yl)-6-methylquinolin-4-yl]-N'-(2-methoxyethyl)ethane-1,2-diamine; 1-[2-(1,1-dioxido-2,3-dihydro-1,4-benzothiazepin-4(5H)-yl)-6-methylquinolin-4-yl]-3-methylpyrrolidin-3-ol; N-[6-chloro-2-(1,1-dioxido-2,3-dihydro-1,4-benzothiazepin-4(5H)-yl)quinolin-4-yl]ethane-1,2-diamine; 2-(1,1-dioxido-2,3-dihydro-1,4-benzothiazepin-4(5H)-yl)-6-methyl-N-(oxetan-3-yl)quinolin-4-amine; N-[(3-aminooxetan-3-yl)methyl]-2-(1,1-dioxido-2,3-dihydro-1,4-benzothiazepin-4(5H)-yl)quinolin-4-amine; 2-(1,1-dioxido-2,3-dihydro-1,4-benzothiazepin-4(5H)-yl)-6-methyl-N-[(3R)-tetrahydrofuran-3-yl]quinolin-4-amine; N-{[3-(aminomethyl)oxetan-3-yl]methyl}-2-(1,1-dioxido-2,3-dihydro-1,4-benzothiazepin-4(5H)-yl)-6-methylquinolin-4-amine; N-{[3-(aminomethyl)oxetan-3-yl]methyl}-6-chloro-2-(1,1-dioxido-2,3-dihydro-1,4-benzothiazepin-4(5H)-yl)quinolin-4-amine; N-{[3-(aminomethyl)oxetan-3-yl]methyl}-2-(1,1-dioxido-2,3-dihydro-1,4-benzothiazepin-4(5H)-yl)quinolin-4-amine; 2-(1,1-dioxido-2,3-dihydro-1,4-benzothiazepin-4(5H)-yl)-6-methyl-N-(oxetan-3-ylmethyl)quinolin-4-amine; N-[(1-aminocyclobutyl)methyl]-2-(1,1-dioxido-2,3-dihydro-1,4-benzothiazepin-4(5H)-yl)-6- methylquinolin-4-amine; N-[2-(1,1-dioxido-2,3-dihydro-1,4-benzothiazepin-4(5H)-yl)-6-methylquinolin-4-yl]pentane-1,5-diamine; N-[2-(1,1-dioxido-2,3-dihydro-1,4-benzothiazepin-4(5H)-yl)-6-methylquinolin-4-yl]hexane-1,6-diamine; N-[2-(1,1-dioxido-2,3-dihydro-1,4-benzothiazepin-4(5H)-yl)-6-methylquinolin-4-yl]-1,1,1-trifluoromethanesulfonamide hydrochloride; N-[2-(1,1-dioxido-2,3-dihydro-1,4-benzothiazepin-4(5H)-yl)-6-methylquinolin-4-yl]pyridazine-3-carboxamide; N-[2-(1,1-dioxido-2,3-dihydro-1,4-benzothiazepin-4(5H)-yl)-6-methylquinolin-4-yl]benzamide; N-[2-(1,1-dioxido-2,3-dihydro-1,4-benzothiazepin-4(5H)-yl)-6-methylquinolin-4-yl]acetamide; N-[2-(1,1-dioxido-2,3-dihydro-1,4-benzothiazepin-4(5H)-yl)-6-methylquinolin-4-yl]piperidine-3-carboxamide; N-[2-(1,1-dioxido-2,3-dihydro-1,4-benzothiazepin-4(5H)-yl)-6-methylquinolin-4-yl]piperidine-4-carboxamide; 3-[2-(1,1-dioxido-2,3-dihydro-1,4-benzothiazepin-4(5H)-yl)-6-methylquinolin-4-yl]-1,1-dimethylurea; 2-(1,1-dioxido-2,3-dihydro-1,4-benzothiazepin-4(5H)-yl)-6-methyl-N-(1,2-oxazol-3-yl)quinolin-4-amine; N-{[3-(aminomethyl)oxetan-3-yl]methyl}-2-(1,1-dioxido-2,3-dihydro-1,4-benzothiazepin-4(5H)-yl)-6-(~2~H_3_)methylquinolin-4-amine; N-[(3-aminooxetan-3-yl)methyl]-6-chloro-2-(2,3-dihydro-1,4-benzothiazepin-4(5H)-yl)quinolin-4-amine; N-[6-chloro-2-(2,3-dihydro-1,4-benzothiazepin-4(5H)-yl)quinolin-4-yl]ethane-1,2-diamine; N-[(3-aminooxetan-3-yl)methyl]-2-(2,3-dihydro-1,4-benzothiazepin-4(5H)-yl)-6-methylquinolin-4-amine; 1-[2-(2,3-dihydro-1,4-benzothiazepin-4(5H)-yl)-6-methylquinolin-4-yl]pyrrolidin-3-amine; N-[2-(2,3-dihydro-1,4-benzothiazepin-4(5H)-yl)-6-methylquinazolin-4-yl]-2,2-difluoropropane-1,3-diamine; 2-(1,1-dioxido-2,3-dihydro-1,4-benzothiazepin-4(5H)-yl)-N-[2-(1,1-dioxidothiomorpholin-4-yl)ethyl]-6-methylquinolin-4-amine; N-[2-(2-aminoethoxy)ethyl]-2-(1,1-dioxido-2,3-dihydro-1,4-benzothiazepin-4(5H)-yl)-6-methylquinolin-4-amine; N~1~-[2-(1,1-dioxido-2,3-dihydro-1,4-benzothiazepin-4(5H)-yl)-6-methylquinolin-4-yl]-2-methylpropane-1,2-diamine; N~1~-[2-(1,1-dioxido-2,3-dihydro-1,4-benzothiazepin-4(5H)-yl)quinolin-4-yl]-2-methylpropane-1,2-diamine; N~1~-[2-(1,1-dioxido-2,3-dihydro-1,4-benzothiazepin-4(5H)-yl)-6-methylquinolin-4-yl]propane-1,2-diamine; 4-[6-methyl-4-(4-methylpiperazin-1-yl)quinolin-2-yl]-2,3,4,5-tetrahydro-1,4-benzothiazepine 1,1-dioxide; 1-{[2-(1,1-dioxido-2,3-dihydro-1,4-benzothiazepin-4(5H)-yl)-6-methylquinolin-4-yl]amino}propan-2-ol; (2S)—N~1~-[2-(1,1-dioxido-2,3-dihydro-1,4-benzothiazepin-4(5H)-yl)-6-methylquinolin-4-yl]propane-1,2-diamine; (2R)—N~1~-[2-(1,1-dioxido-2,3-dihydro-1,4-benzothiazepin-4(5H)-yl)-6-methylquinolin-4-yl]propane-1,2-diamine; N-[(3-aminooxetan-3-yl)methyl]-2-(1,1-dioxido-2,3-dihydro-1,4-benzothiazepin-4(5H)-yl)-7,8-difluoro-6-methylquinolin-4-amine; N-(2,2-difluoroethyl)-N'-[2-(1,1-dioxido-2,3-dihydro-1,4-benzothiazepin-4(5H)-yl)-6-methylquinolin-4-yl]ethane-1,2-diamine; 3-{[2-(1,1-dioxido-2,3-dihydro-1,4-benzothiazepin-4(5H)-yl)-6-methylquinolin-4-yl]amino}oxetan-3-ethanol; N-{[3-(aminomethyl)thietan-3-yl]methyl}-2-(1,1-dioxido-2,3-dihydro-1,4-benzothiazepin-4(5H)-yl)-6-methylquinolin-4-amine; N-{[3-(aminomethyl)-1,1-dioxidothietan-3-yl]methyl}-2-(1,1-dioxido-2,3-dihydro-1,4-benzothiazepin-4(5H)-yl)-6-methylquinolin-4-amine; N-(4,5-dihydro-1H-imidazol-2-yl)-2-(1,1-dioxido-2,3-dihydro-1,4-benzothiazepin-4(5H)-yl)-6-methylquinolin-4-amine; trans-4-{[2-(1,1-dioxido-2,3-dihydro-1,4-benzothiazepin-4(5H)-yl)-6-methylquinolin-4-yl]amino}cyclohexanol; (2S)-2-{[2-(1,1-dioxido-2,3-dihydro-1,4-benzothiazepin-4(5H)-yl)-6-methylquinolin-4-yl]amino}propan-1-ol; trans-1-[2-(1,1-dioxido-2,3-dihydro-1,4-benzothiazepin-4(5H)-yl)-6-methylquinolin-4-yl]-4-methoxypyrrolidin-3-amine; 2-(1,1-dioxido-2,3-dihydro-1,4-benzothiazepin+D154-4(5H)-yl)-N-[trans-4-methoxypyrrolidin-3-yl]-6-methylquinolin-4-amine; 4-{4-[(4aS,7aR)-hexahydropyrrolo[3,4-b][1,4]oxazin-6(2H)-yl]-6-methylquinolin-2-yl}-2,3,4,5-tetrahydro-1,4-benzothiazepine 1,1-dioxide; (3R,4R)-1-[2-(1,1-dioxido-2,3-dihydro-1,4-benzothiazepin-4(5H)-yl)-6-methylquinolin-4-yl]-4-(4-methylpiperazin-1-yl)pyrrolidin-3-ol; N-{2-[(2-amino ethyl)sulfanyl]ethyl}-2-(1,1-dioxido-2,3-dihydro-1,4-benzothiazepin-4(5H)-yl)-6-methylquinolin-4-amine; 1-{1-[2-(1,1-dioxido-2,3-dihydro-1,4-benzothiazepin-4(5H)-yl)-6-methylquinolin-4-yl]piperidin-4-yl}methanamine; 2-{[2-(8-methoxy-1,1-dioxido-2,3-dihydro-1,4-benzothiazepin-4(5H)-yl)quinolin-4-yl]amino}ethanol; N-[2-(1,1-dioxido-2,3-dihydro-1,4-benzothiazepin-4(5H)-yl)-6-methylquinolin-4-yl]propane-1,3-diamine; 4-[6-methyl-4-(morpholin-4-yl)quinolin-2-yl]-2,3,4,5-tetrahydro-1,4-benzothiazepine 1,1-dioxide; 3-{[2-(1,1-dioxido-2,3-dihydro-1,4-benzothiazepin-4(5H)-yl)-6-methylquinolin-4-yl]amino}propan-1-ol; 2-(1,1-dioxido-2,3-dihydro-1,4-benzothiazepin-4(5H)-yl)-6-methyl-N-[2-(piperidin-1-yl)ethyl]quinolin-4-amine; 1-amino-3-{[2-(1,1-dioxido-2,3-dihydro-1,4-benzothiazepin-4(5H)-yl)-6-methylquinolin-4-yl]amino}propan-2-ol; N-[2-(1,1-dioxido-2,3-dihydro-1,4-benzothiazepin-4(5H)-yl)-6-methylquinolin-4-yl]glycine; N-[2-(1,1-dioxido-2,3-dihydro-1,4-benzothiazepin-4(5H)-yl)-6-fluoroquinolin-4-yl]ethane-1,2-diamine; N-[2-(1,1-dioxido-2,3-dihydro-1,4-benzothiazepin-4(5H)-yl)-6-ethylquinolin-4-yl]ethane-1,2-diamine; N-[7-chloro-2-(1,1-dioxido-2,3-dihydro-1,4-benzothiazepin-4(5H)-yl)quinolin-4-yl]propane-1,3-diamine; N-[8-chloro-2-(1,1-dioxido-2,3-dihydro-1,4-benzothiazepin-4(5H)-yl)quinolin-4-yl]propane-1,3-diamine; N-[5-chloro-2-(1,1-dioxido-2,3-dihydro-1,4-benzothiazepin-4(5H)-yl)quinolin-4-yl]propane-1,3-diamine; N-[2-(1,1-dioxido-2,3-dihydro-1,4-benzothiazepin-4(5H)-yl)-6-methylquinolin-4-yl]-2,2-dimethylpropane-1,3-diamine; N-[2-(1,1-dioxido-2,3-dihydro-1,4-benzothiazepin-4(5H)-yl)quinolin-4-yl]ethane-1,2-diamine; N-[2-(1,1-dioxido-2,3-dihydro-1,4-benzothiazepin-4(5H)-yl)-6-methylquinolin-4-yl]ethane-1,2-diamine; N~2~-[2-(1,1-dioxido-2,3-dihydro-1,4-benzothiazepin-4(5H)-yl)-6-methylquinolin-4-yl]-2-methylpropane-1,2-diamine; N~2~-[2-(1,1-dioxido-2,3-dihydro-1,4-benzothiazepin-4(5H)-yl)-6-methylquinolin-4-yl]propane-1,2-diamine; N-[2-(1,1-dioxido-2,3-dihydro-1,4-benzothiazepin-4(5H)-yl)-6-methylquinolin-4-yl]butane-1,4-diamine; N-[2-(1,1-dioxido-2,3-dihydro-1,4-benzothiazepin-4(5H)-yl)-6-nitroquinolin-4-yl]ethane-1,2-diamine; N-[2-(1,1-dioxido-2,3-dihydro-1,4-benzothiazepin-4(5H)-yl)-5-fluoro-6-methylquinolin-4-yl]ethane-1,2-diamine; 2-{[2-(1,1-dioxido-2,3-dihydro-1,4-benzothiazepin-4(5H)-yl)-5-fluoro-6-methylquinolin-4-yl]amino}ethanol; 2-{[2-(1,1-dioxido-2,3-dihydro-1,4-benzothiazepin-4(5H)-yl)-7-fluoro-6-methylquinolin-4-yl]amino}ethanol; N-[2-(1,1-dioxido-2,3-dihydro-1,4-benzothiazepin-4(5H)-yl)-7-fluoro-6-methylquinolin-4-yl]ethane-1,2-diamine; N-[2-(1,1-dioxido-2,3-dihydro-1,4-benzothiazepin-4(5H)-yl)-7,8-difluoro-6-methylquinolin-4-yl]ethane-1,2-diamine; 2-(1,1-dioxido-2,3-dihydro-1,4-benzothiazepin-4(5H)-yl)-N-(2-methoxyethyl)-6-methylquinolin-4-amine; 1-[2-(1,1-dioxido-2,3-dihydro-1,4-benzothiazepin-4(5H)-yl)-6-methylquinolin-4-yl]piperidin-4-amine; 1-[2-(1,1-dioxido-2,3-dihydro-1,4-benzothiazepin-4(5H)-yl)-1,6-naphthyridin-4-yl]pyrrolidin- 3-amine; N-[6-(difluoromethyl)-2-(1,1-dioxido-2,3-dihydro-1,4-benzothiazepin-4(5H)-yl)quinolin-4-yl]propane-1,3-diamine; 6-chloro-2-(1,1-dioxido-2,3-dihydro-1,4-benzothiazepin-4(5H)-yl)-N-ethylquinolin-4-amine; 2-{[6-chloro-2-(1,1-dioxido-2,3-dihydro-1,4-benzothiazepin-4(5H)-yl)quinolin-4-yl]amino}ethanol; N-[6-chloro-2-(1,1-dioxido-2,3-dihydro-1,4-benzothiazepin-4(5H)-yl)quinolin-4-yl]-N'-methylethane-1,2-diamine; N-[2-(1,1-dioxido-2,3-dihydro-1,4-benzothiazepin-4(5H)-yl)-6-(methylsulfanyl)quinolin-4-yl]propane-1,3-diamine; N-[6-bromo-2-(1,1-dioxido-2,3-dihydro-1,4-benzothiazepin-4(5H)-yl)quinolin-4-yl]propane-1,3-diamine; {4-[(2-amino ethyl)amino]-2-(1,1-dioxido-2,3-dihydro-1,4-benzothiazepin-4(5H)-yl)quinolin-6-yl}methanol; 2-{[2-(1,1-dioxido-2,3-dihydro-1,4-benzothiazepin-4(5H)-yl)-6-methylquinolin-4-yl]amino}propane-1,3-diol; 2,2'-{[2-(1,1-dioxido-2,3-dihydro-1,4-benzothiazepin-4(5H)-yl)-6-methylquinolin-4-yl]imino}diethanol; 4-{[2-(1,1-dioxido-2,3-dihydro-1,4-benzothiazepin-4(5H)-yl)-6-methylquinolin-4-yl]amino}-3-hydroxybutanoic acid; 1-amino-3-{[2-(1,1-dioxido-2,3-dihydro-1,4-benzothiazepin-4(5H)-yl)-6-methylquinolin-4-yl]amino}-2-methylpropan-2-ol; 2-(1,1-dioxido-2,3-dihydro-1,4-benzothiazepin-4(5H)-yl)-6-methyl-N-[2-(morpholin-4-yl)ethyl]quinolin-4-amine; 2-{[2-(1,1-dioxido-2,3-dihydro-1,4-benzothiazepin-4(5H)-yl)-1,6-naphthyridin-4-yl]amino}ethanol; N-[2-(1,1-dioxido-2,3-dihydro-1,4-benzothiazepin-4(5H)-yl)-8-methylquinolin-4-yl]nonane-1,9-diamine; N-[2-(1,1-dioxido-2,3-dihydro-1,4-benzothiazepin-4(5H)-yl)-8-methylquinolin-4-yl]decane-1,10-diamine; N-[2-(1,1-dioxido-2,3-dihydro-1,4-benzothiazepin-4(5H)-yl)-6-methylquinolin-4-yl]octane-1,8-diamine; 9-{[2-(1,1-dioxido-2,3-dihydro-1,4-benzothiazepin-4(5H)-yl)-6-methylquinolin-4-yl]amino}nonan-1-ol; N-[2-(1,1-dioxido-2,3-dihydro-1,4-benzothiazepin-4(5H)-yl)-8-methylquinolin-4-yl]octane-1,8-diamine; cis-4-amino-1-[2-(1,1-dioxido-2,3-dihydro-1,4-benzothiazepin-4(5H)-yl)-6-methylquinolin-4-yl]pyrrolidin-3-ol; N-[2-(1,1-dioxido-2,3-dihydro-1,4-benzothiazepin-4(5H)-yl)-6-methylquinolin-4-yl]-L-alanine; N-[2-(1,1-dioxido-2,3-dihydro-1,4-benzothiazepin-4(5H)-yl)-6-methylquinolin-4-yl]-beta-alanine; N-[2-(1,1-dioxido-2,3-dihydro-1,4-benzothiazepin-4(5H)-yl)-6-methylquinolin-4-yl]benzene-1,3-diamine; N-[2-(1,1-dioxido-2,3-dihydro-1,4-benzothiazepin-4(5H)-yl)-6-methylquinolin-4-yl]benzene-1,4-diamine; (3S)-1-[2-(1,1-dioxido-2,3-dihydro-1,4-benzothiazepin-4(5H)-yl)-6-methylquinolin-4-yl]pyrrolidin-3-ol; (3R)-1-[2-(1,1-dioxido-2,3-dihydro-1,4-benzothiazepin-4(5H)-yl)-6-methylquinolin-4-yl]pyrrolidin-3-ol; trans-N-[2-(1,1-dioxido-2,3-dihydro-1,4-benzothiazepin-4(5H)-yl)-6-methylquinolin-4-yl]cyclopentane-1,2-diamine; 1-[2-(1,1-dioxido-2,3-dihydro-1,4-benzothiazepin-4(5H)-yl)-6-methylquinolin-4-yl]piperidin-3-amine; 2-(1,1-dioxido-2,3-dihydro-1,4-benzothiazepin-4(5H)-yl)-N,N,6-trimethylquinolin-4-amine; N-[2-(1,1-dioxido-2,3-dihydro-1,4-benzothiazepin-4(5H)-yl)-6-(trifluoromethoxy)quinolin-4-yl]propane-1,3-diamine; N-[2-(1,1-dioxido-2,3-dihydro-1,4-benzothiazepin-4(5H)-yl)-6-(trifluoromethyl)quinolin-4-yl]propane-1,3-diamine; N-[6-(difluoromethoxy)-2-(1,1-dioxido-2,3-dihydro-1,4-benzothiazepin-4(5H)-yl)quinolin-4-yl]propane-1,3-diamine; N-[2-(1,1-dioxido-2,3-dihydro-1,4-benzothiazepin-4(5H)-yl)-6-methoxyquinolin-4-yl]propane-1,3-diamine; N-[2-(1,1-dioxido-2,3-dihydro-1,4-benzothiazepin-4(5H)-yl)-8-methylquinolin-4-yl]propane-1,3-diamine; N-[2-(1,1-dioxido-2,3-dihydro-1,4-benzothiazepin-4(5H)-yl)-5-methylquinolin-4-yl]propane-1,3-diamine; N-[2-(1,1-dioxido-2,3-dihydro-1,4-benzothiazepin-4(5H)-yl)-7-methylquinolin-4-yl]propane-1,3-diamine; N-{[3-(aminomethyl)oxetan-3-yl]methyl}-2-(1,1-dioxido-2,3-dihydro-1,4-benzothiazepin-4(5H)-yl)-6-fluoroquinolin-4-amine; N-[(3-aminooxetan-3-yl)methyl]-6-methyl-2-(1-oxido-2,3-dihydro-1,4-benzothiazepin-4(5H)-yl)quinolin-4-amine; (+)-N-[(3-aminooxetan-3-yl)methyl]-6-methyl-2-[1-oxido-2,3-dihydro-1,4-benzothiazepin-4(5H)-yl]quinolin-4-amine; (−)-N-[(3-aminooxetan-3-yl)methyl]-6-methyl-2-[1-oxido-2,3-dihydro-1,4-benzothiazepin-4(5H)-yl]quinolin-4-amine; N-[(3-aminooxetan-3-yl)methyl]-6-chloro-2-(1-oxido-2,3-dihydro-1,4-benzothiazepin-4(5H)-yl)quinolin-4-amine; 2,2-difluoro-N-[6-methyl-2-(1-oxido-2,3-dihydro-1,4-benzothiazepin-4(5H)-yl)quinolin-4-yl]propane-1,3-diamine; N-[6-chloro-2-(1-oxido-2,3-dihydro-1,4-benzothiazepin-4(5H)-yl)quinolin-4-yl]-2,2-difluoropropane-1,3-diamine; N-[6-chloro-2-(1-oxido-2,3-dihydro-1,4-benzothiazepin-4(5H)-yl)quinolin-4-yl]ethane-1,2-diamine; N-{[3-(aminomethyl)oxetan-3-yl]methyl}-6-methyl-2-(1-oxido-2,3-dihydro-1,4-benzothiazepin-4(5H)-yl)quinolin-4-amine; N-{[3-(aminomethyl)oxetan-3-yl]methyl}-6-chloro-2-(1-oxido-2,3-dihydro-1,4-benzothiazepin-4(5H)-yl)quinolin-4-amine; N-[6-methyl-2-(1-oxido-2,3-dihydro-1,4-benzothiazepin-4(5H)-yl)quinolin-4-yl]ethane-1,2-diamine; 2-{[6-methyl-2-(1-oxido-2,3-dihydro-1,4-benzothiazepin-4(5H)-yl)quinolin-4-yl]amino}ethanol; trans-4-amino-1-[6-methyl-2-(1-oxido-2,3-dihydro-1,4-benzothiazepin-4(5H)-yl)quinolin-4-yl]pyrrolidin-3-ol; (1R,5S,6S)-3-[2-(1,1-dioxido-2,3-dihydro-1,4-benzothiazepin-4(5H)-yl)-6-methylquinolin-4-yl]-3-azabicyclo[3.1.0]hexan-6-amine; trans-4-amino-1-[2-(1,1-dioxido-2,3-dihydro-1,4-benzothiazepin-4(5H)-yl)-6-methylquinolin-4-yl]pyrrolidin-3-ol; 1-[6-methyl-2-(1-oxido-2,3-dihydro-1,4-benzothiazepin-4(5H)-yl)quinolin-4-yl]pyrrolidin-3-amine; trans-1-[6-chloro-2-(1,1-dioxido-2,3-dihydro-1,4-benzothiazepin-4(5H)-yl)quinolin-4-yl]-4-fluoropyrrolidin-3-amine; trans-4-amino-1-[6-chloro-2-(1,1-dioxido-2,3-dihydro-1,4-benzothiazepin-4(5H)-yl)quinolin-4-yl]pyrrolidin-3-ol; trans-1-[6-chloro-2-(1-oxido-2,3-dihydro-1,4-benzothiazepin-4(5H)-yl)quinolin-4-yl]-4-fluoropyrrolidin-3-amine; 2-[2-(1,1-dioxido-2,3-dihydro-1,4-benzothiazepin-4(5H)-yl)-6-methylquinolin-4-yl]-2-azabicyclo[2.1.1]hexan-5-amine; 2-(8-methoxy-1,1-dioxido-2,3-dihydro-1,4-benzothiazepin-4(5H)-yl)-6-methylquinolin-4-amine; 2-(7-methoxy-1,1-dioxido-2,3-dihydro-1,4-benzothiazepin-4(5H)-yl)-6-methylquinolin-4-amine; N-[2-(1-aminocyclopropyl)ethyl]-2-(1,1-dioxido-2,3-dihydro-1,4-benzothiazepin-4(5H)-yl)-6-methylquinolin-4-amine; 2-(1,1-dioxido-2,3-dihydro-1,4-benzothiazepin-4(5H)-yl)-6-methyl-N-(morpholin-2-ylmethyl)quinolin-4-amine; N-[2-(1,1-dioxido-2,3-dihydro-1,4-benzothiazepin-4(5H)-yl)-6-methylquinolin-4-yl]-N-methylethane-1,2-diamine; N-(azetidin-2-ylmethyl)-2-(1,1-dioxido-2,3-dihydro-1,4-benzothiazepin-4(5H)-yl)-6-methylquinolin-4-amine; 2-(1,1-dioxido-2,3-dihydro-1,4-benzothiazepin-4(5H)-yl)-6-methyl-N-(pyrrolidin-3-yl)quinolin-4-amine; N-[(1-aminocyclopropyl)methyl]-2-(1,1-dioxido-2,3-dihydro-1,4-benzothiazepin-4(5H)-yl)-6-methylquinolin-4-amine; N-(azetidin-3-yl)-6-chloro-2-(1,1-dioxido-2,3-dihydro-1,4-benzothiazepin-4(5H)-yl)quinolin-4-amine; 6-[2-(1,1-dioxido-2,3-dihydro-1,4-benzothiazepin-4(5H)-yl)-6-methylquinolin-4-yl]-2-oxa-6-azaspiro[3.4]octan-8-amine; trans-4-amino-1-[2-(1,1-dioxido-2,3-dihydro-1,4-benzothiazepin-4(5H)-yl)-1,6-naphthyridin-4-yl]pyrrolidin-3-ol; 1-[2-(1,1-dioxido-2,3-dihydro-1,4-benzothiazepin-4(5H)-yl)-6-methylquinolin-4-yl]pyrrolidin-3-amine; N-(azetidin-3-yl)-2-(1,1-dioxido-2,3-dihydro-1,4-benzothiazepin-4

(5H)-yl)-6-methylquinolin-4-amine; 1-[2-(1,1-dioxido-2,3-dihydro-1,4-benzothiazepin-4(5H)-yl)-6-methylquinolin-4-yl]azetidin-3-amine; N-[2-(1,1-dioxido-2,3-dihydro-1,4-benzothiazepin-4(5H)-yl)-6-methylquinolin-4-yl]prolinamide; 2-(1,1-dioxido-2,3-dihydro-1,4-benzothiazepin-4(5H)-yl)-N-(trans-fluoropyrrolidin-3-yl)-6-methylquinolin-4-amine; trans-4-{[2-(1,1-dioxido-2,3-dihydro-1,4-benzothiazepin-4(5H)-yl)quinolin-4-yl]amino}pyrrolidin-3-ol; trans-4-{[2-(1,1-dioxido-2,3-dihydro-1,4-benzothiazepin-4(5H)-yl)-6-methylquinolin-4-yl]amino}pyrrolidin-3-ol; cis-4-{[2-(1,1-dioxido-2,3-dihydro-1,4-benzothiazepin-4(5H)-yl)-6-methylquinolin-4-yl]amino}pyrrolidin-3-ol; N-[trans-4-fluoropyrrolidin-3-yl]-6-methyl-2-(1-oxido-2,3-dihydro-1,4-benzothiazepin-4(5H)-yl)quinolin-4-amine; 4-[(3-aminopropyl)amino]-2-(1,1-dioxido-2,3-dihydro-1,4-benzothiazepin-4(5H)-yl)quinolin-6-ol; 2-({4-[(3-aminopropyl)amino]-2-(1,1-dioxido-2,3-dihydro-1,4-benzothiazepin-4(5H)-yl)quinolin-6-yl}oxy)ethanol; N-[2-(1,1-dioxido-2,3-dihydro-1,4-benzothiazepin-4(5H)-yl)-6-(2-methoxyethoxy)quinolin-4-yl]propane-1,3-diamine; N-[2-(1,1-dioxido-2,3-dihydro-1,4-benzothiazepin-4(5H)-yl)-6-(pyridin-2-yloxy)quinolin-4-yl]propane-1,3-diamine; 3-{[2-(1,1-dioxido-2,3-dihydro-1,4-benzothiazepin-4(5H)-yl)-6-methylquinolin-4-yl]amino}propane-1,2-diol; 3-{[6-chloro-2-(1,1-dioxido-2,3-dihydro-1,4-benzothiazepin-4(5H)-yl)quinolin-4-yl]amino}propane-1,2-diol; 3-{[2-(8-chloro-1,1-dioxido-2,3-dihydro-1,4-benzothiazepin-4(5H)-yl)-6-methylquinolin-4-yl]amino}propane-1,2-diol; 3-{[6-methyl-2-(1-oxido-2,3-dihydro-1,4-benzothiazepin-4(5H)-yl)quinolin-4-yl]amino}propane-1,2-diol; 3-{[6-methyl-2-(5-methyl-1,1-dioxido-2,3-dihydro-1,4-benzothiazepin-4(5H)-yl)quinolin-4-yl]amino}propane-1,2-diol; N-[(3-aminooxetan-3-yl)methyl]-6-methyl-2-[7-(morpholin-4-yl)-1,1-dioxido-2,3-dihydro-1,4-benzothiazepin-4(5H)-yl]quinolin-4-amine; N-[(3-aminooxetan-3-yl)methyl]-2-{1,1-dioxido-7-[4-(propan-2-yl)piperazin-1-yl]-2,3-dihydro-1,4-benzothiazepin-4(5H)-yl}-6-methylquinolin-4-amine; 3-{[4-(4-amino quinolin-2-yl)-1,1-dioxido-2,3,4,5-tetrahydro-1,4-benzothiazepin-8-yl]oxy}propan-1-ol; N-[(3-aminooxetan-3-yl)methyl]-2-(1,1-dioxido-8-phenoxy-2,3-dihydro-1,4-benzothiazepin-4(5H)-yl)-6-methylquinolin-4-amine; N~3~-[2-(1,1-dioxido-2,3-dihydro-1,4-benzothiazepin-4(5H)-yl)-6-methylquinolin-4-yl]-beta-alaninamide; 3-{[2-(1,1-dioxido-2,3-dihydro-1,4-benzothiazepin-4(5H)-yl)-6-methylquinolin-4-yl]amino}butanamide; 3-{[2-(1,1-dioxido-2,3-dihydro-1,4-benzothiazepin-4(5H)-yl)-6-methylquinolin-4-yl]amino}-2-methylpropanamide; N~2~-[2-(1,1-dioxido-2,3-dihydro-1,4-benzothiazepin-4(5H)-yl)-6-methylquinolin-4-yl]-L-alaninamide; N~2~-[2-(1,1-dioxido-2,3-dihydro-1,4-benzothiazepin-4(5H)-yl)-6-methylquinolin-4-yl]glycinamide; N~2~-[2-(1,1-dioxido-2,3-dihydro-1,4-benzothiazepin-4(5H)-yl)-6-methylquinolin-4-yl]-N-methylglycinamide; (2S)-2-amino-3-{[2-(1,1-dioxido-2,3-dihydro-1,4-benzothiazepin-4(5H)-yl)-6-methylquinolin-4-yl]amino}propan-1-ol; (2R)-2-amino-3-{[2-(1,1-dioxido-2,3-dihydro-1,4-benzothiazepin-4(5H)-yl)-6-methylquinolin-4-yl]amino}propan-1-ol; N-[(2-amino-4,5-dihydro-1,3-oxazol-5-yl)methyl]-2-(1,1-dioxido-2,3-dihydro-1,4-benzothiazepin-4(5H)-yl)-6-methylquinolin-4-amine; N-[(2-amino-5-methyl-4,5-dihydro-1,3-oxazol-5-yl)methyl]-2-(1,1-dioxido-2,3-dihydro-1,4-benzothiazepin-4(5H)-yl)-6-methylquinolin-4-amine; N-{[(4R)-2-amino-4,5-dihydro-1,3-oxazol-4-yl]methyl}-2-(1,1-dioxido-2,3-dihydro-1,4-benzothiazepin-4(5H)-yl)-6-methylquinolin-4-amine; N-{[(4S)-2-amino-4,5-dihydro-1,3-oxazol-4-yl]methyl}-2-(1,1-dioxido-2,3-dihydro-1,4-benzothiazepin-4(5H)-yl)-6-methylquinolin-4-amine; cis-5-[2-(1,1-dioxido-2,3-dihydro-1,4-benzothiazepin-4(5H)-yl)-6-methylquinolin-4-yl]-4,5,6,6a-tetrahydro-3aH-pyrrolo[3,4-d][1,3]oxazol-2-amine; 2-(1,1-dioxido-2,3-dihydro-1,4-benzothiazepin-4(5H)-yl)-6-methylquinolin-4-amine; N-[2-(1,1-dioxido-2,3-dihydro-1,4-benzothiazepin-4(5H)-yl)-6-methylquinolin-4-yl]glycinamide; N-[2-(1,1-dioxido-2,3-dihydro-1,4-benzothiazepin-4(5H)-yl)-6-methylquinolin-4-yl]-2-methylalaninamide; N-[2-(1,1-dioxido-2,3-dihydro-1,4-benzothiazepin-4(5H)-yl)-6-methylquinolin-4-yl]alaninamide; 2-amino-N-[2-(1,1-dioxido-2,3-dihydro-1,4-benzothiazepin-4(5H)-yl)-6-methylquinolin-4-yl]butanamide; N-[2-(1,1-dioxido-2,3-dihydro-1,4-benzothiazepin-4(5H)-yl)-6-methylquinolin-4-yl]-2-methoxy-2-methylpropanamide; N~1~-[2-(1,1-dioxido-2,3-dihydro-1,4-benzothiazepin-4(5H)-yl)-6-methylquinolin-4-yl]-4,4,4-trifluorobutane-1,3-diamine; N-[2-(1,1-dioxido-2,3-dihydro-1,4-benzothiazepin-4(5H)-yl)-6-methylquinolin-4-yl]-beta-alaninamide; 2-(1,1-dioxido-2,3-dihydro-1,4-benzothiazepin-4(5H)-yl)-N-{[3-(ethylamino)oxetan-3-yl]methyl}-6-methylquinolin-4-amine; 2-(1,1-dioxido-2,3-dihydro-1,4-benzothiazepin-4(5H)-yl)-6-methyl-N-[1-(oxetan-3-yl)pyrrolidin-3-yl]quinolin-4-amine; N'-[2-(1,1-dioxido-2,3-dihydro-1,4-benzothiazepin-4(5H)-yl)-6-methylquinolin-4-yl]-N-ethyl-N-(oxetan-3-yl)ethane-1,2-diamine; N-[2-(1,1-dioxido-2,3-dihydro-1,4-benzothiazepin-4(5H)-yl)-6-methylquinolin-4-yl]-N'-(oxetan-3-yl)propane-1,3-diamine; 1-[2-(1,1-dioxido-2,3-dihydro-1,4-benzothiazepin-4(5H)-yl)-6-methylquinolin-4-yl]-N-(oxetan-3-yl)pyrrolidin-3-amine; N-[2-(1,1-dioxido-2,3-dihydro-1,4-benzothiazepin-4(5H)-yl)-6-methylquinolin-4-yl]-N'-(oxetan-3-yl)ethane-1,2-diamine; N-[2-(1,1-dioxido-2,3-dihydro-1,4-benzothiazepin-4(5H)-yl)-6-methylquinolin-4-yl]-N'-(pyridin-2-yl)ethane-1,2-diamine; (4R)-1-[2-(1,1-dioxido-2,3-dihydro-1,4-benzothiazepin-4(5H)-yl)-6-methylquinolin-4-yl]-4-hydroxypyrrolidin-2-one; N-[2-(1,1-dioxido-2,3-dihydro-1,4-benzothiazepin-4(5H)-yl)-6-methylquinolin-4-yl]-5-oxopyrrolidine-3-carboxamide; 2-(1,1-dioxido-2,3-dihydro-1,4-benzothiazepin-4(5H)-yl)-6-methyl-N-(1H-pyrazol-3-yl)quinolin-4-amine; N-[2-(1,1-dioxido-2,3-dihydro-1,4-benzothiazepin-4(5H)-yl)-6-methylquinolin-4-yl]pyridine-3-carboxamide; N-[2-(1,1-dioxido-2,3-dihydro-1,4-benzothiazepin-4(5H)-yl)-6-methylquinolin-4-yl]piperidine-2-carboxamide; N-[2-(1,1-dioxido-2,3-dihydro-1,4-benzothiazepin-4(5H)-yl)-6-methylquinolin-4-yl]-2-(pyridin-2-yl)acetamide; N-[2-(1,1-dioxido-2,3-dihydro-1,4-benzothiazepin-4(5H)-yl)-6-methylquinolin-4-yl]methanesulfonamide trifluoroacetate; N-[2-(1,1-dioxido-2,3-dihydro-1,4-benzothiazepin-4(5H)-yl)-6-methylquinolin-4-yl]pyrazine-2-carboxamide; N-[2-(1,1-dioxido-2,3-dihydro-1,4-benzothiazepin-4(5H)-yl)-6-methylquinolin-4-yl]-2-hydroxyacetamide; N-[2-(1,1-dioxido-2,3-dihydro-1,4-benzothiazepin-4(5H)-yl)-6-methylquinolin-4-yl]pyridine-2-carboxamide; N-[2-(1,1-dioxido-2,3-dihydro-1,4-benzothiazepin-4(5H)-yl)-6-methylquinolin-4-yl]azetidine-2-carboxamide; 1-[2-(1,1-dioxido-2,3-dihydro-1,4-benzothiazepin-4(5H)-yl)-6-methylquinolin-4-yl]-3-phenylurea; 1-[2-(1,1-dioxido-2,3-dihydro-1,4-benzothiazepin-4(5H)-yl)-6-methylquinolin-4-yl]-3-ethylurea; N-[6-cyclopropyl-2-(1,1-dioxido-2,3-dihydro-1,4-benzothiazepin-4(5H)-yl)quinolin-4-yl]propane-1,3-diamine; 4-[(3-aminopropyl)amino]-2-(1,1-dioxido-2,3-dihydro-1,4-benzothiazepin-4(5H)-yl)quinoline-6-carbonitrile; N-[2-(1,1-dioxido-2,3-dihydro-1,4-benzothiazepin-4(5H)-yl)-6-ethenylquinolin-4-yl]propane-1,3-diamine; N-[2-(1,1-dioxido-2,3-dihydro-1,4- benzothiazepin-4(5H)-yl)-6-ethynylquinolin-4-yl]propane-1,3-diamine; N-[(3-aminooxetan-3-yl)methyl]-6-methyl-2-(1-oxido-2,3-dihydro-1,4-benzothiazepin-4(5H)-yl)quinazolin-4-amine; N-{[3-(benzylamino)oxetan-3-yl]methyl}-6-methyl-2-(1-oxido-2,3-dihydro-1,4-benzothiazepin-4(5H)-yl)quinazolin-4-amine; 2-fluoro-N-[6-methyl-2-(1-oxido-2,3-dihydro-1,4-benzothiazepin-4(5H)-yl)quinazolin-4-yl]propane-1,3-diamine; N-{[3-(aminomethyl)oxetan-3-yl]methyl}-2-(1,1-dioxido-2,3-dihydro-1,4-benzothiazepin-4(5H)-yl)-6-methylquinazolin-4-amine; 2,2-difluoro-N-[6-methyl-2-(1-oxido-2,3-dihydro-1,4-benzothiazepin-4(5H)-yl)quinazolin-4-yl]propane-1,3-diamine; N-{[3-(aminomethyl)oxetan-3-yl]methyl}-6-chloro-2-(1,1-dioxido-2,3-dihydro-1,4-benzothiazepin-4(5H)-yl)quinazolin-4-amine; N-[2-(1,1-dioxido-2,3-dihydro-1,4-benzothiazepin-4(5H)-yl)-6-methylquinazolin-4-yl]-2,2-difluoropropane-1,3-diamine; N-[2-(1,1-dioxido-2,3-dihydro-1,4-benzothiazepin-4(5H)-yl)-6-methylquinazolin-4-yl]-2-fluoropropane-1,3-diamine; N-[6-methyl-2-(1-oxido-2,3-dihydro-1,4-benzothiazepin-4(5H)-yl)quinazolin-4-yl]propane-1,3-diamine; N-[(3-aminooxetan-3-yl)methyl]-2-(2,3-dihydro-1,4-benzothiazepin-4(5H)-yl)quinazolin-4-amine; N-[(3-aminooxetan-3-yl)methyl]-2-(1-oxido-2,3-dihydro-1,4-benzothiazepin-4(5H)-yl)quinazolin-4-amine; N-[(3-aminooxetan-3-yl)methyl]-2-(1,1-dioxido-2,3-dihydro-1,4-benzothiazepin-4(5H)-yl)quinazolin-4-amine; N-[(3-aminooxetan-3-yl)methyl]-6-chloro-2-(2,3-dihydro-1,4-benzothiazepin-4(5H)-yl)quinazolin-4-amine; N-[(3-aminooxetan-3-yl)methyl]-6-chloro-2-(1-oxido-2,3-dihydro-1,4-benzothiazepin-4(5H)-yl)quinazolin-4-amine; N-[(3-aminooxetan-3-yl)methyl]-6-chloro-2-(1,1-dioxido-2,3-dihydro-1,4-benzothiazepin-4(5H)-yl)quinazolin-4-amine; 2-{[2-(1,1-dioxido-2,3-dihydro-1,4-benzothiazepin-4(5H)-yl)-6-methylquinazolin-4-yl]amino}ethanol; 2-(2,3-dihydro-1,4-benzothiazepin-4(5H)-yl)-6-methylquinazolin-4-amine; 2-(1,1-dioxido-2,3-dihydro-1,4-benzothiazepin-4(5H)-yl)-6-methylquinazolin-4-amine; N~1~-[2-(1,1-dioxido-2,3-dihydro-1,4-benzothiazepin-4(5H)-yl)-6-methylquinazolin-4-yl]-2-methylpropane-1,2-diamine; N-[(3-aminooxetan-3-yl)methyl]-2-(1,1-dioxido-2,3-dihydro-1,4-benzothiazepin-4(5H)-yl)-6-methylquinazolin-4-amine; N-[(1-aminocyclobutyl)methyl]-2-(1,1-dioxido-2,3-dihydro-1,4-benzothiazepin-4(5H)-yl)-6-methylquinazolin-4-amine; N-{[3-(aminomethyl)oxetan-3-yl]methyl}-6-methyl-2-(1-oxido-2,3-dihydro-1,4-benzothiazepin-4(5H)-yl)quinazolin-4-amine; (−)-N-{[3-(aminomethyl)oxetan-3-yl]methyl}-6-methyl-2-[1-oxido-2,3-dihydro-1,4-benzothiazepin-4(5H)-yl]quinazolin-4-amine; (+)-N-{[3-(aminomethyl)oxetan-3-yl]methyl}-6-methyl-2-[1-oxido-2,3-dihydro-1,4-benzothiazepin-4(5H)-yl]quinazolin-4-amine; N~4~-[2-(1,1-dioxido-2,3-dihydro-1,4-benzothiazepin-4(5H)-yl)-6-methylquinazolin-4-yl]-2-fluorobutane-1,4-diamine; N~1~-[2-(1,1-dioxido-2,3-dihydro-1,4-benzothiazepin-4(5H)-yl)-6-methylquinazolin-4-yl]-2-fluorobutane-1,4-diamine; N-{[3-(aminomethyl)oxetan-3-yl]methyl}-2-(2,3-dihydro-1,4-benzothiazepin-4(5H)-yl)-6-methylquinazolin-4-amine; trans-4-fluoro-1-[6-methyl-2-(1-oxido-2,3-dihydro-1,4-benzothiazepin-4(5H)-yl)quinazolin-4-yl]pyrrolidin-3-amine; N-(Azetidin-3-yl)-6-methyl-2-(1,1-dioxido-2,3-dihydro-1,4-benzothiazepin-4(5H)-yl) quinazolin-4-amine; N-(2-{[2-(1,1-dioxido-2,3-dihydro-1,4-benzothiazepin-4(5H)-yl)-6-methylquinolin-4-yl]amino}ethyl)acetamide; N-{[3-({[2-(1,1-dioxido-2,3-dihydro-1,4-benzothiazepin-4(5H)-yl)-6-methylquinolin-4-yl]amino}methyl)oxetan-3-yl]methyl}acetamide; N-(3-{[2-(1,1-dioxido-2,3-dihydro-1,4-benzothiazepin-4(5H)-yl)-6-methylquinolin-4-yl]amino}propyl)acetamide; N-[2-(1,1-dioxido-2,3-dihydro-1,4-benzothiazepin-4(5H)-yl)-6-methylquinazolin-4-yl]acetamide; 1-[2-(1,1-dioxido-2,3-dihydro-1,4-benzothiazepin-4(5H)-yl)-6-methylquinolin-4-yl]-3-methylpyrrolidin-3-amine; N-[(3-aminooxetan-3-yl)methyl]-2-(9-methoxy-1,1-dioxido-2,3-dihydro-1,4-benzothiazepin-4(5H)-yl)-6-methylquinolin-4-amine; 4-(4-{[(3-aminooxetan-3-yl)methyl]amino}-6-methylquinolin-2-yl)-2,3,4,5-tetrahydro-1,4-benzothiazepin-7-ol 1,1-dioxide; 3-{[2-(1,1-dioxido-2,3-dihydro-1,4-benzothiazepin-4(5H)-yl)-6-methylquinolin-4-yl]amino}-2-methylpropane-1,2-diol; 4-{[2-(1,1-dioxido-2,3-dihydro-1,4-benzothiazepin-4(5H)-yl)-6-methylquinolin-4-yl]amino}butane-1,3-diol; N-[6-methyl-2-(2-methyl-1,1-dioxido-2,3-dihydro-1,4-benzothiazepin-4(5H)-yl)quinolin-4-yl]ethane-1,2-diamine; N-[(3-aminooxetan-3-yl)methyl]-6-methyl-2-(2-methyl-1,1-dioxido-2,3-dihydro-1,4-benzothiazepin-4(5H)-yl)quinolin-4-amine; N-[(3-{[2-(1,1-dioxido-2,3-dihydro-1,4-benzothiazepin-4(5H)-yl)-6-methylquinolin-4-yl]amino}oxetan-3-yl)methyl]-2,2,2-trifluoroacetamide; N-[3-(aminomethyl)oxetan-3-yl]-2-(1,1-dioxido-2,3-dihydro-1,4-benzothiazepin-4(5H)-yl)-6-methylquinolin-4-amine; 2-(aminomethyl)-2-{[2-(1,1-dioxido-2,3-dihydro-1,4-benzothiazepin-4(5H)-yl)-6-methylquinolin-4-yl]amino}propane-1,3-diol; 4-amino-1-[2-(1,1-dioxido-2,3-dihydro-1,4-benzothiazepin-4(5H)-yl)-6-methylquinolin-4-yl]pyrrolidin-2-one; 2-(1,1-dioxido-2,3-dihydro-1,4-benzothiazepin-4(5H)-yl)-6-methyl-N-[2-(methylsulfinyl)ethyl]quinolin-4-amine; N-{2-[(2-aminoethyl)sulfonyl]ethyl}-2-(1,1-dioxido-2,3-dihydro-1,4-benzothiazepin-4(5H)-yl)-6-methylquinolin-4-amine; N-[2-(1-imino-1-oxido-1,2,3,5-tetrahydro-4H-1lambda~4~,4-benzothiazepin-4-yl)-6-methylquinolin-4-yl]ethane-1,2-diamine; 2-(1,1-dioxido-2,3-dihydro-1,4-benzothiazepin-4(5H)-yl)-6-methyl-N-[2-(S-methylsulfonimidoyl)ethyl]quinolin-4-amine; trans-4-amino-1-[2-(1-imino-1-oxido-1,2,3,5-tetrahydro-4H-1lambda~4~,4-benzothiazepin-4-yl)-6-methylquinolin-4-yl]pyrrolidin-3-ol; trans-1-[2-(1,1-dioxido-2,3-dihydro-1,4-benzothiazepin-4(5H)-yl)-6-methylquinolin-4-yl]-4-fluoropyrrolidin-3-amine; 1-[2-(1,1-dioxido-2,3-dihydro-1,4-benzothiazepin-4(5H)-yl)-6-methylquinolin-4-yl]pyrrolidine-3-carboxamide; N-[2-(1,1-dioxido-2,3-dihydro-1,4-benzothiazepin-4(5H)-yl)-6-(methylsulfinyl)quinolin-4-yl]propane-1,3-diamine; 4-[(3-aminopropyl)amino]-2-(1,1-dioxido-2,3-dihydro-1,4-benzothiazepin-4(5H)-yl)quinoline-6-carboxamide; 1-{4-[(3-aminopropyl)amino]-2-(1,1-dioxido-2,3-dihydro-1,4-benzothiazepin-4(5H)-yl)quinolin-6-yl}ethanol; 3-{[2-(1,1-dioxido-2,3-dihydro-1,4-benzothiazepin-4(5H)-yl)-6-methylquinolin-4-yl]amino}propanenitrile; 2-(1,1-dioxido-2,3-dihydro-1,4-benzothiazepin-4(5H)-yl)-6-methyl-N-[2-(1H-tetrazol-5-yl)ethyl]quinolin-4-amine; N~4~-(2-aminoethyl)-2-(1,1-dioxido-2,3-dihydro-1,4-benzothiazepin-4(5H)-yl)quinoline-4,6-diamine; 5-[2-(1,1-dioxido-2,3-dihydro-1,4-benzothiazepin-4(5H)-yl)-6-methylquinolin-4-yl]-2-oxa-5,7-diazaspiro[3.4]octan-6-one; 3-{[2-(1,1-dioxido-2,3-dihydro-1,4-benzothiazepin-4(5H)-yl)-6-methylquinazolin-4-yl]amino}propane-1,2-diol; 3-{[6-chloro-2-(1,1-dioxido-2,3-dihydro-1,4-benzothiazepin-4(5H)-yl)quinazolin-4-yl]amino}propane-1,2-diol; N-[2-(2,3-dihydro-1,4-benzothiazepin-4(5H)-yl)-6-methylquinazolin-4-yl]ethane-1,2-diamine; N-[6-methyl-2-(1-oxido-2,3-dihydro-1,4-benzothiazepin-4(5H)-yl)quinazolin-4-yl]ethane-1,2-diamine; N-[2-(1,1-dioxido-2,3-dihydro-1,4-benzothiazepin-4(5H)-yl)-6-methylquinazolin-4-yl]ethane-1,2-diamine; N-[3-(aminomethyl)oxetan-3-yl]-6-methyl-2-(1-oxido-2,3-dihydro-1,4-benzothiazepin-4

(5H)-yl)quinazolin-4-amine; N-(trans-4-fluoropyrrolidin-3-yl)-6-methyl-2-(1-oxido-2,3-dihydro-1,4-benzothiazepin-4 (5H)-yl)quinazolin-4-amine; N-(trans-4-fluoropyrrolidin-3-yl)-6-methyl-2-(1,1-dioxido-2,3-dihydro-1,4-benzothiazepin-4(5H)-yl)quinazolin-4-amine; 1-[6-methyl-2-(1-oxido-2,3-dihydro-1,4-benzothiazepin-4(5H)-yl) quinazolin-4-yl]pyrrolidin-3-amine; N-(azetidin-3-yl)-6-methyl-2-(1,1-dioxido-2,3-dihydro-1,4-benzothiazepin-4 (5H)-yl)quinazolin-4-amine; (4R)-4-{2-[2-(1,1-dioxido-2,3-dihydro-1,4-benzothiazepin-4(5H)-yl)-6-methylquinolin-4-yl]ethyl}-4,5-dihydro-1,3-oxazol-2-amine; 3-[2-(1,1-dioxido-2,3-dihydro-1,4-benzothiazepin-4(5H)-yl)-6-ethylquinolin-4-yl]propanoic acid; 3-[2-(1,1-dioxido-2,3-dihydro-1,4-benzothiazepin-4(5H)-yl)-6-methylquinolin-4-yl]propan-1-amine; 2-{[2-(1,1-dioxido-2,3-dihydro-1,4-benzothiazepin-4(5H)-yl)-6-methylquinolin-4-yl] oxy}ethanamine; 4-[6-methyl-4-(pyrrolidin-3-yloxy) quinolin-2-yl]-2,3,4,5-tetrahydro-1,4-benzothiazepine 1,1-dioxide; 4-[6-methyl-4-(piperidin-4-yloxy)quinolin-2-yl]-2,3,4,5-tetrahydro-1,4-benzothiazepine 1,1-dioxide; 4-(4,6-dimethylquinolin-2-yl)-2,3,4,5-tetrahydro-1,4-benzothiazepine 1,1-dioxide; [2-(1,1-dioxido-2,3-dihydro-1, 4-benzothiazepin-4(5H)-yl)-6-methylquinolin-4-yl] (piperidin-4-yl)methanone; 4-[6-methyl-4-(1H-pyrazol-3-yl)quinolin-2-yl]-2,3,4,5-tetrahydro-1,4-benzothiazepine 1,1-dioxide; 4-[6-methyl-4-(phenylsulfonyl)quinolin-2-yl]-2,3,4,5-tetrahydro-1,4-benzothiazepine 1,1-dioxide; N-(2-aminoethyl)-2-(1,1-dioxido-2,3-dihydro-1,4-benzothiazepin-4(5H)-yl)-6-methylquinoline-4-sulfonamide; methyl 4-({[3-(aminomethyl)oxetan-3-yl]methyl}amino)-2-(1,1-dioxido-2,3-dihydro-1,4-benzothiazepin-4(5H)-yl)quinoline-6-carboxylate; 4-({[3-(aminomethyl)oxetan-3-yl] methyl}amino)-2-(1,1-dioxido-2,3-dihydro-1,4-benzothiazepin-4(5H)-yl)quinoline-6-carboxylic acid; [4-({[3-(aminomethyl)oxetan-3-yl]methyl}amino)-2-(1,1-dioxido-2,3-dihydro-1,4-benzothiazepin-4(5H)-yl)quinolin-6-yl]methanol; N-{[3-(aminomethyl)oxetan-3-yl]methyl}-6-(~2~H_3_)methyl-2-(1-oxido-2,3-dihydro-1,4-benzothiazepin-4(5H)-yl)quinazolin-4-amine; 4-({[3-(aminomethyl)oxetan-3-yl]methyl}amino)-2-(1,1-dioxido-2,3-dihydro-1,4-benzothiazepin-4(5H)-yl)quinazoline-6-carboxylic acid; 4-({[3-(aminomethyl)oxetan-3-yl] methyl}amino)-2-(1-oxido-2,3-dihydro-1,4-benzothiazepin-4(5H)-yl)quinazoline-6-carboxylic acid; [4-({[3-(aminomethyl)oxetan-3-yl]methyl}amino)-2-(1-oxido-2,3-dihydro-1,4-benzothiazepin-4(5H)-yl)quinazolin-6-yl] methanol; [4-({[3-(aminomethyl)oxetan-3-yl] methyl}amino)-2-(1,1-dioxido-2,3-dihydro-1,4-benzothiazepin-4(5H)-yl)quinazolin-6-yl]methanol; N-[(1-aminocyclopropyl)methyl]-2-(1,1-dioxido-2,3-dihydro-1,4-benzothiazepin-4(5H)-yl)-6-methylquinazolin-4-amine; and 2-(1,1-dioxido-2,3-dihydro-1,4-benzothiazepin-4(5H)-yl)-6-methyl-N-(pyrrolidin-3-yl)quinazolin-4-amine.

Another embodiment of invention is (xii) a compound of formula (I) or a pharmaceutically acceptable salt thereof, wherein $R^1$ is hydrogen or halogen;
$R^2$ and $R^4$ are hydrogen;
$R^3$ is hydrogen or halogen;
$R^5$ is hydrogen or halogen;
$R^6$ is hydrogen, halogen, hydroxy, $C_{1-6}$alkoxy or carboxy;
$R^7$ is hydrogen, halogen, $C_{1-6}$alkoxy, $C_{1-6}$alkylaminocarbonyl, $diC_{1-6}$ alkylaminocarbonyl or $C_{1-6}$alkylsulfonyl;
$R^8$ is hydrogen or halogen;
$R^9$ is hydrogen or =O;
$R^{10}$ is hydrogen or =O, provided that $R^9$ and $R^{10}$ are not =O simultaneously;

A is —C—$R^{11}$, wherein $R^{11}$ is hydrogen, halogen, $C_{1-6}$alkyl, $C_{1-6}$alkoxy, trifluoromethyl, trifluoromethoxy, pyridinyloxy, difluoromethoxy or $C_{1-6}$alkylsulfonyl;
X is —$CH_2$—, —O—, NH—, —$CF_2$, —$C(CH_3)(OH)$—, C=O, or —C(=N—$C_{1-6}$alkoxy)-;
Y is —CH— or nitrogen;
Q is hydrogen; halogen; $C_{1-6}$alkyl, once or twice substituted by hydroxy provided that disubstitution of hydroxy is not on the same carbon; amino$(CH_2)_{2-6}$aminosulfonyl; 2-amino-4,5-dihydro-1,3-oxazol-4-ylethyl; or $NR^{12}R^{13}$, wherein one of $R^{12}$ and $R^{13}$ is hydrogen, $C_{1-6}$alkyl or hydroxy$(CH_2)_{2-6}$, and the other one is guanidino$(CH_2)_{2-6}$; 3-aminomethyl-1,1-dioxidothietan-3-ylmethyl; 3-amino-1,1-dioxidothietan-3-ylmethyl; 3-(aminomethyl)thietan-3-ylmethyl; amino$(CH_2)_{2-6}$—O—$(CH_2)_{2-6}$; amino$(CH_2)_{2-10}$; amino$(CH_2)_{1-6}$carbonyl; amino$(CH_2)_{1-6}$difluoromethyl$(CH_2)_{1-6}$; amino$(CH_2)_{1-6}$oxetanyl$(CH_2)_{1-6}$; amino$(CH_2)_{2-6}$sulfonyl$(CH_2)_{2-6}$; 3-aminocyclohexyl; 4-amino cyclohexyl; 2-amino-4,5-dihydro-oxazol-5-yl$(CH_2)_{1-6}$; aminooxetanyl$(CH_2)_{1-6}$; $C_{1-6}$alkylamino$(CH_2)_{2-6}$; $C_{1-6}$alkylamino carbonyl; di$C_{1-6}$alkylamino$(CH_2)_{2-6}$; hydroxy$(CH_2)_{2-6}$; piperazinyl$(CH_2)_{2-6}$; pyrrolidin-3-yl; or

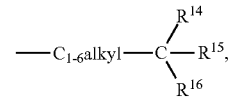

wherein $R^{14}$ is hydrogen, $C_{1-6}$alkyl or hydroxy$(CH_2)_{1-6}$; $R^{15}$ is hydroxy, hydroxy$(CH_2)_{1-6}$ or amino; and $R^{16}$ is $C_{1-6}$alkyl, hydroxy$(CH_2)_{1-6}$ or amino$(CH_2)_{1-6}$;
$R^{12}$ and $R^{13}$, with the nitrogen atom to which they are attached, may form a pyrrolidinyl, piperazinyl or diazepanyl ring; which may be unsubstituted, once or twice substituted by a group selected from $C_{1-6}$alkyl, amino or hydroxy.

Another particular embodiment of invention is (xiii) a compound of formula (I) or a pharmaceutically acceptable salt thereof, wherein $R^1$ is hydrogen or chloro;
$R^2$ and $R^4$ are hydrogen;
$R^3$ is hydrogen or chloro;
$R^5$ is hydrogen or fluoro;
$R^6$ is hydrogen, fluoro, hydroxy, methoxy, ethoxy or carboxy;
$R^7$ is hydrogen, fluoro, bromo, methoxy, dimethylaminocarbonyl, methylsulfonyl or ethylsulfonyl;
$R^8$ is hydrogen or chloro.
A is $CR^{11}$, wherein $R^{11}$ is hydrogen, fluoro, chloro, bromo, methyl, methoxy, trifluoromethyl, trifluoromethoxy, pyridinyloxy, difluoromethoxy or methylsulfonyl;
Q is hydrogen; chloro; hydroxymethyl; hydroxymethyl (hydroxy)ethyl; aminoethylaminosulfonyl; 2-amino-4,5-dihydro-1,3-oxazol-4-ylethyl; or $NR^{12}R^{13}$, wherein one of $R^{12}$ and $R^{13}$ is hydrogen, methyl or hydroxyethyl, and the other one is aminobutyl; 3-aminocyclohexyl; 4-aminocyclohexyl; 2-amino-4,5-dihydro-oxazol-5-yl-methyl; 3-amino-1,1-dioxidothietan-3-ylmethyl; aminoethoxyethyl; aminoethyl; aminoethylsulfonylethyl; aminomethylcarbonyl; aminomethyldifluoromethylethyl; 3-aminomethyl-1,1-dioxidothietan-3-ylmethyl; 3-(aminomethyl)thietan-3-ylmethyl; aminomethyloxetanylmethyl; aminooxetanylmethyl; aminopropyl; dimethylaminoethyl; ethylaminocarbonyl; guanidinoethyl; hydroxyethyl; hydroxypropyl; methylaminoethyl; piperazin-1-ylethyl; pyrrolidin-3-yl; or

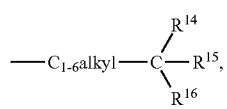

wherein $R^{14}$ is hydrogen, methyl or hydroxymethyl; $R^{15}$ is hydroxy, hydroxymethyl or amino; and $R^{16}$ is methyl, hydroxymethyl or aminomethyl;

$R^{12}$ and $R^{13}$, with the nitrogen atom to which they are attached, may form a pyrrolidinyl, piperazinyl or diazepanyl ring; which may be unsubstituted, once or twice substituted by a group selected from methyl, amino or hydroxy; and all the remaining substituents are as defined above in embodiment (xii).

A particular embodiment of present invention is a compound of formula (I) or a pharmaceutically acceptable salt thereof, selected from: N-[(3-aminooxetan-3-yl)methyl]-2-(5,5-difluoro-1,3,4,5-tetrahydro-2H-2-benzazepin-2-yl)-6-methylquinolin-4-amine; N-[2-(2-aminoethoxy)ethyl]-2-(5,5-difluoro-1,3,4,5-tetrahydro-2H-2-benzazepin-2-yl)-6-methylquinolin-4-amine; N-[2-(5,5-difluoro-1,3,4,5-tetrahydro-2H-2-benzazepin-2-yl)-6-methylquinolin-4-yl]-N'-methylethane-1,2-diamine; 1-amino-3-{[2-(5,5-difluoro-1,3,4,5-tetrahydro-2H-2-benzazepin-2-yl)-6-methylquinolin-4-yl]amino}propan-2-ol; 3-{[2-(5,5-difluoro-1,3,4,5-tetrahydro-2H-2-benzazepin-2-yl)-6-methylquinolin-4-yl]amino}propane-1,2-diol; 3-{[2-(5,5-difluoro-1,3,4,5-tetrahydro-2H-2-benzazepin-2-yl)-6-methylquinolin-4-yl]amino}propan-1-ol; 2-(5,5-difluoro-1,3,4,5-tetrahydro-2H-2-benzazepin-2-yl)-6-methyl-N-[2-(piperazin-1-yl)ethyl]quinolin-4-amine; N~1~-[2-(5,5-difluoro-1,3,4,5-tetrahydro-2H-2-benzazepin-2-yl)-6-methylquinolin-4-yl]propane-1,2-diamine; cis-N-[2-(5,5-difluoro-1,3,4,5-tetrahydro-2H-2-benzazepin-2-yl)-6-methylquinolin-4-yl]cyclohexane-1,4-diamine; 2-(9,9-difluoro-6,7,8,9-tetrahydro-5H-benzo[7]annulen-6-yl)-6-methyl-N-(pyrrolidin-3-yl)quinolin-4-amine; 2,2'-{[2-(5,5-difluoro-1,3,4,5-tetrahydro-2H-2-benzazepin-2-yl)-6-methylquinolin-4-yl]imino}diethanol; N~1~-[2-(5,5-difluoro-1,3,4,5-tetrahydro-2H-2-benzazepin-2-yl)-6-methylquinolin-4-yl]-2-methylpropane-1,2-diamine; 5,5-difluoro-2-[6-methyl-4-(4-methylpiperazin-1-yl)quinolin-2-yl]-2,3,4,5-tetrahydro-1H-2-benzazepine; 1-[2-(9,9-difluoro-6,7,8,9-tetrahydro-5H-benzo[7]annulen-6-yl)-6-methylquinolin-4-yl]-3-ethylurea; N-{[3-(aminomethyl)oxetan-3-yl]methyl}-2-(5,5-difluoro-1,3,4,5-tetrahydro-2H-2-benzazepin-2-yl)-6-methylquinolin-4-amine; 5,5-difluoro-2-[6-methyl-4-(piperazin-1-yl)quinolin-2-yl]-2,3,4,5-tetrahydro-1H-2-benzazepine; 2-[4-(1,4-diazepan-1-yl)-6-methylquinolin-2-yl]-5,5-difluoro-2,3,4,5-tetrahydro-1H-2-benzazepine; N-[2-(5,5-difluoro-1,3,4,5-tetrahydro-2H-2-benzazepin-2-yl)-6-methylquinolin-4-yl]-N-methylethane-1,2-diamine; 1-[2-(5,5-difluoro-1,3,4,5-tetrahydro-2H-2-benzazepin-2-yl)-6-methylquinolin-4-yl]pyrrolidin-3-amine; 2-{[2-(5,5-difluoro-1,3,4,5-tetrahydro-2H-2-benzazepin-2-yl)-6-methylquinolin-4-yl]amino}ethanol; N-[2-(5,5-difluoro-1,3,4,5-tetrahydro-2H-2-benzazepin-2-yl)-6-methylquinolin-4-yl]ethane-1,2-diamine; N-[2-(5,5-difluoro-1,3,4,5-tetrahydro-2H-2-benzazepin-2-yl)-6-methylquinolin-4-yl]cyclohexane-1,3-diamine; N-[2-(5,5-difluoro-1,3,4,5-tetrahydro-2H-2-benzazepin-2-yl)-6-methylquinolin-4-yl]-N,N-dimethylethane-1,2-diamine; N-[2-(5,5-difluoro-1,3,4,5-tetrahydro-2H-2-benzazepin-2-yl)-6-methylquinolin-4-yl]propane-1,3-diamine; N-[2-(5,5-difluoro-1,3,4,5-tetrahydro-2H-2-benzazepin-2-yl)-6-methylquinolin-4-yl]butane-1,4-diamine; trans-4-amino-1-[2-(5,5-difluoro-1,3,4,5-tetrahydro-2H-2-benzazepin-2-yl)-6-methylquinolin-4-yl]pyrrolidin-3-ol; N-{[3-(aminomethyl)-1,1-dioxidothietan-3-yl]methyl}-2-(5,5-difluoro-1,3,4,5-tetrahydro-2H-2-benzazepin-2-yl)-6-methylquinolin-4-amine; N-{2-[(2-amino ethyl)sulfonyl]ethyl}-2-(5,5-difluoro-1,3,4,5-tetrahydro-2H-2-benzazepin-2-yl)-6-methylquinolin-4-amine; N-{[3-(aminomethyl)thietan-3-yl]methyl}-2-(5,5-difluoro-1,3,4,5-tetrahydro-2H-2-benzazepin-2-yl)-6-methylquinazolin-4-amine; N-{[3-(aminomethyl)oxetan-3-yl]methyl}-2-(5,5-difluoro-1,3,4,5-tetrahydro-2H-2-benzazepin-2-yl)-6-methylquinazolin-4-amine; 2-(aminomethyl)-2-({[2-(5,5-difluoro-1,3,4,5-tetrahydro-2H-2-benzazepin-2-yl)-6-methylquinazolin-4-yl]amino}methyl)propane-1,3-diol; 2-(4-{[(3-aminooxetan-3-yl)methyl]amino}-6-methylquinazolin-2-yl)-5-methyl-2,3,4,5-tetrahydro-1H-2-benzazepin-5-ol; N-[(3-aminooxetan-3-yl)methyl]-2-(5,5-difluoro-1,3,4,5-tetrahydro-2H-2-benzazepin-2-yl)-6-methylquinazolin-4-amine; N-[(3-amino-1,1-dioxidothietan-3-yl)methyl]-2(5,5-difluoro-1,3,4,5-tetrahydro-2H-2-benzazepin-2-yl)-6-methylquinazolin-4-amine; N-[2-(5,5-difluoro-1,3,4,5-tetrahydro-2H-2-benzazepin-2-yl)-6-methylquinazolin-4-yl]-2,2-difluoropropane-1,3-diamine; N-[2-(7-bromo-1,3,4,5-tetrahydro-2H-2-benzazepin-2-yl)-6-chloroquinolin-4-yl]ethane-1,2-diamine; 2-{4-[(2-amino ethyl)amino]quinolin-2-yl}-2,3,4,5-tetrahydro-1H-2-benzazepin-8-ol; N-[6-methyl-2-(1,3,4,5-tetrahydro-2H-2-benzazepin-2-yl)quinolin-4-yl]ethane-1,2-diamine; N-[2-(8-fluoro-1,3,4,5-tetrahydro-2H-2-benzazepin-2-yl)-6-methylquinolin-4-yl]ethane-1,2-diamine; N-[6-chloro-2-(1,3,4,5-tetrahydro-2H-2-benzazepin-2-yl)quinolin-4-yl]ethane-1,2-diamine; N-[6-chloro-2-(9-fluoro-1,3,4,5-tetrahydro-2H-2-benzazepin-2-yl)quinolin-4-yl]ethane-1,2-diamine; N-[2-(8-fluoro-1,3,4,5-tetrahydro-2H-2-benzazepin-2-yl)quinolin-4-yl]ethane-1,2-diamine; 1-amino-3-{[2-(1,3,4,5-tetrahydro-2H-2-benzazepin-2-yl)quinolin-4-yl]amino}propan-2-ol trifluoroacetate; N-[2-(1,3,4,5-tetrahydro-2H-2-benzazepin-2-yl)quinolin-4-yl]ethane-1,2-diamine; N-[6-bromo-2-(1,3,4,5-tetrahydro-2H-2-benzazepin-2-yl)quinolin-4-yl]ethane-1,2-diamine; N-[6-methoxy-2-(1,3,4,5-tetrahydro-2H-2-benzazepin-2-yl)quinolin-4-yl]ethane-1,2-diamine; N-[2-(6-chloro-1,3,4,5-tetrahydro-2H-2-benzazepin-2-yl)quinolin-4-yl]ethane-1,2-diamine; N-[2-(7-fluoro-1,3,4,5-tetrahydro-2H-2-benzazepin-2-yl)-6-methylquinolin-4-yl]ethane-1,2-diamine; N-methyl-N'-[2-(1,3,4,5-tetrahydro-2H-2-benzazepin-2-yl)quinolin-4-yl]ethane-1,2-diamine; N-[2-(7-methoxy-1,3,4,5-tetrahydro-2H-2-benzazepin-2-yl)quinolin-4-yl]ethane-1,2-diamine; N-[2-(7-fluoro-1,3,4,5-tetrahydro-2H-2-benzazepin-2-yl)quinolin-4-yl]ethane-1,2-diamine; N-[2-(8-methoxy-1,3,4,5-tetrahydro-2H-2-benzazepin-2-yl)quinolin-4-yl]ethane-1,2-diamine; N-[6-(difluoromethoxy)-2-(1,3,4,5-tetrahydro-2H-2-benzazepin-2-yl)quinolin-4-yl]ethane-1,2-diamine; N-[2-(1,3,4,5-tetrahydro-2H-2-benzazepin-2-yl)-6-(trifluoromethyl)quinolin-4-yl]ethane-1,2-diamine; N-[8-chloro-2-(1,3,4,5-tetrahydro-2H-2-benzazepin-2-yl)quinolin-4-yl]ethane-1,2-diamine; N-[6-fluoro-2-(1,3,4,5-tetrahydro-2H-2-benzazepin-2-yl)quinolin-4-yl]ethane-1,2-diamine; N,N-dimethyl-N'-[2-(1,3,4,5-tetrahydro-2H-2-benzazepin-2-yl)quinolin-4-yl]ethane-1,2-diamine; N-[2-(1,3,4,5-tetrahydro-2H-2-benzazepin-2-yl)-6-(trifluoromethoxy)quinolin-4-yl]ethane-1,2-diamine; N-[6-(methylsulfonyl)-2-(1,3,4,5-tetrahydro-2H-2-benzazepin-2-yl)quinolin-4-yl]ethane-1,2-diamine; 2-{4-[(2-amino ethyl)amino]quinolin-2-yl}-2,3,4,5-tetrahydro-1H-2-benzazepine-8-carboxylic acid; 2-(4-chloroquinolin-2-yl)-2,3,4,5-tetrahydro-1H-2-benzazepine; N-[5-chloro-2-(1,3,4,5-tetrahydro-2H-2-benzazepin-2-yl)quinolin-4-yl]ethane-1,2-diamine; N-{2-[7-(methylsulfonyl)-1,3,4,5-tetrahydro-2H-2-benzazepin-2-yl]quinolin-4-yl}ethane-1,2-diamine; N-{2-[7-(ethylsulfonyl)-1,3,4,5-tetrahydro-2H-2-benzazepin-2-yl]quinolin-4-yl}ethane-1,2-diamine; N-[2-(8-ethoxy-1,3,4,5-tetrahydro-2H-2- benzazepin-2-yl)quinolin-4-yl]ethane-1,2-diamine; N-[6-(pyridin-2-yloxy)-2-(1,3,4,5-tetrahydro-2H-2-benzazepin-2-yl)quinolin-4-yl]ethane-1,2-diamine; 2-{4-[(2-amino ethyl)amino]-6-chloro quinolin-2-yl}-N,N-dimethyl-2,3,4,5-tetrahydro-1H-2-benzazepine-7-carboxamide; 2-{4-[(2-amino ethyl)amino]quinolin-2-yl}-7-bromo-1,2,4,5-tetrahydro-3H-2-benzazepin-3-one; 1-(2-{[2-(1,3,4,5-tetrahydro-2H-2-benzazepin-2-yl)quinolin-4-yl]amino}ethyl) guanidine trifluoroacetate; N-[(2-amino-4,5-dihydro-1,3-oxazol-5-yl)methyl]-2-(1,3,4,5-tetrahydro-2H-2-benzazepin-2-yl)quinolin-4-amine trifluoroacetate; N-[(2-amino-4,5-dihydro-1,3-oxazol-5-yl)methyl]-6-chloro-2-(1,3,4,5-tetrahydro-2H-2-benzazepin-2-yl)quinolin-4-amine; N-[2-(1,3,4,5-tetrahydro-2H-2-benzazepin-2-yl)quinolin-4-yl]glycinamide; 3-[2-(1,3,4,5-tetrahydro-2H-2-benzazepin-2-yl)quinolin-4-yl]propan-1-amine; [2-(1,3,4,5-tetrahydro-2H-2-benzazepin-2-yl)quinolin-4-yl]methanol; 2-(6-chloroquinolin-2-yl)-2,3,4,5-tetrahydro-1H-2-benzazepine; 3-[6-chloro-2-(1,3,4,5-tetrahydro-2H-2-benzazepin-2-yl)quinolin-4-yl]propane-1,2-diol; (4S)-4-{2-[2-(1,3,4,5-tetrahydro-2H-2-benzazepin-2-yl)quinolin-4-yl]ethyl}-4,5-dihydro-1,3-oxazol-2-amine; N-(2-aminoethyl)-2-(1,3,4,5-tetrahydro-2H-2-benzazepin-2-yl)quinoline-4-sulfonamide trifluoroacetate; 4-{4-[(2-aminoethyl)amino]-6-methylquinolin-2-yl}-1,3,4,5-tetrahydro-2H-1,4-benzodiazepin-2-one; N-[6-methyl-2-(1,2,3,5-tetrahydro-4H-1,4-benzodiazepin-4-yl)quinolin-4-yl]ethane-1,2-diamine; N-[2-(2,3-dihydro-1,4-benzoxazepin-4(5H)-yl)quinolin-4-yl]ethane-1,2-diamine; N-[(3-aminooxetan-3-yl)methyl]-2-[(5E)-5-(methoxyimino)-1,3,4,5-tetrahydro-2H-2-benzazepin-2-yl]-6-methylquinolin-4-amine and 2-(4-{[(3-aminooxetan-3-yl)methyl]amino}-6-methylquinazolin-2-yl)-1,2,3,4-tetrahydro-5H-2-benzazepin-5-one.

The compounds of the present invention can be prepared by any conventional means. Suitable processes for synthesizing these compounds as well as their starting materials are provided in the schemes below and in the examples. All substituents, in particular, $R^1$ to $R^{10}$, A, Q, X and Y are as defined above unless otherwise indicated. Furthermore, and unless explicitly otherwise stated, all reactions, reaction conditions, abbreviations and symbols have the meanings well known to a person of ordinary skill in organic chemistry.

ABBREVIATIONS

DMSO-d6: deuterated dimethylsulfoxide
FBS: fetal bovine serum
g: gram
µg: microgram
$EC_{50}$: the concentration of a compound where 50% of its maximal protection effect against viral induced CPE is observed
HPLC: high performance liquid chromatography
Hz: Hertz
$CDCl_3$ deuterated chloroform
$CD_3OD$: deuterated methanol
mg: milligram
MHz: megahertz
mL: milliliter
mmol: millimole
obsd. Observed
µL: microliter
µm: micrometer
µM: micromoles per liter
mm: millimeter
MS (ESI): mass spectroscopy (electron spray ionization)
NMR: nuclear magnetic resonance
TLC: thin layer chromatography General Synthetic Route for 2,4-Dihalogen Quinolines IIIa (Scheme 1)

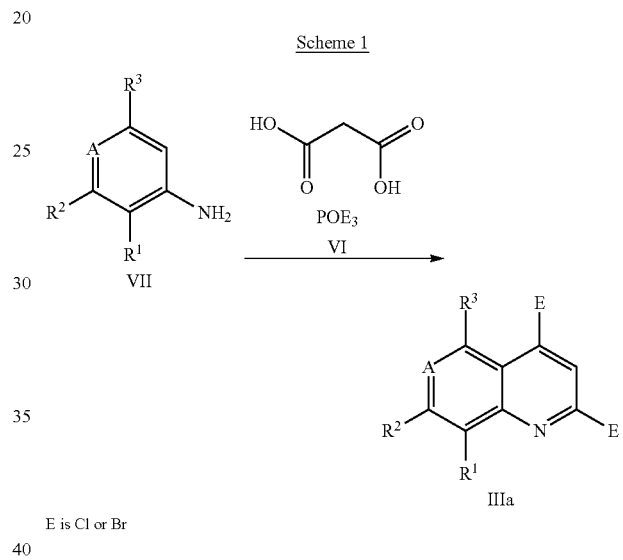

E is Cl or Br

Compounds of interest of formula IIIa can be prepared according to Scheme 1. Starting with various VII, cyclization reaction with propanedioic acid in the presence of VI affords 2,4-dihalogen-quinolines IIIa. The reaction can be carried out at a temperature between 100° C. and 150° C. for 6 to 12 hours. VI can be phosphoryl trichloride or phosphoryl tribromide. General synthetic route for 2,3,4,5-tetrahydro-1,4-benzothiazepines (Scheme 2)

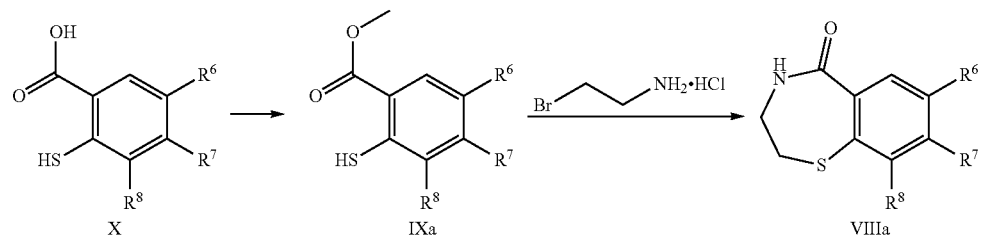

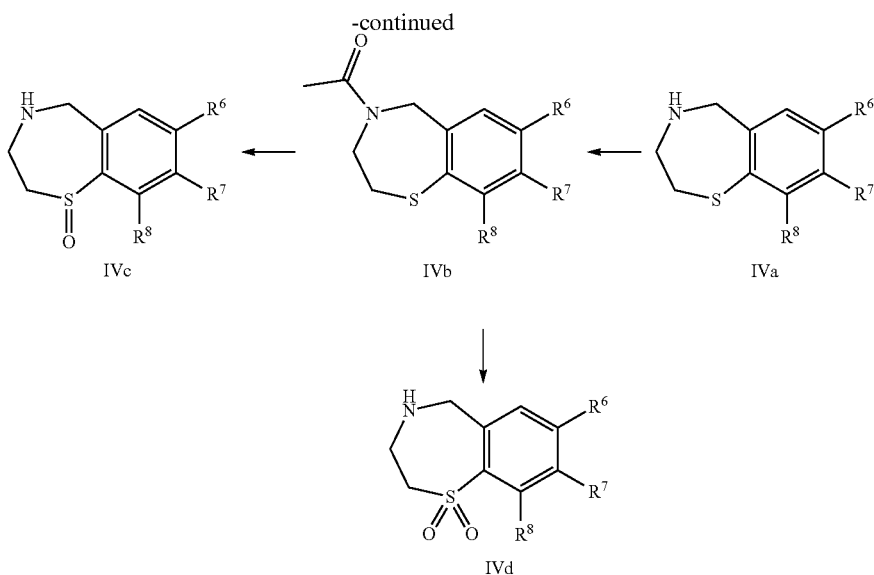

Compounds of interest IVa, IVb, IVc and IVd can be prepared according to Scheme 2. Starting with 2-sulfanylbenzoic acids X, esterification with methanol gives methyl 2-sulfanylbenzoates IXa. Annulation of esters IXa with 2-bromo ethylamine affords 3,4-dihydro-1,4-benzothiazepin-5(2H)-ones VIIIa. Reduction of VIIIa affords 2,3,4,5-tetrahydro-1,4-benzothiazepines IVa. Acylation of IVa generates amides IVb. Oxidation of IVb followed by deacylation affords compounds of interest IVc and IVd.

Methyl 2-sulfanylbenzoates IXa can be prepared by esterification of 2-sulfanylbenzoic acids X. The conversion can be achieved by heating under reflux in the presence of sulfuric acid in methanol overnight or stirring with thionyl chloride in methanol at room temperature for several hours.

3,4-Dihydro-1,4-benzothiazepin-5(2H)-ones VIIIa can be prepared from methyl 2-sulfanylbenzoates IXa by annulation with 2-bromo-ethylamine hydrochloride. The reaction can be carried out with a standard basic agent such as sodium hydride, potassium tert-butoxide in a suitable organic solvent such as tetrahydrofuran, 1,4-dioxane, N,N-dimethylformamide or mixtures thereof, typically at 0° C., followed by stirring at room temperature overnight.

2,3,4,5-Tetrahydro-1,4-benzothiazepines IVa can be prepared by reduction of 3,4-dihydro-1,4-benzothiazepin-5(2H)-ones VIIIa. The reaction can be carried out with a standard reducing agent such as lithium aluminium hydride, boron hydride or combination of sodium borohydride and boron trifluoride in a suitable inert organic solvent such as tetrahydrofuran, diethyl ether or mixtures thereof, typically at 0° C., followed by stirring at a temperature between 25° C. and 70° C. for several hours.

Amides IVb can be prepared by acylation of IVa with acetyl chloride or acetic anhydride. The reaction can be carried out with a suitable base such as triethylamine or pyridine in a suitable inert organic solvent such as dichloromethane, tetrahydrofuran or pyridine at 0° C., followed by stirring at room temperature for 30 minutes.

Compounds IVc can be prepared by oxidation of IVb followed by deacylation. Oxidation can be carried out with 1-2 equivalents of 3-chloroperoxybenzoic acid, in a suitable solvent such as dichloromethane, chloroform, 1,2-dichloroethane, or the mixture thereof, typically at 0° C., followed by stirring at room temperature for 10 to 20 minutes. Deacylation can be achieved by stirring amides with a suitable base such as sodium hydroxide or potassium hydroxide in a mixture of alcohol such as methanol or ethanol and water under reflux overnight.

Compounds IVd can be prepared by oxidation of IVb followed by deacylation. Oxidation can be carried out with 4 equivalents of 3-chloroperoxybenzoic acid, in a suitable solvent such as dichloromethane, chloroform, 1,2-dichloroethane, or the mixture thereof, typically at 0° C., followed by stirring at room temperature for 1 to 2 hours. Deacylation can be achieved by stirring amides with a suitable base such as sodium hydroxide or potassium hydroxide in a mixture of alcohol such as methanol or ethanol and water under reflux overnight.

General Synthetic Route for 5-methyl-2,3,4,5-tetrahydro-1,4-benzothiazepines (Scheme 3)

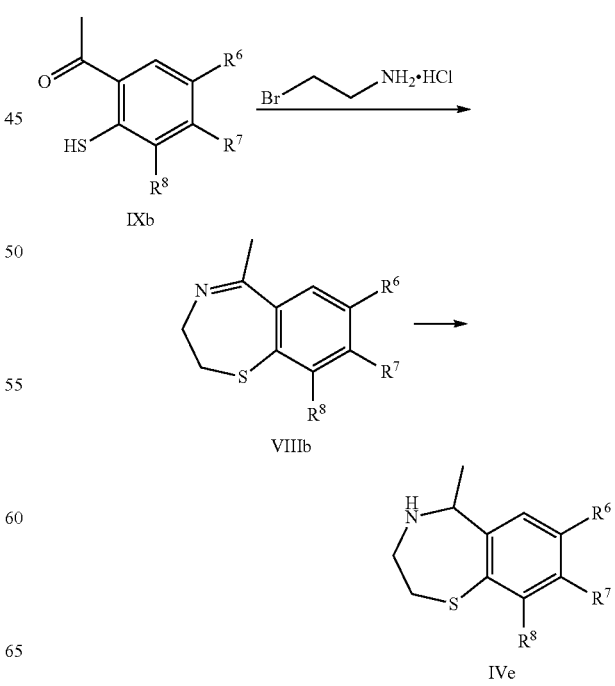

Scheme 3

Compounds of interest IVe can be prepared according to Scheme 3. Starting from 1-(2-sulfanylphenyl)ethanones IXb, annulation of esters IXb with 2-bromo ethylamine hydrochloride affords 5-methyl-2,3-dihydro-1,4-benzothiazepines VIIIb. Reduction of VIIIb affords 5-methyl-2,3,4,5-tetrahydro-1,4-benzothiazepines IVe.

5-Methyl-2,3-dihydro-1,4-benzothiazepine VIIIb can be prepared from 1-(2-sulfanylphenyl)ethanones IXb by annulation with 2-bromo-ethylamine. The reaction can be carried out with a standard basic agent such as sodium hydride, potassium tert-butoxide in a suitable organic solvent such as tetrahydrofuran, 1,4-dioxane, N,N-dimethylformamide or mixtures thereof, typically at 0° C., followed by stirring at room temperature overnight.

5-Methyl-2,3,4,5-tetrahydro-1,4-benzothiazepines IVe can be prepared from reduction of 5-methyl-2,3-dihydro-1,4-benzothiazepines VIIIb. The reaction can be carried out with a reducing reagent such as sodium borohydride in a suitable organic solvent such as methanol, water or mixtures thereof at room temperature for several hours or overnight, followed by treatment with concentrated hydrochloric acid at room temperature for 30 minutes. After neutralization with sodium carbonate or sodium hydroxide, free form of IVe is obtained.

General Synthetic Route for Formulas Iaa (Scheme 4)

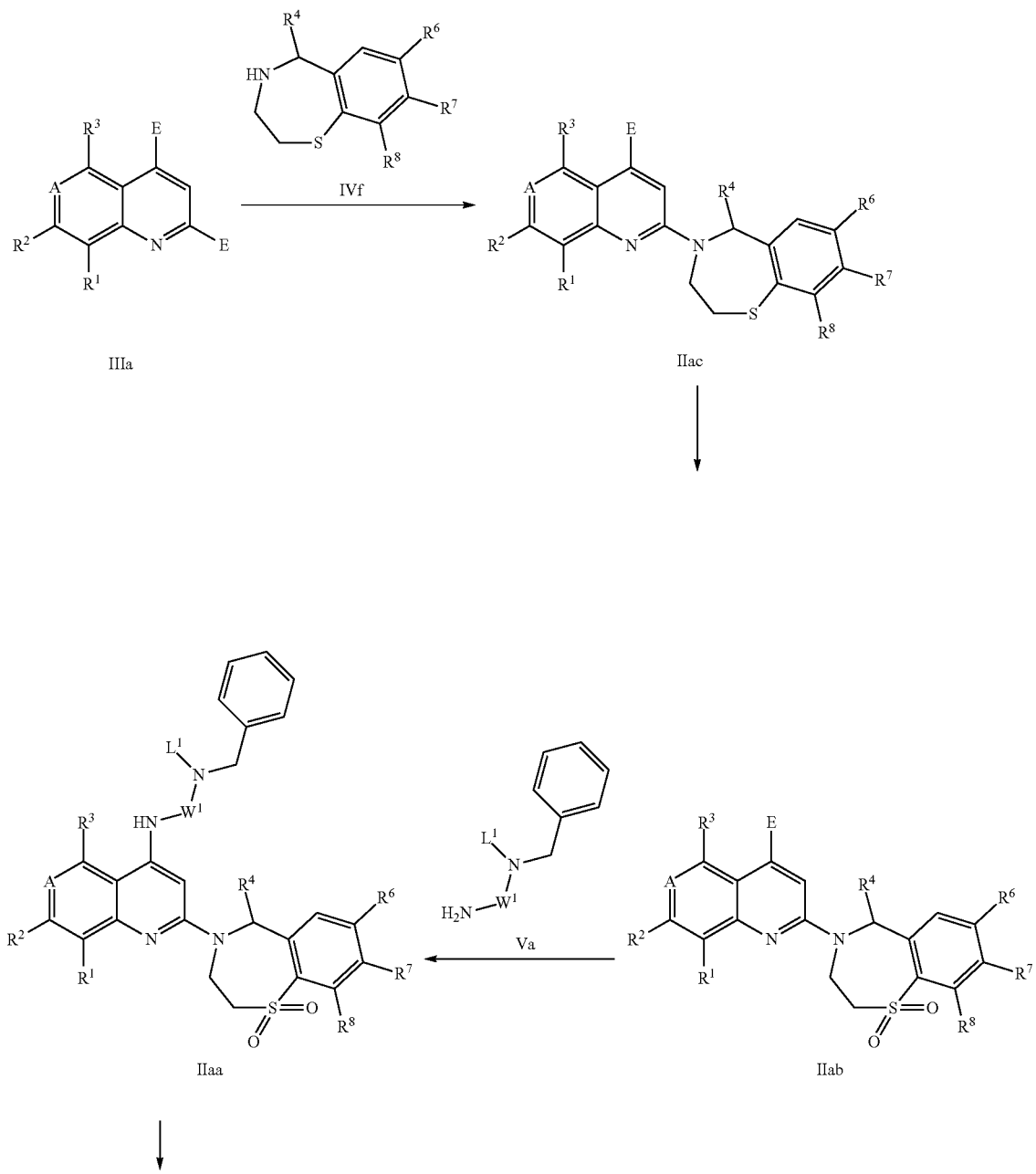

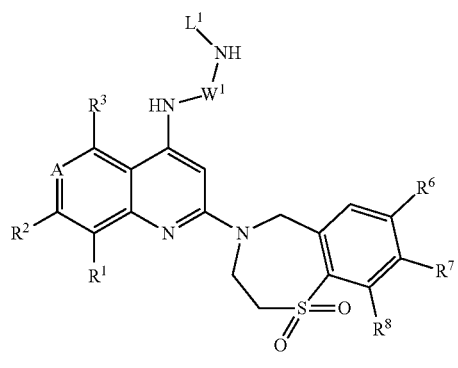

Iaa

E is Cl or Br,

W¹ is (oxetan-3-yl)$C_{1-4}$alkyl, (tetrahydrofuran-3-yl)$C_{1-4}$alkyl, (tetrahydro-2H-pyran-4-yl)$C_{1-4}$alkyl, or ($C_{3-6}$cycloalkyl)$C_{1-4}$alkyl L¹ is H or benzyl, or L¹ and W¹ with the nitrogen atom to which they are attached form 2-Oxa-6-aza-spiro[3.4]oct-8-yl Compounds of interest Iaa can be prepared according to Scheme 4. Coupling of 2,4-dihalogen quinolines IIIa with benzothiazepines IVf followed by oxidation gives 4-halogen quinolines IIab. Coupling of 4-halogen quinolines IIab with various benzyl diamines Va followed by debenzylation generates Iaa.

Quinolines IIac can be prepared by coupling of 2,4-dihalogen quinolines IIIa with benzothiazepines IVf. The reaction can be carried out with or without a solvent such as isopropanol, n-butanol, tert-butanol or the mixture thereof at a temperature between 120° C. and 180° C., typically at 160° C. under microwave irradiation for several hours.

Sulfones IIab can be prepared by oxidation of sulfides IIac. The reaction can be carried out with a suitable oxidant such as 3-chloroperoxybenzoic acid in a suitable inert organic solvent such as dichloromethane typically at 0° C., followed by stirring at room temperature for several hours. Alternatively, the reaction can be carried out with a suitable oxidant such as hydrogen peroxide, sodium periodate or potassium permanganate, in a suitable solvent such as methanol, tetrahydrofuran, water or the mixture thereof, typically at 0° C., followed by stirring at a temperature between room temperature and 70° C. for several hours.

4-Benzyl diamino quinolines IIaa can be prepared by coupling of quinolines IIab with various benzyl diamines Va. The reaction can be carried out in the presence of a palladium catalyst such as 1,1'-bis(diphenylphosphino)ferrocene-palladium (II), palladium (II) acetate, tri(dibenzylideneacetone)dipalladium(0), or palladium (II) chloride in the presence of a phosphine ligand such as triphenyl phosphane, 1,1'-bis(diphenylphosphino)ferrocene, 9,9-dimethyl-4,5-bis(diphenylphosphino)xanthene, or tricyclohexylphosphine, with a suitable base such as sodium carbonate, potassium carbonate, cesium carbonate, sodium tert-butoxide or potassium tert-butoxide, in a suitable inert organic solvent such as toluene, 1,4-dioxane, tetrahydrofuran or N,N-dimethylformamide at a temperature between 100° C. and 160° C. for 1 to 3 hours under microwave irradiation. Alternatively, the reactions can be carried out at a heated temperature such as between 100° C. and 140° C. for a longer reaction time without microwave irradiation.

Compounds of interest Iaa can be prepared by standard debenzylation of IIaa. The reaction can be carried out in the presence of palladium on carbon, palladium hydroxide on carbon or platinum oxide, typically with an acid such as hydrochloric acid, acetic acid or trifluoroacetic acid in a suitable solvent such as methanol, ethanol, tetrahydrofuran, ethyl acetate or the mixture thereof, at room temperature for several hours under hydrogen atmosphere.

General Synthetic Route for Formula Iab and Iac (Scheme 5)

Scheme 5

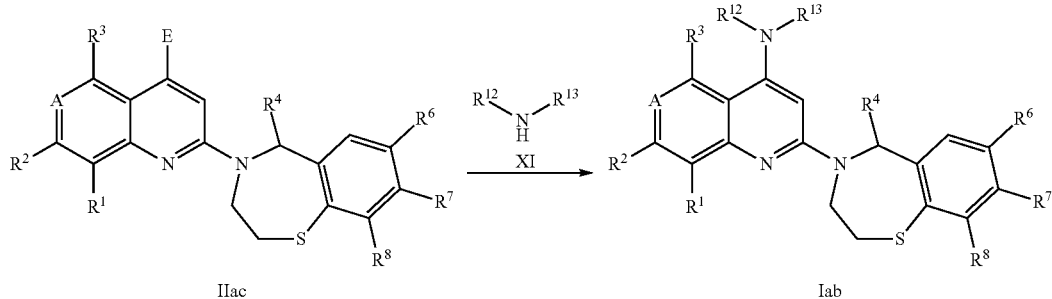

IIac        Iab

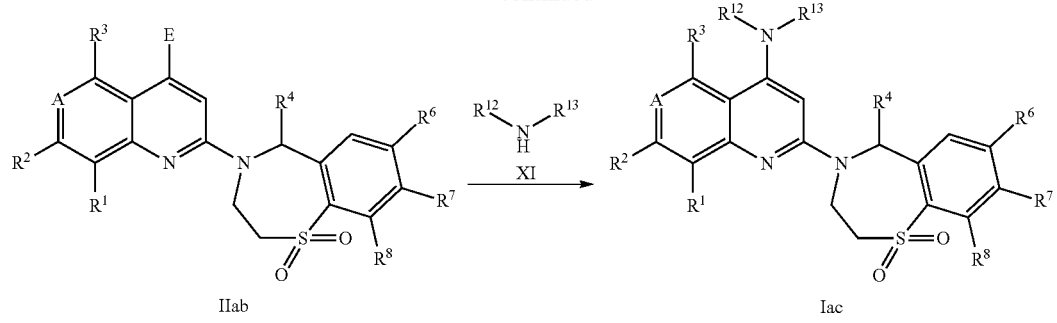

IIab

E is Cl or Br

Iac

Compounds of interest Iab and Iac can be prepared according to Scheme 5. Coupling of 4-halogen quinolines IIac with various amines XI affords Iab. Coupling of 4-halogen quinolines IIab and various amines XI affords 4-amino quinolines Iac. Alternatively, Iac can be obtained by oxidation of the sulfides Iab.

4-Amino quinolines Iab can be prepared by coupling of 4-halogen quinolines IIac with various amines XI in the presence or absence of a palladium catalyst. Palladium-catalyzed coupling reaction can be carried out in the presence of a palladium catalyst such as 1,1'-bis(diphenylphosphino)ferrocene-palladium(II)dichloride, palladium acetate or tris(dibenzylideneacetone) dipalladium(0), in combination with a phosphine ligand such as 1,1'-bis(diphenylphosphino)ferrocene, 2,2'-bis(diphenylphosphino)-1,1'-binaphthalene, 4,5-bis(diphenylphosphino)-9,9-dimethylxanthene or 2-dicyclohexylphosphino-2'-(N,N-dimethylamino)biphenyl, and a base such as sodium tert-butoxide, cesium carbonate or potassium phosphate in a suitable solvent such as 1,4-dioxane or toluene, at a temperature between 100° C. and 140° C. for 1 to 2 hours under microwave irradiation. Alternatively, palladium-catalyzed coupling reaction can be carried out at an elevated temperature such as 110° C. or 120° C. without microwave irradiation for a longer reaction time. Coupling of 4-halogen quinolines IIac with various amines XI in the absence of a palladium catalyst can be carried out with a suitable base such as N,N-diisopropylethylamine or without any base in a suitable solvent such as n-butanol, 1-methyl-2-pyrrolidinone or phenol, at a temperature between 130° C. and 160° C. for 1.5 to 2 hours under microwave irradiation. Alternatively, the reaction can be carried out at an elevated temperature between 150° C. and 180° C. without microwave irradiation for a longer reaction time. Alternatively, the reaction can also be carried out without any base and without any solvent at 160° C. for one to several hours under microwave irradiation.

4-Amino quinolines Iac can be prepared by coupling of 4-halogen quinolines IIab with various amines XI in the presence of a metal catalyst such as a palladium catalyst or copper (I) iodide, or absence of a metal catalyst. Coupling of 4-halogen quinolines IIab with various amines XI in the presence of a palladium catalyst or in the absence of any metal catalyst can be carried out in analogy to coupling of 4-halogen quinolines IIac with various amines XI. Copper(I) iodide catalyzed coupling of 4-halogen quinolines IIab with various amines XI can be carried out in the presence of copper(I) iodide with a ligand such as N,N'-dimethylcyclohexane-1,2-diamine or cyclohexane-1,3-diamine, and a base such as potassium carbonate or potassium phosphate in a suitable solvent such as 1,4-dioxane or diethylene glycol dimethyl ether, at a temperature between 140° C. and 150° C. for 2 to 3 hours under microwave irradiation. Alternatively, the reaction can be carried out at an elevated temperature without microwave irradiation for a longer reaction time.

Alternatively, 4-Amino quinolines Iac can be prepared from oxidation of sulfides Iab. The reaction can be carried out in analogy to oxidation of quinolines IIac in Scheme 4.

General Synthetic Route for Formula Iad (Scheme 6)

Scheme 6

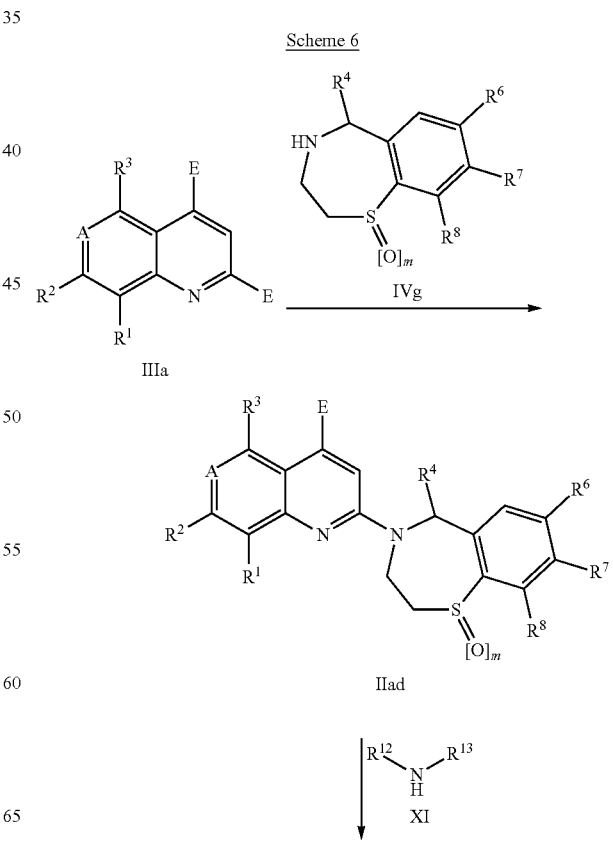

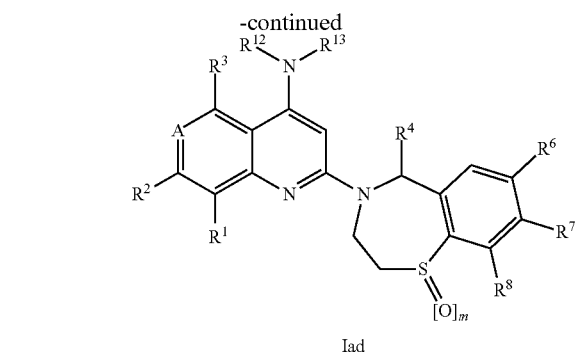

Iad

E is Cl or Br;
m is 1 or 2.

Compounds of interest Iad can be prepared according to Scheme 6. Coupling of 2,4-halogen quinolines a with benzothiazepines IVg affords 2-benzothiazepin-4-halogen quinolines IIad. Coupling of had with various amines XI affords compounds of interest Iad.

2-Benzothiazepin-4-halogen quinolines IIad can be prepared from coupling of 2,4-halogen quinolines IIIa with benzothiazepines IVg. The reaction can be carried out in the absence of solvent or in a suitable solvent such as isopropanol, n-butanol, tert-butanol or the mixtures thereof at a temperature between 120° C. and 180° C., typically at 160° C. under microwave irradiation for several hours.

Compounds of interest of formula had can be prepared from coupling of 2-benzothiazepin-4-halogen quinolines IIad with various amines XI. The reaction can be carried out in the presence of a metal catalyst or in the absence of a metal catalyst in analogy to coupling of 4-halogen quinolines IIab with various amines XI in Scheme 5.

General Synthetic Route for Formula Iae, Iaf and Iag (Scheme 7)

Scheme 7

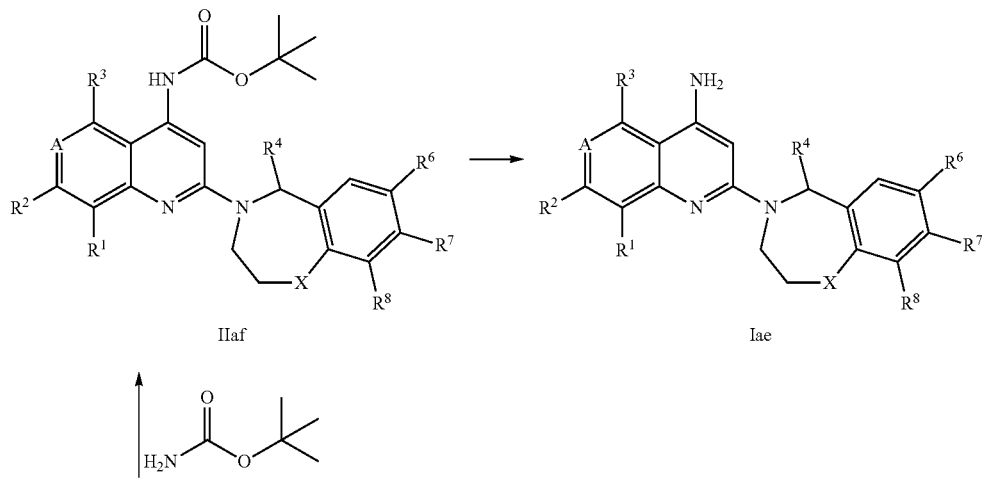

IIaf → Iae

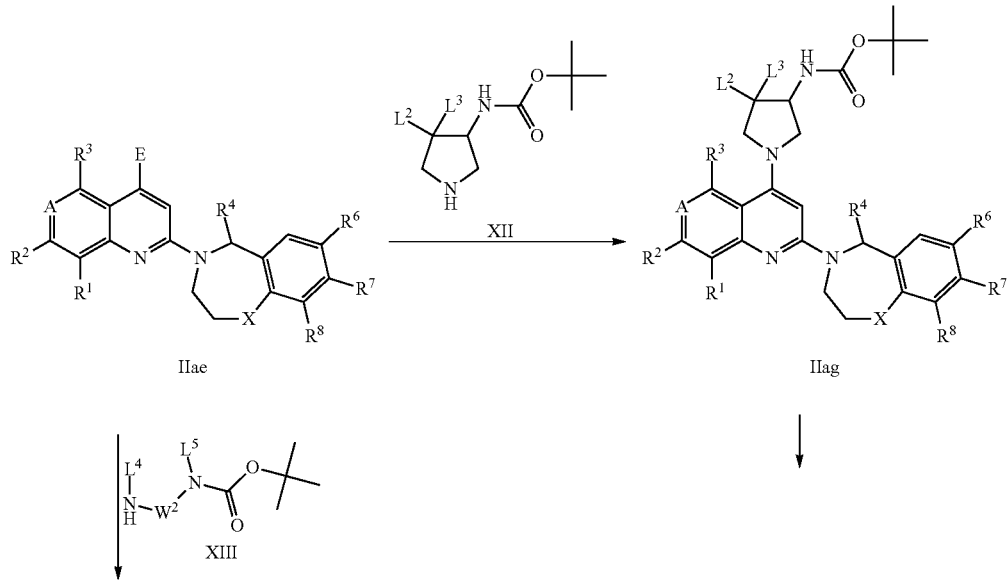

IIae → IIag

XIII

-continued

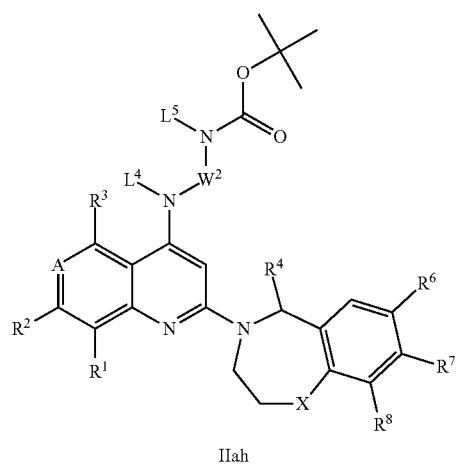

IIah

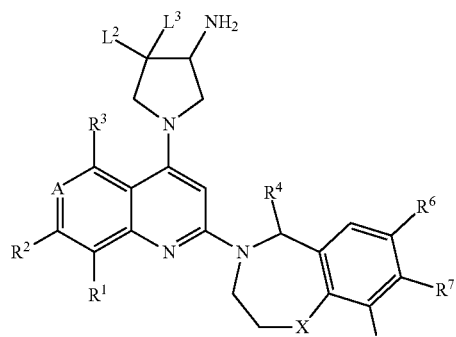

Iaf

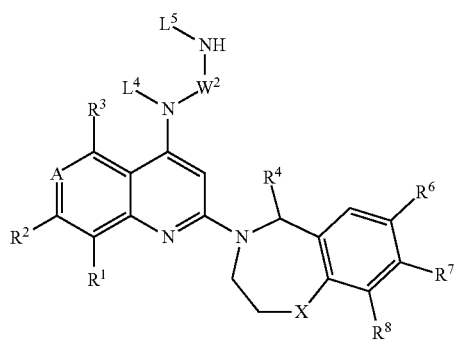

Iag

E is Cl or Br;
$L^2$ is hydrogen;
$L^3$ is hydrogen, hydroxy or fluoro;
$L^2$ and $L^3$ are attached to form 3-oxetanyl;
$L^4$ is hydrogen, or methyl; $L^5$ is hydrogen;
$W^2$ is ethyl, methlcyclopropyl, ethylcyclopropyl, or (morpholin-2-yl)methyl
$L^4$ and $W^2$ with nitrogen they are attached to form azetidin-3-yl, 2-azabicyclo[2.1.1]hexan-5-yl or
(1R, 5S, 6S)-3-azabicyclo[3,1,0]hexan-6-yl
$L^5$ and $W^2$ with nitrogen they are attached to form pyrrolindin-3-yl, azetidin-3-yl, methylazetidin-2-yl,
azetidin-2-yl-carbonyl or pyrrolindin-2-yl-carbonyl.

Compounds of interest Iae, Iaf and Iag can be prepared according to Scheme 7. Coupling of 4-halogen quinolines IIae with various protected amines affords intermediates IIaf, IIag and IIah. Deprotection of IIaf, IIag and IIah affords compounds of interest Iae, Iaf and Iag.

Compounds of interest IIaf, IIag and IIah can be prepared from coupling of 4-halogen quinolines IIae with various protected amines. Coupling of 4-halogen quinolines IIae with various amines such as tert-butyl carbamate, XII or XIII can be carried out in the presence of a metal catalyst or in the absence of a metal catalyst in analogy to coupling of 4-halogen quinolines IIab with various amines XI in Scheme 5.

Compounds of interest Iae, Iaf and Iag can be prepared from deprotection of tert-butyloxycarbonyl of IIaf, IIag and IIah. The reaction can be carried out with a suitable acid such as trifluoroacetic acid or hydrochloric acid in a suitable solvent such as dichloromethane, ethyl acetate or 1,4-dioxane, at 0° C. to room temperature for 4 to 16 hours.

General Synthetic Route for Formula Iah (Scheme 8)

Scheme 8

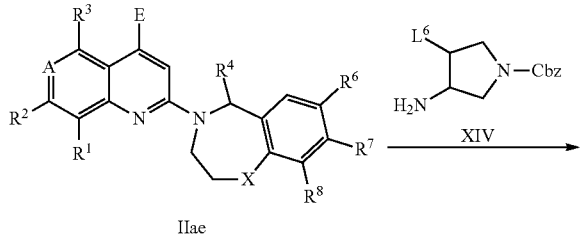

IIae

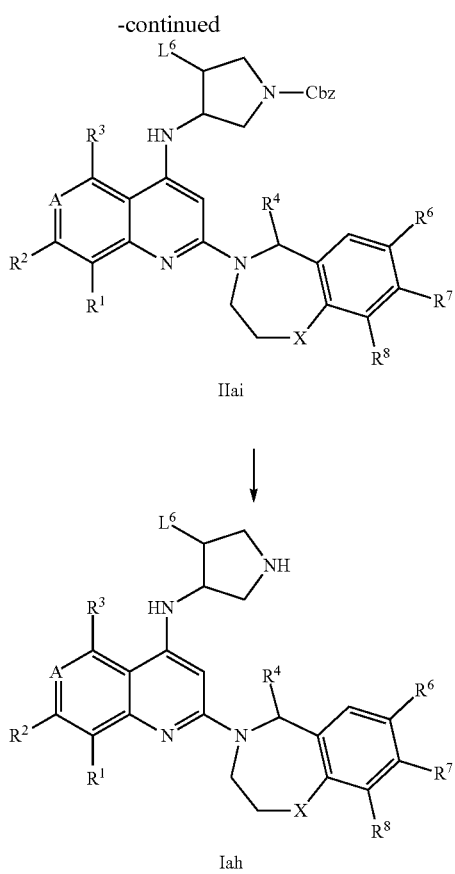

Q is Cl or Br,
L⁶ is hydroxy or fluoro

Compounds of interest Iah can be prepared according to Scheme 8. Coupling of 4-halogen quinolines IIae with various protected amines XIV affords intermediates IIai. Deprotection of benzyloxycarbonyl of IIai affords compounds of interest Iah.

Compounds IIai can be prepared from coupling of 4-halogen quinolines IIae with various amines XIV. The reaction can be carried out in the presence of a metal catalyst or in the absence of a metal catalyst in analogy to coupling of 4-halogen quinolines IIab with various amines XI in Scheme 5. Typically, the reaction can be carried out in the presence of tris(dibenzylideneacetone)dipalladium(0) with 2-dicyclohexylphosphino-2'-(N,N-dimethylamino)biphenyl, and sodium tert-butoxide in a suitable solvent such as 1,4-dioxane, at 120° C. for 2 hours under microwave irradiation.

Compounds of interest Iah can be prepared from deprotection of benzyloxycarbonyl of IIai. The conversion can be achieved under strong acidic conditions, under basic conditions or by hydrogenation. Treating IIai with a mixture of aqueous solution of potassium hydroxide and methanol under reflux for 30 minutes to several hours can generate Iah. Treating IIai under strong acidic conditions such as reflux in 6 N hydrochloride in methanol for several hours can also generate Iah. Hydrogenation of IIai can be carried out in the presence of palladium on carbon or palladium black, under hydrogen atmosphere or with a hydrogen donor such as formic acid or ammonium formate, in a suitable solvent such as methanol or ethanol, at a temperature between room temperature and 80° C. for 15 minutes to several hours.

General Synthetic Route for Formula Iai and Iaj (Scheme 9)

Scheme 9

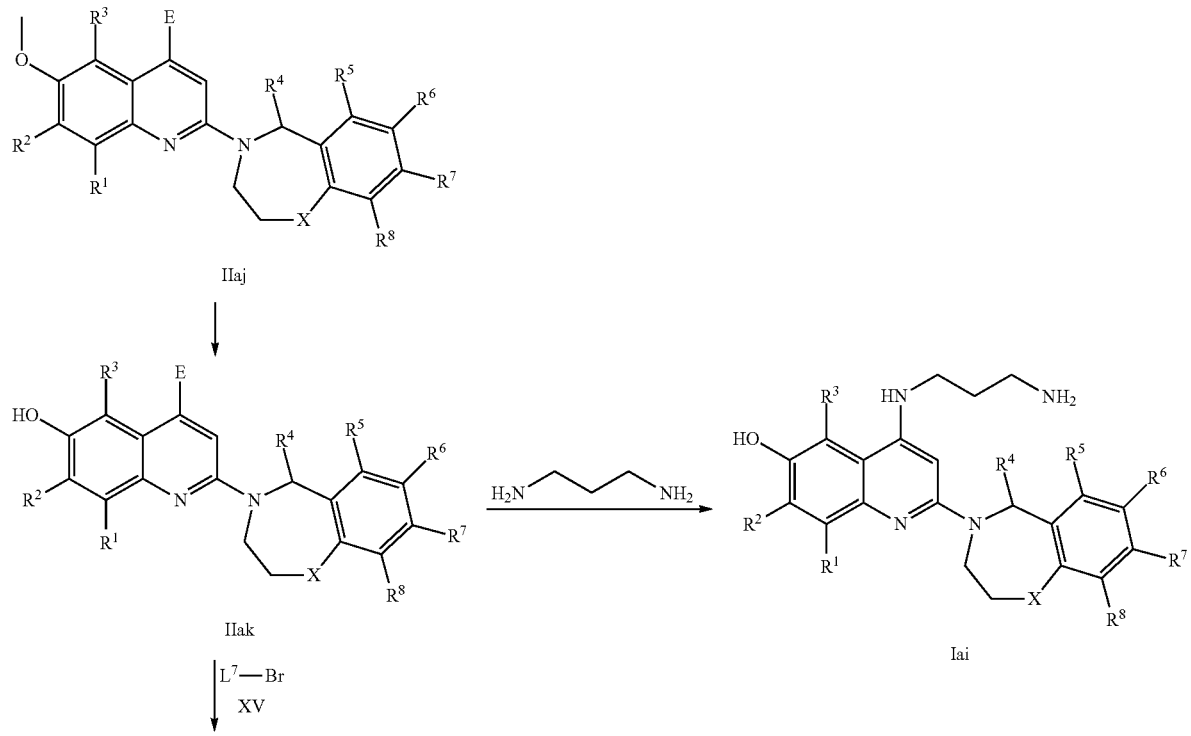

47

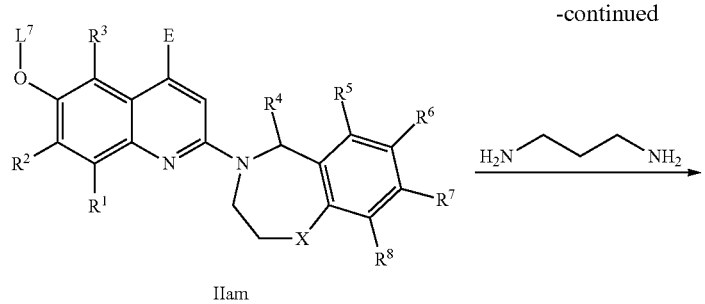

IIam

E is Cl or Br
$L^7$ is hydroxyethyl, methoxyethyl or pyridin-2-yl

48

-continued

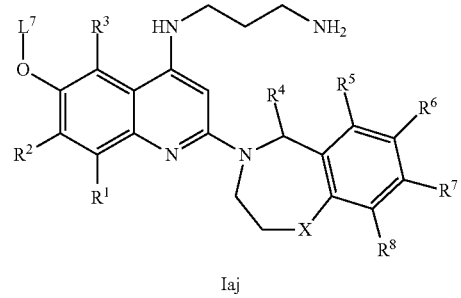

Iaj

Compounds of interest Iai and Iaj can be prepared according to Scheme 8. Demethylation of 6-methoxy quinolines IIaj affords 6-hydroxy quinolines IIak. Reaction of IIak with bromides XV affords IIam. Coupling of 6-hydroxy quinolines IIak with propane-1,3-diamine affords compounds of interest Iai. Coupling of IIam with propane-1,3-diamine affords compounds of interest Iaj.

6-Hydroxy quinolines IIak can be prepared by demethylation of 6-methoxy quinolines IIaj. The reaction can be carried out in an aqueous solution of hydrobromic acid by heating under reflux for 2 days.

IIam can be prepared by reaction of IIak with bromides XV. When $L^7$ is pyridin-2-yl, the reaction can be carried out in the presence of a metal catalyst such as Copper(I) iodide with a ligand such as N,N'-dimethylcyclohexane-1,2-diamine and with a suitable base such as potassium carbonate in a suitable solvent such as 1,2-dimethoxyethane at 120° C. for 1 hours under microwave irradiation. When $L^7$ is substituted alkyl such as hydroxyethyl or methoxyethyl, the reaction can be carried out in the presence of a suitable base such as potassium carbonate in a suitable solvent such as acetone at room temperature overnight.

Compounds of interest Iai and Iaj can be prepared by coupling of IIak and IIam with propane-1,3-diamine separately. The reaction can be carried out at 150° C. for 1.5 hours under microwave irradiation.

General Synthetic Route for Formula Iak (Scheme 10)

Scheme 10

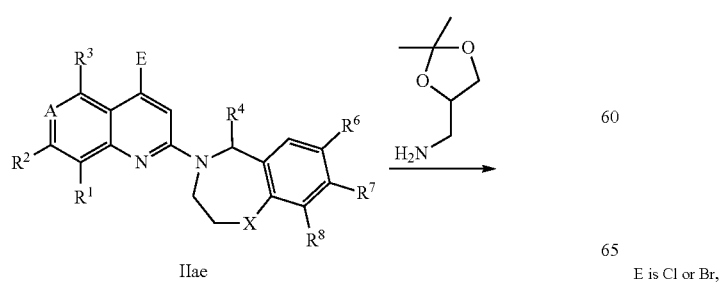

IIae

-continued

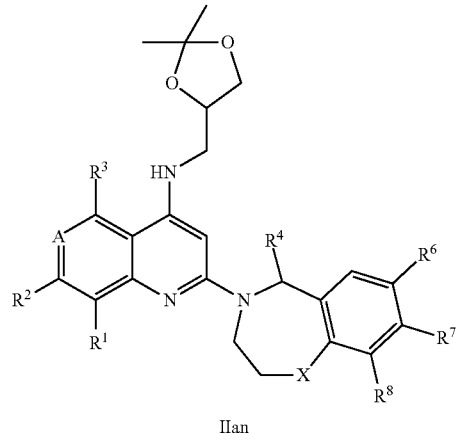

IIan

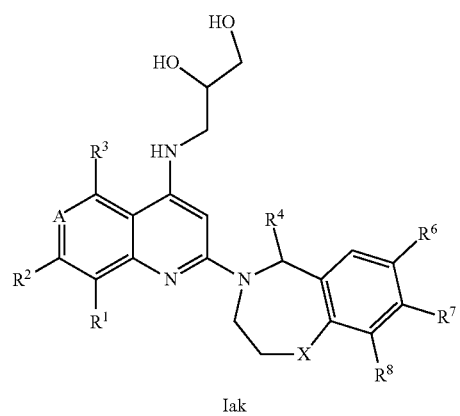

Iak

E is Cl or Br,

Compounds of interest Iak can be prepared according to Scheme 10. Coupling of 4-halogen quinolines IIae with C-(2,2-dimethyl-[1,3]dioxolan-4-yl)-methylamine followed by deprotection affords 4-(2,3-diol-propylamino)-quinolines Iak.

IIan can be obtained by coupling of 4-halogen quinolines IIae with C-(2,2-dimethyl-[1,3]dioxolan-4-yl)-methylamine. The reaction can be carried out in analogy to coupling of 4-halogen quinolines IIab with various amines XI in Scheme 5. Typically the reaction can be carried out by heating a mixture of 4-halogen quinolines IIae and C-(2,2-dimethyl-[1,3]dioxolan-4-yl)-methylamine at 160° C. for 16 hours.

4-(2,3-Diol-propylamino)-quinolines Iak can be prepared by deprotection of IIan. The reaction can be carried out in the presence of an acid such as hydrochloric acid in a suitable solvent such as methanol, ethanol, water or mixtures thereof at room temperature for several hours.

General Synthetic Route for Formula Ial (Scheme 11)

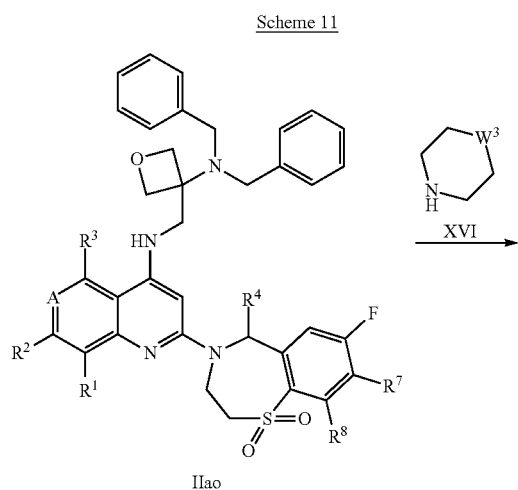

Scheme 11

IIao

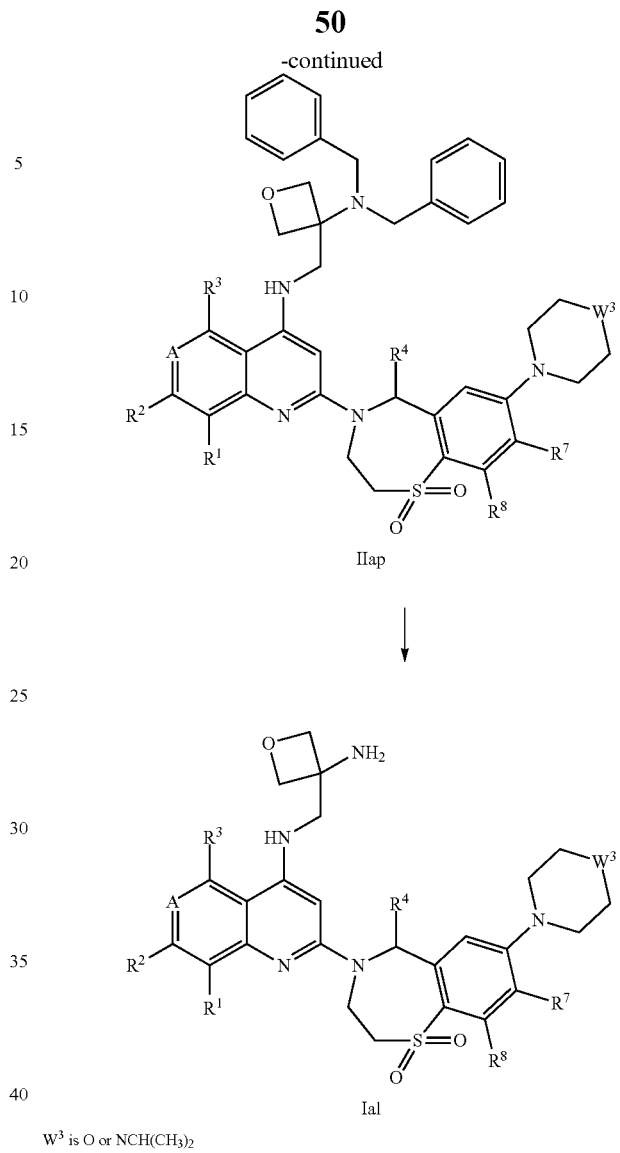

IIap

Ial $W^3$ is O or NCH(CH$_3$)$_2$

Compounds of interest Ial can be prepared according to Scheme 11. Coupling of fluorides IIao with amines XVI followed by debenzylation affords compounds of interest Ial.

Quinolines IIap can be prepared from coupling of fluorides IIao (which can be prepared in analogy to 4-benzyl diamino quinolines IIaa in Scheme 4) with amines XVI. The reaction can be carried out by heating a mixture of fluorides IIao and amines XVI with a suitable solvent such as N,N-dimethyl formamide, N,N-dimethyl acetamide, N-methyl-2-pyrrolidinone, dimethyl sulfoxide or the mixtures thereof, or without any solvent at a temperature between 100° C. and 150° C., typically at 120° C. under microwave irradiation for several hours.

Compounds of interest Ial can be prepared by standard benzyl deprotection of IIap. The reaction can be carried out in analogy to debenzylation of IIaa in Scheme 4.

General Synthetic Route for Formula IIam and Ian (Scheme 12)

Scheme 12
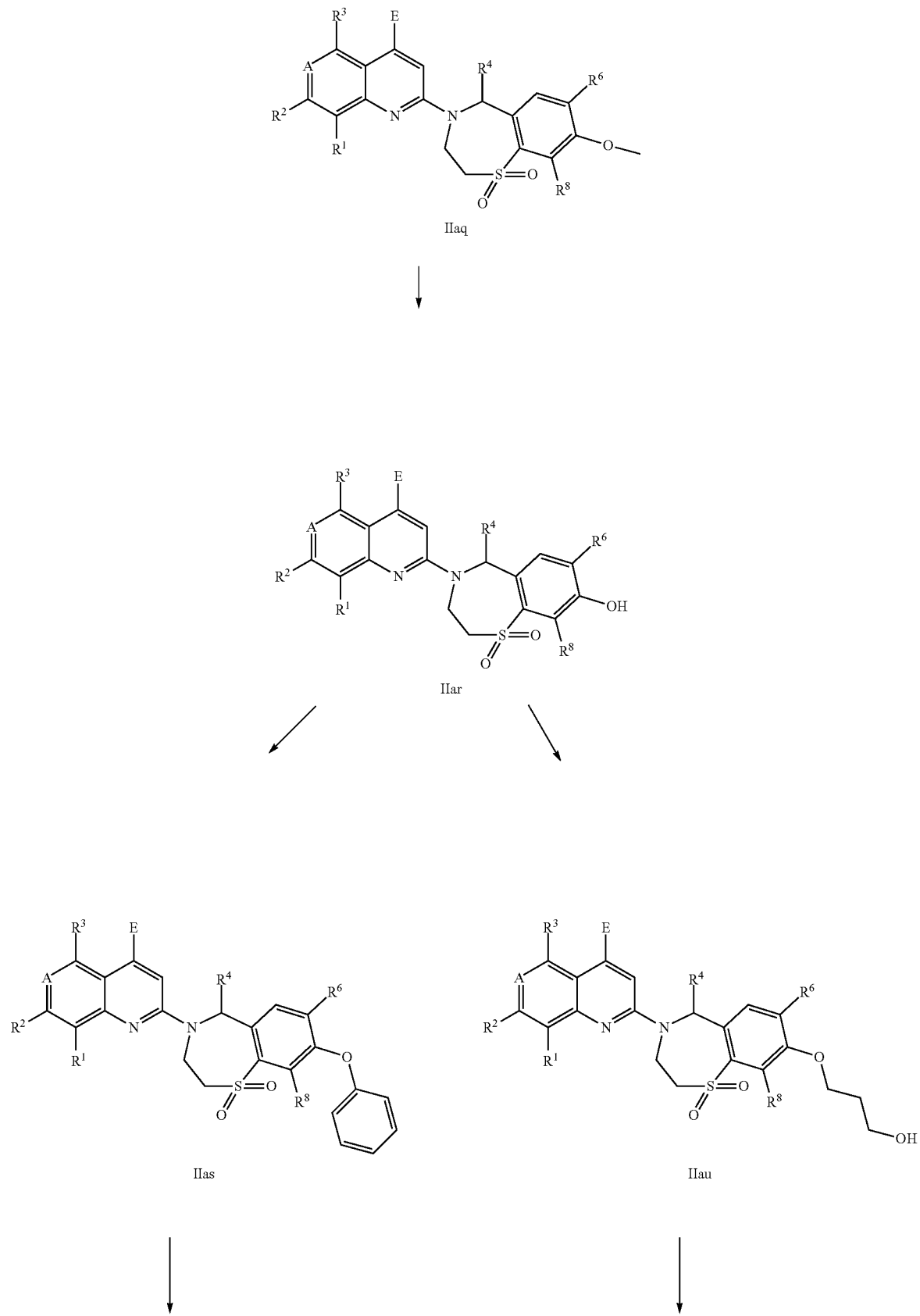

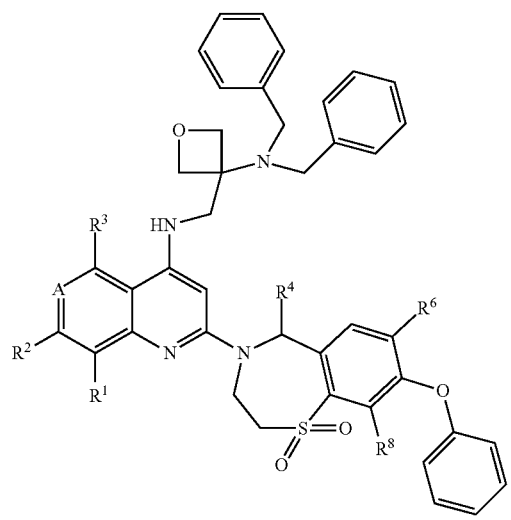

IIat

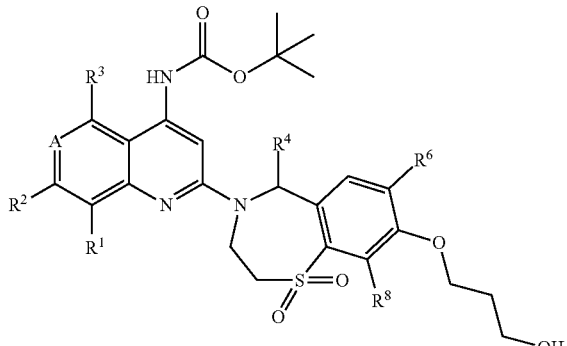

IIav

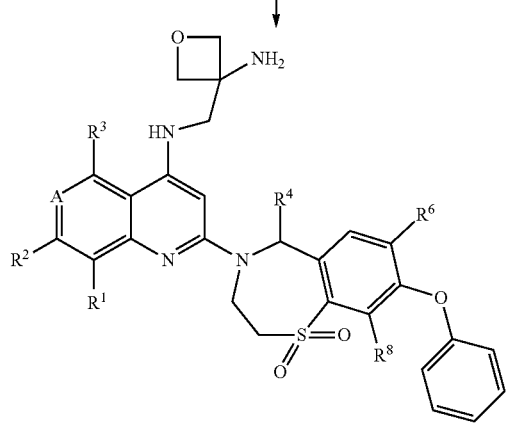

Iam

E is Cl or Br,

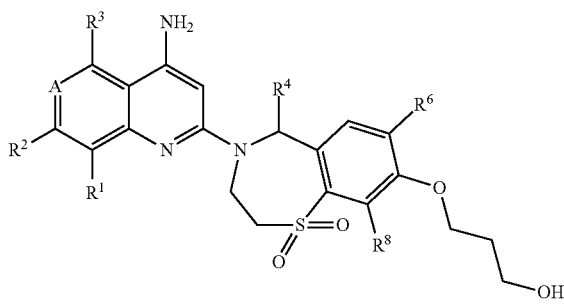

Ian

Compounds of interest Iam and Ian can be prepared according to Scheme 12. Demethylation of IIaq affords IIar. Coupling of IIar with iodobenzene affords 4-phenoxy benzothiazepines IIas. Coupling of IIas with (3-aminomethyl-oxetan-3-yl)-dibenzylamine followed by debenzylation provides 4-[(3-amino-oxetan-3-ylmethyl)-amino]quinolines Iam. Coupling of IIar with 3-bromo-propan-1-ol affords IIau. Coupling of 4-halogen quinolines IIau with carbamic acid tert-butyl ester followed by deprotection of tert-butyloxycarbonyl affords 4-amino quinolines Ian.

IIar can be prepared by demethylation of IIaq. The reaction can be carried out by treating IIaq with a suitable Lewis acid such as tribromoborane, aluminum chloride, aluminum bromide, and stannous chloride in a dry organic inert solvent such as dichloromethane, chloroform, acetonitrile and N,N-dimethylformamide at a temperature between 0 and 80° C., typically at 0° C., for a period of 5 minutes to 3 hours, typically for 1 hour.

IIas can be obtained by coupling of IIar with iodobenzene. The reaction can be carried out by heating in the presence of copper(I) iodide or copper(I) bromide, with a ligand such as N,N-dimethylglycine hydrochloride, (2-pyridyl)acetone or 1,1,1-tris(hydroxymethyl)ethane, and a base such as cesium carbonate, potassium carbonate, or potassium phosphate, in an organic solvent such as dimethyl sulfoxide, N,N-dimethylformamide, acetonitrile or 1,4-dioxane at a temperature between 80° C. and 120° C. for 4 to 24 hours. Typically, the reaction can be carried out by heating in the presence of copper(I) iodide, N,N-dimethylglycine hydrochloride and potassium carbonate in dimethyl sulfoxide at 120° C. for 6 hours.

Iam can be obtained by coupling of IIas with (3-aminomethyl-oxetan-3-yl)-dibenzylamine followed by debenzylation. The reactions can be conducted in analogy to preparation of Iaa from IIab in Scheme 4. Typically, coupling of IIas with (3-aminomethyl-oxetan-3-yl)-dibenzylamine can be carried out in the presence of bis(diphenylphosphino)-ferrocenedichloropalladium(II), 1,1'-bis(diphenylphosphino)-ferrocene and sodium-tert-butoxide in 1,4-dioxane at 120° C. for 2 hours under microwave irradiation. Debenzylation of IIat can be achieved by stirring a solution of IIat in methanol in the presence of palladium hydroxide on carbon and trifluoroacetic acid at room temperature under 2 bar of hydrogen atmosphere for 14 hours.

IIau can be prepared by coupling of IIar with 3-bromopropan-1-ol. The reaction can be carried out with a suitable base such as potassium carbonate, cesium carbonate, sodium tert-butoxide, potassium tert-butoxide, sodium hydride or 1,8-diazabicyclo[5.4.0]undec-7-ene in an inert organic solvent such as dichloromethane, N,N-dimethylformamide, dimethyl sulfoxide or 1-methyl-pyrrolidin-2-one at a temperature between room temperature and 100° C., typically at 70° C. for several hours.

IIav can be prepared by coupling of 4-halogen quinolines IIau with carbamic acid tert-butyl ester. The reaction can be carried out in the presence of a palladium catalyst in analogy to coupling of 4-halogen quinolines IIab with various amines XI in Scheme 5. Typically the reaction can be carried out by heating a mixture of 4-halogen quinolines IIau and carbamic acid tert-butyl ester in the presence of bis(diphenylphosphino)ferrocenedichloropalladium(II), with 1,1'-bis(diphenylphosphino)ferrocene and sodium-tert-butoxide in 1,4-dioxane at 120° C. for 2 hours.

4-Amine quinolines Ian can be obtained by standard deprotection of tert-butyloxycarbonyl of IIav. The reaction can be carried out by treating IIav with a suitable acid such as hydrochloric acid, trifluoroacetic acid, or sulfuric acid in a suitable solvent such as methanol, ethyl acetate, dichloromethane, 1,4-dioxane, water or the mixtures thereof at a temperature between 0° C. and room temperature for 30 minutes to several hours. Typically the reaction can be carried out by treating IIav with trifluoroacetic acid in dichloromethane at room temperature for 6 hours.

General Synthetic Route for Formula Iao (Scheme 12)

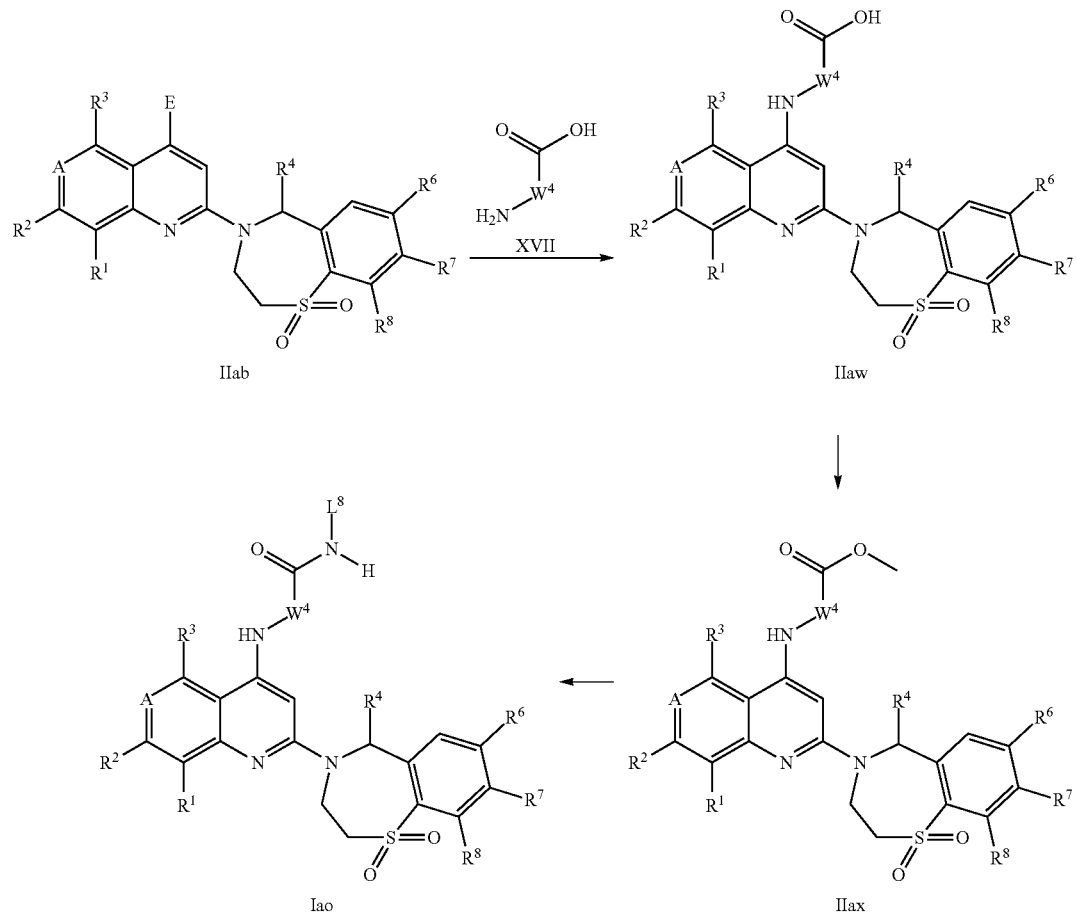

Scheme 12

E is Cl or Br;
W is $CH_2$, $CH(CH_3)$, $CH_2CH(CH_3)$, or $CH(CH_3)CH_2$;
$L^8$ is H or $CH_3$

Compounds of interest Iao can be prepared according to Scheme 13. Coupling of 4-halogen quinolines IIab with various amino acids XVII gives acids IIaw. Esterification of acids IIaw followed by aminolysis affords amides Iao.

Acids IIaw can be prepared by coupling of 4-halogenquinolines IIab with amino acids XVII. The reaction can be carried out in phenol, preferably at 150° C. in a sealed tube overnight.

Esters IIax can be prepared by esterification of carboxylic acids IIaw. The reaction can be carried out by heating IIaw and methanol in the presence of a suitable catalyst such as concentrated sulfuric acid, dry hydrochloride gas, or thionyl chloride for several hours. Typically the reaction can be carried out by heating IIaw and methanol in the presence of thionyl chloride under reflux for 2 hours.

Amides Iao can be prepared by aminolysis of methyl esters IIax. The reaction can be carried out by heating methyl esters IIax with various concentrated amines in alcohol, such as 7N ammonia in methanol or 33% (wt %) methyl amine in absolute ethanol. The reaction can be preferably carried out at 85° C. in a sealed tube overnight.

General Synthetic Route for Formula Iap (Scheme 14)

Scheme 14

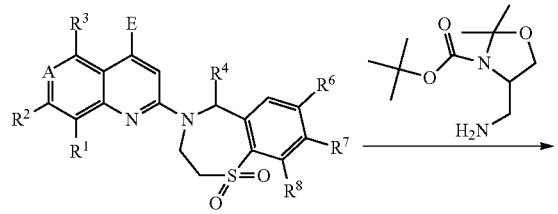

IIab

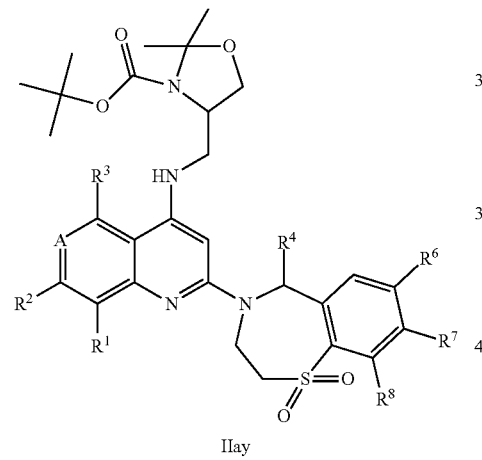

IIay

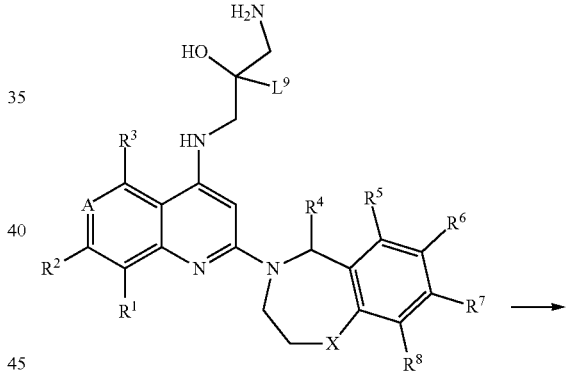

Iap

Compounds of interest Iap can be prepared according to Scheme 14. Coupling of 4-halogen quinolines IIab with 4-aminomethyl-2,2-dimethyl-oxazolidine-3-carboxylic acid tert-butyl ester affords IIay. Cleavage of tert-butyloxycarbonyl and acetal generates amino alcohols Iap.

Oxazolidines can be prepared by coupling of 4-halogen quinolines IIab with 4-aminomethyl-2,2-dimethyl-oxazolidine-3-carboxylic acid tert-butyl ester. The reaction can be carried out in the presence of a palladium catalyst in analogy to coupling of 4-halogen quinolines IIab with various amines XI in Scheme 5. Typically the reaction can be carried out by heating a mixture of 4-halogen quinolines IIab and 4-aminomethyl-2,2-dimethyl-oxazolidine-3-carboxylic acid tert-butyl ester in the presence of bis(diphenylphosphino)ferrocenedichloropalladium(II), with 1,1'-bis(diphenylphosphino)ferrocene and sodium-tert-butoxide in 1,4-dioxane at 120° C. for 1.5 hours.

Amino alcohols Iap can be prepared by acid catalyzed cleavage of tert-butyloxycarbonyl and acetal of acetonides IIay. The reaction is typically carried out in a solution of hydrochloride in ethyl acetate for several hours at room temperature.

General Synthetic Route for Formula Iar (Scheme 15)

Scheme 15

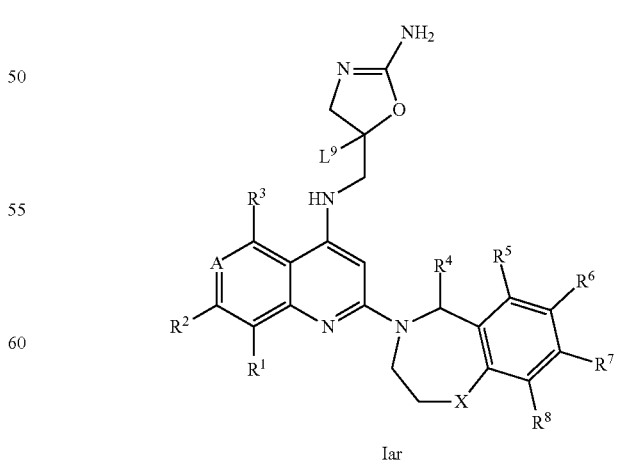

Iar $L^9$ is H or $CH_3$,

Compounds of interest Iar can be prepared according to Scheme 15. Starting with amino alcohols Iaq (prepared in analogue to Idj in Scheme 56), ring closure with cyanogen bromide gives oxazoles Iar. The reaction can be carried out with a suitable base such as sodium acetate, sodium carbonate, potassium acetate or potassium carbonate, in a suitable solvent such as methanol, water, or the mixtures thereof, typically at 0° C., followed by stirring at room temperature for several hours.

General Synthetic Route for Formula Iat (Scheme 16)

Scheme 16

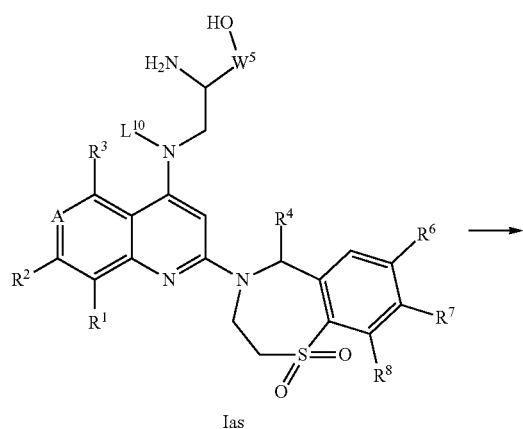

Ias

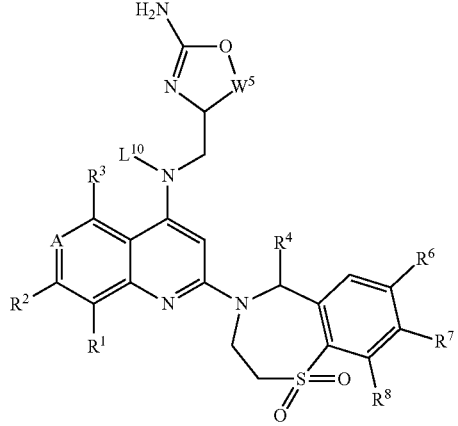

Iat $L^{10}$ is H,
$W^5$ is $CH_2$,
or $L^{10}$ is $CH_2$ and $W^5$ is CH, they attach and form a pyrrolidine ring.

Compounds of interest Iat can be prepared according to Scheme 16. Starting with amino alcohols Ias (prepared in analogue to Iap in Scheme 14 and Iaf in Scheme 7), cyclization with cyanogen bromide affords oxazoles Iat. Compounds of interest Iat can be prepared by cyclization of amino alcohols Ias with a slight excess of cyanogen bromide. The reaction can be carried out in the presence of a suitable base such as sodium acetate, sodium carbonate, potassium acetate or potassium carbonate, in a suitable solvent such as methanol, water, or the mixtures thereof, typically at 0° C., followed by stirring at room temperature for several hours.

General Synthetic Route for Formula Iau (Scheme 17)

Scheme 17

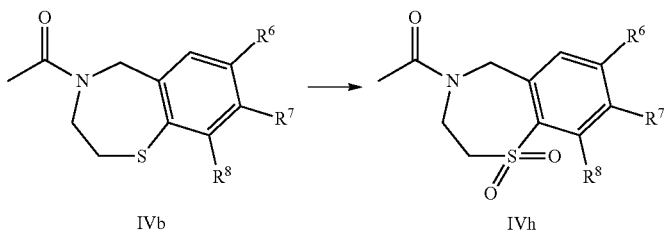

IVb → IVh

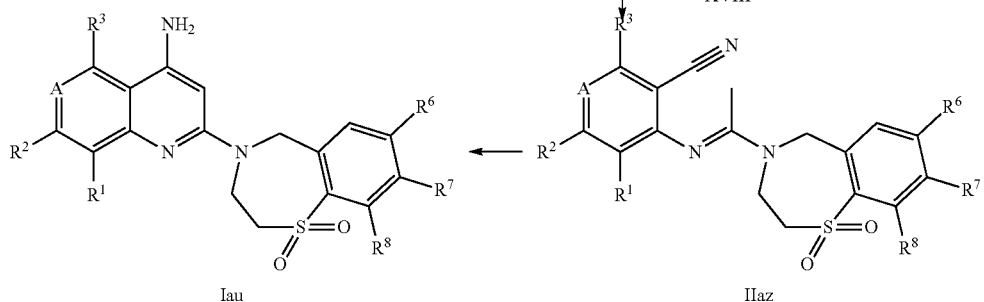

Iau    IIaz

Compounds of interest Iau can be prepared according to Scheme 17. Starting with IVb, oxidation of IVb gives sulfones IVh, which was coupled with 2-aminobenzonitriles XVIII to afford imines IIaz. Ring closure of imines IIaz gives 4-amino quinolines Iau.

Sulfones IVh can be prepared by oxidation of IVb. The reaction can be carried out with a suitable oxidant such as 3-chloroperoxybenzoic acid, hydrogen peroxide, sodium periodate or potassium permanganate, in a suitable solvent such as dichloromethane, acetic acid, water or the mixtures thereof, typically at 0° C., followed by stirring at room temperature for several hours.

Imines IIaz can be prepared by heating a mixture of IVh, 2-aminobenzonitriles XVIII and phosphorous oxychloride. The reaction can be carried out in a suitable inert organic solvent such as dichloromethane, chloroform or the mixtures thereof, typically at 0-10° C., followed by stirring at reflux for 24 hours.

Compounds of interest Iau can be prepared by ring closure of imines IIaz. The reaction can be achieved by treatment of IIaz with Lewis acid such as zinc chloride in N,N-dimethylacetamide at 120-180° C. for several hours in an inert atmosphere.

General Synthetic Route for Formula Iav and Iaw (Scheme 18)

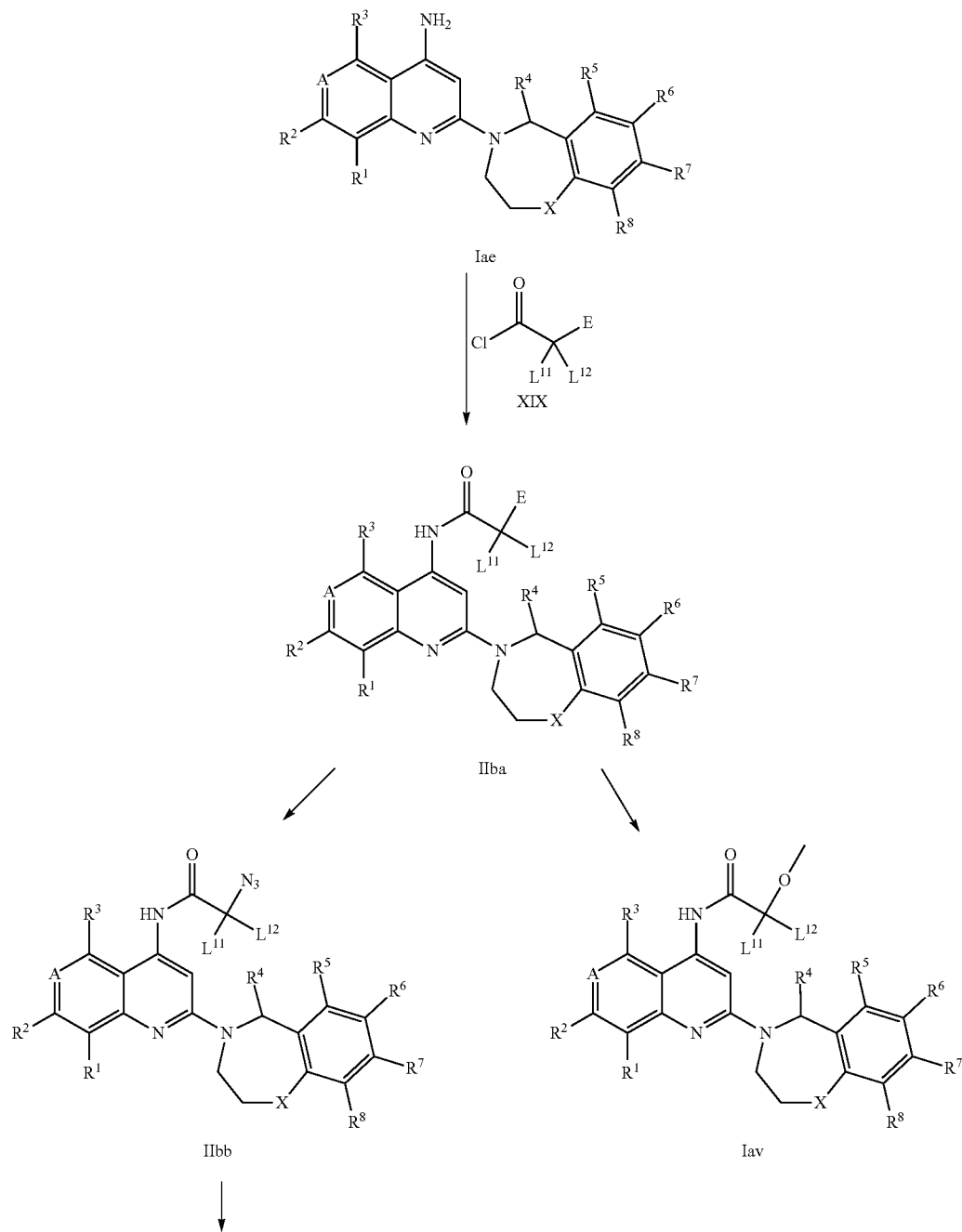

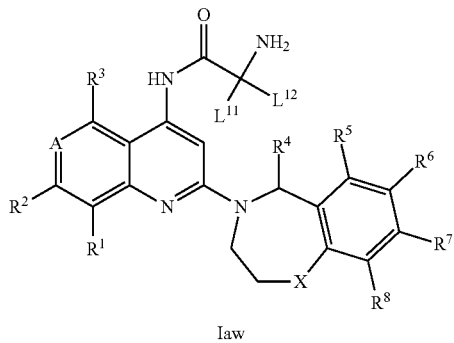

Iaw

E is Cl or Br,
L$^{11}$ is H, or CH$_3$,
L$^{12}$ is H, CH$_3$ or CH$_2$CH$_3$

Compounds of interest Iaw and Iav can be prepared according to Scheme 18. Staring from 4-amino quinolines Iae, acylation of Iae with acyl chlorides XIX gives amides IIba. Reaction of IIba with methanol affords methyl ethers Iav. Reaction of IIba with sodium azide followed by hydrogenation of azides generates compounds of formula Iaw.

Amides IIba can be prepared from 4-amino quinolines Iae by acylation with acy chlorides XIX. The reaction can be carried out with a suitable base such as potassium carbonate, cesium carbonate, sodium hydride or 1,8-diazabicyclo[5.4.0]undec-7-ene in an inert organic solvent such as dichloromethane, tetrahydrofuran or N,N-dimethylformamide, typically at room temperature, followed by stirring at 50-100° C. for several hours.

Methyl ethers Iav can be prepared by reaction of IIba with methanol. The reaction can be realized by refluxing IIba in methanol in the presence of ethylamine overnight.

Azides IIbb can be prepared by reaction of amides IIba with sodium azide. The reaction can be carried out in a suitable solvent such as acetonitrile, N,N-dimethylformamide, dimethyl sulfoxide, water or mixtures thereof, typically at 25-70° C. for several hours.

Amines Iaw can be prepared by hydrogenation of azides IIbb. The reaction can be carried out in the presence of 10% palladium on carbon under hydrogen atmosphere in an organic solvent such as ethyl acetate, methanol, or ethanol, typically at room temperature for several hours.

General Synthetic Route for Formula Iax and Iay (Scheme 19)

Scheme 19

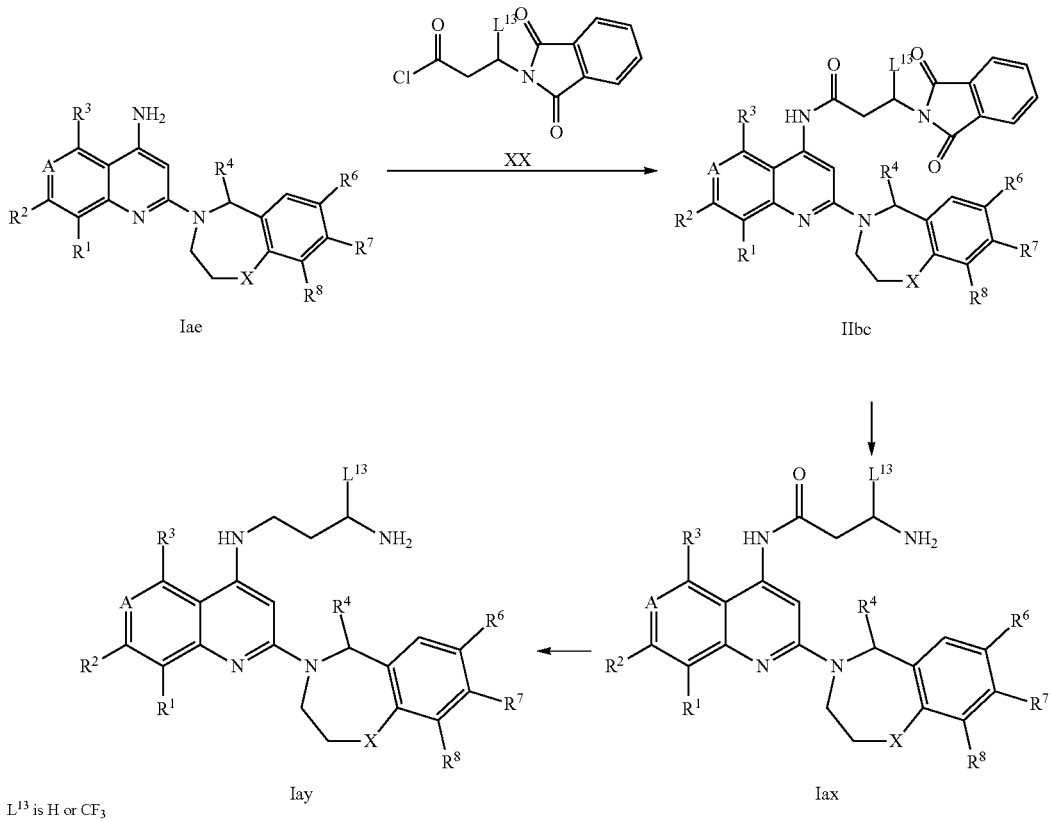

L$^{13}$ is H or CF$_3$

Compounds of interest Iax and Iay can be prepared according to Scheme 19. Starting from 4-aminoquinolines Iae, acylation of Iae with acyl chlorides XX gives IIbc. Cleavage of phthalic protecting group from IIbc generates amides Iax. Reduction of amides of Iax generates Iay.

IIbc can be prepared by acylation of 4-aminoquinolines Iae. The reaction can be carried out by stirring a mixture of Iae and acyl chlorides XX with a suitable base such as N,N-diisopropylethylamine or cesium carbonate, in a suitable organic solvent such as dichloromethane, N,N-dimethylformamide or the mixtures thereof, at room temperature for several hours.

Amides Iax can be prepared by cleavage of phthalic protecting group from IIbc. The reaction can be carried out with a suitable base such as hydrazine, hydrazine acetate or low alkyl amine such as methylamine or n-butylamine in an alcohol solvent such as methanol or ethanol at a temperature between room temperature and 90° C. for several hours. Typically, the reaction can be carried out by heating IIbc with methylamine in ethanol, at 90° C. for 2 hours. Iay can be obtained by reduction of amides of Iax. The reaction can be carried out by heating Iax in a solution of borane-methyl sulfide complex in diethyl ether at 80° C. for several hours.

General Synthetic Route for Formula Iba (Scheme 20)

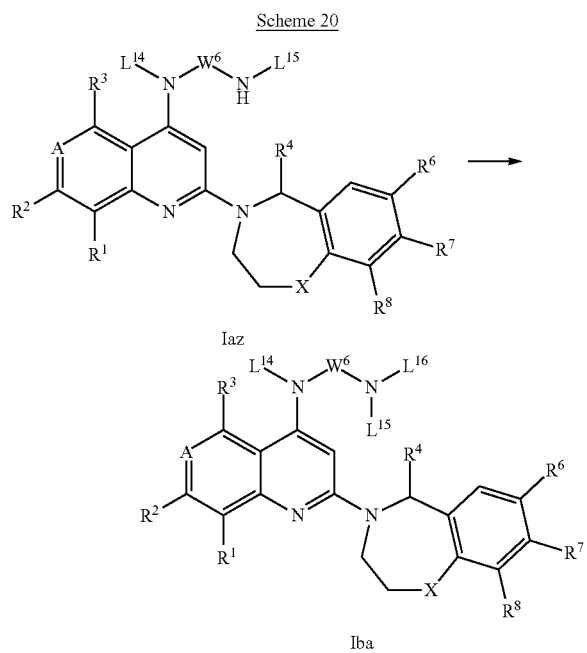

Iaz

Iba $L^{14}$ is H,
$L^{15}$ is H or ethyl,
$L^{16}$ is $CH_2CH_3$, oxetan-3-yl, or pyridin-2-yl,
$W^6$ is $(CH_2)_2$, $(CH_2)_3$, or methyl-oxetan-3-yl,
$L^{14}$ and $W^6$ with nitrogen they are attached to form pyrrolidin-3-yl,
$L^{15}$ and $W^6$ with nitrogen they are attached to form pyrrolidin-3-yl, Compounds of interest Iba can be prepared according to Scheme 20. Starting with amines Iaz (prepared in analogue to Iac in Scheme 5 and Iaf, Iag in Scheme 7), reductive amination with various aldehydes or ketones provides substituted amines Iba when $L^{16}$ is ethyl or oxetan-3-yl; coupling of amines Iaz with 2-bromo-pyridine generates Iba when $L^{16}$ is pyridine-2-yl.

Compounds of interest Iba can be prepared by reductive amination of Iaz with various aldehydes or ketones. This reaction can be carried out with a suitable reducing agent such as sodium triacetoxyborohydride or sodium cyanoborohydride in a suitable organic solvent such as dichloromethane, 1,2-dichloroethane, tetrahydrofuran, methanol or the mixtures thereof, typically with the addition of molecular sieves or acetic acid, at a temperature between room temperature and 70° C. for 2 to 12 hours.

Compounds of interest Iba can also be prepared by coupling of amines Iaz with 2-bromo-pyridine. The reaction is typically performed in N-methylpyrrolidinone with tri(dibenzylideneacetone)dipalladium(0), 4,5-bis(diphenylphosphino)-9,9-dimethylxanthe, cesium carbonate at a temperature between 100° C. and 150° C. for several hours under inert atmosphere.

General Synthetic Route for Formula Ibb (Scheme 21)

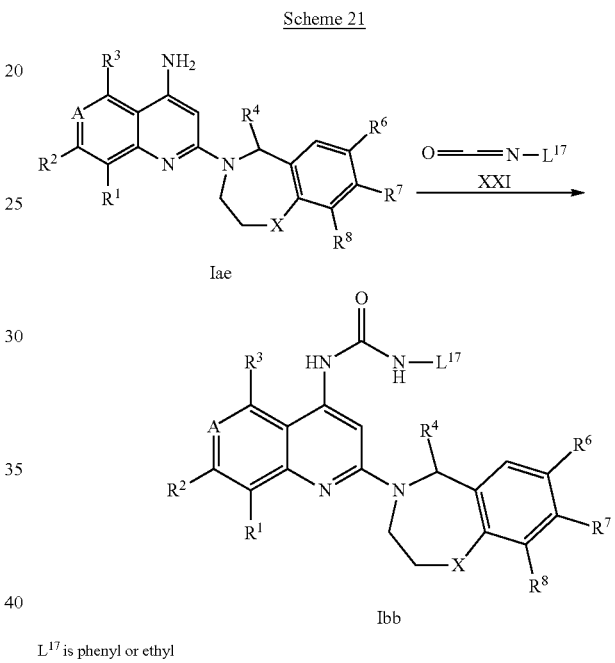

Ibb $L^{17}$ is phenyl or ethyl

Compounds of formula Ibb can be prepared as shown in Scheme 21. Ureas Ibb can be prepared by reaction of 4-amino-quinolines Iae with isocyanides XXI. The reaction can be carried out by stirring 4-amino-quinolines Iae with various isocyanide XXI in the presence of a suitable base such as triethylamine in an organic solvent such as tetrahydrofuran at a temperature between 0° C. to 50° C. for several hours.

General Synthetic Route for Formula Ibc (Scheme 22)

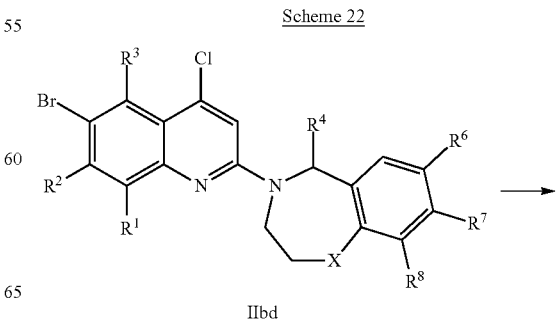

IIbd

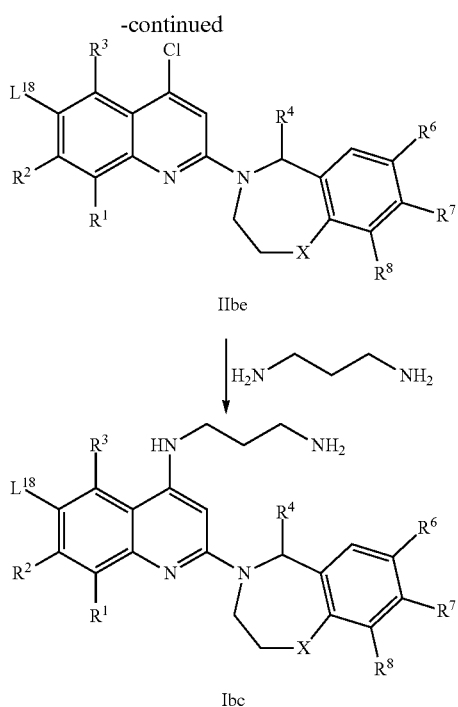

$L^{18}$ is cyclopropyl, cyano, ethenyl, or ethynyl

Compounds of interest of formula Ibc can be prepared according to Scheme 22. Reaction of bromides IIbd with various organoboronic acids or various organometallic reagents affords compounds IIbe. Coupling of IIbe with propane-1,3-diamine affords compounds of interest of formula Ibc.

Compounds IIbe can be prepared from reaction of bromides IIbd with various organoboronic acids or various metal reagents such as zinc cyanide or organostannic reagents. Reaction of bromides IIbd with various organoboronic acids can be carried out in the presence of a palladium catalyst such as tetra(triphenylphosphino)palladium or palladium acetate with a phosphine ligand such as 2,2'-bis(diphenylphosphino)-1,1'-binaphthalene and a base such as potassium carbonate in a suitable solvent such as toluene at 90° C. for 16 hours under argon atmosphere. Reaction of bromides IIbd with various organometallic reagents can be carried out in the presence of a palladium catalyst such as tetra(tri-phenylphosphino)palladium in a suitable solvent such as N,N-dimethylformamide under reflux for 1 to 2 hours under argon atmosphere.

Coupling of halogens IIbe with propane-1,3-diamine can be carried out in analogy to coupling of 4-halogen quinolines IIab with various amines XI in Scheme 5. Typically, the reaction can be carried out with a palladium catalyst such as bis(diphenylphosphino)ferrocenedichloropalladium(II), with a phosphine ligand such as 1,1'-bis(diphenylphosphino) ferrocene, and a suitable base such as sodium-tert-butoxide in a suitable solvent such as 1,4-dioxane, heated at 120° C. for 2 hours under microwave irradiation.

General Synthetic Route for Formula Ibd, Ibe and Ibf (Scheme 23)

Scheme 23

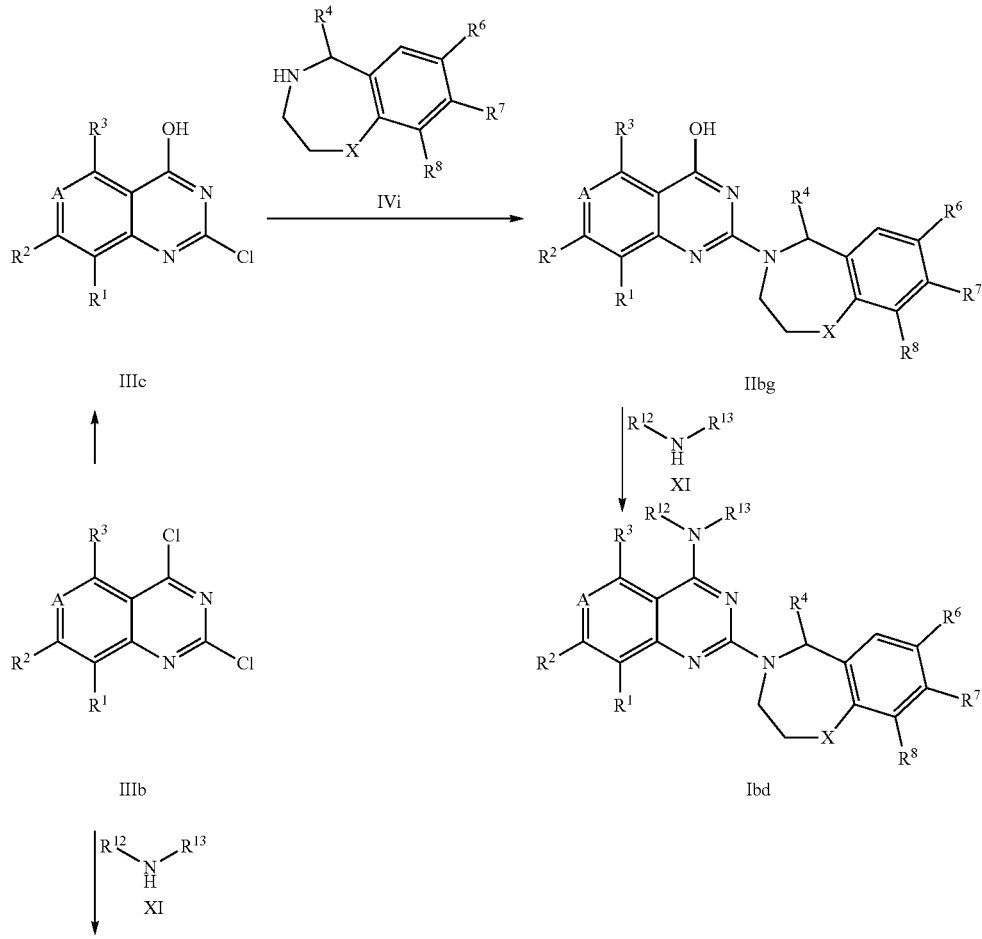

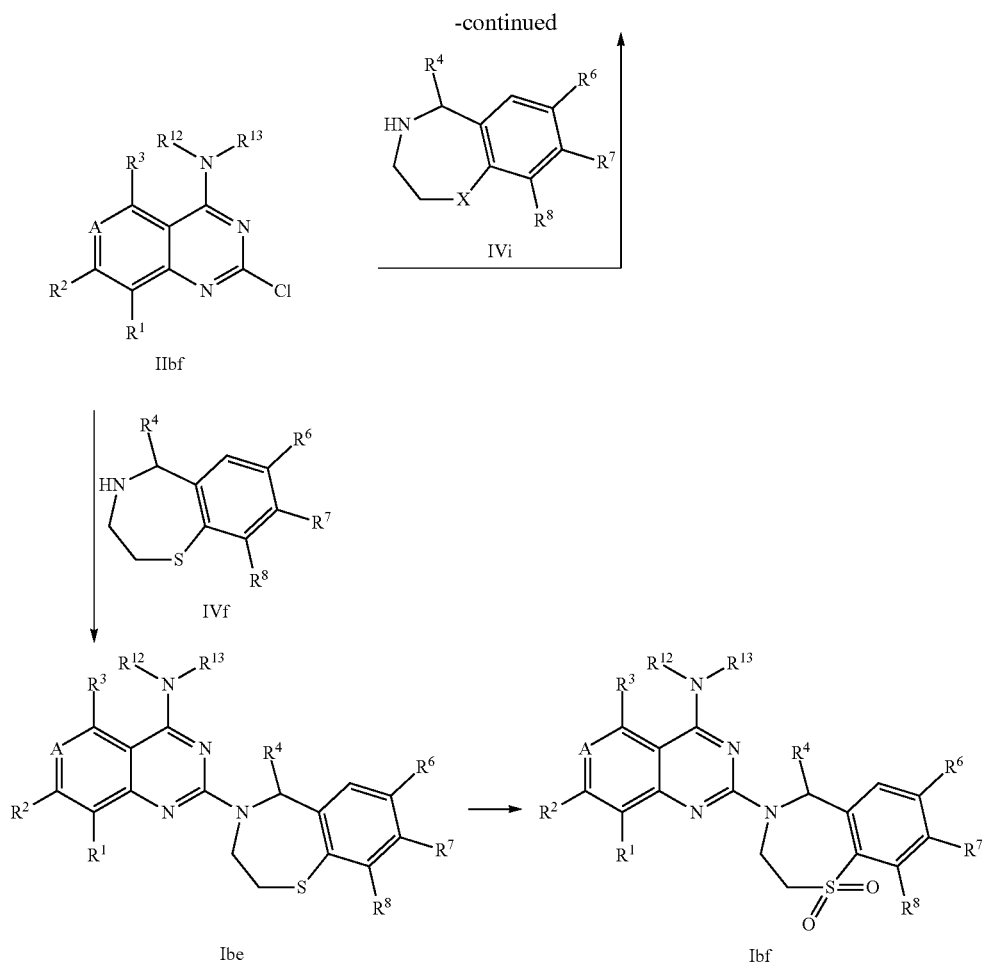

Compounds of interest Ibd, Ibe and Ibf can be prepared according to Scheme 23. Hydrolysis of 2,4-dichloro-quinozalines IIIb affords 2-chloro-4-hydroxy-quinozalines Inc. Coupling of 2,4-dichloro-quinozalines IIIb with various amines XI affords IIbf. Coupling of IIIc with benzoazapines IVi followed by coupling with various amines XI affords compounds of interest Ibd. Coupling of IIbf with benzoazapines IVi affords compounds of interest Ibd. Coupling of IIbf with benzothioazapines IVf affords compounds of interest Ibe. Oxidation of sulfides of Ibe affords compounds of interest Ibf.

2-Chloro-4-hydroxy-quinozalines IIIc can be prepared by hydrolysis of 2,4-dichloro-quinozalines IIIb. The reaction can be carried out in the presence of a suitable base such as sodium hydroxide in a suitable solvent such as tetrahydrofuran, water or mixtures thereof at room temperature for several hours.

4-Hydroxy quinozalines IIbg can be prepared by coupling of IIIc with benzoazapines IVi. The reaction can be carried out in the presence of a suitable base such as triethylamine in a suitable solvent such as toluene or N,N-dimethylformamide at a temperature between 110° C. and 160° C. under microwave irradiation for 30 minutes to 2 hours. Alternatively, the reaction can be carried out at an elevated temperature such as under reflux overnight without microwave irradiation.

2-Chloro-4-amino quinozalines IIbf can be prepared by coupling of IIIb with various amines XI. The reaction can be carried out in the presence of a suitable base such as triethylamine in a suitable solvent such as methanol, tetrahydrofuran, dichloromethane or mixtures thereof at a temperature between 0° C. to room temperature for several hours.

Compounds of interest Ibd can be prepared by coupling of IIbg with various amines XI. The reaction can be carried out in the presence of a suitable base such as 1,8-diazabicyclo[5.4.0]undec-7-ene with a suitable coupling reagents such as benzotriazol-1-yloxytris(dimethylamino)-phosphonium hexafluorophosphate, in a suitable solvent such as N,N-dimethylformamide at room temperature for several hours.

Alternatively, compounds of interest Ibd can be obtained by the coupling of IIbf with benzoazapines IVi. The reaction can be carried out with or without a base such as triethylamine, in a suitable solvent such as n-butanol or N,N-dimethylformamide at a temperature between 130° C. and 160° C. for 30 minutes to several hours under microwave irradiation. Alternatively, this reaction can be carried out with triethylamine in n-butanol in a sealed tube at a lower temperature for several hours, typically at 100° C. for 4 hours.

Compounds of interest Ibe can be prepared by coupling of IIbf with benzothioazapines IVf. The reaction can be carried out without any base or with a suitable base such as triethylamine in a suitable solvent such as n-butanol or N,N-dimethylformamide at a temperature between 130° C. and 160° C. for several hours under microwave irradiation.

Compounds of interest Ibf can be prepared by oxidation of Ibe. The reaction can be carried out with 3-chloroperoxybenzoic acid in dichloromethane or oxone in a mixture solvent such as methanol and tetrahydrofuran at a temperature between 0° C. and room temperature for several hours.

General Synthetic Route for Formula Ibj (Scheme 24)

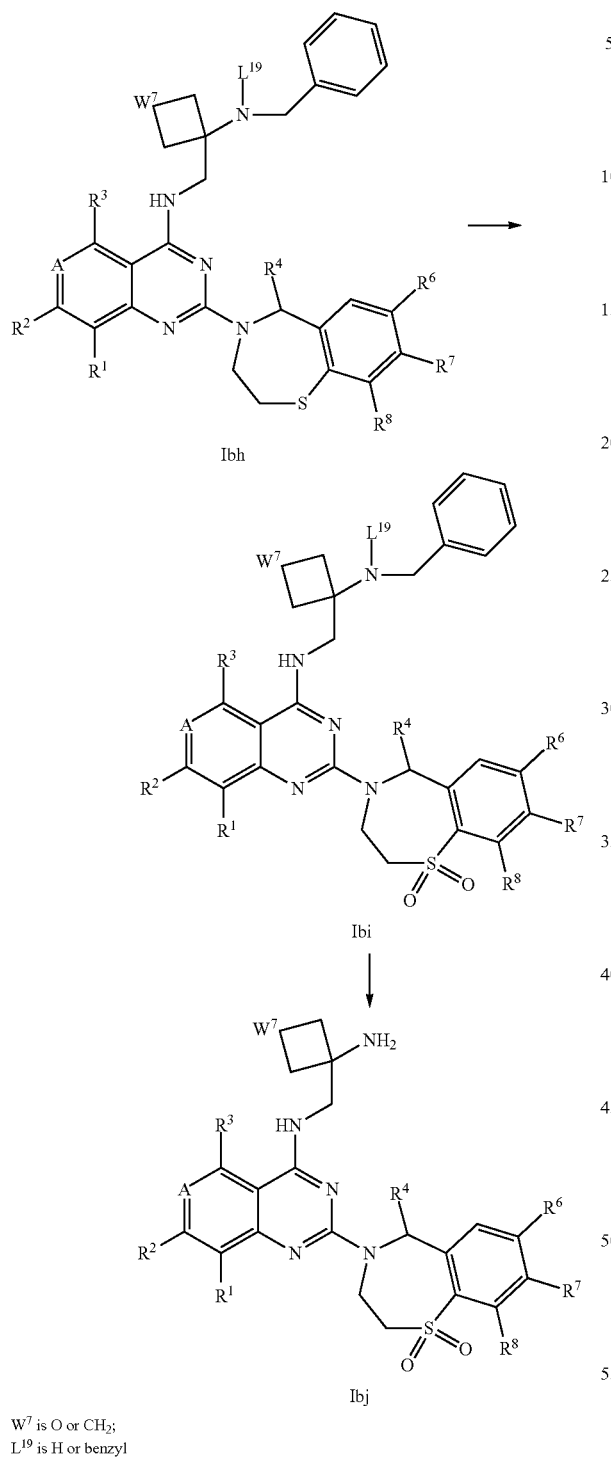

$W^7$ is O or $CH_2$;
$L^{19}$ is H or benzyl

Compounds of interest Ibj can be prepared according to Scheme 24. Starting with Ibh (prepared in analogue to Ibe in Scheme 23), oxidation with a suitable oxidant provides Ibi. Subsequent debenzylation generates amines Ibj.

Ibi can be prepared by oxidation of Ibh. The reaction can be carried out with a suitable oxidant such as 3-chloroperoxybenzoic acid, hydrogen peroxide, sodium periodate or potassium permanganate, in a suitable solvent such as dichloromethane, acetic acid, water or the mixture thereof, typically at 0° C., followed by stirring at room temperature for several hours.

Compounds Ibj can be prepared by standard debenzylation of Ibi. The reaction can be carried out with palladium on carbon, palladium hydroxide on carbon or platinum oxide, typically with an acid such as acetic acid or trifluoroacetic acid in a suitable solvent such as methanol, ethanol, tetrahydrofuran, ethyl acetate or the mixtures thereof, at room temperature under hydrogen atmosphere for several hours.

General Synthetic Route for Formula Ibl (Scheme 25)

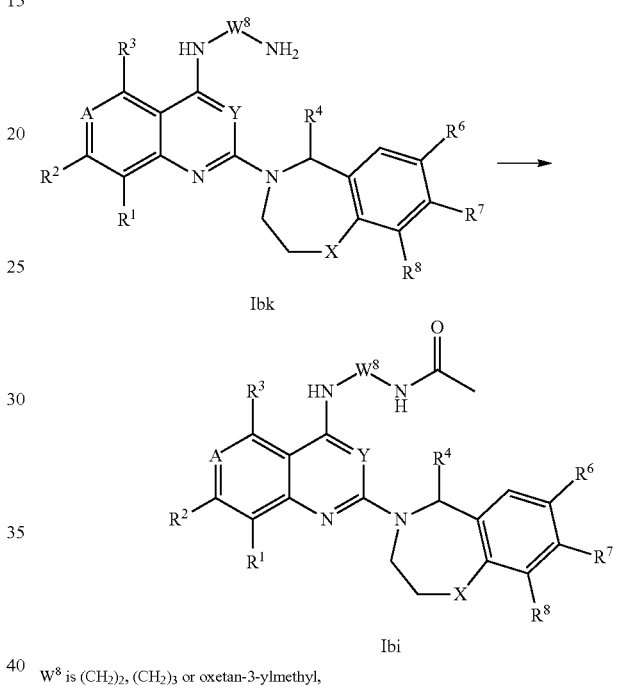

$W^8$ is $(CH_2)_2$, $(CH_2)_3$ or oxetan-3-ylmethyl,

Compounds of interest Ibl can be prepared according to Scheme 25. Starting with amines Ibk (prepared in analogue to Iac in Scheme 5 and Ibf in Scheme 23), acylation with acetic anhydride or acetyl chloride gives acetamides Ibl. The reaction can be carried out with a suitable base such as triethylamine or pyridine in a suitable inert organic solvent such as dichloromethane, tetrahydrofuran or pyridine at 0° C., followed by stirring at room temperature for several hours.

General Synthetic Route for Formula Ibm (Scheme 26)

Scheme 26

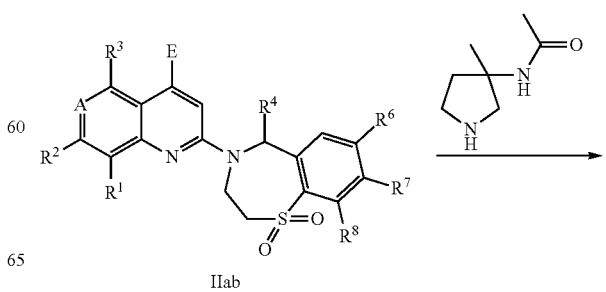

General Synthetic Route for Formula Ibo (Scheme 27)

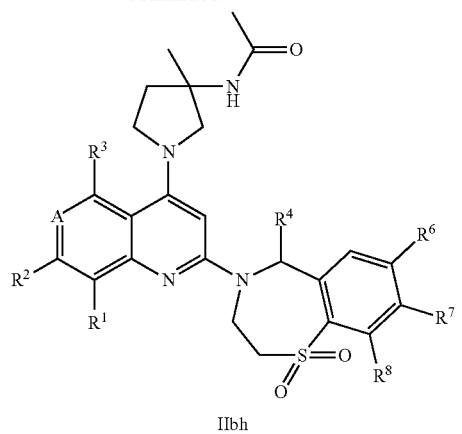

IIbh

↓

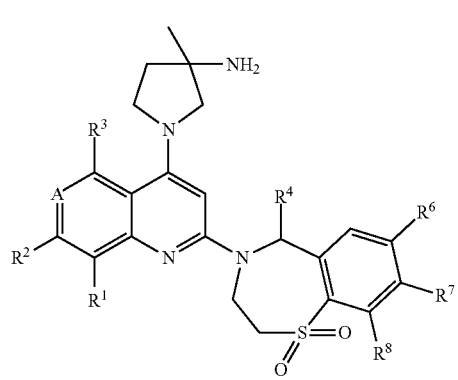

Ibm

E is Cl or Br

Compounds of interest Ibm can be prepared according to Scheme 26. Coupling of 4-halogen-quinolines IIab with N-(3-methyl-pyrrolidin-3-yl)-acetamide affords compounds IIbh. Deactylation of IIbh affords compounds of interest Ibm.

Compounds IIbh can be prepared by coupling of 4-halogen-quinolines IIab with N-(3-methyl-pyrrolidin-3-yl)-acetamide. The reaction can be carried out in the presence of a metal catalyst or in the absence of a metal catalyst in analogy to coupling of 4-halogen quinolines IIab with various amines XI in Scheme 5. Typically, the reaction can be carried out with 1,1'-bis(diphenylphosphino)ferrocene, 1,1'-bis(diphenylphosphino)ferrocenedichloropalladium(II), and sodium-tert-butoxide in 1,4-dioxane at 120° C. for 1.5 hours under microwave irradiation.

Compounds of interest Ibm can be prepared by deactylation of IIbh. The reaction can be carried out in 2 N hydrochloric acid at 100° C. for 16 hours.

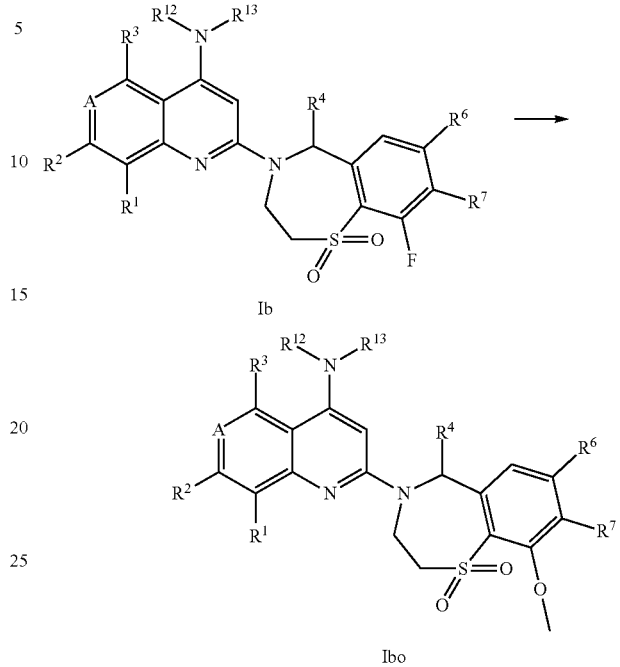

Compounds of interest Ibo can be prepared according to Scheme 27. Starting with fluorides Ibn, substitution of fluoro with methoxy group affords Ibo. The reaction can be carried out by heating of fluorides with sodium methoxide in methanol, typically at 100° C. for 20 minutes under microwave irradiation.

General Synthetic Route for Formula Ibq (Scheme 28)

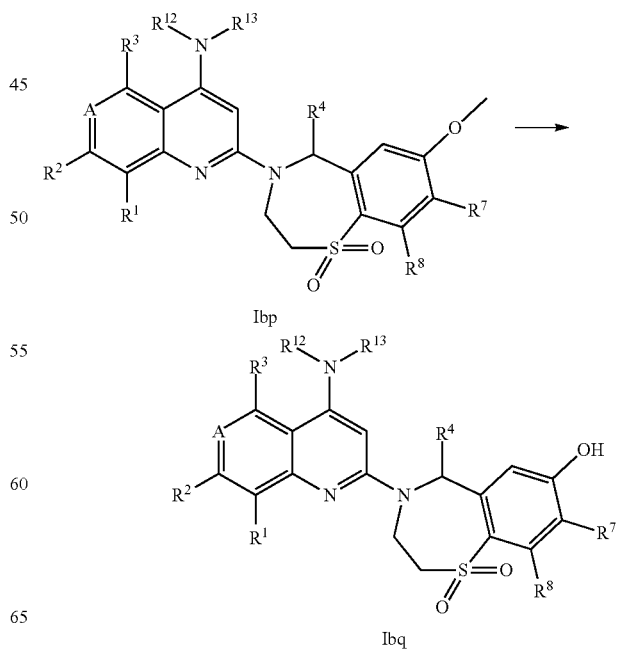

Compounds of interest Ibq can be prepared according to Scheme 28. Demethylation of methoxybenzenes Ibp affords phenols Ibq. The reaction can be carried out by heating of Ibp with potassium hydroxide in dimethylsulfoxide, typically at 100° C. for 20 minutes under microwave irradiation.

General Synthetic Route for Formula Ibr and Ibs (Scheme 29)

acids IIbj affords 1,3-diols Ibr. Coupling of 4-chloroquinolines IIbi with 2-methyl-allyllamine followed by dihydroxylation of alkenes IIbk affords 1,2-diols Ibs.

Acids IIbj can be obtained by coupling of 4-chloroquinolines IIbi with 4-amino-3-hydroxy-butyric acid. Alkenes IIbk can be obtained by coupling of 4-chloro quinolines IIbi with 2-methyl-allylamine. Coupling reaction can be carried out by

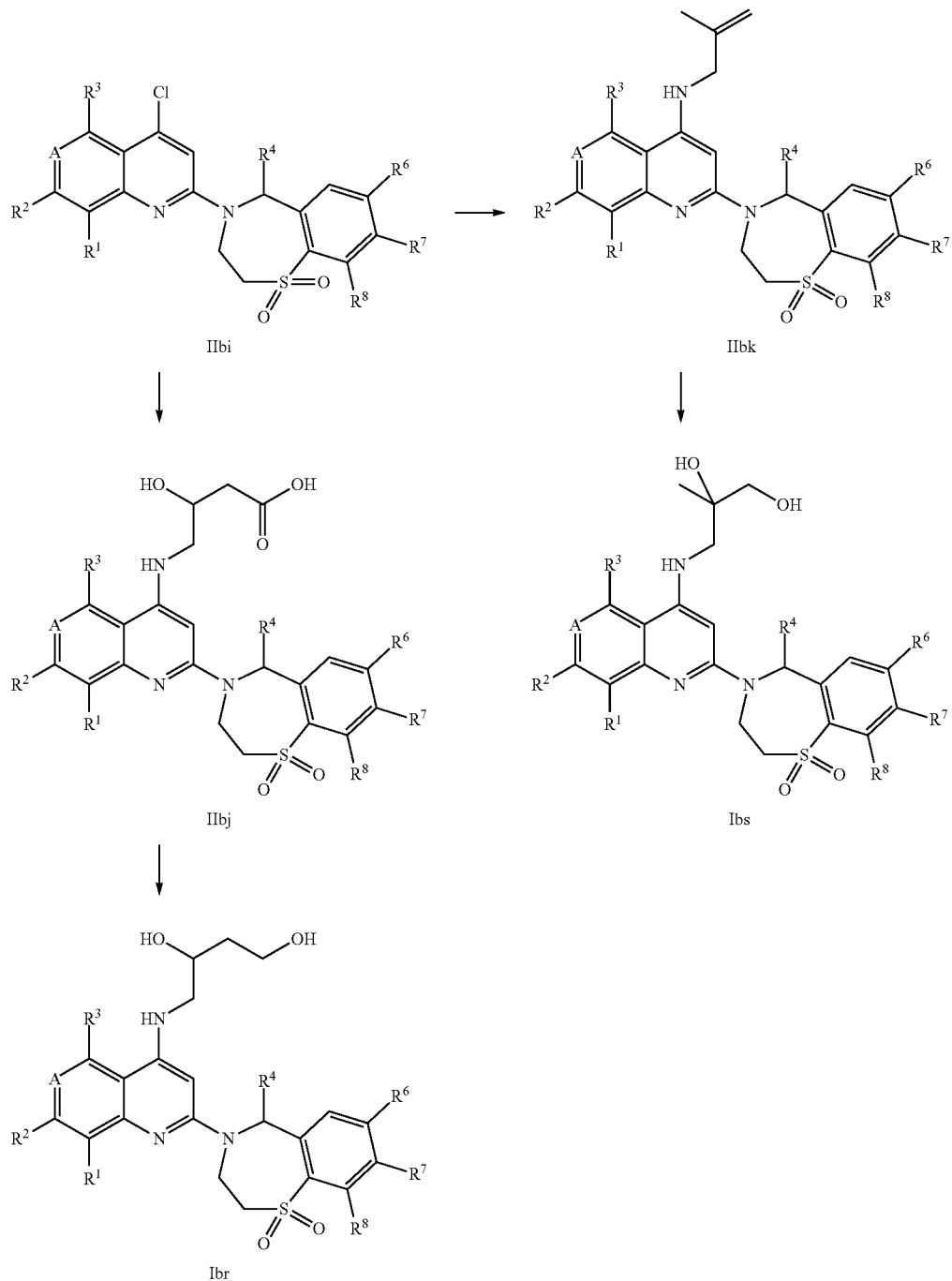

Compounds of interest Ibr and Ibs can be prepared according to Scheme 29. Coupling of 4-chloroquinolines IIbi with 4-amino-3-hydroxy-butyric acid followed by reduction of acids IIbj affords 1,3-diols Ibr. Coupling of 4-chloroquinolines IIbi with 2-methyl-allyllamine followed by dihydroxylation of alkenes IIbk affords 1,2-diols Ibs.

heating 4-chloroquinolines IIbi with amines in a suitable organic solvent such as 1-methyl-2-pyrrolidinone at an elevated temperature, typically at 160° C. for 16 hours.

1,3-Diols Ibr can be prepared by reduction of acids IIbj. The reaction can be carried out by treating acids with sodium borohydride in the presence of iodine in tetrahydrofuran, typically at 0° C., followed by stirring at room temperature for 16 hours.

1,2-Diols Ibs can be prepared by dihydroxylation of alkenes IIbk. The reaction can be accomplished by treating alkenes with 4-methylmorpholine N-oxide monohydrate and osmium tetroxide in acetone at room temperature for 1 hour.

General Synthetic Route for Formula Ibt (Scheme 30)

Scheme 30

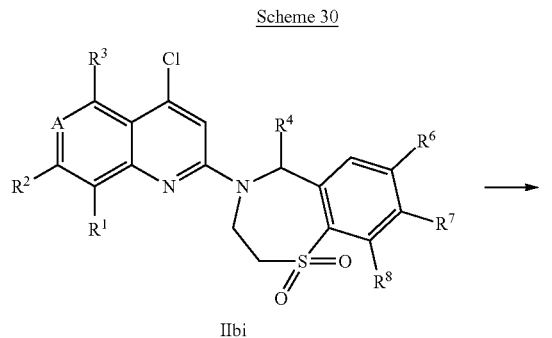

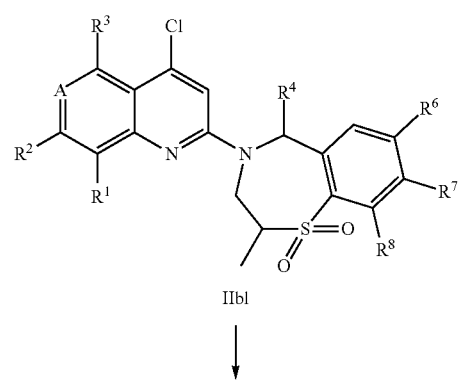

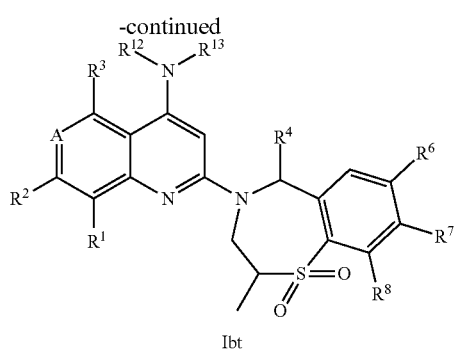

Ibt

Compounds of interest Ibt can be prepared according to Scheme 30. Starting with IIbi, alkylation with methyl iodide followed by coupling with various amines affords compounds of interest Ibt.

Compounds IIbl can be prepared by alkylation of IIbi with methyl iodide. Preferably, compounds can be obtained by deprotonation of α-H of sulfone followed by reaction with methyl iodide. Deprotonation of α-H of sulfone can be carried out by treating sulfone IIbi with n-butyl lithium in tetrahydrofuran at −78° C. under argon atmosphere for 1 hour. Reaction with methyl iodide can be accomplished by addition of methyl iodide to the above reaction mixture at −78° C., followed by stirring at room temperature overnight.

Compounds of interest Ibt can be prepared by coupling of IIbl with various amines. The reaction can be carried out in analogy to coupling of 4-halogen quinolines IIab with various amines XI in Scheme 5. The reaction preferably can be achieved by heating a mixture of IIbl and various amines with or without organic solvent such as N,N-dimethylformamide, 1-methylpyrrolidin-2-one or n-butyl alcohol, under microwave irradiation at 140-160° C. for 1-3 hours.

General Synthetic Route for Formula Ibu, Ibv and Ibw (Scheme 31)

Scheme 31

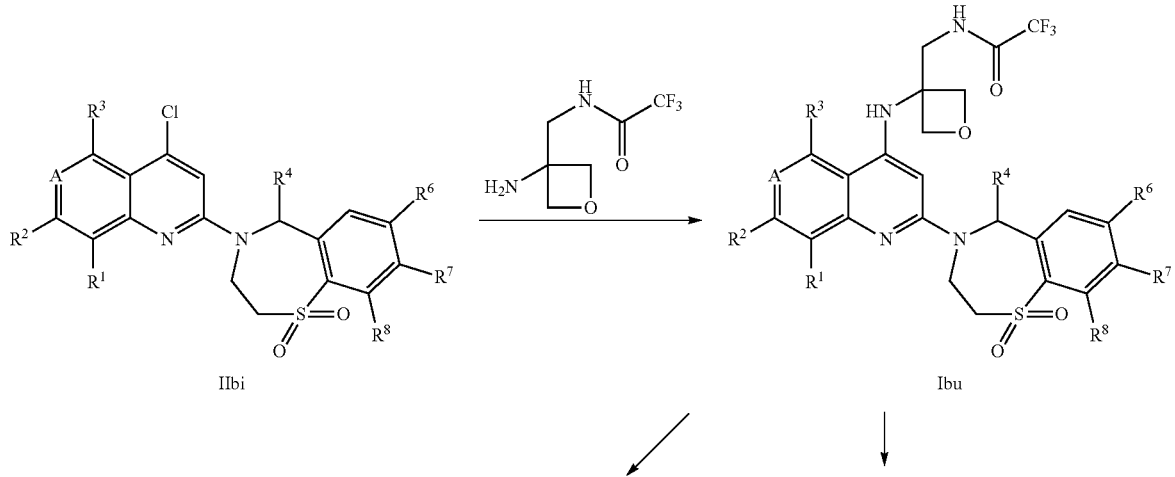

79

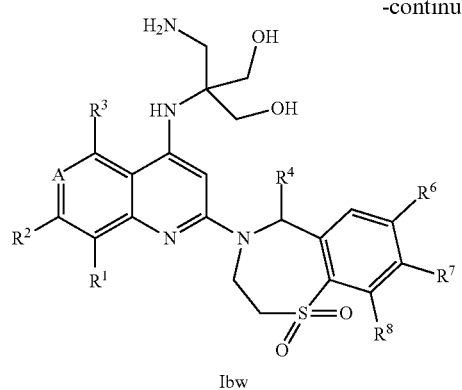

Ibw

80

-continued

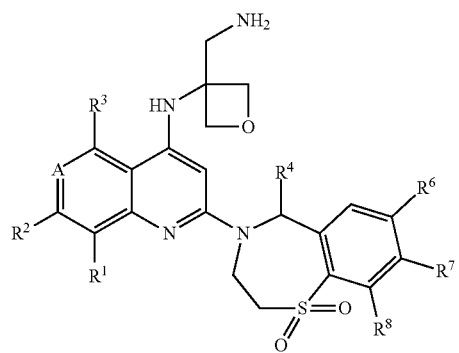

Ibv

Compounds of interest Ibu, Ibv and Ibw can be prepared according to Scheme 31. Coupling of 4-chloroquinolines IIbi with N-(3-amino-oxetan-3-ylmethyl)-2,2,2-trifluoro-acetamide affords Ibu. Standard trifluoroacetyl deprotection of Ibu generates compounds Ibv. Trifluoroacetyl deprotection and hydrolysis of Ibu affords Ibw.

Compounds Ibu can be prepared by coupling of 4-chloroquinolines IIbi with N-(3-amino-oxetan-3-ylmethyl)-trifluoro-acetamide. The reaction can be carried out in the presence of a palladium catalyst such as [1,1'-bis(diphenylphosphino)ferrocene]dichloropalladium(II), (triphenylphosphine)dichloropalladium(II), palladium(II) acetate, or tri(dibenzylideneacetone)dipalladium(0), in combination of a phosphine ligand such as bis(diphenylphosphino)ferrocene, tricyclohexylphosphine, or 9,9-dimethyl-4,5-bis(diphenylphosphino)xanthene, with a suitable base such as sodium tert-butoxide, in a suitable inert organic solvent such as 1,4-dioxane, or N,N-dimethylformamide, at 100-150° C. for 1-3 hours under microwave irradiation. Alternatively, the reactions can be carried out at an elevated temperature such as 100-140° C. for a longer reaction time without microwave irradiation.

Compounds Ibv can be prepared by standard trifluoroacetyl deprotection of Ibu. The reaction can be carried out with potassium carbonate, in a suitable solvent such as the mixture of methanol and water, at room temperature for several hours.

Compounds Ibw can be prepared by trifluoroacetyl deprotection and hydrolysis of Ibu. The reaction is typically carried out with ammonia solution in methanol for several hours at room temperature.

General Synthetic Route for Formula Ibx and Iby (Scheme 32)

Scheme 32

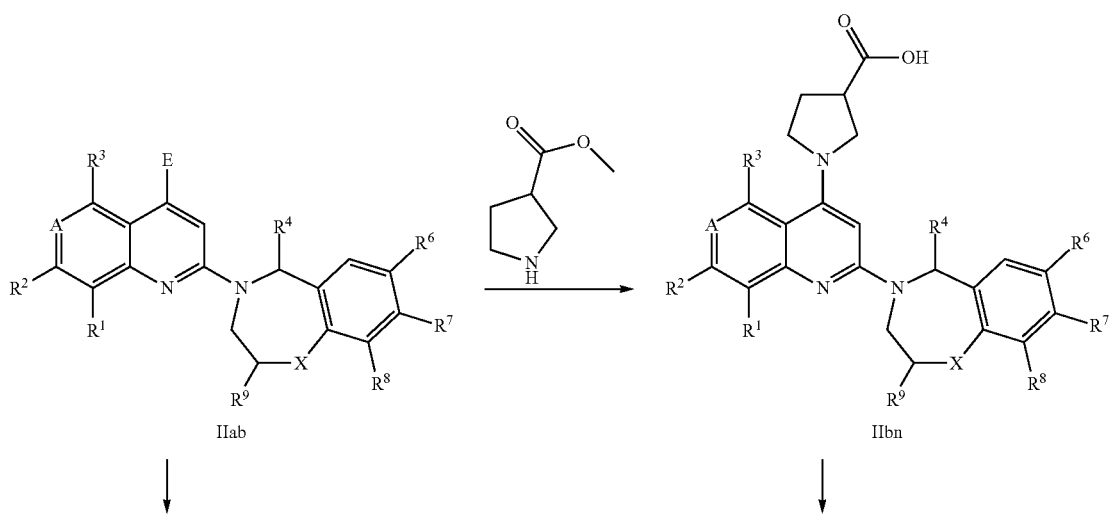

81                                                                          82
-continued

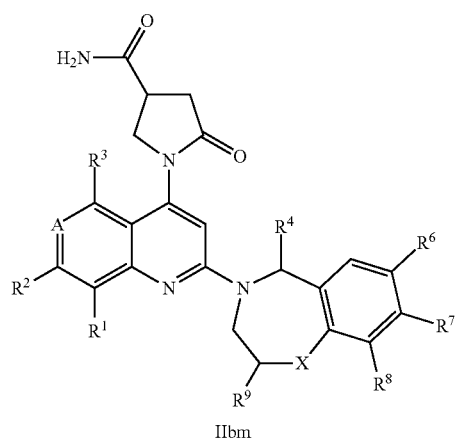
IIbm

IIbo

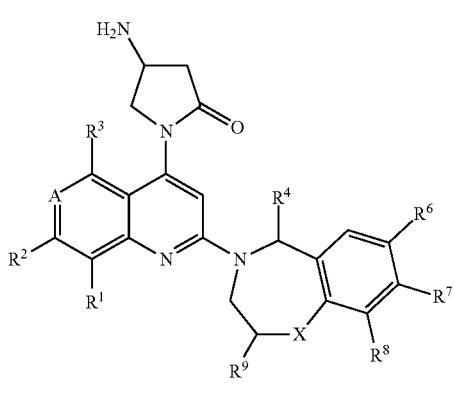
Ibx

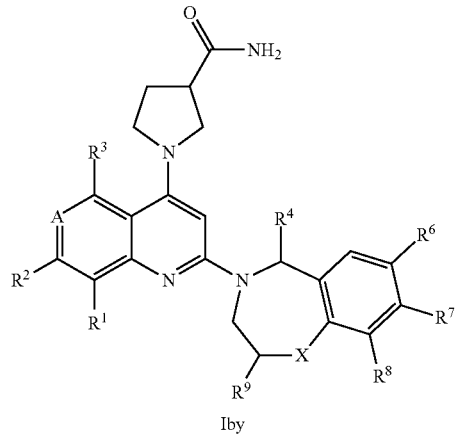
Iby

Compounds of interest Ibx and Iby can be prepared according to Scheme 32. Standard coupling of IIab with 5-oxo-pyrrolidine-3-carboxylic acid amide generates IIbm, followed by rearrangement of amides IIbm gives aminopyrrolidines Ibx. Coupling of halogens IIab with pyrrolidine-3-carboxylic acid methyl ester affords compounds IIbn. Conversion of IIbn to acylchlorides IIbo followed by treatment with ammonia affords compounds of interest Iby.

Amides IIbm can be prepared by copper-mediated coupling reaction of IIab with 5-oxo-pyrrolidine-3-carboxylic acid amide. The reaction can be carried out in the presence of a copper source such as copper(I) iodide and a ligand such as 2,2'-bipyridine, L-proline, N,N-dimethyl glycine, ethylene glycol or trans-N,N'-dimethylcyclohexane-1,2-diamine, with a suitable base such as triethylamine, sodium carbonate, potassium carbonate, cesium carbonate, sodium tert-butoxide, potassium tert-butoxide, sodium hydride or 1,8-diazabicyclo[5.4.0]undec-7-ene. The reaction can be carried out in a suitable organic solvent such as diethylene glycol dimethyl ether, toluene, 1,4-dioxane, N,N-dimethylformamide, dimethyl sulfoxide or 1-methyl-pyrrolidin-2-one at a temperature between 100° C. and 180° C. for several hours under microwave irradiation. Alternatively, the reactions can be carried out at a temperature such as 130° C. for a longer reaction time without microwave irradiation.

Aminopyrrolidines Ibx can be prepared by rearrangement of amides IIbm. The reaction can be typically carried out in the presence of (diacetoxyiodo)benzene in a mixture of acetonitrile and water for several hours at room temperature.

Acids IIbn can be prepared by coupling of halogens IIab with pyrrolidine-3-carboxylic acid methyl ester. The reaction can be carried out with a suitable base such as diisopropylethylamine without any solvent at 140° C. for 1.5 hours under microwave irradiation.

Acyl chlorides IIbo can be prepared by chlorination of IIbn. The reaction can be carried out with such as oxalyl dichloride in the presence of N,N-dimethylformamide, in a suitable solvent such as dichloromethane at 0° C. to room temperature for 16 hours.

Compounds of interest Iby can be prepared by reaction of IIbo with ammonia. The reaction can be carried out in suitable solvent such as dichloromethane at 0° C. to room temperature for 16 hours.

General Synthetic Route for Formula Ibz and Ica (Scheme 33)

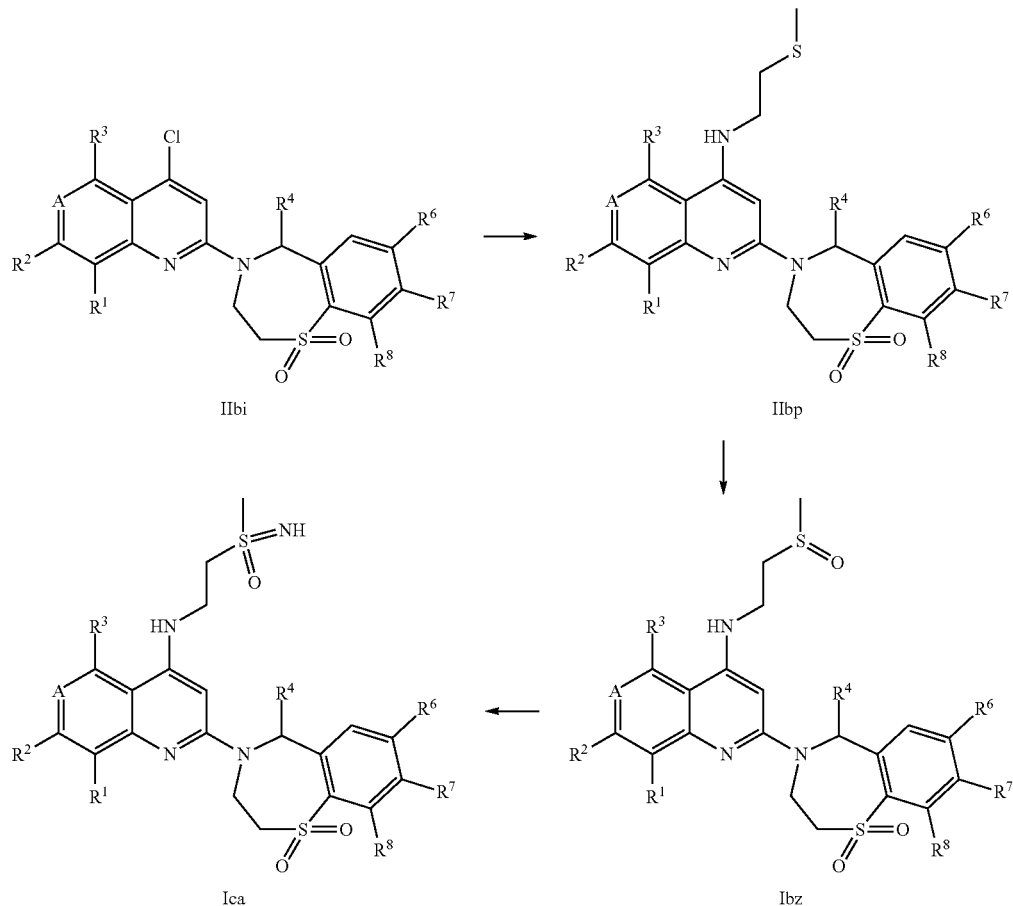

Compounds of interest Ibz and Ica can be prepared according to Scheme 33. Starting with IIbi, coupling with 2-methylsulfanyl-ethylamine gives sulfides IIbp. Selective oxidation of sulfides IIbi gives sulfoxides Ibz. Imination of sulfoxides, followed by hydrolyzation affords compounds of interest Ica.

Sulfides IIbp can be prepared from coupling of 2-benzoazapin-4-chloroquinolines IIbi with 2-methylsulfanyl-ethylamine. The reaction can be carried out in the presence of a palladium catalyst in analogy to coupling of 4-halogen quinolines IIab with various amines XI in Scheme 5. Typically the reaction can be carried out in the presence of tri(dibenzylideneacetone)dipalladium(0), 2-(dicyclohexylphosphino)-2'-(N,N-dimethylamino)biphenyl, and sodium-tert-butoxide in 1,4-dioxane under microwave irradiation at 100° C. for 1.5 hours.

Sulfoxides Ibz can be prepared by oxidation of sulfides IIbp. The reaction preferably can be carried out with a standard oxidant agent such as hydrogen peroxide in a suitable organic solvent such as acetic acid at room temperature for several hours.

Compounds of interest Ica can be prepared by metal-catalyzed imination of sulfoxides followed by hydrolysis. Imination of sulfoxides can be carried out by treating sulfoxides with rhodium (II) acetate and trifluoroacetamide or sulfonylamides in combination with iodobenzene diacetate and magnesium oxide in dichloromethane at room temperature overnight, preferably trifluoroacetamide was used. Hydrolysis can be carried out in the presence of a suitable base, such as potassium carbonate, sodium hydroxide or potassium hydroxide in methanol under reflux for 30 minutes to several hours.

General Synthetic Route for Formula Icc (Scheme 34)

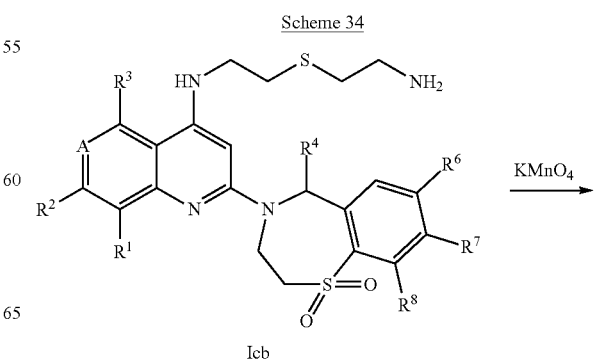

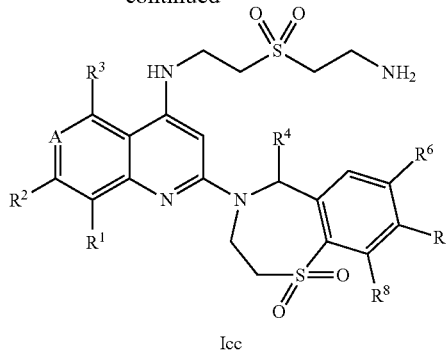

Icc

Compounds of interest Icc can be prepared according to Scheme 34. Starting with sulfides Icb (prepared in analogue to Iac in Scheme 5), oxidation of sulfides affords compounds of interest Icc.

Compounds of interest Icc can be prepared by oxidation of sulfides Icb. The reaction can be carried out in analogy to oxidation of quinolines IIac in Scheme 4. Typically the reaction can be carried out by treating sulfides with potassium permanganate in acetic acid at room temperature for 30 minutes to several hours.

General Synthetic Route for Formula Icd (Scheme 35)

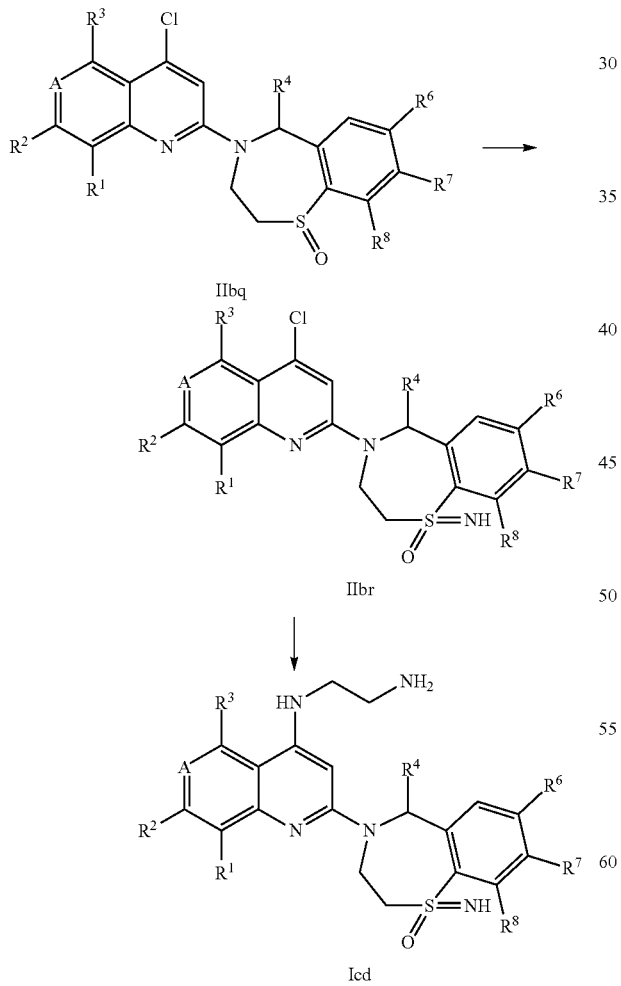

imination of sulfoxides followed by hydrolysis gives sulfoximines IIbr. Coupling of IIbr with various amines affords compounds of interest Icd.

Sulfoximines can be prepared from imination of sulfoxides IIbq followed by hydrolysis. Imination of sulfoxides can be carried out by treating sulfoxides with rhodium (II) acetate and trifluoroacetamide or sulfonylamides in combination with iodobenzene diacetate and magnesium oxide in dichloromethane at room temperature overnight, preferably trifluoroacetamide was used. Hydrolysis can be carried out in the presence of a suitable base, such as potassium carbonate, sodium hydroxide, potassium hydroxide or sodium methoxide in methanol under reflux for 30 minutes to several hours.

Compounds of interest Icd can be prepared by coupling of IIbr with 1,2-ethylenediamine. The reaction can be carried out in analogy to coupling of 4-halogen quinolines IIac with various amines XI in Scheme 5. Typically the reaction can be carried out with or without an organic solvent such as N,N-dimethylformamide, 1-methylpyrrolidin-2-one or n-butyl alcohol at a temperature between 140° C. and 160° C. under microwave irradiation for 1 to 3 hours.

General Synthetic Route for Formula Ice (Scheme 36)

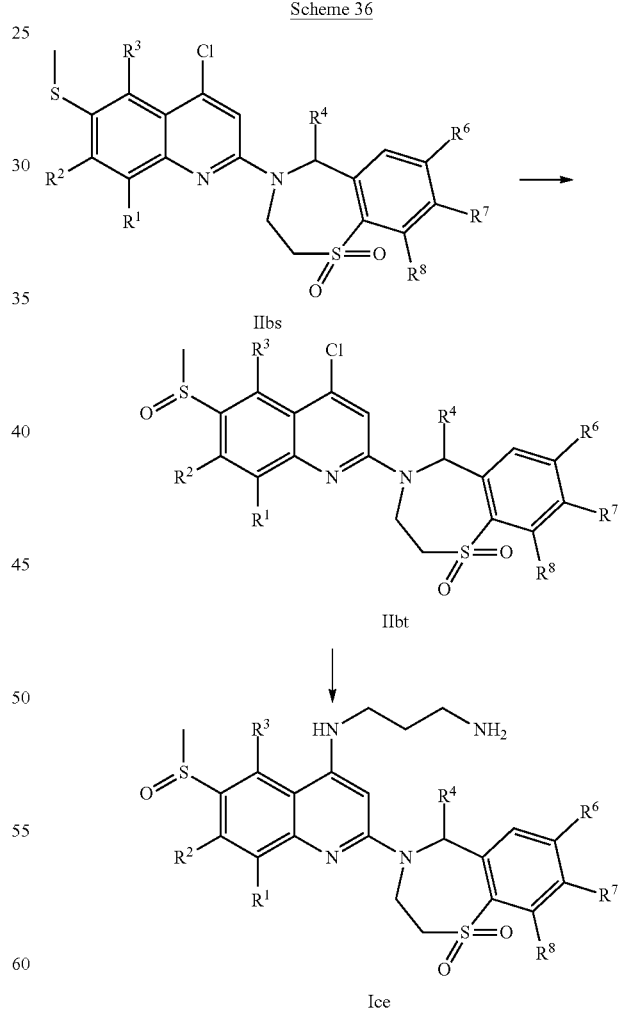

Compounds of interest Ice can be prepared according to Scheme 36. Oxidation of sulfides IIbs followed by coupling of IIbt with propane-1,3-diamine affords compounds of interest Ice.

Compounds of interest Icd can be prepared according to Scheme 35. Starting with sulfoxides IIbq, metal-catalyzed Sulfoxides IIbt can be prepared by oxidation of sulfides IIbs. The reaction can be carried out with a suitable oxidation reagent such as m-chloroperbenzoic acid in a suitable solvent such as dichloromethane at 0° C. for 20 minutes.

Compounds of interest Ice can be prepared by coupling of IIbt with propane-1,3-diamine. The reaction can be carried out in analogy to coupling of 4-halogen quinolines IIac with various amines XI in Scheme 5. Typically, the reaction can be carried out by treating a mixture of IIbt and propane-1,3-diamine without any base and without any solvent at 150° C. for 1 hour under microwave irradiation.

General Synthetic Route for Formula Icf and Icg (Scheme 37)

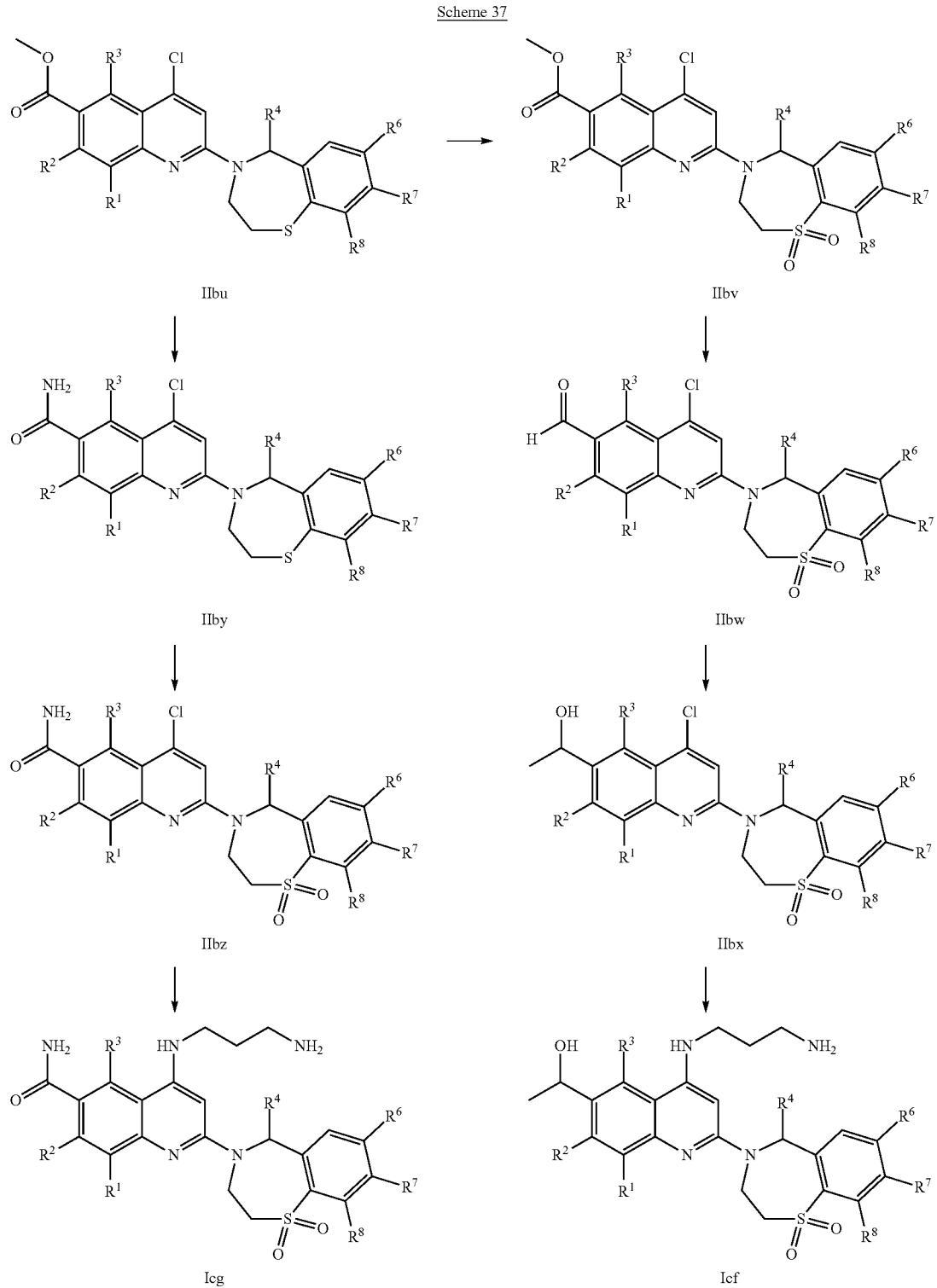

Compounds of interest Icg and Icf can be prepared according to Scheme 37. Amination of IIbu affords amides IIby. Oxidation of sulfides IIby affords sulfones IIbz. Coupling of IIbz with propane-1,3-diamine affords compounds of interest Icg. Oxidation of sulfides IIbu affords sulfones IIbv. Reduction of carboxylic acid esters IIbv followed by Swern-oxidation affords aldehydes IIbw. Methylation of IIbw followed by coupling with propane-1,3-diamine affords compounds of interest Icf.

Amides IIby can be prepared by amination of IIbu. The reaction can be carried out in a solution of ammonia in a suitable solvent such as methanol, tetrahydrofuran or mixture thereof in a sealed tube at a temperature between 100° C. and 150° C. for several hours, typically at 120° C. for 16 hours.

Sulfones IIbz can be prepared by oxidation of sulfides IIby. The reaction can be carried out in analogy to oxidation of quinolines IIac in Scheme 4. Typically, the reaction can be carried out with m-chloroperbenzoic acid in dichloromethane at 0° C. for 2 hours.

Compounds of interest Icg can be prepared by coupling of IIbz with propane-1,3-diamine. The reaction can be carried out in analogy to coupling of 4-halogen-quinolines IIac with various amines XI in Scheme 5. Typically, the reaction can be carried out by treating a mixture of IIbz and propane-1,3-diamine without any base and without any solvent at 120° C. for 1 hour under microwave irradiation.

Sulfones IIbv can be prepared by oxidation of sulfides IIbu. The reaction can be carried out in analogy to oxidation of quinolines IIac in Scheme 4. Typically, the reaction can be carried out with m-chloroperbenzoic acid in dichloromethane at 0° C. for 1 hour.

Aldehydes IIbw can be prepared by reduction of carboxylic acid esters IIbv followed by Swern oxidation. Reduction can be carried out with a standard reducing agent such as sodium boronhydride in a suitable solvent such as tetrahydrofuran, under reflux for several hours to several days, typically 60 hours. Swern oxidation can be carried out with oxalyl dichloride and dimethyl sulfoxide in the presence of triethylamine in a suitable solvent such as dichloromethane at −78° C., then at room temperature for 1 to several hours.

6-(1-Hydroxyethyl)quinolines IIbx can be prepared by methylation of IIbw. The reaction can be carried out with a methylation reagent such as methyl magnesium bromide in tetrahydrofuran at a temperature below 12° C. for 10 minutes to several hours.

Compounds of interest Icg can be prepared by coupling of IIbw with propane-1,3-diamine. The reaction can be carried out in analogy to coupling of 4-halogen quinolines IIac with various amines XI in Scheme 5. Typically, the reaction can be carried out without any metal catalyst and without any solvent at 150° C. for 1.5 hours under microwave irradiation.

General Synthetic Route for Formula Ich and Ici (Scheme 38)

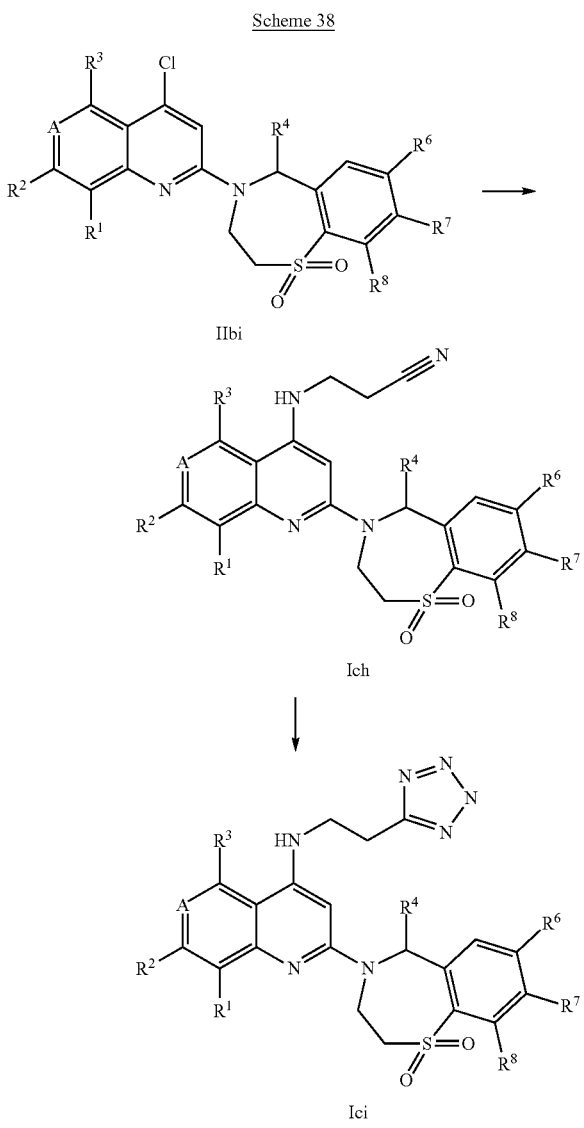

Compounds of interest Ici can be prepared according to Scheme 38. Standard coupling of IIbi with 3-amino-propionitrile generates Ich, cyclization of nitriles with sodium azide affords tetrazoles Ici.

Nitriles Ich can be prepared by coupling reaction of chlorides IIbi with 3-amino-propionitrile. The reaction can be carried out in analogy to coupling of 4-halogen quinolines IIac with various amines XI in Scheme 5. Typically, the reaction can be carried out by heating with tri(dibenzylideneacetone)dipalladium(0), 2,2'-bis(diphenylphosphino)-1,1'-binaphthyl, and sodium tert-butoxide in toluene at 110° C. overnight.

Tetrazoles Ici can be prepared by cyclization of nitriles Ich with sodium azide. The reaction can be typically carried out in the presence of sodium azide and ammonium chloride in N,N-dimethylformamide at a temperature between 60° C. and 100° C., typically at 80° C. for several hours.

General Synthetic Route for Formula Ick (Scheme 39)

Scheme 39

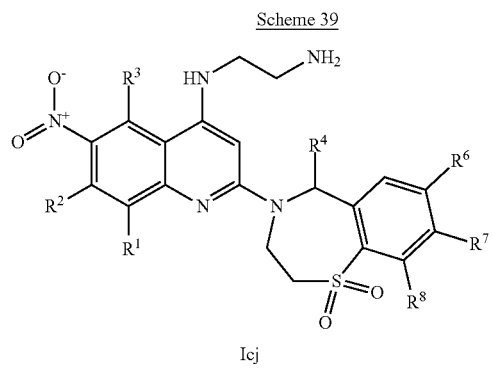

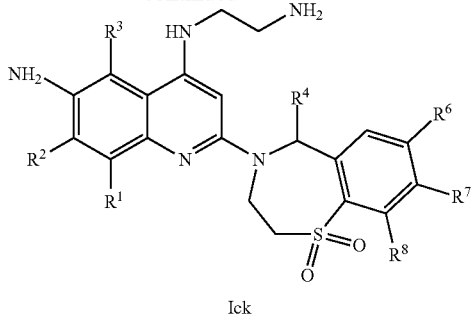

Ick

Compounds of formula Ick can be prepared according to Scheme 39. Reduction of 6-nitro quinolines Icj generates 6-amino-quinolines Ick. The reaction can be carried out with stannous chloride in methanol under reflux overnight.

General Synthetic Route for Formula Icl (Scheme 40)

Scheme 40

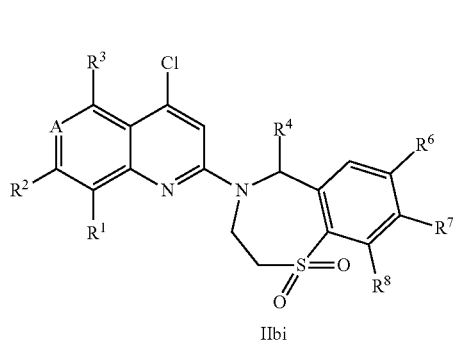

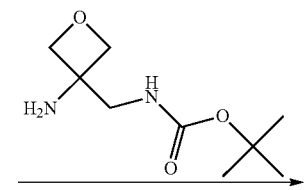

IIbi

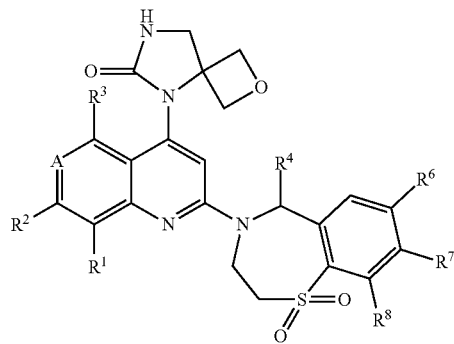

Icl

Compounds of interest Icl can be prepared according to Scheme 40. Starting with IIbi, coupling with (3-amino-oxetan-3-ylmethyl)-carbamic acid tert-butyl ester gives spiral compounds Icl. This reaction can be carried out in the presence of a palladium catalyst such as (triphenylphosphine) dichloropalladium(II), [1,1'-bis(diphenylphosphino)ferrocene]dichloropalladium(II), palladium(II) acetate, or tri(dibenzylideneacetone)dipalladium(0), with a phosphine ligand such as 2,2'-bis(diphenylphosphino)-1,1'-binaphthyl, bis(diphenylphosphino)ferrocene, tricyclohexylphosphine, or 9,9-dimethyl-4,5-bis(diphenylphosphino)xanthene, with a suitable base such as sodium tert-butoxide, in a suitable inert organic solvent such as toluene, dioxane, or N,N-dimethylformamide, at a temperature between 100° C. and 150° C. for 1 to 3 hours under microwave irradiation. Alternatively, the reactions can be carried out at a temperature such as 100° C. to 140° C. for a longer reaction time without microwave irradiation.

General Synthetic Route for Formula Icm (Scheme 41)

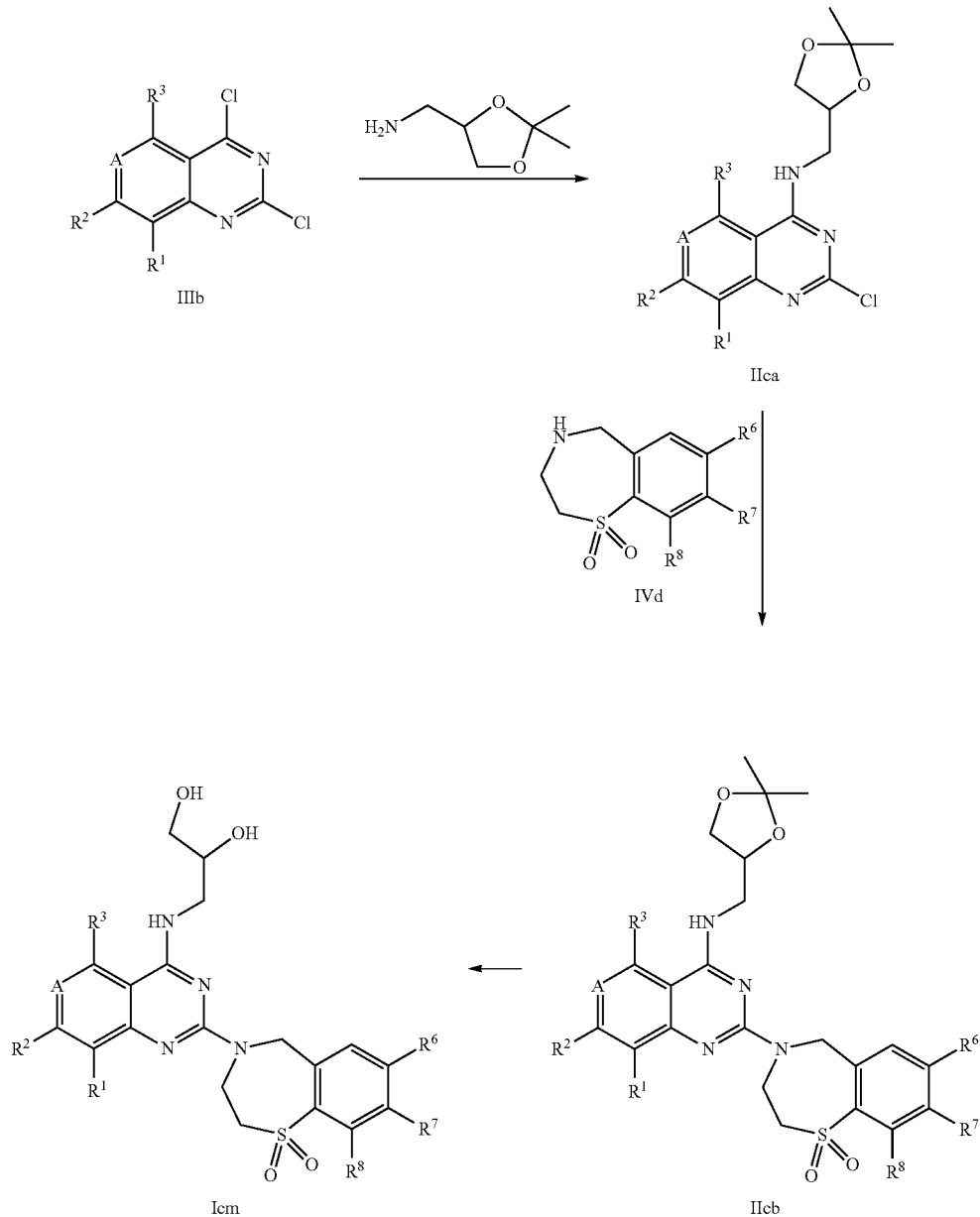

Compounds of interest Icm can be prepared according to Scheme 41. Coupling of 2,4-dichloroquinazolines IIIb with C-(2,2-dimethyl-[1,3]dioxolan-4-yl)-methylamine affords IIca. Reaction of 2-chloro-4-aminoquinazolines IIca with 6,7,8,9-tetrahydro-5-thia-8-aza-benzocycloheptene 5,5-dioxides IVd followed by deprotection affords 4-(2,3-diol-propylamino)-quinolines Iak.

IIca can be obtained by coupling of 2,4-dichloroquinazolines IIIb with C-(2,2-dimethyl-[1,3]dioxolan-4-yl)-methylamine. The reaction can be carried out with a base such as triethylamine in a suitable solvent such as methanol or dichloromethane at room temperature for several hours.

Intermediates IIcb can be prepared by coupling of 2-chloro-4-amino quinazolines IIca with 6,7,8,9-tetrahydro-5-thia-8-aza-benzocycloheptene 5,5-dioxides IVd. The reaction can be carried out in the presence of a base such as triethylamine in N,N-dimethylformamide at a temperature between 120° C. and 180° C., typically at 160° C. for several hours.

4-(2,3-Diol-propylamino)-quinazolines Icm can be prepared by deprotection of IIcb. The reaction can be carried out in the presence of an acid such as hydrochloric acid in a suitable solvent such as methanol, ethanol, water or mixtures thereof at room temperature for several hours.

General Synthetic Route for Formula Icn (Scheme 42)

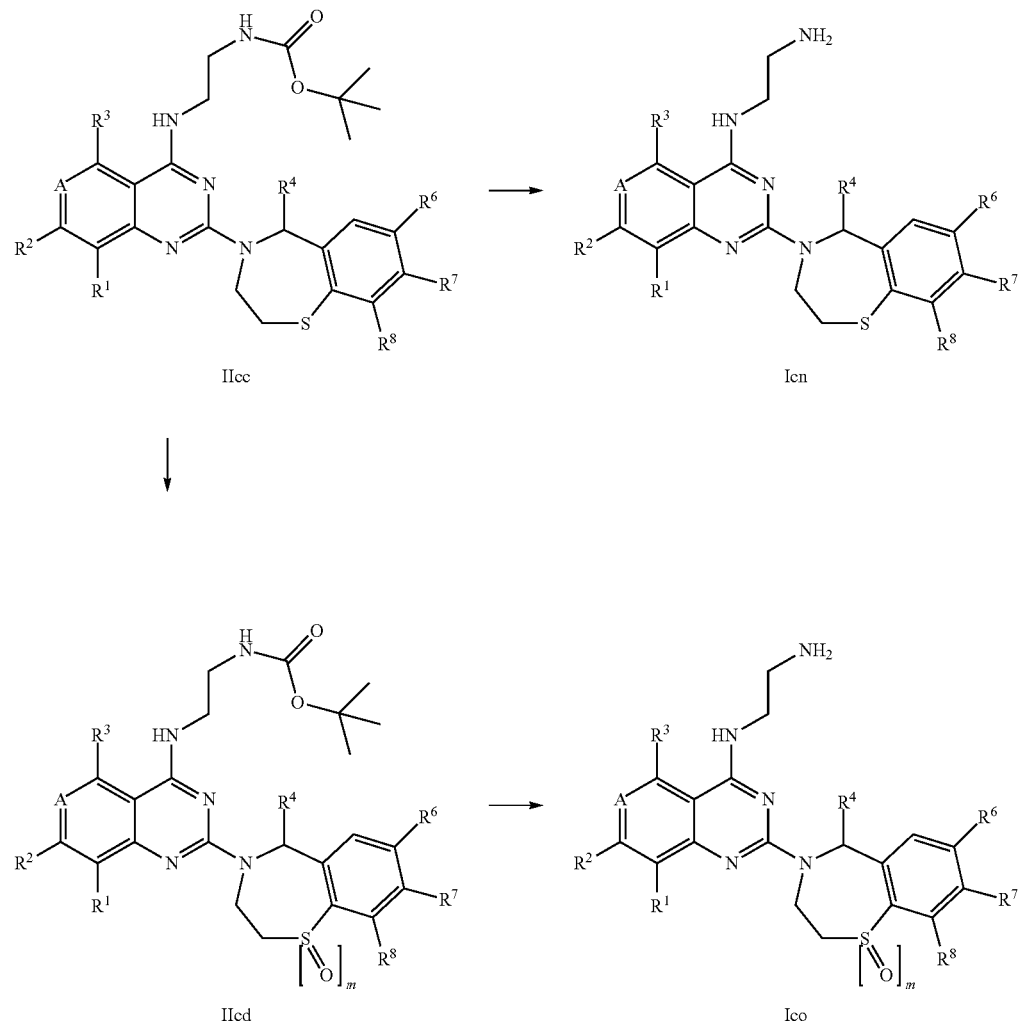

m is 1 or 2

Compounds of interest Icn and Ico can be prepared according to Scheme 42. Starting with IIcc, cleavage of tert-butoxycarbonyl gives compounds of interest Icn. Oxidation of sulfides IIcc generates oxides IIcd, followed by cleavage of tert-butoxycarbonyl generates compounds of interest Ico.

IIcd can be prepared by oxidation of thio group of compounds IIcc. The reaction can be carried out with a suitable oxidant such as oxone, meta-chloroperoxybenzoic acid, hydrogen peroxide, sodium periodate or potassium permanganate, in a suitable solvent such as methanol, dichloromethane, acetic acid, water or the mixtures thereof, typically at 0° C., followed by stirring at room temperature for several hours.

Amines Icn and Ico can be prepared by cleavage of tert-butoxycarbonyl of IIcc and IIcd respectively. The reaction can be typically carried out with trifluoroacetic acid in dichloromethane, or hydrogen chloride in methanol for several hours at room temperature.

General Synthetic Route for Formula Icp (Scheme 43)

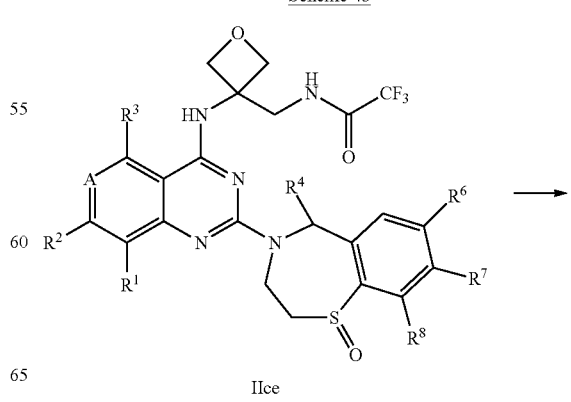

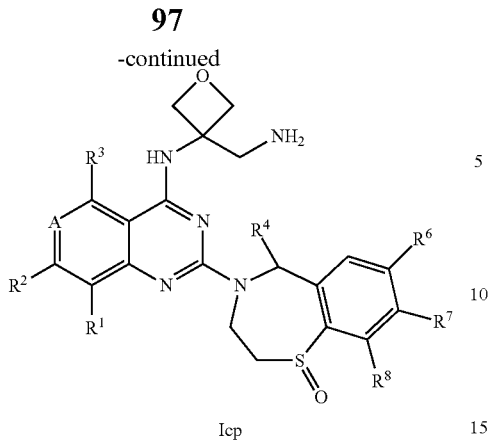

Icp

Compounds of interest Icp can be prepared according to Scheme 43. Starting with IIce, removal of trifluoroacetyl generates amines Icp. The reaction can be carried out with potassium carbonate or sodium hydroxide, in a suitable solvent such as the mixture of ethanol and water, at room temperature for several hours.

General Synthetic Route for Formula Icq and Icr (Scheme 44)

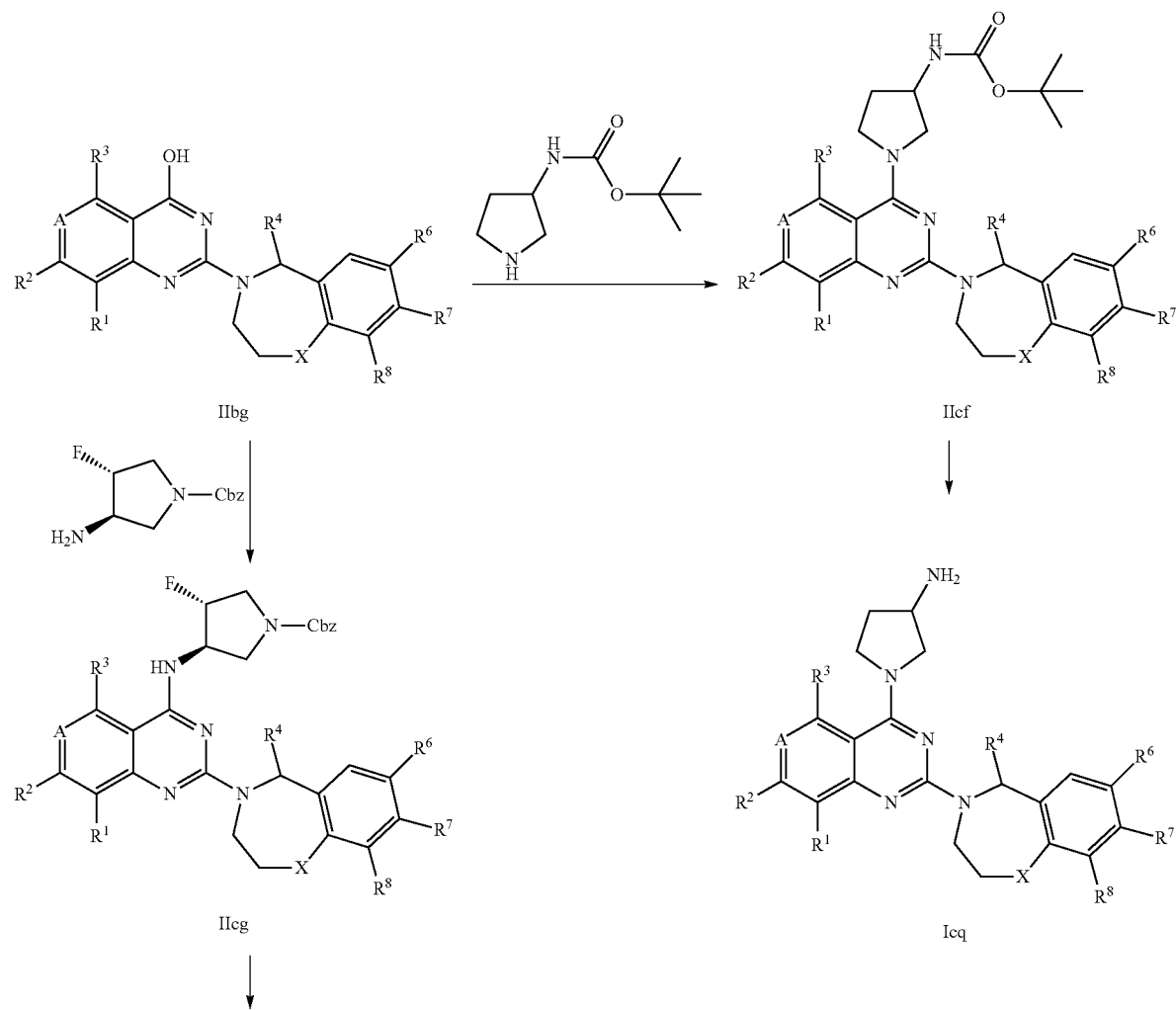

-continued

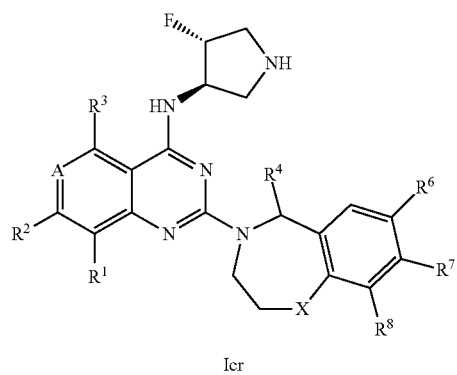

Icr

Compounds of interest Icq and Icr can be prepared according to Scheme 44. Starting with quinazolinones IIbg, coupling reaction with amine gives IIcf, followed by cleavage of tert-butoxycarbonyl of IIcf affords compounds of interest Icq. Starting with quinazolinones IIbg, coupling reaction with amine gives IIcg, followed by cleavage of benzoxycarbonyl of IIcg affords compounds of interest Icr.

IIcf and IIcg can be prepared from coupling reaction of IIbg with 3-(tert-butoxycarbonyl-amino)pyrrolidine and trans-3-amino-4-fluoro-pyrrolidine-1-carboxylic acid benzyl ester separately. The reaction can be carried out in the presence of benzotriazol-1-yloxytris(dimethylamino)phosphonium hexafluorophosphate, with a suitable base such as 1,8-diazabicyclo[5.4.0]undec-7-ene, or triethyl amine, in a solvent such as N,N-dimethylformamide or acetonitrile at room temperature overnight.

Compounds of interest Icq can be prepared by standard cleavage of tert-butoxycarbonyl of IIcf. The reaction can be carried out by treating tert-butyl carbamates IIcf with a suitable acid such as hydrochloric acid, trifluoroacetic acid, or sulfuric acid in a suitable solvent such as methanol, ethyl acetate, dichloromethane, 1,4-dioxane, water or the mixtures thereof at a temperature between 0° C. and room temperature for 30 minutes to several hours. Typically the reaction can be carried out by treating tert-butyl carbamates IIaf with trifluoroacetic acid in dichloromethane at room temperature for 6 hours.

Compounds of interest Icr can be prepared by cleavage of benzyl carbomates IIcg. The conversion can be achieved by hydrogenolysis or under strong acidic conditions. Hydrogenolysis of IIcg can be carried out in the presence of palladium on carbon or palladium black, under hydrogen atmosphere or with a hydrogen donor such as formic acid or ammonium formate, in a suitable solvent such as methanol or ethanol, at a temperature between room temperature and 80° C. for 15 minutes to several hours. Alternatively the conversion can also be achieved by treating IIcg under strong acidic conditions such as reflux in 6 N hydrochloride in methanol for several hours.

General Synthetic Route for Formula Ics (Scheme 45)

Scheme 45

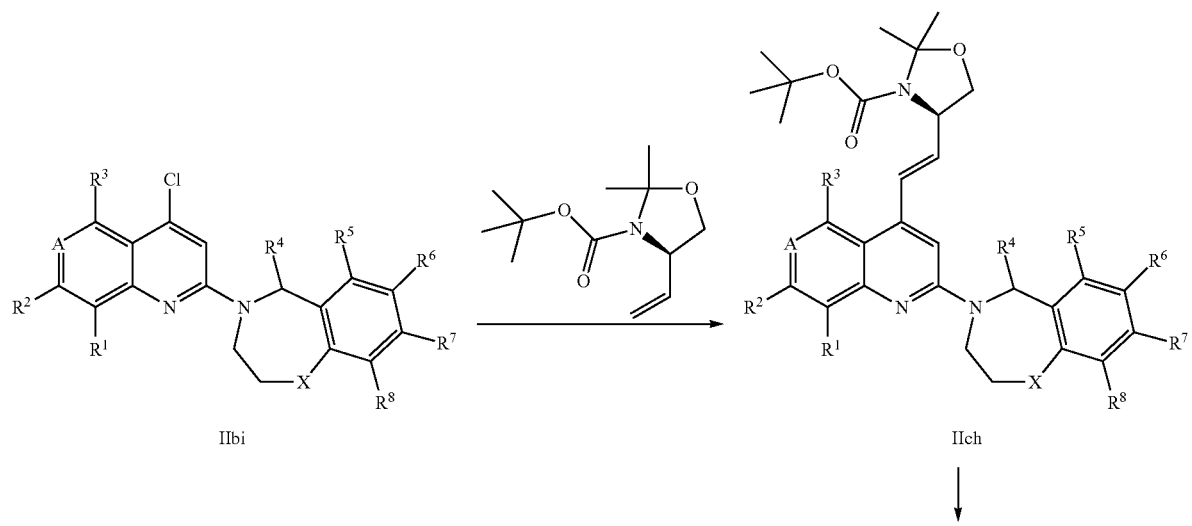

-continued

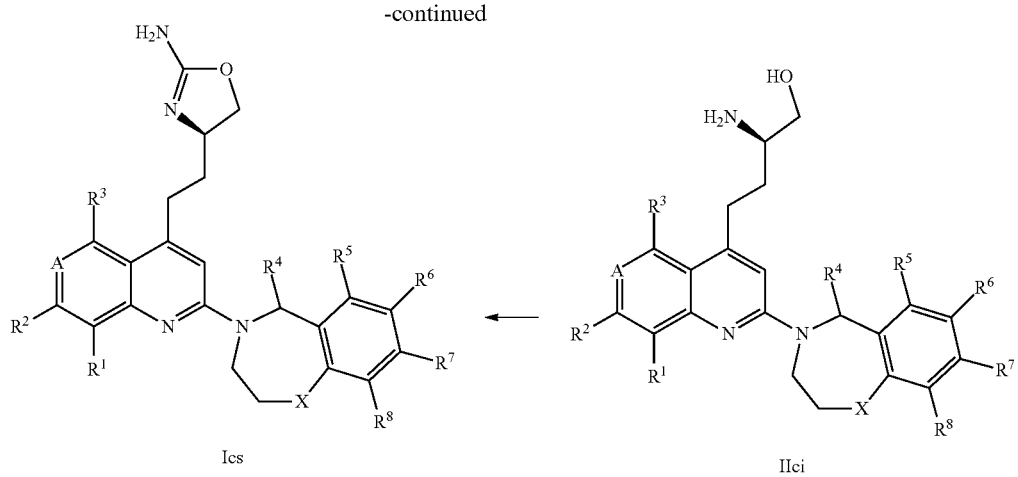

Ics    IIci

Compounds of interest Ics can be prepared according to Scheme 45. Starting with 4-chloro-quinolines IIbi, coupling with (R)-2,2-dimethyl-4-vinyl-oxazolidine-3-carboxylic acid tert-butyl ester gives vinyl quinolines IIch. Subsequent reduction and deprotection of tert-butyloxycarbonyl and acetal of IIch generates amino alcohols IIci, which are then cyclized to compounds of interest Ics.

Vinyl quinolines IIch can be prepared by coupling of 4-chloro-quinolines IIbi with (R)-2,2-dimethyl-4-vinyl-oxazolidine-3-carboxylic acid tert-butyl ester. The reaction can be typically conducted in deoxygenated N,N-dimethylformamide with triethylamine, bis(tri-tert-butylphosphine)palladium(0), at a temperature between 100° C. and 160° C. for several hours under microwave irradiation. Alternatively, the reactions can be carried out at an elevated temperature such as between 100 and 140° C. for a longer reaction time without microwave irradiation.

Amino alcohols IIci can be prepared from vinyl quinolines IIch by hydrogenolysis and deprotection of tert-butyloxycarbonyl and acetal. The hydrogenolysis can be carried out in the presence of 10% palladium on carbon under an atmospheric pressure of hydrogen, in an organic solvent such as ethyl acetate, methanol, or ethanol, typically at room temperature for several hours. Deprotection of acetonides is typically carried out in a solution of hydrochloric acid in ethyl acetate for several hours at room temperature.

Compounds Ics can be prepared from amino alcohols IIci by ring closure with cyanogen bromide. The reaction can be carried out with a suitable base such as sodium acetate, sodium carbonate, potassium acetate or potassium carbonate, in a suitable solvent such as methanol, water, or the mixtures thereof, typically at 0° C., followed by stirring at room temperature for several hours.

General Synthetic Route for Formula Ict, Icu and Icv (Scheme 46)

Scheme 46

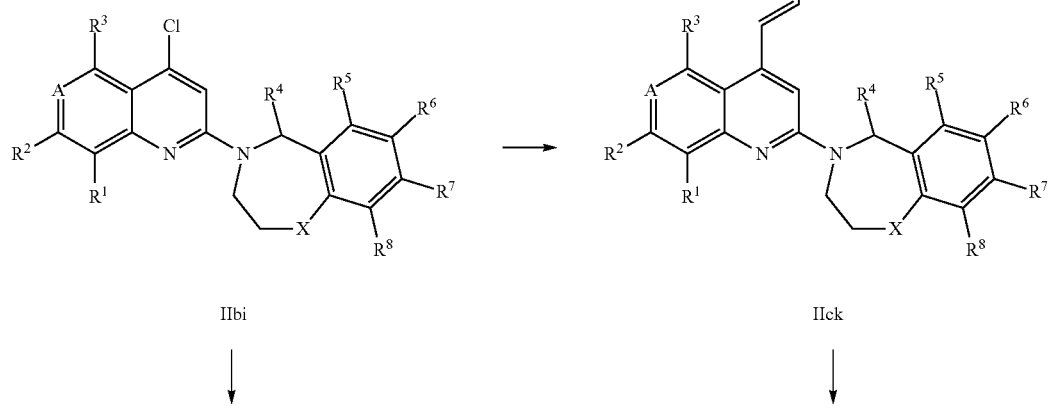

IIbi    IIck

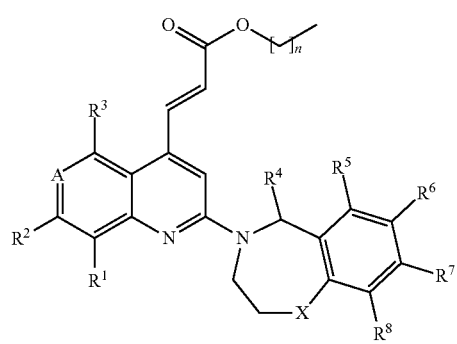

IIcj

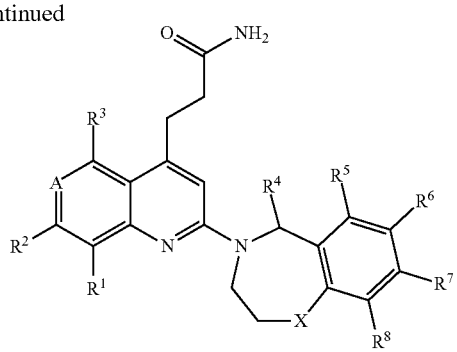

Icu

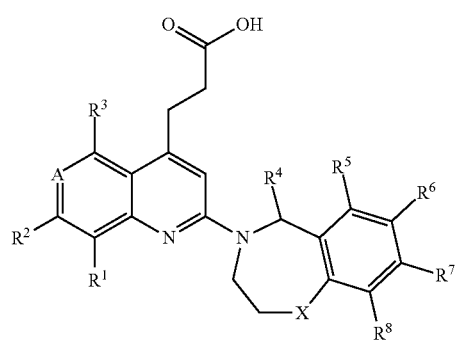

Ict

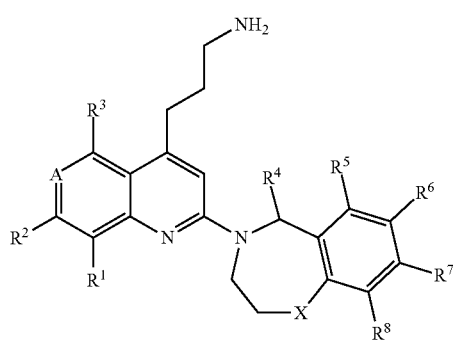

Icv n is 0 or 1

Compounds of interest Ict, Icu and Icv can be prepared according to Scheme 46. Starting with 4-chloro quinolines IIbi, coupling with ethyl acrylate gives alkenes IIcj. Reduction of alkenes IIcj followed by hydrolysis of esters affords compounds of interest Ict. Heck reaction coupling with acrylonitrile gives alkenes IIck. Hydrogenation of alkenes followed by hydrolysis of nitriles affords amides Icu. Alternatively, amides Icu can be formed by aminolysis of esters IIcj. Reduction of amides Icu affords compounds of interest Icv.

Alkenes IIcj and IIck can be prepared by Heck coupling of 4-chloro-quinolines IIbi with ethyl acrylate and acrylonitrile separately. The reaction can be typically conducted in the presence of bis(tri-tert-butylphosphine)palladium(0) with triethylamine in deoxygenated N,N-dimethylformamide, at a temperature between 100° C. and 160° C. for 30 minutes to several hours under microwave irradiation. Alternatively, the reactions can be carried out at an elevated temperature such as between 100° C. and 140° C. for a longer reaction time without microwave irradiation.

Compounds of interest Ict can be prepared by reduction of alkenes IIcj followed by hydrolysis. Reduction can be achieved by treating alkenes IIcj with 2-nitrobenzenesulfonylhydrazide in the presence of triethylamine in dichloromethane at room temperature for several hours. Hydrolysis can be carried out with a suitable base, such as lithium hydroxide, or sodium hydroxide in a mixture of water and organic solvent, such as tetrahydrofuran or methanol at room temperature for several hours.

Amides Icu can be prepared by hydrogenation of alkenes IIck followed by hydrolysis of nitriles. Hydrogenation reaction can be carried out in the presence of palladium on carbon under hydrogen atmosphere in methanol at room temperature for several hours. Hydrolysis can be achieved by treating nitriles with a base such as potassium hydroxide in tert-butanol under reflux for several hours.

Alternatively, amides Icu can be prepared by aminolysis of esters IIcj. The reaction can be typically conducted in an ammonia solution in tetrahydrofuran at a temperature between 25° C. to 70° C. for several hours.

Amines Icv can be prepared by reduction of amides Icu. The reaction can be achieved by treating amides Icu with borane in tetrahydrofuran at an elevated temperature such as 65° C. for several hours.

General Synthetic Route for Formula Icw and Icx (Scheme 47)

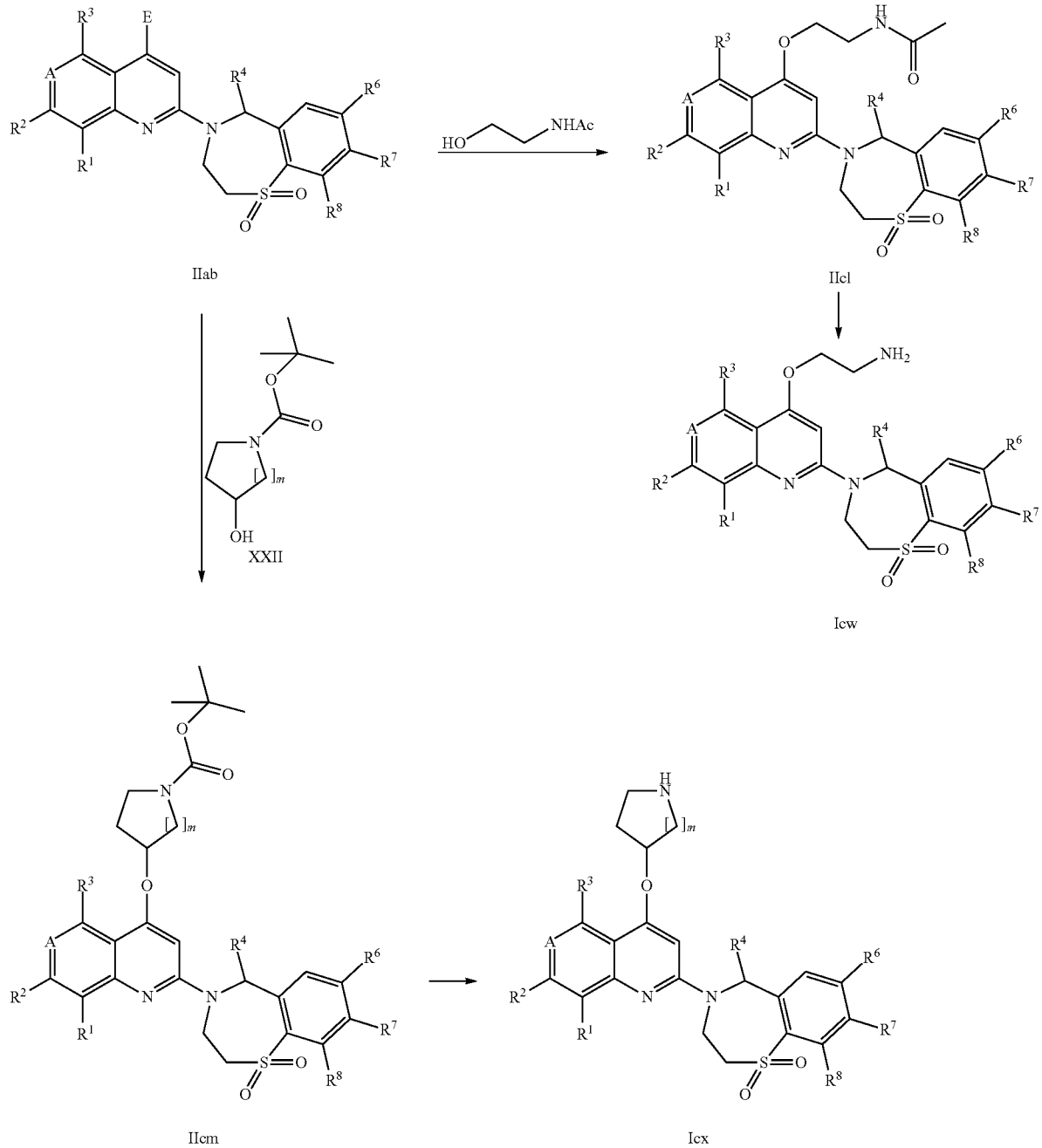

E is Br or cl,
m is 1 or 2

Compounds of interest Icw and Icx can be prepared according to Scheme 47. Coupling of 4-halogen quinolines IIab with N-(2-hydroxyethyl)acetamide followed by deacylation of IIcl affords compounds of interest Icw. Coupling of IIab with protected alcohol XXII followed by cleavage of tert-butyloxycarbonyl affords compounds of interest Icx.

Ethers IIcl and IIcm can be prepared by coupling of 4-halogen quinolines IIab with N-(2-hydroxyethyl)acetamide and XXII separately. The reaction can be carried out with a palladium catalyst such as 1,1'-bis(diphenylphosphino)ferrocene-palladium(II)dichloride in combination with 1,1'-bis(diphenylphosphino)ferrocene and sodium tert-butoxide in a suitable organic solvent such as 1,4-dioxane in a sealed microwave process vial at an elevated temperature such as 130° C. under microwave irradiation for 1 to several hours.

2-Aminoethyl ethers Icw can be prepared by deacylation of IIcl. The reaction can be carried out in an aqueous solution of hydrochloric acid at an elevated temperature such as 80° C. for several hours.

Compounds of interest Icx can be prepared by cleavage of tert-butyloxycarbonyl. The reaction can be carried out with trifluoroacetic acid in dichloromethane or hydrochloride in ethyl acetate at room temperature for several hours.

General Synthetic Route for Formula Icy (Scheme 48)

ried out in the presence of a suitable base such as sodium hydride or potassium carbonate, in an organic solvent such as N,N-dimethylformamide, at an elevated temperature, typically at 70° C. for several hours to overnight.

Carboxylic acids IIco can be prepared from hydrolysis of IIcn. The reaction can be carried out with a suitable base such as lithium hydroxide or sodium hydroxide in a suitable mixed solvent such as tetrahydrofuran and water or methanol and water, at room temperature for several hours.

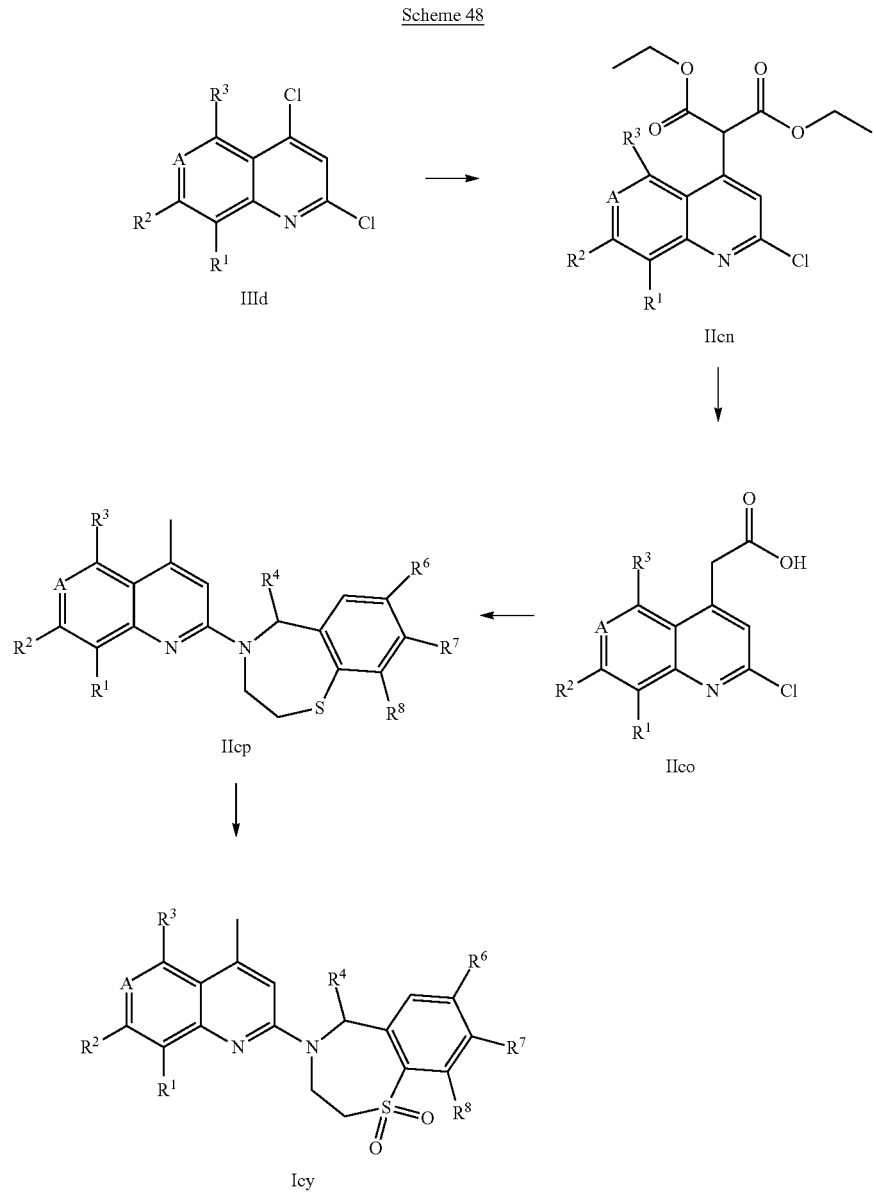

Compounds of interest Icy can be prepared according to Scheme 48. Starting with 2,4-dichloro-quinolines IIId, regioselective nucleophillic replacement with diethyl malonate followed by hydrolysis affords carboxylic acids IIco. Coupling of IIco with benzothiazepines and decarboxylation in a tandem reaction affords 4-methyl-quinolines IIcp. Oxidation of sulfides IIcp affords sulfones Icy.

IIcn can be prepared from regioselective nucleophillic replacement with diethyl malonate. The reaction can be car- IIcp can be obtained by coupling of 2-chloroquinolines IIco with benzothiazepines and decarboxylation in a tandem reaction. The reaction preferably can be carried out with or without an organic solvent such as n-butanol under microwave irradiation at a temperature between 150° C. and 170° C. for several hours.

Compounds of interest Icy can be prepared by oxidation of IIcp. The reaction can be carried out in analogy to oxidation of quinolines IIac in Scheme 4.

General Synthetic Route for Formula Icz (Scheme 49)

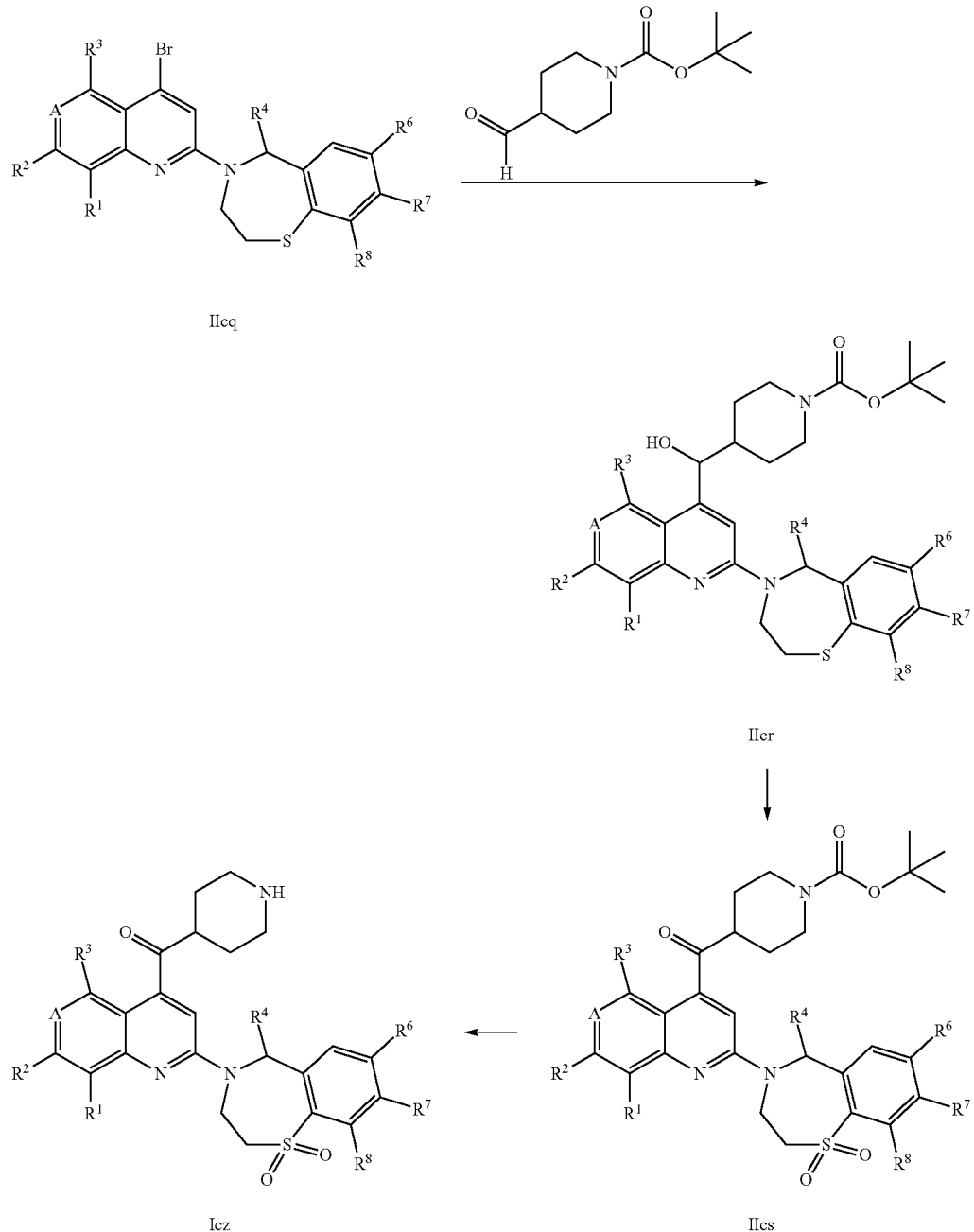

Compounds of interest Icz can be prepared according to Scheme 49. Starting with 4-bromoquinolines IIcq, reaction with a lithium alkylide followed by reaction with 1-tert-butoxy carbonyl-4-piperidinecarboxaldehyde provides the secondary alcohols IIcr. Dess-Martin oxidation of IIcr followed by cleavage of tert-butyl carbamates affords compounds of interest Icz.

IIcr can be obtained by reaction of 4-bromoquinolines IIcq with a lithium alkylide followed by reaction with 1-tert-butoxycarbonyl-4-piperidinecarboxaldehyde. The conversion can be achieved by treating 4-bromo-quinolines IIcq with n-butyllithium and 1-tert-butoxycarbonyl-4-piperidinecarboxaldcehyde in an inert organic solvent such as tetrahydrofuran at −78° C., then at room temperature overnight.

Compounds of interest Icz can be obtained by Dess-Martin oxidation of IIcr followed by cleavage of tert-butyl carbamates. Oxidation of IIcr can be carried out with a suitable oxidant such as Dess-martin reagent in dichloromethane at room temperature overnight, or with manganese dioxide in toluene under reflux for several hours. Cleavage of tert-butyl carbamates can be achieved by treating tert-butyl carbamates IIcs with a suitable acid such as hydrochloric acid, trifluoroacetic acid, or sulfuric acid in a suitable solvent such as methanol, ethyl acetate, dichloromethane, 1,4-dioxane, water or the mixture thereof at a temperature between 0° C. and room temperature for 30 minutes to several hours. Typically the reaction can be carried out by treating tert-butyl carbamates IIcs with trifluoroacetic acid in dichloromethane at room temperature for 6 hours.

General Synthetic Route for Formula Ida (Scheme 50)

Scheme 50

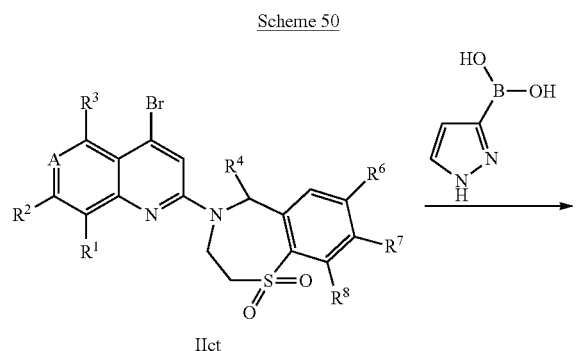

IIct

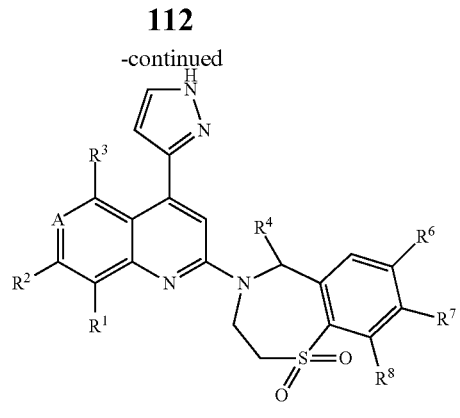

Ida

Compounds of interest Ida can be prepared according to Scheme 50. Coupling of bromides IIct with 1H-pyrazole-3-boronic acid affords Ida. The reaction can be carried out in the presence of a palladium catalyst such as (triphenylphosphine)palladium with sodium carbonate in a suitable organic solvent such as benzene or dimethoxyethane, at a temperature between 80° C. and 120° C., typically at 80° C. for 1 hour under microwave irradiation General Synthetic Route for Formula Ida (Scheme 51)

Scheme 51

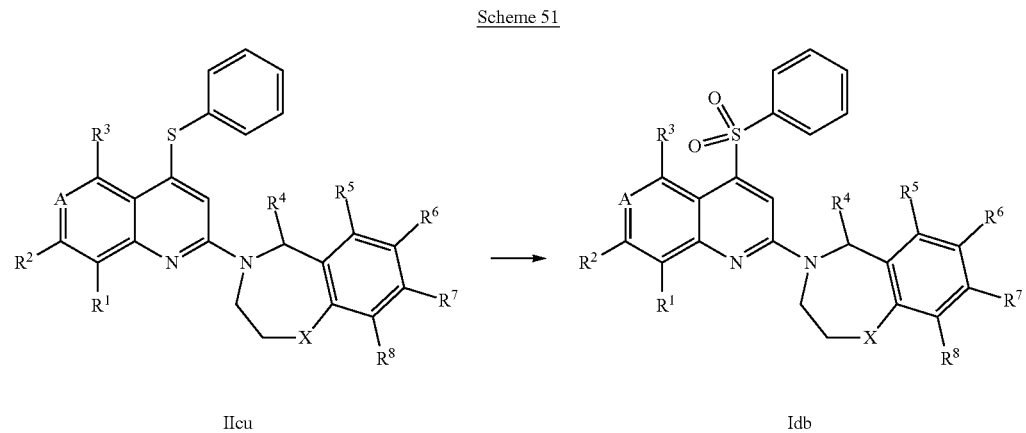

IIcu → Idb

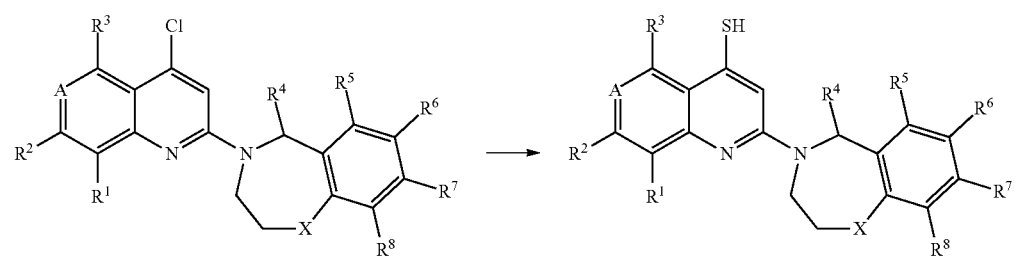

IIbi → IIcv

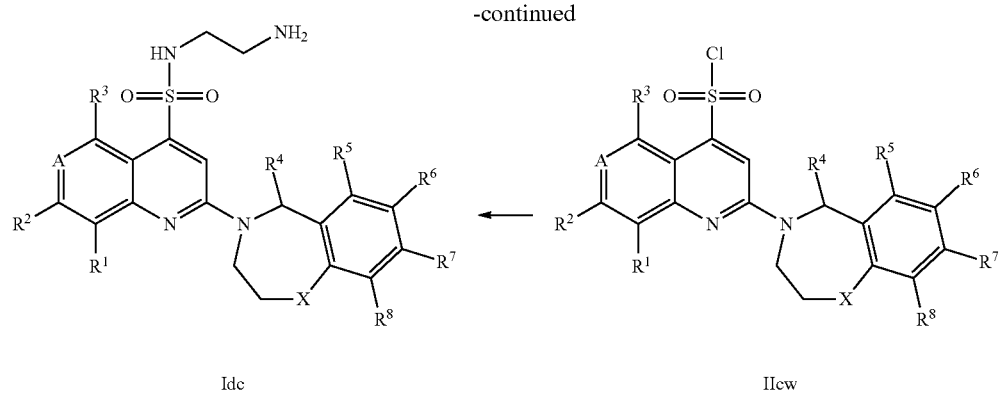

Idc ← IIcw

Compounds of interest Idb and Idc can be prepared according to Scheme 51. Coupling of chlorides IIbi with benzenethiol affords IIcu. Oxidation of IIcu affords compounds of interest Idb. Coupling of chlorides IIbi with sodium methanethiolate affords IIcv. Oxidation and chlorination of IIcv affords sulfonyl chlorides IIcw. Coupling of sulfonyl chlorides IIcw with ethyl-1,2-diamine affords compounds of interest Idc.

Compounds of interest of formula IIcu can be prepared by coupling of chlorides IIbi with benzenethiol. The reaction can be carried out with a suitable base such as N,N-dimethylpyridin-4-amine in a suitable solvent such as ethanol at room temperature for several days.

Sulfones Idb can be prepared by oxidation of IIcu. The reaction can be carried out with a suitable oxidation reagent such as m-chloroperbenzoic acid in a suitable solvent such as dichloromethane at a temperature between 0° C. and room temperature for 1 to several hours.

Thiols IIcv can be prepared by coupling of chlorides IIbi with sodium methanethiolate. The reaction can be carried out in a suitable solvent such as N,N-dimethylformamide under reflux overnight.

Sulfonyl chlorides IIcw can be prepared by oxidation-chlorination of IIcv. The reaction can be carried out in a suitable solvent such as hydrochloric acid by bubbling of chlorine at a temperature between 0° C. and 10° C. for 30 minutes.

Compounds of interest Idc can be prepared by coupling of chlorides IIcw with ethyl-1,2-diamine. The reaction can be carried out with a suitable base such as triethylamine or ethyl-diisopropyl-amine in a suitable solvent such as dichloromethane at a temperature between 0° C. and room temperature overnight.

General Synthetic Route for Formula Idd, Ide and Idf (Scheme 52)

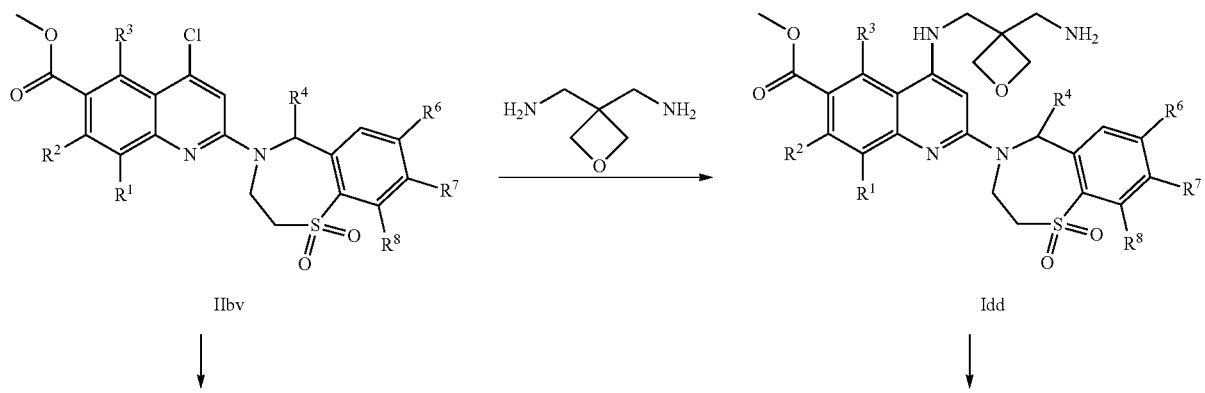

Scheme 52

IIbv → Idd

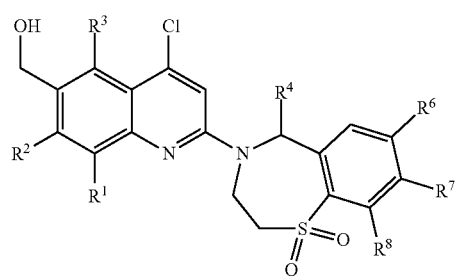

IIcx

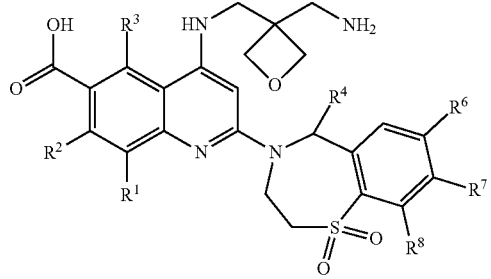

Ide

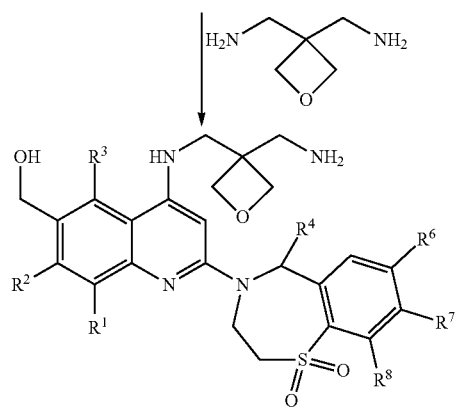

Idf

Compounds of interest Idd, Ide and Idf can be prepared according to Scheme 52. Coupling of chlorides IIbv with C-(3-aminomethyl-oxetan-3-yl)-methylamine generates Idd. Hydrolysis of esters affords carboxylic acids Ide. Reduction of esters IIbv followed by coupling with C-(3-aminomethyl-oxetan-3-yl)-methylamine generates compounds Idf.

Compounds Idd can be prepared by coupling of chlorides IIbv with C-(3-aminomethyl-oxetan-3-yl)-methylamine. The reaction can be carried in analogy to coupling of 4-halogen quinolines IIab with various amines XI in Scheme 5. Typically the reaction can be carried out with tris(dibenzylidene-acetone)dipalladium(0), 2,2'-bis(diphenylphosphino)-1,1'-binaphthyl and sodium tert-butoxide in toluene at 110° C. overnight under nitrogen atmosphere.

Acids Ide can be prepared from hydrolysis of methyl esters Idd. The reaction can be carried out with a suitable base such as sodium hydroxide or lithium hydroxide in a mixture solvent of tetrahydrofuran and water at a temperature between room temperature and 60° C., typically at room temperature for several hours or overnight.

Hydroxides IIcx can be prepared by reduction of esters IIbv. The reaction can be carried out with a standard reduction agent such as lithium aluminium hydride in a suitable solvent such as tetrahydrofuran, at a temperature between 0° C. and room temperature for several hours, typically at room temperature for 2 hours.

Compounds Idf can be prepared by coupling of IIcx with C-(3-aminomethyl-oxetan-3-yl)-methylamine. The reaction can be carried out in analogy to coupling of IIbv with C-(3-aminomethyl-oxetan-3-yl)-methylamine in this scheme.

General Synthetic Route for Formula Idg (Scheme 53)

Scheme 53

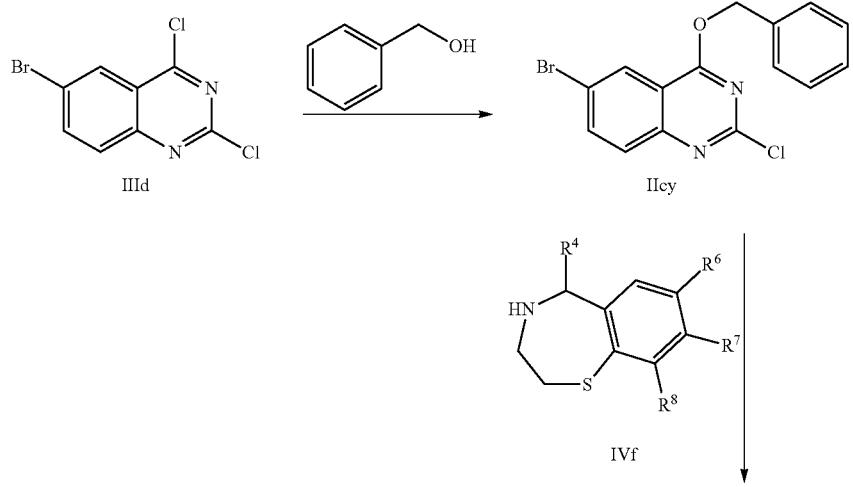

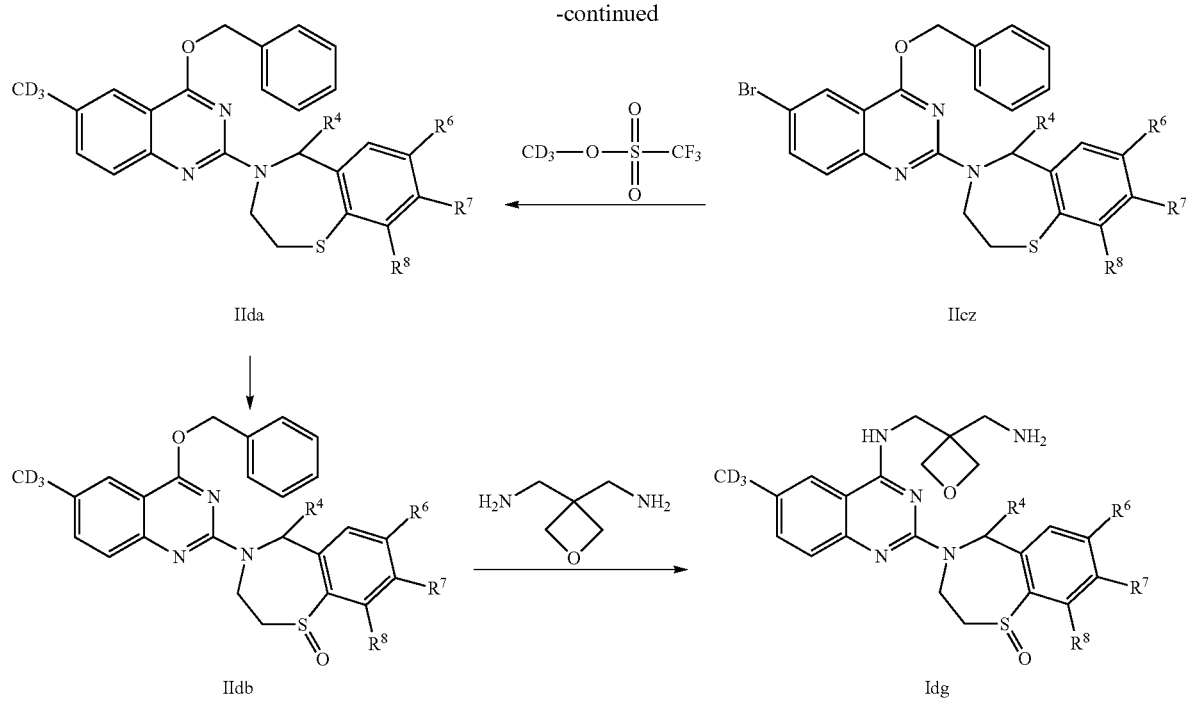

Compounds of interest Idg can be prepared according to Scheme 53. Starting with 2,4-dichloro-quinazolines IIId, reaction with benzyl alcohol followed by coupling with benzothiazepines IVf affords benzyloxy compounds IIcz. Substitution of bromo with methyl-d³ followed by oxidation affords 6-methyl-d³-quinazolines IIdb. Coupling of IIdb with C-(3-aminomethyl-oxetan-3-yl)-methylamine affords compounds of interest Idg.

2-Chloro-4-benzoxy quinazolines IIcy can be prepared by reaction of 2,4-dichloro-quinazolines IIId with benzyl alcohol. The reaction can be carried out in the presence of a suitable base such as sodium hydride in an organic solvent such as tetrahydrofuran, acetonitrile or N,N-dimethylformamide at 0° C. followed by at room temperature for several hours.

IIcz can be prepared by coupling of IIcy with benzothiazepines IVf. The reaction can be carried out without any base and without any solvent at a temperature between 80° C. and 160° C., typically at 80° C. for 10 minutes to 2 hours.

6-Methyl-d³-quinazolines IIda can be prepared by substitution of bromo with methyl-d³. The reaction can be carried out by treating IIcy with n-butyllithium in anhydrous tetrahydrofuran at −78° C. for several minutes under nitrogen followed by stirring with methyl-d³ trifluoromethanesulfonate at −78° C. and then at room temperature for 1 to several hours.

Sulfoxides IIdb can be prepared by oxidation of IIda. The reaction can be carried out by treating IIda with 1-2 equivalents of 3-chloroperoxybenzoic acid in a suitable organic solvent such as dichloromethane, chloroform, 1,2-dichloroethane or the mixtures thereof, typically at 0° C., followed by stirring at room temperature for 10 to 20 minutes.

Compounds of interest Idg can be prepared by coupling of IIdb with C-(3-aminomethyl-oxetan-3-yl)-methylamine. The reaction can be carried out without any solvent and without any base at an elevated temperature such as 170° C. for 20 minutes.

General Synthetic Route for Formula Idh (Scheme 54)

Scheme 54

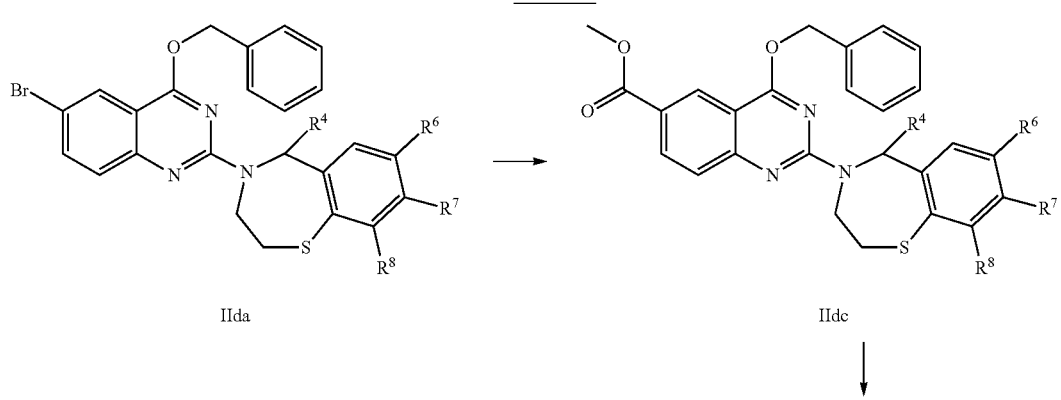

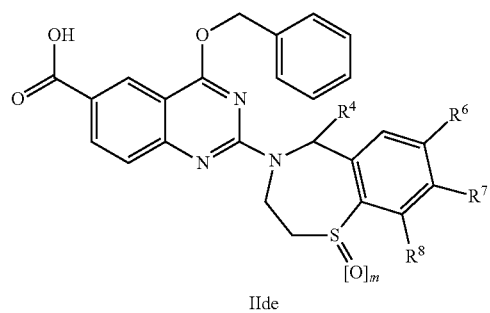

IIde

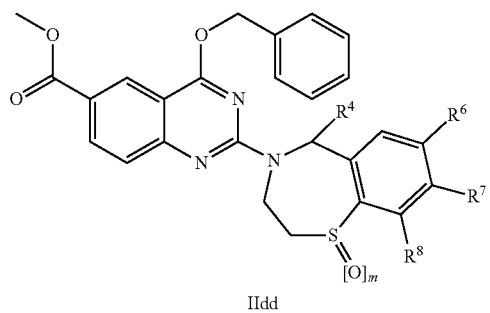

IIdd

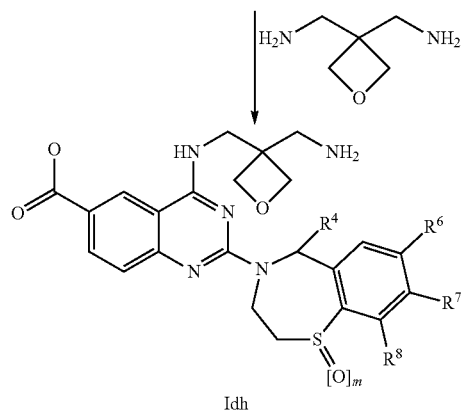

Idh

*m* is 1 or 2

Compounds of interest Idh can be prepared according to Scheme 54. Starting with 6-bromo-quinazolines IIda, carbonylation followed by esterification, oxidation and hydrolysis affords acids IIde. Coupling of IIde with C-(3-aminomethyl-oxetan-3-yl)-methylamine generates compounds of interest Idh.

6-Methoxycarbonyl quinazolines IIdc can be prepared by carbonylation of 6-bromo-quinazolines IIda followed by esterification. Carbonylation can be carried out with dry ice in the presence of n-butyllithium in tetrahydrofuran at −78° C. under nitrogen atmosphere, followed by stirring at room temperature for 1 to several hours. Methyl esterification can be carried out in methanol in the presence of sulfinyl chloride or concentrated sulfuric acid at a temperature between room temperature and 70° C. for 1 to several hours Compounds IIdd can be prepared by oxidation of IIdc. Oxidation can be carried out by treating IIdc with 1-2 equivalent(s) of 3-chloroperoxybenzoic acid in a suitable organic solvent such as dichloromethane, chloroform, 1,2-dichloroethane or mixtures thereof, typically at 0° C., followed by stirring at room temperature for 10 minutes to several hours.

Acids IIde can be prepared by hydrolysis of methyl esters IIdd. The reaction can be carried out with a suitable base such as sodium hydroxide or lithium hydroxide in a mixture of tetrahydrofuran and water at a temperature between room temperature and 60° C., typically at room temperature for several hours or overnight.

Compounds of interest Idh can be prepared by couplin, g of IIde with C-(3-aminomethyl-oxetan-3-yl)-methylamine. The reaction can be carried out without any solvent and without any base at 170° C. for 30 minutes.

General Synthetic Route for Formula Idi (Scheme 55)

Scheme 55

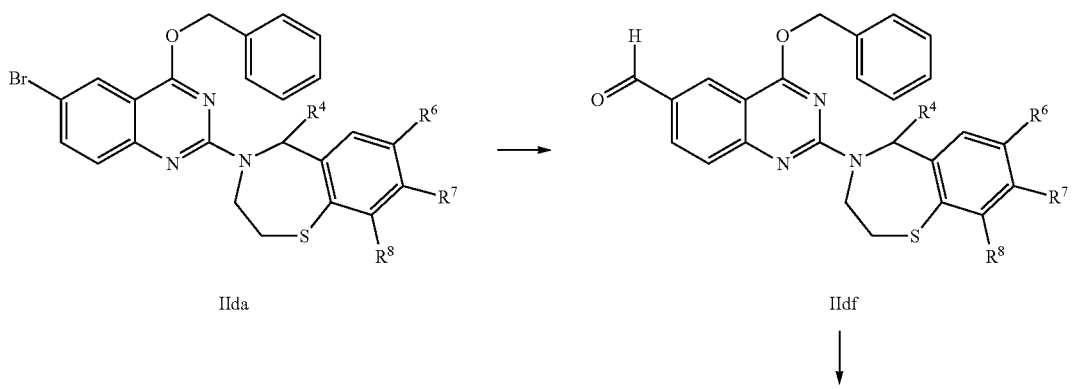

IIda    IIdf

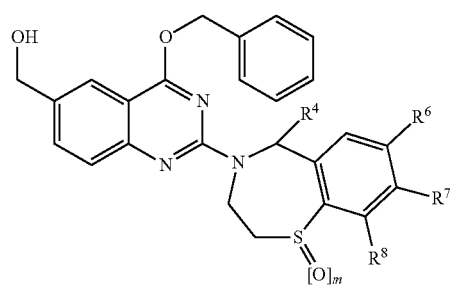

IIdh

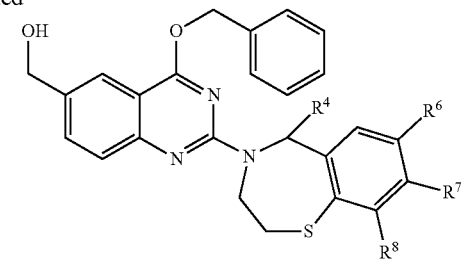

IIdg

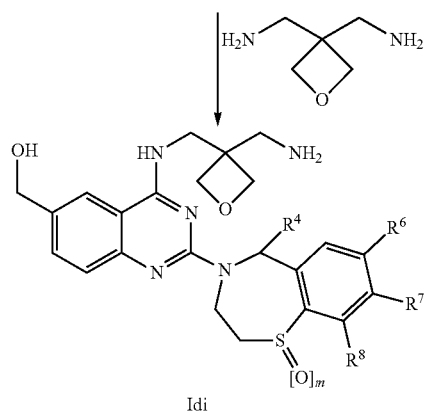

Idi m is 1 or 2

Compounds of Idi can be prepared according to Scheme 55. Starting with 6-bromo quinazolines IIda, Bouveault formylation followed by reduction of aldehyde and oxidation of sulfide affords 4-benzyloxy-6-hydroxymethyl-quinazolines IIdh. Coupling of IIdh with C-(3-aminomethyl-oxetan-3-yl)-methylamine generates compounds of interest Idi.

Aldehydes IIdf can be prepared by Bouveault formylation. The reaction can be carried out by treating bromide with n-butyllithium in anhydrous tetrahydrofuran at −78° C. followed by stirring with anhydrous N,N-dimethylformamide at −78° C. for 30 minutes to several hours.

6-Hydroxymethyl-quinazolines IIdg can be prepared by reduction of aldehydes. The reaction can be carried out with sodium borohydride in a suitable organic solvent such as methanol, tetrahydrofuran or the mixture thereof at 0° C. for 15 minutes to several hours.

IIdh can be prepared by oxidation of sulfides. Oxidation can be carried out with 1-2 equivalents of 3-chloroperoxybenzoic acid in a suitable organic solvent such as dichloromethane, chloroform, 1,2-dichloroethane or mixtures thereof, typically at 0° C., followed by stirring at room temperature for 10 minutes to several hours.

Compounds of interest Idi can be prepared by coupling IIdh with C-(3-aminomethyl-oxetan-3-yl)-methylamine. The reaction can be carried out without any solvent and without any base at 160° C. for 30 minutes.

General Synthetic Route for Formula Idj (Scheme 56)

Scheme 56

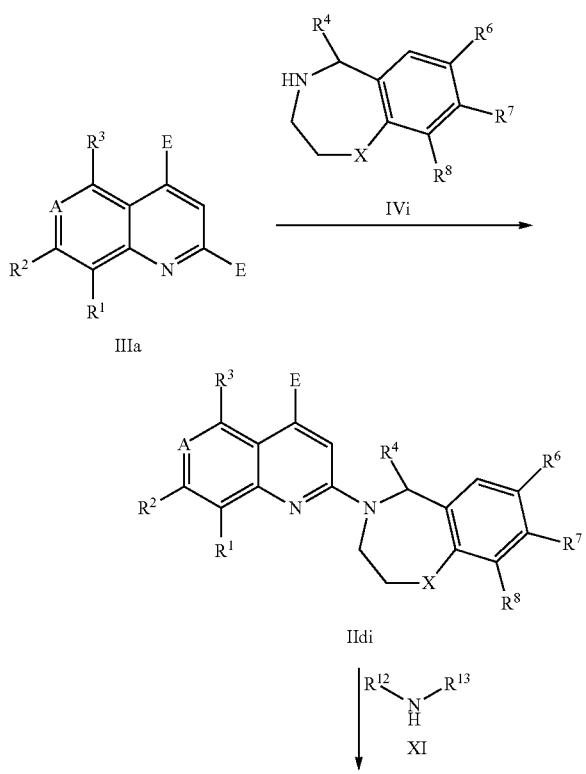

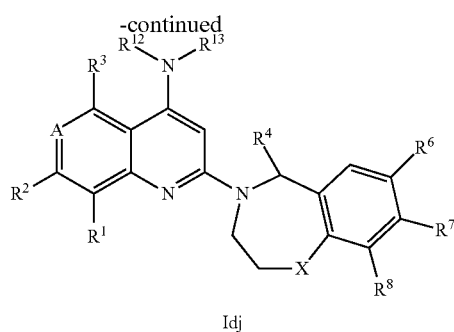

Idj

E is Cl or Br

Compounds of interest Idj can be prepared according to Scheme 56. Starting with 2,4-dihalogen-quinolines IIIa, coupling with benzoazepines IVi affords 2-benzoazepin-4-halogen-qunolines IIdi. Coupling of IIdi with various amines generates compounds of interest Idj.

2-Benzoazepin-4-halogen-qunolines IIdi can be prepared by coupling of 2,4-dihalogen-quinolines IIIa with benzoazepines IVi. The reaction can be carried out with or without a solvent such as n-butanol at 160° C. for several hours under microwave irradiation.

Compounds of interest Idj can be prepared by coupling of IIdi with various amines. The reaction can be carried out in analogy to coupling of 4-halogen-quinolines IIab with various amines XI in Scheme 5. Typically the reaction can be carried out in the presence of 1,1'-bis(diphenylphosphino)ferrocene, 1,1'-bis(diphenylphosphino)ferrocene-palladium (II)dichloride and sodium tert-butoxide in 1,4-dioxane at 120° C. for 1.5 hours under microwave irradiation.

General Synthetic Route for Formula Idk (Scheme 57)

Compounds of interest Idk can be prepared according to Scheme 57. Starting with IIIc, coupling with 1,2,3,4-tetrahydro-benzo[c]azepin-5-one followed by reaction with methyl magnesium bromide affords 5-methyl-5-hydroxy benzothiazepines IIdk. Coupling of IIdk with 3-aminomethyl-oxetan-3-ylamine generates compounds of interest Idk.

2-Benzoazepin-quinolines IIdj can be prepared by coupling of IIIc with 1,2,3,4-tetrahydro-benzo[c]azepin-5-one. The reaction can be carried out in the presence of an organic base such as triethylamine in toluene under reflux overnight.

5-Methyl-5-hydroxy benzothiazepines IIdk can be prepared by reaction of ketones IIdj with methyl magnesium bromide. The conversion can be achieved by stirring of IIdj with methyl magnesium bromide in tetrahydrofuran at 50° C. for several hours.

Compounds of interest Idk can be prepared by coupling of IIdj with 3-aminomethyl-oxetan-3-ylamine. The reaction can be carried out in the presence of a suitable base such as 1,8-diazabicyclo[5.4.0]undec-7-ene with a suitable phosphine ligand such as benzotriazol-1-yloxytris(dimethylamino)-phosphonium hexafluorophosphate, in a suitable solvent such as N,N-dimethylformamide at room temperature for several hours.

Scheme 57

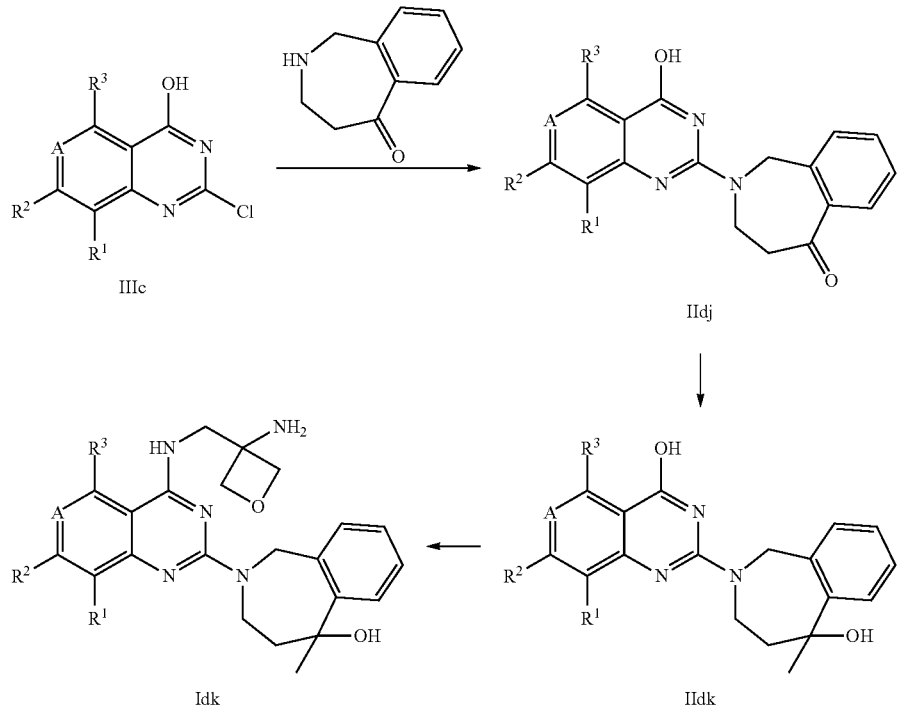

General Synthetic Route for Formula Idl (Scheme 58)

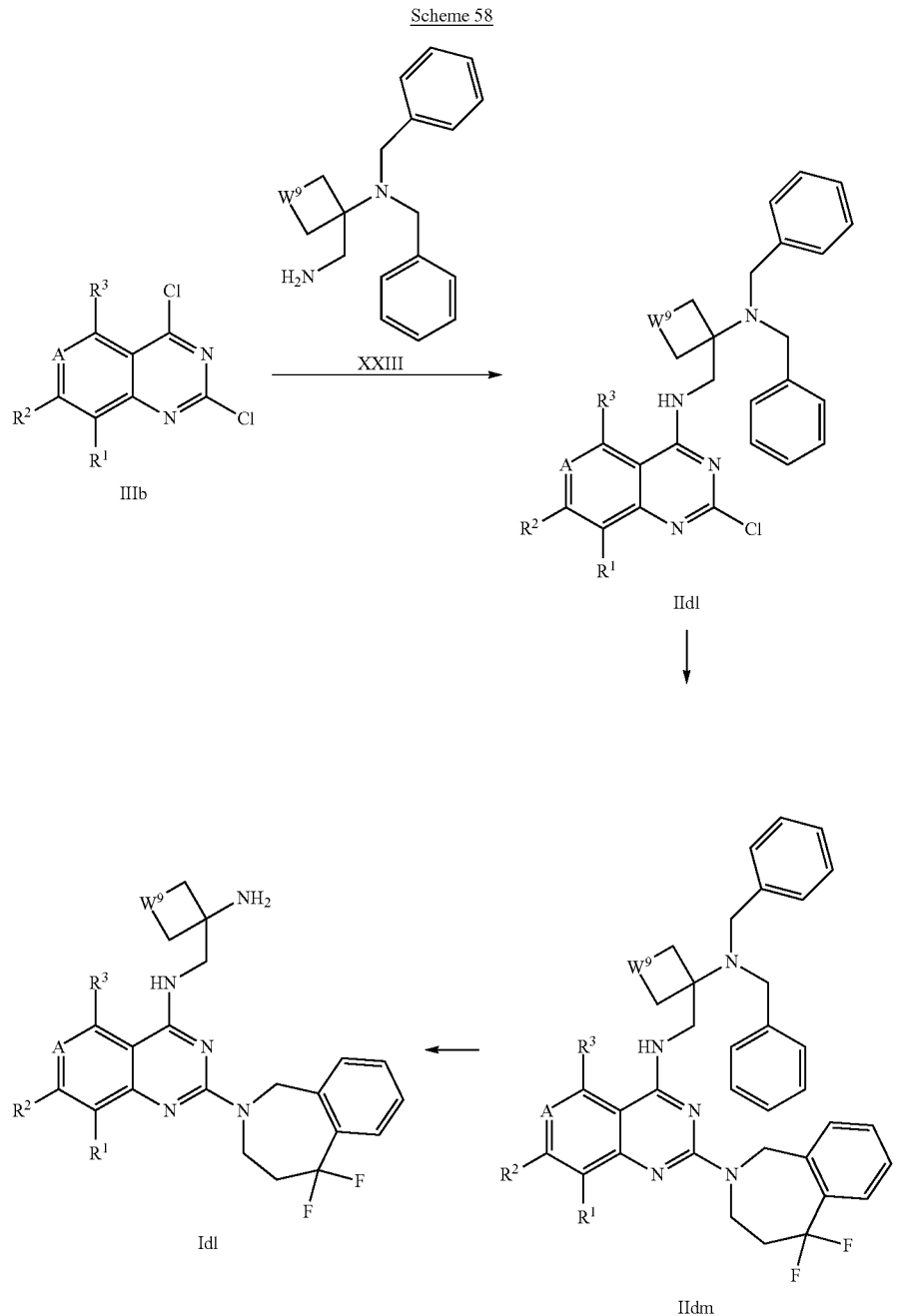

Compounds of interest Idl can be prepared according to Scheme 58. Starting with Mb, reaction with various benzylamino ethylamines XXIII affords IIdl. Substitution of 2-chloro with 5,5-difluoro-2,3,4,5-tetrahydro-1H-benzo[c]azepine followed by deprotection of benzyl generates compounds of interest Idl.

2-Chloro-quinazolines IIdl can be prepared by coupling of IIIb with various amines XXIII. The reaction can be carried out in the presence of a suitable base such as triethylamine in a suitable solvent such as methanol, tetrahydrofuran, dichloromethane or mixtures thereof at a temperature between 0° C. and room temperature for several hours or overnight.

Compounds Idl can be prepared by standard benzyl deprotection of IIdm. The reaction can be carried out with palladium on carbon, palladium hydroxide on carbon or platinum oxide, typically with addition of acetic acid or trifluoroacetic acid in a suitable solvent such as methanol, ethanol, tetrahydrofuran, ethyl acetate or the mixture thereof, at room temperature for several hours under hydrogen atmosphere.

General Synthetic Route for Formula Idm (Scheme 59)

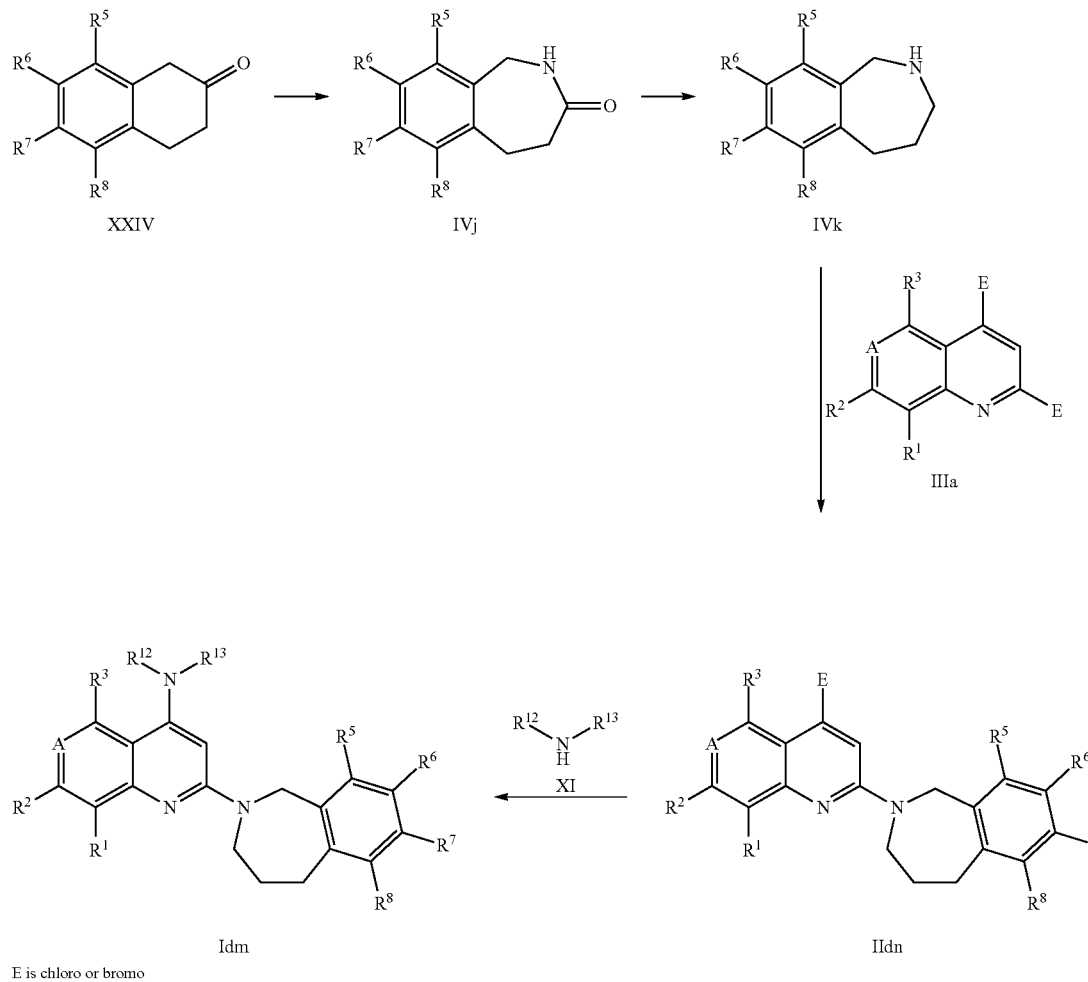

E is chloro or bromo

Compounds of interest Idm can be prepared according to Scheme 59. Starting with naphthalen-2-ones XXIV, ring expansion with hydrazoic acid gives benzoazepin-3-ones IVj. Reduction of lactams IVj to benzoazepines IVk followed by coupling of IVk with 2,4-dihalogen quinolines IIIa gives 4-halogen quinolines IIdn. Coupling of IIdn with various amines XI affords compounds of interest Idm.

Benzoazepin-3-ones IVj can be prepared from ring expansion of naphthalen-2-ones XXIV by using sodium azide. The reaction can be carried out in toluene with a suitable acid such as trifluoromethanesulfonic acid, trifluoroacetic acid or hydrochloric acid, typically at 0° C., followed by stirring at room temperature for several hours.

Benzoazepines IVk can be prepared from benzoazepin-3-ones IVj by reduction of lactams. The reaction can be carried out with standard reducing agent such as lithium aluminium hydride, boron hydride or combination of sodium borohydride and boron trifluoride in a suitable inert organic solvent such as tetrahydrofuran, diethyl ether or mixtures thereof, typically at 0° C., followed by stirring at a temperature between 25° C. and 70° C. for several hours.

4-Halogen quinolines IIdn can be prepared from coupling of benzoazepines IVk and 2,4-dihalogen quinolines IIIa. The reaction can be carried out with a suitable acid such as hydrochloric acid or p-toluenesulfonic acid in a suitable organic solvent such as toluene, dioxane, n-butyl alcohol or 2-methyl-2-pentanol at a temperature between 100° C. and 120° C. for several hours. Alternatively, the reaction can be carried out without acid at a temperature between 100° C. and 160° C. for 1 to 3 hours under microwave irradiation.

Compounds of interest Idm can be prepared by coupling of 4-halogen quinolines IIdn with various amines XI. The reaction can be achieved by microwave irradiation at a temperature between 140° C. and 160° C. for 1 to 3 hours with or without organic solvent such as N,N-dimethylformamide, 1-methylpyrrolidin-2-one or n-butyl alcohol.

B. General Synthetic Route for Formula Idm (Scheme 60)

Scheme 60

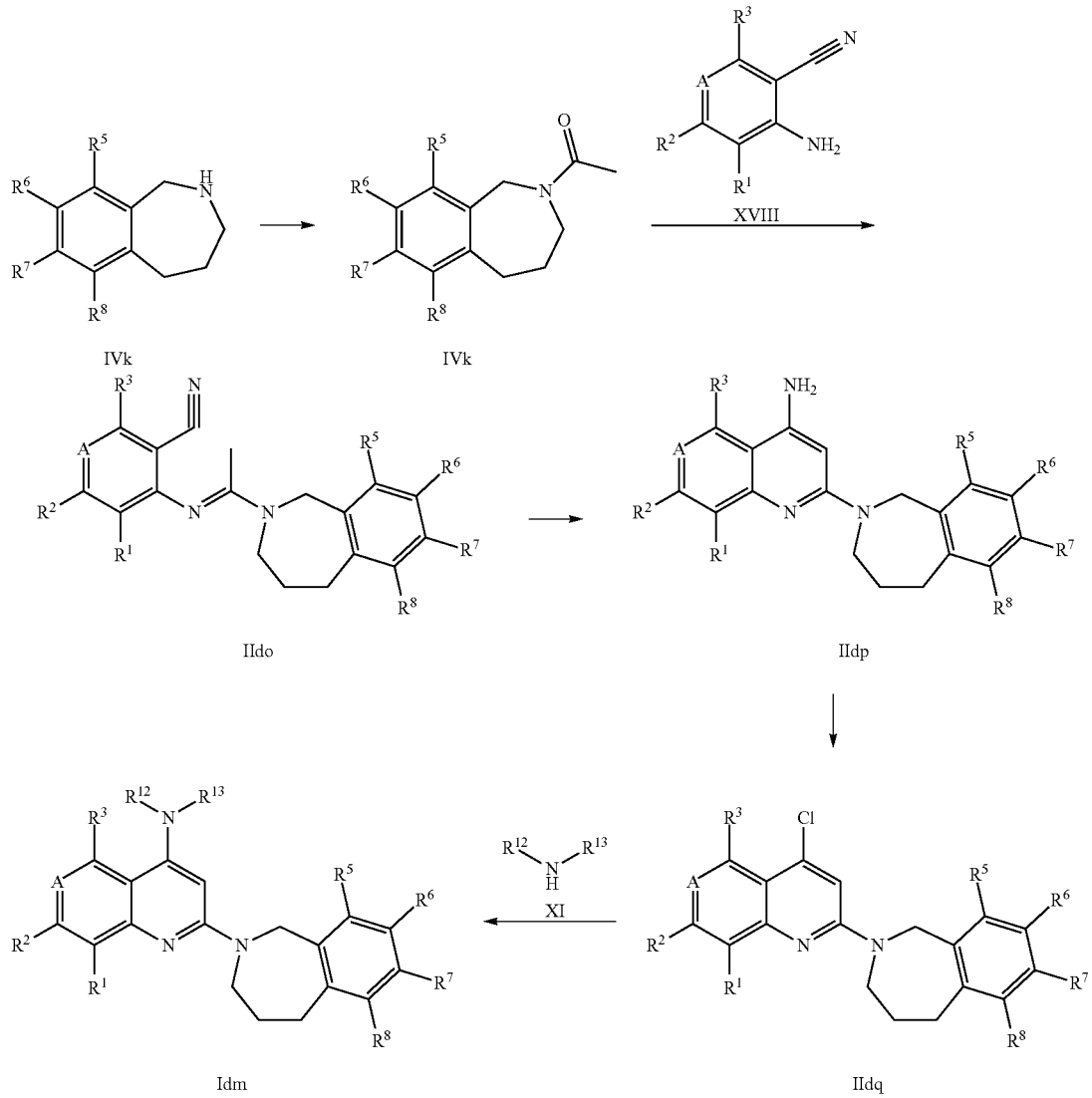

Compounds of interest Idm can be prepared according to Scheme 60. Acylation of benzoazepines IVk, followed by coupling with 2-aminobenzonitriles XVIII provides imines IIdo. Ring closure of imines IIdo gives 4-aminoquinolines IIdp. Sandmeyer reaction of 4-aminoquinolines IIdp provides 4-halogen quinolines IIdq. Coupling of IIdq with various amines XI generates compounds of interest Idm.

Acetyl benzoazepines IVm can be prepared by acylation of benzoazepines IVk with acetyl chloride or acetic anhydride. The reaction can be carried out with a suitable base such as triethylamine or pyridine in a suitable inert organic solvent such as dichloromethane, tetrahydrofuran or pyridine at 0° C., followed by stirring at room temperature for 30 minutes.

Imines IIdo can be prepared by heating a mixture of IVm, 2-aminobenzonitriles XVIII and phosphorous oxychloride. The reaction can be carried out in a suitable inert organic solvent such as dichloromethane, chloroform or the mixtures thereof, typically at a temperature between 0° C. and 10° C., followed by stirring under reflux for 24 hours.

Ring closure of imines IIdo to give 4-aminoquinolines IIdp can be achieved by treatment of IIdo with Lewis acid such as zinc chloride in N,N-dimethyl-acetamide at a temperature between 120° C. and 180° C. for several hours in an inert atmosphere.

Intermediates IIdq can be prepared from 4-aminoquinolines IIdp by using Sandmeyer reaction. The conversion is typically conducted in standard Sandmeyer reaction conditions such as sodium nitrite, hydrochloric acid and sodium chloride or copper(I) chloride in a suitable solvent such as water, typically at −10° C., followed by stirring at room temperature for several hours.

Compounds of interest Idm can be prepared by coupling of IIdq with various amines XI. The reaction can be achieved by microwave irradiation at a temperature between 140° C. and 160° C. for 1-3 hours with or without organic solvent such as N,N-dimethylformamide, 1-methyl-pyrrolidin-2-one or n-butyl alcohol.

General Synthetic Route for Formula Idn (Scheme 61)

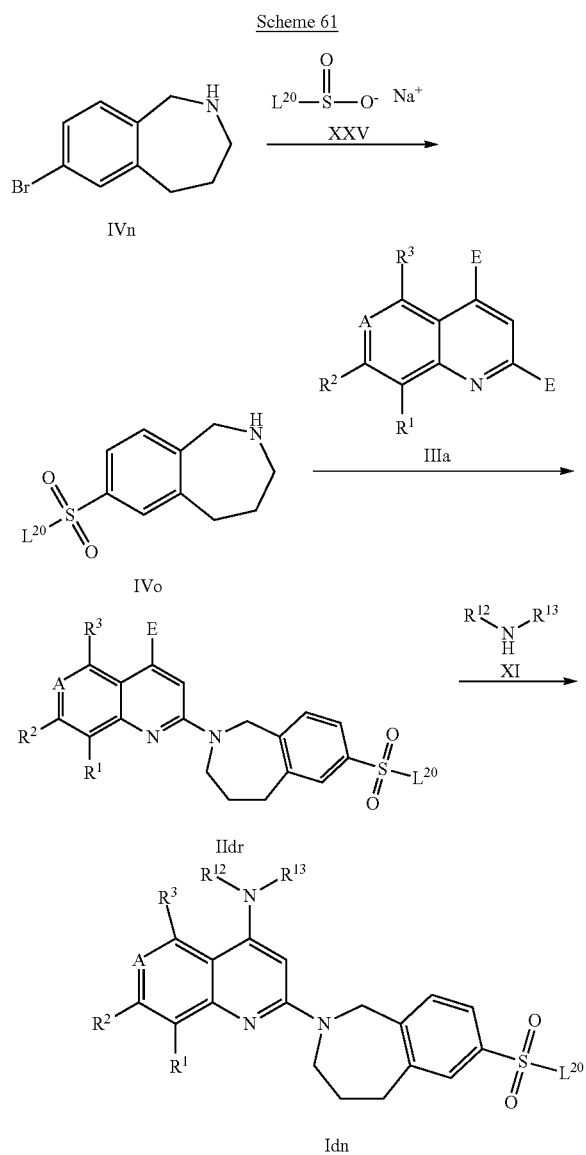

$L^{20}$ is $C_{1-6}$ alkyl;
E is chloro of bromo.

Compounds of interest Idn can be prepared according to Scheme 61. Starting with 7-bromo-2,3,4,5-tetrahydro-1H-benzo[c]azepine IVn, copper-catalyzed coupling with sodium sulfinates XXV gives sulfonyls IVo. Coupling of IVo with 2,4-dihalogen quinolines IIIa gives 4-halogen quinolines IIdr. Coupling of IIdr with various amines XI affords compounds of interest Idn.

The copper-mediated coupling reaction of 7-bromo-2,3,4,5-tetrahydro-1H-benzo[c]azepine IVn with sodium sulfinates XXV illustrated above can be carried out in the presence of a copper source such as copper(I) iodide (CuI), and a ligand such as 2,2'-bipyridine, L-proline, N,N-dimethyl glycine or ethylene glycol, with a suitable base such as triethylamine, sodium carbonate, potassium carbonate, cesium carbonate, sodium tert-butoxide, potassium tert-butoxide, sodium hydride or 1,8-diazabicyclo[5.4.0]undec-7-ene. The reaction can be carried out in a suitable organic solvent such as acetonitrile, toluene, 1,4-dioxane, N,N-dimethylformamide, dimethyl sulfoxide or 1-methyl-pyrrolidin-2-one at a temperature between 100° C. and 180° C. for 15 to 60 minutes under microwave irradiation. Alternatively, the reactions can be carried out at a temperature such as 130° C. for a longer reaction time without the use of microwave irradiation.

Compounds IIdr can be prepared from coupling of benzoazepine IVo and 2,4-dihalogen quinolines IIIa. The reaction can be carried out with a suitable acid such as hydrochloric acid or p-toluenesulfonic acid in a suitable organic solvent such as toluene, dioxane, n-butyl alcohol or 2-methyl-2-pentanol at a temperature between 100° C. and 120° C. for several hours. Alternatively, the reaction can be carried out without acid at a temperature between 100° C. and 160° C. for 1-3 hours under microwave irradiation.

Compounds of interest Idn can be prepared by coupling of IIdr with various amines XI. The reaction can be achieved by microwave irradiation at 140-160° C. for 1-3 hours with or without organic solvent such as N,N-dimethylformamide, 1-methyl-pyrrolidin-2-one or n-butyl alcohol.

D. General Synthetic Route for Formula Ido (Scheme 62)

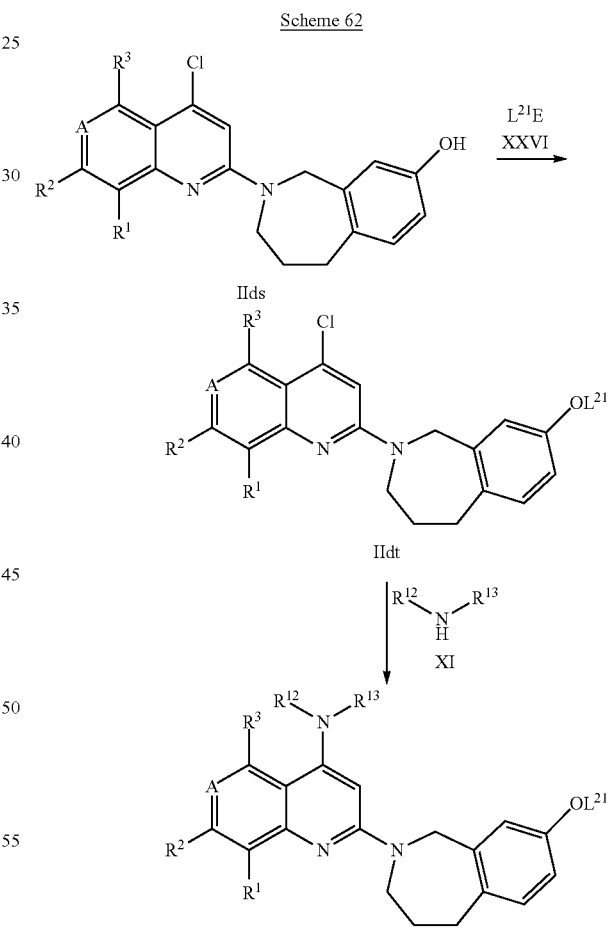

$L^{21}$ is $C_{1-6}$ alkyl;
E is chloro or bromo.

Compounds of interest Ido can be prepared according to Scheme 62. Starting with phenols IIds, alkylation with various XXVI provides IIdt. Coupling of IIdt with various amines XI affords compounds of interest Ido.

Compounds IIdt can be prepared by alkylation of phenols lids with XXVI. The reaction can be carried out with a suitable base such as cesium carbonate, sodium tert-butoxide, potassium tert-butoxide, sodium hydride or 1,8-diazabicyclo[5.4.0]undec-7-ene in an inert organic solvent such as dichloromethane, N,N-dimethylformamide, dimethyl sulfoxide or 1-methyl-pyrrolidin-2-one, typically at room temperature for several hours.

Compounds of interest Ido can be prepared by coupling of IIdt with various amines XI. The reaction can be achieved by microwave irradiation at a temperature between 140° C. and 160° C. for 1 to 3 hours with or without organic solvent such as N,N-dimethylformamide, 1-methyl-pyrrolidin-2-one or n-butyl alcohol.

F. General Synthetic Route for Formula Idp (Scheme 63)

Compounds of interest Idp can be prepared according to Scheme 63. Starting with IIdu, palladium-catalyzed carbonylation gives carboxylic acid methyl esters IIdv. Basic hydrolysis of esters IIdv to acids IIdw followed by coupling with various amines XXVII to furnishes amides IIdx. Coupling of IIdx with various amines XI affords compounds of interest Idp.

Palladium-catalyzed carbonylation of IIdu to the corresponding methyl esters IIdv can be accomplished under an atmosphere of carbon monoxide (1 atmospheric pressure) in methanol. The reaction can be carried out in the presence of a palladium catalyst such as bis(triphenylphosphine)dichloropalladium(II), palladium(II) acetate, tetrakis(triphenylphosphine)palladium(0), or tri(dibenzylideneacetone)dipalladium(0), in the presence or absence of a phosphine ligand

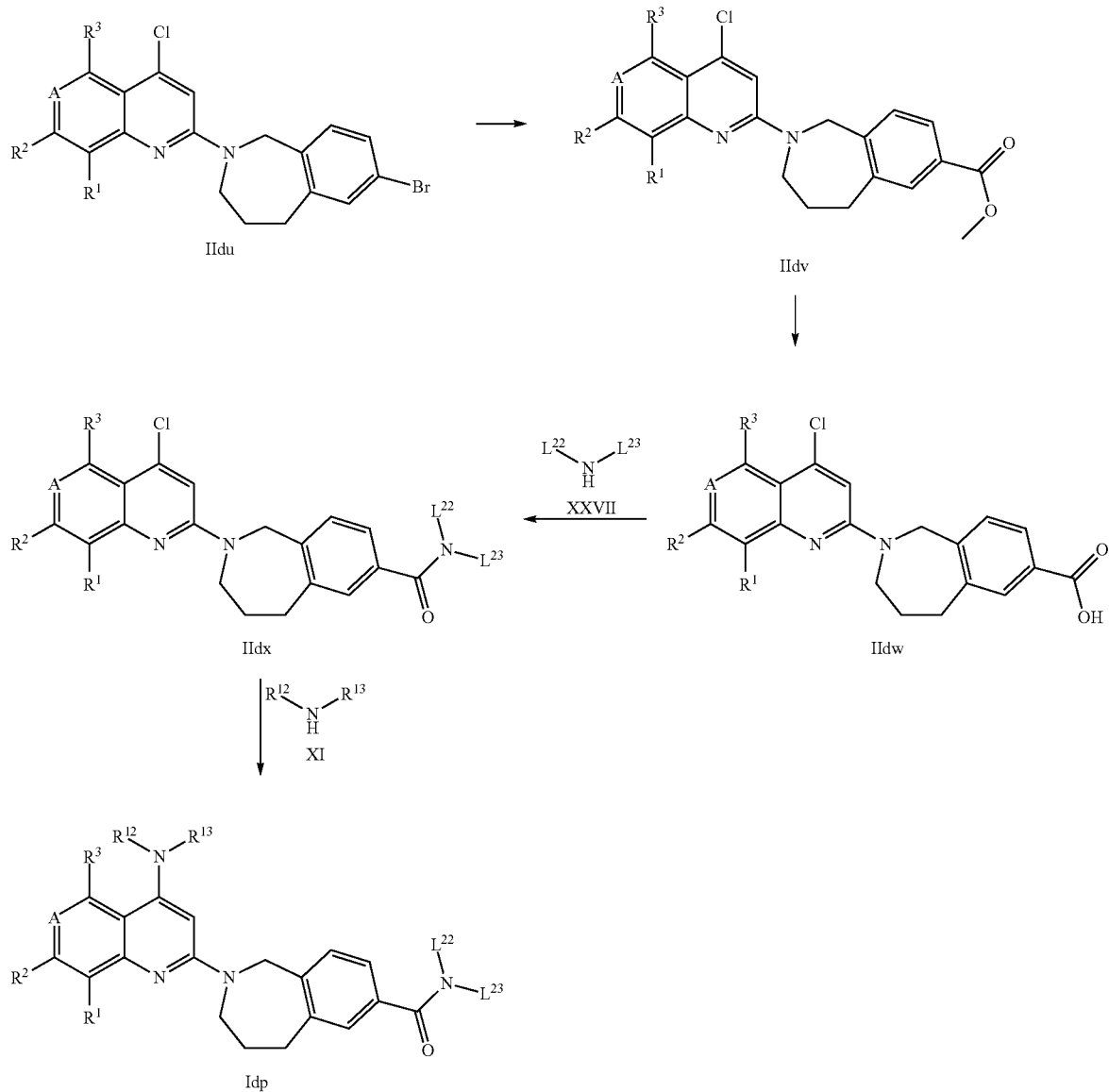

Scheme 63

$L^{22}$ is hydrogen or $C_{1-6}$ alkyl;
$L^{23}$ is hydrogen or $C_{1-6}$ alkyl.

such as tricyclohexylphosphine or triphenylphosphine, and a suitable base such as triethylamine, sodium carbonate or potassium carbonate at a temperature between 60° C. and 120° C. for several hours.

Hydrolysis of the methyl esters IIdv to acids IIdw can be carried out in the presence of an aqueous inorganic base such as lithium hydroxide, sodium hydroxide, or potassium hydroxide in a solvent such as methanol, 1,4-dioxane or tetrahydrofuran at room temperature for several hours.

Amides IIdx can be prepared by coupling various amines XXVII with carboxylic acids IIdw. The reaction is typically conducted with standard peptide coupling reagents such as 1-ethyl-3-(3-dimethylaminopropyl)carbodiimide and 1-hydroxybenzotriazole, bromo-tris-pyrrolidino-phosphonium-hexafluorophosphate and diisopropylethylamine, or O-(7-azabenzotriazol-1-yl)-N,N,N',N'-tetramethyluronium hexafluorophosphate and a base such as triethylamine, or diisopropylethylamine in a suitable inert solvent such as dichloromethane or N,N-dimethylformamide or mixtures thereof at room temperature for several hours.

Compounds of interest Idp can be prepared by coupling of amides IIdx with various amines XI. The reaction can be conducted by microwave irradiation at a temperature between 140° C. and 160° C. for 1 to 3 hours with or without organic solvent such as N,N-dimethylformamide, 1-methyl-pyrrolidin-2-one or n-butyl alcohol.

G. General Synthetic Route for Formula Idq (Scheme 64)

Scheme 64

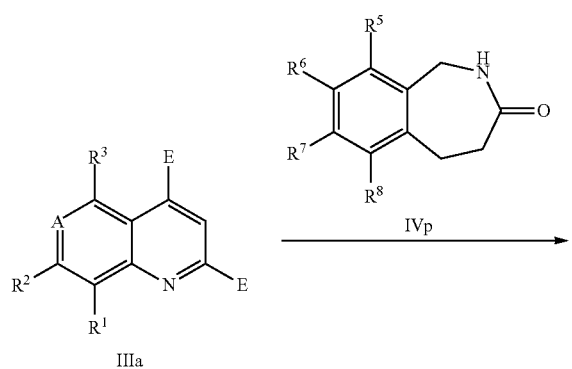

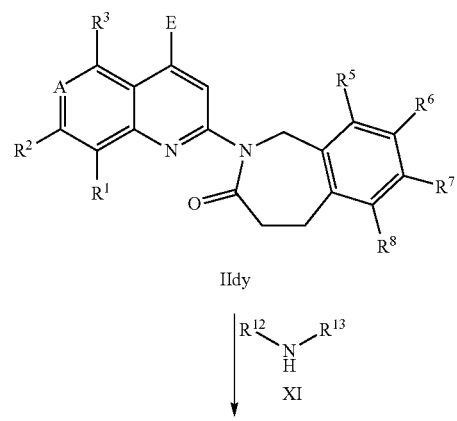

IIdy

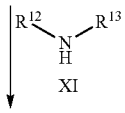

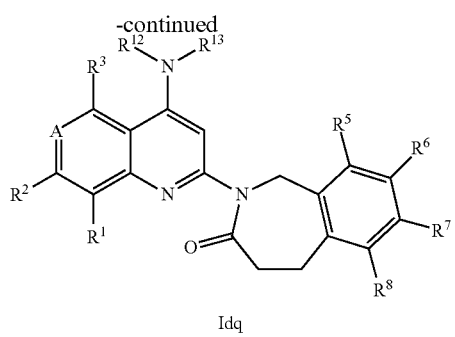

Idq

Compounds of interest Idq can be prepared according to Scheme 64. Palladium-catalyzed coupling of lactams IVp with 2,4-dihalogenquinolines IIIa gives intermediates IIdy. Coupling of IIdy with various amines XI generates compounds of interest Idq.

Intermediates IIdy can be prepared from lactams IVp by coupling with 2,4-dihhalogenquinolines IIIa. The reaction can be carried out typically in the presence of a palladium catalyst such as bis(triphenylphosphine)dichloropalladium (II), palladium(II) acetate, tetrakis(triphenylphosphine)palladium(0), or tri(dibenzylideneacetone)dipalladium(0), in the presence of a phosphine ligand such as tricyclohexylphosphine, or 9,9-dimethyl-4,5-bis(diphenylphosphino)xanthene, with a suitable base such as potassium phosphate tribasic, sodium carbonate or potassium carbonate, in a suitable inert organic solvent such as dioxane, or N,N-dimethylformamide, at a temperature between 100° C. and 150° C. for several hours.

Compounds of interest Idq can be prepared by coupling of IIdy with various amines XI. The reaction can be achieved by microwave irradiation at a temperature between 140° C. and 160° C. for 1 to 3 hours with or without organic solvent such as N,N-dimethylformamide, 1-methyl-pyrrolidin-2-one or n-butyl alcohol.

H. General Synthetic Route for Formula Ids (Scheme 65)

Scheme 65

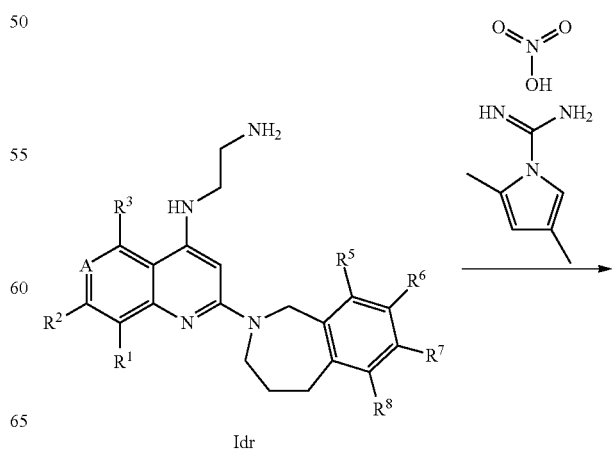

Idr

137

-continued

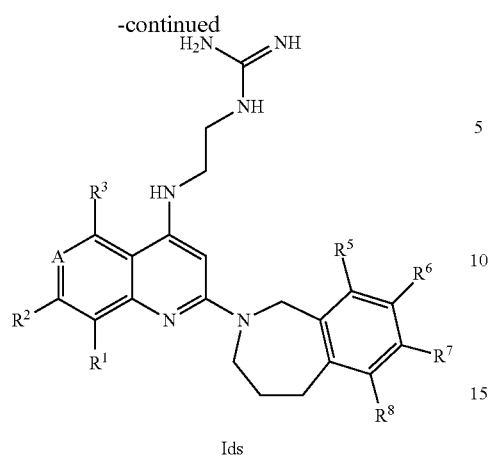

Ids

Compounds of interest Ids can be prepared according to Scheme 65. Starting with diamines Idr (prepared in analogue to Idm in Scheme 59 or Scheme 60), guanidation with 3,5-dimethyl-1H-pyrazole-1-carboximidamide nitrate gives guanidines Ids. The reaction can be carried out in a suitable solvent such as ethanol, typically at a temperature between 70° C. and 90° C. for several hours.

L. General Synthetic Route for Formula Idt (Scheme 66)

Scheme 66

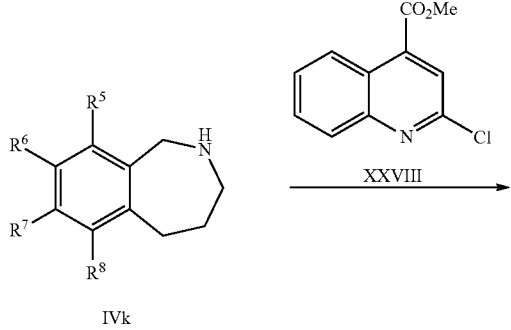

138

-continued

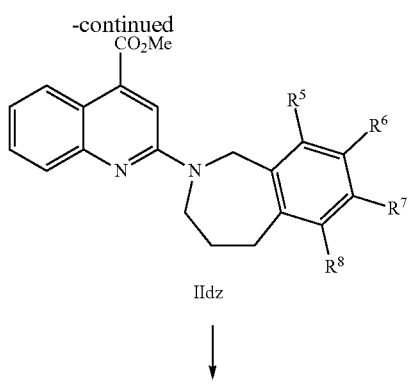

IIdz

↓

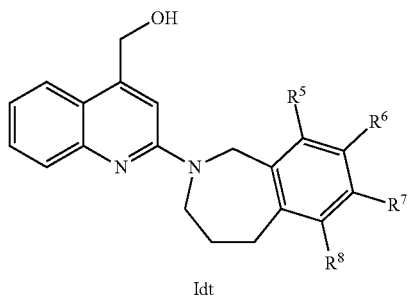

Idt

Compounds of interest Idt can be prepared according to Scheme 66. Starting with benzoazepines IVk, coupling with 2-chloro-quinoline-4-carboxylic acid methyl ester XXVIII gives compounds IIdz, which are in turn reduced to compounds of interest Idt.

Esters IIdz can be prepared from benzoazepines IVk by coupling with 2-chloro-quinoline-4-carboxylic acid methyl ester XXVIII. The reaction can be carried out with a suitable acid such as hydrochloric acid or p-toluenesulfonic acid in a suitable organic solvent such as toluene, dioxane, n-butyl alcohol or 2-methyl-2-pentanol at a temperature between 100° C. and 120° C. for several hours. Alternatively, the reaction can be carried out without acid at a temperature between 100° C. and 160° C. for 1 to 3 hours under microwave irradiation.

Alcohols Idt can be prepared from methyl esters IIdz by reduction. The reaction is typically conducted in a tetrahydrofuran solution of borane at 0° C., followed by stirring at reflux temperature for several hours.

M. General Synthetic Route for Formulas Idu and Idv (Scheme 67)

Scheme 67

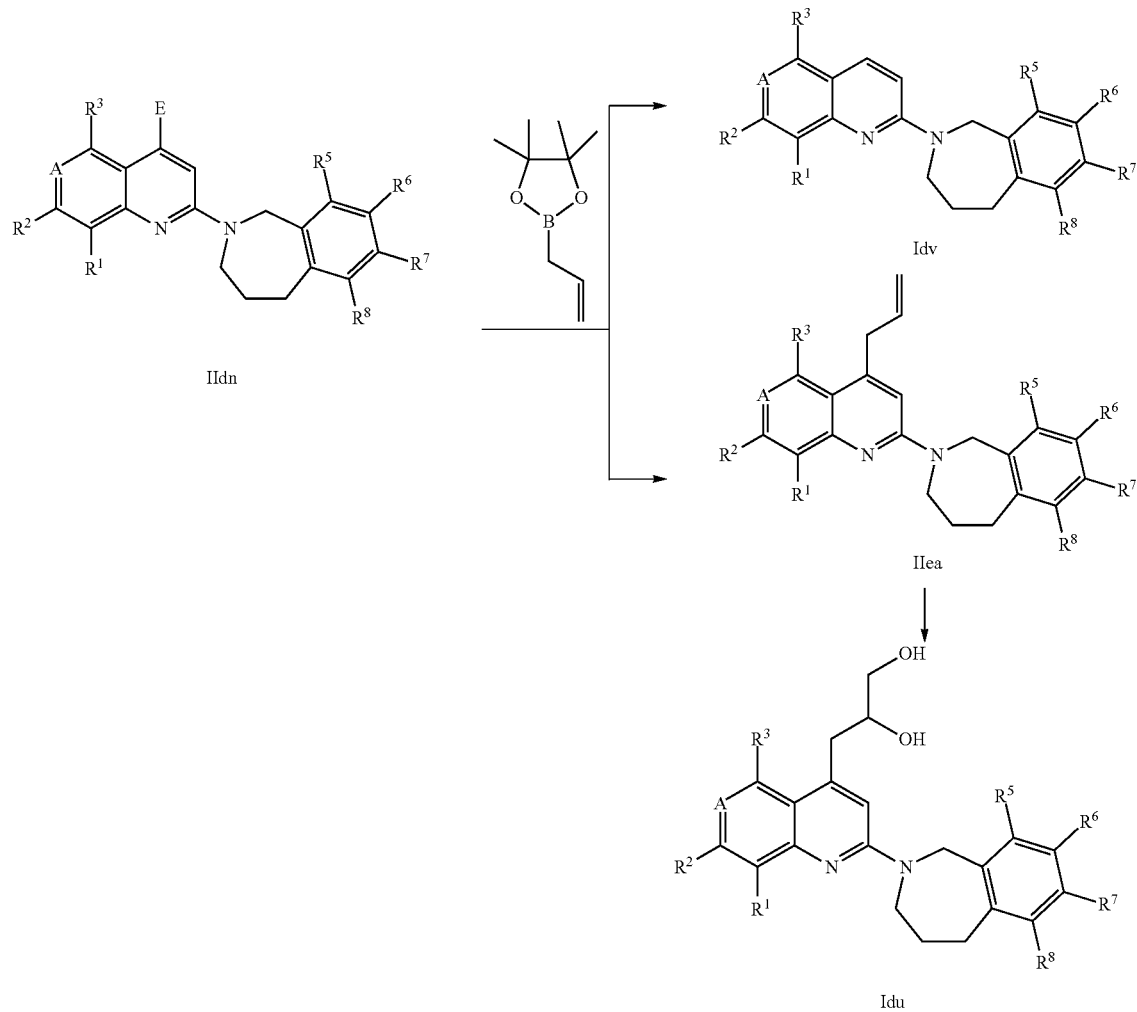

Compounds of interest Idu and Idv can be prepared according to Scheme 67. Starting with 4-halogen quinolines IIdn, Suzuki reaction coupling with 2-allyl-4,4,5,5-tetramethyl-[1,3,2]dioxaborolane gives 4-allyl-quinolines IIea and compounds Idv as a byproduct. 4-Allyl-quinolines IIea are then converted to compounds of interest Idu by Upjohn dihydroxylation.

4-Allyl-quinolines IIea and compounds Idv can be prepared from 4-halogen quinolines IIdn by Suzuki coupling with 2-allyl-4,4,5,5-tetramethyl-[1,3,2]dioxaborolane. The reaction is typically conducted in 1,2-dimethoxyethane and water with potassium carbonate, tetrakis(triphenylphosphine)palladium(0), at a temperature between 80° C. and 140° C. for several hours under microwave irradiation. Alternatively, the reactions can be carried out at a heated temperature such as a temperature between 100° C. and 140° C. for a longer reaction time without the use of microwave irradiation.

Compounds of interest Idu can be prepared from 4-allyl-quinolines IIea by Upjohn dihydroxylation. The reaction can be typically carried out in water with osmium tetroxide and N-methyl morpholine-N-oxide at room temperature for several hours.

P. General Synthetic Route for Formula Idw (Scheme 68)

Scheme 68

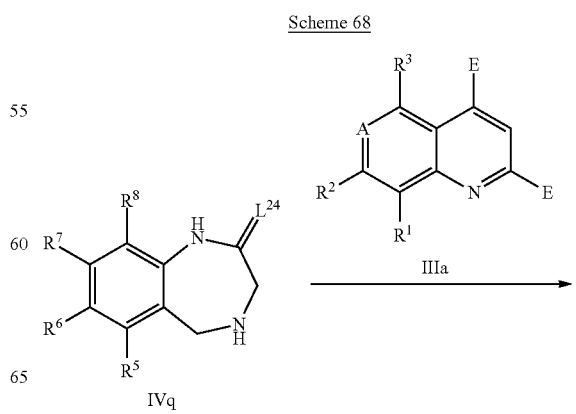

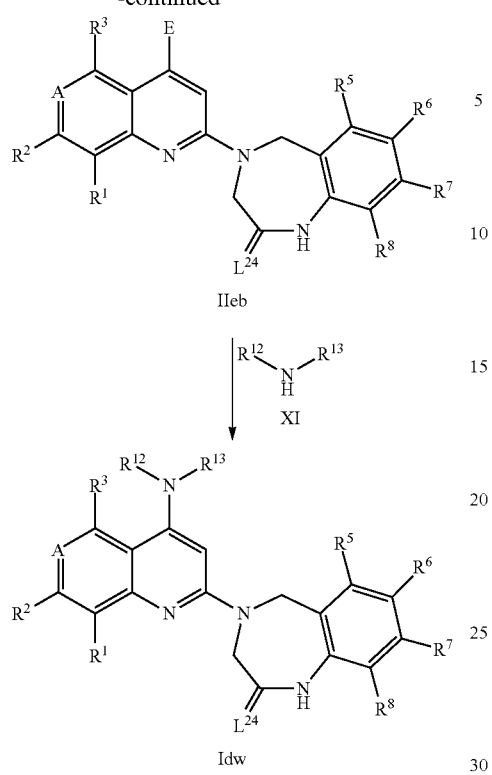

IIeb

↓ $R^{12}\underset{H}{N}R^{13}$
XI

Idw $L^{24}$ is hydrogen or oxygen.

Compounds of interest Idw can be prepared according to Scheme 68. Starting with diazepines IVq, coupling of 2,4-dihalogen quinolines IIIa with IVq furnishes IIeb. Subsequent coupling of IIeb with various amines XI generates compounds of interest Idw.

Compounds IIeb can be prepared from coupling of 2,4-dihalogen quinolines IIIa with diazepines IVq. The reaction can be carried out with a suitable acid such as hydrochloric acid or p-toluenesulfonic acid in a suitable organic solvent such as toluene, dioxane, n-butyl alcohol or 2-methyl-2-pentanol at a temperature between 100° C. and 120° C. for several hours. Alternatively, the reaction can be carried out without acid at a temperature between 100° C. and 160° C. for 1 to 3 hours under microwave irradiation.

Compounds of interest Idw can be prepared by coupling of compounds IIeb with various amines XI. The reaction can be carried out typically in the presence of a palladium catalyst such as [1,1'-bis(diphenylphosphino)ferrocene]dichloropalladium(II), (triphenylphosphine)dichloropalladium(II), palladium(II) acetate, or tri(dibenzylideneacetone)dipalladium (0), in the presence of a phosphine ligand such bis(diphenylphosphino)ferrocene, tricyclohexylphosphine, or 9,9-dimethyl-4,5-bis(diphenylphosphino)xanthene, with a suitable base such as sodium tert-butoxide, in a suitable inert organic solvent such as dioxane, or N,N-dimethylformamide, at a temperature between 100° C. and 150° C. for 1 to 3 hours under microwave irradiation. Alternatively, the reactions can be carried out at a heated temperature such as a temperature between 100° C. and 140° C. for a longer reaction time without the use of microwave irradiation.

R. General Synthetic Route for Formula Idx (Scheme 69)

Scheme 69

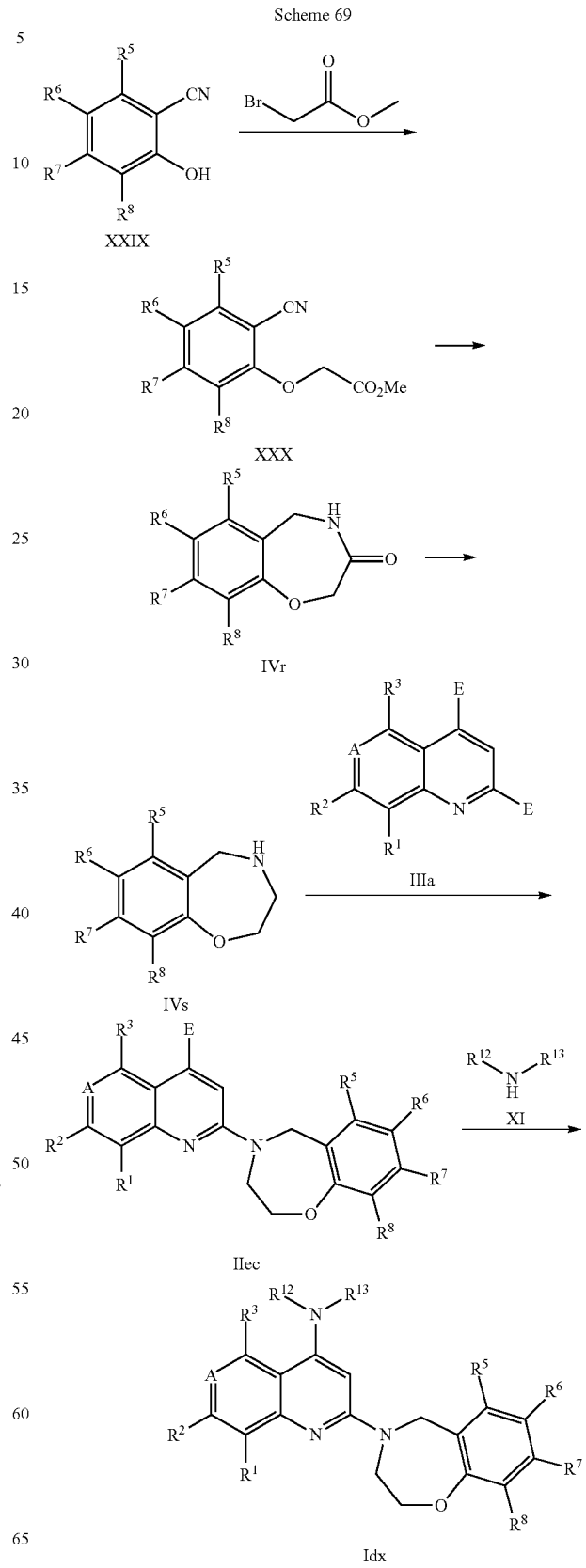

Compounds of interest Idx can be prepared according to Scheme 69. Starting with hydroxybenzonitriles XXIX, alkylation with methyl bromoacetate gives esters XXX. Intramolecular cyclization of compounds XXX gives benzooxazepin-3-ones IVr, which are in turn converted to benzooxazepines IVs by reduction. Coupling of IVs with 2,4-dihalogen quinolines IIIa furnishes IIec. Subsequent coupling of IIec with various amines XI affords compounds of interest Idx.

Esters XXX can be prepared from alkylation of hydroxybenzonitriles XXIX with methyl bromoacetate. The reaction is typically carried out in acetone with potassium carbonate at room temperature for several hours.

Benzooxazepin-3-ones IVr can be prepared from esters XXX by intramolecular cyclization. The reaction can be carried out in methanol with Raney nickel at room temperature for several hours under an atmospheric pressure of hydrogen.

Benzooxazepines IVs can be prepared from benzooxazepin-3-ones IVr by reduction of lactam. The reaction is typically conducted in an inert solvent such as tetrahydrofuran, diethyl ether or mixtures thereof with lithium aluminium hydride, typically at 0° C., followed by stirring at reflux temperature for several hours.

Substituted quinolines IIec can be prepared from coupling of benzooxazepines IVs with 2,4-dihalogen quinolines IIIa. The reaction can be carried out with a suitable base such as potassium carbonate, cesium carbonate, diisopropylethylamine, triethylamine, or 1,8-diazabicyclo[5.4.0]undec-7-ene in an inert organic solvent such as toluene, tetrahydrofuran, 1-methyl-pyrrolidin-2-one or N,N-dimethylformamide, typically at a temperature between 100° C. and 180° C. for 1 to 3 hours under microwave irradiation.

Compounds of interest Idx can be prepared by coupling of substituted quinolines IIec with various amines XI. The reaction can be achieved by microwave irradiation at a temperature between 140° C. and 180° C. for 1 to 3 hours with or without organic solvent such as N,N-dimethylformamide, 1-methyl-pyrrolidin-2-one or n-butyl alcohol.

General Synthetic Route for Formula Idy (Scheme 70)

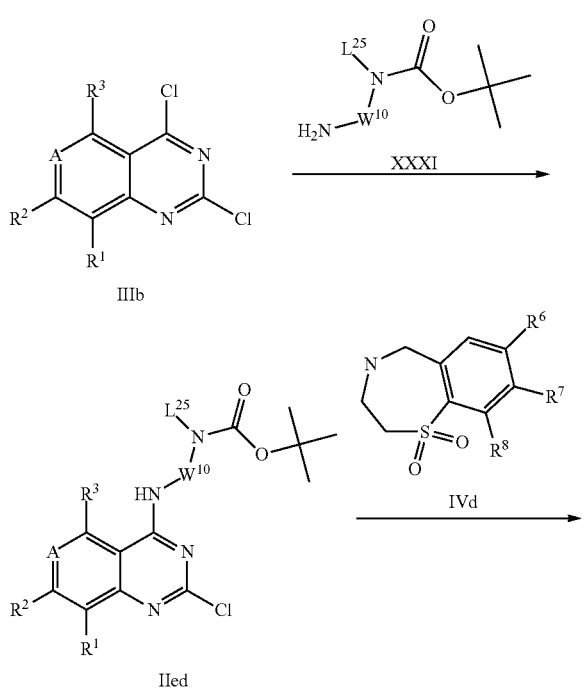

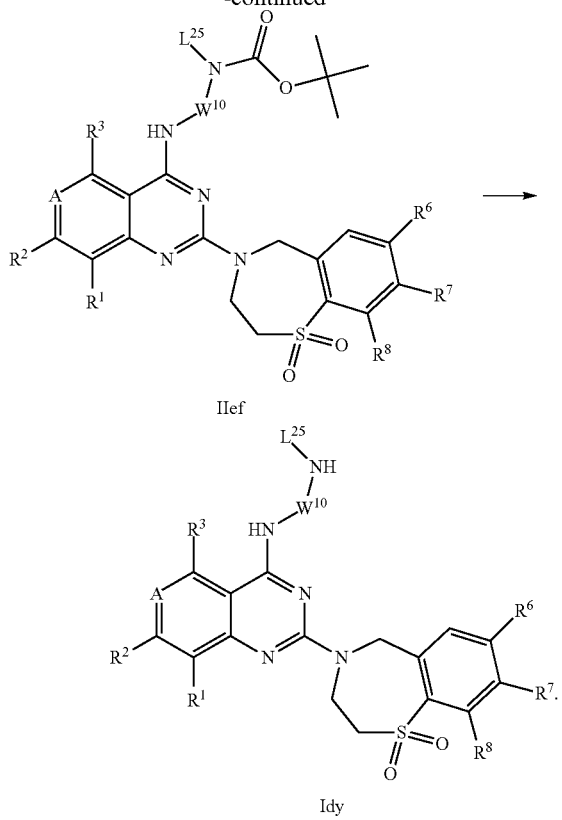

• $W^{10}$ is methylcyclopropyl and $L^{25}$ is hydrogen, or
$W^{10}$ and $L^{25}$ with nitrogen they are attached with form pyrrolindin-3-yl.

Compounds of interest of formula Idy can be prepared according to Scheme 70. Coupling of 2,4-dichloro-quinozalines IIIb with various amines XXXI followed by reaction with 6,7,8,9-tetrahydro-5-thia-8-aza-benzocycloheptene 5,5-dioxides IVd affords 2,4-disubstituted quinozalines IIef. Deprotection of tert-butyloxycarbonyl of IIef generates the target compounds Idy.

2-Chloro-4-amino quinozalines IIed can be prepared by coupling of IIIb with various amines XXXI. The reaction can be carried out in the presence of a suitable base such as triethylamine in a suitable solvent such as methanol, tetrahydrofuran, dichloromethane or mixture thereof at a temperature between 0° C. to room temperature for several hours.

4-Disubstituted quinozalines IIef can be obtained by the coupling of IIed with 6,7,8,9-tetrahydro-5-thia-8-aza-benzocycloheptene 5,5-dioxides IVd. The reaction can be carried out with or without an acid such as 4-methylbenzenesulfonic acid and ammonium chloride, in a suitable solvent such as ethanol or N,N-dimethylformamide at an elevated temperature between 50° C. and 120° C. for several hours, typically at 70° C. overnight.

Compounds of interest of formula Idy can be prepared from deprotection of tert-butyloxycarbonyl of 4 disubstituted quinozalines IIef. The reaction can be carried out with a suitable acid such as trifluoroacetic acid or hydrochloric acid in a suitable solvent such as dichloromethane, ethyl acetate or 1,4-dioxane, at 0° C. to room temperature for 30 minutes to 16 hours.

The invention also relates to a compound of formula (I) for use as therapeutically active substance.

The invention relates to a compound of formula (I) for use as a medicament.

The invention also relates to a pharmaceutical composition comprising a compound of formula (I) and a therapeutically inert carrier.

The invention relates in particular to the use of a compound of formula (I) for the preparation of a medicament for the treatment or prophylaxis of respiratory syncytial virus infection.

Said medicaments, e.g. in the form of pharmaceutical preparations, can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions with an effective amount of a compound as defined above.

The above-mentioned pharmaceutical composition can be obtained by processing the compounds according to this invention with pharmaceutically inert inorganic or organic carriers. For example, lactose, corn starch or derivatives thereof, talc, stearic acids or its salts and the like can be used, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical composition can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage depends on various factors such as manner of administration, species, age and/or individual state of health. The doses to be administered daily are about 5-400 mg/kg, preferably about 10-100 mg/kg, and can be taken singly or distributed over several administrations.

A compound of formula (I) when manufactured according to the above process is also an object of the invention.

This invention relates to the use of a compound of formula (I) for the manufacture of a medicament for treatment or prophylaxis of RSV infection.

The invention further relates to a method for the treatment or prophylaxis of respiratory syncytial virus infection, which method comprises administering an effective amount of a compound of formula (I).

The invention is illustrated by the following examples which have no limiting character. Unless explicitly otherwise stated, all reactions, reaction conditions, abbreviations and symbols have the meanings well known to a person of ordinary skill in organic chemistry.

EXAMPLES

Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp $C_{18}$ (5 μm, OBD™ 30×100 mm) column or SunFire™ Perp $C_{18}$ (5 μm, OBD™ 30×100 mm) column.

LC/MS spectra were obtained using a MicroMass Plateform LC (Waters™ alliance 2795-ZQ2000). Standard LC/MS conditions were as follows (running time 6 minutes):

Acidic condition: A: 0.1% formic acid in $H_2O$; B: 0.1% formic acid in acetonitrile;
Basic condition: A: 0.01% $NH_3.H_2O$ in $H_2O$; B: acetonitrile;
Neutral condition: A: $H_2O$; B: acetonitrile.

Mass spectra (MS): generally only ions which indicate the parent mass are reported, and unless otherwise stated the mass ion quoted is the positive mass ion $(M+H)^+$.

The microwave assisted reactions were carried out in a Biotage Initiator Sixty.

NMR Spectra were obtained using Bruker Avance 400 MHz.

All reactions involving air-sensitive reagents were performed under an argon atmosphere. Reagents were used as received from commercial suppliers without further purification unless otherwise noted.

Intermediate 1-1

2,4-Dichloro-8-methylquinoline

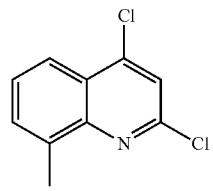

To a three necks round bottom flask equipped with a reflux condenser and thermometer containing phosphoryl chloride (400 mL) was added 2-methylaniline (50 g, 0.47 mol) and propanedioic acid (73 g, 0.7 mol). The mixture was heated and stirred at 95° C. for 16 hours and then 145° C. for 1 hour. The volatiles were evaporated in vacuo and the residual black oil was poured onto crashed ice with stirring. The resulting mixture was extracted with dichloromethane (300 mL×3). The combined organic layers were washed with a saturated aqueous solution of sodium bicarbonate until the water phase was pH 7-8, then washed with brine (300 mL), dried over sodium sulfate, filtered and concentrated in vacuo. The residue was purified by flash column chromatography (3% ethyl acetate in petroleum ether) to afford 65 g of the pure product (yield was 65.3%). MS obsd. $(ESI^+)$ $[(M+H)^+]$ 212.

Intermediate 1-2

2,4-Dichloro-6-(methylsulfanyl)quinoline

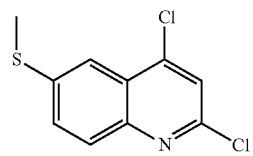

1-(Methylsulfanyl)-4-nitrobenzene

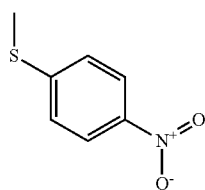

To a suspension of p-nitrothiophenol (20 g, 0.129 mol) in water (150 mL) was added an aqueous solution of sodium hydroxide (75 mL, 2 N) at room temperature. After the mixture was stirred for 15 minutes and cooled to 10° C., methyl iodide (57 g, 25 mL, 0.401 mol) was added slowly. The reaction mixture was allowed to warm to room temperature and stirred for 2.5 hours. The resulting mixture was extracted with diethyl ether (100 mL×3). The organic layers were combined, washed with water (200 mL) and brine (200 mL), dried over calcium sulfate and concentrated in vacuo. The residue was purified by silica gel column chromatography to afford 11 g of 1-(methylsulfanyl)-4-nitrobenzene as a yellow solid.

4-(Methylsulfanyl)aniline

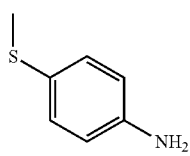

A suspension of 1-(methylsulfanyl)-4-nitrobenzene (10.5 g, 0.062 mol) and Raney nickel (5 g) in methanol (250 ml) was hydrogenated in a round flask equipped with a balloon filled with hydrogen at room temperature for 16 hours. The resulting mixture was filtered and concentrated in vacuo to afford 8.0 g of 4-(methylsulfanyl)aniline as colorless oil.

2,4-Dichloro-6-(methylsulfanyl)quinoline

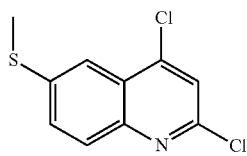

Intermediate 1-2 can be prepared in analogy to Intermediate 1-1 by using 4-(methylsulfanyl)aniline. MS obsd. (ESI$^+$) [(M+H)$^+$] 244.

Intermediate 1-3

6-Bromo-2,4-dichloroquinoline

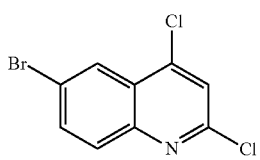 [SMILES: Clc1cc(Cl)c2cc(Br)ccc2n1]

Intermediate 1-3 can be prepared in analogy to Intermediate 1-1 by using 4-bromoaniline. MS obsd. (ESI$^+$) [(M+H)$^+$] 276.

Intermediate 1-4

2,4-Dichloro-5-methylquinoline

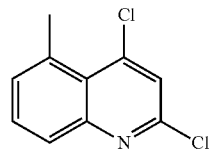

Intermediate 1-4 can be prepared in analogy to intermediate 1-1 by using 3-methylaniline. MS obsd. (ESI$^+$) [(M+H)$^+$] 212.

Intermediate 1-5

2,4-Dichloro-7-methylquinoline

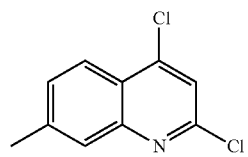

Intermediate 1-5 can be prepared in analogy to intermediate 1-1 by using 3-methylaniline. MS obsd. (ESI$^+$) [(M+H)$^+$] 212.

Intermediate 1-6

2,4-Dichloro-6-fluoro-quinoline

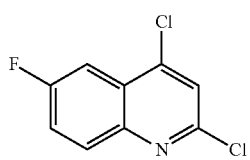 [SMILES: Fc1ccc2nc(Cl)cc(Cl)c2c1]

Intermediate 1-6 can be prepared in analogy to Intermediate 1-1 by using 4-fluoroaniline. MS obsd. (ESI$^+$) [(M+H)$^+$] 216.

Intermediate 1-8

2,4-Dichloro-6-trideuteriomethyl-quinoline

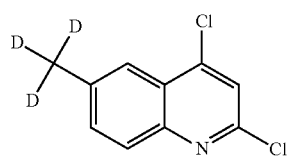 [SMILES: [2H]C([2H])([2H])c1ccc2nc(Cl)cc(Cl)c2c1]

Intermediate 1-8 can be prepared in analogy to Intermediate 1-1 by using 4-trideuteriomethylaniline. MS obsd. (ESI+) [(M+H)+] 215.

Intermediate 1-9

Methyl 2,4-dichloro-quinoline-6-carboxylate

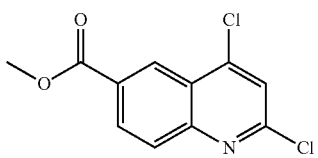 [SMILES: COC(=O)c1ccc2nc(Cl)cc(Cl)c2c1]

Intermediates 1-9 can be prepared in analogy to Intermediate 1-1 by using methyl 4-aminobenzoate. MS obsd. (ESI+) [(M+H)+] 256.

Intermediate 1-10

2,4-Dichloro-7,8-difluoro-6-methylquinoline

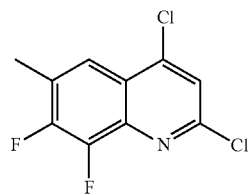

Intermediate 1-10 can be prepared in analogy to Intermediate 1-1 by using 2,3-difluoro-4-methylaniline. MS obsd. (ESI+) [(M+H)+] 248.

Intermediate 1-11

2,4-Dichloro-6-(trifluoromethoxy)quinoline

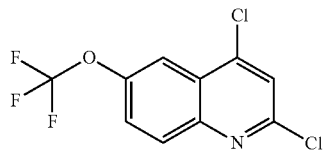 [SMILES: FC(F)(F)Oc1ccc2nc(Cl)cc(Cl)c2c1]

Intermediate 1-11 can be prepared in analogy to Intermediate 1-1 by using 4-(trifluoromethoxy)aniline. MS obsd. (ESI+) [(M+H)+] 282.

Intermediate 1-12

2,4-Dichloro-6-(difluoromethoxy)quinoline

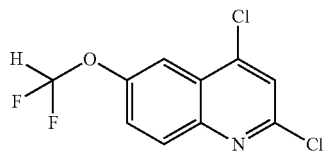 [SMILES: FC(F)Oc1ccc2nc(Cl)cc(Cl)c2c1]

Intermediate 1-12 can be prepared in analogy to Intermediate 1-1 by using 4-(difluoromethoxy)aniline. MS obsd. (ESI+) [(M+H)+] 264.

Intermediate 1-13

2,4-Dichloro-5-fluoro-6-methylquinoline

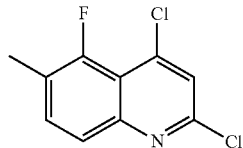

Intermediate 1-13 can be prepared in analogy to Intermediate 1-1 by using 3-fluoro-4-methylaniline. MS obsd. (ESI+) [(M+H)+] 230.

Intermediate 1-14

2,4-Dichloro-7-fluoro-6-methylquinoline

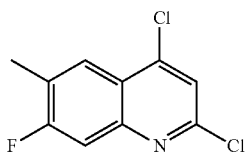

Intermediate 1-14 can be prepared in analogy to Intermediate 1-1 by using 3-fluoro-4-methylaniline. MS obsd. (ESI+) [(M+H)+] 230.

Intermediate 1-15

2,4-Dibromo-6-methylquinoline

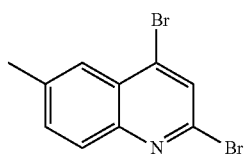

Intermediate 1-15 can be prepared in analogy to Intermediate 1-1 by using 4-methylaniline, propanedioic acid and phosphoryl bromide. MS obsd. (ESI+) [(M+H)+] 300, 1H NMR (400 MHz, CD3OD) δ ppm 7.92 (s, 1 H), 7.91-7.88 (d, J=0.8 Hz, 1 H), 7.80 (s, 1 H), 7.62-7.56 (dd, J=2.0, 8.4 Hz, 1 H), 2.57 (s, 3 H).

Intermediate 1-16

2,4-Dichloro-1,6-naphthyridine

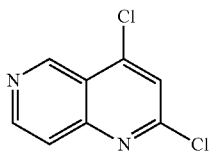 [SMILES: Clc1cc(Cl)c2cnccc2n1]

Methyl 4-aminopyridine-3-carboxylate

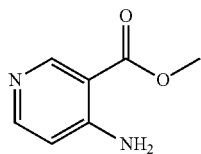

A mixture of compound 4-aminopyridine-3-carboxylic acid (100 g, 0.7 mol) and concentrated sulfuric acid (400 g, 4.0 mol) in absolute methanol (1.5 L) was stirred under reflux for 24 hours. The reaction mixture was concentrated in vacuo. The residue was diluted with ice-water (800 mL), basified with 2 N of aqueous solution of sodium hydroxide to about pH 10 and then extracted with ethyl acetate (300 mL×3). The combined organic layers were washed with water (500 mL), dried over sodium sulfate and concentrated in vacuo to afford the crude product, which was used for next step without further purification.

Methyl 4-(acetylamino)pyridine-3-carboxylate

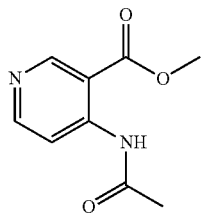

A mixture of methyl 4-aminopyridine-3-carboxylate (100 g, 0.6 mol) and acetic anhydride (240 g, 2.4 mol) in anhydrous 1,4-dioxane (1.2 L) was stirred at room temperature overnight. The reaction mixture was concentrated in vacuo and diluted with water (800 mL). The mixture was neutralized with a saturated aqueous solution of sodium bicarbonate to pH 7. The formed solid was collected by filtration and dried in vacuo to afford 50 g of methyl 4-(acetylamino)pyridine-3-carboxylate as a white solid.

1-Benzyl-4-hydroxy-1,6-naphthyridin-2(1H)-one

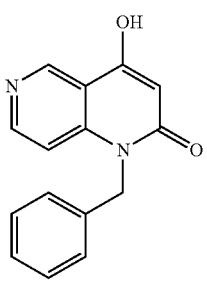 [SMILES: O=c1cc(O)c2cnccc2n1Cc1ccccc1]

A mixture of methyl 4-(acetylamino)pyridine-3-carboxylate (70 g, 0.36 mol) and sodium hydride (50 g, 1.25 mol, 60% in mineral oil) in anhydrous tetrahydrofuran (800 mL) was stirred at room temperature for 30 minutes. To the above mixture was added bromomethylbenzene (60 g, 0.36 mmol) and the resulting mixture was stirred at room temperature overnight. The reaction mixture was poured onto crashed ice (600 mL), concentrated in vacuo, and washed with ethyl acetate (400 mL). The aqueous layer was neutralized by addition of 3 N aqueous solution of hydrochloric acid to pH 7. The formed solid was collected by filtration and dried in vacuo to afford 24 g of 1-benzyl-4-hydroxy-1,6-naphthyridin-2(1H)-one as a pale yellow solid.

1,6-Naphthyridine-2,4(1H,3H)-dione

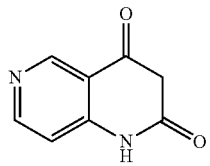

A mixture of 1-benzyl-4-hydroxy-1,6-naphthyridin-2 (1H)-one (21 g, 0.08 mol) and trifluoromethanesulfonic acid (100 mL) was heated with stirring at 120° C. overnight. The reaction mixture was used for the next step directly.

2,4-Dichloro-1,6-naphthyridine

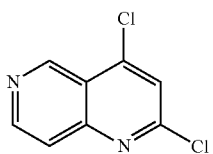

A mixture of 1,6-naphthyridine-2,4(1H,3H)-dione (10 g, 0.06 mol) and phosphoryl chloride (180 g) was heated with stirring at 100° C. for 3 hours. The reaction mixture was cooled to room temperature and concentrated in vacuo. The residue was poured into ice-water (200 g) and extracted with ethyl acetate (200 mL×5). The combined organic layers were dried over sodium sulfate, concentrated in vacuo to afford the crude product. $^1$H NMR (400 MHz, CD$_3$OD) δ ppm 9.57 (s, 1 H), 8.90-8.89 (d, J=5.6 Hz, 1 H), 8.12 (s, 1 H), 7.94-7.93 (d, J=6.0 Hz, 1 H).

Intermediate 1-17

2,4-Dichloro-6-difluoromethylquinoline

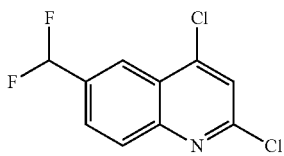 [SMILES: FC(F)c1ccc2nc(Cl)cc(Cl)c2c1]

4-Aminobenzaldehyde

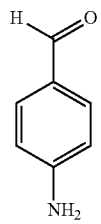

To a solution of 4-nitrobenzaldehyde (2.0 g, 0.133 mol) in acetic acid (150 mL) and water (15 mL) was added iron powder (1.48 g, 0.265 mol). The reaction was stirred overnight at room temperature. The mixture was filtered and extracted with dichloromethane (50 mL×3). Then the organic layer was dried over sodium sulfate, filtered and concentrated in vacuo. The residue was purified by flash column chromatography (eluting with 10% ethyl acetate in petroleum ether) to afford 1.2 g of the pure product (yield was 75%).

2,4-Dichloroquinoline-6-carbaldehyde

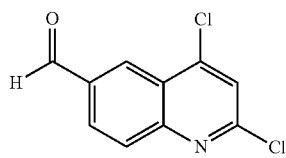 [SMILES: O=Cc1ccc2nc(Cl)cc(Cl)c2c1]

A mixture of 4-aminobenzaldehyde (14 g, 0.116 mol), propanedioic acid (14.4 g, 0.139 mol) and phosphoryl chloride (180 g) was heated with stirring at 95° C. for 16 hours. The reaction mixture was cooled to room temperature and concentrated in vacuo. The residue was purified by flash column chromatography afford 150 mg of the pure product (yield was 0.57%).

2,4-Dichloro-6-difluoromethylquinoline

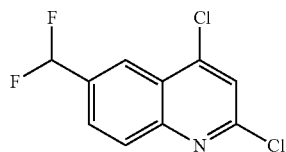 [SMILES: FC(F)c1ccc2nc(Cl)cc(Cl)c2c1]

A mixture of 2,4-dichloroquinoline-6-carbaldehyde (45.2 mg, 0.2 mmol) and diethylaminosulfur trifluoride (32.2 mg, 0.2 mmol) in 1,2-dichloroethane (15 mL) was refluxed overnight. The reaction mixture was cooled to room temperature and concentrated in vacuo. The residue was purified by thin layer chromatography to afford 20 mg of the desired product (yield was 40.3%), MS obsd. (ESI$^+$) [(M+H)$^+$] 248, $^1$H NMR (400 MHz, CDCl$_3$) δ ppm 8.28 (s, 1 H), 8.10-8.05 (d, J=8.8 Hz, 1 H), 7.90-7.82 (d, J=8.4 Hz, 1 H), 7.53 (s, 1 H), 6.95-6.62 (t, J=56 Hz, 1 H).

Intermediate 2-1

2,3,4,5-Tetrahydro-1,4-benzothiazepine

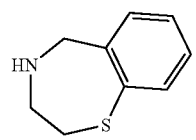 [SMILES: c1ccc2c(c1)CNCCS2]

Methyl 2-sulfanylbenzoate

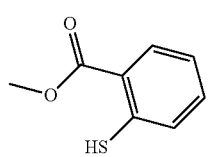

To a cooled solution of concentrated sulfuric acid (72 g) in methanol (1.5 L) at 0° C., was added 2-sulfanylbenzoic acid (300 g, 1.95 mol) in portions under argon atmosphere. After being refluxed with stirring for 18 hours, the reaction mixture was concentrated in vacuo. The residue was diluted with water (800 mL), basified with a saturated aqueous solution of sodium bicarbonate to about pH 7, and extracted with dichloromethane (600 mL×3). The combined organic layers were washed with brine (800 mL), dried over sodium sulfate, filtered and concentrated in vacuo to afford 300 g of methyl 2-sulfanylbenzoate (yield was 91%) as a light yellow oil, which was used for the next step without further purification.

3,4-Dihydro-1,4-benzothiazepin-5(2H)-one

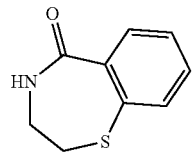 [SMILES: O=C1NCCSc2ccccc21]

To a cooled solution of methyl 2-sulfanylbenzoate (200 g, 1.19 mol) in tetrahydrofuran and N,N-dimethylformamide (2 L, V/V=1/1) was added 2-chloroethanamine hydrochloride (138 g, 1.19 mol) at 0° C. followed by sodium hydride (143 g, 3.57 mol, 60% in mineral oil) in portions. After being stirred at room temperature overnight, the reaction mixture was poured into ice-water and extracted with ethyl acetate (900 mL×4). The organic layers were combined, washed with brine (900 mL×3), dried over sodium sulfate and concentrated in vacuo. The residue was stirred in a mixture solution of ethyl acetate and petroleum ether (300 mL, V/V=1/1) for 1 hour. The solid was collected by filtration and dried in vacuo to afford 100 g of 3,4-dihydro-1,4-benzothiazepin-5(2H)-one (yield was 47%).

2,3,4,5-Tetrahydro-1,4-benzothiazepine

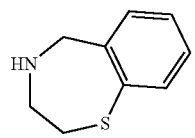 [SMILES: c1ccc2c(c1)CNCCS2]

To a bottle containing a cooled suspension of lithium aluminum hydride (44 g, 1.17 mol) in dry tetrahydrofuran (1.5 L) was added 3,4-dihydro-1,4-benzothiazepin-5(2H)-one (150 g, 0.84 mol) in portions at 0° C. After being refluxed for 18 hours, the reaction mixture was cooled to 0° C., followed by addition of water (25 mL) dropwise. The reaction mixture was then filtered through a pad of celite and washed with dichloromethane. The filtrate was dried over sodium sulfate and evaporated in vacuo to afford 125 g of 2,3,4,5-tetrahydro-1,4-benzothiazepine (yield was 90%), which was used for the next step without further purification.

Intermediate 2-2 and 2-3

8-Methoxy-2,3,4,5-tetrahydro-1,4-benzothiazepine (Intermediate 2-2) and 8-Fluoro-2,3,4,5-tetrahydro-1,4-benzothiazepine (Intermediate 2-3)

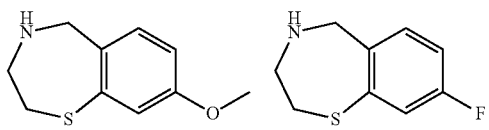

4-Fluoro-2-sulfanylbenzoic acid

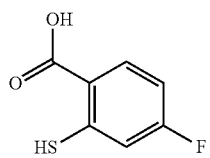

To a cooled solution of 2-amino-4-fluoro-benzoic acid (0.93 g, 6 mmol) in water (3 mL) was added concentrated hydrochloric acid (1.2 mL), then a cold solution of sodium nitrite (0.41 g, 6 mmol) in water (2 mL) was added dropwise at 5° C. After the addition, the mixture was stirred for 30 minutes at that temperature. A cooled solution of disodium disulphide prepared with boiled water (2 mL), sodium sulfide nonahydrate (1.57 g, 6.66 mmol), sulfur (0.2 g, 6.6 mmol) and a solution of sodium hydroxide (0.6 mL, 10 mol/L) was added dropwise into the above mixture at 5° C. After being stirred for 2 hours at room temperature, the mixture was acidified with hydrochloric acid. The formed precipitate was filtered, washed with water, and dried in vacuo to afford 1.4 g of the disulfide derivative as a yellow solid (yield was 70%). MS obsd. (ESI⁻) [(M−H)⁻] 341.

A mixture of disulfide (1.4 g, 4.1 mmol) and zinc powder (0.18 g, 2.76 mmol) in acetic acid (5 mL) was refluxed for 4 hours, and then cooled to room temperature. The formed precipitate was collected by filtration, and then boiled in an aqueous solution of sodium hydroxide (0.15 g in 1.2 mL of water) for 30 minutes. After being cooled to 0° C., the mixture was acidified with hydrochloric acid. The formed solid was collected by filtration, washed with water, and dried in vacuo to afford 0.5 g of the product (yield was 36%). MS obsd. (ESI⁻) [(M−H)⁻] 171.

Methyl 4-fluoro-2-sulfanylbenzoate

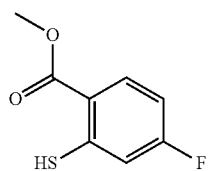

A mixture of 4-fluoro-2-sulfanylbenzoic acid (6.0 g, 34.9 mmol), concentrated sulfuric acid (6 mL) in methanol (200 mL) was refluxed for 18 hours under argon atmosphere. The resulting mixture was concentrated in vacuo. The residue was diluted with ethyl acetate, washed with water, basified with a saturated aqueous solution of sodium bicarbonate to about pH 8. The organic layer was washed with brine, dried over sodium sulfate, and concentrated in vacuo to afford 4.54 g of the crude product as a brown oil (yield was 70%), which was used directly for the next step without further purification. MS obsd. (ESI⁻) [(M−H)⁻] 185.

8-Methoxy-3,4-dihydro-1,4-benzothiazepin-5(2H)-one and 8-Fluoro-3,4-dihydro-1,4-benzothiazepin-5(2H)-one

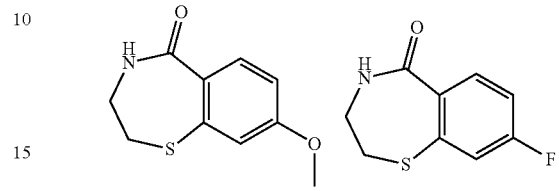

To a solution of methyl 4-fluoro-2-sulfanylbenzoate (3.0 g, 16 mmol) and 2-chloroethanamine hydrochloride (1.88 g, 16 mmol) in N,N-dimethylformamide (30 mL), sodium hydride (1.94 g, 48 mmol, 60% in mineral oil) was added in portions. The reaction mixture was stirred at 100° C. overnight. The solvent was removed under reduced pressure. The residue was diluted with water, then a mixture of ethyl acetate and petroleum ether (1/10, V/V). The resulting mixture was stirred for 1 hour. The resulting precipitate was collected by filtration, washed with diethyl ether and petroleum ether, dried in vacuo to afford a mixture of 8-methoxy-3,4-dihydro-1,4-benzothiazepin-5(2H)-one and 8-fluoro-3,4-dihydro-1,4-benzothiazepin-5(2H)-one. The above mixture was purified by flash column to afford 0.75 g of the product 8-methoxy-3,4-dihydro-1,4-benzothiazepin-5(2H)-one as a pale white solid (yield was 22%), MS obsd. (ESI⁺) [(M+H)⁺] 210, and 0.75 g of the product 8-fluoro-3,4-dihydro-1,4-benzothiazepin-5(2H)-one as a pale white solid (yield was 23%), MS obsd. (ESI⁺) [(M+H)⁺] 198.

Intermediate 2-2

8-Methoxy-2,3,4,5-tetrahydro-1,4-benzothiazepine

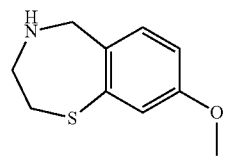

Intermediate 2-2 can be prepared in analogy to intermediate 2-1 by using 8-methoxy-3,4-dihydro-1,4-benzothiazepin-5(2H)-one (yield was 90%). MS obsd. (ESI⁺) [(M+H)⁺] 196.

Intermediate 2-3

8-Fluoro-2,3,4,5-tetrahydro-1,4-benzothiazepine

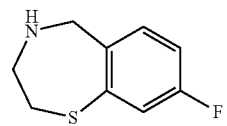 [SMILES: Fc1ccc2c(c1)SCCNC2]

Intermediate 2-3 can be prepared in analogy to intermediate 2-1 by using 8-fluoro-3,4-dihydro-1,4-benzothiazepin-5(2H)-one (yield was 96%). MS obsd. (ESI$^+$) [(M+H)$^+$] 184.

Intermediate 2-4

7-Fluoro-2,3,4,5-tetrahydro-1,4-benzothiazepine

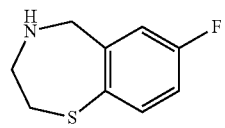 [SMILES: Fc1ccc2c(c1)CNCCS2]

Intermediate 2-4 can be prepared in analogy to intermediate 2-1 by using 5-fluoro-2-sulfanylbenzoic acid. MS obsd. (ESI$^+$) [(M+H)$^+$] 184.

Intermediate 2-5

9-Fluoro-2,3,4,5-tetrahydro-1,4-benzothiazepine

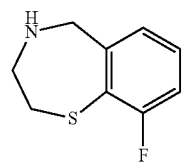 [SMILES: Fc1cccc2c1SCCNC2]

Intermediate 2-5 can be prepared in analogy to intermediate 2-1 by using 3-fluoro-2-sulfanylbenzoic acid. MS obsd. (ESI$^+$) [(M+H)$^+$] 184.

Intermediate 2-6

8-Methyl-2,3,4,5-tetrahydro-1,4-benzothiazepine

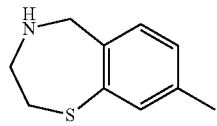

Methyl 2-hydroxy-4-methylbenzoate

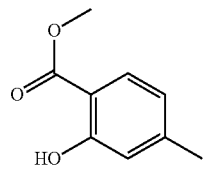

A mixture of 2-hydroxy-4-methylbenzoic acid (100.0 g, 657.2 mmol), concentrated sulfuric acid (50 mL) in methanol (1000 mL) was refluxed for 20 hours under nitrogen atmosphere. The resulting mixture was concentrated in vacuo. The residue was poured into ice-water, extracted with ethyl acetate (1000 mL). The organic layer was washed with saturated sodium bicarbonate, brine, dried over sodium sulfate, concentrated in vacuo to afford 109 g of the crude product of methyl 2-hydroxy-4-methylbenzoate as light brown oil, which was used directly in the next step without further purification.

Methyl 2-[(dimethylcarbamothioyl)oxy]-4-methylbenzoate

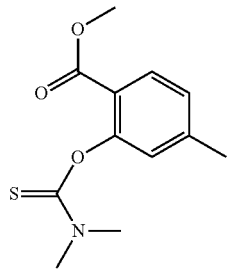 [SMILES: COC(=O)c1ccc(C)cc1OC(=S)N(C)C]

To a solution of methyl 2-hydroxy-4-methylbenzoate (109 g, 657.2 mmol) and 1,4-diazabicyclo[2.2.2]octane (147.4 g, 1314.4 mmol) in N,N-dimethylformamide (300 mL) was added a solution of N,N-dimethylcarbamothioyl chloride (97.5 g, 788.6 mmol) in N,N-dimethylformamide (100 mL) at room temperature. After being heated at 60° C. for 4 hours, the mixture was cooled and poured onto ice. The formed precipitate was collected by filtration, washed with water (300 mL×3) and dried in vacuo to afford 137 g of methyl 2-[(dimethylcarbamothioyl)oxy]-4-methylbenzoate as an off-white solid (yield was 82%).

Methyl 2-[(dimethylcarbamoyl)sulfanyl]-4-methylbenzoate

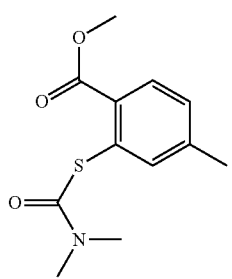 [SMILES: COC(=O)c1ccc(C)cc1SC(=O)N(C)C]

Methyl 2-[(dimethylcarbamothioyl)oxy]-4-methylbenzoate (52.0 g, 205.5 mmol) in a round bottle flask which was vacuumed and backfilled with nitrogen, was heated at 210° C. for 4 hours. The mixture was then cooled to room temperature and used for next step without further purification.

4-Methyl-2-sulfanylbenzoic acid

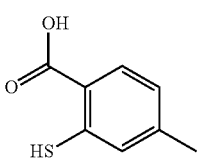

A round bottle flask containing a mixture of methyl 2-[(dimethylcarbamoyl)sulfanyl]-4-methylbenzoate (50 g, 197.6 mmol) and an aqueous solution of sodium hydroxide (120 mL, 4 N) was vacuumed and backfilled with nitrogen 3 times. After being refluxed for 2 hours, the resulting mixture was cooled to 0° C. and acidified with an aqueous solution of hydrochloric acid (45 mL, 6 N). The formed precipitate was collected by filtration, and then dissolved in ethyl acetate (500 mL). The solution was dried over anhydrous sodium sulfate, and concentrated in vacuo to afford 4-methyl-2-sulfanylbenzoic acid as a light yellow solid.

8-Methyl-2,3,4,5-tetrahydro-1,4-benzothiazepine

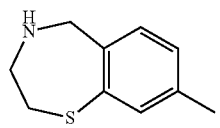

Intermediate 2-6 can be prepared in analogy to intermediate 2-1 by using 4-methyl-2-sulfanylbenzoic acid. MS obsd. (ESI⁺) [(M+H)⁺] 180.

Intermediate 2-7

8-Chloro-2,3,4,5-tetrahydro-1,4-benzothiazepine

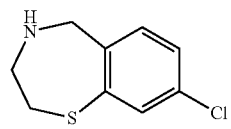 [SMILES: Clc1ccc2c(c1)SCCNC2]

4-Chloro-2-sulfanylbenzoic acid

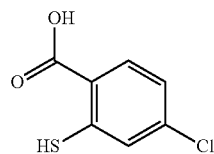 [SMILES: O=C(O)c1ccc(Cl)cc1S]

To a cooled mixture of concentrated hydrochloric acid (6 mL) and ice (10 g) was added slowly a solution of 2-amino-4-chlorobenzoic acid (4 g, 23.3 mmol), sodium hydroxide (0.94 g, 23.5 mmol) and sodium nitrite (1.6 g, 23.3 mmol) in water (30 mL) in an ice bath. The resulting mixture was stirred at 0° C. for 1 hour. A solution of potassium ethoxymethanedithioate (20.8 g, 65.2 mmol) in water (40 mL) in a beaker was heated to 65° C. The cold diazonium salt solution was added slowly to the above hot solution while evolution of gas was observed. After the addition the mixture was cooled to room temperature and acidified to about pH 3 with an aqueous solution of hydrochloric acid (4 N). The aqueous phase was decanted from the resulting semisolid and the sludge was dissolved in 10% aqueous sodium hydroxide (20 mL). The solution was heated for 2 hours at 100° C. followed by addition of sodium hydrosulfite (2 g). The resulting mixture was heated with stirring at 100° C. for an additional 10 minutes, then cooled to room temperature and filtered through a pad of celite. The filtrate was acidified to about pH 4 with concentrated hydrochloric acid. The formed solid was collected by filtration, washed with water, and dissolved in methanol (10 mL) and diethyl ether (150 mL). The solution was dried over sodium sulfate and concentrated in vacuo to afford 2.8 g of 4-chloro-2-sulfanylbenzoic acid as a yellow solid (yield was 63%).

8-Chloro-2,3,4,5-tetrahydro-1,4-benzothiazepine

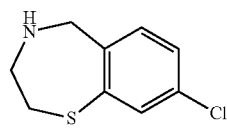 [SMILES: Clc1ccc2c(c1)SCCNC2]

Intermediate 2-7 can be prepared in analogy to intermediate 2-1 by using 4-chloro-2-sulfanylbenzoic acid. MS obsd. (ESI [(M+H)⁺] 200.

Intermediate 3

5-Methyl-2,3,4,5-tetrahydro-1,4-benzothiazepine

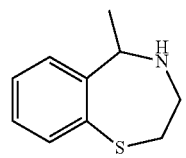

1-(2-Sulfanylphenyl)ethanone

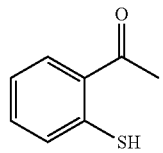

To a stirred suspension of aluminium chloride (10.50 g, 78.8 mmol) in dry benzene (200 mL) was added a solution of 1-[2-(benzylsulfanyl)phenyl]ethan-1-one (11.93 g, 49.2 mmol) in dry benzene (100 mL) dropwise in an ice bath under argon atmosphere. After the reaction mixture being stirred at room temperature overnight, the reaction was quenched by the cautious addition of ice-water. The separated organic layer was washed with water and extracted with 5% aqueous solution of sodium hydroxide (300 mL). The aqueous layer was acidified to about pH 3 with concentrated hydrochloric acid (12 N) and extracted with dichloromethane (300 mL×3). The combined organic layers were washed with brine, dried over anhydrous sodium sulfate, concentrated in vacuo to afford 6.47 g of the crude product 1-(2-sulfanylphenyl)ethanone.

5-Methyl-2,3-dihydro-1,4-benzothiazepine

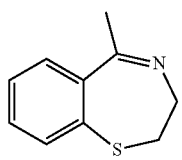

To a solution of 1-(2-sulfanylphenyl)ethanone (6.40 g, 42.05 mmol) in ethanol (80 mL) was added an aqueous solution of potassium hydroxide (7.08 g, 126.14 mmol in 30 mL of water) and an aqueous solution of 2-bromoethanamine hydrobromide (9.48 g, 46.25 mmol in 30 mL of water). After being stirred at room temperature for 6 hours, the reaction mixture was concentrated in vacuo to remove most of ethanol and extracted with dichloromethane (60 mL×3). The combined organic layers were washed with brine (100 mL), dried over anhydrous sodium sulfate, and concentrated in vacuo. The residue was purified by flash column chromatography to give 5.92 g of 5-methyl-2,3-dihydro-1,4-benzothiazepine.

5-Methyl-2,3,4,5-tetrahydro-1,4-benzothiazepine

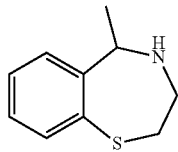

To a solution of 5-methyl-2,3-dihydro-1,4-benzothiazepine (5.92 g, 33.40 mmol) in methanol (100 mL) was added a solution of sodium borohydride (3.16 g, 83.49 mmol) in water (60 mL). After being stirred at room temperature overnight, the reaction mixture was acidified with concentrated hydrochloric acid, and then stirred at room temperature for 30 minutes. After being adjusted to pH 9 with an aqueous solution of sodium hydroxide, the resulting mixture was extracted with ethyl acetate (60 mL×3). The combined organic layers were washed by brine (100 mL), dried over anhydrous sodium sulfate, and concentrated in vacuo to afford 5.6 g of 5-methyl-2,3,4,5-tetrahydro-1,4-benzothiazepine, MS obsd. (ESI$^+$) [(M+H)$^+$] 180.

Intermediate 4

1-(1,1-Dioxido-2,3-dihydro-1,4-benzothiazepin-4 (5H)-yl)ethanone

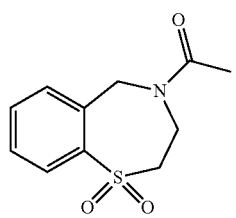 [SMILES: CC(=O)N1CCS(=O)(=O)c2ccccc2C1]

1-(2,3-Dihydro-1,4-benzothiazepin-4(5H)-yl)ethanone

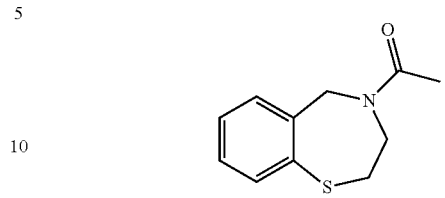

To a solution of 2,3,4,5-tetrahydro-1,4-benzothiazepine (5 g, 30.3 mmol) in dry dichloromethane (100 mL) was added triethylamine (5.06 mL, 36.3 mmol) at room temperature, followed by the dropwise addition of acetic anhydride (3.43 mL, 36.3 mmol) at 0° C. under nitrogen. The resulting solution was stirred for 1 hour whilst allowing the temperature to rise slowly to room temperature. The mixture was washed with brine (50 mL×2), dried over sodium sulfate, filtered and concentrated in vacuo to afford 6.28 g of product as yellow oil, which was used for next step without further purification.

1-(1,1-Dioxido-2,3-dihydro-1,4-benzothiazepin-4 (5H)-yl)ethanone

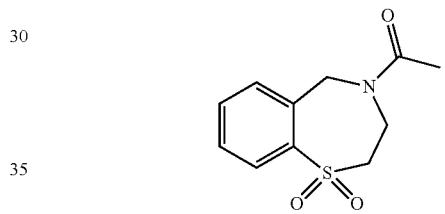

To a cooled solution of 1-(2,3-dihydro-1,4-benzothiazepin-4(5H)-yl)ethanone (6.27 g, 30.2 mmol) in dichloromethane (100 mL) was added a suspension of 3-chloroperoxybenzoic acid (20.9 g, 90.8 mmol, 75% purity) in dichloromethane (50 mL) at 10° C. After the addition, the resulting mixture was stirred for 1 hour whilst allowing the temperature to rise slowly to room temperature. The mixture was washed with a saturated aqueous solution of sodium carbonate (100 mL×2), a saturated aqueous solution of sodium sulfite (100 mL×2) and brine (100 mL). The organic layer was dried over sodium sulfate, filtered and concentrated in vacuo. The residue was stirred in diethyl ether (50 mL) and the solid was collected by filtration and dried in vacuo to afford 6 g of 1-(1,1-dioxido-2,3-dihydro-1,4-benzothiazepin-4(5H)-yl)ethanone as a white powder.

Intermediate 5

2,3,4,5-Tetrahydro-1,4-benzothiazepine 1,1-dioxide

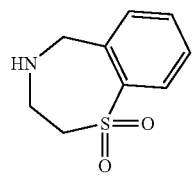 [SMILES: O=S1(=O)CCNCc2ccccc21]

To a solution of 1-(1,1-dioxido-2,3-dihydro-1,4-benzothiazepin-4(5H)-yl)ethanone (240 g, 1.0 mol) in ethanol (1.0 L) was added sodium hydroxide (200 g, 5.0 mol) and water (700 mL). The mixture was refluxed overnight and then concentrated in vacuo. The residue was extracted by ethyl acetate (1500 mL×4). The combined organic layers were extracted by hydrochloric acid (2000 mL, 3 N). The acidic aqueous layer was washed with ethyl acetate (1500 mL×2), then basified with a saturated aqueous solution of sodium bicarbonate to pH >7, and extracted with ethyl acetate (1500 mL×4). The combined organic layers were dried over sodium sulfate, filtered and concentrated in vacuo to afford 151 g of 2,3,4,5-tetrahydro-1,4-benzothiazepine 1,1-dioxide (yield was 76%), MS obsd. (ESI$^+$) [(M+H)$^1$] 198, $^1$H NMR (400 MHz, DMSO-d$^6$) δ ppm 7.89 (dd, J=1.2, 7.6 Hz, 1 H), 7.56 (t, J=7.6 Hz, 1 H), 7.47 (t, J=7.6 Hz, 1 H), 7.42 (d, J=7.6 Hz, 1 H), 4.04 (s, 2 H), 3.32-3.30 (m, 2 H), 3.30-3.25 (m, 2 H), 2.64 (s, 1 H).

Intermediate 6

2,3,4,5-Tetrahydro-1,4-benzothiazepine 1-oxide

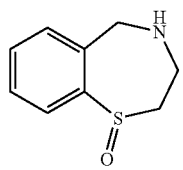 [SMILES: O=S1CCNCc2ccccc21]

1-(1-Oxido-2,3-dihydro-1,4-benzothiazepin-4(5H)-yl)ethanone

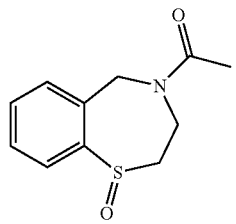

To a cooled solution of 1-(2,3-dihydro-1,4-benzothiazepin-4(5H)-yl)ethanone (70 g, 0.33 mol) in dichloromethane (700 mL) was added a solution of 3-chloroperoxybenzoic acid (67 g, 0.33 mol) in dichloromethane (800 mL) dropwise at 0° C. After the addition, the reaction was stirred at the same temperature for 15 minutes. The resulting reaction mixture was washed with a saturated aqueous solution of sodium carbonate (500 mL×2) and a saturated aqueous solution of sodium sulfite (500 mL×2). The combined aqueous layers were extracted with dichloromethane (200 mL×2), dried over sodium sulfate and concentrated in vacuo. The residue was purified by flash chromatography (eluting with 1-2% methanol in dichloromethane) to afford 57 g of the desired product (yield was 77%).

2,3,4,5-Tetrahydro-1,4-benzothiazepine 1-oxide

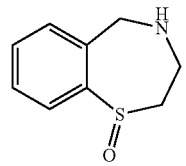 [SMILES: O=S1CCNCc2ccccc21]

Intermediate 6 was prepared in analogy to intermediate 5 by using 1-(1-oxido-2,3-dihydro-1,4-benzothiazepin-4(5H)-yl)ethanone (yield was 66%), MS obsd. (ESI$^+$) [(M+H)$^+$] 181, $^1$H NMR (400 MHz, CD$_3$OD) δ ppm 7.72 (dd, J=1.6, 7.6 Hz, 1 H), 7.52-7.48 (m, 2 H), 7.33 (dd, J=1.6, 7.2 Hz, 1 H), 4.21-4.11 (m, 1 H), 3.82-3.80 (m, 1 H), 3.62-3.50 (m, 2 H), 3.22-3.19 (m, 2 H).

Intermediate 7

(5Z)—N-Methoxy-1,2,3,4-tetrahydro-5H-2-benzazepin-5-imine

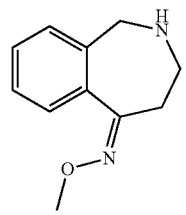

A mixture of 1,2,3,4-tetrahydro-1-benzazepin-5-one (500 mg, 2.530 mmol), O-methyl hydroxylamine hydrochloride (211 mg, 2.530 mmol), sodium acetate (208 mg, 2.530 mmol) and sodium carbonate (536 mg, 5.060 mmol) in ethanol was refluxed for 3 hours. The resulting mixture was concentrated in vacuo to remove ethanol and to the residue was added water (15 mL). The residue in water was extracted with dichloromethane (15 mL×3). The organic layers were combined, dried over sodium sulfate, and concentrated in vacuo to afford 326 mg of the desired product (yield was 67%).

Intermediate 8

5,5-Difluoro-2,3,4,5-tetrahydro-1H-benzazepine

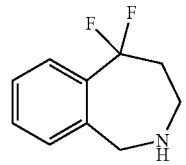 [SMILES: FC1(F)CCNCc2ccccc21]

1-(5,5-Difluoro-1,3,4,5-tetrahydro-2H-2-benzazepin-2-yl)-2,2,2-trifluoroethanone

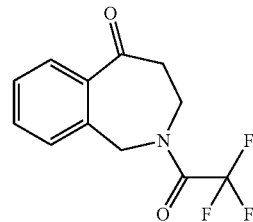 [SMILES: O=C1CCN(C(=O)C(F)(F)F)Cc2ccccc21]

To a cooled solution of 1,2,3,4-tetrahydro-1-benzazepin-5-one hydrochloride (33.7 g, 0.17 mol) in dichloromethane (500 mL) at 0° C., was added triethylamine (52 g, 0.51 mol) dropwise followed by trifluoroacetic anhydride (36 g, 0.17 mmol). After being stirred at room temperature for 3 hours, the resulting mixture was diluted with water (300 mL). The aqueous layer was extracted with dichloromethane (500 mL). The combined organic layers were washed with a saturated aqueous solution of sodium bicarbonate (500 mL) and brine (500 mL), dried over sodium sulfate and concentrated in vacuo. The residue was purified by flash chromatography (eluting with 16% ethyl acetate in petroleum ether) to afford 40 g of the desired product (yield was 89%).

1-(5,5-Difluoro-1,3,4,5-tetrahydro-2H-2-benzazepin-2-yl)-2,2,2-trifluoroethanone

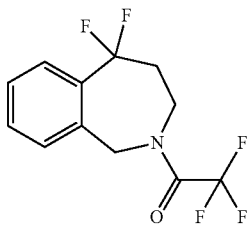 [SMILES: O=C(N1CCC(F)(F)c2ccccc2C1)C(F)(F)F]

A solution of 2-(trifluoroacetyl)-1,2,3,4-tetrahydro-5H-2-benzazepin-5-one (40 g, 0.156 mol) in N,N-diethylaminosulflur trifluoride (104 g, 0.468 mol) was heated at 70° C. for 3 hours. The reaction mixture was poured into ice-water (600 mL) and extracted with dichloromethane (800 mL). The organic layer was washed with a saturated aqueous solution of sodium bicarbonate (500 mL) and brine (500 mL), dried over sodium sulfate, and concentrated in vacuo. The residue was purified by flash chromatography (eluting with 16% ethyl acetate in petroleum ether) to give 33 g of the desired product (yield was 76%).

5,5-Difluoro-2,3,4,5-tetrahydro-1H-benzazepine

To a cooled solution of 1-(5,5-difluoro-1,3,4,5-tetrahydro-2H-2-benzazepin-2-yl)-2,2,2-trifluoroethanone (33 g, 0.184 mmol) in methanol was added an ammonia methanol solution (300 mL, 7 M) at 0° C. After being stirred at 0° C. for 2 hours, the reaction mixture was concentrated in vacuo. The residue was purified by flash chromatography (eluting with 1025% ethyl acetate in petroleum ether) to afford 18 g of the desired product as a purple oil (yield was 83.3%), MS obsd. (ESI+) [(M+H)+] 184, $^1$H NMR (400 MHz, CDCl$_3$) δ ppm 7.64-7.60 (m, 1 H), 7.34-7.25 (m, 2 H), 7.16-7.14 (m, 1 H), 7.01 (s, 2 H), 3.33-3.30 (m, 2 H), 2.33-2.24 (m, 2 H).

Intermediate 9-1

3-(Aminomethyl)-N,N-dibenzyltetrahydrofuran-3-amine

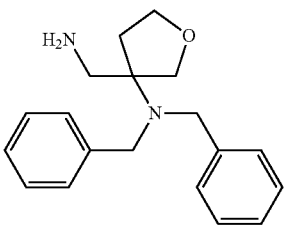 [SMILES: NCC1(N(Cc2ccccc2)Cc2ccccc2)CCOC1]

3-(Dibenzylamino)tetrahydrofuran-3-carbonitrile

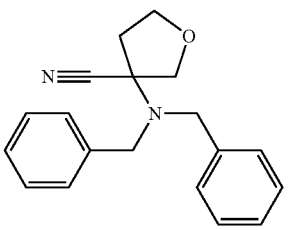 [SMILES: N#CC1(N(Cc2ccccc2)Cc2ccccc2)CCOC1]

To a cooled solution of dibenzylamine (31.9 g, 162 mmol) in acetic acid (100 mL) at 0° C., dihydrofuran-3(2H)-one (7.0 g, 81 mmol) was added followed by trimethylsilyl-formonitrile (14.4 g, 145.8 mmol). After being stirred at room temperature for 16 hours, the reaction mixture was poured into water (100 mL), adjusted to pH 7 with sodium bicarbonate, exacted with ethyl acetate (100 mL×2). The combined organic layers were washed with brine (150 mL), dried over sodium sulfate and concentrated in vacuo. The residue was purified by column chromatography to afford 2.2 g of the desired product (yield was 9.28%).

3-(Aminomethyl)-N,N-dibenzyltetrahydrofuran-3-amine

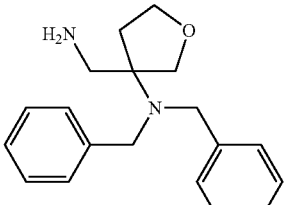

To a cooled solution of 3-(dibenzylamino)tetrahydrofuran-3-carbonitrile (2.2 g, 7.5 mmol) in tetrahydrofuran (50 mL) at 0° C., was added lithium aluminium hydride (855 mg, 22.5 mmol). After the mixture being stirred for 16 hours at room temperature, the reaction was quenched by addition of water (5 mL). The resulting mixture was filtered and the filtrate was concentrated in vacuo to afford 1.3 g of the crude product (yield was 58%).

Intermediate 9-2

3-(Aminomethyl)-N,N-dibenzyloxetan-3-amine

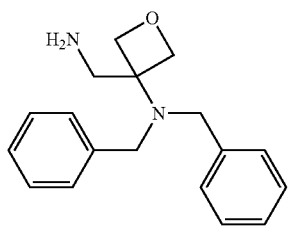 [SMILES: NCC1(N(Cc2ccccc2)Cc2ccccc2)COC1]

Intermediate 9-2 can be prepared in analogy to intermediate 9-1 by using oxetan-3-one. MS obsd. (ESI$^+$) [(M+H)$^+$] 283.

Intermediate 9-3

1-(Aminomethyl)-N,N-dibenzylcyclobutanamine

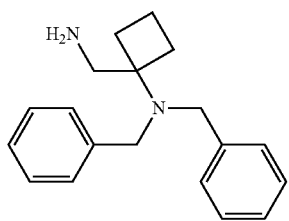 [SMILES: NCC1(N(Cc2ccccc2)Cc2ccccc2)CCC1]

Intermediate 9-3 can be prepared in analogy to intermediate 9-1 by using cyclobutanone. MS obsd. (ESI$^+$) [(M+H)$^+$] 281.

Intermediate 9-4

3-(Aminomethyl)-N,N-dibenzylthietan-3-amine

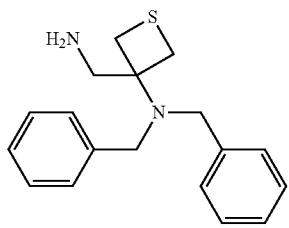 [SMILES: NCC1(N(Cc2ccccc2)Cc2ccccc2)CSC1]

3,3-Dimethoxythietane

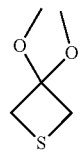

To a solution of 1,3-dibromo-2,2-dimethoxy-propane (102 g, 389 mmol) in N,N-dimethylformamide (1200 mL) was added sodium sulfide (66.8 g, 506 mmol), the mixture was refluxed for 3 days. The mixture was cooled to room temperature, diluted with diethyl ether (1200 mL), washed with water (1200 mL) and brine (1200 mL), dried over sodium sulphate and concentrated in vacuo to afford 40 g of the product as a yellowish oil (yield was 77%).

Thietan-3-one

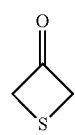

To a solution of 3,3-dimethoxythietane (40 g, 600 mmol) in dichloromethane (2500 mL) was added dioxosilane (160 g). The mixture was refluxed for 2 days. The mixture was cooled to room temperature and filtered through a pad of celite. The filtrate was concentrated in vacuo to afford the desired product.

3-(Aminomethyl)-N,N-dibenzylthietan-3-amine

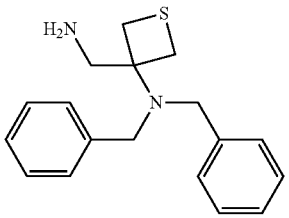 [SMILES: NCC1(N(Cc2ccccc2)Cc2ccccc2)CSC1]

Intermediate 9-4 can be prepared in analogy to intermediate 9-1 by using thietan-3-one. MS obsd. (ESI$^+$) [(M+H)$^+$] 299, $^1$H NMR (400 MHz, CD$_3$OD) δ ppm 7.21-7.14 (m, 8 H), 7.11-7.08 (m, 2 H), 3.74 (s, 4 H), 3.48-3.45 (m, 2 H), 3.26 (s, 2 H), 2.66-2.64 (m, 2 H), 1.49 (s, 2 H).

Intermediate 9-5

1-(Aminomethyl)-N,N-dibenzylcyclohexanamine

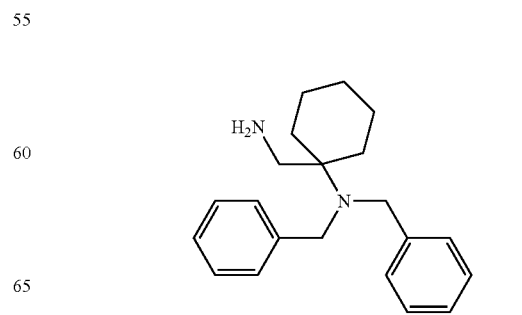

Intermediate 9-5 can be prepared in analogy to intermediate 9-1 by using cyclohexanone. MS obsd. (ESI+) [(M+H)+] 309.

Intermediate 9-6

(4-Aminomethyl-tetrahydropyran-4-yl)-dibenzyl-amine

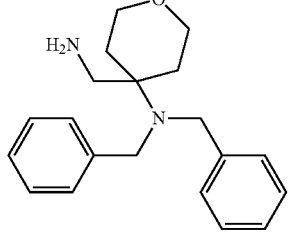 [SMILES: NCC1(N(Cc2ccccc2)Cc2ccccc2)CCCCC1]

Intermediate 9-6 can be prepared in analogy to intermediate 9-1 by using tetrahydropyran-4-one. MS obsd. (ESI+) [(M+H)+] 311.

Intermediate 10

N-[(3-Aminooxetan-3-yl)methyl]-2,2,2-trifluoroacetamide

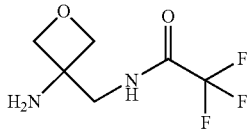 [SMILES: NC1(CNC(=O)C(F)(F)F)COC1]

N-{[3-(Dibenzylamino)oxetan-3-yl]methyl}-2,2,2-trifluoroacetamide

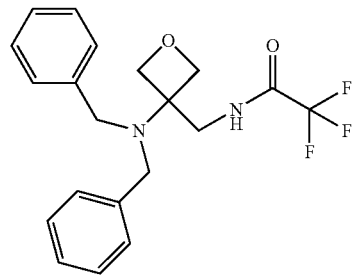 [SMILES: O=C(NCC1(N(Cc2ccccc2)Cc2ccccc2)COC1)C(F)(F)F]

To a solution of 3-(aminomethyl)-N,N-dibenzyloxetan-3-amine (3.0 g, 10.6 mmol) in dichloromethane (30 mL) in an ice bath was added dropwise trifluoroacetic anhydride (2.5 g, 11.7 mmol). After the mixture being stirred at room temperature overnight, the reaction was quenched by addition of a saturated aqueous solution of sodium bicarbonate at 0° C. The resulting mixture was extracted with dichloromethane, dried over sodium sulfate and concentrated in vacuo to afford 4.0 g of the crude product as yellow oil.

N-[(3-Aminooxetan-3-yl)methyl]-2,2,2-trifluoroacetamide

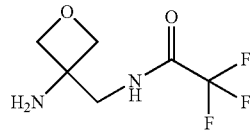 [SMILES: NC1(CNC(=O)C(F)(F)F)COC1]

To a solution of N-{[3-(dibenzylamino)oxetan-3-yl]methyl}-2,2,2-trifluoroacetamide (4.0 g, 10.57 mmol) in methanol (80 mL) was added 20% palladium hydroxide on carbon (0.8 g) and trifluoroacetic acid (one drop). The mixture was stirred at room temperature under hydrogen overnight and then filtered. The filtrate was concentrated in vacuo to afford the crude product as a white solid.

Intermediate 11 tert-Butyl [(3-aminooxetan-3-yl)methyl]carbamate

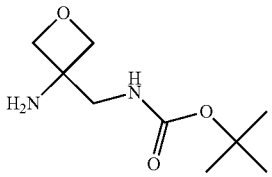

tert-Butyl {[3-(dibenzylamino)oxetan-3-yl]methyl}carbamate

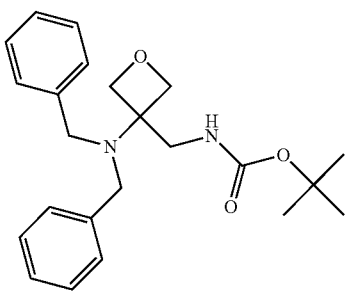 [SMILES: CC(C)(C)OC(=O)NCC1(N(Cc2ccccc2)Cc2ccccc2)COC1]

To a solution of 3-(aminomethyl)-N,N-dibenzyloxetan-3-amine (10.0 g, 35.41 mmol) in tetrahydrofuran (100 mL) was added an aqueous solution of sodium bicarbonate (8.6 g, 102.4 mmol dissolved in 50 mL of water) and a solution of di-tert-butyl dicarbonate (8.9 g, 51.08 mmol) in tetrahydrofuran (30 mL). The mixture was stirred at room temperature overnight, concentrated in vacuo to remove most of the organic solvent, and the aqueous residue was extracted with dichloromethane (100 mL×3). The organic layers were combined, washed with brine (150 mL), dried over sodium sulfate and concentrated in vacuo to afford 13.0 g of the crude product, which was used for the next step without any purification.

tert-Butyl [(3-aminooxetan-3-yl)methyl]carbamate

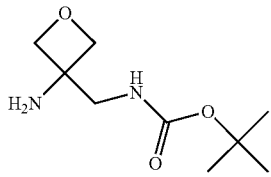

A mixture of tert-butyl {[3-(dibenzylamino)oxetan-3-yl]methyl}carbamate (13.0 g, crude), 20% palladium hydroxide on carbon (2.0 g) and trifluoroacetic acid (0.5 mL) in methanol (20 mL) was stirred overnight under hydrogen atmosphere (1 bar). After being basified with ammonia solution in methanol, the resulting mixture was filtered and concentrated in vacuo to afford 5.8 g of the crude product, which was used for the next step without any purification.

Intermediate 12 tert-Butyl [1-(2-aminoethyl)-cyclopropyl]carbamate

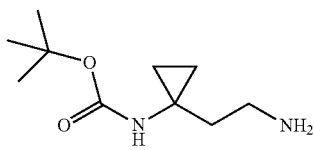

3-(Benzyloxy)propanenitrile

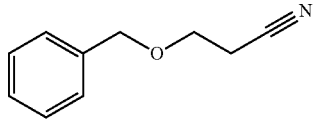 [SMILES: N#CCCOCc1ccccc1]

To a mixture of benzyl alcohol (108 g, 1 mol) and 40% aqueous solution of sodium hydroxide (10 mL) was added prop-2-enenitrile (58.3 g, 1.1 mol) and the mixture was stirred for 6 hours at room temperature. The mixture was neutralized with 1 N hydrochloric acid, and extracted with dichloromethane (300 mL). The organic layer was washed with 5% solution of sodium hydroxide (300 mL) and brine (300 mL), dried over sodium sulfate and concentrated in vacuo to afford 150 g of the desired compound (yield was 93%).

1-[2-(benzyloxy)ethyl]cyclopropanamine

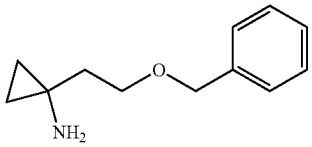 [SMILES: NC1(CCOCc2ccccc2)CC1]

To a solution of 3-(benzyloxy)propanenitrile (16.9 g 105 mmol) in diethyl ether (400 mL) were added titanium isopropoxide (35.7 mL, 115 mmol) and ethyl magnesium bromide (210 mL, 1 M in diethyl ether) successively at room temperature. After being stirred for 0.5 hour, boron trifluoride etherate (27 mL, 525 mmol) was added. After stirring for another 0.5 hour, 10% aqueous solution of sodium hydroxide (ca. 5.5 mL) was introduced to the above mixture. The resulting mixture was acidified with 1N hydrochloric acid to pH 3, and then washed with dichloromethane. The aqueous layer was basified with 5% aqueous solution of sodium hydroxide to pH 8~9 and extracted with dichloromethane (100 mL). The organic layer was washed with brine (100 mL), dried over sodium sulfate and concentrated in vacuo to afford 11 g of 1-[2-(benzyloxy)ethyl]cyclopropanamine (yield was 55%).

2-(1-Aminocyclopropyl)ethanol hydrochloride

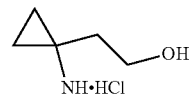

To a mixture of 1-[2-(benzyloxy)ethyl]cyclopropanamine (13.2 g, 69 mmol), 10% palladium on carbon (3.0 g) and propan-2-ol (100 mL) was added a solution of hydrochloride in propan-2-ol (100 mL, 5-6 N). The mixture was shaken at 40° C. under hydrogen pressure of 4 atmospheres until hydrogen uptake ceased. The catalyst was removed by filtration and washed with propan-2-ol. The filtrate was concentrated in vacuo to afford 8.8 g of the salt as a viscous oil (yield was 84.6%).

tert-Butyl [1-(2-hydroxyethyl)cyclopropyl]carbamate

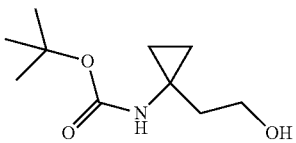

To a solution of 2-(1-amino-cyclopropyl)-ethanol hydrochloride (1:1) (8.8 g, 64.4 mmol) in tetrahydrofuran (63 mL) was added water (1.5 mL), triethylamine (18.3 mL, 130 mmol) and a solution of di-tert-butyl dicarbonate (15.46 g, 70.9 mmol) in tetrahydrofuran (21 mL). The resulting mixture was stirred at room temperature for 16 hours. The mixture was concentrated in vacuo and the residue was dissolved in diethyl ether (100 mL). The organic solution was washed with an aqueous hydrochloric acid solution (0.1 N, 50 mL) and brine (50 mL), dried over sodium sulfate and concentrated in vacuo. The residue was triturated in water and filtered to afford 9.3 g of the pure product as a white solid (yield was 71%).

2-{1-[(tert-Butoxycarbonyl)amino]-cyclopropyl}ethyl methanesulfonate

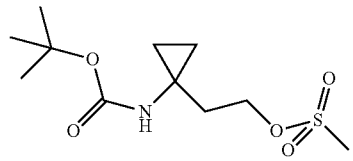 [SMILES: CC(C)(C)OC(=O)NC1(CCOS(C)(=O)=O)CC1]

To a cooled solution of tert-butyl [1-(2-hydroxyethyl)cyclopropyl]carbamate (8.0 g, 0.04 mol) and triethylamine (12.14 g) in anhydrous tetrahydrofuran (120 mL) at −20° C. was added a solution of mesyl chloride (17.8 g) in anhydrous tetrahydrofuran (30 mL). The resulting mixture was allowed to warm to room temperature and stirred at this temperature for 2 hours. The resulting mixture was poured into ice-water (50 mL) and the separated organic layer was washed with brine (100 mL), dried over sodium sulfate and concentrated in vacuo. The residue was triturated with petroleum ether and filtered to give 9.5 g of the pure product as an orange solid (yield was 95%).

tert-Butyl 1-[2-(1,3-dioxo-1,3-dihydro-2H-isoindol-2-yl)ethyl]cyclopropylcarbamate

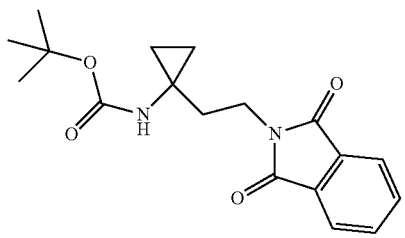 [SMILES: CC(C)(C)OC(=O)NC1(CCN2C(=O)c3ccccc3C2=O)CC1]

To a solution of 2-{1-[(tert-butoxycarbonyl)amino]-cyclopropyl}ethyl methanesulfonate (9.5 g, 344.3 mmol) in anhydrous N,N-dimethylformamide (20 ml) was added potassium 2,3-dihydro-1H-isoindole-1,3-dione (7.0 g, 37 mmol). After being stirred at 150° C. for 18 hours, the resulting mixture was then filtered and washed with diethyl ether (50 mL). The filtrate was washed with brine (50 mL×3), dried over sodium sulfate and concentrated in vacuo. The residue was heated with stirring in water and the precipitate was collected by filtration and dried in vacuo to afford 6.0 g of the pure product as an orange solid (yield was 53%).

tert-Butyl [1-(2-aminoethyl)-cyclopropyl]carbamate

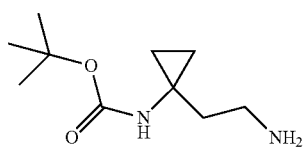

To a solution of tert-butyl 1-[2-(1,3-dioxo-1,3-dihydro-2H-isoindol-2-yl)ethyl]cyclopropylcarbamate (3.3 g, 2.4 mmol) in ethanol (100 mL) was added hydrazine hydrate (5 mL) and the resulting mixture was heated under reflux for 16 hours. The mixture was filtered and washed with diethyl ether. The filtrate was concentrated in vacuo to afford 1.5 g of the pure compound as an orange oil (yield was 75%).

Intermediate 13 tert-Butyl [2-(1-aminocyclopropyl)ethyl]carbamate

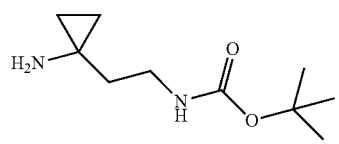

Methyl 1-aminocyclopropanecarboxylate

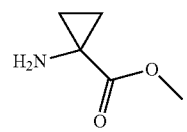

To a solution of 1-aminocyclopropanecarboxylic acid (1.0 g, 9.9 mmol) in methanol (30 mL) was added thionyl chloride (3.5 g, 29.7 mmol) at 0° C. The mixture was heated under reflux for 2 hours and then concentrated in vacuo to afford 1.1 g of the crude product (yield was 100%).

Methyl 1-[(tert-butoxycarbonyl)amino]cyclopropanecarboxylate

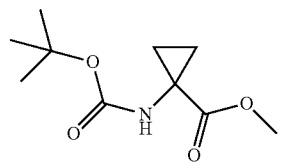

To a cooled mixture of methyl 1-aminocyclopropanecarboxylate (1.1 g, 9.6 mmol) and an aqueous solution of potassium bicarbonate (2.88 g, 28.8 mmol dissolved in 10 mL of water) in ethyl acetate (30 mL) was added a solution of di-tert-butyl dicarbonate (4.15 g, 19.2 mmol) in ethyl acetate (10 mL) at 0° C. The reaction mixture was allowed to warm to room temperature and stirred at this temperature overnight. The separated aqueous layer was extracted with ethyl acetate (20 mL). The combined organic layers were dried over sodium sulfate and concentrated in vauco to afford 2.0 g of the product (yield was 97%).

tert-Butyl [1-(hydroxymethyl)cyclopropyl]carbamate

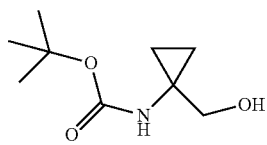

To a cooled solution of methyl 1-[(tert-butoxycarbonyl) amino]cyclopropanecarboxylate (1.2 g, 5.6 mmol) in tetrahydrofuran (10 mL) at 0° C. was added dropwise a solution of lithium borohydride (244 mg, 11.2 mmol) in tetrahydrofuran (10 mL) The reaction mixture was allowed to warm to room temperature and stirred at this temperature overnight. The reaction was quenched by addition of water (10 mL) and the resulting mixture was extracted with dichloromethane. The organic layer was dried over sodium sulfate and concentrated in vacuo to afford 0.8 g of the product (yield was 76.2%).

tert-Butyl [1-(azidomethyl)cyclopropyl]carbamate

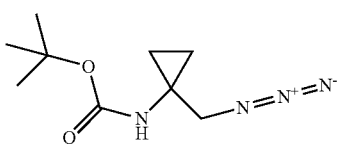

To a solution of tert-butyl [1-(hydroxymethyl)cyclopropyl]carbamate (1 g, 5.3 mmol) in N,N-dimethylformamide (20 mL) was added 1,8-diazabicyclo[5.4.0]undec-7-ene (1.22 g, 8.0 mmol) and diphenylphosphoryl azide (2.33 g, 8.00 mmol). After the mixture was stirred at 80° C. for 3 hours, another batch of 1,8-diazabicyclo[5.4.0]undec-7-ene (1.22 g, 8.0 mmol) and diphenylphosphoryl azide (2.33 g, 8.00 mmol) was introduced and the mixture was stirred at 80° C. for another 2 hours. The resulting mixture was then diluted with water (20 mL) and extracted with ethyl acetate (30 mL×2). The combined organic layers were used for next step directly.

tert-Butyl [1-(aminomethyl)cyclopropyl]carbamate

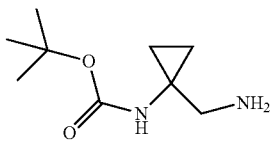

A solution of tert-butyl [1-(azidomethyl)cyclopropyl]carbamate (60 mL, obtained from the above step) was hydrogenated in the presence of 10% palladium on carbon (60 mg) at room temperature overnight under hydrogen atmosphere with hydrogen balloon. The reaction was filtered and concentrated in vacuo to afford 40 mg of the crude product (yield was 40%).

Intermediate 14

(1,1-Dioxidothietane-3,3-diyl)dimethanamine

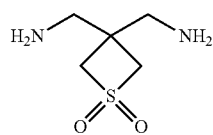

3,3-Bis(azidomethyl)thietane

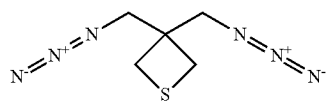 [SMILES: [N-]=[N+]=NCC1(CN=[N+]=[N-])CSC1]

To a mixture of 3,3-bis(bromomethyl)thietane (15.0 g, 0.058 mol) and tetrabutylazanium bromide (0.93 g, 5%) in water (30 mL) was added sodium azide (9.0 g, 0.138 mol). The mixture was stirred at 70° C. overnight, then diluted with water (20 mL) and extracted with dichloromethane (50 mL×3). The combined organic layers were dried over sodium sulfate and concentrated in vacuo to remove most of dichloromethane. The residual solution (in 24 mL of dichloromethane) was used for the next step.

3,3-Bis-azidomethyl-thietane 1,1-dioxide

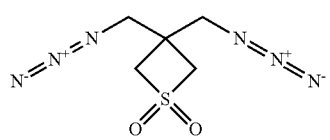 [SMILES: [N-]=[N+]=NCC1(CN=[N+]=[N-])CS(=O)(=O)C1]

To a solution of 3,3-bis(azidomethyl)thietane (2.5 g, 13.59 mmol) in the mixture of formic acid (5 mL) and dichloromethane (6 mL) was added hydrogen peroxide (9.2 g, 81.54 mmol) slowly at 0° C. After being warmed slowly to room temperature and stirred at room temperature overnight, the mixture was diluted with water (10 mL) and extracted with dichloromethane (15 mL×3). The combined organic layers were dried over sodium sulfate and concentrated in vacuo. The residue was purified by flash column chromatography to afford 2.8 g of the desired product as a white solid (yield of two steps was 96%).

(1,1-Dioxidothietane-3,3-diyl)dimethanamine

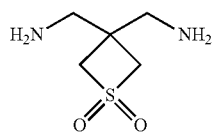

A solution of 3,3-bis-azidomethyl-thietane 1,1-dioxide (1.0 g, 4.63 mmol) in methanol (10 mL) was stirred in the presence of 10% palladium on carbon (0.2 g) under hydrogen atmosphere overnight. The resulting reaction mixture was filtered and the filtrate was concentrated in vacuo to afford 720 mg of the desired product.

Intermediate 15

Thietane-3,3-diyldimethanamine

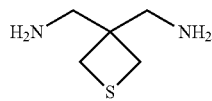

A solution of 3,3-bis(azidomethyl)thietane (2.5 g, 13.59 mmol) in dichloromethane (6 mL) and methanol (50 mL) was stirred in the presence of 10% palladium on carbon (0.8 g) under 25 psi of hydrogen overnight. The resulting mixture was filtered and concentrated in vacuo to afford 1.8 g of the desired product.

Intermediate 16

(3,3-Difluorocyclobutane-1,1-diyl)dimethanamine

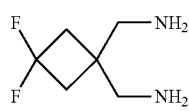

Dipropan-2-yl 3,3-dimethoxycyclobutane-1,1-dicarboxylate

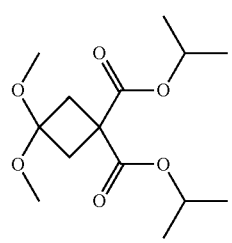 [SMILES: COC1(OC)CC(C(=O)OC(C)C)(C(=O)OC(C)C)C1]

To a stirred suspension of sodium hydride (96.5 g, 2.413 mol, 60% in mineral oil) in dry N,N-dimethylformamide (900 ml) was added 1,3-bis(propan-2-yl) propanedioate (363.3 g, 1.930 mol) dropwise under nitrogen at a rate such that the temperature was maintained below 70° C. On cessation of hydrogen evolution, the mixture was heated to 130° C., to 3-dibromo-2,2-dimethoxypropane (252.8 g, 0.965 mol) was then introduced in one portion. The mixture was heated under reflux for 48 hours. The cooled mixture was poured into a saturated aqueous solution of ammonium chloride (300 mL) and extracted with methyl tert-butyl ether (300 mL). The organic layer was washed with a saturated aqueous solution of sodium bicarbonate and brine, dried over sodium sulfate, and concentrated in vacuo. The residue was distilled in vacuo (oil pump) to afford 52.7 g of dipropan-2-yl 3,3-dimethoxy-cyclobutane-1,1-dicarboxylate as a colorless oil (yield was 58.2%). ¹H NMR (400 MHz, CDCl₃) δ ppm 5.02 (m J=6.4 Hz, 2 H), 3.12 (s, 6 H), 2.66 (s, 4 H), 1.11 (d, J=6.4 Hz, 12 H).

Dipropan-2-yl 3-oxocyclobutane-1,1-dicarboxylate

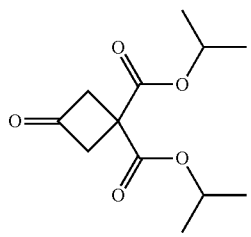 [SMILES: CC(C)OC(=O)C1(C(=O)OC(C)C)CC(=O)C1]

A solution of dipropan-2-yl 3,3-dimethoxycyclobutane-1,1-dicarboxylate (10.0 g, 34.6 mmol) in hydrochloric acid (3 N, 55 mL) was heated at 50° C. for 4 hours. The resulting mixture was neutralized with a saturated aqueous solution of sodium bicarbonate and extracted with ethyl acetate (100 mL). The combined organic layers were dried over sodium sulfate and concentrated in vacuo to afford 6.073 g of dipropan-2-yl 3-oxocyclobutane-1,1-dicarboxylate as a light brown oil (yield was 72.3%).

Dipropan-2-yl 3,3-difluorocyclobutane-1,1-dicarboxylate

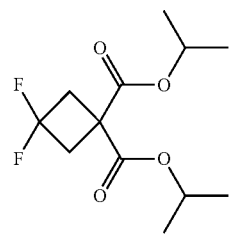 [SMILES: CC(C)OC(=O)C1(C(=O)OC(C)C)CC(F)(F)C1]

To a cooled solution of dipropan-2-yl 3-oxocyclobutane-1,1-dicarboxylate (5.657 g, 23.3 mmol) in dichloromethane (50 ml) at −78° C., was added dropwise a solution of N,N-diethylaminosuflur trifluoride (9.25 ml, 70.05 mmol) in dichloromethane (25 ml) under nitrogen. After the addition, the mixture was allowed to warm up to room temperature and stirred for 24 hours. The mixture was diluted with dichloromethane (50 mL), and washed with 2 N aqueous solution of sodium hydroxide (50 mL) and brine (50 mL). The organic layer was dried over sodium sulfate, and concentrated in vacuo to afford dipropan-2-yl 3,3-difluorocyclobutane-1,1-dicarboxylate as a yellow oil (yield was 68.8%).

3,3-Difluorocyclobutane-1,1-dicarboxylic acid

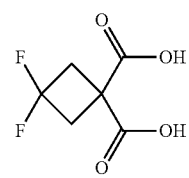

A mixture of 3,3-difluoro-cyclobutane-1,1-dicarboxylic acid diisopropyl ester (5.00 g, 18.9 mmol) and sodium hydroxide (3.00 g, 75.7 mmol) in methanol (20 ml) was stirred at room temperature overnight. The formed off-white solid was collected by filtration, washed with ethyl acetate, and dissolved in water. The aqueous solution was acidified with hydrochloric acid (3 N) to pH 3-4. The mixture was concentrated in vacuo to afford 6.293 g of the crude 3,3-difluorocyclobutane-1,1-dicarboxylic acid as a white solid, which was used for next step without further purification.

3,3-Difluorocyclobutane-1,1-dicarboxamide

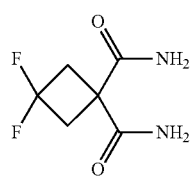

A solution of crude 3,3-difluorocyclobutane-1,1-dicarboxylic acid (6.293 g) in thionyl chloride (50 mL) was heated under reflux for 2 hours. Then the solution was concentrated in vacuo to remove thionyl chloride. To the residue was added dropwise ice-cold ammonium hydroxide (10 mL) and stirred for 0.5 hour. The formed off-white precipitate was collected by filtration. The filtrate was extracted with tetrahydrofuran (three times). The combined organic layers were dried over magnesium sulfate and concentrated in vacuo. The solids were combined to afford 1.858 g of 3,3-difluorocyclobutane-1,1-dicarboxamide as an off-white solid (yield of three steps was 55.2%).

(3,3-Difluorocyclobutane-1,1-diyl)dimethanamine

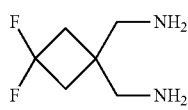

To a cooled solution of 3,3-difluorocyclobutane-1,1-dicarboxamide (1.858 g, 10.4 mmol) in tetrahydrofuran (25 mL) at −10° C., was added slowly lithium aluminium hydride (2.375 g, 62.58 mmol). The reaction was stirred at 0° C. for 4 hours and then heated under reflux for 30 hours. The mixture was cooled and quenched at 0° C. by addition of water (2.5 mL), 15% aqueous solution of sodium hydroxide (7.5 mL) and water (2.5 mL) successively. The resulting mixture was stirred at room temperature for 0.5 hour. The mixture was filtered and the filtrate was concentrated in vacuo to afford 1.137 g of the crude product of (3,3-difluorocyclobutane-1,1-diyl)dimethanamine as a colorless oil (yield was 72.8%).

Intermediate 17

3-(1,3-Dioxo-1,3-dihydro-2H-isoindol-2-yl)-4,4,4-trifluorobutanoyl chloride

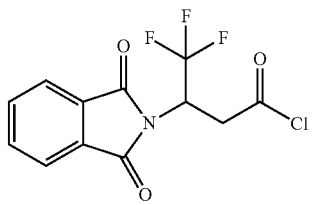 [SMILES: O=C(Cl)CC(N1C(=O)c2ccccc2C1=O)C(F)(F)F]

3-(1,3-Dioxo-1,3-dihydro-2H-isoindol-2-yl)-4,4,4-trifluorobutanoic acid

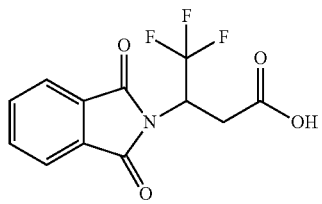 [SMILES: O=C(O)CC(N1C(=O)c2ccccc2C1=O)C(F)(F)F]

A solution of phthalic ahydride (378 mg, 2.54 mmol) and 3-amino-4,4,4-trifluorobutanoic acid (200 mg, 1.27 mmol) in N,N-dimethylformamide (5 mL) was heated at 160° C. under microwave irradiation for 1 hour. The resulting mixture was cooled to room temperature, diluted with water, and extracted with ethyl acetate (30 mL×2). The combined organic layers were washed with brine (50 mL), dried over sodium sulfate and concentrated in vacuo. The residue was purified by flash chromatograph on silica gel (eluting with 50% ethyl acetate in hexane) to afford 270 mg of the product of 3-(1,3-dioxo-1,3-dihydro-2H-isoindol-2-yl)-4,4,4-trifluorobutanoic acid (yield was 37%). MS obsd. (ESI⁺) [(M+H)⁺] 288.

3-(1,3-Dioxo-1,3-dihydro-2H-isoindol-2-yl)-4,4,4-trifluorobutanoyl chloride

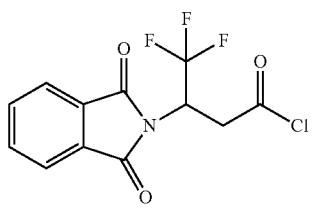 [SMILES: O=C(Cl)CC(N1C(=O)c2ccccc2C1=O)C(F)(F)F]

To a solution of 3-(1,3-dioxo-1,3-dihydro-2H-isoindol-2-yl)-4,4,4-trifluorobutanoic acid (270 mg, 0.94 mmol) in dichloromethane (10 mL) was added oxalyl chloride (0.16 mL, 1.88 mmol), followed by N,N-dimethylformamide (1 drop). After the gas ceased to produce, the reaction mixture was stirred at room temperature for 2 hours. After the mixture was concentrated in vacuo, the residue was diluted with dichloromethane and concentrated in vacuo again to afford 280 mg of the product (yield was 90%), which was used for next step without purification.

Intermediate 18

2-Fluorobutane-1,4-diamine

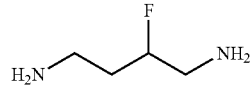

1,4-Dibromo-2-fluorobutane

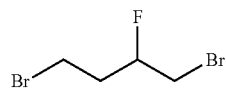

To a solution of 1,4-dibromobutan-2-ol (6.0 g, 25.64 mmol) in dichloromethane (80 mL) was added N,N-diethylaminosuflur trifluoride (6.25 mg, 38.79 mmol). The reaction mixture was stirred at room temperature overnight. The mixture was diluted with ethyl acetate (15 mL), washed with water (15 mL) and brine (15 mL), dried over sodium sulfate, and concentrated in vacuo to afford 4.0 g of 1,4-dibromo-2-fluoro-butane as a yellow oil.

2,2'-(2-Fluorobutane-1,4-diyl)bis(1H-isoindole-1,3(2H)-dione)

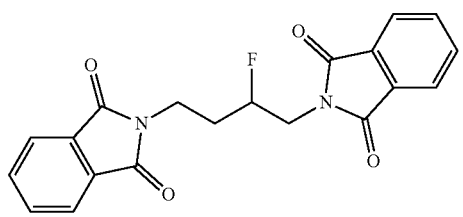 [SMILES: O=C1c2ccccc2C(=O)N1CCC(F)CN1C(=O)c2ccccc2C1=O]

To a solution of 1,4-dibromo-2-fluoro-butane (4.0 g, 17.09 mmol) in N,N-dimethylformamide (60 mL) was added potassium 2,3-dihydro-1H-isoindole-1,3-dione (9.5 g, 51.27 mmol). The reaction mixture was stirred at 100° C. overnight. The mixture was cooled to room temperature, diluted with ethyl acetate (60 mL), washed with water (60 mL), brine (60 mL), dried over sodium sulfate, and concentrated in vacuo to afford 4.5 g of 2,2'-(2-fluorobutane-1,4-diyl)bis(1H-isoindole-1,3(2H)-dione) as a white solid.

2-Fluorobutane-1,4-diamine

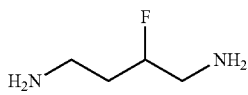

A mixture of 2,2'-(2-fluorobutane-1,4-diyl)bis(1H-isoindole-1,3(2H)-dione) (1.0 g, 2.73 mmol) and hydrazine hydrate (0.68 g, 13.6 mmol) in ethanol (20 mL) was heated under reflux for 16 hours. The resulting mixture was cooled to room temperature and concentrated in vacuo to afford the crude product, which was used for the next step.

Intermediate 19 tert-Butyl (4S)-4-(aminomethyl)-2,2-dimethyl-1,3-oxazolidine-3-carboxylate

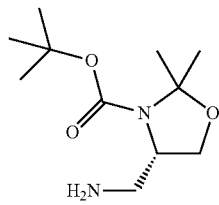 [SMILES: CC(C)(C)OC(=O)N1[C@@H](CN)COC1(C)C]

tert-Butyl (4S)-4-[(benzylamino)methyl]-2,2-dimethyl-1,3-oxazolidine-3-carboxylate

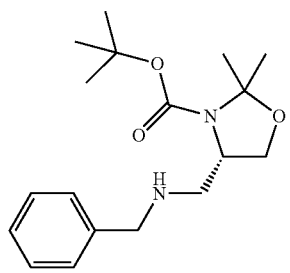 [SMILES: CC(C)(C)OC(=O)N1[C@@H](CNCc2ccccc2)COC1(C)C]

A mixture of tert-butyl (4S)-4-formyl-2,2-dimethyl-1,3-oxazolidine-3-carboxylate (1.0 g, 4.36 mmol), phenylmethanamine (491 mg, 4.58 mmol) and toluene (8 mL) was heated under reflux with stirring for 2 hours. The mixture was concentrated in vacuo. The residue was dissolved in 1,2-dichloroethane (10 mL), to which sodium bis(acetyloxy)boranuidyl acetate (2.31 g, 10.91 mmol) was added. The mixture was stirred at room temperature for two days, then diluted with water (25 mL), extracted with dichloromethane (25 mL×3). The combined organic layers were washed with brine, dried over anhydrous sodium sulfate and concentrated in vacuo. The residue was purified by flash column chromatography to afford 849 mg of the product.

tert-Butyl (4S)-4-(aminomethyl)-2,2-dimethyl-1,3-oxazolidine-3-carboxylate

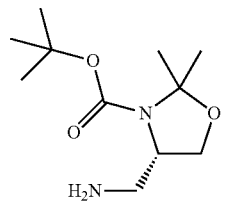 [SMILES: CC(C)(C)OC(=O)N1[C@@H](CN)COC1(C)C]

A mixture of tert-butyl (4S)-4-[(benzylamino)methyl]-2,2-dimethyl-1,3-oxazolidine-3-carboxylate (810 mg, 2.53 mmol), palladium hydroxide on carbon (81 mg) and methanol (20 mL) was stirred at room temperature under hydrogen atmosphere overnight. The catalyst was removed by filtration. The filtrate was concentrated in vacuo. The residue was purified by SPE (12 mL tube, 2 gram of DSC-SCX) to afford the pure product.

Intermediate 20 tert-Butyl 2-oxa-6-azaspiro[3.4]oct-8-ylcarbamate

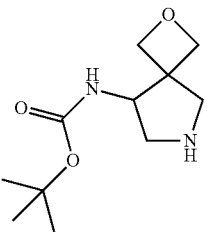 [SMILES: CC(C)(C)OC(=O)NC1CNCC12COC2]

6-Benzyl-8-nitro-2-oxa-6-aza-spiro[3.4]octane

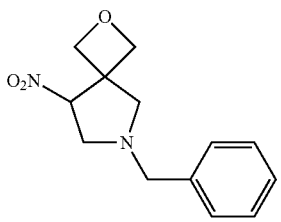

To a solution of benzyl-methoxymethyl-trimethylsilanyl-methyl-amine (3.0 g, 12.6 mmol) and 3-nitromethylene-oxetane (1.38 g, 12.0 mmol) in dichloromethane (60 mL) was added trifluoroacetic acid (0.93 mL, 12.6 mmol) dropwise. The mixture was stirred at room temperature for 2 hours, quenched with sodium carbonate, extracted with dichloromethane. The organic layer was dried over sodium sulfate, concentrated in vacuo. The residue was purified by column chromatography on silica gel to give 2 g of product as colorless oil. It was used for next step without further purification.

6-Benzyl-2-oxa-6-aza-spiro[3.4]oct-8-ylamine

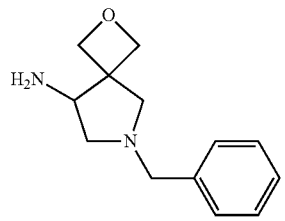 [SMILES: O=[N+]([O-])C1CN(Cc2ccccc2)CC12COC2]

The mixture of 6-benzyl-8-nitro-2-oxa-6-aza-spiro[3.4]octane (2 g, 8.1 mmol), iron powder (2.3 g, 40.5 mmol), ammonium chloride (4.3 g, 81 mmol), methanol (40 mL) and 8 mL of water was heated with stirring for 2 hours at 80° C. The reaction mixture was filtered by a pad of celite. The filtrate was concentrated under reduced pressure, and the residue was used for next step without further purification.

tert-Butyl (6-benzyl-2-oxa-6-azaspiro[3.4]oct-8-yl)carbamate

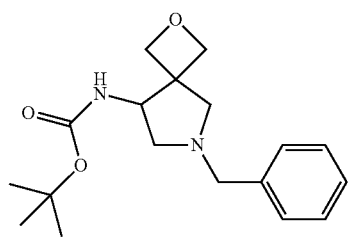 [SMILES: CC(C)(C)OC(=O)NC1CN(Cc2ccccc2)CC12COC2]

To a mixture of 6-benzyl-2-oxa-6-azaspiro[3.4]oct-8-ylamine (prepared above), sodium carbonate (1.46 g, 13.74 mmol), dichloromethane (20 mL) and water (20 mL) was added di-tert-butyl dicarbonate (1.8 g, 8.24 mmol) at room temperature. The mixture was stirred at room temperature overnight. The separated organic layer was dried over sodium sulfate, filtered and concentrated in vacuo. The residue was purified by column chromatography on silica gel to give 1.5 g of product as colorless oil, which was used for next step without further purification.

tert-Butyl 2-oxa-6-azaspiro[3.4]oct-8-ylcarbamate

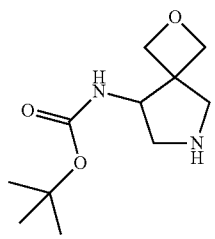

To a solution of 6-benzyl-2-oxa-6-azaspiro[3.4]oct-8-ylamine (1.5 g, 4.71 mmol) in methanol (50 mL) was added palladium hydroxide (20% on carbon, 300 mg). After being stirred at room temperature for 4 hours under a hydrogen atmosphere, the resulting mixture was filtered. The filtrate was concentrated in vacuo to give 900 mg of the product as colorless oil, which was used for next step without further purification.

Intermediate 21

N-(3-Methylpyrrolidin-3-yl)-acetamide

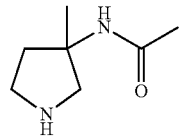

N-(1-Benzyl-3-methylpyrrolidin-3-yl)-acetamide

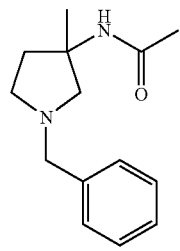 [SMILES: CC(=O)NC1(C)CCN(Cc2ccccc2)C1]

To a solution of 1-benzyl-3-methylpyrrolidin-3-ol (1.0 g, 5.2 mmol) in acetonitrile (10 mL) at 0° C., was added concentrated sulfuric acid (10 mL) slowly. After being stirred for 16 hours at room temperature, the reaction mixture was poured into ice-water. After the reaction mixture was adjusted to pH 7 with a saturated aqueous solution of potassium carbonate, the resulting mixture was exacted with dichloromethane (200 mL×3). The combined organic layers were dried over sodium sulfate, and concentrated in vauo. The residue was purified by preparative HPLC to afford 600 mg of the product (yield was 50%).

N-(3-Methylpyrrolidin-3-yl)-acetamide

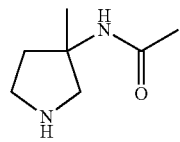

A mixture of N-(1-benzyl-3-methylpyrrolidin-3-yl)-acetamide (600 mg, 2.6 mmol), palladium on carbon (400 mg, 10%) and ethanol (20 mL) was stirred at 40° C. under 50 Psi of hydrogen for 16 hours. The resulting mixture was filtered. The filtrate was concentrated in vacuo to give 200 mg of the desired product (yield was 54%), which was used for next step without any purification.

Intermediate 22

2-Fluoropropane-1,3-diamine

2-Fluoropropanediamide

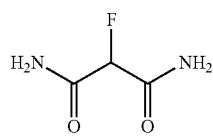

To a solution of 1,3-diethyl 2-difluoropropanedioate (25 g, 140.4 mmol) in methanol (100 mL) under a nitrogen atmosphere was added a solution of ammonia in methanol (80 mL, 7 N, 560 mmol). The resulting mixture was stirred at room temperature overnight and then concentrated in vacuo. The residue was triturated in petroleum ether to afford 16.3 g of 2-fluoropropanediamide as a white solid (yield was 97%). MS obsd. (ESI+) [(M+H)+] 121.

2-Fluoropropane-1,3-diamine

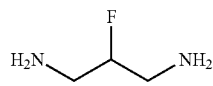

To a solution of 2-fluoropropanediamide (16.3 g, 136 mmol) in tetrahydrofuran (200 mL) was added a solution of boran-tetrahydrofuran complex (800 mL, 800 mmol, 1 M) in tetrahydrofuran. The reaction mixture was heated at 70° C. with stirring overnight, then cooled in an ice bath, stirred with methanol (100 mL) further for 30 minutes, and concentrated in vacuo. The residue was dissolved in methanol (100 mL) and the solution was concentrated in vacuo. To the residue was added water (10 mL), potassium hydroxide was added with cooling until the aqueous solution was saturated. The mixture was extracted by diethyl ether (20 mL×2), and the combined organic layers was dried over potassium hydroxide and concentrated in vacuo to afford 7.5 g of 2-fluoropropane-1,3-diamine (yield was 60%). MS obsd. (ESI+) [(M+H)+] 93.

Intermediate 23

Benzyl 6-oxa-3-azabicyclo[3.1.0]hexane-3-carboxylate

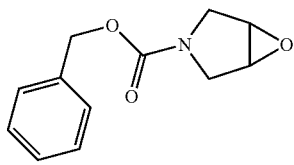 [SMILES: O=C(OCc1ccccc1)N1CC2OC2C1]

To a solution of 1-benzyloxycarbonyl-3-pyrroline (2.5 g) in dichloromethane (60 mL) was added 3-chloroperoxybenzoic acid (6.08 g, 50-60% purity). The reaction was stirred at room temperature for 72 hours, and then a saturated sodium thiosulfate solution (50 mL) was added. After being stirred for additional 30 minutes, the mixture was extracted with chloroform (50 mL×2). The combined organic layers were washed successively with 2 N aqueous solution of sodium hydroxide (50 mL×2) and brine (50 mL), dried over magnesium sulfate and concentrated in vacuo to afford 2.79 g of the crude benzyl 6-oxa-3-azabicyclo[3.1.0]hexane-3-carboxylate as an oil. MS obsd. (ESI+) [(M+H)+] 220.

trans-(±)-Benzyl-3-amino-4-hydroxypyrrolidine-1-carboxylate

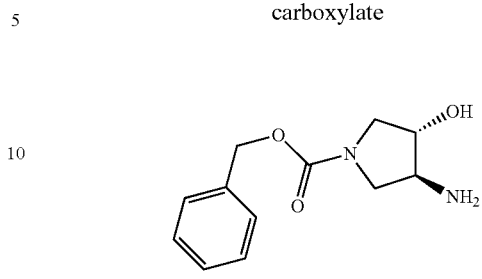

A mixture of the crude benzyl 6-oxa-3-azabicyclo[3.1.0]hexane-3-carboxylate obtained in the above step (2.79 g) and 28% aqueous solution of ammonia (20 mL) was stirred at 40° C. for 2 days in a sealed tube, then 2 N aqueous solution of sodium hydroxide (25 mL) was introduced and the mixture was extracted with chloroform (25 mL×3). The combined organic layers were dried over anhydrous magnesium sulfate and concentrated in vacuo to afford 2.67 g of the crude trans-benzyl-3-amino-4-hydroxypyrrolidine-1-carboxylate as oil. MS obsd. (ESI+) [(M+H)+] 237.

trans-(±)-Benzyl-3-[(tert-butoxycarbonyl)amino]-4-hydroxypyrrolidine-1-carboxylate

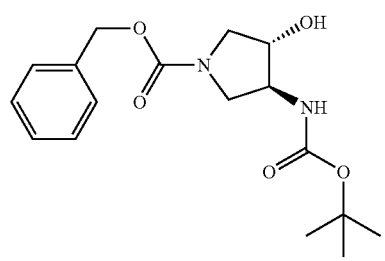 [SMILES: CC(C)(C)OC(=O)N[C@H]1CN(C(=O)OCc2ccccc2)C[C@@H]1O]

To a cooled solution of trans-benzyl-3-amino-4-hydroxypyrrolidine-1-carboxylate (2.67 g) in chloroform (25 mL) was added dropwise a solution of di-tert-butyl dicarbonate (3.7 g) in chloroform (10 mL) in an ice-water bath, and the mixture was stirred at room temperature for 19 hours. The reaction mixture was washed with water and the organic layer was dried over anhydrous magnesium sulfate and concentrated in vacuo. The residue was purified by a column chromatography on silica gel to afford 2.7 g of trans-benzyl-3-[(tert-butoxycarbonyl)amino]-4-hydroxypyrrolidine-1-carboxylate as crystals. MS obsd. (ESI+) [(M+H)+] 337.

trans-(±)-tert-Butyl [4-hydroxypyrrolidin-3-yl]carbamate

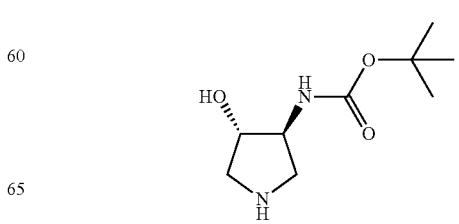

To a solution of trans-3-tert-butoxycarbonylamino-4-hydroxy-pyrrolidine-1-carboxylic acid benzyl ester (3.9 g) in methanol (31 mL) and tetrahydrofuran (7 mL) was added palladium hydroxide (20 wt % Pd on carbon, 500 mg) and the mixture was stirred at room temperature under 40-45 psi of hydrogen atmosphere overnight. The resulting mixture was filtered and the filtrate was concentrated in vacuo. The residue was triturated in the mixture of ethyl acetate and diisopropylether and filtered to remove the insoluable materials. The filtrate was concentrated in vacuo to afford 2.0 g of trans-tert-butyl [4-hydroxypyrrolidin-3-yl]carbamate (yield was 94%) as a powder. MS obsd. (ESI$^+$) [(M+H)$^+$] 203.

Intermediate 24 trans-(±)-Benzyl 3-amino-4-fluoroypyrrolidne-1-carobxylate

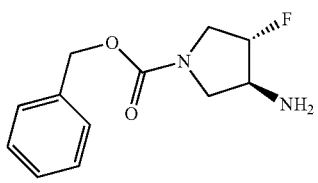 [SMILES: N[C@H]1CN(C(=O)OCc2ccccc2)C[C@@H]1F]

trans-(±)-Benzyl 3-azido-4-fluoroypyrrolidne-1-carobxylate

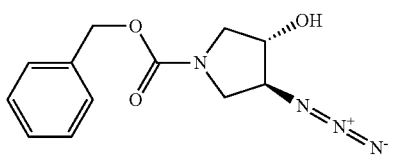 [SMILES: [N-]=[N+]=N[C@H]1CN(C(=O)OCc2ccccc2)C[C@@H]1O]

In a solution of benzyl-6-oxa-3-azabicyclo[3.1.0]hexane-3-carboxylate (2.5 g) in methanol (20 mL) was added water (5 mL), ammonium chloride (550 mg) and sodium azide (1.5 g). The resulting mixture was heated at 65° C. for 21 hours. The solids were removed by filtration and the filtrate was concentrated in vacuo. The residue was poured into 15% aqueous solution of sodium hydroxide (30 mL) and extracted with dichloromethane (50 mL). The organic layers were washed with brine, dried over magnesium sulfate and concentrated in vacuo to afford 2.7 g of trans-(±)benzyl-3-azido-4-hydroxy-pyrrolidne-1-carobxylate. MS obsd. (ESI$^+$) [(M+H)$^+$] 250.

trans-(±)-Benzyl 3-azido-4-fluoroypyrrolidne-1-carobxylate

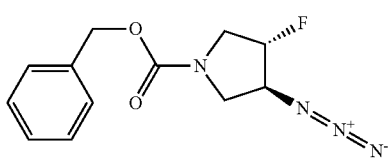 [SMILES: [N-]=[N+]=N[C@H]1CN(C(=O)OCc2ccccc2)C[C@@H]1F]

To a cooled solution of trans-(±)benzyl-3-azido-4-hydroxypyrrolidne-1-carobxylate (6.5 g) in dichloromethane (110 mL) was added diethylaminosulfur trifluoride (6.8 mL) at −78° C. The mixture was stirred at room temperature for 16 hours, and then concentrated in vacuo. The residue was dissolved in ethyl acetate (100 mL), and the solution was washed with a saturated sodium bicarbonate (100 mL) and brine (100 mL), dried over magnesium sulfate and concentrated in vacuo. The residue was purified by column chromatography on silica gel (eluting with 1% methanol in dichloromethane) to yield 5.7 g of trans-(±)benzyl-3-azido-4-fluoroypyrrolidne-1-carobxylate.

trans-(±)-Benzyl 3-amino-4-fluoroypyrrolidne-1-carobxylate

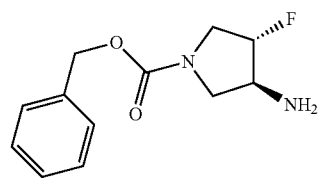 [SMILES: N[C@H]1CN(C(=O)OCc2ccccc2)C[C@@H]1F]

To a solution of trans-(±)benzyl-3-azido-4-fluoroypyrrolidne-1-carobxylate (4.33 g) in tetrahydrofuran (100 mL) and water (10 mL) was added triphenylphospine (4.5 g). The reaction mixture was heated under reflux for 2 hours. The reaction mixture was concentrated in vacuo and the residue was dissolved in ethyl acetate (50 mL). The solution was extracted with 15% aqueous solution of citric acid (30 mL×2) and the aqueous layers were combined, basified with a concentrated aqueous ammonium hydroxide to about pH 9, then extracted with ethyl acetate (50 mL×2). The combined organic layers were washed with brine (50 mL), dried over magnesium sulfate and concentrated in vacuo to afford trans-(±)-benzyl 3-amino-4-fluoroypyrrolidne-1-carobxylate.

Intermediate 25 trans-(±)-tert-Butyl (4-fluoropyrrolidin-3-yl)carbamate

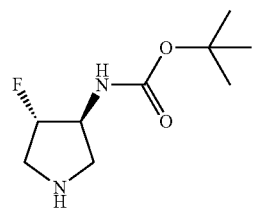

trans-(±)-1-Benzyl-3-[(tert-butoxycarbonyl)amino]-4-fluoropyrrolidine-1-carboxylate

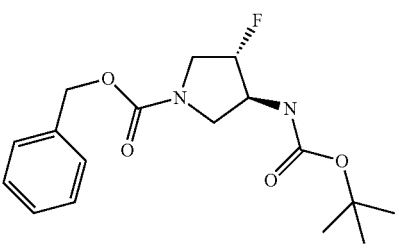 [SMILES: CC(C)(C)OC(=O)N[C@H]1CN(C(=O)OCc2ccccc2)C[C@@H]1F]

To a cooled solution of trans-(±)-benzyl-3-amino-4-fluoropyrrolidne-1-carobxylate (2.39 g) in chloroform (25 mL) was added dropwise a solution of di-tert-butyl dicarbonate (3.7 g) in chloroform (10 mL) in an ice-water bath. The mixture was stirred at room temperature for 19 hours. The reaction mixture was washed with water and the organic layer was dried over anhydrous magnesium sulfate and concentrated in vacuo. The residue was purified by a column chromatography on silica gel to afford 2.9 g of trans-(±)-1-benzyl-3-[(tert-butoxycarbonyl)amino]-4-fluoropyrrolidine-1-carboxylate (yield was 90%) as crystals.

trans-(±)-tert-Butyl (4-fluoropyrrolidin-3-yl) carbamate

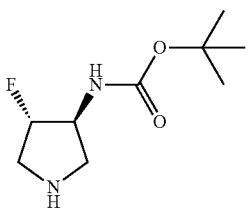

To a solution of trans-(±)-1-benzyl-3-[(tert-butoxycarbonyl)amino]-4-fluoropyrrolidine-1-carboxylate (3.39 g) in methanol (31 mL) and tetrahydrofuran (7 mL) was added palladium hydroxide (20 wt % on carbon, 500 mg) and the mixture was stirred at room temperature under 40-45 psi of hydrogen atmosphere overnight. The resulting mixture was filtered and the filtrate was concentrated in vacuo. The residue was triturated in the mixture of ethyl acetate and diisopropylether and filtered to remove the insoluable materials. The filtrate was concentrated in vacuo to afford 1.5 g of trans-(±)-tert-butyl (4-fluoropyrrolidin-3-yl) carbamate (yield was 74%) as a powder.

Intermediate 26 tert-Butyl (4S)-4-ethenyl-2,2-dimethyl-1,3-oxazolidine-3-carboxylate

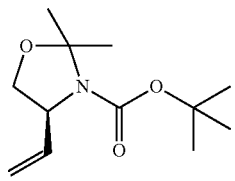 [SMILES: C=C[C@H]1COC(C)(C)N1C(=O)OC(C)(C)C]

3-tert-Butyl 4-methyl (4R)-2,2-dimethyl-1,3-oxazolidine-3,4-dicarboxylate

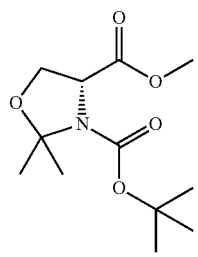 [SMILES: COC(=O)[C@H]1COC(C)(C)N1C(=O)OC(C)(C)C]

A solution of methyl (2R)-2-{[(tert-butoxy)carbonyl]amino}-3-hydroxypropanoate (22 g, 0.1 mol), 2,2-dimethoxypropane (20.8 g, 0.2 mol) and 4-methylbenzene-1-sulfonic acid (0.5 g) in toluene was heated with stirring at 110° C. overnight. The solvent was removed under reduced pressure. The residue was treated with ethyl acetate, washed with water and brine. The organic layer was dried over sodium sulfate, concentrated under reduced pressure. The residue distilled at 0.6 mbar to give 16.5 g of 3-tert-butyl 4-methyl (4R)-2,2-dimethyl-1,3-oxazolidine-3,4-dicarboxylate (yield was 63.6%) as an amber oil.

tert-Butyl (4R)-4-formyl-2,2-dimethyl-1,3-oxazolidine-3-carboxylate

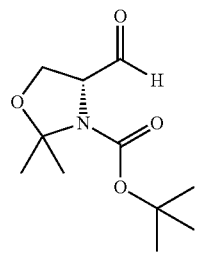 [SMILES: CC(C)(C)OC(=O)N1[C@@H](C=O)COC1(C)C]

To a cooled solution of 3-tert-butyl 4-methyl (4R)-2,2-dimethyl-1,3-oxazolidine-3,4-dicarboxylate (16.5 g, 63.6 mmol) in dry dichloromethane (300 mL) at −78° C., was added a cooled solution of 1.0 M diisobutylaluminium hydride in hexane (127.6 mL, 127.2 mmol) under argon. The rate of addition was adjusted so as to keep the internal temperature below −65° C. and take about 1 hour to complete. The reaction mixture was stirred for an additional 2 hours at −78° C. under argon. The reaction was quenched by slowly adding 60 mL of cold methanol (−78° C.) so as to keep the internal temperature below −65° C. The resulting mixture was extracted with ethyl acetate. The organic layer was washed with brine, dried over sodium sulfate, concentrated under reduced pressure. The residue was distilled at 0.7 mbar to give tert-butyl (4R)-4-formyl-2,2-dimethyl-1,3-oxazolidine-3-carboxylate (10 g, 68.5%) as colorless liquid.

tert-Butyl (4S)-4-ethenyl-2,2-dimethyl-1,3-oxazolidine-3-carboxylate

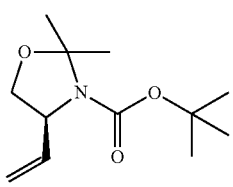 [SMILES: C=C[C@H]1COC(C)(C)N1C(=O)OC(C)(C)C]

To a solution of methyltriphenylphosphonium bromide (3.1 g, 8.64 mmol) in dry tetrahydrofuran (30 mL) was add a solution of sodium bis(trimethylsilyl)amide in hexane (1.0 M, 8.64 mL, 8.64 mmol) under argon. After the reaction was stirred for further 20 minutes, a solution of (4R)-4-formyl-2,2-dimethyl-1,3-oxazolidine-3-carboxylate (1.8 g, 7.86 mmol) in dry tetrahydrofuran (20 mL) was added dropwise. The resulting mixture was stirred at room temperature overnight. The solvent was removed under reduced pressure. The residue was purified by flash column to give tert-butyl (4S)-4-ethenyl-2,2-dimethyl-1,3-oxazolidine-3-carboxylate (1.5 g, 83.9%) as colorless liquid.

Intermediate 27

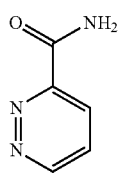

Pyridazine-3-carboxamide

To a cooled solution of pyridazine-3-carboxylic acid (1.0 g, 8.06 mmol) in tetrahydrofuran (40 mL) in a dry-ice bath was added 4-methyl-morpholine (0.9 g, 8.87 mmol) and isopropyl chloroformate (1.1 g, 8.87 mmol) slowly. The reaction was stirred at −30° C. for 6 hours, then an aqueous solution of ammonia (8 mL, 10% W/W) was added. The resulting mixture was stirred at room temperature overnight, washed with a saturated aqueous solution of potassium bisulfate (50 mL). The aqueous layer was extracted with ethyl acetate (30 mL×3). The combined organic layers were dried over sodium sulfate, filtered and concentrated in vacuo to afford 202.5 mg of the desired product (yield was 20.4%). MS obsd. (ESI$^+$) [(M+H)$^+$] 124, $^1$H NMR (400 MHz, CD$_3$OD) δ ppm 9.45-9.35 (t, J=1.6 Hz, 1 H), 8.58 (s, 1 H), 8.23-8.15 (d, J=7.6 Hz, 1 H), 7.98-7.88 (m, 2 H).

Intermediate 28

Oxetane-3,3-diyldimethanamine

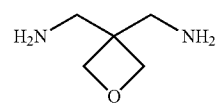

3,3-Bis-azidomethyl-oxetane

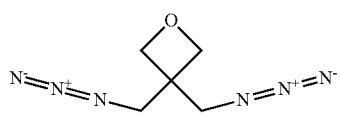 [SMILES: [N-]=[N+]=NCC1(CN=[N+]=[N-])COC1]

A mixture of 3,3-bis(bromomethyl)oxetane (25 g, 100 mmol) and sodium azide (14.3 g, 220 mmol) in water (65 ml) was added tetrabutylazanium bromide (1.61 g, 5 mmol). The reaction mixture was heated with stirring at 70° C. overnight. The reaction mixture was cooled to room temperature and extracted with dichloromethane (50 mL×3). The combined organic layers were washed with water, dried over sodium sulphate and concentrated in vacuo to afford 18.7 g of 3,3-bis-azidomethyl-oxetane as a light yellow oil. The crude product was used for next step without further purification.

Oxetane-3,3-diyldimethanamine

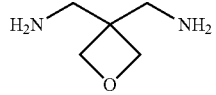

A solution of 3,3-bis-azidomethyl-oxetane (18.7 g) in methanol (15 ml) was stirred in the presence of 10% palladium on carbon (1.8 g) under hydrogen atmosphere at room temperature for 5 hours. The reaction mixture was filtered and the filtrate was concentrated in vacuo to afford oxetane-3,3-diyldimethanamine (12 g) as a light yellow solid.

Intermediate 29

Oxetan-3-ylidene-acetonitrile

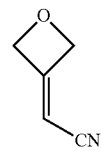

To a solution of oxetan-3-one (5 g, 69.4 mmol) in dry dichloromethane (150 ml) was added (triphenylphosphoranylidene)acetonitrile (20.9 g, 69.4 mmol) at room temperature. After being stirred for 6 hours, the mixture was concentrated in vacuo and the residue was filtered through a pad of silica gel (eluting with 30-50% diethyl ether in pentanes) to afford 5.2 g of oxetan-3-ylidene-acetonitrile as a white solid (yield was 79%).

3-(Benzylamino)oxetan-3-acetonitrile

A mixture of oxetan-3-ylidene-acetonitrile (950 mg, 10 mmol) and phenylmethanamine (1.31 ml, 12 mmol) was heated with stirring at 60° C. for 5 hours under nitrogen. The mixture was concentrated in vacuo. The residue was purified by flash column (eluting with 0-50% ethyl acetate in hexane) to afford 1.65 g of 3-(benzylamino)oxetan-3-acetonitrile as a colorless oil (yield was 81.7%).

3-(Aminoethyl)-N-benzyloxetan-3-amine

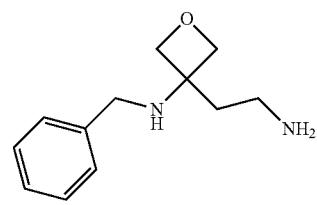 [SMILES: NCCC1(NCc2ccccc2)COC1]

To a cooled slurry of lithium aluminium hydride (327 mg, 8.6 mmol) in anhydrous diethyl ether (40 mL), was added a solution of 3-(benzylamino)oxetan-3-acetonitrile (1.0 g, 4.3 mmol) in anhydrous diethyl ether (10 mL) dropwise at 0° C. After being stirred at 0° C. for 2 hours, the reaction was quenched by introducing disodium sulfate decahydrate slowly. After being stirred for 30 minutes, the mixture was filtered, and the filter cake was washed with ethyl acetate. The filtrate was dried over sodium sulfate and concentrated in vacuo. The residue was purified by flash column to afford 800 mg of 3-(aminoethyl)-N-benzyloxetan-3-amine as a light yellow oil (yield was 79%).

Intermediate 30

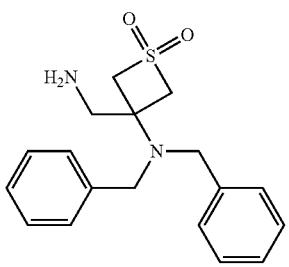 [SMILES: NCC1(N(Cc2ccccc2)Cc2ccccc2)CS(=O)(=O)C1]

The intermediate was prepared in analogy to 1-(1,1-dioxido-2,3-dihydro-1,4-benzothiazepin-4(5H)-yl)ethanone in Intermediate 4 by oxidation of 3-(aminomethyl)-N,N-dibenzylthietan-3-amine (Intermediate 9-4) with 3-chloroperoxybenzoic acid.

The following examples were prepared by the general methods outlined in the schemes above. They are intended to illustrate the meaning of the present invention but should by no means represent a limitation within the meaning of the present invention.

Example 1-1

N-[(3-Aminooxetan-3-yl)methyl]-2-(8-methoxy-1,1-dioxido-2,3-dihydro-1,4-benzothiazepin-4(5H)-yl)-6-methylquinolin-4-amine

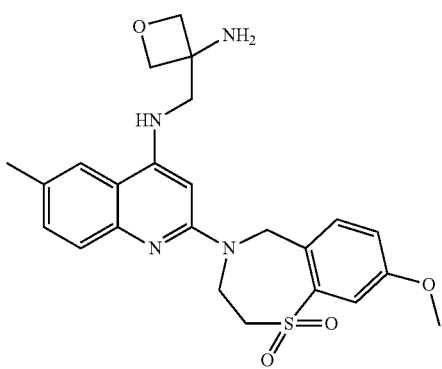

4-(4-Chloro-6-methylquinolin-2-yl)-8-methoxy-2,3,4,5-tetrahydro-1,4-benzothiazepine

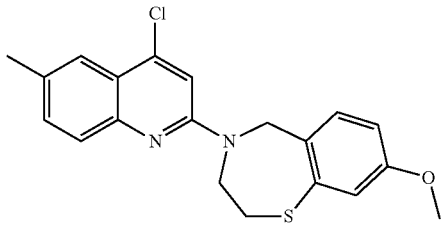

A mixture of 8-methoxy-2,3,4,5-tetrahydro-1,4-benzothiazepine (0.63 g, 3.2 mmol), 2,4-dichloro-6-methylquinoline (0.68 g, 3.2 mmol) and n-butanol (4 mL) was heated with stirring in a 5 mL of microwave process vial for 2.5 hours at 160° C. under microwave irradiation. The solvent was removed by concentration in vacuo. The residue was dissolved in a mixture solvent of ethanol and dichloromethane and then concentrated in vacuo to remove dichloromethane. The formed precipitate was collected by filtration, which was washed with diethyl ether and petroleum ether, dried in vacuo to afford 0.59 g of the product as a pale white solid (yield was 50%). MS obsd. (ESI$^+$) [(M+H)$^+$] 371.

4-(4-Chloro-6-methylquinolin-2-yl)-8-methoxy-2,3,4,5-tetrahydro-1,4-benzothiazepine 1,1-dioxide

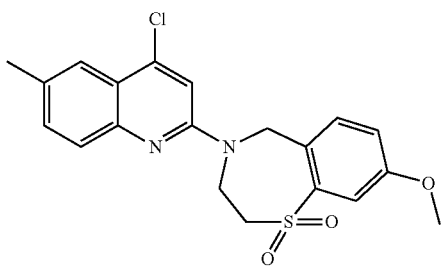

A mixture of 4-(4-chloro-6-methylquinolin-2-yl)-8-methoxy-2,3,4,5-tetrahydro-1,4-benzothiazepine (0.40 g, 1.1 mmol) and sodium metaperiodate (0.71 g, 3.3 mmol) in methanol (15 mL) and water (6 mL) was stirred for 12 hours at room temperature. After removal of the solvent by concentration in vacuo, the residue was dissolved in methanol (15 mL). A solution of potassium permanganate (0.17 g, 1.1 mmol) in water (6 mL) was added dropwise to the above solution which was cooled to 0° C. After being stirred for 2 hours at 0° C., the mixture was extracted with ethyl acetate (10 mL). The organic layer was filtered through a short silica gel column. The filtrate was concentrated in vacuo to afford 0.40 g of the product as a white solid (yield was 90%). MS obsd. (ESI$^+$) [(M+H)$^+$] 403.

N-{[3-(Dibenzylamino)oxetan-3-yl]methyl}-2-(8-methoxy-1,1-dioxido-2,3-dihydro-1,4-benzothiazepin-4(5H)-yl)-6-methylquinolin-4-amine

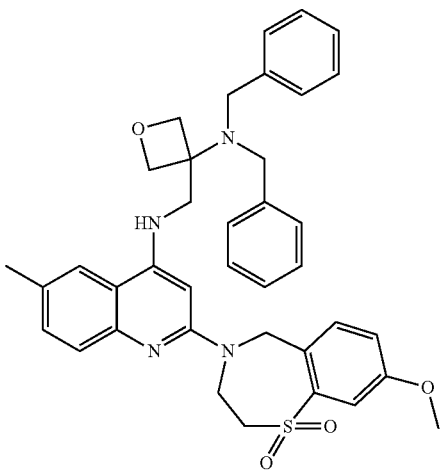

A mixture of 4-(4-chloro-6-methylquinolin-2-yl)-8-methoxy-2,3,4,5-tetrahydro-1,4-benzothiazepine 1,1-dioxide (50 mg, 0.13 mmol), cesium carbonate (80 mg, 0.26 mmol), palladium acetate (2.8 mg, 0.013 mmol), 9,9-dimethyl-4,5-bis(diphenylphosphino)xanthene (11 mg, 0.019 mmol) and 3-(aminomethyl)-N,N-dibenzyloxetan-3-amine (54 mg, 0.19 mmol) in toluene (5 mL) was heated with stirring for 4 hours at 120° C. After being cooled to room temperature, the mixture was concentrated in vacuo. The residue was purified by flash chromatography (eluting with 0.5% triethylamine and 5% methanol in dichloromethane) to afford 50 mg of the product as a white powder (yield was 59%). MS obsd. (ESI$^+$) [(M+H)$^+$] 649. N-[(3-Aminooxetan-3-yl)methyl]-2-(8-methoxy-1,1-dioxido-2,3-dihydro-1,4-benzothiazepin-4(5H)-yl)-6-methylquinolin-4-amine

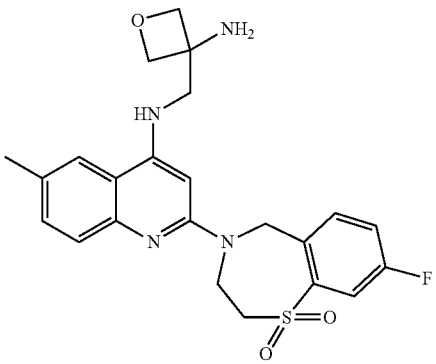 [SMILES: Cc1ccc2nc(N3CCS(=O)(=O)c4cc(F)ccc4C3)cc(NCC3(N)COC3)c2c1]

A mixture of N-{[3-(dibenzylamino)oxetan-3-yl]methyl}-2-(8-methoxy-1,1-dioxido-2,3-dihydro-1,4-benzothiazepin-4(5H)-yl)-6-methylquinolin-4-amine (50 mg, 0.077 mmol), 10% palladium hydroxide on carbon (100 mg) and trifluoroacetic acid (0.2 mL) in methanol (20 mL) was stirred for 12 hours at room temperature under hydrogen atmosphere (1 bar). The resulting mixture was basified with a saturated aqueous solution of sodium bicarbonate to pH >9 and then extracted with dichloromethane (20 mL×2). The combined organic layers were dried over anhydrous sodium sulfate, and then concentrated in vacuo. The residue was purified by preparative HPLC to afford 10 mg of the product (yield was 28%). MS obsd. (ESI$^+$) [(M+H)$^+$] 469, $^1$H NMR (400 MHz, CD$_3$OD) δ ppm 7.82 (d, J=8.34 Hz, 2 H), 7.56 (brs, 2 H), 7.44 (brs, 1 H), 7.18 (d, J=8.59 Hz, 1 H), 6.22 (s, 1 H), 5.27-5.13 (m, 2 H), 4.74-4.55 (m, 4 H), 4.50 (brs, 2 H), 3.86 (s, 3 H), 3.81-3.72 (m, 2 H), 3.71-3.60 (m, 2 H), 2.46 (s, 3 H).

Example 1-2

N-[(3-Aminooxetan-3-yl)methyl]-2-(8-fluoro-1,1-dioxido-2,3-dihydro-1,4-benzothiazepin-4(5H)-yl)-6-methylquinolin-4-amine

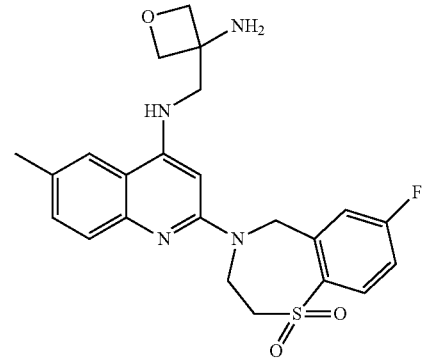 [SMILES: Cc1ccc2nc(N3CCS(=O)(=O)c4ccc(F)cc4C3)cc(NCC3(N)COC3)c2c1]

The title compound was prepared in analogy to Example 1-1 in Scheme 4 by using 2,4-dichloro-6-methylquinoline, 8-fluoro-2,3,4,5-tetrahydro-1,4-benzothiazepine and 3-(aminomethyl)-N,N-dibenzyloxetan-3-amine. MS obsd. (ESI$^+$) [(M+H)$^+$] 457, $^1$H NMR (400 MHz, CD$_3$OD) δ ppm 7.95 (dd, J=8.46, 5.18 Hz, 1 H), 7.77-7.64 (m, 2 H), 7.47 (d, J=8.34 Hz, 1 H), 7.43-7.25 (m, 2 H), 6.20 (s, 1 H), 5.19 (brs, 2 H), 4.68-4.57 (m, 6 H), 3.70 (s, 2 H), 3.67-3.56 (m, 2 H), 2.44 (s, 3 H).

Example 1-3

N-[(3-Aminooxetan-3-yl)methyl]-2-(7-fluoro-1,1-dioxido-2,3-dihydro-1,4-benzothiazepin-4(5H)-yl)-6-methylquinolin-4-amine The title compound was prepared in analogy to Example 1-1 in Scheme 4 by using 2,4-dichloro-6-methylquinoline, 7-fluoro-2,3,4,5-tetrahydro-1,4-benzothiazepine and 3-(aminomethyl)-N,N-dibenzyloxetan-3-amine. MS obsd. (ESI⁺) [(M+H)⁺] 457, ¹H NMR (400 MHz, CD₃OD) δ ppm 8.02 (dd, J=8.72, 5.43 Hz, 1 H), 7.79-7.65 (m, 2 H), 7.46 (d, J=8.34 Hz, 1 H), 7.33 (d, J=8.84 Hz, 1 H), 7.17 (td, J=8.40, 2.65 Hz, 1 H), 6.17 (s, 1 H), 5.17 (brs, 2 H), 4.68-4.41 (m, 6 H), 3.72-3.64 (m, 2 H), 3.64-3.53 (m, 2 H), 2.44 (s, 3 H).

Example 1-4

N-[(3-Aminooxetan-3-yl)methyl]-2-(9-fluoro-1,1-dioxido-2,3-dihydro-1,4-benzothiazepin-4(5H)-yl)-6-methylquinolin-4-amine

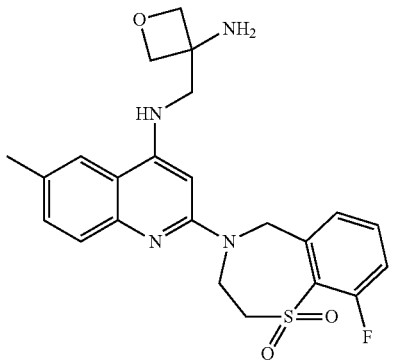 [SMILES: Cc1ccc2nc(N3CCS(=O)(=O)c4c(F)cccc4C3)cc(NCC3(N)COC3)c2c1]

The title compound was prepared in analogy to Example 1-1 in Scheme 4 by using 2,4-dichloro-6-methylquinoline, 9-fluoro-2,3,4,5-tetrahydro-1,4-benzothiazepine and 3-(aminomethyl)-N,N-dibenzyloxetan-3-amine. MS obsd. (ESI⁺) [(M+H)⁺] 457, ¹H NMR (400 MHz, CD₃OD) δ ppm 7.75-7.65 (m, 2 H), 7.60 (td, J=7.96, 4.80 Hz, 1 H), 7.46 (d, J=8.34 Hz, 1 H), 7.32 (dd, J=8.59, 1.77 Hz, 1 H), 7.17 (dd, J=10.36, 8.34 Hz, 1 H), 6.15 (s, 1 H), 5.20 (s, 2 H), 4.68-4.53 (m, 4 H), 4.45 (brs, 2 H), 3.86-3.73 (m, 2 H), 3.65 (s, 2 H), 2.43 (s, 3 H).

Example 1-5

N-[(3-Aminooxetan-3-yl)methyl]-2-(7-methoxy-1,1-dioxido-2,3-dihydro-1,4-benzothiazepin-4(5H)-yl)-6-methylquinolin-4-amine

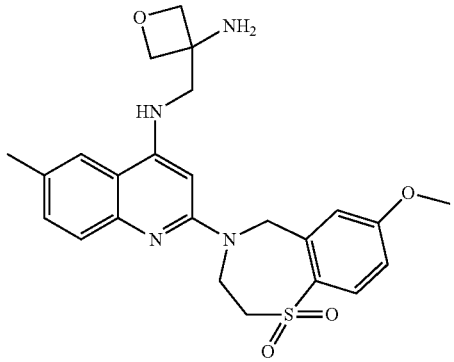

The title compound was prepared in analogy to Example 1-1 in Scheme 4 by using 2,4-dichloro-6-methylquinoline, 7-methoxy-2,3,4,5-tetrahydro-1,4-benzothiazepine and 3-(aminomethyl)-N,N-dibenzyloxetan-3-amine. MS obsd. (ESI⁺) [(M+H)⁺] 469, ¹H NMR (400 MHz, DMSO-d6) δ ppm 7.79 (d, J=8.84 Hz, 1 H), 7.68 (s, 1 H), 7.57 (d, J=2.53 Hz, 1 H), 7.34 (d, J=8.59 Hz, 1 H), 7.30-7.21 (m, 1 H), 6.96 (dd, J=8.72, 2.65 Hz, 1 H), 6.35 (t, J=5.31 Hz, 1 H), 6.19 (s, 1 H), 5.04 (brs, 2 H), 4.45-4.39 (m, 6 H), 3.92-3.75 (m, 3 H), 3.62-3.45 (m, 4 H), 2.37 (s, 3 H).

Example 1-6

N-[(3-Aminooxetan-3-yl)methyl]-2-(8-chloro-1,1-dioxido-2,3-dihydro-1,4-benzothiazepin-4(5H)-yl)-6-methylquinolin-4-amine

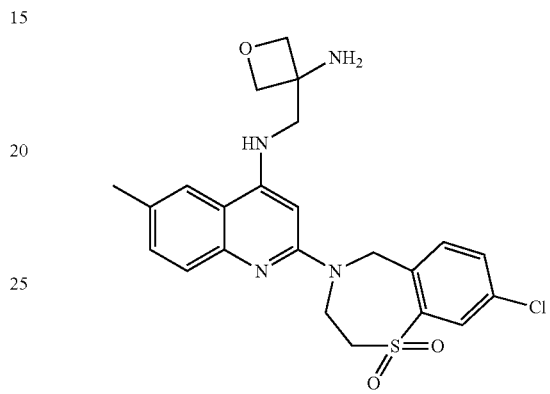

The title compound was prepared in analogy to Example 1-1 in Scheme 4 by using 2,4-dichloro-6-methylquinoline, 8-chloro-2,3,4,5-tetrahydro-1,4-benzothiazepine and 3-(aminomethyl)-N,N-dibenzyloxetan-3-amine. MS obsd. (ESI⁺) [(M+H)⁺] 473, ¹H NMR (400 MHz, CD₃OD) δ ppm 7.99-7.88 (m, 2 H), 7.77 (s, 1 H), 7.64 (dd, J=8.08, 2.27 Hz, 1 H), 7.53 (d, J=8.59 Hz, 1 H), 7.40 (d, J=8.59 Hz, 1 H), 6.19 (s, 1 H), 5.21 (brs, 2 H), 4.84-4.56 (m, 4 H), 4.53 (brs, 2 H), 3.75 (s, 2 H), 3.68 (brs, 2 H), 2.45 (s, 3 H).

Example 1-7

N-[(3-Aminooxetan-3-yl)methyl]-2-(7-methoxy-1,1-dioxido-2,3-dihydro-1,4-benzothiazepin-4(5H)-yl)-quinolin-4-amine

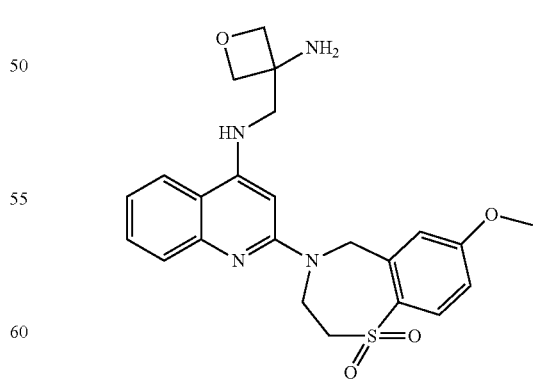

The title compound was prepared in analogy to Example 1-1 in Scheme 4 by using 2,4-dichloroquinoline, 7-methoxy-2,3,4,5-tetrahydro-1,4-benzothiazepine and 3-(aminomethyl)-N,N-dibenzyloxetan-3-amine. MS obsd. (ESI⁺) [(M+

H)+] 455, ¹H NMR (400 MHz, CD₃OD) δ ppm 7.79 (d, J=8.84 Hz, 1 H), 7.68 (s, 1 H), 7.57 (d, J=2.53 Hz, 1 H), 7.34 (d, J=8.59 Hz, 1 H), 7.30-7.21 (m, 1 H), 6.96 (dd, J=8.72, 2.65 Hz, 1 H), 6.35 (t, J=5.31 Hz, 1 H), 6.19 (s, 1 H), 5.04 (brs, 2 H), 4.45 (d, J=5.81 Hz, 2 H), 4.39 (d, J=5.81 Hz, 2 H), 3.92-3.75 (m, 3 H), 3.62-3.45 (m, 4 H), 2.37 (s, 3 H).

Example 2-1

N-[(3-Aminotetrahydrofuran-3-yl)methyl]-2-(1,1-dioxido-2,3-dihydro-1,4-benzothiazepin-4(5H)-yl)-6-methylquinolin-4-amine

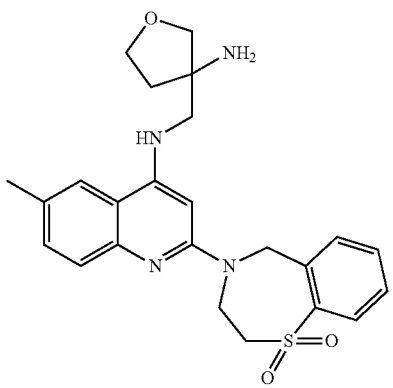 [SMILES: Cc1ccc2nc(N3CCS(=O)(=O)c4ccccc4C3)cc(NCC3(N)CCOC3)c2c1]

N-{[3-(Dibenzylamino)tetrahydrofuran-3-yl]methyl}-2-(1,1-dioxido-2,3-dihydro-1,4-benzothiazepin-4(5H)-yl)-6-methylquinolin-4-amine

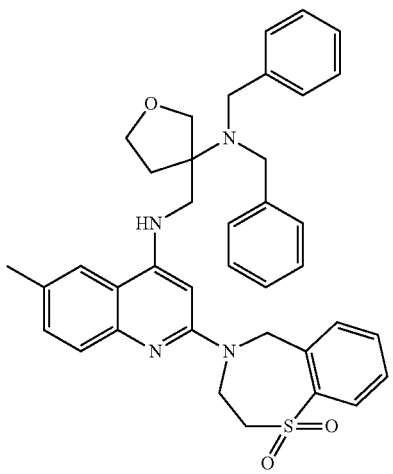 [SMILES: Cc1ccc2nc(N3CCS(=O)(=O)c4ccccc4C3)cc(NCC3(N(Cc4ccccc4)Cc4ccccc4)CCOC3)c2c1]

To a mixture of 4-(4-chloro-6-methylquinolin-2-yl)-2,3,4,5-tetrahydro-1,4-benzothiazepine 1,1-dioxide (400 mg, 1.08 mmol, prepared in analogy to 4-(4-chloro-6-methylquinolin-2-yl)-2,3,4,5-tetrahydro-1,4-benzothiazepine 1,1-dioxide in Example 1-1 by using 2,3,4,5-tetrahydro-1,4-benzothiazepine and 2,4-dichloro-6-methylquinoline), 3-(aminomethyl)-N,N-dibenzyl tetrahydrofuran-3-amine (385 mg, 1.3 mmol), sodium tert-butoxide (207 mg, 2.16 mmol), 1,1'-bis(diphenylphosphino)ferrocene-palladium(II)dichloride (50 mg) and 1,1'-bis(diphenylphosphino)ferrocene (200 mg) in 1,4-dioxane (5 mL) was heated with stirring in a sealed 10 mL of microwave process vial for 1 hour at 120° C. under microwave irradiation. The resulting mixture was concentrated in vacuo. The residue was purified by preparative HPLC to afford 270 mg of the desired product (yield was 39.7%).

N-[(3-Aminotetrahydrofuran-3-yl)methyl]-2-(1,1-dioxido-2,3-dihydro-1,4-benzothiazepin-4(5H)-yl)-6-methylquinolin-4-amine

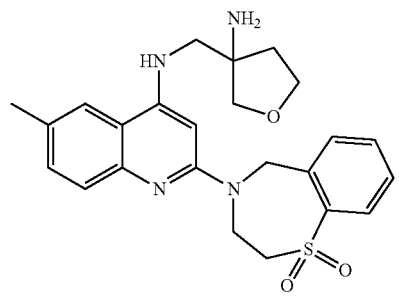 [SMILES: Cc1ccc2nc(N3CCS(=O)(=O)c4ccccc4C3)cc(NCC3(N)CCOC3)c2c1]

A mixture of N-{[3-(dibenzylamino)tetrahydrofuran-3-yl]methyl}-2-(1,1-dioxido-2,3-dihydro-1,4-benzothiazepin-4(5H)-yl)-6-methylquinolin-4-amine (270 mg, 0.43 mmol), 10% palladium hydroxide on active carbon (300 mg) in methanol (20 mL) was stirred for 16 hours at room temperature under hydrogen atmosphere (1 bar). The resulting mixture was concentrated in vacuo. The residue was purified by preparative HPLC to afford 21 mg of the desired product (yield was 10.8%). MS obsd. (ESI⁺) [(M+H)⁺] 453, ¹H NMR (400 MHz, CD₃OD) δ ppm 8.06-7.98 (m, 2 H), 7.89-7.87 (d, J=7.6 Hz, 1 H), 7.75-7.66 (m, 2 H), 7.59-7.56 (m, 2 H), 6.22-6.20 (d, J=8.4 Hz, 1 H), 5.35 (s, 2 H), 4.5 (s, 2 H), 4.08-3.97 (m, 4 H), 3.88-3.73 (m, 3 H), 2.81 (s, 2 H), 2.46 (s, 3 H), 2.31 (s, 2 H).

Example 2-2

N-[(3-Amino oxetan-3-yl)methyl]-2-(1,1-dioxido-2,3-dihydro-1,4-benzothiazepin-4(5H)-yl)-6-methylquinolin-4-amine

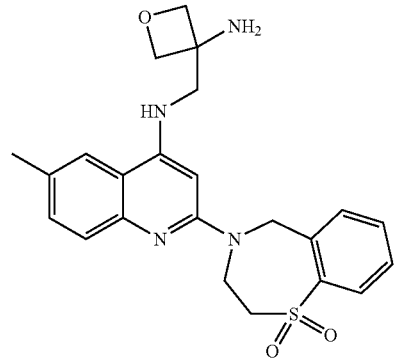 [SMILES: Cc1ccc2nc(N3CCS(=O)(=O)c4ccccc4C3)cc(NCC3(N)COC3)c2c1]

The title compound was prepared in analogy to Example 2-1 in Scheme 4 by using 4-(4-chloro-6-methylquinolin-2-yl)-2,3,4,5-tetrahydro-1,4-benzothiazepine 1,1-dioxide (prepared in analogy to the one in Example 2-1) and 3-(aminomethyl)-N,N-dibenzyloxetan-3-amine. MS obsd. (ESI⁺) [(M+

H)+] 439, ¹H NMR (400 MHz, CD₃OD) δ ppm 7.98 (dd, J=1.2, 7.6 Hz, 1 H), 7.90 (d, J=6.8 Hz, 1 H), 7.66 (s, 1 H), 7.62 (td, J=1.2, 7.6 Hz, 1 H), 7.47-7.43 (m, 2 H), 7.30 (dd, J=1.6, 8.4 Hz, 1 H), 6.20 (s, 1 H), 5.18 (s, 2 H), 4.63 (d, J=6.4 Hz, 2 H), 4.59 (d, J=6.8 Hz, 2 H), 4.59 (brs, 2 H), 3.68 (s, 2 H), 3.59 (t, J=4.4 Hz, 2 H), 2.42 (s, 3 H).

Example 2-3

N-[(4-Aminotetrahydro-2H-pyran-4-yl)methyl]-2-(1,1-dioxido-2,3-dihydro-1,4-benzothiazepin-4(5H)-yl)-6-methylquinolin-4-amine

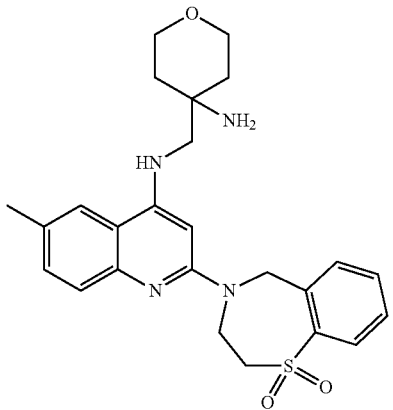 [SMILES: Cc1ccc2nc(N3CCS(=O)(=O)c4ccccc4C3)cc(NCC3(N)CCOCC3)c2c1]

The title compound was prepared in analogy to Example 2-1 in Scheme 4 by using 4-(4-chloro-6-methylquinolin-2-yl)-2,3,4,5-tetrahydro-1,4-benzothiazepine 1,1-dioxide (prepared in analogy to the one in Example 2-1) and 4-(aminomethyl)-N,N-dibenzyltetrahydro-2H-pyran-4-amine. MS obsd. (ESI⁺) [(M+H)⁺] 467, ¹H NMR (400 MHz, CD₃OD) δ ppm 7.98 (d, J=7.2 Hz, 1 H), 7.87 (d, J=7.6 Hz, 1 H), 7.68 (s, 1 H), 7.64-7.60 (m, 1 H), 7.44 (m, 2 H), 7.29 (dd, J=2.0, 8.4 Hz, 1 H), 6.14 (s, 1 H), 5.16 (s, 2 H), 4.54 (brs, 2 H), 3.86-3.74 (m, 4 H), 3.58 (t, J=4.8 Hz, 2 H), 2.42 (s, 3 H), 2.18 (dd, J=2.4, 4.8 Hz, 2 H), 1.88-1.81 (m, 2 H), 1.57 (m, 2 H).

Example 2-4

N-[(3-Aminooxetan-3-yl)methyl]-2-(8-methyl-1,1-dioxido-2,3-dihydro-1,4-benzothiazepin-4(5H)-yl)-quinolin-4-amine

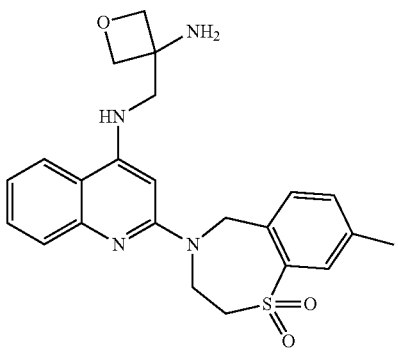 [SMILES: Cc1ccc2c(c1)S(=O)(=O)CCN(c1cc(NCC3(N)COC3)c3ccccc3n1)C2]

The title compound was prepared in analogy to Example 2-1 in Scheme 4 by using 4-(4-chloroquinolin-2-yl)-8-methyl-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 8-methyl-2,3,4,5-tetrahydro-1,4-benzothiazepine and 2,4-dichloroquinoline) and 3-(aminomethyl)-N,N-dibenzyloxetan-3-amine. MS (ESI⁺) [(M+H)⁺] 439, ¹H NMR (400 MHz, CD₃OD) δ ppm 7.91 (d, J=8.34 Hz, 1 H), 7.84 (d, J=7.58 Hz, 1 H), 7.72-7.60 (m, 1 H), 7.49-7.35 (m, 3 H), 7.09 (ddd, J=8.21, 5.18, 3.03 Hz, 1 H), 6.52 (t, J=5.43 Hz, 1 H), 6.22 (s, 1 H), 5.06 (brs, 2 H), 4.45 (d, J=6.06 Hz, 3 H), 4.38 (d, J=6.06 Hz, 3 H), 3.61 (t, J=4.80 Hz, 2 H), 3.56 (d, J=5.31 Hz, 2 H), 2.31 (s, 3 H).

Example 2-5

N-[(3-Aminooxetan-3-yl)methyl]-6-methyl-2-(8-methyl-1,1-dioxido-2,3-dihydro-1,4-benzothiazepin-4(5H)-yl)quinolin-4-amine

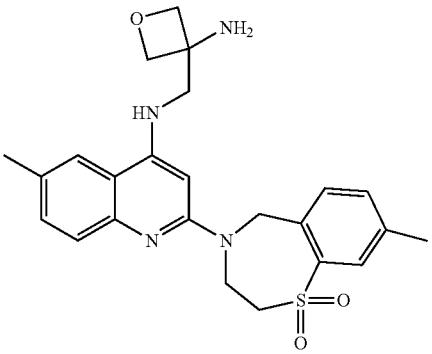

The title compound was prepared in analogy to Example 2-1 in Scheme 4 by using 4-(4-chloro-6-methylquinolin-2-yl)-8-methyl-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 8-methyl-2,3,4,5-tetrahydro-1,4-benzothiazepine and 2,4-dichloro-6-methylquinoline) and 3-(aminomethyl)-N,N-dibenzyloxetan-3-amine. MS obsd. (ESI⁺) [(M+H)⁺] 453, ¹H NMR (400 MHz, CD₃OD) δ ppm 7.82 (d, J=7.83 Hz, 1 H), 7.68 (d, J=3.03 Hz, 2 H), 7.41 (d, J=6.57 Hz, 1 H), 7.33 (d, J=8.59 Hz, 1 H), 7.25 (dd, J=8.59, 1.52 Hz, 1 H), 6.42 (t, J=5.56 Hz, 1 H), 6.19 (s, 1 H), 5.05 (brs, 2 H), 4.45 (d, J=5.81 Hz, 3 H), 4.39 (d, J=6.06 Hz, 3 H), 3.60 (t, J=4.55 Hz, 2 H), 3.55 (d, J=5.31 Hz, 2 H), 2.37 (s, 3 H), 2.31 (s, 3 H).

Example 2-6

2-(1,1-Dioxido-2,3-dihydro-1,4-benzothiazepin-4(5H)-yl)-6-methyl-N-(2-oxa-6-azaspiro[3.4]oct-8-yl)quinolin-4-amine

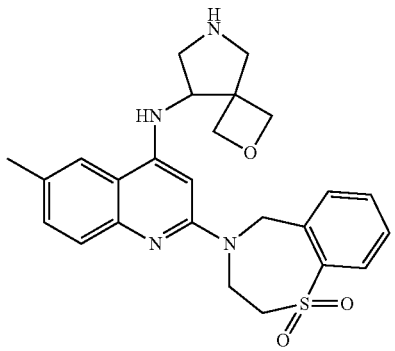 [SMILES: Cc1ccc2nc(N3CCS(=O)(=O)c4ccccc4C3)cc(NC3CNCC34COC4)c2c1]

The title compound was prepared in analogy to Example 2-1 in Scheme 4 by using 4-(4-chloro-6-methylquinolin-2-yl)-2,3,4,5-tetrahydro-1,4-benzothiazepine 1,1-dioxide (prepared in analogy to the one in Example 2-1) and 6-benzyl-2-oxa-6-azaspiro[3.4]oct-8-ylamine. MS obsd. (ESI⁺) [(M+H)⁺] 465, ¹H NMR (400 MHz, CD₃OD) δ ppm 8.11-8.08 (m, 2 H), 7.90-7.88 (d, J=7.2, 1 H), 7.75-7.70 (m, 2 H), 7.65-7.59 (m, 2 H), 6.36 (s, 1 H), 5.38-5.36 (d, J=8.8, 2 H), 5.20-5.10 (m, 1 H), 4.80-4.79 (m, 2 H), 4.74-4.72 (m, 2 H), 4.56-4.54 (d, J=7.2, 2 H), 3.90-3.87 (m, 1 H), 3.81-3.75 (m, 4 H), 3.60-3.50 (m, 1 H), 2.48 (s, 3 H).

Example 2-7

N-[2-(3-Aminooxetan-3-yl)ethyl]-2-(1,1-dioxido-2,3-dihydro-1,4-benzothiazepin-4(5H)-yl)-6-methylquinolin-4-amine

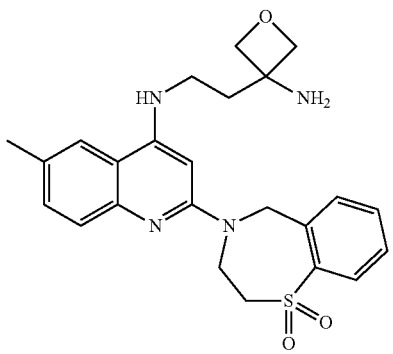 [SMILES: Cc1ccc2nc(N3CCS(=O)(=O)c4ccccc4C3)cc(NCCC3(N)COC3)c2c1]

The title compound was prepared in analogy to Example 2-1 in Scheme 4 by using 4-(4-chloro-6-methylquinolin-2-yl)-2,3,4,5-tetrahydro-1,4-benzothiazepine 1,1-dioxide (prepared in analogy to the one in Example 2-1) and 3-(aminoethyl)-N-benzyloxetan-3-amine. MS obsd. (ESI⁺) [(M+H)⁺] 453, ¹H NMR (400 MHz, DMSO-d6) δ ppm 7.95-7.89 (t, 1 H), 7.89-7.87 (t, 1 H), 7.64-7.60 (m, 2 H), 7.49-7.45 (m, 1 H), 7.31 (d, J=8.4 Hz, 1 H), 7.24-7.21 (m, 1 H), 6.87 (t, J=10.4 Hz, 1 H), 6.05 (s, 1 H), 5.08 (s, 2 H), 4.39 (m, 6 H), 3.63 (t, J=9.2 Hz, 2 H), 3.41-3.36 (m, 2 H), 2.41 (s, 2 H), 2.35 (s, 3 H), 2.08 (t, J=14.4 Hz, 2 H).

Example 2-8

N-[(3-Aminooxetan-3-yl)methyl]-6-methyl-2-(5-methyl-1,1-dioxido-2,3-dihydro-1,4-benzothiazepin-4(5H)-yl)quinolin-4-amine

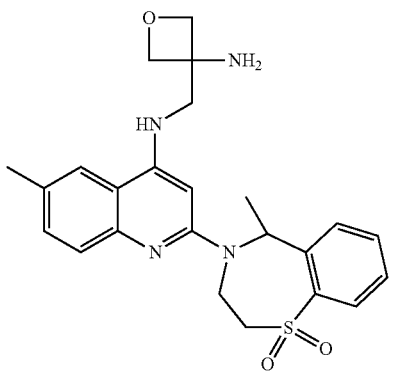 [SMILES: Cc1ccc2nc(N3CCS(=O)(=O)c4ccccc4C3C)cc(NCC3(N)COC3)c2c1]

The title compound was prepared in analogy to Example 2-1 in Scheme 4 by using 4-(4-chloro-6-methylquinolin-2-yl)-5-methyl-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 5-methyl-2,3,4,5-tetrahydro-1,4-benzothiazepine and 2,4-dichloro-6-methylquinoline) and 3-(aminomethyl)-N,N-dibenzyloxetan-3-amine. MS obsd. (ESI⁺) [(M+H)⁺] 453, ¹H NMR (400 MHz, CD₃OD) δ ppm 8.03 (dd, J=7.96, 1.39 Hz, 1 H), 7.90 (d, J=6.57 Hz, 1 H), 7.71-7.64 (m, 2 H), 7.46 (ddd, J=8.15, 6.63, 1.64 Hz, 2 H), 7.33 (dd, J=8.59, 1.77 Hz, 1 H), 6.15 (s, 1 H), 5.86 (d, J=6.82 Hz, 1 H), 4.64-4.53 (m, 4 H), 4.40-4.25 (brs, 2 H), 3.70 (d, J=8.59 Hz, 1 H), 3.62-3.58 (m, 2 H), 3.57-3.49 (m, 1 H), 2.43 (s, 3 H), 2.00 (d, J=7.07 Hz, 3 H).

Example 2-9

N-[(3-Aminooxetan-3-yl)methyl]-2-(8-methoxy-1,1-dioxido-2,3-dihydro-1,4-benzothiazepin-4(5H)-yl)quinolin-4-amine

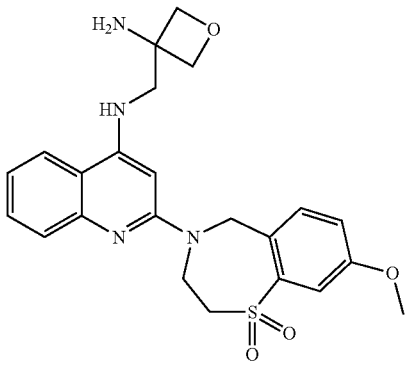 [SMILES: COc1ccc2c(c1)S(=O)(=O)CCN(c1cc(NCC3(N)COC3)c3ccccc3n1)C2]

The title compound was prepared in analogy to Example 2-1 in Scheme 4 by using 4-(4-chloroquinolin-2-yl)-8-methoxy-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 8-methoxy-2,3,4,5-tetrahydro-1,4-benzothiazepine and 2,4-dichloroquinoline) and 3-(aminomethyl)-N,N-dibenzyloxetan-3-amine. MS obsd. (ESI⁺) [(M+H)⁺] 455, ¹H NMR (400 MHz, CD₃OD) δ ppm 7.91-7.74 (m, 2 H), 7.58-7.38 (m, 3 H), 7.22-7.03 (m, 2 H), 6.23 (s, 1 H), 5.12 (brs, 2 H), 4.70-4.46 (m, 6 H), 3.81 (s, 3 H), 3.70 (s, 2 H), 3.65-3.52 (m, 2 H).

Example 2-10

N-[(3-Aminooxetan-3-yl)methyl]-2-(1,1-dioxido-2,3-dihydro-1,4-benzothiazepin-4(5H)-yl)-1,6-naphthyridin-4-amine

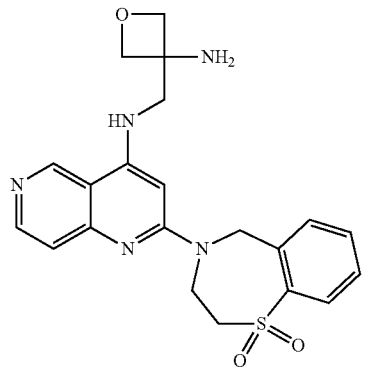 [SMILES: NC1(CNc2cc(N3CCS(=O)(=O)c4ccccc4C3)nc3ccncc23)COC1]

The title compound was prepared in analogy to Example 2-1 in Scheme 4 by using 4-(4-chloro-1,6-naphthyridin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,3,4,5-tetrahydro-1,4-benzothiazepine and 2,4-dichloro-1,6-naphthyridine) and 3-(aminomethyl)-N,N-dibenzyloxetan-3-amine. MS obsd. (ESI$^+$) [(M+H)$^+$] 426, $^1$H NMR (400 MHz, CD$_3$OD) δ ppm 9.15 (s, 1 H), 8.28-8.80 (d, J=6.4 Hz, 1 H), 8.00-7.95 (d, J=1.2 Hz, 1 H), 7.95-7.90 (d, J=7.2 Hz, 1 H), 7.62-7.58 (t, J=0.8 Hz, 1 H), 7.50-7.40 (m, 2 H), 6.31 (s, 1 H), 5.35 (s, 2 H), 4.65-4.58 (m, 6 H), 3.80 (s, 2 H), 3.60-3.50 (t, J=2.8 Hz, 2 H).

Example 2-11

N-[(1-Amino cyclohexyl)methyl]-2-(1,1-dioxido-2,3-dihydro-1,4-benzothiazepin-4(5H)-yl)-6-methylquinolin-4-amine

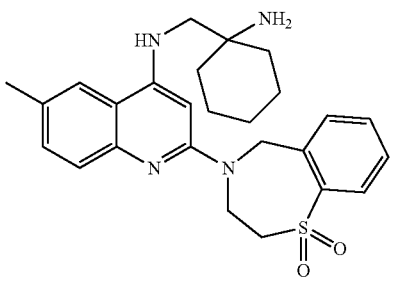 [SMILES: Cc1ccc2nc(N3CCS(=O)(=O)c4ccccc4C3)cc(NCC3(N)CCCCC3)c2c1]

The title compound was prepared in analogy to Example 2-1 in Scheme 4 by using 4-(4-chloro-6-methylquinolin-2-yl)-2,3,4,5-tetrahydro-1,4-benzothiazepine 1,1-dioxide (prepared in analogy to the one in Example 2-1) and 1-(aminomethyl)-N,N-dibenzylcyclohexanamine. MS obsd. (ESI$^+$) [(M+H)$^+$] 465, $^1$H NMR (400 MHz, CDCl$_3$) δ ppm 8.02-7.99 (dd, J=1.2 Hz, 8.0 Hz, 1 H), 7.65-7.63 (d, J=7.6 Hz, 1 H), 7.48-7.46 (m, 2 H), 7.34-7.25 (m, 3 H), 5.86 (s, 1 H), 5.64 (s, 1 H), 5.10 (s, 2 H), 4.56 (s, 2 H), 3.55 (s, 2 H), 3.05-3.04 (d, J=4.8 Hz, 2 H), 2.41 (s, 3 H), 1.98 (s, 4 H), 1.56 (m, 10 H).

Example 3-1

N-{[3-(Aminomethyl)oxetan-3-yl]methyl}-2-(8-fluoro-1,1-dioxido-2,3-dihydro-1,4-benzothiazepin-4(5H)-yl)-6-methylquinolin-4-amine

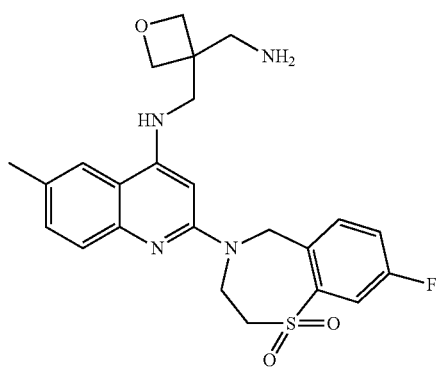 [SMILES: Cc1ccc2nc(N3CCS(=O)(=O)c4cc(F)ccc4C3)cc(NCC3(CN)COC3)c2c1]

A mixture of 8-(4-chloro-6-methylquinolin-2-yl)-8-fluoro-2,3,4,5-tetrahydro-1,4-benzothiazepine 1,1-dioxide (200 mg, 0.51 mmol, prepared in analogy to 4-(4-chloro-6-methylquinolin-2-yl)-2,3,4,5-tetrahydro-1,4-benzothiazepine 1,1-dioxide in Example 2-1 by using 8-fluoro-2,3,4,5-tetrahydro-1,4-benzothiazepine and 2,4-dichloro-6-methylquinoline), sodium tert-butoxide (96 mg, 1.02 mmol), 1,1'-bis(diphenylphosphino)ferrocene-palladium(II)dichloride (42 mg, 0.051 mmol), 1,1'-bis(diphenylphosphino)ferrocene (29 mg, 0.051 mmol), and oxetane-3,3-diyldimethanamine (89 mg, 0.77 mmol) in 1,4-dioxane (2 mL) was heated with stirring in a sealed 5 mL of microwave process via for 1.5 hours at 120° C. under microwave irradiation. The resulting mixture was concentrated in vacuo. The residue was purified by preparative HPLC to afford 48 mg of the product as a white product (yield was 20%). MS obsd. (ESI$^+$) [(M+H)$^+$] 471, $^1$H NMR (400 MHz, CD$_3$OD) δ ppm 7.95 (dd, J=8.34, 5.05 Hz, 1 H), 7.74 (t, J=5.56 Hz, 2 H), 7.54 (d, J=8.59 Hz, 1 H), 7.46-7.29 (m, 2 H), 6.19 (s, 1 H), 5.23 (brs, 2 H), 4.69-4.58 (m, 8 H), 3.78 (s, 2 H), 3.69 (brs, 2 H), 3.41 (s, 2 H), 2.46 (s, 3 H).

Example 3-2

N-{[3-(Benzylamino)oxetan-3-yl]methyl}-6-chloro-2-(7-fluoro-1,1-dioxido-2,3-dihydro-1,4-benzothiazepin-4(5H)-yl)quinolin-4-amine

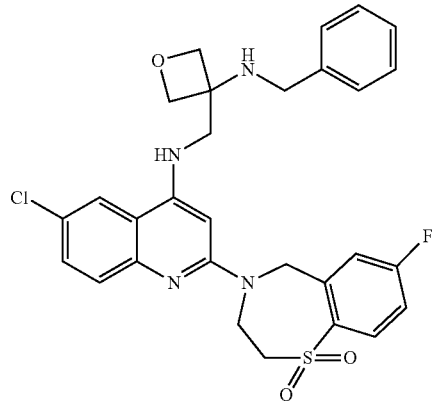 [SMILES: O=S1(=O)CCN(c2cc(NCC3(NCc4ccccc4)COC3)c3cc(Cl)ccc3n2)Cc2cc(F)ccc21]

The title compound was prepared in analogy to Example 3-1 in Scheme 5 by using 4-(4,6-dichloroquinolin-2-yl)-7-fluoro-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 7-fluoro-2,3,4,5-tetrahydro-1,4-benzothiazepine and 2,4,6-trichloroquinoline) and 3-(aminomethyl)-N-benzyloxetan-3-amine. MS obsd. (ESI$^+$) [(M+H)$^+$] 567, $^1$H NMR (400 MHz, CD$_3$OD) δ ppm 7.98 (dd, J=8.72, 5.43 Hz, 1 H), 7.82 (d, J=2.27 Hz, 1 H), 7.71 (dd, J=9.09, 2.53 Hz, 1 H), 7.50 (d, J=8.84 Hz, 1 H), 7.39 (dd, J=8.84, 2.27 Hz, 1 H), 7.33 (d, J=7.07 Hz, 2 H), 7.25-7.16 (m, 2 H), 7.16-7.04 (m, 2 H), 6.13 (s, 1 H), 5.15 (brs, 2 H), 4.71 (d, J=6.57 Hz, 2 H), 4.54 (d, J=6.57 Hz, 4 H), 3.77 (s, 2 H), 3.72 (s, 2 H), 3.56 (t, J=4.93 Hz, 2 H).

Example 3-3

N-[(3-Aminooxetan-3-yl)methyl]-6-chloro-2-(7-fluoro-1,1-dioxido-2,3-dihydro-1,4-benzothiazepin-4(5H)-yl)quinolin-4-amine

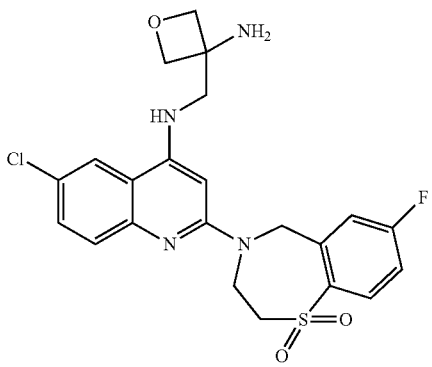 [SMILES: NC1(CNc2cc(N3CCS(=O)(=O)c4ccc(F)cc4C3)nc3ccc(Cl)cc23)COC1]

The title compound was prepared in analogy to Example 3-1 in Scheme 5 by using 4-(4,6-dichloroquinolin-2-yl)-7-fluoro-2,3,4,5-tetrahydro-1,4-benzothiazepine 1,1-dioxide (prepared in analogy to the one in Example 3-2) and 3-(aminomethyl)oxetan-3-amine. MS obsd. (ESI$^+$) [(M+H)$^+$] 477, $^1$H NMR (400 MHz, CD$_3$OD) δ ppm 8.07-7.94 (m, 2 H), 7.72 (dd, J=8.97, 2.65 Hz, 1 H), 7.53 (d, J=8.84 Hz, 1 H), 7.43 (dd, J=8.84, 2.27 Hz, 1 H), 7.15 (td, J=8.46, 2.53 Hz, 1 H), 6.23 (s, 1 H), 5.18 (brs, 2 H), 4.73-4.60 (m, 4 H), 4.51 (brs, 2 H), 3.75 (s, 2 H), 3.59 (t, J=4.67 Hz, 2 H).

Example 3-4

N-{[3-(Aminomethyl)oxetan-3-yl]methyl}-2-(7-methoxy-1,1-dioxido-2,3-dihydro-1,4-benzothiazepin-4(5H)-yl)-quinolin-4-amine

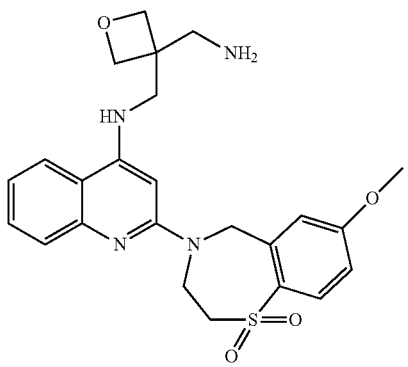 [SMILES: COc1ccc2c(c1)CN(c1cc(NCC3(CN)COC3)c3ccccc3n1)CCS2(=O)=O]

The title compound was prepared in analogy to Example 3-1 in Scheme 5 by using 4-(4-chloroquinolin-2-yl)-7-methoxy-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 7-methoxy-2,3,4,5-tetrahydro-1,4-benzothiazepine and 2,4-dichloroquinoline) and oxetane-3,3-diyldimethanamine. MS obsd. (ESI$^+$) [(M+H)$^+$] 469, $^1$H NMR (400 MHz, CD$_3$OD) δ ppm 8.41 (brs, 3 H), 8.02 (d, J=8.08 Hz, 1 H), 7.97 (d, J=8.84 Hz, 1 H), 7.68 (d, J=8.08 Hz, 1 H), 7.60 (t, J=7.71 Hz, 1 H), 7.44 (d, J=2.53 Hz, 1 H), 7.31 (t, J=7.20 Hz, 1 H), 7.01 (dd, J=8.59, 2.53 Hz, 1 H), 6.19 (s, 1 H), 5.20 (br. s, 2 H), 4.64 (s, 4 H), 4.54 (brs, 2 H), 3.92 (s, 3 H), 3.81 (s, 2 H), 3.69-3.55 (m, 2 H), 3.47 (s, 2 H).

Example 3-5

N-{[3-(Aminomethyl)oxetan-3-yl]methyl}-2-(7-methoxy-1,1-dioxido-2,3-dihydro-1,4-benzothiazepin-4(5H)-yl)-6-methylquinolin-4-amine

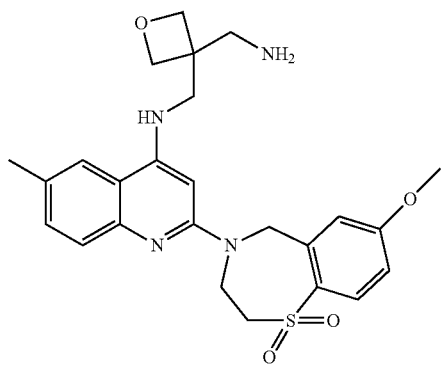

The title compound was prepared in analogy to Example 3-1 in Scheme 5 by using 4-(4-chloro-6-methylquinolin-2-yl)-7-methoxy-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 7-methoxy-2,3,4,5-tetrahydro-1,4-benzothiazepine and 2,4-dichloro-6-methylquinoline) and oxetane-3,3-diyldimethanamine. MS obsd. (ESI$^+$) [(M+H)$^+$] 483, $^1$H NMR (400 MHz, CD$_3$OD) δ ppm 7.89 (d, J=8.59 Hz, 1 H), 7.64 (s, 1 H), 7.51-7.39 (m, 2 H), 7.31 (dd, J=8.59, 1.77 Hz, 1 H), 6.91 (dd, J=8.59, 2.53 Hz, 1 H), 6.14 (s, 1 H), 5.10 (brs, 2 H), 4.69-4.44 (m, 6 H), 3.90 (s, 3 H), 3.74-3.61 (m, 2 H), 3.57-3.52 (m, 2 H), 3.18 (s, 2 H), 2.42 (s, 3 H).

Example 3-6

N-{[3-({[2-(7-Methoxy-1,1-dioxido-2,3-dihydro-1,4-benzothiazepin-4(5H)-yl)-6-methylquinolin-4-yl]amino}methyl)oxetan-3-yl]methyl}acetamide

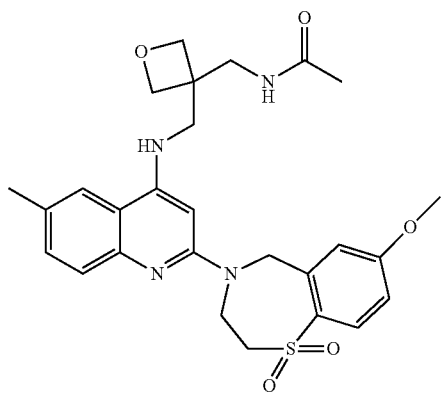

The title compound was prepared in analogy to Example 3-1 in Scheme 5 by using 4-(4-chloro-6-methylquinolin-2-yl)-7-methoxy-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 7-methoxy-2,3,4,5-tetrahydro-1,4-benzothiazepine and 2,4-dichloro-6-methylquinoline) and N-{[3-(aminomethyl)oxetan-3-yl]methyl}acetamide. MS obsd. (ESI⁺) [(M+H)⁺] 525, ¹H NMR (400 MHz, CD$_3$OD) δ ppm 7.91 (d, J=8.59 Hz, 1 H), 7.70 (s, 1 H), 7.47 (d, J=8.59 Hz, 1 H), 7.41 (d, J=2.27 Hz, 1 H), 7.33 (dd, J=8.46, 1.64 Hz, 1 H), 6.94 (d, J=8.59 Hz, 1 H), 6.18 (s, 1 H), 5.12 (s, 2 H), 4.61-4.54 (m, 6 H), 3.90 (s, 3 H), 3.68 (s, 2 H), 3.67-3.63 (m, 2 H), 3.59-3.51 (m, 2 H), 2.44 (s, 3 H), 2.05 (s, 3 H).

Example 3-7

N-{[3-(Aminomethyl)oxetan-3-yl]methyl}-2-(8-methyl-1,1-dioxido-2,3-dihydro-1,4-benzothiazepin-4(5H)-yl)-6-methylquinolin-4-amine

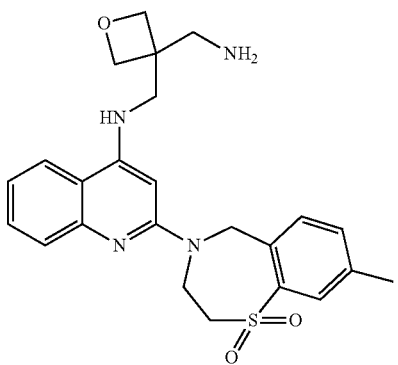 [SMILES: Cc1ccc2c(c1)S(=O)(=O)CCN(c1cc(NCC3(CN)COC3)c3ccccc3n1)C2]

The title compound was prepared in analogy to Example 3-1 in Scheme 5 by using 4-(4-chloroquinolin-2-yl)-8-methyl-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 8-methyl-2,3,4,5-tetrahydro-1,4-benzothiazepine and 2,4-dichloroquinoline) and oxetane-3,3-diyldimethanamine. MS obsd. (ESI⁺) [(M+H)⁺] 453, ¹H NMR (400 MHz, CD$_3$OD) δ ppm 7.86-7.69 (m, 3 H), 7.57-7.49 (m, 1 H), 7.47-7.34 (m, 2 H), 7.19-7.06 (m, 1 H), 6.17 (s, 1 H), 5.11 (brs, 2 H), 4.68-4.39 (m, 6 H), 3.67 (s, 2 H), 3.63 (q, J=7.07 Hz, 1 H), 3.55 (t, J=4.55 Hz, 2 H), 3.15 (s, 2 H), 2.33 (s, 3 H).

Example 3-8

N-{[3-(Aminomethyl)oxetan-3-yl]methyl}-6-methyl-2-(8-methyl-1,1-dioxido-2,3-dihydro-1,4-benzothiazepin-4(5H)-yl)quinolin-4-amine

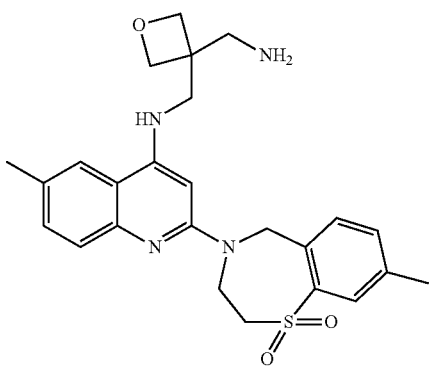

The title compound was prepared in analogy to Example 3-1 in Scheme 5 by using 4-(4-chloro-6-methylquinolin-2-yl)-8-methyl-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 8-methyl-2,3,4,5-tetrahydro-1,4-benzothiazepine and 2,4-dichloro-6-methylquinoline) and oxetane-3,3-diyldimethanamine. MS obsd. (ESI⁺) [(M+H)⁺] 467, ¹H NMR (400 MHz, CD$_3$OD) 7.74-7.62 (m, 2 H), 7.58 (s, 1 H), 7.43 (d, J=8.59 Hz, 1 H), 7.32-7.20 (m, 2 H), 6.07 (s, 1 H), 4.99 (brs, 2 H), 4.62-4.48 (m, 4 H), 4.48-4.18 (m, 2 H), 3.65-3.60 (m, 2 H), 3.44 (brs, 2 H), 3.11 (s, 2 H), 2.43-2.26 (m, 3 H), 2.14 (s, 3 H).

Example 3-9

[3-({[2-(1,1-Dioxido-2,3-dihydro-1,4-benzothiazepin-4(5H)-yl)-6-methylquinolin-4-yl]amino}methyl)oxetan-3-yl]methanol

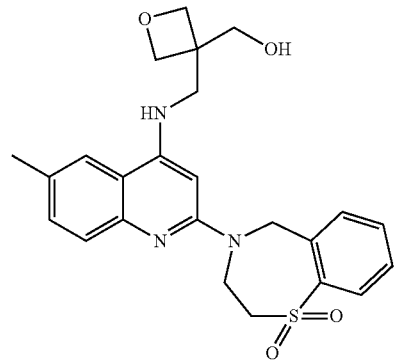 [SMILES: Cc1ccc2nc(N3CCS(=O)(=O)c4ccccc4C3)cc(NCC3(CO)COC3)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 3-(aminomethyl)oxetan-3-yl]methanol. MS obsd. (ESI⁺) [(M+H)⁺] 454, ¹H NMR (400 MHz, CD$_3$OD) δ ppm 8.02-7.96 (m, 1 H), 7.90 (d, J=7.33 Hz, 1 H), 7.68-7.54 (m, 2 H), 7.45 (d, J=8.34 Hz, 2 H), 7.35-7.20 (m, 1 H), 6.19 (s, 1 H), 5.14 (s, 2 H), 4.60 (d, J=6.06 Hz, 3 H), 4.51 (d, J=6.06 Hz, 3 H), 3.98 (s, 2 H), 3.67 (s, 2 H), 3.58 (t, J=4.67 Hz, 2 H), 2.42 (s, 3 H).

Example 3-10

(2S)-3-{[2-(1,1-Dioxido-2,3-dihydro-1,4-benzothiazepin-4(5H)-yl)-6-methylquinolin-4-yl]amino}propane-1,2-diol

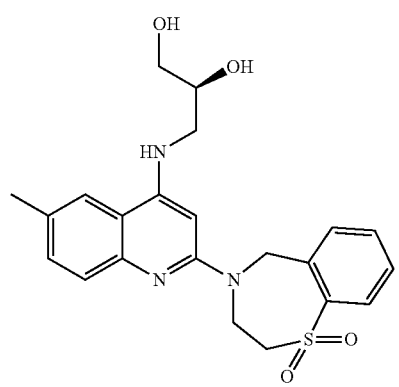 [SMILES: Cc1ccc2nc(N3CCS(=O)(=O)c4ccccc4C3)cc(NC[C@H](O)CO)c2c1]

The title compound was prepared in analogy to Example 3-1 in Scheme 5 by using 4-(4-chloro-6-methylquinolin-2- yl)-2,3,4,5-tetrahydro-1,4-benzothiazepine 1,1-dioxide (prepared in analogy to the one in Example 2-1) and (2S)-3-aminopropane-1,2-diol. MS obsd. (ESI+) [(M+H)+] 428, ¹H NMR (400 MHz, CD₃OD) δ ppm 7.98 (dd, J=7.83, 1.26 Hz, 1 H), 7.89 (d, J=7.33 Hz, 1 H), 7.63 (td, J=7.45, 1.26 Hz, 1 H), 7.57 (s, 1 H), 7.50-7.35 (m, 2 H), 7.29 (dd, J=8.59, 1.77 Hz, 1 H), 6.13 (s, 1 H), 5.14 (s, 2 H), 4.55 (brs, 2 H), 4.04-3.89 (m, 1 H), 3.69 (d, J=5.56 Hz, 2 H), 3.64-3.49 (m, 4 H), 2.41 (s, 3 H).

Example 3-11

(2R)-3-{[2-(1,1-Dioxido-2,3-dihydro-1,4-benzothiazepin-4(5H)-yl)-6-methylquinolin-4-yl]amino}propane-1,2-diol

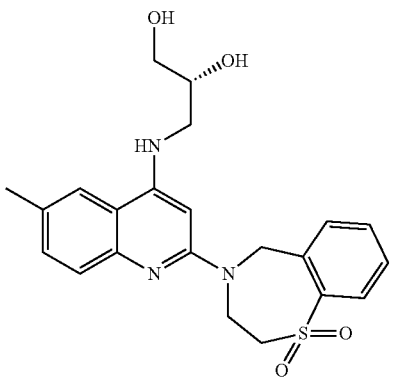 [SMILES: Cc1ccc2nc(N3CCS(=O)(=O)c4ccccc4C3)cc(NC[C@@H](O)CO)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and (2R)-3-aminopropane-1,2-diol. MS obsd. (ESI+) [(M+H)+] 428, ¹H NMR (400 MHz, CD₃OD) δ ppm 7.98 (dd, J=7.83, 1.26 Hz, 1 H), 7.89 (d, J=7.33 Hz, 1 H), 7.63 (td, J=7.45, 1.26 Hz, 1 H), 7.57 (s, 1 H), 7.50-7.35 (m, 2 H), 7.29 (dd, J=8.59, 1.77 Hz, 1 H), 6.13 (s, 1 H), 5.14 (s, 2 H), 4.55 (brs, 2 H), 4.04-3.89 (m, 1 H), 3.69 (d, J=5.56 Hz, 2 H), 3.64-3.49 (m, 4 H), 2.41 (s, 3 H).

Example 3-12

N-{[1-(Aminomethyl)-3,3-difluorocyclobutyl]methyl}-2-(1,1-dioxido-2,3-dihydro-1,4-benzothiazepin-4(5H)-yl)-6-methylquinolin-4-amine

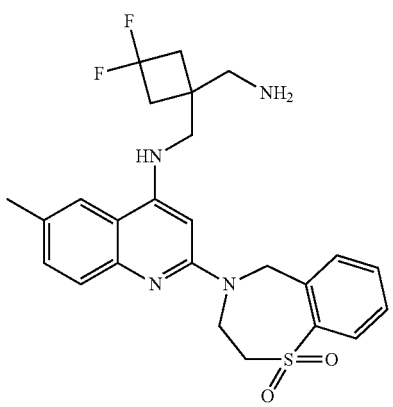 [SMILES: Cc1ccc2nc(N3CCS(=O)(=O)c4ccccc4C3)cc(NCC3(CN)CC(F)(F)C3)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and (3,3-difluorocyclobutane-1,1-diyl)dimethanamine. MS obsd. (ESI+) [(M+H)+] 487, ¹H NMR (400 MHz, CD₃OD) δ ppm 8.11 (dd, J=7.83, 1.01 Hz, 1 H), 8.08 (s, 1 H), 7.89 (d, J=7.07 Hz, 1 H), 7.80-7.68 (m, 2 H), 7.68-7.56 (m, 2 H), 6.15 (s, 1 H), 5.37 (s, 2 H), 4.55 (brs, 2 H), 3.80 (s, 2 H), 3.79-3.67 (m, 2 H), 3.44 (s, 2 H), 2.76 (t, J=12.25 Hz, 4 H), 2.51 (s, 3 H).

Example 3-13

N-[(3-Aminooxetan-3-yl)methyl]-6-chloro-2-(8-methoxy-1,1-dioxido-2,3-dihydro-1,4-benzothiazepin-4(5H)-yl)quinolin-4-amine

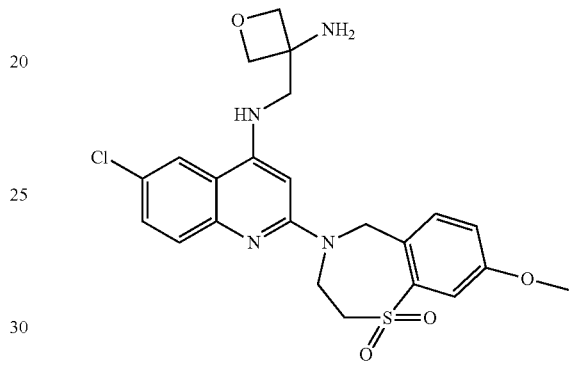

The title compound was prepared in analogy to Example 3-1 in Scheme 5 by using 4-(4,6-dichloroquinolin-2-yl)-8-methoxy-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 8-methoxy-2,3,4,5-tetrahydro-1,4-benzothiazepine and 2,4,6-trichloroquinoline) and 3-(aminomethyl)oxetan-3-amine. MS obsd. (ESI+) [(M+H)+] 489, ¹H NMR (400 MHz, CD₃OD) δ ppm 7.95 (d, J=2.27 Hz, 1 H), 7.83-7.74 (m, 1 H), 7.58-7.44 (m, 2 H), 7.44-7.33 (m, 1 H), 7.14 (dd, J=8.34, 2.78 Hz, 1 H), 6.24 (s, 1 H), 5.11 (brs, 2 H), 4.61 (q, J=6.74 Hz, 6 H), 3.82 (s, 3 H), 3.69 (s, 2 H), 3.63-3.50 (m, 2 H), 2.05 (s, 2 H).

Example 3-14

N-{[3-(Aminomethyl)oxetan-3-yl]methyl}-6-chloro-2-(8-methoxy-1,1-dioxido-2,3-dihydro-1,4-benzothiazepin-4(5H)-yl)quinolin-4-amine

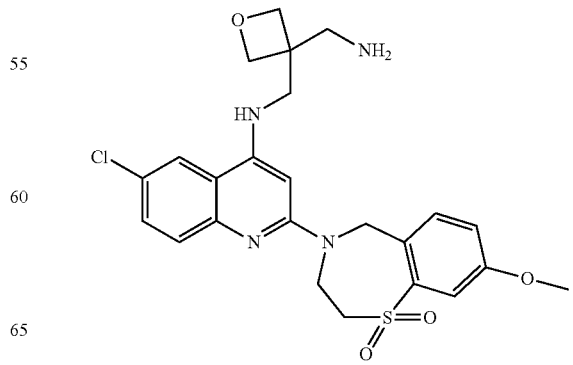

The title compound was prepared in analogy to Example 3-1 in Scheme 5 by using 4-(4,6-dichloroquinolin-2-yl)-8-methoxy-2,3,4,5-tetrahydro-1,4-benzothiazepine 1,1-dioxide (prepared in analogy to the one in Example 3-13) and oxetane-3,3-diyldimethanamine. MS obsd. (ESI⁺) [(M+H)⁺] 503, ¹H NMR (400 MHz, CD₃OD) δ ppm 8.23 (s, 1 H), 7.88 (d, J=8.59 Hz, 1 H), 7.73 (d, J=8.84 Hz, 1 H), 7.65-7.51 (m, 2 H), 7.21 (dd, J=8.34, 2.78 Hz, 1 H), 6.30 (s, 1 H), 5.26 (brs, 2 H), 4.76-4.60 (m, 6 H), 4.56 (brs, 1 H), 3.91 (s, 2 H), 3.85 (s, 3 H), 3.69 (brs, 2 H), 3.52 (s, 2 H).

Example 3-15 trans-N-[2-(1,1-Dioxido-2,3-dihydro-1,4-benzothiazepin-4(5H)-yl)-6-methylquinolin-4-yl]cyclohexane-1,2-diamine

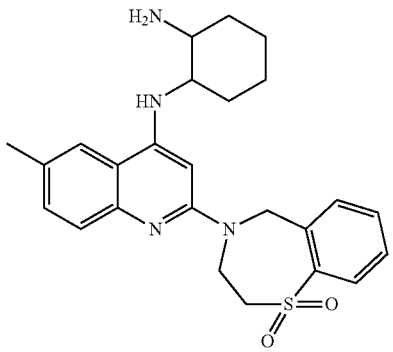 [SMILES: Cc1ccc2nc(N3CCS(=O)(=O)c4ccccc4C3)cc(NC3CCCCC3N)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and trans-cyclohexane-1,2-diamine. MS obsd. (ESI⁺) [(M+H)⁺] 451, ¹H NMR (400 MHz, CD₃OD) δ ppm 8.06-7.96 (d, J=7.8 Hz, 1 H), 7.83 (d, J=7.33 Hz, 1 H), 7.70 (s, 1 H), 7.60 (td, J=7.52, 1.14 Hz, 1 H), 7.50-7.38 (m, 2 H), 7.28 (dd, J=8.46, 1.64 Hz, 1 H), 6.13 (s, 1 H), 5.20-5.11 (m, 2 H), 3.72-3.60 (m, 1 H), 3.58-3.49 (m, 1 H), 3.42-3.35 (m, 2 H), 3.35-3.30 (m, 1 H), 2.87 (td, J=10.17, 3.92 Hz, 1 H), 2.42 (s, 3 H), 2.10 (d, J=5.31 Hz, 1 H), 2.01 (d, J=13.14 Hz, 1 H), 1.89 (d, J=8.08 Hz, 2 H), 1.67-1.56 (m, 1 H), 1.51-1.41 (m, 2 H), 1.32-1.17 (m, 1 H).

Example 3-16

N-[2-(1,1-Dioxido-2,3-dihydro-1,4-benzothiazepin-4(5H)-yl)-6-methylquinolin-4-yl]-cyclohexane-1,3-diamine

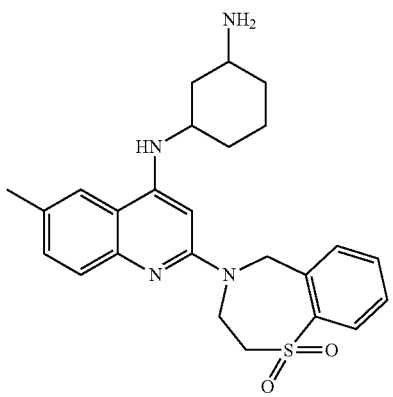 [SMILES: Cc1ccc2nc(N3CCS(=O)(=O)c4ccccc4C3)cc(NC3CCCC(N)C3)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and cyclohexane-1,3-diamine. MS obsd. (ESI⁺) [(M+H)⁺] 451, ¹H NMR (400 MHz, CD₃OD) δ ppm 8.04 (d, J=7.8 Hz, 1 H), 7.57 (d, J=7.3 Hz, 1 H), 7.53-7.47 (m, 2 H), 7.37 (t, J=7.7 Hz, 1 H), 7.32-7.26 (m, 2 H), 5.86 (s, 1 H), 5.16-5.00 (m, 2 H), 3.65-3.50 (brs, 4 H), 3.16 (brs, 1 H), 2.42 (s, 3 H), 2.45-2.38 (m, 1 H), 2.29 (d, J=11.1 Hz, 1 H), 2.03-1.85 (m, 3 H), 1.54-1.42 (m, 1 H), 1.40-1.24 (m, 3 H).

Example 3-17

(R)-1-[2-(1,1-Dioxido-2,3-dihydro-1,4-benzothiazepin-4(5H)-yl)-6-methylquinolin-4-yl]-4,4-dimethylpyrrolidin-3-ol

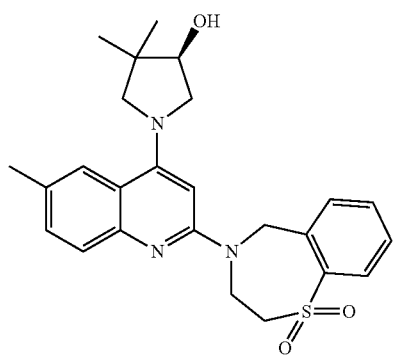 [SMILES: Cc1ccc2nc(N3CCS(=O)(=O)c4ccccc4C3)cc(N3C[C@H](O)C(C)(C)C3)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and (3R)-4,4-dimethylpyrrolidin-3-ol. MS obsd. (ESI⁺) [(M+H)⁺] 452, ¹H NMR (400 MHz, CD₃OD) δ ppm 7.94 (dd, J=7.83, 1.01 Hz, 1 H), 7.83-7.73 (m, 2 H), 7.58 (td, J=7.58, 1.26 Hz, 1 H), 7.47-7.37 (m, 2 H), 7.23 (dd, J=8.59, 1.77 Hz, 1 H), 6.03 (s, 1 H), 5.11 (s, 2 H), 4.02 (dd, J=10.36, 5.31 Hz, 1 H), 3.93 (dd, J=5.05, 3.79 Hz, 1 H), 3.61-3.47 (m, 4 H), 2.37 (s, 3 H), 1.15 (s, 3 H), 1.10-1.05 (m, 3 H).

Example 3-18 cis-N-[2-(1,1-Dioxido-2,3-dihydro-1,4-benzothiazepin-4(5H)-yl)-6-methylquinolin-4-yl]-cyclohexane-1,4-diamine

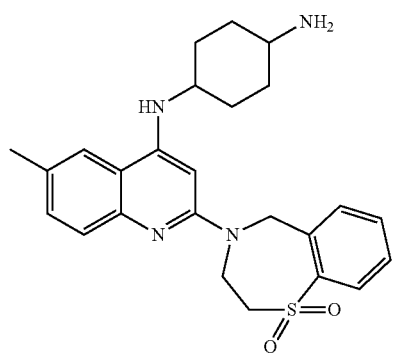 [SMILES: Cc1ccc2nc(N3CCS(=O)(=O)c4ccccc4C3)cc(NC3CCC(N)CC3)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and cis-cyclohexane-1,4-diamine. MS obsd. (ESI$^+$) [(M+H)$^+$] 451, $^1$H NMR (400 MHz, DMSO-d6) δ ppm 7.91-7.85 (m, 2 H), 7.79 (s, 1 H), 7.58 (td, J=7.45, 1.26 Hz, 1 H), 7.51-7.44 (m, 1 H), 7.29 (d, J=8.59 Hz, 1 H), 7.21 (dd, J=8.59, 1.52 Hz, 1 H), 6.17 (d, J=7.58 Hz, 1 H), 6.03 (s, 1 H), 5.06 (brs, 2 H), 4.50 (brs, 1 H), 4.11 (d, J=4.55 Hz, 1 H), 3.67 (d, J=4.80 Hz, 1 H), 3.64-3.56 (m, 2 H), 3.16 (m, 2 H), 3.06 (brs, 1 H), 2.35 (s, 3 H), 1.83-1.44 (m, 8 H).

Example 3-19

N-[2-(1,1-Dioxido-2,3-dihydro-1,4-benzothiazepin-4(5H)-yl)-6-methylquinolin-4-yl]-2,2-difluoropropane-1,3-diamine

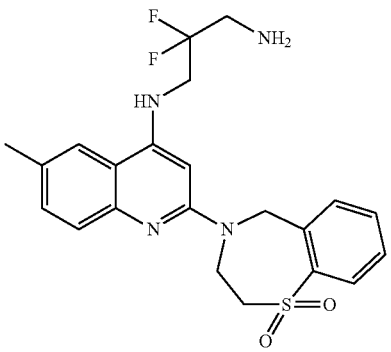 [SMILES: Cc1ccc2nc(N3CCS(=O)(=O)c4ccccc4C3)cc(NCC(F)(F)CN)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 2,2-difluoropropane-1,3-diamine. MS obsd. (ESI$^+$) [(M+H)$^+$] 447, $^1$H NMR (400 MHz, CD$_3$OD) δ ppm 8.09-8.07 (d, 1 H), 7.95 (s, 1 H), 7.86-7.84 (d, 1 H), 7.77-7.69 (m, 2 H), 7.64-7.58 (m, 2 H), 6.26 (s, 1 H), 5.34 (s, 2 H), 4.53 (s, 2 H), 4.23 (t, 2 H), 3.74-3.66 (m, 4 H), 2.48 (s, 3 H).

Example 3-20

N-[6-Chloro-2-(1,1-dioxido-2,3-dihydro-1,4-benzothiazepin-4(5H)-yl)quinolin-4-yl]-2,2-difluoropropane-1,3-diamine

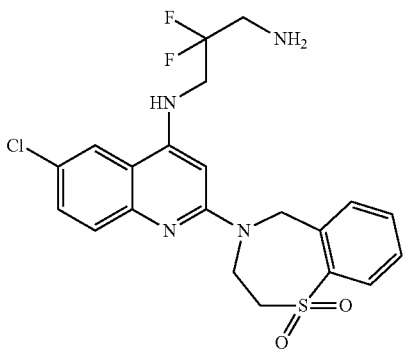 [SMILES: NCC(F)(F)CNc1cc(N2CCS(=O)(=O)c3ccccc3C2)nc2ccc(Cl)cc12]

The title compound was prepared in analogy to Example 3-1 in Scheme 5 by using 4-(4,6-dichloroquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,3,4,5-tetrahydro-1,4-benzothiazepine and 2,4,6-trichloroquinoline) and 2,2-difluoropropane-1,3-diamine. MS obsd. (ESI$^+$) [(M+H)$^+$] 467, $^1$H NMR (400 MHz, DMSO-d6) δ ppm 8.17-8.08 (m, 1 H), 7.94 (d, J=7.07 Hz, 1 H), 7.88 (dd, J=7.83, 1.26 Hz, 1 H), 7.62 (td, J=7.45, 1.26 Hz, 1 H), 7.54-7.39 (m, 3 H), 7.14 (brs, 1 H), 6.33 (s, 1 H), 5.77 (s, 1 H), 5.11 (brs, 2 H), 4.43 (brs, 2 H), 4.03-3.87 (m, 2 H), 3.61 (brs, 2 H), 3.13-3.29 (m, 2 H).

Example 3-21

N-[2-(1,1-Dioxido-2,3-dihydro-1,4-benzothiazepin-4(5H)-yl)-6-methylquinolin-4-yl]-2-fluoropropane-1,3-diamine

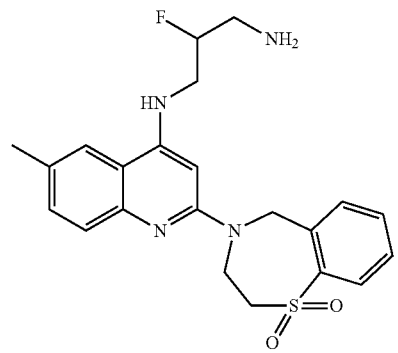 [SMILES: Cc1ccc2nc(N3CCS(=O)(=O)c4ccccc4C3)cc(NCC(F)CN)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 2-fluoropropane-1,3-diamine. MS obsd. (ESI$^+$) [(M+H)$^+$] 429, $^1$H NMR (400 MHz, CD$_3$OD) δ ppm 7.98 (dd, J=7.83, 1.01 Hz, 1 H), 7.84 (d, J=7.58 Hz, 1 H), 7.65-7.57 (m, 2 H), 7.47-7.38 (m, 2 H), 7.29 (dd, J=8.59, 1.77 Hz, 1 H), 6.10 (s, 1 H), 5.14 (s, 2 H), 4.69 (s, 2 H), 3.64 (d, J=5.31 Hz, 1 H), 3.61-3.52 (m, 4 H), 3.04-2.91 (m, 2 H), 2.41 (s, 3 H).

Example 3-22

N-[(3-Aminooxetan-3-yl)methyl]-6-chloro-2-(1,1-dioxido-2,3-dihydro-1,4-benzothiazepin-4(5H)-yl)quinolin-4-amine

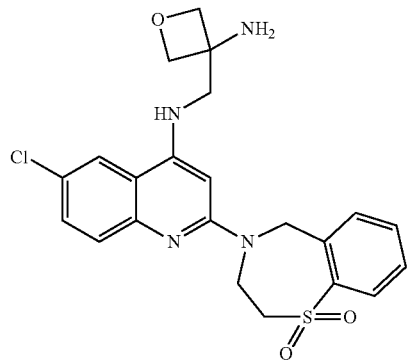 [SMILES: NC1(CNc2cc(N3CCS(=O)(=O)c4ccccc4C3)nc3ccc(Cl)cc23)COC1]

The title compound was prepared in analogy to Example 3-1 in Scheme 5 by using 4-(4,6-dichloroquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,3,4,5-tetrahydro-1,4-benzothiazepine and 2,4,6- trichloroquinoline) and 3-(aminomethyl)oxetan-3-amine. MS obsd. (ESI⁺) [(M+H)⁺] 459, ¹H NMR (400 MHz, CD₃OD) δ ppm 8.34 (s, 1 H), 8.02-8.00 (t, J=4.0, 2.4 Hz, 2 H), 7.92-7.90 (d, J=7.2 Hz, 1 H), 7.65-7.62 (m, 1 H), 7.56-7.54 (d, J=9.2 Hz, 1 H), 7.49-7.44 (m, 2 H), 6.27 (s, 1 H), 5.22 (s, 2 H), 4.67-4.63 (m, 4 H), 4.56 (s, 1 H), 3.78 (s, 2 H), 3.63-3.60 (t, J=4.8 Hz, 2 H).

Example 3-23

[4-{[(3-Aminooxetan-3-yl)methyl]amino}-2-(1,1-dioxido-2,3-dihydro-1,4-benzothiazepin-4(5H)-yl)quinolin-6-yl]methanol

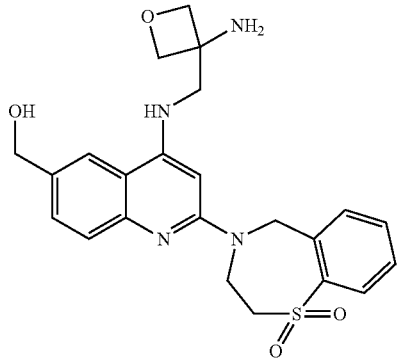 [SMILES: NC1(CNc2cc(N3CCS(=O)(=O)c4ccccc4C3)nc3ccc(CO)cc23)COC1]

Methyl 4-chloro-2-(1,1-dioxido-2,3-dihydro-1,4-benzothiazepin-4(5H)-yl)quinoline-6-carboxylate

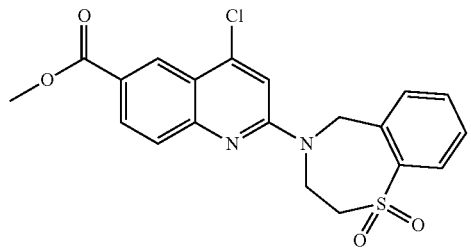 [SMILES: COC(=O)c1ccc2nc(N3CCS(=O)(=O)c4ccccc4C3)cc(Cl)c2c1]

To a cooled solution of methyl 4-chloro-2-(2,3-dihydro-1,4-benzothiazepin-4(5H)-yl)quinoline-6-carboxylate (2.0 g, 5.2 mmol, prepared in analogy to 4-(4-chloro-6-methylquinolin-2-yl)-8-methoxy-2,3,4,5-tetrahydro-1,4-benzothiazepine in Example 1-1 by using methyl 2,4-dichoroquinoline-6-carboxylate and 2,3,4,5-tetrahydro-1,4-benzothiazepine) in dichloromethane (30 mL) was added 3-chloroperoxybenzoic acid (2.63 g, 20.8 mmol) in an ice-bath. After being stirred for 1 hour at 0° C., the reaction mixture was washed with brine, dried over sodium sulfate and concentrated in vacuo to afford 2.0 g of the crude product.

4-Chloro-2-(1,1-dioxido-2,3-dihydro-1,4-benzothiazepin-4(5H)-yl)-quinoline-6-methanol

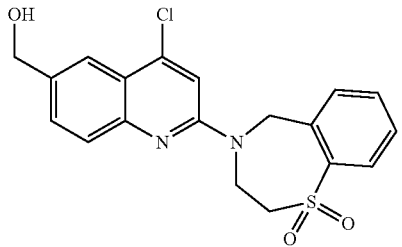 [SMILES: O=S1(=O)CCN(c2cc(Cl)c3cc(CO)ccc3n2)Cc2ccccc21]

To a solution of methyl 4-chloro-2-(1,1-dioxido-2,3-dihydro-1,4-benzothiazepin-4 (5H)-yl)quinoline-6-carboxylate (2.0 g, 4.8 mmol) in tetrahydrofuran (50 mL) was added sodium borohydride (729 mg, 19.2 mmol). After being refluxed for 60 hours, the reaction mixture was diluted with water (30 mL) and extracted with dichloromethane (50 mL×2). The combined organic layers were dried over sodium sulfate and concentrated in vacuo to afford 1.4 g of the crude product.

[4-{[(3-Aminooxetan-3-yl)methyl]amino}-2-(1,1-dioxido-2,3-dihydro-1,4-benzothiazepin-4(5H)-yl)quinolin-6-yl]methanol

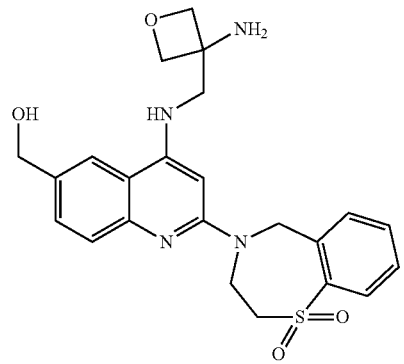 [SMILES: NC1(CNc2cc(N3CCS(=O)(=O)c4ccccc4C3)nc3ccc(CO)cc23)COC1]

The title compound was prepared in analogy to Example 3-1 in Scheme 5 by using 4-chloro-2-(1,1-dioxido-2,3-dihydro-1,4-benzothiazepin-4(5H)-yl)-quinoline-6-methanol and 3-(aminomethyl)oxetan-3-amine. MS obsd. (ESI⁺) [(M+H)⁺] 455, ¹H NMR (400 MHz, CD₃OD) δ ppm 8.33 (s, 1 H), 8.08-8.05 (d, J=11.2 Hz, 2 H), 7.94-7.92 (d, J=7.2 Hz, 1 H), 7.74-7.68 (m, 3 H), 7.57-7.53 (t, J=7.6 Hz, 1 H), 6.26 (s, 1 H), 5.31 (s, 2 H), 4.72 (s, 2 H), 44.57 (s, 4 H), 4.44 (s, 1 H), 3.88 (s, 2 H), 3.77-3.71 (m, 2 H).

Example 3-24

N-[(3-Aminooxetan-3-yl)methyl]-2-(1,1-dioxido-2,3-dihydro-1,4-benzothiazepin-4(5H)-yl)-7-fluoro-6-methylquinolin-4-amine

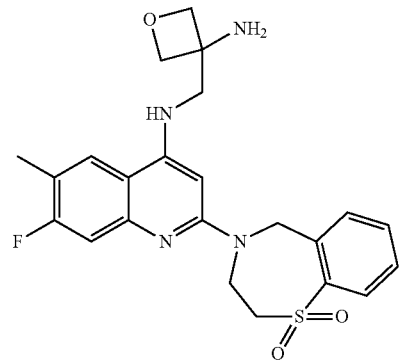 [SMILES: Cc1cc2c(NCC3(N)COC3)cc(N3CCS(=O)(=O)c4ccccc4C3)nc2cc1F]

The title compound was prepared in analogy to Example 3-1 in Scheme 5 by using 4-(4-chloro-7-fluoro-6-methylquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4-dichloro-7-fluoro-6-methylquinoline and 2,3,4,5-tetrahydro-1,4-benzothiazepine) and 3-(aminomethyl)oxetan-3-amine. MS obsd. (ESI⁺) [(M+H)⁺] 457, ¹H NMR (400 MHz, CD₃OD) δ ppm 8.05-8.03 (d, J=8.0 Hz, 1 H), 7.92-7.88 (t, J=8.8, 8.0 Hz, 2 H), 7.68-7.65 (m, 1 H), 7.53-7.49 (t, J=7.6 Hz, 1 H), 7.28-7.25 (d, J=11.6 Hz, 1 H), 6.20 (s, 1 H), 5.24 (s, 2 H), 4.66-4.48 (m, 6 H), 3.82 (s, 2 H), 3.66-3.64 (m, 2 H), 2.68 (s, 3 H).

Example 3-25

N-[(3-Aminooxetan-3-yl)methyl]-2-(1,1-dioxido-2,3-dihydro-1,4-benzothiazepin-4(5H)-yl)-5-fluoro-6-methylquinolin-4-amine

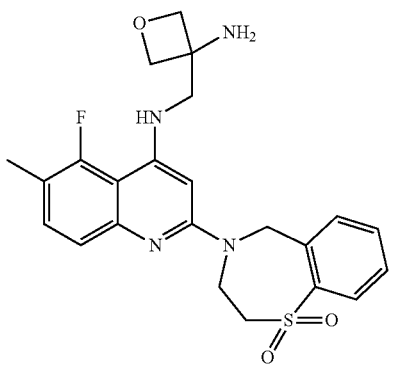 [SMILES: Cc1ccc2nc(N3CCS(=O)(=O)c4ccccc4C3)cc(NCC3(N)COC3)c2c1F]

The title compound was prepared in analogy to Example 3-1 in Scheme 5 by using 4-(4-chloro-5-fluoro-6-methylquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4-dichloro-5-fluoro-6-methylquinoline and 2,3,4,5-tetrahydro-1,4-benzothiazepine) and 3-(aminomethyl)oxetan-3-amine. MS obsd. (ESI$^+$) [(M+H)$^+$] 457, $^1$H NMR (400 MHz, DMSO-d6) δ ppm 7.99-7.97 (d, J=7.2 Hz, 1 H), 7.90-7.88 (m, 1 H), 7.66-7.62 (m, 1 H), 7.51-7.47 (t, J=7.6 Hz, 1 H), 7.29-7.24 (t, J=8.8, 8.4 Hz, 1 H), 7.20-7.18 (d, J=8.4 Hz, 1 H), 6.61-6.57 (d, J=16.0 Hz, 1 H), 6.12 (s, 1 H), 5.11 (s, 2 H), 4.44-4.43 (d, J=6.0 Hz, 2 H), 4.38-4.37 (d, J=6.0 Hz, 2 H), 3.63-3.61 (t, J=4.8, 4.4 Hz, 2 H), 3.53 (s, 2 H), 2.68-2.67 (t, J=2.0, 1.6 Hz, 1 H), 2.34-2.33 (t, J=2.0, 1.6, 1 H), 1.92 (s, 3 H).

Example 3-26

N~1~-[6-Chloro-2-(1,1-dioxido-2,3-dihydro-1,4-benzothiazepin-4(5H)-yl)quinolin-4-yl]-2-methylpropane-1,2-diamine

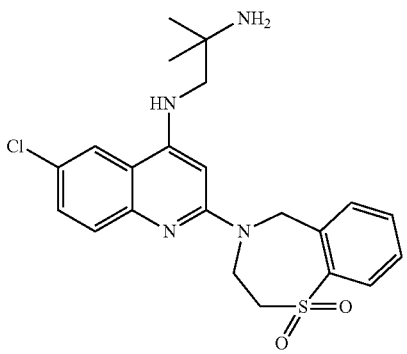 [SMILES: CC(C)(N)CNc1cc(N2CCS(=O)(=O)c3ccccc3C2)nc2ccc(Cl)cc12]

The title compound was prepared in analogy to Example 3-1 in Scheme 5 by using 4-(4,6-dichloroquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4,6-trichloroquinoline and 2,3,4,5-tetrahydro-1,4-benzothiazepine) and 2-methylpropane-1,2-diamine. MS obsd. (ESI$^+$) [(M+H)$^+$] 445, $^1$H NMR (400 MHz, CD$_3$OD) δ ppm 7.98 (d, J=8.0 Hz, 2 H), 7.87 (d, J=7.2 Hz, 1 H), 7.61 (t, J=7.2 Hz, 1 H), 7.49-7.43 (m, 2 H), 7.38 (dd, J=2.0, 8.8 Hz, 1 H), 6.13 (s, 1 H), 5.16 (s, 2 H), 4.54 (brs, 2 H), 3.57 (t, J=4.4 Hz, 2 H), 3.27 (s, 2 H), 1.26 (s, 6 H).

Example 3-27

2-(1,1-Dioxido-2,3-dihydro-1,4-benzothiazepin-4(5H)-yl)-6-methyl-N-(tetrahydro-2H-pyran-4-yl)quinolin-4-amine

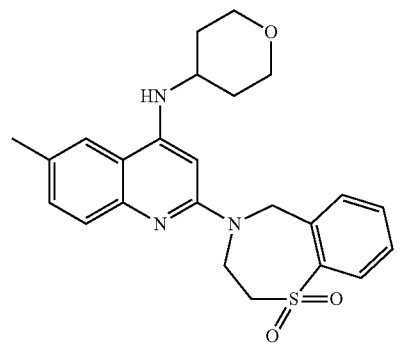 [SMILES: Cc1ccc2nc(N3CCS(=O)(=O)c4ccccc4C3)cc(NC3CCOCC3)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and tetrahydro-2H-pyran-4-ylamine. MS obsd. (ESI$^+$) [(M+H)$^+$] 438, $^1$H NMR (400 MHz, DMSO-d6) δ ppm 7.89 (dd, J=6.95, 3.41 Hz, 2 H), 7.78 (s, 1 H), 7.59 (t, J=7.07 Hz, 1 H), 7.47 (t, J=7.58 Hz, 1 H), 7.31 (d, J=8.59 Hz, 1 H), 7.23 (d, J=8.59 Hz, 1 H), 6.33 (d, J=8.08 Hz, 1 H), 6.09 (s, 1 H), 5.09 (brs, 2 H), 4.44 (brs, 1 H), 3.99 (d, J=9.85 Hz, 2 H), 3.94-3.82 (m, 1 H), 3.69-3.52 (m, 4 H), 2.36 (s, 3 H), 1.85 (d, J=11.87 Hz, 2 H), 1.69-1.44 (m, 2 H).

Example 3-28

2-(1,1-Dioxido-2,3-dihydro-1,4-benzothiazepin-4(5H)-yl)-6-methyl-N-[2-(piperazin-1-yl)ethyl]quinolin-4-amine

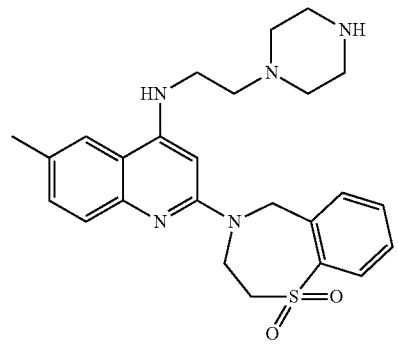 [SMILES: Cc1ccc2nc(N3CCS(=O)(=O)c4ccccc4C3)cc(NCCN3CCNCC3)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 2-(piperazin-1-yl)ethanamine. MS obsd. (ESI$^+$) [(M+H)$^+$] 466, $^1$H NMR (400 MHz, DMSO-d6) ppm 7.925 (d, J=8.0 Hz, 1 H), 7.806 (d, J=7.2 Hz, 1 H), 7.516-7.575 (m, 2 H), 7.359-7.395 (m, 2 H), 7.238 (m, 1 H), 5.98 (s, 1 H), 5.10 (s, 2 H), 4.49 (brs, 2 H), 3.538 (m, 2 H), 3.542 (m, 2 H), 3.44 (t, J=6.57 Hz, 2 H), 3.32 (s, 2 H), 2.89 (t, J=4.80 Hz, 4 H), 2.71 (t, J=6.57 Hz, 2 H), 2.56 (brs, 4 H), 2.37 (s, 3 H).

Example 3-29

2-(1,1-Dioxido-2,3-dihydro-1,4-benzothiazepin-4(5H)-yl)-6-methyl-N-(piperidin-4-ylmethyl)quinolin-4-amine

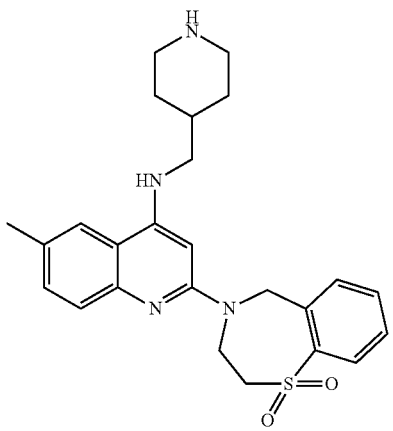 [SMILES: Cc1ccc2nc(N3CCS(=O)(=O)c4ccccc4C3)cc(NCC3CCNCC3)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 1-(piperidin-4-yl)methanamine. MS obsd. (ESI$^+$) [(M+H)$^+$] 451, $^1$H NMR (400 MHz, DMSO-d6) δ ppm 9.89 (brs, 2 H), 7.875 (t, J=8.0 Hz, 2 H), 7.76 (s, 1 H), 7.625 (t, J=6.8 Hz, 1 H), 7.48 (d, J=7.6 Hz, 1 H), 7.30 (d, J=8.4 Hz, 1 H), 7.226 (d, J=1.6 Hz, 1 H), 6.73 (t, J=5.43 Hz, 1 H), 5.07 (brs, 2 H), 4.42 (brs, 2 H), 4.10 (d, J=12.63 Hz, 2 H), 3.63 (m, 2 H), 3.23-3.05 (m, 2 H), 2.50 (s, 2 H), 2.05 (s, 3 H), 1.76-1.66 (m, 3 H), 1.15-0.98 (m, 2 H).

Example 3-30

N-[2-(1,1-Dioxido-2,3-dihydro-1,4-benzothiazepin-4(5H)-yl)-6-methylquinolin-4-yl]heptane-1,7-diamine

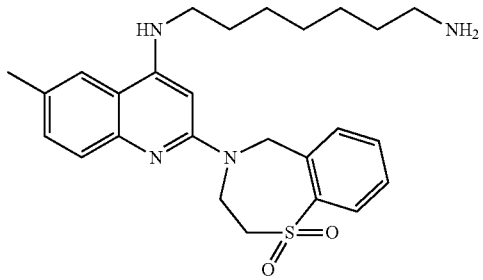 [SMILES: Cc1ccc2nc(N3CCS(=O)(=O)c4ccccc4C3)cc(NCCCCCCCN)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and heptane-1,7-diamine. MS obsd. (ESI$^+$) [(M+H)$^+$] 467, $^1$H NMR (400 MHz, CD$_3$OD) δ ppm 8.07 (dd, J=1.2, 0.8 Hz, 1 H), 7.97 (s, 1 H), 7.92 (d, J=7.6 Hz, 1 H), 7.74-7.68 (m, 2 H), 7.61-7.56 (m, 2 H), 5.91 (s, 1 H), 5.32 (s, 2 H), 4.52 (brs, 2 H), 3.75 (d, J=4.80 Hz, 2 H), 3.31 (d, J=1.60 Hz, 2 H), 2.94 (m, 2 H), 2.45 (s, 3 H), 1.72 (m, 4 H), 1.50 (m, 6 H).

Example 3-31

N-[2-(1,1-Dioxido-2,3-dihydro-1,4-benzothiazepin-4(5H)-yl)-6-methylquinolin-4-yl]-N'-methylethane-1,2-diamine

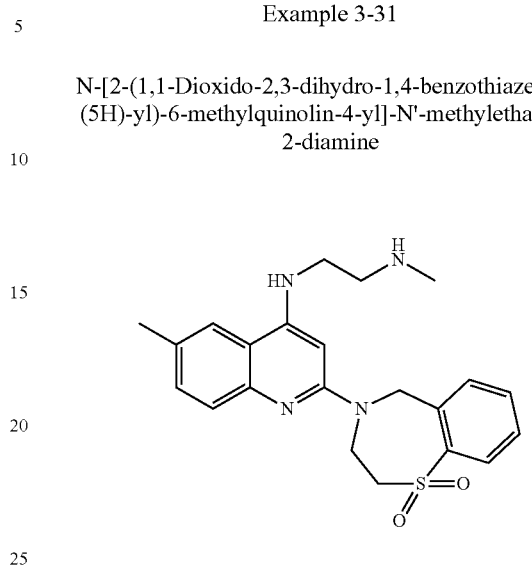

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and N-methylethane-1,2-diamine. MS obsd. (ESI$^+$) [(M+H)$^+$] 411, $^1$H NMR (400 MHz, CD$_3$OD) δ ppm 8.03-8.0 (m, 3 H), 7.87-7.84 (d, J=8.8 Hz, 1 H), 7.71-7.70 (d, J=1.2 Hz, 1 H), 7.57-7.53 (m, 2 H), 6.07 (s, 1 H), 5.40 (s, 2 H), 4.56 (s, 2 H), 3.96-3.93 (dd, J=6.0, 6.4 Hz, 2 H), 3.75-3.73 (q, J=4.4 Hz, 2 H), 3.43-3.40 (q, J=6 Hz, 2 H), 2.80 (s, 3 H), 2.46 (s, 3 H).

Example 3-32

N'-[2-(1,1-Dioxido-2,3-dihydro-1,4-benzothiazepin-4(5H)-yl)-6-methylquinolin-4-yl]-N,N-dimethyl-ethane-1,2-diamine

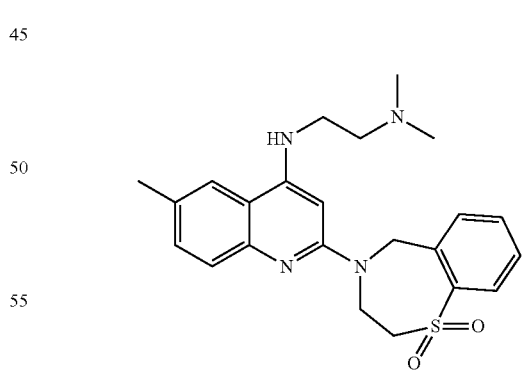

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and N,N-dimethylethane-1,2-diamine. MS obsd. (ESI$^+$) [(M+H)$^+$] 425, $^1$H NMR (400 MHz, CD$_3$OD) δ ppm 8.05-8.01 (m, 3 H), 7.88-7.86 (d, J=8.8 Hz, 1 H), 7.70-7.68 (d, J=1.2 Hz, 1 H), 7.56-7.52 (m, 2 H), 6.05 (s, 1 H), 5.41 (s, 2 H), 4.56 (s, 2 H), 3.96-3.93 (dd, J=6.0, 6.4 Hz, 2 H), 3.75-3.73 (q, J=4.4 Hz, 2 H), 3.43-3.40 (q, J=6.0 Hz, 2 H), 3.01 (s, 3 H), 2.45 (s, 3 H).

Example 3-33

2-(1,1-Dioxido-2,3-dihydro-1,4-benzothiazepin-4(5H)-yl)-N,6-dimethylquinolin-4-amine trifluoroacetate

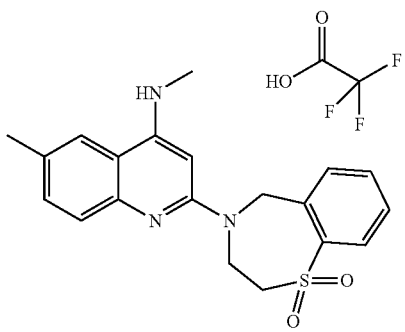

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and methylamine. MS obsd. (ESI$^+$) [(M+H)$^+$] 368, $^1$H NMR (400 MHz, DMSO-d6) δ ppm 11.47 (s, 1 H), 8.45 (brs, 1 H), 7.99 (m, 3 H), 7.75 (m, 2 H), 7.60 (m, 2 H), 5.92 (s, 1 H), 5.33 (s, 2 H), 4.48 (s, 2 H), 3.91 (s, 2 H), 3.02 (s, 3 H), 2.33 (s, 3 H).

Example 3-34

(3S,4S)-1-[2-(1,1-Dioxido-2,3-dihydro-1,4-benzothiazepin-4(5H)-yl)-6-methylquinolin-4-yl]pyrrolidine-3,4-diol

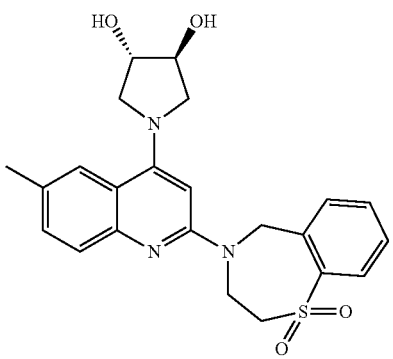 [SMILES: Cc1ccc2nc(N3CCS(=O)(=O)c4ccccc4C3)cc(N3C[C@H](O)[C@@H](O)C3)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and (3S,4S)-pyrrolidine-3,4-diol. MS obsd. (ESI$^+$) [(M+H)$^+$] 440, $^1$H NMR (400 MHz, CD$_3$OD) δ ppm 8.03 (s, 1 H), 8.01 (s, 1 H), 7.80-7.78 (d, J=7.6 Hz, 1 H), 7.67-7.63 (m, 2 H), 7.54-7.50 (m, 2 H), 5.83 (s, 1 H), 5.21 (s, 2 H), 4.45 (s, 2 H), 4.22 (s, 2 H), 4.18-4.15 (m, 2 H), 3.67-3.60 (m, 4 H), 2.41 (s, 3 H).

Example 3-35

2-(1,1-Dioxido-2,3-dihydro-1,4-benzothiazepin-4(5H)-yl)-6-methyl-N-(pyrrolidin-2-ylmethyl)quinolin-4-amine

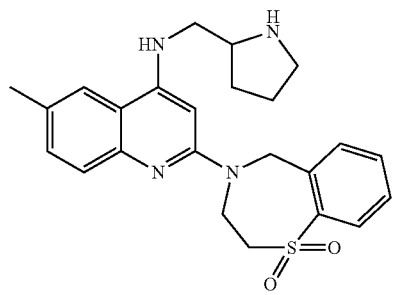 [SMILES: Cc1ccc2nc(N3CCS(=O)(=O)c4ccccc4C3)cc(NCC3CCCN3)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 1-(pyrrolidin-2-yl)methanamine. MS obsd. (ESI$^+$) [(M+H)$^+$] 437, $^1$H NMR (400 MHz, CD$_3$OD) δ ppm 7.96-7.94 (m, 2 H), 7.90 (d, J=7.6 Hz, 1 H), 7.70 (d, J=8.4 Hz, 1 H), 7.61 (t, J=7.6 Hz, 1 H), 7.47-7.45 (m, 2 H), 6.01 (s, 1 H), 5.33-5.25 (m, 2 H), 4.55-4.41 (m, 2 H), 3.96-3.73 (m, 3 H), 3.64 (s, 2 H), 3.38-3.31 (m, 1 H), 3.29-3.27 (m, 1 H), 2.37 (s, 3 H), 2.28-2.21 (m, 1 H), 2.13-1.96 (m, 2 H), 1.89-1.81 (m, 1 H).

Example 3-36

4-[4-(1,4-Diazepan-1-yl)-6-methylquinolin-2-yl]-2,3,4,5-tetrahydro-1,4-benzothiazepine 1,1-dioxide

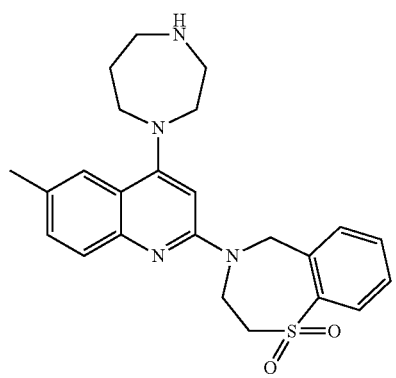 [SMILES: Cc1ccc2nc(N3CCS(=O)(=O)c4ccccc4C3)cc(N3CCCNCC3)c2c1]

The title compound was prepared in analogy to Example 3-1 1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 1,4-diazepine. MS obsd. (ESI$^+$) [(M+H)$^+$] 437, $^1$H NMR (400 MHz, CD$_3$OD) δ ppm 7.99 (d, J=7.2 Hz, 1 H), 7.86 (d, J=7.2 Hz, 1 H), 7.81 (d, J=8.8 Hz, 1 H), 7.72-7.68 (m, 2 H), 7.58-7.51 (m, 2 H), 6.31 (s, 1 H), 5.32 (s, 2 H), 4.54 (s, 2 H), 4.06-4.04 (m, 2 H), 3.90-3.87 (m, 2 H), 3.72 (s, 2 H), 3.63-3.61 (m, 2 H), 3.46-3.42 (m, 2 H), 2.45 (s, 3 H), 2.32 (s, 2 H).

Example 3-37

N-[2-(1,1-Dioxido-2,3-dihydro-1,4-benzothiazepin-4(5H)-yl)-6-methylquinolin-4-yl]-N'-ethylethane-1,2-diamine

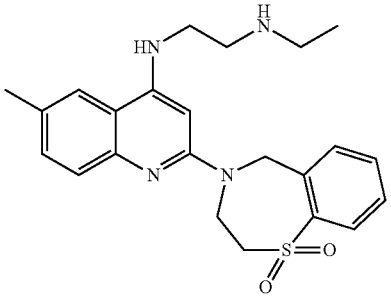 [SMILES: CCNCCNc1cc(N2CCS(=O)(=O)c3ccccc3C2)nc2ccc(C)cc12]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and N-ethylethane-1,2-diamine. MS obsd. (ESI$^+$) [(M+H)$^+$] 425, $^1$H NMR (400 MHz, CD$_3$OD) δ ppm 8.05 (d, J=7.2 Hz, 1 H), 7.99-7.97 (m, 2 H), 7.81 (d, J=8.4 Hz, 1 H), 7.67 (t, J=7.2 Hz, 1 H), 7.51-7.46 (m, 2 H), 6.08 (s, 1 H), 5.37 (s, 2 H), 4.57 (s, 2 H), 3.91 (t, J=6.4 Hz, 2 H), 3.69 (t, J=4.8 Hz, 2 H), 3.37 (t, J=6.4 Hz, 2 H), 3.15 (q, J=7.2 Hz, 2 H), 2.43 (s, 3 H), 1.35 (t, J=7.2 Hz, 3 H).

Example 3-38

2-{[2-(1,1-Dioxido-2,3-dihydro-1,4-benzothiazepin-4(5H)-yl)-6-methylquinolin-4-yl]amino}ethanol

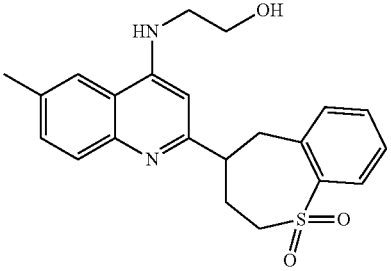 [SMILES: Cc1ccc2nc(C3CCS(=O)(=O)c4ccccc4C3)cc(NCCO)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 2-aminoethanol. MS obsd. (ESI$^+$) [(M+H)$^+$] 398, $^1$H NMR (400 MHz, CD$_3$OD) δ ppm 8.08 (d, J=7.6 Hz, 1 H), 7.91 (s, 1 H), 7.85 (d, J=7.6 Hz, 1 H), 7.74-7.67 (m, 2 H), 7.59-7.56 (m, 2 H), 6.09 (s, 1 H), 5.29 (s, 2 H), 4.51 (s, 2 H), 3.83 (t, J=5.6 Hz, 2 H), 3.74-3.72 (m, 2 H), 3.62 (t, J=5.6 Hz, 2 H), 2.47 (s, 3 H).

Example 3-39

2-(1,1-Dioxido-2,3-dihydro-1,4-benzothiazepin-4(5H)-yl)-6-methyl-N-(piperidin-4-yl)quinolin-4-amine

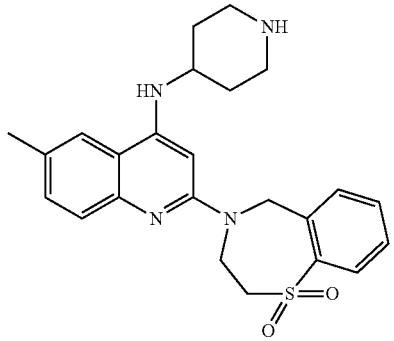 [SMILES: Cc1ccc2nc(N3CCS(=O)(=O)c4ccccc4C3)cc(NC3CCNCC3)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and piperidin-4-amine. MS obsd. (ESI$^+$) [(M+H)$^+$] 437, $^1$H NMR (400 MHz, CD$_3$OD) δ ppm 8.05 (t, J=8 Hz, 2 H), 7.88 (d, J=8 Hz, 1 H), 7.73-7.69 (m, 2 H), 7.59-7.57 (m, 2 H), 6.04 (s, 1 H), 5.33 (s, 2 H), 4.52 (s, 2 H), 4.18-4.11 (m, 1 H), 3.74 (s, 2 H), 3.61-3.57 (m, 2 H), 3.33-3.26 (m, 2 H), 2.46 (s, 3 H), 2.24-2.19 (m, 2 H), 2.01-1.91 (m, 2 H).

Example 3-40

2-(1,1-Dioxido-2,3-dihydro-1,4-benzothiazepin-4(5H)-yl)-6-methyl-N-(piperidin-3-yl)quinolin-4-amine

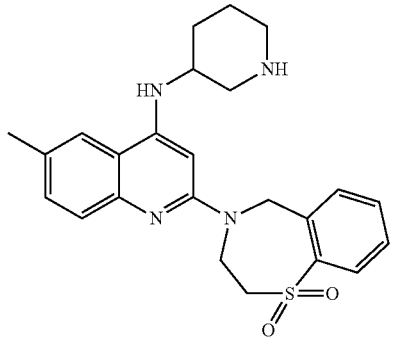 [SMILES: Cc1ccc2nc(N3CCS(=O)(=O)c4ccccc4C3)cc(NC3CCCNC3)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and piperidin-3-amine. MS obsd. (ESI$^+$) [(M+H)$^+$] 437, $^1$H NMR (400 MHz, CD$_3$OD) δ ppm 8.09-8.07 (d, J=8 Hz, 1 H), 7.99 (s, 1 H), 7.89-7.87 (q, J=7.2 Hz, 1 H), 7.73-7.68 (q, J=14 Hz, 2 H), 7.62-7.55 (m, 2 H), 6.14 (s, 1 H), 5.36 (s, 2 H), 4.58-4.51 (m, 2 H), 4.34 (s, 1 H), 3.75 (s, 2 H), 3.63-3.60 (d, J=11.6 Hz, 1 H), 3.47-3.44 (m, 1 H), 3.07-3.02 (d, J=11.6 Hz, 2 H), 2.47 (s, 3 H), 2.17-2.14 (m, 2 H), 2.05-2.00 (m, 1 H), 1.85-1.84 (m, 1 H).

Example 3-41

2-(1,1-Dioxido-2,3-dihydro-1,4-benzothiazepin-4(5H)-yl)-6-methyl-N-(piperidin-2-ylmethyl)quinolin-4-amine

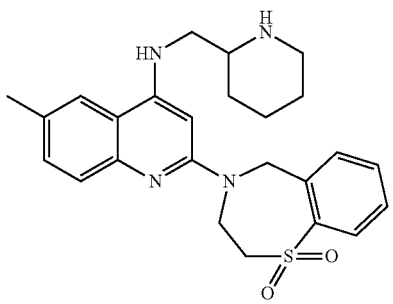 [SMILES: Cc1ccc2nc(N3CCS(=O)(=O)c4ccccc4C3)cc(NCC3CCCCN3)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 1-(piperidin-2-yl)methanamine. MS obsd. (ESI$^+$) [(M+H)$^+$] 451, $^1$H NMR (400 MHz, CD$_3$OD) δ ppm 8.07 (d, J=7.6 Hz, 1 H), 7.93 (s, 1 H), 7.85 (d, J=7.6 Hz, 1 H), 7.73-7.70 (m, 2 H), 7.62-7.58 (m, 2 H), 6.02 (s, 1 H), 5.35 (s, 2 H), 4.51 (s, 2 H), 3.75-3.71 (m, 4 H), 3.51-3.40 (m, 2 H), 2.98-2.92 (m, 1 H), 2.46 (s, 3 H), 2.11-2.05 (m, 1 H), 1.96-1.90 (m, 2 H), 1.78-1.56 (m, 3 H).

Example 3-42

2-[(2-{[2-(1,1-Dioxido-2,3-dihydro-1,4-benzothiazepin-4(5H)-yl)-6-methylquinolin-4-yl]amino}ethyl)amino]ethanol

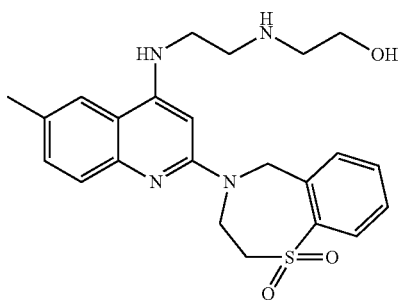 [SMILES: Cc1ccc2nc(N3CCS(=O)(=O)c4ccccc4C3)cc(NCCNCCO)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 2-[(2-aminoethyl)amino]ethanol. MS obsd. (ESI$^+$) [(M+H)$^+$] 441, $^1$H NMR (400 MHz, CD$_3$OD) δ ppm 7.94 (d, J=7.6 Hz, 1 H), 7.81 (d, J=6.8 Hz, 1 H), 7.61-7.57 (m, 2 H), 7.43-7.38 (m, 2 H), 7.24 (d, J=7.6 Hz, 1 H), 6.02 (s, 1 H), 5.12 (s, 2 H), 4.51 (brs, 2 H), 3.69 (t, J=5.2 Hz, 2 H), 3.55-3.52 (m, 2 H), 3.49 (t, J=6.0 Hz, 2 H), 3.01 (t, J=6.0 Hz, 2 H), 2.83 (t, J=5.6 Hz, 2 H), 2.38 (s, 3 H).

Example 3-43

N-[2-(1,1-Dioxido-2,3-dihydro-1,4-benzothiazepin-4(5H)-yl)-6-methylquinolin-4-yl]-2,2,3,3-tetrafluorobutane-1,4-diamine

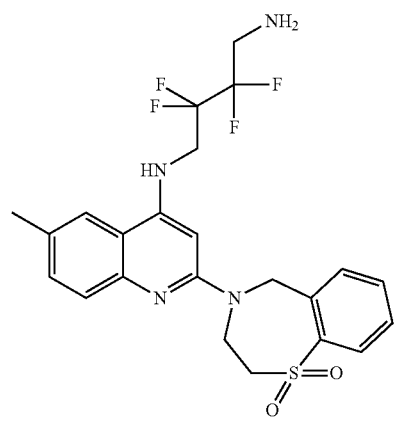 [SMILES: Cc1ccc2nc(N3CCS(=O)(=O)c4ccccc4C3)cc(NCC(F)(F)C(F)(F)CN)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 2,2,3,3-tetrafluorobutane-1,4-diamine. MS obsd. (ESI$^+$) [(M+H)$^+$] 497, $^1$H NMR (400 MHz, CD$_3$OD) δ ppm 7.99 (d, J=6.8 Hz, 1 H), 7.78 (d, J=6.4 Hz, 1 H), 7.58-7.62 (m, 2 H), 7.43-7.47 (m, 2 H), 7.30-7.32 (m, 1 H), 6.19 (s, 1 H), 5.13 (s, 2 H), 4.58 (brs, 2 H), 4.12 (t, J=16 Hz, 2 H), 3.58 (t, J=4.8 Hz 2 H), 3.34-3.20 (m, 2 H), 2.43 (s, 3 H).

Example 3-44

N-[2-(1,1-Dioxido-2,3-dihydro-1,4-benzothiazepin-4(5H)-yl)-6-methylquinolin-4-yl]-N'-(2-methoxyethyl)ethane-1,2-diamine

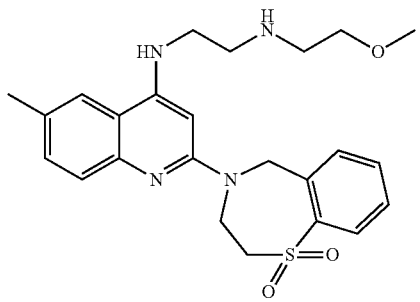

The title compound was prepared in analogy to Example 3-1 1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and N-(2-methoxyethyl)ethane-1,2-diamine. MS obsd. (ESI$^+$) [(M+H)$^+$] 455, $^1$H NMR (400 MHz, CD$_3$OD) δ ppm 8.06-8.04 (d, J=7.6

Hz, 1 H), 7.88-7.86 (m, 2 H), 7.73-7.70 (m, 2 H), 7.59-7.56 (m, 2 H), 6.01 (s, 1 H), 5.33 (s, 2 H), 4.55 (s, 2 H), 3.88-3.78 (m, 2 H), 3.72 (s, 2 H), 3.67-3.65 (t, J=4.8 Hz, 2 H), 3.45-3.42 (t, J=6 Hz, 2 H), 3.38 (s, 3 H), 3.30-3.28 (m, 2 H), 2.45 (s, 3 H).

Example 3-45

1-[2-(1,1-Dioxido-2,3-dihydro-1,4-benzothiazepin-4 (5H)-yl)-6-methylquinolin-4-yl]-3-methylpyrrolidin-3-ol

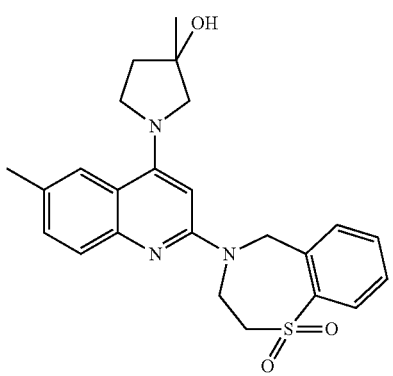 [SMILES: Cc1ccc2nc(N3CCS(=O)(=O)c4ccccc4C3)cc(N3CCC(C)(O)C3)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 3-methylpyrrolidin-3-ol. MS obsd. (ESI+) [(M+H)+] 438, 1H NMR (400 MHz, CD3OD) δ ppm 8.06-8.01 (m, 2 H), 7.84-7.82 (d, J=7.2 Hz, 1 H), 7.74-7.68 (m, 2 H), 7.57-7.53 (m, 2 H), 5.81 (s, 1 H), 5.26 (s, 2 H), 4.49 (s, 2 H), 4.12-3.31 (m, 3 H), 3.27-3.21 (m, 3 H), 2.44 (s, 3 H), 2.08 (s, 2 H), 1.50 (s, 3 H).

Example 3-46

N-[6-Chloro-2-(1,1-dioxido-2,3-dihydro-1,4-benzothiazepin-4(5H)-yl)quinolin-4-yl]ethane-1,2-diamine

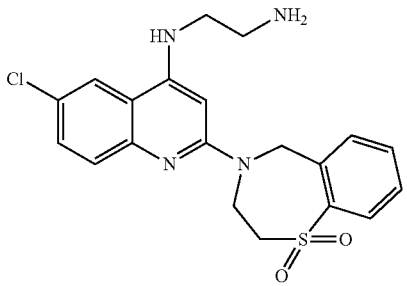 [SMILES: NCCNc1cc(N2CCS(=O)(=O)c3ccccc3C2)nc2ccc(Cl)cc12]

The title compound was prepared in analogy to Example 3-1 in Scheme 5 by using 4-(4,6-dichloroquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4,6-trichloroquinoline and 2,3,4,5-tetrahydro-1,4-benzothiazepine) and ethane-1,2-diamine. MS obsd. (ESI+) [(M+H)+] 417, 1H NMR (400 MHz, CD3OD) δ ppm 8.01- 7.99 (d, J=8.8 Hz, 1 H), 7.90 (s, 1 H), 7.86-7.84 (d, J=7.2 Hz, 1 H), 7.53-7.38 (m, 4 H), 6.10 (s, 1 H), 5.18 (s, 2 H), 3.59-3.40 (m, 4 H), 3.19-3.10 (m, 2 H).

Example 3-47

2-(1,1-Dioxido-2,3-dihydro-1,4-benzothiazepin-4 (5H)-yl)-6-methyl-N-(oxetan-3-yl)quinolin-4-amine

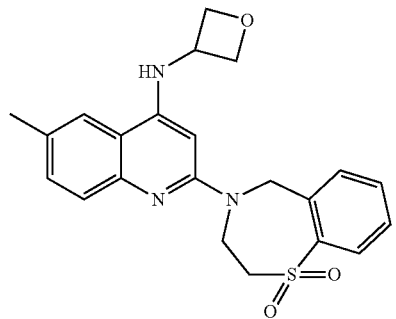 [SMILES: Cc1ccc2nc(N3CCS(=O)(=O)c4ccccc4C3)cc(NC3COC3)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and oxetan-3-amine. MS obsd. (ESI+) [(M+H)+] 410, 1H NMR (400 MHz, CD3OD) δ ppm 7.97 (d, J=1.9 Hz, 1 H), 7.79 (d, J=1.9 Hz, 1 H), 7.72 (s, 1 H), 7.63 (t, J=3.8 Hz, 1 H), 7.44 (t, J=4.3 Hz, 2 H), 7.29 (d, J=2.1 Hz, 1 H), 5.72 (s, 1 H), 5.16 (t, J=3.3 Hz, 2 H), 5.12 (s, 2 H), 4.86 (m, 1 H), 4.72 (t, J=3.0 Hz, 2 H), 4.53 (brs, 2 H), 3.58 (t, J=2.3 Hz, 2 H), 2.43 (s, 3 H).

Example 3-48

N-[(3-Aminooxetan-3-yl)methyl]-2-(1,1-dioxido-2, 3-dihydro-1,4-benzothiazepin-4(5H)-yl)quinolin-4-amine

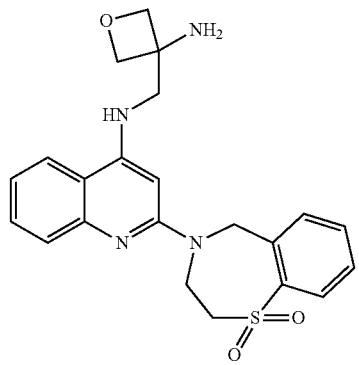 [SMILES: NC1(CNc2cc(N3CCS(=O)(=O)c4ccccc4C3)nc3ccccc23)COC1]

The title compound was prepared in analogy to Example 3-1 in Scheme 5 by using 4-(4-chloroquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4-dichloroquinoline and 2,3,4,5-tetrahydro-1,4-benzothiazepine) and 3-(aminomethyl)oxetan-3-amine. MS obsd. (ESI+) [(M+H)+] 425, 1H NMR (400 MHz, CD3OD) δ ppm 7.96 (d, J=1.8 Hz, 1 H), 7.89 (m, J=5.5 Hz, 2 H), 7.63 (m, J=4.0 Hz, 1 H), 7.44 (m, J=7.6 Hz, 3 H), 7.12-7.08 (m, J=4.1 Hz, 1 H), 6.58 (d, J=0.8 Hz, 1 H), 6.22 (s, 1 H), 5.11 (s, 2 H), 4.48-4.39 (m, J=9.0 Hz, 6 H), 3.65-3.58 (m, J=6.1 Hz, 4 H).

Example 3-49

2-(1,1-Dioxido-2,3-dihydro-1,4-benzothiazepin-4 (5H)-yl)-6-methyl-N-[(3R)-tetrahydrofuran-3-yl] quinolin-4-amine

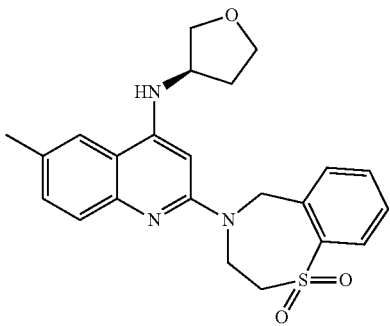 [SMILES: Cc1ccc2nc(N3CCS(=O)(=O)c4ccccc4C3)cc(N[C@@H]3CCOC3)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and (3R)-tetrahydrofuran-3-amine. MS obsd. (ESI+) [(M+H)+] 424, $^1$H NMR (400 MHz, CD$_3$OD) δ ppm 7.89 (t, J=4.4 Hz, 2 H), 7.83 (s, 1 H), 7.65 (t, J=3.7 Hz, 1 H), 7.47 (t, J=3.8 Hz, 1 H), 7.31 (d, J=2.1 Hz, 1 H), 7.24 (d, J=2.1 Hz, 1 H), 6.56 (d, J=1.5 Hz, 1 H), 6.01 (s, 1 H), 5.08 (s, 2 H), 4.40 (brs, 2 H), 4.02 (t, J=3.6 Hz, 1 H), 3.88 (m, J=7.2 Hz, 1 H), 3.80 (m, J=5.4 Hz, 1 H), 3.64 (d, J=4.5 Hz, 3 H), 2.30 (t, J=3.7 Hz, 4 H).

Example 3-50

N-{[3-(Aminomethyl)oxetan-3-yl]methyl}-2-(1,1-dioxido-2,3-dihydro-1,4-benzothiazepin-4(5H)-yl)-6-methylquinolin-4-amine

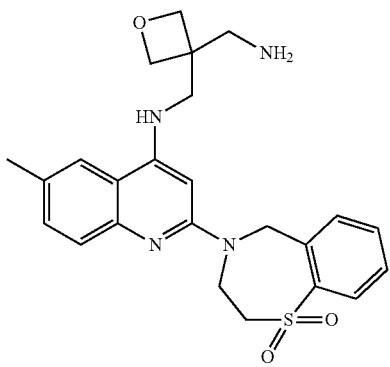

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and oxetane-3,3-diyldimethanamine. MS obsd. (ESI+) [(M+H)+] 453, $^1$H NMR (400 MHz, CD$_3$OD) δ ppm 8.04 (d, J=1.8 Hz, 1 H), 7.90 (d, J=1.9 Hz, 1 H), 7.81 (s, 1 H), 7.67 (t, J=3.6 Hz, 1 H), 7.57 (d, J=2.1 Hz, 1 H), 7.52 (t, J=3.8 Hz, 1 H), 7.43 (d, J=2.1 Hz, 1 H), 6.21 (s, 1 H), 5.26 (s, 2 H), 4.63 (s, 4 H), 4.55 (brs, 2 H), 3.82 (s, 2 H), 3.67 (t, J=2.4 Hz, 2 H), 3.45 (brs, 2 H), 2.46 (s, 3 H).

Example 3-51

N-{[3-(Aminomethyl)oxetan-3-yl]methyl}-6-chloro-2-(1,1-dioxido-2,3-dihydro-1,4-benzothiazepin-4 (5H)-yl)quinolin-4-amine

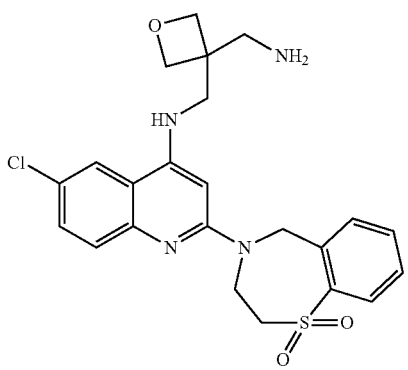

The title compound was prepared in analogy to Example 3-1 in Scheme 5 by using 4-(4,6-dichloroquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4,6-trichloroquinoline and 2,3,4,5-tetrahydro-1,4-benzothiazepine) and oxetane-3,3-diyldimethanamine. MS obsd. (ESI+) [(M+H)+] 473, $^1$H NMR (400 MHz, CD$_3$OD) δ ppm 8.00 (m, J=2.2 Hz, 1 H), 7.89 (t, J=2.9 Hz, 2 H), 7.63 (m, J=4.1, 1 H), 7.45 (m, J=6.5 Hz, 2 H), 7.37 (m, J=2.8 Hz, 1 H), 6.21 (d, 1 H), 5.18 (s, 2 H), 4.56 (m, J=4.6 Hz, 6 H), 3.67 (s, 2 H), 3.58 (t, J=2.4 Hz, 2 H), 3.15 (s, 2 H).

Example 3-52

N-{[3-(Aminomethyl)oxetan-3-yl]methyl}-2-(1,1-dioxido-2,3-dihydro-1,4-benzothiazepin-4(5H)-yl) quinolin-4-amine

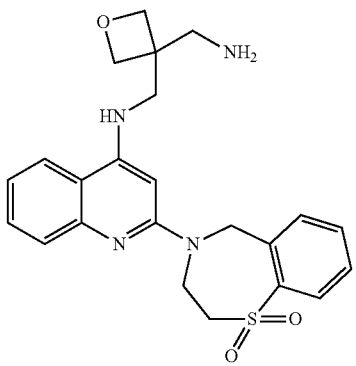 [SMILES: NCC1(CNc2cc(N3CCS(=O)(=O)c4ccccc4C3)nc3ccccc23)COC1]

The title compound was prepared in analogy to Example 3-1 in Scheme 5 by using 4-(4-chloroquinolin-2-yl)-2,3,4,5- tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4-dichloroquinoline and 2,3,4,5-tetrahydro-1,4-benzothiazepine) and oxetane-3,3-diyldimethanamine. MS obsd. (ESI$^+$) [(M+H)$^+$] 439, $^1$H NMR (400 MHz, CD$_3$OD) δ ppm 8.32 (d, J=2.1 Hz, 1 H), 8.11 (t, J=2.0 Hz, 1 H), 8.04 (d, J=1.9 Hz, 1 H), 7.93 (d, J=2.0 Hz, 1 H), 7.77 (m, J=8.3 Hz, 2 H), 7.63 (t, J=3.7 Hz, 1 H), 7.53 (d, J=3.8 Hz, 1 H), 6.30 (s, 1 H), 5.45 (s, 2 H), 4.65 (m, J=5.5 Hz, 6 H), 4.01 (s, 2 H), 3.83 (t, J=2.4 Hz, 2 H), 3.51 (s, 2 H).

Example 3-53

2-(1,1-Dioxido-2,3-dihydro-1,4-benzothiazepin-4 (5H)-yl)-6-methyl-N-(oxetan-3-ylmethyl)quinolin-4-amine

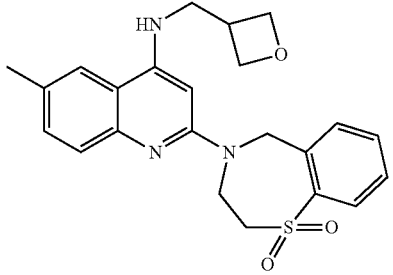 [SMILES: Cc1ccc2nc(N3CCS(=O)(=O)c4ccccc4C3)cc(NCC3COC3)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 1-(oxetan-3-yl)methanamine. MS obsd. (ESI$^+$) [(M+H)$^+$] 424, $^1$H NMR (400 MHz, DMSO-d6) δ ppm 7.93 (d, 1 H), 7.89-7.87 (t, 1 H), 7.69-7.65 (m, 2 H), 7.50-7.46 (t, 1 H), 7.31 (d, 1 H), 7.24-7.21 (m, 1 H), 6.79-6.76 (t, 1 H), 6.04 (s, 1 H), 5.08 (s, 2 H), 4.74-4.70 (m, 2 H), 4.37 (t, 4 H), 3.61 (t, 4 H), 3.28 (m, 1 H), 2.35 (s, 3 H)

Example 3-54

N-[(1-Aminocyclobutyl)methyl]-2-(1,1-dioxido-2,3-dihydro-1,4-benzothiazepin-4(5H)-yl)-6-methylquinolin-4-amine

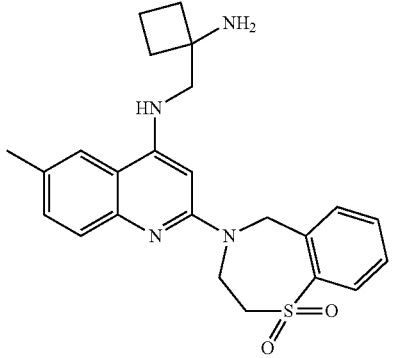 [SMILES: Cc1ccc2nc(N3CCS(=O)(=O)c4ccccc4C3)cc(NCC3(N)CCC3)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 1-(aminomethyl)cyclobutanamine. MS obsd. (ESI$^+$) [(M+H)$^+$] 437, $^1$H NMR (400 MHz, CD$_3$OD) δ ppm 7.97 (m, J=2.0 Hz, 1 H), 7.86 (d, J=1.8 Hz, 1 H), 7.70 (s, 1 H), 7.61 (t, J=3.6 Hz, 1 H), 7.45 (m, J=3.0 Hz, 2 H), 7.30 (m, J=2.5 Hz, 1 H), 6.13 (s, 1 H), 5.18 (s, 2 H), 4.53 (br. s., 2 H), 3.59 (t, J=2.3 Hz, 2 H), 3.46 (s, 2 H), 2.43 (s, 3 H), 2.28-2.22 (m, J=6.3 Hz, 2 H), 2.12-2.03 (m, J=9.2 Hz, 2 H), 1.97-1.82 (m, J=14.7 Hz, 2 H).

Example 3-55

N-[2-(1,1-Dioxido-2,3-dihydro-1,4-benzothiazepin-4 (5H)-yl)-6-methylquinolin-4-yl]pentane-1,5-diamine

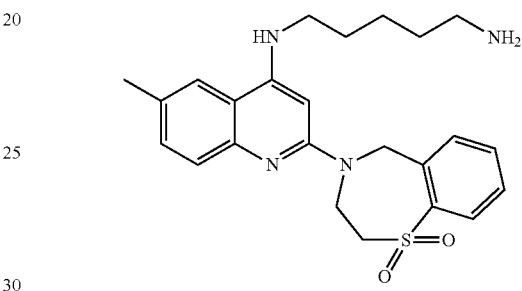

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and pentane-1,5-diamine. MS obsd. (ESI$^+$) [(M+H)$^+$] 439, $^1$H NMR (400 MHz, CDCl$_3$) δ ppm 7.96 (d, J=7.6 Hz, 1 H), 7.54 (d, J=6.8 Hz 1 H), 7.42 (m, 2 H), 7.30 (d, J=6.4 Hz, 1 H), 7.21 (m, 2 H), 5.81 (s, 1 H), 5.03 (s, 2 H), 4.61 (m, 2 H), 3.49 (brs, 2 H), 3.19 (m, 2 H), 2.71 (d, J=6.40 Hz, 2 H), 2.94 (m, 2 H), 2.34 (s, 3 H), 1.61 (s, 2 H), 1.49 (m, 4 H).

Example 3-56

N-[2-(1,1-Dioxido-2,3-dihydro-1,4-benzothiazepin-4 (5H)-yl)-6-methylquinolin-4-yl]hexane-1,6-diamine

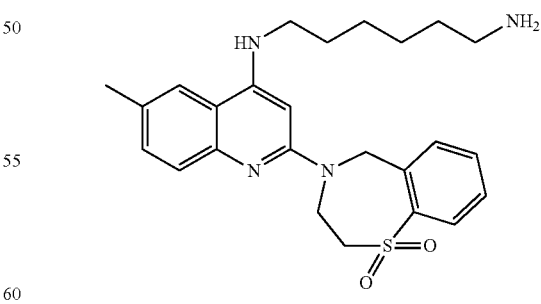

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and hexane-1,6-diamine. MS obsd. (ESI$^+$) [(M+H)$^+$] 453, $^1$H NMR (400 MHz, CD$_3$OD) δ ppm 8.07 (dd, J=1.2, 0.8 Hz, 1 H), 7.97 (s, 1 H), 7.92 (d, J=7.6 Hz, 1 H), 7.80 (d, J=8.8 Hz, 1 H), 7.70 (d, J=1.2 Hz, 1 H), 7.57 (dd, J=7.20, 1.6 Hz, 2 H), 5.91 (s, 1 H), 5.32 (s, 2 H), 4.52 (brs, 2 H), 3.75 (d, J=4.80 Hz, 2 H), 3.31 (d, J=1.60 Hz, 2 H), 2.94 (m, 2 H), 2.45 (s, 3 H), 1.72 (m, 4 H), 1.50 (m, 4 H).

Example 3-57

N-[2-(1,1-Dioxido-2,3-dihydro-1,4-benzothiazepin-4(5H)-yl)-6-methylquinolin-4-yl]-1,1,1-trifluoromethanesulfonamide hydrochloride

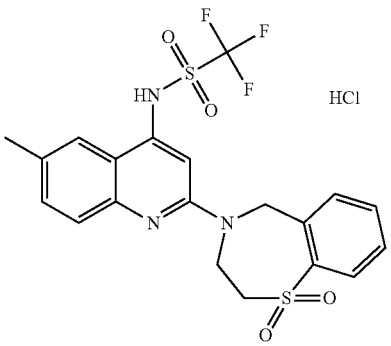 [SMILES: Cc1ccc2nc(N3CCS(=O)(=O)c4ccccc4C3)cc(NS(=O)(=O)C(F)(F)F)c2c1 ; Cl]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 1,1,1-trifluoromethanesulfonamide. MS obsd. (ESI⁺) [(M+H)⁺] 486, ¹H NMR (400 MHz, DMSO-d6) δ ppm 7.99-7.92 (m, 2 H), 7.85-7.80 (d, J=7.2 Hz, 1 H), 7.78-7.73 (d, J=2 Hz, 1 H), 7.72-7.65 (t, J=7.6 Hz, 1 H), 7.62-7.51 (m, 2 H), 7.13 (s, 1 H), 5.07 (s, 2 H), 4.60-4.40 (m, 2 H), 3.98-3.91 (t, J=2.8 Hz, 2 H), 2.39 (s, 3 H).

Example 3-58

N-[2-(1,1-Dioxido-2,3-dihydro-1,4-benzothiazepin-4(5H)-yl)-6-methylquinolin-4-yl]pyridazine-3-carboxamide

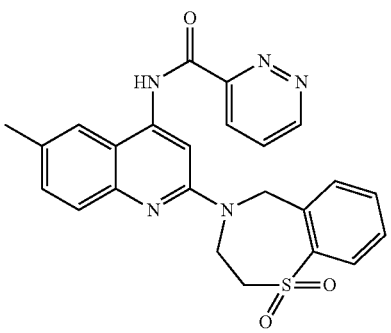 [SMILES: Cc1ccc2nc(N3CCS(=O)(=O)c4ccccc4C3)cc(NC(=O)c3cccnn3)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and pyridazine-3-carboxamide. MS obsd. (ESI⁺) [(M+H)⁺] 460, ¹H NMR (400 MHz, CD₃OD) δ ppm 9.52-9.48 (d, J=8 Hz, 1 H), 8.68 (s, 1 H), 8.62-8.58 (d, J=7.6 Hz, 1 H), 8.10-8.02 (m, 3 H), 7.94 (s, 1 H), 7.88-7.82 (d, J=8 Hz, 1 H), 7.75-7.68 (t, J=7.6 Hz, 2 H), 7.60-7.52 (t, J=7.2 Hz, 1 H), 5.36 (s, 2 H), 4.80-4.55 (m, 2 H), 3.83-3.78 (t, J=2.8 Hz, 2 H), 2.56 (s, 3 H).

Example 3-59

N-[2-(1,1-Dioxido-2,3-dihydro-1,4-benzothiazepin-4(5H)-yl)-6-methylquinolin-4-yl]benzamide

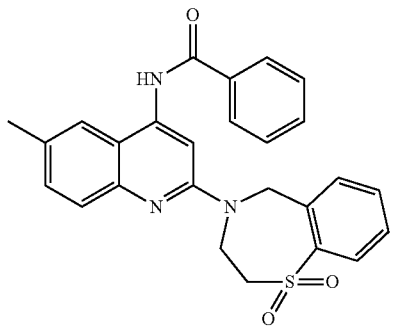 [SMILES: Cc1ccc2nc(N3CCS(=O)(=O)c4ccccc4C3)cc(NC(=O)c3ccccc3)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and benzamide. MS obsd. (ESI⁺) [(M+H)⁺] 458, ¹H NMR (400 MHz, CD₃OD) δ ppm 8.64 (s, 1 H), 8.09-8.04 (m, 5 H), 7.89-7.87 (d, J=8.4 Hz, 1 H), 7.75-7.67 (m, 3 H), 7.62-7.55 (m, 3 H), 5.34 (s, 2 H), 4.62 (s, 2 H), 3.76 (s, 2 H), 2.53 (s, 3 H).

Example 3-60

N-[2-(1,1-Dioxido-2,3-dihydro-1,4-benzothiazepin-4(5H)-yl)-6-methylquinolin-4-yl]acetamide

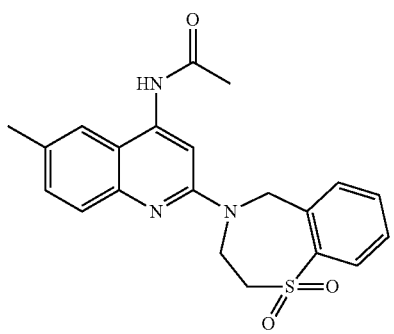 [SMILES: CC(=O)Nc1cc(N2CCS(=O)(=O)c3ccccc3C2)nc2ccc(C)cc12]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and acetamide. MS obsd. (ESI⁺) [(M+H)⁺] 396, ¹H NMR (400 MHz, CD₃OD) δ ppm 8.53 (s, 1 H), 8.10-8.06 (m, 2 H), 7.97-7.85 (d, J=8.4 Hz, 1 H), 7.82-7.80 (d, J=9.2 Hz, 1 H), 7.76-7.72 (m,

Example 3-61

N-[2-(1,1-Dioxido-2,3-dihydro-1,4-benzothiazepin-4(5H)-yl)-6-methylquinolin-4-yl]piperidine-3-carboxamide

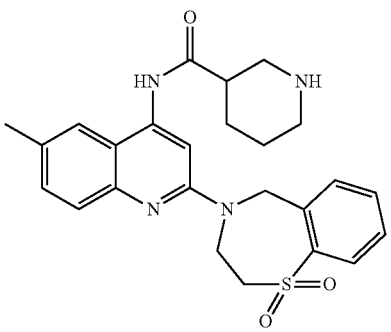 [SMILES: Cc1ccc2nc(N3CCS(=O)(=O)c4ccccc4C3)cc(NC(=O)C3CCCNC3)c2c1]

The title compound was prepared in analogy to Example 3-1 in Scheme 5 by using 4-(4-bromo-6-methylquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 4,6-dibromoquinoline and 2,3,4,5-tetrahydro-1,4-benzothiazepine) and piperidine-3-carboxamide. MS obsd. (ESI$^+$) [(M+H)$^+$] 465, $^1$H NMR (400 MHz, CD$_3$OD) δ ppm 8.47 (s, 1 H), 8.11 (s, 1 H), 8.07-8.05 (d, J=1.2 Hz, 1 H), 7.98-7.96 (d, J=7.2 Hz, 1 H), 7.83-7.80 (d, J=8.4 Hz, 1 H), 7.70-7.64 (m, 2 H), 7.58-7.54 (m, 1 H), 5.29 (s, 1 H), 4.61 (s, 2 H), 3.76 (s, 2 H), 3.55-3.52 (m, 2 H), 3.43-3.34 (m, 3 H), 3.22-3.15 (m, 1 H), 2.52 (s, 3 H), 2.29-2.27 (m, 1 H), 2.06-2.02 (m, 1 H), 1.97-1.89 (m, 2 H).

Example 3-62

N-[2-(1,1-Dioxido-2,3-dihydro-1,4-benzothiazepin-4(5H)-yl)-6-methylquinolin-4-yl]piperidine-4-carboxamide

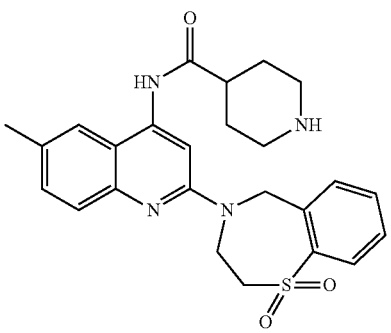 [SMILES: Cc1ccc2nc(N3CCS(=O)(=O)c4ccccc4C3)cc(NC(=O)C3CCNCC3)c2c1]

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and piperidine-4-carboxamide. MS obsd. (ESI$^+$) [(M+H)$^+$] 465, $^1$H NMR (400 MHz, CD$_3$OD) δ ppm 8.50 (s, 1 H), 8.14 (s, 1 H), 8.01-7.98 (d, J=1.2 Hz, 1 H), 7.95-7.93 (d, J=7.2 Hz, 1 H), 7.84-7.82 (d, J=8.8 Hz, 1 H), 7.66-7.61 (m, 2 H), 7.52-7.51 (m, 1 H), 5.23 (s, 1 H), 4.59 (s, 2 H), 3.74 (s, 2 H), 3.57-3.54 (m, 2 H), 3.22-3.10 (m, 4 H), 2.50 (s, 3 H), 2.26-2.22 (m, 2 H), 2.14-2.08 (m, 2 H).

Example 3-63

3-[2-(1,1-Dioxido-2,3-dihydro-1,4-benzothiazepin-4(5H)-yl)-6-methylquinolin-4-yl]-1,1-dimethylurea

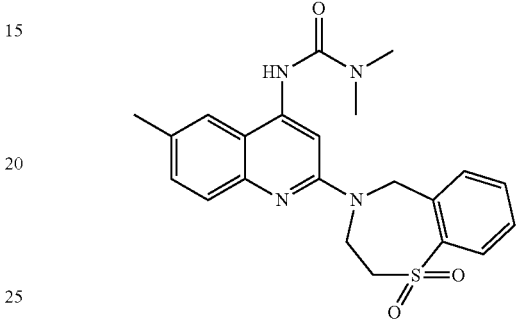

The title compound was prepared in analogy to Example 3-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 1,1-dimethylurea. MS obsd. (ESI$^+$) [(M+H)$^+$] 425, $^1$H NMR (400 MHz, CD$_3$OD) δ ppm 7.83 (d, J=7.6 Hz, 1 H), 7.68 (t, J=3.6 Hz, 2 H), 7.42 (q, J=7.2 Hz, 2 H), 7.23-7.20 (m, 2 H), 7.15 (s, 1 H), 5.00 (s, 2 H), 4.45 (brs, 2 H), 3.42 (s, 2 H), 3.02 (s, 6 H), 2.30 (s, 3 H).

Example 3-64

2-(1,1-Dioxido-2,3-dihydro-1,4-benzothiazepin-4(5H)-yl)-6-methyl-N-(1,2-oxazol-3-yl)quinolin-4-amine

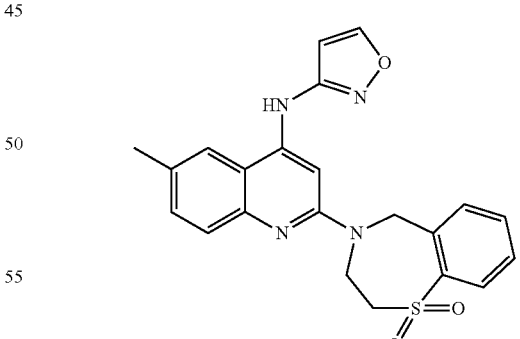

The title compound was prepared in analogy to Example 3-1 in Scheme 5 by using 4-(4-bromo-6-methylquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 4,6-dibromoquinoline and 2,3,4,5-tetrahydro-1,4-benzothiazepine) and 1,2-oxazol-3-amine. MS obsd. (ESI$^+$) [(M+H)$^+$] 421, $^1$H NMR (400 MHz, CD$_3$OD) δ ppm 8.72 (s, 1 H), 8.20 (s, 2 H), 8.14 (d, J=7.2 Hz, 1 H), 8.07 (d, J=7.6 Hz, 1 H), 7.83 (d, J=8.8 Hz, 1 H), 7.63-7.68 (m, 2 H), 7.56 (t, J=7.6 Hz, 1 H), 6.65 (s, 1 H), 5.29 (s, 2 H), 4.61 (s, 2 H), 3.79 (s, 2 H), 2.54 (s, 3 H).

Example 3-65

N-{[3-(Aminomethyl)oxetan-3-yl]methyl}-2-(1,1-dioxido-2,3-dihydro-1,4-benzothiazepin-4(5H)-yl)-6-trideuteriomethylquinolin-4-amine

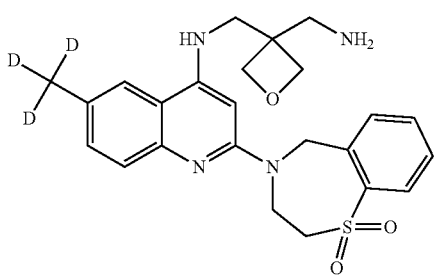 [SMILES: [2H]C([2H])([2H])c1ccc2nc(N3CCS(=O)(=O)c4ccccc4C3)cc(NCC3(CN)COC3)c2c1]

The title compound was prepared in analogy to Example 3-1 in Scheme 5 by using 4-(4-chloro-6-trideuteriomethylquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4-dichloro-6-trideuteriomethylquinoline and 2,3,4,5-tetrahydro-1,4-benzothiazepine) and oxetane-3,3-diyldimethanamine. MS obsd. (ESI$^+$) [(M+H)$^+$] 456, $^1$H NMR (400 MHz, CDCl$_3$) δ ppm 8.04 (d, 1 H), 7.68 (d, 1 H), 7.51 (m, 2 H), 7.36 (t, 1 H), 7.29 (s, 1 H), 7.22 (d, 1 H), 7.08 (s, 1 H), 5.92 (s, 1 H), 5.13 (s, 2 H), 4.57 (s, 6 H), 3.67 (s, 2 H), 3.57 (s, 2 H), 3.34 (s, 2 H).

Example 4-1

N-[(3-Aminooxetan-3-yl)methyl]-6-chloro-2-(2,3-dihydro-1,4-benzothiazepin-4(5H)-yl)quinolin-4-amine

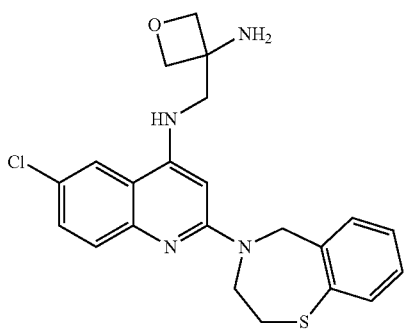 [SMILES: NC1(CNc2cc(N3CCSc4ccccc4C3)nc3ccc(Cl)cc23)COC1]

The title compound was prepared in analogy to Example 3-1 in Scheme 5 by using 4-(4,6-dichloroquinolin-2-yl)-2,3,4,5-tetrahydro-1,4-benzothiazepine (prepared in analogy to 4-(4-chloro-6-methylquinolin-2-yl)-8-methoxy-2,3,4,5-tetrahydro-1,4-benzothiazepine in Example 1-1) and 3-aminomethyl-oxetan-3-ylamine. MS obsd. (ESI$^+$) [(M+H)$^+$] 410, $^1$H NMR (400 MHz, CD$_3$OD) δ ppm 7.94 (s, 1 H), 7.93-7.70 (m, 1 H), 7.50-7.48 (d, J=8.4 Hz, 2 H), 7.40-7.37 (m, 1 H), 7.26-7.22 (m, 1 H), 7.15-7.11 (m, 1 H), 6.20 (s, 1 H), 4.99 (s, 2 H), 4.63-4.61 (d, J=6.8 Hz, 2 H), 4.58-4.57 (d, J=6.4 Hz, 2 H), 4.38 (s, 2 H), 3.65 (s, 2 H), 2.99-2.97 (t, J=4.8 Hz, 2 H).

Example 4-2

N-[6-Chloro-2-(2,3-dihydro-1,4-benzothiazepin-4(5H)-yl)quinolin-4-yl]ethane-1,2-diamine

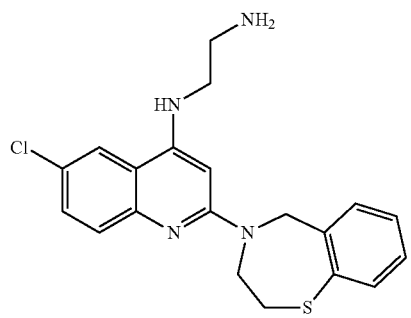 [SMILES: NCCNc1cc(N2CCSc3ccccc3C2)nc2ccc(Cl)cc12]

The title compound was prepared in analogy to Example 4-1 in Scheme 5 by using 4-(4,6-dichloroquinolin-2-yl)-2,3,4,5-tetrahydro-1,4-benzothiazepine (prepared in analogy to the one in Example 4-1) and ethane-1,2-diamine. MS obsd. (ESI$^+$) [(M+H)$^+$] 385, $^1$H NMR (400 MHz, CD$_3$OD) δ ppm 7.901 (s, 1 H), 7.70-7.60 (m, 1 H), 7.55-7.42 (m, 2 H), 7.378-3.350 (dd, J=8.8, 2.4 Hz, 1 H), 7.28-7.16 (m, 1 H), 7.14-7.12 (m, 1 H), 6.05 (s, 1 H), 5.51 (s, 1 H), 4.97 (s, 2 H), 4.38 (s, 2 H), 3.43-3.39 (t, J=6.4 Hz, 2 H), 2.99-2.95 (m, 4 H).

Example 4-3

N-[(3-Aminooxetan-3-yl)methyl]-2-(2,3-dihydro-1,4-benzothiazepin-4(5 H)-yl)-6-methylquinolin-4-amine

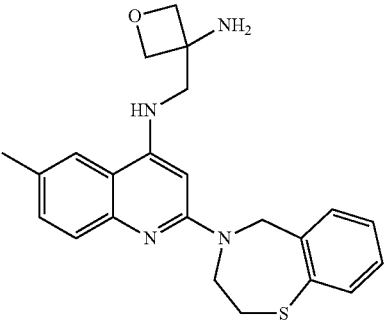 [SMILES: Cc1ccc2nc(N3CCSc4ccccc4C3)cc(NCC3(N)COC3)c2c1]

The title compound was prepared in analogy to Example 4-1 in Scheme 5 by using 4-(4-chloro-6-methylquinolin-2-yl)-2,3,4,5-tetrahydro-1,4-benzothiazepine (prepared in analogy to 4-(4-chloro-6-methylquinolin-2-yl)-8-methoxy-2,3,4,5-tetrahydro-1,4-benzothiazepine in Example 1-1) and 3-aminomethyl-oxetan-3-ylamine. MS obsd. (ESI$^+$) [(M+H)$^+$] 407, $^1$H NMR (400 MHz, CD$_3$OD) δ ppm 7.97 (s, 1 H), 7.74-7.67 (t, 2 H), 7.61 (d, J=8.4 Hz, 1 H), 7.55 (d, J=7.6 Hz, 1 H), 7.32 (t, 1 H), 7.26 (t, 1 H), 6.27 (s, 1 H), 5.19 (s, 2 H), 4.77-4.70 (m, 4 H), 4.35 (s, 2 H), 4.12 (s, 2 H), 3.16 (t, J=9.6 Hz, 2 H), 2.49 (s, 3 H).

Example 4-4

1-[2-(2,3-Dihydro-1,4-benzothiazepin-4(5H)-yl)-6-methylquinolin-4-yl]pyrrolidin-3-amine

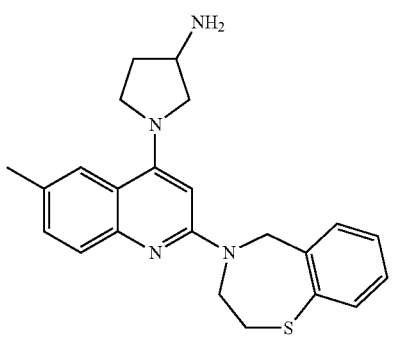 [SMILES: Cc1ccc2nc(N3CCSc4ccccc4C3)cc(N3CCC(N)C3)c2c1]

The title compound was prepared in analogy to Example 4-1 in Scheme 5 by using 4-(4-chloro-6-methylquinolin-2-yl)-2,3,4,5-tetrahydro-1,4-benzothiazepine (prepared in analogy to 4-(4-chloro-6-methylquinolin-2-yl)-8-methoxy-2,3,4,5-tetrahydro-1,4-benzothiazepine in Example 1-1) and pyrrolidin-3-amine. MS obsd. (ESI$^+$) [(M+H)$^+$] 391, $^1$H NMR (400 MHz, CD$_3$OD) δ ppm 8.07 (s, 1 H), 7.79 (d, J=8.4 Hz, 1 H), 7.67-7.57 (m, 3 H), 7.38-7.30 (m, 2 H), 5.96 (s, 1 H), 5.17 (s, 2 H), 4.45-4.35 (m, 2 H), 4.30-4.25 (m, 1 H), 4.20-4.11 (m, 2 H), 4.05-3.91 (m, 2 H), 3.23 (t, J=4.8 Hz, 2 H), 2.51-2.50 (m, 1 H), 2.53 (s, 3 H), 2.40-2.30 (m, 1 H).

Example 5-1

2-(1,1-Dioxido-2,3-dihydro-1,4-benzothiazepin-4(5H)-yl)-N-[2-(1,1-dioxidothiomorpholin-4-yl)ethyl]-6-methylquinolin-4-amine

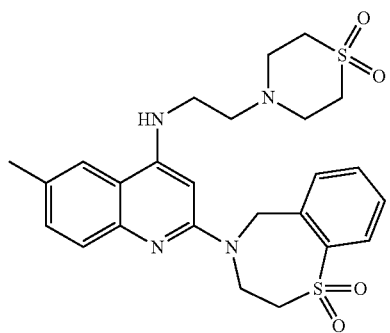 [SMILES: Cc1ccc2nc(N3CCS(=O)(=O)c4ccccc4C3)cc(NCCN3CCS(=O)(=O)CC3)c2c1]

To a solution of 4-(4-chloro-6-methylquinolin-2-yl)-2,3,4,5-tetrahydro-1,4-benzothiazepine 1,1-dioxide (150 mg, 0.40 mmol, prepared in analogy to the one in Example 2-1) in 1,4-dioxane (4 mL) was added tris(dibenzylideneacetone)dipalladium (0) (40 mg, 0.04 mmol), 1,1'-bis(diphenyphosphino)ferrocene (25 mg, 0.04 mmol), sodium tert-butoxide (77 mg, 0.80 mmol) and 2-(1,1-dioxidothio-morpholin-4-yl)ethanamine (107 mg, 0.60 mmol). The resulting mixture was evacuated and refilled with nitrogen, sealed and heated at 120° C. overnight. After being cooled to room temperature, the mixture was filtered and washed with ethyl acetate, the organic layers were combined and concentrated in vacuo, the residue was purified by flash chromatography (eluenting with 2% methanol in dichloromethane) to afford 67 mg of the title compound as a light solid (yield was 40%). MS obsd. (ESI$^+$) [(M+H)$^+$] 515, $^1$H NMR (400 MHz, CDCl$_3$) 8.05 (d, J=7.6 Hz, 1 H), 7.66 (d, J=7.2 Hz, 1 H), 7.53-7.48 (m, 2 H), 7.37-7.28 (m, 2 H), 7.21 (s, 1 H), 5.88 (s, 1 H), 5.26 (m, 1 H), 5.12 (s, 1 H), 4.6 (brs, 1 H), 3.56 (m, 1 H), 3.33 (m, 2 H), 3.14 (m, 8 H), 2.99 (t, J=4.8 Hz, 2 H), 2.46 (s, 3 H), 2.0 (d, J=4.5 Hz, 2 H).

Example 5-2

N-[2-(2-Aminoethoxy)ethyl]-2-(1,1-dioxido-2,3-dihydro-1,4-benzothiazepin-4(5H)-yl)-6-methylquinolin-4-amine

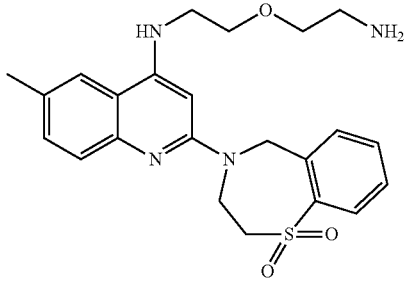 [SMILES: Cc1ccc2nc(N3CCS(=O)(=O)c4ccccc4C3)cc(NCCOCCN)c2c1]

The title compound was prepared in analogy to Example 5-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 2,2'-oxydiethanamine. MS obsd. (ESI$^+$) [(M+H)$^+$] 441, $^1$H NMR (400 MHz, CD$_3$OD) δ ppm 8.08 (dd, J=1.2, 7.6 Hz, 1 H), 7.92 (s, 1 H), 7.83 (d, J=7.2 Hz, 1 H), 7.70-7.67 (m, 2 H), 7.59-7.55 (m, 2 H), 5.96 (s, 1 H), 5.28 (s, 2 H), 4.49 (s, 2 H), 3.81 (t, J=5.2 Hz, 2 H), 3.72-3.68 (m, 6 H), 3.13 (t, J=4.8 Hz, 2 H), 2.45 (s, 3 H).

Example 5-3

N~1~-[2-(1,1-Dioxido-2,3-dihydro-1,4-benzothiazepin-4(5H)-yl)-6-methylquinolin-4-yl]-2-methylpropane-1,2-diamine

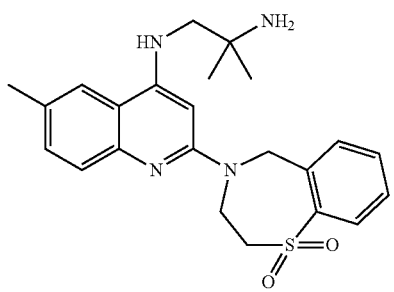 [SMILES: Cc1ccc2nc(N3CCS(=O)(=O)c4ccccc4C3)cc(NCC(C)(C)N)c2c1]

The title compound was prepared in analogy to Example 5-1 in Scheme 5 by using 4-(4-chloro-6-methylquinolin-2- yl)-2,3,4,5-tetrahydro-1,4-benzothiazepine 1,1-dioxide (prepared in analogy to the one in Example 2-1) and 2-methylpropane-1,2-diamine. MS obsd. (ESI+) [(M+H)+] 425, ¹H NMR (400 MHz, CD₃OD) δ ppm 7.97 (d, J=7.83 Hz, 1 H), 7.85 (d, J=7.58 Hz, 1 H), 7.70 (s, 1 H), 7.60 (t, J=7.33 Hz, 1 H), 7.48-7.38 (m, 2 H), 7.29-7.27 (m, 1 H), 6.09 (s, 1 H), 5.15 (brs, 2 H), 3.57 (brs, 2 H), 3.26 (s, 2 H), 2.43 (s, 3 H), 1.34-1.20 (m, 6 H).

Example 5-4

N~1~-[2-(1,1-Dioxido-2,3-dihydro-1,4-benzothiazepin-4(5H)-yl)quinolin-4-yl]-2-methylpropane-1,2-diamine

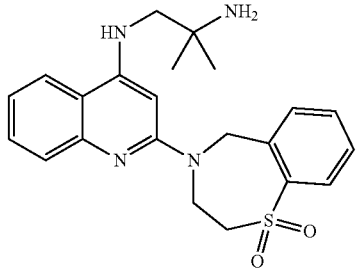 [SMILES: CC(C)(N)CNc1cc(N2CCS(=O)(=O)c3ccccc3C2)nc2ccccc12]

The title compound was prepared in analogy to Example 5-1 in Scheme 5 by using 4-(4-chloroquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using and 2,4-dichloroquinoline 2,3,4,5-tetrahydro-1,4-benzothiazepine) and 2-methylpropane-1,2-diamine. MS obsd. (ESI+) [(M+H)+] 411, ¹H NMR (400 MHz, CD₃OD) δ ppm 8.02-7.93 (m, 1 H), 7.87 (s, 2 H), 7.64-7.57 (m, 1 H), 7.56-7.48 (m, 1 H), 7.42 (s, 2 H), 7.19-7.09 (m, 1 H), 6.11 (s, 1 H), 5.23-5.07 (m, 2 H), 3.63-3.51 (m, 2 H), 3.37 (s, 2 H), 3.33 (m, 2 H), 3.28 (s, 2 H), 1.26 (s, 6 H).

Example 5-5

N~1~-[2-(1,1-Dioxido-2,3-dihydro-1,4-benzothiazepin-4(5H)-yl)-6-methylquinolin-4-yl]propane-1,2-diamine

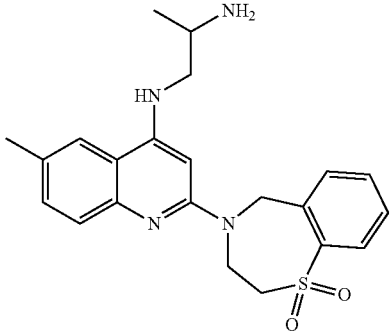

The title compound was prepared in analogy to Example 5-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and propane-1,2-diamine. MS obsd. (ESI+) [(M+H)+] 411, ¹H NMR (400 MHz, CD₃OD) δ ppm 7.91 (dd, J=7.83, 1.01 Hz, 1 H), 7.83 (d, J=7.33 Hz, 1 H), 7.69 (s, 1 H), 7.58 (d, J=1.26 Hz, 1 H), 7.44 (d, J=8.59 Hz, 1 H), 7.38-7.31 (m, 1 H), 7.28 (dd, J=8.59, 1.77 Hz, 1 H), 6.04 (s, 1 H), 5.13 (brs, 2 H), 3.56 (t, J=4.67 Hz, 2 H), 3.52-3.41 (m, 4 H), 3.37 (s, 1 H), 2.41 (s, 3 H), 1.38 (d, J=6.06 Hz, 3 H).

Example 5-6

4-[6-Methyl-4-(4-methylpiperazin-1-yl)quinolin-2-yl]-2,3,4,5-tetrahydro-1,4-benzothiazepine 1,1-dioxide

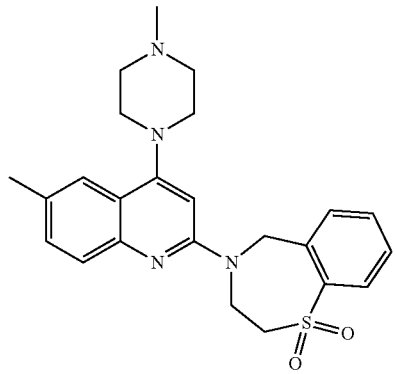 [SMILES: Cc1ccc2nc(N3CCS(=O)(=O)c4ccccc4C3)cc(N3CCN(C)CC3)c2c1]

The title compound was prepared in analogy to Example 5-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 1-methylpiperazine. MS obsd. (ESI+) [(M+H)+] 437, ¹H NMR (400 MHz, CD₃OD) δ ppm 7.90 (dd, J=7.83, 1.01 Hz, 1 H), 7.79 (d, J=7.07 Hz, 1 H), 7.60-7.45 (m, 3 H), 7.34 (td, J=7.64, 1.14 Hz, 1 H), 7.28 (dd, J=8.59, 1.77 Hz, 1 H), 6.54 (s, 1 H), 5.11 (s, 2 H), 3.61-3.50 (m, 2 H), 3.37 (s, 2 H), 3.17 (brs, 4 H), 2.80 (brs, 4 H), 2.46 (s, 3 H), 2.39 (s, 3 H).

Example 5-7

1-{[2-(1,1-Dioxido-2,3-dihydro-1,4-benzothiazepin-4(5H)-yl)-6-methylquinolin-4-yl]amino}propan-2-ol

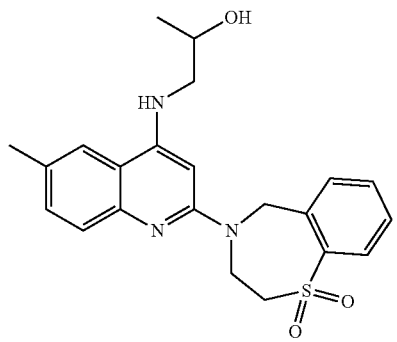 [SMILES: Cc1ccc2nc(N3CCS(=O)(=O)c4ccccc4C3)cc(NCC(C)O)c2c1]

The title compound was prepared in analogy to Example 5-1 in Scheme 5 by using 4-(4-chloro-6-methylquinolin-2-yl)-2,3,4,5-tetrahydro-1,4-benzothiazepine 1,1-dioxide (prepared in analogy to the one in Example 1-1) and 1-aminopropan-2-ol. MS obsd. (ESI⁺) [(M+H)⁺] 412, ¹H NMR (400 MHz, CD₃OD) δ ppm 7.99 (dd, J=7.71, 1.14 Hz, 1 H), 7.84 (d, J=7.07 Hz, 1 H), 7.71 (s, 1 H), 7.64 (td, J=7.58, 1.26 Hz, 1 H), 7.55 (d, J=8.59 Hz, 1 H), 7.50-7.41 (m, 1 H), 7.37 (dd, J=8.59, 1.52 Hz, 1 H), 6.03 (s, 1 H), 5.16 (s, 2 H), 4.08 (dd, J=11.49, 6.44 Hz, 1 H), 3.62 (t, J=4.80 Hz, 2 H), 3.44-3.35 (m, 4 H), 2.42 (s, 3 H), 1.33 (d, J=6.06 Hz, 3 H).

Example 5-8

(2S)—N~1~-[2-(1,1-Dioxido-2,3-dihydro-1,4-benzothiazepin-4(5H)-yl)-6-methylquinolin-4-yl]propane-1,2-diamine

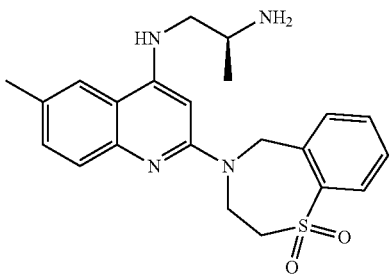 [SMILES: Cc1ccc2nc(N3CCS(=O)(=O)c4ccccc4C3)cc(NC[C@H](C)N)c2c1]

The title compound was prepared in analogy to Example 5-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and (2S)-propane-1,2-diamine. MS obsd. (ESI⁺) [(M+H)⁺] 411, ¹H NMR (400 MHz, CD₃OD) δ ppm 7.86 (d, J=7.58 Hz, 1 H), 7.71 (d, J=7.33 Hz, 1 H), 7.67-7.60 (m, 1 H), 7.49 (t, J=7.33 Hz, 1 H), 7.42 (d, J=8.59 Hz, 1 H), 7.28-7.19 (m, 2 H), 6.07-5.83 (m, 1 H), 5.02 (brs, 2 H), 3.62 (s, 1 H), 3.56-3.46 (m, 2 H), 3.37 (s, 2 H), 3.28-3.11 (m, 4 H), 2.36 (s, 3 H), 0.92-0.80 (m, 2 H).

Example 5-9

(2R)—N~1~-[2-(1,1-Dioxido-2,3-dihydro-1,4-benzothiazepin-4(5H)-yl)-6-methylquinolin-4-yl]propane-1,2-diamine

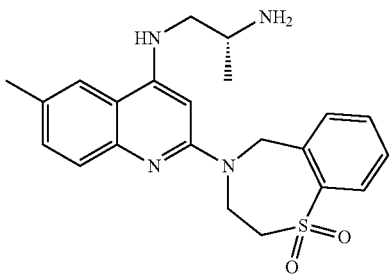 [SMILES: Cc1ccc2nc(N3CCS(=O)(=O)c4ccccc4C3)cc(NC[C@@H](C)N)c2c1]

The title compound was prepared in analogy to Example 5-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and (2R)-propane-1,2-diamine. MS obsd. (ESI⁺) [(M+H)⁺] 411, ¹H NMR (400 MHz, CD₃OD) δ ppm 7.97 (d, J=7.83 Hz, 1 H), 7.82 (d, J=7.58 Hz, 1 H), 7.70-7.55 (m, 2 H), 7.46-7.37 (m, 2 H), 7.33-7.22 (m, 2 H), 6.10-5.99 (m, 1 H), 5.13 (brs, 2 H), 3.65-3.52 (m, 3 H), 3.37 (m, 2 H), 3.31-3.20 (m, 2 H), 2.41 (s, 3 H), 1.32-1.22 (m, 2 H).

Example 5-10

N-[(3-Aminooxetan-3-yl)methyl]-2-(1,1-dioxido-2,3-dihydro-1,4-benzothiazepin-4(5H)-yl)-7,8-difluoro-6-methylquinolin-4-amine

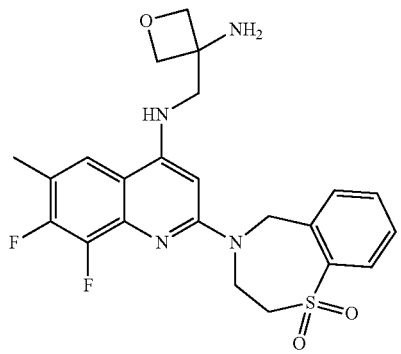 [SMILES: Cc1cc2c(NCC3(N)COC3)cc(N3CCS(=O)(=O)c4ccccc4C3)nc2c(F)c1F]

The title compound was prepared in analogy to Example 5-1 in Scheme 5 by using 4-(4-chloro-6-methyl-7,8-difluoroquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 4-chloro-6-methyl-7,8-dichloroquinoline and 2,3,4,5-tetrahydro-1,4-benzothiazepine) and 3-(aminomethyl)oxetan-3-amine. MS obsd. (ESI⁺) [(M+H)⁺] 475, ¹H NMR (400 MHz, DMSO-d6) δ ppm 8.04 (brs, 1 H), 7.88 (d, J=7.83 Hz, 1 H), 7.62 (t, J=6.82 Hz, 1 H), 7.47 (t, J=7.58 Hz, 1 H), 7.18 (brs, 1 H), 6.31 (brs, 1 H), 5.16 (brs, 1 H), 4.60 (d, J=8.34 Hz, 2 H), 4.05-3.97 (m, 2 H), 3.82 (brs, 2 H), 3.62 (brs, 2 H), 3.17 (m, 2 H), 2.33 (s, 1 H), 1.28-1.13 (m, 3 H).

Example 5-11

N-(2,2-Difluoroethyl)-N'-[2-(1,1-dioxido-2,3-dihydro-1,4-benzothiazepin-4(5H)-yl)-6-methylquinolin-4-yl]ethane-1,2-diamine

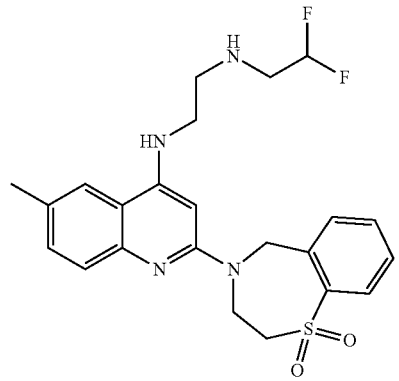 [SMILES: Cc1ccc2nc(N3CCS(=O)(=O)c4ccccc4C3)cc(NCCNCC(F)F)c2c1]

The title compound was prepared in analogy to Example 5-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and N-(2,2-difluoroethyl)ethane-1,2-diamine. MS obsd. (ESI⁺) [(M+H)⁺] 461, ¹H NMR (400 MHz, CD₃OD) δ ppm 7.97 (dd, J=7.83, 1.26 Hz, 1 H), 7.83 (d, J=6.82 Hz, 1 H), 7.60 (td, J=7.45, 1.26 Hz, 2 H), 7.46-7.38 (m, 2 H), 7.28 (dd, J=8.59, 1.77 Hz, 1 H), 6.04 (s, 1 H), 5.13 (s, 2 H), 3.58 (t, J=4.80 Hz, 2 H), 3.46 (t, J=6.19 Hz, 2 H), 3.37 (s, 3 H), 3.10-2.97 (m, 4 H), 2.41 (s, 3 H).

Example 5-12

3-{[2-(1,1-Dioxido-2,3-dihydro-1,4-benzothiazepin-4(5H)-yl)-6-methylquinolin-4-yl]amino}oxetan-3-ethanol

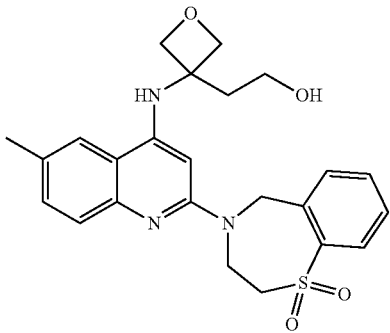 [SMILES: Cc1ccc2nc(N3CCS(=O)(=O)c4ccccc4C3)cc(NC3(CCO)COC3)c2c1]

The title compound was prepared in analogy to Example 5-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 3-aminooxetan-3-ethanol. MS obsd. (ESI$^+$) [(M+H)$^+$] 454, $^1$H NMR (400 MHz, DMSO-d6) δ ppm 7.97 (d, 1 H), 7.89 (d, 1 H), 7.64 (t, 1 H), 7.55 (s, 1 H), 7.49-7.42 (m, 2 H), 7.35-7.32 (m, 1 H), 6.63 (s, 1 H), 5.15 (s, 2 H), 4.50 (d, 2 H), 4.41 (brs, 2 H), 4.39 (d, 4 H), 3.66 (d, 2 H), 2.33 (s, 3 H), 2.27 (t, 2 H).

Example 6-1

N-{[3-(Aminomethyl)thietan-3-yl]methyl}-2-(1,1-dioxido-2,3-dihydro-1,4-benzothiazepin-4(5H)-yl)-6-methylquinolin-4-amine

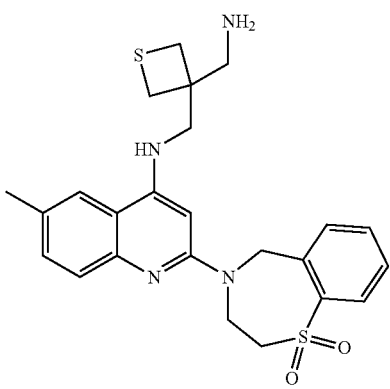 [SMILES: Cc1ccc2nc(N3CCS(=O)(=O)c4ccccc4C3)cc(NCC3(CN)CSC3)c2c1]

A flask containing 4-(4-chloro-6-methylquinolin-2-yl)-2,3,4,5-tetrahydro-1,4-benzothiazepine 1,1-dioxide (250 mg, 0.67 mmol), thietane-3,3-diyldimethanamine (266 mg, 2.01 mmol), tris(dibenzylideneacetone)dipalladium(0) (61.8 mg, 0.067 mmol), 2,2'-bis(diphenylphosphino)-1,1'-binaphthyl (42 mg, 0.067 mmol), sodium tert-butoxide (160 mg, 1.66 mmol) and toluene (15 mL) was evacuated and then filled with nitrogen (balloon). After being stirred at 110° C. overnight, the resulting mixture was diluted with water (15 mL) and extracted with ethyl acetate (15 mL×4). The combined organic layers were dried over sodium sulfate and concentrated in vacuo. The residue was purified by flash column chromatography and preparative HPLC to afford 63 mg of the product as a white solid (yield was 20%). MS obsd. (ESI$^+$) [(M+H)$^+$] 469, $^1$H NMR (400 MHz, CD$_3$OD) δ ppm 7.96-7.94 (m, 1 H), 7.68-7.66 (d, J=7.2 Hz, 1 H), 7.47-7.43 (m, 2 H), 7.31-7.27 (m, 1 H), 7.22-7.21 (d, J=1.6 Hz, 1 H), 7.19 (s, 1 H), 5.88 (s, 1 H), 5.07 (s, 2 H), 4.50 (s, 2 H), 3.55-3.49 (m, 4 H), 3.11 (s, 2 H), 3.06-3.03 (d, J=9.6 Hz, 2 H), 2.94-2.91 (d, J=9.6 Hz, 2 H), 2.31 (s, 3 H).

Example 6-2

N-{[3-(Aminomethyl)-1,1-dioxidothietan-3-yl]methyl}-2-(1,1-dioxido-2,3-dihydro-1,4-benzothiazepin-4(5H)-yl)-6-methylquinolin-4-amine

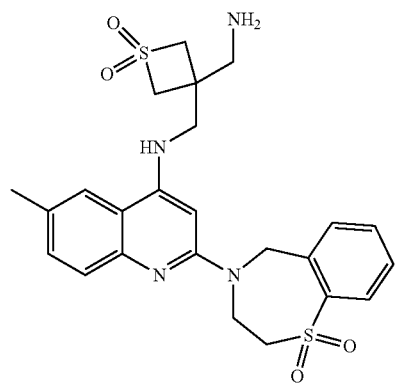 [SMILES: Cc1ccc2nc(N3CCS(=O)(=O)c4ccccc4C3)cc(NCC3(CN)CS(=O)(=O)C3)c2c1]

The title compound was prepared in analogy to Example 6-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and (1,1-dioxidothietane-3,3-diyl)dimethanamine. MS obsd. (ESI$^+$) [(M+H)$^+$] 501, $^1$H NMR (400 MHz, CD$_3$Cl) δ ppm 7.958-7.939 (d, J=7.6 Hz, 1 H), 7.651-7.633 (d, J=7.2 Hz, 1 H), 7.482-7.415 (m, 2 H), 7.308-7.270 (t, J=7.2 Hz, 1 H), 7.235-7.215 (d, J=8.0 Hz, 1 H), 7.134 (s, 1 H), 6.646 (s, 1 H), 5.065 (s, 2 H), 4.701-1.250 (brs, 2 H), 3.924-3.890 (m, 4 H), 3.659-3.646 (d, J=5.2 Hz, 2 H), 3.491 (s, 2 H), 3.320 (s, 2 H), 2.323 (s, 3 H).

Example 7

N-(4,5-Dihydro-1H-imidazol-2-yl)-2-(1,1-dioxido-2,3-dihydro-1,4-benzothiazepin-4(5H)-yl)-6-methylquinolin-4-amine

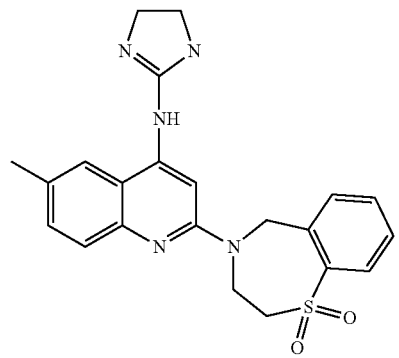 [SMILES: Cc1ccc2nc(N3CCS(=O)(=O)c4ccccc4C3)cc(NC3=NCCN3)c2c1]

A mixture of 4-(4-chloro-6-methylquinolin-2-yl)-2,3,4,5-tetrahydro-1,4-benzothiazepine 1,1-dioxide (150 mg, 0.40 mmol, prepared in analogy to the one in Example 2-1), hydrogen iodide salt of 4,5-dihydro-1H-imidazol-2-amine (110 mg, 0.515 mmol), 4,5-bis(diphenylphosphino)-9,9-dimethylxanthene (25 mg, 0.043 mmol), tris(dibenzylideneacetone)dipalladium(0) (35 mg, 0.038 mmol), cesium carbonate (525 mg, 1.6 mmol) and 1,4-dioxane (3 mL) was heated with stirring in a 5 mL of microwave process vial for 2 hours at 120° C. under microwave irradiation. The resulting mixture was filtered and washed with ethyl acetate. The filtrate was washed with brine, dried over sodium sulfate, and concentrated in vacuo. The residue was purified by preparative HPLC to afford the product as a solid. MS obsd. (ESI$^+$) [(M+H)$^+$] 422, $^1$H NMR (400 MHz, CD$_3$OD) δ ppm 7.68-7.59 (m, 2 H), 7.56 (s, 1 H), 7.50-7.41 (m, 2 H), 7.08 (s, 1 H), 5.23 (brs, 2 H), 4.62 (s, 3 H), 3.76 (s, 3 H), 3.61 (t, J=4.93 Hz, 2 H), 2.68 (s, 4 H), 2.45 (s, 2 H).

Example 8-1 trans-4-{[2-(1,1-Dioxido-2,3-dihydro-1,4-benzothiazepin-4(5H)-yl)-6-methylquinolin-4-yl]amino}cyclohexanol

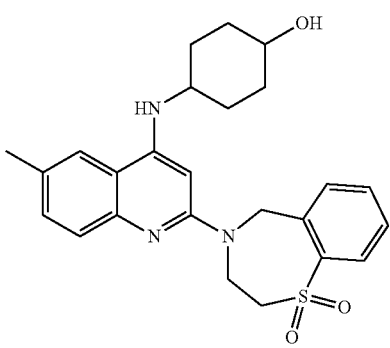 [SMILES: Cc1ccc2nc(N3CCS(=O)(=O)c4ccccc4C3)cc(NC3CCC(O)CC3)c2c1]

A mixture of 4-(4-chloro-6-methylquinolin-2-yl)-2,3,4,5-tetrahydro-1,4-benzothiazepine 1,1-dioxide (140 mg, 0.38 mmol, prepared in analogy to the one in Example 2-1), trans-4-aminocyclohexanol (45 mg, 0.39 mmol), tris(dibenzylideneacetone)dipalladium(0) (35 mg, 0.038 mmol), 2-dicyclohexylphosphino-2'-(N,N-dimethylamino)biphenyl (15 mg, 0.038 mmol), sodium tert-butoxide (38 mg, 0.39 mmol) and 1,4-dioxane (2 mL) was heated with stirring in a 5 mL of microwave process vial for 2 hours at 120° C. under microwave irradiation. The mixture was filtered and washed with ethyl acetate. The filtrate was washed with brine, dried over sodium sulfate, and concentrated in vacuo. The residue was purified by preparative HPLC to afford the product as a solid. MS obsd. (ESI$^+$) [(M+H)$^+$] 452, $^1$H NMR (400 MHz, DMSO-d6) δ ppm 7.98-7.83 (m, 2 H), 7.76 (s, 1 H), 7.64-7.44 (m, 2 H), 7.29 (d, J=8.34 Hz, 1 H), 7.21 (d, J=8.84 Hz, 1 H), 6.22 (d, J=8.34 Hz, 1 H), 6.06 (s, 1 H), 5.09 (brs, 2 H), 4.68 (d, J=4.29 Hz, 1 H), 3.62 (brs, 3 H), 3.49 (d, J=4.55 Hz, 1 H), 2.34 (s, 3 H), 2.03-1.83 (m, 4 H), 1.63-1.45 (m, 2 H), 1.35 (brs, 2 H), 1.24 (brs, 1 H), 1.18 (brs, 1 H).

Example 8-2

(2S)-2-{[2-(1,1-Dioxido-2,3-dihydro-1,4-benzothiazepin-4(5H)-yl)-6-methylquinolin-4-yl]amino}propan-1-ol

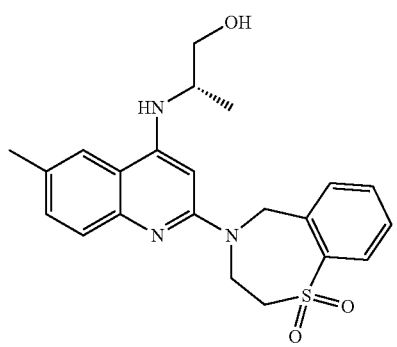 [SMILES: Cc1ccc2nc(N3CCS(=O)(=O)c4ccccc4C3)cc(N[C@@H](C)CO)c2c1]

The title compound was prepared in analogy to Example 8-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and (2S)-2-aminopropan-1-ol. MS obsd. (ESI$^+$) [(M+H)$^+$] 412, $^1$H NMR (400 MHz, DMSO-d6) δ ppm 7.89 (t, J=6.32 Hz, 2 H), 7.75 (s, 1 H), 7.64 (t, J=7.20 Hz, 1 H), 7.55-7.43 (m, 1 H), 7.38-7.27 (m, 1 H), 7.27-7.14 (m, 1 H), 6.16 (d, J=8.08 Hz, 1 H), 6.07 (s, 1 H), 5.07 (brs, 2 H), 4.85 (brs, 1 H), 4.42 (brs, 1 H), 3.85 (dt, J=12.82, 6.35 Hz, 1 H), 3.70-3.47 (m, 3 H), 2.36 (s, 3 H), 1.23 (d, J=6.32 Hz, 3 H).

Example 8-3 trans-1-[2-(1,1-Dioxido-2,3-dihydro-1,4-benzothiazepin-4(5H)-yl)-6-methylquinolin-4-yl]-4-methoxypyrrolidin-3-amine

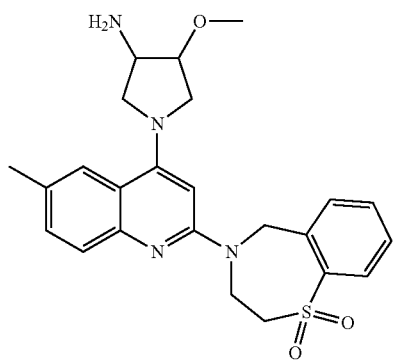 [SMILES: COC1CN(c2cc(N3CCS(=O)(=O)c4ccccc4C3)nc3ccc(C)cc23)CC1N]

The title compound was prepared in analogy to Example 8-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and trans-4-methoxy-3-methylpyrrolidin-3-amine. MS obsd. (ESI$^+$) [(M+H)$^+$] 453, $^1$H NMR (400 MHz, CD$_3$OD) δ ppm 8.00 (dd, J=7.83, 1.26 Hz, 1 H), 7.89-7.78 (m, 2 H), 7.63 (td, J=7.45, 1.26 Hz, 1 H), 7.53 (d, J=8.59 Hz, 1 H), 7.47 (td, J=7.71, 1.01 Hz, 1 H), 7.35 (dd, J=8.59, 1.52 Hz, 1 H), 6.19 (s, 1 H), 5.19 (s, 2 H), 4.53 (brs, 2 H), 4.12 (dd, J=11.12, 5.05 Hz, 1 H), 3.99-3.81 (m, 2 H), 3.73 (brs, 1 H), 3.67-3.56 (m, 2 H), 3.55-3.41 (m, 5 H), 2.43 (s, 3 H).

Example 8-4

2-(1,1-Dioxido-2,3-dihydro-1,4-benzothiazepin-4(5H)-yl)-N-[trans-4-methoxypyrrolidin-3-yl]-6-methylquinolin-4-amine

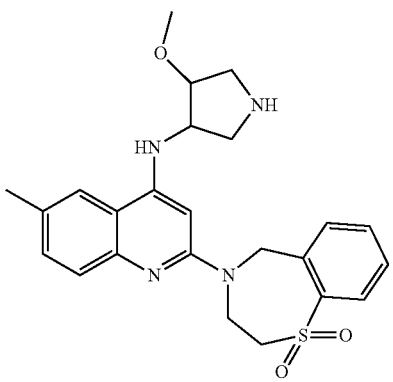 [SMILES: COC1CNCC1Nc1cc(N2CCS(=O)(=O)c3ccccc3C2)nc2ccc(C)cc12]

The title compound was prepared in analogy to Example 8-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and trans-4-methoxy-3-methylpyrrolidin-3-amine. MS obsd. (ESI$^+$) [(M+H)$^+$] 453, $^1$H NMR (400 MHz, CD$_3$OD) δ ppm 8.14 (d, J=7.83 Hz, 1 H), 8.08 (s, 1 H), 7.87 (d, J=7.33 Hz, 1 H), 7.79-7.73 (m, 2 H), 7.69-7.63 (m, 2 H), 6.10 (s, 1 H), 5.36 (q, J=16.67 Hz, 2 H), 4.60 (brs, 2 H), 4.28 (brs, 1 H), 3.93 (dd, J=12.63, 6.82 Hz, 1 H), 3.82 (t, J=4.80 Hz, 2 H), 3.75-3.68 (m, 1 H), 3.68-3.59 (m, 2 H), 3.56 (s, 3 H), 2.51 (s, 3 H).

Example 8-5

4-{4-[(4aS,7aR)-Hexahydropyrrolo[3,4-b][1,4]oxazin-6(2H)-yl]-6-methylquinolin-2-yl}-2,3,4,5-tetrahydro-1,4-benzothiazepine 1,1-dioxide

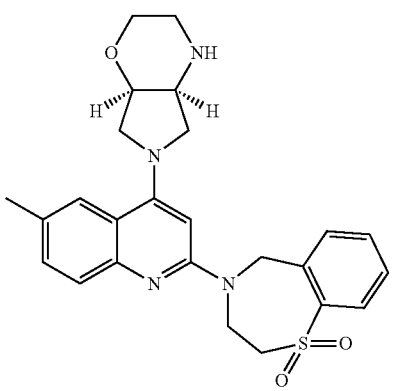 [SMILES: Cc1ccc2nc(N3CCS(=O)(=O)c4ccccc4C3)cc(N3C[C@@H]4NCCO[C@@H]4C3)c2c1]

The title compound was prepared in analogy to Example 8-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and (4aS,7aR)-octahydropyrrolo[3,4-b][1,4]oxazine. MS obsd. (ESI$^+$) [(M+H)$^+$] 465, $^1$H NMR (400 MHz, CD$_3$OD) δ ppm 7.99 (dd, J=7.83, 1.26 Hz, 1 H), 7.85 (d, J=7.33 Hz, 1 H), 7.81 (s, 1 H), 7.63 (td, J=7.52, 1.39 Hz, 1 H), 7.50-7.41 (m, 2 H), 7.28 (dd, J=8.59, 1.77 Hz, 1 H), 6.09 (s, 1 H), 5.16 (s, 2 H), 4.51 (m, 2 H), 4.02-4.15 (m, 3 H), 3.86 (d, J=10.8 Hz, 1 H), 3.68-3.47 (m, 6 H), 3.238 (m, 1 H), 2.72 (m, 1 H), 2.41 (s, 3 H).

Example 8-6

(3R,4R)-1-[2-(1,1-Dioxido-2,3-dihydro-1,4-benzothiazepin-4(5H)-yl)-6-methylquinolin-4-yl]-4-(4-methylpiperazin-1-yl)pyrrolidin-3-ol

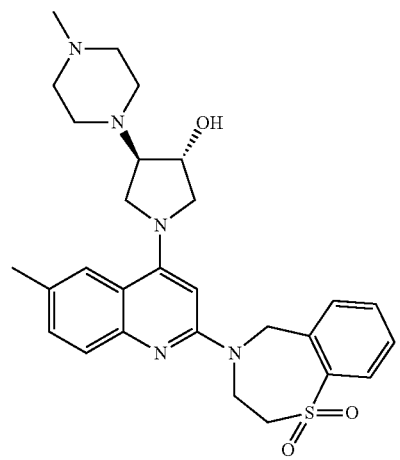 [SMILES: Cc1ccc2nc(N3CCS(=O)(=O)c4ccccc4C3)cc(N3C[C@@H](O)[C@H](N4CCN(C)CC4)C3)c2c1]

The title compound was prepared in analogy to Example 8-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and (3R,4R)-4-(4-methylpiperazin-1-yl)pyrrolidin-3-ol. MS obsd. (ESI$^+$) [(M+H)$^+$] 522, $^1$H NMR (400 MHz, CD$_3$OD) δ ppm 7.99-7.86 (m, 1 H), 7.84-7.75 (m, 1 H), 7.73 (s, 1 H), 7.64-7.52 (m, 1 H), 7.47 (d, J=8.59 Hz, 1 H), 7.43-7.32 (m, 1 H), 7.27 (d, J=8.59 Hz, 1 H), 6.27-6.09 (m, 1 H), 5.10 (brs, 2 H), 4.50 (brs, 1 H), 4.43-4.33 (m, 1 H), 3.81-3.62 (m, 2 H), 3.56 (dd, J=9.85, 4.55 Hz, 3 H), 3.45-3.35 (m, 1 H), 3.02-2.92 (m, 1 H), 2.84 (brs, 2 H), 2.76-2.62 (m, 3 H), 2.57 (brs, 3 H), 2.39 (s, 3 H), 2.32 (s, 3 H).

Example 8-7

N-{2-[(2-Aminoethyl)sulfanyl]ethyl}-2-(1,1-dioxido-2,3-dihydro-1,4-benzothiazepin-4(5H)-yl)-6-methylquinolin-4-amine

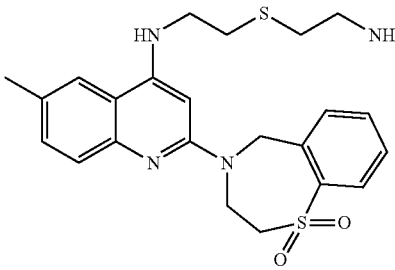

The title compound was prepared in analogy to Example 8-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 2,2'-sulfanediyldiethanamine. MS obsd. (ESI$^+$) [(M+H)$^+$] 457, $^1$H NMR (400 MHz, CD$_3$OD) δ ppm 8.00 (dd, J=7.83, 1.26 Hz, 1 H), 7.84 (d, J=7.33 Hz, 1 H), 7.65 (td, J=7.58, 1.26 Hz, 1 H), 7.57 (s, 1 H), 7.51-7.39 (m, 2 H), 7.29 (dd, J=8.59, 1.77 Hz, 1 H), 6.03 (s, 1 H), 5.14 (s, 2 H), 3.65-3.50 (m, 4 H), 2.92-2.79 (m, 4 H), 2.78-2.68 (m, 2 H), 2.42 (s, 3 H).

Example 9-1

1-{1-[2-(1,1-Dioxido-2,3-dihydro-1,4-benzothiazepin-4(5H)-yl)-6-methylquinolin-4-yl]piperidin-4-yl}methanamine

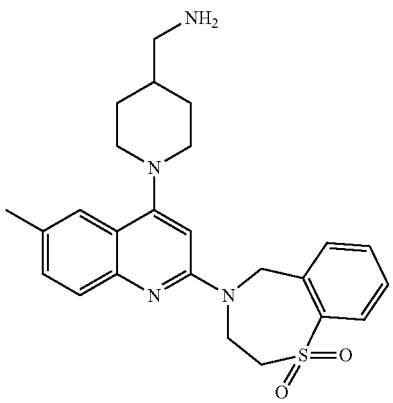 [SMILES: Cc1ccc2nc(N3CCS(=O)(=O)c4ccccc4C3)cc(N3CCC(CN)CC3)c2c1]

A mixture of 4-(4-chloro-6-methylquinolin-2-yl)-2,3,4,5-tetrahydro-1,4-benzothiazepine 1,1-dioxide (75 mg, 0.20 mmol, prepared in analogy to the one in Example 2-1), piperidin-4-yl-methylamine (3 mL) in a 2-5 mL of process vial was heated at 160° C. under microwave irradiation for 1 hour. After being cooled to room temperature, the mixture was concentrated in vacuo to remove the solvent. The residue was purified by preparative HPLC to afford the product as a solid. MS obsd. (ESI$^+$) [(M+H)$^+$] 451, $^1$H NMR (400 MHz, DMSO-d6) δ ppm 7.96-7.81 (m, 2 H), 7.66 (td, J=7.58, 1.26 Hz, 1 H), 7.53-7.39 (m, 3 H), 7.28 (dd, J=8.72, 1.89 Hz, 1 H), 6.58 (s, 1 H), 5.13 (brs, 2 H), 4.42 (brs, 2 H), 3.65 (t, J=4.80 Hz, 2 H), 3.42 (d, J=11.62 Hz, 2 H), 2.72 (t, J=10.99 Hz, 2 H), 2.41-2.27 (m, 3 H), 1.95-1.74 (m, 2 H), 1.61-1.33 (m, 5 H).

Example 9-2

2-{[2-(8-Methoxy-1,1-dioxido-2,3-dihydro-1,4-benzothiazepin-4(5H)-yl)quinolin-4-yl]amino}ethanol

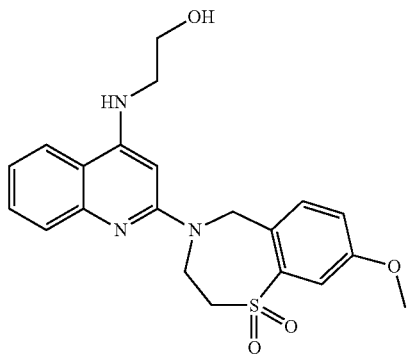 [SMILES: COc1ccc2c(c1)S(=O)(=O)CCN(c1cc(NCCO)c3ccccc3n1)C2]

The title compound was prepared in analogy to Example 9-1 in Scheme 5 by using 4-(4-chloroquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4-dichloroquinoline and 2,3,4,5-tetrahydro-1,4-benzothiazepine) and 2-aminoethanol. MS obsd. (ESI$^+$) [(M+H)$^+$] 414, $^1$H NMR (400 MHz, CD$_3$OD) δ ppm 7.82 (d, J=8.08 Hz, 1 H), 7.76 (d, J=8.34 Hz, 1 H), 7.53 (d, J=2.78 Hz, 2 H), 7.51-7.41 (m, 1 H), 7.22-7.09 (m, 2 H), 6.10 (s, 1 H), 5.11 (s, 2 H), 4.62 (brs, 2 H), 3.83 (s, 3 H), 3.91-3.80 (m, 2 H), 3.61 (brs, 2 H), 3.52 (t, J=5.81 Hz, 2 H).

Example 9-3

N-[2-(1,1-Dioxido-2,3-dihydro-1,4-benzothiazepin-4(5H)-yl)-6-methylquinolin-4-yl]propane-1,3-diamine

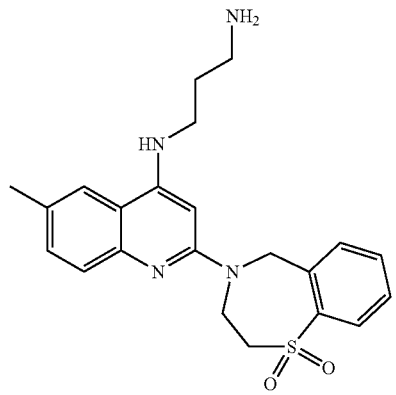 [SMILES: Cc1ccc2nc(N3CCS(=O)(=O)c4ccccc4C3)cc(NCCCN)c2c1]

The title compound was prepared in analogy to Example 9-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and propane-1,3-diamine. MS obsd. (ESI$^+$) [(M+H)$^+$] 411, $^1$H NMR (400 MHz, CD$_3$OD) δ ppm 7.96 (dd, J=7.83, 1.01 Hz, 1 H), 7.81 (d, J=7.07 Hz, 1 H), 7.64-7.54 (m, 2 H), 7.47-7.35 (m, 2 H), 7.26 (dd, J=8.59, 1.77 Hz, 1 H), 5.98 (s, 1 H), 5.12 (s, 2 H), 3.56 (t, J=4.93 Hz, 2 H), 3.39 (t, J=6.82 Hz, 2 H), 2.82 (t, J=6.95 Hz, 2 H), 2.39 (s, 3 H), 1.89 (t, J=6.95 Hz, 2 H).

Example 9-4

4-[6-Methyl-4-(morpholin-4-yl)quinolin-2-yl]-2,3,4,5-tetrahydro-1,4-benzothiazepine 1,1-dioxide

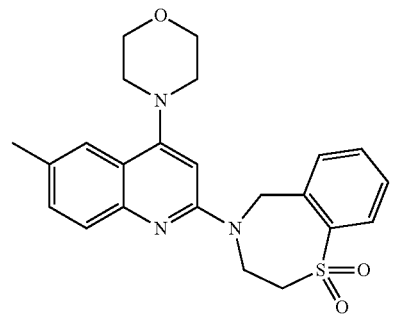 [SMILES: Cc1ccc2nc(N3CCS(=O)(=O)c4ccccc4C3)cc(N3CCOCC3)c2c1]

The title compound was prepared in analogy to Example 9-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and morpholine. MS obsd. (ESI⁺) [(M+H)⁺] 424, ¹H NMR (400 MHz, CDCl₃) δ ppm 8.06 (d, J=8.0 Hz, 1 H), 7.62-7.53 (m, 4 H), 7.40 (t, J=7.6 Hz, 1 H), 7.32 (d, J=7.6 Hz, 1 H), 6.42 (s, 1 H), 5.51 (s, 2 H), 4.60 (brs, 2 H), 4.00 (t, J=4.4 Hz, 4 H), 3.59 (s, 2 H), 3.10 (m, 4 H), 2.44 (s, 3 H).

Example 9-5

3-{[2-(1,1-Dioxido-2,3-dihydro-1,4-benzothiazepin-4(5H)-yl)-6-methylquinolin-4-yl]amino}propan-1-ol

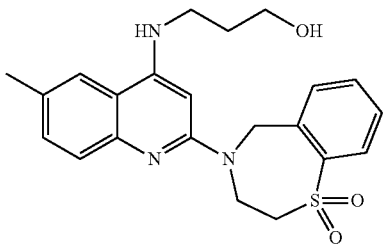 [SMILES: Cc1ccc2nc(N3CCS(=O)(=O)c4ccccc4C3)cc(NCCCO)c2c1]

The title compound was prepared in analogy to Example 9-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 3-propan-1-ol. MS obsd. (ESI⁺) [(M+H)⁺] 412, ¹H NMR (400 MHz, CDCl₃) δ ppm 8.02 (d, J=7.2 Hz, 1 H), 7.71 (m, 1 H), 7.53-7.49 (m, 2 H), 7.38 (t, J=7.2 Hz, 1 H), 7.26 (m, 2 H), 5.31 (s, 1 H), 5.13 (s, 2 H), 4.60 (brs, 2 H), 3.92 (t, J=4.2 Hz, 2 H), 3.52 (s, 2 H), 3.44 (m, 2 H), 2.40 (s, 3 H), 2.00 (m, 2 H).

Example 9-6

2-(1,1-Dioxido-2,3-dihydro-1,4-benzothiazepin-4(5H)-yl)-6-methyl-N-[2-(piperidin-1-yl)ethyl]quinolin-4-amine

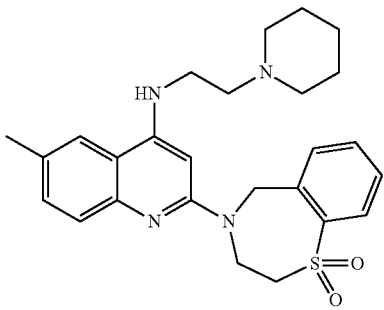 [SMILES: Cc1ccc2nc(N3CCS(=O)(=O)c4ccccc4C3)cc(NCCN3CCCCC3)c2c1]

The title compound was prepared in analogy to Example 9-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 2-(piperidin-1-yl)ethanamine. MS obsd. (ESI⁺) [(M+H)⁺] 465, ¹H NMR (400 MHz, CDCl₃) δ ppm 8.04 (d, J=7.6 Hz, 1 H), 7.67 (d, J=7.6 Hz, 1 H), 7.51 (m, 2 H), 7.38 (t, J=7.6 Hz, 1 H), 7.30 (m, 2 H), 5.74 (m, 1 H), 5.12 (s, 2 H), 4.6 (brs, 2 H), 3.58 (s, 2 H), 3.28 (m, 2 H), 2.75 (t, J=8.4 Hz, 2 H), 2.46 (m, 7 H), 1.62 (m, 4 H), 1.52 (m, 2 H).

Example 9-7

1-Amino-3-{[2-(1,1-dioxido-2,3-dihydro-1,4-benzothiazepin-4(5H)-yl)-6-methylquinolin-4-yl]amino}propan-2-ol

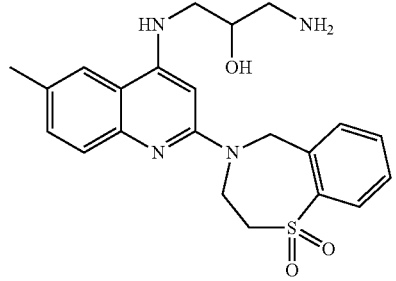 [SMILES: Cc1ccc2nc(N3CCS(=O)(=O)c4ccccc4C3)cc(NCC(O)CN)c2c1]

The title compound was prepared in analogy to Example 9-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 1,3-diaminopropan-2-ol. MS obsd. (ESI⁺) [(M+H)⁺] 427, ¹H NMR (400 MHz, CD₃OD) δ ppm 7.97 (d, J=2.0 Hz, 1 H), 7.86 (d, J=1.8 Hz, 1 H), 7.62 (t, J=3.7 Hz, 1 H), 7.57 (s, 1 H), 7.44 (t, J=3.8 Hz, 2 H), 7.30-7.27 (m, J=2.5 Hz, 1 H), 6.09 (s, 1 H), 5.15 (s, 2 H), 4.53 (brs, 2 H), 3.97-3.91 (m, J=5.8 Hz, 2 H), 3.58 (t, J=2.4 Hz, 2 H), 3.66-3.41 (m, J=3.3 Hz, 2 H), 2.90 (dd, J=4.2, 0.90 Hz, 1 H), 2.77 (dd, J=5.2, 0.9 Hz, 1 H), 2.42 (s, 3 H).

Example 9-8

N-[2-(1,1-Dioxido-2,3-dihydro-1,4-benzothiazepin-4(5H)-yl)-6-methylquinolin-4-yl]glycine

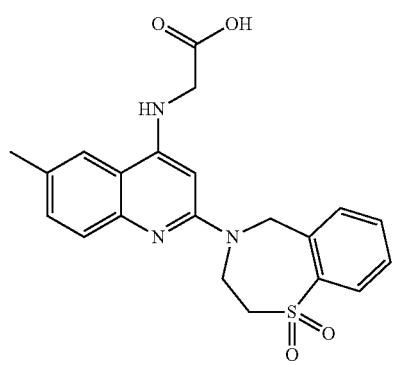 [SMILES: Cc1ccc2nc(N3CCS(=O)(=O)c4ccccc4C3)cc(NCC(=O)O)c2c1]

The title compound was prepared in analogy to Example 9-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and glycine. MS obsd. (ESI⁺) [(M+H)⁺] 412, ¹H NMR (400 MHz, CD₃OD) δ ppm 8.01 (d, J=1.8 Hz, 1 H), 7.89 (d, J=1.9 Hz, 1 H), 7.68 (t, J=2.9 Hz, 2 H), 7.54 (d, J=2.1 Hz, 1 H), 7.48 (t, J=2.2 Hz, 1 H), 7.40 (d, J=0.9 Hz, 1 H), 5.73 (s, 1 H), 5.09 (s, 2 H), 4.36 (brs, 2 H), 3.3 (s, 2 H), 3.58 (s, 2 H), 2.41 (s, 3 H).

Example 9-9

N-[2-(1,1-Dioxido-2,3-dihydro-1,4-benzothiazepin-4 (5H)-yl)-6-fluoro quinolin-4-yl]ethane-1,2-diamine

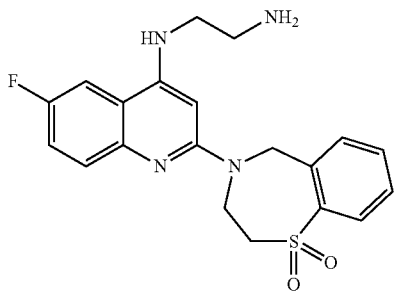 [SMILES: NCCNc1cc(N2CCS(=O)(=O)c3ccccc3C2)nc2ccc(F)cc12]

The title compound was prepared in analogy to Example 9-1 in Scheme 5 by using 4-(4-chloro-6-fluoroquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4-dichloro-6-fluoroquinoline and 2,3,4,5-tetrahydro-1,4-benzothiazepine) and ethane-1,2-diamine. MS obsd. (ESI⁺) [(M+H)⁺] 401, ¹H NMR (400 MHz, CD₃OD) δ ppm 7.98 (d, J=7.6 Hz, 1 H), 7.84 (d, J=7.6 Hz, 1 H), 7.64 (t, J=7.6 Hz, 1 H), 7.58 (dd, J=2.8, 10.8 Hz, 1 H), 7.52 (dd, J=6.4, 8.8 Hz, 1 H), 7.45 (t, J=8.0 Hz, 1 H), 7.22 (td, J=2.8, 8.8 Hz, 1 H), 6.09 (s, 1 H), 5.16 (s, 2 H), 4.55 (brs, 2 H), 3.63-3.57 (m, 2 H), 3.43 (t, J=6.4 Hz, 2 H), 2.97 (t, J=6.4 Hz, 2 H).

Example 9-10

N-[2-(1,1-Dioxido-2,3-dihydro-1,4-benzothiazepin-4 (5H)-yl)-6-ethylquinolin-4-yl]ethane-1,2-diamine

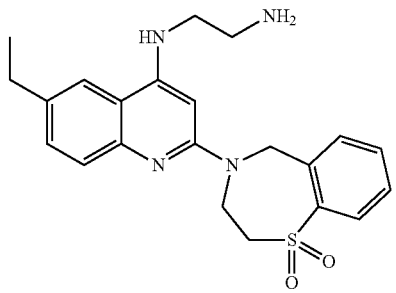 [SMILES: CCc1ccc2nc(N3CCS(=O)(=O)c4ccccc4C3)cc(NCCN)c2c1]

The title compound was prepared in analogy to Example 9-1 in Scheme 5 by using 4-(4-chloro-6-ethylquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 4-chloro-6-ethylquinoline and 2,3,4,5-tetrahydro-1,4-benzothiazepine) and ethane-1,2-diamine. MS obsd. (ESI⁺) [(M+H)⁺] 411, ¹H NMR (400 MHz, CD₃OD) δ ppm 7.98 (d, J=7.6 Hz, 1 H), 7.84 (d, J=7.6 Hz, 1 H), 7.62 (m, 2 H), 7.44 (t, J=8.4 Hz, 2 H), 7.32 (dd, J=1.6, 8.4 Hz, 1 H), 6.03 (s, 1 H), 5.14 (s, 2 H), 4.53 (brs, 2 H), 3.58 (s, 2 H), 3.44 (t, J=6.0 Hz, 2 H), 2.97 (t, J=6.4 Hz, 2 H), 2.72 (q, J=7.6 Hz, 2 H), 1.27 (t, J=7.6 Hz, 3 H).

Example 9-11

N-[7-Chloro-2-(1,1-dioxido-2,3-dihydro-1,4-benzothiazepin-4(5H)-yl)quinolin-4-yl]propane-1,3-diamine

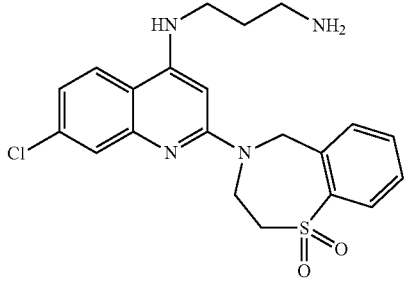 [SMILES: NCCCNc1cc(N2CCS(=O)(=O)c3ccccc3C2)nc2cc(Cl)ccc12]

The title compound was prepared in analogy to Example 9-1 in Scheme 5 by using 4-(4,7-dichloroquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4,7-trichloroquinoline and 2,3,4,5-tetrahydro-1,4-benzothiazepine) and propane-1,3-diamine. MS obsd. (ESI⁺) [(M+H)⁺] 431, ¹H NMR (400 MHz, CD₃OD) δ ppm 8.10-8.05 (m, 2 H), 7.91-7.82 (m, 2 H), 7.80-7.69 (m, 1 H), 7.61-7.50 (m, 1 H), 7.43-7.41 (d, J=7.6 Hz, 1 H), 5.95 (s, 1 H), 5.30 (s, 2 H), 4.5 (s, 2 H), 3.72 (s, 2 H), 3.59-3.56 (t, J=6.4 Hz, 2 H), 3.10-3.06 (t, J=7.6 Hz, 2 H), 2.70-2.10 (t, J=7.2 Hz, 2 H).

Example 9-12

N-[8-Chloro-2-(1,1-dioxido-2,3-dihydro-1,4-benzothiazepin-4(5H)-yl)quinolin-4-yl]propane-1,3-diamine

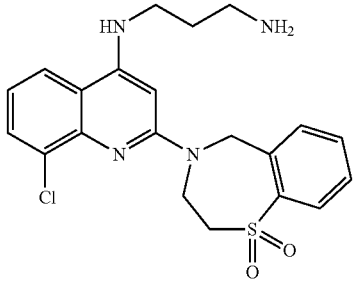 [SMILES: NCCCNc1cc(N2CCS(=O)(=O)c3ccccc3C2)nc2c(Cl)cccc12]

The title compound was prepared in analogy to Example 9-1 in Scheme 5 by using 4-(4,8-dichloroquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4,8-trichloroquinoline and 2,3,4,5-tetrahydro-1,4-benzothiazepine) and propane-1,3-diamine. MS obsd. (ESI⁺) [(M+H)⁺] 431, ¹H NMR (400 MHz, CD₃OD) δ ppm 8.08-8.05 (m, 2 H), 7.94-7.92 (d, J=7.6 Hz, 1 H), 7.85-7.83 (d, J=7.6 Hz, 1 H), 7.71-7.70 (m, 1 H), 7.57-7.56 (m, 1 H), 7.41-7.38 (m, 1 H), 6.00 (s, 1 H), 5.39 (s, 2 H), 4.55 (s, 2 H), 3.74 (s, 2 H), 3.60-3.56 (t, J=6.8 Hz, 2 H), 3.09-3.05 (t, J=7.6 Hz, 2 H), 2.11-2.07 (m, 2 H).

Example 9-13

N-[5-Chloro-2-(1,1-dioxido-2,3-dihydro-1,4-benzothiazepin-4(5H)-yl)quinolin-4-yl]propane-1,3-diamine

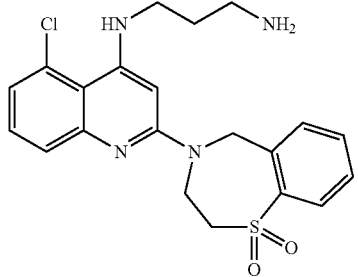 [SMILES: NCCCNc1cc(N2CCS(=O)(=O)c3ccccc3C2)nc2cccc(Cl)c12]

The title compound was prepared in analogy to Example 9-1 in Scheme 5 by using 4-(4,5-dichloroquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4,5-trichloroquinoline and 2,3,4,5-tetrahydro-1,4-benzothiazepine) and propane-1,3-diamine. MS obsd. (ESI$^+$) [(M+H)$^+$] 431, $^1$H NMR (400 MHz, CD$_3$OD) δ ppm 8.08-8.06 (d, J=7.6 Hz, 1 H), 7.94-7.92 (m, 2 H), 7.41-7.26 (m, 5 H), 5.99 (s, 1 H), 5.35 (s, 2 H), 4.55 (s, 2 H), 3.74 (s, 2 H), 3.63-3.61 (m, 2 H), 3.15-3.11 (t, J=7.6 Hz, 2 H), 2.16-2.13 (m, 2 H).

Example 9-14

N-[2-(1,1-Dioxido-2,3-dihydro-1,4-benzothiazepin-4(5H)-yl)-6-methylquinolin-4-yl]-2,2-dimethylpropane-1,3-diamine

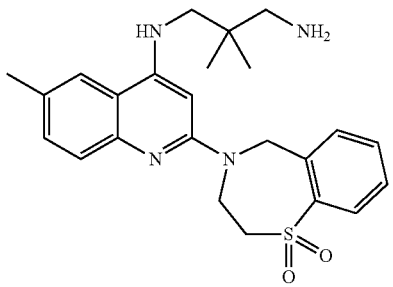 [SMILES: Cc1ccc2nc(N3CCS(=O)(=O)c4ccccc4C3)cc(NCC(C)(C)CN)c2c1]

The title compound was prepared in analogy to Example 9-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 2,2-dimethylpropane-1,3-diamine. MS obsd. (ESI$^+$) [(M+H)$^+$] 439, $^1$H NMR (400 MHz, CD$_3$OD) δ ppm 8.07 (d, J=1.2 Hz, 1 H), 7.99 (s, 1 H), 7.88 (d, J=7.2 Hz, 1 H), 7.73-7.70 (m, 2 H), 7.61-7.57 (m, 2 H), 6.07 (s, 1 H), 5.31 (s, 2 H), 4.50 (s, 2 H), 3.73 (s, 2 H), 3.49 (s, 2 H), 2.99 (s, 2 H), 2.47 (s, 3 H), 1.10 (s, 6 H).

Example 9-15

N-[2-(1,1-Dioxido-2,3-dihydro-1,4-benzothiazepin-4(5H)-yl)quinolin-4-yl]ethane-1,2-diamine

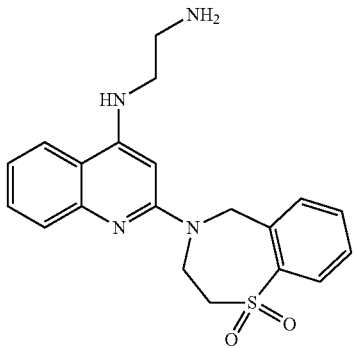 [SMILES: NCCNc1cc(N2CCS(=O)(=O)c3ccccc3C2)nc2ccccc12]

The title compound was prepared in analogy to Example 9-1 in Scheme 5 by using 4-(4-chloroquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4-dichloroquinoline and 2,3,4,5-tetrahydro-1,4-benzothiazepine) and ethane-1,2-diamine. MS obsd. (ESI$^+$) [(M+H)$^+$] 383, $^1$H NMR (400 MHz, CD$_3$OD) δ ppm 7.87 (m, 1 H), 7.81 (d, J=7.83 Hz, 2 H), 7.55 (m, 1 H), 7.47 (m, 1 H), 7.33 (m, 2 H), 7.04 (m, 1 H), 5.94 (m, 1 H), 5.12 (s, 2 H), 3.57 (t, J=4.55 Hz, 2 H), 3.43 (t, J=6.32 Hz, 2 H), 3.33 (m, 2 H), 2.97 (t, J=6.44 Hz, 2 H).

Example 9-16

N-[2-(1,1-Dioxido-2,3-dihydro-1,4-benzothiazepin-4(5H)-yl)-6-methylquinolin-4-yl]ethane-1,2-diamine

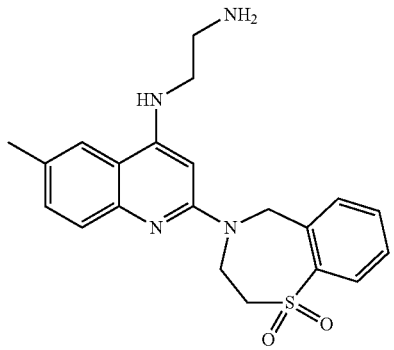 [SMILES: Cc1ccc2nc(N3CCS(=O)(=O)c4ccccc4C3)cc(NCCN)c2c1]

The title compound was prepared in analogy to Example 9-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and ethane-1,2-diamine. MS obsd. (ESI$^+$) [(M+H)$^+$] 397, $^1$H NMR (400 MHz, CD$_3$OD) δ ppm 7.86 (m, 2 H), 7.65-7.50 (m, 2 H), 7.42-7.30 (m, 2 H), 7.28-7.16 (m, 1 H), 6.10-5.95 (m, 1 H), 5.09 (brs, 2 H), 3.64-3.42 (m, 2 H), 3.15-2.98 (m, 2 H), 2.84 (s, 2 H), 2.35 (s, 3 H), 1.20 (s, 2 H).

Example 9-17

N~2~-[2-(1,1-Dioxido-2,3-dihydro-1,4-benzothiazepin-4(5H)-yl)-6-methylquinolin-4-yl]-2-methylpropane-1,2-diamine

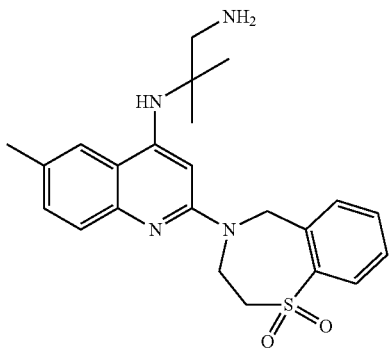 [SMILES: Cc1ccc2nc(N3CCS(=O)(=O)c4ccccc4C3)cc(NC(C)(C)CN)c2c1]

The title compound was prepared in analogy to Example 9-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 2-methylpropane-1,2-diamine. MS obsd. (ESI$^+$) [(M+H)$^+$] 425, $^1$H NMR (400 MHz, CD$_3$OD) δ ppm 7.98 (dd, J=7.83, 1.26 Hz, 1 H), 7.86 (d, J=6.82 Hz, 1 H), 7.70 (s, 1 H), 7.61 (td, J=7.45, 1.26 Hz, 1 H), 7.47-7.42 (m, 2 H), 7.29 (dd, J=8.59, 1.77 Hz, 1 H), 6.09 (s, 1 H), 5.16 (s, 2 H), 3.58 (t, J=4.80 Hz, 2 H), 3.33 (m, 2 H), 3.27 (s, 2 H), 2.43 (s, 3 H), 1.27 (s, 6 H).

Example 9-18

N~2~-[2-(1,1-Dioxido-2,3-dihydro-1,4-benzothiazepin-4(5H)-yl)-6-methylquinolin-4-yl]propane-1,2-diamine

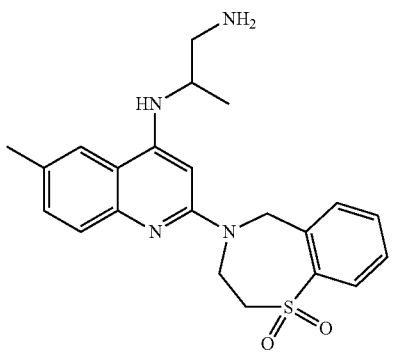 [SMILES: Cc1ccc2nc(N3CCS(=O)(=O)c4ccccc4C3)cc(NC(C)CN)c2c1]

The title compound was prepared in analogy to Example 9-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and propane-1,2-diamine. MS obsd. (ESI$^+$) [(M+H)$^+$] 411, $^1$H NMR (400 MHz, CD$_3$OD) δ ppm 7.97 (dd, J=7.83, 1.01 Hz, 1 H), 7.82 (d, J=7.33 Hz, 1 H), 7.69-7.56 (m, 2 H), 7.46-7.38 (m, 2 H), 7.28 (dd, J=8.46, 1.64 Hz, 1 H), 6.11-5.96 (m, 1 H), 5.13 (s, 2 H), 3.66-3.49 (m, 2 H), 3.30-3.20 (m, 3 H), 2.47-2.39 (m, 3 H), 2.24-2.19 (m, 2 H), 1.32-1.22 (m, 3 H).

Example 9-19

N-[2-(1,1-Dioxido-2,3-dihydro-1,4-benzothiazepin-4(5 H)-yl)-6-methylquinolin-4-yl]butane-1,4-diamine

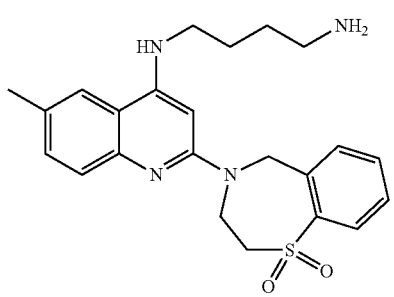 [SMILES: Cc1ccc2nc(N3CCS(=O)(=O)c4ccccc4C3)cc(NCCCCN)c2c1]

The title compound was prepared in analogy to Example 9-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and butane-1,4-diamine. MS obsd. (ESI$^+$) [(M+H)$^+$] 425, $^1$H NMR (400 MHz, CD$_3$OD) δ ppm 8.01-7.95 (m, 1 H), 7.92-7.86 (m, 1 H), 7.83-7.76 (m, 1 H), 7.69-7.61 (m, 1 H), 7.61-7.54 (m, 1 H), 7.50-7.42 (m, 1 H), 7.39-7.31 (m, 1 H), 5.96 (s, 1 H), 5.20 (brs, 2 H), 3.63 (brs, 2 H), 3.47 (brs, 2 H), 3.37 (s, 2 H), 2.42 (s, 3 H), 2.27-2.24 (m, 4 H), 1.86 (d, J=3.28 Hz, 2 H).

Example 9-20

N-[2-(1,1-Dioxido-2,3-dihydro-1,4-benzothiazepin-4(5H)-yl)-6-nitro quinolin-4-yl]ethane-1,2-diamine

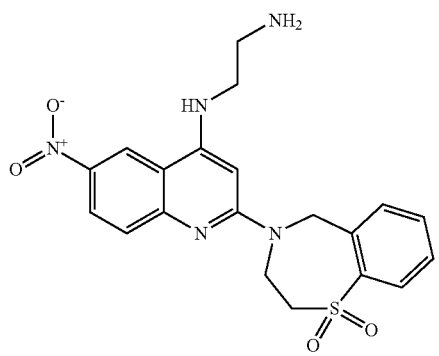 [SMILES: NCCNc1cc(N2CCS(=O)(=O)c3ccccc3C2)nc2ccc([N+](=O)[O-])cc12]

The title compound was prepared in analogy to Example 9-1 in Scheme 5 by using 4-(4-chloro-6-nitroquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4-dichloro-6-nitroquinoline and 2,3,4,5-tetrahydro-1,4-benzothiazepine) and ethane-1,2-diamine. MS obsd. (ESI$^+$) [(M+H)$^+$] 428, $^1$H NMR (400 MHz, CD$_3$OD) δ ppm 9.07 (d, J=2.53 Hz, 1 H), 8.13 (dd, J=9.35, 2.53 Hz, 1 H), 7.96 (d, J=7.58 Hz, 1 H), 7.91 (dd, J=7.71, 1.14 Hz, 1 H), 7.69

(t, J=7.20 Hz, 1H), 7.56-7.41 (m, 2 H), 6.09 (s, 1 H), 5.15 (brs, 2 H), 3.64 (brs, 2 H), 3.34 (brs, 4 H), 2.79 (t, J=6.44 Hz, 2 H).

Example 9-21

N-[2-(1,1-Dioxido-2,3-dihydro-1,4-benzothiazepin-4(5H)-yl)-5-fluoro-6-methylquinolin-4-yl]ethane-1,2-diamine

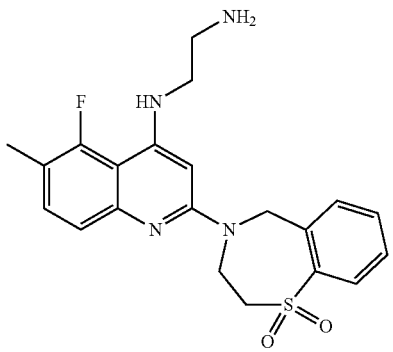 [SMILES: Cc1ccc2nc(N3CCS(=O)(=O)c4ccccc4C3)cc(NCCN)c2c1F]

The title compound was prepared in analogy to Example 9-1 in Scheme 5 by using 4-(4-chloro-5-fluoro-6-methylquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4-dichloro-5-fluoro-6-methylquinoline and 2,3,4,5-tetrahydro-1,4-benzothiazepine) and ethane-1,2-diamine. MS obsd. (ESI$^+$) [(M+H)$^+$] 415, $^1$H NMR (400 MHz, CD$_3$OD) δ ppm 7.98-7.83 (m, 2 H), 7.71-7.60 (m, 1 H), 7.53-7.43 (m, 1 H), 7.32-7.22 (m, 1 H), 7.21-7.11 (m, 1 H), 6.80-6.66 (m, 1 H), 6.01 (s, 1 H), 5.08 (brs, 2 H), 3.61 (t, J=4.67 Hz, 2 H), 3.31-3.26 (m, 3 H), 2.87 (t, J=6.19 Hz, 2 H), 2.22 (d, J=2.53 Hz, 3 H).

Example 9-22

2-{[2-(1,1-Dioxido-2,3-dihydro-1,4-benzothiazepin-4(5H)-yl)-5-fluoro-6-methylquinolin-4-yl]amino}ethanol

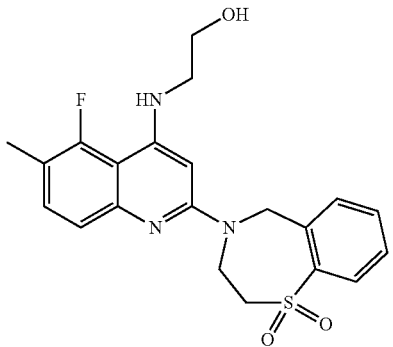 [SMILES: Cc1ccc2nc(N3CCS(=O)(=O)c4ccccc4C3)cc(NCCO)c2c1F]

The title compound was prepared in analogy to Example 9-1 in Scheme 5 by using 4-(4-chloro-5-fluoro-6-methylquinolin-2-yl)-2,3,4,5-tetrahydro-1,4-benzothiazepine 1,1-dioxide (prepared in analogy to the one in Example 9-21) and aminoethanol. MS obsd. (ESI$^+$) [(M+H)$^+$] 416, $^1$H NMR (400 MHz, DMSO-d6) δ ppm 7.94-7.84 (m, 2 H), 7.66 (td, J=7.45, 1.26 Hz, 1 H), 7.49 (td, J=7.71, 1.26 Hz, 1 H), 7.32-7.21 (m, 1 H), 7.21-7.11 (m, 1 H), 6.48 (dt, J=16.93, 4.67 Hz, 1 H), 6.04 (s, 1 H), 5.08 (brs, 2 H), 4.98 (t, J=5.18 Hz, 1 H), 3.67 (q, J=5.31 Hz, 2 H), 3.61 (t, J=4.80 Hz, 2 H), 3.43 (m, 2 H), 2.22 (d, J=2.53 Hz, 3 H).

Example 9-23

2-{[2-(1,1-Dioxido-2,3-dihydro-1,4-benzothiazepin-4(5H)-yl)-7-fluoro-6-methylquinolin-4-yl]amino}ethanol

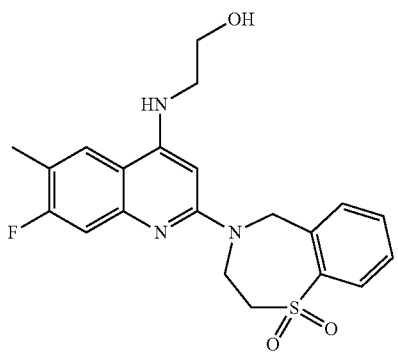 [SMILES: Cc1cc2c(NCCO)cc(N3CCS(=O)(=O)c4ccccc4C3)nc2cc1F]

The title compound was prepared in analogy to Example 9-1 in Scheme 5 by using 4-(4-chloro-7-fluoro-6-methylquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4-dichloro-7-fluoro-6-methylquinoline and 2,3,4,5-tetrahydro-1,4-benzothiazepine) and aminoethanol. MS obsd. (ESI$^+$) [(M+H)$^+$] 416, $^1$H NMR (400 MHz, DMSO-d6) δ ppm 7.93-7.87 (m, 2 H), 7.84 (d, J=8.84 Hz, 1 H), 7.65 (td, J=7.52, 1.14 Hz, 1 H), 7.53-7.43 (m, 1 H), 7.05 (d, J=11.87 Hz, 1 H), 6.71 (t, J=5.56 Hz, 1 H), 6.00 (s, 1 H), 5.07 (brs, 2 H), 4.83 (t, J=5.56 Hz, 1 H), 3.67-3.55 (m, 4 H), 3.42-3.36 (m, 2 H), 2.27 (s, 3 H).

Example 9-24

N-[2-(1,1-Dioxido-2,3-dihydro-1,4-benzothiazepin-4(5H)-yl)-7-fluoro-6-methylquinolin-4-yl]ethane-1,2-diamine

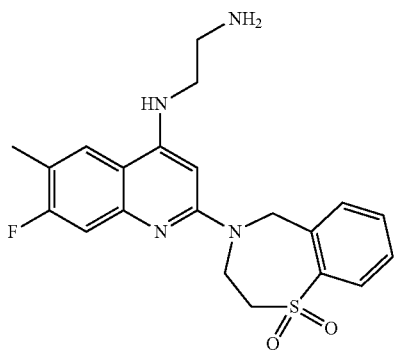 [SMILES: Cc1cc2c(NCCN)cc(N3CCS(=O)(=O)c4ccccc4C3)nc2cc1F]

The title compound was prepared in analogy to Example 9-1 in Scheme 5 by using 4-(4-chloro-7-fluoro-6-methylquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4-dichloro-7-fluoro-6-methylquinoline and 2,3,4,5-tetrahydro-1,4-benzothiazepine) and ethane-1,2-diamine. MS obsd. (ESI⁺) [(M+H)⁺] 415, ¹H NMR (400 MHz, DMSO-d6) δ ppm 7.93 (d, J=6.82 Hz, 1 H), 7.91-7.87 (m, 1 H), 7.82 (d, J=8.84 Hz, 1 H), 7.66 (td, J=7.52, 1.39 Hz, 1 H), 7.48 (td, J=7.71, 1.01 Hz, 1 H), 7.09-7.03 (m, 1 H), 5.99 (s, 1 H), 5.09 (brs, 2 H), 3.61 (m, 2 H), 3.45-3.31 (m, 4 H), 2.90 (t, J=6.32 Hz, 2 H), 2.27 (s, 3 H).

Example 9-25

N-[2-(1,1-Dioxido-2,3-dihydro-1,4-benzothiazepin-4 (5H)-yl)-7,8-difluoro-6-methylquinolin-4-yl]ethane-1,2-diamine

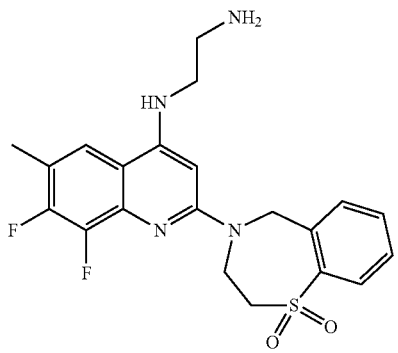

The title compound was prepared in analogy to Example 9-1 in Scheme 5 by using 4-(4-chloro-7,8-difluoro-6-methylquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4-dichloro-7,8-difluoro-6-methylquinoline and 2,3,4,5-tetrahydro-1,4-benzothiazepine) and ethane-1,2-diamine. MS obsd. (ESI⁺) [(M+H)⁺] 433, ¹H NMR (400 MHz, DMSO-d6) δ ppm 8.25 (m, 1 H), 8.08 (m, 1 H), 7.84 (m, 1 H), 7.76 (m, 1 H), 7.53 (m, 1 H), 5.99 (s, 1 H), 5.06 (brs, 2 H), 3.70 (m, 2 H), 3.49-3.30 (m, 4 H), 3.01 (m, 2 H), 2.92 (s, 3 H).

Example 9-26

2-(1,1-Dioxido-2,3-dihydro-1,4-benzothiazepin-4 (5H)-yl)-N-(2-methoxyethyl)-6-methylquinolin-4-amine

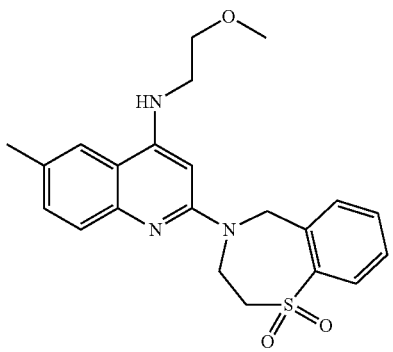 [SMILES: COCCNc1cc(N2CCS(=O)(=O)c3ccccc3C2)nc2ccc(C)cc12]

The title compound was prepared in analogy to Example 9-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 2-methoxyethaneamine. MS obsd. (ESI⁺) [(M+H)⁺] 412, ¹H NMR (400 MHz, CD₃OD) δ ppm 8.12-8.08 (d, J=7.6 Hz, 1 H), 7.90 (s, 1 H), 7.35-7.30 (d, J=7.6 Hz, 1 H), 7.26-7.13 (m, 2 H), 7.11-7.05 (m, 2 H), 6.06 (s, 1 H), 5.27 (s, 2 H), 4.50 (s, 2 H), 4.78-4.62 (m, 6 H), 3.35 (s, 3 H), 2.45 (s, 3 H).

Example 9-27

1-[2-(1,1-Dioxido-2,3-dihydro-1,4-benzothiazepin-4 (5H)-yl)-6-methylquinolin-4-yl]piperidin-4-amine

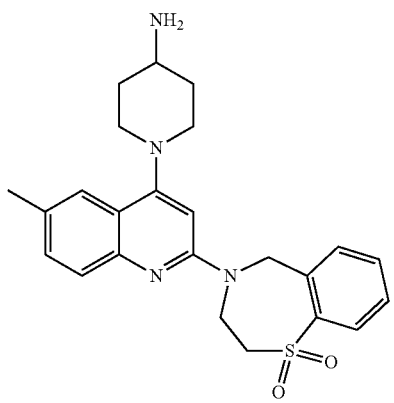 [SMILES: Cc1ccc2nc(N3CCS(=O)(=O)c4ccccc4C3)cc(N3CCC(N)CC3)c2c1]

The title compound was prepared in analogy to Example 9-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and piperidin-4-amine. MS obsd. (ESI⁺) [(M+H)⁺] 437, ¹H NMR (400 MHz, CD₃OD) δ ppm 8.10-8.08 (m, 1 H), 7.84-7.71 (m, 3 H), 7.62-7.59 (m, 3 H), 6.50 (s, 1 H), 5.34 (s, 2 H), 4.57-4.55 (m, 2 H), 3.96-3.86 (m, 2 H), 3.78-3.76 (m, 2 H), 3.48-3.45 (m, 1 H), 3.13-3.08 (m, 2 H), 2.48 (s, 3 H), 2.27-2.23 (m, 2 H), 2.02-1.92 (m, 2 H).

Example 9-28

1-[2-(1,1-Dioxido-2,3-dihydro-1,4-benzothiazepin-4 (5H)-yl)-1,6-naphthyridin-4-yl]pyrrolidin-3-amine

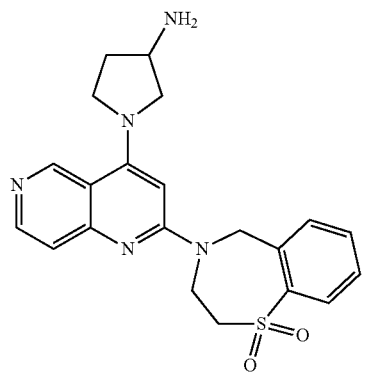 [SMILES: NC1CCN(c2cc(N3CCS(=O)(=O)c4ccccc4C3)nc3ccncc23)C1]

The title compound was prepared in analogy to Example 9-1 in Scheme 5 by using 4-(4-chloro-1,6-naphthyridin-2-yl)-2,3,4,5-tetrahydro-1,4-benzothiazepine 1,1-dioxide (prepared in analogy to 4-(4-chloro-6-methylquinolin-2-yl)-2,3, 4,5-tetrahydro-1,4-benzothiazepine 1,1-dioxide in Example 2-1 by using 2,3,4,5-tetrahydro-1,4-benzothiazepine and 2,4-dichloro-1,6-naphthyridine) and pyrrolidin-3-amine. MS obsd. (ESI⁺) [(M+H)⁺] 410, ¹H NMR (400 MHz, CD₃OD) δ ppm 9.26 (s, 1 H), 8.28-8.20 (d, J=6.4 Hz, 1 H), 8.05-7.98 (d, J=8 Hz, 1 H), 7.90-7.82 (d, J=7.2 Hz, 1 H), 7.70-7.60 (m, 2 H), 7.50-7.42 (t, J=7.2 Hz, 1 H), 6.14 (s, 1 H), 5.26 (s, 2 H), 4.70-4.50 (m, 2 H), 4.20-4.10 (m, 2 H), 4.10-4.00 (m, 1 H), 3.90-3.78 (m, 2 H), 3.60-3.52 (t, J=2.8 Hz, 2 H), 2.60-2.48 (m, 1 H), 2.35-2.25 (m, 1 H).

Example 9-29

N-[6-(Difluoromethyl)-2-(1,1-dioxido-2,3-dihydro-1,4-benzothiazepin-4(5H)-yl)quinolin-4-yl]propane-1,3-diamine

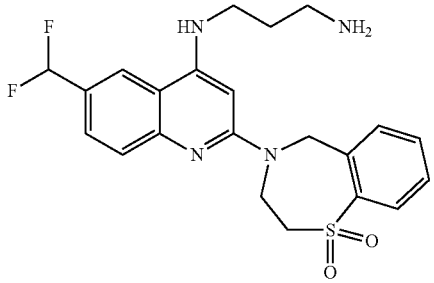 [SMILES: NCCCNc1cc(N2CCS(=O)(=O)c3ccccc3C2)nc2ccc(C(F)F)cc12]

The title compound was prepared in analogy to Example 9-1 in Scheme 5 by using 4-(4-chloro-6-difluoromethylquinolin-2-yl)-2,3,4,5-tetrahydro-1,4-benzothiazepine 1,1-dioxide
(prepared in analogy to 4-(4-chloro-6-methylquinolin-2-yl)-2,3,4,5-tetrahydro-1,4-benzothiazepine 1,1-dioxide in Example 2-1 by using 2,4-dichloro-6-difluoromethylquinoline and 2,3,4,5-tetrahydro-1,4-benzothiazepine) and propane-1,3-diamine. MS obsd. (ESI⁺) [(M+H)⁺] 447, ¹H NMR (400 MHz, CD₃OD) δ ppm 8.39 (s, 1 H), 8.12-8.08 (d, J=7.6 Hz, 1 H), 7.95-7.85 (m, 3 H), 7.78-7.70 (t, J=1.2 Hz, 1 H), 7.65-7.58 (t, J=6.8 Hz, 1 H), 7.03-6.72 (t, J=54.4 Hz, 1 H), 6.03 (s, 1 H), 5.35 (s, 2 H), 4.60-4.49 (m, 2 H), 3.80-3.72 (t, J=2.8 Hz, 2 H), 3.68-3.60 (t, J=6.8 Hz, 2 H), 3.15-3.09 (t, J=7.6 Hz, 2 H), 2.16-2.05 (m, 2 H).

Example 9-30

6-Chloro-2-(1,1-dioxido-2,3-dihydro-1,4-benzothiazepin-4(5H)-yl)-N-ethylquinolin-4-amine

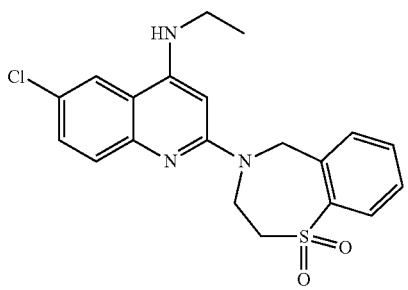 [SMILES: CCNc1cc(N2CCS(=O)(=O)c3ccccc3C2)nc2ccc(Cl)cc12]

The title compound was prepared in analogy to Example 9-1 in Scheme 5 by using 4-(4,6-dichloroquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4,6-trichloroquinoline and 2,3,4,5-tetrahydro-1,4-benzothiazepine) and ethaneamine. MS obsd. (ESI⁺) [(M+H)⁺] 402, ¹H NMR (400 MHz, DMSO-d6) δ ppm 8.07 (s, 1 H), 7.90 (t, J=4.2 Hz, 2 H), 7.65 (t, J=3.5 Hz, 1 H), 7.48 (t, J=3.7 Hz, 1 H), 7.38 (t, J=3.8 Hz, 2 H), 6.03 (s, 1 H), 5.09 (s, 2 H), 4.42 (brs, 2 H), 3.62 (t, J=2.4 Hz, 2 H), 3.3 (m, 2 H), 1.24 (t, 3 H).

Example 9-31

2-{[6-Chloro-2-(1,1-dioxido-2,3-dihydro-1,4-benzothiazepin-4(5H)-yl)quinolin-4-yl]amino}ethanol

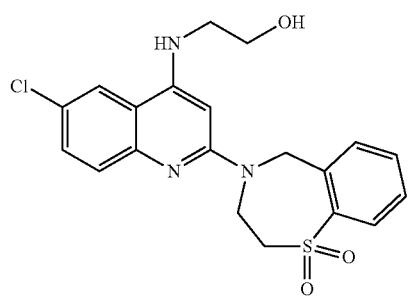 [SMILES: O=S1(=O)CCN(c2cc(NCCO)c3cc(Cl)ccc3n2)Cc2ccccc21]

The title compound was prepared in analogy to Example 9-1 in Scheme 5 by using 4-(4,6-dichloroquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4,6-trichloroquinoline and 2,3,4,5-tetrahydro-1,4-benzothiazepine) and aminoethanol. MS obsd. (ESI⁺) [(M+H)⁺] 418, ¹H NMR (400 MHz, DMSO-d6) δ ppm 8.06 (s, 1 H), 7.90 (t, J=3.9 Hz, 2 H), 7.65 (t, J=3.7 Hz, 1 H), 7.49 (t, J=3.8 Hz, 1 H), 7.39 (t, J=3.6 Hz, 2 H), 6.83 (t, J=4.6 Hz, 1 H), 6.08 (s, 1 H), 5.08 (s, 2 H), 4.81 (t, J=2.8 Hz, 1 H), 4.43 (brs, 2 H), 3.63 (m, 4 H), 3.85 (m, 2 H).

Example 9-32

N-[6-Chloro-2-(1,1-dioxido-2,3-dihydro-1,4-benzothiazepin-4(5H)-yl)quinolin-4-yl]-N'-methylethane-1,2-diamine

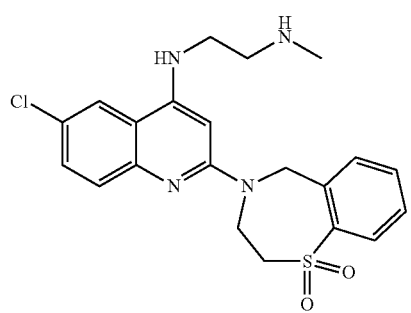 [SMILES: CNCCNc1cc(N2CCS(=O)(=O)c3ccccc3C2)nc2ccc(Cl)cc12]

The title compound was prepared in analogy to Example 9-1 in Scheme 5 by using 4-(4,6-dichloroquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4,6-trichloroquinoline and 2,3,4,5-tetrahydro-1,4-benzothiazepine) and N-methylethane-1,2-diamine. MS obsd. (ESI+) [(M+H)+] 431, ¹H NMR (400 MHz, CD₃OD) δ ppm 7.98 (d, J=2.0 Hz, 1 H), 7.90 (s, 1 H), 7.84 (d, J=1.8 Hz, 1 H), 7.63 (t, J=3.7 Hz, 1 H), 7.46 (t, J=4.1 Hz, 2 H), 7.36 (m, J=2.8 Hz, 1 H), 6.08 (s, 1 H), 5.17 (s, 2 H), 4.55 (brs, 2 H), 3.58 (t, J=2.3 Hz, 2 H), 3.50 (t, J=3.1 Hz, 2 H), 2.96 (t, J=3.1 Hz, 2 H), 2.51 (s, 3 H).

Example 9-33

N-[2-(1,1-Dioxido-2,3-dihydro-1,4-benzothiazepin-4(5H)-yl)-6-(methylsulfanyl)quinolin-4-yl]propane-1,3-diamine

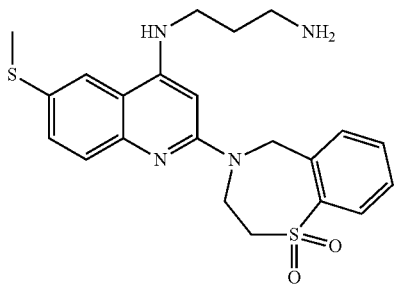 [SMILES: CSc1ccc2nc(N3CCS(=O)(=O)c4ccccc4C3)cc(NCCCN)c2c1]

The title compound was prepared in analogy to Example 9-1 in Scheme 5 by using 4-(4-chloro-6-(methylsulfanyl)quinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4-dichloro-6-(methylsulfanyl)quinoline and 2,3,4,5-tetrahydro-1,4-benzothiazepine) and propane-1,3-diamine. MS obsd. (ESI+) [(M+H)+] 442, ¹H NMR (400 MHz, CD₃OD) δ ppm 8.07 (dd, J=1.2, 8.0 Hz, 1 H), 7.92 (d, J=2.0 Hz, 1 H), 7.84 (d, J=7.6 Hz, 1 H), 7.74-7.69 (m, 2 H), 7.64 (dd, J=2.0, 8.8 Hz, 1 H), 7.57 (t, J=8.0 Hz, 1 H), 5.95 (s, 1 H), 5.30 (s, 2 H), 4.50 (brs, 2 H), 3.72 (t, J=4.8 Hz, 2 H), 3.59 (t, J=6.8 Hz, 2 H), 3.08 (t, J=7.6 Hz, 2 H), 2.55 (s, 3 H), 2.14-2.05 (m, 2 H).

Example 9-34

N-[6-Bromo-2-(1,1-dioxido-2,3-dihydro-1,4-benzothiazepin-4(5H)-yl)quinolin-4-yl]propane-1,3-diamine

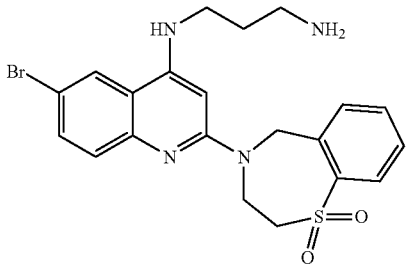 [SMILES: NCCCNc1cc(N2CCS(=O)(=O)c3ccccc3C2)nc2ccc(Br)cc12]

The title compound was prepared in analogy to Example 9-1 in Scheme 5 by using 4-(6-bromo-4-chloroquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 6-bromo-2,4-dichloroquinoline and 2,3,4,5-tetrahydro-1,4-benzothiazepine) and propane-1,3-diamine. MS obsd. (ESI+) [(M+H)+] 475, ¹H NMR (400 MHz, CD₃OD) δ ppm 8.34 (s, 1 H), 8.05-8.04 (d, J=7.6 Hz, 1 H), 7.88-7.86 (d, J=7.6 Hz, 1 H), 7.81-7.79 (d, J=9.2 Hz, 1 H), 7.75-7.69 (m, 2 H), 7.58-7.55 (t, J=7.6 Hz, 1 H), 5.98 (s, 2 H), 5.34 (s, 2 H), 4.52 (s, 2 H), 3.72 (s, 2 H), 3.60-3.57 (t, J=7.2 Hz, 2 H), 3.12-3.08 (t, J=7.6 Hz, 2 H), 2.15-2.08 (m, 2 H).

Example 10

{4-[(2-Aminoethyl)amino]-2-(1,1-dioxido-2,3-dihydro-1,4-benzothiazepin-4(5H)-yl)quinolin-6-yl}methanol

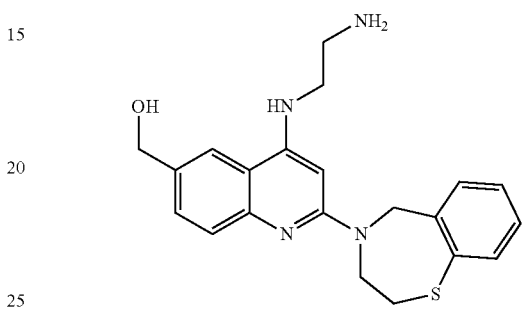

4-Chloro-2-(2,3-dihydro-1,4-benzothiazepin-4(5H)-yl)-quinoline-6-methanol

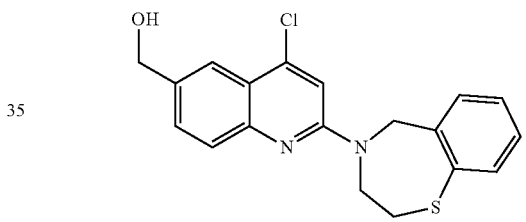

The title compound was prepared in analogy to 4-chloro-2-(1,1-dioxido-2,3-dihydro-1,4-benzothiazepin-4(5H)-yl)-quinoline-6-methanol in Example 3-23 in Scheme 5 by using methyl 4-chloro-2-(2,3-dihydro-1,4-benzothiazepin-4(5H)-yl)quinoline-6-carboxylate (prepared in analogy to 4-(4-chloro-6-methylquinolin-2-yl)-8-methoxy-2,3,4,5-tetrahydro-1,4-benzothiazepine in Example 1-1 in Scheme 4 by using methyl 2,4-dichloro quinoline-6-carboxylate and 2,3,4,5-tetrahydro-1,4-benzothiazepine) and sodium borohydride.

{4-[(2-Aminoethyl)amino]-2-(2,3-dihydro-1,4-benzothiazepin-4(5H)-yl)quinolin-6-yl}methanol

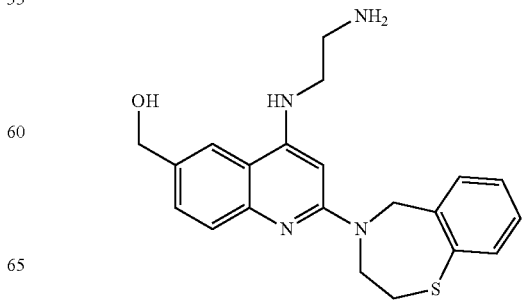

The title compound was prepared in analogy to Example 9-1 in Scheme 5 by using [4-chloro-2-(2,3-dihydro-1,4-benzothiazepin-4(5H)-yl)quinolin-6-yl]methanol and propane-1,3-diamine.

{4-[(2-Aminoethyl)amino]-2-(1,1-dioxido-2,3-dihydro-1,4-benzothiazepin-4(5H)-yl)quinolin-6-yl}methanol

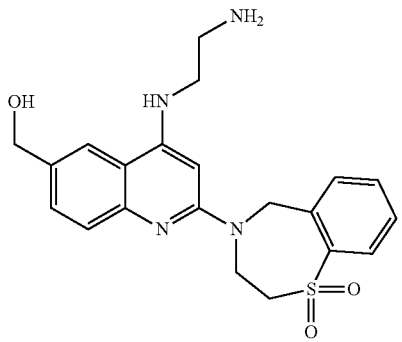 [SMILES: NCCNc1cc(N2CCS(=O)(=O)c3ccccc3C2)nc2ccc(CO)cc12]

To a suspension of {4-[(2-aminoethyl)amino]-2-(2,3-dihydro-1,4-benzothiazepin-4(5H)-yl)quinolin-6-yl}methanol (370 mg, 1.04 mmol) in dichloromethane (10 mL) was added 3-chloroperoxybenzoic acid (384 mg, 2.18 mmol). The resulting mixture was stirred at room temperature for 2 hours. To the mixture was added an aqueous solution of saturated sodium bicarbonate (1 mL) to quench the reaction, and resulting mixture was diluted with dichloromethane (15 mL). The organic phase was separated, washed with saturated sodium bicarbonate and brine, dried over sodium sulfate, and concentrated in vacuo. The residue was purified by flash chromatography to afford 400 mg of the title compound as a yellow solid (yield was 98%). MS obsd. (ESI$^+$) [(M+H)$^+$] 413, $^1$H NMR (400 MHz, DMSO-d6) δ ppm 8.18 (s, 1 H), 7.93 (d, J=7.6 Hz, 1 H), 7.87-7.84 (m, 2 H), 7.64 (m, 1 H), 7.45 (m, 1 H), 7.37 (s, 1 H), 7.33 (s, 1 H), 6.10 (s, 1 H), 5.09 (s, 2 H), 4.52 (brs, 2 H), 3.62 (s, 2 H), 3.37-3.28 (m, 4 H), 3.18 (m, 2 H).

Example 11-1

2-{[2-(1,1-Dioxido-2,3-dihydro-1,4-benzothiazepin-4(5H)-yl)-6-methylquinolin-4-yl]amino}propane-1,3-diol

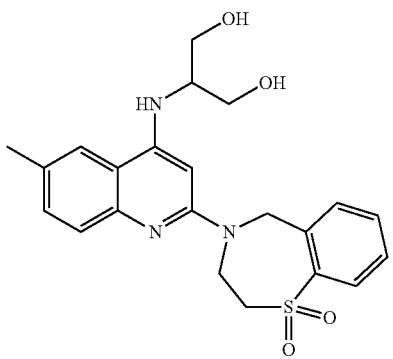 [SMILES: Cc1ccc2nc(N3CCS(=O)(=O)c4ccccc4C3)cc(NC(CO)CO)c2c1]

A solution of 4-(4-chloro-6-methylquinolin-2-yl)-2,3,4,5-tetrahydro-1,4-benzothiazepine 1,1-dioxide (200.0 mg, 0.54 mmol, prepared in analogy to the one in Example 2-1) and 2-aminopropane-1,3-diol (420.0 mg, 4.6 mmol) in 1-methyl-2-pyrrolidinone (1.0 mL) was stirred at 160° C. for 16 hours. After being cooled to room temperature and diluted with water (50 mL), the resulting mixture was extracted with ethyl acetate (100 mL), washed with brine (50 mL×2), dried over anhydrous sodium sulfate and concentrated in vacuo. The residue was purified by preparative HPLC to afford 34.6 mg of the product as a white solid (yield was 15%). MS obsd. (ESI$^+$) [(M+H)$^+$] 428, $^1$H NMR (400 MHz, CD$_3$OD) δ ppm 7.99 (dd, J=7.83, 1.01 Hz, 1 H), 7.86 (d, J=7.07 Hz, 1 H), 7.71-7.58 (m, 2 H), 7.51-7.40 (m, 2 H), 7.36-7.24 (m, 1 H), 6.16 (s, 1 H), 5.16 (s, 2 H), 4.79-4.59 (m, 1 H), 4.54 (brs, 1 H), 3.81 (s, 5 H), 3.69-3.50 (m, 2 H), 2.42 (s, 3 H).

Example 11-2

2,2'-{[2-(1,1-Dioxido-2,3-dihydro-1,4-benzothiazepin-4(5H)-yl)-6-methylquinolin-4-yl]imino}diethanol

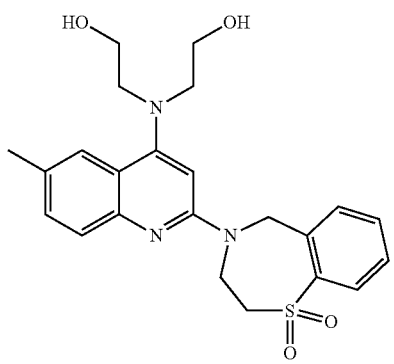 [SMILES: Cc1ccc2nc(N3CCS(=O)(=O)c4ccccc4C3)cc(N(CCO)CCO)c2c1]

The title compound was prepared in analogy to Example 11-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 2,2'-iminodiethanol. MS obsd. (ESI$^+$) [(M+H)$^+$] 442, $^1$H NMR (400 MHz, CD$_3$OD) δ ppm 7.99 (dd, J=7.83, 1.26 Hz, 1 H), 7.81 (s, 1 H), 7.83 (s, 1 H), 7.63 (td, J=7.58, 1.26 Hz, 1 H), 7.56-7.39 (m, 2 H), 7.30 (dd, J=8.46, 1.89 Hz, 1 H), 6.78 (s, 1 H), 5.18 (s, 2 H), 4.57 (brs, 2 H), 3.73-3.56 (m, 6 H), 3.56-3.43 (m, 4 H), 2.42 (s, 3 H).

Example 11-3

4-{[2-(1,1-Dioxido-2,3-dihydro-1,4-benzothiazepin-4(5H)-yl)-6-methylquinolin-4-yl]amino}-3-hydroxybutanoic acid

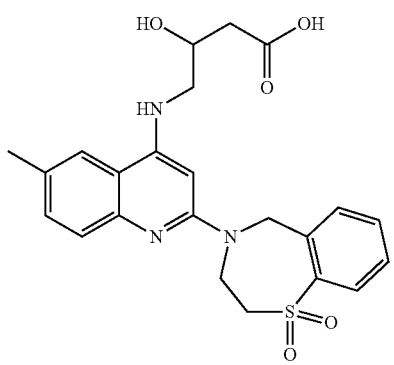 [SMILES: Cc1ccc2nc(N3CCS(=O)(=O)c4ccccc4C3)cc(NCC(O)CC(=O)O)c2c1]

The title compound was prepared in analogy to Example 11-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 4-amino-3-hydroxybutanoic acid. MS obsd. (ESI+) [(M+H)+] 456. ¹H NMR (400 MHz, CD₃OD) δ ppm 8.10 (dd, J=7.83, 1.26 Hz, 1 H), 7.83-8.00 (m, 2 H), 7.80-7.67 (m, 2 H), 7.67-7.52 (m, 2 H), 6.32 (s, 1 H), 5.43-5.27 (m, 2 H), 4.55 (brs, 2 H), 4.39-4.23 (m, 1 H), 3.86-3.66 (m, 3 H), 3.57-3.40 (m, 1 H), 2.78-2.63 (m, 2 H), 2.50 (s, 3 H).

Example 11-4

1-Amino-3-{[2-(1,1-dioxido-2,3-dihydro-1,4-benzothiazepin-4(5H)-yl)-6-methylquinolin-4-yl]amino}-2-methylpropan-2-ol

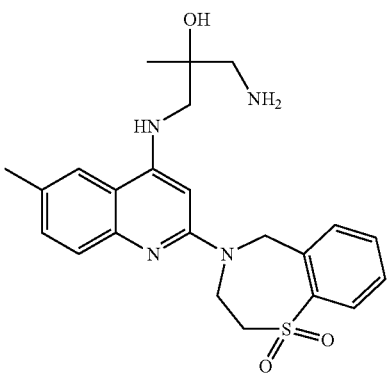 [SMILES: Cc1ccc2nc(N3CCS(=O)(=O)c4ccccc4C3)cc(NCC(C)(O)CN)c2c1]

The title compound was prepared in analogy to Example 11-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 1,3-diamino-2-methylpropan-2-ol. MS obsd. (ESI+) [(M+H)+] 441, ¹H NMR (400 MHz, CD₃OD) δ ppm 7.97 (d, J=7.6 Hz, 1 H), 7.88 (d, J=7.6 Hz, 1 H), 7.60 (t, J=7.6 Hz, 1 H), 7.57 (s, 1 H), 7.43 (m, 2 H), 7.29 (dd, J=1.2, 8.4 Hz, 1 H), 6.18 (s, 1 H), 5.15 (s, 2 H), 4.53 (brs, 2 H), 3.58 (t, J=4.4 Hz, 2 H), 3.34 (m, 2 H), 2.85-2.76 (m, 2 H), 2.42 (s, 3 H), 1.32 (s, 3 H).

Example 12-1

2-(1,1-Dioxido-2,3-dihydro-1,4-benzothiazepin-4(5H)-yl)-6-methyl-N-[2-(morpholin-4-yl)ethyl]quinolin-4-amine

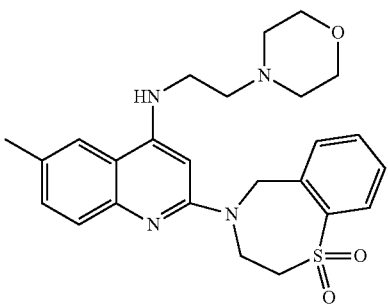 [SMILES: Cc1ccc2nc(N3CCS(=O)(=O)c4ccccc4C3)cc(NCCN3CCOCC3)c2c1]

A mixture of 4-(4-chloro-6-methylquinolin-2-yl)-2,3,4,5-tetrahydro-1,4-benzothiazepine 1,1-dioxide (50 mg, 0.134 mmol, prepared in analogy to the one in Example 2-1), 2-(morpholin-4-yl)ethanamine (78 mg, 0.67 mmol) and n-butanol (5 mL) was heated with stirring in a 10 mL of microwave process vial for 2 hours at 160° C. under microwave irradiation. After being cooled to room temperature, the mixture was diluted with dichloromethane and washed with brine. The organic layer was dried over sodium sulfate and concentrated in vacuo. The residue was purified by column chromatography on silica gel (eluting with 3% methanol in dichloromethane) to afford 35 mg of the product as a light oil (yield was 56%). MS obsd. (ESI+) [(M+H)+] 467, ¹H NMR (400 MHz, CDCl₃) δ ppm 8.05 (d, J=7.6 Hz, 1 H), 7.66 (d, J=7.2 Hz, 1 H), 7.53-7.51 (m, 2 H), 7.38 (m, 1 H), 7.32 (m, 1 H), 5.88 (s, 1 H), 5.56 (s, 2 H), 5.09 (s, 2 H), 4.6 (brs, 2 H) 3.76 (t, J=4.8 Hz, 4 H), 3.50 (brs, 2 H), 3.33 (m, 2 H), 2.82 (m, 2 H), 2.56 (m, 4 H), 2.29 (s, 3 H).

Example 12-2

2-{[2-(1,1-Dioxido-2,3-dihydro-1,4-benzothiazepin-4(5H)-yl)-1,6-naphthyridin-4-yl]amino}ethanol

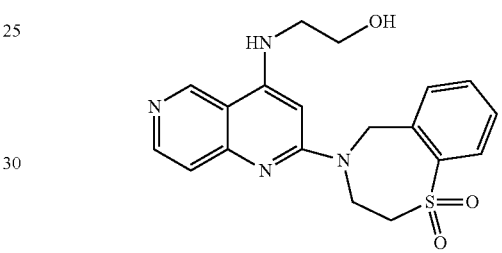

The title compound was prepared in analogy to Example 12-1 in Scheme 5 by using 4-(4-chloro-1,6-naphthyridin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,3,4,5-tetrahydro-1,4-benzothiazepine and 2,4-dichloro-1,6-naphthyridine) and 2-aminoethanol. MS obsd. (ESI+) [(M+H)+] 385, ¹H NMR (400 MHz, CD₃OD) δ ppm 9.66 (s, 1 H), 8.66-8.64 (d, J=6.8 Hz, 1 H), 8.26-8.24 (d, J=6.8 Hz, 1 H), 8.05-8.03 (d, J=7.6 Hz, 1 H), 7.97-7.95 (d, J=7.2 Hz, 1 H), 7.71-7.69 (d, J=7.2 Hz, 1 H), 7.56-7.54 (d, J=7.6 Hz, 1 H), 6.30 (s, 1 H), 5.38 (s, 1 H), 4.72-4.60 (m, 2 H), 3.87-3.86 (m, 2 H), 3.71-3.67 (m, 4 H).

Example 12-3

N-[2-(1,1-Dioxido-2,3-dihydro-1,4-benzothiazepin-4(5H)-yl)-8-methylquinolin-4-yl]nonane-1,9-diamine

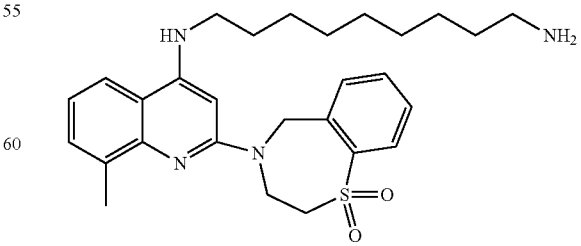

The title compound was prepared in analogy to Example 12-1 in Scheme 5 by using 4-(4-chloro-8-methylquinolin-2-yl)-2,3,4,5-tetrahydro-1,4-benzothiazepine 1,1-dioxide (prepared in analogy to 4-(4-chloro-6-methylquinolin-2-yl)-2,3, 4,5-tetrahydro-1,4-benzothiazepine 1,1-dioxide in Example 2-1 by using 2,4-dichloro-8-methylquinoline and 2,3,4,5-tetrahydro-1,4-benzothiazepine) and nonane-1,9-diamine. MS obsd. (ESI⁺) [(M+H)⁺] 495, ¹H NMR (400 MHz, CD₃OD) δ ppm 8.04-8.03 (m, 1 H), 7.93-7.91 (m, 1 H), 7.82-7.80 (m, 1 H), 7.68-7.70 (m, 1 H), 7.58-7.56 (m, 2 H), 7.40-7.30 (m, 1 H), 5.87 (s, 1 H), 5.30 (s, 2 H), 4.49 (s, 2 H), 3.76-3.75 (m, 2 H), 3.42-3.40 (m, 2 H), 2.90-2.85 (m, 2 H), 2.61 (s, 3 H), 1.70-1.58 (m, 4 H), 1.48-1.31 (m, 10 H).

Example 12-4

N-[2-(1,1-Dioxido-2,3-dihydro-1,4-benzothiazepin-4 (5H)-yl)-8-methylquinolin-4-yl]decane-1,10-diamine

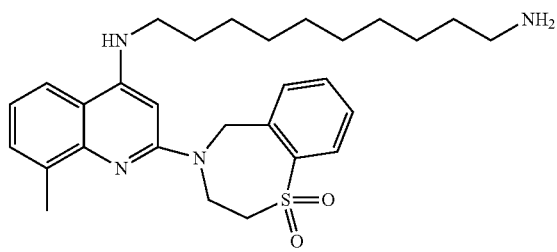 [SMILES: Cc1cccc2c(NCCCCCCCCCCN)cc(N3CCS(=O)(=O)c4ccccc4C3)nc12]

The title compound was prepared in analogy to Example 12-1 in Scheme 5 by using 4-(4-chloro-8-methylquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4-dichloro-8-methylquinoline and 2,3,4,5-tetrahydro-1,4-benzothiazepine) and decane-1,10-diamine. MS obsd. (ESI⁺) [(M+H)⁺] 509, ¹H NMR (400 MHz, CD₃OD) δ ppm 8.08-8.06 (m, 1 H), 7.94-7.93 (m, 1 H), 7.82-7.81 (m, 1 H), 7.72-7.70 (m, 1 H), 7.59-7.57 (m, 2 H), 7.42-7.32 (m, 1 H), 5.89 (s, 1 H), 5.31 (s, 2 H), 4.50 (s, 2 H), 3.78-3.77 (m, 2 H), 3.44-3.42 (m, 2 H), 2.91-2.87 (m, 2 H), 2.63 (s, 3 H), 1.70-1.58 (m, 4 H), 1.48-1.31 (m, 12 H).

Example 12-5

N-[2-(1,1-Dioxido-2,3-dihydro-1,4-benzothiazepin-4 (5H)-yl)-6-methylquinolin-4-yl]octane-1,8-diamine

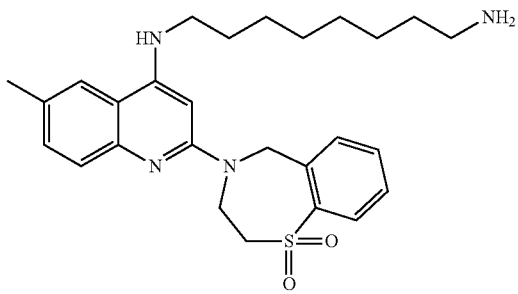 [SMILES: Cc1ccc2nc(N3CCS(=O)(=O)c4ccccc4C3)cc(NCCCCCCCCN)c2c1]

The title compound was prepared in analogy to Example 12-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and octane-1,8-diamine. MS obsd. (ESI⁺) [(M+H)⁺] 481, ¹H NMR (400 MHz, CD₃OD) δ ppm 8.10-8.08 (dd, J=1.2 Hz, 1 H), 7.92 (s, 1 H), 7.86-7.84 (d, J=7.6 Hz, 1 H), 7.71-7.67 (m, 2 H), 7.61-7.55 (m, 2 H), 5.92 (s, 1 H), 5.28 (s, 2 H), 4.52 (s, 2 H), 3.75-3.73 (m, 2 H), 3.50-3.46 (t, 2 H), 2.93-2.83 (t, 2 H), 2.46 (s, 3 H), 1.74-1.64 (m, 4 H), 1.51-1.40 (m, 8 H).

Example 12-6

9-{[2-(1,1-Dioxido-2,3-dihydro-1,4-benzothiazepin-4(5H)-yl)-6-methylquinolin-4-yl]amino}nonan-1-ol

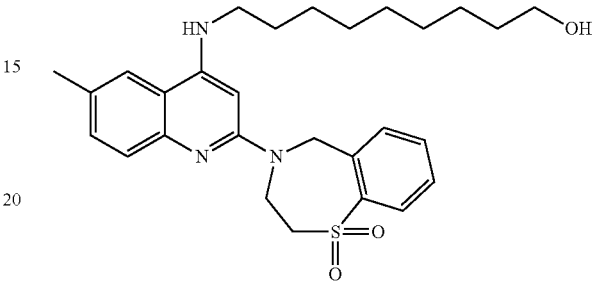

The title compound was prepared in analogy to Example 12-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and 9-aminononanol. MS obsd. (ESI⁺) [(M+H)⁺] 495, ¹H NMR (400 MHz, CD₃OD) δ ppm 8.11-8.09 (dd, J=1.2 Hz, 1 H), 7.92 (s, 1 H), 7.85-7.83 (d, J=7.6 Hz, 1 H), 7.71-7.67 (m, 2 H), 7.61-7.57 (m, 2 H), 5.92 (s, 1 H), 5.28 (s, 2 H), 4.52 (s, 2 H), 3.74 (s, 2 H), 3.50-3.46 (t, 2 H), 2.92-2.89 (t, 2 H), 2.46 (s, 3 H), 1.73-1.63 (m, 4 H), 1.50-1.38 (m, 10 H).

Example 12-7

N-[2-(1,1-Dioxido-2,3-dihydro-1,4-benzothiazepin-4 (5H)-yl)-8-methylquinolin-4-yl]octane-1,8-diamine

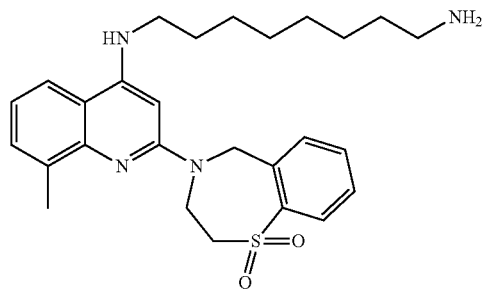 [SMILES: Cc1cccc2c(NCCCCCCCCN)cc(N3CCS(=O)(=O)c4ccccc4C3)nc12]

The title compound was prepared in analogy to Example 12-1 in Scheme 5 by using 4-(4-chloro-8-methylquinolin-2-yl)-2,3,4,5-tetrahydro-1,4-benzothiazepine 1,1-dioxide (prepared in analogy to 4-(4-chloro-6-methylquinolin-2-yl)-2,3, 4,5-tetrahydro-1,4-benzothiazepine 1,1-dioxide in Example 2-1 by using 2,4-dichloro-8-methylquinoline and 2,3,4,5-tetrahydro-1,4-benzothiazepine) and octane-1,8-diamine. MS obsd. (ESI⁺) [(M+H)⁺] 481, ¹H NMR (400 MHz, CD₃OD) δ ppm 8.09-8.07 (d, J=7.6 Hz, 1 H), 7.96-7.94 (d, J=8.4 Hz, 1 H), 7.85-7.83 (d, J=7.6 Hz, 1 H), 7.73-7.70 (m, 2 H), 7.36-7.32 (m, 2 H), 5.90 (s, 1 H), 5.33 (s, 2 H), 4.52-4.51 (m, 2 H), 3.81-3.78 (t, 2 H), 3.47-3.42 (t, 2 H), 2.91-2.89 (t, 2 H), 2.64 (s, 3 H), 1.67-1.63 (m, 4 H), 1.50-1.37 (m, 8 H).

Example 13 cis-4-amino-1-[2-(1,1-Dioxido-2,3-dihydro-1,4-benzothiazepin-4(5H)-yl)-6-methylquinolin-4-yl]pyrrolidin-3-ol

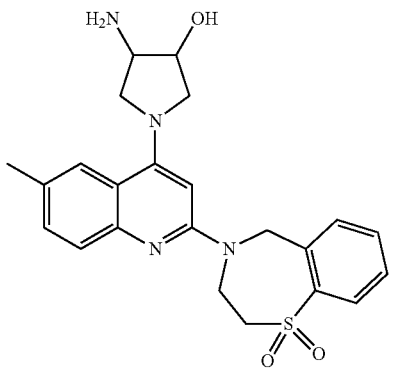 [SMILES: Cc1ccc2nc(N3CCS(=O)(=O)c4ccccc4C3)cc(N3CC(N)C(O)C3)c2c1]

A mixture of 4-(4-chloro-6-methylquinolin-2-yl)-2,3,4,5-tetrahydro-1,4-benzothiazepine 1,1-dioxide (740 mg, 2.0 mmol, prepared in analogy to the one in Example 2-1) and cis-4-aminopyrrolidin-3-ol (600 mg, 6.0 mmol) in n-butanol (0.2 mL) was heated at 180° C. for 3 days. After being cooled to room temperature, the mixture was purified by preparative HPLC to afford the product as a solid. MS obsd. (ESI+) [(M+H)+] 439, $^1$H NMR (400 MHz, CD$_3$OD) δ ppm 8.12 (dd, J=7.83, 1.26 Hz, 1 H), 8.02 (s, 1 H), 7.87 (d, J=7.07 Hz, 1 H), 7.82-7.71 (m, 2 H), 7.67-7.57 (m, 2 H), 5.93 (s, 1 H), 5.33 (s, 2 H), 4.66 (d, J=2.02 Hz, 1 H), 4.56 (brs, 2 H), 4.28-4.17 (m, 2 H), 4.13-3.99 (m, 2 H), 3.91 (s, 1 H), 3.76 (brs, 2 H), 3.37 (s, 3 H), 2.50 (s, 3 H).

Example 14-1

N-[2-(1,1-Dioxido-2,3-dihydro-1,4-benzothiazepin-4(5H)-yl)-6-methylquinolin-4-yl]-L-alanine

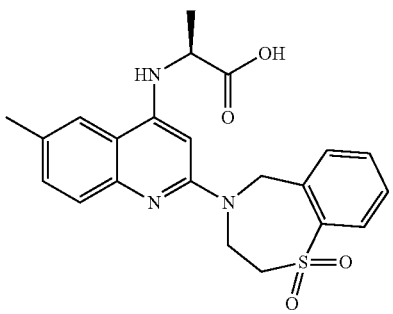 [SMILES: Cc1ccc2nc(N3CCS(=O)(=O)c4ccccc4C3)cc(N[C@@H](C)C(=O)O)c2c1]

The mixture of 4-(4-chloro-6-methylquinolin-2-yl)-2,3,4,5-tetrahydro-1,4-benzothiazepine 1,1-dioxide (150 mg, 0.40 mmol, prepared in analogy to the one in Example 2-1) and L-alanine (360 mg, 4.0 mmol) in phenol (360 mg) was heated at 150° C. overnight. After being cooled to room temperature, the mixture was purified by preparative HPLC to afford the pure product as a solid. MS obsd. (ESI+) [(M+H)+] 426, $^1$H NMR (400 MHz, CD$_3$OD) δ ppm 8.16-7.92 (m, 3 H), 7.84 (d, J=8.34 Hz, 1 H), 7.78-7.62 (m, 1 H), 7.61-7.42 (m, 2 H), 5.86 (s, 1 H), 5.24 (brs, 2 H), 4.65-4.35 (m, 3 H), 3.69 (brs, 2 H), 3.37 (s, 3 H), 2.53-2.39 (m, 3 H), 1.76-1.57 (m, 3 H).

Example 14-2

N-[2-(1,1-Dioxido-2,3-dihydro-1,4-benzothiazepin-4(5H)-yl)-6-methylquinolin-4-1]-beta-alanine

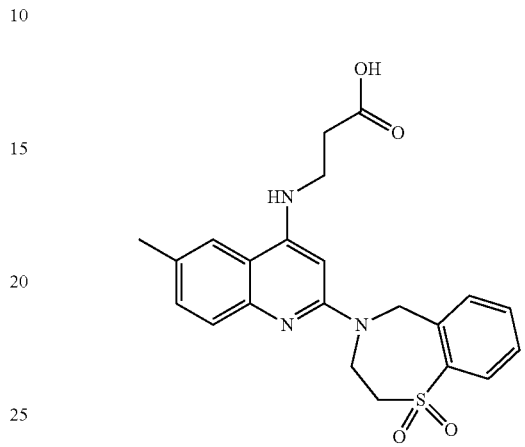

The title compound was prepared in analogy to Example 14-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and beta-alanine. MS obsd. (ESI+) [(M+H)+] 426, $^1$H NMR (400 MHz, CD$_3$OD) δ ppm 8.14-8.08 (m, 1 H), 7.96-7.88 (m, 2 H), 7.77-7.68 (m, 2 H), 7.65-7.57 (m, 2 H), 6.09 (s, 1 H), 5.32 (s, 2 H), 4.56 (brs, 1 H), 3.84-3.71 (m, 4 H), 3.37 (s, 2 H), 2.76 (t, J=6.95 Hz, 2 H), 2.48 (s, 3 H).

Example 15-1

N-[2-(1,1-Dioxido-2,3-dihydro-1,4-benzothiazepin-4(5H)-yl)-6-methylquinolin-4-yl]benzene-1,3-diamine

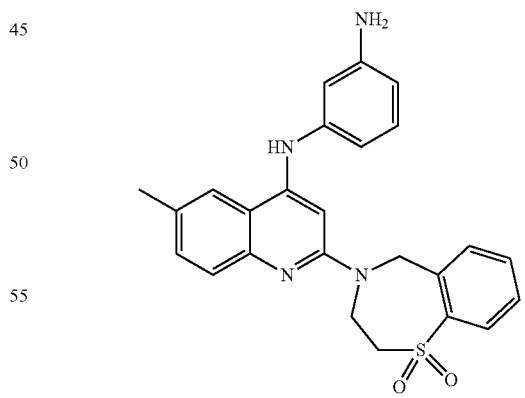

A mixture of 4-(4-chloro-6-methylquinolin-2-yl)-2,3,4,5-tetrahydro-1,4-benzothiazepine 1,1-dioxide (150 mg, 0.40 mmol, prepared in analogy to the one in Example 2-1), benzene-1,3-diamine (86 mg, 0.80 mmol), palladium acetate (18 mg, 0.04 mmol), 2,2'-bis(diphenylphosphino)-1,1'-binaphthalene (50 mg, 0.04 mmol), potassium phosphate (169.6 mg, 0.8 mmol) and 1,4-dioxane (3 mL) in a 2-5 mL of process vial was heated at 140° C. under microwave irradiation for 1.5 hours. After being cooled to room temperature, the mixture was filtered and washed with ethyl acetate. The filtrate was washed with brine, dried over sodium sulfate, and concentrated in vacuo. The residue was purified by preparative HPLC to afford the pure product as a solid. MS obsd. (ESI+) [(M+H)+] 445, $^1$H NMR (400 MHz, DMSO-d6) δ ppm 8.31 (s, 1 H), 7.88 (dd, J=6.06, 1.52 Hz, 2 H), 7.63 (td, J=7.52, 1.14 Hz, 1 H), 7.54-7.46 (m, 1 H), 7.42-7.33 (m, 2 H), 7.33-7.27 (m, 1 H), 7.16 (t, J=7.83 Hz, 1 H), 6.52 (t, J=1.89 Hz, 1 H), 6.49-6.34 (m, 3 H), 5.23 (s, 2 H), 4.86 (s, 2 H), 3.60 (brs, 2 H), 2.38 (s, 3 H).

Example 15-2

N-[2-(1,1-Dioxido-2,3-dihydro-1,4-benzothiazepin-4 (5H)-yl)-6-methylquinolin-4-yl]benzene-1,4-diamine

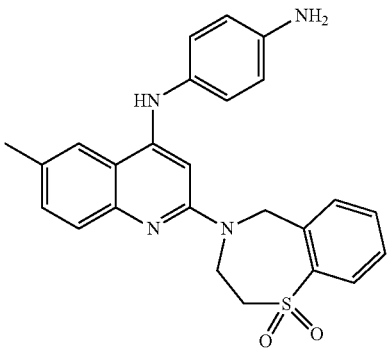 [SMILES: Cc1ccc2nc(N3CCS(=O)(=O)c4ccccc4C3)cc(Nc3ccc(N)cc3)c2c1]

The title compound was prepared in analogy to Example 15-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1 1) and benzene-1,4-diamine. MS obsd. (ESI+) [(M+H)+] 445, $^1$H NMR (400 MHz, DMSO-d6) δ ppm 8.21 (s, 1 H), 7.92-7.83 (m, 2 H), 7.63-7.55 (m, 1 H), 7.53-7.46 (m, 1 H), 7.34 (d, J=8.34 Hz, 1 H), 7.27 (dd, J=8.59, 1.52 Hz, 1 H), 7.15 (d, J=7.58 Hz, 1 H), 6.91 (m, J=8.34 Hz, 2 H), 6.77 (m, J=8.59 Hz, 2 H), 5.97 (s, 1 H), 5.20-5.12 (m, 2 H), 4.76 (brs, 2 H), 3.57 (brs, 2 H), 2.37 (s, 3 H).

Example 15-3

(3S)-1-[2-(1,1-Dioxido-2,3-dihydro-1,4-benzothiazepin-4(5H)-yl)-6-methylquinolin-4-yl]pyrrolidin-3-ol

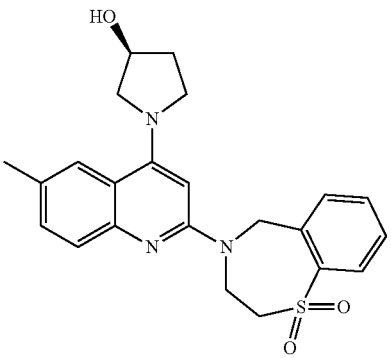 [SMILES: Cc1ccc2nc(N3CCS(=O)(=O)c4ccccc4C3)cc(N3CC[C@H](O)C3)c2c1]

The title compound was prepared in analogy to Example 15-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and (3S)-pyrrolidin-3-ol. MS obsd. (ESI+) [(M+H)+] 424, $^1$H NMR (400 MHz, CD3OD) δ ppm 7.90 (dd, J=7.83, 1.26 Hz, 1 H), 7.80-7.72 (m, 2 H), 7.54 (td, J=7.52, 1.39 Hz, 1 H), 7.43 (d, J=8.59 Hz, 1 H), 7.34 (td, J=7.71, 1.01 Hz, 1 H), 7.23 (dd, J=8.59, 1.77 Hz, 1 H), 6.05 (s, 1 H), 5.06 (s, 2 H), 4.55-4.43 (m, 1 H), 3.84 (dd, J=10.48, 4.42 Hz, 2 H), 3.58-3.43 (m, 4 H), 3.35 (s, 2 H), 2.35 (s, 3 H), 2.11 (dd, J=8.84, 4.55 Hz, 1 H), 2.06-1.97 (m, 1 H).

Example 15-4

(3R)-1-[2-(1,1-Dioxido-2,3-dihydro-1,4-benzothiazepin-4(5H)-yl)-6-methylquinolin-4-yl]pyrrolidin-3-ol

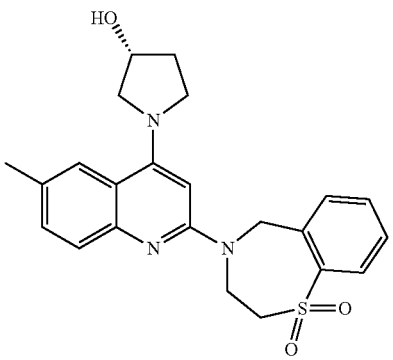 [SMILES: Cc1ccc2nc(N3CCS(=O)(=O)c4ccccc4C3)cc(N3CC[C@@H](O)C3)c2c1]

The title compound was prepared in analogy to Example 15-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and (3R)-pyrrolidin-3-ol. MS obsd. (ESI+) [(M+H)+] 424, $^1$H NMR (400 MHz, CD3OD) δ ppm 7.88 (dd, J=7.83, 1.01 Hz, 1 H), 7.79-7.69 (m, 2 H), 7.52 (td, J=7.52, 1.14 Hz, 1 H), 7.44 (d, J=8.59 Hz, 1 H), 7.33-7.27 (m, 1 H), 7.23 (dd, J=8.59, 1.77 Hz, 1 H), 6.02 (s, 1 H), 5.04 (s, 2 H), 4.55-4.42 (m, 2 H), 3.89-3.76 (m, 2 H), 3.59-3.42 (m, 4 H), 3.37 (s, 2 H), 2.35 (s, 3 H), 2.16-1.97 (m, 2 H).

Example 15-5 trans-N-[2-(1,1-Dioxido-2,3-dihydro-1,4-benzothiazepin-4(5H)-yl)-6-methylquinolin-4-yl]cyclopentane-1,2-diamine

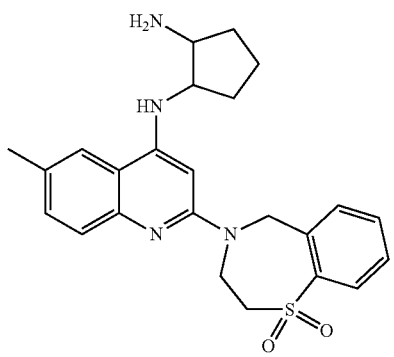 [SMILES: Cc1ccc2nc(N3CCS(=O)(=O)c4ccccc4C3)cc(NC3CCCC3N)c2c1]

The title compound was prepared in analogy to Example 15-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and trans-cyclopentane-1,2-diamine. MS obsd. (ESI+) [(M+H)+] 437, $^1$H NMR (400 MHz, CD$_3$OD) δ ppm 8.03 (d, J=7.83 Hz, 1 H), 7.93-7.81 (m, 2 H), 7.67 (t, J=7.45 Hz, 1 H), 7.61 (d, J=8.59 Hz, 1 H), 7.51 (t, J=7.71 Hz, 1 H), 7.47 (d, J=7.58 Hz, 1 H), 6.04 (s, 1 H), 5.25 (s, 2 H), 4.66 (brs, 1 H), 4.40 (brs, 1 H), 4.27 (d, J=7.07 Hz, 1 H), 3.84 (q, J=7.66 Hz, 1 H), 3.75-3.65 (m, 2 H), 2.45 (s, 3 H), 2.40-2.24 (m, 2 H), 2.08-1.79 (m, 3 H), 1.58 (dd, J=13.01, 7.71 Hz, 1 H).

Example 16-1

1-[2-(1,1-Dioxido-2,3-dihydro-1,4-benzothiazepin-4 (5H)-yl)-6-methylquinolin-4-yl]piperidin-3-amine

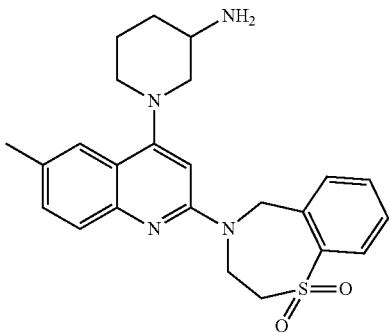 [SMILES: Cc1ccc2nc(N3CCS(=O)(=O)c4ccccc4C3)cc(N3CCCC(N)C3)c2c1]

A mixture of 4-(4-chloro-6-methylquinolin-2-yl)-2,3,4,5-tetrahydro-1,4-benzothiazepine 1,1-dioxide (0.2 g, 0.54 mmol, prepared in analogy to the one in Example 2-1), piperidin-3-ylamine hydrochloric acid salt (0.275 g, 1.6 mmol) and N,N-diisopropylethylamine (1 mL) was heated at 160° C. under microwave irradiation for 1 hour. After being cooled to room temperature, the mixture was purified by preparative HPLC and SPE. After SPE separation, the eluent was concentrated in vacuo to remove the organic solution. The residue was dried by lyophylization to give 52.3 mg of the desired product (yield was 22.3%). MS obsd. (ESI+) [(M+H)+] 437, $^1$H NMR (400 MHz, CD$_3$OD) δ ppm 8.09-8.07 (d, J=8 Hz, 1 H), 7.87-7.85 (q, J=7.2 Hz, 1 H), 7.85-7.82 (m, 1 H), 7.73-7.68 (q, J=14 Hz, 2 H), 7.62-7.55 (m, 2 H), 6.56 (s, 1 H), 5.37 (s, 2 H), 4.57 (s, 2 H), 3.90-3.88 (d, J=9.6 Hz, 1 H), 3.75 (s, 2 H), 3.67-3.66 (m, 1 H), 3.51-3.48 (d, J=11.6 Hz, 1 H), 3.26-3.24 (d, J=9.6 Hz, 1 H), 3.24-3.14 (m, 1 H), 2.49 (s, 3 H), 2.26-2.22 (m, 1 H), 2.14-2.10 (m, 1 H), 1.99-1.92 (m, 1 H), 1.91-1.78 (m, 1 H).

Example 16-2

2-(1,1-Dioxido-2,3-dihydro-1,4-benzothiazepin-4 (5H)-yl)-N,N,6-trimethylquinolin-4-amine

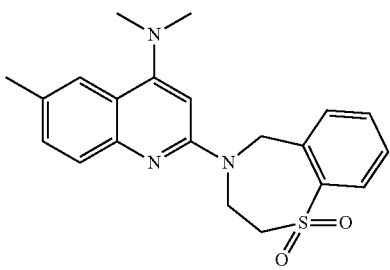 [SMILES: Cc1ccc2nc(N3CCS(=O)(=O)c4ccccc4C3)cc(N(C)C)c2c1]

The title compound was prepared in analogy to Example 16-1 in Scheme 5 by using 4-(4-chloro-6-methylquinolin-2-yl)-2,3,4,5-tetrahydro-1,4-benzothiazepine 1,1-dioxide (prepared in analogy to the one in Example 2-1) and dimethylamine. MS obsd. (ESI+) [(M+H)+] 382, $^1$H NMR (400 MHz, CD$_3$OD) δ ppm 8.07 (d, J=7.6 Hz, 1 H), 7.85-7.83 (m, 2 H), 7.73-7.70 (m, 2 H), 7.58-7.55 (m, 2 H), 6.14 (s, 1 H), 5.30 (s, 2 H), 4.51 (s, 2 H), 3.72-3.70 (m, 2 H), 3.29 (s, 6 H), 2.45 (s, 3 H).

Example 17-1

N-[2-(1,1-Dioxido-2,3-dihydro-1,4-benzothiazepin-4 (5H)-yl)-6-(trifluoromethoxy)quinolin-4-yl]propane-1,3-diamine

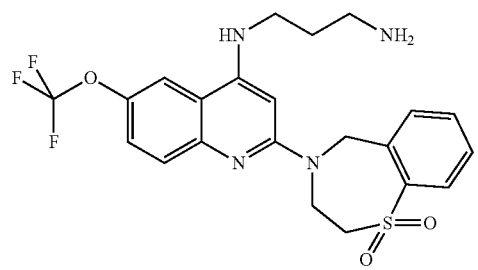 [SMILES: NCCCNc1cc(N2CCS(=O)(=O)c3ccccc3C2)nc2ccc(OC(F)(F)F)cc12]

4-(4-Chloro-6-(trifluoromethoxy)quinolin-2-yl)-2,3, 4,5-tetrahydro-1,4-benzothiazepine 1,1-dioxide

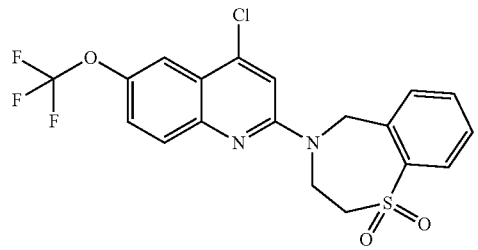 [SMILES: O=S1(=O)CCN(c2cc(Cl)c3cc(OC(F)(F)F)ccc3n2)Cc2ccccc21]

A mixture of 2,4-dichloro-6-(trifluoromethoxy)quinoline (250 mg, 0.89 mmol), 2,3,4,5-tetrahydro-1,4-benzothiazepine 1,1-dioxide (210 mg, 1.06 mmol) and n-butanol (2 mL) was heated with stirring in a 5 mL of microwave process vial for 3 hours at 150° C. under microwave irradiation. The mixture was filtered. The formed solid was collected by filtration and washed with 10 mL of mixture solution of petroleum ether and ethyl acetate (V/V=10/1) to afford 0.3 g of the product (yield was 77%).

N-[2-(1,1-Dioxido-2,3-dihydro-1,4-benzothiazepin-4(5 H)-yl)-6-(trifluoromethoxy)quinolin-4-yl]propane-1,3-diamine

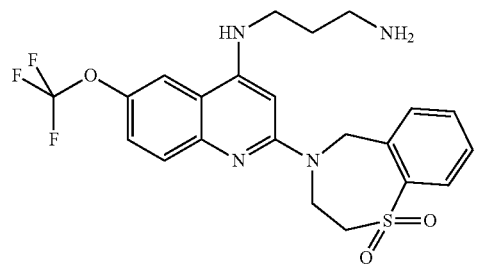 [SMILES: NCCCNc1cc(N2CCS(=O)(=O)c3ccccc3C2)nc2ccc(OC(F)(F)F)cc12]

The title compound was prepared in analogy to Example 3-1 in Scheme 5 by using 4-(4-chloro-6-(trifluoromethoxy)quinolin-2-yl)-2,3,4,5-tetrahydro-1,4-benzothiazepine 1,1-dioxide and propane-1,3-diamine. MS obsd. (ESI$^+$) [(M+H)$^+$] 481, $^1$H NMR (400 MHz, CD$_3$OD) δ ppm 8.16-8.15 (d, J=2.4 Hz, 1 H), 8.09-8.07 (dd, J=5.2, 8.0 Hz, 1 H), 7.94-7.92 (d, J=10 Hz, 1 H), 7.90-7.88 (d, J=8 Hz, 1 H), 7.72-7.70 (m, 2 H), 7.58-7.55 (m, 1 H), 6.03 (s, 1 H), 5.34 (s, 2 H), 4.55 (s, 2 H), 3.75 (s, 2 H), 3.62-3.59 (t, J=6.8 Hz, 2 H), 3.14-3.10 (t, J=8.0 Hz, 2 H), 2.15-2.11 (m, 2 H).

Example 17-2

N-[2-(1,1-Dioxido-2,3-dihydro-1,4-benzothiazepin-4(5H)-yl)-6-(trifluoromethyl)quinolin-4-yl]propane-1,3-diamine

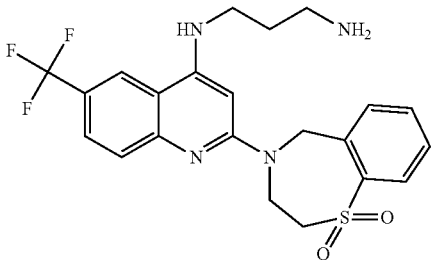 [SMILES: NCCCNc1cc(N2CCS(=O)(=O)c3ccccc3C2)nc2ccc(C(F)(F)F)cc12]

The title compound was prepared in analogy to Example 17-1 in Scheme 6 by using 4-(4-chloro-6-(trifluoromethyl)quinolin-2-yl)-2,3,4,5-tetrahydro-1,4-benzothiazepine 1,1-dioxide (prepared in analogy to 4-(4-chloro-6-(trifluoromethoxy)quinolin-2-yl)-2,3,4,5-tetrahydro-1,4-benzothiazepine 1,1-dioxide in Example 17-1 by using 2,4-dichloro-6-(trifluoromethyl)quinoline and 2,3,4,5-tetrahydro-1,4-benzothiazepine 1,1-dioxide) and propane-1,3-diamine. MS obsd. (ESI$^+$) [(M+H)$^+$] 465, $^1$H NMR (400 MHz, CD$_3$OD) δ ppm 8.57 (s, 1 H), 8.09-8.07 (dd, J=6.4, 7.6 Hz, 1 H), 7.98-9.97 (d, J=1.6 Hz, 2 H), 7.95-7.87 (d, J=7.2 Hz, 1 H), 7.74-7.70 (m, 1 H), 7.60-7.58 (m, 1 H), 6.04 (s, 1 H), 5.34 (s, 2 H), 4.55 (s, 2 H), 3.75 (s, 2 H), 3.62-3.59 (t, J=6.8 Hz, 2 H), 3.12-3.08 (t, J=8 Hz, 2 H), 2.14-2.10 (t, J=8 Hz, 2 H).

Example 17-3

N-[6-(Difluoromethoxy)-2-(1,1-dioxido-2,3-dihydro-1,4-benzothiazepin-4(5H)-yl)quinolin-4-yl]propane-1,3-diamine

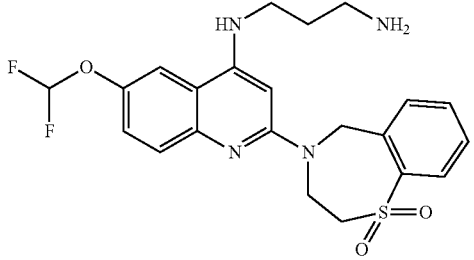 [SMILES: NCCCNc1cc(N2CCS(=O)(=O)c3ccccc3C2)nc2ccc(OC(F)F)cc12]

The title compound was prepared in analogy to Example 17-1 in Scheme 6 by using 4-(4-chloro-6-(difluoromethoxy)quinolin-2-yl)-2,3,4,5-tetrahydro-1,4-benzothiazepine 1,1-dioxide (prepared in analogy to 4-(4-chloro-6-(trifluoromethoxy)quinolin-2-yl)-2,3,4,5-tetrahydro-1,4-benzothiazepine 1,1-dioxide in Example 17-1 by using 2,4-dichloro-6-(difluoromethoxy)quinoline and 2,3,4,5-tetrahydro-1,4-benzothiazepine 1,1-dioxide) and propane-1,3-diamine. MS obsd. (ESI$^+$) [(M+H)$^+$] 463, $^1$H NMR (400 MHz, CD$_3$OD) δ ppm 8.02-8.00 (d, J=7.6 Hz, 1 H), 7.98-7.90 (d, J=2 Hz, 1 H), 7.84-7.82 (d, J=8.4 Hz, 2 H), 7.68-7.64 (t, J=7.6 Hz, 1 H), 7.54-7.50 (m, 1 H), 7.05-6.68 (d, J=73.6 Hz, 2 H), 5.95 (s, 1 H), 5.28 (s, 2 H), 4.48 (s, 2 H), 3.68 (s, 2 H), 3.57-3.54 (t, J=6.8 Hz, 2 H), 3.08-3.04 (t, J=7.6 Hz, 2 H), 2.11-2.04 (m, 2 H).

Example 17-4

N-[2-(1,1-Dioxido-2,3-dihydro-1,4-benzothiazepin-4(5H)-yl)-6-methoxyquinolin-4-yl]propane-1,3-diamine

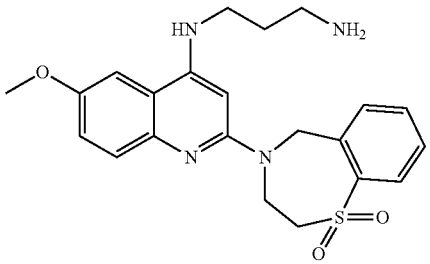 [SMILES: COc1ccc2nc(N3CCS(=O)(=O)c4ccccc4C3)cc(NCCCN)c2c1]

The title compound was prepared in analogy to Example 17-1 in Scheme 6 by using 4-(4-chloro-6-methoxyquinolin-2-yl)-2,3,4,5-tetrahydro-1,4-benzothiazepine 1,1-dioxide (prepared in analogy to 4-(4-chloro-6-(trifluoromethoxy)quinolin-2-yl)-2,3,4,5-tetrahydro-1,4-benzothiazepine 1,1-dioxide in Example 17-1 by using 2,4-dichloro-6-methoxyquinoline and 2,3,4,5-tetrahydro-1,4-benzothiazepine 1,1-dioxide) and propane-1,3-diamine. MS obsd. (ESI$^+$) [(M+H)$^+$] 427, $^1$H NMR (400 MHz, CD$_3$OD) δ ppm 8.01-7.99 (d, J=8 Hz, 1 H), 7.83-7.81 (d, J=7.2 Hz, 1 H), 7.71-7.64 (m, 2 H), 7.52-7.50 (d, J=7.6 Hz, 2 H), 7.30-7.27 (d, J=9.2 Hz, 1 H), 5.90 (s, 1 H), 5.25 (s, 2 H), 4.46 (s, 2 H), 3.83 (s, 3 H), 3.66 (s, 2 H), 3.56 (s, 2 H), 3.08-3.07 (t, J=7.2 Hz, 2 H), 2.09-2.06 (d, J=5.2 Hz, 2 H).

Example 17-5

N-[2-(1,1-Dioxido-2,3-dihydro-1,4-benzothiazepin-4(5H)-yl)-8-methylquinolin-4-yl]propane-1,3-diamine

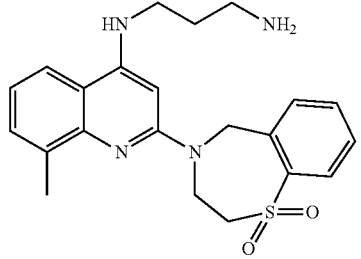 [SMILES: Cc1cccc2c(NCCCN)cc(N3CCS(=O)(=O)c4ccccc4C3)nc12]

The title compound was prepared in analogy to Example 17-1 in Scheme 6 by using 4-(4-chloro-8-methylquinolin-2-yl)-2,3,4,5-tetrahydro-1,4-benzothiazepine 1,1-dioxide (prepared in analogy to 4-(4-chloro-6-(trifluoromethoxy)quinolin-2-yl)-2,3,4,5-tetrahydro-1,4-benzothiazepine 1,1-dioxide in Example 17-1 by using 2,4-dichloro-8-methylquinoline and 2,3,4,5-tetrahydro-1,4-benzothiazepine 1,1-dioxide) and propane-1,3-diamine. MS obsd. (ESI⁺) [(M+H)⁺] 411, ¹H NMR (400 MHz, CD₃OD) δ ppm 8.33 (s, 1 H), 8.08-8.02 (m, 2 H), 7.83-7.86 (d, J=7.2 Hz, 1 H), 7.74-7.72 (t, J=8.4 Hz, 1 H), 7.62-7.58 (q, J=7.2 Hz, 2 H), 7.34-7.28 (t, J=7.6 Hz, 1 H), 5.98 (s, 2 H), 5.40 (s, 2 H), 4.58 (s, 2 H), 3.79 (s, 2 H), 3.64-3.61 (t, J=6.8 Hz, 2 H), 3.09-3.05 (dd, J=7.6, 8.4 Hz, 2 H), 2.67 (s, 3 H), 2.10-2.06 (d, J=7.2 Hz, 2 H).

Example 17-6 and 17-7

N-[2-(1,1-Dioxido-2,3-dihydro-1,4-benzothiazepin-4(5H)-yl)-5-methylquinolin-4-yl]propane-1,3-diamine and N-[2-(1,1-Dioxido-2,3-dihydro-1,4-benzothiazepin-4(5H)-yl)-7-methylquinolin-4-yl]propane-1,3-diamine

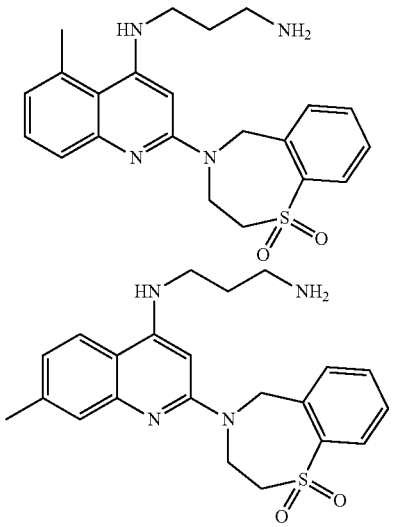

A mixture of the title compound prepared in analogy to Example 17-1 by using propane-1,3-diamine and a mixture of 4-(4-chloro-5-methylquinolin-2-yl)-2,3,4,5-tetrahydro-1,4-benzothiazepine 1,1-dioxide and 4-(4-chloro-7-methylquinolin-2-yl)-2,3,4,5-tetrahydro-1,4-benzothiazepine 1,1-dioxide (prepared in analogy to 4-(4-chloro-6-(trifluoromethoxy)quinolin-2-yl)-2,3,4,5-tetrahydro-1,4-benzothiazepine 1,1-dioxide in Example 17-1 by using a mixture of 2,4-dichloro-5-methylquinoline and 2,4-dichloro-7-methylquinoline and propane-1,3-diamine) was purified by preparative HPLC and SPE to give the pure title compounds N-[2-(1,1-dioxido-2,3-dihydro-1,4-benzothiazepin-4(5H)-yl)-5-methylquinolin-4-yl]propane-1,3-diamine and N-[2-(1,1-dioxido-2,3-dihydro-1,4-benzothiazepin-4(5H)-yl)-7-methylquinolin-4-yl]propane-1,3-diamine.

N-[2-(1,1-Dioxido-2,3-dihydro-1,4-benzothiazepin-4(5H)-yl)-5-methylquinolin-4-yl]propane-1,3-diamine, MS obsd. (ESI⁺) [(M+H)⁺] 411, ¹H NMR (400 MHz, CD₃OD) δ ppm 8.15-7.98 (d, J=7.6 Hz, 1 H), 7.85-7.80 (d, J=7.2 Hz, 1 H), 7.70-7.60 (q, J=6.4 Hz, 2 H), 7.55-7.48 (t, J=7.6 Hz, 2 H), 7.21-7.18 (d, J=6.8 Hz, 1 H), 5.87 (s, 1 H), 5.26 (s, 2 H), 4.70-4.40 (m, 2 H), 3.71-3.65 (t, J=2.8 Hz, 2 H), 3.58-3.50 (t, J=7.2 Hz, 2 H), 3.12-3.05 (t, J=7.6 Hz, 2 H), 2.82 (s, 3 H), 2.12-2.03 (m, 2 H).

N-[2-(1,1-Dioxido-2,3-dihydro-1,4-benzothiazepin-4(5H)-yl)-7-methylquinolin-4-yl]propane-1,3-diamine, MS obsd. (ESI⁺) [(M+H)⁺] 411, ¹H NMR (400 MHz, CD₃OD) δ ppm 8.10-8.02 (m, 1 H), 8.00-7.95 (d, J=8.8 Hz, 1 H), 7.88-7.81 (d, J=7.2 Hz, 1 H), 7.70-7.65 (t, J=1.2 Hz, 1 H), 7.57 (s, 1 H), 7.57-7.50 (t, J=16 Hz, 1 H), 7.30-7.22 (d, J=8.4 Hz, 1 H), 5.88 (s, 1 H), 5.29 (s, 2 H), 4.60-4.40 (m, 2 H), 3.72-3.68 (t, J=1.2 Hz, 2 H), 3.60-3.50 (t, J=2.8 Hz, 2 H), 3.10-3.02 (t, J=7.6 Hz, 2 H), 2.45 (s, 3 H), 2.11-2.02 (m, 2 H).

Example 17-8

N-{[3-(Aminomethyl)oxetan-3-yl]methyl}-2-(1,1-dioxido-2,3-dihydro-1,4-benzothiazepin-4(5H)-yl)-6-fluoroquinolin-4-amine

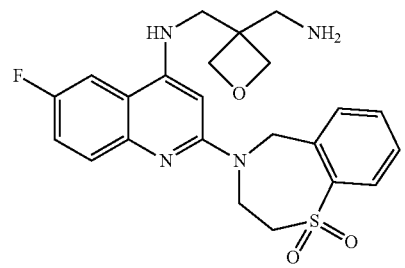 [SMILES: NCC1(CNc2cc(N3CCS(=O)(=O)c4ccccc4C3)nc3ccc(F)cc23)COC1]

The title compound was prepared in analogy to Example 17-1 in Scheme 6 by using 4-(4-chloro-8-fluoroquinolin-2-yl)-2,3,4,5-tetrahydro-1,4-benzothiazepine 1,1-dioxide (prepared in analogy to 4-(4-chloro-6-(trifluoromethoxy)quinolin-2-yl)-2,3,4,5-tetrahydro-1,4-benzothiazepine 1,1-dioxide in Example 17-1 by using 2,4-dichloro-8-fluoroquinoline and 2,3,4,5-tetrahydro-1,4-benzothiazepine 1,1-dioxide) and oxetane-3,3-diyldimethanamine. MS obsd. (ESI⁺) [(M+H)⁺] 457, ¹H NMR (400 MHz, CD₃OD) δ ppm 8.08 (d, J=7.2 Hz, 1 H), 8.03 (dd, J=2.4, 9.6 Hz, 1 H), 7.91-7.84 (m, 2 H), 7.70 (t, J=7.2 Hz, 1 H), 7.57 (t, J=7.6 Hz, 2 H), 6.23 (s, 1 H), 5.35 (s, 2 H), 4.63 (d, J=7.2 Hz, 2 H), 4.56-4.51 (m, 4 H), 3.92 (s, 2 H), 3.74 (s, 2 H), 3.47 (s, 2 H).

Example 18-1

N-[(3-Aminooxetan-3-yl)methyl]-6-methyl-2-(1-oxido-2,3-dihydro-1,4-benzothiazepin-4(5H)-yl)quinolin-4-amine

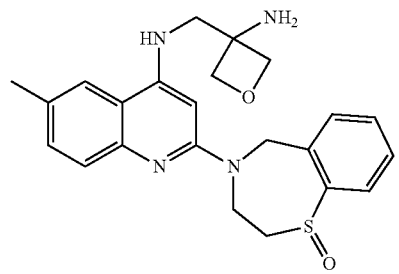 [SMILES: Cc1ccc2nc(N3CCS(=O)c4ccccc4C3)cc(NCC3(N)COC3)c2c1]

4-(4-Chloro-6-methylquinolin-2-yl)-2,3,4,5-tetrahydro-1,4-benzothiazepine 1-oxide

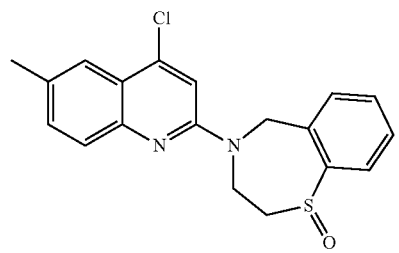 [SMILES: Cc1ccc2nc(N3CCS(=O)c4ccccc4C3)cc(Cl)c2c1]

The title compound was prepared in analogy to 4-(4-chloro-6-(trifluoromethoxy)quinolin-2-yl)-2,3,4,5-tetrahydro-1,4-benzothiazepine 1,1-dioxide in Example 17-1 in Scheme 6 by using 2,4-dichloro-6-methylquinoline and 2,3,4,5-tetrahydro-1,4-benzothiazepine 1-oxide. N-[(3-Aminooxetan-3-yl)methyl]-2-(1-oxido-2,3-dihydro-1,4-benzothiazepin-4(5H)-yl)-6-methylquinolin-4-amine

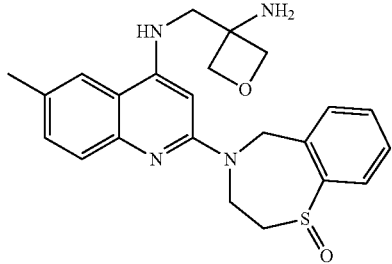 [SMILES: Cc1ccc2nc(N3CCS(=O)c4ccccc4C3)cc(NCC3(N)COC3)c2c1]

A mixture of 4-(4-chloro-6-methylquinolin-2-yl)-2,3,4,5-tetrahydro-1,4-benzothiazepine 1-oxide (2 g, 5.6 mmol), 3-aminomethyloxetan-3-ylamine (572 mg, 5.6 mmol), tri(dibenzylideneacetone)dipalladium(0) (256 mg, 0.28 mmol), 2,2'-bis(diphenylphosphino)-1,1'-binaphthalene (348.7 mg, 0.56 mmol), sodium tert-butoxide (1.08 g, 11.2 mmol) and toluene (20 mL) was heated with stirring in a 30 mL of sealed tube for 20 hours at 110° C. under nitrogen. The resulting mixture was diluted with ethyl acetate and washed with water. The organic layer was dried over sodium sulfate, filtered and concentrated in vacuo. The residue was purified by column chromatography on silica gel to give 1.5 g of the product as off-white foam.

Example 18-2 and Example 18-3

(+)-N-[(3-Aminooxetan-3-yl)methyl]-6-methyl-2-[1-oxido-2,3-dihydro-1,4-benzothiazepin-4(5H)-yl]quinolin-4-amine and (−)-N-[(3-aminooxetan-3-yl)methyl]-6-methyl-2-[1-oxido-2,3-dihydro-1,4-benzothiazepin-4(5H)-yl]quinolin-4-amine

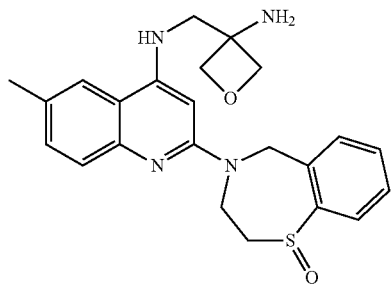
(+)

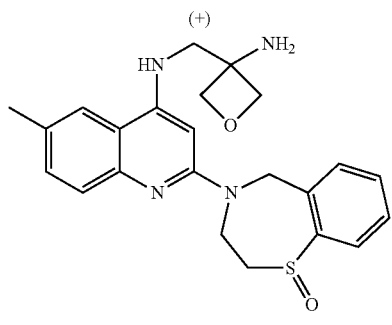
(−)

The chiral separation of Example 18-1 (column: IA; flow rate: 15 mL/min; gradient: 50% hexane in ethanol with 0.4% of triethylamine) gives (+)-N-[(3-aminooxetan-3-yl)methyl]-6-methyl-2-[1-oxido-2,3-dihydro-1,4-benzothiazepin-4(5H)-yl]quinolin-4-amine, MS obsd. (ESI⁺) [(M+H)⁺] 423, ¹H NMR (400 MHz, CD₃OD) δ ppm 7.74 (d, J=7.6 Hz, 1 H), 7.70-7.66 (m, 2 H), 7.48-7.43 (m, 2 H), 7.39 (t, J=7.2 Hz, 1 H), 7.29 (dd, J=1.6, 8.4 Hz, 1 H), 6.16 (s, 1 H), 5.21 (d, J=16.0 Hz, 1 H), 4.72 (brs, 2 H), 4.62 (d, J=6.8 Hz, 2 H), 4.57 (dd, J=2.4, 6.4 Hz, 2 H), 4.43 (brs, 1 H), 3.66 (s, 2 H), 3.42 (m, 2 H), 2.41 (s, 3 H); and (−)-N-[(3-aminooxetan-3-yl)methyl]-6-methyl-2-[1-oxido-2,3-dihydro-1,4-benzothiazepin-4(5H)-yl]quinolin-4-amine, MS obsd. (ESI⁺) [(M+H)⁺] 423, ¹H NMR (400 MHz, CD₃OD) δ ppm 7.70 (d, J=7.6 Hz, 1 H), 7.65 (m, 2 H), 7.47-7.38 (m, 2 H), 7.33 (t, J=7.2 Hz, 1 H), 7.27 (dd, J=1.6, 8.4 Hz, 1 H), 6.12 (s, 1 H), 5.15 (d, J=16.0 Hz, 1 H), 4.64 (brs, 2 H), 4.60 (d, J=6.4 Hz, 2 H), 4.55 (dd, J=2.8, 6.4 Hz, 2 H), 4.43 (brs, 1 H), 3.63 (s, 2 H), 3.34 (m, 2 H), 2.38 (s, 3 H).

Example 18-4

N-[(3-Aminooxetan-3-yl)methyl]-6-chloro-2-(1-oxido-2,3-dihydro-1,4-benzothiazepin-4 (5H)-yl)quinolin-4-amine

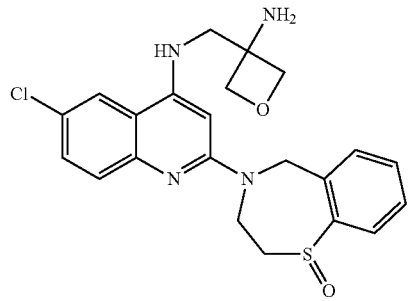 [SMILES: NC1(CNc2cc(N3CCS(=O)c4ccccc4C3)nc3ccc(Cl)cc23)COC1]

The title compound was prepared in analogy to Example 18-1 in Scheme 6 by using 4-(4,6-dichloroquinolin-2-yl)-2,3,4,5-tetrahydro-1,4-benzothiazepine 1-oxide (prepared in analogy to 4-(4-chloro-6-methylquinolin-2-yl)-2,3,4,5-tetrahydro-1,4-benzothiazepine 1-oxide in Example 18-1 by using 2,4,6-trichloroquinoline and 2,3,4,5-tetrahydro-1,4-benzothiazepine 1-oxide) and 3-aminomethyloxetan-3-ylamine. MS obsd. (ESI⁺) [(M+H)⁺] 443, ¹H NMR (400 MHz, CD₃OD) δ ppm 7.94 (d, J=2.02 Hz, 1 H), 7.77 (d, J=7.83 Hz, 1 H), 7.71 (d, J=8.59 Hz, 1 H), 7.52-7.34 (m, 4 H), 6.22 (s, 1 H), 5.25 (d, J=15.92 Hz, 2 H), 4.78 (brs, 2 H), 4.65-4.52 (m, 4 H), 3.66 (s, 2 H), 3.47-3.38 (m, 2 H).

Example 18-5

N-[2-(1-Oxido-2,3-dihydro-1,4-benzothiazepin-4(5H)-yl)-6-methylquinolin-4-yl]-2,2-difluoropropane-1,3-diamine

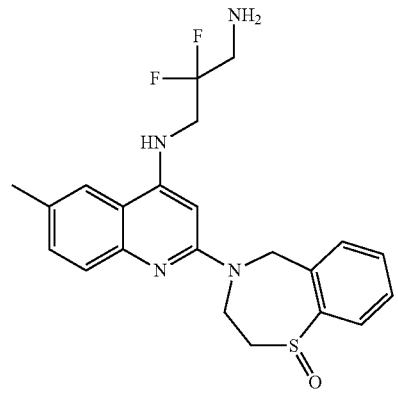 [SMILES: Cc1ccc2nc(N3CCS(=O)c4ccccc4C3)cc(NCC(F)(F)CN)c2c1]

The title compound was prepared in analogy to Example 18-1 in Scheme 6 by using 4-(4-chloro-6-methylquinolin-2-yl)-2,3,4,5-tetrahydro-1,4-benzothiazepine 1-oxide (prepared in analogy to the one in Example 18-1) and 2,2-difluoropropane-1,3-diamine. MS obsd. (ESI⁺) [(M+H)⁺] 431, ¹H NMR (400 MHz, CD₃OD) δ ppm 7.93 (s, 1 H), 7.81-7.79 (m, 1 H), 7.76-7.74 (d, 2 H), 7.62-7.52 (m, 3 H), 6.25 (s, 1 H), 5.45-5.41 (d, 1 H), 5.05 (d, 1 H), 4.75 (m, 1 H), 4.45 (m, 1 H), 4.23-4.16 (m, 2 H), 3.72-3.64 (t, 2 H), 3.50 (m, 2 H), 2.47 (s, 3 H).

Example 18-6

N-[6-Chloro-2-(1-oxido-2,3-dihydro-1,4-benzothiazepin-4(5H)-yl)quinolin-4-yl]-2,2-difluoropropane-1,3-diamine

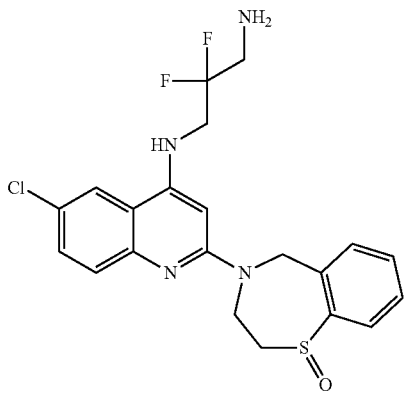 [SMILES: NCC(F)(F)CNc1cc(N2CCS(=O)c3ccccc3C2)nc2ccc(Cl)cc12]

The title compound was prepared in analogy to Example 18-1 in Scheme 6 by using 4-(4,6-dichloroquinolin-2-yl)-2,3,4,5-tetrahydro-1,4-benzothiazepine 1-oxide (prepared in analogy to 4-(4-chloro-6-methylquinolin-2-yl)-2,3,4,5-tetrahydro-1,4-benzothiazepine 1-oxide in Example 18-1 by using 2,4,6-trichloroquinoline and 2,3,4,5-tetrahydro-1,4-benzothiazepine 1-oxide) and 2,2-difluoropropane-1,3-diamine. MS obsd. (ESI⁺) [(M+H)⁺] 451, ¹H NMR (400 MHz, CD₃OD) δ ppm 8.21 (s, 1 H), 7.86-7.81 (m, 2 H), 7.77-7.74 (m, 2 H), 7.58 (m, 2 H), 6.32 (s, 1 H), 5.45 (d, 1 H), 5.05 (d, 1 H), 4.75 (m, 1 H), 4.48 (m, 1 H), 4.20 (m, 2 H), 3.68 (t, 2 H), 3.50 (m, 2 H).

Example 18-7

N-[6-Chloro-2-(1-oxido-2,3-dihydro-1,4-benzothiazepin-4(5H)-yl)quinolin-4-yl]ethane-1,2-diamine

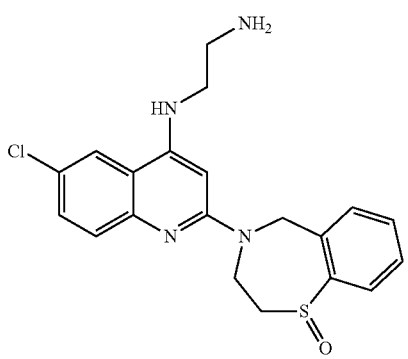 [SMILES: NCCNc1cc(N2CCS(=O)c3ccccc3C2)nc2ccc(Cl)cc12]

The title compound was prepared in analogy to Example 18-1 in Scheme 6 by using 4-(4,6-dichloroquinolin-2-yl)-2,3,4,5-tetrahydro-1,4-benzothiazepine 1-oxide (prepared in analogy to 4-(4-chloro-6-methylquinolin-2-yl)-2,3,4,5-tetrahydro-1,4-benzothiazepine 1-oxide in Example 18-1 by using 2,4,6-trichloroquinoline and 2,3,4,5-tetrahydro-1,4-benzothiazepine 1-oxide) and ethane-1,3-diamine. MS obsd. (ESI⁺) [(M+H)⁺] 401, ¹H NMR (400 MHz, CD₃OD) δ ppm 7.91 (d, J=2.0 Hz, 1 H), 7.76-7.74 (d, J=7.8 Hz, 2 H), 7.53-7.38 (m, 4 H), 6.10 (s, 1 H), 5.29-5.25 (d, J=15.2 Hz, 1 H), 4.62 (s, 3 H), 3.57 (m, 4 H), 3.19-3.10 (m, 2 H).

Example 18-8

N-{[3-(Aminomethyl)oxetan-3-yl]methyl}-6-methyl-2-(1-oxido-2,3-dihydro-1,4-benzothiazepin-4(5H)-yl)quinolin-4-amine

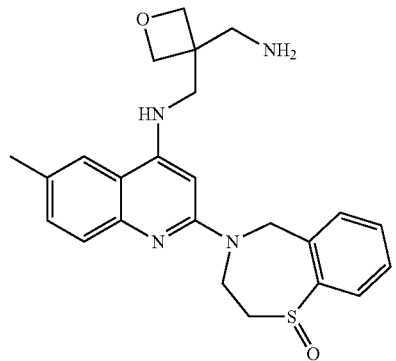 [SMILES: Cc1ccc2nc(N3CCS(=O)c4ccccc4C3)cc(NCC3(CN)COC3)c2c1]

The title compound was prepared in analogy to Example 18-1 in Scheme 6 by using 4-(4-chloro-6-methylquinolin-2-yl)-2,3,4,5-tetrahydro-1,4-benzothiazepine 1-oxide (prepared in analogy to the one in Example 18-1) and oxetane-3,3-diyldimethanamine. MS obsd. (ESI⁺) [(M+H)⁺] 437, ¹H NMR (400 MHz, CD₃OD) δ ppm 8.11 (s, 1 H), 7.86-7.75 (m, 3 H), 7.59-7.51 (m, 3 H), 7.67 (t, J=3.6 Hz, 1 H), 7.57 (d, J=2.1 Hz, 1 H), 6.22 (s, 1 H), 5.45 (d, J=16.4 Hz, 1 H), 5.10 (brs, 1 H), 4.76 (brs, 1 H), 4.60 (m, 4 H), 3.94 (d, 2 H), 4.52 (s, 2 H), 3.47 (s, 2 H), 2.46 (s, 3 H).

Example 18-9

N-{[3-(Aminomethyl)oxetan-3-yl]methyl}-6-chloro-2-(1-oxido-2,3-dihydro-1,4-benzothiazepin-4(5H)-yl)quinolin-4-amine

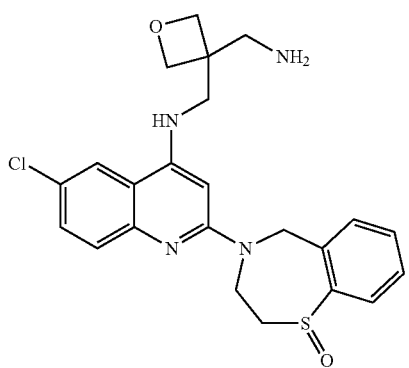 [SMILES: NCC1(CNc2cc(N3CCS(=O)c4ccccc4C3)nc3ccc(Cl)cc23)COC1]

The title compound was prepared in analogy to Example 18-1 in Scheme 6 by using 4-(4,6-dichloroquinolin-2-yl)-2, 3,4,5-tetrahydro-1,4-benzothiazepine 1-oxide (prepared in analogy to 4-(4-chloro-6-methylquinolin-2-yl)-2,3,4,5-tetrahydro-1,4-benzothiazepine 1-oxide in Example 18-1 by using 2,4,6-trichloroquinoline and 2,3,4,5-tetrahydro-1,4-benzothiazepine 1-oxide) and oxetane-3,3-diyldimethanamine. MS obsd. (ESI$^+$) [(M+H)$^+$] 457, $^1$H NMR (400 MHz, CD$_3$OD) δ ppm 8.31 (d, 1 H), 7.85-7.74 (m, 4 H), 7.60-7.55 (m, 2 H), 6.22 (s, 1 H), 5.45 (d, 1 H), 5.11 (d, 1 H), 4.68 (brs, 1 H), 4.65-4.56 (m, 4 H), 4.47 (d, 1 H), 3.91 (m, 2 H), 3.55 (m, 2 H), 3.47 (s, 2 H).

Example 18-10

N-[6-Methyl-2-(1-oxido-2,3-dihydro-1,4-benzothiazepin-4(5H)-yl)quinolin-4-yl]ethane-1,2-diamine

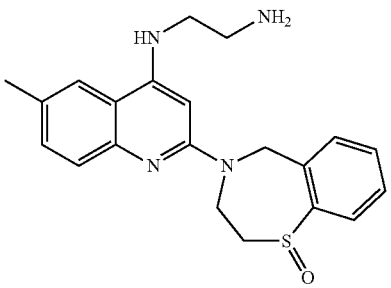 [SMILES: Cc1ccc2nc(N3CCS(=O)c4ccccc4C3)cc(NCCN)c2c1]

The title compound was prepared in analogy to Example 18-1 in Scheme 6 by using 4-(4-chloro-6-methylquinolin-2-yl)-2,3,4,5-tetrahydro-1,4-benzothiazepine 1-oxide (prepared in analogy to the one in Example 18-1) and ethane-1,2-amine. MS obsd. (ESI$^+$) [(M+H)$^+$] 381, $^1$H NMR (400 MHz, CD$_3$OD) δ ppm 7.89 (s, 1 H), 7.81-7.76 (m, 2 H), 7.73-7.70 (m, 1 H), 7.59-7.49 (m, 3 H), 6.02 (s, 1 H), 5.44-5.40 (m, 1 H), 5.04-5.01 (m, 1 H), 4.75-4.71 (m, 1 H), 4.48-4.44 (m, 1 H), 3.84-3.81 (t, 2 H), 3.51 (s, 2 H), 3.33-3.28 (m, 2 H), 2.45 (s, 3 H).

Example 18-11

2-{[6-Methyl-2-(1-oxido-2,3-dihydro-1,4-benzothiazepin-4(5H)-yl)quinolin-4-yl]amino}ethanol

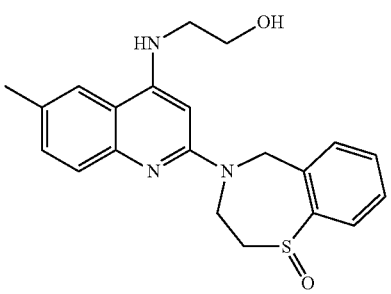 [SMILES: Cc1ccc2nc(N3CCS(=O)c4ccccc4C3)cc(NCCO)c2c1]

The title compound was prepared in analogy to Example 18-1 in Scheme 6 by using 4-(4-chloro-6-methylquinolin-2-yl)-2,3,4,5-tetrahydro-1,4-benzothiazepine 1-oxide (prepared in analogy to the one in Example 18-1) and 2-aminoethanol. MS obsd. (ESI$^+$) [(M+H)$^+$] 382, $^1$H NMR (400 MHz, CD$_3$OD) δ ppm 7.92 (s, 1 H), 7.85-7.80 (d, J=8.4 Hz, 1 H), 7.80-7.75 (d, J=7.6 Hz, 1 H), 7.75-7.70 (d, J=7.2 Hz, 1 H), 7.61-7.50 (m, 3 H), 6.10 (s, 1 H), 5.48-5.39 (m, 1 H), 5.08-4.95 (m, 1 H), 4.80-4.70 (m, 1 H), 4.52-4.42 (m, 1 H), 3.88-3.80 (t, J=5.6 Hz, 2 H), 3.65-3.60 (t, J=5.6 Hz, 2 H), 3.59-3.40 (m, 2 H), 2.46 (s, 3 H).

Example 19-1 trans-4-Amino-1-[6-methyl-2-(1-oxido-2,3-dihydro-1,4-benzothiazepin-4(5H)-yl)quinolin-4-yl]pyrrolidin-3-ol

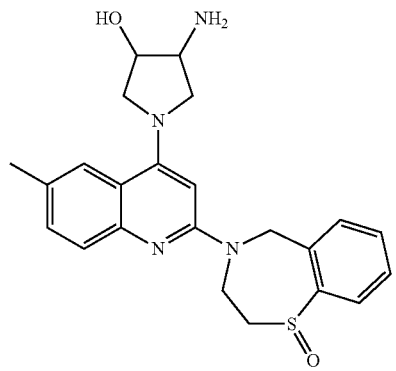 [SMILES: Cc1ccc2nc(N3CCS(=O)c4ccccc4C3)cc(N3CC(N)C(O)C3)c2c1]

tert-Butyl {trans-1-[6-methyl-2-(1-oxido-2,3-dihydro-1,4-benzothiazepin-4(5H)-yl)quinolin-4-yl]-4-hydroxypyrrolidin-3-yl}carboxylate

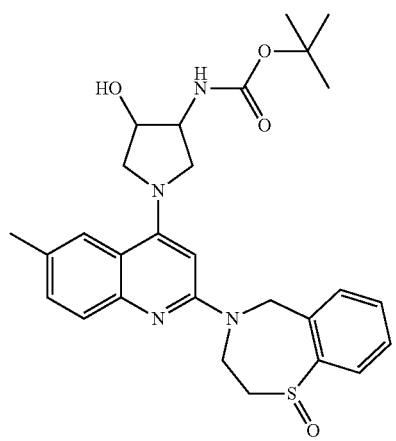 [SMILES: Cc1ccc2nc(N3CCS(=O)c4ccccc4C3)cc(N3CC(O)C(NC(=O)OC(C)(C)C)C3)c2c1]

A mixture of 4-(4-chloro-6-methylquinolin-2-yl)-2,3,4,5-tetrahydro-1,4-benzothiazepine 1-oxide (200 mg, 0.56 mmol, prepared in analogy to the one in Example 18-1), tert-butyl [trans-4-hydroxypyrrolidin-3-yl]carbamate (125 mg, 0.62 mmol), tris(2-benzylidene acetone) palladium(II) (50 mg, 0.055 mmol), 2-dicyclohexylphosphino-2-(N,N-dimethylamino)biphenyl (30 mg, 0.076 mmol), sodium tert-butoxide (60 mg, 0.625 mmol) and 1,4-dioxane (3 mL) in a 2-5 mL of process vial was heated at 120° C. under microwave irradiation for 2 hours. After being cooled to room temperature, the mixture was filtered and washed with ethyl acetate. The filtrate was washed with brine, dried over sodium sulfate, and concentrated in vacuo. The residue was purified by flash column chromatography (eluting with 10% methanol in dichloromethane) to afford 230 mg of the product as a white solid (yield was 80%).

trans-4-Amino-1-[6-methyl-2-(1-oxido-2,3-dihydro-1,4-benzothiazepin-4(5H)-yl)quinolin-4-yl]pyrrolidin-3-ol

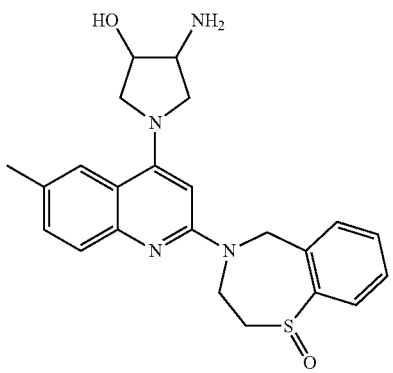 [SMILES: Cc1ccc2nc(N3CCS(=O)c4ccccc4C3)cc(N3CC(N)C(O)C3)c2c1]

To a solution of tert-butyl {trans-1-[6-methyl-2-(1-oxido-2,3-dihydro-1,4-benzothiazepin-4(5H)-yl)quinolin-4-yl]-4-hydroxypyrrolidin-3-yl}carboxylate (230 mg, 0.54 mmol) in dichloromethane (5 mL) was added trifluoroacetic acid (2 mL). After being stirred at room temperature for 3 hours, the resulting mixture was concentrated in vacuo. The residue was purified by preparative HPLC to afford the pure product as a solid. MS obsd. (ESI$^+$) [(M+H)$^+$] 423, $^1$H NMR (400 MHz, CD$_3$OD) δ ppm 7.95 (s, 1 H), 7.80-7.76 (d, J=7.2 Hz, 1 H), 7.76-7.70 (m, 2 H), 7.60-7.52 (m, 2 H), 7.52-7.43 (m, 1 H), 5.91 (s, 1 H), 5.42-5.30 (m, 1 H), 5.02-4.90 (m, 1 H), 4.80-4.68 (m, 1 H), 4.56-4.50 (m, 1 H), 4.50-4.20 (m, 3 H), 3.96-3.88 (m, 1 H), 3.86-3.80 (m, 1 H), 3.80-3.70 (m, 1 H), 3.56-3.38 (m, 2 H), 2.43 (s, 3 H).

Example 19-2

(1R,5S,6S)-3-[2-(1,1-Dioxido-2,3-dihydro-1,4-benzothiazepin-4(5H)-yl)-6-methylquinolin-4-yl]-3-azabicyclo[3.1.0]hexan-6-amine

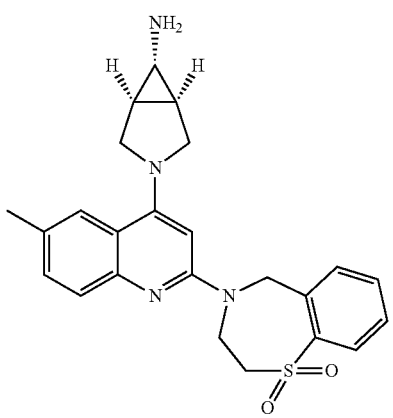 [SMILES: Cc1ccc2nc(N3CCS(=O)(=O)c4ccccc4C3)cc(N3C[C@@H]4[C@@H](N)[C@@H]4C3)c2c1]

The title compound was prepared in analogy to Example 19-1 in Scheme 7 by using 4-(4-chloro-6-methylquinolin-2-yl)-2,3,4,5-tetrahydro-1,4-benzothiazepine 1,1-dioxide (prepared in analogy to 4-(4-chloro-6-(trifluoromethoxy)quinolin-2-yl)-2,3,4,5-tetrahydro-1,4-benzothiazepine 1,1-dioxide in Example 17-1 by using 2,4-dichloro-6-methylquinoline and 2,3,4,5-tetrahydro-1,4-benzothiazepine 1,2-dioxide) and tert-butyl (1R,5S,6S)-3-azabicyclo[3.1.0]hex-6-ylcarbamate. MS obsd. (ESI$^+$) [(M+H)$^+$] 435, $^1$H NMR (400 MHz, CD$_3$OD) δ ppm 7.98 (dd, J=7.83, 1.01 Hz, 1 H), 7.82 (d, J=7.07 Hz, 1 H), 7.71-7.56 (m, 2 H), 7.51-7.39 (m, 2 H), 7.27 (dd, J=8.59, 1.77 Hz, 1 H), 6.31 (s, 1 H), 5.15 (s, 2 H), 4.56 (brs, 2 H), 3.83 (d, J=9.60 Hz, 2 H), 3.58 (t, J=4.93 Hz, 2 H), 3.38 (d, J=9.60 Hz, 2 H), 2.55 (s, 1 H), 2.40 (s, 3 H), 1.76-1.62 (m, 2 H).

Example 19-3 trans-4-Amino-1-[2-(1,1-dioxido-2,3-dihydro-1,4-benzothiazepin-4(5H)-yl)-6-methylquinolin-4-yl]pyrrolidin-3-ol

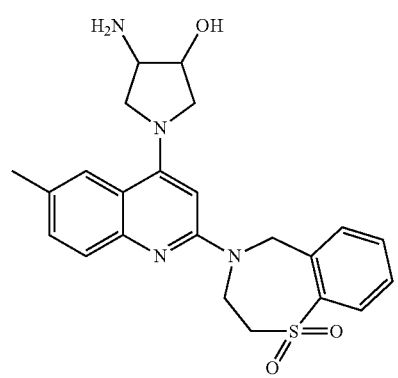 [SMILES: Cc1ccc2nc(N3CCS(=O)(=O)c4ccccc4C3)cc(N3CC(N)C(O)C3)c2c1]

The title compound was prepared in analogy to Example 19-1 in Scheme 7 by using 4-(4-chloro-6-methylquinolin-2-yl)-2,3,4,5-tetrahydro-1,4-benzothiazepine 1,1-dioxide (prepared in analogy to 4-(4-chloro-6-(trifluoromethoxy)quinolin-2-yl)-2,3,4,5-tetrahydro-1,4-benzothiazepine 1,1-dioxide in Example 17-1 by using 2,4-dichloro-6-methylquinoline and 2,3,4,5-tetrahydro-1,4-benzothiazepine 1,2-dioxide) and tert-butyl trans-(4-hydroxypyrrolidin-3-yl)carbamate. MS obsd. (ESI$^+$) [(M+H)$^+$] 439, $^1$H NMR (400 MHz, CD$_3$OD) δ ppm 7.92-7.83 (m, 2 H), 7.76 (s, 1 H), 7.67-7.59 (m, 1 H), 7.47 (t, J=7.45 Hz, 1 H), 7.37 (d, J=8.59 Hz, 1 H), 7.23 (dd, J=8.46, 1.39 Hz, 1 H), 6.03 (s, 1 H), 5.18-4.96 (m, 3 H), 4.41 (brs, 2 H), 4.04-3.83 (m, 3 H), 3.62 (t, J=4.80 Hz, 2 H), 3.35-3.25 (d, J=9.85 Hz, 2 H), 2.35 (s, 3 H).

Example 19-4

1-[6-Methyl-2-(1-oxido-2,3-dihydro-1,4-benzothiazepin-4(5H)-yl)quinolin-4-yl]pyrrolidin-3-amine

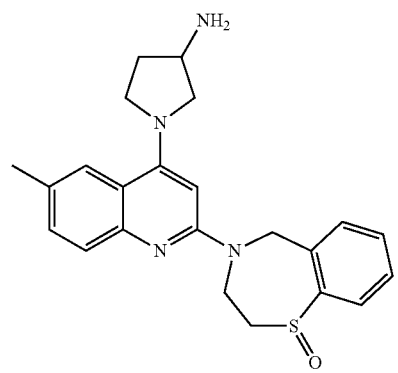 [SMILES: Cc1ccc2nc(N3CCS(=O)c4ccccc4C3)cc(N3CCC(N)C3)c2c1]

The title compound was prepared in analogy to Example 19-1 in Scheme 7 by using 4-(4-chloro-6-methylquinolin-2-yl)-2,3,4,5-tetrahydro-1,4-benzothiazepine 1-oxide (prepared in analogy to the one in Example 18-1) and tert-butyl pyrrolidin-3-ylcarbamate. MS obsd. (ESI⁺) [(M+H)⁺] 407, ¹H NMR (400 MHz, CD₃OD) δ ppm 7.81 (s, 1 H), 7.71 (t, J=8.21 Hz, 2 H), 7.57-7.36 (m, 3 H), 7.27 (dd, J=8.59, 1.77 Hz, 1 H), 6.11 (s, 1 H), 5.21 (d, J=16.17 Hz, 1 H), 4.76 (d, J=15.92 Hz, 2 H), 4.50 (brs, 1 H), 3.88-3.71 (m, 2 H), 3.71-3.53 (m, 2 H), 3.53-3.36 (m, 3 H), 2.40 (s, 3 H), 2.26 (dq, J=12.63, 6.23 Hz, 1 H), 1.98-1.78 (m, 1 H).

Example 19-5 trans-1-[6-Chloro-2-(1,1-dioxido-2,3-dihydro-1,4-benzothiazepin-4(5H)-yl)quinolin-4-yl]-4-fluoropyrrolidin-3-amine

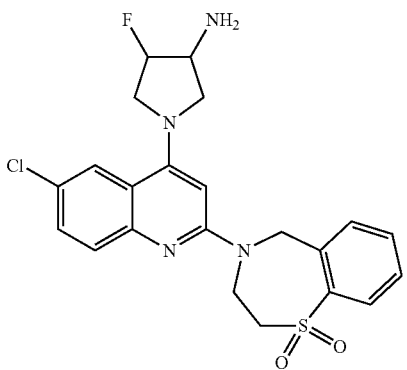 [SMILES: NC1CN(c2cc(N3CCS(=O)(=O)c4ccccc4C3)nc3ccc(Cl)cc23)CC1F]

The title compound was prepared in analogy to Example 19-1 in Scheme 7 by using 4-(4,6-dichloroquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1) and tert-butyl trans-(4-fluoropyrrolidin-3-yl)carbamate. MS obsd. (ESI⁺) [(M+H)⁺] 461, ¹H NMR (400 MHz, CD₃OD) δ ppm 8.03-7.96 (m, 2 H), 7.86 (d, J=7.58 Hz, 1 H), 7.63 (td, J=7.45, 1.26 Hz, 1 H), 7.54 (d, J=9.09 Hz, 1 H), 7.46 (td, J=7.71, 1.01 Hz, 1 H), 7.39 (dd, J=9.09, 2.27 Hz, 1 H), 6.25 (s, 1 H), 5.14-5.25 (m, 2 H), 5.05 (brs, 1 H), 4.55 (brs, 2 H), 4.18-4.27 (dd, J=12.25, 3.92 Hz, 1 H), 4.01 (dd, J=8.97, 5.18 Hz, 1 H), 3.78-3.55 (m, 4 H), 3.40-3.30 (m, 1 H).

Example 19-6 trans-4-Amino-1-[6-chloro-2-(1,1-dioxido-2,3-dihydro-1,4-benzothiazepin-4(5 H)-yl)quinolin-4-yl]pyrrolidin-3-ol

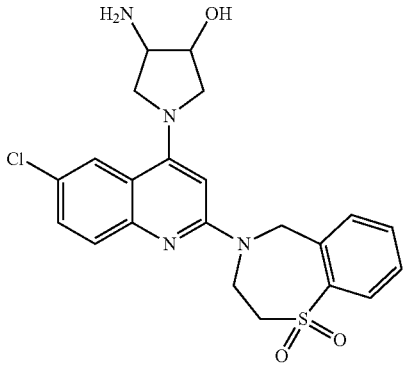 [SMILES: NC1CN(c2cc(N3CCS(=O)(=O)c4ccccc4C3)nc3ccc(Cl)cc23)CC1O]

The title compound was prepared in analogy to Example 19-1 in Scheme 7 by using 4-(4,6-dichloroquinolin-2-yl)-2,3,4,5-tetrahydro-1,4-benzothiazepine 1,1-dioxide (prepared in analogy to 4-(4-chloro-6-(trifluoromethoxy)quinolin-2-yl)-2,3,4,5-tetrahydro-1,4-benzothiazepine 1,1-dioxide in Example 17-1 by using 2,4,6-trichloro-quinoline and 2,3,4,5-tetrahydro-1,4-benzothiazepine 1,2-dioxide) and tert-butyl (trans-4-hydroxypyrrolidin-3-yl)carbamate. MS obsd. (ESI⁺) [(M+H)⁺] 459, ¹H NMR (400 MHz, CD₃OD) δ ppm 8.03-7.96 (m, 2 H), 7.85 (d, J=7.33 Hz, 1 H), 7.66-7.60 (m, 1 H), 7.53 (d, J=9.09 Hz, 1 H), 7.49-7.42 (m, 1 H), 7.38 (dd, J=8.97, 2.15 Hz, 1 H), 6.20 (s, 1 H), 5.18 (brs, 2 H), 4.70-4.40 (b, 2 H), 4.21 (brs, 1 H), 4.10 (dd, J=10.74, 4.93 Hz, 1 H), 3.97 (dd, J=9.60, 5.56 Hz, 1 H), 3.59 (d, J=3.28 Hz, 2 H), 3.54-3.49 (m, 1 H), 3.48-3.39 (m, 2 H).

Example 19-7 trans-1-[6-Chloro-2-(1-oxido-2,3-dihydro-1,4-benzothiazepin-4(5H)-yl)quinolin-4-yl]-4-fluoropyrrolidin-3-amine

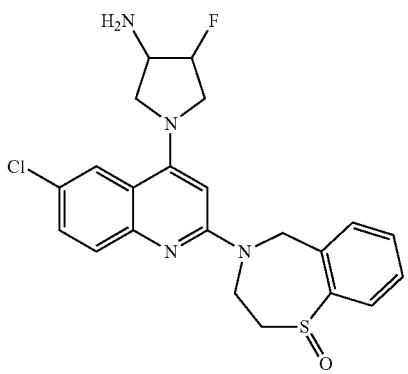 [SMILES: NC1CN(c2cc(N3CCS(=O)c4ccccc4C3)nc3ccc(Cl)cc23)CC1F]

The title compound was prepared in analogy to Example 19-1 in Scheme 7 by using 4-(4,6-dichloroquinolin-2-yl)-2,3,4,5-tetrahydro-1,4-benzothiazepine 1-oxide (prepared in analogy to 4-(4-chloro-6-methylquinolin-2-yl)-2,3,4,5-tetrahydro-1,4-benzothiazepine 1-oxide in Example 18-1) and tert-butyl (trans-4-fluoropyrrolidin-3-yl)carbamate. MS obsd. (ESI⁺) [(M+H)⁺] 445, ¹H NMR (400 MHz, CD₃OD) δ ppm 7.98 (d, J=2.27 Hz, 1 H), 7.78-7.68 (m, 2 H), 7.55 (dd, J=9.09, 1.52 Hz, 1 H), 7.52-7.42 (m, 2 H), 7.39 (dd, J=9.09, 2.27 Hz, 1 H), 6.28-6.21 (m, 1 H), 5.25 (d, J=15.66 Hz, 1 H), 5.10-4.95 (m, 1 H), 4.90-4.54 (m, 2 H), 4.65-4.40 (m, 1 H), 4.30-4.10 (m, 1 H), 4.05-3.59 (m, 1 H), 3.55-3.51 (m, 2 H), 3.40-3.35 (m, 3 H).

Example 19-8

2-[2-(1,1-Dioxido-2,3-dihydro-1,4-benzothiazepin-4(5H)-yl)-6-methylquinolin-4-yl]-2-azabicyclo[2.1.1]hexan-5-amine

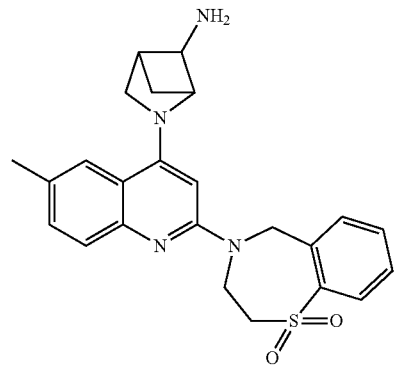 [SMILES: Cc1ccc2nc(N3CCS(=O)(=O)c4ccccc4C3)cc(N3CC4CC3C4N)c2c1]

The title compound was prepared in analogy to Example 19-1 in Scheme 7 by using 4-(4-chloro-6-methylquinolin-2-yl)-2,3,4,5-tetrahydro-1,4-benzothiazepine 1,1-dioxide (prepared in analogy to 4-(4-chloro-6-(trifluoromethoxy)quinolin-2-yl)-2,3,4,5-tetrahydro-1,4-benzothiazepine 1,1-dioxide in Example 17-1 by using 2,4-dichloro-6-methylquinoline and 2,3,4,5-tetrahydro-1,4-benzothiazepine 1,2-dioxide) and tert-butyl 2-azabicyclo[2.1.1]hex-5-ylcarbamate. MS obsd. (ESI$^+$) [(M+H)$^+$] 435, $^1$H NMR (400 MHz, CD$_3$OD) δ ppm 7.99 (dd, J=7.83, 1.01 Hz, 1 H), 7.86-7.74 (m, 2 H), 7.61 (td, J=7.58, 1.26 Hz, 1 H), 7.54-7.39 (m, 2 H), 7.33 (dd, J=8.59, 1.77 Hz, 1 H), 6.43 (s, 1 H), 5.22-5.06 (m, 2 H), 4.38 (d, J=6.32 Hz, 1 H), 3.95 (d, J=8.59 Hz, 1 H), 3.67-3.52 (m, 2 H), 3.42-3.35 (m, 1 H), 3.05 (d, J=8.59 Hz, 1 H), 2.91-2.77 (m, 1 H), 2.45 (s, 3 H), 1.67 (d, J=7.83 Hz, 1 H), 1.39-1.26 (m, 2 H), 1.19 (d, J=7.83 Hz, 1 H).

Example 20-1

2-(8-Methoxy-1,1-dioxido-2,3-dihydro-1,4-benzothiazepin-4(5H)-yl)-6-methylquinolin-4-amine

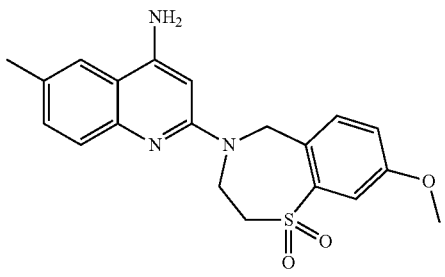

tert-Butyl [2-(8-Methoxy-1,1-dioxido-2,3-dihydro-1,4-benzothiazepin-4(5H)-yl)-6-methylquinolin-4-yl]carbamate

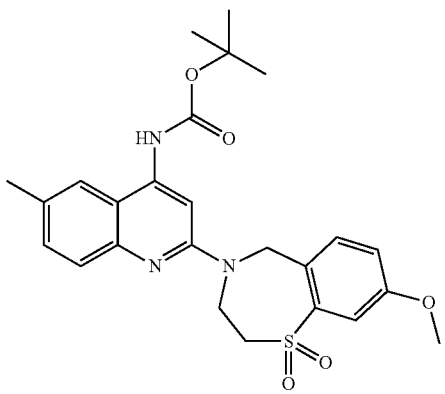

A mixture solution of 4-(4-chloro-6-methylquinolin-2-yl)-8-methoxy-2,3,4,5-tetrahydro-1,4-benzothiazepine 1,1-dioxide (60.0 mg, 0.15 mmol, prepared in analogy to 4-(4-chloro-6-(trifluoromethoxy)quinolin-2-yl)-2,3,4,5-tetrahydro-1,4-benzothiazepine 1,1-dioxide in Example 17-1 by using 2,4-dichloro-6-methylquinoline and 8-methoxy-2,3,4,5-tetrahydro-1,4-benzothiazepine 1,2-dioxide), tert-butyl carbamate (45.0 mg, 0.37 mmol), 1,1'-bis(diphenylphosphino)ferrocene (11.2 mg, 0.02 mmol), 1,1'-bis(diphenylphosphino)ferrocenedichloropalladium(II) (15.0 mg, 0.02 mmol), and sodium tert-butoxide (75.0 mg, 0.72 mmol) in 1,4-dioxane (2.0 mL) was heated with stirring at 120° C. for 2 hours. After being cooled to room temperature, the reaction mixture was extracted with ethyl acetate (100 mL), washed with brine (50 mL×2), dried over anhydrous sodium sulfate and concentrated in vacuo to afford 59.9 mg of the crude product as yellow oil. MS obsd. (ESI$^+$) [(M+H)$^+$] 484.

2-(8-Methoxy-1,1-dioxido-2,3-dihydro-1,4-benzothiazepin-4(5H)-yl)-6-methylquinolin-4-amine

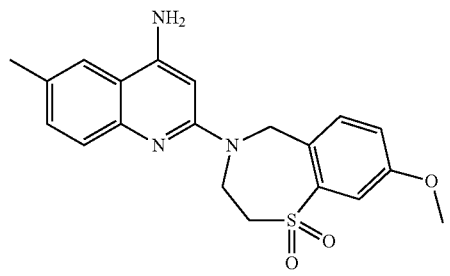

A mixture solution of tert-butyl [2-(8-methoxy-1,1-dioxido-2,3-dihydro-1,4-benzothiazepin-4(5H)-yl)-6-methylquinolin-4-yl]carbamate (59.0 mg, 0.12 mmol) and trifluoroacetic acid (0.5 mL) in dichloromethane (2.0 mL) was stirred at room temperature for 6 hours. Then the reaction mixture was extracted with ethyl acetate (100 mL). The organic layer was washed with brine (50 mL×2), dried over anhydrous sodium sulfate and then concentrated in vacuo. The residue was purified by preparative HPLC to afford 10.2 mg of the product as a white solid (yield was 21.5%). MS obsd. (ESI$^+$) [(M+H)$^+$] 384, $^1$H NMR (400 MHz, CD$_3$OD) δ ppm 7.72 (d, J=8.34 Hz, 1 H), 7.58 (s, 1 H), 7.50 (d, J=2.78 Hz, 1 H), 7.43 (d, J=8.34 Hz, 1 H), 7.29 (dd, J=8.46, 1.89 Hz, 1 H), 7.12 (dd, J=8.34, 2.78 Hz, 1 H), 6.27 (s, 1 H), 5.02 (s, 2 H), 4.47 (brs, 2 H), 3.82 (s, 3 H), 3.56 (t, J=4.80 Hz, 2 H), 2.42 (s, 3 H).

Example 20-2

2-(7-Methoxy-1,1-dioxido-2,3-dihydro-1,4-benzothiazepin-4(5H)-yl)-6-methylquinolin-4-amine

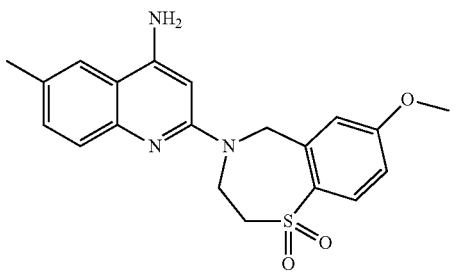

The title compound was prepared in analogy to Example 20-1 in Scheme 7 by using 4-(4-chloro-6-methylquinolin-2-yl)-7-methoxy-2,3,4,5-tetrahydro-1,4-benzothiazepine 1,1-dioxide (prepared in analogy to 4-(4-chloro-6-(trifluoromethoxy)quinolin-2-yl)-2,3,4,5-tetrahydro-1,4-benzothiazepine 1,1-dioxide in Example 17-1 by using 2,4-dichloro-6-methylquinoline and 7-methoxy-2,3,4,5-tetrahydro-1,4-benzothiazepine 1,2-dioxide) and tert-butyl carbamate. MS obsd. (ESI⁺) [(M+H)⁺] 384, ¹H NMR (400 MHz, CD₃OD) δ ppm 7.87 (d, J=8.84 Hz, 1 H), 7.59 (s, 1 H), 7.44 (d, J=8.59 Hz, 1 H), 7.35 (d, J=2.53 Hz, 1 H), 7.30 (dd, J=8.59, 1.77 Hz, 1 H), 6.88 (dd, J=8.72, 2.65 Hz, 1 H), 6.27 (s, 1 H), 5.04 (s, 2 H), 4.46 (brs, 2 H), 3.89 (s, 3 H), 3.52 (t, J=4.67 Hz, 2 H), 2.42 (s, 3 H).

Example 20-3

[2-(1-Amino-cyclopropyl)-ethyl]-[2-(1,1-dioxido-2,3-dihydro-1,4-benzothiazepin-4(5H)-yl)-6-methylquinolin-4-yl]-amine

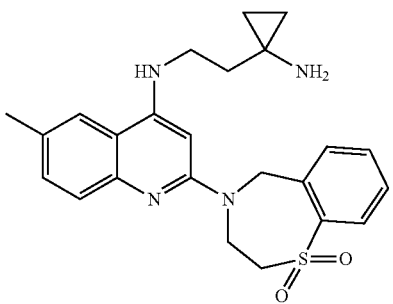 [SMILES: Cc1ccc2nc(N3CCS(=O)(=O)c4ccccc4C3)cc(NCCC3(N)CC3)c2c1]

The title compound was prepared in analogy to Example 20-1 in Scheme 7 by using 4-(4-chloro-6-methylquinolin-2-yl)-2,3,4,5-tetrahydro-1,4-benzothiazepine 1,1-dioxide (prepared in analogy to 4-(4-chloro-6-(trifluoromethoxy)quinolin-2-yl)-2,3,4,5-tetrahydro-1,4-benzothiazepine 1,1-dioxide in Example 17-1 by using 2,4-dichloro-6-methylquinoline and 2,3,4,5-tetrahydro-1,4-benzothiazepine 1,2-dioxide) and tert-butyl 1-(2-aminoethyl)-cyclopropylcarbamate. MS obsd. (ESI⁺) [(M+H)⁺] 437, ¹H NMR (400 MHz, CDCl₃) δ ppm 7.95-7.93 (dd, J=1.2, 8.0 Hz, 1 H), 7.59-7.57 (d, J=6 Hz, 1 H), 7.42-7.38 (m, 2 H), 7.29-7.25 (m, 1 H), 7.21-7.18 (m, 2 H), 6.40 (s, 1 H), 5.79 (s, 1 H), 4.5 (s, 2 H), 3.48 (s, 2 H), 3.35 (s, 2 H), 2.44 (s, 3 H), 2.31 (s, 3 H), 1.77-1.74 (d, J=6 Hz, 2 H), 1.54 (s, 2 H), 0.56-0.50 (m, 2 H).

Example 21-1

2-(1,1-Dioxido-2,3-dihydro-1,4-benzothiazepin-4(5H)-yl)-6-methyl-N-(morpholin-2-ylmethyl)quinolin-4-amine

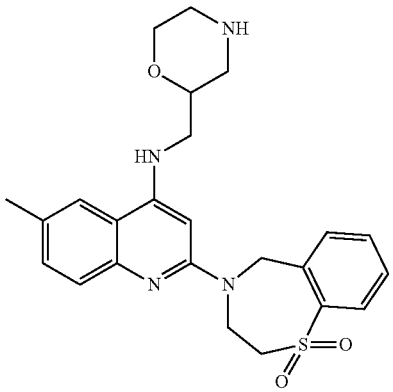 [SMILES: Cc1ccc2nc(N3CCS(=O)(=O)c4ccccc4C3)cc(NCC3CNCCO3)c2c1]

tert-Butyl 2-{[2-(1,1-dioxido-2,3-dihydro-1,4-benzothiazepin-4(5H)-yl)-6-methylquinolin-4-ylamino]-methyl}-morpholine-4-carboxylate

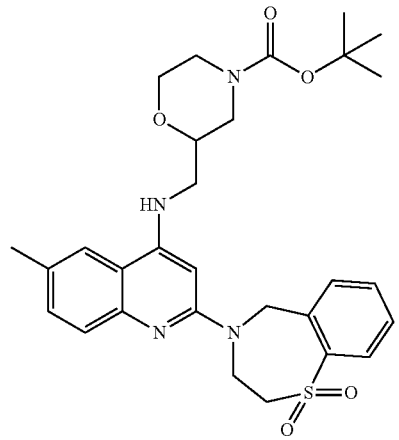 [SMILES: Cc1ccc2nc(N3CCS(=O)(=O)c4ccccc4C3)cc(NCC3CN(C(=O)OC(C)(C)C)CCO3)c2c1]

A mixture of 4-(4-chloro-6-methylquinolin-2-yl)-2,3,4,5-tetrahydro-1,4-benzothiazepine 1,1-dioxide (682 mg, 1.83 mmol, prepared in analogy to 4-(4-chloro-6-(trifluoromethoxy)quinolin-2-yl)-2,3,4,5-tetrahydro-1,4-benzothiazepine 1,1-dioxide in Example 17-1 by using 2,4-dichloro-6-methylquinoline and 2,3,4,5-tetrahydro-1,4-benzothiazepine 1,2-dioxide) in 1,4-dioxane (5 mL) was added tert-butyl 2-(aminomethyl)morpholine-4-carboxylate (395 mg, 1.83 mmol), 1,1'-bis(diphenylphosphino)ferrocene-dichloropalladium(II) (146 mg, 0.18 mmol), 1,1'-bis(diphenylphosphino)ferrocene (100 mg, 0.18 mmol) and sodium tert-butoxide (350 mg, 3.66 mmol) under Argon protection. The mixture was heated with stirring under microwave irridiation at 120° C. for 1.5 hours. The reaction mixture was concentrated in vacuo and the residue was purified by preparative HPLC to give 100 mg of the desired product (yield was 10%).

2-(1,1-Dioxido-2,3-dihydro-1,4-benzothiazepin-4(5H)-yl)-6-methyl-N-(morpholin-2-ylmethyl)quinolin-4-amine

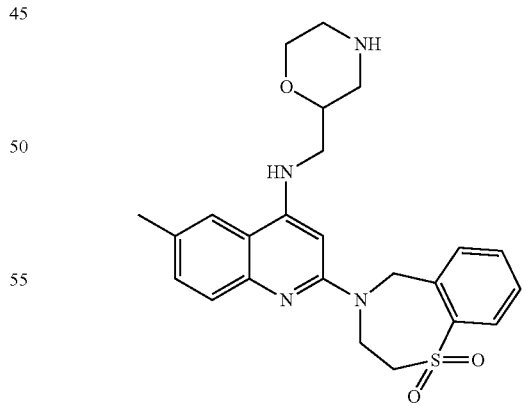

To a solution of tert-butyl 2-{[2-(1,1-dioxido-2,3-dihydro-1,4-benzothiazepin-4(5H)-yl)-6-methylquinolin-4-ylamino]-methyl}-morpholine-4-carboxylate (100 mg, 0.18 mmol) in ethyl acetate (10 mL) was added a solution of hydrochloride in ethyl acetate (4 N, 30 mL) in an ice-water bath dropwise. After being stirred at room temperature for 4 hours, the mixture was concentrated in vacuo. The residue was purified by preparative HPLC to afford trifluoroacetic acid salt of the desired product. The trifluoroacetic acid salt was flashed through SPE column with methanol to remove the trifluoroacetic acid. The solution was concentrated in vacuo and then dried by lyopylization to give 46.94 mg of the desired product (yield was 60%). MS obsd. (ESI⁺) [(M+H)⁺] 453, ¹H NMR (400 MHz, CD₃OD) δ ppm 8.04 (d, J=7.6 Hz, 1 H), 7.90-7.86 (m, 2 H), 7.72-7.68 (m, 2 H), 7.56-7.50 (m, 2 H), 6.11 (s, 1 H), 5.29 (s, 2 H), 4.55-4.49 (m, 2 H), 4.11-4.01 (m, 2 H), 3.88-3.81 (m, 1 H), 3.71-3.62 (m, 4 H), 3.42-3.39 (m, 1 H), 3.33-3.21 (s, 1 H), 3.28-3.01 (m, 2 H), 2.45 (s, 3 H).

Example 21-2

N-[2-(1,1-Dioxido-2,3-dihydro-1,4-benzothiazepin-4 (5H)-yl)-6-methylquinolin-4-yl]-N-methylethane-1,2-diamine

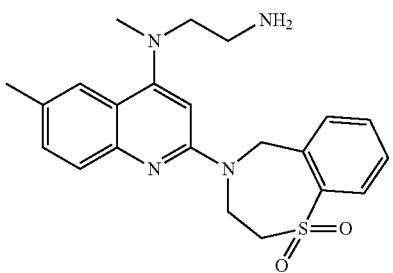 [SMILES: Cc1ccc2nc(N3CCS(=O)(=O)c4ccccc4C3)cc(N(C)CCN)c2c1]

The title compound was prepared in analogy to Example 21-1 in Scheme 7 by using 4-(4-chloro-6-methylquinolin-2-yl)-2,3,4,5-tetrahydro-1,4-benzothiazepine 1,1-dioxide (prepared in analogy to 4-(4-chloro-6-(trifluoromethoxy)quinolin-2-yl)-2,3,4,5-tetrahydro-1,4-benzothiazepine 1,1-dioxide in Example 17-1 by using 2,4-dichloro-6-methylquinoline and 2,3,4,5-tetrahydro-1,4-benzothiazepine 1,2-dioxide) and tert-butyl N-[2-(methylamino)ethyl]carbamate. MS obsd. (ESI⁺) [(M+H)⁺] 411, 1H NMR (400 MHz, CD₃OD) δ ppm 7.92 (dd, J=1.6, 7.6 Hz, 1 H), 7.86 (d, J=7.6 Hz, 2 H), 7.74 (s, 1 H), 7.61 (t, J=7.6 Hz, 1 H), 7.54 (d, J=8.4 Hz, 1 H), 7.40 (t, J=7.6 Hz, 1 H), 7.33 (dd, J=2.0, 8.8 Hz, 1 H), 6.66 (s, 1 H), 5.20 (s, 2 H), 4.51 (brs, 2 H), 3.59-3.53 (m, 4 H), 3.24 (t, J=6.4 Hz, 2 H), 2.93 (s, 3 H), 2.42 (s, 3 H).

Example 21-3

N-(Azetidin-2-ylmethyl)-2-(1,1-dioxido-2,3-dihydro-1,4-benzothiazepin-4(5H)-yl)-6-methylquinolin-4-amine

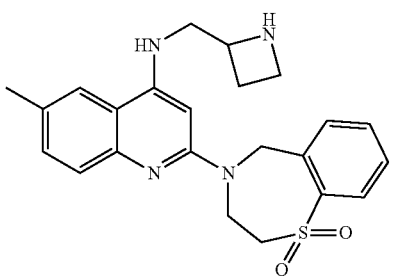 [SMILES: Cc1ccc2nc(N3CCS(=O)(=O)c4ccccc4C3)cc(NCC3CCN3)c2c1]

The title compound was prepared in analogy to Example 21-1 in Scheme 7 by using 4-(4-chloro-6-methylquinolin-2-yl)-2,3,4,5-tetrahydro-1,4-benzothiazepine 1,1-dioxide (prepared in analogy to 4-(4-chloro-6-(trifluoromethoxy)quinolin-2-yl)-2,3,4,5-tetrahydro-1,4-benzothiazepine 1,1-dioxide in Example 17-1 by using 2,4-dichloro-6-methylquinoline and 2,3,4,5-tetrahydro-1,4-benzothiazepine 1,2-dioxide) and tert-butyl 2-(aminomethyl)azetidine-1-carboxylate. MS obsd. (ESI⁺) [(M+H)⁺] 423, ¹H NMR (400 MHz, CD₃OD) δ ppm 8.09-8.02 (d, J=4 Hz, 1 H), 7.89 (s, 1 H), 7.85-7.79 (d, J=4 Hz, 1 H), 7.72-7.65 (m, 2 H), 7.60-7.50 (m, 2 H), 6.00 (s, 1 H), 5.31 (s, 2 H), 4.85-4.75 (m, 1 H), 4.60-4.40 (m, 2 H), 4.13-3.95 (m, 3 H), 3.92-3.85 (dd, J=2.8, 12.8 Hz, 1 H), 3.75-3.66 (t, J=2.8 Hz, 2 H), 2.72-2.60 (m, 1 H), 2.52-2.42 (m, 1 H), 2.42 (s, 3 H).

Example 21-4

2-(1,1-Dioxido-2,3-dihydro-1,4-benzothiazepin-4 (5H)-yl)-6-methyl-N-(pyrrolidin-3-yl)quinolin-4-amine

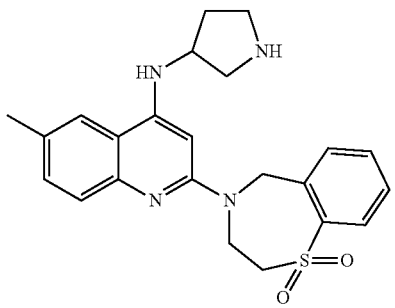 [SMILES: Cc1ccc2nc(N3CCS(=O)(=O)c4ccccc4C3)cc(NC3CCNC3)c2c1]

The title compound was prepared in analogy to Example 21-1 in Scheme 7 by using 4-(4-chloro-6-methylquinolin-2-yl)-2,3,4,5-tetrahydro-1,4-benzothiazepine 1,1-dioxide (prepared in analogy to 4-(4-chloro-6-(trifluoromethoxy)quinolin-2-yl)-2,3,4,5-tetrahydro-1,4-benzothiazepine 1,1-dioxide in Example 17-1 by using 2,4-dichloro-6-methylquinoline and 2,3,4,5-tetrahydro-1,4-benzothiazepine 1,2-dioxide) and tert-butyl 3-aminopyrrolidine-1-carboxylate. MS obsd. (ESI⁺) [(M+H)⁺] 423, ¹H NMR (400 MHz, CD₃OD) δ ppm 8.16 (s, 1 H), 8.12-8.10 (q, J=1.2 Hz, 1 H), 7.96-7.94 (d, J=7.6 Hz, 1 H), 7.80-7.74 (m, 2 H), 7.74-7.60 (m, 2 H), 6.04 (s, 1 H), 5.39 (s, 2 H), 4.84-4.82 (m, 2 H), 4.58 (s, 2 H), 3.81-3.77 (dd, J=6.4, 4.4 Hz, 2 H), 3.62-3.52 (m, 3 H), 2.67-2.30 (m, 1 H), 2.61-2.54 (m, 1 H), 2.50 (s, 3 H).

Example 21-5

(1-Amino-cyclopropylmethyl)-[2-(5,5-dioxo-5,6,7,9-tetrahydro-5λ⁶-thia-8-aza-benzocyclohepten-8-yl)-6-methyl-quinolin-4-yl]-amine

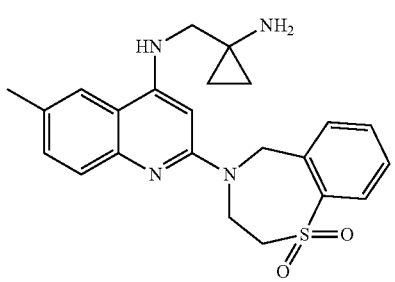 [SMILES: Cc1ccc2nc(N3CCS(=O)(=O)c4ccccc4C3)cc(NCC3(N)CC3)c2c1]

The title compound was prepared in analogy to Example 21-1 in Scheme 7 by using 4-(4-chloro-6-methylquinolin-2-- yl)-2,3,4,5-tetrahydro-1,4-benzothiazepine 1,1-dioxide (prepared in analogy to 4-(4-chloro-6-(trifluoromethoxy) quinolin-2-yl)-2,3,4,5-tetrahydro-1,4-benzothiazepine 1,1-dioxide in Example 17-1 by using 2,4-dichloro-6-methylquinoline and 2,3,4,5-tetrahydro-1,4-benzothiazepine 1,2-dioxide) and tert-butyl 1-(aminomethyl)cyclopropane carbamate. MS obsd. (ESI$^+$) [(M+H)$^+$] 423, $^1$H NMR (400 MHz, CD$_3$OD) δ ppm 7.98-7.90 (d, J=8 Hz, 1 H), 7.82-7.78 (d, J=7.6 Hz, 1 H), 7.69 (s, 1 H), 7.60-7.52 (t, J=1.2 Hz, 1 H), 7.42-7.36 (m, 2 H), 7.29-7.22 (d, J=7.2 Hz, 1 H), 6.00 (s, 1 H), 5.11 (s, 2 H), 4.65-4.50 (m, 2 H), 3.60-3.50 (t, J=2.8 Hz, 2 H), 3.40-3.30 (d, J=4.4 Hz, 2 H), 2.39 (s, 3 H), 0.70-0.60 (m, 4 H).

Example 22

N-(Azetidin-3-yl)-6-chloro-2-(1,1-dioxido-2,3-dihydro-1,4-benzothiazepin-4(5H)-yl)quinolin-4-amine

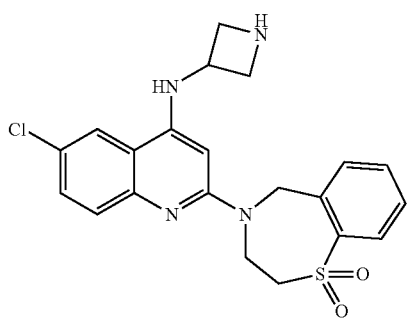 [SMILES: O=S1(=O)CCN(c2cc(NC3CNC3)c3cc(Cl)ccc3n2)Cc2ccccc21]

tert-Butyl 3-[6-chloro-2-(1,1-dioxido-2,3-dihydro-1,4-benzothiazepin-4(5H)-yl)-quinolin-4-ylamino]-azetidine-1-carboxylate

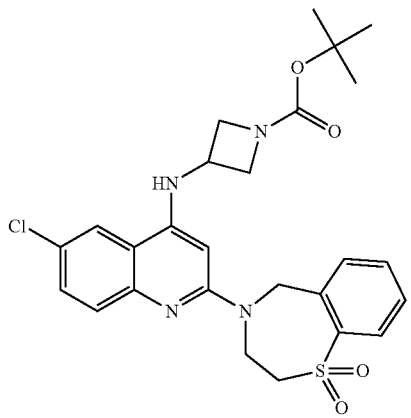 [SMILES: CC(C)(C)OC(=O)N1CC(Nc2cc(N3CCS(=O)(=O)c4ccccc4C3)nc3ccc(Cl)cc23)C1]

The title compound was prepared in analogy to tert-butyl 2-{[2-(1,1-dioxido-2,3-dihydro-1,4-benzothiazepin-4(5H)-yl)-6-methylquinolin-4-ylamino]-methyl}-morpholine-4-carboxylate in Example 21-1 by using 4-(4,6-dichloroquinolin-2-yl)-2,3,4,5-tetrahydro-1,4-benzothiazepine 1,1-dioxide and tert-butyl 3-aminoazetidine-1-carboxylate.

N-(Azetidin-3-yl)-6-chloro-2-(1,1-dioxido-2,3-dihydro-1,4-benzothiazepin-4(5H)-yl)quinolin-4-amine

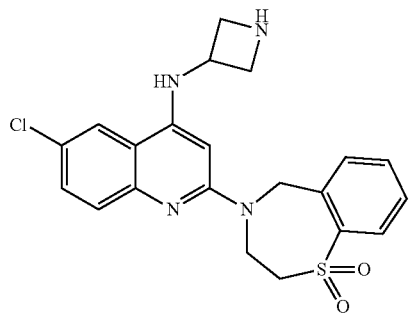 [SMILES: O=S1(=O)CCN(c2cc(NC3CNC3)c3cc(Cl)ccc3n2)Cc2ccccc21]

A mixture of tert-butyl 3-[6-chloro-2-(1,1-dioxido-2,3-dihydro-1,4-benzothiazepin-4(5H)-yl)-quinolin-4-ylamino]-azetidine-1-carboxylate (120 mg, 0.2 mmol) and a solution of hydrochloride in 1,4-dioxane (4 N, 20 mL) was stirred at room temperature for 16 hours. The resulting mixture was concentrated in vacuo. The residue was purified by preparative HPLC to afford 50 mg of the desired product (yield was 51%). MS obsd. (ESI$^+$) [(M+H)$^+$] 429, $^1$H NMR (400 MHz, CD$_3$OD) δ ppm 8.31 (s, 1 H), 8.08-8.06 (d, J=8 Hz, 1 H), 7.87-7.80 (m, 2 H), 7.73-7.68 (m, 2 H), 7.55-7.53 (m, 1 H), 5.84 (s, 1 H), 5.30 (s, 2 H), 4.99-4.96 (m, 1 H), 4.59-4.52 (m, 4 H), 4.32-4.27 (m, 2 H), 3.72 (s, 2 H).

Example 23

6-[2-(1,1-Dioxido-2,3-dihydro-1,4-benzothiazepin-4(5 H)-yl)-6-methylquinolin-4-yl]-2-oxa-6-azaspiro[3.4]octan-8-amine

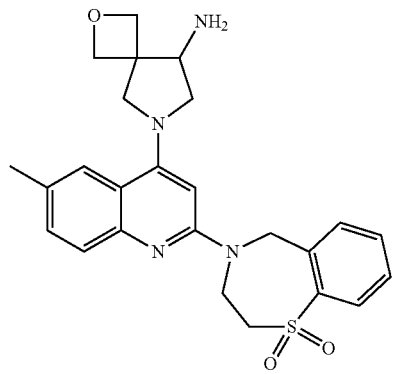 [SMILES: Cc1ccc2nc(N3CCS(=O)(=O)c4ccccc4C3)cc(N3CC(N)C4(COC4)C3)c2c1]

tert-Butyl 6-[2-(1,1-dioxido-2,3-dihydro-1,4-benzothiazepin-4(5 H)-yl)-6-methylquinolin-4-yl]-2-oxa-6-azaspiro[3.4]octan-8-carbamate

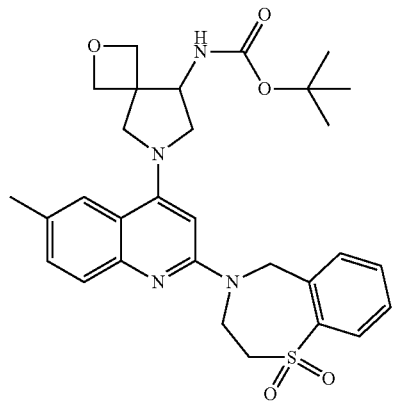 [SMILES: Cc1ccc2nc(N3CCS(=O)(=O)c4ccccc4C3)cc(N3CC(NC(=O)OC(C)(C)C)C4(COC4)C3)c2c1]

A mixture of tert-butyl 2-oxa-6-azaspiro[3.4]oct-8-ylcarbamate (459 mg, 2.0 mmol), 4-(4-chloro-6-methylquinolin-2-yl)-2,3,4,5-tetrahydro-1,4-benzothiazepine 1,1-dioxide (500 mg, 1.34 mmol, prepared in analogy to 4-(4-chloro-6-(trifluoromethoxy)quinolin-2-yl)-2,3,4,5-tetrahydro-1,4-benzothiazepine 1,1-dioxide in Example 17-1 by using 2,4-dichloro-6-methylquinoline and 2,3,4,5-tetrahydro-1,4-benzothiazepine 1,2-dioxide), tri(dibenzylideneacetone) dipalladium(0) (61.3 mg, 0.067 mmol), 2'-(dicyclohexylphosphino)-N,N-dimethyl[1,1'-biphenyl]-2-amine (52.7 mg, 0.134 mmol), sodium tert-butoxide (192.2 mg, 2.0 mmol) and 1,4-dioxane (6 mL) was heated with stirring in a 20 mL of microwave process vial for 3 hours at 100° C. The mixture was diluted with ethyl acetate and washed with water. The organic layer was dried over sodium sulfate and concentrated in vacuo. The residue was purified by column chromatography on silica gel to give 700 mg of the product as a white solid, which was used for next step without further purification.

6-[2-(1,1-Dioxido-2,3-dihydro-1,4-benzothiazepin-4(5 H)-yl)-6-methylquinolin-4-yl]-2-oxa-6-azaspiro[3.4]octan-8-amine

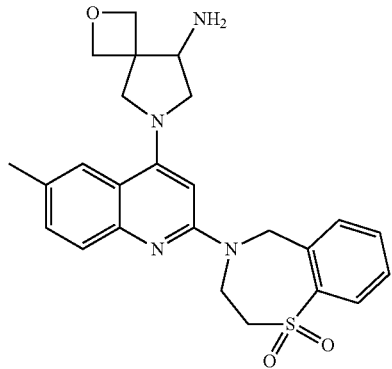 [SMILES: Cc1ccc2nc(N3CCS(=O)(=O)c4ccccc4C3)cc(N3CC(N)C4(COC4)C3)c2c1]

To a solution of tert-butyl 6-[2-(1,1-dioxido-2,3-dihydro-1,4-benzothiazepin-4(5 H)-yl)-6-methylquinolin-4-yl]-2-oxa-6-azaspiro[3.4]octan-8-carbamate (700 mg, 1.24 mmol) in dichloromethane (10 mL) was added trifluoroacetic acid (5 mL) at 0° C. The resulting mixture was stirred at room temperature for further 30 minutes. The reaction was quenched with a saturated aqueous solution of sodium carbonate, and the mixture was extracted with dichloromethane. The organic layer was dried over sodium sulfate, filtered and concentrated in vacuo. The residue was purified by preparative HPLC to give 80 mg of the product as a white solid. MS obsd. (ESI+) [(M+H)+] 465, $^1$H NMR (400 MHz, CD$_3$OD) δ ppm 7.97 (d, J=7.6 Hz, 1 H), 7.83 (d, J=7.6 Hz, 1 H), 7.79 (s, 1 H), 7.63 (m, 1 H), 7.52 (d, J=8.4 Hz, 1 H), 7.44 (m, 1 H), 7.35 (m, 1 H), 6.10 (s, 1 H), 5.17 (s, 2 H), 4.95 (d, J=6.8 Hz, 1 H), 4.68-4.62 (m, 3 H), 4.50 (brs, 2 H), 4.10 (d, J=8.8 Hz, 1 H), 3.91-3.81 (m, 3 H), 3.60 (m, 2 H), 3.45 (m 1 H), 2.41 (s, 3 H).

Example 24 trans-4-Amino-1-[2-(1,1-dioxido-2,3-dihydro-1,4-benzothiazepin-4(5H)-yl)-1,6-naphthyridin-4-yl]pyrrolidin-3-ol

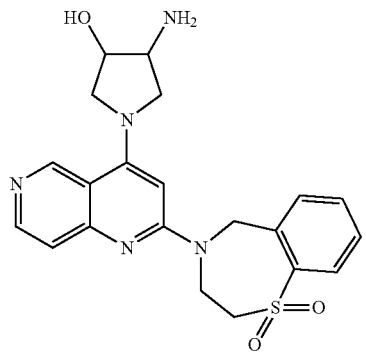 [SMILES: NC1CN(c2cc(N3CCS(=O)(=O)c4ccccc4C3)nc3ccncc23)CC1O]

tert-Butyl trans-1-[2-(1,1-dioxido-2,3-dihydro-1,4-benzothiazepin-4(5H)-yl)-1,6-naphthyridin-4-yl]-3-hydroxypyrrolidin-4-carbamate

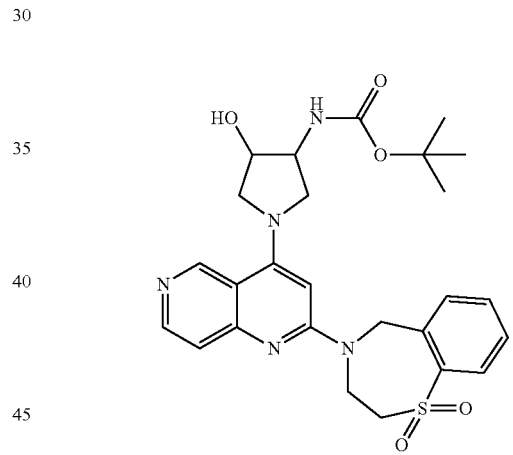

To a solution of -(4-chloro-1,6-naphthyridin-2-yl)-2,3,4,5-tetrahydro-1,4-benzothiazepine 1,1-dioxide (300 mg, 0.84 mmol, prepared in analogy to 4-(4-chloro-6-methylquinolin-2-yl)-2,3,4,5-tetrahydro-1,4-benzothiazepine 1,1-dioxide in Example 2-1 by using 2,3,4,5-tetrahydro-1,4-benzothiazepine and 2,4-dichloro-1,6-naphthyridine) in 1,4-dioxane (5 mL) was added tert-butyl (trans-4-hydroxypyrrolidin-3-yl)carbamate (204 mg, 1.02 mmol), tri(dibenzylideneacetone) dipalladium(0) (39 mg, 0.042 mmol), (2'-dicyclohexylphosphanyl-biphenyl-2-yl)-dimethyl-amine (24 mg, 0.063 mmol) and sodium tert-butoxide (114 mg, 1.17 mmol) under Ar protection. The reaction mixture was heated with stirring in a 10 mL of microwave process vial for 2 hours at 120° C. The reaction mixture was concentrated in vacuo. The residue was purified by preparative HPLC to give 45 mg of the desired product (yield was 10%).

trans-4-Amino-1-[2-(1,1-dioxido-2,3-dihydro-1,4-benzothiazepin-4(5H)-yl)-1,6-naphthyridin-4-yl]pyrrolidin-3-ol

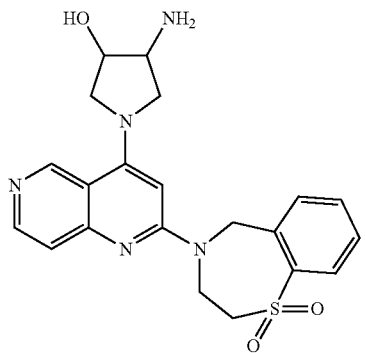 [SMILES: NC1CN(c2cc(N3CCS(=O)(=O)c4ccccc4C3)nc3ccncc23)CC1O]

To a solution of tert-butyl trans-1-[2-(1,1-dioxido-2,3-dihydro-1,4-benzothiazepin-4(5H)-yl)-1,6-naphthyridin-4-yl]-3-hydroxypyrrolidin-4-carbamate (45 mg, 0.08 mmol) in ethyl acetate (10 mL) was added a solution of hydrochloride in ethyl acetate (4 N, 30 mL) in an ice-water bath dropwise. After being stirred at room temperature for 4 hours, the mixture was concentrated in vacuo. The residue was purified by preparative HPLC to give the trifluoroacetic acid salt of the desired product. The trifluoroacetic acid salt was flashed through SPE column with methanol. The solution was concentrated in vacuo and dried by lyopylization to afford 10.9 mg of the desired product (yield was 30%). MS obsd. (ESI$^+$) [(M+H)$^+$] 426, $^1$H NMR (400 MHz, CD$_3$OD) δ ppm 9.23 (s, 1 H), 8.23 (d, J=7.2 Hz, 1 H), 7.99 (d, J=7.6 Hz, 1 H), 7.87 (d, J=7.2 Hz, 1 H), 7.66-7.64 (m, 2 H), 7.48 (t, J=7.6 Hz, 1 H), 6.16 (s, 1 H), 5.25 (s, 2 H), 4.70-4.40 (m, 3 H), 4.26-4.18 (m, 2 H), 3.87-3.85 (m, 1 H), 3.81-3.78 (m, 1 H), 3.71-3.68 (m, 1 H), 3.55 (t, J=4.8 Hz, 2 H).

Example 25

1-[2-(1,1-Dioxido-2,3-dihydro-1,4-benzothiazepin-4(5H)-yl)-6-methylquinolin-4-yl]pyrrolidin-3-amine

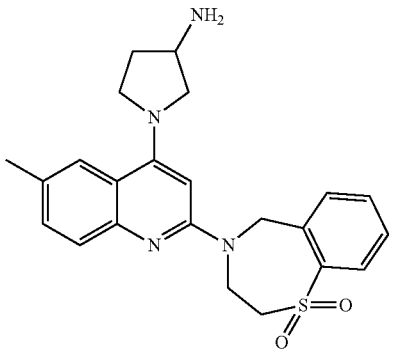 [SMILES: Cc1ccc2nc(N3CCS(=O)(=O)c4ccccc4C3)cc(N3CCC(N)C3)c2c1]

A mixture of 4-(4-chloro-6-methylquinolin-2-yl)-2,3,4,5-tetrahydro-1,4-benzothiazepine 1,1-dioxide (0.3 g, 0.8 mmol, prepared in analogy to 4-(4-chloro-6-(trifluoromethoxy)quinolin-2-yl)-2,3,4,5-tetrahydro-1,4-benzothiazepine 1,1-dioxide in Example 17-1 by using 2,4-dichloro-6-methylquinoline and 2,3,4,5-tetrahydro-1,4-benzothiazepine 1,2-dioxide) and tert-butyl pyrrolidine-3-carbamate (0.3 g, 1.6 mmol) was heated with stirring in a 10 mL of microwave process vial for 1 hour at 140° C. The resulting mixture was purified by preparative HPLC and SPE. After SPE separation, the eluent was concentrated in vacuo to remove the organic solution. The residue was dried by lyophylization to afford 82.9 mg of the desired product (yield was 25%). MS obsd. (ESI$^+$) [(M+H)$^+$] 423, $^1$H NMR (400 MHz, CD$_3$OD) δ ppm 8.09-8.08 (dd, J=4.0, 8.0 Hz, 1 H), 8.02 (s, 1 H), 7.85-7.83 (q, J=7.6 Hz, 1 H), 7.77-7.70 (m, 2 H), 7.61-7.56 (m, 2 H), 5.90 (s, 1 H), 5.30 (s, 2 H), 4.52 (s, 2 H), 4.30-4.26 (m, 1 H), 4.17-4.11 (m, 2 H) 3.99-3.96 (m, 2 H), 3.74 (s, 2 H), 2.57-2.52 (m, 1 H), 2.47 (s, 3 H), 2.35-2.28 (m, 1 H).

Example 26-1

N-(Azetidin-3-yl)-2-(1,1-dioxido-2,3-dihydro-1,4-benzothiazepin-4(5H)-yl)-6-methylquinolin-4-amine

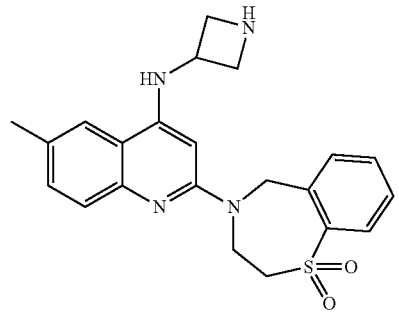 [SMILES: Cc1ccc2nc(N3CCS(=O)(=O)c4ccccc4C3)cc(NC3CNC3)c2c1]

tert-Butyl 3-[1,1-dioxido-2,3-dihydro-1,4-benzothiazepin-4(5H)-yl)-6-methylquinolin-4-ylamino]-azetidine-1-carboxylate

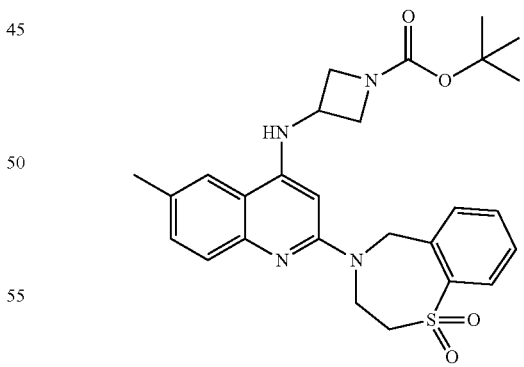

A mixture of 8-(4-bromo-6-methylquinolin-2-yl)-2,3,4,5-tetrahydro-1,4-benzothiazepine 1,1-dioxide (900 mg, 2.16 mmol, prepared in analogy to the one in Example 2-1) and tert-butyl 3-aminoazetidine-1-carboxylate (1.86 g, 10.77 mmol) was heated with stirring in a 10 mL of microwave process vial for 1 hour at 150° C. The resulting mixture was purified by preparative HPLC to afford 110 mg of the desired product (yield was 7%).

309

N-(Azetidin-3-yl)-2-(1,1-dioxido-2,3-dihydro-1,4-benzothiazepin-4(5H)-yl)-6-methylquinolin-4-amine

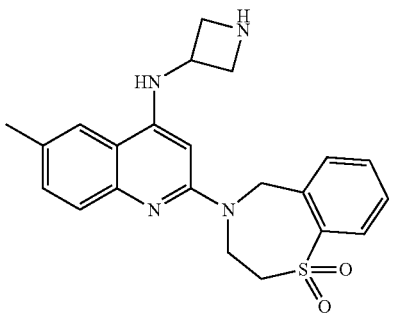 [SMILES: Cc1ccc2nc(N3CCS(=O)(=O)c4ccccc4C3)cc(NC3CNC3)c2c1]

To a solution of tert-butyl 3-[1,1-dioxido-2,3-dihydro-1,4-benzothiazepin-4(5H)-yl)-6-methylquinolin-4-ylamino]-azetidine-1-carboxylate (110 mg, 0.22 mmol) in ethyl acetate (10 mL) was added a solution of hydrochloride in ethyl acetate (4 N, 30 mL) in an ice-water bath dropwise. After being stirred at room temperature for 4 hours, the mixture was concentrated in vacuo. The residue was purified by preparative HPLC to give the trifluoroacetic acid salt of the desired product. The trifluoroacetic acid salt was flashed through SPE column with methanol. The solution was concentrated in vacuo and dried by lyopylization to afford 29 mg of the desired product (yield was 33%). MS obsd. (ESI$^+$) [(M+H)$^+$] 409, $^1$H NMR (400 MHz, CD$_3$OD) δ ppm 8.09 (d, J=7.2 Hz, 1 H), 8.02 (s, 1 H), 7.84-7.82 (m, 1 H), 7.76-7.72 (m, 2 H), 7.65-7.60 (m, 2 H), 5.79 (s, 1 H), 5.33 (s, 2 H), 4.96-4.92 (m, 1 H), 4.55-4.50 (m, 4 H), 4.31-4.28 (m, 2 H), 3.76 (s, 2 H), 2.49 (s, 3 H).

Example 26-2

1-[2-(1,1-Dioxido-2,3-dihydro-1,4-benzothiazepin-4(5H)-yl)-6-methylquinolin-4-yl]azetidin-3-amine

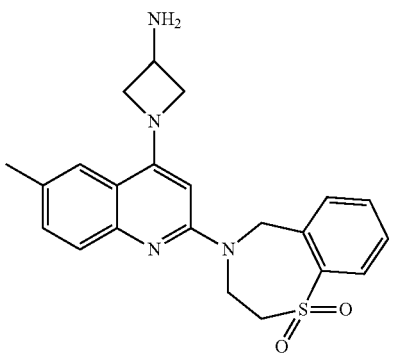 [SMILES: Cc1ccc2nc(N3CCS(=O)(=O)c4ccccc4C3)cc(N3CC(N)C3)c2c1]

The title compound was prepared in analogy to Example 26-1 in Scheme 7 by using 4-(4-chloro-6-methylquinolin-2-yl)-2,3,4,5-tetrahydro-1,4-benzothiazepine 1,1-dioxide (prepared in analogy to the one in Example 2-1) and tert-butyl azetidin-3-ylcarbamate. MS obsd. (ESI$^+$) [(M+H)$^+$] 409, $^1$H NMR (400 MHz, CD$_3$OD) δ ppm 8.03-8.00 (d, J=7.6 Hz, 1 H), 7.87 (s, 1 H), 7.80-7.78 (d, J=7.6 Hz, 1 H), 7.67-7.62 (m, 2 H), 7.56-7.50 (m, 2 H), 6.00 (s, 1 H), 5.29 (s, 2 H), 4.47 (s, 2 H), 3.97-3.89 (m, 3 H), 3.82-3.69 (m, 4 H), 2.40 (s, 3 H).

Example 27

N-[2-(1,1-Dioxido-2,3-dihydro-1,4-benzothiazepin-4(5H)-yl)-6-methylquinolin-4-yl]prolinamide

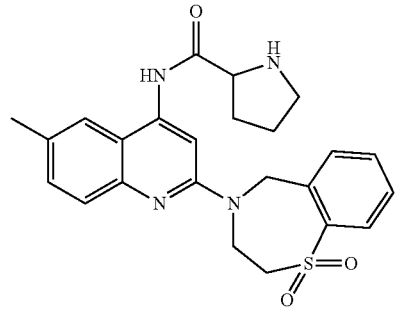 [SMILES: Cc1ccc2nc(N3CCS(=O)(=O)c4ccccc4C3)cc(NC(=O)C3CCCN3)c2c1]

tert-Butyl 2-{[2-(1,1-dioxido-2,3-dihydro-1,4-benzothiazepin-4(5H)-yl)-6-methylquinolin-4-yl]carbamoyl}pyrrolidine-1-carboxylate

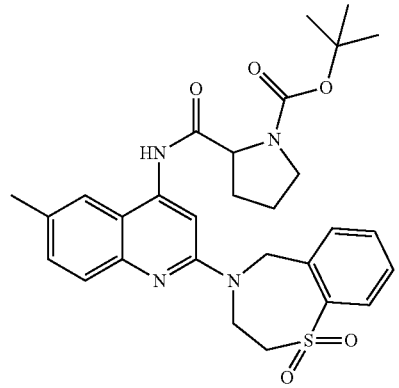 [SMILES: Cc1ccc2nc(N3CCS(=O)(=O)c4ccccc4C3)cc(NC(=O)C3CCCN3C(=O)OC(C)(C)C)c2c1]

To a solution of 4-(4-chloro-6-methylquinolin-2-yl)-2,3,4,5-tetrahydro-1,4-benzothiazepine 1,1-dioxide (0.60 g, 1.6 mmol, prepared in analogy to the one in Example 2-1), tert-butyl 2-carbamoylpyrrolidine-1-carboxylate (0.34 g, 1.6 mmol), 1,1'-bis(diphenylphosphino)ferrocene-palladium(II) dichloride (0.13 g, 0.16 mmol), 1,1'-bis(diphenylphosphino)ferrocene (0.089 g, 0.16 mmol) and sodium tert-butoxide (0.307 g, 3.2 mmol) in 1,4-dioxane (25 mL) was heated with stirring for 1.5 hours at 120° C. under microwave irradiation. The reaction mixture was filtered and concentrated in vacuo. The residue was purified by preparative TLC (eluting with 50% ethyl acetate in petroleum ether, V/V=1:1) to give 250 mg of the desired product (yield was 29%).

311

N-[2-(1,1-Dioxido-2,3-dihydro-1,4-benzothiazepin-4(5H)-yl)-6-methylquinolin-4-yl]prolinamide

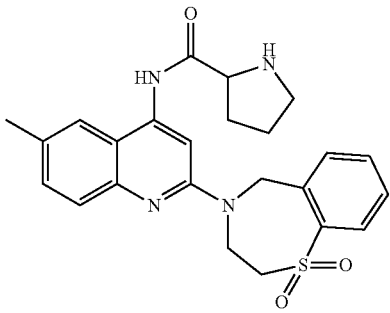 [SMILES: Cc1ccc2nc(N3CCS(=O)(=O)c4ccccc4C3)cc(NC(=O)C3CCCN3)c2c1]

To a solution of tert-butyl 2-{[2-(1,1-dioxido-2,3-dihydro-1,4-benzothiazepin-4(5H)-yl)-6-methylquinolin-4-yl]carbamoyl}pyrrolidine-1-carboxylate (250 mg, 0.44 mmol) in ethyl acetate (5 mL) was added a solution of hydrochloride in ethyl acetate (4 N, 20 mL) dropwise in an ice-water bath. After being stirred at room temperature for 14 hours, the reaction mixture was concentrated in vacuo. The residue was purified by preparative TLC to give 104.8 mg of the desired product (yield was 48%). MS obsd. (ESI$^+$) [(M+H)$^+$] 451, $^1$H NMR (400 MHz, DMSO-d6) δ ppm 7.96 (s, 1 H), 7.88-7.84 (m, 2 H), 7.63-7.59 (m, 1 H), 7.54 (s, 1 H) 7.49-7.44 (m, 2 H), 7.39-7.37 (m, 2 H), 7.00 (s, 1 H), 5.04 (s, 2 H), 4.40 (s, 2 H), 4.16-4.12 (t, J=5.2 Hz, 1 H), 3.64 (s, 2 H) 3.15-3.01 (m, 3 H), 2.39 (s, 3 H), 2.23-2.20 (m, 1 H), 1.95-1.90 (m, 1 H), 1.80-1.75 (m, 1 H).

Example 28-1

2-(1,1-Dioxido-2,3-dihydro-1,4-benzothiazepin-4(5H)-yl)-N-trans-(4-fluoropyrrolidin-3-yl)-6-methylquinolin-4-amine

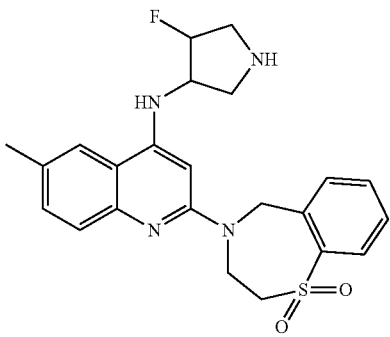 [SMILES: Cc1ccc2nc(N3CCS(=O)(=O)c4ccccc4C3)cc(NC3CNCC3F)c2c1]

Benzyl trans-3-{[2-(1,1-dioxido-2,3-dihydro-1,4-benzothiazepin-4(5H)-yl)-6-methylquinolin-4-yl]amino}-4-fluoropyrrolidine-1-carboxylate

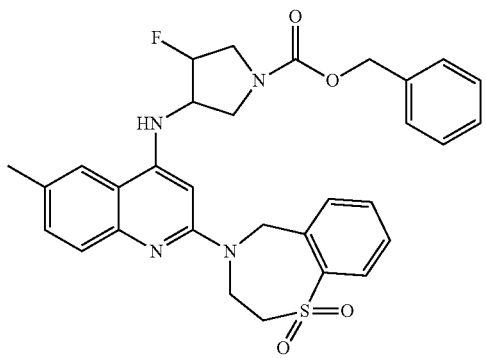 [SMILES: Cc1ccc2nc(N3CCS(=O)(=O)c4ccccc4C3)cc(NC3CN(C(=O)OCc4ccccc4)CC3F)c2c1]

312

The title compound was prepared in analogy to Example 8-1 in Scheme 7 by using 4-(4-chloro-6-methylquinolin-2-yl)-2,3,4,5-tetrahydro-1,4-benzothiazepine 1,1-dioxide (prepared in analogy to the one in Example 2-1) and benzyl trans-3-amino-4-fluoropyrrolidine-1-carboxylare.

2-(1,1-Dioxido-2,3-dihydro-1,4-benzothiazepin-4(5H)-yl)-N-(trans-4-fluoropyrrolidin-3-yl)-6-methylquinolin-4-amine

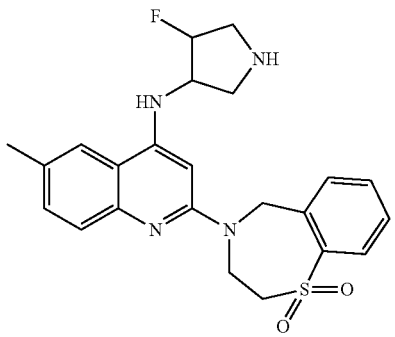 [SMILES: Cc1ccc2nc(N3CCS(=O)(=O)c4ccccc4C3)cc(NC3CNCC3F)c2c1]

To a suspension of benzyl trans-3-{[2-(1,1-dioxido-2,3-dihydro-1,4-benzothiazepin-4(5H)-yl)-6-methylquinolin-4-yl]amino}-4-fluoropyrrolidine-1-carboxylate (320 mg, 0.557 mmol) in methanol (5 mL) was added an aqueous solution of potassium hydroxide (40%, 5 mL). The suspension was heated under reflux for 30 minutes. The organic solvent was removed by concentration in vacuo. The residue was purified by preparative HPLC to afford the pure product as a solid. MS obsd. (ESI$^+$) [(M+H)$^+$] 441, $^1$H NMR (400 MHz, CD$_3$OD) δ ppm 8.01 (d, J=6.57 Hz, 1 H), 7.85 (d, J=7.33 Hz, 1 H), 7.67 (s, 1 H), 7.63 (t, J=7.07 Hz, 1 H), 7.53-7.40 (m, 2 H), 7.30 (d, J=8.84 Hz, 1 H), 6.18 (s, 1 H), 5.15 (s, 2 H), 5.10 (brs, 1 H), 4.97 (brs, 1 H), 3.60 (dd, J=12.00, 6.44 Hz, 3 H), 3.28 (brs, 1 H), 3.23 (dd, J=8.84, 5.31 Hz, 1 H), 3.18-3.12 (m, 1 H), 3.04 (dd, J=12.00, 4.67 Hz, 1 H), 2.42 (s, 3 H).

Example 28-2 trans-4-{[2-(1,1-Dioxido-2,3-dihydro-1,4-benzothiazepin-4(5H)-yl)quinolin-4-yl]amino}pyrrolidin-3-ol

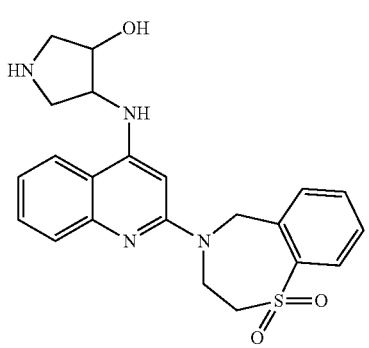 [SMILES: O=S1(=O)CCN(c2cc(NC3CNCC3O)c3ccccc3n2)Cc2ccccc21]

The title compound was prepared in analogy to Example 28-1 in Scheme 8 by using 4-(4-bromoquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1) and benzyl trans-3-amino-4-hydroxypyrrolidine-1-carboxylate. MS obsd. (ESI$^+$) [(M+H)$^+$] 439, $^1$H NMR (400 MHz, CD$_3$OD) δ ppm 8.29-8.22 (d, J=7.6 Hz, 1 H), 8.12-8.08 (d, J=1.2 Hz, 1 H), 7.98-7.92 (d, J=7.6 Hz, 1 H), 7.88-7.82 (d, J=0.8 Hz, 1 H), 7.80-7.71 (m, 2 H), 7.62-7.58 (t, J=1.2 Hz, 1 H), 7.50-7.42 (t, J=6.8 Hz, 1 H), 6.20 (s, 1 H), 5.45-5.30 (q, J=7.2 Hz, 2 H), 4.62-4.52 (m, 2 H), 4.52-4.45 (m, 2 H), 4.05-3.95 (q, J=4.4 Hz, 1 H), 3.80-3.75 (t, J=2.8 Hz, 2 H), 3.75-3.68 (m, 1 H), 3.62-3.55 (dd, J=2.8, 12.8 Hz, 1 H), 3.48-3.40 (d, J=7.6 Hz, 1 H).

Example 28-3 trans-4-{[2-(1,1-Dioxido-2,3-dihydro-1,4-benzothi-azepin-4(5H)-yl)-6-methylquinolin-4-yl]amino}pyrrolidin-3-ol

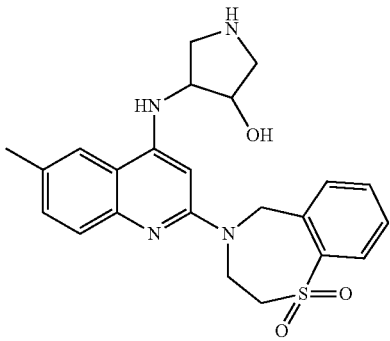 [SMILES: Cc1ccc2nc(N3CCS(=O)(=O)c4ccccc4C3)cc(NC3CNCC3O)c2c1]

The title compound was prepared in analogy to Example 28-1 in Scheme 8 by using 4-(4-bromo-6-methylquinolin-2-yl)-2,3,4,5-tetrahydro-1,4-benzothiazepine 1,1-dioxide (prepared in analogy to the one in Example 2-1) and benzyl (3S,4S)-3-amino-4-hydroxypyrrolidine-1-carboxylate. MS obsd. (ESI$^+$) [(M+H)$^+$] 439, $^1$H NMR (400 MHz, CD$_3$OD) δ ppm 8.13-8.10 (d, J=7.6 Hz, 1 H), 8.06 (s, 1 H), 7.95-7.90 (d, J=7.2 Hz, 1 H), 7.78-7.70 (m, 2 H), 7.65-7.58 (m, 2 H), 6.16 (s, 1 H), 5.3 (q, J=1.2 Hz, 2 H), 4.65-4.40 (m, 2 H), 4.50-4.40 (m, 2 H), 4.12-3.95 (m, 1 H), 3.80-3.68 (m, 3 H), 3.60-3.50 (m, 1 H), 3.48-3.40 (d, J=7.2 Hz, 1 H), 2.47 (s, 3 H).

Example 28-4 cis-4-{[2-(1,1-Dioxido-2,3-dihydro-1,4-benzothiaz-epin-4(5H)-yl)-6-methylquinolin-4-yl]amino}pyrrolidin-3-ol

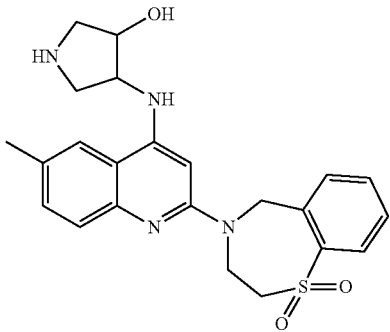 [SMILES: Cc1ccc2nc(N3CCS(=O)(=O)c4ccccc4C3)cc(NC3CNCC3O)c2c1]

The title compound was prepared in analogy to Example 28-1 in Scheme 8 by using 4-(4-bromo-6-methylquinolin-2-yl)-2,3,4,5-tetrahydro-1,4-benzothiazepine 1,1-dioxide (prepared in analogy to the one in Example 2-1) and benzyl cis-3-amino-4-hydroxypyrrolidine-1-carboxylate. MS obsd. (ESI$^+$) [(M+H)$^+$] 439, $^1$H NMR (400 MHz, CD$_3$OD) δ ppm 8.12-8.07 (m, 2 H), 7.98-7.90 (d, J=7.6 Hz, 1 H), 7.78-7.70 (m, 2 H), 7.63-7.58 (m, 2 H), 6.16 (s, 1 H), 5.41-5.28 (m, 2 H), 4.61-4.50 (m, 2 H), 4.48 (s, 2 H), 4.02-3.93 (q, J=6 Hz, 1 H), 3.78-3.68 (m, 3 H), 3.60-3.50 (dd, J=2.8, 12.8 Hz, 1 H), 3.48-3.40 (d, J=3.6 Hz, 1 H), 2.46 (s, 3 H).

Example 28-5

N-[trans-4-Fluoropyrrolidin-3-yl]-6-methyl-2-(1-oxido-2,3-dihydro-1,4-benzothiazepin-4(5H)-yl)quinolin-4-amine

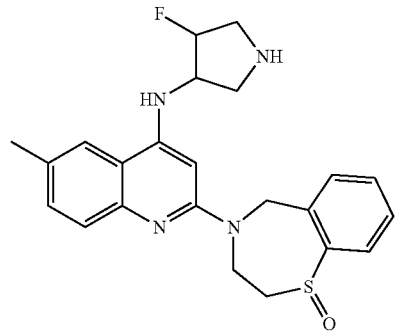 [SMILES: Cc1ccc2nc(N3CCS(=O)c4ccccc4C3)cc(NC3CNCC3F)c2c1]

The title compound was prepared in analogy to Example 28-1 in Scheme 8 by using 4-(4-chloro-6-methylquinolin-2-yl)-2,3,4,5-tetrahydro-1,4-benzothiazepine 1-oxide (prepared in analogy to the one in Example 18-1) and benzyl trans-3-amino-4-fluoropyrrolidine-1-carboxylare. MS obsd. (ESI$^+$) [(M+H)$^+$] 425, $^1$H NMR (400 MHz, CD$_3$OD) δ ppm 7.75 (m, 3 H), 7.50 (m, 3 H), 7.35 (d, J=8.4 Hz, 1 H), 6.16 (brs, 1 H), 5.28-4.97 (m, 3 H), 4.61 (s, 1 H), 4.28 (m, 1 H), 3.64 (m, 1 H), 3.47 (s, 2 H), 3.30-3.08 (m, 2 H), 2.43 (s, 3 H).

Example 29

4-[(3-Aminopropyl)amino]-2-(1,1-dioxido-2,3-dihydro-1,4-benzothiazepin-4(5H)-yl)quinolin-6-ol

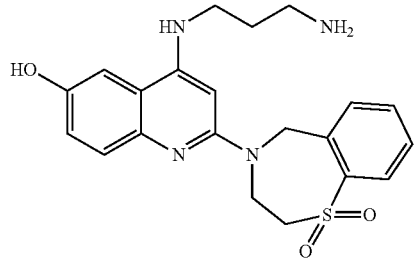 [SMILES: NCCCNc1cc(N2CCS(=O)(=O)c3ccccc3C2)nc2ccc(O)cc12]

4-Chloro-2-(1,1-dioxido-2,3-dihydro-1,4-benzothi-azepin-4(5H)-yl)-quinolin-6-ol

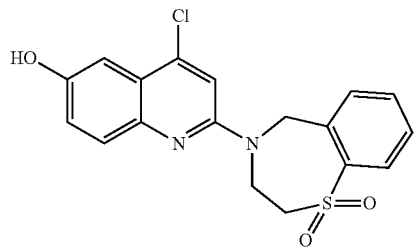 [SMILES: O=S1(=O)CCN(c2cc(Cl)c3cc(O)ccc3n2)Cc2ccccc21]

A mixture of 4-(4-chloro-6-methoxyquinolin-2-yl)-2,3,4,5-tetrahydro-1,4-benzothiazepine 1,1-dioxide (5.0 g, 12.85 mmol, prepared in analogy to 4-(4-chloro-6-methylquinolin-2-yl)-2,3,4,5-tetrahydro-1,4-benzothiazepine 1,1-dioxide in Example 2-1 by using 2,4-dichloro-6-methoxyquinoline and 2,3,4,5-tetrahydro-1,4-benzothiazepine) and hydrobromic acid (350 mL, 48%) was refluxed for 2 days. The resulting mixture was basified with an aqueous solution of sodium hydroxide (4 N) to about pH 9 and extracted with ethyl acetate (250 mL×3). The combined organic layers were dried over sodium sulfate and concentrated in vacuo. The residue was purified by preparative HPLC to afford 3.0 g of the desired product (yield was 62.2%).

4-[(3-Aminopropyl)amino]-2-(1,1-dioxido-2,3-dihydro-1,4-benzothiazepin-4(5H)-yl)quinolin-6-ol

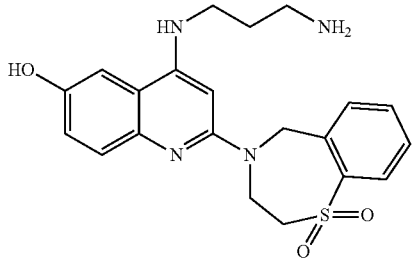 [SMILES: NCCCNc1cc(N2CCS(=O)(=O)c3ccccc3C2)nc2ccc(O)cc12]

A mixture of 4-chloro-2-(1,1-dioxido-2,3-dihydro-1,4-benzothiazepin-4(5H)-yl)-quinolin-6-ol (400 mg, 1.067 mmol) and propane-1,3-diamine (158 mg, 2.134 mmol) was heated with stirring for 1.5 hours at 150° C. under microwave irradiation. The reacting mixture was purified by preparative HPLC and SPE to give 118.8 mg of the desired product (yield was 27%). MS obsd. (ESI+)[(M+H)+] 413, $^1$H NMR (400 MHz, CD$_3$OD) δ ppm 8.10-8.05 (d, J=7.6 Hz, 1 H), 7.85-7.80 (d, J=8 Hz, 1 H), 7.71-7.62 (m, 2 H), 7.60-7.52 (t, J=7.2 Hz, 1 H), 7.40-7.35 (m, 1 H), 7.26-7.20 (dd, J=2.8 Hz, 12.8 Hz, 1 H), 5.91 (s, 1 H), 5.27 (s, 2 H), 4.52-4.42 (m, 2 H), 3.72-3.68 (t, J=2.8 Hz, 2 H), 3.60-3.52 (t, J=6.8 Hz, 2 H), 3.10-3.02 (t, J=7.2 Hz, 2 H), 2.10-2.00 (m, 2 H);

Example 30-1

2-({4-[(3-Aminopropyl)amino]-2-(1,1-dioxido-2,3-dihydro-1,4-benzothiazepin-4(5 H)-yl)quinolin-6-yl}oxy)ethanol

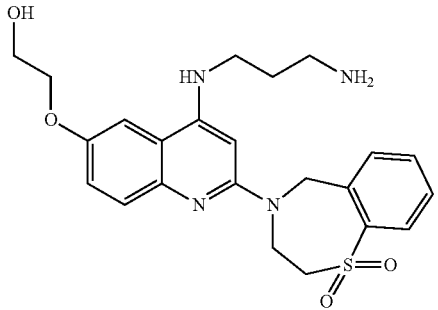 [SMILES: NCCCNc1cc(N2CCS(=O)(=O)c3ccccc3C2)nc2ccc(OCCO)cc12]

2-[4-Chloro-2-(1,1-dioxido-2,3-dihydro-1,4-benzothiazepin-4(5H)-yl)-quinolin-6-yloxy]-ethanol

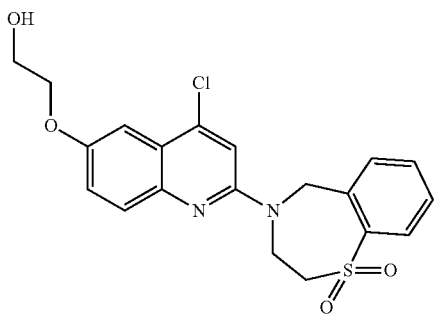 [SMILES: O=S1(=O)CCN(c2cc(Cl)c3cc(OCCO)ccc3n2)Cc2ccccc21]

A mixture of 4-chloro-2-(1,1-dioxido-2,3-dihydro-1,4-benzothiazepin-4(5H)-yl)-quinolin-6-ol (250 mg, 0.67 mmol, prepared in analogy to the one in Example 29), 2-bromo-ethanol (166.7 mg, 1.33 mmol), and potassium carbonate (277 mg, 2.01 mmol) in acetone (30 mL) was stirred at room temperature overnight and then refluxed for 12 hours. The reacting mixture was filtered and concentrated in vacuo. The residue was purified by preparative TLC to afford 230 mg of the desired product (yield was 82%).

2-({4-[(3-Aminopropyl)amino]-2-(1,1-dioxido-2,3-dihydro-1,4-benzothiazepin-4(5H)-yl)quinolin-6-yl}oxy)ethanol

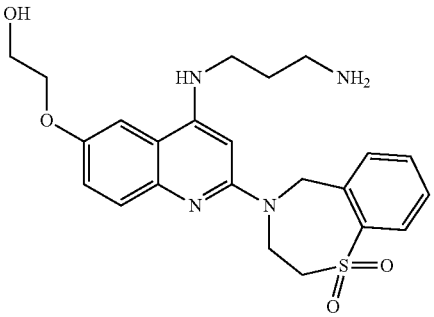 [SMILES: NCCCNc1cc(N2CCS(=O)(=O)c3ccccc3C2)nc2ccc(OCCO)cc12]

A mixture of 2-{[4-chloro-2-(1,1-dioxido-2,3-dihydro-1,4-benzothiazepin-4 (5H)-yl)quinolin-6-yl]oxy}ethanol (250 mg, 0.6 mmol) and propane-1,3-diamine (88.8 mg, 1.2 mmol) was heated for 1.5 hours at 150° C. under microwave irradiation. The reacting mixture was purified by preparative HPLC and SPE to afford 98.2 mg of the desired product (yield was 35.8%). MS obsd. (ESI+) [(M+H)+] 457, $^1$H NMR (400 MHz, CD$_3$OD) δ ppm 8.10-8.02 (d, J=8 Hz, 1 H), 7.88-7.80 (d, J=7.6 Hz, 1 H), 7.77-7.68 (q, J=9.6 Hz, 2 H), 7.60-7.50 (m, 2 H), 7.42-7.38 (m, 1 H), 5.94 (s, 1 H), 5.29 (s, 2 H), 4.55-4.42 (m, 2 H), 4.18-4.10 (t, J=4.4 Hz, 2 H), 3.90-3.85 (t, J=4.4 Hz, 2 H), 3.76-3.68 (t, J=4.4 Hz, 2 H), 3.62-3.55 (t, J=6.8 Hz, 2 H), 3.12-3.05 (t, J=7.6 Hz, 2 H), 2.15-2.00 (m, 2 H).

Example 30-2

N-[2-(1,1-Dioxido-2,3-dihydro-1,4-benzothiazepin-4(5H)-yl)-6-(2-methoxyethoxy)quinolin-4-yl]propane-1,3-diamine

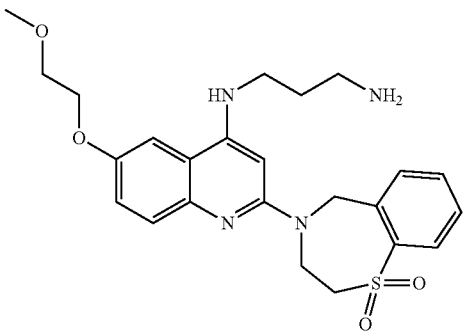 [SMILES: COCCOc1ccc2nc(N3CCS(=O)(=O)c4ccccc4C3)cc(NCCCN)c2c1]

The title compound was prepared in analogy to Example 30-1 by using 4-chloro-2-(1,1-dioxido-2,3-dihydro-1,4-benzothiazepin-4(5H)-yl)quinolin-6-ol (prepared in analogy to the one in Example 29), 1-bromo-2-methoxyethane and propane-1,3-diamine. MS obsd. (ESI+) [(M+H)+] 471, $^1$H NMR (400 MHz, CD$_3$OD) δ ppm 8.10-8.05 (d, J=8 Hz, 1 H), 7.90-7.83 (d, J=7.6 Hz, 1 H), 7.77-7.68 (q, J=9.2 Hz, 2 H), 7.60-7.52 (m, 2 H), 7.42-7.36 (m, 1 H), 5.95 (s, 1 H), 5.30 (s, 2 H), 4.56-4.45 (m, 2 H), 4.22-4.18 (t, J=2.8 Hz, 2 H), 3.80-3.75 (t, J=2.8 Hz, 2 H), 3.75-3.70 (t, J=4.4 Hz, 2 H), 3.65-3.58 (t, J=6.8 Hz, 2 H), 3.42 (s, 3 H), 3.15-3.09 (t, J=7.6 Hz, 2 H), 2.16-2.05 (m, 2 H).

Example 31

N-[2-(1,1-Dioxido-2,3-dihydro-1,4-benzothiazepin-4 (5H)-yl)-6-(pyridin-2-yloxy)quinolin-4-yl]propane-1,3-diamine

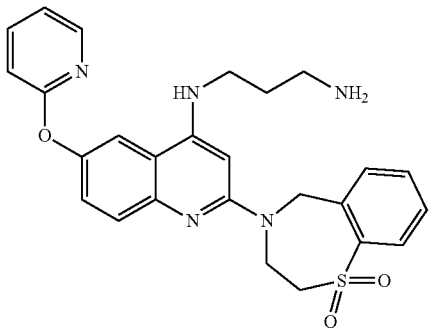 [SMILES: NCCCNc1cc(N2CCS(=O)(=O)c3ccccc3C2)nc2ccc(Oc3ccccn3)cc12]

8-[4-Chloro-6-(pyridin-2-yloxy)-quinolin-2-yl]-2,3,4,5-tetrahydro-1,4-benzothiazepine 1,1-dioxide

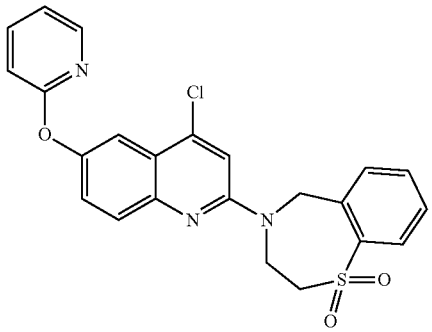 [SMILES: O=S1(=O)CCN(c2cc(Cl)c3cc(Oc4ccccn4)ccc3n2)Cc2ccccc21]

A mixture of 4-chloro-2-(1,1-dioxido-2,3-dihydro-1,4-benzothiazepin-4(5H)-yl)quinolin-6-ol (400 mg, 1.067 mmol), 2-bromo-pyridine (337 mg, 2.134 mmol, prepared in analogy to the one in Example 29), copper(I) iodide (40 mg, 0.107 mmol), N,N'-dimethyl-cyclohexane-1,2-diamine (2.0 mg, 0.107 mmol) and potassium carbonate (250 mg, 2.134 mmol) in 1,2-dimethoxyethane (5 mL) was heated at 120° C. for 1 hour under microwave irridiation. The resulting mixture was filtered and concentrated in vacuo. The residue was purified by preparative HPLC to afford 300 mg of the desired product (yield was 62.2%).

N-[2-(1,1-Dioxido-2,3-dihydro-1,4-benzothiazepin-4 (5H)-yl)-6-(pyridin-2-yloxy)quinolin-4-yl]propane-1,3-diamine

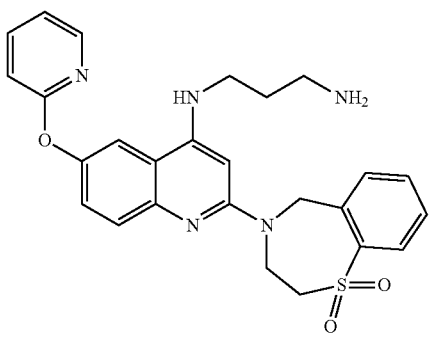 [SMILES: NCCCNc1cc(N2CCS(=O)(=O)c3ccccc3C2)nc2ccc(Oc3ccccn3)cc12]

The title compound was prepared in analogy to Example 30-1 in Scheme 9 by using 8-[4-chloro-6-(pyridin-2-yloxy)-quinolin-2-yl]-2,3,4,5-tetrahydro-1,4-benzothiazepine 1,1-dioxide and propane-1,3-diamine. MS obsd. (ESI$^+$) [(M+H)$^+$] 490, $^1$H NMR (400 MHz, CD$_3$OD) δ ppm 8.10-8.02 (m, 2 H), 7.92-7.90 (m, 1 H), 7.88-7.80 (m, 3 H), 7.71-7.65 (t, J=7.2 Hz, 1 H), 7.60-7.48 (m, 2 H), 7.15-7.09 (t, J=0.8 Hz, 1 H), 7.06-7.00 (d, J=8.4 Hz, 1 H), 5.96 (s, 1 H), 5.31 (s, 2 H), 4.55-4.42 (m, 2 H), 3.78-3.69 (t, J=2.8 Hz, 2 H), 3.60-3.50 (t, J=6.8 Hz, 2 H), 3.08-3.00 (t, J=7.6 Hz, 2 H), 2.10-2.00 (m, 2 H).

Example 32-1

3-{[2-(1,1-Dioxido-2,3-dihydro-1,4-benzothiazepin-4(5H)-yl)-6-methylquinolin-4-yl]amino}propane-1,2-diol

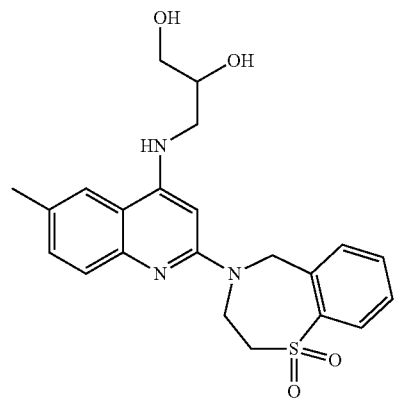 [SMILES: Cc1ccc2nc(N3CCS(=O)(=O)c4ccccc4C3)cc(NCC(O)CO)c2c1]

A mixture of 4-(4-chloro-6-methylquinolin-2-yl)-2,3,4,5-tetrahydro-1,4-benzothiazepine 1,1-dioxide (200.0 mg, 0.54 mmol, prepared in analogy to the one in Example 2-1) and 1-(2,2-dimethyl-1,3-dioxolan-4-yl)methanamine (0.5 mL, 3.8 mmol) was heated with stirring at 160° C. for 16 hours. After being cooled to room temperature, the resulting reaction mixture was diluted with methanol (2.0 mL). Concentrated hydrochloric acid (12.0 N, 0.5 mL) was introduced to the above mixture. The resulting mixture was stirred at room temperature for 1 hour, and then extracted with ethyl acetate (100 mL). The organic layer was washed with brine (50 mL×2), dried over anhydrous sodium sulfate and concentrated in vacuo. The residue was purified by preparative HPLC to afford 69.2 mg of the product as a white solid (yield was 30%). MS obsd. (ESI$^+$) [(M+H)$^+$] 428, $^1$H NMR (400 MHz, CD$_3$OD) δ ppm 7.98 (dd, J=7.83, 1.26 Hz, 1 H), 7.89 (d, J=7.33 Hz, 1 H), 7.63 (td, J=7.45, 1.26 Hz, 1 H), 7.57 (s, 1 H), 7.50-7.35 (m, 2 H), 7.29 (dd, J=8.59, 1.77 Hz, 1 H), 6.13 (s, 1 H), 5.14 (s, 2 H), 4.55 (brs, 2 H), 4.04-3.89 (m, 1 H), 3.69 (d, J=5.56 Hz, 2 H), 3.64-3.49 (m, 4 H), 2.41 (s, 3 H).

Example 32-2

3-{[6-Chloro-2-(1,1-dioxido-2,3-dihydro-1,4-benzothiazepin-4(5H)-yl)quinolin-4-yl]amino}propane-1,2-diol

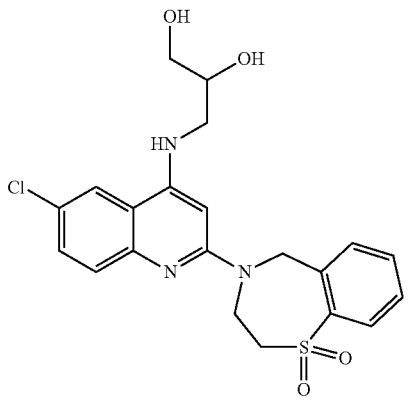 [SMILES: O=S1(=O)CCN(c2cc(NCC(O)CO)c3cc(Cl)ccc3n2)Cc2ccccc21]

The title compound was prepared in analogy to Example 32-1 in Scheme 10 by using 4-(4,6-dichloroquinolin-2-yl)-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4,6-triochloroquinoline and 2,3,4,5-tetrahydro-1,4-benzothiazepine) and 1-(2,2-dimethyl-1,3-dioxolan-4-yl)methanamine. MS obsd. (ESI+) [(M+H)+] 448. 1H NMR (400 MHz, CD3OD) δ ppm 8.23 (d, J=2.02 Hz, 1 H), 8.12 (dd, J=7.83, 1.01 Hz, 1 H), 7.97 (d, J=6.82 Hz, 1 H), 7.87-7.80 (m, 1 H), 7.80-7.68 (m, 2 H), 7.66-7.54 (m, 1 H), 6.30 (s, 1 H), 5.32 (s, 2 H), 4.56 (brs, 2 H), 4.04-3.83 (m, 1 H), 3.83-3.60 (m, 5 H), 3.54 (dd, J=14.27, 7.20 Hz, 1 H).

Example 32-3

3-{[2-(8-Chloro-1,1-dioxido-2,3-dihydro-1,4-benzothiazepin-4(5H)-yl)-6-methylquinolin-4-yl]amino}propane-1,2-diol

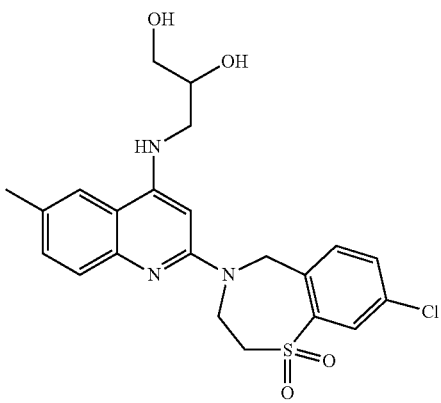 [SMILES: Cc1ccc2nc(N3CCS(=O)(=O)c4cc(Cl)ccc4C3)cc(NCC(O)CO)c2c1]

The title compound was prepared in analogy to Example 32-1 in Scheme 10 by using 4-(4-chloro-6-methylquinolin-2-yl)-8-chloro-2,3,4,5-tetrahydro-1,4-benzothiazepine 1,1-dioxide (prepared in analogy to 4-(4-chloro-6-methylquinolin-2-yl)-2,3,4,5-tetrahydro-1,4-benzothiazepine 1,1-dioxide in Example 2-1 by using 2,4-dichloro-6-methylquinoline and 8-chloro-2,3,4,5-tetrahydro-1,4-benzothiazepine) and 1-(2,2-dimethyl-1,3-dioxolan-4-yl)methanamine. MS obsd. (ESI+) [(M+H)+] 462. 1H NMR (400 MHz, CD3OD) δ ppm 8.04 (d, J=2.27 Hz, 1 H), 7.94 (d, J=10.36 Hz, 2 H), 7.67-7.82 (m, 2 H), 7.61 (dd, J=8.59, 1.26 Hz, 1 H), 6.21 (s, 1 H), 5.28 (s, 2 H), 4.54 (brs, 2 H), 4.02-3.90 (m, 1 H), 3.80 (brs, 2 H), 3.76-3.61 (m, 3 H), 3.54 (dd, J=14.15, 7.33 Hz, 1 H), 2.50 (s, 3 H).

Example 32-4

3-{[6-Methyl-2-(1-oxido-2,3-dihydro-1,4-benzothiazepin-4(5H)-yl)quinolin-4-yl]amino}propane-1,2-diol

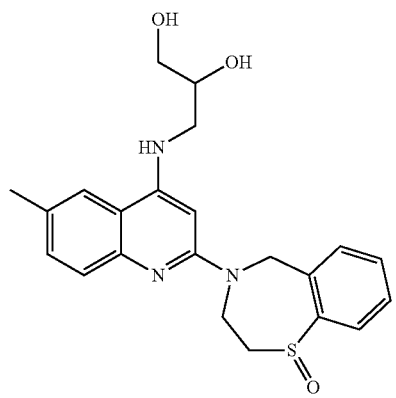 [SMILES: Cc1ccc2nc(N3CCS(=O)c4ccccc4C3)cc(NCC(O)CO)c2c1]

The title compound was prepared in analogy to Example 32-1 in Scheme 5 by using 4-(4-chloro-6-methylquinolin-2-yl)-2,3,4,5-tetrahydro-1,4-benzothiazepine 1-oxide (prepared in analogy to the one in Example 18-1) and 1-(2,2-dimethyl-1,3-dioxolan-4-yl)methanamine. MS obsd. (ESI+) [(M+H)+] 412. 1H NMR (400 MHz, CD3OD) δ ppm 7.78 (d, J=7.33 Hz, 1 H), 7.74 (dd, J=7.58, 1.26 Hz, 1 H), 7.62 (s, 1 H), 7.55-7.39 (m, 3 H), 7.33 (dd, J=8.34, 1.52 Hz, 1 H), 6.13 (s, 1 H), 5.24 (dd, J=16.04, 2.91 Hz, 2 H), 4.82 (d, J=7.58 Hz, 1 H), 4.76 (d, J=14.15 Hz, 2 H), 4.06-3.83 (m, 1 H), 3.75-3.63 (m, 2 H), 3.63-3.52 (m, 1 H), 3.45 (d, J=3.79 Hz, 2 H), 3.37 (td, J=6.88, 4.42 Hz, 1 H), 2.43 (s, 3 H).

Example 32-5

3-{[6-Methyl-2-(5-methyl-1,1-dioxido-2,3-dihydro-1,4-benzothiazepin-4(5H)-yl)quinolin-4-yl]amino}propane-1,2-diol

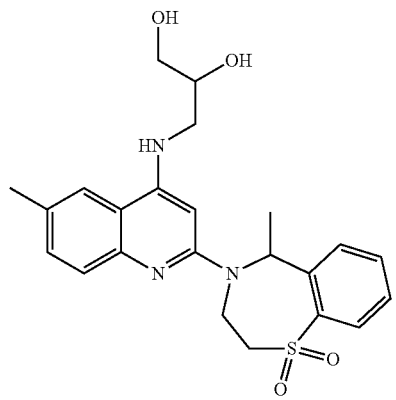 [SMILES: Cc1ccc2nc(N3CCS(=O)(=O)c4ccccc4C3C)cc(NCC(O)CO)c2c1]

4-(4-Chloro-6-methylquinolin-2-yl)-5-methyl-2,3,4,5-tetrahydro-1,4-benzothiazepine

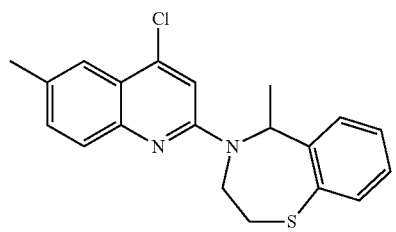 [SMILES: Cc1ccc2nc(N3CCSc4ccccc4C3C)cc(Cl)c2c1]

A mixture of 5-methyl-2,3,4,5-tetrahydro-1,4-benzothiazepine (1.0 g, 5.58 mmol) and 2,4-dichloro-6-methylquinoline (1.7 g, 8.02 mmol) was heated with stirring in a 2 mL of microwave process vial for 5 hours at 170° C. under microwave irradiation. The solvent was removed by concentration in vacuo. The residue was purified by flash column chromatography to give 560 mg of the mixture of 5-methyl-2,3,4,5-tetrahydro-1,4-benzothiazepine and 4-(4-chloro-6-methylquinolin-2-yl)-5-methyl-2,3,4,5-tetrahydro-1,4-benzothiazepine.

4-(4-Chloro-6-methylquinolin-2-yl)-5-methyl-2,3,4,5-tetrahydro-1,4-benzothiazepine 1,1-dioxide

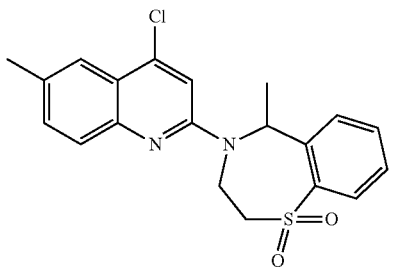 [SMILES: Cc1ccc2nc(N3CCS(=O)(=O)c4ccccc4C3C)cc(Cl)c2c1]

To a solution of the above mixture of 5-methyl-2,3,4,5-tetrahydro-1,4-benzothiazepine and 4-(4-chloro-6-methylquinolin-2-yl)-5-methyl-2,3,4,5-tetrahydro-1,4-benzothiazepine (427 mg) in dichloromethane was added a solution of 3-chloroperbenzoic acid (693 mg, 3.01 mmol) in dichloromethane in an ice bath. After being stirred for 1.5 hours in an ice bath, the reaction mixture was washed with a saturated aqueous solution of sodium bicarbonate and brine. The organic layer was dried over anhydrous sodium sulfate, and concentrated in vacuo. The residue was purified by flash column chromatography to give 130 mg of the product.

3-{[6-Methyl-2-(5-methyl-1,1-dioxido-2,3-dihydro-1,4-benzothiazepin-4(5H)-yl)quinolin-4-yl]amino}propane-1,2-diol

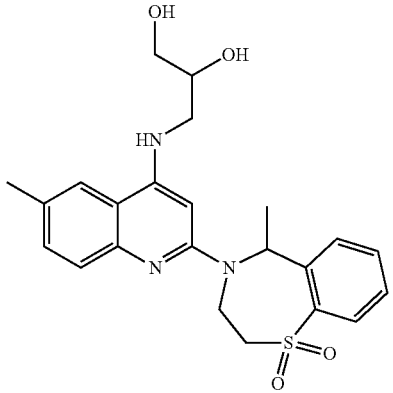 [SMILES: Cc1ccc2nc(N3CCS(=O)(=O)c4ccccc4C3C)cc(NCC(O)CO)c2c1]

The title compound was prepared in analogy to Example 32-1 in Scheme 10 by using 4-(4-chloro-6-methylquinolin-2-yl)-5-methyl-2,3,4,5-tetrahydro-1,4-benzothiazepine 1,1-dioxide and 1-(2,2-dimethyl-1,3-dioxolan-4-yl)methanamine. MS obsd. (ESI$^+$) [(M+H)$^+$] 453, $^1$H NMR (400 MHz, CD$_3$OD) δ ppm 8.03 (dd, J=7.96, 1.39 Hz, 1 H), 7.90 (d, J=6.57 Hz, 1 H), 7.71-7.64 (m, 2 H), 7.46 (ddd, J=8.15, 6.63, 1.64 Hz, 2 H), 7.33 (dd, J=8.59, 1.77 Hz, 1 H), 6.15 (s, 1 H), 5.86 (d, J=6.82 Hz, 1 H), 4.64-4.53 (m, 4 H), 3.70 (d, J=8.59 Hz, 1 H), 3.62-3.58 (m, 2 H), 3.57-3.49 (m, 1 H), 2.43 (s, 3 H), 2.00 (d, J=7.07 Hz, 3 H).

Example 33-1

N-[(3-Aminooxetan-3-yl)methyl]-2-(7-morpholin-4-yl-1,1-dioxido-2,3-dihydro-1,4-benzothiazepin-4(5H)-yl)-6-methylquinolin-4-amine

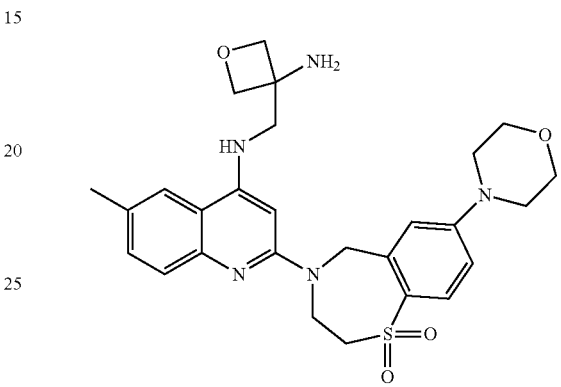

N-{[3-(Dibenzylamino)oxetan-3-yl]methyl}-6-methyl-2-[7-(morpholin-4-yl)-1,1-dioxido-2,3-dihydro-1,4-benzothiazepin-4(5H)-yl]quinolin-4-amine

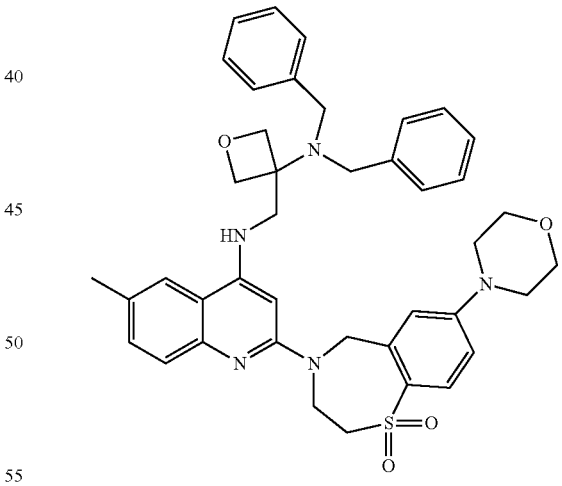

A mixture of N-{[3-(dibenzylamino)oxetan-3-yl]methyl}-6-methyl-2-[7-fluoro-1,1-dioxido-2,3-dihydro-1,4-benzothiazepin-4(5H)-yl]quinolin-4-amine (100 mg, 0.16 mmol, prepared in analogy to N-{[3-(dibenzylamino)oxetan-3-yl]methyl}-2-(8-methoxy-1,1-dioxido-2,3-dihydro-1,4-benzothiazepin-4(5H)-yl)-6-methylquinolin-4-amine in Example 1-1 by using 2,4-dichloro-6-methylquinoline, 7-fluoro-2,3,4,5-tetrahydro-1,4-benzothiazepine and 3-(aminomethyl)-N,N-dibenzyloxetan-3-amine) and morpholine (0.5 mL) was heated with stirring in a sealed 2 mL of microwave process via for 3 hours at 120° C. under microwave irradiation. The resulting mixture was concentrated in vacuo to afford 111 mg of the crude product which was used in next step without purification. MS obsd. (ESI⁺) [(M+H)⁺] 704.

N-[(3-Aminooxetan-3-yl)methyl]-2-[(7-morpholin-4-yl)-1,1-dioxido-2,3-dihydro-1,4-benzothiazepin-4(5H)-yl]-6-methylquinolin-4-amine

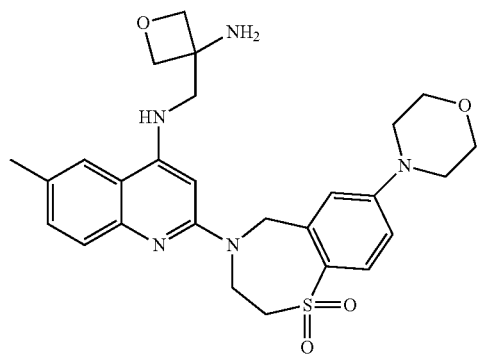 [SMILES: Cc1ccc2nc(N3CCS(=O)(=O)c4ccc(N5CCOCC5)cc4C3)cc(NCC3(N)COC3)c2c1]

A mixture of N-{[3-(dibenzylamino)oxetan-3-yl]methyl}-6-methyl-2-[7-(morpholin-4-yl)-1,1-dioxido-2,3-dihydro-1,4-benzothiazepin-4(5H)-yl]quinolin-4-amine (100 mg, 0.14 mmol), 10% palladium hydroxide on active carbon (100 mg) and trifluoroacetic acid (0.5 mL) in methanol (20 mL) was stirred for 12 hours under hydrogen (1 bar). Then the mixture was basified with a saturated aqueous solution of sodium bicarbonate, and extracted with dichloromethane. The organic layer was dried over anhydrous sodium sulfate, and concentrated in vacuo. The residue was purified by preparative HPLC to afford 30 mg of the product (yield was 40%). MS obsd. (ESI⁺) [(M+H)⁺] 524, ¹HNMR ((400 MHz, CD₃OD) δ ppm 7.72-7.60 (m, 2 H), 7.56 (d, J=2.27 Hz, 1 H), 7.33 (d, J=8.34 Hz, 1 H), 7.25 (dd, J=8.46, 1.39 Hz, 1 H), 6.85 (dd, J=8.84, 2.53 Hz, 1 H), 6.30-6.03 (m, 2 H), 5.00 (brs, 2 H), 4.53-4.31 (m, 4 H), 3.86-3.68 (m, 4 H), 3.51 (d, J=14.40 Hz, 4 H), 3.33-3.19 (m, 6 H), 2.41 (brs, 1 H), 2.37 (s, 3 H).

Example 33-2

N-[(3-Aminooxetan-3-yl)methyl]-2-{1,1-dioxido-7-[4-(propan-2-yl)piperazin-1-yl]-2,3-dihydro-1,4-benzothiazepin-4(5H)-yl}-6-methylquinolin-4-amine

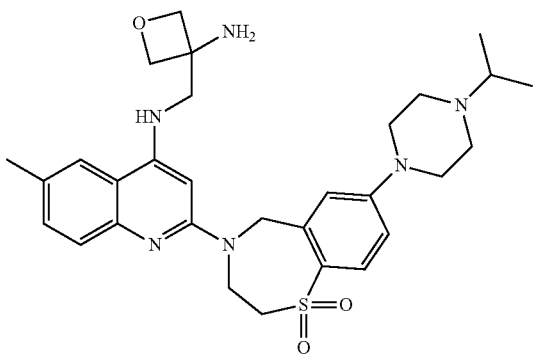 [SMILES: Cc1ccc2nc(N3CCS(=O)(=O)c4ccc(N5CCN(C(C)C)CC5)cc4C3)cc(NCC3(N)COC3)c2c1]

The title compound was prepared in analogy to Example 33-1 in Scheme 11 by using N-{[3-(dibenzylamino)oxetan-3-yl]methyl}-6-methyl-2-[7-fluoro-1,1-dioxido-2,3-dihydro-1,4-benzothiazepin-4(5H)-yl]quinolin-4-amine (prepared in analogy to the one in Example 33-1) and 4-(propan-2-yl)piperazine. MS obsd. (ESI⁺) [(M+H)⁺] 565, ¹HNMR ((400 MHz, CD₃OD) δ ppm 7.82-7.67 (m, 2 H), 7.58 (d, J=8.59 Hz, 1 H), 7.46 (d, J=2.53 Hz, 1 H), 7.35 (dd, J=8.59, 1.52 Hz, 1 H), 6.72 (dd, J=8.97, 2.15 Hz, 1 H), 6.14 (s, 1 H), 5.11 (brs, 2 H), 4.62 (q, J=6.57 Hz, 4 H), 4.56-4.36 (m, 2 H), 3.82-3.65 (m, 2 H), 3.54 (brs, 2 H), 3.50-3.39 (m, 4 H), 2.90-2.88 (m, 1 H), 2.88-2.72 (m, 4 H), 2.50-2.40 (m, 3 H), 1.26-1.11 (m, 6 H).

Example 34

3-{[4-(4-Aminoquinolin-2-yl)-1,1-dioxido-2,3,4,5-tetrahydro-1,4-benzothiazepin-8-yl]oxy}propan-1-ol

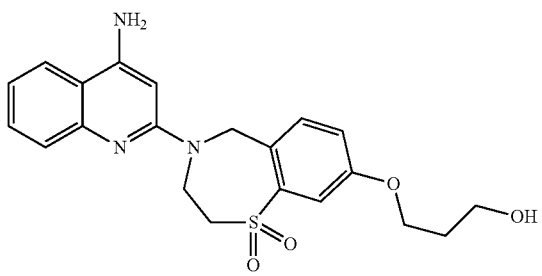 [SMILES: Nc1cc(N2CCS(=O)(=O)c3cc(OCCCO)ccc3C2)nc2ccccc12]

4-(4-Chloroquinolin-2-yl)-2,3,4,5-tetrahydro-1,4-benzothiazepin-8-ol 1,1-dioxide

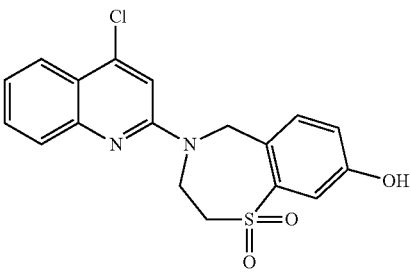 [SMILES: O=S1(=O)CCN(c2cc(Cl)c3ccccc3n2)Cc2ccc(O)cc21]

To a stirred solution of 4-(4-chloroquinolin-2-yl)-8-methoxy-2,3,4,5-tetrahydro-1,4-benzothiazepine 1,1-dioxide (2.0 g, 5.15 mmol, prepared in analogy to 4-(4-chloro-6-methylquinolin-2-yl)-2,3,4,5-tetrahydro-1,4-benzothiazepine 1,1-dioxide in Example 2-1) in dry methylene chloride (70.0 mL) was added a solution of boron tribromide (2.5 ml, 25.7 mmol) in dry methylene chloride (10 ml) at 0° C. After being stirred at 0° C. for 1 hour, the reaction was quenched by addition of a saturated aqueous sodium bicarbonate solution (30 mL). The mixture was extracted with ethyl acetate (100 mL×2). The combined organic layers were washed with a saturated aqueous sodium bicarbonate solution (20 mL×3) and brine (20 mL×3), dried over anhydrous sodium sulfate and concentrated in vacuo to afford 1.95 g of the crude product as a white solid. MS obsd. (ESI⁺) [(M+H)⁺] 375.

325

3-{[4-(4-Chloroquinolin-2-yl)-1,1-dioxido-2,3,4,5-tetrahydro-1,4-benzothiazepin-8-yl]oxy}propan-1-ol

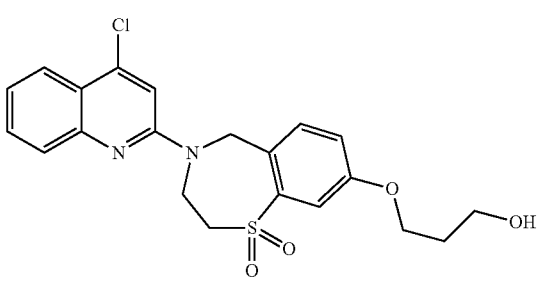 [SMILES: O=S1(=O)CCN(c2cc(Cl)c3ccccc3n2)Cc2ccc(OCCCO)cc21]

A mixture of 4-(4-chloroquinolin-2-yl)-2,3,4,5-tetrahydro-1,4-benzothiazepin-8-ol 1,1-dioxide (374.0 mg, 1.0 mmol), 3-bromo-propan-1-ol (0.37 mL, 3.0 mmol) and potassium carbonate (415.0 mg, 3.0 mmol) in N,N-dimethylformamide (1.5 mL) was heated with stirring at 70° C. for 2 hours. After being cooled to room temperature, the resulting mixture was extracted with ethyl acetate (150 mL×2). The combined organic layers were washed with water (50 mL×2) and a saturated aqueous ammonium chloride solution (50 mL×2), dried over anhydrous sodium sulfate and then concentrated in vacuo to afford 421.6 mg of the crude product as a yellow oil which was used for next step without further purification. MS obsd. (ESI$^+$) [(M+H)$^+$] 433.

tert-Butyl {2-[8-(3-hydroxypropoxy)-1,1-dioxido-2,3-dihydro-1,4-benzothiazepin-4(5H)-yl]quinolin-4-yl}carbamate

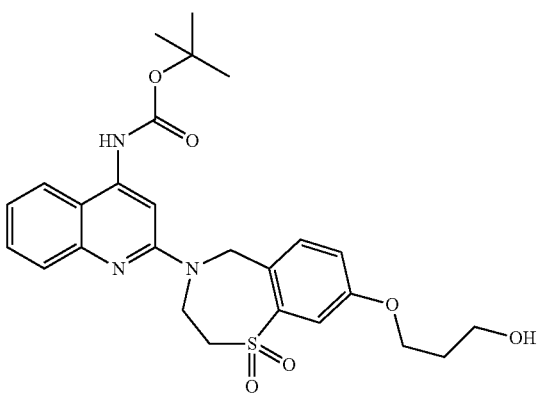 [SMILES: CC(C)(C)OC(=O)Nc1cc(N2CCS(=O)(=O)c3cc(OCCCO)ccc3C2)nc2ccccc12]

A mixture solution of 3-{[4-(4-chloroquinolin-2-yl)-1,1-dioxido-2,3,4,5-tetrahydro-1,4-benzothiazepin-8-yl]oxy}propan-1-ol (300.0 mg, 0.70 mmol), tert-butyl carbamate (175.0 mg, 1.5 mmol), 1,1'-bis(diphenylphosphino)ferrocene (70.0 mg, 0.113 mmol), 1,1'-bis(diphenylphosphino)ferrocenedichloropalladium(II) (70.0 mg, 0.075 mmol) and sodium tert-butoxide (232.0 mg, 2.25 mmol) in 1,4-dioxane (2.0 mL) was heated with stirring at 120° C. for 2 hours under microwave irridiation. After being cooled to room temperature, the reaction mixture was extracted with ethyl acetate (100 mL). The organic layer was washed with brine (50 mL×2), dried over anhydrous sodium sulfate and concentrated in vacuo to afford 359.1 mg of the crude product as yellow oil which was used for next step without further purification. MS obsd. (ESI$^+$) [(M+H)$^+$] 514.

326

3-{[4-(4-Aminoquinolin-2-yl)-1,1-dioxido-2,3,4,5-tetrahydro-1,4-benzothiazepin-8-yl]oxy}propan-1-ol

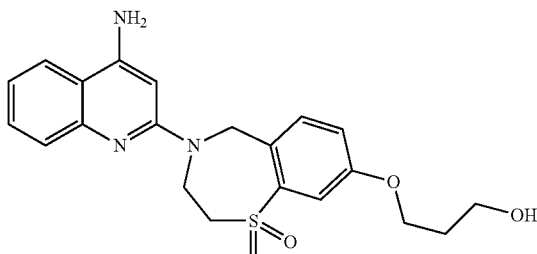

A mixture solution of tert-butyl {2-[8-(3-hydroxypropoxy)-1,1-dioxido-2,3-dihydro-1,4-benzothiazepin-4(5H)-yl]quinolin-4-yl}carbamate (359.1 mg, the crude product of the above step) and trifluoroacetic acid (1.0 mL) in dichloromethane (2.0 mL) was stirred at room temperature for 6 hours. The reaction mixture was diluted with water (10 mL) and extracted with ethyl acetate (100 mL). The organic layer was washed with brine (50 mL×2), dried over anhydrous sodium sulfate and concentrated in vacuo. The residue was purified by preparative HPLC to afford 14.2 mg of the desired product as a white solid (yield was 4.9%). MS obsd. (ESI$^+$) [(M+H)$^+$] 414, $^1$HNMR ((400 MHz, CD$_3$OD) δ ppm 7.82-7.67 (m, 2 H), 7.54-7.48 (m, 2 H), 7.48-7.39 (m, 1 H), 7.19-7.06 (m, 2 H), 6.30 (s, 1 H), 5.04 (s, 2 H), 4.78-4.34 (m, 2 H), 4.11 (t, J=6.32 Hz, 2 H), 3.71 (t, J=6.19 Hz, 2 H), 3.62-3.49 (m, 2 H), 2.11-1.78 (m, 2 H).

Example 35

N-[(3-Aminooxetan-3-yl)methyl]-2-(1,1-dioxido-8-phenoxy-2,3-dihydro-1,4-benzothiazepin-4(5H)-yl)-6-methylquinolin-4-amine

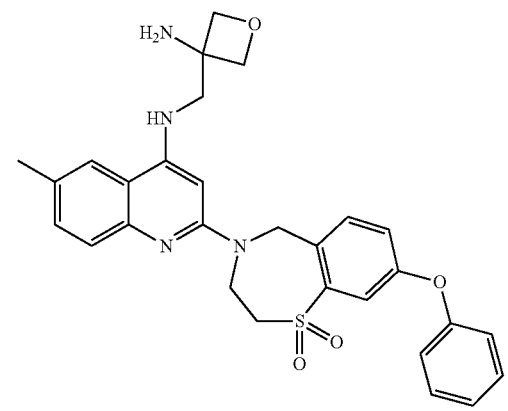 [SMILES: Cc1ccc2nc(N3CCS(=O)(=O)c4cc(Oc5ccccc5)ccc4C3)cc(NCC3(N)COC3)c2c1]

4-(4-Chloro-6-methylquinolin-2-yl)-8-phenoxy-2,3,4,5-tetrahydro-1,4-benzothiazepine 1,1-dioxide

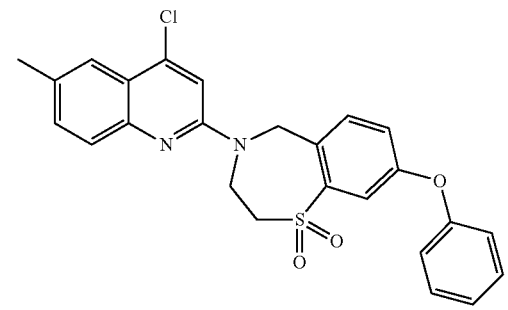 [SMILES: Cc1ccc2nc(N3CCS(=O)(=O)c4cc(Oc5ccccc5)ccc4C3)cc(Cl)c2c1]

327

A mixture of 4-(4-chloro-6-methylquinolin-2-yl)-2,3,4,5-tetrahydro-1,4-benzothiazepin-8-ol 1,1-dioxide (250.0 mg, 0.65 mmol, prepared in analogy to 4-(4-chloroquinolin-2-yl)-2,3,4,5-tetrahydro-1,4-benzothiazepin-8-ol 1,1-dioxide in Example 34), iodo-benzene (0.1 mL, 0.089 mmol), copper(I) iodide (74.0 mg, 0.35 mmol), N,N-dimethylglycine hydrochloride (72.0 mg, 0.52 mmol) and potassium carbonate (267.0 mg, 1.9 mmol) in dimethyl sulfoxide (1.5 mL). The reaction mixture was heated with stirring at 120° C. for 6 hours. After being cooled to room temperature, the reaction mixture was extracted with ethyl acetate (150 mL×2), washed with water (50 mL×2) and a saturated aqueous ammonium chloride solution (50 mL×2), dried over anhydrous sodium sulfate and then concentrated in vacuo to afford 298.0 mg of the crude product as a yellow oil which was used for next step without further purification. MS obsd. (ESI$^+$) [(M+H)$^+$] 465.

N-{[3-(Dibenzylamino)oxetan-3-yl]methyl}-2-(1,1-dioxido-8-phenoxy-2,3-dihydro-1,4-benzothiazepin-4(5H)-yl)-6-methylquinolin-4-amine

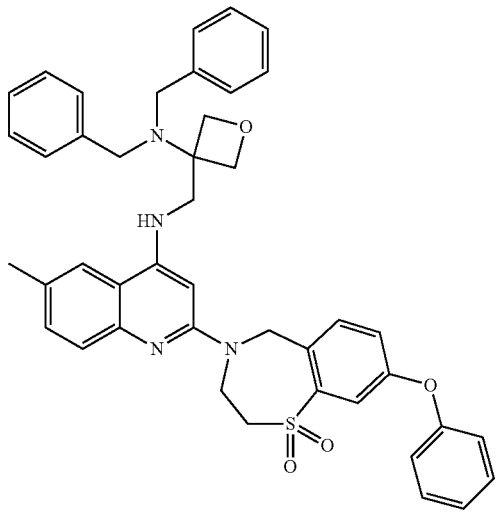 [SMILES: Cc1ccc2nc(N3CCS(=O)(=O)c4cc(Oc5ccccc5)ccc4C3)cc(NCC3(N(Cc4ccccc4)Cc4ccccc4)COC3)c2c1]

A mixture solution of 4-(4-chloro-6-methylquinolin-2-yl)-8-phenoxy-2,3,4,5-tetrahydro-1,4-benzothiazepine 1,1-dioxide (167.0 mg, 0.36 mmol), (3-(aminomethyl)-N,N-dibenzyloxetan-3-amine (609.0 mg, 2.16 mmol), 1,1'-bis(diphenylphosphino)-ferrocenedichloropalladium(II) (15.0 mg, 0.02 mmol), 1,1'-bis(diphenylphosphino)-ferrocene (11.2 mg, 0.02 mmol) and sodium tert-butoxide (75.0 mg, 0.72 mmol) in 1,4-dioxane (2.0 mL) was heated with stirring at 120° C. for 2 hours under microwave irridiation. After being cooled to room temperature, the reaction mixture was extracted with ethyl acetate (100 mL). The organic layer was washed with brine (50 mL×2), dried over anhydrous sodium sulfate and concentrated in vacuo. The residue was purified by ISCO combi-flash chromatography (gradient elution, 20-60% ethyl acetate in petroleum ether) to afford 134.6 mg of the desired product as a light yellow solid (yield was 52.6%). MS obsd. (ESI$^+$) [(M+H)$^+$] 711.

328

N-[(3-Aminooxetan-3-yl)methyl]-2-(1,1-dioxido-8-phenoxy-2,3-dihydro-1,4-benzothiazepin-4(5H)-yl)-6-methylquinolin-4-amine

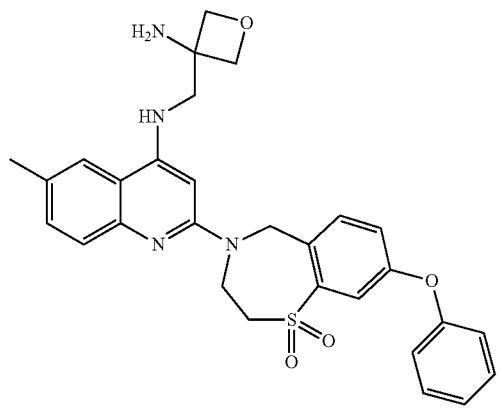 [SMILES: Cc1ccc2nc(N3CCS(=O)(=O)c4cc(Oc5ccccc5)ccc4C3)cc(NCC3(N)COC3)c2c1]

A mixture of N-{[3-(dibenzylamino)oxetan-3-yl]methyl}-2-(1,1-dioxido-8-phenoxy-2,3-dihydro-1,4-benzothiazepin-4(5H)-yl)-6-methylquinolin-4-amine (90 mg, 0.13 mmol), palladium hydroxide on carbon (40 mg) and trifluoroacetic acid (0.1 mL) in methanol (30.0 mL) was stirred at room temperature under hydrogen (2 bar) for 14 hours. Then the reaction mixture was filtered and concentrated in vacuo. The residue was purified by preparative HPLC to afford 10.5 mg of the desired product as a white solid (yield was 15.2%). MS obsd. (ESI$^+$) [(M+H)$^+$] 531, $^1$H NMR (400 MHz, CD$_3$OD) δ ppm 7.86 (d, J=8.34 Hz, 1 H), 7.69 (s, 1 H), 7.52 (d, J=2.53 Hz, 1 H), 7.45 (d, J=8.59 Hz, 1 H), 7.42-7.35 (m, 2 H), 7.31 (dd, J=8.46, 1.64 Hz, 1 H), 7.25-7.13 (m, 2 H), 7.06-6.97 (m, 2 H), 6.21 (s, 1 H), 5.14 (brs, 2 H), 4.70-4.46 (m, 6 H), 3.68 (s, 2 H), 3.60 (brs, 2 H), 2.44 (s, 3 H).

Example 36-1

N$^3$-[2-(1,1-Dioxido-2,3-dihydro-1,4-benzothiazepin-4(5H)-yl)-6-methylquinolin-4-yl]-beta-alaninamide

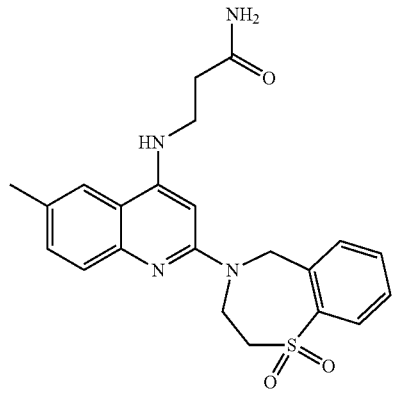 [SMILES: Cc1ccc2nc(N3CCS(=O)(=O)c4ccccc4C3)cc(NCCC(N)=O)c2c1]

Methyl N-[2-(1,1-dioxido-2,3-dihydro-1,4-benzothiazepin-4(5H)-yl)-6-methylquinolin-4-yl]-beta-alaninate

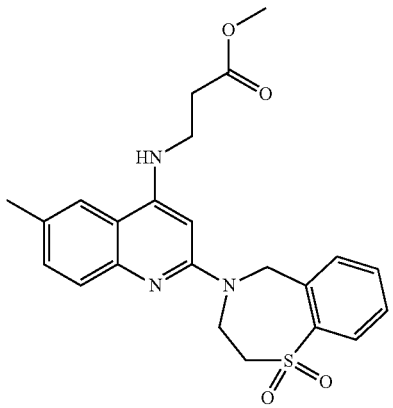 [SMILES: COC(=O)CCNc1cc(N2CCS(=O)(=O)c3ccccc3C2)nc2ccc(C)cc12]

To a solution of N-[2-(1,1-dioxido-2,3-dihydro-1,4-benzothiazepin-4(5H)-yl)-6-methylquinolin-4-yl]-beta-alanine (85 mg, 0.2 mmol, prepared in analogy to the one in Example 14-2) in methanol (10 mL) at 0° C. was added thionyl chloride (1.5 mL) carefully. The mixture was stirred at room temperature for 20 minutes, and then refluxed at 80° C. for 2 hours. After being cooled to room temperature, the mixture was concentrated in vacuo. The residue was dissolved in dichloromethane, washed with a saturated aqueous solution of sodium bicarbonate, water and brine, then dried over sodium sulfate, and concentrated in vacuo to afford the crude product which was directly used for the next step without further purification.

$N^{\sim}3^{\sim}$-[2-(1,1-Dioxido-2,3-dihydro-1,4-benzothiazepin-4(5H)-yl)-6-methylquinolin-4-yl]-beta-alaninamide

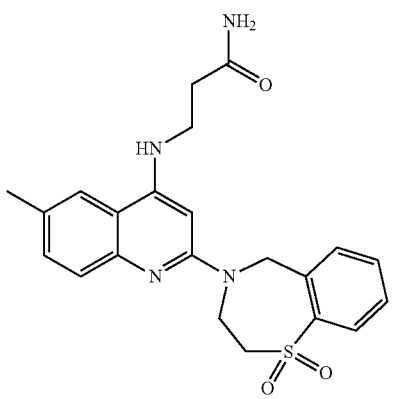 [SMILES: Cc1ccc2nc(N3CCS(=O)(=O)c4ccccc4C3)cc(NCCC(N)=O)c2c1]

A mixture of methyl N-[2-(1,1-dioxido-2,3-dihydro-1,4-benzothiazepin-4(5H)-yl)-6-methylquinolin-4-yl]-beta-alaninate and a solution of ammonia in methanol (7 N, 10 mL) was heated with stirring at 85° C. in a sealed tube overnight. The resulting mixture was concentrated in vacuo. The residue was purified by preparative HPLC to afford 59.2 mg of the desired product as a solid. MS obsd. (ESI$^+$) [(M+H)$^+$] 425, $^1$H NMR (400 MHz, DMSO-d6) δ ppm 7.95 (d, J=6.82 Hz, 1 H), 7.88 (dd, J=7.83, 1.26 Hz, 1 H), 7.66-7.60 (m, 2 H), 7.50-7.42 (m, 2 H), 7.31 (d, J=8.59 Hz, 1 H), 7.22 (dd, J=8.46, 1.64 Hz, 1 H), 6.97 (brs, 1 H), 6.73 (t, J=5.68 Hz, 1 H), 6.06 (s, 1 H), 5.06 (brs, 2 H), 4.40 (brs, 2 H), 3.68-3.56 (m, 2 H), 3.51 (q, J=6.65 Hz, 2 H), 2.42 (t, J=7.07 Hz, 2 H), 2.34 (s, 3 H).

Example 36-2

3-{[2-(1,1-Dioxido-2,3-dihydro-1,4-benzothiazepin-4(5H)-yl)-6-methylquinolin-4-yl]amino}butanamide

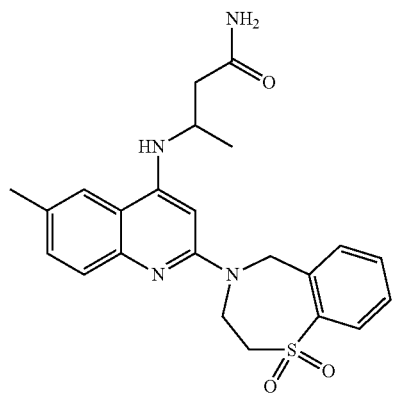 [SMILES: Cc1ccc2nc(N3CCS(=O)(=O)c4ccccc4C3)cc(NC(C)CC(N)=O)c2c1]

The title compound was prepared in analogy to Example 36-1 in Scheme 13 by using 3-{[2-(1,1-dioxido-2,3-dihydro-1,4-benzothiazepin-4(5H)-yl)-6-methylquinolin-4-yl]amino}butanoic acid (prepared in analogy to N-[2-(1,1-dioxido-2,3-dihydro-1,4-benzothiazepin-4(5H)-yl)-6-methylquinolin-4-yl]-beta-alanine in Example 14-2). MS obsd. (ESI$^+$) [(M+H)$^+$] 439, $^1$H NMR (400 MHz, CD$_3$OD) δ ppm 8.07 (dd, J=7.83, 1.26 Hz, 1 H), 7.98 (d, J=7.6 Hz, 1 H), 7.95 (brs, 1 H), 7.74-7.66 (m, 2 H), 7.62-7.51 (m, 2 H), 6.14 (s, 1 H), 5.29 (s, 2 H), 4.43-4.64 (m, 2 H), 4.38 (q, J=8 Hz, 1 H), 3.72 (brs, 2 H), 2.68 (dd, J=14.65, 5.56 Hz, 1 H), 2.54 (dd, J=14.65, 7.07 Hz, 1 H), 2.46 (s, 3 H), 1.41 (d, J=6.32 Hz, 3 H).

Example 36-3

3-{[2-(1,1-Dioxido-2,3-dihydro-1,4-benzothiazepin-4(5H)-yl)-6-methylquinolin-4-yl]amino}-2-methylpropanamide

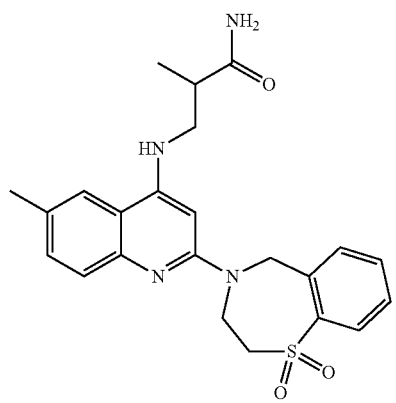 [SMILES: Cc1ccc2nc(N3CCS(=O)(=O)c4ccccc4C3)cc(NCC(C)C(N)=O)c2c1]

The title compound was prepared in analogy to Example 36-1 by using 3-{[2-(1,1-dioxido-2,3-dihydro-1,4-benzothiazepin-4(5H)-yl)-6-methylquinolin-4-yl]amino}-2-methylpropanoic acid (prepared in analogy to N-[2-(1,1-dioxido-2, 3-dihydro-1,4-benzothiazepin-4(5H)-yl)-6-methylquinolin-4-yl]-beta-alanine in Example 14-2). MS obsd. (ESI⁺) [(M+H)⁺] 439, ¹H NMR (400 MHz, DMSO-d6) δ ppm 8.17 (s, 1 H), 7.99-7.82 (m, 2 H), 7.72-7.57 (m, 2 H), 7.54-7.43 (m, 1 H), 7.38 (brs, 1 H), 7.32 (d, J=8.34 Hz, 1 H), 7.23 (dd, J=8.59, 1.52 Hz, 1 H), 6.94 (s, 1 H), 6.03 (s, 1 H), 5.08 (brs, 2 H), 4.52 (brs, 3 H), 4.30 (brs, 1 H), 3.70-3.55 (m, 2 H), 3.50 (dt, J=13.26, 6.51 Hz, 2 H), 3.25-3.15 (m, 2 H), 2.67 (q, J=6.91 Hz, 1 H), 2.41-2.26 (m, 3 H), 1.13 (d, J=7.07 Hz, 3 H).

Example 36-4

N~2~-[2-(1,1-dioxido-2,3-dihydro-1,4-benzothiazepin-4(5H)-yl)-6-methylquinolin-4-yl]-L-alaninamide

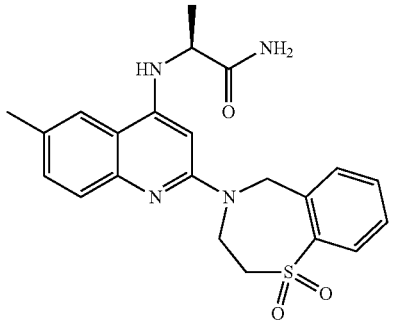 [SMILES: Cc1ccc2nc(N3CCS(=O)(=O)c4ccccc4C3)cc(N[C@@H](C)C(N)=O)c2c1]

The title compound was prepared in analogy to Example 36-1 by using N-[2-(1,1-dioxido-2,3-dihydro-1,4-benzothiazepin-4(5H)-yl)-6-methylquinolin-4-yl]-L-alanine (prepared in analogy to N-[2-(1,1-dioxido-2,3-dihydro-1,4-benzothiazepin-4(5H)-yl)-6-methylquinolin-4-yl]-beta-alanine in Example 14-2). MS obsd. (ESI⁺) [(M+H)⁺] 425, ¹H NMR (400 MHz, DMSO-d6) δ ppm 7.91-7.81 (m, 3 H), 7.68 (s, 1 H), 7.54 (brs, 1 H), 7.48 (d, J=7.33 Hz, 1 H), 7.33 (d, J=8.34 Hz, 1 H), 7.26 (d, J=8.08 Hz, 1 H), 7.18 (brs, 1 H), 6.61 (d, J=6.32 Hz, 1 H), 5.89 (s, 1 H), 4.99 (brs, 2 H), 4.08 (brs, 2 H), 3.59 (brs, 3 H), 2.35 (brs, 3 H), 1.49 (d, J=6.82 Hz, 3 H).

Example 36-5

N~2~-(1,1-Dioxido-2,3-dihydro-1,4-benzothiazepin-4(5H)-yl)-6-methylquinolin-4-yl]glycinamide

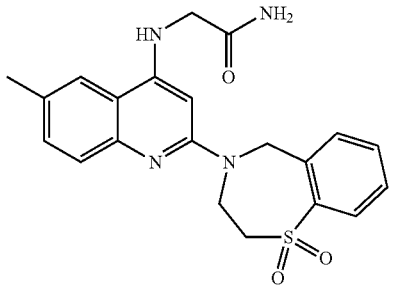 [SMILES: Cc1ccc2nc(N3CCS(=O)(=O)c4ccccc4C3)cc(NCC(N)=O)c2c1]

The title compound was prepared in analogy to Example 36-1 by using N~2~-[2-(1,1-Dioxido-2,3-dihydro-1,4-benzothiazepin-4(5H)-yl)-6-methylquinolin-4-yl]glycine (prepared in analogy to N-[2-(1,1-dioxido-2,3-dihydro-1,4-benzothiazepin-4(5H)-yl)-6-methylquinolin-4-yl]-beta-alanine in Example 14-2). MS obsd. (ESI⁺) [(M+H)⁺] 411, ¹H NMR (400 MHz, DMSO-d6) δ ppm 7.87 (d, J=7.83 Hz, 1 H), 7.82 (d, J=7.33 Hz, 1 H), 7.74-7.64 (m, 2 H), 7.52-7.41 (m, 2 H), 7.36-7.30 (m, 1 H), 7.30-7.19 (m, 2 H), 7.10 (t, J=5.56 Hz, 1 H), 5.87 (s, 1 H), 5.00 (brs, 2 H), 3.86 (d, J=5.81 Hz, 2 H), 3.59 (brs, 2 H), 3.32 (s, 2 H), 2.41-2.32 (s, 3 H).

Example 36-6

N~2~-[2-(1,1-Dioxido-2,3-dihydro-1,4-benzothiazepin-4(5H)-yl)-6-methylquinolin-4-yl]-N-methylglycinamide

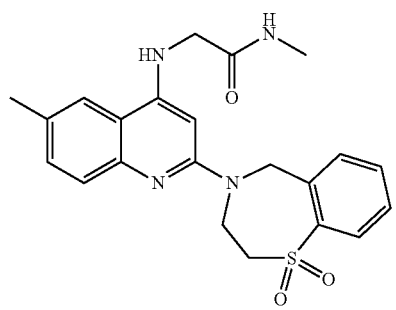 [SMILES: CNC(=O)CNc1cc(N2CCS(=O)(=O)c3ccccc3C2)nc2ccc(C)cc12]

The title compound was prepared in analogy to Example 36-1 by using N~2~-[2-(1,1-dioxido-2,3-dihydro-1,4-benzothiazepin-4(5H)-yl)-6-methylquinolin-4-yl]glycine (prepared in analogy to N-[2-(1,1-dioxido-2,3-dihydro-1,4-benzothiazepin-4(5H)-yl)-6-methylquinolin-4-yl]-beta-alanine in Example 14-2) and a solution of methylamine in ethanol. MS obsd. (ESI⁺) [(M+H)⁺] 425, ¹H NMR (400 MHz, DMSO-d6) δ ppm 7.90-7.82 (m, 2 H), 7.77 (d, J=7.58 Hz, 1 H), 7.70 (s, 1 H), 7.61 (td, J=7.45, 1.52 Hz, 1 H), 7.51-7.46 (m, 1 H), 7.34 (d, J=8.34 Hz, 1 H), 7.26 (dd, J=8.46, 1.64 Hz, 1 H), 7.15 (t, J=5.94 Hz, 1 H), 5.86 (s, 1 H), 5.00 (brs, 2 H), 3.90 (d, J=5.81 Hz, 2 H), 3.59 (brs, 2 H), 3.32 (s, 2 H), 2.62 (d, J=4.55 Hz, 3 H), 2.37 (s, 3 H).

Example 37-1

(2S)-2-Amino-3-{[2-(1,1-dioxido-2,3-dihydro-1,4-benzothiazepin-4(5H)-yl)-6-methylquinolin-4-yl]amino}propan-1-ol

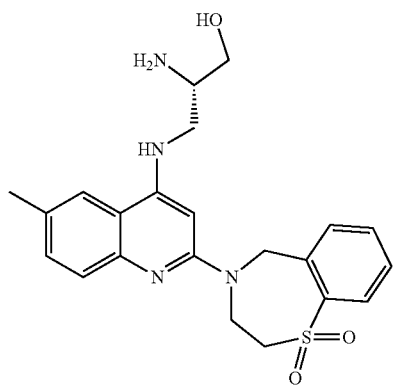 [SMILES: Cc1ccc2nc(N3CCS(=O)(=O)c4ccccc4C3)cc(NC[C@H](N)CO)c2c1]

333 tert-Butyl (2S)-4-({[2-(1,1-dioxido-2,3-dihydro-1,4-benzothiazepin-4(5H)-yl)-6-methylquinolin-4-yl]amino}methyl)-2,2-dimethyl-1,3-oxazolidine-3-carboxylate

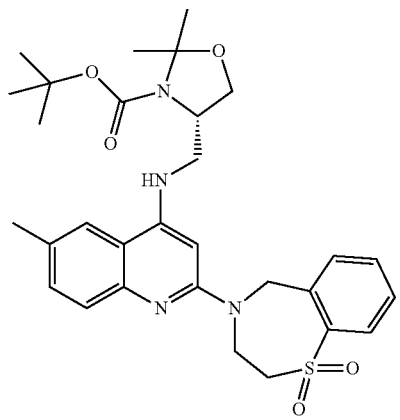 [SMILES: Cc1ccc2nc(N3CCS(=O)(=O)c4ccccc4C3)cc(NC[C@H]3COC(C)(C)N3C(=O)OC(C)(C)C)c2c1]

A mixture of 4-(4-chloro-6-methylquinolin-2-yl)-2,3,4,5-tetrahydro-1,4-benzothiazepine 1,1-dioxide (332 mg, 0.890 mmol), tert-butyl (2S)-4-aminomethyl-2,2-dimethyl-1,3-oxazolidine-3-carboxylate (205 mg, 0.890 mmol), 1,1'-bis(diphenylphosphino)ferrocene-palladium(II)dichloride (73 mg, 0.089 mmol), 1,1'-bis(diphenylphosphino)ferrocene (49 mg, 0.089 mmol), sodium tert-butoxide (171.1 mg, 1.780 mmol) and 1,4-dioxane (4 mL) was heated at 120° C. for 1.5 hours under microwave irradiation. The reaction mixture was concentrated in vacuo. The residue was purified by flash column chromatography to afford 251 mg of the desired product.

(2S)-2-Amino-3-{[2-(1,1-dioxido-2,3-dihydro-1,4-benzothiazepin-4(5H)-yl)-6-methylquinolin-4-yl]amino}propan-1-ol

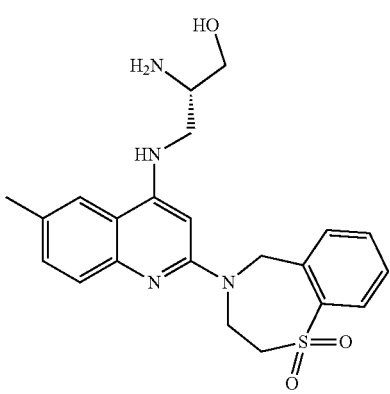 [SMILES: Cc1ccc2nc(N3CCS(=O)(=O)c4ccccc4C3)cc(NC[C@H](N)CO)c2c1]

A mixture of tert-butyl 4-({[2-(1,1-dioxido-2,3-dihydro-1,4-benzothiazepin-4(5H)-yl)-6-methylquinolin-4-yl]amino}methyl)-2,2-dimethyl-1,3-oxazolidine-3-carboxylate (251 mg) and a solution of hydrochloride in ethyl acetate (13 mL, 4 N) was stirred at room temperature overnight. The reaction mixture was concentrated in vacuo. The residue was dissolved in water, and basified with a saturated aqueous solution of sodium bicarbonate to about pH 9, and extracted with ethyl acetate (20 mL×3). The combined organic layers were washed with brine, dried over anhydrous sodium sulfate, concentrated in vacuo. The residue was purified by preparative HPLC to give 74.6 mg of the desired product as a white solid. MS obsd. (ESI$^+$) [(M+H)$^+$] 427, $^1$H NMR (400 MHz, CD$_3$OD) δ ppm 8.04 (dd, J=1.2, 8.0 Hz, 1 H), 7.98 (d, J=7.2 Hz, 1 H), 7.86 (s, 1 H), 7.72-7.66 (m, 2 H), 7.55-7.46 (m, 2 H), 6.20 (s, 1 H), 5.31 (s, 2 H), 4.57 (s, 2 H), 3.93-3.62 (m, 7 H), 2.47 (s, 3 H).

Example 37-2

(2R)-2-Amino-3-{[2-(1,1-dioxido-2,3-dihydro-1,4-benzothiazepin-4(5H)-yl)-6-methylquinolin-4-yl]amino}propan-1-ol

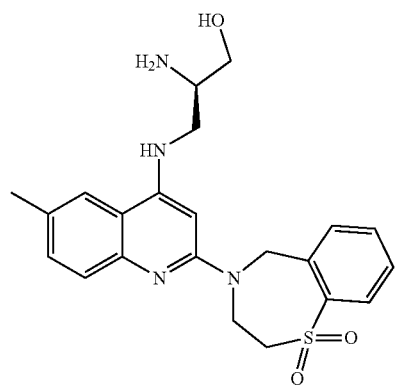 [SMILES: Cc1ccc2nc(N3CCS(=O)(=O)c4ccccc4C3)cc(NC[C@@H](N)CO)c2c1]

The title compound was prepared in analogy to Example 37-1 in Scheme 14 by using 4-(4-chloro-6-methylquinolin-2-yl)-2,3,4,5-tetrahydro-1,4-benzothiazepine 1,1-dioxide, tert-butyl (2R)-4-aminomethyl-2,2-dimethyl-1,3-oxazolidine-3-carboxylate. MS obsd. (ESI$^+$) [(M+H)$^+$] 427, $^1$H NMR (400 MHz, CD$_3$OD) δ ppm 8.02 (d, J=6.8 Hz, 1 H), 7.96 (d, J=8.4 Hz, 1 H), 7.80 (s, 1 H), 7.68 (dd, J=6.0, 7.6 Hz, 1 H), 7.58 (d, J=8.4 Hz, 1 H), 7.50 (m, 1 H), 7.41 (d, J=8.4 Hz, 1 H), 6.19 (s, 1 H), 5.27 (s, 2 H), 4.57 (s, 2 H), 3.92-3.60 (m, 7 H), 2.45 (s, 3 H).

Example 38-1

N-[(2-Amino-4,5-dihydro-1,3-oxazol-5-yl)methyl]-2-(1,1-dioxido-2,3-dihydro-1,4-benzothiazepin-4(5H)-yl)-6-methylquinolin-4-amine

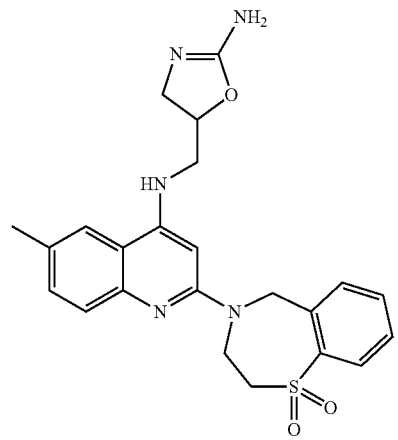 [SMILES: Cc1ccc2nc(N3CCS(=O)(=O)c4ccccc4C3)cc(NCC3CN=C(N)O3)c2c1]

A mixture of 1-amino-3-{[2-(1,1-dioxido-2,3-dihydro-1,4-benzothiazepin-4(5H)-yl)-6-methylquinolin-4-yl]amino}propan-2-ol (80 mg, 0.18 mmol, prepared in analogy to Example 9-7) and potassium acetate (89 mg, 0.91 mmol) in a mixture solution of methanol and water (7 ml, V/V=6/1) was added cyanogen bromide (89 mg, 0.84 mmol) at 0° C. After being stirred at room temperature for 3 hours, the mixture was stirred further with concentrated hydrochloric acid (3 mL) for 1 hour, and then concentrated in vacuo. The residue was dissolved in a saturated aqueous solution of sodium bicarbonate (10 mL) and extracted with dichloromethane (15 mL×3). The combined organic layers were dried over sodium sulfate and concentrated in vacuo. The residue was purified by flash column (10% methanol in dichloromethane) to afford 32 mg of the desired product as a white solid. MS obsd. (ESI$^+$) [(M+H)$^+$] 452, $^1$H NMR (400 MHz, DMSO-d6) δ ppm 7.92-7.87 (m, J=4.6 Hz, 2 H), 7.72 (s, 1 H), 7.65-7.62 (t, J=3.7 Hz, 1 H), 7.49-7.45 (t, J=3.9 Hz, 1 H), 7.32 (d, J=2.1 Hz, 1 H), 7.23 (d, J=2.1 Hz, 1 H), 6.85 (t, J=2.6 Hz, 1 H), 6.46 (brs, 2 H), 6.10 (s, 1 H), 5.10 (s, 2 H), 4.82-4.77 (m, J=4.8 Hz, 1 H), 4.49 (brs, 2 H), 3.75 (m, 1 H), 3.63 (s, 2 H), 3.52 (m, 3 H), 2.35 (s, 3 H).

Example 38-2

N-[(2-Amino-5-methyl-4,5-dihydro-1,3-oxazol-5-yl)methyl]-2-(1,1-dioxido-2,3-dihydro-1,4-benzothiazepin-4(5H)-yl)-6-methylquinolin-4-amine

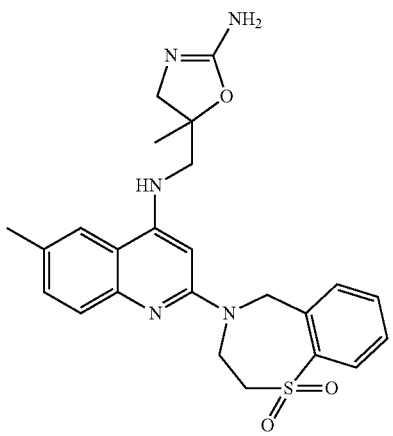 [SMILES: Cc1ccc2nc(N3CCS(=O)(=O)c4ccccc4C3)cc(NCC3(C)CN=C(N)O3)c2c1]

To a mixture of 1-amino-3-{[2-(1,1-dioxido-2,3-dihydro-1,4-benzothiazepin-4(5H)-yl)-6-methylquinolin-4-yl]amino}-2-methylpropan-2-ol (200 mg, 0.45 mmol, prepared in analogy to Example 11-4) and potassium acetate (240 mg, 2.4 mmol) in methanol (8 mL) and water (2 mL) which was cooled to 0° C., a cooled solution of cyanogen bromide (52.3 mg, 0.5 mmol) in methanol (2 mL) was added. After being stirred at room temperature for 4 hours, the reaction mixture was concentrated in vacuo. The residue was diluted with ethyl acetate (50 mL), washed with water (50 mL), dried over sodium sulfate, and concentrated in vacuo. The residue was purified by column chromatography on silica gel to give 80 mg of the product as a white powder. MS obsd. (ESI$^+$) [(M+H)$^+$] 466, $^1$H NMR (400 MHz, CD$_3$OD) δ ppm 7.95 (d, J=7.6 Hz, 1 H), 7.83 (d, J=7.2 Hz, 1 H), 7.60 (m, 2 H), 7.46-7.39 (m, 2 H), 7.29 (dd, J=1.6, 8.8 Hz, 1 H), 6.19 (s, 1 H), 5.18-5.09 (m, 2 H), 4.51 (brs, 2 H), 3.82 (d, J=11.2 Hz, 1 H), 3.65 (s, 2 H), 2.57 (m, 3 H), 2.41 (s, 3 H), 1.62 (s, 3 H).

Example 38-3

N-{[(4R)-2-Amino-4,5-dihydro-1,3-oxazol-4-yl]methyl}-2-(1,1-dioxido-2,3-dihydro-1,4-benzothiazepin-4(5H)-yl)-6-methylquinolin-4-amine

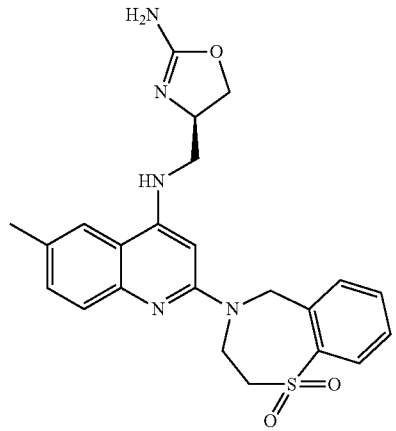 [SMILES: Cc1ccc2nc(N3CCS(=O)(=O)c4ccccc4C3)cc(NC[C@@H]3COC(N)=N3)c2c1]

The title compound was prepared in analogy to Example 38-1 in Scheme 15 by using (2R)-2-amino-3-{[2-(1,1-dioxido-2,3-dihydro-1,4-benzothiazepin-4(5H)-yl)-6-methylquinolin-4-yl]amino}propan-1-ol (prepared in analogy to Example 37-2). MS obsd. (ESI$^+$) [(M+H)$^+$] 452, $^1$H NMR (400 MHz, CD$_3$OD) δ ppm 7.98 (d, J=7.2 Hz, 1 H), 7.87 (d, J=7.2 Hz, 1 H), 7.64-7.58 (m, 2 H), 7.47-7.41 (m, 2 H), 7.28 (dd, J=2.0, 8.8 Hz, 1 H), 6.09 (s, 1 H), 5.16 (s, 2 H), 4.58 (brs, 2 H), 4.40 (t, J=8.0 Hz, 1 H), 4.29 (td, J=5.6, 12.8 Hz, 1 H), 4.20 (dd, J=6.0, 8.0 Hz, 1 H), 3.58 (t, J=4.8 Hz, 2 H), 3.45-3.35 (m, 2 H), 2.42 (s, 3 H).

Example 38-4

N-{[(4S)-2-Amino-4,5-dihydro-1,3-oxazol-4-yl]methyl}-2-(1,1-dioxido-2,3-dihydro-1,4-benzothiazepin-4(5 H)-yl)-6-methylquinolin-4-amine

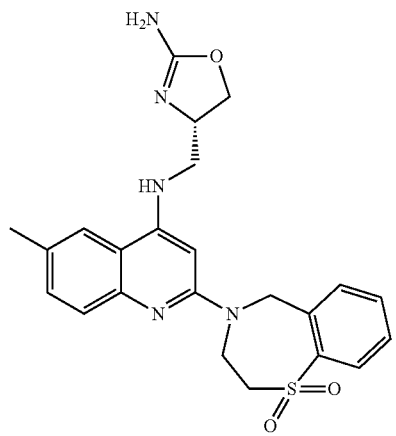 [SMILES: Cc1ccc2nc(N3CCS(=O)(=O)c4ccccc4C3)cc(NC[C@H]3COC(N)=N3)c2c1]

The title compound was prepared in analogy to Example 38-1 in Scheme 15 by using (2S)-2-amino-3-{[2-(1,1-dioxido-2,3-dihydro-1,4-benzothiazepin-4(5H)-yl)-6-methylquinolin-4-yl]amino}propan-1-ol (prepared in analogy to Example 37-1). MS obsd. (ESI⁺) [(M+H)⁺] 452, ¹H NMR (400 MHz, CD₃OD) δ ppm 7.98 (d, J=7.2 Hz, 1 H), 7.87 (d, J=7.2 Hz, 1 H), 7.64-7.58 (m, 2 H), 7.47-7.41 (m, 2 H), 7.28 (dd, J=2.0, 8.8 Hz, 1 H), 6.09 (s, 1 H), 5.16 (s, 2 H), 4.58 (brs, 2 H), 4.40 (t, J=8.0 Hz, 1 H), 4.29 (td, J=5.6, 12.8 Hz, 1 H), 4.20 (dd, J=6.0, 8.0 Hz, 1 H), 3.58 (t, J=4.8 Hz, 2 H), 3.45-3.35 (m, 2 H), 2.42 (s, 3 H).

Example 38-5 cis-5-[2-(1,1-Dioxido-2,3-dihydro-1,4-benzothiazepin-4(5H)-yl)-6-methylquinolin-4-yl]-4,5,6,6a-tetrahydro-3aH-pyrrolo[3,4-d][1,3]oxazol-2-amine

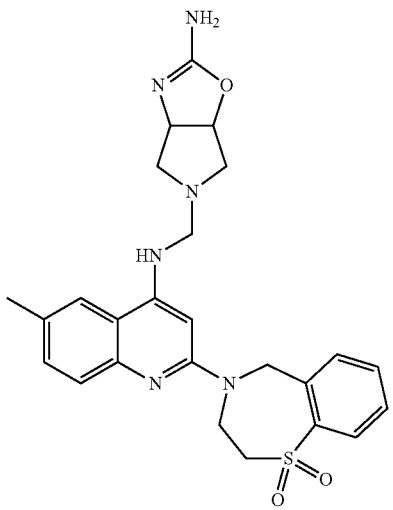 [SMILES: Cc1ccc2nc(N3CCS(=O)(=O)c4ccccc4C3)cc(NCN3CC4N=C(N)OC4C3)c2c1]

To a mixture of cis-4-amino-1-[2-(1,1-dioxido-2,3-dihydro-1,4-benzothiazepin-4(5H)-yl)-6-methylquinolin-4-yl]pyrrolidin-3-ol (90 mg 0.20 mmol, prepared in analogy to Example 19-3 in Scheme 7 by using 4-(4-chloro-6-methylquinolin-2-yl)-2,3,4,5-tetrahydro-1,4-benzothiazepine 1,1-dioxide and tert-butyl [cis-4-hydroxypyrrolidin-3-yl]carbamate) and sodium acetate (82 mg, 1.0 mmol) in methanol (10 mL) at 0° C. was added cyanogen bromide (105 mg, 1 mmol). The mixture was stirred overnight gradually from 0° C. to room temperature, and then concentrated in vacuo. The residue was purified by preparative HPLC to afford the pure product as a solid. MS obsd. (ESI⁺) [(M+H)⁺] 464, ¹H NMR (400 MHz, CD₃OD) δ ppm 8.09 (d, J=7.33 Hz, 1 H), 7.98 (d, J=7.58 Hz, 1 H), 7.89 (brs, 1 H), 7.79-7.70 (m, 2 H), 7.66-7.56 (m, 2 H), 6.50 (s, 1 H), 5.89-5.84 (m, 1 H), 5.41 (brs, 2 H), 4.97-5.02 (m, 1 H), 4.63 (brs, 2 H), 4.31 (brs, 1 H), 4.12 (brs, 1 H), 3.77 (brs, 2 H), 3.62-3.42 (b, 2 H), 2.54-2.48 (m, 3 H).

Example 39

2-(1,1-Dioxido-2,3-dihydro-1,4-benzothiazepin-4(5H)-yl)-6-methylquinolin-4-amine

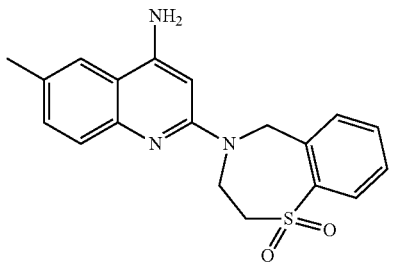 [SMILES: Cc1ccc2nc(N3CCS(=O)(=O)c4ccccc4C3)cc(N)c2c1]

2-{[(1E)-1-(1,1-Dioxido-2,3-dihydro-1,4-benzothiazepin-4(5H)-yl)ethylidene]amino}-5-methylbenzonitrile

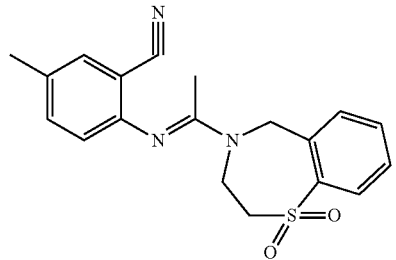 [SMILES: C/C(=N\c1ccc(C)cc1C#N)N1CCS(=O)(=O)c2ccccc2C1]

To a stirred solution of 1-(1,1-dioxido-2,3-dihydro-1,4-benzothiazepin-4(5H)-yl)ethanone (6.0 g, 25.0 mmol) in dry dichloromethane (100 mL) was added phosphorus oxychloride (2.5 mL, 27.3 mmol) at 10° C. After being stirred for 20 minutes at room temperature, a solution of 2-amino-5-methylbenzonitrile (3.3 g, 25.0 mmol) in dry dichloromethane (40 mL) was added and the resulting suspension was heated under reflux for 24 hours. After being cooled to room temperature, the reaction mixture was diluted with water (50 mL), basified with a saturated aqueous solution of sodium bicarbonate to about pH 8. The separated aqueous layer was extracted with dichloromethane (100 mL). The combined organic layers were washed with brine, dried over sodium sulfate and concentrated in vacuo. The residue was purified by column chromatography on silica gel (eluting with 16% ethyl acetate in petroleum ether) to give 1.5 g of the product as a white solid.

2-(1,1-Dioxido-2,3-dihydro-1,4-benzothiazepin-4(5H)-yl)-6-methylquinolin-4-amine

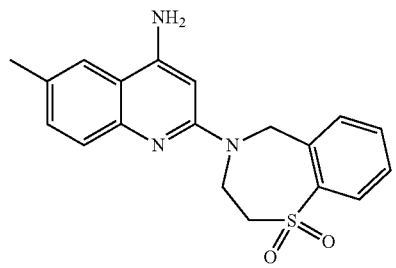 [SMILES: Cc1ccc2nc(N3CCS(=O)(=O)c4ccccc4C3)cc(N)c2c1]

A mixture of 2-{[(1E)-1-(1,1-dioxido-2,3-dihydro-1,4-benzothiazepin-4(5H)-yl)ethylidene]amino}-5-methylbenzonitrile (1.5 g, 4.24 mmol), zinc chloride (578 mg, 4.24 mmol) and N,N-dimethylacetamide (4 mL) was heated with stirring at 160° C. for 3 hours under argon. After the reaction mixture was cooled to about 40° C., an aqueous solution of sodium hydroxide (2 N, 20 mL) was introduced. After being stirred for 10 minutes at room temperature, the reaction mixture was poured into water. The formed solid was collected by filtration, and dried in vacuo to give 1.5 g of the product as a brown powder. MS obsd. (ESI⁺) [(M+H)⁺] 354, ¹H NMR (400 MHz, DMSO-d6) δ ppm 7.90-7.84 (m, 2 H), 7.66-7.62 (m, 2 H), 7.48 (t, J=7.2 Hz, 1 H), 7.32 (d, J=8.4 Hz, 1 H), 7.23 (dd, J=1.6, 8.8 Hz, 1 H), 6.29 (s, 2 H), 6.23 (s, 1 H), 4.97 (s, 2 H), 4.36 (brs, 2 H), 3.60 (t, J=4.8 Hz, 2 H), 2.34 (s, 3 H).

Example 40-1

N-[2-(1,1-Dioxido-2,3-dihydro-1,4-benzothiazepin-4 (5H)-yl)-6-methylquinolin-4-yl]glycinamide

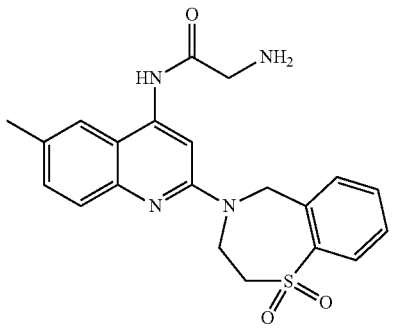 [SMILES: Cc1ccc2nc(N3CCS(=O)(=O)c4ccccc4C3)cc(NC(=O)CN)c2c1]

2-Chloro-N-[2-(1,1-dioxido-2,3-dihydro-1,4-benzothiazepin-4(5H)-yl)-6-methylquinolin-4-yl]acetamide

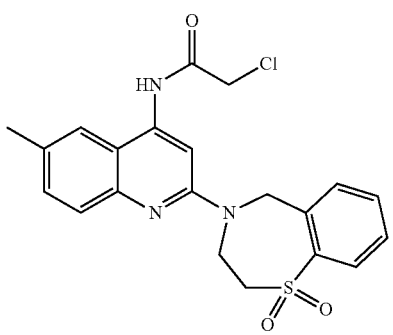 [SMILES: Cc1ccc2nc(N3CCS(=O)(=O)c4ccccc4C3)cc(NC(=O)CCl)c2c1]

To a solution of 2-(1,1-dioxido-2,3-dihydro-1,4-benzothiazepin-4(5H)-yl)-6-methylquinolin-4-amine (500 mg, 1.4 mmol) in chloroform (10 mL) was added 1,8-diazabicyclo[5.4.0]undec-7-ene (0.41 mL, 2.8 mmol) followed by chloroacetyl chloride (0.17 mL, 2.1 mmol) at room temperature. The resulting solution was heated with stirring at 70° C. for 2 hours under nitrogen. After being cooled to room temperature, the reaction was diluted with ethyl acetate (50 mL), washed with water (50 mL×3), dried over sodium sulfate and concentrated in vacuo. The residue was purified by column chromatography on silica gel (eluting with 25% ethyl acetate in petroleum ether) to give 120 mg of the product as an off-white solid.

2-Azido-N-[2-(1,1-dioxido-2,3-dihydro-1,4-benzothiazepin-4(5H)-yl)-6-methylquinolin-4-yl]acetamide

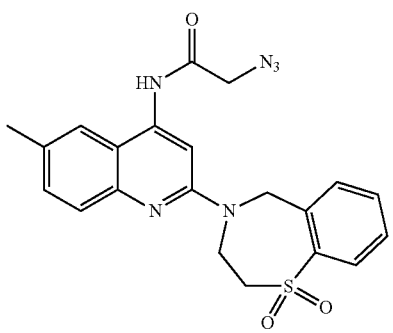 [SMILES: Cc1ccc2nc(N3CCS(=O)(=O)c4ccccc4C3)cc(NC(=O)CN=[N+]=[N-])c2c1]

To a solution of 2-chloro-N-[2-(1,1-dioxido-2,3-dihydro-1,4-benzothiazepin-4(5H)-yl)-6-methylquinolin-4-yl]acetamide (120 mg, 0.28 mmol) in acetonitrile (3 mL) was added sodium azide (72 mg, 1.1 mmol). The resulting mixture was stirred at room temperature for 6 hours. The reaction was diluted with ethyl acetate (20 mL), washed with water (10 mL), dried over sodium sulfate, and concentrated in vacuo. The residue was purified by column chromatography on silica gel (20% ethyl acetate in petroleum ether) to give 110 mg of the product as a white powder.

N-[2-(1,1-Dioxido-2,3-dihydro-1,4-benzothiazepin-4 (5H)-yl)-6-methylquinolin-4-yl]glycinamide

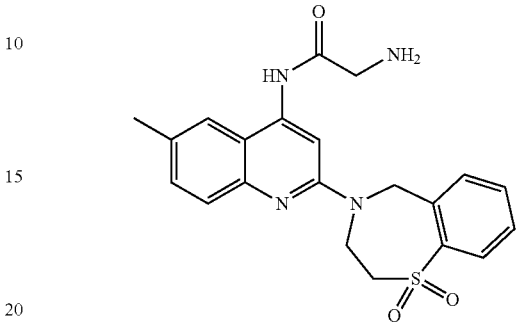

To a solution of 2-azido-N-[2-(1,1-dioxido-2,3-dihydro-1,4-benzothiazepin-4(5H)-yl)-6-methylquinolin-4-yl]acetamide (110 mg, 0.25 mmol) in methanol was added 10% palladium on carbon (507 mg). After being stirred at room temperature overnight under a hydrogen atmosphere, the resulting mixture was filtered. The filtrate was concentrated in vacuo. The residue was purified by preparative HPLC to afford 30 mg of the product as a white powder. MS obsd. (ESI$^+$) [(M+H)$^+$] 411, $^1$H NMR (400 MHz, CD$_3$OD) δ ppm 8.51 (s, 1 H), 8.12 (s, 1 H), 8.07 (d, J=7.6 Hz, 1 H), 8.00 (d, J=7.6 Hz, 1 H), 7.87 (d, J=8.8 Hz, 1 H), 7.67-7.12 (m, 2 H), 7.57 (t, J=8.0 Hz, 1 H), 5.31 (s, 2 H), 4.66 (brs, 2 H), 4.25 (s, 2 H), 3.78 (s, 2 H), 2.52 (s, 3 H).

Example 40-2

N-[2-(1,1-Dioxido-2,3-dihydro-1,4-benzothiazepin-4 (5H)-yl)-6-methylquinolin-4-yl]-2-methylalaninamide

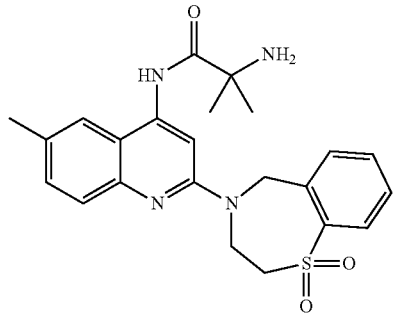 [SMILES: Cc1ccc2nc(N3CCS(=O)(=O)c4ccccc4C3)cc(NC(=O)C(C)(C)N)c2c1]

2-Bromo-N-[2-(1,1-dioxido-2,3-dihydro-1,4-benzothiazepin-4(5H)-yl)-6-methylquinolin-4-yl]-2-methylpropanamide

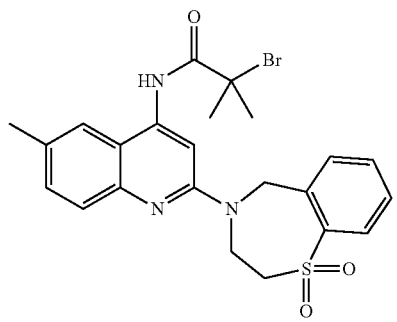 [SMILES: Cc1ccc2nc(N3CCS(=O)(=O)c4ccccc4C3)cc(NC(=O)C(C)(C)Br)c2c1]

To a solution of 2-(1,1-dioxido-2,3-dihydro-1,4-benzothiazepin-4(5H)-yl)-6-methylquinolin-4-amine (200 mg, 0.566 mmol) in chloroform (10 mL) was added triethylamine (0.124 mL), followed by 2-bromo-2-methylpropionyl chloride (286 mg, 1.30 mmol). The resulting mixture was heated at 110° C. for 2 hours under microwave irradiation. After being cooled to room temperature, the mixture was concentrated in vacuo. The residue was diluted with ethyl acetate (35 mL), washed with brine and dried over sodium sulfate, and concentrated in vacuo. The residue was purified by flash chromatography to afford 180 mg of the title compound as a light solid (yield was 63%).

2-Azido-N-[2-(1,1-dioxido-2,3-dihydro-1,4-benzothiazepin-4(5H)-yl)-6-methylquinolin-4-yl]-2-methylpropanamide

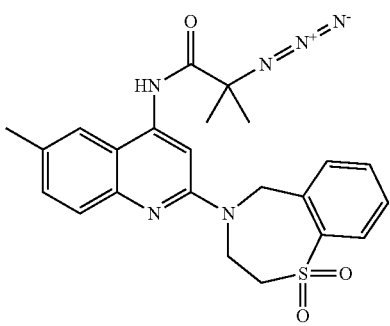 [SMILES: Cc1ccc2nc(N3CCS(=O)(=O)c4ccccc4C3)cc(NC(=O)C(C)(C)N=[N+]=[N-])c2c1]

To a solution of 2-bromo-N-[2-(1,1-dioxido-2,3-dihydro-1,4-benzothiazepin-4(5H)-yl)-6-methylquinolin-4-yl]-2-methylpropanamide (160 mg, 0.319 mmol) in actonitrile (15 mL) was added sodium azide (62 mg, 0.958 mmol). After being refluxed overnight, the resulting mixture was concentrated in vacuo. The residue was diluted with ethyl acetate (40 mL), washed with brine, dried over sodium sulfate, and concentrated in vacuo to afford 160 mg of the crude product.

N-[2-(1,1-Dioxido-2,3-dihydro-1,4-benzothiazepin-4(5H)-yl)-6-methylquinolin-4-yl]-2-methylalaninamide

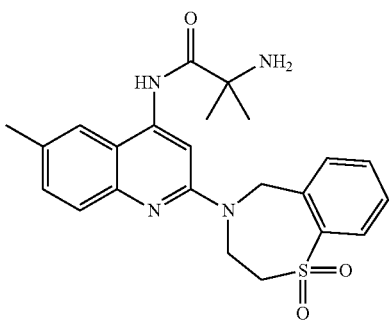 [SMILES: Cc1ccc2nc(N3CCS(=O)(=O)c4ccccc4C3)cc(NC(=O)C(C)(C)N)c2c1]

To a solution 2-azido-N-[2-(1,1-dioxido-2,3-dihydro-1,4-benzothiazepin-4(5H)-yl)-6-methylquinolin-4-yl]-2-methylpropanamide (160 mg, 0.345 mmol) in ethyl acetate (25 mL) was added 10% palladium on carbon (100 mg), the flask was degassed and refilled with hydrogen (repeated for three times). After being stirred at room temperature overnight under a hydrogen atmosphere, the resulting mixture was filtered. The filtrate was concentrated in vacuo. The residue was purified by flash chromatography to afford 110 mg of the title compound (yield was 73%). MS obsd. (ESI$^+$) [(M+H)$^+$] 439, $^1$H NMR (400 MHz, CDCl$_3$) δ ppm 11.05 (s, 1 H), 8.30 (s, 1 H), 8.02 (dd, J=0.8, 7.6 Hz, 1 H), 7.89 (d, J=7.2 Hz, 1 H), 7.59 (d, J=8.8 Hz, 1 H), 7.53 (t, J=7.6 Hz, 1 H), 7.37 (m, 3 H), 5.17 (s, 2 H), 4.6 (brs., 2 H), 3.56 (s, 2 H), 2.48 (s, 3 H), 1.56 (s, 6 H).

Example 40-3

N-[2-(1,1-Dioxido-2,3-dihydro-1,4-benzothiazepin-4(5H)-yl)-6-methylquinolin-4-yl]alaninamide

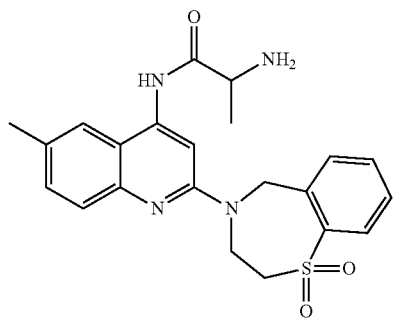 [SMILES: Cc1ccc2nc(N3CCS(=O)(=O)c4ccccc4C3)cc(NC(=O)C(C)N)c2c1]

The title compound was prepared in analogy to Example 40-2 in Scheme 18 by using 2-(1,1-dioxido-2,3-dihydro-1,4-benzothiazepin-4(5H)-yl)-6-methylquinolin-4-amine, 2-bromopropionyl chloride and sodium azide. MS obsd. (ESI$^+$) [(M+H)$^+$] 425, $^1$H NMR (400 MHz, CD$_3$OD) δ ppm 8.07-7.85 (m, 3 H), 7.64-7.51 (m, 2 H), 7.46-7.35 (m, 2 H), 5.22-5.08 (m, 2 H), 4.51-4.42 (m, 1 H), 3.65-3.53 (m, 2 H), 3.37 (s, 3 H), 2.51-2.40 (m, 3 H), 1.73 (d, J=7.07 Hz, 1 H), 1.30 (d, J=2.78 Hz, 2 H).

Example 40-4

2-Amino-N-[2-(1,1-dioxido-2,3-dihydro-1,4-benzothiazepin-4(5H)-yl)-6-methylquinolin-4-yl]butanamide

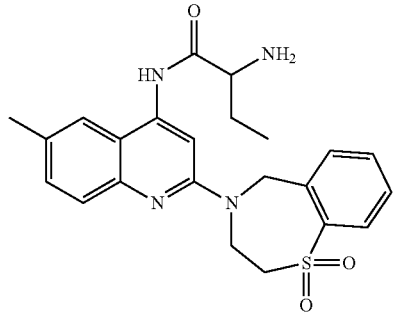 [SMILES: CCC(N)C(=O)Nc1cc(N2CCS(=O)(=O)c3ccccc3C2)nc2ccc(C)cc12]

The title compound was prepared in analogy to Example 40-2 in Scheme 18 by using 2-(1,1-dioxido-2,3-dihydro-1,4- benzothiazepin-4(5H)-yl)-6-methylquinolin-4-amine, 2-bromobutyryl chloride and sodium azide. MS obsd. (ESI⁺) [(M+H)⁺] 439, ¹H NMR (400 MHz, CD₃OD) δ ppm 8.07 (m, 3 H), 7.53 (m, 2 H), 7.45 (m, 2 H), 5.33 (m, 2 H), 4.32 (m, 1 H), 3.59 (m, 2 H), 3.37 (s, 3 H), 2.44 (m, 2 H), 1.70 (d, J=8.02 Hz, 1 H), 1.38 (d, J=2.56 Hz, 2 H), 1.22 (m, 3 H).

Example 41

N-[2-(1,1-Dioxido-2,3-dihydro-1,4-benzothiazepin-4(5H)-yl)-6-methylquinolin-4-yl]-2-methoxy-2-methylpropanamide

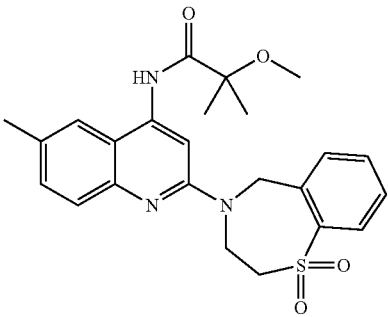 [SMILES: COC(C)(C)C(=O)Nc1cc(N2CCS(=O)(=O)c3ccccc3C2)nc2ccc(C)cc12]

To a solution of 2-bromo-N-[2-(1,1-dioxido-2,3-dihydro-1,4-benzothiazepin-4(5H)-yl)-6-methylquinolin-4-yl]-2-methylpropanamide (80 mg, 0.159 mmol, prepared in Example 40-2) in methanol (5 mL) was added ethylamine (1 mL), the resulting mixture was heated under reflux overnight. After being cooled to room temperature, the resulting mixture was concentrated in vacuo. The residue was purified by preparative TLC (eluting with 33% ethyl acetate in hexanes) to afford 15 mg of the title compound as a light powder (yield was 21%). MS obsd. (ESI⁺) [(M+H)⁺] 454, ¹H NMR (400 MHz, CD₃OD) δ ppm 7.94-7.89 (m, 3 H), 7.58 (m, 2 H), 7.43-7.39 (m, 3 H), 5.17 (s, 2 H), 4.50 (brs, 2 H), 3.59 (m, 2 H), 3.50 (s, 3 H), 2.46 (s, 3 H), 1.56 (s, 6 H).

Example 42-1

N~1~-[2-(1,1-Dioxido-2,3-dihydro-1,4-benzothiazepin-4(5H)-yl)-6-methylquinolin-4-yl]-4,4,4-trifluorobutane-1,3-diamine

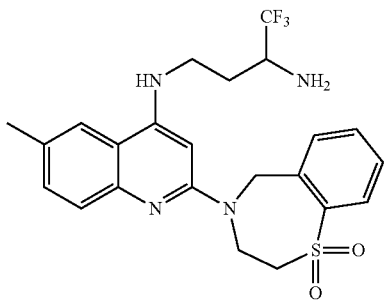 [SMILES: Cc1ccc2nc(N3CCS(=O)(=O)c4ccccc4C3)cc(NCCC(N)C(F)(F)F)c2c1]

N-[2-(1,1-Dioxido-2,3-dihydro-1,4-benzothiazepin-4(5H)-yl)-6-methylquinolin-4-yl]-3-(1,3-dioxo-1,3-dihydro-2H-isoindol-2-yl)-4,4,4-trifluorobutanamide

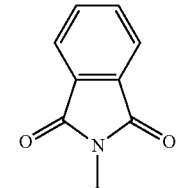

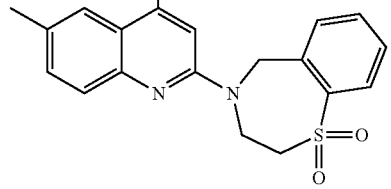

To a solution of 2-(1,1-dioxido-2,3-dihydro-1,4-benzothiazepin-4(5H)-yl)-6-methylquinolin-4-amine (200 mg, 0.565 mmol, prepared in analogy to the one in Example 2-1) in N,N-dimethylformamide (6 mL) was added a solution of 3-(1,3-dioxo-1,3-dihydro-2H-isoindol-2-yl)-4,4,4-trifluorobutanoyl chloride (670 mg, 2.3 mmol) in dichloromethane (4 mL) followed by N,N-diisopropylethylamine (0.3 mL). The resulting mixture was stirred at room temperature for 1 hour and heated at 85° C. for additional 2 hours. After being cooled to room temperature, the resulting mixture was evaporated in vacuo. The residue was diluted with water and extracted with ethyl acetate (20 mL×2). The combined organic layers were washed with brine, dried over sodium sulfate and concentrated in vacuo. The residue was purified by flash chromatography to afford 230 mg of the product as a solid (yield was 66%).

3-Amino-N-[2-(1,1-dioxido-2,3-dihydro-1,4-benzothiazepin-4(5H)-yl)-6-methylquinolin-4-yl]-4,4,4-trifluorobutanamide

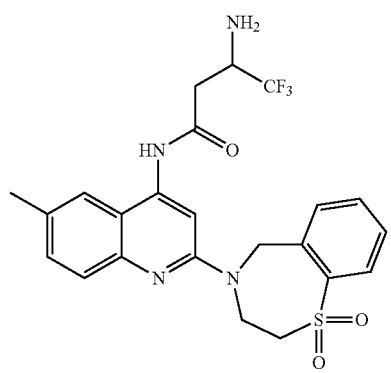 [SMILES: Cc1ccc2nc(N3CCS(=O)(=O)c4ccccc4C3)cc(NC(=O)CC(N)C(F)(F)F)c2c1]

To a solution of N-[2-(1,1-dioxido-2,3-dihydro-1,4-benzothiazepin-4(5H)-yl)-6-methylquinolin-4-yl]-3-(1,3-dioxo-1,3-dihydro-2H-isoindol-2-yl)-4,4,4-trifluorobutanamide (25 mg, 0.04 mmol) in ethanol (3 mL) was added a solution of methylamine (30% in ethanol, 0.3 mL). The resulting mixture was heated at 90° C. for 2 hours. After being cooled to room temperature, the mixture was concentrated in vacuo. The residue was purified by flash chromatography (eluting with 50% ethyl acetate in hexanes) to afford 15 mg of the title compound as light solid (yield was 80%).

N~1~-[2-(1,1-Dioxido-2,3-dihydro-1,4-benzothiazepin-4(5H)-yl)-6-methylquinolin-4-yl]-4,4,4-trifluorobutane-1,3-diamine

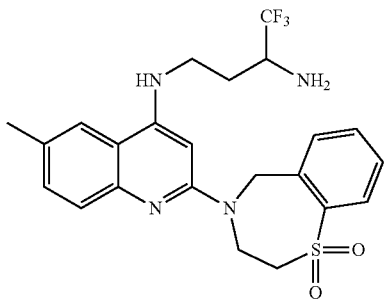 [SMILES: Cc1ccc2nc(N3CCS(=O)(=O)c4ccccc4C3)cc(NCCC(N)C(F)(F)F)c2c1]

To a solution of 3-amino-N-[2-(1,1-dioxido-2,3-dihydro-1,4-benzothiazepin-4(5H)-yl)-6-methylquinolin-4-yl]-4,4,4-trifluorobutanamide (120 mg, 0.245 mmol) was added a solution of borane-methyl sulfide complex in methyl sulfide (5 M, 1.0 mL). The resulting solution was heated at 85° C. for 2 hours. After being cooled to room temperature, the mixture was acidified by careful addition of an aqueous solution of hydrochloric acid (1 M) to about pH 4, and then stirred at room temperature overnight. The resulting mixture was concentrated in vacuo. The residue was neutralized with a 10% aqueous solution of sodium hydroxide to pH >9, and then extracted with dichloromethane (20 mL×3). The combined organic layers were washed with brine, dried over sodium sulfate, and concentrated in vacuo. The residue was purified by flash chromatography to afford 60 mg of the title product as a solid (yield was 65%). MS obsd. (ESI$^+$) [(M+H)$^+$] 479, $^1$H NMR (400 MHz, CDCl$_3$) δ ppm 8.04 (d, J=7.6 Hz, 1 H), 7.65 (d, J=7.6 Hz, 1 H), 7.50-7.49 (m, 2 H), 7.38 (t, J=7.2 Hz, 1 H), 7.30 (m, 1 H), 6.06 (s, 1 H), 5.93 (s, 1 H), 5.12 (s, 1 H), 3.63 (m, 3 H), 4.62 (brs, 2 H), 3.45 (m, 1 H), 3.33 (m, 1 H), 2.42 (s, 3 H), 2.22 (m, 1 H), 2.03 (s, 1 H), 1.82 (m, 1 H).

Example 42-2

N-[2-(1,1-Dioxido-2,3-dihydro-1,4-benzothiazepin-4(5H)-yl)-6-methylquinolin-4-yl]-beta-alaninamide

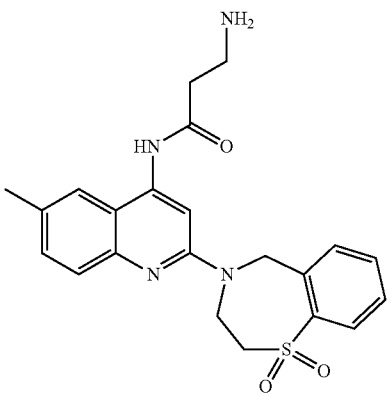 [SMILES: Cc1ccc2nc(N3CCS(=O)(=O)c4ccccc4C3)cc(NC(=O)CCN)c2c1]

The title compound was prepared in analogy to 3-amino-N-[2-(1,1-dioxido-2,3-dihydro-1,4-benzothiazepin-4(5H)-yl)-6-methylquinolin-4-yl]-4,4,4-trifluorobutanamide in Example 42-1 in Scheme 19 by using 2-(1,1-dioxido-2,3-dihydro-1,4-benzothiazepin-4(5H)-yl)-6-methylquinolin-4-amine and 3-(1,3-dioxo-1,3-dihydro-2H-isoindol-2-yl)propanoyl chloride. MS obsd. (ESI$^+$) [(M+H)$^+$] 425, $^1$H NMR (400 MHz, CDCl$_3$) δ ppm 8.00 (d, J=7.83 Hz, 1 H), 8.29 (s, 1 H), 7.85 (d, J=7.33 Hz, 1 H), 7.61-7.47 (m, 4 H), 7.34 (d, J=12.13 Hz, 2 H), 5.12 (s, 2 H), 3.55 (brs, 2 H), 3.23 (d, J=5.56 Hz, 2 H), 2.62 (brs, 2 H), 2.44 (brs, 3 H), 1.66-2.10 (m, 2 H).

Example 43

2-(1,1-Dioxido-2,3-dihydro-1,4-benzothiazepin-4(5H)-yl)-N-{[3-(ethylamino)oxetan-3-yl]methyl}-6-methylquinolin-4-amine

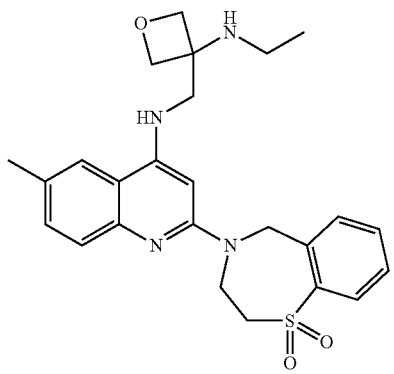 [SMILES: CCNC1(CNc2cc(N3CCS(=O)(=O)c4ccccc4C3)nc3ccc(C)cc23)COC1]

To a stirred solution of N-[(3-aminooxetan-3-yl)methyl]-2-(1,1-dioxido-2,3-dihydro-1,4-benzothiazepin-4(5H)-yl)-6-methylquinolin-4-amine (200 mg, 0.46 mmol, prepared in analogy to Example 2-2), acetaldehyde (25.6 μL, 0.46 mmol) and acetic acid (270 μL) in methanol (8 mL) was added dropwize a solution of sodium cyanoborohydride (34 mg, 0.54 mmol) in tetrahydrofuran (0.5 mL). After being stirred for 12 hours at room temperature, the reaction mixture was diluted with ethyl acetate, washed with water and a saturated aqueous solution of sodium bicarbonate, dried over sodium sulfate, and concentrated in vacuo. The residue was purified by preparative HPLC to afford 42 mg of the desired product as a white solid (yield was 20%). MS obsd. (ESI$^+$) [(M+H)$^+$] 467, $^1$H NMR (400 MHz, DMSO-d6) δ ppm 7.95 (d, J=1.9 Hz, 1 H), 7.89-7.87 (t, J=2.2 Hz, 1 H), 7.64-7.58 (m, J=6.0 Hz, 2 H), 7.49-7.45 (m, J=4.0 Hz, 1 H), 7.35 (d, J=2.1 Hz, 1 H), 7.27-7.24 (m, J=2.5 Hz, 1 H), 6.17 (s, 1 H), 5.11 (s, 2 H), 4.52 (d, 2 H), 4.37 (d, 4 H), 3.62-3.45 (t, J=2.4 Hz, 2 H), 3.58 (d, 2 H), 2.53 (m, 2 H), 2.37 (s, 3 H), 1.07-1.03 (t, J=3.6 Hz, 3 H).

Example 44-1

2-(1,1-Dioxido-2,3-dihydro-1,4-benzothiazepin-4(5H)-yl)-6-methyl-N-[1-(oxetan-3-yl)pyrrolidin-3-yl]quinolin-4-amine

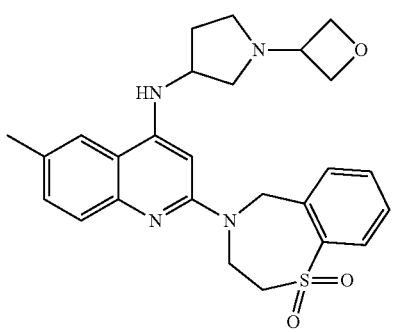 [SMILES: Cc1ccc2nc(N3CCS(=O)(=O)c4ccccc4C3)cc(NC3CCN(C4COC4)C3)c2c1]

To a solution of [2-(1,1-dioxido-2,3-dihydro-1,4-benzothiazepin-4(5H)-yl)-6-methyl-N-(pyrrolidin-3-yl)quinolin-4-amine (21 mg, 0.05 mmol, prepared in analogy to Example 21-4) and oxetan-3-one (7.2 mg, 0.10 mmol) in tetrahydrofuran (2 mL) was added acetic acid (8.6 μL, 0.15 mmol). After the mixture being stirred at 55° C. for 1 hour, sodium triacetoxyborohydride (21 mg, 0.10 mmol) was added to the mixture. After being stirred for 2 hours at 65° C., the reaction mixture was concentrated in vacuo. The residue was portioned between ethyl acetate and a saturated aqueous solution of sodium carbonate. The separated organic layer was washed with water, dried over sodium sulfate, and concentrated in vacuo. The residue was purified by preparative HPLC to afford 10 mg of the product as a white solid. MS obsd. (ESI+) [(M+H)+] 479, $^1$H NMR (400 MHz, CD$_3$OD) δ ppm 8.30 (d, J=1.9 Hz, 1 H), 7.84 (d, J=1.8 Hz, 1 H), 7.78 (s, 1 H), 7.68-7.64 (t, J=3.7 Hz, 1 H), 7.53-7.49 (t, J=3.7 Hz, 2 H), 7.39 (d, J=1.7 Hz, 1 H), 5.98 (s, 1 H), 5.20 (s, 2 H), 4.83-4.78 (m, J=4.7 Hz, 2 H), 4.69-4.60 (m, J=8.4 Hz, 2 H), 4.55 (brs, 2 H), 4.37 (s, 1 H), 3.80-3.74 (m, J=4.1 Hz, 1 H), 3.65-3.61 (m, J=4.2 Hz, 2 H), 2.96-2.89 (m, J=6.6 Hz, 2 H), 2.75-2.72 (m, J=3.3 Hz, 1 H), 2.63-2.47 (m, J=15.9 Hz, 2 H), 2.45 (s, 3 H), 1.95 (m, 1 H).

Example 44-2

N'-[2-(1,1-Dioxido-2,3-dihydro-1,4-benzothiazepin-4(5H)-yl)-6-methylquinolin-4-yl]-N-ethyl-N-(oxetan-3-yl)ethane-1,2-diamine

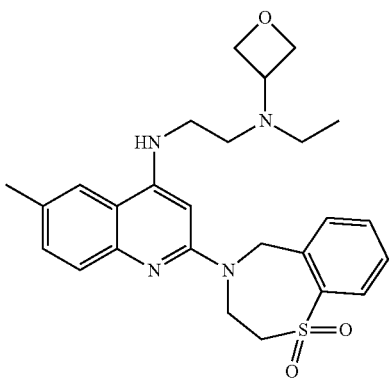 [SMILES: CCN(CCNc1cc(N2CCS(=O)(=O)c3ccccc3C2)nc2ccc(C)cc12)C1COC1]

The title compound was prepared in analogy to Example 44-1 in Scheme 20 by using N-[2-(1,1-dioxido-2,3-dihydro-1,4-benzothiazepin-4(5H)-yl)-6-methylquinolin-4-yl]-N'-ethylethane-1,2-diamine (prepared in analogy to Example 3-37) and oxetan-3-one. MS obsd. (ESI+) [(M+H)+] 481, $^1$H NMR (400 MHz, CD$_3$OD) δ ppm 8.02 (d, J=7.6 Hz, 1 H), 7.87 (d, J=7.2 Hz, 1 H), 7.66 (t, 2 H), 7.50 (t, 2 H), 7.36 (d, J=7.6 Hz, 1 H), 6.04 (s, 1 H), 5.20 (s, 2 H), 4.68-4.50 (m, 6 H), 4.07-4.00 (m, 1 H), 3.65 (s, 2 H), 3.45 (t, J=12.4 Hz, 2 H), 2.84 (t, J=12.8 Hz, 2 H), 2.73-2.67 (m, 2 H), 2.45 (s, 3 H), 1.07 (t, 3 H).

Example 45-1

N-[2-(1,1-Dioxido-2,3-dihydro-1,4-benzothiazepin-4(5H)-yl)-6-methylquinolin-4-yl]-N'-(oxetan-3-yl)propane-1,3-diamine

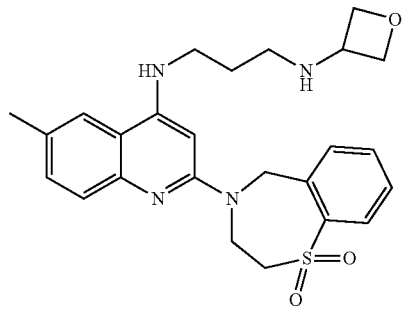 [SMILES: Cc1ccc2nc(N3CCS(=O)(=O)c4ccccc4C3)cc(NCCCNC3COC3)c2c1]

To a stirred of N-[2-(1,1-dioxido-2,3-dihydro-1,4-benzothiazepin-4(5H)-yl)-6-methylquinolin-4-yl]propane-1,3-diamine (84 mg, 0.2 mmol, prepared in analogy to Example 9-3), oxetan-3-one (15 mg, 0.21 mmol) and ethyldiisopropylamine (43 μL, 0.25 mmol) in dichloromethane (10 mL) was added molecular sieves (4 Å, 84 mg) followed by sodium triacetoxyborohydride (63.6 mg, 0.3 mmol). After being stirred at room temperature overnight, another batch of sodium triacetoxyborohydride (63.6 mg, 0.3 mmol) was added and the mixture was heated under reflux for 2 hours. The reaction mixture was cooled, washed with brine, dried over sodium sulfate and concentrated in vacuo. The residue was purified by preparative HPLC to afford 26 mg of N-[2-(1,1-dioxido-2,3-dihydro-1,4-benzothiazepin-4(5H)-yl)-6-methylquinolin-4-yl]-N'-(oxetan-3-yl)propane-1,3-diamine as a white solid. MS obsd. (ESI+) [(M+H)+] 467, $^1$H NMR (400 MHz, CD$_3$OD) δ ppm 8.05 (d, J=7.6 Hz, 1 H), 7.87 (d, J=7.6 Hz, 1 H), 7.34 (s, 1 H), 7.68 (t, J=14.8 Hz, 1 H), 7.58-7.51 (m, 2 H), 7.45 (d, 1 H), 5.99 (s, 1 H), 5.24 (s, 2 H), 4.85 (t, J=3.3 Hz, 2 H), 4.85 (t, J=13.6 Hz, 2 H), 4.55 (m, 4 H), 4.06-4.00 (m, 1 H), 3.67 (s, 2 H), 3.50 (t, J=13.2 Hz, 2 H), 2.74 (t, J=13.6 Hz, 2 H), 2.45 (s, 3 H), 1.98-1.91 (m, 2 H).

Example 45-2

1-[2-(1,1-Dioxido-2,3-dihydro-1,4-benzothiazepin-4(5H)-yl)-6-methylquinolin-4-yl]-N-(oxetan-3-yl)pyrrolidin-3-amine

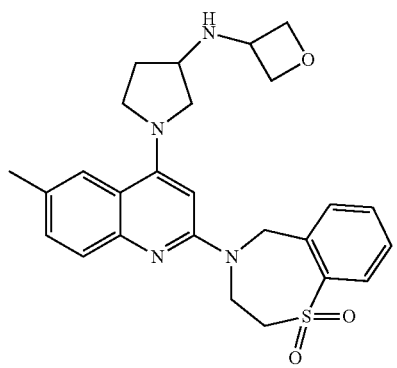 [SMILES: Cc1ccc2nc(N3CCS(=O)(=O)c4ccccc4C3)cc(N3CCC(NC4COC4)C3)c2c1]

The title compound was prepared in analogy to Example 45-1 in Scheme 20 by using 1-[2-(1,1-dioxido-2,3-dihydro-1,4-benzothiazepin-4(5H)-yl)-6-methylquinolin-4-yl]pyrrolidin-3-amine and oxetan-3-one (prepared in analogy to Example 25) and oxetan-3-one. MS obsd. (ESI⁺) [(M+H)⁺] 479, ¹H NMR (400 MHz, CD₃OD) δ ppm 7.99-7.97 (m, J=2.2 Hz, 1 H), 7.83-7.80 (t, J=2.9 Hz, 2 H), 7.64-7.60 (m, J=4.1 Hz, 1 H), 7.47-7.43 (m, J=4.5 Hz, 2 H), 7.29-7.26 (m, J=2.5 Hz, 1 H), 6.12 (s, 1 H), 5.15 (s, 2 H), 4.85 (m, 2 H), 4.56 (m, 4 H), 4.14 (m, 1 H), 3.73 (m, 2 H), 3.60 (m, 3 H), 3.42 (m, 2 H), 2.40 (s, 3 H), 2.21 (m, 1 H), 1.87 (m, 1 H).

Example 45-3

N-[2-(1,1-Dioxido-2,3-dihydro-1,4-benzothiazepin-4(5H)-yl)-6-methylquinolin-4-yl]-N'-(oxetan-3-yl)ethane-1,2-diamine

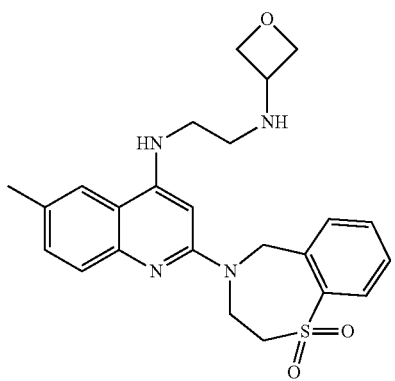 [SMILES: Cc1ccc2nc(N3CCS(=O)(=O)c4ccccc4C3)cc(NCCNC3COC3)c2c1]

The title compound was prepared in analogy to Example 45-1 in Scheme 20 by using N-[2-(1,1-dioxido-2,3-dihydro-1,4-benzothiazepin-4(5H)-yl)-6-methylquinolin-4-yl]-N'-(oxetan-3-yl)ethane-1,2-diamine (prepared in analogy to Example 9-16) and oxetan-3-one. MS obsd. (ESI⁺) [(M+H)⁺] 453, ¹H NMR (400 MHz, CD₃OD) δ ppm 8.09 (t, J=2.0 Hz, 1 H), 7.87 (d, J=1.7 Hz, 2 H), 7.74-7.70 (m, J=4.0 Hz, 1 H), 7.64 (d, J=2.1 Hz, 1 H), 7.61-7.54 (m, J=6.8 Hz, 2 H), 6.03 (s, 1 H), 5.29 (s, 2 H), 4.85 (t, J=3.3 Hz, 2 H), 4.51 (t, J=3.1 Hz, 4 H), 4.06 (brs, 1 H), 3.73 (s, 2 H), 3.57 (t, J=3.0 Hz, 2 H), 2.93 (brs, 2 H), 2.48 (s, 3 H).

Example 46

N-[2-(1,1-Dioxido-2,3-dihydro-1,4-benzothiazepin-4(5H)-yl)-6-methylquinolin-4-yl]-N'-(pyridin-2-yl)ethane-1,2-diamine

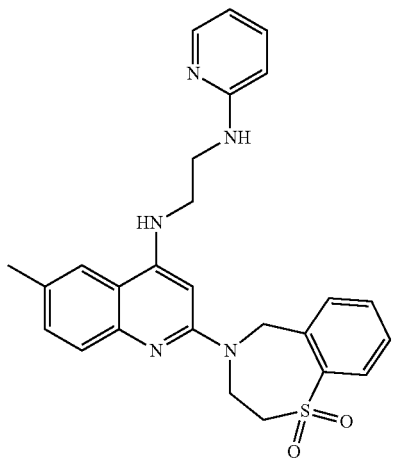 [SMILES: Cc1ccc2nc(N3CCS(=O)(=O)c4ccccc4C3)cc(NCCNc3ccccn3)c2c1]

A mixture of N-[2-(1,1-dioxido-2,3-dihydro-1,4-benzothiazepin-4(5H)-yl)-6-methylquinolin-4-yl]ethane-1,2-diamine (150 mg, 0.38 mol, prepared in analogy to Example 9-16), 2-bromo-pyridine (60 mg, 0.38 mol), tri(dibenzylideneacetone)dipalladium(0) (17.4 mg, 0.019 mmol), 4,5-bis(diphenylphosphino)-9,9-dimethylxanthe (22 mg, 0.038 mmol), cesium carbonate (247.6 mg, 0.76 mmol) and N-methylpyrrolidinone (3 mL) was heated with stirring at 150° C. for 6 hours under nitrogen. The mixture was diluted with ethyl acetate, washed with water, dried over sodium sulfate, filtered, concentrated in vacuo. The residue was purified by preparative HPLC to give 10 mg of produce as an off-white solid. MS obsd. (ESI⁺) [(M+H)⁺] 474, ¹H NMR (400 MHz, DMSO-d6) δ ppm 8.1 (d, J=6.4 Hz, 1 H), 7.96 (dd, J=1.2, 8.0 Hz, 1 H), 7.81 (d, J=6.8 Hz, 1 H), 7.54-7.39 (m, 5 H), 7.27 (dd, J=2.0, 8.8 Hz, 1 H), 6.63-6.56 (m, 2 H), 6.07 (s, 1 H), 5.10 (s, 2 H), 4.52 (brs, 2 H), 3.69 (t, J=6.4 Hz, 2 H), 3.55 (m, 4 H), 2.40 (s, 3 H).

Example 47-1

(4R)-1-[2-(1,1-Dioxido-2,3-dihydro-1,4-benzothiazepin-4(5H)-yl)-6-methylquinolin-4-yl]-4-hydroxypyrrolidin-2-one

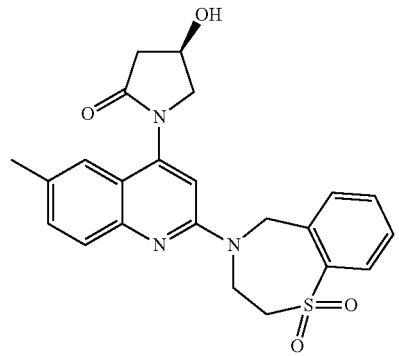 [SMILES: Cc1ccc2nc(N3CCS(=O)(=O)c4ccccc4C3)cc(N3C[C@H](O)CC3=O)c2c1]

A mixture of 4-(4-bromo-6-methylquinolin-2-yl)-2,3,4,5-tetrahydro-1,4-benzothiazepine 1,1-dioxide (400 mg, 0.96 mol, prepared in analogy to 4-(4-chloro-6-(trifluoromethoxy)quinolin-2-yl)-2,3,4,5-tetrahydro-1,4-benzothiazepine 1,1-dioxide in Example 17-1), (4R)-4-hydroxypyrrolidin-2-one (116.3 mg, 1.15 mmol), copper(I) iodide (90 mg, 0.47 mmol), potassium carbonate (265 mg, 1.92 mmol), trans-N,N'-dimethylcyclohexane-1,2-diamine (0.1 mL, 0.63 mmol) and diethylene glycol dimethyl ether (10 mL) was heated with stirring in a 10 mL of microwave process vial for 2 hours at 140° C. The mixture was diluted with dichloromethane, washed with water. The aqueous was back extracted with dichloromethane. The combined organic layer was dried over sodium sulfate, filtered, concentrated in vacuo. The residue was purified by column chromatography on silica gel to give 160 mg of produce as a gray solid. MS obsd. (ESI⁺) [(M+H)⁺] 438, ¹H NMR (400 MHz, DMSO-d6) δ ppm 7.96 (d, J=7.2 Hz, 1 H), 7.88 (dd, J=1.2, 8.0 Hz, 1 H), 7.64 (td, J=1.2, 7.6 Hz, 1 H), 7.56 (d, J=8.8 Hz, 1 H), 7.48 (dd, J=6.8, 7.6 Hz, 1 H), 7.40 (m, 2 H), 7.24 (s, 1 H), 5.51 (d, J=3.6 Hz, 1 H), 5.13 (s, 2 H), 5.55 (d, J=2.4 Hz, 1 H), 4.41 (brs, 2 H), 4.08 (dd, J=4.8, 10.0 Hz, 1 H), 3.66 (s, 2 H), 3.52 (d, J=9.6 Hz, 1 H), 2.87 (dd, J=6.4, 16.8 Hz, 1 H), 2.36 (dd, J=2.0, 16.8 Hz, 1 H), 2.36 (s, 3 H).

Example 47-2

N-[2-(1,1-Dioxido-2,3-dihydro-1,4-benzothiazepin-4 (5H)-yl)-6-methylquinolin-4-yl]-5-oxopyrrolidine-3-carboxamide

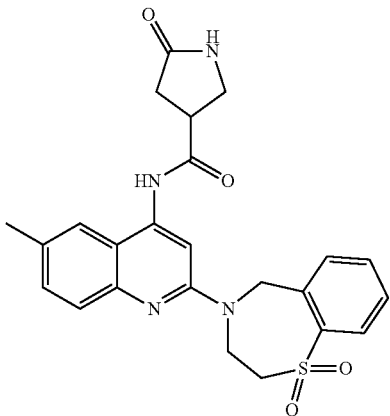 [SMILES: Cc1ccc2nc(N3CCS(=O)(=O)c4ccccc4C3)cc(NC(=O)C3CNC(=O)C3)c2c1]

A mixture of 4-(4-bromo-6-methylquinolin-2-yl)-2,3,4,5-tetrahydro-1,4-benzothiazepine 1,1-dioxide (500 mg, 1.19 mol, prepared in analogy to 4-(4-chloro-6-(trifluoromethoxy) quinolin-2-yl)-2,3,4,5-tetrahydro-1,4-benzothiazepine 1,1-dioxide in Example 17-1), 5-oxopyrrolidine-3-carboxamide (307 mg, 2.39 mmol), copper(I) iodide (23 mg, 0.12 mmol), potassium carbonate (497 mg, 3.60 mmol), trans-N,N'-dimethylcyclohexane-1,2-diamine (0.038 mL, 0.24 mmol) and diethylene glycol dimethyl ether (10 mL) was heated with stirring in a 10 mL microwave process vial for 3 hours at 140° C. under microwave irridiation. The mixture was diluted with dichloromethane, washed with water. The aqueous layer was back extracted with dichloromethane. The combined organic layers were dried over sodium sulfate, filtered, and concentrated in vacuo. The residue was purified by column chromatography on silica gel to give 40 mg of N-[2-(1,1-dioxido-2,3-dihydro-1,4-benzothiazepin-4(5H)-yl)-6-methylquinolin-4-yl]-5-oxopyrrolidine-3-carboxamide as light brown solid. MS obsd. (ESI$^+$) [(M+H)$^+$] 451, $^1$H NMR (400 MHz, DMSO-d6) δ ppm 9.98 (s, 1 H), 7.88 (m, 3 H), 7.81 (s, 1 H), 7.70 (s, 1 H), 7.64 (td, J=1.2, 7.6 Hz, 1 H), 7.47 (d, J=8.8 Hz, 1 H), 7.46 (dd, J=0.8, 7.6 Hz, 1 H), 7.38 (dd, J=1.6, 8.4 Hz, 1 H), 5.08 (s, 2 H), 4.42 (brs, 2 H), 3.73-3.57 (m, 4 H), 3.43 (dd, J=6.0, 9.6 Hz, 1 H), 3.32 (s, 1 H), 2.48 (m, 1 H), 2.42 (s, 3 H).

Example 47-3

2-(1,1-Dioxido-2,3-dihydro-1,4-benzothiazepin-4 (5H)-yl)-6-methyl-N-(1H-pyrazol-3-yl)quinolin-4-amine

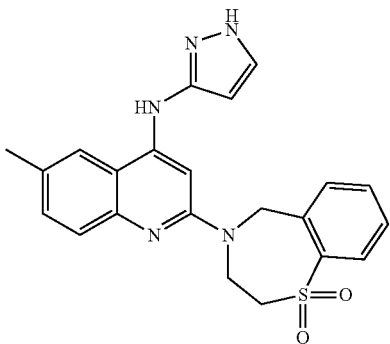 [SMILES: Cc1ccc2nc(N3CCS(=O)(=O)c4ccccc4C3)cc(Nc3cc[nH]n3)c2c1]

The title compound was prepared in analogy to Example 47-1 in Scheme 5 by using 4-(4-bromo-6-methylquinolin-2-yl)-2,3,4,5-tetrahydro-1,4-benzothiazepine 1,1-dioxide (prepared in analogy to 4-(4-chloro-6-(trifluoromethoxy)quinolin-2-yl)-2,3,4,5-tetrahydro-1,4-benzothiazepine 1,1-dioxide in Example 17-1) and 1H-pyrazol-3-amine. MS obsd. (ESI$^+$) [(M+H)$^+$] 420, $^1$H NMR (400 MHz, CD$_3$OD) δ ppm 8.22 (s, 1 H), 8.15-8.14 (d, J=2.8 Hz, 1 H), 8.04-8.02 (d, J=8 Hz, 1 H), 7.90-7.88 (d, J=7.2 Hz, 1 H), 7.85-7.83 (d, J=8.8 Hz, 1 H), 7.71-7.70 (m, 1 H), 7.64-7.61 (d, J=8.4 Hz, 1 H), 7.60-7.51 (t, J=8 Hz, 1 H), 7.30 (s, 1 H), 6.27 (s, 1 H), 5.34 (s, 2 H), 4.59 (s, 2 H), 3.74 (s, 2 H), 2.45 (s, 3 H).

Example 47-4

N-[2-(1,1-Dioxido-2,3-dihydro-1,4-benzothiazepin-4 (5H)-yl)-6-methylquinolin-4-yl]pyridine-3-carboxamide

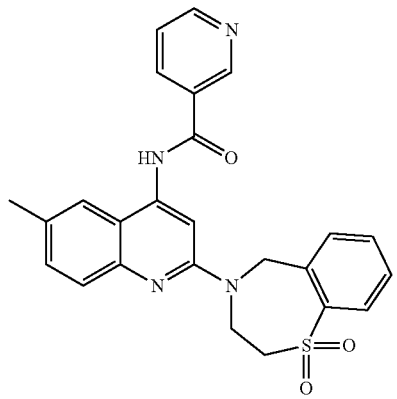 [SMILES: Cc1ccc2nc(N3CCS(=O)(=O)c4ccccc4C3)cc(NC(=O)c3cccnc3)c2c1]

The title compound was prepared in analogy to Example 47-1 in Scheme 5 by using 4-(4-bromo-6-methylquinolin-2-yl)-2,3,4,5-tetrahydro-1,4-benzothiazepine 1,1-dioxide (prepared in analogy to 4-(4-chloro-6-(trifluoromethoxy)quinolin-2-yl)-2,3,4,5-tetrahydro-1,4-benzothiazepine 1,1-dioxide in Example 17-1) and pyridine-3-carboxamide. MS obsd. (ESI$^+$) [(M+H)$^+$] 459, $^1$H NMR (400 MHz, CD$_3$OD) δ ppm 9.17 (s, 1 H), 8.80 (s, 1 H), 8.52 (s, 1 H), 8.44-8.42 (d, J=8 Hz, 1 H), 8.08-8.06 (d, J=8 Hz, 1 H), 7.99-7.96 (d, J=9.6 Hz, 2 H), 7.90-7.88 (d, J=8.4 Hz, 1 H), 7.70-7.48 (m, 4 H), 5.29 (s, 2 H), 4.72 (s, 2 H), 3.64 (s, 2 H), 2.49 (s, 3 H).

Example 47-5

N-[2-(1,1-Dioxido-2,3-dihydro-1,4-benzothiazepin-4 (5H)-yl)-6-methylquinolin-4-yl]piperidine-2-carboxamide

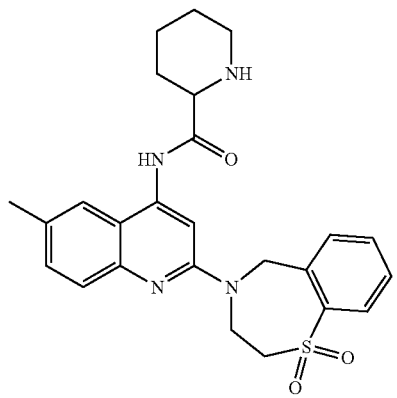 [SMILES: Cc1ccc2nc(N3CCS(=O)(=O)c4ccccc4C3)cc(NC(=O)C3CCCCN3)c2c1]

The title compound was prepared in analogy to Example 47-1 in Scheme 5 by using 4-(4-bromo-6-methylquinolin-2-yl)-2,3,4,5-tetrahydro-1,4-benzothiazepine 1,1-dioxide (prepared in analogy to 4-(4-chloro-6-(trifluoromethoxy)quinolin-2-yl)-2,3,4,5-tetrahydro-1,4-benzothiazepine 1,1-dioxide in Example 17-1) and piperidine-2-carboxamide. MS obsd. (ESI⁺) [(M+H)⁺] 465, ¹H NMR (400 MHz, CD₃OD) δ ppm 8.33 (s, 1 H), 8.07-8.05 (d, J=6.8 Hz, 1 H), 8.02 (s, 1 H), 7.95-7.93 (d, J=7.6 Hz, 1 H), 7.80-7.78 (d, J=8.4 Hz, 1 H), 7.66-7.62 (q, J=8.8 Hz, 2 H), 7.56-7.52 (dd, J=7.2, 15.6 Hz, 1 H), 5.28 (s, 2 H), 4.61 (s, 2 H), 4.34-4.31 (dd, J=2.4, 12.8 Hz, 1 H), 3.74 (s, 2 H), 3.56-3.53 (d, J=12.8 Hz, 1 H), 3.18-3.11 (m, 1 H), 2.51 (s, 3 H), 2.46-2.43 (d, J=14 Hz, 1 H), 2.07-1.99 (m, 2 H), 1.88-1.76 (m, 1 H).

Example 47-6

N-[2-(1,1-Dioxido-2,3-dihydro-1,4-benzothiazepin-4 (5H)-yl)-6-methylquinolin-4-yl]-2-(pyridin-2-yl) acetamide

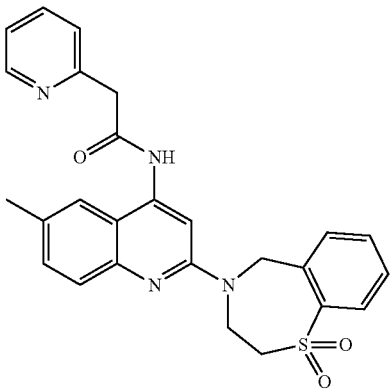 [SMILES: Cc1ccc2nc(N3CCS(=O)(=O)c4ccccc4C3)cc(NC(=O)Cc3ccccn3)c2c1]

The title compound was prepared in analogy to Example 47-1 in Scheme 5 by using 4-(4-bromo-6-methylquinolin-2-yl)-2,3,4,5-tetrahydro-1,4-benzothiazepine 1,1-dioxide (prepared in analogy to 4-(4-chloro-6-(trifluoromethoxy)quinolin-2-yl)-2,3,4,5-tetrahydro-1,4-benzothiazepine 1,1-dioxide in Example 17-1) and 2-(pyridin-2-yl)acetamide. MS obsd. (ESI⁺) [(M+H)⁺] 473, ¹H NMR (400 MHz, CD₃OD) δ ppm 8.53 (s, 1 H), 8.15 (s, 2 H), 8.06-8.04 (d, J=7.6 Hz, 1 H), 7.85-7.54 (m, 8 H), 5.26 (s, 2 H), 4.61 (s, 2 H), 3.57 (s, 2 H), 2.56 (s, 3 H).

Example 47-7

N-[2-(1,1-Dioxido-2,3-dihydro-1,4-benzothiazepin-4 (5H)-yl)-6-methylquinolin-4-yl]methanesulfonamide trifluoroacetate

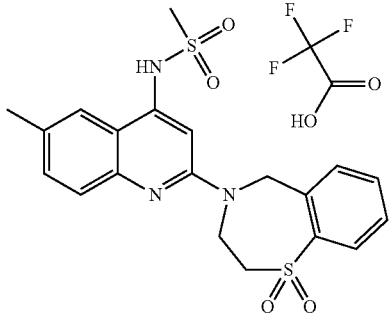

The title compound was prepared in analogy to Example 47-1 in Scheme 5 by using 4-(4-bromo-6-methylquinolin-2-yl)-2,3,4,5-tetrahydro-1,4-benzothiazepine 1,1-dioxide (prepared in analogy to 4-(4-chloro-6-(trifluoromethoxy)quinolin-2-yl)-2,3,4,5-tetrahydro-1,4-benzothiazepine 1,1-dioxide in Example 17-1) and methanesulfonamide. MS obsd. (ESI⁺) [(M+H)⁺] 432, ¹H NMR (400 MHz, DMSO-d6) δ ppm 7.98-7.90 (m, 2 H), 7.88-7.82 (d, J=7.2 Hz, 1 H), 7.72-7.65 (t, J=2 Hz, 1 H), 7.65-7.58 (d, J=7.6 Hz, 1 H), 7.58-7.51 (t, J=2.4 Hz, 1 H), 7.48-7.42 (d, J=7.6 Hz, 1 H), 7.01 (s, 1 H), 5.10 (s, 2 H), 4.60-4.40 (m, 2 H), 3.82-3.75 (t, J=2.8 Hz, 2 H), 3.10 (s, 3 H), 2.38 (s, 3 H).

Example 47-8

N-[2-(1,1-Dioxido-2,3-dihydro-1,4-benzothiazepin-4 (5H)-yl)-6-methylquinolin-4-yl]pyrazine-2-carboxamide

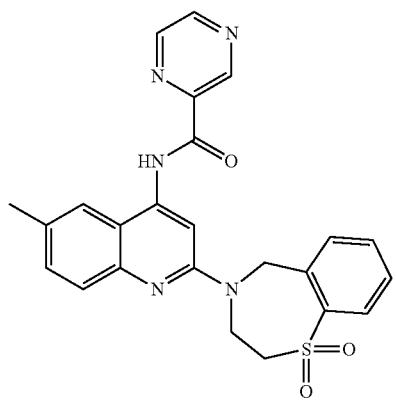

The title compound was prepared in analogy to Example 47-1 in Scheme 5 by using 4-(4-bromo-6-methylquinolin-2-yl)-2,3,4,5-tetrahydro-1,4-benzothiazepine 1,1-dioxide (prepared in analogy to 4-(4-chloro-6-(trifluoromethoxy)quinolin-2-yl)-2,3,4,5-tetrahydro-1,4-benzothiazepine 1,1-dioxide in Example 17-1) and pyrazine-2-carboxamide. MS obsd. (ESI⁺) [(M+H)⁺] 460, ¹H NMR (400 MHz, CD₃OD) δ ppm 9.53 (s, 1 H), 8.97 (s, 1 H), 8.86 (s, 1 H), 8.72 (s, 1 H), 8.10-8.08 (dd, J=5.2, 11.2 Hz, 2 H), 7.94-7.90 (dd, J=8.8, 14.8 Hz, 2 H), 7.76-7.72 (d, J=7.6 Hz, 2 H), 7.60-7.56 (d, J=8 Hz, 1 H), 5.37 (s, 2 H), 4.70 (s, 2 H), 3.81 (s, 2 H), 2.56 (s, 3 H).

Example 47-9

N-[2-(1,1-Dioxido-2,3-dihydro-1,4-benzothiazepin-4 (5H)-yl)-6-methylquinolin-4-yl]-2-hydroxyacetamide

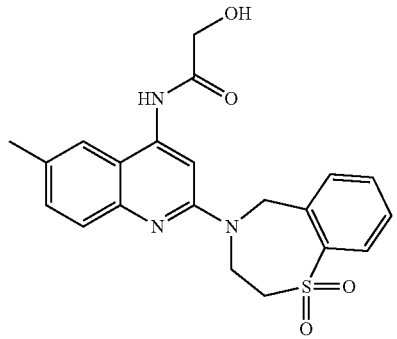 [SMILES: Cc1ccc2nc(N3CCS(=O)(=O)c4ccccc4C3)cc(NC(=O)CO)c2c1]

The title compound was prepared in analogy to Example 47-1 in Scheme 5 by using 4-(4-bromo-6-methylquinolin-2-yl)-2,3,4,5-tetrahydro-1,4-benzothiazepine 1,1-dioxide (prepared in analogy to 4-(4-chloro-6-(trifluoromethoxy)quinolin-2-yl)-2,3,4,5-tetrahydro-1,4-benzothiazepine 1,1-dioxide in Example 17-1) and 2-hydroxyacetamide. MS obsd. (ESI$^+$) [(M+H)$^+$] 412, $^1$H NMR (400 MHz, CD$_3$OD) δ ppm 8.54 (s, 1 H), 8.05 (dd, J=1.2, 7.6 Hz, 1 H), 7.97 (d, J=7.2 Hz, 1 H), 7.81 (s, 2 H), 7.70-7.66 (m, 2 H), 7.54 (t, J=7.6 Hz, 1 H), 5.27 (s, 2 H), 4.62 (s, 2 H), 4.36 (s, 2 H), 3.76 (s, 2 H), 2.51 (s, 3 H).

Example 48

N-[2-(1,1-Dioxido-2,3-dihydro-1,4-benzothiazepin-4(5H)-yl)-6-methylquinolin-4-yl]pyridine-2-carboxamide

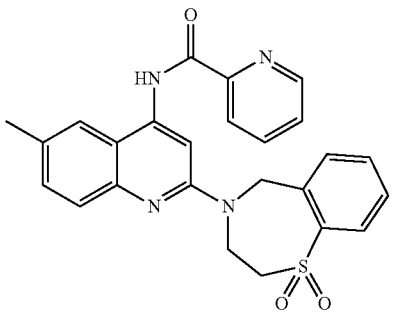 [SMILES: Cc1ccc2nc(N3CCS(=O)(=O)c4ccccc4C3)cc(NC(=O)c3ccccn3)c2c1]

A mixture of pyridine-2-carboxylic acid amide (99 mg, 0.8 mmol), 4-(4-chloro-6-methylquinolin-2-yl)-2,3,4,5-tetrahydro-1,4-benzothiazepine 1,1-dioxide (300 mg, 0.8 mmol, prepared in analogy to 4-(4-chloro-6-(trifluoromethoxy)quinolin-2-yl)-2,3,4,5-tetrahydro-1,4-benzothiazepine 1,1-dioxide in Example 17-1), cyclohexane-1,3-diamine (90 mg, 0.08 mmol), copper(I) iodide (1.5 mg, 0.008 mmol) and potassium phosphate (340 mg, 1.6 mmol) in 1,4-dioxane (3 mL) was heated in a 5 mL of microwave process vial for 3 hours at 150° C. The reaction mixture was concentrated in vacuo. The residue was purified by preparative HPLC and SPE to give 26 mg of the desired product (yield was 7.1%). MS obsd. (ESI$^+$) [(M+H)$^+$] 451, $^1$H NMR (400 MHz, CD$_3$OD) δ ppm 8.90-8.82 (d, J=8 Hz, 1 H), 8.77 (s, 1 H), 8.47-8.40 (d, J=7.6 Hz, 1 H), 8.20-8.13 (t, J=6.4 Hz, 1 H), 8.13-8.08 (d, J=7.6 Hz, 2 H), 7.92-7.85 (m, 2 H), 7.80-7.70 (q, J=8.4 Hz, 3 H), 7.62-7.56 (t, J=7.2 Hz, 1 H), 5.37 (s, 2 H), 4.80-4.50 (m, 2 H), 3.82-3.78 (t, J=2.8 Hz, 2 H), 2.60 (s, 3 H).

Example 49

N-[2-(1,1-Dioxido-2,3-dihydro-1,4-benzothiazepin-4(5H)-yl)-6-methylquinolin-4-yl]azetidine-2-carboxamide

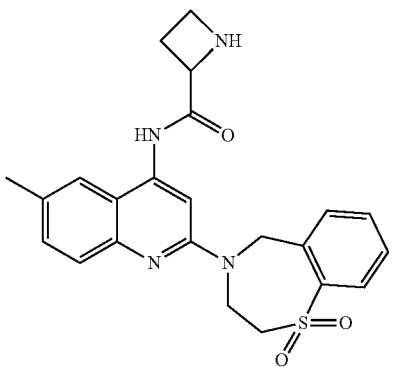 [SMILES: Cc1ccc2nc(N3CCS(=O)(=O)c4ccccc4C3)cc(NC(=O)C3CCN3)c2c1]

tert-Butyl 2-{[2-(1,1-dioxido-2,3-dihydro-1,4-benzothiazepin-4(5H)-yl)-6-methylquinolin-4-yl]carbamoyl}azetidine-1-carboxylate

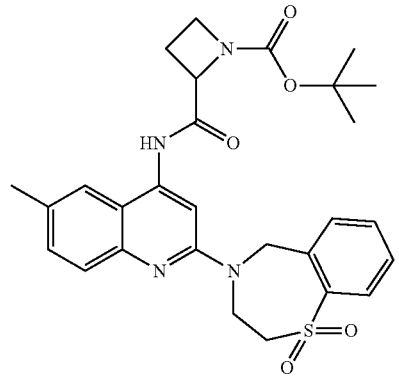 [SMILES: Cc1ccc2nc(N3CCS(=O)(=O)c4ccccc4C3)cc(NC(=O)C3CCN3C(=O)OC(C)(C)C)c2c1]

The title compound was prepared in analogy to Example 48-1 in Scheme 5 by using 4-(4-bromo-6-methylquinolin-2-yl)-2,3,4,5-tetrahydro-1,4-benzothiazepine 1,1-dioxide (prepared in analogy to 4-(4-chloro-6-(trifluoromethoxy)quinolin-2-yl)-2,3,4,5-tetrahydro-1,4-benzothiazepine 1,1-dioxide in Example 17-1) and tert-butyl 2-carbamoylazetidine-1-carboxylate.

N-[2-(1,1-Dioxido-2,3-dihydro-1,4-benzothiazepin-4(5H)-yl)-6-methylquinolin-4-yl]azetidine-2-carboxamide

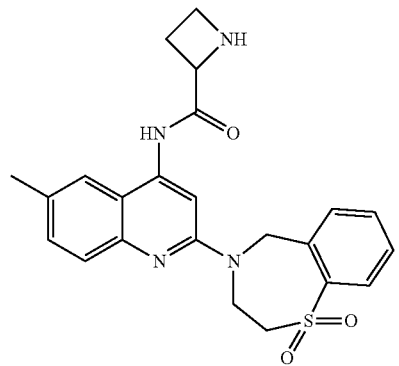 [SMILES: Cc1ccc2nc(N3CCS(=O)(=O)c4ccccc4C3)cc(NC(=O)C3CCN3)c2c1]

To a solution of tert-butyl 2-{[2-(1,1-dioxido-2,3-dihydro-1,4-benzothiazepin-4(5H)-yl)-6-methylquinolin-4-yl]carbamoyl}azetidine-1-carboxylate (80 mg, 0.15 mmol) in ethyl acetate (10 mL) was added a solution of hydrochloride in ethyl acetate (4 N, 30 mL) dropwise in an ice-water bath. After being stirred at room temperature for 4 hours, the resulting mixture was concentrated in vacuo and purified by preparative HPLC to give the trifluoroacetic acid salt of the desired product. The trifluoroacetic acid salt was flashed through SPE column with methanol. The eluent was concentrated in vacuo and dried by lyopylization to give 30.79 mg of the desired product (yield was 47%). MS obsd. (ESI$^+$) [(M+H)$^+$] 437, $^1$H NMR (400 MHz, CD$_3$OD) δ ppm 8.35 (s, 1 H), 8.04 (dd, J=1.2, 7.6 Hz, 1 H), 7.98 (d, J=7.6 Hz, 1 H), 7.93 (s, 1 H), 7.75 (d, J=8.8 Hz, 1 H), 7.67 (t, J=7.6 Hz, 1 H), 7.59 (d, J=9.6 Hz, 1 H), 7.53 (t, J=8.8 Hz, 1 H), 5.47-5.43 (m, 1 H), 5.28 (s, 2 H), 4.61 (brs, 2 H), 4.25-4.18 (m, 1 H), 4.14-4.10 (m, 1 H), 3.73 (s, 2 H), 3.04-2.98 (m, 1 H), 2.76-2.72 (m, 1 H), 2.49 (s, 3 H).

Example 50-1

1-[2-(1,1-Dioxido-2,3-dihydro-1,4-benzothiazepin-4(5H)-yl)-6-methylquinolin-4-yl]-3-phenylurea

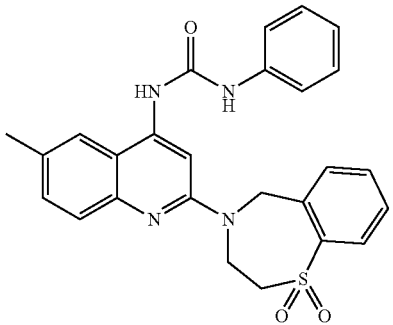 [SMILES: Cc1ccc2nc(N3CCS(=O)(=O)c4ccccc4C3)cc(NC(=O)Nc3ccccc3)c2c1]

To a solution of 2-(1,1-dioxido-2,3-dihydro-1,4-benzothiazepin-4(5H)-yl)-6-methylquinolin-4-amine (180 mg, 0.5 mmol, prepared in analogy to 4-(4-chloro-6-(trifluoromethoxy)quinolin-2-yl)-2,3,4,5-tetrahydro-1,4-benzothiazepine 1,1-dioxide in Example 17-1) and triethylamine (103 mg) in tetrahydrofuran (15 mL) was added a solution of isocyanato-benzene (59.6 mg, 0.5 mmol) in tetrahydrofuran (5 mL) at 0° C. The reaction was stirred at room temperature overnight and then heated at 50° C. for additional 5 hours. The reaction mixture was concentrated in vacuo and the residue was purified by preparative HPLC and SPE to give 17.6 mg of the desired product (yield was 7.5%). MS obsd. (ESI$^+$) [(M+H)$^+$] 473, $^1$H NMR (400 MHz, CD$_3$OD) δ ppm 8.55 (s, 1 H), 8.12-8.03 (m, 2 H), 7.92 (s, 1 H), 7.86-7.81 (d, J=8.4 Hz, 1 H), 7.76-7.68 (m, 2 H), 7.66-7.57 (m, 3 H), 7.45-7.38 (t, J=7.6 Hz, 2 H), 7.20-7.12 (t, J=2.0 Hz, 1 H), 5.32 (s, 2 H), 4.61-4.40 (m, 2 H), 3.82-3.75 (t, J=2.8 Hz, 2 H), 2.56 (s, 3 H).

Example 50-2

1-[2-(1,1-Dioxido-2,3-dihydro-1,4-benzothiazepin-4(5H)-yl)-6-methylquinolin-4-yl]-3-ethylurea

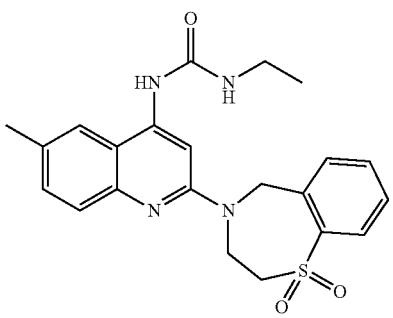 [SMILES: CCNC(=O)Nc1cc(N2CCS(=O)(=O)c3ccccc3C2)nc2ccc(C)cc12]

The title compound was prepared in analogy to Example 50-1 by using 2-(1,1-dioxido-2,3-dihydro-1,4-benzothiazepin-4(5H)-yl)-6-methylquinolin-4-amine (prepared in analogy to 4-(4-chloro-6-(trifluoromethoxy)quinolin-2-yl)-2,3,4,5-tetrahydro-1,4-benzothiazepine 1,1-dioxide in Example 17-1) and ethylisocyanate. MS obsd. (ESI$^+$) [(M+H)$^+$] 425, $^1$H NMR (400 MHz, CD$_3$OD) δ ppm 8.44 (s, 1 H), 8.09-8.03 (d, J=8 Hz, 1 H), 7.99-7.93 (d, J=7.6 Hz, 1 H), 7.86 (s, 1 H), 7.80-7.74 (d, J=8.8 Hz, 1 H), 7.72-7.62 (m, 2 H), 7.60-7.51 (t, J=8.4 Hz, 1 H), 5.24 (s, 2 H), 4.62-4.50 (m, 2 H), 3.78-3.70 (m, 2 H), 3.40-3.32 (q, J=7.2 Hz, 2 H), 2.49 (s, 3 H), 1.28-1.20 (t, J=7.2 Hz, 3 H).

Example 51

N-[6-Cyclopropyl-2-(1,1-dioxido-2,3-dihydro-1,4-benzothiazepin-4(5H)-yl)quinolin-4-yl]propane-1,3-diamine

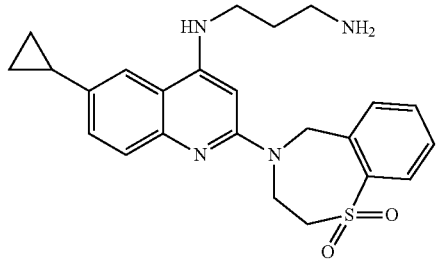 [SMILES: NCCCNc1cc(N2CCS(=O)(=O)c3ccccc3C2)nc2ccc(C3CC3)cc12]

4-(4-Chloro-6-cyclopropylquinolin-2-yl)-2,3,4,5-tetrahydro-1,4-benzothiazepine 1,1-dioxide

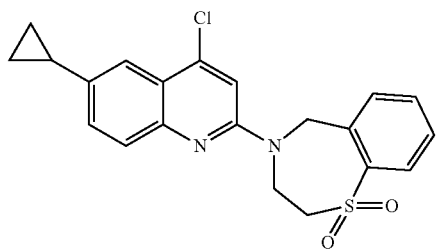 [SMILES: O=S1(=O)CCN(c2cc(Cl)c3cc(C4CC4)ccc3n2)Cc2ccccc21]

To a solution of 4-(6-bromo-4-chloroquinolin-2-yl)-2,3,4,5-tetrahydro-1,4-benzothiazepine 1,1-dioxide (1.0 g, 2.3 mmol, prepared in analogy to 4-(4-chloro-6-(trifluoromethoxy)quinolin-2-yl)-2,3,4,5-tetrahydro-1,4-benzothiazepine 1,1-dioxide in Example 17-1) in toluene (150 mL) was added cyclopropylboronic acid (200 mg, 2.3 mmol), palladium acetate (52 mg, 0.23 mmol), 2,2'-bis(diphenylphosphino)-1,1'-binaphthyl (143 mg, 0.23 mmol) and potassium carbonate (320 mg, 2.3 mmol) under argon protection. After being heated at 90° C. for 16 hours, the reaction mixture was concentrated in vacuo. The residue was dissolved in dichloromethane (100 mL), and the solution was washed with water (50 mL×3), dried over sodium sulfate, filtered and concentrated in vacuo. The residue was purified by column chromatography (eluting with 16% ethyl acetate in petroleum ether) to afford 300 mg of the desired product (yield was 33%).

N-[6-Cyclopropyl-2-(1,1-dioxido-2,3-dihydro-1,4-benzothiazepin-4(5H)-yl)quinolin-4-yl]propane-1,3-diamine

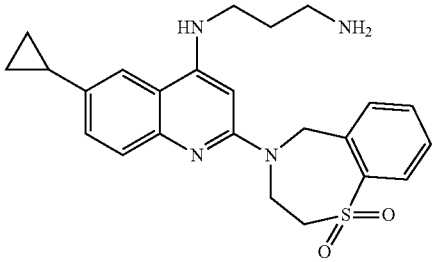 [SMILES: NCCCNc1cc(N2CCS(=O)(=O)c3ccccc3C2)nc2ccc(C3CC3)cc12]

A mixture of 4-(4-chloro-6-cyclopropylquinolin-2-yl)-2,3,4,5-tetrahydro-1,4-benzothiazepine 1,1-dioxide (300 mg, 0.75 mmol) and propane-1,3-diamine (700 mg, 7.5 mmol) was heated with stirring in a 10 mL of microwave process vial for 1.5 hours at 150° C. under microwave irradiation. The reaction mixture was purified by preparative HPLC to give the trifluoroacetic acid salt of the desired product. The trifluoroacetic acid salt was flashed through SPE column with methanol. The eluent was concentrated in vacuo and dried by lyopylization to give 119.4 mg of the desired product (yield was 36%). MS obsd. (ESI$^+$) [(M+H)$^+$] 437, $^1$H NMR (400 MHz, CD$_3$OD) δ ppm 8.05 (d, J=7.6 Hz, 1 H), 7.84 (d, J=7.2 Hz, 1 H), 7.81 (d, J=1.2 Hz, 1 H), 7.67-7.69 (m, 2 H), 7.55 (t, J=7.6 Hz, 1 H), 7.46 (d, J=8.8 Hz, 1 H), 5.92 (s, 1 H), 5.29 (s, 2 H), 4.48 (brs, 2 H), 3.70 (s, 2 H), 3.59 (t, J=6.8 Hz, 2 H), 3.08 (t, J=8.0 Hz, 2 H), 2.12-2.07 (m, 2 H), 2.05-1.98 (m, 1 H), 1.03 (dd, J=2.0 Hz, 8.4 Hz, 2 H), 0.78-0.76 (m, 2 H).

Example 52

4-[(3-Aminopropyl)amino]-2-(1,1-dioxido-2,3-dihydro-1,4-benzothiazepin-4(5H)-yl)quinoline-6-carbonitrile

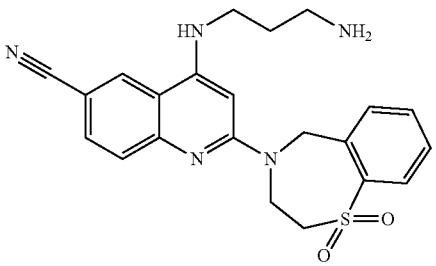 [SMILES: N#Cc1ccc2nc(N3CCS(=O)(=O)c4ccccc4C3)cc(NCCCN)c2c1]

4-(4-Chloro-6-ethynylquinolin-2-yl)-2,3,4,5-tetrahydro-1,4-benzothiazepine 1,1-dioxide

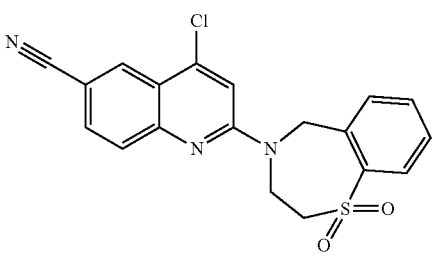 [SMILES: N#Cc1ccc2nc(N3CCS(=O)(=O)c4ccccc4C3)cc(Cl)c2c1]

To a degassed solution of 4-(6-bromo-4-chloroquinolin-2-yl)-2,3,4,5-tetrahydro-1,4-benzothiazepine 1,1-dioxide (880 mg, 2 mmol, prepared in analogy to 4-(4-chloro-6-(trifluoromethoxy)quinolin-2-yl)-2,3,4,5-tetrahydro-1,4-benzothiazepine 1,1-dioxide in Example 17-1) in N,N-dimethylformamide (50 mL), zinc cyanide (280 mg, 2.4 mmol) and tetrakis(triphenylphosphine)palladium(0) (232 mg, 0.2 mmol) was added under argon. After being refluxed for 2 hours, the reaction mixture was concentrated in vacuo and the residue was portioned in ethyl acetate (100 mL) and water (100 mL). After being stirred vigorously for 1 hour, the separated aqueous layer was extracted with ethyl acetate (100 mL×2). The combined organic layers were dried over sodium sulfate and concentrated in vacuo to afford 0.6 g of the crude product.

4-[(3-Aminopropyl)amino]-2-(1,1-dioxido-2,3-dihydro-1,4-benzothiazepin-4(5H)-yl)quinoline-6-carbonitrile

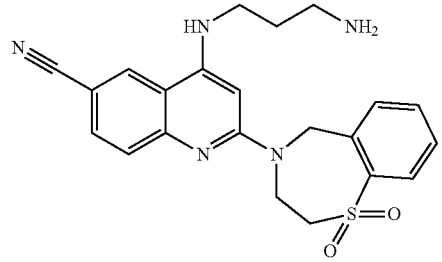 [SMILES: N#Cc1ccc2nc(N3CCS(=O)(=O)c4ccccc4C3)cc(NCCCN)c2c1]

A mixture of 4-(4-chloro-6-ethynylquinolin-2-yl)-2,3,4,5-tetrahydro-1,4-benzothiazepine 1,1-dioxide (300 mg, 0.7 mmol), propane-1,3-diamine (64 mg, 0.8 mmol), 1,1'-bis(diphenylphosphino)ferrocene-palladium(II)dichloride (65 mg, 0.08 mmol), 1,1'-bis(diphenylphosphino)ferrocene (45 mg, 0.08 mmol) and sodium tert-butoxide (307 mg, 3.2 mmol) in 1,4-dioxane (3 mL) was heated with stirring in a sealed 5 mL of microwave process vial for 1.5 hours at 120° C. under microwave irradiation. The resulting mixture was concentrated in vacuo. The residue was purified by preparative HPLC and SPE. After SPE separation, the eluent was concentrated in vacuo and the residue was dried by lyophylization to afford 65.2 mg of the desired product (yield was 20%). MS obsd. (ESI$^+$) [(M+H)$^+$] 422, $^1$H NMR (400 MHz, CD$_3$OD) δ ppm 8.60 (s, 1 H), 8.10-8.08 (d, J=8 Hz, 1 H), 7.99-7.86 (m, 3 H), 7.74-7.70 (t, J=7.2 Hz, 1 H), 7.61-7.57 (t, J=7.6 Hz, 1 H), 6.05 (s, 2 H), 5.35 (s, 2 H), 4.56 (s, 2 H), 3.75 (s, 2 H), 3.62-3.59 (t, J=6.8 Hz, 2 H), 3.14-3.10 (t, J=8 Hz, 2 H), 2.15-2.11 (t, J=7.6 Hz, 2 H).

Example 53

N-[2-(1,1-Dioxido-2,3-dihydro-1,4-benzothiazepin-4(5H)-yl)-6-ethenylquinolin-4-yl]propane-1,3-diamine

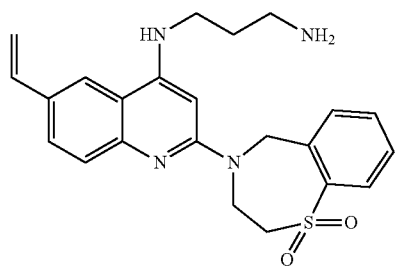 [SMILES: C=Cc1ccc2nc(N3CCS(=O)(=O)c4ccccc4C3)cc(NCCCN)c2c1]

361

4-(4-Chloro-6-ethenylquinolin-2-yl)-2,3,4,5-tetrahydro-1,4-benzothiazepine 1,1-dioxide

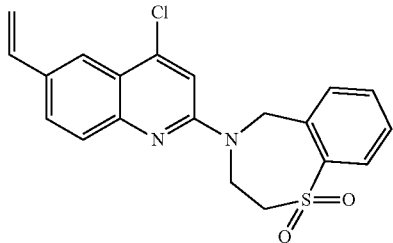 [SMILES: C=Cc1ccc2nc(N3CCS(=O)(=O)c4ccccc4C3)cc(Cl)c2c1]

To a degassed solution of 4-(6-bromo-4-chloroquinolin-2-yl)-2,3,4,5-tetrahydro-1,4-benzothiazepine 1,1-dioxide (880 mg, 2 mmol, prepared in analogy to 4-(4-chloro-6-(trifluoromethoxy)quinolin-2-yl)-2,3,4,5-tetrahydro-1,4-benzothiazepine 1,1-dioxide in Example 17-1) in N,N-dimethylformamide (50 mL), tributyl(vinyl)tin (760 mg, 2.4 mmol) and tetrakis(triphenylphosphine)palladium(0) (232 mg, 0.2 mmol) was added under argon. After being refluxed for 2 hours, the reaction mixture was concentrated in vacuo and the residue was portioned in ethyl acetate (100 mL) and a saturated aqueous solution of potassium fluoride (100 mL). After the mixture being stirred vigorously for 1 hour, the separated aqueous layer was extracted with ethyl acetate (100 mL×2). The combined organic layers were dried over sodium sulfate and concentrated in vacuo to afford 0.4 g of the crude product.

N-[2-(1,1-Dioxido-2,3-dihydro-1,4-benzothiazepin-4(5H)-yl)-6-ethenylquinolin-4-yl]propane-1,3-diamine

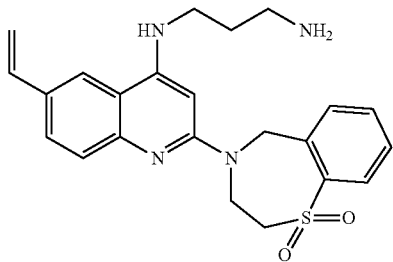 [SMILES: C=Cc1ccc2nc(N3CCS(=O)(=O)c4ccccc4C3)cc(NCCCN)c2c1]

The title compound was prepared in analogy to Example 52 in Scheme 22 by using 4-(4-chloro-6-ethenylquinolin-2-yl)-2,3,4,5-tetrahydro-1,4-benzothiazepine 1,1-dioxide and propane-1,3-diamine. MS obsd. (ESI$^+$) [(M+H)$^+$] 423, $^1$H NMR (400 MHz, CD$_3$OD) δ ppm 8.12 (s, 1 H), 8.05-8.02 (q, J=8 Hz, 1 H), 7.89-7.81 (m, 2 H), 7.77-7.70 (m, 2 H), 7.56-7.54 (t, J=4.4 Hz, 1 H), 6.80-6.74 (m, 1 H), 5.95-5.90 (m, 2 H), 5.36-5.30 (m, 3 H), 4.51 (s, 2 H), 3.71 (s, 2 H), 3.61-3.60 (t, J=3.2 Hz, 2 H), 3.11-3.10 (t, J=5.2 Hz, 2 H), 2.13-2.11 (t, J=5.6 Hz, 2 H).

Example 54

N-[2-(1,1-Dioxido-2,3-dihydro-1,4-benzothiazepin-4(5H)-yl)-6-ethynylquinolin-4-yl]propane-1,3-diamine

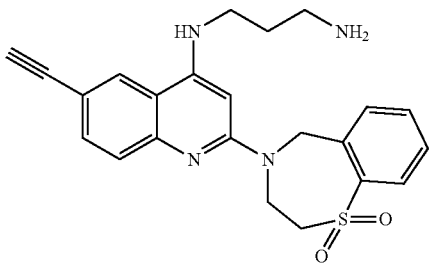 [SMILES: C#Cc1ccc2nc(N3CCS(=O)(=O)c4ccccc4C3)cc(NCCCN)c2c1]

362

4-(4-chloro-6-ethynylquinolin-2-yl)-2,3,4,5-tetrahydro-1,4-benzothiazepine 1,1-dioxide

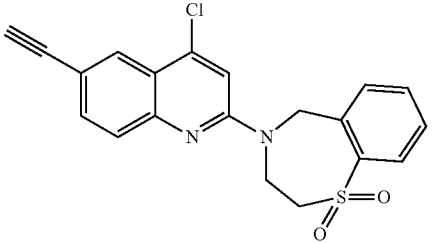 [SMILES: C#Cc1ccc2nc(N3CCS(=O)(=O)c4ccccc4C3)cc(Cl)c2c1]

To a degassed solution of 4-(6-bromo-4-chloroquinolin-2-yl)-2,3,4,5-tetrahydro-1,4-benzothiazepine 1,1-dioxide (880 mg, 2 mmol, prepared in analogy to 4-(4-chloro-6-(trifluoromethoxy)quinolin-2-yl)-2,3,4,5-tetrahydro-1,4-benzothiazepine 1,1-dioxide in Example 17-1) in N,N-dimethylformamide (50 mL), tributyl(ethynyl)tin (760 mg, 2.4 mmol) and tetrakis(triphenylphosphine)palladium(0) (232 mg, 0.2 mmol) was added under argon. After being refluxed for 2 hours, the reaction mixture was concentrated in vacuo and the residue was portioned in a mixture of ethyl acetate (100 mL) and a saturated aqueous solution of potassium fluoride (100 mL). After the mixture being stirred vigorously for 1 hour, the separated aqueous layer was extracted with ethyl acetate (100 mL×2). The combined organic layers were dried over sodium sulfate and concentrated in vacuo to afford 0.45 g of the crude product.

N-[2-(1,1-Dioxido-2,3-dihydro-1,4-benzothiazepin-4(5H)-yl)-6-ethynylquinolin-4-yl]propane-1,3-diamine

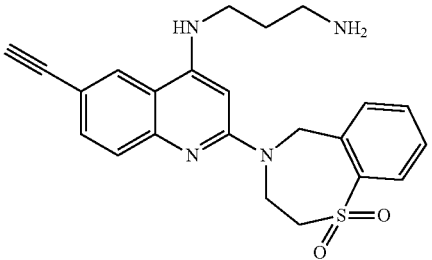 [SMILES: C#Cc1ccc2nc(N3CCS(=O)(=O)c4ccccc4C3)cc(NCCCN)c2c1]

The title compound was prepared in analogy to Example 52 in Scheme 22 by using 4-(4-chloro-6-ethynylquinolin-2-yl)-2,3,4,5-tetrahydro-1,4-benzothiazepine 1,1-dioxide and propane-1,3-diamine. MS obsd. (ESI$^+$) [(M+H)$^+$] 421, $^1$H NMR (400 MHz, CD$_3$OD) δ ppm 8.25 (s, 1 H), 8.01-7.99 (d, J=7.6 Hz, 1 H), 7.94-7.92 (d, J=7.2 Hz, 1 H), 7.87-7.85 (d, J=8.8 Hz, 1 H), 7.82-7.79 (m, 1 H), 7.65-7.61 (m, 1 H), 7.50-7.47 (m, 1 H), 7.32 (s, 1 H), 5.30 (s, 2 H), 3.65-3.60 (m, 6 H), 2.70 (s, 3 H), 2.14-2.11 (t, J=5.2 Hz, 2 H).

Example 55-1

N-[(3-Aminooxetan-3-yl)methyl]-6-methyl-2-(1-oxido-2,3-dihydro-1,4-benzothiazepin-4(5H)-yl)quinazolin-4-amine

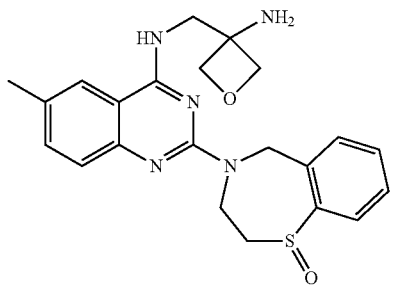 [SMILES: Cc1ccc2nc(N3CCS(=O)c4ccccc4C3)nc(NCC3(N)COC3)c2c1]

N-(3-Aminooxetan-3-ylmethyl)-2-chloro-6-methylquinazolin-4-amine

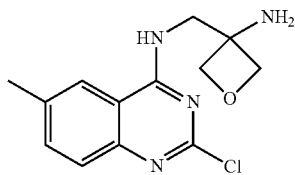 [SMILES: Cc1ccc2nc(Cl)nc(NCC3(N)COC3)c2c1]

A solution of 2,4-dichloro-6-methylquinazoline (645 mg, 3 mmol) and 3-(aminomethyl)oxetan-3-amine (340 mg, 3.3 mmol) in methanol (15 mL) was stirred at room temperature overnight. After the resulting mixture was concentrated in vacuo, the residue was purified by column chromatography (eluting with 10% methanol in dichloromethane) to afford the desired product.

N-[(3-Aminooxetan-3-yl)methyl]-6-methyl-2-(1-oxido-2,3-dihydro-1,4-benzothiazepin-4(5H)-yl)quinazolin-4-amine

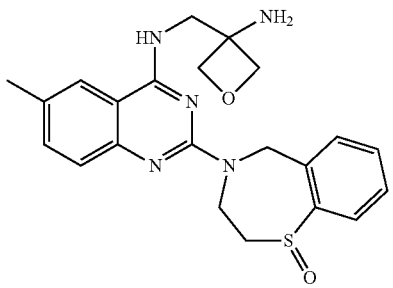 [SMILES: Cc1ccc2nc(N3CCS(=O)c4ccccc4C3)nc(NCC3(N)COC3)c2c1]

A mixture of N-(3-aminooxetan-3-ylmethyl)-2-chloro-6-methylquinazolin-4-amine (140 mg, 0.5 mmol) and 2,3,4,5-tetrahydro-1,4-benzothiazepine 1-oxide (270 mg, 1.5 mmol) in n-butanol (10 mL) was heated at 160° C. for 30 minutes. After the resulting mixture was concentrated in vacuo, the residue was purified by preparative HPLC to afford the pure product as a solid. MS obsd. (ESI$^+$) [(M+H)$^+$] 424, $^1$H NMR (400 MHz, CD$_3$OD) δ ppm 8.01 (s, 1 H), 7.83-7.79 (m, 2 H), 7.66-7.52 (m, 4 H), 5.45-5.41 (d, 1 H), 5.10 (brs, 1 H), 4.80-4.72 (m, 6 H), 4.39 (s, 2 H), 3.51 (s, 2 H), 2.45 (s, 3 H).

Example 55-2

N-{[3-(Benzylamino)oxetan-3-yl]methyl}-6-methyl-2-(1-oxido-2,3-dihydro-1,4-benzothiazepin-4(5H)-yl)quinazolin-4-amine

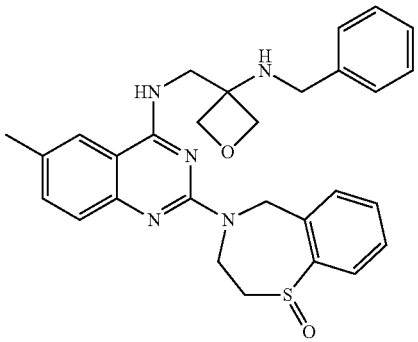 [SMILES: Cc1ccc2nc(N3CCS(=O)c4ccccc4C3)nc(NCC3(NCc4ccccc4)COC3)c2c1]

The title compound was prepared in analogy to Example 55-1 in Scheme 23 by using 2,4-dichloro-6-methylquinazoline, 3-(aminomethyl)-N-benzyloxetan-3-amine and 2,3,4,5-tetrahydro-1,4-benzothiazepine 1-oxide. MS obsd. (ESI$^+$) [(M+H)$^+$] 514, $^1$H NMR (400 MHz, CD$_3$OD) δ ppm 8.06 (s, 1 H), 7.81-7.77 (m, 2 H), 7.66-7.56 (m, 4 H), 7.47-7.45 (m, 2 H), 7.31-7.29 (m, 3 H), 5.45-5.35 (d, 1 H), 5.10 (brs, 1 H), 4.82-4.80 (m, 6 H), 4.71-4.69 (m, 2 H), 4.16 (s, 2 H), 3.51 (m, 2 H), 2.46 (s, 3 H).

Example 55-3

2-Fluoro-N-[6-methyl-2-(1-oxido-2,3-dihydro-1,4-benzothiazepin-4(5H)-yl)quinazolin-4-yl]propane-1,3-diamine

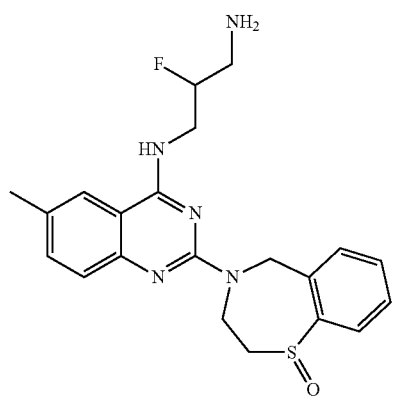 [SMILES: Cc1ccc2nc(N3CCS(=O)c4ccccc4C3)nc(NCC(F)CN)c2c1]

The title compound was prepared in analogy to Example 55-1 in Scheme 23 by using 2,4-dichloro-6-methylquinazoline, 2-fluoropropane-1,3-diamine and 2,3,4,5-tetrahydro-1,4-benzothiazepine 1-oxide. MS obsd. (ESI$^+$) [(M+H)$^+$] 414, $^1$H NMR (400 MHz, CD$_3$OD) δ ppm (d, J=7.6 Hz, 1 H), 7.79 (s, 1 H), 7.70-7.20 (m, 6 H), 5.56 (m, 1 H), 4.85-4.55 (m, 3 H), 4.48-4.32 (brs, 1 H), 3.91-3.71 (brs, 2 H), 3.40-3.11 (m, 2 H), 2.93-2.72 (m, 2 H), 2.24 (s, 3 H), 1.68 (s, 2 H).

Example 55-4

N-[2-(2,3-Dihydro-1,4-benzothiazepin-4(5H)-yl)-6-methylquinazolin-4-yl]-2,2-difluoropropane-1,3-diamine

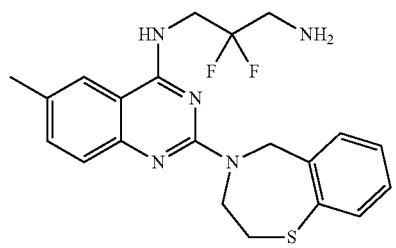 [SMILES: Cc1ccc2nc(N3CCSc4ccccc4C3)nc(NCC(F)(F)CN)c2c1]

The title compound was prepared in analogy to Example 55-1 in Scheme 23 by using 2,4-dichloro-6-methylquinazoline, 2,2-difluoropropane-1,3-diamine and 2,3,4,5-tetrahydro-1,4-benzothiazepine. MS obsd. (ESI$^+$) [(M+H)$^+$] 416, $^1$H NMR (400 MHz, CD$_3$OD) δ ppm 7.96 (s, 1 H), 7.80-7.68 (m, 1 H), 7.60-7.58 (m, 2 H), 7.51-7.49 (m, 1 H), 7.30-7.27 (t, 1 H), 7.24-7.20 (t, 1 H), 5.15 (s, 2 H), 4.37-4.31 (m, 4 H), 3.51-3.49 (m, 4 H), 3.14 (s, 2 H), 2.45 (s, 3 H).

Example 56-1

N-{[3-(Aminomethyl)oxetan-3-yl]methyl}-2-(1,1-dioxido-2,3-dihydro-1,4-benzothiazepin-4(5H)-yl)-6-methylquinazolin-4-amine

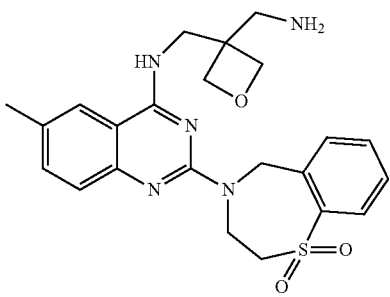 [SMILES: Cc1ccc2nc(N3CCS(=O)(=O)c4ccccc4C3)nc(NCC3(CN)COC3)c2c1]

N-{[3-(Aminomethyl)oxetan-3-yl]methyl}-2-chloro-6-methylquinazolin-4-amine

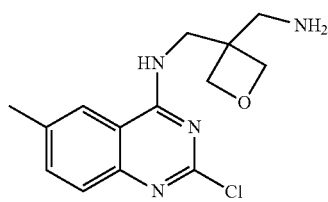 [SMILES: Cc1ccc2nc(Cl)nc(NCC3(CN)COC3)c2c1]

To a mixture of oxetane-3,3-diyldimethanamine (1.16 g, 10.0 mmol) and triethylamine (1.4 mL, 10 mol) in dichloromethane (15 mL) was added dropwise of a solution of 2,4-dichloro-6-methylquinazoline (500 mg, 2.36 mmol) in dichloromethane (5 mL). After being stirred at room temperature overnight, the resulting mixture was diluted with water (50 mL), and extracted with dichloromethane. The organic layer was washed with brine, dried over anhydrous sodium sulfate, and concentrated in vacuo. The residue was purified by flash column chromatography (eluting with 10% methanol in dichloromethane) to afford 300 mg of the desired product as a white solid.

N-{[3-(Aminomethyl)oxetan-3-yl]methyl}-2-(1,1-dioxido-2,3-dihydro-1,4-benzothiazepin-4(5H)-yl)-6-methylquinazolin-4-amine

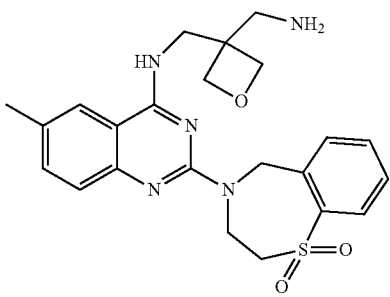 [SMILES: Cc1ccc2nc(N3CCS(=O)(=O)c4ccccc4C3)nc(NCC3(CN)COC3)c2c1]

The title compound was prepared in analogy to Example 55-1 in Scheme 23 by using N-{[3-(aminomethyl)oxetan-3-yl]methyl}-2-chloro-6-methylquinazolin-4-amine and 2,3,4,5-tetrahydro-1,4-benzothiazepine 1,2-dioxide. MS obsd. (ESI$^+$) [(M+H)$^+$] 454, $^1$H NMR (400 MHz, CD$_3$OD) δ ppm 7.99 (dd, J=7.83, 1.26 Hz, 1 H), 7.88 (d, J=7.33 Hz, 1 H), 7.67 (s, 1 H), 7.62 (td, J=7.58, 1.26 Hz, 1 H), 7.50-7.37 (m, 2 H), 7.37-7.30 (m, 1 H), 5.21 (brs, 2 H), 4.66 (d, J=6.06 Hz, 2 H), 4.57 (d, J=6.06 Hz, 1 H), 4.51 (d, J=6.32 Hz, 2 H), 4.06 (s, 2 H), 3.53 (t, J=5.05 Hz, 2 H), 3.05 (s, 2 H), 2.40 (s, 3 H).

Example 56-2

2,2-Difluoro-N-[6-methyl-2-(1-oxido-2,3-dihydro-1,4-benzothiazepin-4(5H)-yl)quinazolin-4-yl]propane-1,3-diamine

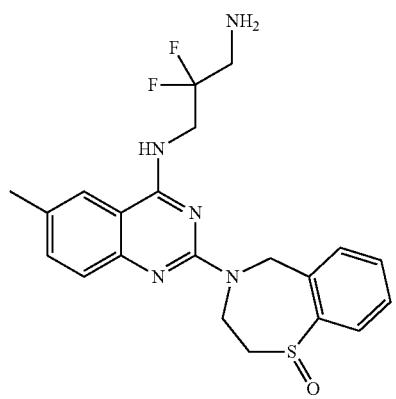 [SMILES: Cc1ccc2nc(N3CCS(=O)c4ccccc4C3)nc(NCC(F)(F)CN)c2c1]

The title compound was prepared in analogy to Example 56-1 in Scheme 23 by using 2,4-dichloro-6-methylquinazoline, 2,2-difluoropropane-1,3-diamine and 2,3,4,5-tetrahydro-1,4-benzothiazepine 1-oxide. MS obsd. (ESI$^+$) [(M+H)$^+$] 432, $^1$H NMR (400 MHz, CD$_3$OD) δ ppm 7.98 (s, 1 H), 7.82-7.80 (d, 1 H), 7.74-7.69 (m, 2 H), 7.63-7.53 (m, 3 H), 5.40 (d, 1 H), 5.10 (m, 1 H), 4.75 (m, 1 H), 4.60-4.33 (m, 3 H), 3.63 (m, 4 H), 2.45 (s, 3 H).

Example 56-3

N-{[3-(aminomethyl)oxetan-3-yl]methyl}-6-chloro-2-(1,1-dioxido-2,3-dihydro-1,4-benzothiazepin-4(5H)-yl)quinazolin-4-amine

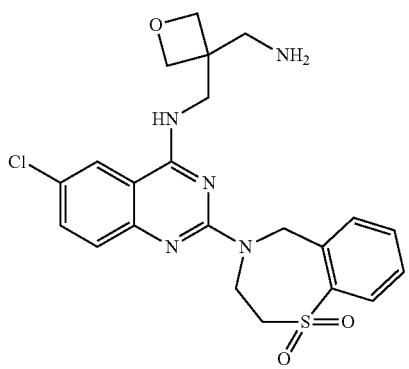 [SMILES: NCC1(CNc2nc(N3CCS(=O)(=O)c4ccccc4C3)nc3ccc(Cl)cc23)COC1]

The title compound was prepared in analogy to Example 56-1 in Scheme 23 by using 2,4,6-trichloroquinazoline, oxetane-3,3-diyldimethanamine and 2,3,4,5-tetrahydro-1,4-benzothiazepine 1,1-dioxide. MS obsd. (ESI⁺) [(M+H)⁺] 474, ¹H NMR (400 MHz, CD₃OD) δ ppm 7.99 (d, J=6.82 Hz, 1 H), 7.94 (d, J=2.53 Hz, 1 H), 7.88 (d, J=7.07 Hz, 1 H), 7.66-7.59 (m, 1 H), 7.52-7.42 (m, 2 H), 7.42-7.36 (m, 1 H), 5.21 (brs, 2 H), 4.69-4.56 (m, 5 H), 4.51 (d, J=6.32 Hz, 2 H), 4.05 (brs, 2 H), 3.52 (t, J=5.05 Hz, 2 H), 3.04 (s, 2 H).

Example 56-4

N-[2-(1,1-Dioxido-2,3-dihydro-1,4-benzothiazepin-4 (5H)-yl)-6-methylquinazolin-4-yl]-2,2-difluoropropane-1,3-diamine

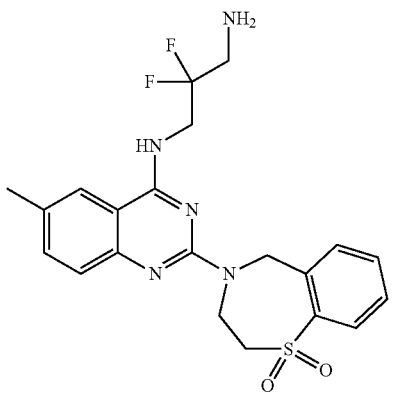 [SMILES: Cc1ccc2nc(N3CCS(=O)(=O)c4ccccc4C3)nc(NCC(F)(F)CN)c2c1]

The title compound was prepared in analogy to Example 56-1 in Scheme 23 by using 2,4-dichloro-6-methylquinazoline, 2,2-difluoropropane-1,3-diamine and 2,3,4,5-tetrahydro-1,4-benzothiazepine 1,1-dioxide. MS obsd. (ESI⁺) [(M+H)⁺] 448, ¹H NMR (400 MHz, CD₃OD) δ ppm 8.06-8.04 (dd, J=1.2, 7.6 Hz, 1 H), 7.99 (s, 1 H), 7.84-7.82 (d, J=7.6 Hz, 1 H), 7.72-7.67 (m, 2 H), 7.63-7.58 (m, 1 H), 7.56-7.54 (dd, J=1.2, 8 Hz, 1 H), 5.35 (s, 2 H), 4.54 (s, 2 H), 4.44-4.37 (t, J=14 Hz, 2 H), 3.72-3.64 (m, 4 H), 2.46 (s, 3 H).

Example 56-5

N-[2-(1,1-Dioxido-2,3-dihydro-1,4-benzothiazepin-4 (5H)-yl)-6-methylquinazolin-4-yl]-2-fluoropropane-1,3-diamine

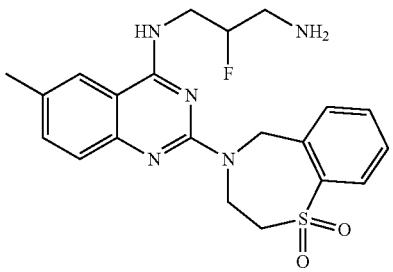 [SMILES: Cc1ccc2nc(N3CCS(=O)(=O)c4ccccc4C3)nc(NCC(F)CN)c2c1]

The title compound was prepared in analogy to Example 56-1 in Scheme 23 by using 2,4-dichloro-6-methylquinazoline, 2-fluoropropane-1,3-diamine and 2,3,4,5-tetrahydro-1,4-benzothiazepine 1,1-dioxide. MS obsd. (ESI⁺) [(M+H)⁺] 430, ¹H NMR (400 MHz, CD₃OD) δ ppm 8.06-8.04 (d, J=7.6 Hz, 1 H), 7.93 (s, 1 H), 7.81-7.79 (d, J=7.6 Hz, 1 H), 7.69-7.65 (t, J=8 Hz, 2 H), 7.60-7.53 (m, 2 H), 5.32 (s, 2 H), 5.17-5.03 (d, J=28 Hz, 1 H), 4.52 (s, 2 H), 4.20-3.92 (m, 2 H), 3.67 (s, 2 H), 3.47-3.36 (m, 2 H), 2.44 (s, 3 H).

Example 56-6

N-[6-Methyl-2-(1-oxido-2,3-dihydro-1,4-benzothiazepin-4(5H)-yl)quinazolin-4-yl]propane-1,3-diamine

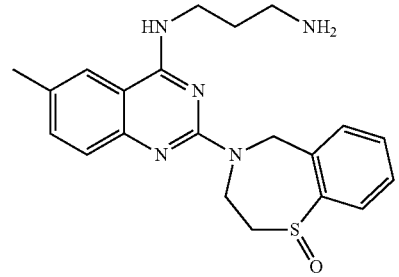 [SMILES: Cc1ccc2nc(N3CCS(=O)c4ccccc4C3)nc(NCCCN)c2c1]

The title compound was prepared in analogy to Example 56-1 in Scheme 23 by using 2,4-dichloro-6-methylquinazoline, propane-1,3-diamine and 2,3,4,5-tetrahydro-1,4-benzothiazepine 1-oxide. MS obsd. (ESI⁺) [(M+H)⁺] 396, ¹H NMR (400 MHz, CD₃OD) δ ppm 7.92 (s, 1 H), 7.81-7.79 (d, J=7.6 Hz, 1 H), 7.74-7.72 (d, J=7.6 Hz, 1 H), 7.64-7.50 (m, 4 H), 5.43-5.39 (d, J=15.6 Hz, 1 H), 5.12-5.05 (m, 1 H), 4.81-4.72 (m, 1 H), 4.53-4.46 (m, 2 H), 3.84-3.82 (m, 2 H), 3.52-3.48 (m, 2 H), 3.31-3.29 (m, 2 H), 2.43 (s, 3 H), 2.17-2.11 (m, 2 H).

Example 57-1

N-[(3-Aminooxetan-3-yl)methyl]-2-(2,3-dihydro-1, 4-benzothiazepin-4(5H)-yl)quinazolin-4-amine

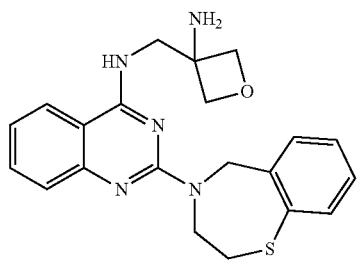 [SMILES: NC1(CNc2nc(N3CCSc4ccccc4C3)nc3ccccc23)COC1]

N-[(3-Aminooxetan-3-yl)methyl]-2-chloroquinazolin-4-amine

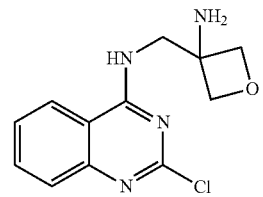 [SMILES: NC1(CNc2nc(Cl)nc3ccccc23)COC1]

To a solution of 2,4-dichloroquinazoline (1.0 g, 5.024 mmol) in methanol (15 mL) was added 3-(aminomethyl)

oxetan-3-amine (855 mg, 60%, 5.024 mmol) and triethylamine (101 mg, 1.005 mmol). After being stirred at room temperature overnight, the mixture was concentrated in vacuo. The residue was purified by flash column chromatography to afford 1.2 g of the desired product as a white solid (yield was 92%).

N-[(3-Aminooxetan-3-yl)methyl]-2-(2,3-dihydro-1,4-benzothiazepin-4(5H)-yl)quinazolin-4-amine

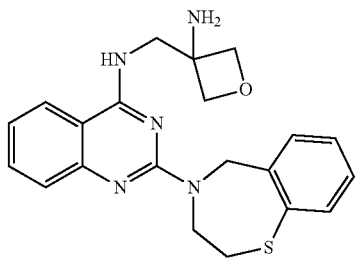 [SMILES: NC1(CNc2nc(N3CCSc4ccccc4C3)nc3ccccc23)COC1]

To a solution of N-[(3-aminooxetan-3-yl)methyl]-2-chloroquinazolin-4-amine (200 mg, 0.756 mmol) in N,N-dimethylformamide (4 mL) was added 2,3,4,5-tetrahydro-1,4-benzothiazepine (125 mg, 0.756 mmol) and triethylamine (230 mg, 2.268 mmol). After being heated at 130° C. for 4 hours under microwave irradiation, the reaction mixture was poured into water and extracted with ethyl acetate. The organic layer was dried with sodium sulfate, and concentrated in vacuo. The residue was purified by preparative HPLC to afford 42 mg of the desired product as a white solid (yield was 14%). MS obsd. (ESI$^+$) [(M+H)$^+$] 394, $^1$H NMR (400 MHz, CD$_3$OD) δ ppm 7.75-7.73 (t, J=6.4, 1.2 Hz, 1 H), 7.56-7.53 (m, 1 H), 7.52-7.47 (m, 2 H), 7.43-7.41 (d, J=8.0 Hz, 1 H), 7.24-7.20 (m, 1 H), 7.15-7.08 (m, 2 H), 5.06 (s, 2 H), 4.69-4.67 (d, J=6.8 Hz, 2 H), 4.55-4.53 (d, J=6.4 Hz, 2 H), 4.42 (s, 2 H), 4.09 (s, 2 H), 2.97-2.95 (t, J=4.8, 4.4 Hz, 2 H).

Example 57-2

N-[(3-Aminooxetan-3-yl)methyl]-2-(1-oxido-2,3-dihydro-1,4-benzothiazepin-4(5H)-yl)quinazolin-4-amine

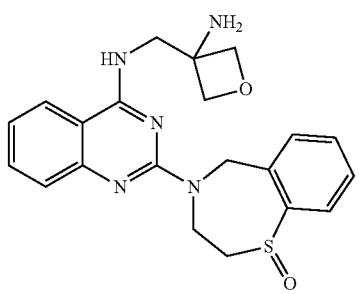 [SMILES: NC1(CNc2nc(N3CCS(=O)c4ccccc4C3)nc3ccccc23)COC1]

The title compound was prepared in analogy to Example 57-1 in Scheme 23 by using 2,4-dichloroquinazoline, 3-(aminomethyl)oxetan-3-amine and 2,3,4,5-tetrahydro-1,4-benzothiazepine 1-oxide. MS obsd. (ESI$^+$) [(M+H)$^+$] 410, $^1$H NMR (400 MHz, CD$_3$OD) δ ppm 7.91-7.90 (t, J=7.2, 0.8 Hz, 1 H), 7.81-7.74 (m, 2 H), 7.58-7.54 (m, 1 H), 7.51-7.43 (m, 3 H), 7.16-7.12 (m, 1 H), 5.32-5.28 (d, J=15.2 Hz, 2 H), 4.68-4.53 (m, 6 H), 4.10 (s, 2 H), 3.37-3.34 (m, 2 H).

Example 57-3

N-[(3-Aminooxetan-3-yl)methyl]-2-(1,1-dioxido-2,3-dihydro-1,4-benzothiazepin-4(5H)-yl)quinazolin-4-amine

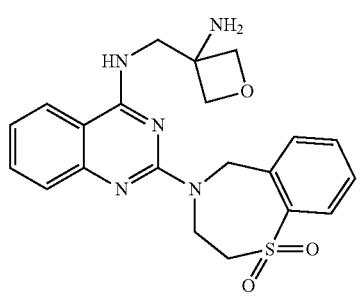 [SMILES: NC1(CNc2nc(N3CCS(=O)(=O)c4ccccc4C3)nc3ccccc23)COC1]

The title compound was prepared in analogy to Example 57-1 in Scheme 23 by using 2,4-dichloroquinazoline, 3-(aminomethyl)oxetan-3-amine and 2,3,4,5-tetrahydro-1,4-benzothiazepine 1,1-dioxide. MS obsd. (ESI$^+$) [(M+H)$^+$] 426, $^1$H NMR (400 MHz, CD$_3$OD) δ ppm 7.98-7.93 (m, 1 H), 7.91-7.88 (m, 2 H), 7.64-7.60 (m, 1 H), 7.57-7.51 (m, 1 H), 7.48-7.41 (m, 2 H), 7.15-7.11 (m, 1 H), 5.24 (s, 2 H), 4.67-4.54 (m, 6 H), 4.09 (s, 2 H), 3.55-3.50 (m, 2 H).

Example 57-4

N-[(3-Aminooxetan-3-yl)methyl]-6-chloro-2-(2,3-dihydro-1,4-benzothiazepin-4(5H)-yl)quinazolin-4-amine

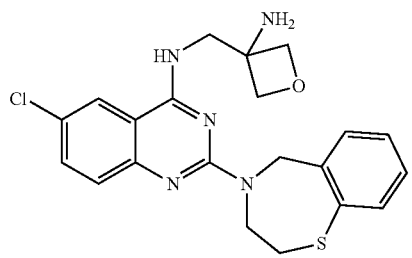 [SMILES: NC1(CNc2nc(N3CCSc4ccccc4C3)nc3ccc(Cl)cc23)COC1]

The title compound was prepared in analogy to Example 57-1 in Scheme 23 by using 2,4,6-trichloroquinazoline, 3-(aminomethyl)oxetan-3-amine and 2,3,4,5-tetrahydro-1,4-benzothiazepine. MS obsd. (ESI$^+$) [(M+H)$^+$] 428, $^1$H NMR (400 MHz, DMSO-d6) δ ppm 8.18 (s, 1 H), 7.97 (s, 1 H), 7.70 (s, 1 H), 7.51-7.44 (m, 2 H), 7.27-7.21 (m, 2 H), 7.16-7.12 (t, J=7.2 Hz, 1 H), 4.93 (s, 2 H), 4.50-4.35 (m, 5 H), 3.97-3.80 (m, 2 H), 2.96-2.87 (m, 2 H), 2.69-2.67 (m, 1 H), 2.35-2.33 (m, 1 H), 2.10 (s, 2 H).

Example 57-5

N-[(3-Aminooxetan-3-yl)methyl]-6-chloro-2-(1-oxido-2,3-dihydro-1,4-benzothiazepin-4(5H)-yl)quinazolin-4-amine

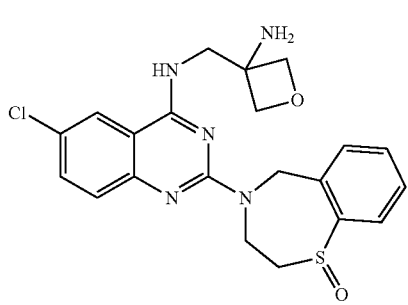 [SMILES: NC1(CNc2nc(N3CCS(=O)c4ccccc4C3)nc3ccc(Cl)cc23)COC1]

The title compound was prepared in analogy to Example 57-1 in Scheme 23 by using 2,4,6-trichloroquinazoline, 3-(aminomethyl)oxetan-3-amine and 2,3,4,5-tetrahydro-1,4-benzothiazepine 1-oxide. MS obsd. (ESI$^+$) [(M+H)$^+$] 444, $^1$H NMR (400 MHz, CD$_3$OD) δ ppm 8.57 (s, 1 H), 8.01-7.73 (m, 2 H), 7.52-7.40 (m, 4 H), 5.31-5.28 (d, J=15.2 Hz, 1 H), 4.66-4.53 (m, 6 H), 4.08 (s, 2 H), 3.51-3.50 (m, 2 H), 1.36-1.31 (m, 1 H).

Example 57-6

N-[(3-Aminooxetan-3-yl)methyl]-6-chloro-2-(1,1-dioxido-2,3-dihydro-1,4-benzothiazepin-4(5H)-yl)quinazolin-4-amine

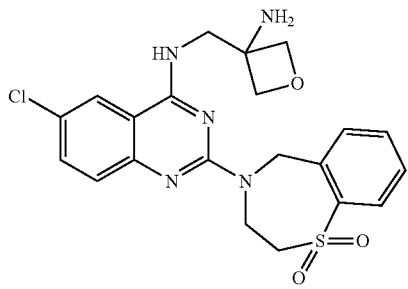 [SMILES: NC1(CNc2nc(N3CCS(=O)(=O)c4ccccc4C3)nc3ccc(Cl)cc23)COC1]

The title compound was prepared in analogy to Example 57-1 in Scheme 23 by using 2,4,6-trichloroquinazoline, 3-(aminomethyl)oxetan-3-amine and 2,3,4,5-tetrahydro-1,4-benzothiazepine 1,1-dioxide. MS obsd. (ESI$^+$) [(M+H)$^+$] 460, $^1$H NMR (400 MHz, CD$_3$OD) δ ppm 8.00-7.98 (t, J=2.0, 4.8 Hz, 2 H), 7.91-7.89 (d, J=7.2 Hz, 1 H), 7.64-7.60 (t, J=7.2 Hz, 1 H), 7.51-7.44 (m, 2 H), 7.40-7.38 (d, J=9.2 Hz, 1 H), 5.22 (s, 2 H), 4.65-4.62 (t, J=6.4, 5.6 Hz, 4 H), 4.56-4.54 (d, J=6.4 Hz, 2 H), 4.08 (s, 2 H), 3.54-3.51 (t, J=5.2, 4.8 Hz, 2 H).

Example 57-7

2-{[2-(1,1-Dioxido-2,3-dihydro-1,4-benzothiazepin-4(5H)-yl)-6-methylquinazolin-4-yl]amino}ethanol

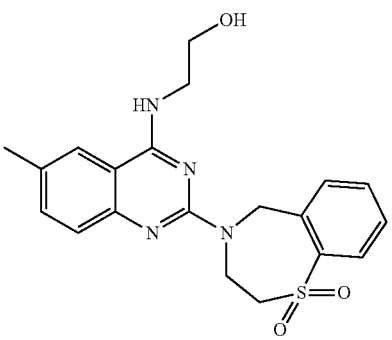 [SMILES: Cc1ccc2nc(N3CCS(=O)(=O)c4ccccc4C3)nc(NCCO)c2c1]

The title compound was prepared in analogy to Example 57-1 in Scheme 23 by using 2,4-diichloro-6-methylquinazoline, 2-aminoethanol and 2,3,4,5-tetrahydro-1,4-benzothiazepine 1,1-dioxide. MS obsd. (ESI$^+$) [(M+H)$^+$] 410, $^1$HNMR (400 MHz, CD$_3$OD) δ ppm 7.98 (dd, J=1.2, 7.6 Hz, 1 H), 7.83 (d, J=6.8 Hz, 1 H), 7.63-7.59 (m, 2 H), 7.44 (td, J=0.8, 7.6 Hz, 1 H), 7.38 (dd, J=1.6, 8.4 Hz, 1 H), 7.31 (d, J=8.4 Hz, 1 H), 5.20 (s, 2 H), 4.58 (brs, 2 H), 3.82-3.78 (m, 4 H), 3.53 (t, J=5.2 Hz, 2 H), 2.39 (s, 3 H).

Example 58

2-(2,3-Dihydro-1,4-benzothiazepin-4(5H)-yl)-6-methylquinazolin-4-amine

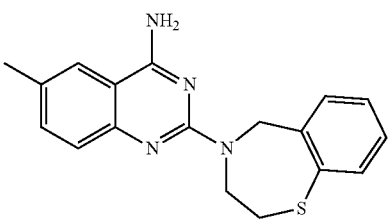 [SMILES: Cc1ccc2nc(N3CCSc4ccccc4C3)nc(N)c2c1]

2-Chloro-6-methylquinazolin-4-amine

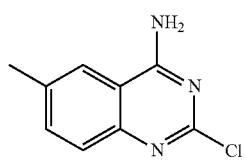

A mixture of 2,4-dichloro-6-methylquinazoline (500 mg, 2.348 mmol) and a solution of ammonia in tetrahydrofuran (20 mL, 3.0 M) was stirred in an ice-bath for 2 hours. The resulting mixture was concentrated in vauco to afford 454 mg of the crude product as a white solid.

2-(2,3-Dihydro-1,4-benzothiazepin-4(5H)-yl)-6-methylquinazolin-4-amine

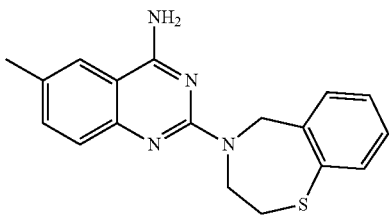 [SMILES: Cc1ccc2nc(N3CCSc4ccccc4C3)nc(N)c2c1]

To a solution of 2-chloro-6-methylquinazolin-4-amine (454 mg, 2.345 mmol) in n-butanol (5 mL) was added 2,3,4,5-tetrahydro-1,4-benzothiazepine (388 mg, 2.345 mmol). After being heated at 150° C. for 1.5 hours under microwave irradiation, the reaction mixture was filtered and the collected solid was washed with ether to afford 756 mg of the product as a white solid. MS obsd. (ESI$^+$) [(M+H)$^+$] 323, $^1$H NMR (400 MHz, DMSO-d6) δ ppm 7.92 (s, 1 H), 7.83-7.81 (d, J=8.0 Hz, 1 H), 7.62-7.60 (d, J=8.0 Hz, 1 H), 7.53-7.49 (m, 2 H), 7.29-7.25 (m, 1 H), 7.22-7.19 (m, 1 H), 4.98 (s, 2 H), 4.25 (s, 2 H), 2.98 (s, 2 H), 2.35 (s, 3 H).

Example 59

2-(1,1-Dioxido-2,3-dihydro-1,4-benzothiazepin-4(5H)-yl)-6-methylquinazolin-4-amine

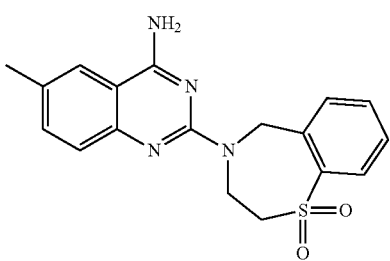 [SMILES: Cc1ccc2nc(N3CCS(=O)(=O)c4ccccc4C3)nc(N)c2c1]

To a solution of oxone (670 mg, 1.117 mmol) in water (2.5 mL), which was cooled below 0° C. in an ice-bath, was added a solution of 2-(2,3-dihydro-1,4-benzothiazepin-4(5H)-yl)-6-methylquinazolin-4-amine (300 mg, 0.930 mmol) in methanol (15 mL) and tetrahydrofuran (3 mL) dropwise. The resulting mixture was stirred below 0° C. for 2 hours. The formed precipitate was collected by filtration, washed with water and dried in vacuo to afford the desired product as a white solid. MS obsd. (ESI$^+$) [(M+H)$^+$] 355, $^1$H NMR (400 MHz, DMSO-d6) δ ppm 7.91-7.86 (m, 2 H), 7.77 (s, 1 H), 7.64-7.60 (t, J=16.0 Hz, 1 H), 7.51-7.48 (m, 2 H), 7.37-7.35 (d, J=8.0 Hz, 1 H), 5.06 (s, 2 H), 4.37 (s, 2 H), 3.59 (s, 2 H), 2.31 (s, 3 H).

Example 60

N$^-$1$^-$-[2-(1,1-Dioxido-2,3-dihydro-1,4-benzothiazepin-4(5H)-yl)-6-methylquinazolin-4-yl]-2-methylpropane-1,2-diamine

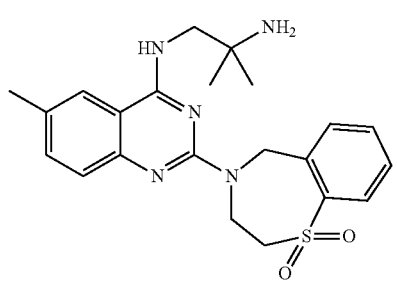 [SMILES: Cc1ccc2nc(N3CCS(=O)(=O)c4ccccc4C3)nc(NCC(C)(C)N)c2c1]

N$^-$1$^-$-(2-Chloro-6-methylquinazolin-4-yl)-2-methylpropane-1,2-diamine

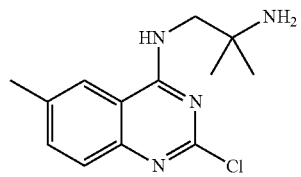 [SMILES: Cc1ccc2nc(Cl)nc(NCC(C)(C)N)c2c1]

A solution of 2,4-dichloro-6-methylquinazoline (500 mg, 2.35 mmol) and 2-methylpropane-1,2-diamine (365 μL, 3.52 mmol) in methanol (10 mL) was stirred at room temperature for 1 hour. The reaction mixture was diluted with ethyl acetate (30 mL) and stirred for 30 minutes. The formed solid was collected by filtration and dried in vacuo to afford 500 mg of the desired product as a white solid (yield was 80.6%).

N$^-$1$^-$-[2-(1,1-Dioxido-2,3-dihydro-1,4-benzothiazepin-4(5H)-yl)-6-methylquinazolin-4-yl]-2-methylpropane-1,2-diamine

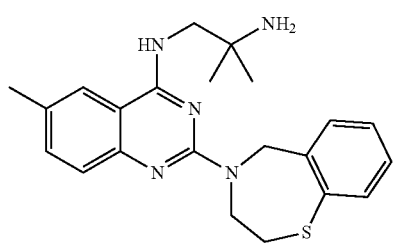 [SMILES: Cc1ccc2nc(N3CCSc4ccccc4C3)nc(NCC(C)(C)N)c2c1]

A mixture of N$^-$1$^-$-(2-chloro-6-methylquinazolin-4-yl)-2-methylpropane-1,2-diamine (300 mg, 1.14 mmol) and 2,3,4,5-tetrahydro-1,4-benzothiazepine (226 mg, 1.25 mmol) in n-butanol (3 mL) was heated in the microwave at 160° C. for 2 hours. The resulting mixture was concentrated in vacuo. The residue was purified by flash column chromatography (eluting with 0-10% methanol in dichloromethane) to afford 300 mg of the desired product as a white solid (yield was 67%).

375

N~1~-[2-(1,1-Dioxido-2,3-dihydro-1,4-benzothiaz-epin-4(5H)-yl)-6-methylquinazolin-4-yl]-2-methyl-propane-1,2-diamine

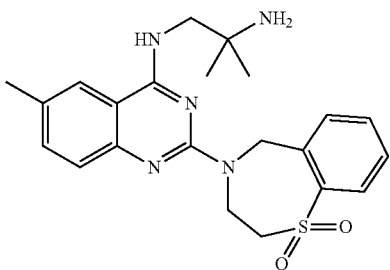 [SMILES: Cc1ccc2nc(N3CCS(=O)(=O)c4ccccc4C3)nc(NCC(C)(C)N)c2c1]

To a stirred solution of N~1~-[2-(1,1-dioxido-2,3-dihydro-1,4-benzothiazepin-4(5H)-yl)-6-methylquinazolin-4-yl]-2-methylpropane-1,2-diamine (240 mg, 0.61 mmol) in dichloromethane (15 mL) was added 3-chloroperoxybenzoic acid (263 mg, 1.53 mmol) at 0° C. After being stirred at 0° C. for 20 minutes, the reaction mixture was washed with a saturated aqueous solution of sodium carbonate and brine, dried over sodium sulfate, and concentrated in vacuo. The residue was purified by flash column chromatography (eluting with 10% methanol in dichloromethane) to afford 100 mg of the desired product as a white solid (yield was 38.6%). MS obsd. (ESI⁺) [(M+H)⁺] 426, ¹H NMR (400 MHz, CD₃OD) δ ppm 7.99 (d, J=1.9 Hz, 1 H), 7.86 (d, J=1.8 Hz, 1 H), 7.73 (s, 1 H), 7.60 (t, J=2.7 Hz, 1 H), 7.47-7.40 (m, J=6.9 Hz, 2 H), 7.36-7.33 (m, 1 H), 5.20 (s, 2 H), 4.58 (brs, 2 H), 3.72 (s, 2 H), 3.52 (m, 2 H), 2.41 (s, 3 H), 1.30 (s, 6 H).

Example 61-1

N-[(3-Aminooxetan-3-yl)methyl]-2-(1,1-dioxido-2,3-dihydro-1,4-benzothiazepin-4(5H)-yl)-6-methylquinazolin-4-amine

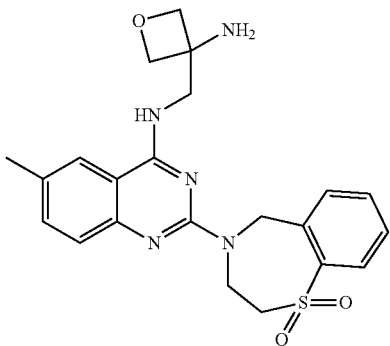 [SMILES: Cc1ccc2nc(N3CCS(=O)(=O)c4ccccc4C3)nc(NCC3(N)COC3)c2c1]

376

N-{[3-(Dibenzylamino)oxetan-3-yl]methyl}-2-(2,3-dihydro-1,4-benzothiazepin-4(5H)-yl)-6-methylquinazolin-4-amine

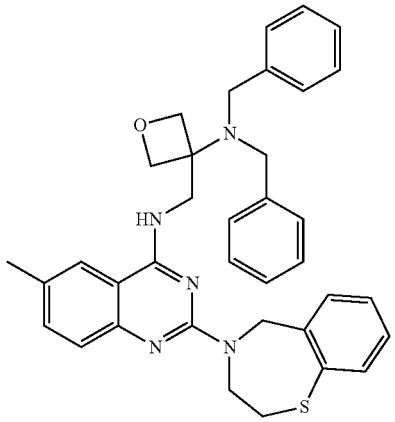 [SMILES: Cc1ccc2nc(N3CCSc4ccccc4C3)nc(NCC3(N(Cc4ccccc4)Cc4ccccc4)COC3)c2c1]

A mixture of (2-chloro-6-methylquinazolin-4-yl)-[3-(dibenzylamino)oxetan-3-ylmethyl]-amine (2 g, 4.4 mmol, prepared in analogy to N-(3-aminooxetan-3-ylmethyl)-2-chloro-6-methylquinazolin-4-amine in Example 55-1), 2,3,4,5-tetrahydro-1,4-benzothiazepine (720 mg, 4.4 mmol), triethylamine (1.2 mL, 8.6 mmol) in N,N-dimethylformamide (20 mL) was heated with stirring in a 30 mL of microwave process vial for 2 hours at 150° C. The reaction mixture was diluted with ethyl acetate, washed with water and brine. The organic layer was dried over sodium sulfate, filtered and concentrated in vacuo. The residue was purified by column chromatography on silica gel to give 1.7 g of the product as a white solid.

N-{[3-(Dibenzylamino)oxetan-3-yl]methyl}-2-(1,1-dioxido-2,3-dihydro-1,4-benzothiazepin-4(5H)-yl)-6-methylquinazolin-4-amine

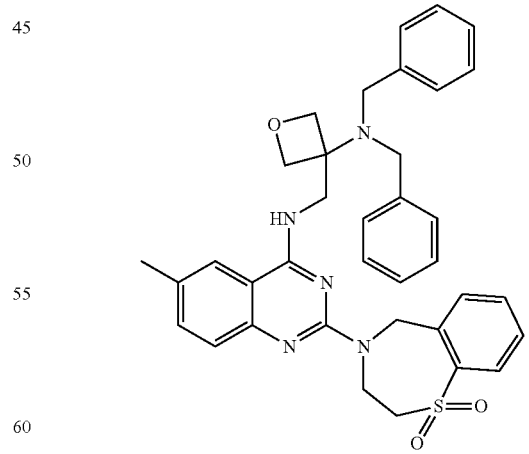

To a solution of N-{[3-(dibenzylamino)oxetan-3-yl]methyl}-2-(2,3-dihydro-1,4-benzothiazepin-4(5H)-yl)-6-methylquinazolin-4-amine (1.7 g, 2.89 mmol) in dichloromethane (30 mL) was added 3-chloroperbenzoic acid (75%, 1.33 g, 5.8 mmol) at 0° C. The resulting mixture was stirred for 1 hour whilst allowing the temperature to rise slowly to room temperature. The reaction mixture was then washed with a saturated aqueous solution of sodium carbonate, a saturated aqueous solution of sodium sulfite and brine. The organic layer was dried over sodium sulfate, filtered, and concentrated in vacuo. The residue was purified by column chromatography on silica gel to give 1.4 g of the product as a white solid.

N-[(3-Aminooxetan-3-yl)methyl]-2-(1,1-dioxido-2,3-dihydro-1,4-benzothiazepin-4(5H)-yl)-6-methylquinazolin-4-amine

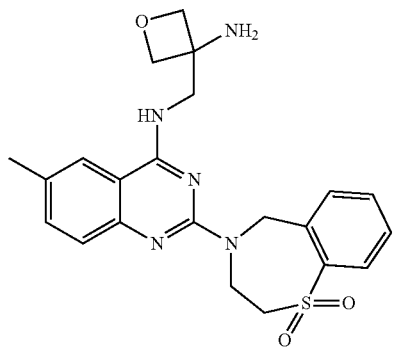 [SMILES: Cc1ccc2nc(N3CCS(=O)(=O)c4ccccc4C3)nc(NCC3(N)COC3)c2c1]

To a solution of N-{[3-(dibenzylamino)oxetan-3-yl]methyl}-2-(1,1-dioxido-2,3-dihydro-1,4-benzothiazepin-4(5H)-yl)-6-methylquinazolin-4-amine (1.4 g, 2.26 mmol) in methanol was added palladium hydroxide (20% on carbon, 200 mg). After being stirred at room temperature overnight under a hydrogen atmosphere, the resulting mixture was filtered. The filtrate was concentrated in vacuo. The residue was purified by column chromatography on silica gel to afford 300 mg of the product as off-white foam. MS obsd. (ESI$^+$) [(M+H)$^+$] 440, $^1$H NMR (400 MHz, CD$_3$OD) δ ppm 7.97 (d, J=7.6 Hz, 1 H), 7.86 (d, J=7.2 Hz, 1 H), 7.69 (s, 1 H), 7.58 (t, J=7.2 Hz, 1 H), 7.44-7.34 (m, 3 H), 5.21 (s, 2 H), 4.66 (d, J=6.4 Hz, 2 H), 4.60 (br.s., 2 H), 4.56 (d, J=6.4 Hz, 2 H), 4.10 (s, 2 H), 3.52 (t, J=5.2 Hz, 2 H), 2.39 (s, 3 H).

Example 61-2

N-[(1-Aminocyclobutyl)methyl]-2-(1,1-dioxido-2,3-dihydro-1,4-benzothiazepin-4(5H)-yl)-6-methylquinazolin-4-amine

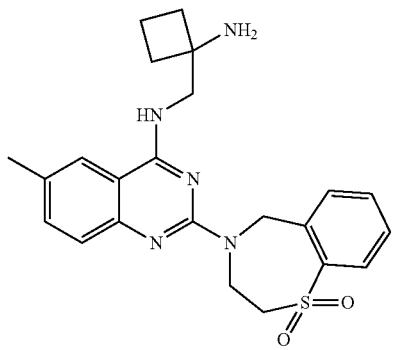 [SMILES: Cc1ccc2nc(N3CCS(=O)(=O)c4ccccc4C3)nc(NCC3(N)CCC3)c2c1]

N-[(1-Benzylamino-cyclobutyl)methyl]-2-(1,1-dioxido-2,3-dihydro-1,4-benzothiazepin-4 (5H)-yl)-6-methylquinazolin-4-amine

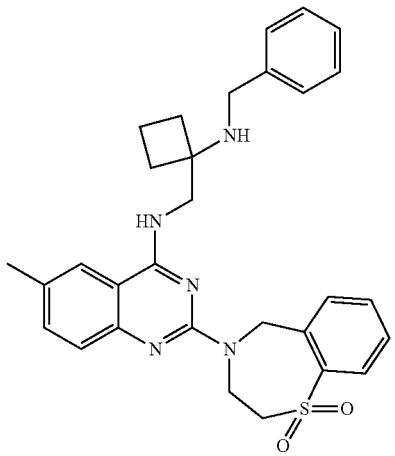 [SMILES: Cc1ccc2nc(N3CCS(=O)(=O)c4ccccc4C3)nc(NCC3(NCc4ccccc4)CCC3)c2c1]

The title compound was prepared in analogy to N-{[3-(dibenzylamino)oxetan-3-yl]methyl}-2-(1,1-dioxido-2,3-dihydro-1,4-benzothiazepin-4(5H)-yl)-6-methylquinazolin-4-amine in Example 61-1 in Scheme 24 by using 2,4-dichloro-6-methylquinazoline, 1-(aminomethyl)-N-dibenzylcyclobutanamine and 2,3,4,5-tetrahydro-1,4-benzothiazepine.

N-[(1-Aminocyclobutyl)methyl]-2-(1,1-dioxido-2,3-dihydro-1,4-benzothiazepin-4(5H)-yl)-6-methylquinazolin-4-amine

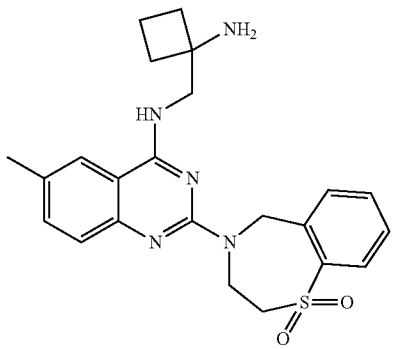 [SMILES: Cc1ccc2nc(N3CCS(=O)(=O)c4ccccc4C3)nc(NCC3(N)CCC3)c2c1]

A mixture of N-[(1-benzylamino-cyclobutyl)methyl]-2-(1,1-dioxido-2,3-dihydro-1,4-benzothiazepin-4(5H)-yl)-6-methylquinazolin-4-amine (220 mg, 0.417 mmol), 10% of palladium hydroxide on carbon (30 mg), and trifluoroacetic acid (160 μL) in methanol (20 mL) was stirred at room temperature for 24 hours under a hydrogen atmosphere. The resulting mixture was filtered, and the filtrate was adjusted to pH 8-9 by the addition of a solution of ammonia in methanol (7 M), and concentrated in vacuo. The residue was purified by preparative HPLC to give 105 mg of the product as a white solid. MS obsd. (ESI$^+$) [(M+H)$^+$] 438, $^1$H NMR (400 MHz, CD$_3$OD) δ ppm 7.98 (d, J=7.6 Hz, 1 H), 7.86 (d, J=7.6 Hz, 1 H), 7.73 (s, 1 H), 7.60 (t, J=7.6 Hz, 1 H), 7.47-7.32 (m, 3 H), 5.33 (s, 2 H), 4.58 (brs, 2 H), 3.84 (s, 2 H), 3.53 (t, J=4.8 Hz, 2 H), 2.41 (s, 3 H), 2.21 (m, 2 H), 2.04-1.97 (m, 2 H), 1.91-1.82 (m, 2 H).

Example 62-1

N-{[3-(Aminomethyl)oxetan-3-yl]methyl}-6-methyl-2-(1-oxido-2,3-dihydro-1,4-benzothiazepin-4(5H)-yl)quinazolin-4-amine

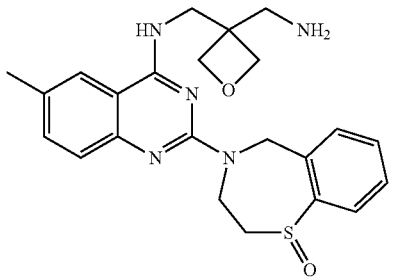 [SMILES: Cc1ccc2nc(N3CCS(=O)c4ccccc4C3)nc(NCC3(CN)COC3)c2c1]

2-Chloro-6-methylquinazolin-4(3H)-one

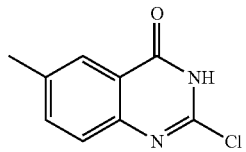

To a solution of 2,4-dichloro-6-methylquinazoline (2.13 g, 10 mmol) in tetrahydrofuran (20 mL) was added sodium hydroxide (2 N, 20 mL). After being stirred at room temperature for 4 hours, the reaction mixture was chilled and acidified to pH 5 with acetic acid. The formed solid was collected by filtration, washed with water, and dried in vacuo to afford 1.7 g of the desired product as a white solid (yield was 87.6%).

6-Methyl-2-(1-oxido-2,3-dihydro-1,4-benzothiazepin-4(5H)-yl)quinazolin-4(3H)-one

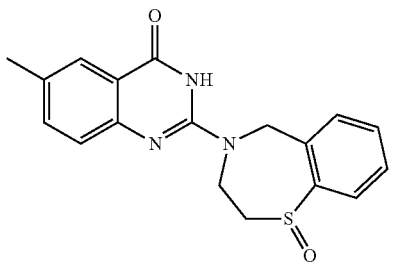 [SMILES: Cc1ccc2nc(N3CCS(=O)c4ccccc4C3)[nH]c(=O)c2c1]

To a stirred solution of 2-chloro-6-methylquinazolin-4 (3H)-one (15 g, 77.3 mmol) and 2,3,4,5-tetrahydro-1,4-benzothiazepine 1-oxide (16.8 g, 103 mmol) in toluene (200 mL) was added triethylamine (16.1 mL, 116 mmol). After being refluxed overnight, the reaction mixture was cooled to room temperature. The formed solid was collected by filtration, washed with ethanol (50 mL) and ethyl acetate (100 mL), and then dried in vacuo to afford 21.0 g of the desired product as a white solid (yield was 80%).

N-{[3-(Aminomethyl)oxetan-3-yl]methyl}-6-methyl-2-(1-oxido-2,3-dihydro-1,4-benzothiazepin-4(5H)-yl)quinazolin-4-amine

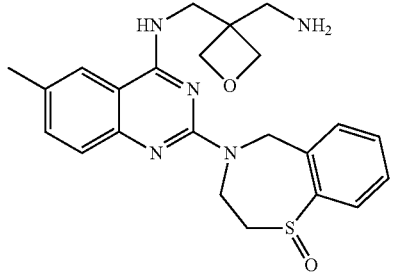 [SMILES: Cc1ccc2nc(N3CCS(=O)c4ccccc4C3)nc(NCC3(CN)COC3)c2c1]

To a solution of 6-methyl-2-(1-oxido-2,3-dihydro-1,4-benzothiazepin-4(5H)-yl)quinazolin-4(3H)-one (10 g, 29.5 mmol) and benzotriazol-1-yloxytris(dimethylamino)phosphonium hexafluorophosphate (16.9 g, 38.3 mmol) in N,N-dimethylformamide (140 mL) was added 1,8-diazabicyclo[5.4.0]undec-7-ene (6.7 g, 44.2 mmol) at room temperature. After being stirred for 10 minutes, (3-aminomethyl-oxetan-3-yl)-methylamine (5.1 g, 44.2 mmol) was added. The mixture was stirred for 4 hours at room temperature and diluted with water (150 mL). The separated aqueous layer was extracted with ethyl acetate (100 mL×6). The organic layers were combined and washed with brine, dried over sodium sulfate, and then concentrated in vacuo. The residue was purified by flash column chromatography (eluting with 10% methanol in dichloromethane) to afford 9.0 g of the impure product (purity was 90%). The impure product was purified by preparative HPLC to afford 6.0 g of the desired product as a white solid. MS obsd. (ESI$^+$) [(M+H)$^+$] 438, $^1$H NMR (400 MHz, CD$_3$OD) δ ppm 8.02 (s, 1 H), 7.82-7.79 (m, 2 H), 7.64 (d, J=1.6 Hz, 1 H), 7.60-7.57 (m, 3 H), 5.44 (d, 1 H), 5.13 (brs, 1 H), 4.77 (brs, 1 H), 4.66-4.59 (m, 4 H), 4.51 (brs, 1 H), 4.24 (s, 2 H), 3.55 (brs, 2 H), 3.44 (s, 2 H), 2.44 (s, 3 H).

Example 62-2 and Example 62-3

(−)-N-{[3-(Aminomethyl)oxetan-3-yl]methyl}-6-methyl-2-[(1-oxido-2,3-dihydro-1,4-benzothiazepin-4(5H)-yl]quinazolin-4-amine and (+)-N-{[3-(Aminomethyl)oxetan-3-yl]methyl}-6-methyl-2-[1-oxido-2,3-dihydro-1,4-benzothiazepin-4(5H)-yl]quinazolin-4-amine

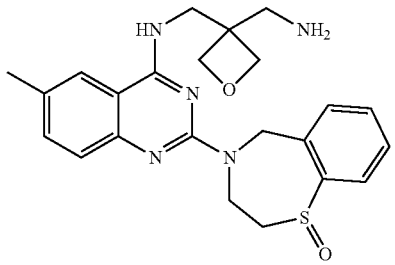

(−)

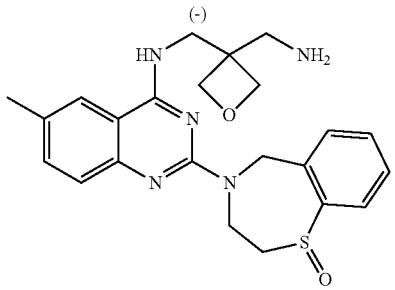

(+)

The chiral separation of Example 62-1 (column: IA; flow rate: 15 mL/min; gradient: 50% hexane in ethanol with 0.4% of triethylamine) affords (−)-N-{[3-(aminomethyl)oxetan-3-yl]methyl}-6-methyl-2-[1-oxido-2,3-dihydro-1,4-benzothiazepin-4(5H)-yl]quinazolin-4-amine, MS obsd. (ESI$^+$) [(M+H)$^+$] 438, and (+)-N-{[3-(aminomethyl)oxetan-3-yl]methyl}-6-methyl-2-[1-oxido-2,3-dihydro-1,4-benzothiazepin-4(5H)-yl]quinazolin-4-amine, MS obsd. (ESI$^+$) [(M+H)$^+$] 438.

Example 62-4 and Example 62-5

N$^4$~-[2-(1,1-Dioxido-2,3-dihydro-1,4-benzothiazepin-4(5H)-yl)-6-methylquinazolin-4-yl]-2-fluorobutane-1,4-diamine and N$^1$~-[2-(1,1-Dioxido-2,3-dihydro-1,4-benzothiazepin-4(5H)-yl)-6-methylquinazolin-4-yl]-2-fluorobutane-1,4-diamine

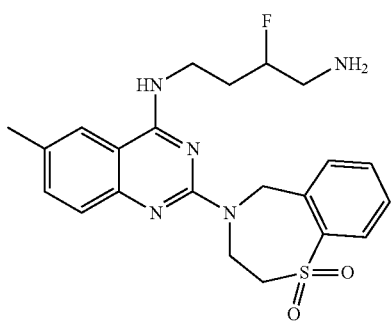

A

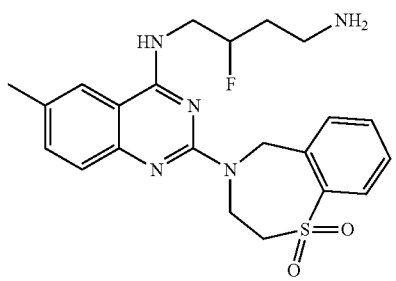

B

The title compound was prepared in analogy to Example 62-1 in Scheme 23 by using 2-chloro-6-methylquinazolin-4(3H)-one, 2,3,4,5-tetrahydro-1,4-benzothiazepine 1,1-dioxide and 2-fluorobutane-1,4-diamine. 8.65 mg of compound A and 3.54 mg of compound B were obtained.

A: MS obsd. (ESI$^+$) [(M+H)$^+$] 444, $^1$H NMR (400 MHz, CD$_3$OD) δ ppm 8.03-7.90 (d, J=3 Hz, 1 H), 7.65 (s, 1 H), 7.50-7.40 (t, 1 H), 7.40-7.30 (m, 3 H), 7.15 (s, 1 H), 5.95 (s, 1 H), 5.10 (s, 2 H), 4.75-4.50 (d, J=52 Hz, 2 H), 3.75 (s, 2 H), 3.40 (s, 2 H), 2.97-2.87 (m, 2 H), 2.34 (s, 3 H), 1.90 (s, 2 H).

B: MS obsd. (ESI$^+$) [(M+H)$^+$] 444, $^1$H NMR (400 MHz, CD$_3$OD) δ ppm 8.03-7.90 (d, J=4 Hz, 1 H), 7.70 (s, 1 H), 7.45-7.35 (t, 1 H), 7.33-7.25 (m, 3 H), 6.10 (s, 1 H), 5.15 (s, 2 H), 4.90-4.50 (m, 3 H), 4.00-3.65 (m, 2 H), 3.40 (s, 2 H), 2.95-2.70 (m, 2 H), 2.30 (s, 3 H), 2.11-1.65 (m, 2 H).

Example 62-6

N-{[3-(Aminomethyl)oxetan-3-yl]methyl}-2-(2,3-dihydro-1,4-benzothiazepin-4(5H)-yl)-6-methylquinazolin-4-amine

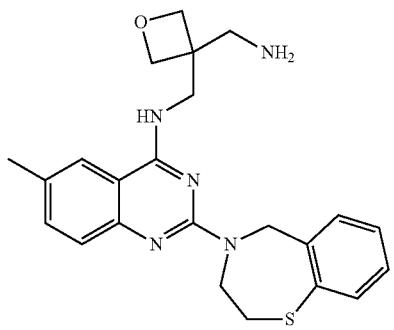 [SMILES: Cc1ccc2nc(N3CCSc4ccccc4C3)nc(NCC3(CN)COC3)c2c1]

The title compound was prepared in analogy to Example 62-1 in Scheme 23 by using 2-chloro-6-methylquinazolin-4(3H)-one, 2,3,4,5-tetrahydro-1,4-benzothiazepine and oxetane-3,3-diyldimethanamine. MS obsd. (ESI$^+$) [(M+H)$^+$] 422. $^1$H NMR (400 MHz, CD$_3$OD) δ ppm 7.66 (dd, J=1.6, 7.2 Hz, 1 H), 7.62 (s, 1 H), 7.44 (dd, J=1.2, 7.6 Hz, 1 H), 7.34-7.29 (m, 2 H), 7.18 (m, 1 H), 7.08 (m, 1 H), 4.99 (s, 2 H), 4.63 (d, J=6.4 Hz, 2 H), 4.45 (d, J=6.4 Hz, 2 H), 4.34 (s, 2 H), 4.02 (s, 2 H), 2.98 (s, 2 H), 2.90 (m, 2 H), 2.36 (s, 3 H).

Example 62-7 trans-4-Fluoro-1-[6-methyl-2-(1-oxido-2,3-dihydro-1,4-benzothiazepin-4(5H)-yl)quinazolin-4-yl]pyrrolidin-3-amine

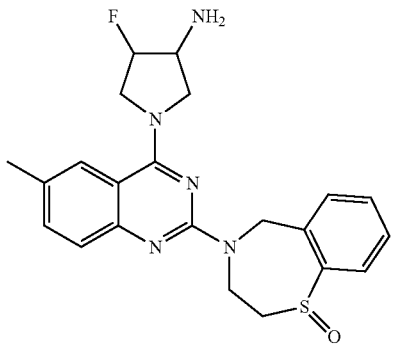 [SMILES: Cc1ccc2nc(N3CCS(=O)c4ccccc4C3)nc(N3CC(N)C(F)C3)c2c1]

The title compound was prepared in analogy to Example 62-1 in Scheme 23 by using 2-chloro-6-methylquinazolin-4(3H)-one, 2,3,4,5-tetrahydro-1,4-benzothiazepine 1-oxide and trans-4-fluoropyrrolidin-3-amine. MS obsd. (ESI$^+$) [(M+H)$^+$] 426. $^1$H NMR (400 MHz, CD$_3$OD) 7.82 (s, 1 H), 7.71 (d, J=6.8 Hz, 1 H), 7.42 (m, 4 H), 5.26 (d, J=15.2 Hz, 1 H), 5.07 (d, J=51.2 Hz, 1 H), 4.78 (brs, 1 H), 4.43 (m, 2 H), 4.29 (m, 1 H), 4.06 (t, J=11.2 Hz, 1 H), 3.86 (d, J=12 Hz, 1 H), 3.75 (m, 1 H), 3.40 (m, 2 H), 2.40 (s, 3 H).

Example 63-1

N-(2-{[2-(1,1-Dioxido-2,3-dihydro-1,4-benzothiazepin-4(5H)-yl)-6-methylquinolin-4-yl]amino}ethyl)acetamide

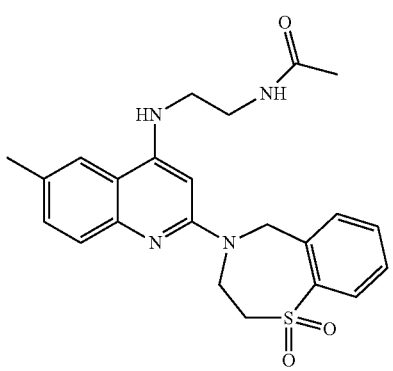 [SMILES: CC(=O)NCCNc1cc(N2CCS(=O)(=O)c3ccccc3C2)nc2ccc(C)cc12]

To a solution of N-[2-(1,1-dioxido-2,3-dihydro-1,4-benzothiazepin-4(5H)-yl)-6-methylquinolin-4-yl]ethane-1,2-diamine (39 mg, 0.1 mmol, prepared in analogy to Example 9-11) in dichloromethane (5 mL) was added acetic anhydride (12 mg, 0.12 mmol) at 0° C. The reaction mixture was stirred at room temperature for 2 hours and then concentrated in vacuo. The residue was diluted with a saturated aqueous solution of sodium bicarbonate (5 mL), and extracted with dichloromethane (10 mL×2). The combined organic layers were washed with brine (10 mL), dried over sodium sulfate, filtered and concentrated in vacuo. The residue was purified by flash column chromatography (eluting with 10% methanol in dichloromethane) to afford 21 mg of the desired product as a white solid (yield was 48%). MS obsd. (ESI$^+$) [(M+H)$^+$] 439, $^1$H NMR (400 MHz, CD$_3$OD) δ ppm 8.16 (s, 1 H), 7.95 (d, J=1.8 Hz, 2 H), 7.86 (d, J=1.9 Hz, 1 H), 7.62 (t, J=3.6 Hz, 2 H), 7.46 (t, J=3.8 Hz, 1 H), 7.31 (d, J=2.1 Hz, 1 H), 7.22 (d, J=2.1 Hz, 1 H), 6.84 (s, 1 H), 6.20 (s, 1 H), 5.10 (s, 2 H), 4.43 (brs, 2 H), 3.62 (s, 2 H), 3.32 (m, 4 H), 2.34 (s, 3 H), 1.89 (s, 3 H).

Example 63-2

N-{[3-({[2-(1,1-Dioxido-2,3-dihydro-1,4-benzothiazepin-4(5H)-yl)-6-methylquinolin-4-yl]amino}methyl)oxetan-3-yl]methyl}acetamide

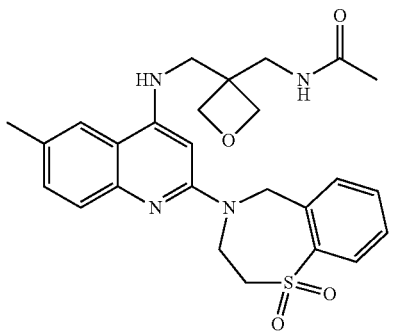 [SMILES: CC(=O)NCC1(CNc2cc(N3CCS(=O)(=O)c4ccccc4C3)nc3ccc(C)cc23)COC1]

The title compound was prepared in analogy to Example 63-1 in Scheme 25 by using N-{[3-(aminomethyl)oxetan-3-yl]methyl}-2-(1,1-dioxido-2,3-dihydro-1,4-benzothiazepin-4(5H)-yl)-6-methylquinolin-4-amine (prepared in analogy to Example 3-50) and acetic anhydride. MS obsd. (ESI$^+$) [(M+H)$^+$] 495, $^1$H NMR (400 MHz, CD$_3$OD) δ ppm 8.00 (d, J=7.6 Hz, 1 H), 7.89 (d, J=7.2 Hz, 1 H), 7.66 (t, 2 H), 7.46 (t, 2 H), 7.32-7.30 (m, 1 H), 6.22 (s, 1 H), 5.17 (s, 2 H), 4.56-4.51 (m, 6 H), 3.67 (d, 4 H), 3.60 (t, J=9.6 Hz, 2 H), 2.43 (s, 3 H), 2.06 (s, 3 H).

Example 63-3

N-(3-{[2-(1,1-Dioxido-2,3-dihydro-1,4-benzothiazepin-4(5H)-yl)-6-methylquinolin-4-yl]amino}propyl)acetamide

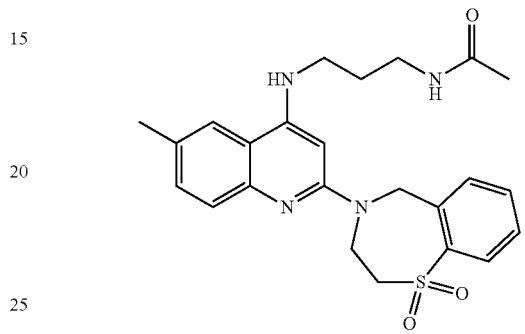

The title compound was prepared in analogy to Example 63-1 in Scheme 25 by using N-[2-(1,1-dioxido-2,3-dihydro-1,4-benzothiazepin-4(5H)-yl)-6-methylquinolin-4-yl]propane-1,3-diamine (prepared in analogy to Example 9-3) and acetic anhydride. MS obsd. (ESI$^+$) [(M+H)$^+$] 453, $^1$H NMR (400 MHz, CD$_3$OD) δ ppm 8.00-7.97 (m, 1 H), 7.81 (d, J=7.2 Hz, 1 H), 7.76-7.64 (m, 2 H), 7.46-7.42 (m, 2 H), 7.30-7.28 (m, 1 H), 5.99 (s, 1 H), 5.14 (s, 2 H), 4.54 (brs, 2 H), 3.58 (t, 2 H), 3.36 (m, 4 H), 2.42 (s, 3 H), 2.00 (s, 3 H), 1.94-1.87 (m, 2 H).

Example 63-4

N-[2-(1,1-Dioxido-2,3-dihydro-1,4-benzothiazepin-4(5H)-yl)-6-methylquinazolin-4-yl]acetamide

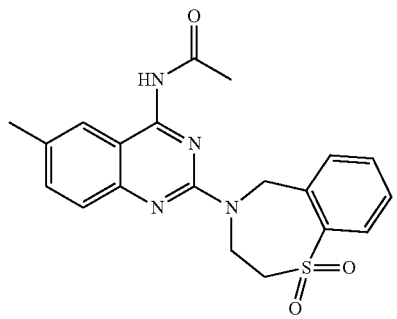 [SMILES: CC(=O)Nc1nc(N2CCS(=O)(=O)c3ccccc3C2)nc2ccc(C)cc12]

A mixture of 2-(1,1-dioxido-2,3-dihydro-1,4-benzothiazepin-4(5H)-yl)-6-methylquinazolin-4-amine (50 mg, 0.14 mmol, prepared in analogy to Example 59) and acetic anhydride (2 mL) was heated with stirring at 110° C. for 2 hours under nitrogen. The reaction mixture was diluted with ethyl acetate, washed with a saturated aqueous solution of sodium carbonate and brine, dried over sodium sulfate, filtered and concentrated in vacuo. The residue was purified by column chromatography on silica gel to give 30 mg of the product as a white powder. MS obsd. (ESI$^+$) [(M+H)$^+$] 397, $^1$H NMR (400 MHz, CD$_3$OD) δ ppm 7.87 (d, J=7.6 Hz, 1 H), 7.80 (s, 1 H), 7.56 (m, 3 H), 7.28 (m, 1 H), 7.21 (m, 1 H), 5.11 (s, 2 H), 4.48 (s, 2 H), 2.99 (s, 2 H), 2.47 (s, 6 H).

Example 64

1-[2-(1,1-Dioxido-2,3-dihydro-1,4-benzothiazepin-4 (5H)-yl)-6-methylquinolin-4-yl]-3-methylpyrrolidin-3-amine

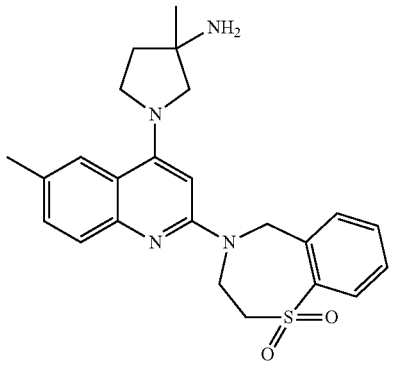 [SMILES: Cc1ccc2nc(N3CCS(=O)(=O)c4ccccc4C3)cc(N3CCC(C)(N)C3)c2c1]

N-{1-[2-(1,1-Dioxido-2,3-dihydro-1,4-benzothiazepin-4(5H)-yl)-6-methylquinolin-4-yl]-3-methylpyrrolidin-3-yl}acetamide

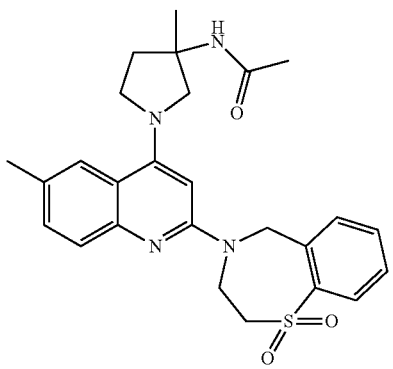 [SMILES: CC(=O)NC1(C)CCN(c2cc(N3CCS(=O)(=O)c4ccccc4C3)nc3ccc(C)cc23)C1]

The title compound was prepared in analogy to Example 3-1 in Scheme 26 by using 4-(4-chloro-6-methylquinolin-2-yl)-2-methyl-2,3,4,5-tetrahydro-1,4-benzothiazepine 1,1-dioxide (prepared in analogy to the one in Example 2-1) and N-(3-methylpyrrolidin-3-yl)acetamide.

1-[2-(1,1-Dioxido-2,3-dihydro-1,4-benzothiazepin-4 (5H)-yl)-6-methylquinolin-4-yl]-3-methylpyrrolidin-3-amine

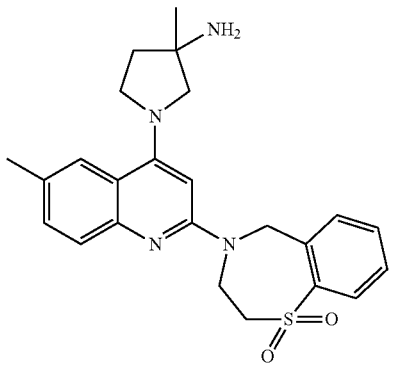 [SMILES: Cc1ccc2nc(N3CCS(=O)(=O)c4ccccc4C3)cc(N3CCC(C)(N)C3)c2c1]

A mixture of N-{1-[2-(1,1-dioxido-2,3-dihydro-1,4-benzothiazepin-4(5H)-yl)-6-methylquinolin-4-yl]-3-methylpyrrolidin-3-yl}acetamide (102 mg, 0.21 mmol) and hydrochloric acid (2 N, 120 mL) was heated with stirring at 100° C. for 16 hours. After being cooled to room temperature, the reaction mixture was adjusted to pH 9 with a saturated aqueous solution of potassium carbonate and exacted with dichloromethane (200 mL×3). The combined organic layers were dried over sodium sulfate, and concentrated in vacuo. The residue was purified by preparative HPLC to afford 2.6 mg of the product (yield was 2.8%). MS obsd. (ESI$^+$) [(M+H)$^+$] 437, $^1$H NMR (400 MHz, CD$_3$OD) δ ppm 8.10-8.08 (d, J=7.6 Hz, 1 H), 8.01 (s, 1 H), 7.85-7.83 (d, J=7.6 Hz, 1 H), 7.76-7.71 (m, 2 H), 7.60-7.58 (m, 2 H), 5.92 (s, 1 H), 5.31 (s, 2 H), 4.51 (s, 2 H), 4.22-3.97 (m, 4 H), 3.75-3.73 (d, J=8 Hz, 2 H), 2.47 (s, 3 H), 3.11-3.08 (m, 2 H), 2.47-2.31 (m, 2 H), 1.63 (s, 3 H).

Example 65

N-[(3-Aminooxetan-3-yl)methyl]-2-(9-methoxy-1,1-dioxido-2,3-dihydro-1,4-benzothiazepin-4(5H)-yl)-6-methylquinolin-4-amine

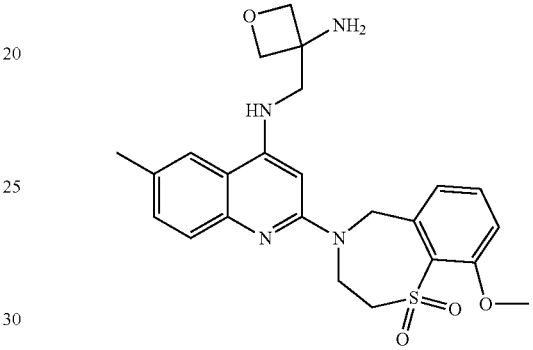

A mixture of N-[(3-aminooxetan-3-yl)methyl]-2-(9-fluoro-1,1-dioxido-2,3-dihydro-1,4-benzothiazepin-4(5H)-yl)-6-methylquinolin-4-amine (20 mg, 0.044 mmol, prepared in analogy to Example 1-4) and sodium methoxide (24 mg, 0.44 mmol) in methanol (2 mL) was heated with stirring in a sealed 5 mL of microwave process via for 20 minutes at 100° C. under microwave irradiation. The resulting mixture was concentrated in vacuo. The residue was purified by preparative HPLC to afford 6 mg of the product (yield was 29%). MS obsd. (ESI$^+$) [(M+H)$^+$] 469, $^1$H NMR (400 MHz, CD$_3$OD) δ ppm 7.67 (s, 1 H), 7.62-7.52 (m, 1 H), 7.47 (d, J=8.59 Hz, 1 H), 7.41 (d, J=7.07 Hz, 1 H), 7.31 (dd, J=8.46, 1.89 Hz, 1 H), 7.16 (d, J=7.83 Hz, 1 H), 5.99 (s, 1 H), 5.08 (s, 2 H), 4.63-4.49 (m, 4 H), 4.31 (t, J=5.56 Hz, 2 H), 3.98-3.81 (m, 5 H), 3.54 (s, 2 H), 2.43 (s, 3 H).

Example 66

4-(4-{[(3-Aminooxetan-3-yl)methyl]amino}-6-methylquinolin-2-yl)-2,3,4,5-tetrahydro-1,4-benzothiazepin-7-ol 1,1-dioxide

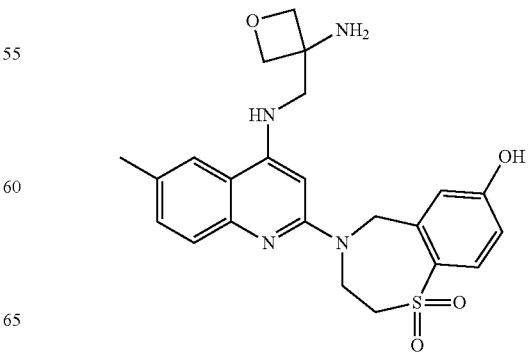

A mixture of N-[(3-aminooxetan-3-yl)methyl]-2-(7-methoxy-1,1-dioxido-2,3-dihydro-1,4-benzothiazepin-4(5H)-yl)-6-methylquinolin-4-amine (20 mg, 0.044 mmol, prepared in analogy to Example 1-5), potassium hydroxide (24 mg, 0.44 mmol) in dimethylsulfoxide (2 mL) was heated with stirring in a sealed 5 mL of microwave process via for 20 minutes at 100° C. under microwave irradiation. The resulting mixture was purified by preparative HPLC to afford 6 mg of the product (yield was 30%). MS obsd. (ESI+) [(M+H)+] 455, ¹HNMR (400 MHz, CD₃OD) δ ppm 7.77 (d, J=8.59 Hz, 1 H), 7.67 (s, 1 H), 7.45 (d, J=8.59 Hz, 1 H), 7.31 (dd, J=8.46, 1.64 Hz, 1 H), 7.18 (d, J=2.53 Hz, 1 H), 6.72 (dd, J=8.59, 2.27 Hz, 1 H), 6.19 (s, 1 H), 5.03 (s, 2 H), 4.68 (d, J=6.57 Hz, 2 H), 4.61 (d, J=6.57 Hz, 2 H), 3.66 (s, 2 H), 3.50 (brs, 2 H), 3.30 (m, 2 H), 2.43 (s, 3 H).

Example 67

3-{[2-(1,1-Dioxido-2,3-dihydro-1,4-benzothiazepin-4(5H)-yl)-6-methylquinolin-4-yl]amino}-2-methyl-propane-1,2-diol

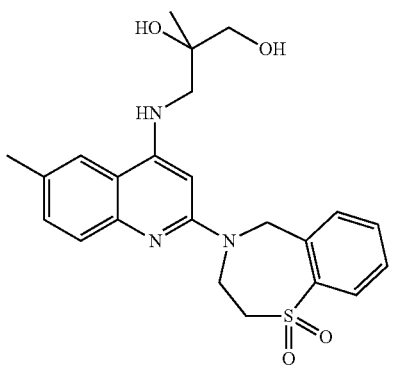 [SMILES: Cc1ccc2nc(N3CCS(=O)(=O)c4ccccc4C3)cc(NCC(C)(O)CO)c2c1]

2-(1,1-Dioxido-2,3-dihydro-1,4-benzothiazepin-4(5H)-yl)-6-methyl-N-(2-methylprop-2-en-1-yl)quinolin-4-amine

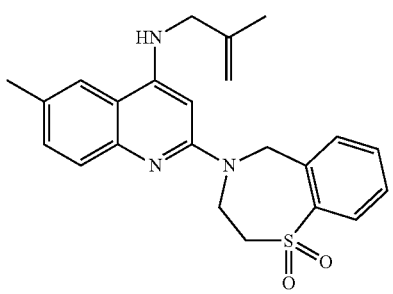 [SMILES: C=C(C)CNc1cc(N2CCS(=O)(=O)c3ccccc3C2)nc2ccc(C)cc12]

A solution of 4-(4-chloro-6-methylquinolin-2-yl)-2,3,4,5-tetrahydro-1,4-benzothiazepine 1,1-dioxide (372.0 mg, 1.0 mmol, prepared in analogy to 4-(4-chloro-6-(trifluoromethoxy)quinolin-2-yl)-2,3,4,5-tetrahydro-1,4-benzothiazepine 1,1-dioxide in Example 17-1) and 2-methylprop-2-en-1-amine (213.0 mg, 3.0 mmol) in 1-methyl-2-pyrrolidinone (1.0 mL) was heated with stirring at 160° C. for 36 hours. The reaction mixture was cooled to room temperature, diluted with water (10 mL) and extracted with ethyl acetate (100 mL). The organic layer was washed with brine (50 mL×2), dried over anhydrous sodium sulfate and then concentrated in vacuo to afford 407.0 mg of the product as a light yellow solid. MS obsd. (ESI+) [(M+H)+] 408.

3-{[2-(1,1-Dioxido-2,3-dihydro-1,4-benzothiazepin-4(5H)-yl)-6-methylquinolin-4-yl]amino}-2-methyl-propane-1,2-diol

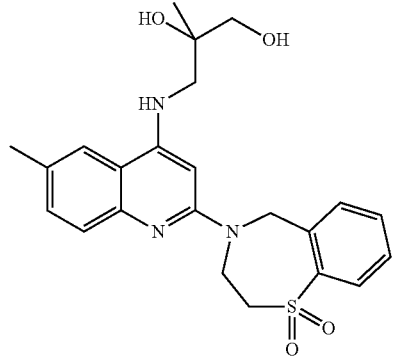 [SMILES: Cc1ccc2nc(N3CCS(=O)(=O)c4ccccc4C3)cc(NCC(C)(O)CO)c2c1]

A mixture solution of 2-(1,1-dioxido-2,3-dihydro-1,4-benzothiazepin-4(5H)-yl)-6-methyl-N-(2-methylprop-2-en-1-yl)quinolin-4-amine (200.0 mg, 0.49 mmol), 4-methylmorpholine N-oxide monohydrate (67.2 mg, 0.58 mmol) and osmium tetroxide (6.4 mg, 0.024 mmol) in acetone (10 mL) was stirred at room temperature for 1 hour. After being quenched by adding sodium bisulfite, the resulting mixture was extracted with ethyl acetate (100 mL). The organic layer was washed with brine (50 mL×2), dried over anhydrous sodium sulfate and then concentrated in vacuo. The residue was purified by preparative HPLC to afford 25.1 mg of the desired product as a light yellow solid (yield was 11.6%), MS obsd. (ESI+) [(M+H)+] 442, ¹H NMR (400 MHz, CD₃OD) δ ppm 7.96 (dd, J=7.83, 1.01 Hz, 1 H), 7.89 (d, J=7.33 Hz, 1H), 7.60 (td, J=7.45, 1.26 Hz, 1 H), 7.54 (s, 1 H), 7.50-7.34 (m, 2 H), 7.28 (dd, J=8.59, 1.77 Hz, 1 H), 6.22 (s, 1 H), 5.13 (brs, 2 H), 4.52 (brs, 2 H), 3.66-3.46 (m, 4 H), 3.40 (s, 2 H), 3.33 (dt, J=3.28, 1.64 Hz, 2 H), 2.41 (s, 3 H), 1.31 (s, 3 H).

Example 68

4-{[2-(1,1-Dioxido-2,3-dihydro-1,4-benzothiazepin-4(5H)-yl)-6-methylquinolin-4-yl]amino}butane-1,3-diol

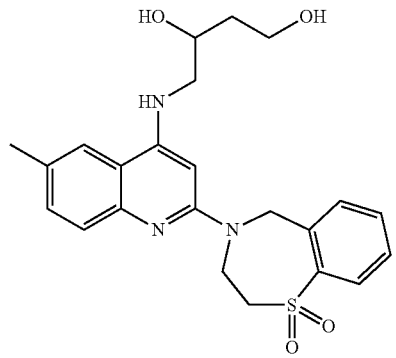 [SMILES: Cc1ccc2nc(N3CCS(=O)(=O)c4ccccc4C3)cc(NCC(O)CCO)c2c1]

A solution of 4-{[2-(1,1-dioxido-2,3-dihydro-1,4-benzothiazepin-4(5H)-yl)-6-methylquinolin-4-yl]amino}-3-hydroxybutanoic acid (50.0 mg, 0.11 mmol, prepared in analogy to Example 11-3), sodium borohydride (100.0 g, 2.6 mmol) and iodine (300.0 mg, 1.2 mmol) in tetrahydrofuran (10.0 mL) was stirred at room temperature for 16 hours. The reaction mixture was diluted with water (20 mL) and extracted with ethyl acetate (100 mL). The organic layer was washed with brine (50 mL×2), dried over anhydrous sodium sulfate and then concentrated in vacuo. The residue was purified by preparative HPLC to afford 20.0 mg of the desired product as a light yellow solid (yield was 41.2%). MS obsd. (ESI$^+$) [(M+H)$^+$] 442, $^1$H NMR (400 MHz, CD$_3$OD) δ ppm 8.04 (d, J=7.58 Hz, 1 H), 7.90 (d, J=7.58 Hz, 1 H), 7.81 (brs, 1 H), 7.75-7.59 (m, 2 H), 7.59-7.41 (m, 2 H), 6.10 (s, 1 H), 5.25 (brs, 2 H), 4.53 (brs, 2 H), 4.12 (brs, 1 H), 3.82 (t, J=5.94 Hz, 2 H), 3.68 (brs, 2 H), 3.55 (dd, J=13.77, 4.17 Hz, 1 H), 3.44 (dd, J=13.64, 7.33 Hz, 1 H), 2.45 (s, 3 H), 1.97-1.73 (m, 2 H).

Example 69-1

N-[6-Methyl-2-(2-methyl-1,1-dioxido-2,3-dihydro-1,4-benzothiazepin-4(5H)-yl)quinolin-4-yl]ethane-1,2-diamine

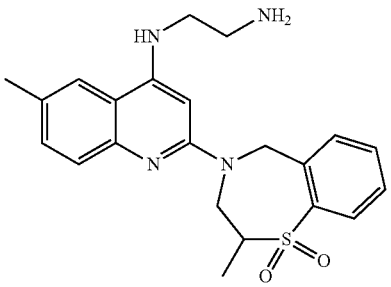 [SMILES: Cc1ccc2nc(N3Cc4ccccc4S(=O)(=O)C(C)C3)cc(NCCN)c2c1]

4-(4-Chloro-6-methylquinolin-2-yl)-2-methyl-2,3,4,5-tetrahydro-1,4-benzothiazepine 1,1-dioxide

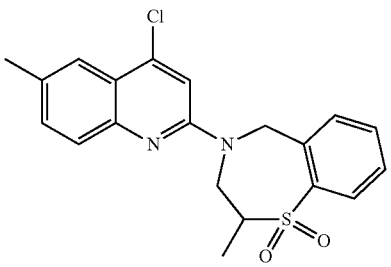 [SMILES: Cc1ccc2nc(N3Cc4ccccc4S(=O)(=O)C(C)C3)cc(Cl)c2c1]

To a cooled solution of 4-(4-chloro-6-methylquinolin-2-yl)-2,3,4,5-tetrahydro-1,4-benzothiazepine 1,1-dioxide (186 mg, 0.5 mmol, prepared in analogy to 4-(4-chloro-6-(trifluoromethoxy)quinolin-2-yl)-2,3,4,5-tetrahydro-1,4-benzothiazepine 1,1-dioxide in Example 17-1) in dry tetrahydrofuran (10 mL) was added n-butyllithium (0.47 mL, 1.6 N) at −78° C. under argon. After being stirred at −78° C. for 1 hour, a solution of methyl iodide in dry tetrahydrofuran (5 mL) was added to the reaction mixture dropwise at −78° C. Then the mixture was stirred overnight whilst allowing the temperature to rise slowly to room temperature. The resulting reaction mixture was poured into a saturated aqueous solution of ammonium chloride (20 mL) and extracted with ethyl acetate (50 mL). The organic layer was dried over sodium sulfate and concentrated in vacuo. The residue was purified by flash column chromatography (eluting with 20% ethyl acetate in petroleum ether) to afford the desired product.

N-[6-Methyl-2-(2-methyl-1,1-dioxido-2,3-dihydro-1,4-benzothiazepin-4(5H)-yl)quinolin-4-yl]ethane-1,2-diamine

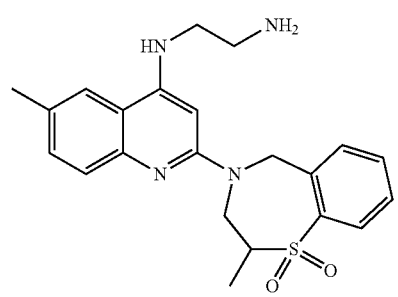 [SMILES: Cc1ccc2nc(N3Cc4ccccc4S(=O)(=O)C(C)C3)cc(NCCN)c2c1]

The title compound was prepared in analogy to Example 9-1 in Scheme 30 by using 4-(4-chloro-6-methylquinolin-2-yl)-2-methyl-2,3,4,5-tetrahydro-1,4-benzothiazepine 1,1-dioxide and ethane 1,2-diamine. MS obsd. (ESI$^+$) [(M+H)$^+$] 411, $^1$H NMR (400 MHz, CD$_3$OD) δ ppm 8.01 (d, J=7.83 Hz, 1 H), 7.85 (brs, 1 H), 7.70-7.60 (m, 2 H), 7.52-7.40 (m, 2 H), 7.30 (dd, J=8.59, 1.77 Hz, 1 H), 6.03 (s, 1 H), 5.13 (brs, 2 H), 3.67-3.57 (m, 1 H), 3.56-3.48 (m, 2 H), 3.31-3.30 (m, 3 H), 3.15-3.04 (m, 2 H), 2.42 (s, 3 H), 1.51 (brs, 2 H).

Example 69-2

N-[(3-Aminooxetan-3-yl)methyl]-6-methyl-2-(2-methyl-1,1-dioxido-2,3-dihydro-1,4-benzothiazepin-4(5H)-yl)quinolin-4-amine

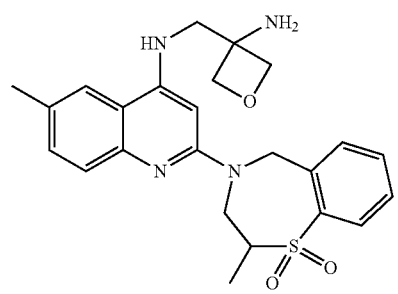 [SMILES: Cc1ccc2nc(N3Cc4ccccc4S(=O)(=O)C(C)C3)cc(NCC3(N)COC3)c2c1]

The title compound was prepared in analogy to Example 69-1 in Scheme 30 by using 4-(4-chloro-6-methylquinolin-2-yl)-2-methyl-2,3,4,5-tetrahydro-1,4-benzothiazepine 1,1-dioxide and 3-(aminomethyl)oxetan-3-amine. MS obsd. (ESI$^+$) [(M+H)$^+$] 453, $^1$H NMR (400 MHz, CD$_3$OD) δ ppm 8.01 (d, J=7.83 Hz, 1 H), 7.92 (brs, 1 H), 7.66 (s, 2 H), 7.52-7.41 (m, 2 H), 7.30 (dd, J=8.59, 1.77 Hz, 1 H), 6.19 (s, 1 H), 5.18 (brs, 1 H), 5.10 (brs, 1 H), 4.66-4.55 (m, 4 H), 3.68 (d, J=2.02 Hz, 2 H), 3.65-3.57 (m, 1 H), 3.35-3.30 (m, 3 H), 2.43 (s, 3 H), 1.60-1.40 (brs, 2 H).

Example 70

N-[(3-{[2-(1,1-Dioxido-2,3-dihydro-1,4-benzothiazepin-4(5H)-yl)-6-methylquinolin-4-yl]amino}oxetan-3-yl)methyl]-2,2,2-trifluoroacetamide

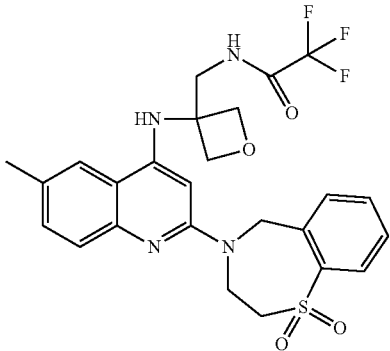 [SMILES: Cc1ccc2nc(N3CCS(=O)(=O)c4ccccc4C3)cc(NC3(CNC(=O)C(F)(F)F)COC3)c2c1]

A solution of 4-(4-chloro-6-methylquinolin-2-yl)-2,3,4,5-tetrahydro-1,4-benzothiazepine 1,1-dioxide (500 mg, 1.341 mmol, prepared in analogy to 4-(4-chloro-6-(trifluoromethoxy)quinolin-2-yl)-2,3,4,5-tetrahydro-1,4-benzothiazepine 1,1-dioxide in Example 17-1), N-[(3-aminooxetan-3-yl)methyl]-2,2,2-trifluoroacetamide (570 mg, 70%, 2.01 mmol), 1,1'-bis(diphenylphosphino)ferrocene-palladium(II) dichloride (99 mg, 0.134 mmol), 1,1'-bis(diphenylphosphino)ferrocene (75 mg, 0.134 mmol), and sodium tert-butoxide (258 mg, 2.682 mmol) in 1,4-dioxane (8 mL) was heated with stirring in a sealed 10 mL of microwave process vial for 1.5 hours at 120° C. under microwave irradiation. The reaction mixture was poured into water and extracted with ethyl acetate. The organic layer was dried over sodium sulfate and concentrated in vacuo. The residue was purified by flash column chromatography (eluting with 1-10% methanol in dichloromethane) to afford 190 mg of the desired product (yield was 26%). MS obsd. (ESI$^+$) [(M+H)$^+$] 535, $^1$H NMR (400 MHz, CD$_3$OD) δ ppm 7.98 (m, 1 H), 7.82 (d, J=6.8 Hz, 1 H), 7.66 (s, 1 H), 7.59 (td, J=0.8, 7.6 Hz, 1 H), 7.47-7.42 (m, 2 H), 7.32 (dd, J=1.6, 8.8 Hz, 1 H), 5.70 (s, 1 H), 5.18 (s, 2 H), 4.86 (m, 4 H), 4.52 (s, 2 H), 3.87 (s, 2 H), 3.60 (t, J=4.8 Hz, 2 H), 2.43 (s, 3 H).

Example 71

N-[3-(Aminomethyl)oxetan-3-yl]-2-(1,1-dioxido-2,3-dihydro-1,4-benzothiazepin-4(5H)-yl)-6-methylquinolin-4-amine

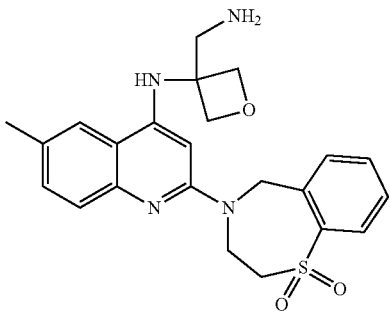 [SMILES: Cc1ccc2nc(N3CCS(=O)(=O)c4ccccc4C3)cc(NC3(CN)COC3)c2c1]

To a solution of N-[(3-{[2-(1,1-dioxido-2,3-dihydro-1,4-benzothiazepin-4(5H)-yl)-6-methylquinolin-4-yl]amino}oxetan-3-yl)methyl]-2,2,2-trifluoroacetamide (190 mg, 0.355 mmol) in methanol (15 mL) was added an aqueous solution of potassium carbonate (197 mg, 1.42 mmol, dissolved in 2 mL of water). After being stirred at room temperature overnight, the resulting mixture was concentrated in vacuo to remove methanol. The residue was diluted with water (5 mL) and extracted with dichloromethane (15 mL). The organic layer was dried over sodium sulfate and concentrated in vacuo. The residue was purified by preparative HPLC to give 23 mg of the desired product as a white solid (yield was 14.8%). MS obsd. (ESI$^+$) [(M+H)$^+$] 439, $^1$H NMR (400 MHz, CD$_3$OD) δ ppm 7.98-7.96 (m, 1 H), 7.58-7.56 (d, J=6.8 Hz, 1 H), 7.44-7.40 (m, 2 H), 7.32-7.30 (t, 1 H), 7.19 (m, 2 H), 5.99 (s, 1 H), 5.54 (s, 1 H), 4.98-4.97 (d, J=6.0, 4 H), 4.64-4.63 (m, 3 H), 3.51 (s, 2 H), 3.30 (s, 2 H), 2.34 (s, 3 H).

Example 72

2-(Aminomethyl)-2-{[2-(1,1-dioxido-2,3-dihydro-1,4-benzothiazepin-4(5H)-yl)-6-methylquinolin-4-yl]amino}propane-1,3-diol

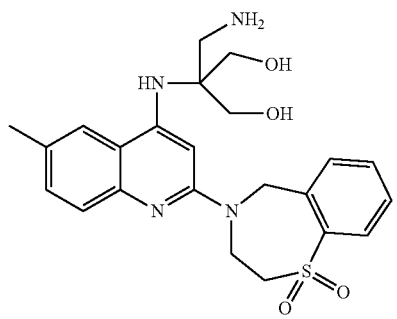 [SMILES: Cc1ccc2nc(N3CCS(=O)(=O)c4ccccc4C3)cc(NC(CN)(CO)CO)c2c1]

A mixture of N-[(3-{[2-(1,1-dioxido-2,3-dihydro-1,4-benzothiazepin-4(5H)-yl)-6-methylquinolin-4-yl]amino}oxetan-3-yl)methyl]-2,2,2-trifluoroacetamide (269 mg, 0.503 mmol) and a solution of ammonia in methanol (7 M, 10 mL,) was stirred at room temperature overnight. The resulting mixture was concentrated in vacuo and the residue was purified by preparative HPLC to afford 58 mg of the product as a white solid (yield was 25%). MS obsd. (ESI$^+$) [(M+H)$^+$] 457, $^1$H NMR (400 MHz, CD$_3$OD) δ ppm 8.11-8.09 (t, J=6.4, 1.2 Hz, 1 H), 8.00-7.96 (m, 1 H), 7.86 (s, 1 H), 7.76-7.73 (m, 2 H), 7.64-7.60 (m, 2 H), 6.49 (s, 1 H), 5.33 (s, 2 H), 4.55 (s, 2 H), 3.82 (s, 2 H), 3.77-3.75 (m, 6 H), 2.49 (s, 3 H).

Example 73

4-Amino-1-[2-(1,1-dioxido-2,3-dihydro-1,4-benzothiazepin-4(5H)-yl)-6-methylquinolin-4-yl]pyrrolidin-2-one

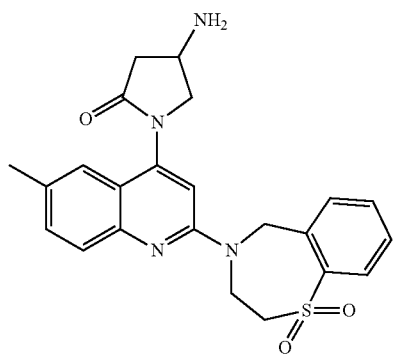 [SMILES: Cc1ccc2nc(N3CCS(=O)(=O)c4ccccc4C3)cc(N3CC(N)CC3=O)c2c1]

To a solution of 1-[2-(1,1-dioxido-2,3-dihydro-1,4-benzothiazepin-4(5H)-yl)-6-methylquinolin-4-yl]-5-oxopyrrolidine-3-carboxamide (100 mg, 0.22 mmol, byproduct of Example 47-2) in acetonitrile (2 mL) and water (2 mL) was added (diacetoxyiodo)benzene (91 mg, 0.28 mmol). The mixture was stirred at room temperature overnight. The reaction mixture was diluted with water, acidified with concentrated hydrochloride acid (12 N), and extracted with dichloromethane. The organic layer was dried over sodium sulfate, filtered and concentrated in vacuo. The residue was purified by column chromatography on silica gel (eluting with 1-10% methanol in dichloromethane) to give 10 mg of the product as a white solid. MS obsd. (ESI$^+$) [(M+H)$^+$] 437, $^1$H NMR (400 MHz, DMSO-d6) δ ppm 7.94-7.87 (m, 2 H), 7.60 (td, J=1.2, 7.2 Hz, 1 H), 7.55 (d, J=8.8 Hz, 1 H), 7.47-7.43 (m, 2 H), 7.37 (dd, J=2.0, 8.8 Hz, 1 H), 7.22 (s, 1 H), 5.13 (s, 2 H), 4.42 (brs, 2 H), 4.02 (dd, J=2.0, 9.6 Hz, 1 H), 3.87 (td, J=3.6, 6.8 Hz, 1 H), 3.62 (dd, J=4.8, 9.6 Hz, 2 H), 3.45 (dd, J=3.2, 9.6 Hz, 1 H), 3.14-3.13 (m, 1 H), 2.85 (dd, J=7.2, 16.8 Hz, 1 H), 2.36 (s, 3 H).

Example 74

2-(1,1-Dioxido-2,3-dihydro-1,4-benzothiazepin-4(5H)-yl)-6-methyl-N-[2-(methylsulfinyl)ethyl]quinolin-4-amine

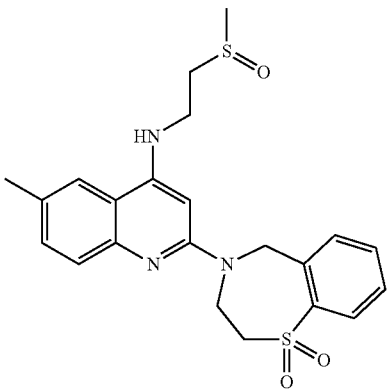 [SMILES: Cc1ccc2nc(N3CCS(=O)(=O)c4ccccc4C3)cc(NCCS(C)=O)c2c1]

2-(1,1-Dioxido-2,3-dihydro-1,4-benzothiazepin-4(5H)-yl)-6-methyl-N-[2-(methylsulfanyl)ethyl]quinolin-4-amine

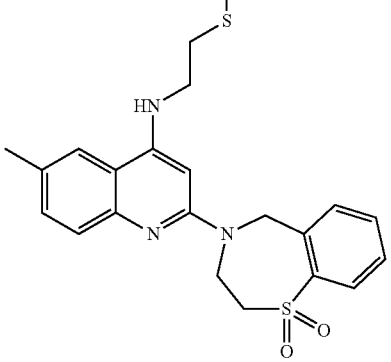

A dried microwave process vial capped with a rubber septum was purged with argon and charged with tris(dibenzylideneacetone)dipalladium(0) (2.88 mg, 0.005 mmol), 1-(N,N-dimethylamino)-1'-(dicyclohexylphosphino)biphenyl (5.90 mg, 0.015 mmol) and sodium tert-butoxide (134 mg, 1.4 mmol). The tube was purged with argon, and a solution of 4-(4-chloro-6-methylquinolin-2-yl)-2,3,4,5-tetrahydro-1,4-benzothiazepine 1,1-dioxide (370 mg, 1.0 mmol, prepared in analogy to 4-(4-chloro-6-(trifluoromethoxy)quinolin-2-yl)-2,3,4,5-tetrahydro-1,4-benzothiazepine 1,1-dioxide in Example 17-1) and 2-(methylthio)ethylamine (128 mg, 1.4 mmol) in 1,4-dioxane (2.0 mL) was added. The mixture was heated with stirring in a sealed 5 mL of microwave process vial for 2 hour at 120° C. under microwave irradiation. After being cooled to room temperature, the reaction mixture was diluted with ethyl acetate, filtered through celite and concentrated in vacuo. The residue was purified by flash chromatography on silica gel (eluting with 1-10% methanol in dichloromethane) to afford 341 mg of the desired product (yield was 80%). MS obsd. (ESI$^+$) [(M+H)$^+$] 428.

2-(1,1-Dioxido-2,3-dihydro-1,4-benzothiazepin-4(5H)-yl)-6-methyl-N-[2-(methylsulfinyl)ethyl]quinolin-4-amine

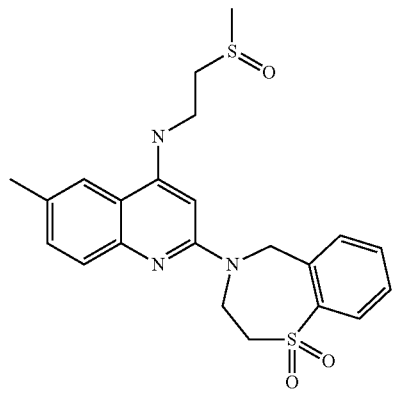 [SMILES: Cc1ccc2nc(N3CCS(=O)(=O)c4ccccc4C3)cc(NCCS(C)=O)c2c1]

To a solution of 2-(1,1-dioxido-2,3-dihydro-1,4-benzothiazepin-4(5H)-yl)-6-methyl-N-[2-(methylsulfanyl)ethyl]quinolin-4-amine (300 mg, 0.70 mmol) in acetic acid (2 mL) was added hydrogen peroxide (0.5 mL) at room temperature. The mixture was stirred at room temperature for 2 hours. The resulting mixture was diluted with ethyl acetate (10 mL), washed with a saturated aqueous solution of sodium bicarbonate, dried over sodium sulfate, and concentrated in vacuo. The residue was purified by preparative HPLC to afford the desired product. MS obsd. (ESI$^+$) [(M+H)$^+$] 444, $^1$H NMR (400 MHz, DMSO-d6) δ ppm 7.99 (d, J=7.07 Hz, 1 H), 7.88 (dd, J=7.83, 1.26 Hz, 1 H), 7.70-7.60 (m, 2 H), 7.47 (td, J=7.64, 1.14 Hz, 1 H), 7.34 (d, J=8.34 Hz, 1 H), 7.25 (dd, J=8.34, 1.52 Hz, 1 H), 6.98 (t, J=5.56 Hz, 1 H), 6.14 (s, 1 H), 5.09 (brs, 2 H), 4.5 (brs, 2 H), 3.81-3.56 (m, 4 H), 3.20-3.07 (m, 1 H), 3.04-2.92 (m, 1 H), 2.65 (s, 3 H), 2.35 (s, 3 H).

Example 75

N-{2-[(2-Aminoethyl)sulfonyl]ethyl}-2-(1,1-dioxido-2,3-dihydro-1,4-benzothiazepin-4(5H)-yl)-6-methylquinolin-4-amine

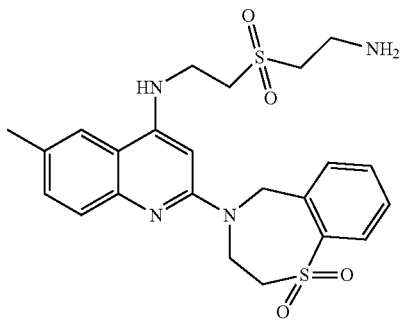 [SMILES: Cc1ccc2nc(N3CCS(=O)(=O)c4ccccc4C3)cc(NCCS(=O)(=O)CCN)c2c1]

To a solution of N-{2-[(2-aminoethyl)sulfanyl]ethyl}-2-(1,1-dioxido-2,3-dihydro-1,4-benzothiazepin-4(5H)-yl)-6-methylquinolin-4-amine (40 mg, 0.087 mmol, prepared in analogy to Example 3-1 by using 4-(4-chloro-6-methylquinolin-2-yl)-2,3,4,5-tetrahydro-1,4-benzothiazepine 1,1-dioxide and 2-[(2-aminoethyl)sulfanyl]ethylamine) in acetic acid (2 mL), potassium permanganate (15 mg, 0.08 mmol) was added. After being stirred at room temperature for 30 minutes, the mixture was concentrated in vacuo. The residue was purified by preparative HPLC to afford the pure product as a solid. MS obsd. (ESI⁺) [(M+H)⁺] 489, ¹H NMR (400 MHz, CD₃OD) δ ppm 7.99 (dd, J=7.83, 1.26 Hz, 1 H), 7.93 (d, J=7.58 Hz, 1 H), 7.65 (td, J=7.45, 1.26 Hz, 1 H), 7.54 (s, 1 H), 7.49-7.41 (m, 2 H), 7.30 (dd, J=8.46, 1.64 Hz, 1 H), 6.13 (s, 1 H), 5.16 (s, 2 H), 4.63 (brs, 1 H), 4.56 (brs, 1 H), 3.91 (t, J=6.82 Hz, 2 H), 3.60 (t, J=4.67 Hz, 2 H), 3.55-3.45 (m, 2 H), 3.31-3.27 (m, 2 H), 3.20-3.06 (m, 2 H), 2.41 (s, 3 H).

Example 76

N-[2-(1-Imino-1-oxido-1,2,3,5-tetrahydro-4H-1lambda~4~,4-benzothiazepin-4-yl)-6-methylquinolin-4-yl]ethane-1,2-diamine

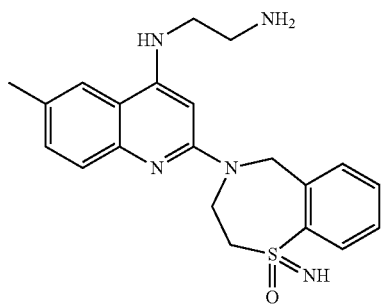 [SMILES: Cc1ccc2nc(N3CCS(=N)(=O)c4ccccc4C3)cc(NCCN)c2c1]

N-[4-(4-Chloro-6-methylquinolin-2-yl)-1-oxido-2,3,4,5-tetrahydro-1H-1lambda~4~,4-benzothiazepin-1-ylidene]-2,2,2-trifluoroacetamide

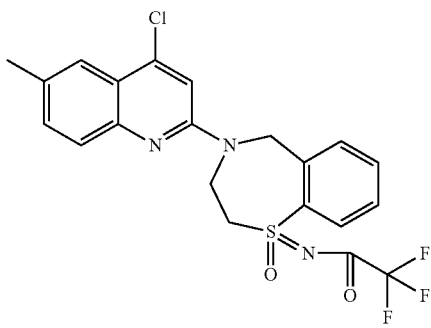 [SMILES: Cc1ccc2nc(N3CCS(=O)(=NC(=O)C(F)(F)F)c4ccccc4C3)cc(Cl)c2c1]

To a suspension of 4-(4-chloro-6-methylquinolin-2-yl)-2,3,4,5-tetrahydro-1,4-benzothiazepine 1-oxide (357 mg, 1.0 mmol, prepared in analogy to the one in Example 18-1), trifluoroacetamide (226 mg, 2.0 mmol), magnesium oxide (160 mg, 4.0 mmol) and rhodium(II) acetate (11 mg, 2.5 mol) in dichloromethane (10 mL) was added (diacetoxyiodo)benzene (483 mg, 1.5 mmol). After being stirred at room temperature overnight, the resulting mixture was concentrated in vacuo. The residue was purified by flash column chromatography (eluting with 20-33% ethyl acetate in petroleum ether) to afford 234 mg of the pure product (yield was 50%). MS obsd. (ESI⁺) [(M+H)⁺] 468.

4-(4-Chloro-6-methylquinolin-2-yl)-2,3,4,5-tetrahydro-1H-1lambda~4~,4-benzothiazepin-1-imine 1-oxide

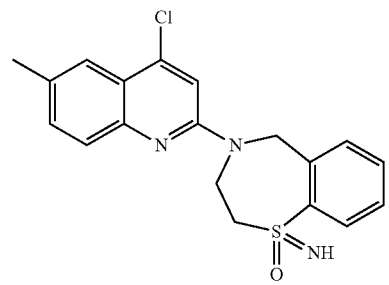 [SMILES: Cc1ccc2nc(N3CCS(=N)(=O)c4ccccc4C3)cc(Cl)c2c1]

To a solution of N-[4-(4-chloro-6-methylquinolin-2-yl)-1-oxido-2,3,4,5-tetrahydro-1H-1lambda~4~,4-benzothiazepin-1-ylidene]-2,2,2-trifluoroacetamide (234 mg, 0.50 mmol) in methanol (10 mL) was added potassium carbonate (690 mg, 5.0 mmol). After being stirred at room temperature for 30 minutes, the reaction mixture was concentrated in vacuo. The residue was purified by column chromatography (eluting with 20-33% ethyl acetate in petroleum ether) to afford the N-unsubstituted sulfoximines. MS obsd. (ESI⁺) [(M+H)⁺] 372.

N-[2-(1-Imino-1-oxido-1,2,3,5-tetrahydro-4H-1lambda~4~,4-benzothiazepin-4-yl)-6-methylquinolin-4-yl]ethane-1,2-diamine

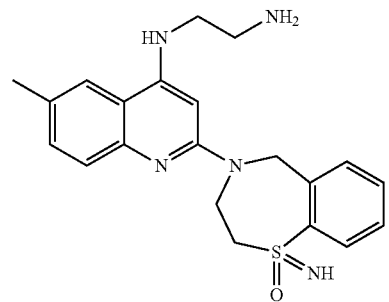 [SMILES: Cc1ccc2nc(N3CCS(=N)(=O)c4ccccc4C3)cc(NCCN)c2c1]

The title compound was prepared in analogy to Example 9-1 in Scheme 35 by using 4-(4-chloro-6-methylquinolin-2-yl)-2,3,4,5-tetrahydro-1H-1lambda~4~,4-benzothiazepin-1-imine 1-oxide and ethane 1,2-diamine. MS obsd. (ESI⁺) [(M+H)⁺] 396, ¹H NMR (400 MHz, DMSO-d6) δ ppm 7.91 (d, J=8.08 Hz, 1 H), 7.83 (d, J=7.58 Hz, 1 H), 7.70 (s, 1 H), 7.58-7.52 (m, 1 H), 7.44-7.37 (m, 1 H), 7.30 (d, J=8.59 Hz, 1 H), 7.21 (dd, J=8.46, 1.64 Hz, 1 H), 6.63 (t, J=5.43 Hz, 1 H), 6.01 (s, 1 H), 5.11 (brs, 2 H), 4.61 (brs, 1 H), 4.10 (brs, 1 H), 3.49-3.36 (m, 2 H), 3.31 (q, J=6.23 Hz, 3 H), 2.86-2.76 (m, 3 H), 2.34 (s, 3 H).

Example 77

2-(1,1-Dioxido-2,3-dihydro-1,4-benzothiazepin-4(5H)-yl)-6-methyl-N-[2-(S-methylsulfonimidoyl)ethyl]quinolin-4-amine

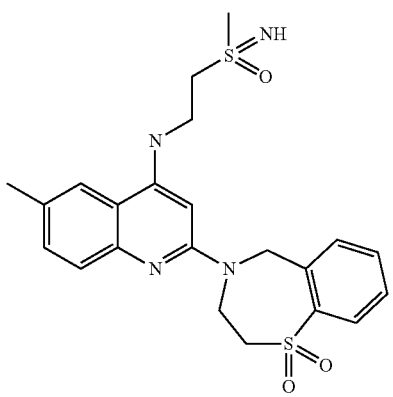 [SMILES: Cc1ccc2nc(N3CCS(=O)(=O)c4ccccc4C3)cc(NCCS(C)(=N)=O)c2c1]

The title compound was prepared in analogy to Example 76 in Scheme 33 by using 2-(1,1-dioxido-2,3-dihydro-1,4-benzothiazepin-4(5H)-yl)-6-methyl-N-[2-(methylsulfinyl)ethyl]quinolin-4-amine (prepared in analogy to Example 74) and trifluoroacetamide. MS obsd. (ESI+) [(M+H)+] 459, 1H NMR (400 MHz, CD3OD) δ ppm 8.04 (d, J=7.33 Hz, 1 H), 7.96 (d, J=7.33 Hz, 1 H), 7.73-7.66 (m, 2 H), 7.60-7.55 (m, 1 H), 7.52 (s, 1 H), 7.46-7.40 (m, 1 H), 6.17 (s, 1 H), 5.26 (brs, 2 H), 4.50 (brs, 2 H), 3.98 (t, J=6.69 Hz, 2 H), 3.68 (brs, 2 H), 3.59 (t, J=6.82 Hz, 2 H), 3.14 (s, 3 H), 2.45 (s, 3 H).

Example 78-1 trans-4-Amino-1-[2-(1-imino-1-oxido-1,2,3,5-tetrahydro-4H-1lambda~4~,4-benzothiazepin-4-yl)-6-methylquinolin-4-yl]pyrrolidin-3-ol

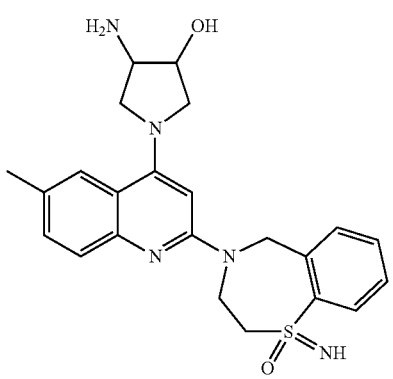 [SMILES: Cc1ccc2nc(N3CCS(=N)(=O)c4ccccc4C3)cc(N3CC(N)C(O)C3)c2c1]

A mixture of 4-(4-chloro-6-methylquinolin-2-yl)-2,3,4,5-tetrahydro-1H-1lambda~4~,4-benzothiazepin-1-imine 1-oxide (100 mg, 0.27 mmol), tert-butyl (trans-4-hydroxypyrrolidin-3-yl)carbamate (164 mg, 0.81 mmol) and n-butanol (0.2 mL) was stirred at 160° C. overnight. After the mixture being cooled to room temperature, to the above mixture was added dichloromethane (10 mL) and trifluoroacetic acid (10 mL). The mixture was stirred further until the reaction finished monitoring by TLC, and then concentrated in vacuo. The residue was dissolved in dichloromethane and the solution was washed with an aqueous solution of sodium hydroxide (10% W/W) and brine, dried over sodium sulfate, and concentrated in vacuo. The residue was purified by preparative HPLC to afford the product as a solid. MS obsd. (ESI+) [(M+H)+] 438, 1H NMR (400 MHz, CD3OD) δ ppm 8.05 (d, J=7.83 Hz, 1 H), 7.84 (s, 1 H), 7.81 (s, 1 H), 7.61 (t, J=7.45 Hz, 1 H), 7.52 (d, J=8.59 Hz, 1 H), 7.49-7.43 (m, 1 H), 7.36-7.30 (m, 1 H), 6.14 (s, 1 H), 5.31-5.16 (m, 2 H), 4.25 (brs, 1 H), 4.17-4.05 (m, 1 H), 4.05-3.94 (m, 1 H), 3.62 (d, J=10.61 Hz, 2 H), 3.70-3.58 (m, 2 H), 3.57-3.41 (m, 3 H), 2.43 (s, 3 H).

Example 78-2 trans-1-[2-(1,1-Dioxido-2,3-dihydro-1,4-benzothiazepin-4(5H)-yl)-6-methylquinolin-4-yl]-4-fluoropyrrolidin-3-amine

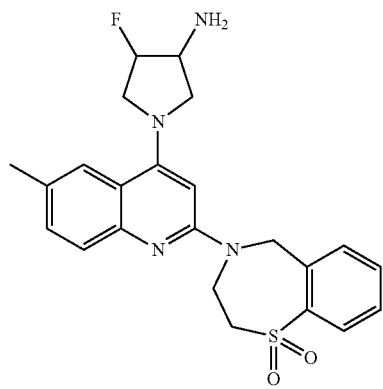 [SMILES: Cc1ccc2nc(N3CCS(=O)(=O)c4ccccc4C3)cc(N3CC(N)C(F)C3)c2c1]

The title compound was prepared in analogy to Example 78-1 in Scheme 7 by using 4-(4-chloro-6-methylquinolin-2-yl)-2,3,4,5-tetrahydro-1,4-benzothiazepine 1,1-dioxide and tert-butyl (trans-4-fluoropyrrolidin-3-yl)carbamate. MS obsd. (ESI+) [(M+H)+] 441, 1H NMR (400 MHz, CD3OD) δ ppm 7.98 (dd, J=7.71, 1.89 Hz, 1 H), 7.91-7.75 (m, 2 H), 7.62 (t, J=7.45 Hz, 1 H), 7.52 (d, J=8.59 Hz, 1 H), 7.45 (td, J=7.58, 3.28 Hz, 1 H), 7.32 (d, J=8.59 Hz, 1 H), 6.19 (s, 1 H), 5.18 (brs, 2 H), 5.06 (m, 1 H), 4.53 (brs, 2 H), 4.17 (m, 1 H), 4.03 (dd, J=9.98, 5.43 Hz, 1 H), 3.81-3.54 (m, 4 H), 3.45-3.35 (m, 1 H), 2.42 (s, 3 H).

Example 79

1-[2-(1,1-Dioxido-2,3-dihydro-1,4-benzothiazepin-4(5H)-yl)-6-methylquinolin-4-yl]pyrrolidine-3-carboxamide

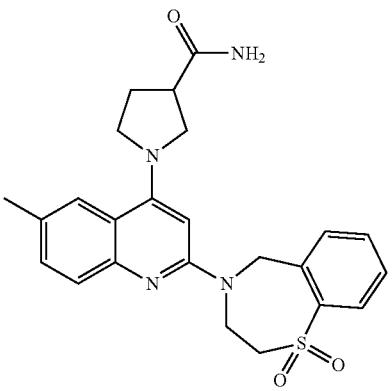 [SMILES: Cc1ccc2nc(N3CCS(=O)(=O)c4ccccc4C3)cc(N3CCC(C(N)=O)C3)c2c1]

1-[2-(1,1-Dioxido-2,3-dihydro-1,4-benzothiazepin-4 (5H)-yl)-6-methylquinolin-4-yl]pyrrolidine-3-carboxylic acid

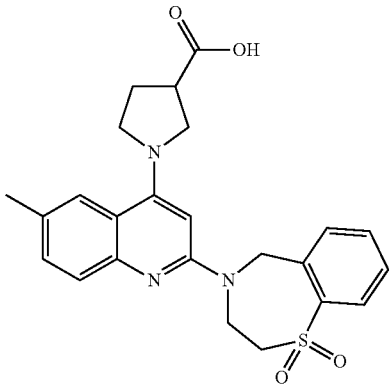 [SMILES: Cc1ccc2nc(N3CCS(=O)(=O)c4ccccc4C3)cc(N3CCC(C(=O)O)C3)c2c1]

A mixture of 4-(4-chloro-6-methylquinolin-2-yl)-2,3,4,5-tetrahydro-1,4-benzothiazepine 1,1-dioxide (500 mg, 1.34 mmol, prepared in analogy to 4-(4-chloro-6-(trifluoromethoxy)quinolin-2-yl)-2,3,4,5-tetrahydro-1,4-benzothiazepine 1,1-dioxide in Example 17-1) and methylpyrrolidine-3-carboxylate (173 mg, 1.34 mmol) and N,N-diisopropylethylamine (346 mg, 2.68 mmol) was heated with stirring in a sealed 10 mL of microwave process vial for 1.5 hours at 140° C. under microwave irradiation. The resulting mixture was purified by preparative HPLC to afford 120 mg of the pure product (yield was 19.8%).

1-[2-(1,1-Dioxido-2,3-dihydro-1,4-benzothiazepin-4 (5H)-yl)-6-methylquinolin-4-yl]pyrrolidine-3-carbonyl chloride

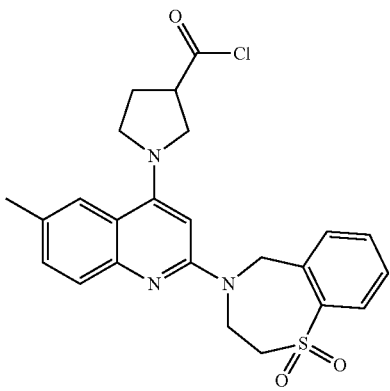 [SMILES: Cc1ccc2nc(N3CCS(=O)(=O)c4ccccc4C3)cc(N3CCC(C(=O)Cl)C3)c2c1]

To a cooled solution of 1-[2-(1,1-dioxido-2,3-dihydro-1,4-benzothiazepin-4(5H)-yl)-6-methylquinolin-4-yl]pyrrolidine-3-carboxylic acid (120 mg, 0.26 mmol) in dichloromethane (20 mL) was added two drops of N,N-dimethylformamide followed by oxalyl chloride (30.6 µL, 0.39 mmol) at 0° C. After being stirred for 16 hours at room temperature, the reaction mixture was concentrated in vacuo to afford 100 mg of the crude product which was used for the next step without any further purification.

1-[2-(1,1-Dioxido-2,3-dihydro-1,4-benzothiazepin-4 (5H)-yl)-6-methylquinolin-4-yl]pyrrolidine-3-carboxamide

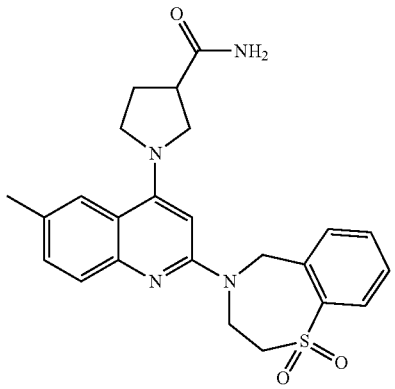 [SMILES: Cc1ccc2nc(N3CCS(=O)(=O)c4ccccc4C3)cc(N3CCC(C(N)=O)C3)c2c1]

To a cooled solution of 1-[2-(1,1-dioxido-2,3-dihydro-1,4-benzothiazepin-4(5H)-yl)-6-methylquinolin-4-yl]pyrrolidine-3-carbonyl chloride (100 mg, 0.21 mmol) in dichloromethane (20 mL) was added a saturated solution of ammonia in dichloromethane (10 mL) slowly at 0° C. After being stirred for 16 hours at room temperature, the mixture was concentrated in vacuo. The residue was purified by preparative HPLC to afford 13 mg of the desired product (yield was 13.5%). MS obsd. (ESI$^+$) [(M+H)$^+$] 451, $^1$H NMR (400 MHz, CD$_3$OD) δ ppm 8.08-8.05 (m, 2 H), 7.33-7.31 (d, J=7.6 Hz, 1 H), 7.70-7.67 (m, 2 H), 7.57-7.55 (m, 2 H), 5.85 (s, 1 H), 5.25 (s, 2 H), 4.5 (s, 2 H), 4.03-3.94 (m, 4 H), 3.71 (s, 2 H), 3.29-3.21 (m, 1 H), 2.45 (s, 3 H), 2.41-2.32 (m, 1 H), 2.31-2.21 (m, 1 H).

Example 80

N-[2-(1,1-Dioxido-2,3-dihydro-1,4-benzothiazepin-4 (5H)-yl)-6-(methylsulfinyl)quinolin-4-yl]propane-1,3-diamine

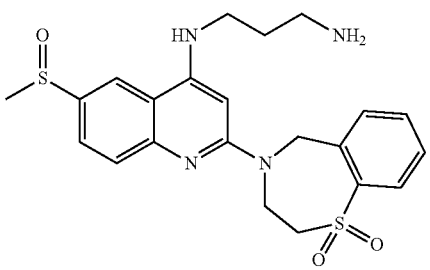 [SMILES: CS(=O)c1ccc2nc(N3CCS(=O)(=O)c4ccccc4C3)cc(NCCCN)c2c1]

4-[4-Chloro-6-(methylsulfinyl)quinolin-2-yl]-2,3,4,5-tetrahydro-1,4-benzothiazepine 1,1-dioxide

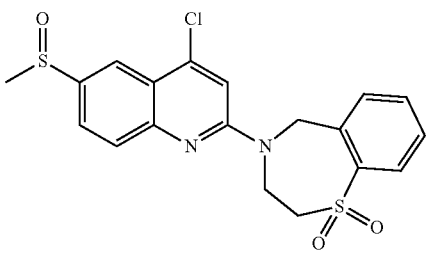 [SMILES: CS(=O)c1ccc2nc(N3CCS(=O)(=O)c4ccccc4C3)cc(Cl)c2c1]

To a cooled solution of 4-[4-Chloro-6-(methylsulfanyl)quinolin-2-yl]-2,3,4,5-tetrahydro-1,4-benzothiazepine 1,1-dioxide (800 mg, 1.98 mmol, prepared in analogy to 4-(4-chloro-6-methylquinolin-2-yl)-2,3,4,5-tetrahydro-1,4-benzothiazepine 1,1-dioxide in Example 17-1) in dichloromethane (70 mL) was added a solution of 3-chloroperoxybenzoic acid (400 mg, 198 mmol, purity 85%) in dichloromethane (30 mL) dropwise at 0° C. After being stirred at 0° C. for 20 minutes, the reaction mixture was washed with a saturated aqueous solution of sodium bicarbonate (100 mL), a saturated aqueous solution of sodium thiosulphate (100 mL×3) and brine (100×2). The organic layer was dried over sodium sulfate, filtered and concentrated in vacuo to afford 500 mg of the desired product (yield was 60%).

N-[2-(1,1-Dioxido-2,3-dihydro-1,4-benzothiazepin-4(5H)-yl)-6-(methylsulfinyl)quinolin-4-yl]propane-1,3-diamine

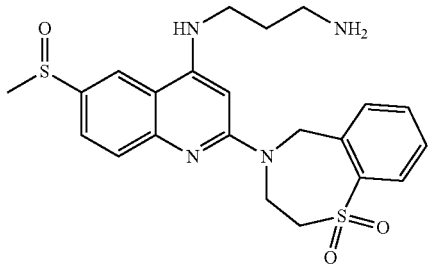 [SMILES: CS(=O)c1ccc2nc(N3CCS(=O)(=O)c4ccccc4C3)cc(NCCCN)c2c1]

A mixture of 4-[4-chloro-6-(methylsulfinyl)quinolin-2-yl]-2,3,4,5-tetrahydro-1,4-benzothiazepine 1,1-dioxide (300 mg, 0.71 mmol) and propane-1,3-diamine (67525 mg, 7.1 mmol) was heated with stirring in a sealed 10 mL of microwave process vial for 1 hour at 150° C. under microwave irradiation. The reaction mixture was purified by preparative HPLC to afford the trifluoroacetic acid salt of the desired product. The trifluoroacetic acid salt was flashed through SPE column with methanol. The eluent was concentrated in vacuo and dried by lyopylization to afford 256.8 mg of the desired product (yield was 78%). MS obsd. (ESI$^+$) [(M+H)$^+$] 459, $^1$H NMR (400 MHz, CD$_3$OD) δ ppm 8.44 (s, 1 H), 8.05-7.96 (m, 3 H), 7.88 (d, J=7.6 Hz, 1 H), 7.71 (t, J=7.6 Hz, 1 H), 7.55 (t, J=7.6 Hz, 1 H), 6.02 (s, 1 H), 5.33 (s, 2 H), 4.54 (s, 2 H), 3.74 (s, 2 H), 3.61 (t, J=6.0 Hz, 2 H), 3.11 (t, J=8.0 Hz, 2 H), 2.82 (s, 3 H), 2.16-2.09 (m, 2 H).

Example 81

4-[(3-Aminopropyl)amino]-2-(1,1-dioxido-2,3-dihydro-1,4-benzothiazepin-4(5H)-yl)quinoline-6-carboxamide

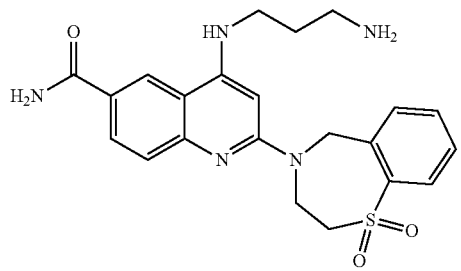 [SMILES: NCCCNc1cc(N2CCS(=O)(=O)c3ccccc3C2)nc2ccc(C(N)=O)cc12]

4-Chloro-2-(2,3-dihydro-1,4-benzothiazepin-4(5H)-yl)quinoline-6-carboxamide

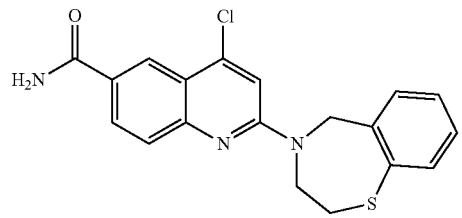 [SMILES: NC(=O)c1ccc2nc(N3CCSc4ccccc4C3)cc(Cl)c2c1]

To a mixture of methyl 4-chloro-2-(2,3-dihydro-1,4-benzothiazepin-4(5H)-yl)quinoline-6-carboxylate (400 mg, 1.04 mmol, prepared in analogy to 4-(4-chloro-6-methylquinolin-2-yl)-8-methoxy-2,3,4,5-tetrahydro-1,4-benzothiazepine in Example 1-1) in tetrahydrofuran (5 mL) and a saturated solution of ammonia in methanol (30 mL) was heated with stirring for 16 hours at 120° C. in a sealed tube. The reaction mixture was concentrated in vacuo to afford 300 mg of the product (yield was 78%).

4-Chloro-2-(1,1-dioxido-2,3-dihydro-1,4-benzothiazepin-4(5H)-yl)quinoline-6-carboxamide

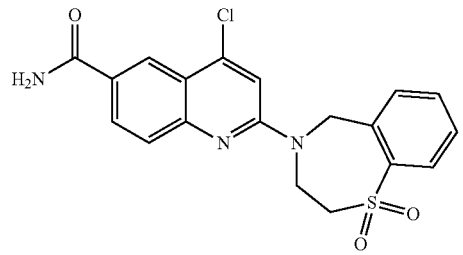 [SMILES: NC(=O)c1ccc2nc(N3CCS(=O)(=O)c4ccccc4C3)cc(Cl)c2c1]

To a cooled solution of 4-chloro-2-(2,3-dihydro-1,4-benzothiazepin-4(5H)-yl)quinoline-6-carboxamide (300 mg, 0.81 mmol) in dichloromethane (50 mL) was added 3-chloroperoxybenzoic acid (418 mg, 70% purity, 1.70 mmol) at 0° C. After being stirred for 2 hours at 0° C., the reaction mixture was washed with a saturated aqueous solution of sodium thiosulphate (50 mL), dried over sodium sulfate, and concentrated in vacuo to afford 300 mg of the crude product.

4-[(3-Aminopropyl)amino]-2-(1,1-dioxido-2,3-dihydro-1,4-benzothiazepin-4(5H)-yl)quinoline-6-carboxamide

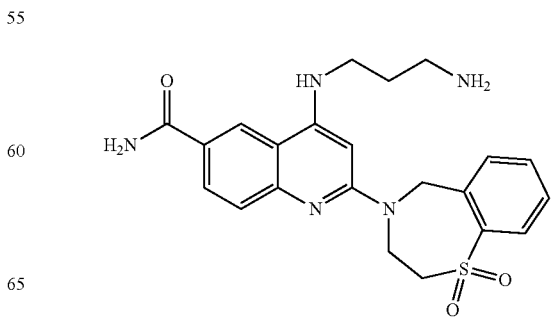

A mixture of 4-chloro-2-(1,1-dioxido-2,3-dihydro-1,4-benzothiazepin-4 (5H)-yl)quinoline-6-carboxamide (300 mg, 0.75 mmol) and propane-1,3-diamine (306 mg, 4.14 mmol) was heated with stirring in a sealed 10 mL of microwave process vial for 1 hour at 120° C. under microwave irradiation. The reaction mixture was purified by preparative HPLC to afford 23.5 mg of the desired product (yield was 7.2%). MS obsd. (ESI+) [(M+H)+] 440, $^1$H NMR (400 MHz, $CD_3OD$) δ ppm 8.70-8.69 (d, J=1.6 Hz, 1 H), 8.18-8.15 (m, 1 H), 8.10-8.08 (dd, J=1.2, 7.6 Hz, 1 H), 7.88-7.84 (t, J=6.8 Hz, 2 H), 7.73-7.72 (m, 1 H), 7.60-7.59 (m, 1 H), 6.01 (s, 1 H), 5.34 (s, 2 H), 4.55 (s, 2 H), 3.75 (s, 2 H), 3.64-3.60 (t, J=6.8 Hz, 1 H), 3.11-3.09 (m, 2 H), 2.18-2.09 (m, 2 H).

Example 82

1-{4-[(3-Aminopropyl)amino]-2-(1,1-dioxido-2,3-dihydro-1,4-benzothiazepin-4(5H)-yl)quinolin-6-yl}ethanol

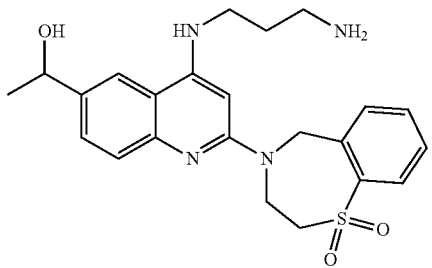 [SMILES: CC(O)c1ccc2nc(N3CCS(=O)(=O)c4ccccc4C3)cc(NCCCN)c2c1]

4-Chloro-2-(1,1-dioxido-2,3-dihydro-1,4-benzothiazepin-4(5H)-yl)quinoline-6-carbaldehyde

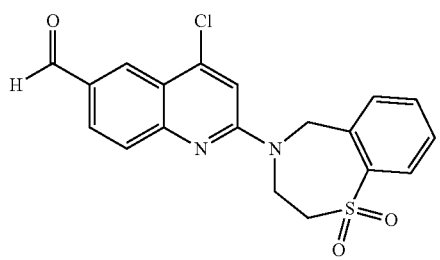 [SMILES: O=Cc1ccc2nc(N3CCS(=O)(=O)c4ccccc4C3)cc(Cl)c2c1]

To a solution of oxalyl dichloride (36.3 mg, 0.29 mmol) in dichloromethane (10 mL) was added a solution of dimethyl sulphoxide (0.1 mL, 0.57 mmol) in dichloromethane (10 mL) at −78° C. dropwise. After the mixture being stirred for 10 minutes at −78° C., a solution of 4-chloro-2-(1,1-dioxido-2,3-dihydro-1,4-benzothiazepin-4(5H)-yl)-quinoline-6-methanol (100 mg, 0.26 mmol, prepared in analogy to the one in Example 3-23) in dichloromethane (5 mL) was added dropwise. After the mixture being stirred for further 1 hour at −78° C., triethylamine (0.2 mL, 1.3 mmol) was. The resulting mixture was stirred at −78° C. for 1 hour and then at room temperature for further 1 hour. The reaction was washed with brine, dried over sodium sulfate and concentrated in vacuo to afford 70 mg of the product.

1-[4-Chloro-2-(1,1-dioxido-2,3-dihydro-1,4-benzothiazepin-4(5H)-yl)quinolin-6-yl]ethanol

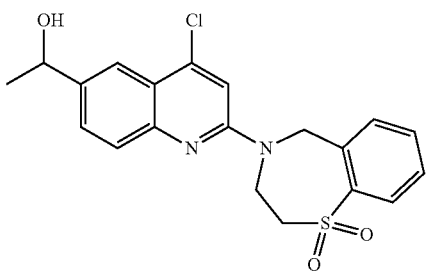 [SMILES: CC(O)c1ccc2nc(N3CCS(=O)(=O)c4ccccc4C3)cc(Cl)c2c1]

To a cooled solution of 4-chloro-2-(1,1-dioxido-2,3-dihydro-1,4-benzothiazepin-4(5H)-yl)-quinoline-6-carbaldehyde (100 mg, 0.26 mmol) in tetrahydrofuran (20 mL) was added a solution of methyl magnesium bromide in tetrahydrofuran (0.13 mL, 0.39 mmol, 3 M) at 0° C. dropwise. After being stirred for 20 minutes at the temperature below 12° C., the mixture was concentrated in vacuo. The residue was purified by preparative TLC to give 100 mg of the desired product (yield was 96%).

1-{4-[(3-Aminopropyl)amino]-2-(1,1-dioxido-2,3-dihydro-1,4-benzothiazepin-4(5H)-yl)quinolin-6-yl}ethanol

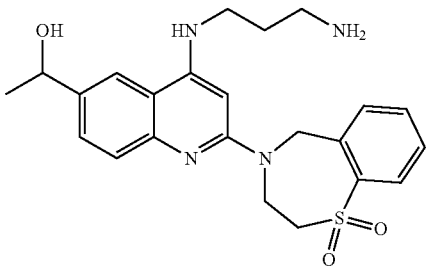 [SMILES: CC(O)c1ccc2nc(N3CCS(=O)(=O)c4ccccc4C3)cc(NCCCN)c2c1]

A mixture of 1-[4-chloro-2-(1,1-dioxido-2,3-dihydro-1,4-benzothiazepin-4(5H)-yl)quinolin-6-yl]ethanol (150 mg, 0.387 mmol) and propane-1,3-diamine (55 mg, 0.74 mmol) was heated with stirring in a sealed 0.5 mL of microwave process vial for 1.5 hours at 150° C. under microwave irradiation. The reaction mixture was purified by preparative HPLC and SPE to afford 70.2 mg of the desired product (yield was 41.2%). MS obsd. (ESI+) [(M+H)+] 441, $^1$H NMR (400 MHz, $CD_3OD$) δ ppm 8.10-8.05 (m, 2 H), 7.86-7.80 (d, J=7.6 Hz, 1 H), 7.78-7.75 (m, 2 H), 7.72-7.62 (t, J=1.2 Hz, 1 H), 7.60-7.50 (t, J=1.2 Hz, 1 H), 5.94 (s, 1 H), 5.30 (s, 2 H), 4.98-4.92 (m, 1 H), 4.58-4.45 (m, 2 H), 3.78-3.70 (t, J=2.8 Hz, 2 H), 3.62-3.53 (t, J=4.4 Hz, 2 H), 3.10-3.02 (t, J=6.8 Hz, 2 H), 2.12-2.02 (m, 2 H), 1.50-1.40 (d, J=6.4 Hz, 3 H).

Example 83

3-{[2-(1,1-Dioxido-2,3-dihydro-1,4-benzothiazepin-4(5H)-yl)-6-methylquinolin-4-yl]amino}propanenitrile

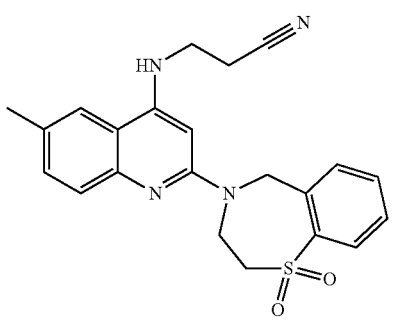 [SMILES: Cc1ccc2nc(N3CCS(=O)(=O)c4ccccc4C3)cc(NCCC#N)c2c1]

A flask containing 4-(4-chloro-6-methylquinolin-2-yl)-2,3,4,5-tetrahydro-1,4-benzothiazepine 1,1-dioxide (500 mg, 1.34 mmol, prepared in analogy to 4-(4-chloro-6-(trifluoromethoxy)quinolin-2-yl)-2,3,4,5-tetrahydro-1,4-benzothiazepine 1,1-dioxide in Example 17-1), 3-aminopropionitrile (140 mg, 2.01 mmol), tris(dibenzylideneacetone)dipalladium(0) (61.8 mg, 0.068 mmol), 2,2'-bis(diphenylphosphino)-1,1'-binaphthyl (83.3 mg, 0.134 mmol), sodium tert-butoxide (257 mg, 2.68 mmol) and toluene (15 ml) was evacuated and then filled with nitrogen (balloon). After being stirred at 110° C. overnight, the resulting mixture was diluted with water (15 mL), and extracted with ethyl acetate (15 mL×4). The combined organic layers were dried over sodium sulfate and concentrated in vacuo. The residue was purified by flash column chromatography (eluting with 10% methanol in dichloromethane) to afford 380 mg of the product as a white solid (yield was 70%). MS obsd. (ESI$^+$) [(M+H)$^+$] 407, $^1$H NMR (400 MHz, CD$_3$OD) δ ppm 8.02-8.00 (m, 1 H), 7.90 (d, J=7.2 Hz, 1 H), 7.69-7.63 (m, 2 H), 7.51-7.45 (m, 2 H), 7.34-7.31 (m, 1 H), 6.10 (s, 1 H), 5.19 (s, 2 H), 4.55 (brs, 2 H), 3.73 (t, J=13.2 Hz, 2 H), 3.63 (t, J=10 Hz, 2 H), 2.85 (t, 2 H), 2.44 (s, 3 H).

Example 84

2-(1,1-Dioxido-2,3-dihydro-1,4-benzothiazepin-4(5H)-yl)-6-methyl-N-[2-(1H-tetrazol-5-yl)ethyl]quinolin-4-amine

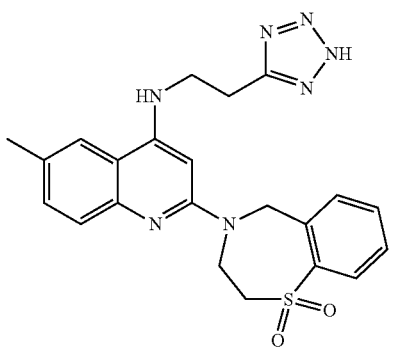 [SMILES: Cc1ccc2nc(N3CCS(=O)(=O)c4ccccc4C3)cc(NCCc3nn[nH]n3)c2c1]

A mixture of 3-{[2-(1,1-dioxido-2,3-dihydro-1,4-benzothiazepin-4(5H)-yl)-6-methylquinolin-4-yl]amino}propanenitrile (100 mg, 0.25 mmol), sodium azide (48 mg, 0.98 mmol), dimethyl formamide (2 ml) and ammonium chloride (52.6 mg, 0.98 mmol) was heated at 80° C. in an oil bath overnight. The resulting mixture was diluted with water and extracted with dichloromethane (10 mL×3). The combined organic layers were washed with brine, dried over sodium sulfate and concentrated in vacuo. The residue was purified by flash column chromatography (eluting with 10% methanol in dichloromethane) to afford 20 mg of the desired product as a white solid. MS obsd. (ESI$^+$) [(M+H)$^+$] 450, $^1$H NMR (400 MHz, CD$_3$OD) δ ppm 8.06 (m, 1 H), 7.92 (t, 1 H), 7.86 (s, 1 H), 7.60 (m, 1 H), 7.58-7.52 (m, 3 H), 5.89 (s, 1 H), 5.27 (s, 2 H), 4.52 (brs, 2 H), 3.86 (t, 2 H), 3.72 (t, 2 H), 3.33 (t, 2 H), 2.47 (s, 3 H).

Example 85

N$^{-4-}$-(2-Aminoethyl)-2-(1,1-dioxido-2,3-dihydro-1,4-benzothiazepin-4(5H)-yl)quinoline-4,6-diamine

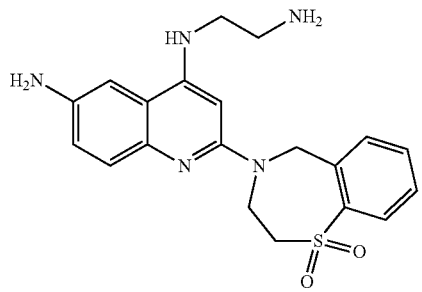 [SMILES: NCCNc1cc(N2CCS(=O)(=O)c3ccccc3C2)nc2ccc(N)cc12]

To a solution of N-[2-(1,1-dioxido-2,3-dihydro-1,4-benzothiazepin-4(5H)-yl)-6-nitroquinolin-4-yl]ethane-1,2-diamine (50 mg, 0.11 mmol, prepared in analogy to N-[2-(1,1-dioxido-2,3-dihydro-1,4-benzothiazepin-4(5H)-yl)-6-methylquinolin-4-yl]ethane-1,2-diamine in Example 9-11) in methanol (20 mL) was added tin(II) chloride (102.8 mg, 0.55 mmol). After being refluxed overnight, the resulting mixture was cooled to room temperature, diluted with dichloromethane, washed with brine, dried over anhydrous sodium sulfate and concentrated in vacuo. The residue was purified by preparative HPLC to afford 11 mg of the desired product (yield was 25%). MS obsd. (ESI$^+$) [(M+H)$^+$] 398, $^1$H NMR (400 MHz, CD$_3$OD) δ ppm 7.95 (d, J=8.08 Hz, 1 H), 7.79 (d, J=7.58 Hz, 1 H), 7.60 (t, J=7.45 Hz, 1 H), 7.47-7.37 (m, 1 H), 7.35 (d, J=8.84 Hz, 1 H), 7.06-6.95 (m, 2 H), 6.00 (s, 1 H), 5.10 (s, 2 H), 3.56 (brs, 2 H), 3.41 (t, J=6.44 Hz, 2 H), 2.96 (t, J=6.44 Hz, 2 H), 1.29 (brs, 2 H).

Example 86

5-[2-(1,1-Dioxido-2,3-dihydro-1,4-benzothiazepin-4(5H)-yl)-6-methylquinolin-4-yl]-2-oxa-5,7-diazaspiro[3.4]octan-6-one

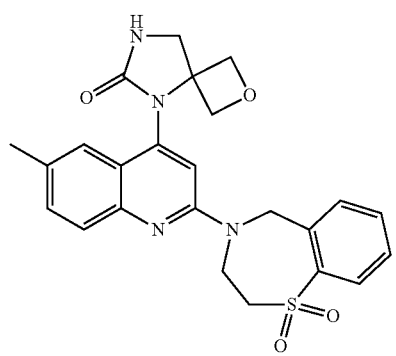 [SMILES: Cc1ccc2nc(N3CCS(=O)(=O)c4ccccc4C3)cc(N3C(=O)NCC34COC4)c2c1]

A mixture of 4-(4-chloro-6-methylquinolin-2-yl)-2,3,4,5-tetrahydro-1,4-benzothiazepine 1,1-dioxide (372 mg, 1.0 mmol, prepared in analogy to the one in Example 17-1), tert-butyl [(3-aminooxetan-3-yl)methyl]carbamate (202 mg, 1.0 mmol), tris(dibenzylideneacetone)dipalladium(0) (91 mg, 0.10 mmol), 2,2'-bis(diphenylphosphino)-1,1'-binaphthyl (62 mg, 0.10 mmol) and sodium tert-buoxide (192 mg, 2.0 mmol) in toluene (10 mL) was heated at 110° C. overnight. The resulting mixture was diluted with water (20 mL), and extracted with dichloromethane (20 mL×3). The combined organic layers were washed with brine (50 mL), dried over sodium sulfate, and concentrated in vacuo. The residue was purified by preparative HPLC to afford 15 mg of the title compound. MS obsd. (ESI$^+$) [(M+H)$^+$] 465, $^1$H NMR (400 MHz, DMSO-d6) δ ppm 8.15 (s, 1 H), 7.98-7.96 (d, J=7.2 Hz, 1 H), 7.90-7.87 (m, 1 H), 7.68-7.64 (m, 1 H), 7.53-7.46 (m, 2 H), 7.37-7.34 (m, 2 H), 7.17 (s, 1 H), 5.14 (s, 2 H), 4.80-4.74 (m, 4 H), 4.44 (s, 2 H), 4.27 (s, 2 H), 3.66-3.64 (t, J=4.8, 4.4 Hz, 2 H), 2.36 (s, 3 H).

Example 87-1

3-{[2-(1,1-Dioxido-2,3-dihydro-1,4-benzothiazepin-4(5H)-yl)-6-methylquinazolin-4-yl]amino}propane-1,2-diol

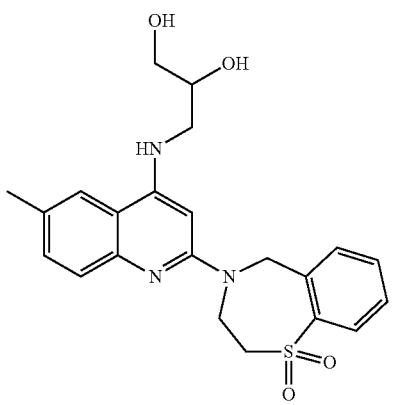 [SMILES: Cc1ccc2nc(N3CCS(=O)(=O)c4ccccc4C3)cc(NCC(O)CO)c2c1]

2-Chloro-N-[(2,2-dimethyl-1,3-dioxolan-4-yl)methyl]-6-methylquinazolin-4-amine

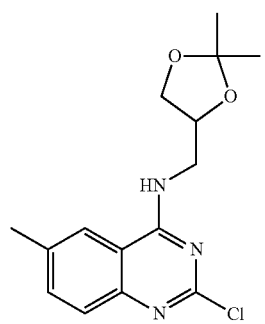

A solution of 2,4-dichloro-6-methylquinazoline (300.0 mg, 1.4 mmol), triethylamine (0.5 mL) and 2,2-dimethyl-1,3-dioxolane-4-methanamine (0.2 mL, 1.5 mmol) in methanol (2.0 mL) was stirred at room temperature for 16 hours. The reaction mixture was diluted with ethyl acetate (100 mL), washed with brine (50 mL×2), dried over anhydrous sodium sulfate and then concentrated in vacuo to afford 431 mg of the crude product as a white solid. MS obsd. (ESI$^+$) [(M+H)$^+$] 308.

3-{[2-(1,1-Dioxido-2,3-dihydro-1,4-benzothiazepin-4(5H)-yl)-6-methylquinazolin-4-yl]amino}propane-1,2-diol

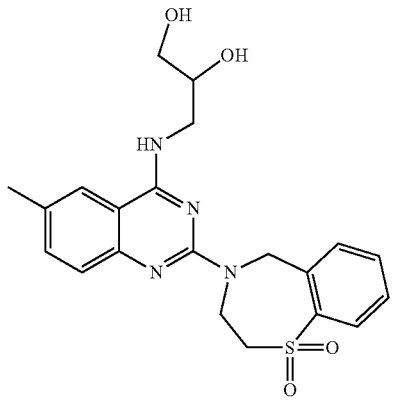 [SMILES: Cc1ccc2nc(N3CCS(=O)(=O)c4ccccc4C3)nc(NCC(O)CO)c2c1]

A solution of 2-chloro-N-[(2,2-dimethyl-1,3-dioxolan-4-yl)methyl]-6-methylquinazolin-4-amine (431.2 mg, 1.4 mmol) and triethylamine (0.8 mL), 2,3,4,5-tetrahydro-1,4-benzothiazepine 1,1-dioxide (296.1 mg, 1.5 mmol) in N,N-dimethyl-formamide (1.0 mL) was stirred at 160° C. for 4 hours. After being cooled to room temperature, the reaction mixture was dissolved in methanol (2.0 mL). To the above mixture, concentrated hydrochloric acid (0.5 mL) was added, and the resulting mixture was stirred at room temperature for 1 hour, and then extracted with ethyl acetate (100 mL). The organic layer was washed with brine (50 mL×2), dried over anhydrous sodium sulfate and concentrated in vacuo. The residue was purified by preparative HPLC to afford 59.2 mg of the product as a white solid (yield was 10%). MS obsd. (ESI$^+$) [(M+H)$^+$] 429, $^1$H NMR (400 MHz, CD$_3$OD) δ ppm 7.98 (dd, J=7.83, 1.01 Hz, 1 H), 7.90 (d, J=7.58 Hz, 1 H), 7.66-7.55 (m, 2 H), 7.50-7.35 (m, 2 H), 7.35-7.28 (m, 1 H), 5.21 (brs, 2 H), 4.56 (brs, 2 H), 4.05-3.95 (m, 1 H), 3.86 (dd, J=13.26, 4.42 Hz, 1 H), 3.73-3.56 (m, 3 H), 3.53 (t, J=5.05 Hz, 2 H), 2.39 (s, 3 H).

Example 87-2

3-[6-Chloro-2-(1,1-Dioxido-2,3-dihydro-1,4-benzothiazepin-4(5H)-yl))-quinazolin-4-ylamino]-propane-1,2-diol

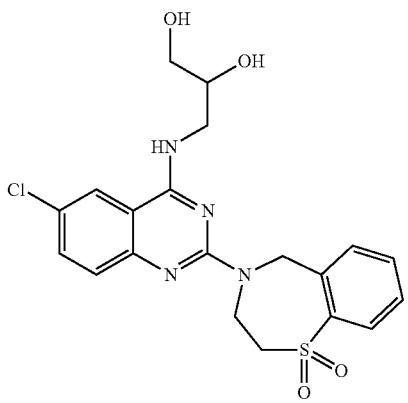 [SMILES: O=S1(=O)CCN(c2nc(NCC(O)CO)c3cc(Cl)ccc3n2)Cc2ccccc21]

The title compound was prepared in analogy to Example 87-1 in Scheme 41 by using 2,4,6-trichloroquinazoline, 2,2-dimethyl-1,3-dioxolane-4-methanamine and 2,3,4,5-tetrahydro-1,4-benzothiazepine 1,1-dioxide. MS obsd. (ESI+) [(M+H)+] 449, ¹H NMR (400 MHz, CD₃OD) δ ppm 7.98 (d, J=7.83 Hz, 1 H), 7.95-7.84 (m, 2 H), 7.62 (t, J=7.33 Hz, 1 H), 7.53-7.41 (m, 2 H), 7.37 (d, J=8.84 Hz, 1 H), 5.21 (brs, 2 H), 4.61 (brs, 2 H), 4.01 (brs, 1 H), 3.85 (brs, 1 H), 3.65 (brs, 3 H), 3.52 (t, J=4.67 Hz, 3 H).

Example 88-1

N-[2-(2,3-Dihydro-1,4-benzothiazepin-4(5H)-yl)-6-methylquinazolin-4-yl]ethane-1,2-diamine

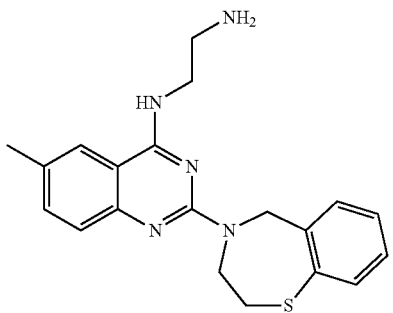 [SMILES: Cc1ccc2nc(N3CCSc4ccccc4C3)nc(NCCN)c2c1]

tert-Butyl {2-[(2-chloro-6-methylquinazolin-4-yl)amino]ethyl}carbamate

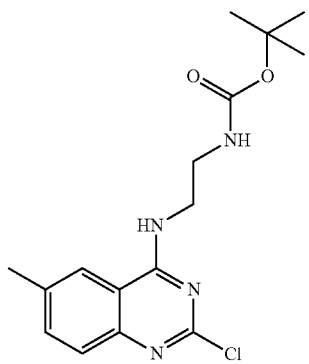 [SMILES: Cc1ccc2nc(Cl)nc(NCCNC(=O)OC(C)(C)C)c2c1]

A mixture of 2,4-dichloro-6-methylquinazoline (700 mg, 3.29 mmol), tert-butyl N-(2-aminoethyl)carbamate (2.6 g, 16.4 mmol) and methanol (35 mL) was stirred at room temperature for 1 hour. The resulting mixture was concentrated in vacuo and the residue was purified by flash column chromatography to afford 1.0 g of the product as a white solid (yield was 91%).

tert-Butyl {2-[2-(2,3-dihydro-1,4-benzothiazepin-4(5H)-yl)-6-methylquinazolin-4-yl]amino ethyl}carbamate

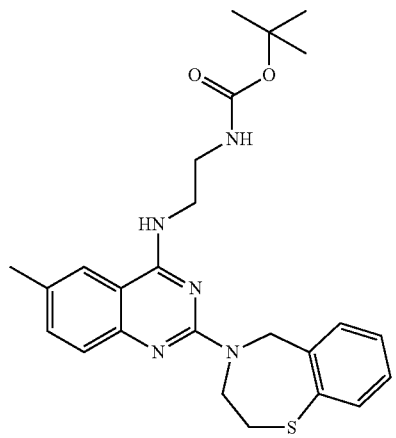 [SMILES: Cc1ccc2nc(N3CCSc4ccccc4C3)nc(NCCNC(=O)OC(C)(C)C)c2c1]

To a solution of tert-butyl {2-[(2-chloro-6-methylquinazolin-4-yl)amino]ethyl}carbamate (460 mg, 1.366 mmol) in n-butanol (6 mL) was added 2,3,4,5-tetrahydro-1,4-benzothiazepine (248 mg, 1.50 mmol) and triethylamine (276 mg, 2.732 mmol). The mixture was heated with stirring at 100° C. in a sealed tube for 4 hours, and then concentrated in vacuo. The residue was purified by flash column chromatography to afford 350 mg of the desired product as a white solid (yield was 55%).

N-[2-(2,3-Dihydro-1,4-benzothiazepin-4(5H)-yl)-6-methylquinazolin-4-yl]ethane-1,2-diamine

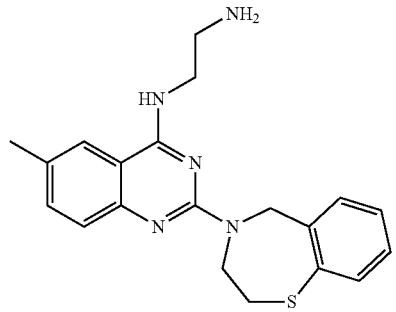 [SMILES: Cc1ccc2nc(N3CCSc4ccccc4C3)nc(NCCN)c2c1]

To a cooled solution of trifluoroacetic acid in dichloromethane (2 mL, V/V=1/4) was added tert-butyl {2-[2-(2,3-dihydro-1,4-benzothiazepin-4(5H)-yl)-6-methylquinazolin-4-yl]aminoethyl}carbamate (120 mg, 0.258 mmol) in an ice bath. The mixture was stirred for 3 hours whilst allowing the temperature of the mixture rising naturally to room temperature, and then concentrated in vacuo. The residue was dissolved in water (10 mL), and washed with dichloromethane (10 mL). The aqueous layer was adjusted to pH 10 with a saturated aqueous solution of sodium carbonate and extracted with ethyl acetate (20 mL×2). The organic extracts were dried with sodium sulfate, concentrated in vacuo to afford 68 mg of the product as a white solid (yield was 72%). MS obsd. (ESI$^+$) [(M+H)$^+$] 366, $^1$H NMR (400 MHz, CD$_3$OD) δ ppm 7.67-7.64 (t, J=12.0 Hz, 2 H), 7.49-7.47 (d, J=8.4 Hz, 1 H), 7.38-7.30 (m, 2 H), 7.23-7.19 (dd, J=8.4, 7.6 Hz, 2 H), 7.13-7.09 (dd, J=8.8 Hz, 1 H), 5.04 (s, 2 H), 4.38 (s, 2 H), 3.75-3.72 (m, 2 H), 2.98-2.92 (m, 4 H), 2.39 (s, 3 H).

Example 88-2

(1-Amino-cyclopropylmethyl)-[6-methyl-2-(1-oxido-2,3-dihydro-1,4-benzothiazepin-4(5H)-yl)-quinolin-4-yl]-amine

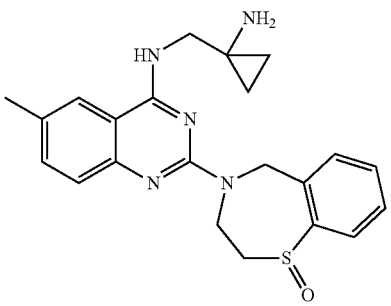 [SMILES: Cc1ccc2nc(N3CCS(=O)c4ccccc4C3)nc(NCC3(N)CC3)c2c1]

The title compound was prepared in analogy to Example 88-1 in Scheme 42 by using 2,4-dichloro-6-methylquinazoline, tert-butyl [1-(aminomethyl)cyclopropyl]carbamate and 2,3,4,5-tetrahydro-1,4-benzothiazepine 1-oxide. MS obsd. (ESI$^+$) [(M+H)$^+$] 408, $^1$H NMR (400 MHz, CDCl$_3$) δ ppm 7.766-7.748 (d, J=7.2 Hz, 1 H), 7.632 (s, 1 H), 7.410-7.328 (m, 5 H), 5.936 (s, 1 H), 5.333-5.295 (d, J=15.2 Hz, 1 H), 4.924 (m, 2 H), 4.400 (s, 1 H), 3.644 (s, 2 H), 3.332 (s, 2 H), 2.398 (s, 3 H), 0.740-0.678 (m, 4 H).

Example 89

N-[6-Methyl-2-(1-oxido-2,3-dihydro-1,4-benzothiazepin-4(5H)-yl)quinazolin-4-yl]ethane-1,2-diamine

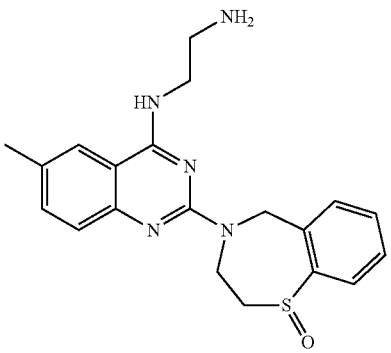 [SMILES: Cc1ccc2nc(N3CCS(=O)c4ccccc4C3)nc(NCCN)c2c1]

tert-Butyl {2-[2-(1-oxido-2,3-dihydro-1,4-benzothiazepin-4(5H)-yl)-6-methylquinazolin-4-yl]amino ethyl}carbamate

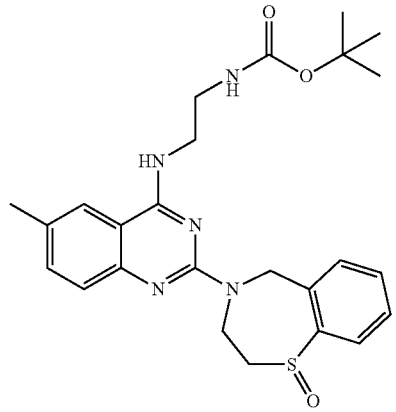 [SMILES: Cc1ccc2nc(N3CCS(=O)c4ccccc4C3)nc(NCCNC(=O)OC(C)(C)C)c2c1]

To a solution of oxone (120 mg, 0.200 mmol) in water (0.7 mL) which was cooled below 0° C. in an ice bath, was added a solution of tert-butyl {2-[2-(2,3-dihydro-1,4-benzothiazepin-4(5H)-yl)-6-methylquinazolin-4-yl] aminoethyl}carbamate (155 mg, 0.333 mmol) in methanol (3 mL) dropwise. The mixture was stirred below 0° C. about 20 minutes. The formed precipitate was collected by filtration, washed with water and purified by flash column chromatography to afford 124 mg of the product as a white solid (yield was 77%).

N-[6-Methyl-2-(1-oxido-2,3-dihydro-1,4-benzothiazepin-4(5H)-yl)quinazolin-4-yl]ethane-1,2-diamine

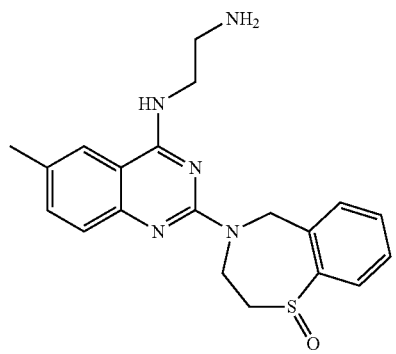 [SMILES: Cc1ccc2nc(N3CCS(=O)c4ccccc4C3)nc(NCCN)c2c1]

The title compound was prepared in analogy to Example 88-1 in Scheme 42 by using tert-butyl {2-[2-(1-oxido-2,3-dihydro-1,4-benzothiazepin-4(5H)-yl)-6-methylquinazolin-4-yl]aminoethyl}carbamate (150 mg, yield was 86%). MS obsd. (ESI$^+$) [(M+H)$^+$] 382, $^1$H NMR (400 MHz, CD$_3$OD) δ ppm 7.74-7.72 (t, J=8.0 Hz, 2 H), 7.66-7.62 (d, J=16.0 Hz, 1 H), 7.49-7.44 (m, 2 H), 7.42-7.40 (m, 1 H), 7.38-7.33 (m, 1 H), 5.29-5.25 (d, J=16.0 Hz, 1 H), 4.81-4.70 (m, 1 H), 4.58-4.51 (m, 1 H), 3.79-3.70 (m, 2 H), 3.53-3.34 (m, 4 H), 3.03-3.00 (m, 2 H), 2.40 (s, 3 H).

Example 90

N-[2-(1,1-Dioxido-2,3-dihydro-1,4-benzothiazepin-4(5H)-yl)-6-methylquinazolin-4-yl]ethane-1,2-diamine

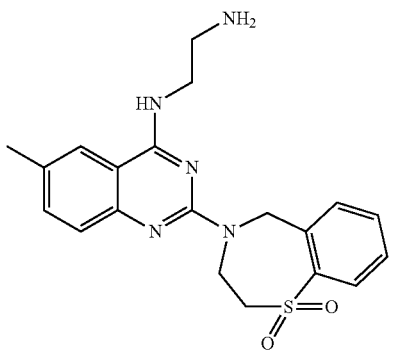 [SMILES: Cc1ccc2nc(N3CCS(=O)(=O)c4ccccc4C3)nc(NCCN)c2c1]

tert-Butyl {2-[2-(1,1-dioxido-2,3-dihydro-1,4-benzothiazepin-4(5H)-yl)-6-methylquinazolin-4-yl]aminoethyl}carbamate

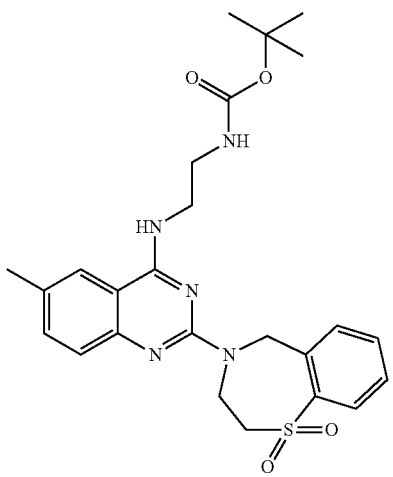 [SMILES: Cc1ccc2nc(N3CCS(=O)(=O)c4ccccc4C3)nc(NCCNC(=O)OC(C)(C)C)c2c1]

To a solution of tert-butyl {2-[2-(2,3-dihydro-1,4-benzothiazepin-4(5H)-yl)-6-methylquinazolin-4-yl]aminoethyl}carbamate (190 mg, 0.408 mmol) in dichloromethane (10 mL) was added dropwise a solution of 3-chloroperbenzoic acid (228.6 mg, 1.02 mmol) in dichloromethane (6 mL) in an ice bath. After the mixture being stirred in an ice bath for 2 hours, the reaction was quenched by the addition of a saturated aqueous solution of sodium thiosulphate. The separated organic layer was washed by a saturated aqueous solution of sodium bicarbonate and brine, dried over anhydrous sodium sulfate, and concentrated in vacuo. The residue was purified by flash column chromatography (eluting with 20-40% ethyl acetate in petroleum ether) to give 170 mg of the product.

N-[2-(1,1-Dioxido-2,3-dihydro-1,4-benzothiazepin-4(5H)-yl)-6-methylquinazolin-4-yl]ethane-1,2-diamine

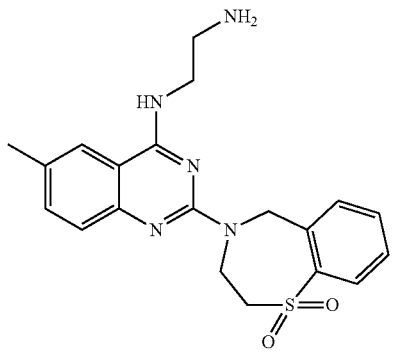 [SMILES: Cc1ccc2nc(N3CCS(=O)(=O)c4ccccc4C3)nc(NCCN)c2c1]

The title compound was prepared in analogy to Example 88-1 in Scheme 42 by using tert-butyl {2-[2-(1,1-dioxido-2,3-dihydro-1,4-benzothiazepin-4(5H)-yl)-6-methylquinazolin-4-yl]aminoethyl}carbamate. MS obsd. (ESI$^+$) [(M+H)$^+$] 398, $^1$H NMR (400 MHz, CD$_3$OD) δ ppm 7.98 (d, J=6.8 Hz, 1 H), 7.83 (d, J=7.6 Hz, 1 H), 7.65 (s, 1 H), 7.61 (dd, J=6.8, 7.6 Hz, 1 H), 7.44 (t, J=7.2 Hz, 1 H), 7.38 (dd, J=1.6, 8.4 Hz, 1 H), 7.31 (d, J=8.4 Hz, 1 H), 5.20 (s, 2 H), 4.58 (brs, 2 H), 3.73 (t, J=6.4 Hz, 2 H), 3.54-3.48 (m, 2 H), 2.97 (t, J=6.4 Hz, 2 H), 2.39 (s, 3 H).

Example 91

N-[3-(Aminomethyl)oxetan-3-yl]-6-methyl-2-(1-oxido-2,3-dihydro-1,4-benzothiazepin-4(5H)-yl)quinazolin-4-amine

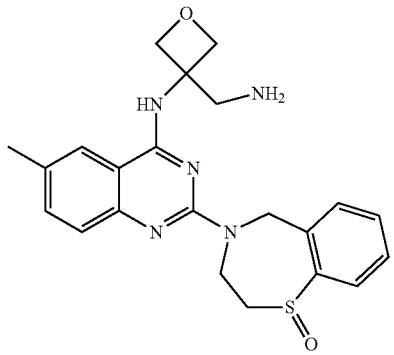 [SMILES: Cc1ccc2nc(N3CCS(=O)c4ccccc4C3)nc(NC3(CN)COC3)c2c1]

2,2,2-Trifluoro-N-[(3-{[6-methyl-2-(1-oxido-2,3-dihydro-1,4-benzothiazepin-4(5H)-yl)quinazolin-4-yl]amino}oxetan-3-yl)methyl]acetamide

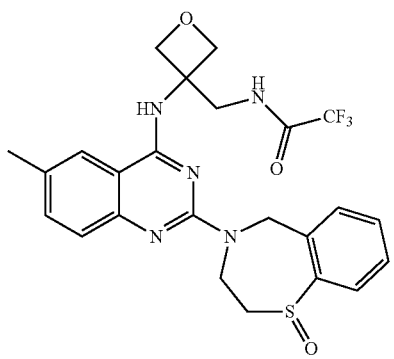 [SMILES: Cc1ccc2nc(N3CCS(=O)c4ccccc4C3)nc(NC3(CNC(=O)C(F)(F)F)COC3)c2c1]

The title compound was prepared as a light white solid in analogy to Example 62-1 in Scheme 23 by using 2-chloro-6-methylquinazolin-4(3H)-one, 2,3,4,5-tetrahydro-1,4-benzothiazepine 1-oxide and N-[(3-aminooxetan-3-yl)methyl]-2,2,2-trifluoroacetamide (yield was 80%).

N-[3-(Aminomethyl)oxetan-3-yl]-6-methyl-2-(1-oxido-2,3-dihydro-1,4-benzothiazepin-4(5H)-yl)quinazolin-4-amine

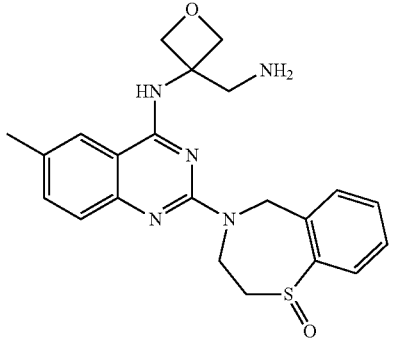 [SMILES: Cc1ccc2nc(N3CCS(=O)c4ccccc4C3)nc(NC3(CN)COC3)c2c1]

To a stirred of 2,2,2-trifluoro-N-[(3-{[6-methyl-2-(1-oxido-2,3-dihydro-1,4-benzothiazepin-4(5H)-yl)quinazolin-4-yl]amino}oxetan-3-yl)methyl]acetamide (70 mg, 0.135 mmol) in ethanol (5 mL) was added an aqueous solution of sodium hydroxide (5 N, 1 mL). After being stirred at room temperature overnight, the resulting mixture was diluted with water (15 mL), and extracted with dichloromethane (15 mL×3). The organic layers were combined, washed with brine, dried over sodium sulfate, and concentrated in vacuo. The residue was purified by preparative HPLC to afford 7 mg of the desired product as a white solid. MS obsd. (ESI$^+$) [(M+H)$^+$] 424, $^1$H NMR (400 MHz, CD$_3$OD) δ ppm 7.97 (s, 1 H), 7.83-7.78 (m, 2 H), 7.71-7.68 (m, 1 H), 7.61-7.54 (m, 3 H), 5.45 (d, 1 H), 5.15 (brs, 1 H), 4.81-4.74 (m, 5 H), 4.51 (brs, 3 H), 3.54 (brs, 2 H), 2.45 (s, 3 H).

Example 92-1

N-(trans-4-Fluoropyrrolidin-3-yl)-6-methyl-2-(1-oxido-2,3-dihydro-1,4-benzothiazepin-4(5H)-yl)quinazolin-4-amine

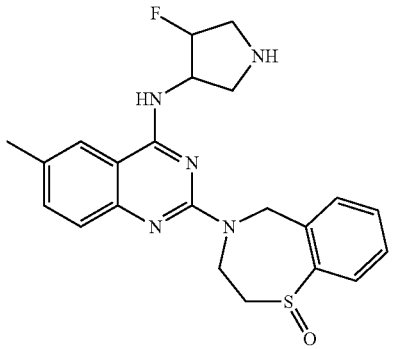 [SMILES: Cc1ccc2nc(N3CCS(=O)c4ccccc4C3)nc(NC3CNCC3F)c2c1]

Benzyl trans-3-fluoro-4-{[6-methyl-2-(1-oxido-2,3-dihydro-1,4-benzothiazepin-4 (5H)-yl)quinazolin-4-yl]amino}pyrrolidine-1-carboxylate

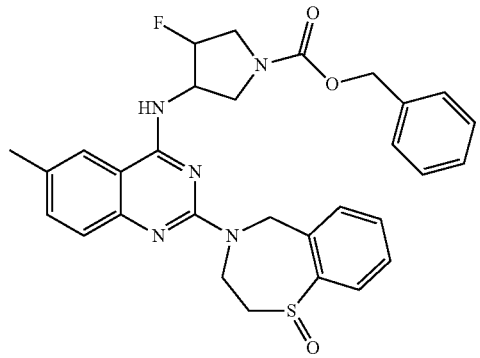 [SMILES: Cc1ccc2nc(N3CCS(=O)c4ccccc4C3)nc(NC3CN(C(=O)OCc4ccccc4)CC3F)c2c1]

A suspension of 6-methyl-2-(1-oxido-2,3-dihydro-1,4-benzothiazepin-4 (5H)-yl)quinazolin-4(3H)-one (600 mg, 1.77 mmol, prepared in analogy to the one in Example 91), benzotriazol-1-yloxytris(dimethylamino)phosphonium hexafluorophosphate (1.02 g, 2.3 mmol), and 1,8-diazabicyclo[5.4.0]undec-7-ene (400 mg, 2.6 mmol) in anhydrous N,N-dimethylformamide (10 mL) was stirred at room temperature for 10 minutes. Then a solution of benzyl trans-3-amino-4-fluoropyrrolidine-1-carboxylate (500 mg, 2.1 mmol) in N,N-dimethylformamide (5 mL) was added dropwise. After being heated at 60° C. overnight, the mixture was diluted with water (50 mL), extracted with dichloromethane (50 mL). The organic layer was washed with brine, dried over anhydrous sodium sulfate, and concentrated in vacuo. The residue was purified by flash column chromatography (gradient eluting with 10% to 25% ethyl acetate in dichloromethane) to afford 415 mg of the desired product as a yellow solid (yield was 41.8%).

N-(trans-4-Fluoropyrrolidin-3-yl)-6-methyl-2-(1-oxido-2,3-dihydro-1,4-benzothiazepin-4 (5H)-yl)quinazolin-4-amine

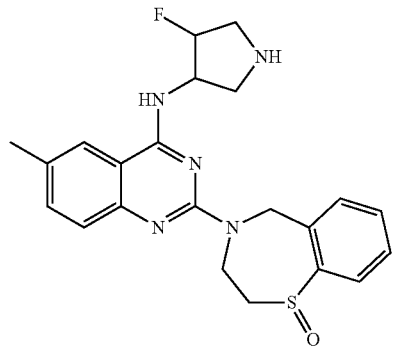 [SMILES: Cc1ccc2nc(N3CCS(=O)c4ccccc4C3)nc(NC3CNCC3F)c2c1]

A mixture of benzyl trans-3-fluoro-4-{[6-methyl-2-(1-oxido-2,3-dihydro-1,4-benzothiazepin-4(5H)-yl)quinazolin-4-yl]amino}pyrrolidine-1-carboxylate (200 mg, 0.35 mmol) and an aqueous solution of hydrochloric acid (5 mL, 6 N) was refluxed for 6 hours. The resulting mixture was basified by adding an aqueous solution of sodium hydroxide (1 N) to pH 10, and then extracted with dichloromethane (50 mL). The organic layer was washed with brine, dried over anhydrous sodium sulfate and concentrated in vacuo. The residue was purified by preparative HPLC to afford the desired compound as a yellow solid. MS obsd. (ESI+) [(M+H)+] 426, ¹H NMR (400 MHz, CD₃OD) δ ppm 7.76 (m, 3 H), 7.45 (m, 4 H), 5.32 (m, 3 H), 4.61 (s, 3 H), 3.70-3.11 (m, 6 H), 2.41 (s, 3 H).

Example 92-2

N-(trans-4-Fluoropyrrolidin-3-yl)-6-methyl-2-(1,1-dioxido-2,3-dihydro-1,4-benzothiazepin-4(5H)-yl)quinazolin-4-amine

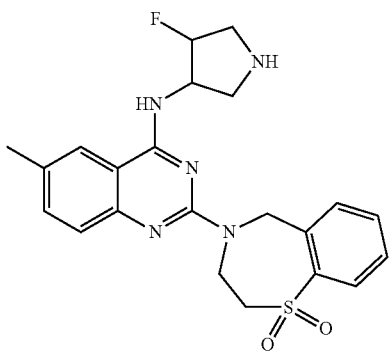 [SMILES: Cc1ccc2nc(N3CCS(=O)(=O)c4ccccc4C3)nc(NC3CNCC3F)c2c1]

The title compound was prepared in analogy to Example 92-1 in Scheme 44 by using 6-methyl-2-(1,1-dioxido-2,3-dihydro-1,4-benzothiazepin-4(5H)-yl)quinazolin-4(3H)-one (prepared in analogy to 6-methyl-2-(1-oxido-2,3-dihydro-1,4-benzothiazepin-4(5H)-yl)quinazolin-4(3H)-one in Example 91) and benzyl trans-3-amino-4-fluoropyrrolidine-1-carboxylate. MS obsd. (ESI+) [(M+H)+] 442, ¹H NMR (400 MHz, CDCl₃) δ ppm 8.40-8.02 (d, J=7.6 Hz, 1 H), 7.83-7.81 (d, J=7.2 Hz, 1 H), 7.52-7.49 (m, 1 H), 7.37-7.35 (d, J=10.8 Hz, 3 H), 7.22 (s, 1 H), 5.41 (s, 1 H), 5.30-5.00 (brs, 2 H), 4.90-4.55 (brs, 2 H), 3.70-3.68 (d, J=5.2 Hz, 1 H), 3.48 (s, 2 H), 3.31-3.25 (brs, 2 H) 2.95 (s, 1 H), 2.38 (s, 3 H), 2.20-2.18 (d, J=8.8 Hz, 1 H).

Example 93-1

1-[6-Methyl-2-(1-oxido-2,3-dihydro-1,4-benzothiazepin-4(5H)-yl)quinazolin-4-yl]pyrrolidin-3-amine

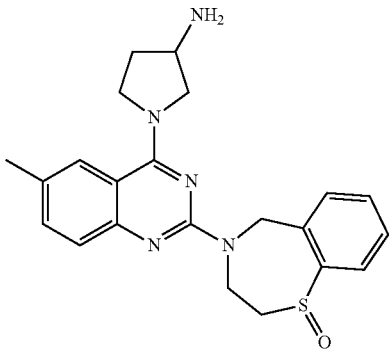 [SMILES: Cc1ccc2nc(N3CCS(=O)c4ccccc4C3)nc(N3CCC(N)C3)c2c1]

tert-Butyl {1-[6-methyl-2-(1-oxido-2,3-dihydro-1,4-benzothiazepin-4(5H)-yl)quinazolin-4-yl]pyrrolidin-3-yl}carbamate

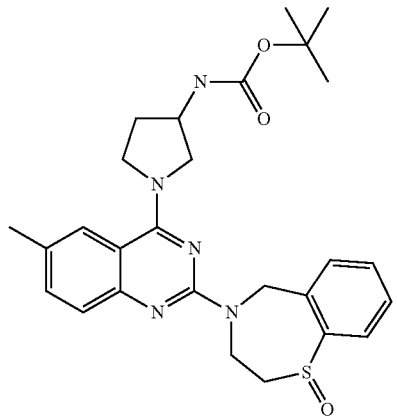 [SMILES: Cc1ccc2nc(N3CCS(=O)c4ccccc4C3)nc(N3CCC(NC(=O)OC(C)(C)C)C3)c2c1]

The title compound was prepared in analogy to benzyl (3S,4S)-3-fluoro-4-{[6-methyl-2-(1-oxido-2,3-dihydro-1,4-benzothiazepin-4(5H)-yl)quinazolin-4-yl]amino}pyrrolidine-1-carboxylate in Example 92 by using 6-methyl-2-(1-oxido-2,3-dihydro-1,4-benzothiazepin-4(5H)-yl)quinazolin-4(3H)-one and tert-butyl (pyrrolidin-3-yl)carbamate.

1-[6-Methyl-2-(1-oxido-2,3-dihydro-1,4-benzothiazepin-4(5H)-yl)quinazolin-4-yl]pyrrolidin-3-amine

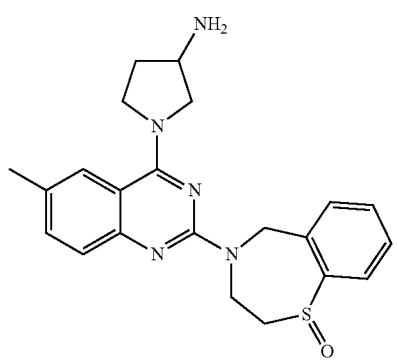 [SMILES: Cc1ccc2nc(N3CCS(=O)c4ccccc4C3)nc(N3CCC(N)C3)c2c1]

The title compound was prepared in analogy to Example 90 in Scheme 44 by using tert-butyl {1-[6-methyl-2-(1-oxido-2,3-dihydro-1,4-benzothiazepin-4(5H)-yl)quinazolin-4-yl]pyrrolidin-3-yl}carbamate. MS obsd. (ESI+) [(M+H)+] 408, ¹H NMR (400 MHz, CD₃OD) δ ppm 7.73 (s, 1 H), 7.64 (dd, J=7.2, 1.6 Hz, 2 H), 7.41-7.28 (m, 4 H), 5.16 (d, J=15.2 Hz, 1 H), 4.70 (m, 2 H), 4.39 (s, 1 H), 3.86 (m, 2 H), 3.59 (m, 2 H), 3.37 (brs, 1 H), 2.31 (s, 3 H), 2.15 (m, 1 H), 1.82 (m, 1 H), 1.24 (brs, 1 H).

Example 93-2

N-(Azetidin-3-yl)-6-methyl-2-(1,1-dioxido-2,3-dihydro-1,4-benzothiazepin-4(5H)-yl)quinazolin-4-amine

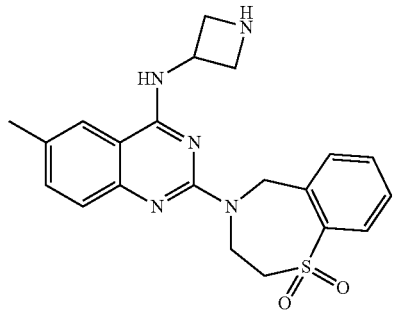 [SMILES: Cc1ccc2nc(N3CCS(=O)(=O)c4ccccc4C3)nc(NC3CNC3)c2c1]

The title compound was prepared in analogy to Example 93-1 in Scheme 44 by using 6-methyl-2-(1,1-dioxido-2,3-dihydro-1,4-benzothiazepin-4(5H)-yl)quinazolin-4(3H)-one and tert-butyl 3-aminoazetidine-1-carboxylate. MS obsd. (ESI$^+$) [(M+H)$^+$] 410.1, $^1$H NMR (400 MHz, DMSO-d6) δ ppm 8.24 (s, 1 H), 7.87 (s, 2 H), 7.79 (s, 1 H), 7.62 (brs, 1 H), 7.45 (s, 1 H), 7.34 (d, J=8.4 Hz, 1 H), 7.22 (brs, 1 H), 5.06-4.42 (m, 5 H), 3.85 (brs, 1 H), 3.59 (m, 5 H), 2.32 (s, 3 H).

Example 94

(4R)-4-{2-[2-(1,1-Dioxido-2,3-dihydro-1,4-benzothiazepin-4(5H)-yl)-6-methylquinolin-4-yl]ethyl}-4,5-dihydro-1,3-oxazol-2-amine

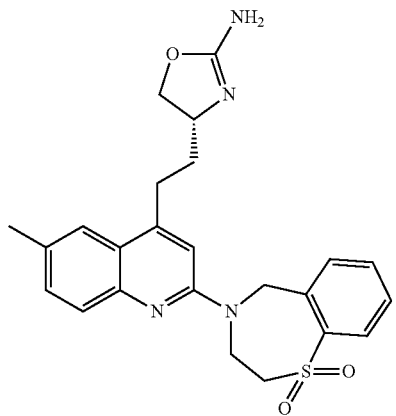 [SMILES: Cc1ccc2nc(N3CCS(=O)(=O)c4ccccc4C3)cc(CC[C@@H]3COC(N)=N3)c2c1]

tert-Butyl (4R)-4-{(2E)-[2-(1,1-dioxido-2,3-dihydro-1,4-benzothiazepin-4(5H)-yl)-6-methylquinolin-4-yl]-vinyl}-2,2-dimethyl-1,3-oxazolidine-3-carboxylate

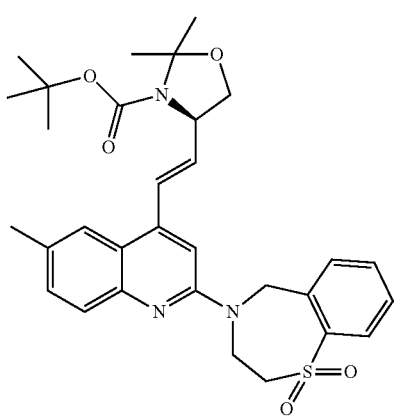 [SMILES: Cc1ccc2nc(N3CCS(=O)(=O)c4ccccc4C3)cc(/C=C/[C@@H]3COC(C)(C)N3C(=O)OC(C)(C)C)c2c1]

To a vial containing a mixture of 4-(4-chloro-6-methylquinolin-2-yl)-2,3,4,5-tetrahydro-1,4-benzothiazepine 1,1-dioxide (200 mg, 0.536 mmol, prepared in analogy to 4-(4-chloro-6-(trifluoromethoxy)quinolin-2-yl)-2,3,4,5-tetrahydro-1,4-benzothiazepine 1,1-dioxide in Example 17-1), tert-butyl (4R)-4-ethenyl-2,2-dimethyl-1,3-oxazolidine-3-carboxylate (146 mg, 0.643 mmol), triethylamine (0.5 mL) and N,N-dimethylformamide (1 mL), which was evacuated and filled with argon, di(tri-tert-butylphosphine)palladium (0) (13.7 mg, 0.0268 mmol) was added. The vial was caped and heated at 110° C. for 30 minutes under microwave irradiation. The reaction mixture was poured into water (30 mL) and extracted with ethyl acetate (20 mL×3). The organic layers were combined, washed with brine, dried over sodium sulfate and concentrated in vacuo. The residue was purified by flash column chromatography (eluting with 50% ethyl acetate in hexanes) to afford 180 mg of the desired product as a white solid (yield was 60%).

(3R)-2-Amino-4-[2-(1,1-dioxido-2,3-dihydro-1,4-benzothiazepin-4(5H)-yl))-6-methyl-quinolin-4-yl]-butan-1-ol

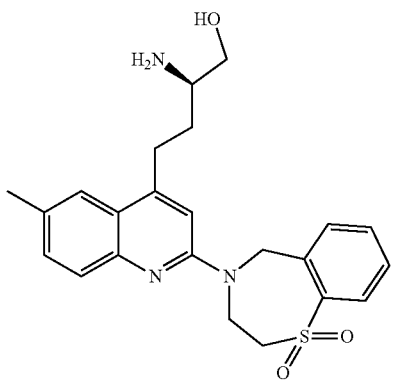 [SMILES: Cc1ccc2nc(N3CCS(=O)(=O)c4ccccc4C3)cc(CC[C@@H](N)CO)c2c1]

A solution of tert-butyl (4R)-4-{(2E)-[2-(1,1-dioxido-2,3-dihydro-1,4-benzothiazepin-4(5H)-yl)-6-methylquinolin-4-yl]-vinyl}-2,2-dimethyl-1,3-oxazolidine-3-carboxylate (180 mg, 0.32 mmol) in methanol was hydrogenated over 10% palladium on carbon (30 mg) under atmospheric pressure for 2 hours at room temperature. The reaction mixture was filtered and the filtrate was concentrated in vacuo. The residue was dissolved in a solution of hydrochloride in ethyl acetate (2 N, 10 mL) and the solution was stirred at room temperature for 2 hours. The reaction mixture was basified with an aqueous solution of sodium bicarbonate (2 N) to pH 8 and then extracted with ethyl acetate (15 mL×3). The combined layers was dried over sodium sulfate and concentrated in vacuo. The residue was purified by flash column chromatography (eluting with 10% methanol in dichloromethane) to afford 90 mg of the desired product as a white solid (yield was 66.2%).

(4R)-4-{2-[2-(1,1-Dioxido-2,3-dihydro-1,4-benzothiazepin-4(5H)-yl)-6-methylquinolin-4-yl]ethyl}-4,5-dihydro-1,3-oxazol-2-amine

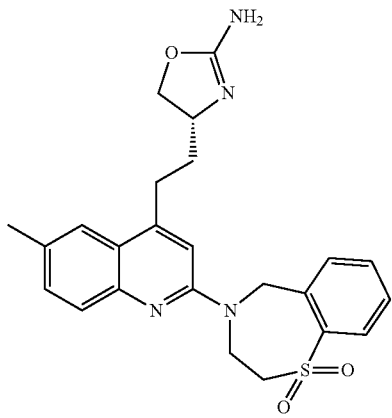 [SMILES: Cc1ccc2nc(N3CCS(=O)(=O)c4ccccc4C3)cc(CC[C@@H]3COC(N)=N3)c2c1]

The title compound was prepared in analogy to Example 38-1 in Scheme 45 by using (3R)-2-amino-4-[2-(1,1-dioxido-2,3-dihydro-1,4-benzothiazepin-4(5H)-yl))-6-methylquinolin-4-yl]-butan-1-ol and cyanogen bromide. MS obsd. (ESI+) [(M+H)+] 451, ¹H NMR (400 MHz, DMSO-d6) δ ppm 7.89 (m, J=4.7 Hz, 2 H), 7.72 (s, 1 H), 7.63 (t, J=3.7 Hz, 1 H), 7.47 (t, J=3.9 Hz, 1 H), 7.32 (d, J=2.1 Hz, 1 H), 7.23 (d, J=2.1 Hz, 1 H), 6.85 (t, J=2.6 Hz, 1 H), 6.10 (s, 1 H), 5.15 (s, 2 H), 4.53 (brs, 2 H), 3.97-3.91 (m, J=5.8 Hz, 2 H), 3.58 (t, J=2.4 Hz, 2 H), 3.66-3.41 (m, J=3.3 Hz, 2 H), 2.90 (dd, J=4.2, 0.9, Hz, 1 H), 2.77 (dd, J=5.2, 0.9 Hz, 1 H), 2.42 (s, 3 H).

Example 95

3-[2-(1,1-Dioxido-2,3-dihydro-1,4-benzothiazepin-4(5H)-yl)-6-ethylquinolin-4-yl]propanoic acid

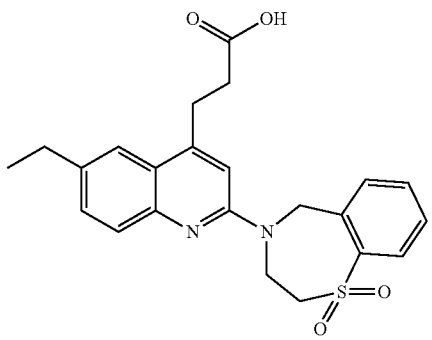 [SMILES: CCc1ccc2nc(N3CCS(=O)(=O)c4ccccc4C3)cc(CCC(=O)O)c2c1]

Ethyl (2E)-3-[2-(1,1-dioxido-2,3-dihydro-1,4-benzothiazepin-4(5H)-yl)-6-ethylquinolin-4-yl]prop-2-enoate

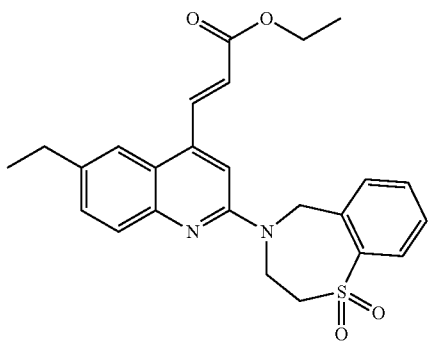 [SMILES: CCOC(=O)/C=C/c1cc(N2CCS(=O)(=O)c3ccccc3C2)nc2ccc(CC)cc12]

A mixture of 4-(4-chloro-6-ethylquinolin-2-yl)-2,3,4,5-tetrahydro-1,4-benzothiazepine 1,1-dioxide (300 mg, 0.78 mmol), ethyl prop-2-enoate (170 mg, 1.70 mmol), triethylamine (1 mL) and N,N-dimethylformamide (2 mL), bis(tri-tert-butylphosphine)palladium(0) (15 mg, 0.02 mmol) was heated with stirring in a 10 mL of microwave process vial for 30 minutes at 100° C. under microwave irradiation. The reaction mixture was poured into water (5 mL) and extracted with ethyl acetate (10 mL×3). The organic layers were combined, washed with brine, dried over sodium sulfate and concentrated in vacuo. The residue was purified by flash chromatography on silica gel (eluting with 20-40% ethyl acetate in petroleum ether) to afford 280 mg of the product as a white solid (yield was 80%). MS obsd. (ESI+) [(M+H)+] 451.

Ethyl 3-[2-(1,1-dioxido-2,3-dihydro-1,4-benzothiazepin-4(5H)-yl)-6-ethylquinolin-4-yl]propanoate

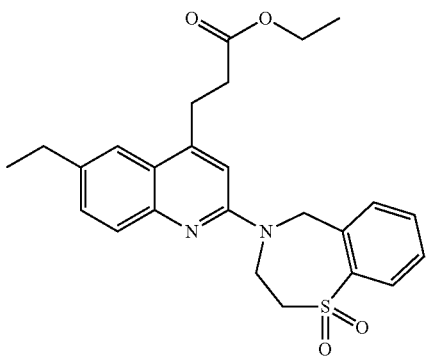 [SMILES: CCOC(=O)CCc1cc(N2CCS(=O)(=O)c3ccccc3C2)nc2ccc(CC)cc12]

To a 25 mL of dry round bottom flask containing a solution of ethyl (2E)-3-[2-(1,1-dioxido-2,3-dihydro-1,4-benzothiazepin-4(5H)-yl)-6-ethylquinolin-4-yl]prop-2-enoate (300 mg, 0.67 mmol) in dichloromethane (5 mL) was added 2-nitrophenylsulfonylhydrazide (2.91 g, 13.4 mmol) followed by a solution of triethylamine (5 mL) in dichloromethane (10 mL) under nitrogen. The suspension was gently stirred for 6 hour at room temperature under nitrogen, and then concentrated in vacuo. The residue was purified by flash column chromatography on silica gel (eluting with 20-40% ethyl acetate in petroleum ether) to afford 151 mg of the desired product (yield was 50%). MS obsd. (ESI+) [(M+H)+] 453.

3-[2-(1,1-dioxido-2,3-dihydro-1,4-benzothiazepin-4(5H)-yl)-6-ethylquinolin-4-yl]propanoic acid

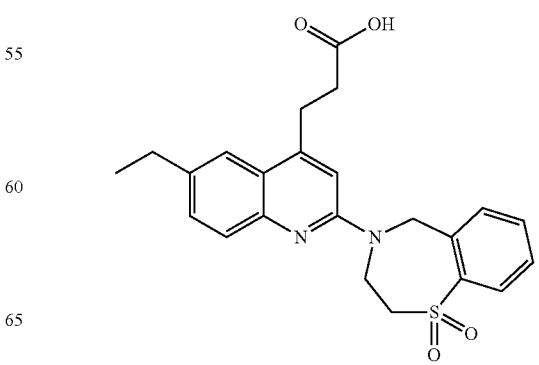

To a solution of ethyl 3-[2-(1,1-dioxido-2,3-dihydro-1,4-benzothiazepin-4(5H)-yl)-6-ethylquinolin-4-yl]propanoate (100 mg, 0.22 mmol) in methanol (2 mL) was added an aqueous solution of lithium hydroxide (20.6 mg in 2 mL of water) and the resulting mixture was stirred at room temperature for 4 hours. The reacting mixture was acidified to pH 4 with an aqueous solution of hydrochloric acid (5 N), and then extracted with ethyl acetate (10 mL×3). The organic layers were dried over sodium sulfate and concentrated in vacuo. The residue was purified by flash column chromatography (eluting with 1-10% methanol in dichlorometane) to afford 50 mg of the product as a white solid. MS (ESI$^+$) [(M+H)$^+$] 425, $^1$H NMR (400 MHz, DMSO-d6) δ ppm 8.08 (brs, 2 H), 7.94 (d, J=7.58 Hz, 1 H), 7.80 (brs, 1 H), 7.72 (t, J=7.07 Hz, 1 H), 7.57 (d, J=7.33 Hz, 2 H), 7.37 (brs, 1 H), 5.38 (m, 2 H), 4.56 (brs, 2 H), 3.94-3.69 (m, 2 H), 3.26 (brs, 2 H), 2.81-2.64 (m, 4 H), 1.22 (t, J=7.58 Hz, 3 H).

Example 96

3-[2-(1,1-Dioxido-2,3-dihydro-1,4-benzothiazepin-4 (5H)-yl)-6-methylquinolin-4-yl]propan-1-amine

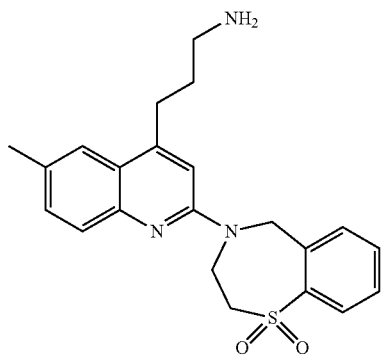 [SMILES: Cc1ccc2nc(N3CCS(=O)(=O)c4ccccc4C3)cc(CCCN)c2c1]

3-[2-(1,1-Dioxido-2,3-dihydro-1,4-benzothiazepin-4 (5H)-yl)-6-methylquinolin-4-yl]-propionitrile

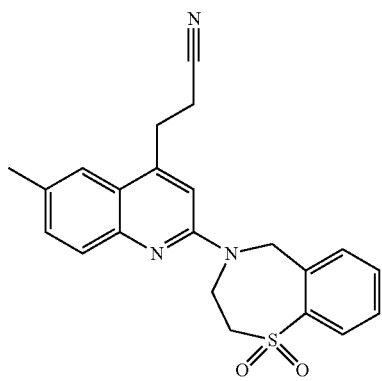 [SMILES: Cc1ccc2nc(N3CCS(=O)(=O)c4ccccc4C3)cc(CCC#N)c2c1]

The title compound was prepared in analogy to ethyl 3-[2-(1,1-dioxido-2,3-dihydro-1,4-benzothiazepin-4(5H)-yl)-6-ethylquinolin-4-yl]propanoate in Example 95 in Scheme 46 by using 4-(4-chloro-6-ethylquinolin-2-yl)-2,3,4,5-tetrahydro-1,4-benzothiazepine 1,1-dioxide and acrylonitrile.

3-[2-(1,1-dioxido-2,3-dihydro-1,4-benzothiazepin-4 (5H)-yl)-6-methylquinolin-4-yl]propanamide

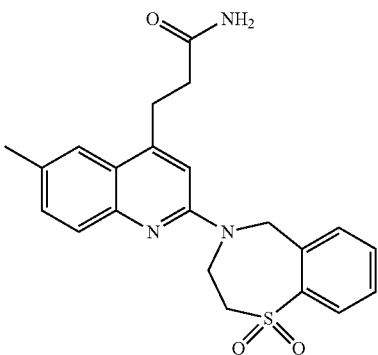 [SMILES: Cc1ccc2nc(N3CCS(=O)(=O)c4ccccc4C3)cc(CCC(N)=O)c2c1]

A solution of 3-[2-(1,1-dioxido-2,3-dihydro-1,4-benzothiazepin-4(5H)-yl)-6-methylquinolin-4-yl]-propionitrile (150 mg, 0.38 mmol), and powdered potassium hydroxide (172 mg, 3.07 mmol) in tert-butanol (8 mL) was heated with stirring under reflux for 1.5 hours. After being cooled to room temperature, the reaction mixture was diluted with water (15 mL) and extracted with ethyl acetate (15 mL×3). The combined organic layers were dried over sodium sulfate and concentrated in vacuo. The residue was purified by flash column (eluting with 5% methanol in dichloromethane) to afford 125 mg of the product as a white solid.

3-[2-(1,1-Dioxido-2,3-dihydro-1,4-benzothiazepin-4 (5H)-yl)-6-methylquinolin-4-yl]propan-1-amine

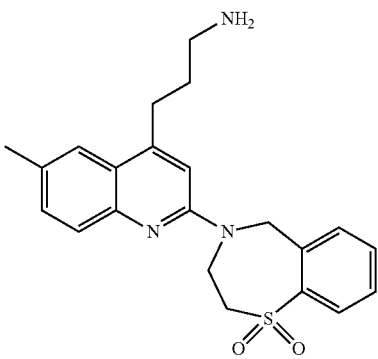 [SMILES: Cc1ccc2nc(N3CCS(=O)(=O)c4ccccc4C3)cc(CCCN)c2c1]

To a solution of 3-[2-(1,1-dioxido-2,3-dihydro-1,4-benzothiazepin-4(5H)-yl)-6-methylquinolin-4-yl]-propionamide (30 mg, 0.073 mmol) in tetrahydrofuran (2 mL) was added a solution of borane in tetrahydrofuran (1 mL, 2 M) in an ice bath. The mixture was stirred at 65° C. for 3 hours and then cooled naturally to room temperature. The reaction was quenched with methanol and the mixture was concentrated in vacuo. The residue was purified by preparative HPLC to afford 6.3 mg of the desired product. MS obsd. (ESI$^+$) [(M+H)$^+$] 396, $^1$H NMR (400 MHz, CD$_3$OD) δ ppm 7.99 (dd, J=1.2, 8.0 Hz, 1 H), 7.88 (d, J=7.2 Hz, 1 H), 7.64-7.56 (m, 3 H), 7.45 (dd, J=6.8, 7.6 Hz, 1 H), 7.37 (dd, J=1.6, 8.4 Hz, 1 H), 7.06 (s, 1 H), 5.22 (s, 2 H), 4.57 (brs, 2 H), 3.61 (t, J=4.8 Hz, 2 H), 3.07 (t, J=8.0 Hz, 2 H), 2.94 (t, J=7.6 Hz, 2 H), 2.45 (s, 3 H), 2.04-1.96 (m, 2 H).

Example 97

2-{[2-(1,1-Dioxido-2,3-dihydro-1,4-benzothiazepin-4(5H)-yl)-6-methylquinolin-4-yl]oxy}ethanamine

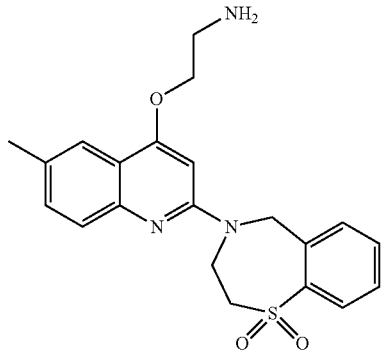 [SMILES: Cc1ccc2nc(N3CCS(=O)(=O)c4ccccc4C3)cc(OCCN)c2c1]

N-(2-{[2-(1,1-Dioxido-2,3-dihydro-1,4-benzothiazepin-4(5H)-yl)-6-methylquinolin-4-yl]oxy}ethyl)acetamide

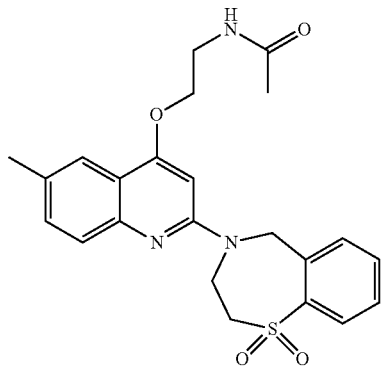 [SMILES: CC(=O)NCCOc1cc(N2CCS(=O)(=O)c3ccccc3C2)nc2ccc(C)cc12]

A mixture of N-(2-hydroxyethyl)-acetamide (247 mg, 2.4 mmol), 4-(4-bromo-6-methylquinolin-2-yl)-2,3,4,5-tetrahydro-1,4-benzothiazepine 1,1-dioxide (1000 mg, 2.4 mmol, prepared in analogy to 4-(4-chloro-6-(trifluoromethoxy) quinolin-2-yl)-2,3,4,5-tetrahydro-1,4-benzothiazepine 1,1-dioxide in Example 17-1), 1,1'-bis(diphenylphosphino)ferrocene-palladium(II)dichloride (190.4 mg, 0.24 mmol), 1,1'-bis(diphenylphosphino)ferrocene (129.3 mg, 0.24 mmol) and sodium tert-butoxide (460.8 mg, 4.8 mmol) in 1,4-dioxane (5 mL) was heated with stirring in a sealed 10 mL of microwave process vial for 1 hour at 130° C. under microwave irradiation. The reaction mixture was concentrated in vacuo and the residue was purified by preparative HPLC to afford 20 mg of the desired product (yield was 1.9%).

2-{[2-(1,1-Dioxido-2,3-dihydro-1,4-benzothiazepin-4(5H)-yl)-6-methylquinolin-4-yl]oxy}ethanamine

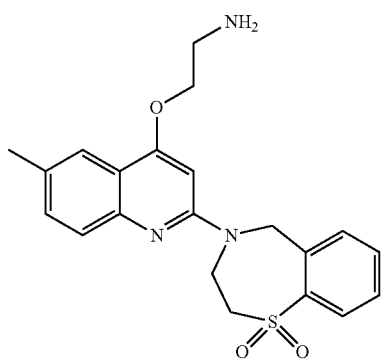 [SMILES: Cc1ccc2nc(N3CCS(=O)(=O)c4ccccc4C3)cc(OCCN)c2c1]

A mixture of N-(2-{[2-(1,1-dioxido-2,3-dihydro-1,4-benzothiazepin-4(5H)-yl)-6-methylquinolin-4-yl]oxy}ethyl)acetamide (15 mg, 0.03 mmol) and an aqueous solution of hydrochloric acid (10 mL, 37% W/W) was heated with stirring at 80° C. for 3 hours. The reaction mixture was purified by preparative HPLC and SPE to give 9.3 mg of the desired product (yield was 68.5%). MS obsd. (ESI⁺) [(M+H)⁺] 398, ¹H NMR (400 MHz, CD₃OD) δ ppm 8.11 (s, 1 H), 8.10-8.06 (d, J=7.6 Hz, 1 H), 7.93-7.88 (d, J=7.2 Hz, 1 H), 7.82-7.76 (d, J=8 Hz, 1 H), 7.73-7.68 (t, J=7.6 Hz, 1 H), 7.65-7.60 (d, J=6.8 Hz, 1 H), 7.60-7.53 (t, J=7.2 Hz, 1 H), 6.68 (s, 1 H), 5.41 (s, 2 H), 4.70-4.65 (m, 2 H), 4.65-4.45 (m, 2 H), 3.80-3.72 (t, J=2.8 Hz, 2 H), 3.62-3.58 (t, J=4.4 Hz, 2 H), 2.47 (s, 3 H).

Example 98-1

4-[6-Methyl-4-(pyrrolidin-3-yloxy)quinolin-2-yl]-2,3,4,5-tetrahydro-1,4-benzothiazepine 1,1-dioxide

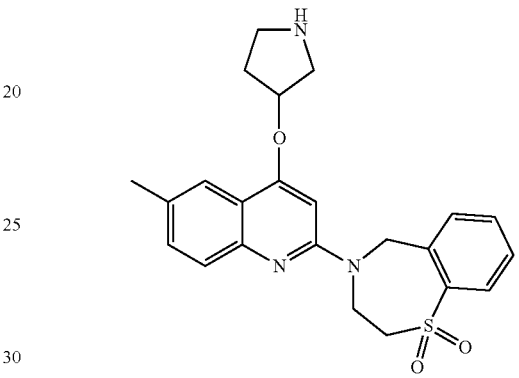

tert-Butyl 3-{[2-(1,1-dioxido-2,3-dihydro-1,4-benzothiazepin-4(5H)-yl)-6-methylquinolin-4-yl]oxy}pyrrolidine-1-carboxylate

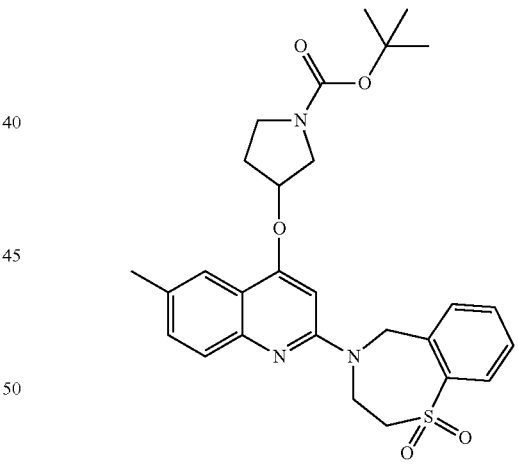

A mixture of tert-butyl 3-hydroxypyrrolidine-1-carboxylate (134.7 mg, 0.72 mmol), 4-(4-bromo-6-methylquinolin-2-yl)-2,3,4,5-tetrahydro-1,4-benzothiazepine 1,1-dioxide (300 mg, 0.72 mmol, prepared in analogy to 4-(4-chloro-6-(trifluoromethoxy)quinolin-2-yl)-2,3,4,5-tetrahydro-1,4-benzothiazepine 1,1-dioxide in Example 17-1), 1,1'-bis(diphenylphosphino)ferrocene-palladium(II)dichloride (57.12 mg, 0.07 mmol), 1,1'-bis(diphenylphosphino)ferrocene (38.78 mg, 0.07 mmol) and sodium tert-butoxide (138.24 mg, 1.44 mmol) in 1,4-dioxane (5 mL) was heated with stirring in a sealed 10 mL of microwave process vial for 1 hour at 130° C. under microwave irradiation. The reaction mixture was concentrated in vacuo and the residue was purified by preparative HPLC to afford 20 mg of the desired product (yield was 5.3%).

427

4-[6-Methyl-4-(pyrrolidin-3-yloxy)quinolin-2-yl]-2,3,4,5-tetrahydro-1,4-benzothiazepine 1,1-dioxide

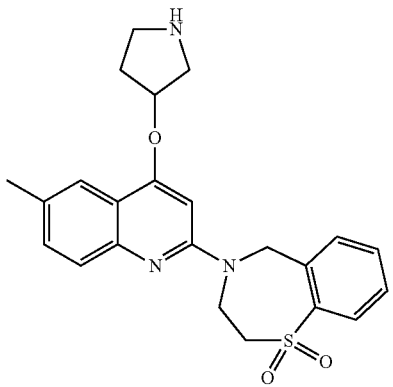 [SMILES: Cc1ccc2nc(N3CCS(=O)(=O)c4ccccc4C3)cc(OC3CCNC3)c2c1]

A mixture of tert-butyl 3-{[2-(1,1-dioxido-2,3-dihydro-1,4-benzothiazepin-4(5H)-yl)-6-methylquinolin-4-yl]oxy}pyrrolidine-1-carboxylate (50 mg, 0.096 mmol) and a solution of hydrochloride in ethyl acetate (30 mL, 4 M) was stirred at room temperature for 8 hours. The resulting mixture was concentrated in vacuo and the residue was purified by preparative HPLC and SPE to afford 18.4 mg of the desired product (yield was 45.3%). MS obsd. (ESI$^+$) [(M+H)$^+$] 424, $^1$H NMR (400 MHz, CD$_3$OD) δ ppm 8.11-8.08 (d, J=6.4 Hz, 1 H), 7.95-7.88 (m, 2 H), 7.78-7.70 (m, 2 H), 7.68-7.56 (m, 2 H), 6.62 (s, 1 H), 5.75-5.70 (m, 1 H), 5.40 (s, 2 H), 4.70-4.50 (m, 2 H), 3.80-3.70 (m, 4 H), 3.65-3.48 (m, 2 H), 2.60-2.50 (m, 1 H), 2.46 (s, 3 H), 2.46-2.35 (m, 1 H).

Example 98-2

8-[6-Methyl-4-(piperidin-4-yloxy)-quinolin-2-yl]-2,3,4,5-tetrahydro-1,4-benzothiazepine 1,1-dioxide

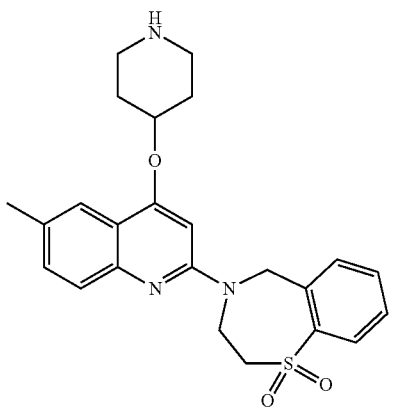 [SMILES: Cc1ccc2nc(N3CCS(=O)(=O)c4ccccc4C3)cc(OC3CCNCC3)c2c1]

The title compound was prepared in analogy to Example 98-1 in Scheme 47 by using 4-(4-bromo-6-methylquinolin-2-yl)-2,3,4,5-tetrahydro-1,4-benzothiazepine 1,1-dioxide (prepared in analogy to 4-(4-chloro-6-(trifluoromethoxy)quinolin-2-yl)-2,3,4,5-tetrahydro-1,4-benzothiazepine 1,1-dioxide in Example 17-1) and tert-butyl 4-hydroxypiperidine-1-carboxylate. MS obsd. (ESI$^+$) [(M+H)$^+$] 438, $^1$H NMR (400 MHz, CD$_3$OD) δ ppm 8.10-8.05 (d, J=8 Hz, 1 H), 7.92 (s, 1 H), 7.90-7.85 (d, J=7.6 Hz, 1 H), 7.80-7.75 (d, J=8.8 Hz, 1 H), 7.75-7.68 (t, J=7.6 Hz, 1 H), 7.68-7.62 (d, J=9.2 Hz, 1 H), 7.60-7.55 (t, J=7.6 Hz, 1 H), 6.64 (s, 1 H), 5.38 (s, 2 H), 5.32-5.26 (m, 1 H), 4.65-4.40 (m, 2 H), 3.82-3.72 (t, J=2.8 Hz, 2 H), 3.52-3.40 (m, 2 H), 3.40-3.30 (m, 2 H), 2.47 (s, 3 H), 3.36-3.28 (m, 2 H), 3.20-3.10 (m, 2 H).

Example 99

4-(4,6-Dimethylquinolin-2-yl)-2,3,4,5-tetrahydro-1,4-benzothiazepine 1,1-dioxide

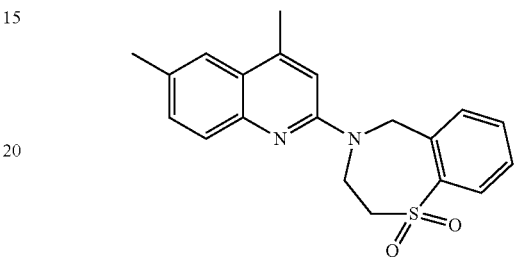

Diethyl (2-chloro-6-methylquinolin-4-yl)propanedioate

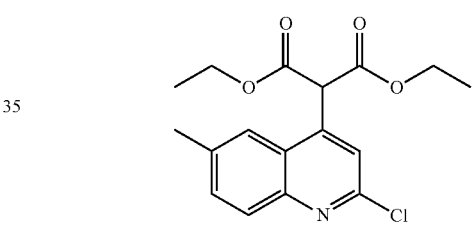

To a solution of 2,4-dichloro-6-methylquinoline (2.11 g, 10 mmol) and 1,3-diethyl propanedioate (2.64 g, 20 mmol) in N,N-dimethylformamide (40 mL) was added anhydrous potassium carbonate (2.8 g, 20 mmol). The mixture was stirred at 70° C. for 3 hours, then poured into ice/water (100 mL) and extracted with ethyl acetate (100 mL×3). The combined organic layers were washed with brine (150 mL×2), dried over sodium sulfate. The residue was purified by flash column chromatography on silica gel (eluting with 20-30% ethyl acetate in petroleum ether) to afford 1.34 g of the desired product (yield was 40%). MS obsd. (ESI$^+$) [(M+H)$^+$] 336.

(2-Chloro-6-methylquinolin-4-yl)acetic acid

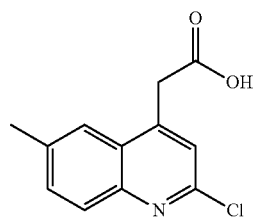 [SMILES: Cc1ccc2nc(Cl)cc(CC(=O)O)c2c1]

To a solution of diethyl (2-chloro-6-methylquinolin-4-yl)propanedioate (100 mg, 0.30 mmol) in methanol (2 mL) was added an aqueous solution of sodium hydroxide (2 N, 2 mL) and the resulting mixture was stirred at room temperature overnight. The reaction was then acidified to pH 4 with an aqueous solution of hydrochloric acid (5 N), and extracted with ethyl acetate (10 mL×3). The organic layer was dried over sodium sulfate and concentrated in vacuo to afford the desired product as a white solid. MS (ESI⁺) [(M+H)⁺] 236.

4-(4,6-Dimethylquinolin-2-yl)-2,3,4,5-tetrahydro-1,4-benzothiazepine

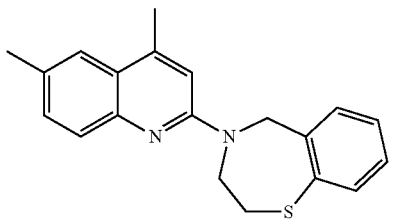 [SMILES: Cc1ccc2nc(N3CCSc4ccccc4C3)cc(C)c2c1]

A solution of (2-chloro-6-methylquinolin-4-yl)acetic acid (118 mg, 0.5 mmol) and 2,3,4,5-tetrahydro-1,4-benzothiazepine (247 mg, 1.5 mmol) in n-butanol (0.2 mL) was heated with stirring in a sealed 0.5 mL of microwave process vial for 2 hours at 160° C. After being cooled to room temperature, the reaction mixture was diluted with dichloromethane (50 mL), washed with a saturated aqueous solution of sodium carbonate (50 mL) and brine (50 mL), dried over anhydrous sodium sulfate and concentrated in vacuo. The residue was purified by flash column chromatography on silica gel (eluting with 20-30% ethyl acetate in petroleum ether) to afford 100 mg of the desired product (yield was 62%). MS (ESI⁺) [(M+H)⁺] 321.

4-(4,6-Dimethylquinolin-2-yl)-2,3,4,5-tetrahydro-1,4-benzothiazepine 1,1-dioxide

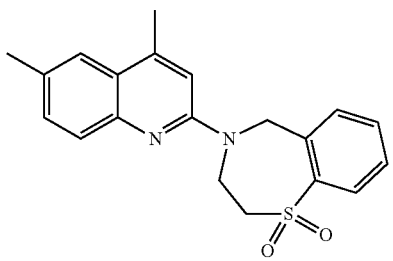 [SMILES: Cc1ccc2nc(N3CCS(=O)(=O)c4ccccc4C3)cc(C)c2c1]

To a solution of 4-(4,6-dimethylquinolin-2-yl)-2,3,4,5-tetrahydro-1,4-benzothiazepine (100 mg, 0.31 mmol) in dichloromethane (10 mL) was added 3-chloroperbenzoic acid (167 mg, 70% purity, 0.78 mmol) at room temperature for 4 hours. The resulting mixture was washed with a saturated aqueous solution of sodium carbonate (10 mL), dried over sodium sulfate and concentrated in vacuo. The residue was purified by preparative HPLC to afford the desired product. MS (ESI⁺) [(M+H)⁺] 353, ¹H NMR (400 MHz, DMSO-d6) δ ppm 7.99 (d, J=7.58 Hz, 1 H), 7.88 (d, J=7.33 Hz, 1 H), 7.65 (t, J=7.20 Hz, 1 H), 7.60-7.42 (m, 3 H), 7.35 (d, J=8.34 Hz, 1 H), 7.18 (s, 1 H), 5.12 (brs, 2 H), 4.43 (brs, 2 H), 3.65 (brs, 2 H), 2.53 (s, 3 H), 2.39 (s, 3 H).

Example 100

[2-(1,1-Dioxido-2,3-dihydro-1,4-benzothiazepin-4(5H)-yl)-6-methylquinolin-4-yl](piperidin-4-yl)methanone

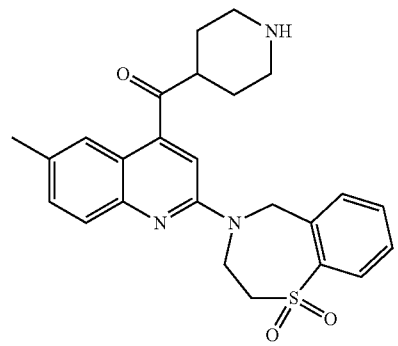 [SMILES: Cc1ccc2nc(N3CCS(=O)(=O)c4ccccc4C3)cc(C(=O)C3CCNCC3)c2c1]

tert-Butyl 4-{[2-(2,3-dihydro-1,4-benzothiazepin-4(5H)-yl)-6-methylquinolin-4-yl](hydroxy)methyl}piperidine-1-carboxylate

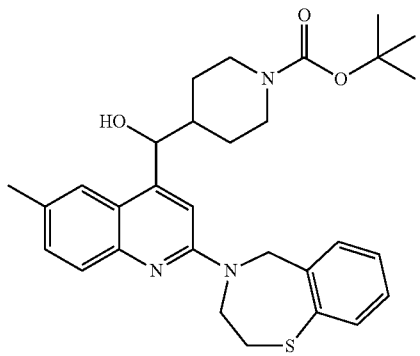 [SMILES: Cc1ccc2nc(N3CCSc4ccccc4C3)cc(C(O)C3CCN(C(=O)OC(C)(C)C)CC3)c2c1]

To a solution of 4-(4-bromo-6-methylquinolin-2-yl)-2,3,4,5-tetrahydro-1,4-benzothiazepine (385 mg, 1.0 mmol, prepared in analogy to 4-(4-chloro-6-(trifluoromethoxy)quinolin-2-yl)-2,3,4,5-tetrahydro-1,4-benzothiazepine 1,1-dioxide in Example 17-1) in tetrahydrofuran (10 mL) which was cooled to −78° C., butyl lithium (0.8 mL, 1.3 mmol) was added slowly and the mixture was stirred for 5 minutes, followed by the addition of a solution of tert-butyl 4-formylpiperidine-1-carboxylate (153 mg, 1.3 mmol) in tetrahydrofuran (5 mL) slowly. After being stirred further at −78° C. for 2 hours, the reaction mixture was diluted with a saturated aqueous solution of ammonium chloride (10 mL) and extracted with dichloromethane (20 mL×2). The organic layers were combined, dried over sodium sulfate and concentrated in vacuo. The residue was purified by flash column chromatography on silica gel (eluting with 20-40% ethyl acetate in petroleum ether) to afford 360 mg of the desired product (yield was 70%). MS (ESI⁺) [(M+H)⁺] 520.

tert-Butyl 4-{[2-(1,1-dioxido-2,3-dihydro-1,4-benzothiazepin-4(5H)-yl)-6-methylquinolin-4-yl](hydroxy)methyl}piperidine-1-carboxylate

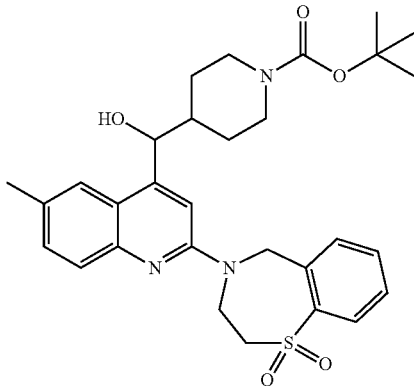 [SMILES: Cc1ccc2nc(N3CCS(=O)(=O)c4ccccc4C3)cc(C(O)C3CCN(C(=O)OC(C)(C)C)CC3)c2c1]

To a solution of tert-butyl 4-{[2-(2,3-dihydro-1,4-benzothiazepin-4(5H)-yl)-6-methylquinolin-4-yl](hydroxy)methyl}piperidine-1-carboxylate (519 mg, 1.0 mmol) in dichloromethane (10 mL) was added 3-chloroperbenzoic acid (537 mg, 70% purity, 2.2 mmol). After being stirred at room temperature for 4 hours, to the above mixture was added a saturated aqueous solution of sodium thiosulfate (3 mL). The separated organic layer was washed with a saturated aqueous solution of sodium carbonate (5 mL) and brine (5 mL), dried over sodium sulfate and concentrated in vacuo. The residue was purified by flash column chromatography on silica gel (eluting with 20-50% ethyl acetate in petroleum ether) to afford 300 mg of the desired product. MS (ESI⁺) [(M+H)⁺] 552.

tert-Butyl 4-{[2-(1,1-dioxido-2,3-dihydro-1,4-benzothiazepin-4(5H)-yl)-6-methylquinolin-4-yl]carbonyl}piperidine-1-carboxylate

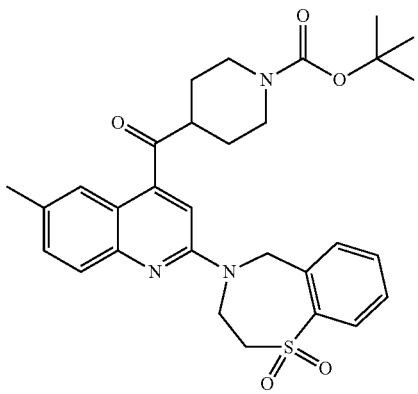 [SMILES: Cc1ccc2nc(N3CCS(=O)(=O)c4ccccc4C3)cc(C(=O)C3CCN(C(=O)OC(C)(C)C)CC3)c2c1]

To a solution of tert-butyl 4-{[2-(1,1-dioxido-2,3-dihydro-1,4-benzothiazepin-4(5H)-yl)-6-methylquinolin-4-yl](hydroxy)methyl}piperidine-1-carboxylate (200 mg, 0.36 mmol) in dichloromethane (10 mL) was added Dess-Martin reagents (226 mg, 0.54 mmol). The resulting mixture was stirred at room temperature until the reaction was complete monitoring by LC/MS and then concentrated in vacuo. The residue was purified by flash column chromatography on silica gel (eluting with 20-30% ethyl acetate in petroleum ether) to afford 150 mg of the desired product. MS (ESI⁺) [(M+H)⁺] 550.

[2-(1,1-Dioxido-2,3-dihydro-1,4-benzothiazepin-4(5H)-yl)-6-methylquinolin-4-yl](piperidin-4-yl)methanone

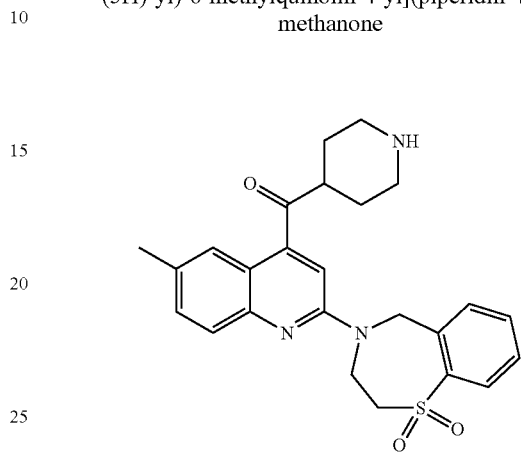

To a solution of tert-butyl 4-{[2-(1,1-dioxido-2,3-dihydro-1,4-benzothiazepin-4(5H)-yl)-6-methylquinolin-4-yl]carbonyl}piperidine-1-carboxylate (100 mg, 0.18 mmol) in dichloromethane (1 mL) was added trifluoroacetic acid (1 mL). The resulting mixture was stirred at room temperature until the reaction was complete monitoring by LC/MS and then concentrated in vacuo. The residue was purified by flash column chromatography on silica gel (eluting with 1-10% methanol in dichloromethane) to afford 60 mg of the desired product. MS (ESI⁺) [(M+H)⁺] 450, ¹H NMR (400 MHz, CD₃OD) δ ppm 8.01 (dd, J=7.83, 1.26 Hz, 1 H), 7.90 (d, J=7.07 Hz, 1 H), 7.68-7.56 (m, 2 H), 7.51-7.38 (m, 3 H), 7.34 (s, 1 H), 5.26 (brs, 2 H), 4.5 (brs, 2 H), 3.70-3.58 (m, 2 H), 3.37 (s, 2 H), 3.35-3.32 (m, 1 H), 3.14-3.03 (m, 2 H), 2.71 (td, J=12.25, 2.78 Hz, 2 H), 2.40 (s, 3 H), 1.79 (m, 2 H), 1.69-1.51 (m, 2 H).

Example 101

4-[6-Methyl-4-(1H-pyrazol-3-yl)quinolin-2-yl]-2,3,4,5-tetrahydro-1,4-benzothiazepine 1,1-dioxide

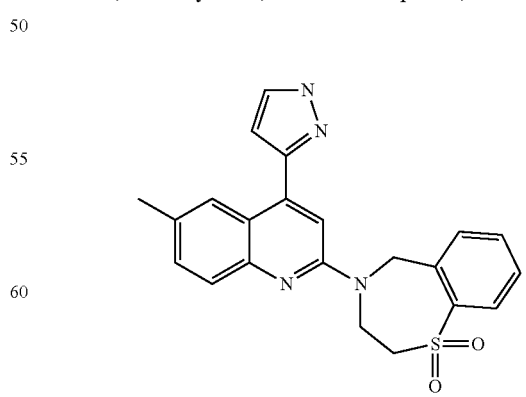

To a solution of 8-(4-bromo-6-methylquinolin-2-yl)-2,3,4,5-tetrahydro-1,4-benzothiazepine 1,1-dioxide (115 mg, 0.28 mmol, prepared in analogy to 4-(4-chloro-6-(trifluoromethoxy)quinolin-2-yl)-2,3,4,5-tetrahydro-1,4-benzothiazepine 1,1-dioxide in Example 17-1) in dimethoxyethane (8 mL) was added (triphenylphosphine) palladium (20 mg). After the mixture was stirred for 10 minutes, 1H-pyrazole-3-boric acid (107 mg, 0.84 mmol) was added followed by an aqueous solution of sodium carbonate (1 M, 0.5 mL). The resulting mixture was sealed and heated with stirring in a sealed 10 mL of microwave process vial for 1 hour at 80° C. under microwave irradiation. The reaction mixture was then purified by preparative HPLC to afford 36.5 mg of the desired product (yield was 10.8%). MS (ESI$^+$) [(M+H)$^+$] 405, $^1$H NMR (400 MHz, CD$_3$OD) δ ppm 8.41 (s, 1 H), 8.09-8.02 (m, 2 H), 7.95 (s, 2 H), 7.69-7.53 (m, 4 H), 6.99 (s, 1 H), 5.48 (s, 2 H), 4.67 (s, 2 H), 3.81 (s, 2 H), 3.34 (s, 1 H), 2.44 (s, 3 H).

Example 102

4-[6-Methyl-4-(phenylsulfonyl)quinolin-2-yl]-2,3,4,5-tetrahydro-1,4-benzothiazepine 1,1-dioxide

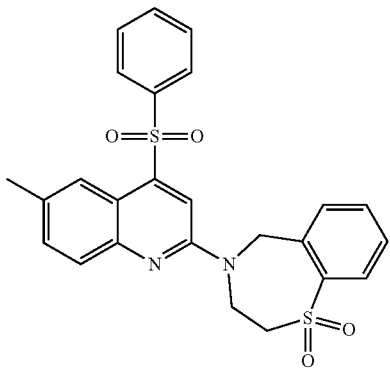 [SMILES: Cc1ccc2nc(N3CCS(=O)(=O)c4ccccc4C3)cc(S(=O)(=O)c3ccccc3)c2c1]

4-[6-Methyl-4-(phenylsulfanyl)quinolin-2-yl]-2,3,4,5-tetrahydro-1,4-benzothiazepine 1,1-dioxide

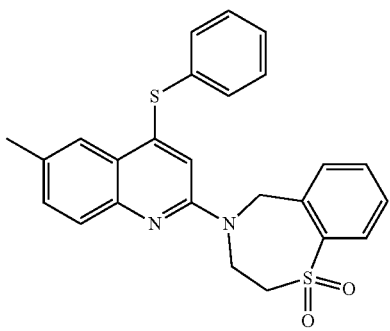 [SMILES: Cc1ccc2nc(N3CCS(=O)(=O)c4ccccc4C3)cc(Sc3ccccc3)c2c1]

A mixture of 4-(4-chloro-6-methylquinolin-2-yl)-2,3,4,5-tetrahydro-1,4-benzothiazepine 1,1-dioxide (1.8 g, 5.0 mmol, prepared in analogy to the one in Example 17-1), benzenethiol (0.66 g, 6.0 mmol) and N,N-dimethylpyridin-4-amine (0.74 g, 6 mmol) in dry ethanol (40 mL) was stirred at room temperature for 3 days. The reaction mixture was filtered and concentrated in vacuo. The residue was purified by silica gel column (gradient eluting with 10-20% ethyl acetate in hexanes) to afford 1.0 g of the desired product (yield was 45%).

4-[6-Methyl-4-(phenylsulfonyl)quinolin-2-yl]-2,3,4,5-tetrahydro-1,4-benzothiazepine 1,1-dioxide

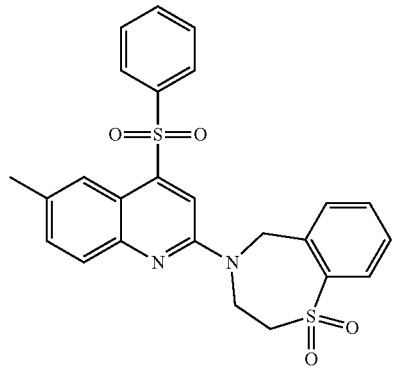 [SMILES: Cc1ccc2nc(N3CCS(=O)(=O)c4ccccc4C3)cc(S(=O)(=O)c3ccccc3)c2c1]

A mixture solution of 4-[6-methyl-4-(phenylsulfanyl)quinolin-2-yl]-2,3,4,5-tetrahydro-1,4-benzothiazepine 1,1-dioxide (223 mg, 0.5 mmol) and 3-chloroperbenzoic acid (340 mg, 2 mmol) in dry dichloromethane (30 mL) was stirred at 0° C. for 2 hours. After the reaction was quenched with a saturated aqueous solution of sodium thiosulphate (15 mL), the resulting mixture was stirred further at room temperature for 15 minutes. The separated organic layer was washed with a saturated aqueous solution of sodium bicarbonate (15 mL) and a saturated aqueous solution of sodium thiosulphate (15 mL), dried over sodium sulfate and concentrated in vacuo. The residue was purified by preparative HPLC to afford 168 mg of the desired product (yield was 70%). MS (ESI$^+$) [(M+H)$^+$] 479, $^1$H NMR (400 MHz, CDCl$_3$) δ ppm 8.11-8.08 (dd, J=1.2, 8 Hz, 1 H), 8.05 (s, 1 H), 7.91-7.89 (t, J=3.6 Hz, 3 H), 7.75-7.38 (d, J=6.8 Hz, 1 H), 7.65-7.58 (m, 3 H), 7.53-7.45 (m, 3 H), 7.41-7.39 (dd, J=1.6, 8.4 Hz, 1 H), 5.25 (s, 2 H), 5.15-4.20 (brs, 2 H), 3.58 (s, 2 H), 2.42 (s, 3 H).

Example 103

N-(2-Aminoethyl)-2-(1,1-dioxido-2,3-dihydro-1,4-benzothiazepin-4(5H)-yl)-6-methylquinoline-4-sulfonamide

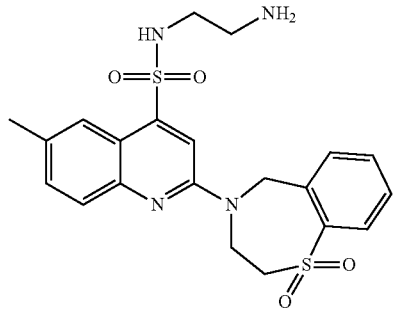 [SMILES: Cc1ccc2nc(N3CCS(=O)(=O)c4ccccc4C3)cc(S(=O)(=O)NCCN)c2c1]

2-(1,1-Dioxido-2,3-dihydro-1,4-benzothiazepin-4(5H)-yl)-6-methylquinoline-4-thiol

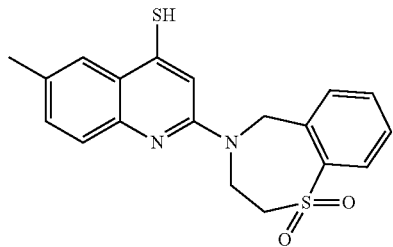 [SMILES: Cc1ccc2nc(N3CCS(=O)(=O)c4ccccc4C3)cc(S)c2c1]

To a solution of 4-(4-chloro-6-methylquinolin-2-yl)-2,3,4,5-tetrahydro-1,4-benzothiazepine 1,1-dioxide (1.5 g, 4 mmol, prepared in analogy to the one in Example 17-1) in dry N,N-dimethylformamide (100 mL) was added sodium methanethiolate (1.4 g, 20 mmol) under argon protection. The reaction was stirred at 130° C. for 16 hours. The reaction mixture was cooled to 50° C. and concentrated in vacuo. The residue was dissolved in cooled water (150 mL) and carefully acidified with 20% of hydrochloric acid to pH 4~5 under argon atmosphere. The resultant solution was extracted with cooled dichloromethane (150 mL×3). The combined organic layer was washed with cooled brine (100 mL×2) and concentrated in vacuo at room temperature to afford the crude product, which was used for next step without further purification.

2-(1,1-Dioxido-2,3-dihydro-1,4-benzothiazepin-4(5H)-yl)-6-methylquinoline-4-sulfonyl chloride

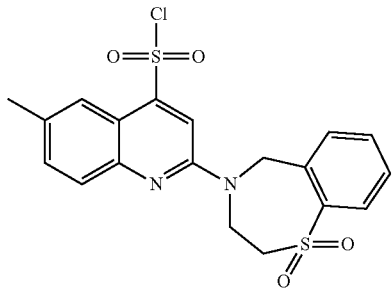 [SMILES: Cc1ccc2nc(N3CCS(=O)(=O)c4ccccc4C3)cc(S(=O)(=O)Cl)c2c1]

Gaseous chlorine was passed through a well stirred solution of 2-(1,1-dioxido-2,3-dihydro-1,4-benzothiazepin-4(5H)-yl)-6-methylquinoline-4-thiol (the crude product from the above step) in concentrated hydrochloric acid (10 mL) at −10° C. at such a rate that temperature was maintained between −5° C.~−10° C. After been stirred for 30 minutes, the passage of chlorine was discontinued and the mixture was poured onto ice (10 g) followed by the addition of sodium bicarbonate (8 g) in small portions. The resulting mixture was extracted with cooled dichloromethane (100 mL×3). The combined organic layer was washed with cooled water (100 mL), dried over sodium sulfate and filtered. The filtrate was used for the next step without further purification.

N-(2-Aminoethyl)-2-(1,1-dioxido-2,3-dihydro-1,4-benzothiazepin-4(5H)-yl)-6-methylquinoline-4-sulfonamide

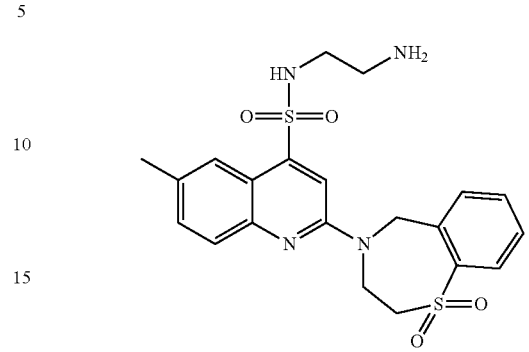

To a cooled solution of ethane-1,2-diamine (320 mg, 5.4 mmol) in dichloromethane (50 mL) was added triethylamine (3 drops) followed by 2-(1,1-dioxido-2,3-dihydro-1,4-benzothiazepin-4(5H)-yl)-6-methylquinoline-4-sulfonyl chloride (the filtrate from the above step) at 0° C. The resulting mixture was stirred at room temperature for 16 hours and concentrated in vacuo. The residue was purified by preparative HPLC to afford 56.38 mg of the desired product (yield of three steps was 3.1%). MS (ESI$^+$) [(M+H)$^+$] 461, $^1$H NMR (400 MHz, CD$_3$OD) δ ppm 8.11 (s, 1 H), 7.99-7.97 (d, J=8.4 Hz, 1 H), 7.85-7.83 (d, J=7.6 Hz, 1 H), 7.67-7.63 (m, 3 H), 7.49-7.45 (m, 2 H), 5.25 (s, 2 H), 4.76-4.03 (m, 2 H), 3.63-3.59 (t, 2 H), 3.03-3.00 (m, 4 H), 2.46 (s, 3 H).

Example 104

Methyl 4-({[3-(aminomethyl)oxetan-3-yl]methyl}amino)-2-(1,1-dioxido-2,3-dihydro-1,4-benzothiazepin-4(5H)-yl)quinoline-6-carboxylate

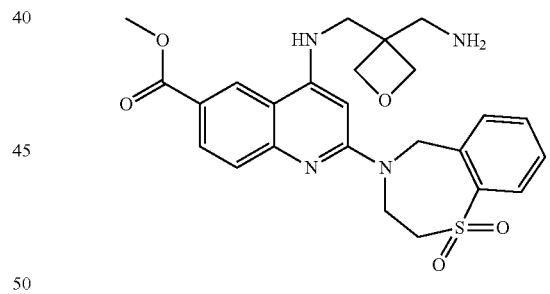

Methyl 4-chloro-2-(1,1-dioxido-2,3-dihydro-1,4-benzothiazepin-4(5H)-yl)quinoline-6-carboxylate

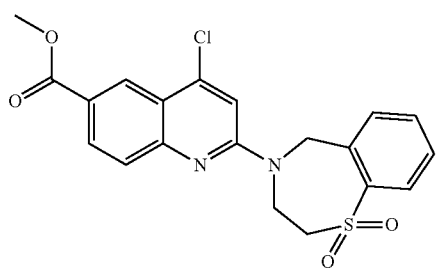 [SMILES: COC(=O)c1ccc2nc(N3CCS(=O)(=O)c4ccccc4C3)cc(Cl)c2c1]

To a stirred solution of methyl 4-chloro-2-(2,3-dihydro-1,4-benzothiazepin-4(5H)-yl)quinoline-6-carboxylate (1.5 g, 3.9 mmol) in dichloromethane (20 ml) was added 3-chloroperbenzoic acid (1.68 g, 9.7 mmol) at 0° C. The reaction mixture was stirred at 0° C. for 20 minutes and the reaction was quenched with a saturated aqueous solution of sodium carbonate (10 mL). The separated organic layer was washed with a saturated aqueous solution of sodium carbonate (10 mL) and brine (10 mL), dried over sodium sulfate and concentrated in vacuo. The residue was purified by flash column chromatography (eluting with 5% methanol in dichloromethane) to afford 1.38 g of the desired product as a white solid (yield was 85%).

Methyl 4-({[3-(aminomethyl)oxetan-3-yl]methyl}amino)-2-(1,1-dioxido-2,3-dihydro-1,4-benzothiazepin-4(5H)-yl)quinoline-6-carboxylate

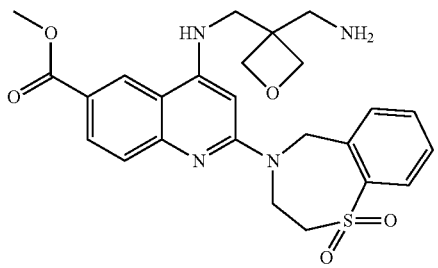 [SMILES: COC(=O)c1ccc2nc(N3CCS(=O)(=O)c4ccccc4C3)cc(NCC3(CN)COC3)c2c1]

The title compound was prepared in analogy to Example 6-1 in Scheme 52 by using methyl 4-chloro-2-(1,1-dioxido-2,3-dihydro-1,4-benzothiazepin-4(5H)-yl)quinoline-6-carboxylate and oxetane-3,3-diyldimethanamine. MS obsd. (ESI$^+$) [(M+H)$^+$] 497, $^1$H NMR (400 MHz, DMSO-d6) δ ppm 8.57 (d, 1 H), 7.95 (d, 1 H), 7.85 (m, 2 H), 7.71 (t, 1 H), 7.61 (m, 1 H), 7.46-7.38 (m, 2 H), 6.18 (s, 1 H), 5.07 (s, 2 H), 4.32 (m, 6 H), 3.80 (s, 3 H), 3.55 (m, 4 H), 2.95 (s, 2 H).

Example 105

4-({[3-(Aminomethyl)oxetan-3-yl]methyl}amino)-2-(1,1-dioxido-2,3-dihydro-1,4-benzothiazepin-4(5H)-yl)quinoline-6-carboxylic acid

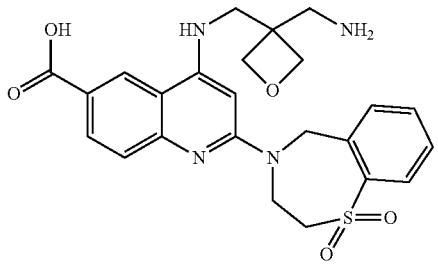 [SMILES: NCC1(CNc2cc(N3CCS(=O)(=O)c4ccccc4C3)nc3ccc(C(=O)O)cc23)COC1]

To a stirred solution of methyl 4-({[3-(aminomethyl)oxetan-3-yl]methyl}amino)-2-(1,1-dioxido-2,3-dihydro-1,4-benzothiazepin-4(5H)-yl)quinoline-6-carboxylate (100 mg, 0.2 mmol) in tetrahydrofuran and water (4 mL, V/V=3/1) was added sodium hydroxide (40 mg, 1.0 mmol). After being stirred at room temperature overnight, the resulting mixture was concentrated in vacuo to remove the organic solvent. The residual aqueous solution was acidified with an aqueous solution of citric acid (5 mL, 20%) and extracted with dichloromethane (15 mL×3). The combined organic layers were dried over anhydrous sodium sulfate and concentrated in vacuo to afford a sticky solid, which was purified by flash column chromatography (eluting with 5% methanol in dichloromethane) to afford 20 mg of the desire product as a solid. MS obsd. (ESI$^+$) [(M+H)$^+$] 483, $^1$H NMR (400 MHz, DMSO-d6) δ ppm 8.78 (s, 1 H), 8.01 (d, 1 H), 7.90 (m, 2 H), 7.61 (t, 1 H), 7.47 (t, 1 H), 7.32 (d, 1 H), 6.29 (s, 1 H), 5.76 (s, 2 H), 4.40 (m, 6 H), 3.78 (s, 2 H), 3.62 (s, 2 H), 3.17 (m, 2 H).

Example 106

[4-({[3-(Aminomethyl)oxetan-3-yl]methyl}amino)-2-(1,1-dioxido-2,3-dihydro-1,4-benzothiazepin-4(5H)-yl)quinolin-6-yl]methanol

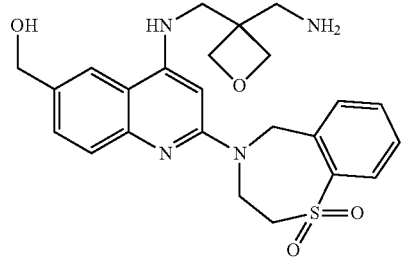 [SMILES: NCC1(CNc2cc(N3CCS(=O)(=O)c4ccccc4C3)nc3ccc(CO)cc23)COC1]

[4-Chloro-2-(1,1-dioxido-2,3-dihydro-1,4-benzothiazepin-4(5H)-yl)quinolin-6-yl]methanol

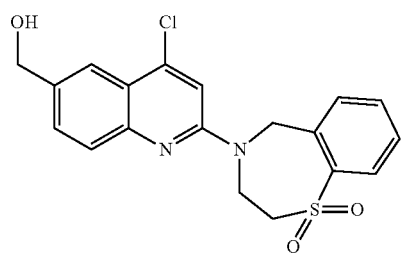 [SMILES: O=S1(=O)CCN(c2cc(Cl)c3cc(CO)ccc3n2)Cc2ccccc21]

To a slurry of lithium aluminum hydride (46 mg, 1.21 mmol) in tetrahydrofuran (5 mL) was added a solution of methyl 4-chloro-2-(1,1-dioxido-2,3-dihydro-1,4-benzothiazepin-4(5H)-yl)quinoline-6-carboxylate (400 mg, 0.96 mmol) in tetrahydrofuran (10 mL) at 0° C. under a nitrogen atmosphere. After being allowed to warm to room temperature and stirred for 2 hours, the reaction mixture was cooled to 0° C. and treated with water (0.2 mL) to quench the reaction. The resulting mixture was stirred for 30 minutes, dried over anhydrous sodium sulfate, filtered and concentrated in vacuo to afford 321 mg of the desired product as a white solid (yield was 86%).

439

[4-({[3-(Aminomethyl)oxetan-3-yl]methyl}amino)-2-(1,1-dioxido-2,3-dihydro-1,4-benzothiazepin-4(5H)-yl)quinolin-6-yl]methanol

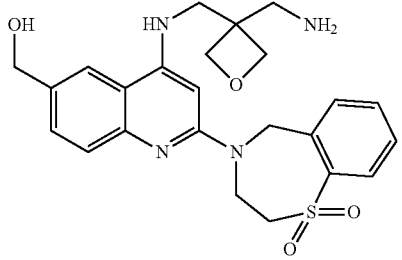 [SMILES: NCC1(CNc2cc(N3CCS(=O)(=O)c4ccccc4C3)nc3ccc(CO)cc23)COC1]

The title compound was prepared in analogy to Example 6-1 in Scheme 52 by using [4-chloro-2-(1,1-dioxido-2,3-dihydro-1,4-benzothiazepin-4(5H)-yl)quinolin-6-yl]methanol and oxetane-3,3-diyldimethanamine. MS obsd. (ESI$^+$) [(M+H)$^+$] 469, $^1$H NMR (400 MHz, DMSO-d6) δ ppm 7.93 (d, 1 H), 7.83 (m, 1 H), 7.75 (s, 1 H), 7.59 (m, 1 H), 7.42 (m, 1 H), 7.34 (s, 2 H), 7.25 (t, 1 H), 6.13 (s, 1 H), 5.10 (t, 1 H), 5.04 (s, 2 H), 4.47 (d, 2 H), 4.34 (m, 6 H), 3.58 (d, 2 H), 3.52 (d, 2 H), 2.96 (t, 2 H), 1.79 (m, 2 H).

Example 107

N-{[3-(Aminomethyl)oxetan-3-yl]methyl}-6-trideuteriomethyl-2-(1-oxido-2,3-dihydro-1,4-benzothiazepin-4(5H)-yl)quinazolin-4-amine

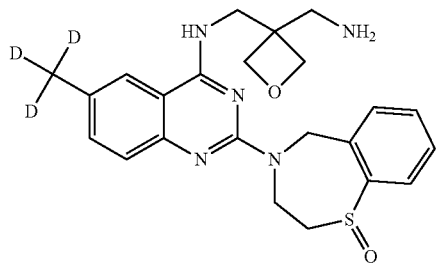 [SMILES: [2H]C([2H])([2H])c1ccc2nc(N3CCS(=O)c4ccccc4C3)nc(NCC3(CN)COC3)c2c1]

4-(Benzyloxy)-6-bromo-2-chloroquinazoline

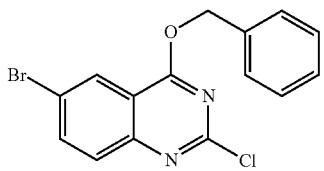 [SMILES: Clc1nc(OCc2ccccc2)c2cc(Br)ccc2n1]

To a cooled solution of 6-bromo-2,4-dichloroquinazoline (1.39 g, 5 mmol) in tetrahydrofuran (50 mL) was added a solution of benzyl alcohol (0.52 mL, 5 mmol) and sodium hydride (210 mg, 5.25 mmol, 60% in mineral oil) in tetrahydrofuran (15 mL) dropwise at 0° C. After being stirred at room temperature for 2 hours, the reaction mixture was poured into cold water (10 mL) and then extracted with ethyl acetate (50 mL). The organic layer was dried over magnesium sulfate and concentrated in vacuo to afford 1.73 g of the desired product as a yellow solid (yield was 99%).

440

4-[4-(Benzyloxy)-6-bromoquinazolin-2-yl]-2,3,4,5-tetrahydro-1,4-benzothiazepine

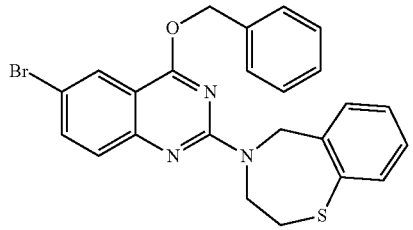 [SMILES: Brc1ccc2nc(N3CCSc4ccccc4C3)nc(OCc3ccccc3)c2c1]

A mixture of 4-(benzyloxy)-6-bromo-2-chloroquinazoline (700 mg, 2.0 mmol) and 2,3,4,5-tetrahydro-1,4-benzothiazepine (990 mg, 6.0 mmol) was heated at 80° C. for 10 minutes. The resulting reaction mixture was cooled to room temperature and purified by silica gel column chromatography (eluting with dichloromethane) to afford 600 mg of the desired product as a white solid (yield was 62.7%).

4-[4-(Benzyloxy)-6-trideuteriomethylquinazolin-2-yl]-2,3,4,5-tetrahydro-1,4-benzothiazepine

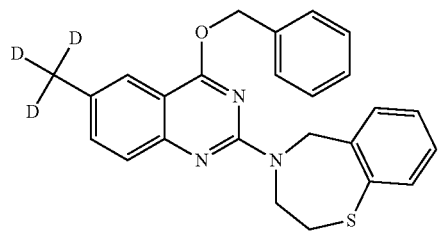 [SMILES: [2H]C([2H])([2H])c1ccc2nc(N3CCSc4ccccc4C3)nc(OCc3ccccc3)c2c1]

To a cooled solution of 4-[4-(benzyloxy)-6-bromoquinazolin-2-yl]-2,3,4,5-tetrahydro-1,4-benzothiazepine (239 mg, 0.50 mmol) in anhydrous tetrahydrofuran (10 mL) was added n-butyllithium (0.5 mL, 0.80 mmol) in tetrahydrofuran dropwise over 5 minutes under a nitrogen atmosphere at −78° C., followed by addition of methyl-d$^3$ trifluoromethanesulfonate (134 mg, 0.80 mmol) dropwise at −78° C. over 5 minutes. After being stirred for 1 hour at −78° C., the reaction mixture was allowed to warm to room temperature and stirred for another 1 hour. The reaction was quenched with deuterated water (5 mL). The resulting mixture was extracted with ethyl acetate (20 mL). The organic layer was dried over sodium sulfate and concentrated in vacuo to afford the desired compound.

4-[4-(Benzyloxy)-6-trideuteriomethylquinazolin-2-yl]-2,3,4,5-tetrahydro-1,4-benzothiazepine 1-oxide

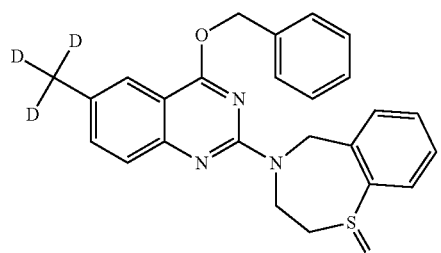

To a solution of 4-[4-(benzyloxy)-6-trideuteriomethylquinazolin-2-yl]-2,3,4,5-tetrahydro-1,4-benzothiazepine (417 mg, 1.0 mmol) in dichloromethane (10 mL) was added 3-chloroperoxybenzoic acid (233 mg, 1.0 mmol, 75%). After being stirred for 1 hour, the mixture was washed with a saturated aqueous solution of sodium thiosulphate (3 mL), 10% aqueous solution of sodium hydroxide (5 mL) and brine (5 mL). The organic layer was dried over sodium sulfate and concentrated in vacuo. The residue was purified by silica gel column chromatography (eluting with 10% ethyl acetate in dichloromethane) to afford the desired product as a white solid.

N-{[3-(aminomethyl)oxetan-3-yl]methyl}-6-trideuteriomethyl-2-(1-oxido-2,3-dihydro-1,4-benzothiazepin-4(5H)-yl)quinazolin-4-amine

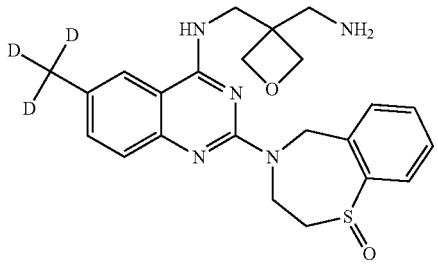 [SMILES: [2H]C([2H])([2H])c1ccc2nc(N3CCS(=O)c4ccccc4C3)nc(NCC3(CN)COC3)c2c1]

A mixture of 4-[4-(benzyloxy)-6-trideuteriomethylquinazolin-2-yl]-2,3,4,5-tetrahydro-1,4-benzothiazepine 1-oxide (700 mg, 1.62 mmol) and oxetane-3,3-diyldimethanamine (752 mg, 6.5 mmol) was heated at 170° C. for 20 minutes, then the mixture was cooled to room temperature and then purified by preparative HPLC to afford 60 mg of the desired product as a white solid (yield was 8.4%). MS obsd. (ESI$^+$) [(M+H)$^+$] 441, $^1$H NMR (400 MHz, CD$_3$OD) δ ppm 7.78-7.73 (m, 2 H), 7.69-7.67 (m, 1 H), 7.62-7.45 (m, 2 H), 7.44-7.40 (m, 1 H), 7.38-7.34 (m, 1 H), 5.27 (d, J=16 Hz, 1 H), 4.77 (brs, 1 H), 4.68-4.64 (m, 2 H), 4.52-4.47 (m, 2 H), 4.11-4.01 (m, 2 H), 3.49-3.35 (m, 2 H), 3.50-3.40 (m, 1 H), 3.40-3.34 (m, 1 H), 3.04 (s, 2 H).

Example 108-1

4-({[3-(Aminomethyl)oxetan-3-yl]methyl}amino)-2-(1-oxido-2,3-dihydro-1,4-benzothiazepin-4(5H)-yl)quinazoline-6-carboxylic acid

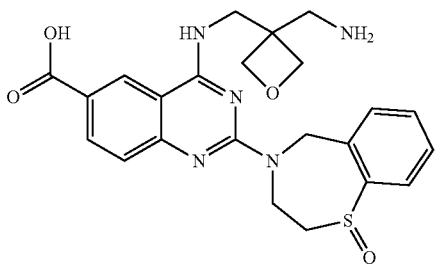 [SMILES: NCC1(CNc2nc(N3CCS(=O)c4ccccc4C3)nc3ccc(C(=O)O)cc23)COC1]

Methyl 4-(benzyloxy)-2-(2,3-dihydro-1,4-benzothiazepin-4(5H)-yl)quinazoline-6-carboxylate

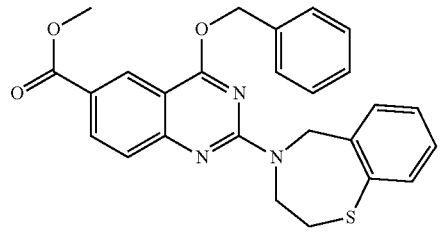 [SMILES: COC(=O)c1ccc2nc(N3CCSc4ccccc4C3)nc(OCc3ccccc3)c2c1]

To a solution of 4-(4-benzyloxy-6-bromoquinazolin-2-yl)-2,3,4,5-tetrahydro-1,4-benzothiazepine (239 mg, 0.5 mmol) in anhydrous tetrahydrofuran (10 mL) was added n-butyllithium (0.5 mL, 0.8 mmol) in tetrahydrofuran dropwise at −78° C. under nitrogen atmosphere over 5 minutes followed by addition of dry ice (2.5 mmol) at −78° C. After being stirred for 1 hour at −78° C., the reaction mixture was allowed to warm to room temperature and stirred for another 1 hour. The reaction was quenched by addition of a saturated solution of ammonium chloride (10 mL) and extracted with ethyl acetate (25 mL). The organic layer was dried over sodium sulfate and concentrated in vacuo to afford the crude product of the acid. To a solution of the above crude acid in methanol (15 mL) was added sulfinyl chloride (2 mL) at 0° C., then the mixture was heat at 70° C. for 1 hour. The reaction mixture was cooled to room temperature and concentrated in vacuo. The residue was dissolved in ethyl acetate, and the solution was washed with a saturated aqueous solution of sodium bicarbonate, dried over sodium sulfate and concentrated in vacuo. The residue was purified by flash column chromatography (eluting with 10% ethyl acetate in dichloromethane) to afford the desired methyl ester.

Methyl 4-(benzyloxy)-2-(1-oxido-2,3-dihydro-1,4-benzothiazepin-4(5H)-yl)quinazoline-6-carboxylate and Methyl 4-(benzyloxy)-2-(1,1-dioxido-2,3-dihydro-1,4-benzothiazepin 4(5H)-yl)quinazoline-6-carboxylate

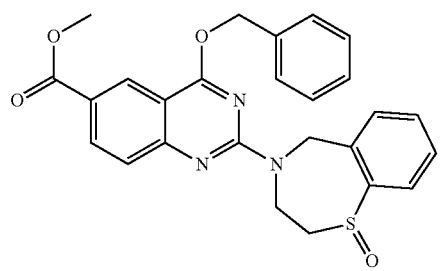

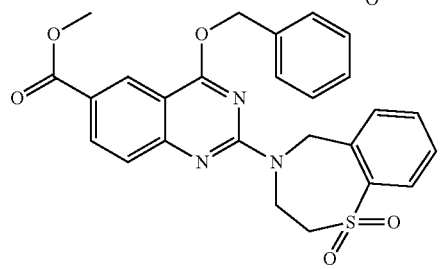

To a solution of methyl 4-(benzyloxy)-2-(2,3-dihydro-1,4-benzothiazepin-4(5H)-yl)quinazoline-6-carboxylate (800 mg, 1.75 mmol) in dichloromethane was added m-chloroperoxybenzoic acid (602 mg, 2.625 mmol, 75% purity) slowly, then the mixture was stirred at room temperature for 1 hour. The reaction mixture was washed with a saturated aqueous solution of sodium thiosulphate, and 10% aqueous solution of sodium hydroxide, and brine. The resulting organic layer was dried over sodium sulfate and concentrated in vacuo. The residue was purified by flash column chromatography (eluting with 10% ethyl acetate in dichloromethane) to afford 350 mg of methyl 4-(benzyloxy)-2-(1-oxido-2,3-dihydro-1,4-benzothiazepin-4(5H)-yl)quinazoline-6-carboxylate and 400 mg of methyl 4-(benzyloxy)-2-(1,1-dioxido-2,3-dihydro-1,4-benzothiazepin-4(5H)-yl)quinazoline-6-carboxylate.

4-(Benzyloxy)-2-(1-oxido-2,3-dihydro-1,4-benzothiazepin-4(5H)-yl)quinazoline-6-carboxylic acid

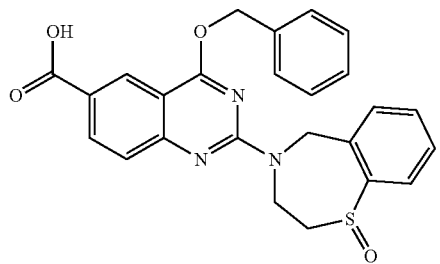 [SMILES: O=C(O)c1ccc2nc(N3CCS(=O)c4ccccc4C3)nc(OCc3ccccc3)c2c1]

To the solution of methyl 4-(benzyloxy)-2-(1-oxido-2,3-dihydro-1,4-benzothiazepin-4(5H)-yl)quinazoline-6-carboxylate (350 mg, 0.74 mmol) in the mixture of tetrahydrofuran and water (10 mL, V/V=4:1) was added lithium hydroxide (178 mg, 7.4 mmol). The resulting mixture was stirred at room temperature overnight and then acidified with hydrochloric acid (2 N), extracted with ethyl acetate. The organic layer was dried over sodium sulfate and concentrated in vacuo. The residue was purified by flash column chromatography (eluting with 10% ethyl acetate in dichloromethane) to afford 4-(benzyloxy)-2-(1-oxido-2,3-dihydro-1,4-benzothiazepin-4(5H)-yl)quinazoline-6-carboxylic MS obsd. (ESI$^+$) [(M+H)$^+$] 460.

4-({[3-(Aminomethyl)oxetan-3-yl]methyl}amino)-2-(1-oxido-2,3-dihydro-1,4-benzothiazepin-4(5H)-yl)quinazoline-6-carboxylic acid

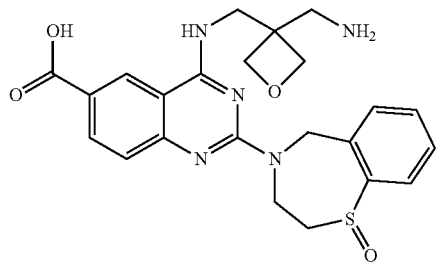 [SMILES: NCC1(CNc2nc(N3CCS(=O)c4ccccc4C3)nc3ccc(C(=O)O)cc23)COC1]

A mixture of 4-(benzyloxy)-2-(1-oxido-2,3-dihydro-1,4-benzothiazepin-4 (5H)-yl)quinazoline-6-carboxylic acid (170 mg, 0.37 mmol) and oxetane-3,3-diyldimethanamine (128 mg, 1.11 mmol) was heated at 170° C. for 30 minutes. Then the reaction mixture was cooled to room temperature and purified by preparative HPLC to afford 4-({[3-(Aminomethyl)oxetan-3-yl]methyl}amino)-2-(1-oxido-2,3-dihydro-1,4-benzothiazepin-4(5H)-yl)quinazoline-6-carboxylic acid, MS obsd. (ESI$^+$) [(M+H)$^+$] 468, $^1$H NMR (400 MHz, DMSO-d6) δ ppm 8.91-8.61 (m, 2 H), 8.09-8.00 (m, 1 H), 7.77-7.74 (m, 1 H), 7.68-7.65 (m, 1 H), 7.51-7.42 (m, 2 H), 7.27-7.13 (m, 1 H), 5.26-5.17 (m, 2 H), 4.89-4.68 (m, 4 H), 452-4.45 (m, 2 H), 4.40-4.31 (m, 2 H), 4.10-3.84 (m, 2 H), 3.20-3.01 (m, 2 H).

Example 108-2

4-({[3-(Aminomethyl)oxetan-3-yl]methyl}amino)-2-(1,1-dioxido-2,3-dihydro-1,4-benzothiazepin-4(5H)-yl)quinazoline-6-carboxylic acid

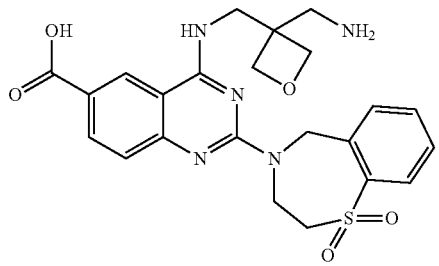 [SMILES: NCC1(CNc2nc(N3CCS(=O)(=O)c4ccccc4C3)nc3ccc(C(=O)O)cc23)COC1]

The title compound was prepared in analogy to Example 108-1 in Scheme 54 by using 4-(benzyloxy)-2-(1,1-dioxido-2,3-dihydro-1,4-benzothiazepin-4(5H)-yl)quinazoline-6-carboxylic acid and oxetane-3,3-diyldimethanamine, MS obsd. (ESI$^+$) [(M+H)$^+$] 484, $^1$H NMR (400 MHz, DMSO-d6) δ ppm 8.95 (brs, 1 H), 8.68 (m, 1 H), 8.04 (d, J=9.1 Hz, 1 H), 7.77-7.73 (m, 2 H), 7.68-7.63 (m, 1 H), 7.48-7.43 (m, 1 H), 7.24-7.19 (m, 1 H), 5.11 (brs, 2 H), 4.59-4.30 (brs, 6 H), 4.20 (m, 1 H), 4.0 (m, 1 H), 3.58 (brs, 2 H), 3.12 (m, 2 H).

Example 109-1 and Example 109-2

[4-({[3-(Aminomethyl)oxetan-3-yl]methyl}amino)-2-(1-oxido-2,3-dihydro-1,4-benzothiazepin-4(5H)-yl)quinazolin-6-yl]methanol and [4-({[3-(Aminomethyl)oxetan-3-yl]methyl}amino)-2-(1,1-dioxido-2,3-dihydro-1,4-benzothiazepin-4(5H)-yl)quinazolin-6-yl]methanol

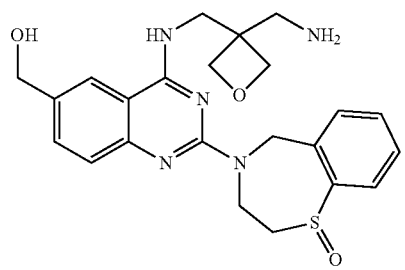

-continued

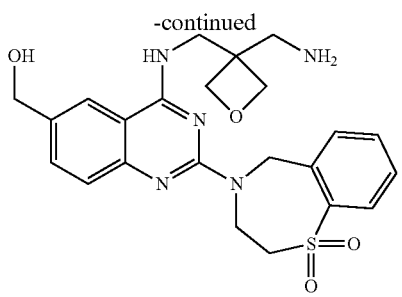

4-(Benzyloxy)-2-(2,3-dihydro-1,4-benzothiazepin-4(5H)-yl)quinazoline-6-carbaldehyde

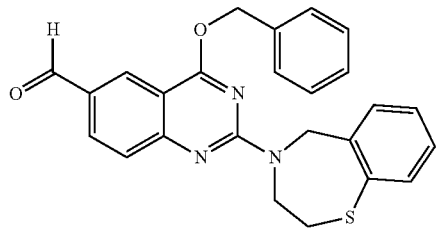 [SMILES: O=Cc1ccc2nc(N3CCSc4ccccc4C3)nc(OCc3ccccc3)c2c1]

To a cooled solution of 4-(4-benzyloxy-6-bromoquinazolin-2-yl)-2,3,4,5-tetrahydro-1,4-benzothiazepine (500 mg, 1.048 mmol) in anhydrous tetrahydrofuran (10 mL) was added anhydrous N,N-dimethylformamide (150 μL, 1.94 mmol) at −78° C. After being stirred at −78° C. for 30 minutes, the mixture was warmed to room temperature, diluted with water (10 mL) and extracted with ethyl acetate (20 mL×3). The combined organic layers were washed with a saturated aqueous solution of ammonium chloride (40 mL) and brine (40 mL), dried over anhydrous sodium sulfate, and concentrated in vacuo to afford 410 mg of the crude product as a yellow solid. MS obsd. (ESI⁺) [(M+H)⁺] 428.

[4-(Benzyloxy)-2-(2,3-dihydro-1,4-benzothiazepin-4(5H)-yl)quinazolin-6-yl]methanol

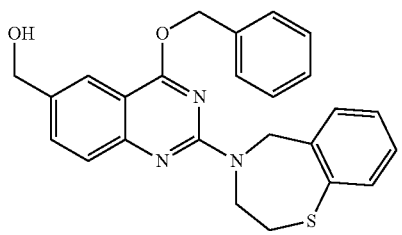 [SMILES: OCc1ccc2nc(N3CCSc4ccccc4C3)nc(OCc3ccccc3)c2c1]

To a solution of 4-(benzyloxy)-2-(2,3-dihydro-1,4-benzothiazepin-4(5H)-yl)quinazoline-6-carbaldehyde (3.0 g, 7.0 mmol) in methanol (20 mL) and tetrahydrofuran (20 mL) was added sodium borohydride (270 mg, 7.13 mmol) at 0° C. After being stirred at 0° C. for 15 minutes, the resulting mixture was warmed to room temperature, diluted with water (10 mL) and extracted with ethyl acetate (20 mL×3). The combined organic layers were washed with a saturated aqueous solution of ammonium chloride (40 mL) and brine (40 mL), dried over anhydrous sodium sulfate, and concentrated in vacuo to afford 2.85 g of the desired product as a yellow solid (yield was 95%), MS obsd. (ESI⁺) [(M+H)⁺] 430.

[4-(Benzyloxy)-2-(1-oxido-2,3-dihydro-1,4-benzothiazepin-4(5H)-yl)quinazolin-6-yl]methanol and [4-(Benzyloxy)-2-(1,1-dioxido-2,3-dihydro-1,4-benzothiazepin-4(5H)-yl)quinazolin-6-yl]methanol

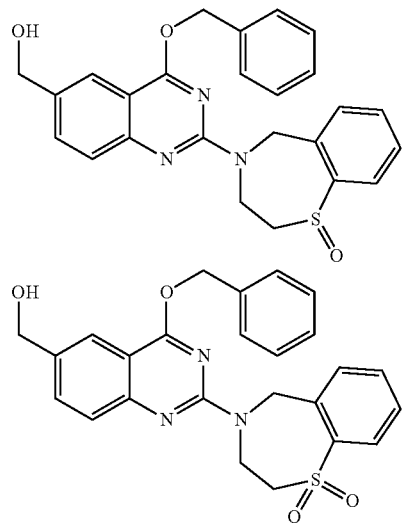

To a solution of [4-(benzyloxy)-2-(2,3-dihydro-1,4-benzothiazepin-4(5H)-yl)quinazolin-6-yl]methanol (1.0 g, 2.33 mmol) in dichloromethane (20 mL) was added 3-chloroperoxybenzoic acid (536 mg, 2.33 mmol, 75% purity) at 0° C. After being stirred at 0° C. for 15 minutes, the mixture was warmed to room temperature, diluted with water, extracted with dichloromethane (20 mL×3). The combined organic layers were washed with a saturated aqueous solution of sodium bicarbonate (40 mL) and brine (40 mL), dried over anhydrous sodium sulfate, and concentrated in vacuo to afford 0.90 g of the mixture of [4-(benzyloxy)-2-(1-oxido-2,3-dihydro-1,4-benzothiazepin-4(5H)-yl)quinazolin-6-yl]methanol and [4-(benzyloxy)-2-(1,1-dioxido-2,3-dihydro-1,4-benzothiazepin-4(5H)-yl)quinazolin-6-yl]methanol as a yellow solid.

[4-({[3-(Aminomethyl)oxetan-3-yl]methyl}amino)-2-(1-oxido-2,3-dihydro-1,4-benzothiazepin-4(5H)-yl)quinazolin-6-yl]methanol and [4-({[3-(Aminomethyl)oxetan-3-yl]methyl}amino)-2-(1,1-dioxido-2,3-dihydro-1,4-benzothiazepin-4(5H)-yl)quinazolin-6-yl]methanol

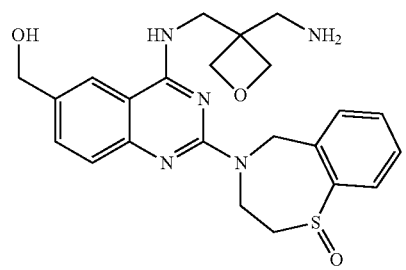

-continued

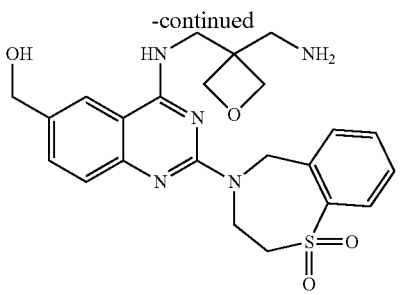

A mixture of [4-(benzyloxy)-2-(1-oxido-2,3-dihydro-1,4-benzothiazepin-4(5H)-yl)quinazolin-6-yl]methanol and [4-(benzyloxy)-2-(1,1-dioxido-2,3-dihydro-1,4-benzothiazepin-4(5H)-yl)quinazolin-6-yl]methanol (700 mg, about 1.57 mmol) and oxetane-3,3-diyldimethanamine (700 mg, 6.03 mmol) was heated at 160° C. for 30 minutes. After being cooled to room temperature, the reaction mixture was diluted with water (10 mL), extracted with dichloromethane (20 mL×3). The organic layers were washed with brine (40 mL), dried over anhydrous sodium sulfate and concentrated in vacuo. The residue was purified by preparative HPLC to afford [4-({[3-(aminomethyl)oxetan-3-yl]methyl}amino)-2-(1-oxido-2,3-dihydro-1,4-benzothiazepin-4(5H)-yl)quinazolin-6-yl]methanol, MS obsd. (ESI⁺) [(M+H)⁺] 454, ¹H NMR (400 MHz, DMSO-d6) δ ppm 8.139 (s, 1 H), 7.918 (s, 1 H), 7.71 (m, 2 H), 7.48 (m, 3 H), 7.316 (d, J=8 Hz, 1 H), 5.21 (m, 2 H), 4.75 (m, 2 H), 4.51 (m, 4 H), 4.369 (s, 3 H), 3.93 (brs, 1 H), 3.15 (brs, 2 H), 2.989 (s, 2 H), and [4-({[3-(aminomethyl)oxetan-3-yl]methyl}amino)-2-(1,1-dioxido-2,3-dihydro-1,4-benzothiazepin-4(5H)-yl)quinazolin-6-yl]methanol, MS obsd. (ESI⁺) [(M+H)⁺] 470, ¹H NMR (400 MHz, DMSO-d6) δ ppm 8.197 (s, 1 H), 7.789 (m, 3 H), 7.62 (t, J=7.2 Hz, 1 H), 7.48 (m, 2 H), 7.316 (s, 1 H), 5.12 (m, 3 H), 4.48 (m, 8 H), 3.917 (s, 2 H), 3.569 (brs, 2 H), 2.951 (brs, 2 H).

Example 110-1

N-[(3-Aminooxetan-3-yl)methyl]-2-(5,5-difluoro-1,3,4,5-tetrahydro-2H-2-benzazepin-2-yl)-6-methylquinolin-4-amine

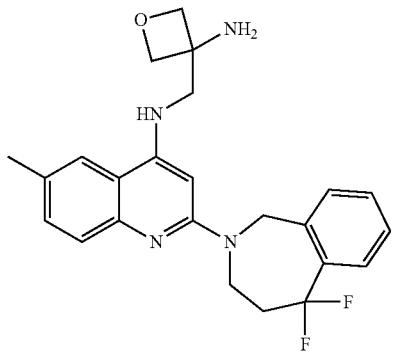 [SMILES: Cc1ccc2nc(N3CCC(F)(F)c4ccccc4C3)cc(NCC3(N)COC3)c2c1]

2-(4-Chloro-6-methylquinolin-2-yl)-5,5-difluoro-2,3,4,5-tetrahydro-1H-benzo[c]azepine

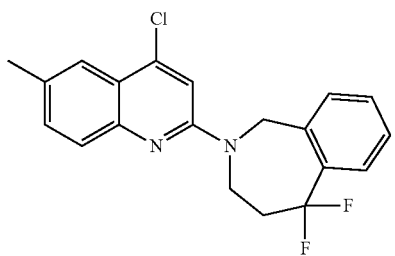 [SMILES: Cc1ccc2nc(N3CCC(F)(F)c4ccccc4C3)cc(Cl)c2c1]

A solution of 2,4-dichloro-6-methylquinoline (500 mg, 2.358 mmol) and 5,5-difluoro-2,3,4,5-tetrahydro-1H-benzazepine (432 mg, 2.358 mmol) in n-butanol (10 mL) was heated at 160° C. for 5 hours under microwave irradiation. The resulting reaction mixture was poured into water (10 mL) and extracted with ethyl acetate (20 mL×3). The combined organic layers were dried over sodium sulfate and concentrated in vacuo. The residue was purified by flash column chromatography (eluting with 20% ethyl acetate in petroleum ether) to afford 550 mg of the desired product as a solid (yield was 65%).

N-[(3-Aminooxetan-3-yl)methyl]-2-(5,5-difluoro-1,3,4,5-tetrahydro-2H-2-benzazepin-2-yl)-6-methylquinolin-4-amine

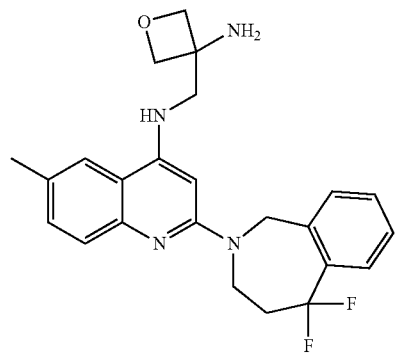 [SMILES: Cc1ccc2nc(N3CCC(F)(F)c4ccccc4C3)cc(NCC3(N)COC3)c2c1]

A solution of 2-(4-chloro-6-methylquinolin-2-yl)-5,5-difluoro-2,3,4,5-tetrahydro-1H-benzazepine (250 mg, 0.697 mmol), 3-(aminomethyl)oxetan-3-amine (119 mg, 0.697 mmol, purity: 60%), 1,1'-bis(diphenylphosphino)ferrocene (39 mg, 0.0697 mmol), 1,1'-bis(diphenylphosphino)ferrocene-palladium(II)dichloride (51 mg, 0.0697 mmol), sodium tert-butoxide (134 mg, 1.394 mmol). in 1,4-dioxane (10 mL) was heated at 120° C. for 1.5 hours under microwave irradiation. The resulting reaction mixture was poured into water (10 mL) and extracted with dichloromethane (20 mL×3), the combined organic layers were dried over sodium sulfate and concentrated in vacuo. The residue was purified by flash column chromatography (eluting with 0-10% methanol in dichloromethane) and preparative HPLC to afford 14 mg of the product as a white solid (yield was 4.4%). MS obsd. (ESI⁺) [(M+H)⁺] 425, ¹H NMR (400 MHz, CD₃OD) δ ppm 7.67-7.65 (d, J=6.8 Hz, 2 H), 7.61-7.59 (d, J=7.6 Hz, 1 H), 7.46-7.39 (m, 2 H), 7.33-7.29 (m, 2 H), 6.15 (s, 1 H), 4.91 (s, 2 H), 4.63-4.61 (d, J=6.4 Hz, 2 H), 4.58-4.56 (d, J=6.4 Hz, 2 H), 4.32-4.29 (t, J=5.5, 5.6 Hz, 2 H), 3.64 (s, 2 H), 2.55-2.45 (m, 2 H), 2.42 (s, 3 H).

Example 110-2

N-[2-(2-Aminoethoxy)ethyl]-2-(5,5-difluoro-1,3,4,5-tetrahydro-2H-2-benzazepin-2-yl)-6-methylquinolin-4-amine

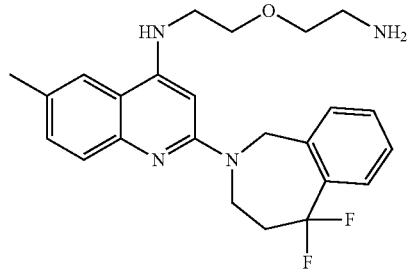 [SMILES: Cc1ccc2nc(N3CCC(F)(F)c4ccccc4C3)cc(NCCOCCN)c2c1]

449

The title compound was prepared in analogy to Example 110-1 in Scheme 56 by using 2-(4-chloro-6-methylquinolin-2-yl)-5,5-difluoro-2,3,4,5-tetrahydro-1H-benzazepine and 2-(2-aminoethoxy)ethan-1-amine. MS obsd. (ESI⁺) [(M+H)⁺] 427, ¹H NMR (400 MHz, CD₃OD) δ ppm 7.60-7.50 (d, J=7.2 Hz 1 H), 7.50-7.40 (d, J=9.2 Hz, 1 H), 7.40-7.30 (d, J=7.6 Hz, 1 H), 7.30-7.15 (m, 5 H), 5.85 (s, 1 H), 5.05 (s, 1 H), 4.75 (s, 2 H), 4.30 (s, 2 H), 3.75-3.65 (m, 2 H), 3.55-3.45 (m, 2 H), 3.40-3.30 (m, 2 H), 2.90-2.80 (t, 2 H), 2.50-2.40 (m, 2 H), 2.35 (s, 3 H).

Example 110-3

N-[2-(5,5-Difluoro-1,3,4,5-tetrahydro-2H-2-benzazepin-2-yl)-6-methylquinolin-4-yl]-N'-methylethane-1,2-diamine

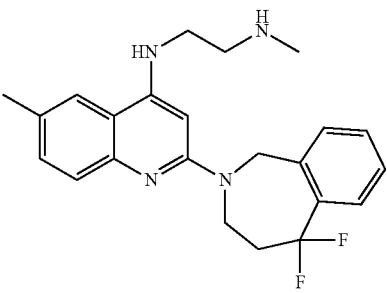 [SMILES: CNCCNc1cc(N2CCC(F)(F)c3ccccc3C2)nc2ccc(C)cc12]

The title compound was prepared in analogy to Example 110-1 in Scheme 56 by using 2-(4-chloro-6-methylquinolin-2-yl)-5,5-difluoro-2,3,4,5-tetrahydro-1H-benzazepine and (2-aminoethyl)(methyl)amine. MS obsd. (ESI⁺) [(M+H)⁺] 397, ¹H NMR (400 MHz, CD₃OD) δ ppm 7.60-7.50 (d, J=7.2 Hz, 1 H), 7.45-7.30 (m, 2 H), 7.30-7.10 (m, 5 H), 5.85 (s, 1 H), 5.25 (s, 1 H), 4.80 (s, 2 H), 4.30 (s, 2 H), 3.35-3.20 (m, 2 H), 2.97-2.85 (m, 2 H), 2.50-2.40 (m, 5 H), 2.35 (s, 3 H).

Example 110-4

1-Amino-3-{[2-(5,5-difluoro-1,3,4,5-tetrahydro-2H-2-benzazepin-2-yl)-6-methylquinolin-4-yl]amino}propan-2-ol

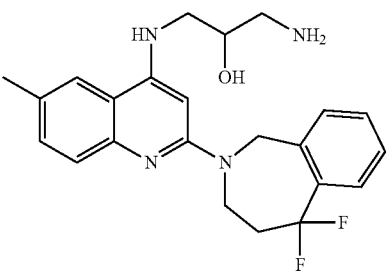 [SMILES: Cc1ccc2nc(N3CCC(F)(F)c4ccccc4C3)cc(NCC(O)CN)c2c1]

The title compound was prepared in analogy to Example 110-1 in Scheme 56 by using 2-(4-chloro-6-methylquinolin-2-yl)-5,5-difluoro-2,3,4,5-tetrahydro-1H-benzazepine and 1,3-diaminopropan-2-ol. MS obsd. (ESI⁺) [(M+H)⁺] 413, ¹H NMR (400 MHz, CD₃OD) δ ppm 7.60-7.50 (d, J=7.6 Hz, 1 H), 7.45-7.35 (m, 2 H), 7.30-7.10 (m, 5 H), 5.85 (s, 1 H), 5.20 (s, 1 H), 4.78 (s, 2 H), 4.30 (s, 2 H), 3.85-3.75 (m, 1 H), 3.35-3.20 (m, 1 H), 3.20-3.10 (m, 1 H), 3.00-2.90 (m, 1 H), 2.75-2.65 (m, 1 H), 2.45-2.35 (m, 2 H), 2.32 (s, 3 H).

Example 110-5

3-{[2-(5,5-Difluoro-1,3,4,5-tetrahydro-2H-2-benzazepin-2-yl)-6-methylquinolin-4-yl]amino}propane-1,2-diol

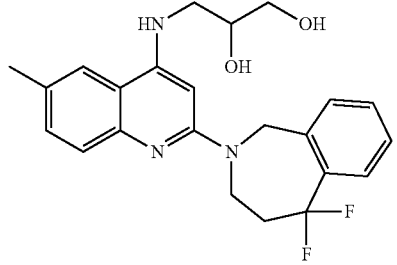 [SMILES: Cc1ccc2nc(N3CCC(F)(F)c4ccccc4C3)cc(NCC(O)CO)c2c1]

The title compound was prepared in analogy to Example 110-1 in Scheme 56 by using 2-(4-chloro-6-methylquinolin-2-yl)-5,5-difluoro-2,3,4,5-tetrahydro-1H-benzazepine and 3-aminopropane-1,2-diol. MS obsd. (ESI⁺) [(M+H)⁺] 414, ¹H NMR (400 MHz, CDCl₃) δ ppm 7.60-7.50 (d, J=7.6 Hz, 1 H), 7.50-7.40 (d, J=8.4 Hz, 2 H), 7.35-7.25 (d, J=8.4 Hz, 2 H), 7.25-7.10 (m, 2 H) 5.85 (s, 1 H), 5.20 (s, 1 H), 4.78 (s, 2 H), 4.20 (s, 2 H), 3.95-3.85 (m, 1 H), 3.70-3.50 (m, 2 H), 3.20-3.10 (m, 2 H), 2.50-2.40 (m, 2 H), 2.32 (s, 3 H).

Example 110-6

3-{[2-(5,5-Difluoro-1,3,4,5-tetrahydro-2H-2-benzazepin-2-yl)-6-methylquinolin-4-yl]amino}propan-1-ol

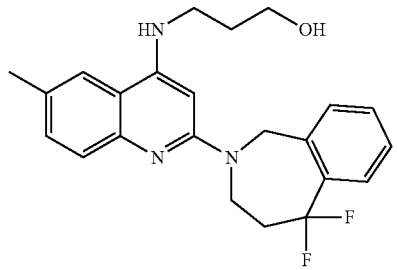 [SMILES: Cc1ccc2nc(N3CCC(F)(F)c4ccccc4C3)cc(NCCCO)c2c1]

The title compound was prepared in analogy to Example 110-1 in Scheme 56 by using 2-(4-chloro-6-methylquinolin-2-yl)-5,5-difluoro-2,3,4,5-tetrahydro-1H-benzazepine and 3-aminopropane-1-ol. MS obsd. (ESI⁺) [(M+H)⁺] 398, ¹H NMR (400 MHz, CD₃Cl) δ ppm 7.60-7.40 (m, 3 H), 7.35-7.25 (m, 4 H), 5.85 (s, 1 H), 4.80 (s, 2 H), 4.30 (s, 2 H), 3.90-3.80 (m, 2 H), 3.45-3.30 (m, 2 H), 2.55-2.45 (m, 2 H), 2.38 (s, 3 H).

Example 110-7

2-(5,5-Difluoro-1,3,4,5-tetrahydro-2H-2-benzazepin-2-yl)-6-methyl-N-[2-(piperazin-1-yl)ethyl]quinolin-4-amine

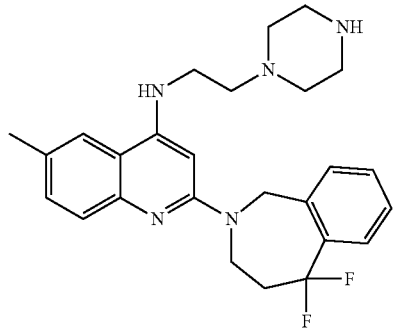 [SMILES: Cc1ccc2nc(N3CCC(F)(F)c4ccccc4C3)cc(NCCN3CCNCC3)c2c1]

The title compound was prepared in analogy to Example 110-1 in Scheme 56 by using 2-(4-chloro-6-methylquinolin-2-yl)-5,5-difluoro-2,3,4,5-tetrahydro-1H-benzazepine and 2-(piperazin-1-yl)ethan-1-amine. MS obsd. (ESI⁺) [(M+H)⁺] 452, ¹H NMR (400 MHz, CD₃Cl) δ ppm 7.52-7.44 (d, J=8.8 Hz, 1 H), 7.41-7.40 (m, 2 H), 7.25-7.10 (m, 4 H), 5.80 (s, 1 H), 5.51 (s, 1 H), 4.79 (s, 2 H), 4.26 (s, 2 H), 3.21-3.17 (m, 2 H), 2.86-2.84 (m, 4 H), 2.70-2.67 (m, 2 H), 2.44-2.42 (m, 6 H), 2.35 (s, 3 H).

Example 110-8

N~1~-[2-(5,5-Difluoro-1,3,4,5-tetrahydro-2H-2-benzazepin-2-yl)-6-methylquinolin-4-yl]propane-1,2-diamine

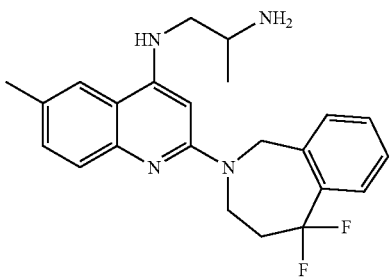 [SMILES: Cc1ccc2nc(N3CCC(F)(F)c4ccccc4C3)cc(NCC(C)N)c2c1]

The title compound was prepared in analogy to Example 110-1 in Scheme 56 by using 2-(4-chloro-6-methylquinolin-2-yl)-5,5-difluoro-2,3,4,5-tetrahydro-1H-benzazepine and propane-1,2-diamine. MS obsd. (ESI⁺) [(M+H)⁺] 397, ¹H NMR (400 MHz, CD₃Cl) δ ppm 7.54-7.52 (d, J=7.6 Hz, 1 H), 7.47-7.45 (d, J=8.4 Hz, 1 H), 7.40-7.38 (d, J=7.6 Hz, 1 H), 7.25-7.16 (m, 4 H) 5.85 (s, 1 H), 5.25 (s, 1 H), 4.78 (s, 2 H), 4.29-4.24 (m, 2 H), 3.22-3.17 (m, 2 H), 2.91-2.89 (m, 1 H), 2.46-2.33 (m, 2 H), 2.32 (s, 3 H), 1.20-1.18 (m, 3 H).

Example 110-9 cis-N-[2-(5,5-Difluoro-1,3,4,5-tetrahydro-2H-2-benzazepin-2-yl)-6-methylquinolin-4-yl]cyclohexane-1,4-diamine

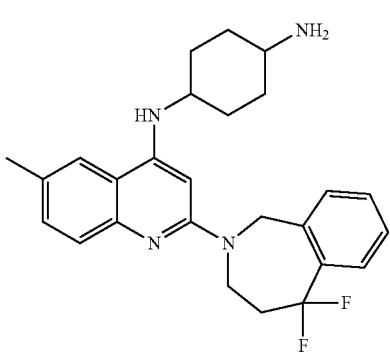 [SMILES: Cc1ccc2nc(N3CCC(F)(F)c4ccccc4C3)cc(NC3CCC(N)CC3)c2c1]

The title compound was prepared in analogy to Example 110-1 in Scheme 56 by using 2-(4-chloro-6-methylquinolin-2-yl)-5,5-difluoro-2,3,4,5-tetrahydro-1H-benzazepine and cis-cyclohexane-1,4-diamine. MS obsd. (ESI⁺) [(M+H)⁺] 437, ¹H NMR (400 MHz, CD₃OD) δ ppm 7.60-7.50 (d, J=7.6 Hz, 1 H), 7.50-7.40 (d, J=8.4 Hz, 1 H), 7.40-7.30 (d, J=7.6 Hz, 1 H), 7.30-7.15 (m, 5 H), 5.95 (s, 1 H), 4.80-4.70 (d, J=4.0 Hz, 2 H), 4.60 (s, 2 H), 4.05 (s, 1 H), 3.10 (s, 1 H), 2.70-2.60 (m, 1 H), 2.50-2.40 (m, 2 H), 2.35 (s, 3 H), 2.05 (s, 2 H), 1.80 (s, 2 H), 1.50-1.30 (m, 4 H).

Example 110-10

2-(9,9-Difluoro-6,7,8,9-tetrahydro-5H-benzo[7]annulen-6-yl)-6-methyl-N-(pyrrolidin-3-yl)quinolin-4-amine

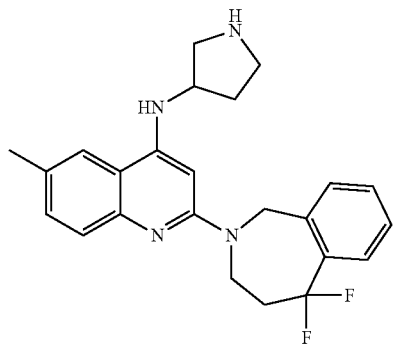 [SMILES: Cc1ccc2nc(N3CCC(F)(F)c4ccccc4C3)cc(NC3CCNC3)c2c1]

The title compound was prepared in analogy to Example 110-1 in Scheme 56 by using 2-(4-chloro-6-methylquinolin-2-yl)-5,5-difluoro-2,3,4,5-tetrahydro-1H-benzazepine and pyrrolidin-3-amine. MS obsd. (ESI⁺) [(M+H)⁺] 409, ¹H NMR (400 MHz, CD₃OD) δ ppm 7.60-7.50 (d, J=7.6 Hz, 1 H), 7.50-7.40 (d, J=8.8 Hz, 1 H), 7.40-7.30 (d, J=7.2 Hz, 1 H), 7.30-7.20 (m, 4 H), 5.85 (s, 1 H), 4.75 (s, 2 H), 4.30 (s, 2 H), 4.05 (s, 1 H), 3.65 (s, 1 H), 3.30-3.20 (m, 1 H), 3.20-2.90 (m, 3 H), 2.50-2.40 (m, 2 H), 2.35 (s, 3 H), 2.20-2.10 (m, 2 H).

Example 110-11

2,2'-{[2-(5,5-Difluoro-1,3,4,5-tetrahydro-2H-2-benzazepin-2-yl)-6-methylquinolin-4-yl]imino}diethanol

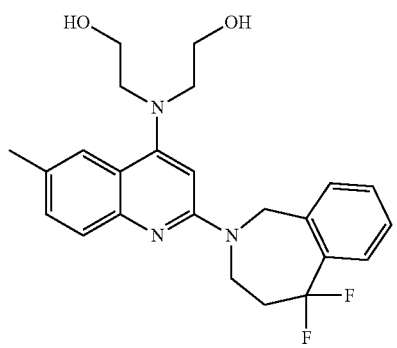 [SMILES: Cc1ccc2nc(N3CCC(F)(F)c4ccccc4C3)cc(N(CCO)CCO)c2c1]

The title compound was prepared in analogy to Example 110-1 in Scheme 56 by using 2-(4-chloro-6-methylquinolin-2-yl)-5,5-difluoro-2,3,4,5-tetrahydro-1H-benzazepine and 2,2'-iminodiethanol. MS obsd. (ESI⁺) [(M+H)⁺] 428, ¹H NMR (400 MHz, CD₃OD) δ ppm 7.90-7.70 (m, 2 H), 7.70-7.60 (m, 2 H), 7.50-7.30 (m, 3 H), 6.40 (s, 1 H), 5.85 (s, 2 H), 4.65 (s, 2 H), 4.15 (s, 2 H), 3.85 (s, 3 H), 3.58 (s, 2 H), 3.25 (s, 2 H), 2.60-2.50 (m, 3 H), 2.35 (s, 3 H).

Example 110-12

N~1~-[2-(5,5-Difluoro-1,3,4,5-tetrahydro-2H-2-benzazepin-2-yl)-6-methylquinolin-4-yl]-2-methyl-propane-1,2-diamine

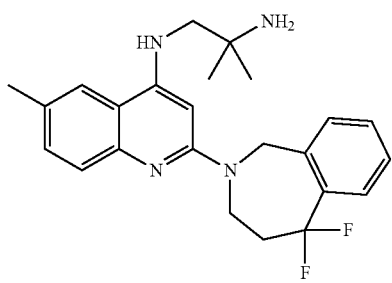 [SMILES: Cc1ccc2nc(N3CCC(F)(F)c4ccccc4C3)cc(NCC(C)(C)N)c2c1]

The title compound was prepared in analogy to Example 110-1 in Scheme 56 by using 2-(4-chloro-6-methylquinolin-2-yl)-5,5-difluoro-2,3,4,5-tetrahydro-1H-benzazepine and 2-methylpropane-1,2-diamine. MS obsd. (ESI$^+$) [(M+H)$^+$] 411, $^1$H NMR (400 MHz, CD$_3$OD) δ ppm 8.06 (s, 1 H), 7.79-7.69 (m, 3 H), 7.61-7.58 (dd, J=8.8, 1.6 Hz, 1 H), 7.53-7.49 (t, J=7.6 Hz, 1 H), 7.46-7.42 (t, J=7.6 Hz, 1 H), 6.13 (s, 1 H), 5.12 (s, 2 H), 4.24-4.21 (t, J=5.6 Hz, 2 H), 3.76 (s, 2 H), 2.73-2.64 (m, 2 H), 2.48 (s, 3 H), 1.42 (s, 6 H).

Example 110-13

5,5-Difluoro-2-[6-methyl-4-(4-methylpiperazin-1-yl)quinolin-2-yl]-2,3,4,5-tetrahydro-1H-2-benzazepine

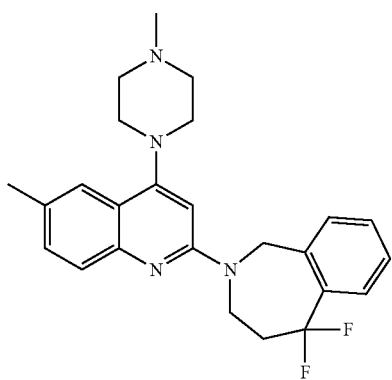 [SMILES: Cc1ccc2nc(N3CCC(F)(F)c4ccccc4C3)cc(N3CCN(C)CC3)c2c1]

The title compound was prepared in analogy to Example 110-1 in Scheme 56 by using 2-(4-chloro-6-methylquinolin-2-yl)-5,5-difluoro-2,3,4,5-tetrahydro-1H-benzazepine and 1-methylpiperazine. MS obsd. (ESI$^+$) [(M+H)$^+$] 423, $^1$H NMR (400 MHz, CD$_3$OD) δ ppm 7.93-7.91 (d, J=8.4 Hz, 1 H), 7.77-7.75 (d, J=7.6 Hz, 1 H), 7.71-7.69 (d, J=7.6 Hz, 1 H), 7.69 (s, 1 H), 7.62-7.60 (d, J=7.6 Hz, 1 H), 7.56-7.52 (t, J=8 Hz, 1 H), 7.49-7.45 (t, J=8 Hz, 1 H), 6.58 (s, 1 H), 5.18 (s, 2 H), 4.32-4.29 (t, J=6 Hz, 2 H), 3.97-3.89 (m, 2 H), 3.77-3.68 (m, 2H), 3.61-3.51 (m, 2 H), 3.50-3.39 (m, 2 H), 3.03 (s, 3 H), 2.79-2.67 (m, 2 H), 2.49 (s, 3 H).

Example 110-14

1-[2-(9,9-Difluoro-6,7,8,9-tetrahydro-5H-benzo[7]annulen-6-yl)-6-methylquinolin-4-yl]-3-ethylurea

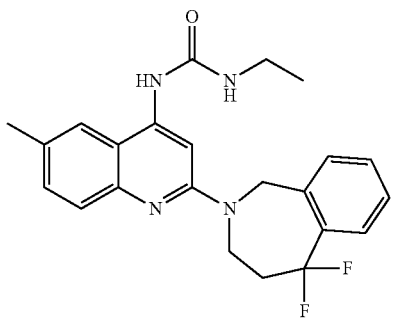 [SMILES: CCNC(=O)Nc1cc(N2CCC(F)(F)c3ccccc3C2)nc2ccc(C)cc12]

The title compound was prepared in analogy to Example 110-1 in Scheme 56 by using 2-(4-chloro-6-methylquinolin-2-yl)-5,5-difluoro-2,3,4,5-tetrahydro-1H-benzazepine and ethylurea. MS obsd. (ESI$^+$) [(M+H)$^+$] 411, $^1$H NMR (400 MHz, CDCl$_3$) δ ppm 12.30 (s, 1 H), 9.62-9.55 (m, 1 H), 8.40-8.20 (m, 1 H), 7.82-7.70 (m, 2 H), 7.60-7.38 (m, 4 H), 7.12 (s, 1 H), 5.00-4.80 (m, 2 H), 4.50-4.10 (m, 2 H), 3.42-3.30 (m, 2 H), 2.70-2.50 (m, 2 H), 1.92 (s, 3 H), 1.31-1.20 (t, J=7.2 Hz, 3 H).

Example 110-15

N-{[3-(Aminomethyl)oxetan-3-yl]methyl}-2-(5,5-difluoro-1,3,4,5-tetrahydro-2H-2-benzazepin-2-yl)-6-methylquinolin-4-amine

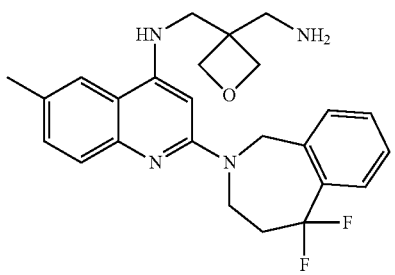 [SMILES: Cc1ccc2nc(N3CCC(F)(F)c4ccccc4C3)cc(NCC3(CN)COC3)c2c1]

The title compound was prepared in analogy to Example 110-1 in Scheme 56 by using 2-(4-chloro-6-methylquinolin-2-yl)-5,5-difluoro-2,3,4,5-tetrahydro-1H-benzazepine and oxetane-3,3-diyldimethanamine. MS obsd. (ESI$^+$) [(M+H)$^+$] 439, $^1$H NMR (400 MHz, CDCl$_3$) δ ppm 8.08 (s, 1 H), 7.80 (m, 3 H), 7.67 (d, 1 H), 7.60 (t, 1 H), 7.54 (t, 1 H), 6.18 (s, 1 H), 5.16 (s, 2 H), 4.68-4.62 (m, 4 H), 4.32 (t, 2 H), 3.94 (s, 2 H), 3.54 (s, 2 H), 2.78 (m, 2 H), 2.54 (s, 3 H).

Example 111-1

5,5-Difluoro-2-[6-methyl-4-(piperazin-1-yl)quinolin-2-yl]-2,3,4,5-tetrahydro-1H-2-benzazepine

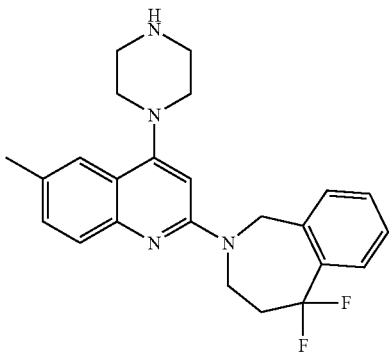 [SMILES: Cc1ccc2nc(N3CCC(F)(F)c4ccccc4C3)cc(N3CCNCC3)c2c1]

A mixture of 2-(4-chloro-6-methylquinolin-2-yl)-5,5-difluoro-2,3,4,5-tetrahydro-1H-benzazepine (100 mg, 0.279 mmol) and piperazine (300 mg, 3.488 mmol) was heated at 150° C. for 2 hours under microwave irradiation. The resulting reaction mixture was purified by preparative HPLC followed by SPE. The eluent was concentrated in vacuo and the residue was dried by lyophilization to afford 38.87 mg of the desired product (yield was 34.1%). MS obsd. (ESI$^+$) [(M+H)$^+$] 409, $^1$H NMR (400 MHz, CD$_3$OD) δ ppm 7.65-7.58 (d, J=7.6 Hz, 1 H), 7.55-7.45 (t, 2 H), 7.40-7.30 (d, J=7.6 Hz, 1 H), 7.38-7.25 (m, 2 H), 7.28-7.20 (m, 1 H), 6.35 (s, 1 H), 4.75 (s, 2 H), 4.34 (s, 2 H), 3.20-3.00 (m, 8 H), 2.60-2.45 (m, 2 H), 2.43 (s, 3 H).

Example 111-2

2-[4-(1,4-Diazepan-1-yl)-6-methylquinolin-2-yl]-5,5-difluoro-2,3,4,5-tetrahydro-1H-2-benzazepine

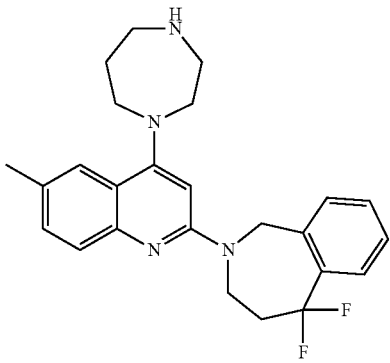 [SMILES: Cc1ccc2nc(N3CCC(F)(F)c4ccccc4C3)cc(N3CCCNCC3)c2c1]

The title compound was prepared in analogy to Example 111-1 in Scheme 56 by using 2-(4-chloro-6-methylquinolin-2-yl)-5,5-difluoro-2,3,4,5-tetrahydro-1H-benzazepine and [1,4]diazepane. MS obsd. (ESI$^+$) [(M+H)$^+$] 423, $^1$H NMR (400 MHz, CD$_3$Cl) δ ppm 7.60-7.58 (d, J=6.8 Hz, 1 H), 7.55-7.53 (m, 1 H), 7.45-7.43 (d, J=7.2 Hz, 1 H), 7.34-7.24 (m, 3 H), 6.41 (s, 1 H), 4.85 (s, 2 H), 4.33-4.32 (d, J=5.2 Hz, 2 H), 3.43-3.40 (m, 4 H), 3.17-3.14 (m, 4 H), 2.51-2.47 (m, 2 H), 2.41 (s, 3 H), 2.20 (brs, 1 H), 2.04-2.01 (m, 2 H).

Example 111-3

N-[2-(5,5-Difluoro-1,3,4,5-tetrahydro-2H-2-benzazepin-2-yl)-6-methylquinolin-4-yl]-N-methylethane-1,2-diamine

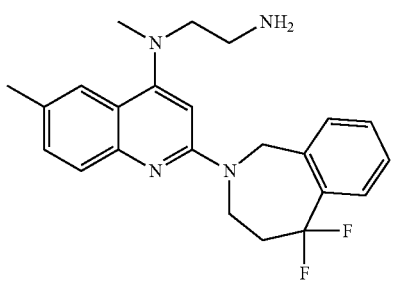 [SMILES: Cc1ccc2nc(N3CCC(F)(F)c4ccccc4C3)cc(N(C)CCN)c2c1]

The title compound was prepared in analogy to Example 111-1 in Scheme 56 by using 2-(4-chloro-6-methylquinolin-2-yl)-5,5-difluoro-2,3,4,5-tetrahydro-1H-benzazepine and (2-aminoethyl)(methyl)amine. MS obsd. (ESI$^+$) [(M+H)$^+$] 397, $^1$H NMR (400 MHz, CD$_3$OD) δ ppm 7.60-7.50 (d, J=7.2 Hz, 1 H), 7.45-7.35 (m, 2 H), 7.30-7.10 (m, 5 H), 5.85 (s, 1 H), 5.25 (s, 1 H), 4.78 (s, 2 H), 4.30 (s, 2 H), 3.35-3.20 (m, 2 H), 2.97-2.80 (m, 2 H), 2.50-2.35 (m, 5 H), 2.40-2.30 (s, 3 H).

Example 111-4

1-[2-(5,5-Difluoro-1,3,4,5-tetrahydro-2H-2-benzazepin-2-yl)-6-methylquinolin-4-yl]pyrrolidin-3-amine

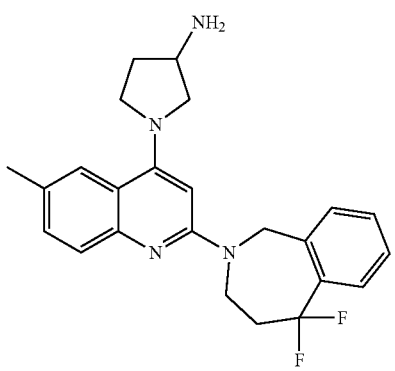 [SMILES: Cc1ccc2nc(N3CCC(F)(F)c4ccccc4C3)cc(N3CCC(N)C3)c2c1]

The title compound was prepared in analogy to Example 111-1 in Scheme 56 by using 2-(4-chloro-6-methylquinolin-2-yl)-5,5-difluoro-2,3,4,5-tetrahydro-1H-benzazepine and pyrrolidin-3-amine. MS obsd. (ESI$^+$) [(M+H)$^+$] 409, $^1$H NMR (400 MHz, CD$_3$OD) δ ppm 7.65 (s, 1 H), 7.62-7.55 (d, J=7.6 Hz, 1 H), 7.55-7.45 (d, J=8.8 Hz, 1 H), 7.45-7.40 (d, J=7.2 Hz, 1 H), 7.40-7.30 (t, 1 H), 7.30-7.20 (m, 3 H), 5.85 (s, 1 H), 4.85 (s, 2 H), 4.30 (s, 2 H), 3.80-3.70 (m, 3 H), 3.60-3.50 (m, 2 H), 3.40-3.30 (m, 1 H), 2.50-2.40 (m, 2 H), 2.35 (s, 3 H), 2.30-2.10 (m, 1 H).

Example 111-5

2-{[2-(5,5-Difluoro-1,3,4,5-tetrahydro-2H-2-benzazepin-2-yl)-6-methylquinolin-4-yl]amino}ethanol

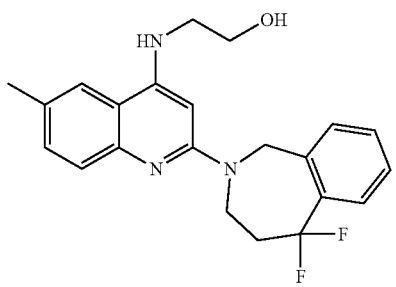 [SMILES: Cc1ccc2nc(N3CCC(F)(F)c4ccccc4C3)cc(NCCO)c2c1]

The title compound was prepared in analogy to Example 111-1 in Scheme 56 by using 2-(4-chloro-6-methylquinolin-2-yl)-5,5-difluoro-2,3,4,5-tetrahydro-1H-benzazepine and 2-aminoethanol. MS obsd. (ESI$^+$) [(M+H)$^+$] 384, $^1$H NMR (400 MHz, CD$_3$OD) δ ppm 7.60-7.40 (m, 3 H), 7.35-7.20 (m, 4 H), 5.87 (s, 1 H), 4.88-4.87 (d, J=16.4 Hz, 2 H), 4.33 (s, 2 H), 3.90-3.87 (m, 2 H), 3.41-3.37 (m, 2 H), 2.52-2.47 (m, 2 H), 2.38 (s, 3 H), 2.00-1.97 (m, 2 H).

Example 111-6

N-[2-(5,5-Difluoro-1,3,4,5-tetrahydro-2H-2-benzazepin-2-yl)-6-methylquinolin-4-yl]ethane-1,2-diamine

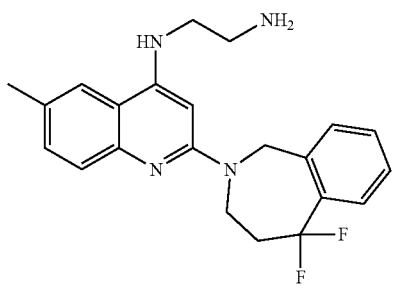 [SMILES: Cc1ccc2nc(N3CCC(F)(F)c4ccccc4C3)cc(NCCN)c2c1]

The title compound was prepared in analogy to Example 111-1 in Scheme 56 by using 2-(4-chloro-6-methylquinolin-2-yl)-5,5-difluoro-2,3,4,5-tetrahydro-1H-benzazepine and ethane-1,2-diamine. MS obsd. (ESI$^+$) [(M+H)$^+$] 383, $^1$H NMR (400 MHz, CD$_3$OD) δ ppm 7.89 (s, 1 H), 7.72-7.70 (d, J=6.8 Hz, 1 H), 7.70-7.67 (d, J=6.8 Hz, 2 H), 7.65-7.42 (m, 3 H), 6.00 (s, 1 H), 5.02 (s, 2 H), 4.23-4.20 (t, 2 H), 3.88-3.78 (t, 2 H), 3.58-3.55 (t, 2 H), 2.71-2.61 (m, 2 H), 2.46 (s, 3 H).

Example 111-7

N-[2-(5,5-Difluoro-1,3,4,5-tetrahydro-2H-2-benzazepin-2-yl)-6-methylquinolin-4-yl]cyclohexane-1,3-diamine

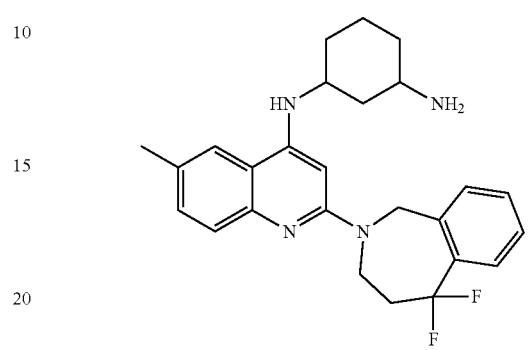

The title compound was prepared in analogy to Example 111-1 in Scheme 56 by using 2-(4-chloro-6-methylquinolin-2-yl)-5,5-difluoro-2,3,4,5-tetrahydro-1H-benzazepine and cyclohexane-1,3-diamine. MS obsd. (ESI$^+$) [(M+H)$^+$] 437, $^1$H NMR (400 MHz, CD$_3$OD) δ ppm 8.01-7.97 (d, J=15.2 Hz, 1 H), 7.69-7.65 (m, 3 H), 7.55-7.41 (m, 3 H), 5.92-5.91 (d, J=2.4 Hz, 2 H), 5.02-4.92 (m, 2 H), 4.31-4.10 (m, 2 H), 3.83-3.60 (m, 1 H), 3.41-3.32 (m, 1 H), 2.69-2.63 (m, 2 H), 2.45-2.43 (m, 3 H), 2.38-2.32 (m, 1 H), 2.19-2.11 (m, 1 H), 2.10-1.98 (m, 2 H), 1.70-1.65 (m, 2 H), 1.44-1.29 (m, 2 H).

Example 111-8

N'-[2-(5,5-Difluoro-1,3,4,5-tetrahydro-2H-2-benzazepin-2-yl)-6-methylquinolin-4-yl]-N,N-dimethylethane-1,2-diamine

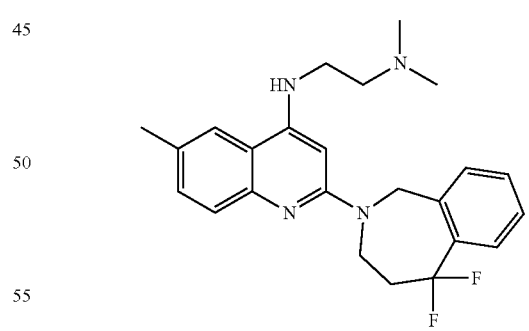

The title compound was prepared in analogy to Example 111-1 in Scheme 56 by using 2-(4-chloro-6-methylquinolin-2-yl)-5,5-difluoro-2,3,4,5-tetrahydro-1H-benzazepine and N,N-dimethylethane-1,2-diamine. MS obsd. (ESI$^+$) [(M+H)$^+$] 411, $^1$H NMR (400 MHz, CDCl$_3$) δ ppm 7.61 (s, 2 H), 7.59 (s, 1 H), 7.46-7.44 (d, J=8.4 Hz, 1 H), 7.37-7.42 (m, 1 H), 7.31-7.29 (m, 2 H), 5.93 (s, 1 H), 4.88 (s, 2 H), 4.25 (m, 2 H), 3.45-3.41 (t, J=6.4 Hz, 2 H), 2.69-2.65 (t, J=6.4 Hz, 2 H), 2.53-2.44 (m, 2 H), 2.39 (s, 3 H), 2.34 (s, 3 H).

Example 111-9

N-[2-(5,5-Difluoro-1,3,4,5-tetrahydro-2H-2-benzazepin-2-yl)-6-methylquinolin-4-yl]propane-1,3-diamine

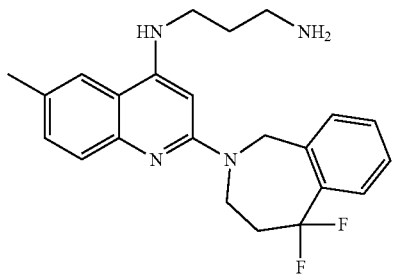 [SMILES: Cc1ccc2nc(N3CCC(F)(F)c4ccccc4C3)cc(NCCCN)c2c1]

The title compound was prepared in analogy to Example 111-1 in Scheme 56 by using 2-(4-chloro-6-methylquinolin-2-yl)-5,5-difluoro-2,3,4,5-tetrahydro-1H-benzazepine and propane-1,3-diamine. MS obsd. (ESI$^+$) [(M+H)$^+$] 397, $^1$H NMR (400 MHz, CD$_3$OD) δ ppm 7.60-7.52 (m, 3 H), 7.40-7.32 (t, J=2.4 Hz, 2 H), 7.30-7.20 (m, 2 H), 5.92 (s, 1 H), 4.30-4.20 (m, 2 H), 3.38-3.30 (t, J=6.8 Hz, 2 H), 2.81-2.74 (t, J=7.2 Hz, 2 H), 2.51-2.40 (m, 2 H), 2.37 (s, 3 H), 1.90-1.80 (m, 2 H), 1.32-1.25 (m, 2 H).

Example 111-10

N-[2-(5,5-Difluoro-1,3,4,5-tetrahydro-2H-2-benzazepin-2-yl)-6-methylquinolin-4-yl]butane-1,4-diamine

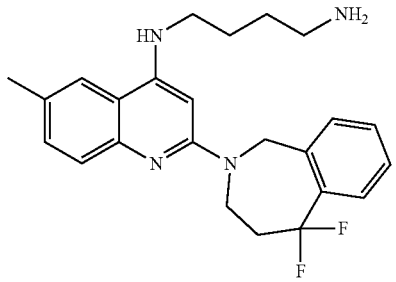 [SMILES: Cc1ccc2nc(N3CCC(F)(F)c4ccccc4C3)cc(NCCCCN)c2c1]

The title compound was prepared in analogy to Example 111-1 in Scheme 56 by using 2-(4-chloro-6-methylquinolin-2-yl)-5,5-difluoro-2,3,4,5-tetrahydro-1H-benzazepine and butane-1,4-diamine. MS obsd. (ESI$^+$) [(M+H)$^+$] 411, $^1$H NMR (400 MHz, CD$_3$OD) δ ppm 7.60-7.52 (m, 3 H), 7.40-7.35 (t, J=2.4 Hz, 2 H), 7.32-7.20 (m, 2 H), 5.90 (s, 1 H), 4.30-4.20 (m, 2 H), 3.35-3.25 (m, 2 H), 2.78-2.68 (t, J=7.2 Hz, 2 H), 2.51-2.40 (m, 2 H), 2.37 (s, 3 H), 1.78-1.68 (m, 2 H), 1.68-1.58 (m, 2 H), 1.32-1.25 (m, 2 H).

Example 111-11 trans-4-Amino-1-[2-(5,5-difluoro-1,3,4,5-tetrahydro-2H-2-benzazepin-2-yl)-6-methylquinolin-4-yl]pyrrolidin-3-ol

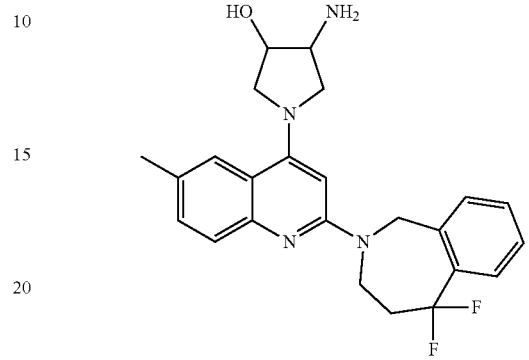

The title compound was prepared in analogy to Example 111-1 in Scheme 56 by using 2-(4-chloro-6-methylquinolin-2-yl)-5,5-difluoro-2,3,4,5-tetrahydro-1H-benzazepine and tert-butyl [(3S,4S)-4-hydroxypyrrolidin-3-yl]carbamate. MS obsd. (ESI$^+$) [(M+H)$^+$] 425, $^1$H NMR (400 MHz, CD$_3$OD) δ ppm 7.75 (s, 1 H), 7.65-7.55 (m, 2 H), 7.50-7.40 (d, J=7.6 Hz, 1 H), 7.42-7.35 (t, 1 H), 7.35-7.25 (m, 2 H), 5.60 (s, 1 H), 4.80 (s, 2 H), 4.60-4.50 (m, 1 H), 4.25-4.15 (m, 1 H), 4.15-4.00 (m, 3 H), 3.90-3.80 (m, 1 H), 3.80-3.70 (m, 1 H), 3.65-3.55 (m, 1 H), 3.30 (s, 2 H), 2.60-2.40 (m, 2 H), 2.30 (s, 3 H).

Example 112-1

N-{[3-(Aminomethyl)-1,1-dioxidothietan-3-yl]methyl}-2-(5,5-difluoro-1,3,4,5-tetrahydro-2H-2-benzazepin-2-yl)-6-methylquinolin-4-amine

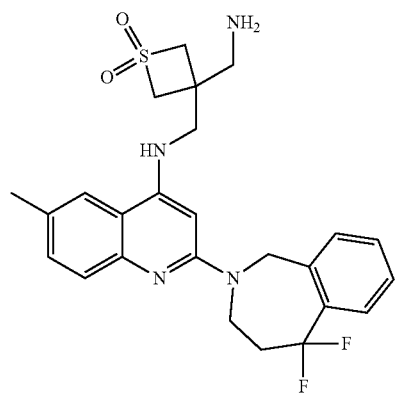 [SMILES: Cc1ccc2nc(N3CCC(F)(F)c4ccccc4C3)cc(NCC3(CN)CS(=O)(=O)C3)c2c1]

A mixture solution of 2-(4-chloro-6-methyl-quinolin-2-yl)-5,5-difluoro-2,3,4,5-tetrahydro-1H-benzazepine (218 mg, 0.609 mmol), (1,1-dioxidothietane-3,3-diyl)dimethanamine (110 mg, 0.670 mmol), (tris(dibenzylideneacetone)dipalladium(0) (56 mg, 0.061 mmol), 2,2'-bis(diphenylphosphino)-1,1'-binaphthalene (38 mg, 0.061 mmol) and sodium

Example 112-2

N-[(3-Aminooxetan-3-yl)methyl]-2-[(5E)-5-(methoxyimino)-1,3,4,5-tetrahydro-2H-2-benzazepin-2-yl]-6-methylquinolin-4-amine

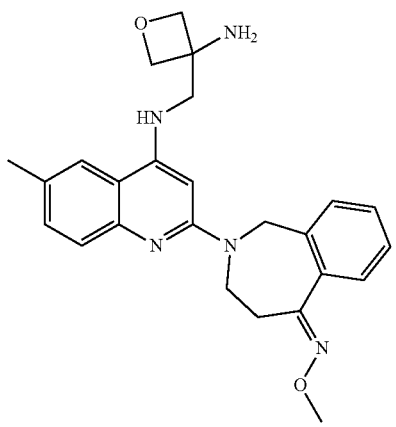 [SMILES: CO/N=C1\CCN(c2cc(NCC3(N)COC3)c3cc(C)ccc3n2)Cc2ccccc21]

(5E)-2-(4-Chloro-6-methylquinolin-2-yl)-N-methoxy-1,2,3,4-tetrahydro-5H-2-benzazepin-5-imine

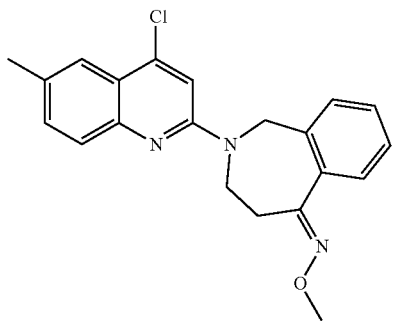 [SMILES: CO/N=C1\CCN(c2cc(Cl)c3cc(C)ccc3n2)Cc2ccccc21]

The title compound was prepared in analogy to 2-(4-chloro-6-methylquinolin-2-yl)-5,5-difluoro-2,3,4,5-tetrahydro-1H-benzazepine in Example 110-1 in Scheme 56 by using 2,4-dichoro-6-methylquinoline and N-methoxy-1,2,3,4-tetrahydro-5H-2-benzazepin-5-imine. N-[(3-Aminooxetan-3-yl)methyl]-2-[(5E)-5-(methoxyimino)-1,3,4,5-tetrahydro-2H-2-benzazepin-2-yl]-6-methylquinolin-4-amine

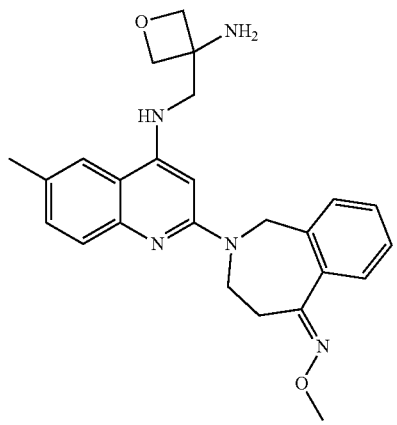 [SMILES: CO/N=C1\CCN(c2cc(NCC3(N)COC3)c3cc(C)ccc3n2)Cc2ccccc21]

The title compound was prepared in analogy to Example 112-1 in Scheme 56 by using (5E)-2-(4-chloro-6-methylquinolin-2-yl)-N-methoxy-1,2,3,4-tetrahydro-5H-2-benzazepin-5-imine and 3-(aminomethyl)oxetan-3-amine. MS obsd. (ESI$^+$) [(M+H)$^+$] 432, $^1$H NMR (400 MHz, CD$_3$OD) δ ppm 7.965 (s, 1 H), 7.706-7.684 (d, J=8.8 Hz, 1 H), 7.609-7.586 (m, 3 H), 7.453-7.376 (m, 2 H), 6.100 (s, 1 H), 5.035 (s, 2 H), 4.695-4.623 (m, 4 H), 4.014-3.987 (m, 4 H), 3.928 (s, 3 H), 3.258-3.242 (m, 2 H), 2.471 (s, 3 H).

Example 113

N-{2-[(2-Aminoethyl)sulfonyl]ethyl}-2-(5,5-difluoro-1,3,4,5-tetrahydro-2H-2-benzazepin-2-yl)-6-methylquinolin-4-amine

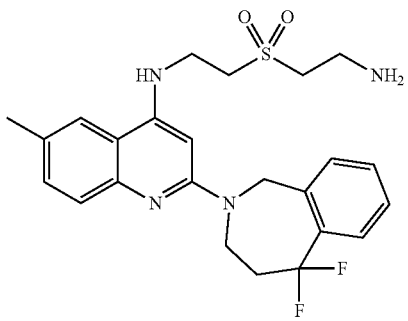 [SMILES: Cc1ccc2nc(N3CCC(F)(F)c4ccccc4C3)cc(NCCS(=O)(=O)CCN)c2c1]

N-{2-[(2-Aminoethyl)sulfanyl]ethyl}-2-(5,5-difluoro-1,3,4,5-tetrahydro-2H-2-benzazepin-2-yl)-6-methylquinolin-4-amine

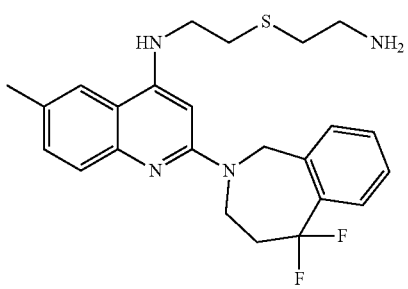 [SMILES: Cc1ccc2nc(N3CCC(F)(F)c4ccccc4C3)cc(NCCSCCN)c2c1]

A mixture of 2-(4-chloro-6-methylquinolin-2-yl)-5,5-difluoro-2,3,4,5-tetrahydro-1H-benzazepine (160 mg, 0.447 mmol) and 2-[(2-aminoethyl)sulfanyl]ethan-1-amine (1.5 mL) was heated at 150° C. for 8 hours. The resulting reaction mixture was concentrated in vacuo. The residue was dissolved in dichloromethane (20 mL), washed with a saturated aqueous solution of sodium bicarbonate (20 mL) and brine (20 mL), dried over sodium sulfate and concentrated in vacuo. The residue was purified by flash column chromatography (eluting with 10-20% methanol in dichloromethane) to afford 180 mg of the desired product as oil (yield was 91.1%), MS obsd. (ESI$^+$) [(M+H)$^+$] 443.

N-{2-[(2-Aminoethyl)sulfonyl]ethyl}-2-(5,5-difluoro-1,3,4,5-tetrahydro-2H-2-benzazepin-2-yl)-6-methylquinolin-4-amine

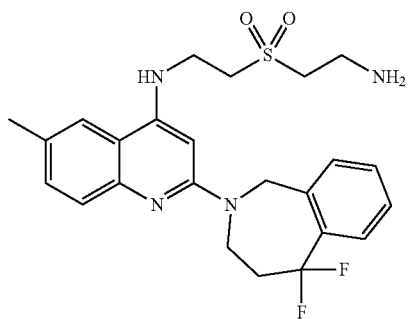 [SMILES: Cc1ccc2nc(N3CCC(F)(F)c4ccccc4C3)cc(NCCS(=O)(=O)CCN)c2c1]

To a solution of N-{2-[(2-aminoethyl)sulfanyl]ethyl}-2-(5,5-difluoro-1,3,4,5-tetrahydro-2H-2-benzazepin-2-yl)-6-methylquinolin-4-amine (120 mg, 0.271 mmol) in acetic acid (2 mL) was added potassium permanganate (60 mg, 0.38 mmol). After being stirred at room temperature for 30 minutes, the resulting mixture was concentrated in vacuo. The residue was purified by preparative HPLC to afford 5 mg of the desired product as a solid. MS obsd. (ESI$^+$) [(M+H)$^+$] 475, $^1$H NMR (400 MHz, CD$_3$OD) δ ppm 7.81 (s, 1 H), 7.77-7.68 (m, 2 H), 7.676 (s, 1 H), 7.56 (dd, J=7.2, 1.2 Hz, 2 H), 7.47 (t, J=7.6 Hz, 1 H), 6.08 (s, 1 H), 5.07 (brs, 2 H), 4.60 (brs, 2 H), 4.27 (t, J=5.6 Hz, 2 H), 4.01 (t, J=6.4 Hz, 2 H), 3.62 (t, J=6.8 Hz, 2 H), 3.53 (m, 2 H), 3.42 (m, 2 H), 2.48 (s, 3 H).

Example 114-1

2-(4-{[(3-Aminooxetan-3-yl)methyl]amino}-6-methylquinazolin-2-yl)-1,2,3,4-tetrahydro-5H-2-benzazepin-5-one

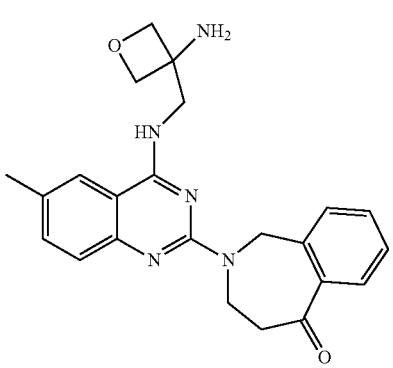 [SMILES: Cc1ccc2nc(N3CCC(=O)c4ccccc4C3)nc(NCC3(N)COC3)c2c1]

2-(4-Hydroxy-6-methylquinazolin-2-yl)-1,2,3,4-tetrahydro-5H-2-benzazepin-5-one

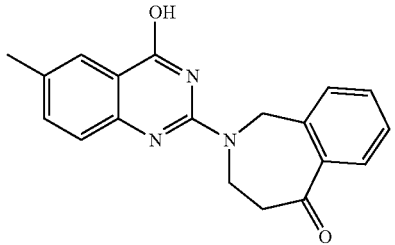 [SMILES: Cc1ccc2nc(N3CCC(=O)c4ccccc4C3)nc(O)c2c1]

To a stirred solution of 2-chloro-4(3H)-quinazolinone (580 mg, 3.0 mmol) and 1,2,3,4-tetrahydro-5H-2-benzazepin-5-one (591 mg, 3.0 mmol) in toluene (20 mL) was added triethylamine (626 µL, 4.5 mmol). After being refluxed overnight, the resulting reaction mixture was cooled and the formed solid was collected by filtration, washed with ethanol (10 mL) and ethyl acetate (10 mL), and dried in vacuo to afford 775 mg of the desired product as a white solid (yield was 81%).

2-(4-{[(3-Aminooxetan-3-yl)methyl]amino}-6-methylquinazolin-2-yl)-1,2,3,4-tetrahydro-5H-2-benzazepin-5-one

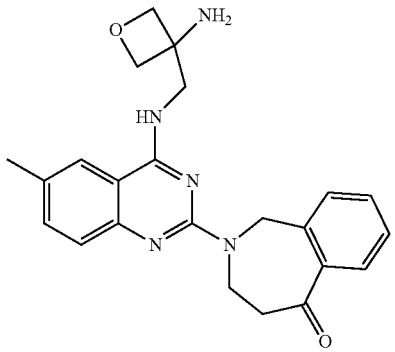 [SMILES: Cc1ccc2nc(N3CCC(=O)c4ccccc4C3)nc(NCC3(N)COC3)c2c1]

The title compound was prepared in analogy to Example 62-1 in Scheme 23 by using 2-(4-hydroxy-6-methylquinazolin-2-yl)-1,2,3,4-tetrahydro-5H-2-benzazepin-5-one and 3-(aminomethyl)oxetan-3-amine. MS obsd. (ESI$^+$) [(M+H)$^+$] 404, $^1$H NMR (400 MHz, CD$_3$OD) δ ppm 7.94 (s, 1 H), 7.90 (d, 1 H), 7.75 (d, 1 H), 7.65-7.55 (m, 3 H), 7.45 (t, 1 H), 5.40 (s, 2 H), 4.77-7.72 (m, 4 H), 4.40 (s, 2 H), 4.05 (brs, 2 H), 3.35 (t, 2 H), 2.43 (s, 3 H).

Example 114-2

N-{[3-(Aminomethyl)thietan-3-yl]methyl}-2-(5,5-difluoro-1,3,4,5-tetrahydro-2H-2-benzazepin-2-yl)-6-methylquinazolin-4-amine

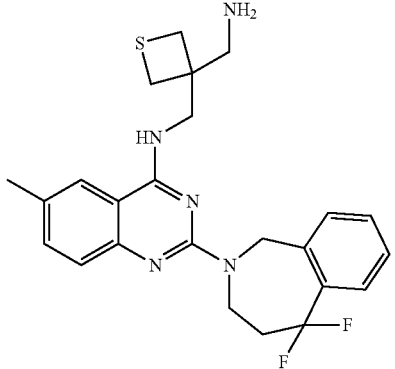 [SMILES: Cc1ccc2nc(N3CCC(F)(F)c4ccccc4C3)nc(NCC3(CN)CSC3)c2c1]

The title compound was prepared in analogy to Example 114-1 in Scheme 23 by using 2-chloro-4(3H)-quinazolinone, 5,5-difluoro-2,3,4,5-tetrahydro-1H-benzazepine and thietane-3,3-diyldimethanamine. MS obsd. (ESI$^+$) [(M+H)$^+$] 456, $^1$H NMR (400 MHz, CD$_3$OD) δ ppm 7.701-7.683 (d, J=7.2 Hz, 1 H), 7.605 (s, 1 H), 7.574-7.554 (d, J=8.0 Hz, 1 H), 7.392-7.336 (m, 2 H), 7.298-7.251 (t, J=8.4, 10.4 Hz, 2 H), 4.990 (s, 2 H), 4.309-4.283 (t, J=4.8, 5.6 Hz, 2 H), 4.035 (s, 2 H), 3.119-3.095 (d, J=9.6 Hz, 2 H), 3.016-2.992 (d, J=9.6 Hz, 2 H), 2.849 (s, 2 H), 2.478-2.413 (m, 2 H), 2.356 (s, 3 H).

Example 114-3

N-{[3-(Aminomethyl)oxetan-3-yl]methyl}-2-(5,5-difluoro-1,3,4,5-tetrahydro-2H-2-benzazepin-2-yl)-6-methylquinazolin-4-amine

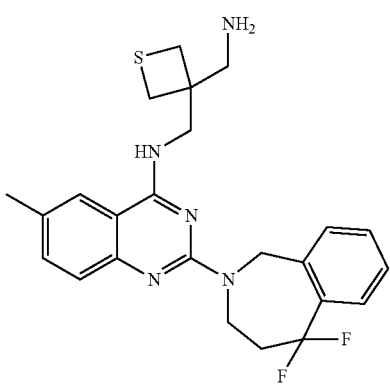 [SMILES: Cc1ccc2nc(N3CCC(F)(F)c4ccccc4C3)nc(NCC3(CN)CSC3)c2c1]

The title compound was prepared in analogy to Example 114-1 in Scheme 23 by using 2-chloro-4(3H)-quinazolinone, 5,5-difluoro-2,3,4,5-tetrahydro-1H-benzazepine and oxetane-3,3-diyldimethanamine. MS obsd. (ESI$^+$) [(M+H)$^+$] 440, $^1$H NMR (400 MHz, CD$_3$OD) δ ppm 8.00 (s, 1 H), 7.67 (m, 3 H), 7.56 (d, 1 H), 7.45 (m, 2 H), 5.14 (s, 2 H), 4.64 (d, 2 H), 4.58 (d, 2 H), 4.21 (s, 4 H), 3.41 (s, 2 H), 2.63 (brs, 2 H), 2.44 (s, 3 H).

Example 114-4

2-(Aminomethyl)-2-({[2-(5,5-difluoro-1,3,4,5-tetrahydro-2H-2-benzazepin-2-yl)-6-methylquinazolin-4-yl]amino}methyl)propane-1,3-diol

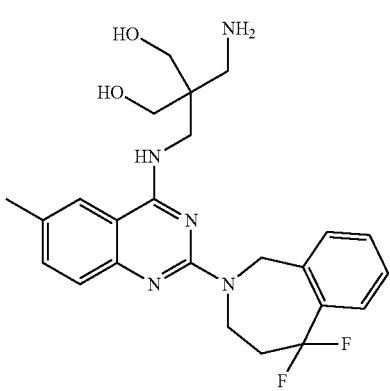 [SMILES: Cc1ccc2nc(N3CCC(F)(F)c4ccccc4C3)nc(NCC(CN)(CO)CO)c2c1]

The title compound was formed when purification of Example 114-3 by preparative HPLC in acid condition. MS obsd. (ESI$^+$) [(M+H)$^+$] 458, $^1$H NMR (400 MHz, CD$_3$OD) δ ppm 7.96 (s, 1 H), 7.63-7.75 (m, 4 H), 7.50 (t, 1 H), 7.43 (t, 1 H), 5.17 (s, 2 H), 4.27 (s, 2 H), 3.94 (s, 2 H), 3.76 (m, 4 H), 3.25 (s, 2 H), 2.68 (s, 2 H), 2.45 (s, 3 H).

Example 115

2-(4-{[(3-Aminooxetan-3-yl)methyl]amino}-6-methylquinazolin-2-yl)-5-methyl-2,3,4,5-tetrahydro-1H-2-benzazepin-5-ol

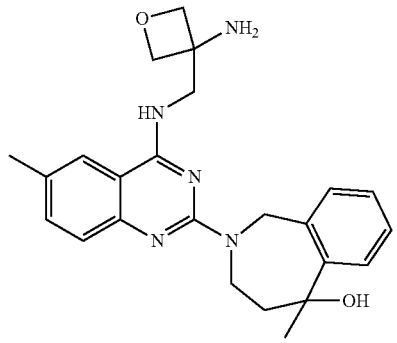 [SMILES: Cc1ccc2nc(N3CCC(C)(O)c4ccccc4C3)nc(NCC3(N)COC3)c2c1]

2-(5-Hydroxy-5-methyl-1,3,4,5-tetrahydro-benzoazepin-2-yl)-6-methyl-3H-quinazolin-4-one

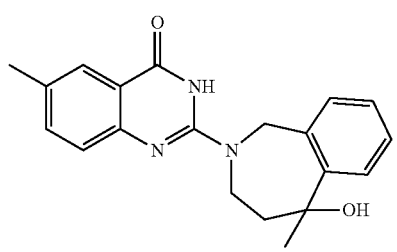 [SMILES: Cc1ccc2nc(N3CCC(C)(O)c4ccccc4C3)[nH]c(=O)c2c1]

To a suspension of 2-(4-hydroxy-6-methylquinazolin-2-yl)-1,2,3,4-tetrahydro-5H-2-benzazepin-5-one (500 mg, 1.57 mmol) in tetrahydrofuran (15 mL), a solution of methyl magnesium bromide in tetrahydrofuran (3 M, 0.57 ml, 1.72 mmol) was added at 0° C. The reaction mixture was heated at 50° C. for 4 hours, and then poured into a saturated aqueous solution of ammonium chloride (10 mL) and stirred for 10 minutes. The resulting mixture was extracted with dichloromethane (15 mL×3). The combined organic layers were dried over sodium sulfate and concentrated in vacuo. The residue was purified by flash column chromatography (eluting with 50% ethyl acetate in hexanes) to afford 350 mg of the desired product as a white solid (yield was 66.5%).

2-(4-{[(3-Aminooxetan-3-yl)methyl]amino}-6-methylquinazolin-2-yl)-5-methyl-2,3,4,5-tetrahydro-1H-2-benzazepin-5-ol

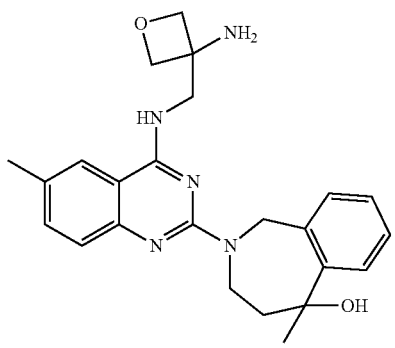 [SMILES: Cc1ccc2nc(N3CCC(C)(O)c4ccccc4C3)nc(NCC3(N)COC3)c2c1]

The title compound was prepared in analogy to Example 114-1 in Scheme 57 by using 2-(5-hydroxy-5-methyl-1,3,4,5-tetrahydro-benzoazepin-2-yl)-6-methyl-3H-quinazolin-4-one and 3-(aminomethyl)oxetan-3-amine. MS obsd. (ESI$^+$) [(M+H)$^+$] 420, $^1$H NMR (400 MHz, CD$_3$OD) δ ppm 7.95 (s, 1 H), 7.66 (d, 2 H), 7.57 (d, 1 H), 7.51 (d, 1 H), 7.30 (m, 2 H), 5.31 (d, 2 H), 4.80 (m, 4 H), 4.73 (d, 2 H), 4.39 (brs, 2 H), 3.97 (brs, 2 H), 2.45 (s, 3 H), 1.64 (s, 3 H).

Example 116-1

N-[(3-Aminooxetan-3-yl)methyl]-2-(5,5-difluoro-1,3,4,5-tetrahydro-2H-2-benzazepin-2-yl)-6-methylquinazolin-4-amine

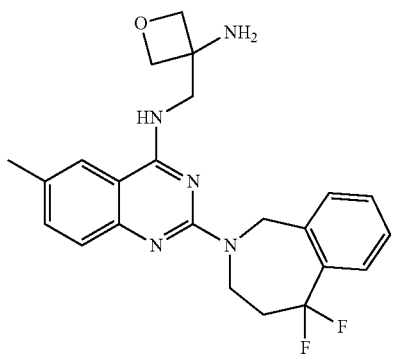 [SMILES: Cc1ccc2nc(N3CCC(F)(F)c4ccccc4C3)nc(NCC3(N)COC3)c2c1]

2-Chloro-N-{[3-(dibenzylamino)oxetan-3-yl]methyl}-6-ethylquinazolin-4-amine

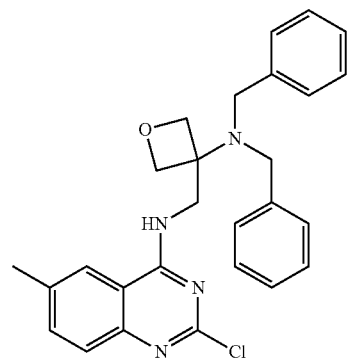 [SMILES: Cc1ccc2nc(Cl)nc(NCC3(N(Cc4ccccc4)Cc4ccccc4)COC3)c2c1]

A solution of 2,4-dichloro-6-methylquinazoline (1.0 g, 4.69 mmol) in methanol (10 mL) was added 3-(aminomethyl)-N,N-dibenzyloxetan-3-amine (1.4 g, 5.16 mmol, 60% purity) and triethylamine (0.1 g, 1 mmol). After being stirred at room temperature overnight, the mixture was concentrated in vacuo. The residue was purified by flash column chromatography (eluting with 20% ethyl acetate in petroleum ether) to afford 1.6 g of the product as a white solid (yield was 76%).

N-{[3-(Dibenzylamino)oxetan-3-yl]methyl}-2-(5,5-difluoro-1,3,4,5-tetrahydro-2H-2-benzazepin-2-yl)-6-methylquinazolin-4-amine

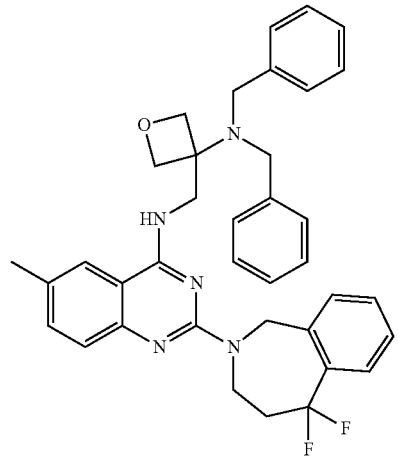 [SMILES: Cc1ccc2nc(N3CCC(F)(F)c4ccccc4C3)nc(NCC3(N(Cc4ccccc4)Cc4ccccc4)COC3)c2c1]

To a solution of 2-chloro-N-{[3-(dibenzylamino)oxetan-3-yl]methyl}-6-methylquinazolin-4-amine (200 mg, 0.436 mmol) in N,N-dimethylformamide (3 mL) was added 5,5-difluoro-1,3,4,5-tetrahydro-2H-2-benzazepine (80 mg, 0.436 mmol) and triethylamine (89 mg, 0.872 mmol). The mixture was heated at 120° C. for 30 minutes under microwave irradiation. The reaction was poured into water (10 mL) and extracted with dichloromethane (15 mL×3). The combined organic layers were dried over sodium sulfate and concentrated in vacuo. The residue was purified by flash column chromatography (eluting with 20% ethyl acetate in petroleum ether) to afford 190 mg of the product as a brown solid (yield was 72%).

N-[(3-Aminooxetan-3-yl)methyl]-2-(5,5-difluoro-1,3,4,5-tetrahydro-2H-2-benzazepin-2-yl)-6-methylquinazolin-4-amine

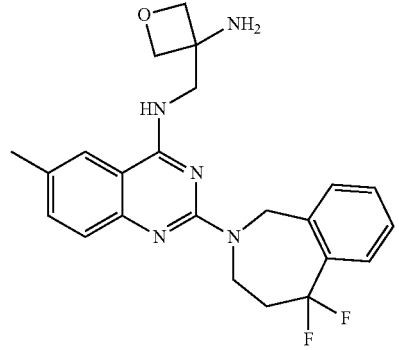 [SMILES: Cc1ccc2nc(N3CCC(F)(F)c4ccccc4C3)nc(NCC3(N)COC3)c2c1]

A solution of N-{[3-(dibenzylamino)oxetan-3-yl]methyl}-2-(5,5-difluoro-1,3,4,5-tetrahydro-2H-2-benzazepin-2-yl)-6-methylquinazolin-4-amine (190 mg, 0.314 mmol) and trifluororacetic acid (1 drop) in methanol was stirred in the presence of palladium hydroxide on carbon (50 mg) at room temperature under hydrogen atmosphere overnight. The resulting mixture was filtered, concentrated in vacuo. The residue was purified by preparative HPLC to afford 32 mg of the product as a white solid (yield was 24%). MS obsd.

(ESI⁺) [(M+H)⁺] 426, ¹H NMR (400 MHz, CD₃OD) δ ppm 7.696 (s, 1 H), 7.654-7.636 (d, J=7.2 Hz, 1 H), 7.607-7.588 (d, J=7.6 Hz, 1 H), 7.404-7.367 (m, 2 H), 7.341-7.283 (m, 2 H), 5.011 (s, 2 H), 4.683-4.626 (m, 2 H), 4.556-4.540 (d, J=6.4 Hz, 2 H), 4.335-4.307 (t, J=5.6 Hz, 2 H), 4.084 (s, 2 H), 5.528-2.432 (m, 2 H), 2.398 (s, 3 H).

Example 116-2

N-[(3-Amino-1,1-dioxidothietan-3-yl)methyl]-2-(5,5-difluoro-1,3,4,5-tetrahydro-2H-2-benzazepin-2-yl)-6-methylquinazolin-4-amine

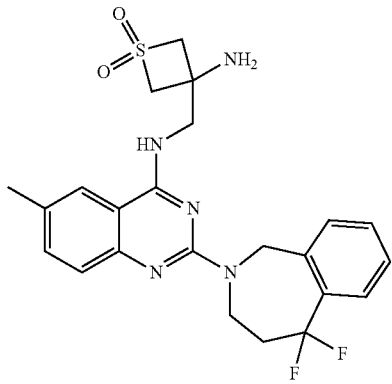 [SMILES: Cc1ccc2nc(N3CCC(F)(F)c4ccccc4C3)nc(NCC3(N)CS(=O)(=O)C3)c2c1]

The title compound was prepared in analogy to Example 116-1 in Scheme 57 by using 2,4-dichloro-6-methylquinazoline, 3-(aminomethyl)-N,N-dibenzyl(1,1-dioxido)thietan-3-amine and 5,5-difluoro-1,3,4,5-tetrahydro-2H-2-benzazepine. MS obsd. (ESI⁺) [(M+H)⁺] 474, ¹H NMR (400 MHz, CD₃OD) δ ppm 7.73 (s, 1 H), 7.65 (d, 1 H), 7.60 (d, 1 H), 7.29-7.45 (m, 4 H), 5.02 (s, 2 H), 4.04-4.62 (m, 2 H), 4.34 (t, 2 H), 4.12 (t, 2 H), 4.01-4.04 (m, 2 H), 2.47 (m, 2 H), 2.41 (s, 3 H).

Example 117

N-[2-(5,5-Difluoro-1,3,4,5-tetrahydro-2H-2-benzazepin-2-yl)-6-methylquinazolin-4-yl]-2,2-difluoropropane-1,3-diamine

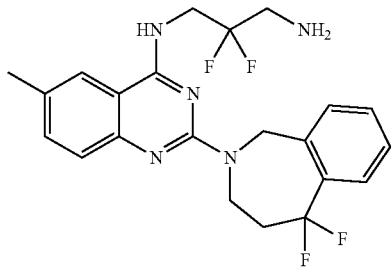 [SMILES: Cc1ccc2nc(N3CCC(F)(F)c4ccccc4C3)nc(NCC(F)(F)CN)c2c1]

N-(2-Chloro-6-methylquinazolin-4-yl)-2,2-difluoropropane-1,3-diamine

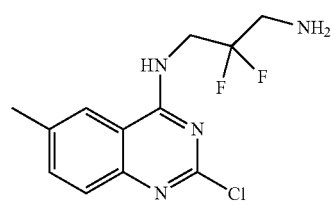 [SMILES: Cc1ccc2nc(Cl)nc(NCC(F)(F)CN)c2c1]

To a solution of 2,2-difluoropropane-1,3-diamine (1.1 g, 10 mmol) and triethylamine (1.4 mL, 10 mol) in dichloromethane (15 mL) was added a solution of 2,4-dichloro-6-methylquinazoline (500 mg, 2.36 mmol) in dichloromethane (5 mL) dropwise. After being stirred at room temperature overnight, the resulting mixture was poured into water (50 mL) and extracted with dichloromethane (50 mL×2). The combined organic layers were washed with brine (50 mL), dried over anhydrous sodium sulfate and concentrated in vacuo. The residue was purified by flash column chromatography (eluting with 10-25% methanol in dichloromethane) to afford 41.8 mg of the desired product as a white solid (yield was 62%). MS obsd. (ESI⁺) [(M+H)⁺] 287.

N-[2-(5,5-Difluoro-1,3,4,5-tetrahydro-2H-2-benzazepin-2-yl)-6-methylquinazolin-4-yl]-2,2-difluoropropane-1,3-diamine

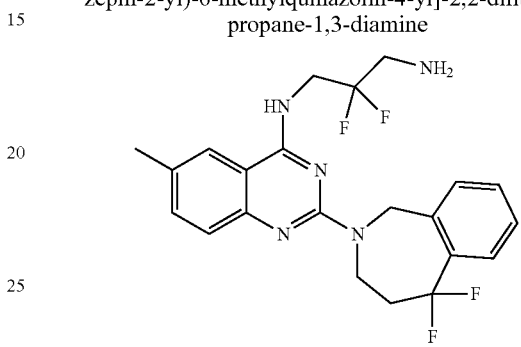

A solution of N-(2-chloro-6-methylquinazolin-4-yl)-2,2-difluoropropane-1,3-diamine (97 mg, 0.34 mmol) and 5,5-difluoro-2,3,4,5-tetrahydro-1H-benzazepine (310 mg, 1.70 mmol) in n-butanol (1 mL) was heated at 160° C. for 30 minutes. The resulting reaction mixture was purified by preparative HPLC to afford 24.3 mg of the desired compound as a white solid. MS obsd. (ESI⁺) [(M+H)⁺] 434, ¹H NMR (400 MHz, CD₃OD) δ ppm 7.96 (s, 1 H), 7.68 (d, J=7.2 Hz, 2 H), 7.58 (m, 2 H), 7.46 (m, 2 H), 5.12 (s, 2 H), 4.36 (t, J=13.6 Hz, 2 H), 4.23 (s, 2 H), 3.58 (t, J=16 Hz, 2 H), 2.67 (brs, 2 H), 2.44 (s, 3 H).

Example 118-1

N-[2-(7-Bromo-1,3,4,5-tetrahydro-2H-2-benzazepin-2-yl)-6-chloroquinolin-4-yl]ethane-1,2-diamine

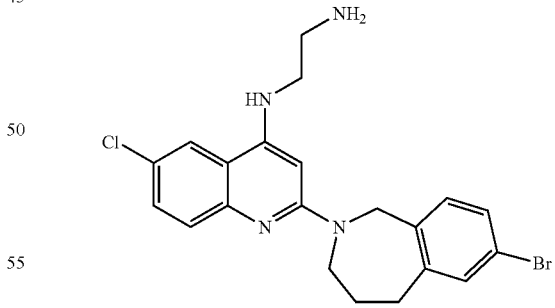

7-Bromo-1,2,4,5-tetrahydro-3H-2-benzazepin-3-one

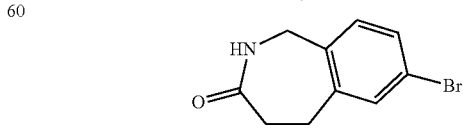

To a cooled solution of 6-bromo-3,4-dihydro-1H-naphthalen-2-one (100 g, 0.44 mol) in toluene was added sodium azide (150 g, 2.2 mol) followed by addition of trifluoromethanesulfonic acid (200 mL) dropwise. When the addition was completed, the ice bath was removed and the mixture was stirred at room temperature overnight. The reaction was poured into ice-water, basified with potassium carbonate to pH >10 slowly, and then extracted with dichloromethane (1000 mL×3). The organic layers were combined and dried over sodium sulfate, and then concentrated under reduced pressure to give a residue which was separated by column chromatography on silica gel to give 35 g of crude product. It was used for next step without further purification. MS obsd. (ESI$^+$) [(M+H)$^+$] 240.

7-Bromo-2,3,4,5-tetrahydro-1H-2-benzazepine

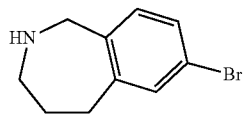

To a solution of 7-bromo-1,2,4,5-tetrahydro-3H-2-benzazepin-3-one (35 g, 146 mmol) in 1,2-dimethoxyethane (400 mL) was added a solution of borane dimethyl sulfide complex (1.0 M in tetrahydrofuran, 40 mL) under nitrogen and the resulting mixture was stirred under reflux overnight. The reaction was quenched with methanol, acidified with 2 M hydrochloric acid and then stirred for further 2 hours. The resulting mixture was concentrated in vacuo and the residue was purified by preparative HPLC to give 4.6 g of product. MS obsd. (ESI$^+$) [(M+H)$^+$] 226. $^1$H NMR (400 MHz, CDCl$_3$) δ ppm 7.21 (d, J=5 Hz, 1 H), 7.15-7.13 (dd, J=2.0, 8.0 Hz, 1 H), 6.89 (d, J=8 Hz, 1 H), 3.79 (s, 2 H), 3.11-3.08 (m, 2 H), 2.82-2.79 (m, 2 H), 2.38 (brs, 1 H), 1.63-1.61 (m, 2 H).

7-Bromo-2-(4,6-dichloroquinolin-2-yl)-2,3,4,5-tetrahydro-1H-2-benzazepine

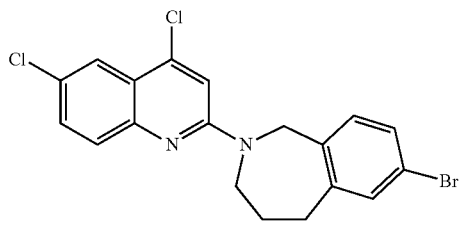 [SMILES: Clc1ccc2nc(N3CCCc4cc(Br)ccc4C3)cc(Cl)c2c1]

The mixture of 2,4,6-trichloroquinoline (300 mg, 1.29 mmol), 7-bromo-2,3,4,5-tetrahydro-1H-2-benzazepine (291 mg, 1.29 mmol) and n-butanol (3 mL) was heated with stirring in a 10 mL microwave process vial for 1 hour at 160° C. under microwave irradiation. The mixture was cooled to room temperature and diluted with ethyl acetate (10 mL), and then washed with water (10 mL). The organic layer was dried over sodium sulfate and evaporated to give a residue which was purified by column chromatography on silica gel to give 222 mg of product as a white solid (yield was 41%). MS obsd. (ESI$^+$) [(M+H)$^+$] 421.

N-[2-(7-Bromo-1,3,4,5-tetrahydro-2H-2-benzazepin-2-yl)-6-chloroquinolin-4-yl]ethane-1,2-diamine

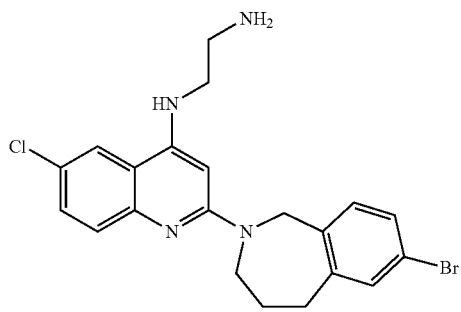 [SMILES: NCCNc1cc(N2CCCc3cc(Br)ccc3C2)nc2ccc(Cl)cc12]

The mixture of 7-bromo-2-(4,6-dichloroquinolin-2-yl)-2,3,4,5-tetrahydro-1H-2-benzazepine (200 mg, 0.47 mmol) and ethane-1,2-diamine (0.5 mL) was heated with stirring in a 5 mL microwave process vial for 2 hours at 160° C. under microwave irradiation. The solvent was removed under reduced pressure, and the residue was purified by preparative HPLC to give 38 mg of product (yield was 18%). MS obsd. (ESI$^+$) [(M+H)$^+$] 445, $^1$H NMR (400 MHz, CD$_3$OD) δ ppm 7.90 (d, J=2.4 Hz, 1 H), 7.49 (d, J=8.8 Hz, 1 H), 7.41 (m, 1 H), 7.35 (m, 1 H), 7.31 (m, 2 H), 5.99 (s, 1 H), 4.80 (s, 2 H), 4.13 (m, 2 H), 3.40 (m, 2 H), 3.00 (m, 4 H), 1.90 (m, 2 H).

Example 118-2

2-{4-[(2-Aminoethyl)amino]quinolin-2-yl}-2,3,4,5-tetrahydro-1H-2-benzazepin-8-ol

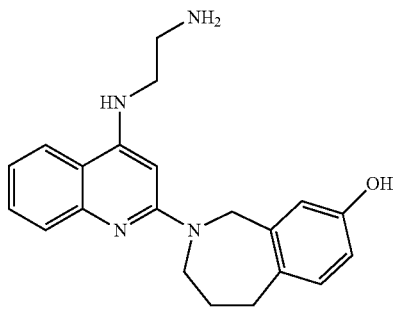 [SMILES: NCCNc1cc(N2CCCc3ccc(O)cc3C2)nc2ccccc12]

The title compound was prepared in analogy to Example 118-1 in Scheme 59 by using 2,3,4,5-tetrahydro-1H-2-benzazepine-8-ol (commercial available) and 2,4-dichloroquinoline (commercial available) instead of 7-bromo-2,3,4,5-tetrahydro-1H-2-benzazepine and 2,4-trichloroquinoline respectively. MS obsd. (ESI$^+$) [(M+H)$^+$] 349. $^1$H NMR (400 MHz, CD$_3$OD) δ ppm 7.82 (d, J=8.0 Hz, 1 H), 7.55 (d, J=8.0 Hz, 1 H), 7.43 (m, 1 H), 7.13 (m, 1 H), 6.96 (m, 2 H), 6.56 (m, 1 H), 6.00 (s, 1 H), 4.72 (s, 2 H), 4.13 (m, 2 H), 3.43 (t, J=6.4 Hz, 2 H), 2.96 (m, 4 H), 1.87 (m, 2 H).

Example 118-3

N-[6-Methyl-2-(1,3,4,5-tetrahydro-2H-2-benzazepin-2-yl)quinolin-4-yl]ethane-1,2 diamine

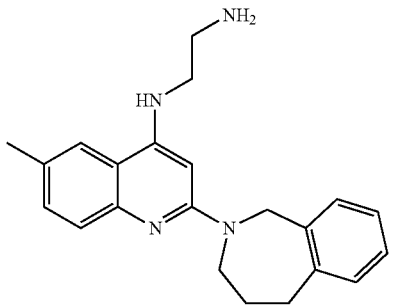 [SMILES: Cc1ccc2nc(N3CCCc4ccccc4C3)cc(NCCN)c2c1]

The title compound was prepared in analogy to Example 118-1 in Scheme 59 by using 2,3,4,5-tetrahydro-1H-2-benzazepine (commercial available) and 2,4-dichloro-6-methylquinoline (commercial available) instead of 7-bromo-2,3,4,5-tetrahydro-1H-2-benzazepine and 2,4,6-trichloroquinoline respectively. MS obsd. (ESI⁺) [(M+H)⁺] 347. ¹H NMR (400 MHz, DMSO-d6) δ ppm 7.68 (s, 1 H), 7.55 (d, J=6.8 Hz, 1 H), 7.29 (d, J=8.4 Hz, 1 H), 7.21 (d, J=6.8 Hz, 1 H), 7.13-7.05 (m, 3 H), 6.67 (brs, 1 H), 6.00 (s, 1 H), 4.79 (s, 2 H), 4.11 (brs, 2 H), 3.52 (s, 2 H), 3.05-2.99 (m, 4 H), 2.35 (s, 3 H), 1.77 (s, 2 H).

Example 118-4

N-[2-(8-Fluoro-1,3,4,5-tetrahydro-2H-2-benzazepin-2-yl)-6-methylquinolin-4-yl]ethane-1,2-diamine

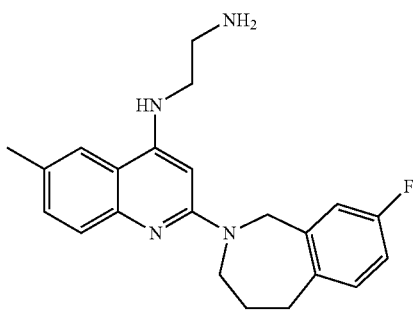 [SMILES: Cc1ccc2nc(N3CCCc4ccc(F)cc4C3)cc(NCCN)c2c1]

The title compound was prepared in analogy to Example 118-1 in Scheme 59 by using 8-fluoro-2,3,4,5-tetrahydro-1H-2-benzazepine (commercial available) and 2,4-dichloro-6-methylquinoline (commercial available) instead of 7-bromo-2,3,4,5-tetrahydro-1H-2-benzazepine and 2,4,6-trichloroquinoline respectively. MS obsd. (ESI⁺) [(M+H)⁺] 365. ¹H NMR (400 MHz, CD₃OD) δ ppm 7.68 (s, 1 H), 7.48 (d, J=8.4 Hz, 1 H), 7.28 (m, 2 H), 7.12 (m, 1 H), 6.83 (m, 1 H), 5.93 (s, 1 H), 4.80 (s, 2 H), 4.09 (s, 2 H), 3.46 (t, J=6.0 Hz, 2 H), 3.00 (m, 4 H), 2.40 (s, 3 H), 1.90 (m, 2 H).

Example 118-5

N-[6-Chloro-2-(1,3,4,5-tetrahydro-2H-2-benzazepin-2-yl)quinolin-4-yl]ethane-1,2-diamine

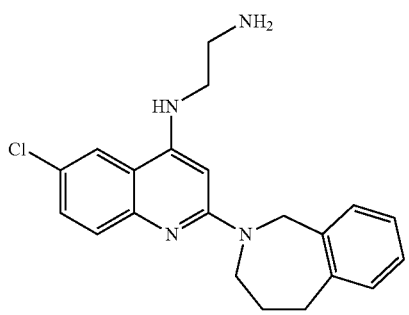 [SMILES: NCCNc1cc(N2CCCc3ccccc3C2)nc2ccc(Cl)cc12]

The title compound was prepared in analogy to Example 118-1 in Scheme 59 by using 2,3,4,5-tetrahydro-1H-2-benzazepine (commercial available) instead of 7-bromo-2,3,4,5-tetrahydro-1H-2-benzazepine. MS obsd. (ESI⁺) [(M+H)⁺] 367. ¹H NMR (400 MHz, CD₃OD) δ ppm 7.87 (d, J=2.4 Hz, 1 H), 7.47-7.42 (m, 2 H), 7.34 (dd, J=9.0, 2.2 Hz, 1 H), 7.15-7.09 (m, 3 H), 5.99 (s, 1 H), 4.76 (s, 2 H), 4.11 (brs, 2 H), 3.38-3.32 (m, 2 H), 3.00-2.93 (m, 4 H), 1.87 (t, J=5.2 Hz, 2 H).

Example 118-6

N-[6-Chloro-2-(9-fluoro-1,3,4,5-tetrahydro-2H-2-benzazepin-2-yl)quinolin-4-yl]ethane-1,2-diamine

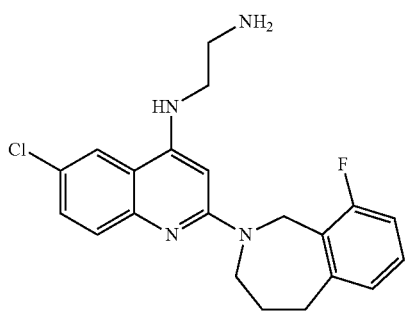 [SMILES: NCCNc1cc(N2CCCc3cccc(F)c3C2)nc2ccc(Cl)cc12]

The title compound was prepared in analogy to Example 118-1 in Scheme 59 by using 9-fluoro-2,3,4,5-tetrahydro-1H-2-benzazepine (commercial available) instead of 7-bromo-2,3,4,5-tetrahydro-1H-2-benzazepine. MS obsd. (ESI⁺) [(M+H)⁺] 385. ¹H NMR (400 MHz, CD₃OD) δ ppm 7.90 (d, J=2.0 Hz, 1 H), 7.47 (d, J=8.8 Hz, 1 H), 7.36 (dd, J=8.8, 2.4 Hz, 1 H), 7.13 (m, 1H), 7.00 (m, 2 H), 6.11 (s, 1 H), 4.91 (s, 2 H), 4.21 (s, 2 H), 3.45 (t, J=6.0 Hz, 2 H), 3.10 (m, 2 H), 3.00 (t, J=6.0 Hz, 2 H), 1.89 (m, 2 H).

Example 118-7

N-[2-(8-Fluoro-1,3,4,5-tetrahydro-2H-2-benzazepin-2-yl)quinolin-4-yl]ethane-1,2-diamine

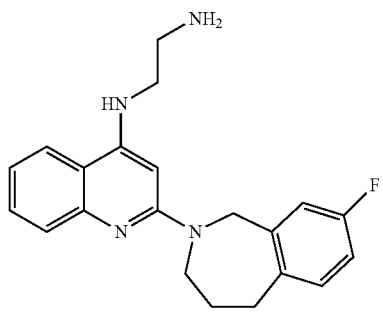 [SMILES: NCCNc1cc(N2CCCc3ccc(F)cc3C2)nc2ccccc12]

The title compound was prepared in analogy to Example 118-1 in Scheme 59 by using 8-fluoro-2,3,4,5-tetrahydro-1H-2-benzazepine (commercial available) and 2,4-dichloroquinoline (commercial available) instead of 7-bromo-2,3,4,5-tetrahydro-1H-2-benzazepine and 2,4,6-trichloroquinoline respectively. MS obsd. (ESI$^+$) [(M+H)$^+$] 351. $^1$H NMR (400 MHz, CD$_3$OD) δ ppm 7.90 (d, J=7.6 Hz, 1 H), 7.58 (d, J=8.0 Hz, 1 H), 7.52 (t, J=6.8, 1.2 Hz, 1 H), 7.19 (m, 2 H), 7.02 (m, 2 H), 6.07 (s, 1 H), 4.21 (s, 2 H), 3.52 (t, J=6.0 Hz, 2 H), 4.91 (s, 2 H), 3.12 (m, 2 H), 3.06 (m, 2 H), 1.94 (m, 2 H).

Example 118-8

1-Amino-3-{[2-(1,3,4,5-tetrahydro-2H-2-benzazepin-2-yl)quinolin-4-yl]amino}propan-2-ol trifluoroacetate (salt)

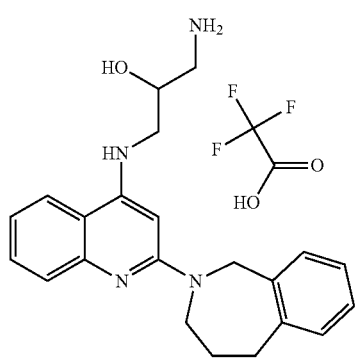

The title compound was prepared in analogy to Example 118-1 in Scheme 59 by using 2,3,4,5-tetrahydro-1H-2-benzazepine (commercial available), 2,4-dichloroquinoline (commercial available) and 1,3-diamino-propan-2-ol (commercial available) instead of 7-bromo-2,3,4,5-tetrahydro-1H-2-benzazepine, 2,4,6-trichloroquinoline and ethane-1,2-diamine respectively. MS obsd. (ESI$^+$) [(M+H)$^+$] 363. $^1$H NMR (400 MHz, CD$_3$OD CD$_3$OD) δ ppm 8.05-8.03 (d, J=7.6 Hz, 1 H), 7.78-7.76 (d, J=7.6 Hz, 1 H), 7.72-7.68 (m, 1 H), 7.52-7.50 (m, 1 H), 7.44-7.40 (m, 1 H), 7.23-7.19 (m, 3 H), 6.12 (s, 1 H), 4.97 (s, 2 H), 4.16-4.11 (m, 3 H), 3.56-3.55 (d, J=6 Hz, 2 H), 3.20-3.16 (dd, J=2.8, 12.8 Hz, 1 H), 3.11-3.08 (m, 2 H), 2.99-2.94 (m, 1 H), 1.99-1.98 (m, 2 H).

Example 118-9

N-[2-(1,3,4,5-Tetrahydro-2H-2-benzazepin-2-yl)quinolin-4-yl]ethane-1,2-diamine

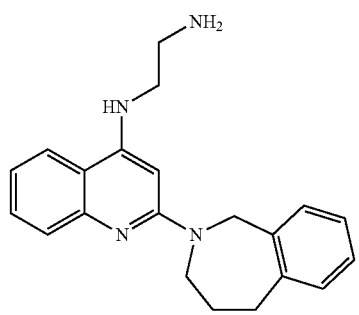 [SMILES: NCCNc1cc(N2CCCc3ccccc3C2)nc2ccccc12]

The title compound was prepared in analogy to Example 118-1 in Scheme 59 by using 2,3,4,5-tetrahydro-1H-2-benzazepine (commercial available) and 2,4-dichloroquinoline (commercial available) instead of 7-bromo-2,3,4,5-tetrahydro-1H-2-benzazepine and 2,4,6-trichloroquinoline respectively. MS obsd. (ESI$^+$) [(M+H)$^+$] 333. $^1$H NMR (400 MHz, CD$_3$OD) δ ppm 7.91-7.89 (m, 1 H), 7.62-7.60 (m, 1 H), 7.52-7.45 (m, 2 H), 7.21-7.12 (m, 3 H), 5.96 (s, 1 H), 4.10 (s, 2 H), 3.51-3.47 (t, J=6.0 Hz, 1 H), 3.04-2.98 (m, 5 H), 2.84 (s, 2 H), 1.94-1.91 (m, 2 H).

Example 118-10

N-[6-Bromo-2-(1,3,4,5-tetrahydro-2H-2-benzazepin-2-yl)quinolin-4-yl]ethane-1,2-diamine

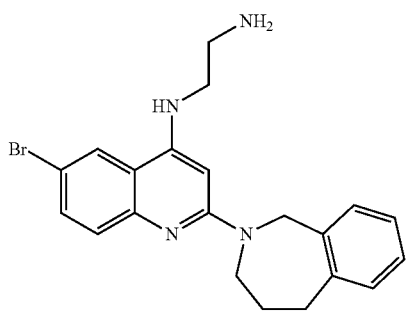

The title compound was prepared in analogy to Example 118-1 in Scheme 59 by using 2,3,4,5-tetrahydro-1H-2-benzazepine (commercial available) and 6-bromo-2,4-dichloroquinoline (commercial available) instead of 7-bromo-2,3,4,5-tetrahydro-1H-2-benzazepine and 2,4,6-trichloroquinoline respectively. MS obsd. (ESI$^+$) [(M+H)$^+$] 411. $^1$H NMR (400 MHz, CD$_3$OD) δ ppm 8.05 (d, J=2.0 Hz, 1 H), 7.52-7.42 (m, 3 H), 7.16-7.12 (m, 3 H), 6.03 (s, 1 H), 4.83 (s, 2 H), 4.15 (brs, 2 H), 3.48 (t, J=6.0 Hz, 2 H), 3.07-3.03 (m, 4 H), 1.94 (t, J=5.2 Hz, 2 H).

Example 118-11

N-[6-Methoxy-2-(1,3,4,5-tetrahydro-2H-2-benzazepin-2-yl)quinolin-4-yl]ethane-1,2-diamine

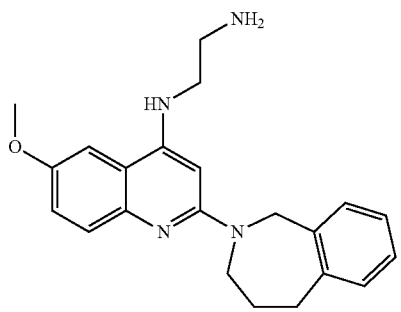 [SMILES: COc1ccc2nc(N3CCCc4ccccc4C3)cc(NCCN)c2c1]

The title compound was prepared in analogy to Example 118-1 in Scheme 59 by using 2,3,4,5-tetrahydro-1H-2-benzazepine (commercial available) and 2,4-dichloro-6-methoxyquinoline (commercial available) instead of 7-bromo-2,3,4,5-tetrahydro-1H-2-benzazepine and 2,4,6-trichloroquinoline respectively. MS obsd. (ESI$^+$) [(M+H)$^+$] 363. $^1$H NMR (400 MHz, CD$_3$OD) δ ppm 7.60 (d, J=9.2 Hz, 1 H), 7.50 (d, J=6.4 Hz, 1 H), 7.42 (d, J=2.4 Hz, 1 H), 7.25-7.18 (m, 4 H), 6.01 (s, 1 H), 4.93 (s, 2 H), 4.13 (brs, 2 H), 3.89 (s, 3 H), 3.53 (t, J=6.4 Hz, 2 H), 3.10-3.01 (m, 4 H), 1.96 (s, 2 H).

Example 118-12

N-[2-(6-Chloro-1,3,4,5-tetrahydro-2H-2-benzazepin-2-yl)quinolin-4-yl]ethane-1,2-diamine

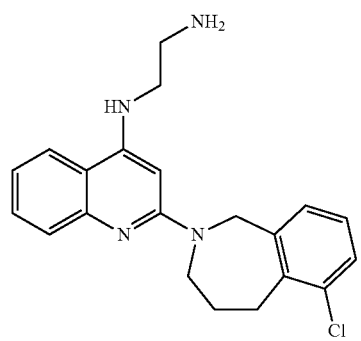 [SMILES: NCCNc1cc(N2CCCc3c(Cl)cccc3C2)nc2ccccc12]

The title compound was prepared in analogy to Example 118-1 in Scheme 59 by using 5-chloro-3,4-dihydro-1H-naphthalen-2-one (commercial available) and 2,4-dichloroquinoline (commercial available) instead of 6-bromo-3,4-dihydro-1H-naphthalen-2-one and 2,4,6-trichloroquinoline respectively. MS obsd. (ESI$^+$) [(M+H)$^+$] 367. $^1$H NMR (400 MHz, CD$_3$OD) δ ppm 7.82 (d, J=8.0 Hz, 1 H), 7.53 (d, J=8.4 Hz, 1 H), 7.43 (m, 2 H), 7.25 (d, J=8.4 Hz, 1 H), 7.12 (m, 2 H), 5.96 (s, 1 H), 4.87 (s, 2 H), 4.10 (s, 2 H), 3.41 (m, 2 H), 3.25 (m, 2 H), 2.95 (m, 2 H), 1.94 (m, 2 H).

Example 118-13

N-[2-(7-Fluoro-1,3,4,5-tetrahydro-2H-2-benzazepin-2-yl)-6-methylquinolin-4-yl]ethane-1,2-diamine

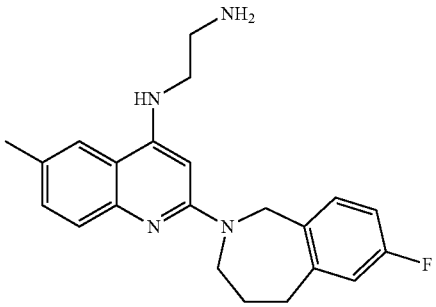 [SMILES: Cc1ccc2nc(N3CCCc4cc(F)ccc4C3)cc(NCCN)c2c1]

The title compound was prepared in analogy to Example 118-1 in Scheme 59 by using 6-fluoro-3,4-dihydro-1H-naphthalen-2-one (commercial available) and 2,4-dichloro-6-methylquinoline (commercial available) instead of 6-bromo-3,4-dihydro-1H-naphthalen-2-one and 2,4,6-trichloroquinoline respectively. MS obsd. (ESI$^+$) [(M+H)$^+$] 365. $^1$H NMR (400 MHz, CD$_3$OD) δ ppm 7.82 (s, 1 H), 7.58 (d, J=8.4 Hz, 1 H), 7.45 (m, 1 H), 7.17 (m, 1 H), 6.94 (m, 1 H), 6.84 (m, 1 H), 6.03 (d, J=4.0 Hz, 1 H), 4.87 (s, 2 H), 3.95 (m, 4 H), 3.56 (t, J=6.4 Hz, 2 H), 3.10 (m, 4 H), 2.48 (s, 3 H).

Example 118-14

N-Methyl-N'-[2-(1,3,4,5-tetrahydro-2H-2-benzazepin-2-yl)quinolin-4-yl]ethane-1,2-diamine

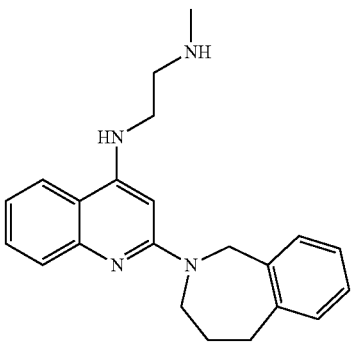 [SMILES: CNCCNc1cc(N2CCCc3ccccc3C2)nc2ccccc12]

The title compound was prepared in analogy to Example 118-1 in Scheme 59 by using 2,3,4,5-tetrahydro-1H-2-benzazepine (commercial available), 2,4-dichloroquinoline (commercial available) and N-methyl-ethane-1,2-diamine (commercial available) instead of 7-bromo-2,3,4,5-tetrahydro-1H-2-benzazepine, 2,4,6-trichloroquinoline and ethane-1,2-diamine respectively. MS obsd. (ESI$^+$) [(M+H)$^+$] 347. $^1$H NMR (400 MHz, DMSO-d6) δ ppm 8.42 (brs, 2 H), 7.88 (s, 1 H), 7.55 (d, J=6.4 Hz, 1 H), 7.47 (s, 2 H), 7.16-7.11 (m, 4 H), 6.01 (s, 1 H), 4.87 (s, 2 H), 4.14 (s, 2 H), 3.63 (s, 2 H), 3.20 (t, J=5.6 Hz, 2 H), 3.02 (s, 2 H), 2.67 (s, 3 H), 1.80 (s, 2 H).

Example 118-15

N-[2-(7-Methoxy-1,3,4,5-tetrahydro-2H-2-benza-zepin-2-yl)quinolin-4-yl]ethane-1,2-diamine

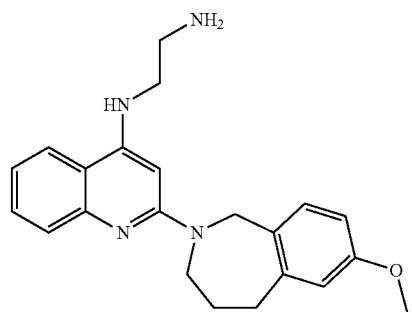 [SMILES: COc1ccc2c(c1)CCCN(c1cc(NCCN)c3ccccc3n1)C2]

The title compound was prepared in analogy to Example 118-1 in Scheme 59 by using 7-methoxy-2,3,4,5-tetrahydro-1H-2-benzazepine (commercial available) and 2,4-dichloroquinoline (commercial available) instead of 7-bromo-2,3,4,5-tetrahydro-1H-2-benzazepine and 2,4,6-trichloroquinoline respectively. MS obsd. (ESI$^+$) [(M+H)$^+$] 363. $^1$H NMR (400 MHz, CD$_3$OD) δ ppm 8.00 (d, J=6.0 Hz, 1 H), 7.70 (d, J=8.0 Hz, 1 H), 7.63 (t, J=6.0 Hz, 1 H), 7.43 (d, J=8.0 Hz, 1 H), 7.34 (m, 1 H), 6.80 (m, 1 H), 6.76 (m, 1 H), 6.00 (s, 1 H), 4.87 (s, 2 H), 4.13 (m, 2 H), 3.76 (s, 3 H), 3.59 (m, 2 H), 3.09 (m, 4 H), 1.97 (m, 2 H).

Example 118-16

N-[2-(7-Fluoro-1,3,4,5-tetrahydro-2H-2-benzazepin-2-yl)quinolin-4-yl]ethane-1,2-diamine

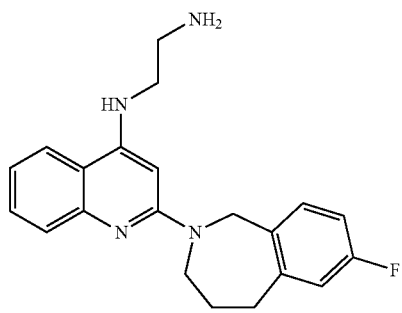 [SMILES: NCCNc1cc(N2CCCc3cc(F)ccc3C2)nc2ccccc12]

The title compound was prepared in analogy to Example 118-1 in Scheme 59 by using 6-fluoro-3,4-dihydro-1H-naphthalen-2-one (commercial available) and 2,4-dichloroquinoline (commercial available) instead of 6-bromo-3,4-dihydro-1H-naphthalen-2-one and 2,4,6-trichloroquinoline respectively. MS obsd. (ESI$^+$) [(M+H)$^+$] 351. $^1$H NMR (400 MHz, CD$_3$OD) δ ppm 7.92 (d, J=8.4 Hz, 1 H), 7.63 (d, J=8.0 Hz, 1 H), 7.55-7.49 (m, 2 H), 7.24 (m, 1 H), 6.96-6.91 (m, 2 H), 5.97 (s, 1 H), 4.86 (s, 2 H), 4.12 (s, 2 H), 3.55 (t, J=6.0 Hz, 2 H), 3.08 (m, 4 H), 1.95 (m, 2 H).

Example 118-17

N-[2-(8-Methoxy-1,3,4,5-tetrahydro-2H-2-benza-zepin-2-yl)quinolin-4-yl]ethane-1,2-diamine

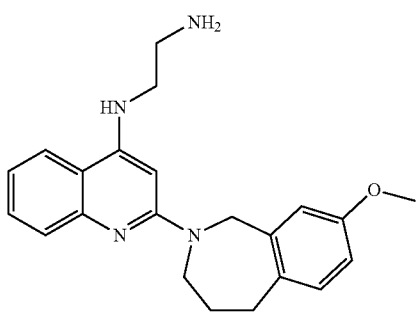 [SMILES: COc1ccc2c(c1)CN(c1cc(NCCN)c3ccccc3n1)CCC2]

The title compound was prepared in analogy to Example 118-1 in Scheme 59 1 by using 8-methoxy-2,3,4,5-tetrahydro-1H-2-benzazepine (commercial available) and 2,4-dichloroquinoline (commercial available) instead of 7-bromo-2,3,4,5-tetrahydro-1H-2-benzazepine and 2,4,6-trichloroquinoline respectively. MS obsd. (ESI$^+$) [(M+H)$^+$] 363. $^1$H NMR (400 MHz, CD$_3$OD) δ ppm 8.08 (d, J=8.4 Hz, 1 H), 7.82 (d, J=8.0 Hz, 1 H), 7.75 (t, J=7.2 Hz, 1 H), 7.46 (t, J=8.0 Hz, 1 H), 7.19 (m, 1 H), 7.13 (m, 1 H), 6.81 (m, 1 H), 6.05 (s, 1 H), 4.96 (s, 2 H), 4.15 (m, 2 H), 3.82 (m, 5 H), 3.29 (m, 2 H), 3.07 (m, 2 H), 1.99 (m, 2 H).

Example 118-18

N-[6-(Difluoromethoxy)-2-(1,3,4,5-tetrahydro-2H-2-benzazepin-2-yl)quinolin-4-yl]ethane-1,2-diamine

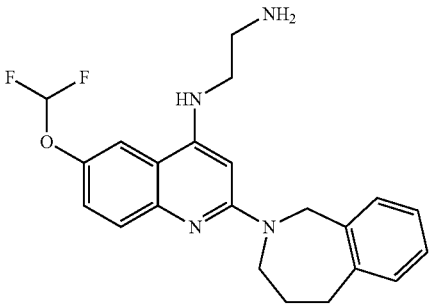 [SMILES: NCCNc1cc(N2CCCc3ccccc3C2)nc2ccc(OC(F)F)cc12]

The title compound was prepared in analogy to Example 118-1 in Scheme 59 by using 2,3,4,5-tetrahydro-1H-2-benzazepine (commercial available) and 2,4-dichloro-6-difluoromethoxyquinoline (commercial available) instead of 7-bromo-2,3,4,5-tetrahydro-1H-2-benzazepine and 2,4,6-trichloroquinoline respectively. MS obsd. (ESI$^+$) [(M+H)$^+$] 399. $^1$H NMR (400 MHz, CD$_3$OD) δ ppm 7.63 (d, J=2.4 Hz, 1 H), 7.55 (d, J=9.2 Hz, 1 H), 7.47 (d, J=6.8 Hz, 1 H), 7.27 (dd, J=8.8, 2.4 Hz, 1 H), 7.18-7.12 (m, 3 H), 6.79 (t, J=74.4 Hz, 1 H, HCF$_2$O—), 6.03 (s, 1 H), 4.82 (s, 2 H), 4.15 (brs, 2 H), 3.46 (t, J=6.2 Hz, 2 H), 3.06-3.00 (m, 4 H), 1.91 (t, J=5.2 Hz, 2 H).

Example 118-19

N-[2-(1,3,4,5-Tetrahydro-2H-2-benzazepin-2-yl)-6-(trifluoromethyl)quinolin-4-yl]ethane-1,2-diamine

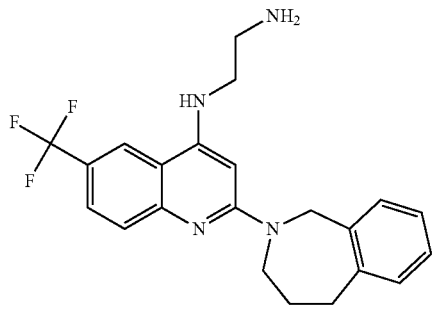 [SMILES: NCCNc1cc(N2CCCc3ccccc3C2)nc2ccc(C(F)(F)F)cc12]

The title compound was prepared in analogy to Example 118-1 in Scheme 59 by using 2,3,4,5-tetrahydro-1H-2-benzazepine (commercial available) and 2,4-dichloro-6-trifluoromethylquinoline (commercial available) instead of 7-bromo-2,3,4,5-tetrahydro-1H-2-benzazepine and 2,4,6-trichloroquinoline respectively. MS obsd. (ESI$^+$) [(M+H)$^+$] 401. $^1$H NMR (400 MHz, DMSO-d6) δ ppm 8.36 (s, 1 H), 7.57-7.45 (m, 3 H), 7.12 (brs, 3 H), 6.99 (s, 1 H), 6.03 (s, 1 H), 4.81 (s, 2 H), 4.15 (brs, 2 H), 3.29 (brs, 2 H), 3.01 (s, 2 H), 2.82 (s, 2 H), 1.77 (s, 2 H).

Example 118-20

N-[8-Chloro-2-(1,3,4,5-tetrahydro-2H-2-benzazepin-2-yl)quinolin-4-yl]ethane-1,2-diamine

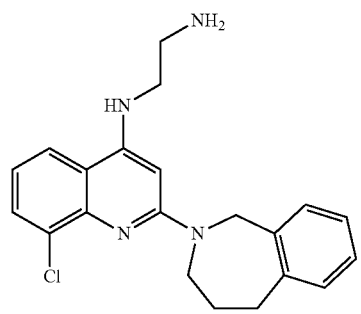 [SMILES: NCCNc1cc(N2CCCc3ccccc3C2)nc2c(Cl)cccc12]

The title compound was prepared in analogy to Example 118-1 in Scheme 59 by using 2,3,4,5-tetrahydro-1H-2-benzazepine (commercial available) and 2,4,8-trichloroquinoline (commercial available) instead of 7-bromo-2,3,4,5-tetrahydro-1H-2-benzazepine and 2,4,6-trichloroquinoline respectively. MS obsd. (ESI$^+$) [(M+H)$^+$] 367. $^1$H NMR (400 MHz, CD$_3$OD) δ ppm 7.24 (d, J=8.0 Hz, 1 H), 7.60 (d, J=6.8 Hz, 1 H), 7.55 (d, J=7.6 Hz, 1 H), 7.13-7.09 (m, 3 H), 6.98 (t, J=8.0 Hz, 1 H), 6.03 (s, 1 H), 4.89 (s, 2 H), 4.20 (brs, 2 H), 3.46 (t, J=6.0 Hz, 2 H), 3.07-3.02 (m, 4 H), 1.92 (t, J=5.2 Hz, 2 H).

Example 118-21

N-[6-Fluoro-2-(1,3,4,5-tetrahydro-2H-2-benzazepin-2-yl)quinolin-4-yl]ethane-1,2-diamine

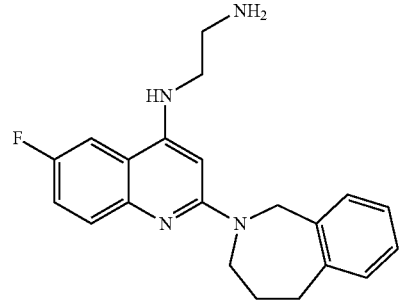 [SMILES: NCCNc1cc(N2CCCc3ccccc3C2)nc2ccc(F)cc12]

The title compound was prepared in analogy to Example 118-1 in Scheme 59 by using 2,3,4,5-tetrahydro-1H-2-benzazepine (commercial available) and 2,4-dichloro-6-fluoroquinoline (commercial available) instead of 7-bromo-2,3,4,5-tetrahydro-1H-2-benzazepine and 2,4,6-trichloroquinoline respectively. MS obsd. (ESI$^+$) [(M+H)$^+$] 351. $^1$H NMR (400 MHz, CD$_3$OD) δ ppm 7.60-7.52 (m, 2 H), 7.47 (d, J=6.8 Hz, 1 H), 7.26-7.21 (m, 1 H), 7.17-7.12 (m, 3 H), 6.04 (s, 1 H), 4.82 (s, 2 H), 4.15 (brs, 2 H), 3.45 (t, J=6.4 Hz, 2 H), 3.06-2.99 (m, 4 H), 1.91 (t, J=5.4 Hz, 2 H).

Example 118-22

N,N-Dimethyl-N'-[2-(1,3,4,5-tetrahydro-2H-2-benzazepin-2-yl)quinolin-4-yl]ethane-1,2-diamine

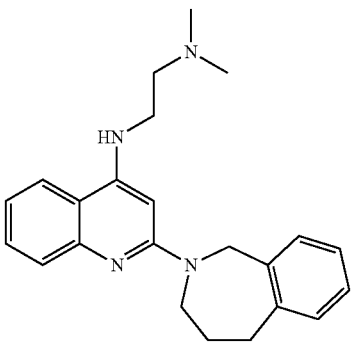 [SMILES: CN(C)CCNc1cc(N2CCCc3ccccc3C2)nc2ccccc12]

The title compound was prepared in analogy to Example 118-1 in Scheme 59 by using 2,3,4,5-tetrahydro-1H-2-benzazepine (commercial available), 2,4-dichloroquinoline (commercial available) and N,N-dimethyl-ethane-1,2-diamine (commercial available) instead of 7-bromo-2,3,4,5-tetrahydro-1H-2-benzazepine, 2,4,6-trichloroquinoline and ethane-1,2-diamine respectively. MS obsd. (ESi$^+$) [(M+H)$^+$] 361. $^1$H NMR (400 MHz, DMSO-d6) δ ppm 7.90 (d, J=3.6 Hz, 1 H), 7.56-7.46 (m, 3 H), 7.15-7.11 (m, 4 H), 5.89 (s, 1 H), 4.87 (s, 2 H), 4.14 (s, 2 H), 3.53 (s, 2 H), 3.05 (s, 2 H), 2.91 (s, 2 H), 2.53 (s, 6 H), 1.80 (s, 2 H).

Example 118-23

N-[2-(1,3,4,5-Tetrahydro-2H-2-benzazepin-2-yl)-6-(trifluoromethoxy)quinolin-4-yl]ethane-1,2-diamine

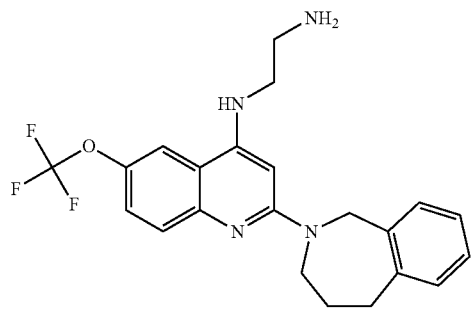 [SMILES: NCCNc1cc(N2CCCc3ccccc3C2)nc2ccc(OC(F)(F)F)cc12]

The title compound was prepared in analogy to Example 118-1 in Scheme 59 by using 2,3,4,5-tetrahydro-1H-2-benzazepine (commercial available) and 2,4-dichloro-6-trifluoromethoxyquinoline (commercial available) instead of 7-bromo-2,3,4,5-tetrahydro-1H-2-benzazepine and 2,4,6-trichloroquinoline respectively. MS obsd. (ESI$^+$) [(M+H)$^+$] 417. $^1$H NMR (400 MHz, CD$_3$OD) δ ppm 7.80 (d, J=2.0 Hz, 1 H), 7.56 (d, J=9.2 Hz, 1 H), 7.48 (d, J=6.8 Hz, 1 H), 7.33 (d, J=10.0 Hz, 1 H), 7.18-7.12 (m, 3 H), 6.06 (s, 1 H), 4.83 (s, 2 H), 4.16 (brs, 2 H), 3.46 (t, J=6.2 Hz, 2 H), 3.06-3.00 (m, 4 H), 1.91 (t, J=5.2 Hz, 2 H).

Example 118-24

N-[6-(Methylsulfonyl)-2-(1,3,4,5-tetrahydro-2H-2-benzazepin-2-yl)quinolin-4-yl]ethane-1,2-diamine

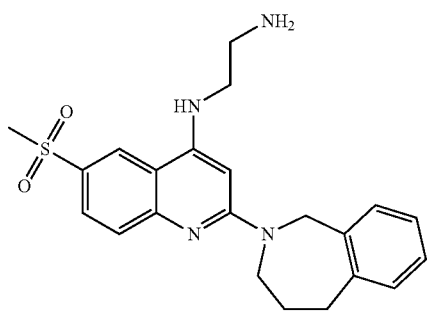 [SMILES: CS(=O)(=O)c1ccc2nc(N3CCCc4ccccc4C3)cc(NCCN)c2c1]

The title compound was prepared in analogy to Example 118-1 in Scheme 59 by using 2,3,4,5-tetrahydro-1H-2-benzazepine (commercial available) and 2,4-dichloro-6-methanesulfonylquinoline (commercial available) instead of 7-bromo-2,3,4,5-tetrahydro-1H-2-benzazepine and 2,4,6-trichloroquinoline respectively. MS obsd. (ESI$^+$) [(M+H)$^+$] 411. $^1$H NMR (400 MHz, DMSO-d6) δ ppm 8.518 (s, 0.5 H), 8.514 (s, 0.5 H), 7.76-7.73 (m, 1 H), 7.61 (d, J=6.4 Hz, 0.5 H), 7.52 (d, J=6.8 Hz, 0.5 H), 7.47-7.34 (m, 1 H), 7.13-7.07 (m, 3 H), 6.23 (s, 0.5 H), 6.04 (s, 0.5 H), 4.83 (d, J=6.4 Hz, 2 H), 4.34 (brs, 2 H), 3.15 (brs, 4 H), 3.00 (s, 2 H), 2.81 (t, J=6.4 Hz, 1 H), 1.76 (brs, 2 H).

Example 118-25

2-{4-[(2-Aminoethyl)amino]quinolin-2-yl}-2,3,4,5-tetrahydro-1H-2-benzazepine-8-carboxylic acid

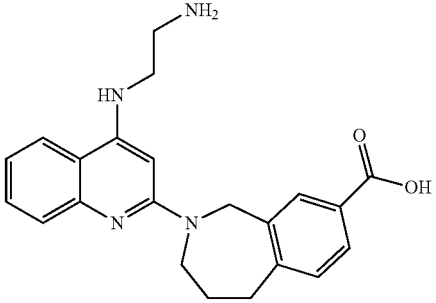 [SMILES: NCCNc1cc(N2CCCc3ccc(C(=O)O)cc3C2)nc2ccccc12]

The title compound was prepared in analogy to Example 118-1 in Scheme 59 by using 2,3,4,5-tetrahydro-1H-2-benzazepine-8-carboxylic acid (commercial available) and 2,4-dichloroquinoline (commercial available) instead of 7-bromo-2,3,4,5-tetrahydro-1H-2-benzazepine and 2,4,6-trichloroquinoline respectively. MS obsd. (ESI$^+$) [(M+H)$^+$] 377. $^1$H NMR (400 MHz, CD$_3$OD) δ ppm 8.57 (s, 1 H), 8.07 (s, 1 H), 7.84 (d, J=7.6 Hz, 1 H), 7.74 (dd, J=6.0 Hz, 1 H), 7.58 (d, J=8.4 Hz, 1 H), 7.47 (m, 1 H), 7.18 (m, 2 H), 6.10 (s, 1 H), 4.24 (brs, 2 H), 3.62 (m, 2 H), 3.26 (m, 2 H), 3.16 (m, 4 H), 1.91 (m, 2 H).

Example 118-26

2-(4-Chloroquinolin-2-yl)-2,3,4,5-tetrahydro-1H-2-benzazepine

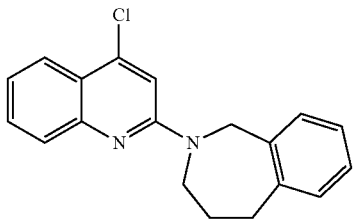 [SMILES: Clc1cc(N2CCCc3ccccc3C2)nc2ccccc12]

The title compound was prepared in Scheme 1 by using 2,3,4,5-tetrahydro-1H-2-benzazepine (commercial available) and 2,4-dichloroquinoline (commercial available) instead of 7-bromo-2,3,4,5-tetrahydro-1H-2-benzazepine and 2,4,6-trichloroquinoline respectively. MS obsd. (ESI$^+$) [(M+H)$^+$] 309. $^1$H NMR (400 MHz, CDCl$_3$) δ ppm 7.92-7.88 (dd, J=1.2, 8.0 Hz, 1 H), 7.65 (d, J=8 Hz, 1 H), 7.53-7.45 (m, 2 H), 7.24-7.10 (m, 5 H), 4.81 (s, 2 H), 4.09 (brs, 2 H), 3.02-2.97 (m, 2 H), 1.94-1.88 (m, 2 H).

Example 119

N-[5-Chloro-2-(1,3,4,5-tetrahydro-2H-2-benzazepin-2-yl)quinolin-4-yl]ethane-1,2-diamine

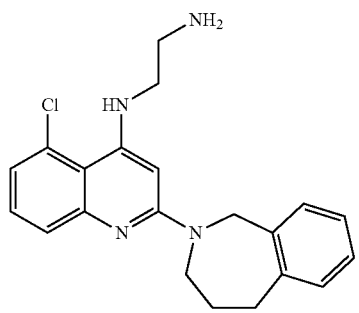 [SMILES: NCCNc1cc(N2CCCc3ccccc3C2)nc2cccc(Cl)c12]

1-(1,3,4,5-Tetrahydro-2H-2-benzazepin-2-yl)ethanone

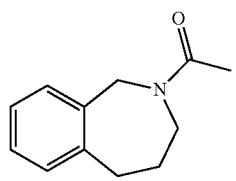

A suspension of 2,3,4,5-tetrahydro-1H-2-benzazepine hydrochloride (10 g, 54.4 mmol) in dry dichloromethane (450 mL) was stirred at 0° C. Triethylamine (18.21 mL, 130.6 mmol) was added followed by the dropwise addition of acetic anhydride (6.18 mL, 65.3 mmol) in dry dichloromethane (50 mL). The reaction was then stirred for 1 hour whilst allowing the temperature to rise slowly to room temperature. The resulting mixture was washed with 1 N hydrochloric acid (200 mL) and brine (200 mL), dried over sodium sulfate and concentrated in vacuo to give 10 g of product as colorless oil (yield was 97%). It was used in next step without further purification. MS obsd. (ESI$^+$) [(M+H)$^+$] 190.

2-Chloro-6-{[1-(1,3,4,5-tetrahydro-2H-2-benzazepin-2-yl)ethylidene]amino}benzonitrile

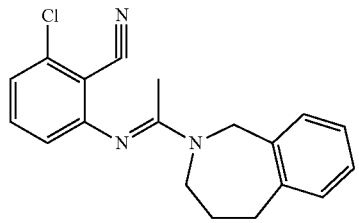 [SMILES: C/C(=N\c1cccc(Cl)c1C#N)N1CCCc2ccccc2C1]

Phosphorus oxychloride (2.93 mL, 32.0 mmol) was added to a stirred solution of 1-(1,3,4,5-tetrahydro-2H-2-benzazepin-2-yl)ethanone (5.5 g, 29.0 mmol) in dry dichloromethane (100 mL) at 10° C. After that, the mixture was stirred for 20 minutes at room temperature. Then a solution of 2-amino-6-chloro-benzonitrile (4.43 g, 29.0 mmol) in dry dichloromethane (40 mL) was added and the resulting suspension was heated under reflux for 24 hours. After the reaction mixture was cooled to room temperature, water (50 mL) was added followed by saturated sodium bicarbonate to pH 8. The organic layer was separated and the aqueous was extracted with dichloromethane (100 mL). The organic fraction was washed with brine and dried over sodium sulfate, and then evaporated in vacuo to give a residue which was precipitated in ether. The solid was collected by filtration and dried in vacuo to give 6 g of product as a brown powder (yield was 63.7%). It was used in the next step without further purification. MS obsd. (ESI$^+$) [(M+H)$^+$] 324.

5-Chloro-2-(1,3,4,5-tetrahydro-2H-2-benzazepin-2-yl)quinolin-4-amine

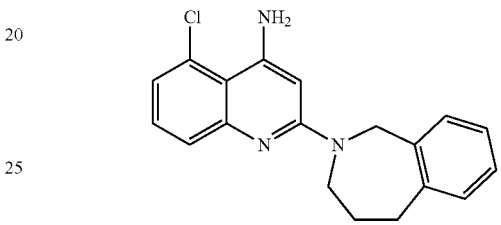

The mixture of 2-chloro-6-{[1-(1,3,4,5-tetrahydro-2H-2-benzazepin-2-yl)ethylidene]amino}benzonitrile (6 g, 18.5 mmol), zinc chloride (2.52 g, 18.5 mmol) and N,N-dimethylacetamide (18 mL) was heated with stirring at 160° C. for 3 hours under argon. After the reaction was allowed to cool to about 40° C., sodium hydroxide (2 N, 20 mL) was added and then stirred for 10 minutes at room temperature. The reaction mixture was poured into water and the solid was collected by filtration, washed with water and dried in vacuo to give 5 g of product as an off-white powder (yield was 83.3%). MS obsd. (ESI$^+$) [(M+H)$^+$] 324.

2-(4,5-Dichloroquinolin-2-yl)-2,3,4,5-tetrahydro-1H-2-benzazepine

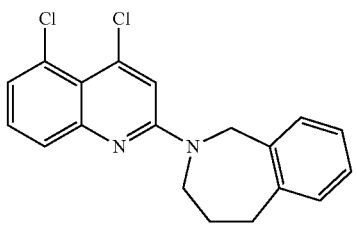 [SMILES: Clc1cccc2nc(N3CCCc4ccccc4C3)cc(Cl)c12]

To the suspension of 5-chloro-2-(1,3,4,5-tetrahydro-2H-2-benzazepin-2-yl)quinolin-4-amine (1.5 g, 4.6 mmol) in concentrated hydrochloric acid (10 mL) was added a solution of sodium nitrite (390 mg, 5.6 mmol) in water at −10° C. After the addition, the reaction mixture was stirred for further 30 minutes, and then sodium chloride (2 g) was added. The resulting mixture was stirred at room temperature overnight and neutralized with saturated sodium bicarbonate, extracted with dichloromethane (50 mL×2). The organic layers were combined and dried over sodium sulfate, and then concentrated under reduced pressure to give the crude product. It was used in next step without further purification.

N-[5-Chloro-2-(1,3,4,5-tetrahydro-2H-2-benzazepin-2-yl)quinolin-4-yl]ethane-1,2-diamine

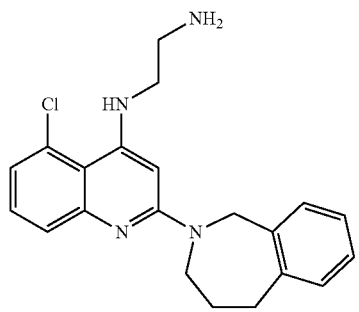 [SMILES: NCCNc1cc(N2CCCc3ccccc3C2)nc2cccc(Cl)c12]

The mixture of 2-(4,5-dichloroquinolin-2-yl)-2,3,4,5-tetrahydro-1H-2-benzazepine prepared above and ethane-1,2-diamine (2 mL) was heated with stirring in a 10 mL microwave process vial for 2 hours at 150° C. under microwave irradiation. The reaction mixture was diluted with ethyl acetate (20 mL), and then washed with water (20 mL). The organic fraction was dried over sodium sulfate, and concentrated under reduced pressure to give a residue which was purified by preparative HPLC to give 20 mg of product as a white powder. MS obsd. (ESI$^+$) [(M+H)$^+$] 367. $^1$H NMR (400 MHz, CD$_3$OD) δ ppm 7.46-7.42 (m, 2 H), 7.27-7.23 (m, 1 H), 7.16-7.11 (m, 3 H), 7.02 (66, J=7.6, 1.2 Hz, 1 H), 5.97 (s, 1 H), 4.79 (s, 2 H), 4.13 (brs, 2 H), 3.38-3.21 (m, 2 H), 3.04-3.02 (m, 2 H), 2.96 (t, J=6.0 Hz, 2 H), 1.91-1.86 (m, 2 H).

Example 120-1

N-{2-[7-(Methylsulfonyl)-1,3,4,5-tetrahydro-2H-2-benzazepin-2-yl]quinolin-4-yl}ethane-1,2-diamine

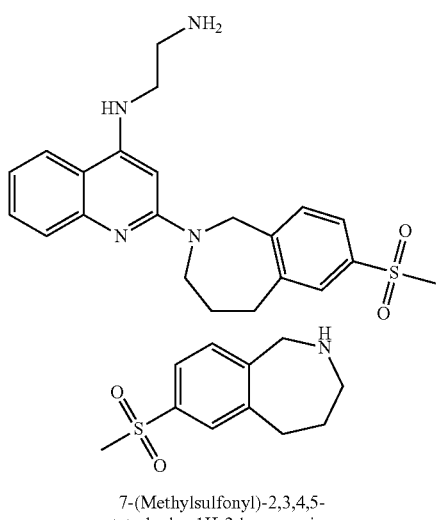

7-(Methylsulfonyl)-2,3,4,5-tetrahydro-1H-2-benzazepine

The mixture of 7-bromo-2,3,4,5-tetrahydro-1H-2-benzazepine (226 mg, 1.0 mmol), sodium methanesulfinate (120 mg, 1.2 mmol), copper(I) iodide (19 mg, 0.1 mmol), L-proline (23 mg, 0.2 mmol), sodium hydroxide (8.0 mg, 0.2 mmol) and dimethyl sulfoxide (2 mL) was heated in a sealed tube for 20 hours at 95° C. The resulting mixture was diluted with water, and extracted with ethyl acetate (30 mL×3). The organic layers were combined and washed with brine (40 mL×3), and then dried over sodium sulfate. The solvent was removed under reduced pressure and the residue was purified by column chromatography on silica gel (methanol/dichloromethane, 1:20) to give 144 mg of product as a light-brown viscous oil (yield was 63.9%). MS obsd. (ESI$^+$) [(M+H)$^+$] 226.

2-(4-Chloroquinolin-2-yl)-7-(methylsulfonyl)-2,3,4, 5-tetrahydro-1H-2-benzazepine

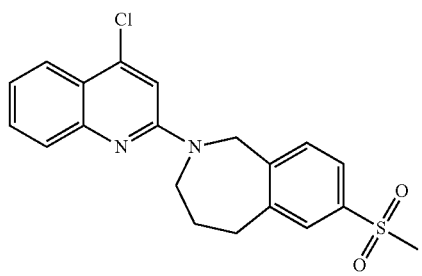 [SMILES: CS(=O)(=O)c1ccc2c(c1)CCCN(c1cc(Cl)c3ccccc3n1)C2]

The mixture of 2,4-dichloroquinoline (126 mg, 0.637 mmol), 7-(methylsulfonyl)-2,3,4,5-tetrahydro-1H-2-benzazepine (144 mg, 0.637 mmol), triethylamine (0.106 mL, 0.765 mmol) and N-methyl-2-pyrrolidone (2 mL) was heated with stirring in a sealed tube for 4 hours at 100° C. The resulting mixture was diluted with water and extracted with ethyl acetate (15 mL×3). The organic layers were combined and washed with brine (15 mL×3), and then dried over sodium sulfate. The solvent was removed under reduced pressure and the residue was purified by column chromatography on silica gel (ethyl acetate/petroleum ether, 1:5) to afford 55.6 mg of product as a white solid (yield was 22.5%). MS obsd. (ESI$^+$) [(M+H)$^+$] 387.

N-{2-[7-(Methylsulfonyl)-1,3,4,5-tetrahydro-2H-2-benzazepin-2-yl]quinolin-4-yl}ethane-1,2-diamine

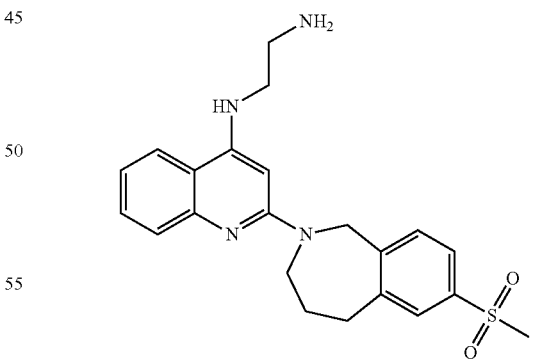

The mixture of 2-(4-chloroquinolin-2-yl)-7-(methylsulfonyl)-2,3,4,5-tetrahydro-1H-2-benzazepine (55.6 mg, 0.144 mmol) and ethane-1,2-diamine (1 mL) was heated with stirring in a 10 mL microwave process vial for 2 hours at 150° C. under microwave irradiation. The solvent was removed in vacuo and the residue was purified by preparative HPLC to give 27.5 mg of product as a light-yellow solid (yield was 46.5%). MS obsd. (ESI$^+$) [(M+H)$^+$] 411. $^1$H NMR (400 MHz, CD$_3$OD) δ ppm 7.82-7.73 (m, 4 H), 7.53 (d, J=7.6 Hz, 1 H), 7.45-7.40 (m, 1 H), 7.12-7.08 (m, 1 H), 5.98 (s, 1 H), 4.96 (s, 2 H), 4.16 (s, 2 H), 3.41 (t, J=6.4 Hz, 2 H), 3.16 (brs, 2 H), 3.06 (s, 3 H), 2.97 (t, J=6.4 Hz, 2 H), 1.96 (brs, 2 H).

Example 120-2

N-{2-[7-(Ethylsulfonyl)-1,3,4,5-tetrahydro-2H-2-benzazepin-2-yl]quinolin-4-yl}ethane-1,2-diamine

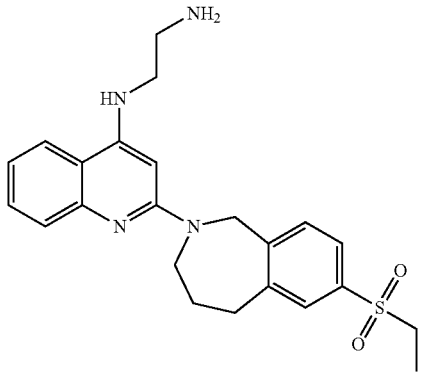 [SMILES: CCS(=O)(=O)c1ccc2c(c1)CCCN(c1cc(NCCN)c3ccccc3n1)C2]

The title compound was prepared in analogy to Example 120-1 by using sodium ethanesulfinate (commercial available) instead of sodium methanesulfinate. MS obsd. (ESI$^+$) [(M+H)$^+$] 424. $^1$H NMR (400 MHz, CD$_3$OD) δ ppm 7.81-7.76 (m, 2 H), 7.70-7.67 (m, 2 H), 7.53 (d, J=7.6 Hz, 1 H), 7.43-7.39 (m, 1 H), 7.10-7.06 (m, 1 H), 5.97 (s, 1 H), 4.93 (s, 2 H), 4.14 (s, 2 H), 3.39 (t, J=6.4 Hz, 2 H), 3.16-3.10 (m, 4 H), 2.95 (t, J=6.4 Hz, 2 H), 1.94 (brs, 2 H), 1.16 (t, J=7.2 Hz, 3 H).

Example 121

N-[2-(8-Ethoxy-1,3,4,5-tetrahydro-2H-2-benzazepin-2-yl)quinolin-4-yl]ethane-1,2-diamine

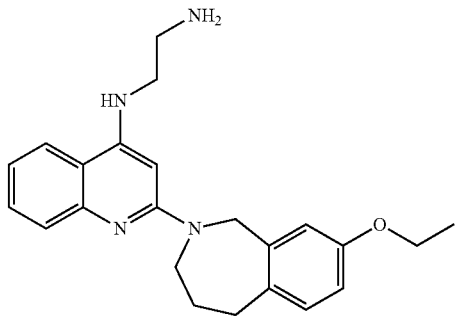 [SMILES: CCOc1ccc2c(c1)CN(c1cc(NCCN)c3ccccc3n1)CCC2]

2-(4-Chloroquinolin-2-yl)-8-ethoxy-2,3,4,5-tetrahydro-1H-2-benzazepine

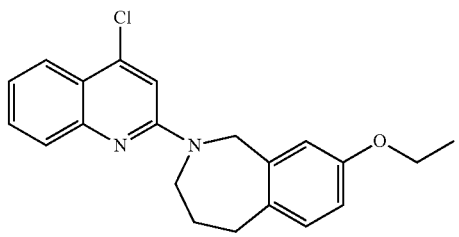 [SMILES: CCOc1ccc2c(c1)CN(c1cc(Cl)c3ccccc3n1)CCC2]

To a solution of 2-(4-chloroquinolin-2-yl)-2,3,4,5-tetrahydro-1H-2-benzazepin-8-ol (36 mg, 0.11 mmol) in 5 mL of dry N,N-dimethylformamide was added sodium hydride (8 mg, 0.17 mmol), then bromoethane (18.5 mg, 0.17 mmol) was added dropwise under nitrogen. After the addition, the reaction was stirred at room temperature for further 1 hour. The resulting mixture was diluted with dichloromethane (10 mL), washed with brine and then dried over sodium sulfate. The solvent was removed in vacuo and the residue was purified by column chromatography on silica gel to give 28 mg of product. MS obsd. (ESI$^+$) [(M+H)$^+$] 353.

N-[2-(8-Ethoxy-1,3,4,5-tetrahydro-2H-2-benzazepin-2-yl)quinolin-4-yl]ethane-1,2-diamine

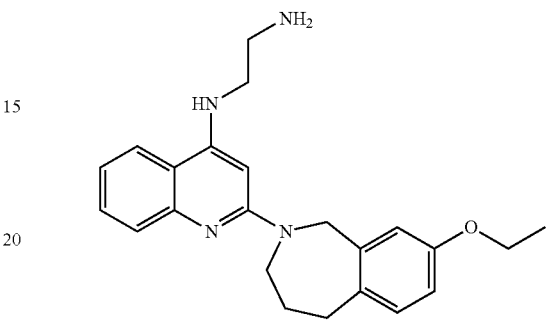

The mixture of 2-(4-chloroquinolin-2-yl)-8-ethoxy-2,3,4,5-tetrahydro-1H-2-benzazepine (28 mg, 0.79 mmol) and ethane-1,2-diamine (0.5 mL) was heated with stirring in a 5 mL microwave process vial for 2 hours at 160° C. under microwave irradiation. The solvent was removed under reduced pressure and the residue was purified by preparative HPLC to give 12 mg of product (yield was 40%). MS obsd. (ESI$^+$) [(M+H)$^+$] 377. $^1$H NMR (400 MHz, CD$_3$OD) δ ppm 7.88 (d, J=7.6 Hz, 1 H,), 7.62 (d, J=8.0 Hz, 1 H), 7.57 (m, 1 H), 7.51 (d, J=8.4 Hz, 1 H), 7.38 (m, 1 H), 7.19 (m, 2 H), 6.00 (s, 1 H), 4.78 (s, 2 H), 4.12 (m, 2 H), 3.99 (q, J=6.8 Hz, 2 H), 3.48 (m, 2 H), 2.98 (m, 4 H), 1.94 (m, 2 H), 1.34 (t, J=6.8 Hz, 3 H).

Example 122

N-[6-(Pyridin-2-yloxy)-2-(1,3,4,5-tetrahydro-2H-2-benzazepin-2-yl)quinolin-4-yl]ethane-1,2-diamine

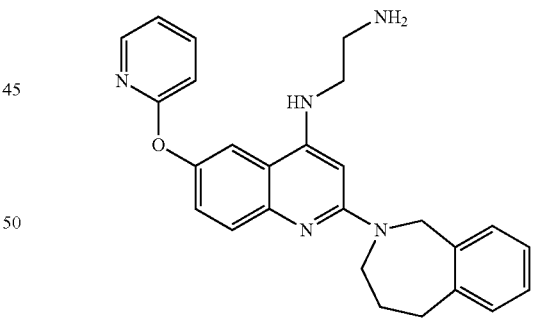

4-Chloro-2-(1,3,4,5-tetrahydro-2H-2-benzazepin-2-yl)quinolin-6-ol

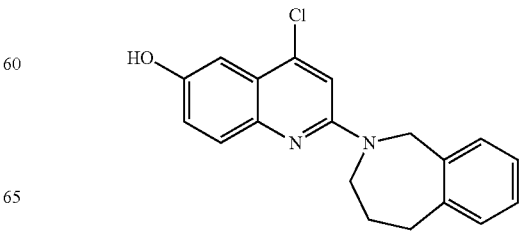

To a solution of 2-(4-chloro-6-methoxy-quinolin-2-yl)-2,3,4,5-tetrahydro-1H-2-benzazepine (800 mg, 2.37 mmol) in 15 mL of dichloromethane was added slowly a solution of boron tribromide (0.558 mL, 5.9 mmol). The resulting mixture was stirred at room temperature for 30 minutes, followed by stirring at 40° C. for 2 hours. After cooled to room temperature, the reaction mixture was carefully quenched with sodium bicarbonate (20 mL), and then extracted with dichloromethane (10 mL×3). The organic layers were combined and washed with brine (20 ml), then dried over sodium sulfate. The solvent was removed in vacuo and the residue was purified by flash column chromatography on silica gel (ethyl acetate/hexane, 1:5) to give 500 mg of product (yield was 65%).

2-[4-Chloro-6-(pyridin-2-yloxy)quinolin-2-yl]-2,3,4,5-tetrahydro-1H-2-benzazepine

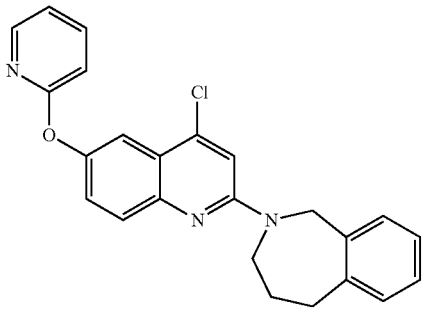 [SMILES: Clc1cc(N2CCCc3ccccc3C2)nc2ccc(Oc3ccccn3)cc12]

The mixture of 4-chloro-2-(1,3,4,5-tetrahydro-2H-2-benzazepin-2-yl)quinolin-6-ol (200 mg, 0.617 mmol), 2-fluoropyridine (180 mg, 1.85 mmol), potassium carbonate (73 mg, 0.53 mmol) and dry dimethylsulfoxide was heated with stirring in a sealed tube for 40 minutes at 130° C. under microwave irradiation. The resulting mixture was cooled to room temperature, then diluted with water (10 mL) and extracted with ethyl acetate (10 mL×2). The combined organic layer was washed with brine (10 mL×3), and then dried over sodium sulfate. The solvent was removed in vacuo and the residue was purified by column chromatography on silica gel (ethyl acetate/petroleum ether, 1:5) to give 110 mg of product as a yellow solid (yield was 45%).

N-[6-(Pyridin-2-yloxy)-2-(1,3,4,5-tetrahydro-2H-2-benzazepin-2-yl)quinolin-4-yl]ethane-1,2-diamine

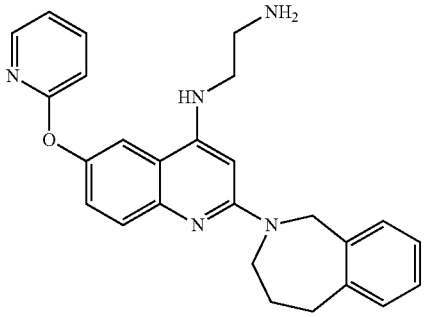 [SMILES: NCCNc1cc(N2CCCc3ccccc3C2)nc2ccc(Oc3ccccn3)cc12]

The mixture of 2-[4-chloro-6-(pyridin-2-yloxy)quinolin-2-yl]-2,3,4,5-tetrahydro-1H-2-benzazepine (40 mg, 0.1 mmol) and ethane-1,2-diamine (2 mL) was heated with stirring in a 5 mL microwave process vial for 3 hours at 180° C. under microwave irradiation. The solvent was removed under reduced pressure and the residue was purified by preparative HPLC to give 7 mg of product as a yellow powder. MS obsd. (ESI$^+$) [(M+H)$^+$] 426. $^1$H NMR (400 MHz, CD$_3$OD) δ ppm 8.12 (d, J=3.2 Hz, 1 H), 7.82-7.78 (m, 1 H), 7.66 (d, J=2.8 Hz, 1 H), 7.61 (d, J=8.8 Hz, 1 H), 7.48 (d, J=6.8 Hz, 1 H), 7.23 (dd, J=5.2, 2.4 Hz, 1 H), 7.16-7.08 (m, 4 H), 6.90 (d, J=8.4 Hz, 1 H), 6.04 (s, 1 H), 4.83 (s, 2 H), 4.16 (brs, 2 H), 3.41 (t, J=6.2 Hz, 2 H), 3.05 (t, J=4.8 Hz, 2 H), 2.94 (t, J=6.2 Hz, 2 H), 1.96-1.91 (m, 2 H).

Example 123

2-{4-[(2-Aminoethyl)amino]-6-chloroquinolin-2-yl}-N,N-dimethyl-2,3,4,5-tetrahydro-1H-2-benzazepine-7-carboxamide

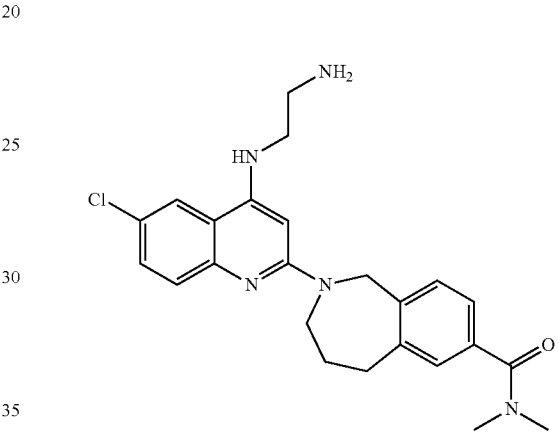

Methyl 2-(4,6-dichloroquinolin-2-yl)-2,3,4,5-tetrahydro-1H-2-benzazepine-7-carboxylate

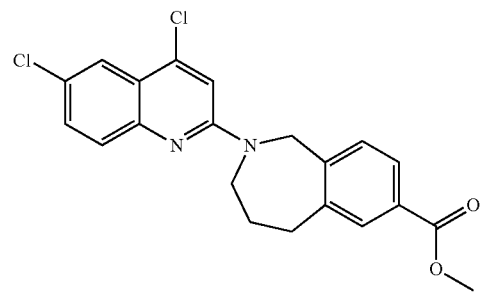 [SMILES: COC(=O)c1ccc2c(c1)CCCN(c1cc(Cl)c3cc(Cl)ccc3n1)C2]

7-Bromo-2-(4,6-dichloroquinolin-2-yl)-2,3,4,5-tetrahydro-1H-benzazepine (200 mg, 0.47 mmol), triethylamine (94 mg, 0.94 mmol) and tetrakis(triphenylphosphine)palladium (0) (49.2 mg, 0.047 mmol) were added into 10 mL of dry methanol. The resulting mixture was stirred under reflux overnight under carbon monoxide. After cooled to room temperature, the reaction was diluted with ethyl acetate (30 mL), and then washed with water. The organic fraction was dried over sodium sulfate and concentrated in vacuo to give a residue which was purified by column chromatography on silica gel (ethyl acetate/petroleum ether, 1:5) to give 156 mg of product (yield was 83%). MS obsd. (ESI$^+$) [(M+H)$^+$] 401.

493

2-(4,6-Dichloroquinolin-2-yl)-2,3,4,5-tetrahydro-1H-2-benzazepine-7-carboxylic acid

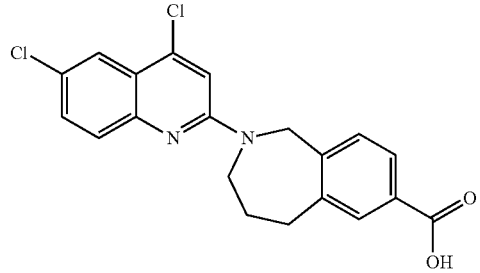 [SMILES: O=C(O)c1ccc2c(c1)CCCN(c1cc(Cl)c3cc(Cl)ccc3n1)C2]

Methyl 2-(4,6-dichloroquinolin-2-yl)-2,3,4,5-tetrahydro-1H-2-benzazepine-7-carboxylate (156 mg, 0.39 mmol) was added into the mixture of methanol (5 mL) and sodium hydroxide (5 M, 2 mL). The reaction mixture was stirred at room temperature overnight. After that, the reaction was diluted with 20 mL of water, acidified with 2 M of hydrochloric acid to pH 6 and diluted with ethyl acetate (30 mL). The organic layer was separated and washed with water. The solvent was dried over sodium sulfate and concentrated in vacuo to give a residue which was purified by column chromatography on silica gel to give 135 mg of product. MS obsd. (ESI$^+$) [(M+H)$^+$] 387.

2-(4,6-Dichloroquinolin-2-yl)-N,N-dimethyl-2,3,4,5-tetrahydro-1H-2-benzazepine-7-carboxamide

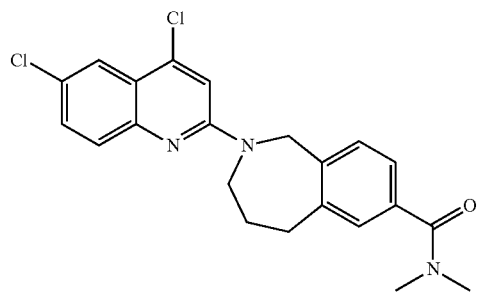 [SMILES: CN(C)C(=O)c1ccc2c(c1)CCCN(c1cc(Cl)c3cc(Cl)ccc3n1)C2]

The mixture of 2-(4,6-dichloroquinolin-2-yl)-2,3,4,5-tetrahydro-1H-2-benzazepine-7-carboxylic acid (135 mg, 0.35 mmol), dimethylamine hydrochloride (34.2 mg, 0.42 mmol), triethylamine (105 mg, 1.05 mmol), O-(7-azabenzotriazol-1-yl)-N,N,N',N'-tetramethyluronium hexafluorophosphate (159 mg, 0.42 mmol) and 5 mL of dichloromethane was stirred at room temperature overnight under nitrogen. The reaction was diluted with ethyl acetate (20 mL), washed with water and dried over sodium sulfate. The solvent was removed in vacuo and the residue was purified by column chromatography to give 133 mg of product as a white solid. (yield was 92%). MS obsd. (ESI$^+$) [(M+H)$^+$] 414.

494

2-{4-[(2-Aminoethyl)amino]-6-chloroquinolin-2-yl}-N,N-dimethyl-2,3,4,5-tetrahydro-1H-2-benzazepine-7-carboxamide

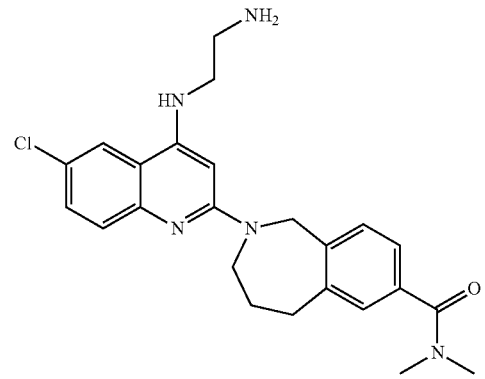 [SMILES: CN(C)C(=O)c1ccc2c(c1)CCCN(c1cc(NCCN)c3cc(Cl)ccc3n1)C2]

The mixture of 2-(4,6-dichloroquinolin-2-yl)-N,N-dimethyl-2,3,4,5-tetrahydro-1H-2-benzazepine-7-carboxamide (133 mg, 0.32 mmol) and ethane-1,2-diamine (2 mL) was heated with stirring in a 5 mL microwave process vial for 3 hours at 180° C. under microwave irradiation. The solvent was removed under reduced pressure and the residue was purified by preparative HPLC to give 11 mg of product as a white solid. MS obsd. (ESI$^+$) [(M+H)$^+$] 438. $^1$H NMR (400 MHz, CD$_3$OD) δ ppm 7.89 (s, 1 H), 7.60 (d, J=8.0 Hz, 1 H), 7.49 (d, J=8.8 Hz, 1 H), 7.38 (m, 1 H), 7.22 (m, 2 H), 6.01 (s, 1 H), 4.80 (s, 2 H), 4.16 (m, 2 H), 3.44 (t, J=6.4 Hz, 2 H), 3.11-2.97 (m, 10 H), 1.93 (m, 2 H).

Example 124

2-{4-[(2-Aminoethyl)amino]quinolin-2-yl}-7-bromo-1,2,4,5-tetrahydro-3H-2-benzazepin-3-one

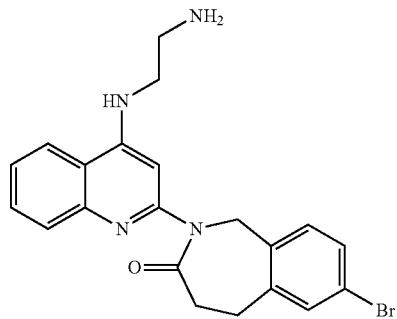 [SMILES: NCCNc1cc(N2Cc3ccc(Br)cc3CCC2=O)nc2ccccc12]

7-Bromo-2-(4-chloroquinolin-2-yl)-1,2,4,5-tetrahydro-3H-2-benzazepin-3-one

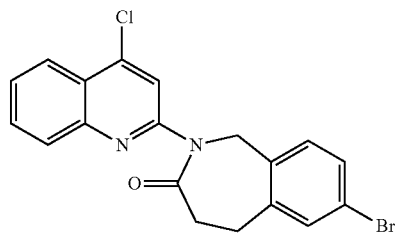 [SMILES: O=C1CCc2cc(Br)ccc2CN1c1cc(Cl)c2ccccc2n1]

To a solution of 2,4-dichloroquinoline (196 mg, 1.0 mmol) in dioxane (4 mL) was added 7-bromo-1,2,4,5-tetrahydro-3H-2-benzazepin-3-one (161 mg, 1.0 mmol), followed by tris(dibenzylideneacetone)dipalladium(0) (28 mg, 0.03 mmol), 9,9-dimethyl-4,5-bis(diphenylphosphino)xanthene (65 mg, 0.11 mmol), and potassium phosphate tribasic (212 mg, 1.0 mmol). The resultant mixture was refilled with nitrogen and heated at 130° C. overnight. After cooled to room temperature, the mixture was diluted with acetonitrile (10 mL), filtered, and washed with acetonitrile. The filtrate was concentrated under reduced pressure to give a residue which was purified by column chromatography on silica gel (hexane/ethyl acetate/ammonium hydroxide solution, 80:19:1) to give 165 mg of product as a white solid (yield was 42%). MS obsd. (ESI$^+$) [(M+H)$^+$] 401.

2-{4-[(2-Aminoethyl)amino]quinolin-2-yl}-7-bromo-1,2,4,5-tetrahydro-3H-2-benzazepin-3-one

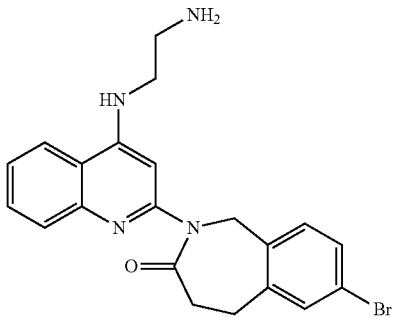 [SMILES: NCCNc1cc(N2Cc3ccc(Br)cc3CCC2=O)nc2ccccc12]

To a solution of 7-bromo-2-(4-chloroquinolin-2-yl)-1,2,4,5-tetrahydro-3H-2-benzazepin-3-one (40 mg, 0.1 mmol) was added ethane-1,2-diamine (0.5 mL) in a microwave vessel, which was degassed and refilled with nitrogen. The resultant mixture was heated at 170° C. under microwave irradiation for 30 minutes. After cooled to room temperature, the mixture was diluted with methanol (10 mL) and concentrated under reduced pressure to give a residue which was purified by preparative HPLC to afford 42 mg of product as a solid (yield was 98%). MS obsd. (ESI$^+$) [(M+H)$^+$] 424. $^1$H NMR (400 MHz, CD$_3$OD) δ ppm 7.99 (d, J=8.0 Hz, 1 H), 7.73 (d, J=8.0 Hz, 1 H), 7.58 (m, 2 H), 7.47 (s, 2 H), 7.32 (td, J=1.2, 8.8 Hz, 1 H), 6.04 (s, 1 H), 5.48 (s, 2 H), 3.42 (t, J=6.4 Hz, 2 H), 3.11 (t, J=7.6 Hz, 2 H), 2.98 (t, J=6.0 Hz, 2 H), 2.86 (t, J=7.2 Hz, 2 H).

Example 125

1-(2-{[2-(1,3,4,5-Tetrahydro-2H-2-benzazepin-2-yl)quinolin-4-yl]amino}ethyl)guanidine trifluoroacetate

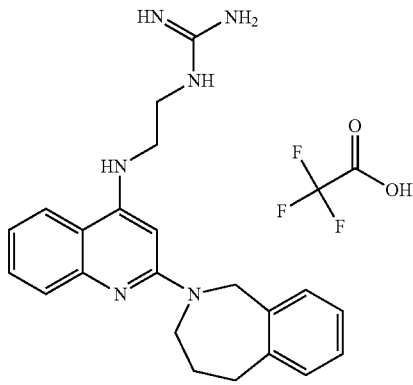 [SMILES: N=C(N)NCCNc1cc(N2CCCc3ccccc3C2)nc2ccccc12 ; O=C(O)C(F)(F)F]

To a solution of N-[2-(1,3,4,5-tetrahydro-2H-2-benzazepin-2-yl)quinolin-4-yl]ethane-1,2-diamine (200 mg, 0.6 mmol) and 3,5-dimethyl-1H-pyrazole-1-carboximidamide nitrate (122 mg, 0.6 mmol) in ethanol (15 mL) was refluxed by heating for overnight. After cooled to room temperature, the reaction mixture was concentrated under reduced pressure, diluted with water (15 mL), and then extracted with dichloromethane (50 mL×2). The dichloromethane fractions were combined and dried over sodium sulfate, and then concentrated under reduced pressure to give a residue which was purified by preparative HPLC to give 35.78 mg of product as a white solid. MS obsd. (ESI$^+$) [(M+H)$^+$] 375. $^1$H NMR (400 MHz, CD$_3$OD) δ ppm 8.07-8.04 (brs, 1 H), 7.80-7.69 (m, 2 H), 7.51-7.41 (m, 2 H), 7.26-7.20 (m, 3 H), 6.00 (s, 1 H), 4.98 (s, 2 H), 4.14 (s, 2 H), 3.71-3.67 (m, 2 H), 3.58-3.55 (t, J=6.4 Hz, 2 H), 3.13-3.10 (m, 2 H), 2.01 (s, 2 H).

Example 126-1

N-[(2-Amino-4,5-dihydro-1,3-oxazol-5-yl)methyl]-2-(1,3,4,5-tetrahydro-2H-2-benzazepin-2-yl)quinolin-4-amine trifluoroacetate

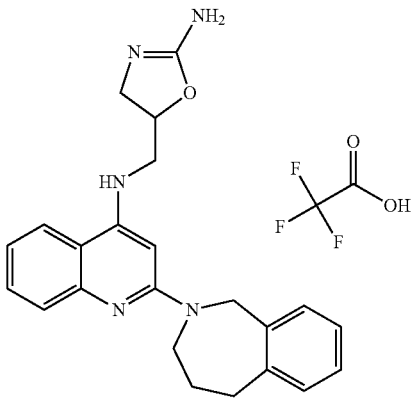 [SMILES: NC1=NCC(CNc2cc(N3CCCc4ccccc4C3)nc3ccccc23)O1 ; O=C(O)C(F)(F)F]

The mixture of 1-amino-3-{[2-(1,3,4,5-tetrahydro-2H-2-benzazepin-2-yl)quinolin-4-yl]amino}propan-2-ol (690 mg, 1.9 mmol) and potassium acetate (490 mg, 5 mmol) in methanol (7 mL) and water (1.75 mL) was stirred at 0° C. A cooled solution of cyanogen bromide (212 mg, 2 mmol) in methanol (1 mL) was added to the above mixture and the resultant mixture was stirred at room temperature for 4 hours. The reaction mixture was concentrated and diluted with ethyl acetate (50 mL), and then washed with water (50 mL). The organic fraction was dried over sodium sulfate, and concentrated under reduced pressure to give a residue which was purified by preparative HPLC to give 73 mg of product as a white powder (yield was 10%). MS obsd. (ESI$^+$) [(M+H)$^+$] 388. $^1$H NMR (400 MHz, CD$_3$OD) δ ppm 8.06-8.04 (dd, J=8.4, 1.2 Hz, 1 H), 7.80-7.78 (d, J=8.4 Hz, 1 H), 7.72 (m, 1 H), 7.50 (m, 1 H), 7.42 (m, 1 H), 7.23 (m, 3 H), 6.11 (s, 1 H), 5.42 (m, 1 H), 4.99 (s, 2 H), 4.11 (m, 3 H), 3.93 (d, J=5.6 Hz, 2 H), 3.77 (dd, J=9.6, 6.8 Hz, 1 H), 3.09 (m, 2 H), 2.00 (d, J=5.6 Hz, 2 H).

Example 126-2

N-[(2-Amino-4,5-dihydro-1,3-oxazol-5-yl)methyl]-6-chloro-2-(1,3,4,5-tetrahydro-2H-2-benzazepin-2-yl)quinolin-4-amine

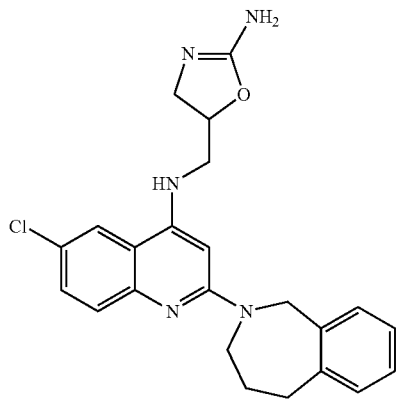 [SMILES: NC1=NCC(CNc2cc(N3CCCc4ccccc4C3)nc3ccc(Cl)cc23)O1]

The title compound was prepared in analogy to Example 9-1 by using 1-amino-3-{6-chloro-[2-(1,3,4,5-tetrahydro-2H-2-benzazepin-2-yl)quinolin-4-yl]amino}propan-2-ol [It was prepared in Scheme 1 by using 2,3,4,5-tetrahydro-1H-2-benzazepine (commercial available) and 1,3-diamino-propan-2-ol (commercial available) instead of 7-bromo-2,3,4,5-tetrahydro-1H-2-benzazepine and ethane-1,2-diamine respectively.] instead of 1-amino-3-{[2-(1,3,4,5-tetrahydro-2H-2-benzazepin-2-yl)quinolin-4-yl]amino}propan-2-ol. MS obsd. (ESI$^+$) [(M+H)$^+$] 422. $^1$H NMR (400 MHz, CD$_3$OD) δ ppm 8.17 (s, 1 H), 7.82 (d, J=8.8 Hz, 1 H), 7.69 (m, 1 H), 7.52 (s, 1 H), 7.22 (m, 3 H), 6.15 (s, 1 H), 5.42 (m, 1 H), 4.99 (s, 2 H), 4.11 (m, 3 H), 3.94 (d, J=5.6 Hz, 2 H), 3.77 (dd, J=9.6, 6.8 Hz, 1 H), 3.09 (m, 2 H), 2.00 (d, J=5.6 Hz, 2 H).

Example 127

N-[2-(1,3,4,5-Tetrahydro-2H-2-benzazepin-2-yl)quinolin-4-yl]glycinamide

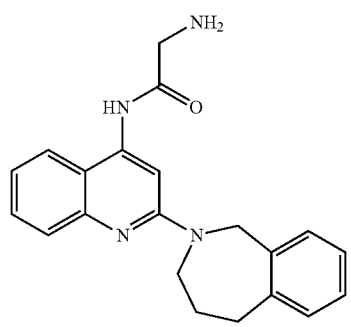 [SMILES: NCC(=O)Nc1cc(N2CCCc3ccccc3C2)nc2ccccc12]

2-Chloro-N-[2-(1,3,4,5-tetrahydro-2H-2-benzazepin-2-yl)quinolin-4-yl]acetamide

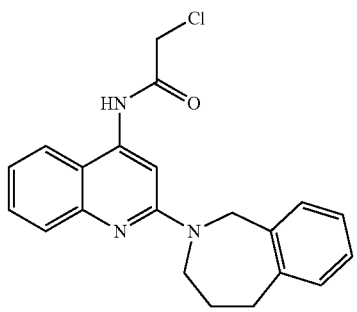 [SMILES: O=C(CCl)Nc1cc(N2CCCc3ccccc3C2)nc2ccccc12]

To the solution of 2-(1,3,4,5-tetrahydro-2H-2-benzazepin-2-yl)quinolin-4-amine (500 mg, 1.73 mmol) was added 1,8-diazabicyclo[5.4.0]undec-7-ene (0.52 mL, 3.48 mmol) followed by chloroacetyl chloride (0.21 mL, 2.64 mmol) at room temperature. The resulting solution was heated with stirring at 70° C. for 2 hours under nitrogen. After cooled to room temperature, the reaction was diluted with ethyl acetate (50 mL), and then washed with water (50 mL×3). The organic phase was dried over sodium sulfate and concentrated under reduced pressure to give a residue which was purified by column chromatography on silica gel (ethyl acetate/petroleum ether, 1:4) to give 140 mg of product as an off-white solid (yield was 22.1%). MS obsd. (ESI$^+$) [(M+H)$^+$] 366.

2-Azido-N-[2-(1,3,4,5-tetrahydro-2H-2-benzazepin-2-yl)quinolin-4-yl]acetamide

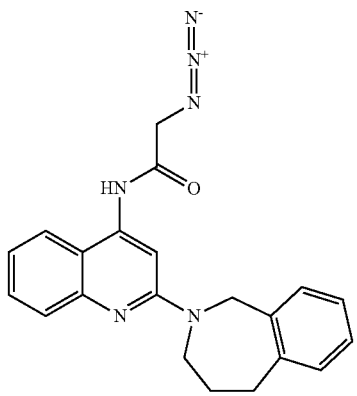 [SMILES: [N-]=[N+]=NCC(=O)Nc1cc(N2CCCc3ccccc3C2)nc2ccccc12]

To a solution of 2-chloro-N-[2-(1,3,4,5-tetrahydro-2H-2-benzazepin-2-yl)quinolin-4-yl]acetamide (70 mg, 0.19 mmol) in acetonitrile (2 mL) was added sodium azide (62 mg, 0.95 mmol). The resulting mixture was stirred at room temperature for 6 hours. The reaction was diluted with ethyl acetate (20 mL), and then washed with water (10 mL). The ethyl acetate fraction was dried over sodium sulfate, and then concentrated under reduced pressure to give a residue which was purified by column chromatography on silica gel (ethyl acetate/petroleum ether, 1:4) to give 65 mg of product as a white powder (yield was 91.8%). MS obsd. (ESI$^+$) [(M+H)$^+$] 373.

N-[2-(1,3,4,5-Tetrahydro-2H-2-benzazepin-2-yl)quinolin-4-yl]glycinamide

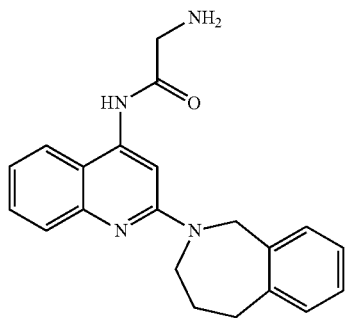 [SMILES: NCC(=O)Nc1cc(N2CCCc3ccccc3C2)nc2ccccc12]

To a solution of 2-azido-N-[2-(1,3,4,5-tetrahydro-2H-2-benzazepin-2-yl)quinolin-4-yl]acetamide (65 mg, 0.17 mmol) in methanol was added palladium (10% on carbon, 7 mg). After being stirred at room temperature overnight under a hydrogen atmosphere, the resulting mixture was filtered. The filtrate was concentrated in vacuo and the residue was purified by preparative HPLC to afford 30 mg of product as a white powder (yield was 60.5%). MS obsd. (ESI$^+$) [(M+H)$^+$] 347. $^1$H NMR (400 MHz, DMSO-d6) δ ppm 8.08 (s, 1 H), 7.78 (d, J=8.0 Hz, 1 H), 7.55-7.49 (m, 3 H), 7.23-7.20 (m, 1 H), 7.15-7.08 (m, 3 H), 4.79 (s, 2 H), 4.13 (brs, 2 H), 3.45 (brs, 2 H), 3.04 (brs, 2 H), 1.79 (brs, 2 H).

Example 128

3-[2-(1,3,4,5-Tetrahydro-2H-2-benzazepin-2-yl)quinolin-4-yl]propan-1-amine

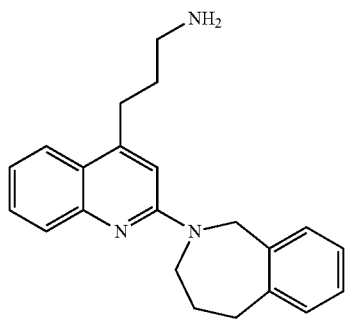 [SMILES: NCCCc1cc(N2CCCc3ccccc3C2)nc2ccccc12]

Methyl (2E)-3-[2-(1,3,4,5-tetrahydro-2H-2-benzazepin-2-yl)quinolin-4-yl]prop-2-enoate

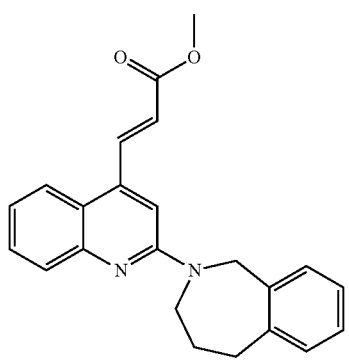 [SMILES: COC(=O)/C=C/c1cc(N2CCCc3ccccc3C2)nc2ccccc12]

The mixture of 2-(4-chloroquinolin-2-yl)-2,3,4,5-tetrahydro-1H-2-benzazepine (1.5 g, 4.86 mmol), acrylic acid methyl ester (0.88 ml, 9.7 mmol), triethylamine (6 mL) and N,N-dimethylformamide (6 mL), bis(tri-tert-butylphosphine)palladium(0) (124 mg, 0.243 mmol) was heated with stirring in a 20 mL of microwave process vial for 30 minutes at 100° C. under argon. The reaction mixture was poured into water (30 mL) and extracted with ethyl acetate (20 mL×3). The organic layers were combined, washed with brine, dried over sodium sulfate and concentrated in vacuo to give a residue which was purified by flash column to afford 1.41 g of product as a white solid (yield was 81%). MS obsd. (ESI$^+$) [(M+H)$^+$] 359.

Methyl 3-[2-(1,3,4,5-tetrahydro-2H-2-benzazepin-2-yl)quinolin-4-yl]propanoate

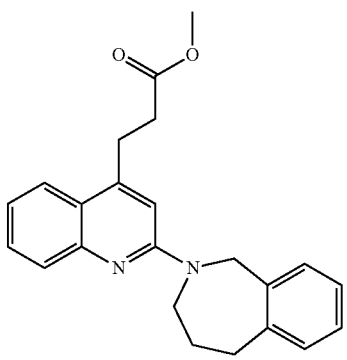 [SMILES: COC(=O)CCc1cc(N2CCCc3ccccc3C2)nc2ccccc12]

To a solution of methyl (2E)-3-[2-(1,3,4,5-tetrahydro-2H-2-benzazepin-2-yl)quinolin-4-yl]prop-2-enoate (1.4 g, 3.91 mmol) in 30 mL of methanol was added 10% palladium on carbon (70 mg). After being vigorously stirred under hydrogen (balloon) for 3 hours, the reaction was filtered and the filtrate was concentrated in vacuo to give 1.4 g of product as a white solid (yield was 98%). MS obsd. (ESI$^+$) [(M+H)$^+$] 361.

3-[2-(1,3,4,5-Tetrahydro-2H-2-benzazepin-2-yl)quinolin-4-yl]propanoic acid

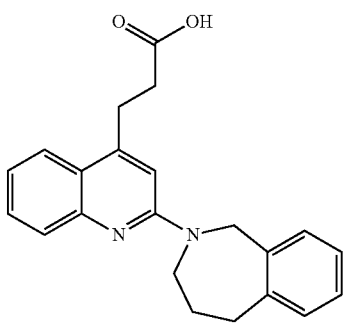 [SMILES: O=C(O)CCc1cc(N2CCCc3ccccc3C2)nc2ccccc12]

To a solution of methyl 3-[2-(1,3,4,5-tetrahydro-2H-2-benzazepin-2-yl)quinolin-4-yl]propanoate (1.4 g, 3.89 mmol) in methanol (10 mL) was added an aqueous solution of sodium hydroxide (4 N, 16 mL) and the resulting mixture was stirred at room temperature for 4 hours. The reaction was acidified to pH 4 with 5 N hydrochloric acid, and then extracted with ethyl acetate (10 mL×3). The organic layer was dried over sodium sulfate and concentrated in vacuo to give a residue which was purified by flash column chromatography to afford 1.1 g of product as a white solid (yield was 82%). MS obsd. (ESI$^+$) [(M+H)$^+$] 347.

3-[2-(1,3,4,5-Tetrahydro-2H-2-benzazepin-2-yl)quinolin-4-yl]propanamide

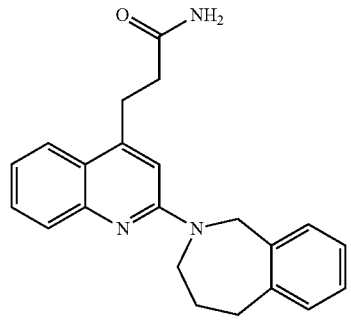 [SMILES: NC(=O)CCc1cc(N2CCCc3ccccc3C2)nc2ccccc12]

To a solution of 3-[2-(1,3,4,5-tetrahydro-2H-2-benzazepin-2-yl)quinolin-4-yl]propanoic acid (300 mg, 0.867 mmol) in dichloromethane (10 mL) was added oxalyl chloride (0.123 mL, 1.3 mmol) and one drop of N,N-dimethylformamide at 0° C. The resulting mixture was warmed to room temperature and stirred for further 2 hours. The solvent was removed under reduced pressure and the residue was dissolved in dichloromethane (5 mL), to which a tetrahydrofuran solution of ammonia (4 N, 5 mL) was added at 0° C., followed by stirring at room temperature overnight. The reaction was concentrated in vacuo to dryness and purified by flash column to afford 50 mg of product as a white solid. It was used in next step without further purification. MS obsd. (ESI$^+$) [(M+H)$^+$] 346.

3-[2-(1,3,4,5-Tetrahydro-2H-2-benzazepin-2-yl)quinolin-4-yl]propan-1-amine

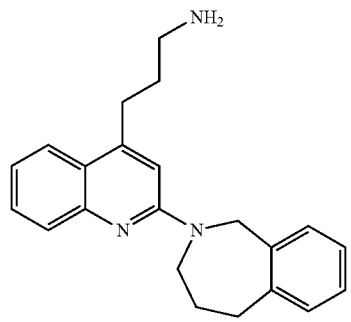 [SMILES: NCCCc1cc(N2CCCc3ccccc3C2)nc2ccccc12]

To the mixture of 3-[2-(1,3,4,5-tetrahydro-2H-2-benzazepin-2-yl)quinolin-4-yl]propanamide (50 mg, 0.145 mmol) in tetrahydrofuran (5 mL) was added a tetrahydrofuran solution of borane (1.5 mL, 1.5 mmol) at 0° C., followed by stirring at 70° C. for 4 hours. After being quenched with methanol (5 mL) at 0° C., the resulting mixture was concentrated in vacuo to give a residue which was purified by flash column (ethyl acetate/hexane, 3:7) to afford 10 mg of product as a white solid. MS obsd. (ESI$^+$) [(M+H)$^+$] 332. $^1$H NMR (400 MHz, DMSO-d6) δ ppm 7.79 (d, J=7.2 Hz, 1 H), 7.57-7.52 (m, 2 H), 7.47-7.43 (m, 1 H), 7.18-7.04 (m, 5 H), 5.24 (brs, 2 H), 4.85 (s, 2 H), 4.14 (brs, 2 H), 3.03 (brs, 2 H), 2.93 (t, J=7.2 Hz, 2 H), 1.89-1.82 (m, 4 H).

Example 129

[2-(1,3,4,5-Tetrahydro-2H-2-benzazepin-2-yl)quinolin-4-yl]methanol

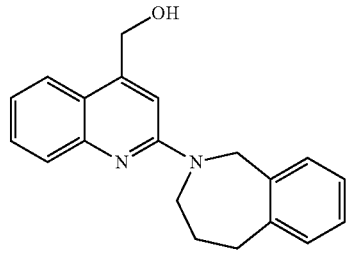 [SMILES: OCc1cc(N2CCCc3ccccc3C2)nc2ccccc12]

Methyl 2-(1,3,4,5-tetrahydro-2H-2-benzazepin-2-yl)quinoline-4-carboxylate

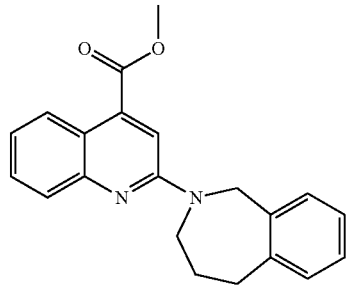 [SMILES: COC(=O)c1cc(N2CCCc3ccccc3C2)nc2ccccc12]

The mixture of 2-chloroquinoline-4-carboxylic acid methyl ester (3 g, 13.5 mmol), 2,3,4,5-tetrahydro-1H-2-benzazepine hydrochloride (3 g, 16.3 mmol), potassium carbonate (4.5 g, 32.6 mmol), tetrabutylammonium iodide (300 mg) and toluene (60 mL) was heated with stirring at 110° C. for 5 days. The solvent was removed under reduced pressure to give a residue which was purified by column chromatography on silica gel (ethyl acetate/petroleum ether, 1:4) to give 1.97 g of product as a yellow solid. MS obsd. (ESI$^+$) [(M+H)$^+$] 333.

[2-(1,3,4,5-Tetrahydro-2H-2-benzazepin-2-yl)quinolin-4-yl]methanol

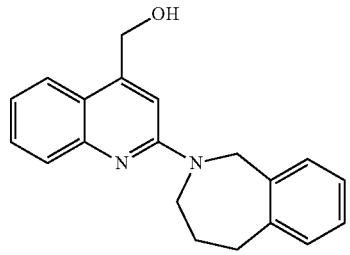 [SMILES: OCc1cc(N2CCCc3ccccc3C2)nc2ccccc12]

To the mixture of methyl 2-(1,3,4,5-tetrahydro-2H-2-benzazepin-2-yl)quinoline-4-carboxylate (30 mg, 0.087 mmol) in tetrahydrofuran (2 mL) was added a tetrahydrofuran solution of borane (1.5 mL, 1.5 mmol) at 0° C. After being stirred at 70° C. for 4 hours, the mixture was quenched with methanol (5 mL) at 0° C. The solvent was removed in vacuo to give a residue which was purified by flash column (ethyl acetate/hexane, 3:7) to afford 16 mg of product as a white solid. MS obsd. (ESI$^+$) [(M+H)$^+$] 305. $^1$H NMR (400 MHz, DMSO-d6) δ ppm 7.70 (d, J=8.0 Hz, 1 H), 7.56-7.44 (m, 3 H), 7.25 (s, 1 H), 7.16-7.07 (m, 4 H), 5.44 (t, J=4.2 Hz, 1 H), 4.86 (s, 2 H), 4.85 (s, 2 H), 4.18 (brs, 2 H), 3.04 (brs, 2 H), 1.80 (brs, 2 H).

Example 130-1

2-(6-Chloroquinolin-2-yl)-2,3,4,5-tetrahydro-1H-2-benzazepine

2-[6-Chloro-4-(prop-2-en-1-yl)quinolin-2-yl]-2,3,4,5-tetrahydro-1H-2-benzazepine

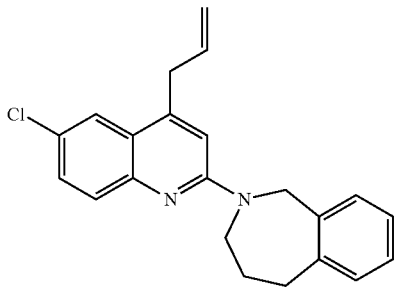 [SMILES: C=CCc1cc(N2CCCc3ccccc3C2)nc2ccc(Cl)cc12]

The mixture of 2-(4,6-dichloroquinolin-2-yl)-2,3,4,5-tetrahydro-1H-2-benzazepine (200 mg, 0.58 mmol), 2-allyl-4,4,5,5-tetramethyl-[1,3,2]dioxaborolane (0.164 mL, 0.87 mmol), tetrakis(triphenylphosphine)palladium(0) (68 mg, 0.058 mmol), potassium carbonate (241 mg, 1.74 mmol), 1,2-dimethoxyethane (3 mL) and water (1 mL) was heated with stirring in a 10 mL of microwave process vial for 3 hours at 120° C. under microwave irradiation. The resulting mixture was diluted with ethyl acetate (20 mL), and then washed with water (20 mL). The ethyl acetate fraction was dried over sodium sulfate, and then concentrated under reduced pressure to give a residue which was separated by column chromatography on silica gel (ethyl acetate/petroleum ether, 0.1:5) to afford 2-[6-chloro-4-(prop-2-en-1-yl)quinolin-2-yl]-2,3,4,5-tetrahydro-1H-2-benzazepine (20 mg) and 2-(6-chloroquinolin-2-yl)-2,3,4,5-tetrahydro-1H-2-benzazepine (50 mg).

2-[6-chloro-4-(prop-2-en-1-yl)quinolin-2-yl]-2,3,4,5-tetrahydro-1H-2-benzazepine MS obsd. (ESI⁺) [(M+H)⁺] 349.

2-(6-chloroquinolin-2-yl)-2,3,4,5-tetrahydro-1H-2-benzazepine

MS obsd. (ESI⁺) [(M+H)⁺] 309. ¹H NMR (400 MHz, DMSO-d6) δ ppm 7.93 (d, J=9.2 Hz, 1 H), 7.72 (brs, 1 H), 7.56-7.51 (m, 2 H), 7.47-7.44 (m, 1 H), 7.29 (d, J=9.6 Hz, 1 H), 7.14-7.08 (m, 3 H), 4.85 (brs, 2 H), 4.14 (brs, 2 H), 3.03 (brs, 2 H), 1.78 (brs, 2 H).

Example 130-2

3-[6-Chloro-2-(1,3,4,5-tetrahydro-2H-2-benzazepin-2-yl)quinolin-4-yl]propane-1,2-diol

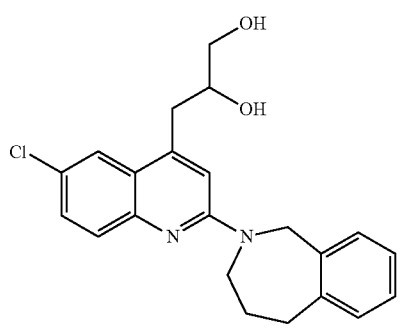 [SMILES: OCC(O)Cc1cc(N2CCCc3ccccc3C2)nc2ccc(Cl)cc12]

To a solution of 2-[6-chloro-4-(prop-2-en-1-yl)quinolin-2-yl]-2,3,4,5-tetrahydro-1H-2-benzazepine (20 mg, 0.057 mmol) in acetone (2 mL) and water (1 mL) was added N-methyl morpholine-N-oxide (50% in water, 15.5 mg, 0.057 mmol) followed by osmium tetroxide (0.14 mg, 0.0005 mmol). The resulting mixture was stirred at room temperature overnight. The solvent was removed under reduced pressure and the residue was purified by column chromatography on silica gel (ethyl acetate/petroleum ether, 3:2) to give 14 mg of product as colorless oil. MS obsd. (ESI⁺) [(M+H)⁺] 383. ¹H NMR (400 MHz, CD₃OD) δ ppm 7.82 (d, J=2.0 Hz, 1 H), 7.58 (d, J=8.8 Hz, 1 H), 7.50 (d, J=6.8 Hz, 1 H), 7.40 (dd, J=9.2, 2.4 Hz, 1 H), 7.14-7.08 (m, 4 H), 4.84 (brs, 2 H), 4.21 (brs, 1 H), 4.10 (brs, 1 H), 3.91-3.88 (m, 1 H), 3.58-3.55 (m, 2 H), 3.21 (dd, J=14.0, 4.4 Hz, 1 H), 3.04 (d, J=6.4 Hz, 2 H), 2.87 (dd, J=14.0, 8.4 Hz, 1 H), 1.91-1.86 (m, 2 H).

Example 131

(4S)-4-{2-[2-(1,3,4,5-Tetrahydro-2H-2-benzazepin-2-yl)quinolin-4-yl]ethyl}-4,5-dihydro-1,3-oxazol-2-amine

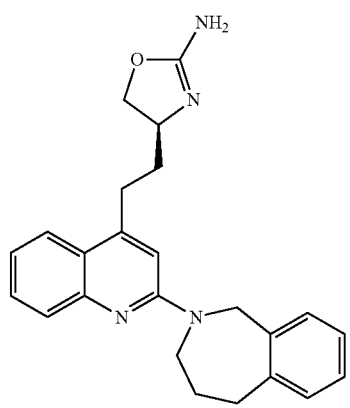 [SMILES: NC1=N[C@@H](CCc2cc(N3CCCc4ccccc4C3)nc3ccccc23)CO1]

tert-Butyl (4S)-2,2-dimethyl-4-{(E)-2-[2-(1,3,4,5-tetrahydro-2H-2-benzazepin-2-yl)quinolin-4-yl]ethenyl}-1,3-oxazolidine-3-carboxylate

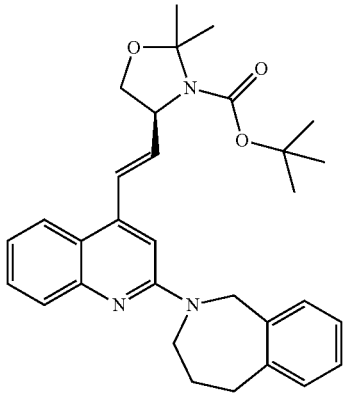 [SMILES: CC(C)(C)OC(=O)N1[C@@H](/C=C/c2cc(N3CCCc4ccccc4C3)nc3ccccc23)COC1(C)C]

The mixture of 2-(4-chloroquinolin-2-yl)-2,3,4,5-tetrahydro-1H-2-benzazepine (310 mg, 1.0 mmol), (S)-2,2-dimethyl-4-vinyl-oxazolidine-3-carboxylic acid tert-butyl ester (273 mg, 1.2 mmol), bis(tri-tert-butylphosphine)palladium (0) (51 mg, 0.1 mmol), methyl dicyclohexylamine (293 mg, 1.5 mmol) and N,N-dimethylformamide (6 mL) was heated with stirring in a 20 mL microwave process vial for 2.5 hours at 120° C. under microwave irradiation. The reaction mixture was diluted with ethyl acetate and washed with brine. The organic layer was dried over sodium sulfate, and then concentrated under reduced pressure to give a residue which was purified by flash column to give 380 mg of product as a white solid (yield was 76%). MS obsd. (ESI$^+$) [(M+H)$^+$] 500.

tert-Butyl (4S)-2,2-dimethyl-4-{2-[2-(1,3,4,5-tetrahydro-2H-2-benzazepin-2-yl)quinolin-4-yl]ethyl}-1,3-oxazolidine-3-carboxylate

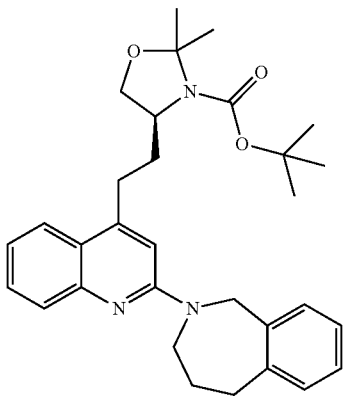 [SMILES: CC(C)(C)OC(=O)N1[C@@H](CCc2cc(N3CCCc4ccccc4C3)nc3ccccc23)COC1(C)C]

The mixture of tert-butyl (4S)-2,2-dimethyl-4-{(E)-2-[2-(1,3,4,5-tetrahydro-2H-2-benzazepin-2-yl)quinolin-4-yl]ethenyl}-1,3-oxazolidine-3-carboxylate (380 mg, 0.76 mmol), palladium hydroxide (20% on carbon, 50 mg) and ethanol (15 mL) was stirred at room temperature for 4 hours under hydrogen. The solid was filtered by a pad of silica gel and the filtrate was concentrated in vacuo to give 340 mg of product as a white solid (yield was 89%). MS obsd. (ESI$^+$) [(M+H)$^+$] 502.

(2S)-2-Amino-4-[2-(1,3,4,5-tetrahydro-2H-2-benzazepin-2-yl)quinolin-4-yl]butan-1-ol

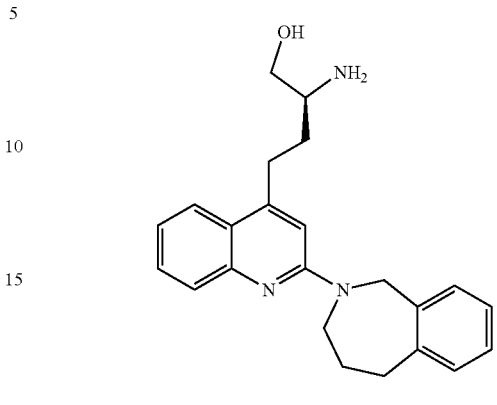

To the solution of tert-butyl (4S)-2,2-dimethyl-4-{2-[2-(1,3,4,5-tetrahydro-2H-2-benzazepin-2-yl)quinolin-4-yl]ethyl}-1,3-oxazolidine-3-carboxylate (340 mg, 0.68 mmol) in ethyl acetate was introduced hydrochloric acid gas for 30 minutes. After being stirred at room temperature overnight, the reaction was poured into ice-water then neutralized with saturated sodium carbonate. The organic layer was separated, dried over sodium sulfate, and then concentrated in vacuo to give the product. It was used in next step without further purification. MS obsd. (ESI$^+$) [(M+H)$^+$] 362.

(4S)-4-{2-[2-(1,3,4,5-Tetrahydro-2H-2-benzazepin-2-yl)quinolin-4-yl]ethyl}-4,5-dihydro-1,3-oxazol-2-amine

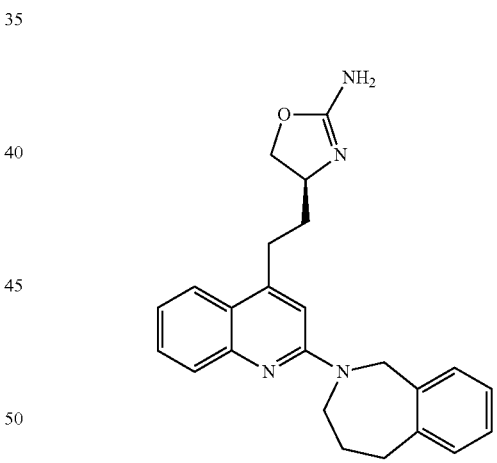

To the stirred mixture of (2S)-2-amino-4-[2-(1,3,4,5-tetrahydro-2H-2-benzazepin-2-yl)quinolin-4-yl]butan-1-ol (110 mg, 0.3 mmol), potassium acetate (90 mg, 0.91 mmol), methanol (8 mL) and water (2 mL) was added a solution of cyanogen bromide (32.3 mg, 0.3 mmol) in cold methanol (2 mL) at 0° C. After the addition, the resulting mixture was stirred at room temperature for 24 hours. The solvent was removed under reduced pressure to give a residue which was purified by preparative HPLC to give 40 mg of product as a white solid (yield was 34.5%). MS obsd. (ESI$^+$) [(M+H)$^+$] 387. $^1$H NMR (400 MHz, DMSO-d6) δ ppm 7.77 (d, J=7.2 Hz, 1 H), 7.56-7.43 (m, 3 H), 7.17-7.04 (m, 4 H), 5.91 (brs, 1 H), 4.84 (s, 2 H), 4.21 (t, J=8.0 Hz, 2 H), 4.13 (brs, 2 H), 3.87 (t, J=7.2 Hz, 1 H), 3.77 (t, J=7.2 Hz, 1 H), 3.01 (brs, 2 H), 2.94-2.89 (m, 1 H), 1.78 (brs, 2 H), 1.72-1.67 (m, 2 H).

Example 132

N-(2-Aminoethyl)-2-(1,3,4,5-tetrahydro-2H-2-benzazepin-2-yl)quinoline-4-sulfonamide trifluoroacetate

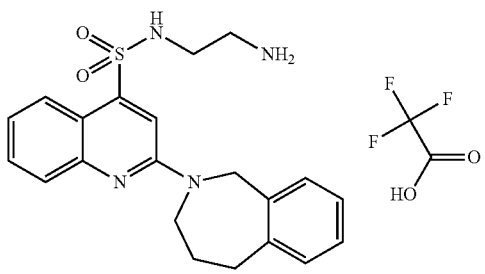 [SMILES: NCCNS(=O)(=O)c1cc(N2CCCc3ccccc3C2)nc2ccccc12 ; O=C(O)C(F)(F)F]

2-(1,3,4,5-Tetrahydro-2H-2-benzazepin-2-yl)quinoline-4-thiol

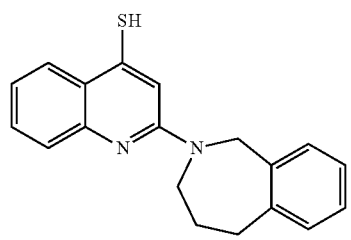 [SMILES: Sc1cc(N2CCCc3ccccc3C2)nc2ccccc12]

A mixture of 2-(4-chloroquinolin-2-yl)-2,3,4,5-tetrahydro-1H-2-benzazepine (2 g, 6.47 mmol) and sodium thiomethoxide (2.4 g, 34 mmol) in dry N,N-dimethylformamide (20 mL) was heated with stirring overnight under reflux. The reaction mixture was cooled to 50° C. and the volatile components were evaporated under reduced pressure to give a residue which was dissolved in 30 mL of chilled water and carefully acidified with 20% hydrochloride aid to pH 4-5 under argon. The resultant solution was extracted with chilled dichloromethane (30 mL×3). The dichloromethane fractions were combined and washed with chilled brine (30 mL×2) and then concentrated under reduced pressure at room temperature to give the crude product. It was used in next step without further purification.

2-(1,3,4,5-Tetrahydro-2H-2-benzazepin-2-yl)quinoline-4-sulfonyl chloride

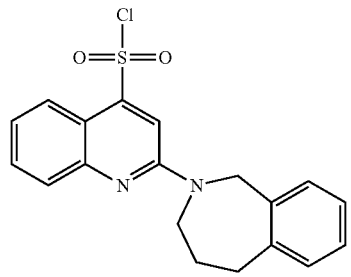 [SMILES: O=S(=O)(Cl)c1cc(N2CCCc3ccccc3C2)nc2ccccc12]

Gaseous chlorine was passed through a well stirred solution of 2-(1,3,4,5-tetrahydro-2H-2-benzazepin-2-yl)quinoline-4-thiol (2 g, 6.5 mmol) in concentrated hydrochloric acid (17 mL) at −10° C. at such a rate that temperature was maintained between −5 and −10° C. The passage of chlorine was discontinued after 30 minutes. The mixture was poured into ice (30 g) followed by addition of sodium bicarbonate (4 g) in small portions. The resultant mixture was extracted with chilled dichloromethane (30 mL×3). The dichloromethane fractions were combined and washed with chilled water (20 mL), and then dried over sodium sulfate, filtered and the filtrate was used in next step without further purification.

N-(2-Aminoethyl)-2-(1,3,4,5-tetrahydro-2H-2-benzazepin-2-yl)quinoline-4-sulfonamide trifluoroacetate

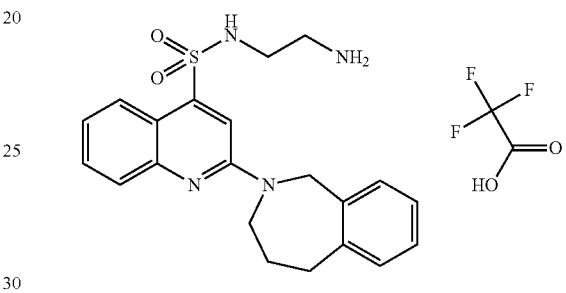

To a solution of ethane-1,2-diamine (500 mg, 8.3 mmol) in dichloromethane (20 mL) was added a cold triethylamine (5 drops) in an ice-water bath, followed by the addition of the solution of 2-(1,3,4,5-tetrahydro-2H-2-benzazepin-2-yl)quinoline-4-sulfonyl chloride (400 mg, 0.9 mmol) in dichloromethane (20 mL) prepared above slowly. After being stirred overnight, the solvent was removed under reduced pressure, and the residue was purified by preparative HPLC to give 43.6 mg of product (yield was 12.2%). MS obsd. (ESI+) [(M+H)+] 397. $^1$H NMR (400 MHz, CD$_3$OD) δ ppm 8.37-8.35 (m, 1 H), 7.88-7.82 (m, 2 H), 7.71 (m, 1 H), 7.48-7.42 (m, 2 H), 7.18-7.17 (m, 3 H), 5.02 (s, 2 H), 4.23 (s, 2 H), 3.09-3.03 (m, 6 H), 1.98 (s, 2 H).

Example 133-1

4-{4-[(2-Aminoethyl)amino]-6-methylquinolin-2-yl}-1,3,4,5-tetrahydro-2H-1,4-benzodiazepin-2-one

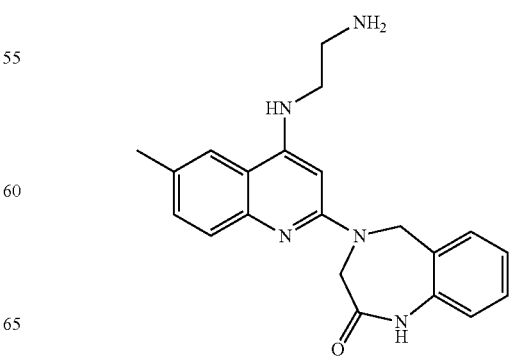

4-(4-Chloro-6-methylquinolin-2-yl)-1,3,4,5-tetrahydro-2H-1,4-benzodiazepin-2-one

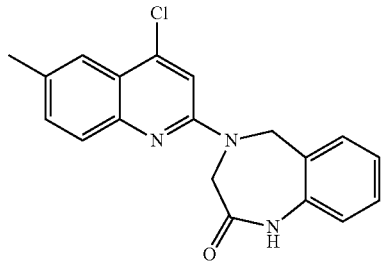 [SMILES: Cc1ccc2nc(N3CC(=O)Nc4ccccc4C3)cc(Cl)c2c1]

The mixture of 2,4-dichloro-6-methyl-quinoline (422 mg, 2 mmol), 1,3,4,5-tetrahydro-2H-1,4-benzodiazepin-2-one (298 mg, 2 mmol) and n-butyl alcohol (15 mL) was heated with stirring in a 20 mL microwave process vial for 3 hours at 160° C. under microwave irradiation. After cooling, the solvent was removed in vacuo and the residue was purified by column chromatography on silica gel (methanol/dichloromethane, 1:20) to give the product. MS obsd. (ESI$^+$) [(M+H)$^+$] 338.

4-{4-[(2-Aminoethyl)amino]-6-methylquinolin-2-yl}-1,3,4,5-tetrahydro-2H-1,4-benzodiazepin-2-one

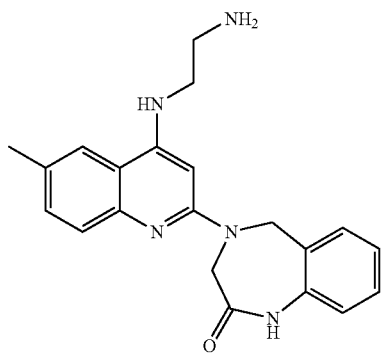 [SMILES: Cc1ccc2nc(N3CC(=O)Nc4ccccc4C3)cc(NCCN)c2c1]

The mixture of 4-(4-chloro-6-methylquinolin-2-yl)-1,3,4,5-tetrahydro-2H-1,4-benzodiazepin-2-one (60 mg, 1 mmol), [1,1'-bis(diphenylphosphino)ferrocene]dichloropalladium (II), (8.2 mg, 0.01 mmol), bis(diphenylphosphino)ferrocene (6 mg, 0.01 mmol) and sodium tert-butoxide (20 mg, 0.2 mmol) and 1,4-dioxane (2 mL) was heated with stirring in a 10 mL microwave process vial for 1 hour at 120° C. under microwave irradiation. After cooling, the mixture was filtered and washed with ethyl acetate. The filtrate was washed with brine, dried over sodium sulfate, and concentrated in vacuo to give a residue which was purified by preparative HPLC to afford the product as a solid. MS obsd. (ESI$^+$) [(M+H)$^+$] 362. $^1$H NMR (400 MHz, CD$_3$OD) δ ppm 7.64 (s, 1 H), 7.44-7.40 (m, 2 H), 7.28 (dd, J=1.6, 8.4 Hz, 1 H), 7.18 (dd, J=1.6, 8.0 Hz, 1 H), 7.09 (dd, J=0.8, 8.0 Hz, 1 H), 6.98 (dd, J=0.8, 8.0 Hz, 1 H), 6.00 (s, 1 H), 4.87 (s, 2 H), 4.72 (s, 2 H), 3.40 (t, J=6.4 Hz, 2 H), 2.95 (t, J=6.4 Hz, 2 H), 2.40 (s, 3 H).

Example 133-2

N-[6-Methyl-2-(1,2,3,5-tetrahydro-4H-1,4-benzodiazepin-4-yl)quinolin-4-yl]ethane-1,2-diamine

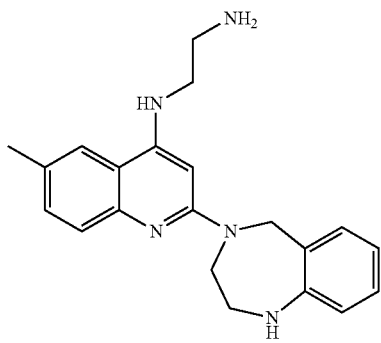 [SMILES: Cc1ccc2nc(N3CCNc4ccccc4C3)cc(NCCN)c2c1]

The title compound was prepared in analogy to Example 16-1 by using 2,3,4,5-tetrahydro-1H-1,4-benzodiazepine (commercial available) instead of 1,3,4,5-tetrahydro-2H-1,4-benzodiazepin-2-one. MS obsd. (ESI$^+$) [(M+H)+] 348. $^1$H NMR (400 MHz, CD$_3$OD) δ ppm 7.90 (s, 1 H), 7.67 (d, J=8.4 Hz, 1 H), 7.58 (d, J=8.4 Hz, 1 H), 7.42 (d, J=7.2 Hz, 1 H), 7.12 (t, J=8.0 Hz, 1 H), 6.88 (t, J=7.2 Hz, 1 H), 6.82 (d, J=8.0 Hz, 1 H), 5.95 (s, 1 H), 4.87 (s, 2 H), 4.00 (t, J=4.8 Hz, 2 H), 3.72 (t, J=6.0 Hz, 2 H), 3.46 (t, J=4.8 Hz, 2 H), 3.18 (t, J=6.0 Hz, 2 H), 2.49 (s, 3 H).

Example 134

N-[2-(2,3-Dihydro-1,4-benzoxazepin-4(5H)-yl)quinolin-4-yl]ethane-1,2-diamine

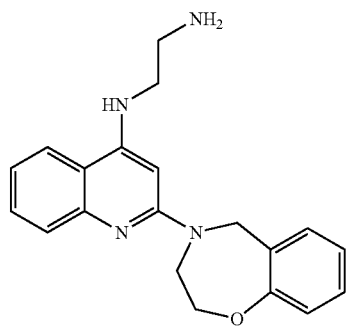 [SMILES: NCCNc1cc(N2CCOc3ccccc3C2)nc2ccccc12]

Methyl (2-cyanophenoxy)acetate

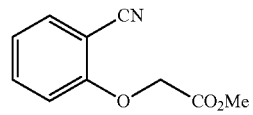 [SMILES: COC(=O)COc1ccccc1C#N]

To the mixture of 2-hydroxybenzonitrile (40 g, 0.34 mol) and potassium carbonate (51.6 g, 0.374 mol) in 850 mL of acetone was added methyl bromoacetate (51.7 g, 0.34 mol) slowly at room temperature. After being stirred at room temperature overnight, the solid was filtered off. The filtrate was concentrated under reduced pressure and the residue was dissolved in ethyl acetate. The organic layer was washed with water then brine, dried over sodium sulfate, filtered and concentrated under reduced pressure to give a residue which was recrystallized in methanol to give 40 g of product as a white solid.

4,5-Dihydro-1,4-benzoxazepin-3(2H)-one

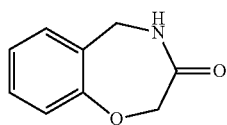 [SMILES: O=C1COc2ccccc2CN1]

The methanol solution of methyl (2-cyanophenoxy)acetate (40 g, 0.209 mol) was added to the mixture of Raney Ni (80 g) in 500 mL of methanol. The reaction mixture was stirred at room temperature overnight under hydrogen atmosphere. Raney Ni was removed by filtration, and the filtrated was concentrated under reduced pressure to give a residue which was purified by column chromatography on silica gel (methanol/dichloromethane, 1:50) to give 23 g of product. MS obsd. (ESI$^+$) [(M+H)$^+$] 164.

2,3,4,5-Tetrahydro-1,4-benzoxazepine

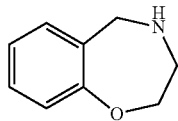 [SMILES: c1ccc2c(c1)CNCCO2]

To the suspension of lithium aluminium hydride (15.2 g, 0.4 mol) in 600 mL of ether was added a solution of 4,5-dihydro-1,4-benzoxazepin-3(2H)-one (16.3 g, 0.1 mol) in 60 mL of tetrahydrofuran at room temperature. After being heated with stirring under reflux overnight, water was added dropwise to quench the reaction at 0° C., The resulting mixture was diluted with ethyl acetate, and then filtered by a pad of celite. The filtrate was concentrated under reduced pressure, followed by the addition of hydrochloric acid ethyl acetate solution. The hydrochloride was collected by filtration, washed with ethyl acetate then ether, and then dried in vacuo to give 13.5 g of product. MS obsd. (ESI$^+$) [(M+H)$^+$] 150.

4-(4-Chloroquinolin-2-yl)-2,3,4,5-tetrahydro-1,4-benzoxazepine

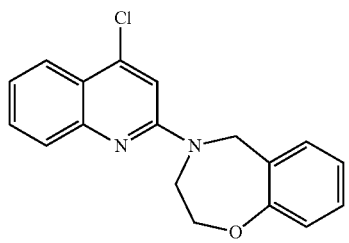 [SMILES: Clc1cc(N2CCOc3ccccc3C2)nc2ccccc12]

The mixture of 2,4-dichloroquinoline (198 mg, 0.1 mmol), 2,3,4,5-tetrahydro-1,4-benzoxazepine hydrochloride (186 mg, 0.1 mmol), diisopropylethylamine (0.4 mL) and 5 mL of N-methyl-2-pyrrolidone was heated with stirring at 100° C. overnight. The mixture was cooled to room temperature, diluted with brine, and extracted with ethyl acetate (30 mL×3). The organic layers were combined and washed with brine. The solvent was dried over sodium sulfate and removed under reduced pressure to give a residue which was purified by column chromatography on silica gel to give 119 mg of product as a white solid. MS obsd. (ESI$^+$) [(M+H)$^+$] 311.

N-[2-(2,3-Dihydro-1,4-benzoxazepin-4(5H)-yl) quinolin-4-yl]ethane-1,2-diamine

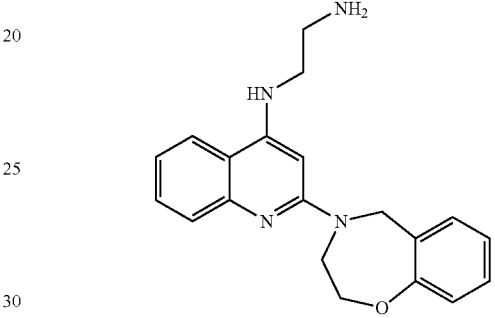

The mixture of 4-(4-chloroquinolin-2-yl)-2,3,4,5-tetrahydro-1,4-benzoxazepine (100 mg, 0.32 mmol) and 1.6 mL of ethane-1,2-diamine was heated with stirring in a 5 mL microwave process vial for 3 hours at 150° C. under microwave irradiation. The mixture was concentrate in vacuo to give a residue which was purified by preparative HPLC to give 31 mg of product as a white solid. MS obsd. (ESI$^+$) [(M+H)$^+$] 335. $^1$H NMR (400 MHz, CD$_3$OD) δ ppm 8.61 (s, 1 H), 7.90 (d, J=7.6 Hz, 1 H), 7.60-7.51 (m, 3 H), 7.23 (brs, 2 H), 7.09-6.98 (m, 2 H), 6.05 (s, 1 H), 4.89 (s, 2 H), 4.27 (s, 2 H), 4.25 (s, 2 H), 3.61 (s, 2 H), 3.15 (s, 2 H).

Example 135-1

N-[(1-Aminocyclopropyl)methyl]-2-(1,1-dioxido-2,3-dihydro-1,4-benzothiazepin-4(5H)-yl)-6-methylquinazolin-4-amine

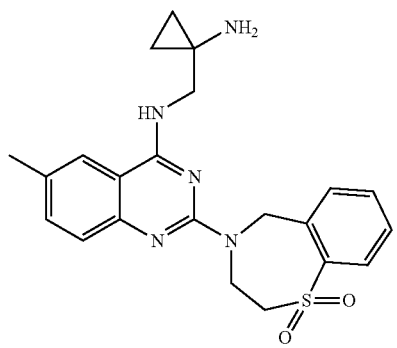 [SMILES: Cc1ccc2nc(N3CCS(=O)(=O)c4ccccc4C3)nc(NCC3(N)CC3)c2c1]

513 tert-Butyl (1-{[(2-chloro-6-methylquinazolin-4-yl)amino]methyl}cyclopropyl)carbamate

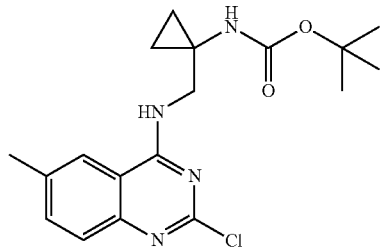 [SMILES: Cc1ccc2nc(Cl)nc(NCC3(NC(=O)OC(C)(C)C)CC3)c2c1]

To a solution of tert-butyl [1-(aminomethyl)cyclopropyl]carbamate (0.92 g, 4.9 mmol) in tetrahydrofuran (50 mL) was added triethylamine (1.3 mL, 9.4 mmol) followed by 2,4-dichloro-6-methylquinazoline (1.0 g, 4.7 mmol) in portions at room temperature. After being stirred at room temperature overnight, the resultant mixture was concentrated in vacuo to remove 20 mL of solvent and then stirred vigorously with water (200 mL). The formed solid was collected by filtration and washed with water and ether, then dried in vacuo to afford 1.5 g of the product as a white powder.

tert-Butyl [({2-[2-(1,1-dioxido-2,3-dihydro-1,4-benzothiazepin-4(5H)-yl)-6-methylquinazolin-4-yl]amino}methyl)cyclopropyl]carbamate

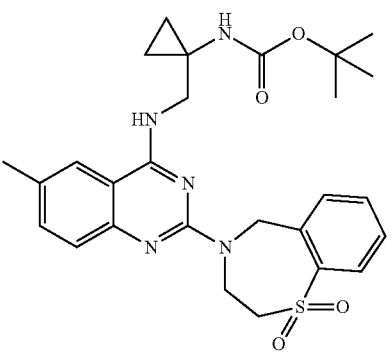 [SMILES: Cc1ccc2nc(N3CCS(=O)(=O)c4ccccc4C3)nc(NCC3(NC(=O)OC(C)(C)C)CC3)c2c1]

A mixture of tert-butyl (1-{[(2-chloro-6-methylquinazolin-4-yl)amino]methyl}cyclopropyl)carbamate (1.5 g, 4.1 mmol), 2,3,4,5-tetrahydro-1,4-benzothiazepine 1,1-dioxide (0.82 g, 4.1 mmol) and catalytic amount of ammonium chloride in ethanol (40 mL) was heated with stirring at 70° C. overnight. The reaction mixture was then cooled to room temperature. The formed solid was collected by filtration, then washed with ethanol and dried in vacuo. The crude solid (1.5 g) was suspended in dichloromethane (50 mL) and basified with 1 N of sodium hydroxide. The organic phase was separated and used for the next step directly.

514

(1-Amino-cyclopropylmethyl)-[2-(5,5-dioxo-5,6,7,9-tetrahydro-5lambda*6*-thia-8-aza-benzocyclohepten-8-yl)-6-methyl-quinazolin-4-yl]-amine

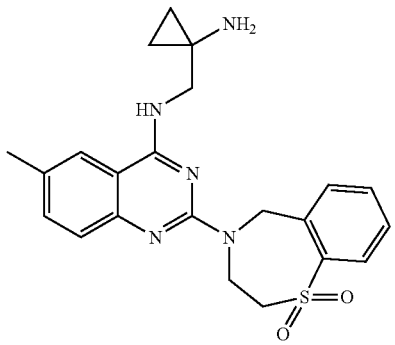 [SMILES: Cc1ccc2nc(N3CCS(=O)(=O)c4ccccc4C3)nc(NCC3(N)CC3)c2c1]

To the solution obtained above was added trifluoroacetic acid (10 mL) and the mixture was stirred at room temperature for 30 minutes. The reaction was quenched with saturated aqueous solution of sodium carbonate. The organic layer was separated and dried over sodium sulfate, filtrated and concentrated in vacuo. The residue was stirred with methanol. The produced white solid was collected by filtration and dried in vacuo to afford 400 mg of the product as a white powder. MS obsd. (ESI$^+$) [(M+H)$^+$] 424, $^1$H NMR (400 MHz, DMSO-$d_6$) δ ppm 7.95-7.85 (m, 2 H), 7.74 (br. s., 2 H), 7.62 (t, J=7.00 Hz, 1 H), 7.47 (t, J=8.30 Hz, 1 H), 7.35 (dd, J=8.53, 1.51 Hz, 1 H), 7.23 (d, J=7.78 Hz, 1 H), 5.07 (br. s., 2 H), 4.44 (br. s., 2 H), 3.32 (s, 2 H), 2.35 (s, 3 H), 2.04 (s, 2 H), 0.52 (d, J=30.62 Hz, 4 H).

Example 135-2

2-(1,1-Dioxido-2,3-dihydro-1,4-benzothiazepin-4(5H)-yl)-6-methyl-N-(pyrrolidin-3-yl)quinazolin-4-amine

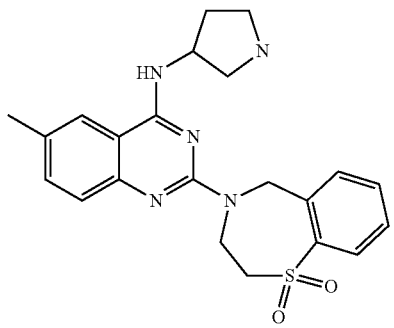 [SMILES: Cc1ccc2nc(N3CCS(=O)(=O)c4ccccc4C3)nc(NC3CCNC3)c2c1]

The title compound was prepared in analogy to Example 135-1 in Scheme 70 by using 2,4-dichloro-6-methylquinazoline, tert-butyl 3-aminopyrrolidine-1-carboxylate, 2,3,4,5-tetrahydro-1,4-benzothiazepine 1,1-dioxide and trifluoroacetic acid instead of 2,4-dichloro-6-methylquinazoline, tert-butyl [1-(aminomethyl)cyclopropyl]carbamate, 2,3,4,5-tetrahydro-1,4-benzothiazepine 1,1-dioxide and trifluoroacetic acid. MS obsd. (ESI+) [(M+H)+] 424, $^1$H NMR (400 MHz, DMSO-d$_6$) δ ppm 7.92-7.82 (m, 2 H), 7.78 (br. s., 1 H), 7.69-7.56 (m, 2 H), 7.48 (t, J=7.53 Hz, 1 H), 7.34 (dd, J=8.53, 1.25 Hz, 1 H), 7.22 (d, J=6.78 Hz, 1 H), 5.08 (br. s., 2 H), 4.47 (br. s., 2 H), 3.48-2.54 (m, 7 H), 2.33 (s, 3 H), 2.25-2.00 (m, 1 H), 1.81-1.68 (m, 1 H).

Example 136

Viral cytopathic effect (CPE) assay: To measure anti-RSV activity of compounds, 96-well plates are seeded with 6×10$^3$ cells per well in Dulbecco's modified Eagle's medium (DMEM) containing 10% fetal bovine serum (FBS). Cells are infected the next day with sufficient RSV Long strain (ATCC) to produce an approximately 80-90% cytopathic effect after 6 days, in the presence of serial half-log diluted compound in a total volume of 200 µL per well. The viability of cells is assessed after 6 days using Cell Counting kit-8 (Dojindo Molecular Technologies). The absorbance at 450 nm and referenced at 630 nm is measured to determine 50% effective concentration (EC$_{50}$).

The compounds of the present invention were tested for their anti-RSV activity, and the activation as described herein. The Examples were tested in the above assay and found to have EC$_{50}$ of about 0.0001 µM to about 10 µM. Particular compound of formula (I) were found to have EC$_{50}$ of about 0.0001 µM to about 1 µM. Further particular compound of formula (I) were found to have EC$_{50}$ of about 0.0001 µM to about 0.1 µM.

Results of CPE assays are given in Table 1.

TABLE 1

| Example | EC50 (µM, Long Strain) |
| --- | --- |
| 1-1 | 0.002 |
| 1-2 | 0.007 |
| 1-3 | 0.072 |
| 1-4 | 0.004 |
| 1-5 | 0.004 |
| 1-6 | 0.022 |
| 1-7 | 0.022 |
| 2-1 | 0.024 |
| 2-2 | 0.002 |
| 2-3 | 2.805 |
| 2-4 | 0.081 |
| 2-5 | 0.006 |
| 2-6 | 0.021 |
| 2-7 | 0.234 |
| 2-8 | 0.055 |
| 2-9 | 0.007 |
| 2-10 | 0.005 |
| 2-11 | 0.008 |
| 3-1 | 0.006 |
| 3-2 | 3.051 |
| 3-3 | 3.552 |
| 3-4 | 0.006 |
| 3-5 | 0.002 |
| 3-6 | 0.058 |
| 3-7 | 0.009 |
| 3-8 | 0.002 |
| 3-9 | 0.248 |
| 3-10 | 0.053 |
| 3-11 | 0.054 |
| 3-12 | 1.654 |
| 3-13 | 0.099 |
| 3-14 | 0.017 |
| 3-15 | 0.482 |
| 3-16 | 0.075 |
| 3-17 | 5.053 |
| 3-18 | 0.024 |
| 3-19 | 0.009 |
| 3-20 | 0.507 |
| 3-21 | 0.006 |
| 3-22 | 0.032 |
| 3-23 | 0.002 |
| 3-24 | 0.021 |
| 3-25 | 0.022 |
| 3-26 | 0.876 |
| 3-27 | 1.394 |
| 3-28 | 0.149 |
| 3-29 | 0.022 |
| 3-30 | 7.81 |
| 3-31 | 0.014 |
| 3-32 | 0.037 |
| 3-33 | 0.426 |
| 3-34 | 0.085 |
| 3-35 | 0.013 |
| 3-36 | 0.092 |
| 3-37 | 0.017 |
| 3-38 | 0.0439 |
| 3-39 | 0.030 |
| 3-40 | 0.022 |
| 3-41 | 0.071 |
| 3-42 | 0.007 |
| 3-43 | 2.394 |
| 3-44 | 0.012 |
| 3-45 | 5.229 |
| 3-46 | 0.053 |
| 3-47 | 0.101 |
| 3-48 | 0.023 |
| 3-49 | 0.099 |
| 3-50 | 0.0004 |
| 3-51 | 0.004 |
| 3-52 | 0.005 |
| 3-53 | 0.261 |
| 3-54 | 0.114 |
| 3-55 | 0.027 |
| 3-56 | 0.716 |
| 3-57 | 7.534 |
| 3-58 | 0.184 |
| 3-59 | 1.083 |
| 3-60 | 0.617 |
| 3-61 | 0.118 |
| 3-62 | 0.589 |
| 3-63 | 9.899 |
| 3-64 | 0.874 |
| 3-65 | 0.002 |
| 4-1 | 0.269 |
| 4-2 | 0.098 |
| 4-3 | 0.026 |
| 4-4 | 0.208 |
| 4-5 | 5.258 |
| 5-1 | 9.197 |
| 5-2 | 0.211 |
| 5-3 | 0.015 |
| 5-4 | 0.326 |
| 5-5 | 0.014 |
| 5-6 | 2.062 |
| 5-7 | 0.941 |
| 5-8 | 0.022 |
| 5-9 | 0.018 |
| 5-10 | 0.397 |
| 5-11 | 0.526 |
| 5-12 | 6.249 |
| 6-1 | 0.025 |
| 6-2 | 0.908 |
| 7 | 1.418 |
| 8-1 | 5.513 |
| 8-2 | 0.817 |
| 8-3 | 0.9 |
| 8-4 | 0.064 |
| 8-5 | 0.074 |
| 8-6 | 3.767 |
| 8-7 | 0.322 |
| 9-1 | 2.35 |
| 9-2 | 4.77 |
| 9-3 | 0.001 |
| 9-4 | 8.874 |
| 9-5 | 0.179 |

TABLE 1-continued

| Example | EC50 (μM, Long Strain) |
|---|---|
| 9-6 | 0.275 |
| 9-7 | 0.002 |
| 9-8 | 3.478 |
| 9-9 | 0.157 |
| 9-10 | 0.037 |
| 9-11 | 0.953 |
| 9-12 | 2.663 |
| 9-13 | 0.701 |
| 9-14 | 0.025 |
| 9-15 | 0.012 |
| 9-16 | 0.005 |
| 9-17 | 0.025 |
| 9-18 | 0.01 |
| 9-19 | 0.0007 |
| 9-20 | 0.760 |
| 9-21 | 0.021 |
| 9-22 | 0.872 |
| 9-23 | 3.022 |
| 9-24 | 0.024 |
| 9-25 | 4.084 |
| 9-26 | 7.204 |
| 9-27 | 0.797 |
| 9-28 | 0.003 |
| 9-29 | 0.024 |
| 9-30 | 8.591 |
| 9-31 | 2.427 |
| 9-32 | 0.063 |
| 9-33 | 0.057 |
| 9-34 | 0.024 |
| 10 | 0.003 |
| 11-1 | 0.069 |
| 11-2 | 7.022 |
| 11-3 | 0.922 |
| 11-4 | 0.004 |
| 12-1 | 0.536 |
| 12-2 | 0.315 |
| 12-3 | 6.256 |
| 12-4 | 0.764 |
| 12-5 | 0.448 |
| 12-6 | 9.214 |
| 12-7 | 0.226 |
| 13 | 0.026 |
| 14-1 | 2.194 |
| 14-2 | 8.792 |
| 15-1 | 7.892 |
| 15-2 | 7.994 |
| 15-3 | 2.697 |
| 15-4 | 0.257 |
| 15-5 | 0.740 |
| 16-1 | 2.567 |
| 16-2 | 9.642 |
| 17-1 | 5.538 |
| 17-2 | 0.616 |
| 17-3 | 2.17 |
| 17-4 | 0.071 |
| 17-5 | 1.504 |
| 17-6 | 0.086 |
| 17-7 | 0.642 |
| 17-8 | 0.021 |
| 18-1 | 0.003 |
| 18-2 | 0.024 |
| 18-3 | 0.014 |
| 18-4 | 0.061 |
| 18-5 | 0.057 |
| 18-6 | 0.061 |
| 18-7 | 0.023 |
| 18-8 | 0.0007 |
| 18-9 | 0.005 |
| 18-10 | 0.011 |
| 18-11 | 0.619 |
| 19-1 | 0.043 |
| 19-2 | 0.011 |
| 19-3 | 0.006 |
| 19-4 | 0.02 |
| 19-5 | 3.073 |
| 19-6 | 0.054 |
| 19-7 | 6.856 |
| 19-8 | 2.749 |
| 20-1 | 0.073 |
| 20-2 | 0.31 |
| 20-3 | 0.093 |
| 21-1 | 0.023 |
| 21-2 | 0.161 |
| 21-3 | 0.015 |
| 21-4 | 0.004 |
| 21-5 | 0.007 |
| 22 | 0.036 |
| 23 | 5.185 |
| 24 | 0.016 |
| 25 | 0.002 |
| 26-1 | 0.005 |
| 26-2 | 0.179 |
| 27 | 2.393 |
| 28-1 | 0.007 |
| 28-2 | 0.007 |
| 28-3 | 0.001 |
| 28-4 | 0.001 |
| 28-5 | 0.003 |
| 29 | 0.042 |
| 30-1 | 0.317 |
| 30-2 | 0.218 |
| 31 | 0.702 |
| 32-1 | 0.019 |
| 32-2 | 2.454 |
| 32-3 | 1.991 |
| 32-4 | 0.272 |
| 32-5 | 2.58 |
| 33-1 | 0.044 |
| 33-2 | 0.627 |
| 34 | 2.086 |
| 35 | 2.791 |
| 36-1 | 0.073 |
| 36-2 | 1.474 |
| 36-3 | 2.153 |
| 36-4 | 0.138 |
| 36-5 | 0.026 |
| 36-6 | 0.264 |
| 37-1 | 0.005 |
| 37-2 | 0.043 |
| 38-1 | 0.01 |
| 38-2 | 0.302 |
| 38-3 | 0.074 |
| 38-4 | 0.064 |
| 38-5 | 6.652 |
| 39 | 0.092 |
| 40-1 | 0.039 |
| 40-2 | 4.655 |
| 40-3 | 0.917 |
| 40-4 | 2.646 |
| 41 | 2.629 |
| 42-1 | 8.947 |
| 42-2 | 0.037 |
| 43 | 0.017 |
| 44-1 | 0.084 |
| 44-2 | 1.547 |
| 45-1 | 0.021 |
| 45-2 | 0.253 |
| 45-3 | 0.031 |
| 46 | 0.682 |
| 47-1 | 7.881 |
| 47-2 | 5.822 |
| 47-3 | 5.692 |
| 47-4 | 0.993 |
| 47-5 | 0.835 |
| 47-6 | 2.312 |
| 47-7 | 3.4107 |
| 47-8 | 0.432 |
| 47-9 | 0.192 |
| 48 | 0.009 |
| 49 | 0.721 |
| 50-1 | 0.931 |
| 50-2 | 2.423 |
| 51 | 0.056 |
| 52 | 0.419 |

TABLE 1-continued

| Example | EC50 (μM, Long Strain) |
|---|---|
| 53 | 0.094 |
| 54 | 4.798 |
| 55-1 | 0.007 |
| 55-2 | 0.202 |
| 55-3 | 0.006 |
| 56-1 | 0.002 |
| 56-2 | 0.023 |
| 56-3 | 0.004 |
| 56-4 | 0.027 |
| 56-5 | 0.022 |
| 56-6 | 0.002 |
| 57-1 | 0.067 |
| 57-2 | 0.018 |
| 57-3 | 0.023 |
| 57-4 | 0.239 |
| 57-5 | 0.027 |
| 57-6 | 0.037 |
| 57-7 | 0.081 |
| 58 | 2.772 |
| 59 | 0.746 |
| 60 | 0.018 |
| 61-1 | 0.005 |
| 61-2 | 0.097 |
| 62-1 | 0.0003 |
| 62-2 | 0.0017 |
| 62-3 | 0.0013 |
| 62-4 | 0.019 |
| 62-5 | 0.017 |
| 62-6 | 0.006 |
| 62-7 | 0.186 |
| 63-1 | 3.133 |
| 63-2 | 2.021 |
| 63-3 | 0.007 |
| 63-4 | 0.797 |
| 64 | 0.035 |
| 65 | 0.322 |
| 66 | 0.002 |
| 67 | 0.585 |
| 68 | 2.012 |
| 69-1 | 0.007 |
| 69-2 | 0.007 |
| 70 | 0.071 |
| 71 | 0.005 |
| 72 | 0.002 |
| 73 | 6.978 |
| 74 | 1.936 |
| 75 | 0.002 |
| 76 | 0.006 |
| 77 | 8.78 |
| 78-1 | 0.016 |
| 78-2 | 0.25 |
| 79 | 2.791 |
| 80 | 5.479 |
| 81 | 0.353 |
| 82 | 0.014 |
| 83 | 0.662 |
| 84 | 2.965 |
| 85 | 0.008 |
| 86 | 2.222 |
| 87-1 | 0.096 |
| 87-2 | 9.31 |
| 88 | 0.007 |
| 89 | 0.007 |
| 90 | 0.005 |
| 91 | 0.004 |
| 92-1 | 0.009 |
| 92-2 | 0.019 |
| 93-1 | 0.005 |
| 93-2 | 0.009 |
| 94 | 6.527 |
| 95 | 3.039 |
| 96 | 2.833 |
| 97 | 0.177 |
| 98-1 | 0.778 |
| 98-2 | 3.163 |
| 99 | 2.999 |
| 100 | 9.191 |
| 101 | 8.579 |
| 102 | 9.76 |
| 103 | 0.202 |
| 104 | 0.89 |
| 105 | 1.084 |
| 106 | 0.002 |
| 107 | 0.001 |
| 108-1 | 0.488 |
| 108-2 | 2.474 |
| 109-1 | 0.00088 |
| 109-2 | 0.0015 |
| 110-1 | 0.017 |
| 110-2 | 2.607 |
| 110-3 | 0.161 |
| 110-4 | 0.06 |
| 110-5 | 1.655 |
| 110-6 | 4.278 |
| 110-7 | 1.178 |
| 110-8 | 0.081 |
| 110-9 | 1.367 |
| 110-10 | 0.099 |
| 110-11 | 6.753 |
| 110-12 | 0.072 |
| 110-13 | 3.679 |
| 110-14 | 0.648 |
| 110-15 | 0.004 |
| 111-1 | 2.007 |
| 111-2 | 1.345 |
| 111-3 | 0.0768 |
| 111-4 | 0.066 |
| 111-5 | 1.64 |
| 111-6 | 0.062 |
| 111-7 | 0.873 |
| 111-8 | 0.283 |
| 111-9 | 0.047 |
| 111-10 | 0.107 |
| 111-11 | 0.588 |
| 112-1 | 3.739 |
| 112-2 | 0.092 |
| 113 | 0.733 |
| 114-1 | 0.007 |
| 114-2 | 0.975 |
| 114-3 | 0.004 |
| 114-4 | 0.186 |
| 115 | 0.01 |
| 116-1 | 0.005 |
| 116-2 | 0.309 |
| 117 | 5.97 |
| 118-1 | 1.975 |
| 118-2 | 0.048 |
| 118-3 | 0.063 |
| 118-4 | 0.104 |
| 118-5 | 0.178 |
| 118-6 | 0.173 |
| 118-7 | 0.166 |
| 118-8 | 0.223 |
| 118-9 | 0.202 |
| 118-10 | 0.289 |
| 118-11 | 0.323 |
| 118-12 | 0.448 |
| 118-13 | 0.463 |
| 118-14 | 0.616 |
| 118-15 | 0.626 |
| 118-16 | 0.695 |
| 118-17 | 0.806 |
| 118-18 | 0.973 |
| 118-19 | 1.236 |
| 118-20 | 1.129 |
| 118-21 | 1.382 |
| 118-22 | 2.227 |
| 118-23 | 2.641 |
| 118-24 | 6.451 |
| 118-25 | 7.623 |
| 118-26 | 7.754 |
| 119 | 6.656 |

TABLE 1-continued

| Example | EC50 (μM, Long Strain) |
|---------|------------------------|
| 120-1   | 2.193                  |
| 120-2   | 1.785                  |
| 121     | 1.103                  |
| 122     | 3.125                  |
| 123     | 3.144                  |
| 124     | 6.102                  |
| 125     | 2.521                  |
| 126-1   | 0.790                  |
| 126-2   | 0.638                  |
| 127     | 6.249                  |
| 128     | 7.174                  |
| 129     | 7.875                  |
| 130-1   | 6.836                  |
| 130-2   | 7.269                  |
| 131     | 2.523                  |
| 132     | 7.814                  |
| 133-1   | 0.31                   |
| 133-2   | 0.186                  |
| 134     | 0.25                   |
| 135-1   | 0.006                  |
| 135-2   | 0.018                  |

Example A

A compound of formula (I) can be used in a manner known per se as the active ingredient for the production of tablets of the following composition:

| Per tablet | |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula (I) can be used in a manner known per se as the active ingredient for the production of capsules of the following composition:

| Per capsule | |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

The invention claimed is:
1. A compound of formula (I)

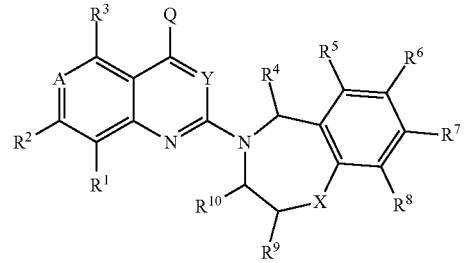

Wherein
$R^1$ is hydrogen, halogen, or $C_{1-6}$alkyl;
$R^2$ is hydrogen, halogen, or $C_{1-6}$alkyl;
$R^3$ is hydrogen, halogen, or $C_{1-6}$alkyl;
$R^4$ is hydrogen, or $C_{1-6}$alkyl;
$R^5$ is hydrogen, or halogen;
$R^6$ is hydrogen, halogen, hydroxy, $C_{1-6}$alkoxy, carboxy, morpholinyl, or 4-$C_{0-6}$alkylpiperazin-1-yl;
$R^7$ is hydrogen, halogen, $C_{1-6}$alkyl, $C_{1-6}$alkoxy, $C_{1-6}$alkylaminocarbonyl, di$C_{1-6}$alkylaminocarbonyl, $C_{1-6}$alkylsulfonyl, phenoxy, or hydroxy$(CH_2)_{2-6}$—O—;
$R^8$ is hydrogen, halogen, or $C_{1-6}$alkoxy;
$R^9$ is hydrogen, $C_{1-6}$alkyl, or =O;
$R^{10}$ is hydrogen, or =O, provided that $R^9$ and $R^{10}$ are not =O simultaneously;
A is nitrogen, or —C—$R^{11}$, wherein $R^{11}$ is hydrogen, halogen, $C_{1-6}$alkyl, cycloalkyl, $C_{1-6}$alkoxy, trifluoromethyl, trifluoromethoxy, pyridinyloxy, $C_{1-6}$alkoxy$(CH_2)_{1-6}$—O—, difluoromethoxy, cyano, nitro, amino, vinyl, acetylenyl, aminocarbonyl, hydroxy$(CH_2)_{2-6}$—O—, $C_{1-6}$alkylsulfinyl, $C_{1-6}$alkylsulfonyl, hydroxy$(CH_2)_{1-6}$, deuterated$C_{1-6}$alkyl, carboxyl, $C_{1-6}$alkoxycarbonyl, hydroxy, difluoromethyl, —CH(hydroxy)$C_{1-6}$alkyl, or $C_{1-6}$alkylsulfanyl;
X is —$CH_2$—, —O—, —NH—, —$CF_2$—, —C($C_{1-6}$alkyl)(OH)—, —S—, —C(=O)—, —C(=NOC$_{0-6}$alkyl)-, —S(=O)—, —S($O_2$)— or —S(=O)(NH)—;
Y is —CH—, or nitrogen;
Q is hydrogen; halogen; $C_{1-6}$alkyl, unsubstituted or once or twice substituted by amino or hydroxy, provided that di-substitution is not on the same carbon; amino$(CH_2)_{2-6}$aminosulfonyl; 2-amino-4,5-dihydro-1,3-oxazol-4-yl$(CH_2)_{1-6}$; carboxy$(CH_2)_{1-6}$; phenylsulfonyl; piperidin-4-yl-carbonyl; 1H-pyrazol-3-yl; pyrrolidin-3-yloxy; piperidin-4-yloxy; amino$(CH_2)_{2-6}$—O—; or $NR^{12}R^{13}$, wherein one of $R^{12}$ and $R^{13}$ is hydrogen, $C_{1-6}$alkyl, or hydroxy$(CH_2)_{2-6}$, and the other one is {1-[amino$(CH_2)_{0-6}$]-3,3-difluorocyclobutyl}$(CH_2)_{1-6}$; guanidino$(CH_2)_{2-6}$; (S—$C_{1-6}$alkylsulfonimidoyl)$(CH_2)_{2-6}$; 2-oxa-6-aza-spiro[3.4]oct-8-yl; {3-[amino$(CH_2)_{0-6}$]tetrahydrofuran-3-yl}$(CH_2)_{1-6}$; 3-aminomethyl-1,1-dioxidothietan-3-ylmethyl; 3-amino-1,1-dioxidothietan-3-ylmethyl; 3-(aminomethyl)thietan-3-ylmethyl;(1,1-dioxidothiomorpholin-4-yl)ethyl; $C_{0-6}$alkyl(oxetanyl)N$(CH_2)_{2-6}$; 4,5-dihydro-1H-imidazol-2-yl; amino$(CH_2)_{2-6}$—O—$(CH_2)_{2-6}$; amino$(CH_2)_{2-10}$; amino$(CH_2)_{1-6}$difluoromethyl$(CH_2)_{1-6}$; amino$(CH_2)_{1-6}$difluoromethyldifluoromethyl$(CH_2)_{1-6}$; amino$(CH_2)_{1-6}$fluoromethyl$(CH_2)_{1-6}$; amino$(CH_2)_{1-6}$oxetanyl$(CH_2)_{0-6}$; amino$(CH_2)_{0-6}$oxetanyl$(CH_2)_{1-6}$;

amino(CH$_2$)$_{2-6}$sulfanyl(CH$_2$)$_{2-6}$; amino(CH$_2$)$_{2-6}$sulfonyl(CH$_2$)$_{2-6}$; amino(CH$_2$)$_{0-6}$carbonyl(CH$_2$)$_{0-6}$; aminocycloalkyl(CH$_2$)$_{0-6}$; 2-aminodihydrooxazol-4-yl(CH$_2$)$_{1-6}$; 2-aminodihydrooxazol-5-yl(CH$_2$)$_{1-6}$; (2-amino-5-methyl-4,5-dihydro-1,3-oxazol-5-yl)methyl; aminophenyl; 4-aminotetrahydropyran-4-yl(CH$_2$)$_{1-6}$; azetidin-2-yl(CH$_2$)$_{1-6}$; azetidin-3-yl(CH$_2$)$_{0-6}$; azetidinylcarbonyl; C$_{1-6}$alkoxy(CH$_2$)$_{2-6}$; C$_{1-6}$alkoxy(CH$_2$)$_{2-6}$amino(CH$_2$)$_{2-6}$; C$_{1-6}$alkyl; C$_{1-6}$alkylamino(CH$_2$)$_{2-6}$; C$_{1-6}$alkylaminocarbonyl(CH$_2$)$_{0-6}$; C$_{1-6}$alkylaminooxetanyl(CH$_2$)$_{1-6}$; C$_{1-6}$alkylcarbonyl; C$_{1-6}$alkylcarbonylamino(CH$_2$)$_{2-6}$; C$_{1-6}$alkylcarbonylamino(CH$_2$)$_{1-6}$oxetanyl(CH$_2$)$_{0-6}$; C$_{1-6}$alkylsulfinyl(CH$_2$)$_{2-6}$; C$_{1-6}$alkylsulfonyl; carboxy(CH$_2$)$_{1-6}$; cyano(CH$_2$)$_{1-6}$; diC$_{1-6}$alkylamino(CH$_2$)$_{2-6}$;diC$_{1-6}$alkylaminocarbonyl; difluoromethyl(CH$_2$)$_{1-6}$amino(CH$_2$)$_{2-6}$; hydrogen; hydroxy(CH$_2$)$_{2-10}$; hydroxy(CH$_2$)$_{2-6}$amino(CH$_2$)$_{2-6}$; hydroxy(CH$_2$)$_{1-6}$carbonyl; hydroxy(CH$_2$)$_{0-6}$oxetanyl(CH$_2$)$_{1-6}$; hydroxy(CH$_2$)$_{1-6}$oxetanyl(CH$_2$)$_{0-6}$; hydroxycycloalkyl; isoxazolyl; morpholin-2-yl(CH$_2$)$_{1-6}$; morpholin-4-yl(CH$_2$)$_{2-6}$; oxetanyl(CH$_2$)$_{0-6}$; N-oxetanylpyrrolidin-3-yl; oxo-pyrrolidinylcarbonyl; phenylaminocarbonyl; phenyl(CH$_2$)$_{0-6}$aminooxetanyl(CH$_2$)$_{1-6}$; phenylcarbonyl; piperazinyl(CH$_2$)$_{2-6}$; piperidin-1-yl(CH$_2$)$_{2-6}$; piperidin-2-yl(CH$_2$)$_{1-6}$; piperidin-3-yl(CH$_2$)$_{0-6}$; piperidin-4-yl(CH$_2$)$_{0-6}$; piperidinylcarbonyl; pyrazinylcarbonyl; pyrazol-3-yl; pyridazinylcarbonyl; pyridinyl(CH$_2$)$_{0-6}$carbonyl; pyridinylamino(CH$_2$)$_{2-6}$; pyrrolidin-3-yl, unsubstituted or 4-substituted by halogen; pyrrolidin-4-yl, unsubstituted or 3-substituted by hydroxy or C$_{1-6}$alkoxy;pyrrolidin-2-yl(CH$_2$)$_{1-6}$; pyrrolidinylcarbonyl; tetrahydrofuran-3-yl; tetrahydropyran-4-yl; tetrazolyl(CH$_2$)$_{2-6}$; trifluoromethylcarbonylamino(CH$_2$)$_{1-6}$oxetanyl; trifluoromethylsulfonyl;

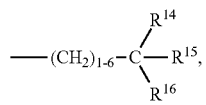

wherein R$^{14}$ is hydrogen, C$_{1-6}$alkyl or hydroxy(CH$_2$)$_{1-6}$; R$^{15}$ is hydroxy, C$_{1-6}$alkyl, hydroxy(CH$_2$)$_{1-6}$ or amino; and R$^{16}$ is C$_{1-6}$alkyl, trifluoromethyl, hydroxy(CH$_2$)$_{1-6}$, amino(CH$_2$)$_{1-6}$, aminocarboxy or carboxy(CH$_2$)$_{1-6}$;

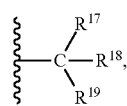

wherein R$^{17}$ is hydrogen, C$_{1-6}$alkyl or hydroxy(CH$_2$)$_{1-6}$; R$^{18}$ is hydroxy(CH$_2$)$_{1-6}$ or C$_{1-6}$alkyl; R$^{19}$ is hydroxy(CH$_2$)$_{1-6}$, amino(CH$_2$)$_{1-6}$, carboxy or aminocarboxy(CH$_2$)$_{0-6}$; or

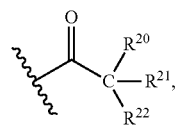

wherein R$^{20}$ is hydrogen or C$_{1-6}$alkyl; R$^{21}$ is C$_{1-6}$alkyl; R$^{22}$ is C$_{1-6}$alkoxy or amino;

R$^{12}$ and R$^{13}$, with the nitrogen atom to which they are attached, may form a pyrrolidinyl, piperazinyl, piperidinyl, morpholinyl, azetidinyl, diazepanyl or oxopyrrolidinyl ring; which may be unsubstituted, once or twice substituted by a group selected from halogen, C$_{1-6}$alkyl, C$_{1-6}$alkoxy, gemdimethyl, amino, aminocarbonyl, hydroxy, oxetanylamino, C$_{1-6}$alkylpiperazinyl, and amino(CH$_2$)$_{1-6}$;

R$^{12}$ and R$^{13}$, with the nitrogen atom to which they are attached may form a bridge ring or a spiral ring selected from 2-oxa-6-aza-spiro[3.4]octan-6-yl, 2-oxa-5,7-diazaspiro[3.4]octan-6-one-5-yl, (4aS,7aR)-hexahydropyrrolo[3,4-b][1,4]oxazin-6(2H)-yl, 4,5,6,6a-tetrahydro-3aH-pyrrolo[3,4-d][1,3]oxazol-5-yl, 2-aza-bicyclo[2.1.1]hexan-2-yl, and 3-aza-bicyclo[3.1.0]hexan-3-yl; which may be unsubstituted or further substituted by amino;

and pharmaceutically acceptable salt and stereoisomers thereof.

2. The compound according to claim 1 or a pharmaceutically acceptable salt thereof, wherein R$^1$ is hydrogen, halogen or C$_{1-6}$alkyl;
R$^2$ is hydrogen, halogen or C$_{1-6}$alkyl;
R$^3$ is hydrogen, halogen or C$_{1-6}$alkyl;
R$^4$ is hydrogen or C$_{1-6}$alkyl;
R$^5$ is hydrogen;
R$^6$ is hydrogen, halogen, hydroxy, C$_{1-6}$alkoxy, morpholinyl or 4-C$_{0-6}$alkylpiperazin-1-yl;
R$^7$ is hydrogen, halogen, C$_{1-6}$alkyl, C$_{1-6}$alkoxy, phenoxy or hydroxy(CH$_2$)$_{2-6}$—O—;
R$^8$ is hydrogen, halogen or C$_{1-6}$alkoxy;
R$^9$ is hydrogen or C$_{1-6}$alkyl;
R$^{10}$ is hydrogen;
A is nitrogen or —C—R$^{11}$, wherein R$^{11}$ is hydrogen, halogen, C$_{1-6}$ alkyl, cycloalkyl, C$_{1-6}$alkoxy, trifluoromethyl, trifluoromethoxy, pyridinyloxy, C$_{1-6}$alkoxy(CH$_2$)$_{1-6}$—O—, difluoromethoxy, cyano, nitro, amino, vinyl, acetylenyl, aminocarbonyl, hydroxy(CH$_2$)$_{2-6}$—O—, C$_{1-6}$alkylsulfinyl, hydroxy(CH$_2$)$_{1-6}$, deuteratedC$_{1-6}$ alkyl, carboxyl, alkoxycarbonyl, hydroxy, difluoromethyl, —CH(hydroxy)C$_{1-6}$alkyl or C$_{1-6}$alkylsulfanyl;
X is S, S=O, SO$_2$ or S(O)NH;
Y is —CH— or nitrogen;
Q is C$_{1-6}$alkyl, unsubstituted or once substituted by amino; amino(CH$_2$)$_{2-6}$aminosulfonyl; 2-amino-4,5-dihydro-1,3-oxazol-4-ylethyl; carboxy(CH$_2$)$_{1-6}$; phenylsulfonyl; piperidin-4-yl-carbonyl; 1H-pyrazol-3-yl; pyrrolidin-3-yloxy; piperidin-4-yloxy; amino(CH$_2$)$_{2-6}$—O—; or
NR$^{12}$R$^{13}$, wherein one of R$^{12}$ and R$^{13}$ is hydrogen, C$_{1-6}$alkyl or hydroxy(CH$_2$)$_{2-6}$, and the other one is {1-[amino(CH$_2$)$_{0-6}$]-3,3-difluorocyclobutyl}(CH$_2$)$_{1-6}$; (S—C$_{1-6}$alkylsulfonimidoyl)(CH$_2$)$_{2-6}$; {3-[amino(CH$_2$)$_{0-6}$]tetrahydrofuran-3-yl}(CH$_2$)$_{1-6}$; (2-amino-5-methyl-4,5-dihydro-1,3-oxazol-5-yl)methyl; 3-aminomethyl-1,1-dioxidothietan-3-ylmethyl; 3-(aminomethyl)thietan-3-ylmethyl; (1,1-dioxidothiomorpholin-4-yl)ethyl; C$_{0-6}$alkyl(oxetanyl)N(CH$_2$)$_{2-6}$; 4,5-dihydro-1H-imidazol-2-yl; amino(CH$_2$)$_{2-6}$—O—(CH$_2$)$_{2-6}$; amino(CH$_2$)$_{2-10}$; amino(CH$_2$)$_{0-6}$carbonyl(CH$_2$)$_{0-6}$; amino(CH$_2$)$_{1-6}$difluoromethyl(CH$_2$)$_{1-6}$; amino(CH$_2$)$_{1-6}$difluoromethyldifluoromethyl(CH$_2$)$_{1-6}$; amino(CH$_2$)$_{1-6}$fluoromethyl(CH$_2$)$_{1-6}$; amino(CH$_2$)$_{1-6}$oxetanyl(CH$_2$)$_{0-6}$; amino(CH$_2$)$_{0-6}$oxetanyl(CH$_2$)$_{1-6}$; amino(CH$_2$)$_{2-6}$sulfanyl(CH$_2$)$_{2-6}$; amino(CH$_2$)$_{2-6}$sulfonyl(CH$_2$)$_{2-6}$; 1-aminocyclobutylmethyl; 2-aminocyclohexyl; 3-aminocyclohexyl; 4-aminocyclohexyl; 1-aminocyclohexylmethyl; 2-aminocyclopentyl;

1-aminocyclopropylethyl; 1-aminocyclopropylmethyl; (2-amino-4,5-dihydro-oxazol-5-yl)($CH_2$)$_{1-6}$, (2-amino-4,5-dihydro-oxazol-4-yl)($CH_2$)$_{1-6}$; aminophenyl; 4-aminotetrahydropyran-4-yl($CH_2$)$_{1-6}$; azetidin-2-yl ($CH_2$)$_{1-6}$; azetidin-3-yl($CH_2$)$_{0-6}$; azetidin-3-ylcarbonyl; $C_{1-6}$alkoxy($CH_2$)$_{2-6}$; $C_{1-6}$alkoxy($CH_2$)$_{2-6}$amino ($CH_2$)$_{2-6}$; $C_{1-6}$alkyl; $C_{1-6}$alkylamino($CH_2$)$_{2-6}$; $C_{1-6}$alkylaminooxetanyl($CH_2$)$_{1-6}$; $C_{1-6}$alkylcarbonyl; $C_{1-6}$alkylaminocarbonyl($CH_2$)$_{0-6}$; $C_{1-6}$alkylcarbonylamino ($CH_2$)$_{2-6}$; $C_{1-6}$alkylcarbonylamino($CH_2$)$_{1-6}$oxetanyl ($CH_2$)$_{0-6}$; $C_{1-6}$alkylsulfinyl($CH_2$)$_{2-6}$; $C_{1-6}$alkylsulfonyl; carboxy($CH_2$)$_{1-6}$; cyano($CH_2$)$_{1-6}$; di$C_{1-6}$alkylamino ($CH_2$)$_{2-6}$; di$C_{1-6}$alkylaminocarbonyl; difluoromethyl ($CH_2$)$_{1-6}$amino($CH_2$)$_{2-6}$; hydrogen; hydroxy($CH_2$)$_{2-10}$; hydroxy($CH_2$)$_{2-6}$amino($CH_2$)$_{2-6}$; hydroxy($CH_2$)$_{1-6}$carbonyl; hydroxy($CH_2$)$_{1-6}$oxetanyl($CH_2$)$_{0-6}$; hydroxy ($CH_2$)$_{0-6}$oxetanyl($CH_2$)$_{1-6}$; 4-hydroxycyclohexyl; isoxazol-3-yl; morpholin-2-yl($CH_2$)$_{1-6}$; morpholin-4-yl ($CH_2$)$_{2-6}$; 2-oxa-6-aza-spiro[3.4]oct-8-yl; oxetanyl ($CH_2$)$_{0-6}$; N-oxetanylpyrrolidin-3-yl; oxopyrrolidinylcarbonyl; phenylaminocarbonyl; phenyl ($CH_2$)$_{0-6}$aminooxetanyl($CH_2$)$_{1-6}$; phenylcarbonyl; piperazinyl($CH_2$)$_{2-6}$; piperidin-1-yl($CH_2$)$_{2-6}$; piperidin-2-yl($CH_2$)$_{1-6}$; piperidin-3-yl($CH_2$)$_{0-6}$; piperidin-4-yl ($CH_2$)$_{0-6}$; piperidinylcarbonyl; pyrazinylcarbonyl; pyrazol-3-yl; pyridazinylcarbonyl; pyridinyl($CH_2$)$_{0-6}$ carbonyl; pyridinylamino($CH_2$)$_{2-6}$; pyrrolidin-3-yl, unsubstituted or 4-substituted by halogen; pyrrolidin-4-yl, unsubstituted or 3-substituted by hydroxy or $C_{1-6}$alkoxy; pyrrolidin-2-yl($CH_2$)$_{1-6}$; pyrrolidinylcarbonyl; tetrahydrofuran-3-yl; tetrahydropyran-4-yl; tetrazolyl($CH_2$)$_{2-6}$; trifluoromethylcarbonylamino($CH_2$)$_{1-6}$ oxetanyl; trifluoromethylsulfonyl;

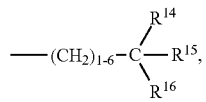

wherein $R^{14}$ is hydrogen or $C_{1-6}$alkyl; $R^{15}$ is hydroxy, $C_{1-6}$alkyl or amino; and $R^{16}$ is $C_{1-6}$alkyl, trifluoromethyl, hydroxy($CH_2$)$_{1-6}$, amino($CH_2$)$_{1-6}$, aminocarbonyl or carboxy($CH_2$)$_{1-6}$;

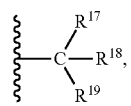

wherein $R^{17}$ is hydrogen, $C_{1-6}$alkyl or hydroxy($CH_2$)$_{1-6}$; $R^{18}$ is hydroxy($CH_2$)$_{1-6}$ or $C_{1-6}$alkyl; $R^{19}$ is hydroxy ($CH_2$)$_{1-6}$, amino($CH_2$)$_{1-6}$, carboxy or aminocarbonyl ($CH_2$)$_{0-6}$; or

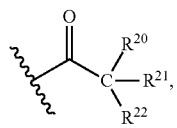

wherein $R^{20}$ is hydrogen or $C_{1-6}$alkyl; $R^{21}$ is $C_{1-6}$alkyl; $R^{22}$ is $C_{1-6}$alkoxy or amino;

$R^{12}$ and $R^{13}$, with the nitrogen atom to which they are attached, may form a pyrrolidinyl, piperazinyl, piperidinyl, morpholinyl, azetidinyl, diazepanyl or oxopyrrolidinyl ring; which may be unsubstituted, once or twice substituted by a group selected from halogen, $C_{1-6}$alkyl, $C_{1-6}$alkoxy, gemdimethyl, amino, aminocarbonyl, hydroxy, oxetanylamino, $C_{1-6}$alkylpiperazinyl, and amino($CH_2$)$_{1-6}$; or $R^{12}$ and $R^{13}$, with the nitrogen atom to which they are attached may form a bridge ring or a spiral ring selected from 2-oxa-6-aza-spiro[3.4]octan-6-yl, 2-oxa-5,7-diazaspiro[3.4]octan-6-one-5-yl, (4aS,7aR)-hexahydropyrrolo[3,4-b][1,4]oxazin-6(2H)-yl, 4,5,6,6a-tetrahydro-3aH-pyrrolo[3,4-d][1,3]oxazol-5-yl, 2-aza-bicyclo[2.1.1]hexan-2-yl and 3-aza-bicyclo[3.1.0]hexan-3-yl; which may be unsubstituted or further substituted by amino.

3. The compound according to claim 1 or a pharmaceutically acceptable salt thereof, wherein $R^1$, $R^2$ or $R^3$ are hydrogen, fluoro, chloro or methyl;

$R^4$ is hydrogen or methyl;

$R^5$ is hydrogen;

$R^6$ is hydrogen, fluoro, hydroxy, methoxy, morpholinyl or 4-(propan-2-yl)piperazin-1-yl;

$R^7$ is hydrogen, fluoro, chloro, methyl, methoxy, ethoxy, hydroxyethoxy or phenoxy;

$R^8$ is hydrogen, fluoro or methoxy;

$R^9$ is hydrogen or methyl;

$R^{10}$ is hydrogen;

A is nitrogen or —C—$R^{11}$, wherein $R^{11}$ is hydrogen, fluoro, chloro, bromo, methyl, ethyl, cyclopropyl, methoxy, trifluoromethyl, trifluoromethoxy, pyridinyloxy, methoxyethoxy, difluoromethoxy, cyano, nitro, amino, vinyl, acetylenyl, aminocarbonyl, hydroxyethoxy, methylsulfanyl, methylsulfinyl, hydroxymethyl, deuteratedmethyl, carboxyl, methoxycarbonyl, hydroxy, difluoromethyl, methylCH(hydroxy)- or methylsulfonyl;

X is S, S=O, $SO_2$ or S(O)NH;

Y is —CH— or nitrogen;

Q is 2-amino-4,5-dihydro-1,3-oxazol-4-ylethyl; aminoethoxy; aminoethylaminosulfonyl; aminopropyl; carboxyethyl; methyl; phenylsulfonyl; piperidin-4-yl-carbonyl; piperidin-4-yloxy; 1H-pyrazol-3-yl; pyrrolidin-3-yloxy; or NR$^{12}$R$^{13}$, wherein one of $R^{12}$ and $R^{13}$ is hydrogen, methyl or hydroxyethyl, and the other one is aminobutyl; aminocarbonylethyl; aminocarbonylmethyl; 1-aminocyclobutylmethyl; 2-aminocyclohexyl; 3-aminocyclohexyl; 4-aminocyclohexyl; 1-aminocyclohexylmethyl; 2-aminocyclopentyl; 1-aminocyclopropylethyl; 1-aminocyclopropylmethyl; aminodecyl; (2-amino-4,5-dihydro-oxazol-5-yl)methyl; (2-amino-4,5-dihydro-oxazol-4-yl)methyl; aminoethoxyethyl; aminoethyl; aminoethylcarbonyl; aminoethylfluoromethylmethyl; aminoethylsulfanylethyl; aminoethylsulfonylethyl; aminoheptyl; aminohexyl; aminomethylcarbonyl; (1-aminomethyl-3,3-difluorocyclobutyl)methyl; aminomethyldifluoromethyldifluoromethylmethyl; aminomethyldifluoromethylmethyl; (2-amino-5-methyl-4,5-dihydro-1,3-oxazol-5-yl) methyl; 3-aminomethyl-1,1-dioxidothietan-3-ylmethyl; aminomethylfluoromethylethyl; aminomethylfluoromethylmethyl; aminomethyloxetanyl; aminomethyloxetanylmethyl; 3-(aminomethyl)thietan-3-ylmethyl; aminononyl; aminooctyl; aminooxetanylethyl; aminooxetanylmethyl; aminopentyl; aminophenyl; aminopropyl; 4-aminotetrahydropyran-4-ylmethyl; 3-aminotetrahydrofuran-3-ylmethyl;azetidin-3-yl; azetidin- 3-ylcarbonyl; azetidin-2-ylmethyl; azetidin-3-ylmethyl; carboxyethyl; carboxymethyl; cyanoethyl; difluoromethylmethylaminoethyl; 4,5-dihydro-1H-imidazol-2-yl; dimethylaminocarbonyl; dimethylaminoethyl; (1,1-dioxidothiomorpholin-4-yl)ethyl; ethyl; ethylaminocarbonyl; ethylaminoethyl; ethylaminooxetanylmethyl; ethyl(oxetanyl)aminoethyl; hydrogen; 4-hydroxycyclohexyl; hydroxyethyl; hydroxyethylaminoethyl; hydroxyethyloxetanyl; hydroxymethylcarbonyl; hydroxymethyloxetanylmethyl; hydroxynonyl; hydroxypropyl; isoxazol-3-yl; methoxyethyl; methoxyethylaminoethyl; methyl; methylaminocarbonylmethyl; methylaminoethyl; methylcarbonyl; methylcarbonylaminoethyl; methylcarbonylaminomethyloxetanylmethyl; methylcarbonylaminopropyl; methylsulfinylethyl; 2-(S-methylsulfonimidoyl)ethyl; methylsulfonyl; morpholin-4-ylethyl; morpholin-2-ylmethyl; 2-oxa-6-aza-spiro[3.4]oct-8-yl; oxetanyl; oxetanylaminoethyl; oxetanylaminopropyl; oxetanylmethyl; N-oxetanylpyrrolidin-3-yl; oxo-pyrrolidin-4-ylcarbonyl; phenylaminocarbonyl; phenylcarbonyl; phenylmethylaminooxetanylmethyl; piperazin-1-ylethyl; piperidin-2-ylcarbonyl; piperidin-3-ylcarbonyl; piperidin-4-ylcarbonyl; piperidin-3-yl; piperidin-4-yl; piperidin-1-ylethyl; piperidin-2-ylmethyl; pyrazin-2-ylcarbonyl; pyrazol-3-yl; pyridazin-3-ylcarbonyl; pyridine-2-ylmethylcarbonyl; pyridine-2-ylaminoethyl; pyridine-2-ylcarbonyl; pyridine-3-ylcarbonyl; pyrrolidin-3-yl, unsubstituted or 4-substituted by fluoro; pyrrolidin-4-yl, unsubstituted or 3-substituted by hydroxy or methoxy; pyrrolidin-2-ylmethyl; pyrrolidin-2-ylcarbonyl; tetrahydrofuran-3-yl; tetrahydropyran-4-yl; tetrazolylethyl; trifluoromethylsulfonyl; trifluoromethylcarbonylaminomethyloxetanyl;

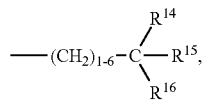

wherein $R^{14}$ is hydrogen or methyl; $R^{15}$ is hydroxy, methyl or amino; and $R^{16}$ is methyl, trifluoromethyl, hydroxymethyl, hydroxyethyl, aminomethyl, aminocarbonyl or carboxymethyl;

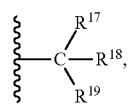

wherein $R^{17}$ is hydrogen, methyl or hydroxymethyl; $R^{18}$ is hydroxymethyl or methyl; $R^{19}$ is hydroxymethyl, aminomethyl, carboxy, aminocarbonyl or aminocarbonylmethyl; or

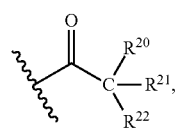

wherein $R^{20}$ is hydrogen or methyl; $R^{21}$ is methyl or ethyl; $R^{22}$ is methoxy or amino;

$R^{12}$ and $R^{13}$, with the nitrogen atom to which they are attached, may form a pyrrolidinyl, piperazinyl, piperidinyl, morpholinyl, azetidinyl, diazepanyl or oxopyrrolidinyl ring; which may be unsubstituted, once or twice substituted by a group selected from fluoro, methyl, methoxy, gemdimethyl, amino, aminocarbonyl, hydroxy, oxetanylamino, methylpiperazinyl and aminomethyl; or $R^{12}$ and $R^{13}$, with the nitrogen atom to which they are attached may form a bridge ring or a spiral ring selected from 2-oxa-6-aza-spiro[3.4]octan-6-yl, 2-oxa-5,7-diazaspiro[3.4]octan-6-one-5-yl, (4aS,7aR)-hexahydropyrrolo[3,4-b][1,4]oxazin-6(2H)-yl, 4,5,6,6a-tetrahydro-3aH-pyrrolo[3,4-d][1,3]oxazol-5-yl, 2-aza-bicyclo[2.1.1]hexan-2-yl or 3-aza-bicyclo[3.1.0]hexan-3-yl; which may be unsubstituted or further substituted by amino.

4. The compound according to any one of claim 1 or a pharmaceutically acceptable salt thereof, wherein
$R^1$, $R^2$, $R^3$, $R^4$, $R^5$, $R^6$, $R^7$, $R^8$, $R^9$ and $R^{10}$ are hydrogen;
A is —C—$R^{11}$, wherein $R^{11}$ is hydrogen, halogen or $C_{1-6}$alkyl;
X is S;
Y is —CH— or nitrogen;
Q is $NR^{12}R^{13}$, wherein one of $R^{12}$ and $R^{13}$ is hydrogen, and the other one is amino$(CH_2)_{2-6}$; amino$(CH_2)_{1-6}$difluoromethyl$(CH_2)_{1-6}$; amino$(CH_2)_{0-6}$oxetanyl$(CH_2)_{1-6}$ or hydrogen; or
$R^{12}$ and $R^{13}$, with the nitrogen atom to which they are attached, may form a pyrrolidinyl ring, which may be once substituted by amino.

5. The compound according to claim 4 or a pharmaceutically acceptable salt thereof, wherein $R^1$, $R^2$, $R^3$, $R^4$, $R^5$, $R^6$, $R^7$, $R^8$, $R^9$ and $R^{10}$ are hydrogen;
A is —C—$R^{11}$, wherein $R^{11}$ is hydrogen, chloro or methyl;
Q is $NR^{12}R^{13}$, wherein one of $R^{12}$ and $R^{13}$ is hydrogen, and the other one is aminoethyl; aminomethyldifluoromethylmethyl; aminomethyloxetanylmethyl; aminooxetanylmethyl or hydrogen; or
$R^{12}$ and $R^{13}$, with the nitrogen atom to which they are attached, may form a pyrrolidinyl ring, which may be once substituted by amino.

6. The compound according to any one of claim 1 or a pharmaceutically acceptable salt thereof, wherein
$R^1$, $R^2$, $R^3$, $R^4$, $R^5$, $R^6$, $R^7$, $R^8$, $R^9$ and $R^{10}$ are hydrogen;
A is —C—$R^{11}$, wherein $R^{11}$ is hydrogen, halogen, $C_{1-6}$alkyl, hydroxy$(CH_2)_{1-6}$, deuteratedmethyl or carboxyl;
X is S=O;
Y is —CH— or nitrogen;
Q is $NR^{12}R^{13}$, wherein one of $R^{12}$ and $R^{13}$ is hydrogen; and the other one is amino$(CH_2)_{2-6}$; amino$(CH_2)_{1-6}$difluoromethyl$(CH_2)_{1-6}$; amino$(CH_2)_{1-6}$fluoromethyl$(CH_2)_{1-6}$; amino$(CH_2)_{1-6}$oxetanyl; amino$(CH_2)_{1-6}$oxetanyl$(CH_2)_{1-6}$; aminooxetanyl$(CH_2)_{1-6}$; hydroxy$(CH_2)_{2-10}$; phenyl$(CH_2)_{1-6}$aminooxetanyl$(CH_2)_{1-6}$; pyrrolidin-3-yl, 4-substituted by halogen; or

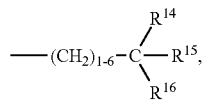

wherein $R^{14}$ is hydrogen, $R^{15}$ is hydroxy, and $R^{16}$ is hydroxy$(CH_2)_{1-6}$; or $R^{12}$ and $R^{13}$, with the nitrogen atom to which they are attached, may form a pyrrolidinyl ring, which may be once or twice substituted by a group selected from halogen, amino and hydroxyl.

7. The compound according to claim 6 or a pharmaceutically acceptable salt thereof, wherein $R^1$, $R^2$, $R^3$, $R^4$, $R^5$, $R^6$, $R^7$, $R^8$, $R^9$ and $R^{10}$ are hydrogen;

A is —C—$R^{11}$, wherein $R^{11}$ is hydrogen, chloro, methyl, hydroxymethyl, deuteratedmethyl or carboxyl;

Q is $NR^{12}R^{13}$, wherein one of $R^{12}$ and $R^{13}$ is hydrogen, and the other one is aminoethyl; aminomethyldifluoromethylmethyl; aminomethylfluoromethylmethyl; aminomethyloxetanyl; aminomethyloxetanylmethyl; aminooxetanylmethyl; aminopropyl; hydroxyethyl; phenylmethylaminooxetanylmethyl; pyrrolidin-3-yl, 4-substituted by fluoro; or

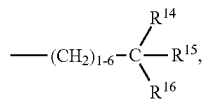

wherein $R^{14}$ is hydrogen, $R^{15}$ is hydroxy, and $R^{16}$ is hydroxymethyl; or $R^{12}$ and $R^{13}$, with the nitrogen atom to which they are attached, may form a pyrrolidinyl ring, which may be once or twice substituted by a group selected from fluoro, amino and hydroxyl.

8. The compound according to any one of claim 1 or a pharmaceutically acceptable salt thereof, wherein $R^1$, $R^2$, and $R^3$ are hydrogen, halogen or $C_{1-6}$alkyl;

$R^4$ is hydrogen or $C_{1-6}$alkyl;

$R^5$ is hydrogen;

$R^6$ is hydrogen, halogen, hydroxy, $C_{1-6}$alkoxy, morpholinyl or 4-(propan-2-yl)piperazin-1-yl;

$R^7$ is hydrogen, halogen, $C_{1-6}$alkyl, $C_{1-6}$alkoxy, hydroxy$(CH_2)_{2-6}$—O—, or phenoxy;

$R^8$ is hydrogen, halogen or $C_{1-6}$alkoxy;

$R^9$ is hydrogen or $C_{1-6}$alkyl;

$R^{10}$ is hydrogen;

A is nitrogen or —C—$R^{11}$, wherein $R^{11}$ is hydrogen, halogen, $C_{1-6}$alkyl, $C_{1-6}$alkoxy, trifluoromethyl, trifluoromethoxy, pyridinyloxy, $C_{1-6}$alkoxy$(CH_2)_{1-6}$—O—, difluoromethoxy, nitro, cycloalkyl, cyano, amino, vinyl, acetylenyl, aminocarbonyl, hydroxy$(CH_2)_{2-6}$—O—, $C_{1-6}$alkylsulfanyl, $C_{1-6}$alkylsulfinyl, hydroxy$(CH_2)_{1-6}$, deuteratedmethyl, carboxyl, $C_{1-6}$alkoxycarbonyl, hydroxy, difluoromethyl or methylCH(hydroxy)-;

X is $SO_2$;

Y is —CH— or nitrogen;

Q is 2-amino-4,5-dihydro-1,3-oxazol-4-ylethyl; amino$(CH_2)_{2-6}$—O—; amino$(CH_2)_{2-6}$aminosulfonyl; $C_{1-6}$alkyl, unsubstituted or once substituted by amino; carboxy$(CH_2)_{1-6}$; phenylsulfonyl; piperidin-4-yl-carbonyl; piperidin-4-yloxy; 1H-pyrazol-3-yl; pyrrolidin-3-yloxy; or $NR^{12}R^{13}$, wherein one of $R^{12}$ and $R^{13}$ is hydrogen, $C_{1-6}$alkyl or hydroxy$(CH_2)_{2-6}$; and the other one is {1-[amino$(CH_2)_{0-6}$]-3,3 difluorocyclobutyl}$(CH_2)_{1-6}$; (S—$C_{1-6}$alkylsulfonimidoyl)$(CH_2)_{2-6}$; 3-aminotetrahydrofuran-3-yl$(CH_2)_{1-6}$; (2-amino-5-methyl-4,5-dihydro-1,3-oxazol-5-yl)methyl; 3-aminomethyl-1,1-dioxidothietan-3-ylmethyl; 3-(aminomethyl)thietan-3-ylmethyl; (1,1-dioxidothiomorpholin-4-yl)ethyl; $C_{0-6}$alkyl(oxetanyl)N$(CH_2)_{2-6}$; 4,5-dihydro-1H-imidazol-2-yl; amino$(CH_2)_{2-6}$—O—$(CH_2)_{2-6}$; amino$(CH_2)_{2-10}$; amino$(CH_2)_{1-6}$carbonyl; aminocarbonyl$(CH_2)_{1-6}$; amino$(CH_2)_{1-6}$difluoromethyl$(CH_2)_{1-6}$; amino$(CH_2)_{1-6}$difluoromethyldifluoromethyl$(CH_2)_{1-6}$; amino$(CH_2)_{1-6}$fluoromethyl$(CH_2)_{1-6}$; amino$(CH_2)_{1-6}$oxetanyl$(CH_2)_{0-6}$; amino$(CH_2)_{0-6}$oxetanyl$(CH_2)_{1-6}$; amino$(CH_2)_{2-6}$sulfanyl$(CH_2)_{2-6}$; amino$(CH_2)_{2-6}$sulfonyl$(CH_2)_{2-6}$; 1-aminocyclobutylmethyl; 2-aminocyclohexyl; 3-aminocyclohexyl; 4-aminocyclohexyl; 1-aminocyclohexylmethyl; 2-aminocyclopentyl; 1-aminocyclopropylethyl; 1-aminocyclopropylmethyl; (2-amino-4,5-dihydro-oxazol-5-yl)$(CH_2)_{1-6}$; (2-amino-4,5-dihydro-oxazol-4-yl)$(CH_2)_{1-6}$; aminophenyl; 4-aminotetrahydropyran-4-yl$(CH_2)_{1-6}$; azetidin-2-yl$(CH_2)_{1-6}$; azetidin-3-yl$(CH_2)_{0-6}$; azetidin-3-ylcarbonyl; $C_{1-6}$alkoxy$(CH_2)_{2-6}$; $C_{1-6}$alkoxy$(CH_2)_{2-6}$amino$(CH_2)_{2-6}$; $C_{1-6}$alkyl; $C_{1-6}$alkylamino$(CH_2)_{2-6}$; $C_{1-6}$alkylaminooxetanyl$(CH_2)_{1-6}$; $C_{1-6}$alkylcarbonyl; $C_{1-6}$alkylcarbonylamino$(CH_2)_{2-6}$; $C_{1-6}$alkylcarbonylamino$(CH_2)_{1-6}$oxetanyl$(CH_2)_{0-6}$; $C_{1-6}$alkylsulfinyl$(CH_2)_{2-6}$; $C_{1-6}$alkylsulfonyl; carboxy$(CH_2)_{1-6}$; cyano$(CH_2)_{1-6}$; $C_{1-6}$alkylaminocarbonyl$(CH_2)_{0-6}$; di$C_{1-6}$alkylamino$(CH_2)_{2-6}$; di$C_{1-6}$alkylaminocarbonyl; difluoromethyl$(CH_2)_{1-6}$amino$(CH_2)_{2-6}$; hydrogen; hydroxy$(CH_2)_{2-10}$; hydroxy$(CH_2)_{2-6}$amino$(CH_2)_{2-6}$; hydroxy$(CH_2)_{1-6}$carbonyl; hydroxy$(CH_2)_{1-6}$oxetanyl$(CH_2)_{0-6}$; 4-hydroxycyclohexyl; isoxazol-3-yl; morpholin-2-yl$(CH_2)_{1-6}$; morpholin-4-yl$(CH_2)_{2-6}$; 2-oxa-6-aza-spiro[3.4]oct-8-yl; oxetanyl$(CH_2)_{0-6}$; N-oxetanylpyrrolidin-3-yl; oxopyrrolidin-4-ylcarbonyl; phenylaminocarbonyl; phenyl$(CH_2)_{1-6}$aminooxetanyl$(CH_2)_{1-6}$; phenylcarbonyl; piperazinyl$(CH_2)_{2-6}$; piperidin-1-yl$(CH_2)_{2-6}$; piperidin-2-yl$(CH_2)_{1-6}$; piperidin-3-yl$(CH_2)_{0-6}$; piperidin-4-yl$(CH_2)_{0-6}$; piperidin-2-ylcarbonyl; piperidin-3-ylcarbonyl; piperidin-4-ylcarbonyl; pyrazin-2-ylcarbonyl; pyrazol-3-yl; pyridazin-3-ylcarbonyl; pyridine-2-yl$(CH_2)_{0-6}$carbonyl; pyridine-3-yl$(CH_2)_{0-6}$carbonyl; pyridine-2-ylamino$(CH_2)_{2-6}$; pyrrolidin-3-yl, unsubstituted or 4-substituted by halogen; pyrrolidin-4-yl, unsubstituted or 3-substituted by hydroxy or $C_{1-6}$alkoxy; pyrrolidin-2-yl$(CH_2)_{1-6}$; pyrrolidin-2-ylcarbonyl; tetrahydrofuran-3-yl; tetrahydropyran-4-yl; tetrazolyl$(CH_2)_{2-6}$; trifluoromethylcarbonylamino$(CH_2)_{1-6}$oxetanyl; trifluoromethylsulfonyl;

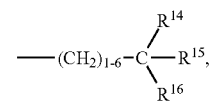

wherein $R^{14}$ is hydrogen or $C_{1-6}$alkyl; $R^{15}$ is hydroxy, $C_{1-6}$alkyl or amino; and $R^{16}$ is $C_{1-6}$alkyl, trifluoromethyl, hydroxy$(CH_2)_{1-6}$, amino$(CH_2)_{1-6}$, aminocarbonyl or carboxy$(CH_2)_{1-6}$;

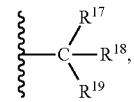

wherein $R^{17}$ is hydrogen, $C_{1-6}$alkyl or hydroxy$(CH_2)_{1-6}$; $R^{18}$ is hydroxy$(CH_2)_{1-6}$ or $C_{1-6}$alkyl; $R^{19}$ is hydroxy$(CH_2)_{1-6}$, amino$(CH_2)_{1-6}$, carboxy or aminocarbonyl$(CH_2)_{0-6}$; or

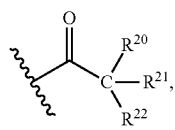

wherein $R^{20}$ is hydrogen or $C_{1-6}$alkyl; $R^{21}$ is $C_{1-6}$alkyl; $R^{22}$ is $C_{1-6}$alkoxy or amino;

$R^{12}$ and $R^{13}$, with the nitrogen atom to which they are attached, may form a pyrrolidinyl, piperazinyl, piperidinyl, morpholinyl, azetidinyl, diazepanyl or oxopyrrolidinyl ring; which may be unsubstituted, once or twice substituted by a group selected from halogen, $C_{1-6}$alkyl, $C_{1-6}$alkoxy, gemdimethyl, amino, aminocarbonyl, hydroxy, oxetanylamino, $C_{1-6}$alkylpiperazinyl and amino$(CH_2)_{1-6}$; or $R^{12}$ and $R^{13}$, with the nitrogen atom to which they are attached may form a bridge ring or a spiral ring selected from 2-oxa-6-aza-spiro[3.4]octan-6-yl, 2-oxa-5,7-diazaspiro[3.4]octan-6-one-5-yl, (4aS,7aR)-hexahydropyrrolo[3,4-b][1,4]oxazin-6(2H)-yl, 4,5,6,6a-tetrahydro-3aH-pyrrolo[3,4-d][1,3]oxazol-5-yl, 2-aza-bicyclo[2.1.1]hexan-2-yl or 3-aza-bicyclo[3.1.0]hexan-3-yl; which may be unsubstituted or further substituted by amino.

9. The compound according to claim 8 or a pharmaceutically acceptable salt thereof, wherein $R^1$, $R^2$, and $R^3$ are hydrogen, fluoro, chloro or methyl;
$R^4$ is hydrogen or methyl;
$R^5$ is hydrogen;
$R^6$ is hydrogen, fluoro, hydroxy, methoxy, morpholinyl or 4-(propan-2-yl)piperazin-1-yl;
$R^7$ is hydrogen, fluoro, chloro, methyl, methoxy, hydroxyethoxy, or phenoxy;
$R^8$ is hydrogen, fluoro or methoxy;
$R^9$ is hydrogen or methyl;
$R^{10}$ is hydrogen;
A is nitrogen or —C—$R^{11}$, wherein $R^{11}$ is hydrogen, fluoro, chloro, bromo, methyl, ethyl, methoxy, trifluoromethyl, trifluoromethoxy, pyridinyloxy, methoxyethoxy, difluoromethoxy, nitro, cyclopropyl, cyano, amino, vinyl, acetylenyl, aminocarbonyl, hydroxyethoxy, methylsulfanyl, methylsulfinyl, hydroxymethyl, deuteratedmethyl, carboxyl, methoxycarbonyl, hydroxy, difluoromethyl or methylCH(hydroxy)-;
Y is —CH— or nitrogen;
Q is 2-amino-4,5-dihydro-1,3-oxazol-4-ylethyl; aminoethoxy; aminoethylaminosulfonyl; aminopropyl; carboxyethyl; methyl; phenylsulfonyl; piperidin-4-yl-carbonyl; piperidin-4-yloxy; 1H-pyrazol-3-yl; pyrrolidin-3-yloxy; or
NR$^{12}$R$^{13}$, wherein one of $R^{12}$ and $R^{13}$ is hydrogen, methyl or hydroxyethyl, and the other one is aminobutyl; aminocarbonylethyl; aminocarbonylmethyl; 1-aminocyclobutylmethyl; 2-aminocyclohexyl; 3-aminocyclohexyl; 4-aminocyclohexyl; 1-aminocyclohexylmethyl; 2-aminocyclopentyl; 1-aminocyclopropylethyl; 1-aminocyclopropylmethyl; aminodecyl; (2-amino-4,5-dihydro-oxazol-5-yl)methyl; (2-amino-4,5-dihydro-oxazol-4-yl)methyl; aminoethoxyethyl; aminoethyl; aminoethylcarbonyl; aminoethylfluoromethylmethyl; aminoethylsulfanylethyl; aminoethylsulfonylethyl; aminoheptyl; aminohexyl; aminomethylcarbonyl; (1-aminomethyl-3,3-difluorocyclobutyl)methyl; aminomethyldifluoromethyldifluoromethylmethyl; aminomethyldifluoromethylmethyl; (2-amino-5-methyl-4,5-dihydro-1,3-oxazol-5-yl)methyl; 3-aminomethyl-1,1-dioxidothietan-3-ylmethyl; aminomethylfluoromethylethyl; aminomethylfluoromethylmethyl; aminomethyloxetanyl; aminomethyloxetanylmethyl; 3-(aminomethyl)thietan-3-ylmethyl; aminononyl; aminooctyl; aminooxetanylethyl; aminooxetanylmethyl; aminopentyl; aminophenyl; aminopropyl; 4-aminotetrahydropyran-4-ylmethyl; 3-aminotetrahydrofuran-3-ylmethyl; azetidin-3-yl; azetidin-3-ylcarbonyl; azetidin-2-ylmethyl; azetidin-3-ylmethyl; carboxyethyl; carboxymethyl; cyanoethyl; difluoromethylmethylaminoethyl; 4,5-dihydro-1H-imidazol-2-yl; dimethylaminocarbonyl; dimethylaminoethyl; (1,1-dioxidothiomorpholin-4-yl)ethyl; ethyl; ethylaminocarbonyl; ethylaminoethyl; ethylaminooxetanylmethyl; ethyl (oxetanyl)aminoethyl; hydrogen; 4-hydroxycyclohexyl; hydroxyethyl; hydroxyethylaminoethyl; hydroxyethyloxetanyl; hydroxymethylcarbonyl; hydroxymethyloxetanylmethyl; hydroxynonyl; hydroxypropyl; isoxazol-3-yl; methoxyethyl; methoxyethylaminoethyl; methyl; methylaminocarbonylmethyl; methylaminoethyl; methylcarbonyl; methylcarbonylaminoethyl; methylcarbonylaminomethyloxetanylmethyl; methylcarbonylaminopropyl; methylsulfinylethyl; 2-(S-methylsulfonimidoyl)ethyl; methylsulfonyl; morpholin-4-ylethyl; morpholin-2-ylmethyl; 2-oxa-6-aza-spiro[3.4]oct-8-yl; oxetanyl; oxetanylaminoethyl; oxetanylaminopropyl; oxetanylmethyl; N-oxetanylpyrrolidin-3-yl; oxo-pyrrolidin-4-ylcarbonyl; phenylaminocarbonyl; phenylcarbonyl; phenylmethylaminooxetanylmethyl; piperazin-1-ylethyl; piperidin-2-ylcarbonyl; piperidin-3-ylcarbonyl; piperidin-4-ylcarbonyl; piperidine-3-yl; piperidine-4-yl; piperidin-1-ylethyl; piperidin-2-ylmethyl; pyrazin-2-ylcarbonyl; pyrazol-3-yl; pyridazin-3-ylcarbonyl; pyridine-2-ylmethylcarbonyl; pyridine-2-ylaminoethyl; pyridine-2-ylcarbonyl; pyridine-3-ylcarbonyl; pyrrolidin-3-yl, unsubstituted or 4-substituted by fluoro; pyrrolidin-4-yl, unsubstituted or 3-substituted by hydroxy or methoxy; pyrrolidin-2-ylmethyl; pyrrolidin-2-ylcarbonyl; tetrahydrofuran-3-yl; tetrahydropyran-4-yl; tetrazolylethyl; trifluoromethylsulfonyl; trifluoromethylcarbonylaminomethyloxetanyl;

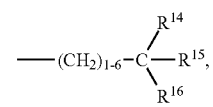

wherein $R^{14}$ is hydrogen or methyl; $R^{15}$ is hydroxy, methyl or amino; and $R^{16}$ is methyl, trifluoromethyl, hydroxymethyl, hydroxyethyl, aminomethyl, aminocarbonyl or carboxymethyl;

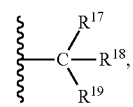

wherein $R^{17}$ is hydrogen, methyl or hydroxymethyl; $R^{18}$ is hydroxymethyl or methyl; $R^{19}$ is hydroxymethyl, aminomethyl, carboxy, aminocarbonyl or aminocarbonylmethyl; or

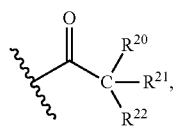

wherein R²⁰ is hydrogen or methyl; R²¹ is methyl or ethyl; R²² is methoxy or amino;

R¹² and R¹³, with the nitrogen atom to which they are attached, may form a pyrrolidinyl, piperazinyl, piperidinyl, morpholinyl, azetidinyl, diazepanyl or oxopyrrolidinyl ring; which may be unsubstituted, once or twice substituted by a group selected from fluoro, methyl, methoxy, gemdimethyl, amino, aminocarbonyl, hydroxy, oxetanylamino, methylpiperazinyl and aminomethyl; or R¹² and R¹³, with the nitrogen atom to which they are attached may form a bridge ring or a spiral ring selected from 2-oxa-6-aza-spiro[3.4]octan-6-yl, 2-oxa-5,7-diazaspiro[3.4]octan-6-one-5-yl, (4aS,7aR)-hexahydropyrrolo[3,4-b][1,4]oxazin-6(2H)-yl, 4,5,6,6a-tetrahydro-3aH-pyrrolo[3,4-d][1,3]oxazol-5-yl, 2-aza-bicyclo[2.1.1]hexan-2-yl or 3-aza-bicyclo[3.1.0]hexan-3-yl; which may be unsubstituted or further substituted by amino.

10. The compound according to any one of claim 1 or a pharmaceutically acceptable salt thereof, wherein
R¹, R², R³, R⁴, R⁵, R⁶, R⁷, R⁸, R⁹, and R¹⁰ are hydrogen;
A is —C—R¹¹, wherein R¹¹ is C₁₋₆alkyl;
X is S(O)NH;
Y is —CH—;
Q is NR¹²R¹³, wherein one of R¹² and R¹³ is hydrogen; and the other one is amino(CH₂)₂₋₆; or
R¹² and R¹³, with the nitrogen atom to which they are attached, may form a pyrrolidinyl ring, which may be twice substituted by a group selected from amino and hydroxyl.

11. The compound according to claim 10 or a pharmaceutically acceptable salt thereof, wherein
R¹, R², R³, R⁴, R⁵, R⁶, R⁷, R⁸, R⁹, and R¹⁰ are hydrogen;
A is —C—R¹¹, wherein R¹¹ is methyl;
Q is NR¹²R¹³, wherein one of R¹² and R¹³ is hydrogen; and the other one is aminoethyl; or
R¹² and R¹³, with the nitrogen atom to which they are attached, may form a pyrrolidinyl ring, which may be twice substituted by a group selected from amino and hydroxyl.

12. The compound according to claim 1 or a pharmaceutically acceptable salt thereof, selected from the group consisting of:
N-[(3-aminooxetan-3-yl)methyl]-2-(8-methoxy-1,1-dioxido-2,3-dihydro-1,4-benzothiazepin-4(5H)-yl)-6-methylquinolin-4-amine; N-[(3-aminooxetan-3-yl)methyl]-2-(8-fluoro-1,1-dioxido-2,3-dihydro-1,4-benzothiazepin-4(5H)-yl)-6-methylquinolin-4-amine; N-[(3-aminooxetan-3-yl)methyl]-2-(7-fluoro-1,1-dioxido-2,3-dihydro-1,4-benzothiazepin-4(5H)-yl)-6-methylquinolin-4-amine; N-[(3-aminooxetan-3-yl)methyl]-2-(9-fluoro-1,1-dioxido-2,3-dihydro-1,4-benzothiazepin-4(5H)-yl)-6-methylquinolin-4-amine; N-[(3-aminooxetan-3-yl)methyl]-2-(7-methoxy-1,1-dioxido-2,3-dihydro-1,4-benzothiazepin-4(5H)-yl)-6-methylquinolin-4-amine; N-[(3-aminooxetan-3-yl)methyl]-2-(8-chloro-1,1-dioxido-2,3-dihydro-1,4-benzothiazepin-4(5H)-yl)-6-methylquinolin-4-amine; N-[(3-aminooxetan-3-yl)methyl]-2-(7-methoxy-1,1-dioxido-2,3-dihydro-1,4-benzothiazepin-4(5H)-yl)quinolin-4-amine; N-[(3-aminotetrahydrofuran-3-yl)methyl]-2-(1,1-dioxido-2,3-dihydro-1,4-benzothiazepin-4(5H)-yl)-6-methylquinolin-4-amine; N-[(3-aminooxetan-3-yl)methyl]-2-(1,1-dioxido-2,3-dihydro-1,4-benzothiazepin-4(5H)-yl)-6-methylquinolin-4-amine; and N-[(4-aminotetrahydro-2H-pyran-4-yl)methyl]-2-(1,1-dioxido-2,3-dihydro-1,4-benzothiazepin-4(5H)-yl)-6-methylquinolin-4-amine.

13. The compound according to claim 1 or a pharmaceutically acceptable salt thereof, selected from the group consisting of:
N-[(3-aminooxetan-3-yl)methyl]-2-(8-methyl-1,1-dioxido-2,3-dihydro-1,4-benzothiazepin-4(5H)-yl)quinolin-4-amine; N-[(3-aminooxetan-3-yl)methyl]-6-methyl-2-(8-methyl-1,1-dioxido-2,3-dihydro-1,4-benzothiazepin-4(5H)-yl)quinolin-4-amine; 2-(1,1-dioxido-2,3-dihydro-1,4-benzothiazepin-4(5H)-yl)-6-methyl-N-(2-oxa-6-azaspiro[3.4]oct-8-yl)quinolin-4-amine; N-[2-(3-aminooxetan-3-yl)ethyl]-2-(1,1-dioxido-2,3-dihydro-1,4-benzothiazepin-4(5H)-yl)-6-methylquinolin-4-amine; N-[(3-aminooxetan-3-yl)methyl]-6-methyl-2-(5-methyl-1,1-dioxido-2,3-dihydro-1,4-benzothiazepin-4(5H)-yl)quinolin-4-amine; N-[(3-aminooxetan-3-yl)methyl]-2-(8-methoxy-1,1-dioxido-2,3-dihydro-1,4-benzothiazepin-4(5H)-yl)quinolin-4-amine; N-[(3-aminooxetan-3-yl)methyl]-2-(1,1-dioxido-2,3-dihydro-1,4-benzothiazepin-4(5H)-yl)-1,6-naphthyridin-4-amine; N-[(1-aminocyclohexyl)methyl]-2-(1,1-dioxido-2,3-dihydro-1,4-benzothiazepin-4(5H)-yl)-6-methylquinolin-4-amine; N-{[3-(aminomethyl)oxetan-3-yl]methyl}-2-(8-fluoro-1,1-dioxido-2,3-dihydro-1,4-benzothiazepin-4(5H)-yl)-6-methylquinolin-4-amine; and N-{[3-(benzylamino)oxetan-3-yl]methyl}-6-chloro-2-(7-fluoro-1,1-dioxido-2,3-dihydro-1,4-benzothiazepin-4(5H)-yl)quinolin-4-amine.

14. The compound according to claim 1 or a pharmaceutically acceptable salt thereof, selected from the group consisting of:
N-[(3-aminooxetan-3-yl)methyl]-6-chloro-2-(7-fluoro-1,1-dioxido-2,3-dihydro-1,4-benzothiazepin-4(5H)-yl)quinolin-4-amine; N-{[3-(aminomethyl)oxetan-3-yl]methyl}-2-(7-methoxy-1,1-dioxido-2,3-dihydro-1,4-benzothiazepin-4(5H)-yl)quinolin-4-amine; N-{[3-(aminomethyl)oxetan-3-yl]methyl}-2-(7-methoxy-1,1-dioxido-2,3-dihydro-1,4-benzothiazepin-4(5H)-yl)-6-methylquinolin-4-amine; N-{[3-({2-(7-methoxy-1,1-dioxido-2,3-dihydro-1,4-benzothiazepin-4(5H)-yl)-6-methylquinolin-4-yl]amino}methyl)oxetan-3-yl]methyl}acetamide; N-{[3-(aminomethyl)oxetan-3-yl]methyl}-2-(8-methyl-1,1-dioxido-2,3-dihydro-1,4-benzothiazepin-4(5H)-yl)quinolin-4-amine; N-{[3-(aminomethyl)oxetan-3-yl]methyl}-6-methyl-2-(8-methyl-1,1-dioxido-2,3-dihydro-1,4-benzothiazepin-4(5H)-yl)quinolin-4-amine; [3-({[2-(1,1-dioxido-2,3-dihydro-1,4-benzothiazepin-4(5H)-yl)-6-methylquinolin-4-yl]amino}methyl)oxetan-3-yl]methanol; (2S)-3-{[2-(1,1-dioxido-2,3-dihydro-1,4-benzothiazepin-4(5H)-yl)-6-methylquinolin-4-yl]amino}propane-1,2-diol; and (2R)-3-{[2-(1,1-dioxido-2,3-dihydro-1,4-benzothiazepin-4(5H)-yl)-6-methylquinolin-4-yl]amino}propane-1,2-diol.

15. The compound according to claim 1 or a pharmaceutically acceptable salt thereof, selected from the group consisting of:

N-{[1-(aminomethyl)-3,3-difluorocyclobutyl]methyl}-2-(1,1-dioxido-2,3-dihydro-1,4-benzothiazepin-4(5H)-yl)-6-methylquinolin-4-amine; N-[(3-aminooxetan-3-yl)methyl]-6-chloro-2-(8-methoxy-1,1-dioxido-2,3-dihydro-1,4-benzothiazepin-4(5H)-yl)quinolin-4-amine; N-{[3-(aminomethyl)oxetan-3-yl]methyl}-6-chloro-2-(8-methoxy-1,1-dioxido-2,3-dihydro-1,4-benzothiazepin-4(5H)-yl)quinolin-4-amine; trans-N-[2-(1,1-dioxido-2,3-dihydro-1,4-benzothiazepin-4(5H)-yl)-6-methylquinolin-4-yl]cyclohexane-1,2-diamine; N-[2-(1,1-dioxido-2,3-dihydro-1,4-benzothiazepin-4(5H)-yl)-6-methylquinolin-4-yl]cyclohexane-1,3-diamine; (3R)-1-[2-(1,1-dioxido-2,3-dihydro-1,4-benzothiazepin-4(5H)-yl)-6-methylquinolin-4-yl]-4,4-dimethylpyrrolidin-3-ol; cis-N-[2-(1,1-dioxido-2,3-dihydro-1,4-benzothiazepin-4(5H)-yl)-6-methylquinolin-4-yl]cyclohexane-1,4-diamine; N-[2-(1,1-dioxido-2,3-dihydro-1,4-benzothiazepin-4(5H)-yl)-6-methylquinolin-4-yl]-2,2-difluoropropane-1,3-diamine; N-[6-chloro-2-(1,1-dioxido-2,3-dihydro-1,4-benzothiazepin-4(5H)-yl)quinolin-4-yl]-2,2-difluoropropane-1,3-diamine; and N-[2-(1,1-dioxido-2,3-dihydro-1,4-benzothiazepin-4(5H)-yl)-6-methylquinolin-4-yl]-2-fluoropropane-1,3-diamine.

16. The compound according to claim 1 or a pharmaceutically acceptable salt thereof, selected from the group consisting of:

N-[(3-aminooxetan-3-yl)methyl]-6-chloro-2-(1,1-dioxido-2,3-dihydro-1,4-benzothiazepin-4(5H)-yl)quinolin-4-amine; [4-{[(3-aminooxetan-3-yl)methyl]amino}-2-(1,1-dioxido-2,3-dihydro-1,4-benzothiazepin-4(5H)-yl)quinolin-6-yl]methanol; N-[(3-aminooxetan-3-yl)methyl]-2-(1,1-dioxido-2,3-dihydro-1,4-benzothiazepin-4(5H)-yl)-7-fluoro-6-methylquinolin-4-amine; N-[(3-aminooxetan-3-yl)methyl]-2-(1,1-dioxido-2,3-dihydro-1,4-benzothiazepin-4(5H)-yl)-5-fluoro-6-methylquinolin-4-amine; N~1~-[6-chloro-2-(1,1-dioxido-2,3-dihydro-1,4-benzothiazepin-4(5H)-yl)quinolin-4-yl]-2-methylpropane-1,2-diamine; 2-(1,1-dioxido-2,3-dihydro-1,4-benzothiazepin-4(5H)-yl)-6-methyl-N-(tetrahydro-2H-pyran-4-yl)quinolin-4-amine; 2-(1,1-dioxido-2,3-dihydro-1,4-benzothiazepin-4(5H)-yl)-6-methyl-N-[2-(piperazin-1-yl)ethyl]quinolin-4-amine; 2-(1,1-dioxido-2,3-dihydro-1,4-benzothiazepin-4(5H)-yl)-6-methyl-N-(piperidin-4-ylmethyl)quinolin-4-amine; N-[2-(1,1-dioxido-2,3-dihydro-1,4-benzothiazepin-4(5H)-yl)-6-methylquinolin-4-yl]heptane-1,7-diamine; and N-[2-(1,1-dioxido-2,3-dihydro-1,4-benzothiazepin-4(5H)-yl)-6-methylquinolin-4-yl]-N'-methylethane-1,2-diamine.

17. The compound according to claim 1 or a pharmaceutically acceptable salt thereof, selected from the group consisting of:

N'-[2-(1,1-dioxido-2,3-dihydro-1,4-benzothiazepin-4(5H)-yl)-6-methylquinolin-4-yl]-N,N-dimethylethane-1,2-diamine; 2-(1,1-dioxido-2,3-dihydro-1,4-benzothiazepin-4(5H)-yl)-N,6-dimethylquinolin-4-amine trifluoroacetate; (3S,4S)-1-[2-(1,1-dioxido-2,3-dihydro-1,4-benzothiazepin-4(5H)-yl)-6-methylquinolin-4-yl]pyrrolidine-3,4-diol; 2-(1,1-dioxido-2,3-dihydro-1,4-benzothiazepin-4(5H)-yl)-6-methyl-N-(pyrrolidin-2-ylmethyl)quinolin-4-amine; 4-[4-(1,4-diazepan-1-yl)-6-methylquinolin-2-yl]-2,3,4,5-tetrahydro-1,4-benzothiazepine 1,1-dioxide; N-[2-(1,1-dioxido-2,3-dihydro-1,4-benzothiazepin-4(5H)-yl)-6-methylquinolin-4-yl]-N'-ethylethane-1,2-diamine; 2-{[2-(1,1-dioxido-2,3-dihydro-1,4-benzothiazepin-4(5H)-yl)-6-methylquinolin-4-yl]amino}ethanol; 2-(1,1-dioxido-2,3-dihydro-1,4-benzothiazepin-4(5H)-yl)-6-methyl-N-(piperidin-4-yl)quinolin-4-amine; 2-(1,1-dioxido-2,3-dihydro-1,4-benzothiazepin-4(5H)-yl)-6-methyl-N-(piperidin-3-yl)quinolin-4-amine; 2-(1,1-dioxido-2,3-dihydro-1,4-benzothiazepin-4(5H)-yl)-6-methyl-N-(piperidin-2-ylmethyl)quinolin-4-amine; and 2-[(2-{[2-(1,1-dioxido-2,3-dihydro-1,4-benzothiazepin-4(5H)-yl)-6-methylquinolin-4-yl]amino}ethyl)amino]ethanol.

18. The compound according to claim 1 or a pharmaceutically acceptable salt thereof, selected from the group consisting of:

N-[2-(1,1-dioxido-2,3-dihydro-1,4-benzothiazepin-4(5H)-yl)-6-methylquinolin-4-yl]-2,2,3,3-tetrafluorobutane-1,4-diamine; N-[2-(1,1-dioxido-2,3-dihydro-1,4-benzothiazepin-4(5H)-yl)-6-methylquinolin-4-yl]-N'-(2-methoxyethyl)ethane-1,2-diamine; 1-[2-(1,1-dioxido-2,3-dihydro-1,4-benzothiazepin-4(5H)-yl)-6-methylquinolin-4-yl]-3-methylpyrrolidin-3-ol; N-[6-chloro-2-(1,1-dioxido-2,3-dihydro-1,4-benzothiazepin-4(5H)-yl)quinolin-4-yl]ethane-1,2-diamine; 2-(1,1-dioxido-2,3-dihydro-1,4-benzothiazepin-4(5H)-yl)-6-methyl-N-(oxetan-3-yl)quinolin-4-amine; N-[(3-aminooxetan-3-yl)methyl]-2-(1,1-dioxido-2,3-dihydro-1,4-benzothiazepin-4(5H)-yl)quinolin-4-amine; 2-(1,1-dioxido-2,3-dihydro-1,4-benzothiazepin-4(5H)-yl)-6-methyl-N-[(3R)-tetrahydrofuran-3-yl]quinolin-4-amine; N-{[3-(aminomethyl)oxetan-3-yl]methyl}-2-(1,1-dioxido-2,3-dihydro-1,4-benzothiazepin-4(5H)-yl)-6-methylquinolin-4-amine; N-{[3-(aminomethyl)oxetan-3-yl]methyl}-6-chloro-2-(1,1-dioxido-2,3-dihydro-1,4-benzothiazepin-4(5H)-yl)quinolin-4-amine; and N-{[3-(aminomethyl)oxetan-3-yl]methyl}-2-(1,1-dioxido-2,3-dihydro-1,4-benzothiazepin-4(5H)-yl)quinolin-4-amine.

19. The compound according to claim 1 or a pharmaceutically acceptable salt thereof, selected from the group consisting of:

2-(1,1-dioxido-2,3-dihydro-1,4-benzothiazepin-4(5H)-yl)-6-methyl-N-(oxetan-3-ylmethyl)quinolin-4-amine; N-[(1-aminocyclobutyl)methyl]-2-(1,1-dioxido-2,3-dihydro-1,4-benzothiazepin-4(5H)-yl)-6-methylquinolin-4-amine; N-[2-(1,1-dioxido-2,3-dihydro-1,4-benzothiazepin-4(5H)-yl)-6-methylquinolin-4-yl]pentane-1,5-diamine; N-[2-(1,1-dioxido-2,3-dihydro-1,4-benzothiazepin-4(5H)-yl)-6-methylquinolin-4-yl]hexane-1,6-diamine; N-[2-(1,1-dioxido-2,3-dihydro-1,4-benzothiazepin-4(5H)-yl)-6-methylquinolin-4-yl]-1,1,1-trifluoromethanesulfonamide hydrochloride; N-[2-(1,1-dioxido-2,3-dihydro-1,4-benzothiazepin-4(5H)-yl)-6-methylquinolin-4-yl]pyridazine-3-carboxamide; N-[2-(1,1-dioxido-2,3-dihydro-1,4-benzothiazepin-4(5H)-yl)-6-methylquinolin-4-yl]benzamide; N-[2-(1,1-dioxido-2,3-dihydro-1,4-benzothiazepin-4(5H)-yl)-6-methylquinolin-4-yl]acetamide; N-[2-(1,1-dioxido-2,3-dihydro-1,4-benzothiazepin-4(5H)-yl)-6-methylquinolin-4-yl]piperidine-3-carboxamide; N-[2-(1,1-dioxido-2,3-dihydro-1,4-benzothiazepin-4(5H)-yl)-6-methylquinolin-4-yl]piperidine-4-carboxamide; and 3-[2-(1,1-dioxido-2,3-dihydro-1,4-benzothiazepin-4(5H)-yl)-6-methylquinolin-4-yl]-1,1-dimethylurea.

20. The compound according to claim 1 or a pharmaceutically acceptable salt thereof, selected from the group consisting of:

2-(1,1-dioxido-2,3-dihydro-1,4-benzothiazepin-4(5H)-yl)-6-methyl-N-(1,2-oxazol-3-yl)quinolin-4-amine; N-{[3-(aminomethyl)oxetan-3-yl]methyl}-2(1,1-dioxido-2,3-dihydro-1,4-benzothiazepin-4(5H)-yl)-6-(~2~H_3_)methylquinolin-4-amine; N-[(3-aminooxetan-3-yl)methyl]-6-chloro-2-(2,3-dihydro-1,4-benzothiazepin-4(5H)-yl)quinolin-4-amine; N-[6-chloro-2-(2,3-dihydro-1,4-benzothiazepin-4(5H)-yl)quinolin-4-yl]ethane-1,2-diamine; N-[(3-aminooxetan-3-yl)methyl]-2-(2,3-dihydro-1,4-benzothiazepin-4(5H)-yl)-6-methylquinolin-4-amine; 1-[2-(2,3-dihydro-1,4-benzothiazepin-4(5H)-yl)-6-methylquinolin-4-yl]pyrrolidin-3-amine; N-[2-(2,3-dihydro-1,4-benzothiazepin-4(5H)-yl)-6-methylquinazolin-4-yl]-2,2-difluoropropane-1,3-diamine; 2-(1,1-dioxido-2,3-dihydro-1,4-benzothiazepin-4(5H)-yl)-N-[2-(1,1-dioxidothiomorpholin-4-yl)ethyl]-6-methylquinolin-4-amine; N-[2-(2-aminoethoxy)ethyl]-2-(1,1-dioxido-2,3-dihydro-1,4-benzothiazepin-4(5H)-yl)-6-methylquinolin-4-amine; N~1~-[2-(1,1-dioxido-2,3-dihydro-1,4-benzothiazepin-4(5H)-yl)-6-methylquinolin-4-yl]-2-methylpropane-1,2-diamine; and N~1~-[2-(1,1-dioxido-2,3-dihydro-1,4-benzothiazepin-4(5H)-yl)quinolin-4-yl]-2-methylpropane-1,2-diamine.

21. The compound according to claim 1 or a pharmaceutically acceptable salt thereof, selected from the group consisting of:

N~1~-[2-(1,1-dioxido-2,3-dihydro-1,4-benzothiazepin-4(5H)-yl)-6-methylquinolin-4-yl]propane-1,2-diamine; 4-[6-methyl-4-(4-methylpiperazin-1-yl)quinolin-2-yl]-2,3,4,5-tetrahydro-1,4-benzothiazepine 1,1-dioxide; 1-{[2-(1,1-dioxido-2,3-dihydro-1,4-benzothiazepin-4(5H)-yl)-6-methylquinolin-4-yl]amino}propan-2-ol; (2S)—N~1~-[2-(1,1-dioxido-2,3-dihydro-1,4-benzothiazepin-4(5H)-yl)-6-methylquinolin-4-yl]propane-1,2-diamine; (2R)—N~1~-[2-(1,1-dioxido-2,3-dihydro-1,4-benzothiazepin-4(5H)-yl)-6-methylquinolin-4-yl]propane-1,2-diamine; N-[(3-aminooxetan-3-yl)methyl]-2-(1,1-dioxido-2,3-dihydro-1,4-benzothiazepin-4(5H)-yl)-7,8-difluoro-6-methylquinolin-4-amine; N-(2,2-difluoroethyl)-N'-[2-(1,1-dioxido-2,3-dihydro-1,4benzothiazepin-4(5H)-yl)-6-methylquinolin-4-yl]ethane-1,2-diamine; 3-{[2-(1,1-dioxido-2,3-dihydro-1,4-benzothiazepin-4(5H)-yl)-6-methylquinolin-4-yl]amino}oxetan-3-ethanol; N-{[3-(aminomethyl)thietan-3-yl]methyl}-2-(1,1-dioxido-2,3-dihydro-1,4-benzothiazepin-4(5H)-yl)-6-methylquinolin-4-amine; and N-{[3-(aminomethyl)-1,1-dioxidothietan-3-yl]methyl}-2-(1,1-dioxido-2,3-dihydro-1,4-benzothiazepin-4(5H)-yl)-6-methylquinolin-4-amine.

22. The compound according to claim 1 or a pharmaceutically acceptable salt thereof, selected from the group consisting of:

N-(4,5-dihydro-1H-imidazol-2-yl)-2-(1,1-dioxido-2,3-dihydro-1,4-benzothiazepin-4(5H)-yl)-6-methylquinolin-4-amine; trans-4-{[2-(1,1-dioxido-2,3-dihydro-1,4-benzothiazepin-4(5H)-yl)-6-methylquinolin-4-yl]amino}cyclohexanol; (2S)-2-{[2-(1,1-dioxido-2,3-dihydro-1,4-benzothiazepin-4(5H)-yl)-6-methylquinolin-4-yl]amino}propan-1-ol; trans-1-[2-(1,1-dioxido-1,4-benzothiazepin-4(5H)-yl)-6-methylquinolin-4-yl]-4-methoxypyrrolidin-3-amine; 2-(1,1-dioxido-2,3-dihydro-1,4-benzothiazepin-4(5H)-yl)-N-[trans-4-methoxypyrrolidin-3-yl]-6-methylquinolin-4-amine; 4-{4-[(4aS,7aR)-hexahydropyrrolo[3,4-b][1,4]oxazin-6(2H)-yl]-6-methylquinolin-2-yl}-2,3,4,5-tetrahydro-1,4-benzothiazepine 1,1-dioxide; (3R,4R)-1-[21,1-dioxido-2,3-dihydro-1,4-benzothiazepin-4(5H)-yl)-6-methylquinolin-4-yl]-4-(4-methylpiperazin-1-yl)pyrrolidin-3-ol; N-{2-[(2-aminoethyl)sulfanyl]ethyl}-2-(1,1-dioxido-2,3-dihydro-1,4-benzothiazepin-4(5H)-yl)-6-methylquinolin-4-amine; 1-{1-[2-(1,1-dioxido-2,3-dihydro-1,4-benzothiazepin-4(5H)-yl)-6-methylquinolin-4-yl]piperidin-4-yl}methanamine; and 2-{[2-(8-methoxy-1,1-dioxido-2,3-dihydro-1,4-benzothiazepin-4(5H)-yl)quinolin-4-yl]amino}ethanol.

23. The compound according to claim 1 or a pharmaceutically acceptable salt thereof, selected from the group consisting of:

N-[2-(1,1-dioxido-2,3-dihydro-1,4-benzothiazepin-4(5H)-yl)-6-methylquinolin-4-yl]propane-1,3-diamine; 4-[6-methyl-4-(morpholin-4-yl)quinolin-2-yl]-2,3,4,5-tetrahydro-1,4-benzothiazepine 1,1-dioxide; 3-{[2-(1,1-dioxido-2,3-dihydro-1,4-benzothiazepin-4(5H)-yl)-6-methylquinolin-4-yl]amino}propan-1-ol; 2-(1,1-dioxido-2,3-dihydro-1,4-benzothiazepin-4(5H)-yl)-6-methyl-N-[2-(piperidin-1-yl)ethyl]quinolin-4-amine; 1-amino-3-{[2-(1,1-dioxido-2,3-dihydro-1,4-benzothiazepin-4(5H)-yl)-6-methylquinolin-4-yl]amino}propan-2-ol; N-[2-(1,1-dioxido-2,3-dihydro-1,4-benzothiazepin-4(5H)-yl)-6-methylquinolin-4-yl]glycine; N-[2-(1,1-dioxido-2,3-dihydro-1,4-benzothiazepin-4(5H)-yl)-6-fluoroquinolin-4-yl]ethane-1,2-diamine; N-[2-(1,1-dioxido-2,3-dihydro-1,4-benzothiazepin-4(5H)-yl)-6-ethylquinolin-4-yl]ethane-1,2-diamine; N-[7-chloro-2-(1,1-dioxido-2,3-dihydro-1,4-benzothiazepin-4(5H)-yl)quinolin-4-yl]propane-1,3-diamine; N-[8-chloro-2-(1,1-dioxido-2,3-dihydro-1,4-benzothiazepin-4(5H)-yl)quinolin-4-yl]propane-1,3-diamine; and N-[5-chloro-2-(1,1-dioxido-2,3-dihydro-1,4-benzothiazepin-4(5H)-yl)quinolin-4-yl]propane-1,3-diamine.

24. The compound according to claim 1 or a pharmaceutically acceptable salt thereof, selected from the group consisting of:

N-[2-(1,1-dioxido-2,3-dihydro-1,4-benzothiazepin-4(5H)-yl)-6-methylquinolin-4-yl]-2,2-dimethylpropane-1,3-diamine; N-[2-(1,1-dioxido-2,3-dihydro-1,4-benzothiazepin-4(5H)-yl)quinolin-4-yl]ethane-1,2-diamine; N-[2-(1,1-dioxido-2,3-dihydro-1,4-benzothiazepin-4(5H)-yl)-6-methylquinolin-4-yl]ethane-1,2-diamine; N~2~-[2-(1,1-dioxido-2,3-dihydro-1,4-benzothiazepin-4(5H)-yl)-6-methylquinolin-4-yl]-2-methylpropane-1,2-diamine; N~2~-[2-(1,1-dioxido-2,3-dihydro-1,4-benzothiazepin-4(5H)-yl)-6-methylquinolin-4-yl]propane-1,2-diamine; N-[2-(1,1-dioxido-2,3-dihydro-1,4-benzothiazepin-4(5H)-yl)-6-methylquinolin-4-yl]butane-1,4-diamine; N-[2-(1,1-dioxido-2,3-dihydro-1,4-benzothiazepin-4(5H)-yl)-6-nitro quinolin-4-yl]ethane-1,2-diamine; N-[2-(1,1-dioxido-2,3-dihydro-1,4-benzothiazepin-4(5H)-yl)-5-fluoro-6-methylquinolin-4-yl]ethane-1,2-diamine; 2-{[2-(1,1-dioxido-2,3-dihydro-1,4-benzothiazepin-4(5H)-yl)-5-fluoro-6-methylquinolin-4-yl]amino}ethanol; 2-{[2-(1,1-dioxido-2,3-dihydro-1,4-benzothiazepin-4(5H)-yl)-7-fluoro-6-methylquinolin-4-yl]amino}ethanol; and N-[2-(1,1-dioxido-2,3-dihydro-1,4-benzothiazepin-4 (5H)-yl)-7-fluoro-6-methylquinolin-4-yl]ethane-1,2-diamine.

25. The compound according to claim 1 or a pharmaceutically acceptable salt thereof, selected from the group consisting of:

N-[2-(1,1-dioxido-2,3-dihydro-1,4-benzothiazepin-4 (5H)-yl)-7,8-difluoro-6-methylquinolin-4-yl]ethane-1,2-diamine; 2-(1,1-dioxido-2,3-dihydro-1,4-benzothiazepin-4(5H)-yl)-N-(2-methoxyethyl)-6-methylquinolin-4-amine; 1-[2-(1,1-dioxido-2,3-dihydro-1,4-benzothiazepin-4(5H)-yl)-6-methylquinolin-4-yl]piperidin-4-amine; 1-[2-(1,1-dioxido-2,3-dihydro-1,4-benzothiazepin-4(5H)-yl)-1,6-naphthyridin-4-yl]pyrrolidin-3-amine; N-[6-(difluoromethyl)-2-(1,1-dioxido-2,3-dihydro-1,4-benzothiazepin-4(5H)-yl)quinolin-4-yl]propane-1,3-diamine; 6-chloro-2-(1,1-dioxido-2,3-dihydro-1,4-benzothiazepin-4(5H)-yl)-N-ethylquinolin-4-amine; 2-{[6-chloro-2-(1,1-dioxido-2,3-dihydro-1,4-benzothiazepin-4(5H)-yl)quinolin-4-yl]amino}ethanol; N-[6-chloro-2-(1,1-dioxido-2,3-dihydro-1,4-benzothiazepin-4 (5H)-yl)quinolin-4-yl]-N'-methylethane-1,2-diamine; N-[2-(1,1-dioxido-2,3-dihydro-1,4-benzothiazepin-4(5H)-yl)-6-(methylsulfanyl)quinolin-4-yl]propane-1,3-diamine; N-[6-bromo-2-(1,1-dioxido-2,3-dihydro-1,4-benzothiazepin-4(5H)-yl)quinolin-4-yl]propane-1,3-diamine; and {4-[(2-aminoethyl)amino]-2-(1,1-dioxido-2,3-dihydro-1,4-benzothiazepin-4(5H)-yl)quinolin-6-yl}methanol.

26. The compound according to claim 1 or a pharmaceutically acceptable salt thereof, selected from the group consisting of:

2-{[2-(1,1-dioxido-2,3-dihydro-1,4-benzothiazepin-4 (5H)-yl)-6-methylquinolin-4-yl]amino}propane-1,3-diol; 2,2'-{[2-(1,1-dioxido-2,3-dihydro-1,4-benzothiazepin-4(5H)-yl)-6-methylquinolin-4-yl]imino}diethanol; 4-{[2-(1,1-dioxido-2,3-dihydro-1,4-benzothiazepin-4 (5H)-yl)-6-methylquinolin-4-yl]amino}-3-hydroxybutanoic acid; 1-amino-3-{[2-(1,1-dioxido-2,3-dihydro-1,4-benzothiazepin-4(5H)-yl)-6-methylquinolin-4-yl]amino}-2-methylpropan-2-ol; 2-(1,1-dioxido-2,3-dihydro-1,4-benzothiazepin-4(5H)-yl)-6-methyl-N-[2-(morpholin-4-yl)ethyl]quinolin-4-amine; 2-{[2-(1,1-dioxido-2,3-dihydro-1,4-benzothiazepin-4(5H)-yl)-1,6-naphthyridin-4-yl]amino}ethanol; N-[2-(1,1-dioxido-2,3-dihydro-1,4-benzothiazepin-4 (5H)-yl)-8-methylquinolin-4-yl]nonane-1,9-diamine; N-[2-(1,1-dioxido-2,3-dihydro-1,4-benzothiazepin-4 (5H)-yl)-8-methylquinolin-4-yl]decane-1,10-diamine; N-[2-(1,1-dioxido-2,3-dihydro-1,4-benzothiazepin-4 (5H)-yl)-6-methylquinolin-4-yl]octane-1,8-diamine; 9-{[2-(1,1-dioxido-2,3-dihydro-1,4-benzothiazepin-4 (5H)-yl)-6-methylquinolin-4-yl]amino}nonan-1-ol; and N-[2-(1,1-dioxido-2,3-dihydro-1,4-benzothiazepin-4(5H)-yl)-8-methylquinolin-4-yl]octane-1,8-diamine.

27. The compound according to claim 1 or a pharmaceutically acceptable salt thereof, selected from the group consisting of:

cis-4-amino-1-[2-(1,1-dioxido-2,3-dihydro-1,4-benzothiazepin-4(5H)-yl)-6-methylquinolin-4-yl]pyrrolidin-3-ol; N-[2-(1,1-dioxido-2,3-dihydro-1,4-benzothiazepin-4(5H)-yl)-6-methylquinolin-4-yl]-L-alanine; N-[2-(1,1-dioxido-2,3-dihydro-1,4-benzothiazepin-4(5H)-yl)-6-methylquinolin-4-yl]-beta-alanine; N-[2-(1,1-dioxido-2,3-dihydro-1,4-benzothiazepin-4(5H)-yl)-6-methylquinolin-4-yl]benzene-1,3-diamine; N-[2-(1,1-dioxido-2,3-dihydro-1,4-benzothiazepin-4(5H)-yl)-6-methylquinolin-4-yl]benzene-1,4-diamine; (3S)-1-[2-(1,1-dioxido-2,3-dihydro-1,4-benzothiazepin-4(5H)-yl)-6-methylquinolin-4-yl]pyrrolidin-3-ol; (3R)-1-[2-(1,1-dioxido-2,3-dihydro-1,4-benzothiazepin-4(5H)-yl)-6-methylquinolin-4-yl]pyrrolidin-3-ol; trans-N-[2-(1,1-dioxido-2,3-dihydro-1,4-benzothiazepin-4(5H)-yl)-6-methylquinolin-4-yl]cyclopentane-1,2-diamine; 1-[2-(1,1-dioxido-2,3-dihydro-1,4-benzothiazepin-4 (5H)-yl)-6-methylquinolin-4-yl]piperidin-3-amine; 2-(1,1-dioxido-2,3-dihydro-1,4-benzothiazepin-4(5H)-yl)-N,N,6-trimethylquinolin-4-amine; N-[2-(1,1-dioxido-2,3-dihydro-1,4-benzothiazepin-4(5H)-yl)-6-(trifluoromethoxy)quinolin-4-yl]propane-1,3-diamine; and N-[2-(1,1-dioxido-2,3-dihydro-1,4-benzothiazepin-4(5H)-yl)-6-(trifluoromethyl)quinolin-4-yl]propane-1,3-diamine.

28. The compound according to claim 1 or a pharmaceutically acceptable salt thereof, selected from the group consisting of:

N-[6-(difluoromethoxy)-2-(1,1-dioxido-2,3-dihydro-1,4-benzothiazepin-4(5H)-yl)quinolin-4-yl]propane-1,3-diamine; N-[2-(1,1-dioxido-2,3-dihydro-1,4-benzothiazepin-4(5H)-yl)-6-methoxyquinolin-4-yl]propane-1,3-diamine; N-[2-(1,1-dioxido-2,3-dihydro-1,4-benzothiazepin-4(5H)-yl)-8-methylquinolin-4-yl]propane-1,3-diamine; N-[2-(1,1-dioxido-2,3-dihydro-1,4-benzothiazepin-4(5H)-yl)-8-methylquinolin-4-yl]propane-1,3-diamine; N-[2-(1,1-dioxido-2,3-dihydro-1,4-benzothiazepin-4(5H)-yl)-7-methylquinolin-4-yl]propane-1,3-diamine; N-{[3-(aminomethyl)oxetan-3-yl]methyl}-2-(1,1-dioxido-2,3-dihydro-1,4-benzothiazepin-4(5H)-yl)-6-fluoroquinolin-4-amine; N-[(3-aminooxetan-3-yl)methyl]-6-methyl-2-(1-oxido-2,3-dihydro-1,4-benzothiazepin-4(5H)-yl)quinolin-4-amine; (+)-N-[(3-aminooxetan-3-yl)methyl]-6-methyl-2-[1-oxido-2,3-dihydro-1,4-benzothiazepin-4(5H)-yl]quinolin-4-amine; (−)-N-[(3-aminooxetan-3-yl)methyl]-6-methyl-2-[1-oxido-2,3-dihydro-1,4-benzothiazepin-4(5H)-yl]quinolin-4-amine; N-[(3-aminooxetan-3-yl)methyl]-6-chloro-2-(1-oxido-2,3-dihydro-1,4-benzothiazepin-4(5H)-yl)quinolin-4-amine; and 2,2-difluoro-N-[6-methyl-2-(1-oxido-2,3-dihydro-1,4-benzothiazepin-4(5H)-yl)quinolin-4-yl]propane-1,3-diamine.

29. The compound according to claim 1 or a pharmaceutically acceptable salt thereof, selected from the group consisting of:

N-[6-chloro-2-(1-oxido-2,3-dihydro-1,4-benzothiazepin-4(5H)-yl)quinolin-4-yl]-2,2-difluoropropane-1,3-diamine; N-[6-chloro-2-(1-oxido-2,3-dihydro-1,4-benzothiazepin-4(5H)-yl)quinolin-4-yl]ethane-1,2-diamine; N-{[3-(aminomethyl)oxetan-3-yl]methyl}-6-methyl-2-(1-oxido-2,3-dihydro-1,4-benzothiazepin-4 (5H)-yl)quinolin-4-amine; N-{[3-(aminomethyl)oxetan-3-yl]methyl}-6-chloro-2-(1-oxido-2,3-dihydro-1,4-benzothiazepin-4(5H)-yl)quinolin-4-amine; N-[6-methyl-2-(1-oxido-2,3-dihydro-1,4-benzothiazepin-4 (5H)-yl)quinolin-4-yl]ethane-1,2-diamine; 2-{[6-methyl-2-(1-oxido-2,3-dihydro-1,4-benzothiazepin-4 (5H)-yl)quinolin-4-yl]amino}ethanol; trans-4-amino-1-[6-methyl-2-(1-oxido-2,3-dihydro-1,4-benzothiazepin-4(5H)-yl)quinolin-4-yl]pyrrolidin-3-ol; (1R,5S,6S)-3-[2-(1,1-dioxido-2,3-dihydro-1,4-benzothiazepin-4(5H)-yl)-6-methylquinolin-4-yl]-3-azabicyclo[3.1.0]hexan-6-amine; trans-4-amino-1-[2-

(1,1-dioxido-2,3-dihydro-1,4-benzothiazepin-4(5H)-yl)-6-methylquinolin-4-yl]pyrrolidin-3-ol; and 1-[6-methyl-2-(1-oxido-2,3-dihydro-1,4-benzothiazepin-4(5H)-yl)quinolin-4-yl]pyrrolidin-3-amine.

30. The compound according to claim 1 or a pharmaceutically acceptable salt thereof, selected from the group consisting of:

trans-1-[6-chloro-2-(1,1-dioxido-2,3-dihydro-1,4-benzothiazepin-4(5H)-yl)quinolin-4-yl]-4-fluoropyrrolidin-3-amine; trans-4-amino-1-[6-chloro-2-(1,1-dioxido-2,3-dihydro-1,4-benzothiazepin-4(5H)-yl)quinolin-4-yl]pyrrolidin-3-ol; trans-1-[6-chloro-2-(1-oxido-2,3-dihydro-1,4-benzothiazepin-4(5H)-yl)quinolin-4-yl]-4-fluoropyrrolidin-3-amine; 2-[2-(1,1-dioxido-2,3-dihydro-1,4-benzothiazepin-4(5H)-yl)-6-methylquinolin-4-yl]-2-azabicyclo[2.1.1]hexan-5-amine; 2-(8-methoxy-1,1-dioxido-2,3-dihydro-1,4-benzothiazepin-4(5H)-yl)-6-methylquinolin-4-amine; 2-(7-methoxy-1,1-dioxido-2,3-dihydro-1,4-benzothiazepin-4(5H)-yl)-6-methylquinolin-4-amine; N-[2-(1-aminocyclopropyl)ethyl]-2-(1,1-dioxido-2,3-dihydro-1,4-benzothiazepin-4(5H)-yl)-6-methylquinolin-4-amine; 2-(1,1-dioxido-2,3-dihydro-1,4-benzothiazepin-4(5H)-yl)-6-methyl-N-(morpholin-2-ylmethyl)quinolin-4-amine; N-[2-(1,1-dioxido-2,3-dihydro-1,4-benzothiazepin-4(5H)-yl)-6-methylquinolin-4-yl]-N-methylethane-1,2-diamine; and N-(azetidin-2-ylmethyl)-2-(1,1-dioxido-2,3-dihydro-1,4-benzothiazepin-4(5H)-yl)-6-methylquinolin-4-amine.

31. The compound according to claim 1 or a pharmaceutically acceptable salt thereof, selected from the group consisting of:

2-(1,1-dioxido-2,3-dihydro-1,4-benzothiazepin-4(5H)-yl)-6-methyl-N-(pyrrolidin-3-yl)quinolin-4-amine; N-[(1-aminocyclopropyl)methyl]-2-(1,1-dioxido-2,3-dihydro-1,4-benzothiazepin-4(5H)-yl)-6-methylquinolin-4-amine; N-(azetidin-3-yl)-6-chloro-2-(1,1-dioxido-2,3-dihydro-1,4-benzothiazepin-4(5H)-yl)quinolin-4-amine; 6-[2-(1,1-dioxido-2,3dihydro-1,4-benzothiazepin-4(5H)-yl)-6-methylquinolin-4-yl]-2-oxa-6-azaspiro[3.4]octan-8-amine; trans-4-amino-1-[2-(1,1-dioxido-2,3-dihydro-1,4-benzothiazepin-4(5H)-yl)-1,6-naphthyridin-4-yl]pyrrolidin-3-ol; 1-[2-(1,1-dioxido-2,3-dihydro-1,4-benzothiazepin-4(5H)-yl)-6-methylquinolin-4-yl]pyrrolidin-3-amine; N-(azetidin-3-yl)-2-(1,1-dioxido-2,3-dihydro-1,4-benzothiazepin-4(5H)-yl)-6-methylquinolin-4-amine; 1-[2-(1,1-dioxido-2,3-dihydro-1,4-benzothiazepin-4(5H)-yl)-6-methylquinolin-4-yl]azetidin-3-amine; N-[2-(1,1-dioxido-2,3-dihydro-1,4-benzothiazepin-4(5H)-yl)-6-methylquinolin-4-yl]prolinamide; 2-(1,1-dioxido-2,3-dihydro-1,4-benzothiazepin-4(5H)-yl)-N-(trans-4-fluoropyrrolidin-3-yl)-6-methylquinolin-4-amine; and trans-4-{[2-(1,1-dioxido-2,3-dihydro-1,4-benzothiazepin-4(5H)-yl)quinolin-4-yl]amino}pyrrolidin-3-ol.

32. The compound according to claim 1 or a pharmaceutically acceptable salt thereof, selected from the group consisting of:

trans-4-{[2-(1,1-dioxido-2,3-dihydro-1,4-benzothiazepin-4(5H)-yl)-6-methylquinolin-4-yl]amino}pyrrolidin-3-ol; cis-4-{[2-(1,1-dioxido-2,3-dihydro-1,4-benzothiazepin-4(5H)-yl)-6-methylquinolin-4-yl]amino}pyrrolidin-3-ol; N-[trans-4-fluoropyrrolidin-3-yl]-6-methyl-2-(1-oxido-2,3-dihydro-1,4-benzothiazepin-4(5H)-yl)quinolin-4-amine; 4-[(3-aminopropyl)amino]-2-(1,1-dioxido-2,3-dihydro-1,4-benzothiazepin-4(5H)-yl)quinolin-6-ol; 2-({4-[(3-aminopropyl)amino]-2-(1,1-dioxido-2,3-dihydro-1,4-benzothiazepin-4(5H)-yl)quinolin-6-yl}oxy)ethanol; N-[2-(1,1-dioxido-2,3-dihydro-1,4-benzothiazepin-4(5H)-yl)-6-(2-methoxyethoxy)quinolin-4-yl]propane-1,3-diamine; N-[2-(1,1-dioxido-2,3-dihydro-1,4-benzothiazepin-4(5H)-yl)-6-(pyridin-2-yloxy)quinolin-4-yl]propane-1,3-diamine; 3-{[2-(1,1-dioxido-2,3-dihydro-1,4-benzothiazepin-4(5H)-yl)-6-methylquinolin-4-yl]amino}propane-1,2-diol; 3-{[6-chloro-2-(1,1-dioxido-2,3-dihydro-1,4-benzothiazepin-4(5H)-yl)quinolin-4-yl]amino}propane-1,2-diol; and 3-{[2-(8-chloro-1,1-dioxido-2,3-dihydro-1,4-benzothiazepin-4(5H)-yl)-6-methylquinolin-4-yl]amino}propane-1,2-diol.

33. The compound according to claim 1 or a pharmaceutically acceptable salt thereof, selected from the group consisting of:

3-{[6-methyl-2-(1-oxido-2,3-dihydro-1,4-benzothiazepin-4(5H)-yl)quinolin-4-yl]amino}propane-1,2-diol; 3-{[6-methyl-2-(5-methyl-1,1-dioxido-2,3-dihydro-1,4-benzothiazepin-4(5H)-yl)quinolin-4-yl]amino}propane-1,2-diol; N-[(3-aminooxetan-3-yl)methyl]-6-methyl-2-[7-(morpholin-4-yl)-1,1-dioxido-2,3-dihydro-1,4-benzothiazepin-4(5H)-yl]quinolin-4-amine; N-[(3-aminooxetan-3-yl)methyl]-2-{1,1-dioxido-7-[4-(propan-2-yl)piperazin-1-yl]-2,3-dihydro-1,4-benzothiazepin-4(5H)-yl}-6-methylquinolin-4-amine; 3-{[4-(4-aminoquinolin-2-yl)-1,1-dioxido-2,3,4,5-tetrahydro-1,4-benzothiazepin-8-yl]oxy}propan-1-ol; N-[(3-aminooxetan-3-yl)methyl]-2-(1,1-dioxido-8-phenoxy-2,3-dihydro-1,4-benzothiazepin-4(5H)-yl)-6-methylquinolin-4-amine; N~3~-[2-(1,1-dioxido-2,3-dihydro-1,4-benzothiazepin-4(5H)-yl)-6-methylquinolin-4-yl]-beta-alaninamide; 3-{[2-(1,1-dioxido-2,3-dihydro-1,4-benzothiazepin-4(5H)-yl)-6-methylquinolin-4-yl]amino}butanamide; 3-{[2-(1,1-dioxido-2,3-dihydro-1,4-benzothiazepin-4(5H)-yl)-6-methylquinolin-4-yl]amino}-2-methylpropanamide; and N~2~-[2-(1,1-dioxido-2,3-dihydro-1,4-benzothiazepin-4(5H)-yl)-6-methylquinolin-4-yl]-L-alaninamide.

34. The compound according to claim 1 or a pharmaceutically acceptable salt thereof, selected from the group consisting of:

N~2~-[2-(1,1-dioxido-2,3-dihydro-1,4-benzothiazepin-4(5H)-yl)-6-methylquinolin-4-yl]glycinamide; N~2~-[2-(1,1-dioxido-2,3-dihydro-1,4-benzothiazepin-4(5H)-yl)-6-methylquinolin-4-yl]-N-methylglycinamide; (2S)-2-amino-3-{[2-(1,1-dioxido-2,3-dihydro-1,4-benzothiazepin-4(5H)-yl)-6-methylquinolin-4-yl]amino}propan-1-ol; (2R)-2-amino-3-{[2-(1,1-dioxido-2,3-dihydro-1,4-benzothiazepin-4(5H)-yl)-6-methylquinolin-4-yl]amino}propan-1-ol; N-[(2-amino-4,5-dihydro-1,3-oxazol-5-yl)methyl]-2-(1,1-dioxido-2,3-dihydro-1,4-benzothiazepin-4(5H)-yl)-6-methylquinolin-4-amine; N-[(2-amino-5-methyl-4,5-dihydro-1,3-oxazol-5-yl)methyl]-2-(1,1-dioxido-2,3-dihydro-1,4-benzothiazepin-4(5H)-yl)-6-methylquinolin-4-amine; N-{[(4R)-2-amino-4,5-dihydro-1,3-oxazol-4-yl]methyl}-2-(1,1-dioxido-2,3-dihydro-1,4benzothiazepin-4(5H)-yl)-6-methylquinolin-4-amine; N-{[(4S)-2-amino-4,5-dihydro-1,3-oxazol-4-yl]methyl}-2-(1,1-dioxido-2,3-dihydro-1,4-benzothiazepin-4(5H)-yl)-6-methylquinolin-4-amine; and cis-5-[2-(1,1-dioxido-2,3-dihydro-1,4-benzothiazepin-4(5H)-yl)-6- methylquinolin-4-yl]-4,5,6,6a-tetrahydro-3aH-pyrrolo[3,4-d][1,3]oxazol-2-amine.

35. The compound according to claim 1 or a pharmaceutically acceptable salt thereof, selected from the group consisting of:

2-(1,1-dioxido-2,3-dihydro-1,4-benzothiazepin-4(5H)-yl)-6-methylquinolin-4-amine; N-[2-(1,1-dioxido-2,3-dihydro-1,4-benzothiazepin-4(5H)-yl)-6-methylquinolin-4-yl]glycinamide; N-[2-(1,1-dioxido-2,3-dihydro-1,4-benzothiazepin-4(5H)-yl)-6-methylquinolin-4-yl]-2-methylalaninamide; N-[2-(1,1-dioxido-2,3-dihydro-1,4-benzothiazepin-4(5H)-yl)-6-methylquinolin-4-yl]alaninamide; 2-amino-N-[2-(1,1-dioxido-2,3-dihydro-1,4-benzothiazepin-4(5H)-yl)-6-methylquinolin-4-yl]butanamide; N-[2-(1,1-dioxido-2,3-dihydro-1,4-benzothiazepin-4(5H)-yl)-6-methylquinolin-4-yl]-2-methoxy-2-methylpropanamide; N~1~-[2-(1,1-dioxido-2,3-dihydro-1,4-benzothiazepin-4(5H)-yl)-6-methylquinolin-4-yl]-4,4,4-trifluorobutane-1,3-diamine; N-[2-(1,1-dioxido-2,3-dihydro-1,4-benzothiazepin-4(5H)-yl)-6-methylquinolin-4-yl]-beta-alaninamide; 2-(1,1-dioxido-2,3-dihydro-1,4-benzothiazepin-4(5H)-yl)-N-{[3-(ethylamino)oxetan-3-yl]methyl}-6-methylquinolin-4-amine; 2-(1,1-dioxido-2,3-dihydro-1,4-benzothiazepin-4(5H)-yl)-6-methyl-N-[1-(oxetan-3-yl)pyrrolidin-3-yl]quinolin-4-amine; and N'-[2-(1,1-dioxido-2,3-dihydro-1,4-benzothiazepin-4(5H)-yl)-6-methylquinolin-4-yl]-N-ethyl-N-(oxetan-3-yl)ethane-1,2-diamine.

36. The compound according to claim 1 or a pharmaceutically acceptable salt thereof, selected from the group consisting of:

N-[2-(1,1-dioxido-2,3-dihydro-1,4-benzothiazepin-4(5H)-yl)-6-methylquinolin-4-yl]-N'-(oxetan-3-yl)propane-1,3-diamine; 1-[2-(1,1-dioxido-2,3-dihydro-1,4-benzothiazepin-4(5H)-yl)-6-methylquinolin-4-yl]-N-(oxetan-3-yl)pyrrolidin-3-amine; N-[2-(1,1-dioxido-2,3-dihydro-1,4-benzothiazepin-4(5H)-yl)-6-methylquinolin-4-yl]-N'-(oxetan-3-yl)ethane-1,2-diamine; N-[2-(1,1-dioxido-2,3-dihydro-1,4-benzothiazepin-4(5H)-yl)-6-methylquinolin-4-yl]-N'-(pyridin-2-yl)ethane-1,2-diamine; (4R)-1-[2-(1,1-dioxido-2,3-dihydro-1,4-benzothiazepin-4(5H)-yl)-6-methylquinolin-4-yl]-4-hydroxypyrrolidin-2-one; N-[2-(1,1-dioxido-2,3-dihydro-1,4-benzothiazepin-4(5H)-yl)-6-methylquinolin-4-yl]-5-oxopyrrolidine-3-carboxamide; 2-(1,1-dioxido-2,3-dihydro-1,4-benzothiazepin-4(5H)-yl)-6-methyl-N-(1H-pyrazol-3-yl)quinolin-4-amine; N-[2-(1,1-dioxido-2,3-dihydro-1,4-benzothiazepin-4(5H)-yl)-6-methylquinolin-4-yl]pyridine-3-carboxamide; N-[2-(1,1-dioxido-2,3-dihydro-1,4-benzothiazepin-4(5H)-yl)-6-methylquinolin-4-yl]piperidine-2-carboxamide; and N-[2-(1,1-dioxido-2,3-dihydro-1,4-benzothiazepin-4(5H)-yl)-6-methylquinolin-4-yl]-2-(pyridin-2-yl)acetamide.

37. The compound according to claim 1 or a pharmaceutically acceptable salt thereof, selected from the group consisting of:

N-[2-(1,1-dioxido-2,3-dihydro-1,4-benzothiazepin-4(5H)-yl)-6-methylquinolin-4-yl]methanesulfonamide trifluoroacetate; N-[2-(1,1-dioxido-2,3-dihydro-1,4-benzothiazepin-4(5H)-yl)-6-methylquinolin-4-yl]pyrazine-2-carboxamide; N-[2-(1,1-dioxido-2,3-dihydro-1,4-benzothiazepin-4(5H)-yl)-6-methylquinolin-4-yl]-2-hydroxyacetamide; N-[2-(1,1-dioxido-2,3-dihydro-1,4-benzothiazepin-4(5H)-yl)-6-methylquinolin-4-yl]pyridine-2-carboxamide; N-[2-(1,1-dioxido-2,3-dihydro-1,4-benzothiazepin-4(5H)-yl)-6-methylquinolin-4-yl]azetidine-2-carboxamide; 1-[2-(1,1-dioxido-2,3-dihydro-1,4-benzothiazepin-4(5H)-yl)-6-methylquinolin-4-yl]-3-phenylurea; 1-[2-(1,1-dioxido-2,3-dihydro-1,4-benzothiazepin-4(5H)-yl)-6-methylquinolin-4-yl]-3-ethylurea; N-[6-cyclopropyl-2-(1,1-dioxido-2,3-dihydro-1,4-benzothiazepin-4(5H)-yl)quinolin-4-yl]propane-1,3-diamine; 4-[(3-aminopropyl)amino]-2-(1,1-dioxido-2,3-dihydro-1,4-benzothiazepin-4(5H)-yl)quinoline-6-carbonitrile; N-[2-(1,1-dioxido-2,3-dihydro-1,4-benzothiazepin-4(5H)-yl)-6-ethenylquinolin-4-yl]propane-1,3-diamine; and N-[2-(1,1-dioxido-2,3-dihydro-1,4-benzothiazepin-4(5H)-yl)-6-ethynylquinolin-4-yl]propane-1,3-diamine.

38. The compound according to claim 1 or a pharmaceutically acceptable salt thereof, selected from the group consisting of:

N-[(3-aminooxetan-3-yl)methyl]-6-methyl-2-(1-oxido-2,3-dihydro-1,4-benzothiazepin-4(5H)-yl)quinazolin-4-amine; N-{[3-(benzylamino)oxetan-3-yl]methyl}-6-methyl-2-(1-oxido-2,3-dihydro-1,4-benzothiazepin-4(5H)-yl)quinazolin-4-amine; 2-fluoro-N-[6-methyl-2-(1-oxido-2,3-dihydro-1,4-benzothiazepin-4(5H)-yl)quinazolin-4-yl]propane-1,3-diamine; N-{[3-(aminomethyl)oxetan-3-yl]methyl}-2-(1,1-dioxido-2,3-dihydro-1,4-benzothiazepin-4(5H)-yl)-6-methylquinazolin-4-amine; 2,2-difluoro-N-[6-methyl-2-(1-oxido-2,3-dihydro-1,4-benzothiazepin-4(5H)-yl)quinazolin-4-yl]propane-1,3-diamine; N-{[3-(aminomethyl)oxetan-3-yl]methyl}-6-chloro-2-(1,1-dioxido-2,3-dihydro-1,4-benzothiazepin-4(5H)-yl)quinazolin-4-amine; N-[2-(1,1-dioxido-2,3-dihydro-1,4-benzothiazepin-4(5H)-yl)-6-methylquinazolin-4-yl]-2,2-difluoropropane-1,3-diamine; N-[2-(1,1-dioxido-2,3-dihydro-1,4-benzothiazepin-4(5H)-yl)-6-methylquinazolin-4-yl]-2-fluoropropane-1,3-diamine; N-[6-methyl-2-(1-oxido-2,3-dihydro-1,4-benzothiazepin-4(5H)-yl)quinazolin-4-yl]propane-1,3-diamine; N-[(3-aminooxetan-3-yl)methyl]-2-(2,3-dihydro-1,4-benzothiazepin-4(5H)-yl)quinazolin-4-amine; and N-[(3-aminooxetan-3-yl)methyl]-2-(1-oxido-2,3-dihydro-1,4-benzothiazepin-4(5H)-yl)quinazolin-4-amine.

39. The compound according to claim 1 or a pharmaceutically acceptable salt thereof, selected from the group consisting of:

$R^{11}$; N-[(3-aminooxetan-3-yl)methyl]-6-chloro-2-(2,3-dihydro-1,4-benzothiazepin-4(5H)-yl)quinazolin-4-amine; N-[(3-aminooxetan-3-yl)methyl]-6-chloro-2-(1-oxido-2,3-dihydro-1,4-benzothiazepin-4(5H)-yl)quinazolin-4-amine; N-[(3-amino oxetan-3-yl)methyl]-6-chloro-2-(1,1-dioxido-2,3-dihydro-1,4-benzothiazepin-4(5H)-yl)quinazolin-4-amine; 2-{[2-(1,1-dioxido-2,3-dihydro-1,4-benzothiazepin-4(5H)-yl)-6-methylquinazolin-4-yl]amino}ethanol; 2-(2,3-dihydro-1,4-benzothiazepin-4(5H)-yl)-6-methylquinazolin-4-amine; 2-(1,1-dioxido-2,3-dihydro-1,4-benzothiazepin-4(5H)-yl)-6-methylquinazolin-4-amine; N~1~-[2-(1,1-dioxido-2,3-dihydro-1,4-benzothiazepin-4(5H)-yl)-6-methylquinazolin-4-yl]-2-methylpropane-1,2-diamine; N-[(1-aminocyclobutyl)methyl]-2-(1,1-dioxido-2,3-dihydro-1,4-benzothiazepin-4(5H)-yl)-6-methylquinazolin-4-amine; and N-{[3-(aminomethyl)oxetan-3-yl]methyl}-6-methyl-2-(1-oxido-2,3-dihydro-1,4-benzothiazepin-4(5H)-yl)quinazolin-4-amine.

40. The compound according to claim 1 or a pharmaceutically acceptable salt thereof, selected from the group consisting of:

(−)-N-{[3-(aminomethyl)oxetan-3-yl]methyl}-6-methyl-2-[1-oxido-2,3-dihydro-1,4-benzothiazepin-4(5H)-yl]quinazolin-4-amine; (+)-N-{[3-(aminomethyl)oxetan-3-yl]methyl}-6-methyl-2-[1-oxido-2,3-dihydro-1,4-benzothiazepin-4(5H)-yl]quinazolin-4-amine; N~4~-[2-(1,1-dioxido-2,3-dihydro-1,4-benzothiazepin-4(5H)-yl)-6-methylquinazolin-4-yl]-2-fluorobutane-1,4-diamine; N~1~-[2-(1,1-dioxido-2,3-dihydro-1,4-benzothiazepin-4(5H)-yl)-6-methylquinazolin-4-yl]-2-fluorobutane-1,4-diamine; N-{[3-(aminomethyl)oxetan-3-yl]methyl}-2-(2,3-dihydro-1,4-benzothiazepin-4(5H)-yl)-6-methylquinazolin-4-amine; trans-4-fluoro-1-[6-methyl-2-(1-oxido-2,3-dihydro-1,4-benzothiazepin-4(5H)-yl)quinazolin-4-yl]pyrrolidin-3-amine; N-(Azetidin-3-yl)-6-methyl-2-(1,1-dioxido-2,3-dihydro-1,4-benzothiazepin-4(5H)-yl)quinazolin-4-amine; N-(2-{[2-(1,1-dioxido-2,3-dihydro-1,4-benzothiazepin-4(5H)-yl)-6-methylquinolin-4-yl]amino}ethyl)acetamide; N-{3-({[2-(1,1-dioxido-2,3-dihydro-1,4-benzothiazepin-4(5H)-yl)-6-methylquinolin-4-yl]amino}methyl)oxetan-3-yl]methyl}acetamide; and N-(3-{[2-(1,1-dioxido-2,3-dihydro-1,4-benzothiazepin-4(5H)-yl)-6-methylquinolin-4-yl]amino}propyl)acetamide.

41. The compound according to claim 1 or a pharmaceutically acceptable salt thereof, selected from the group consisting of:

N-[2-(1,1-dioxido-2,3-dihydro-1,4-benzothiazepin-4(5H)-yl)-6-methylquinazolin-4-yl]acetamide; 1-[2-(1,1-dioxido-2,3-dihydro-1,4-benzothiazepin-4(5H)-yl)-6-methylquinolin-4-yl]-3-methylpyrrolidin-3-amine; N-[(3-aminooxetan-3-yl)methyl]-2-(9-methoxy-1,1-dioxido-2,3-dihydro-1,4-benzothiazepin-4(5H)-yl)-6-methylquinolin-4-amine; 4-(4-{[(3-aminooxetan-3-yl)methyl]amino}-6-methylquinolin-2-yl)-2,3,4,5-tetrahydro-1,4-benzothiazepin-7-ol 1,1-dioxide; 3-{[2-(1,1-dioxido-2,3-dihydro-1,4-benzothiazepin-4(5H)-yl)-6-methylquinolin-4-yl]amino}-2-methylpropane-1,2-diol; 4-{[2-(1,1-dioxido-2,3-dihydro-1,4-benzothiazepin-4(5H)-yl)-6-methylquinolin-4-yl]amino}butane-1,3-diol; N-[6-methyl-2-(2-methyl-1,1-dioxido-2,3-dihydro-1,4-benzothiazepin-4(5H)-yl)quinolin-4-yl]ethane-1,2-diamine; N-[(3-aminooxetan-3-yl)methyl]-6-methyl-2-(2-methyl-1,1-dioxido-2,3-dihydro-1,4-benzothiazepin-4(5H)-yl)quinolin-4-amine; N-[(3-{[2-(1,1-dioxido-2,3-dihydro-1,4-benzothiazepin-4(5H)-yl)-6-methylquinolin-4-yl]amino}oxetan-3-yl)methyl]-2,2,2-trifluoroacetamide; N-[3-(aminomethyl)oxetan-3-yl]-2-(1,1-dioxido-2,3-dihydro-1,4-benzothiazepin-4(5H)-yl)-6-methylquinolin-4-amine; and 2-(aminomethyl)-2-{[2-(1,1-dioxido-2,3-dihydro-1,4-benzothiazepin-4(5H)-yl)-6-methylquinolin-4-yl]amino}propane-1,3-diol.

42. The compound according to claim 1 or a pharmaceutically acceptable salt thereof, selected from the group consisting of:

4-amino-1-[2-(1,1-dioxido-2,3-dihydro-1,4-benzothiazepin-4(5H)-yl)-6-methylquinolin-4-yl]pyrrolidin-2-one; 2-(1,1-dioxido-2,3-dihydro-1,4-benzothiazepin-4(5H)-yl)-6-methyl-N-[2-(methylsulfinyl)ethyl]quinolin-4-amine; N-{2-[(2-amino ethyl)sulfonyl]ethyl}-2-(1,1-dioxido-2,3-dihydro-1,4-benzothiazepin-4(5H)-yl)-6-methylquinolin-4-amine; N-[2-(1-imino-1-oxido-1,2,3,5-tetrahydro-4H-1lambda~4~,4-benzothiazepin-4-yl)-6-methylquinolin-4-yl]ethane-1,2-diamine; 2-(1,1-dioxido-2,3-dihydro-1,4-benzothiazepin-4(5H)-yl)-6-methyl-N-[2-(S-methylsulfonimidoyl)ethyl]quinolin-4-amine; trans-4-amino-1-[2-(1-imino-1-oxido-1,2,3,5-tetrahydro-4H-1lambda~4~,4-benzothiazepin-4-yl)-6-methylquinolin-4-yl]pyrrolidin-3-ol; trans-1-[2-(1,1-dioxido-2,3-dihydro-1,4-benzothiazepin-4(5H)-yl)-6-methylquinolin-4-yl]-4-fluoropyrrolidin-3-amine; 1-[2-(1,1-dioxido-2,3-dihydro-1,4-benzothiazepin-4(5H)-yl)-6-methylquinolin-4-yl]pyrrolidine-3-carboxamide; N-[2-(1,1-dioxido-2,3-dihydro-1,4-benzothiazepin-4(5H)-yl)-6-(methylsulfinyl)quinolin-4-yl]propane-1,3-diamine; 4-[(3-aminopropyl)amino]-2-(1,1-dioxido-2,3-dihydro-1,4-benzothiazepin-4(5H)-yl)quinoline-6-carboxamide; and 1-{4-[(3-aminopropyl)amino]-2-(1,1-dioxido-2,3-dihydro-1,4-benzothiazepin-4(5H)-yl)quinolin-6-yl}ethanol.

43. The compound according to claim 1 or a pharmaceutically acceptable salt thereof, selected from the group consisting of:

3-{[2-(1,1-dioxido-2,3-dihydro-1,4-benzothiazepin-4(5H)-yl)-6-methylquinolin-4-yl]amino}propanenitrile; 2-(1,1-dioxido-2,3-dihydro-1,4-benzothiazepin-4(5H)-yl)-6-methyl-N-[2-(1H-tetrazol-5-yl)ethyl]quinolin-4-amine; N~4~-(2-aminoethyl)-2-(1,1-dioxido-2,3-dihydro-1,4-benzothiazepin-4(5H)-yl)quinoline-4,6-diamine; 5-[2-(1,1-dioxido-2,3-dihydro-1,4-benzothiazepin-4(5H)-yl)-6-methylquinolin-4-yl]-2-oxa-5,7-diazaspiro[3.4]octan-6-one; 3-{[2-(1,1-dioxido-2,3-dihydro-1,4-benzothiazepin-4(5H)-yl)-6-methylquinazolin-4-yl]amino}propane-1,2-diol; 3-{[6-chloro-2-(1,1-dioxido-2,3-dihydro-1,4-benzothiazepin-4(5H)-yl)quinazolin-4-yl]amino}propane-1,2-diol; N-[2-(2,3-dihydro-1,4-benzothiazepin-4(5H)-yl)-6-methylquinazolin-4-yl]ethane-1,2-diamine; N-[6-methyl-2-(1-oxido-2,3-dihydro-1,4-benzothiazepin-4(5H)-yl)quinazolin-4-yl]ethane-1,2-diamine; N-[2-(1,1-dioxido-2,3-dihydro-1,4-benzothiazepin-4(5H)-yl)-6-methylquinazolin-4-yl]ethane-1,2-diamine; and N-[3-(aminomethyl)oxetan-3-yl]-6-methyl-2-(1-oxido-2,3-dihydro-1,4-benzothiazepin-4(5H)-yl)quinazolin-4-amine.

44. The compound according to claim 1 or a pharmaceutically acceptable salt thereof, selected from the group consisting of:

N-(trans-4-fluoropyrrolidin-3-yl)-6-methyl-2-(1-oxido-2,3-dihydro-1,4-benzothiazepin-4(5H)-yl)quinazolin-4-amine; N-(trans-4-fluoropyrrolidin-3-yl)-6-methyl-2-(1,1-dioxido-2,3-dihydro-1,4-benzothiazepin-4(5H)-yl)quinazolin-4-amine; 1-[6-methyl-2-(1-oxido-2,3-dihydro-1,4-benzothiazepin-4(5H)-yl)quinazolin-4-yl]pyrrolidin-3-amine; N-(azetidin-3-yl)-6-methyl-2-(1,1-dioxido-2,3-dihydro-1,4-benzothiazepin-4(5H)-yl)quinazolin-4-amine; (4R)-4-{2-[2-(1,1-dioxido-2,3-dihydro-1,4-benzothiazepin-4(5H)-yl)-6-methylquinolin-4-yl]ethyl}-4,5-dihydro-1,3-oxazol-2-amine; 3-[2-(1,1-dioxido-2,3-dihydro-1,4-benzothiazepin-4(5H)-yl)-6-ethylquinolin-4-yl]propanoic acid; 3-[2-(1,1-dioxido-2,3-dihydro-1,4-benzothiazepin-4(5H)-yl)-6-methylquinolin-4-yl]propan-1-amine; 2-{[2-(1,1-dioxido-2,3-dihydro-1,4-benzothiazepin-4(5H)-yl)-6-methylquinolin-4-yl]oxy}ethanamine; 4-[6-methyl-4-(pyrrolidin-3-yloxy)quinolin-2-yl]-2,3,4,5-tetrahydro-1,4-benzothiazepine 1,1-dioxide; 4-[6-methyl-4-(piperidin-4-yloxy)quinolin-2-yl]-2,3,4,5-tetrahydro-1,4-benzothiazepine 1,1- dioxide; 4-(4,6-dimethylquinolin-2-yl)-2,3,4,5-tetrahydro-1,4-benzothiazepine 1,1-dioxide; and [2-(1,1-dioxido-2,3-dihydro-1,4-benzothiazepin-4(5H)-yl)-6-methylquinolin-4-yl](piperidin-4-yl)methanone.

45. The compound according to claim 1 or a pharmaceutically acceptable salt thereof, selected from the group consisting of:
4-[6-methyl-4-(1H-pyrazol-3-yl)quinolin-2-yl]-2,3,4,5-tetrahydro-1,4-benzothiazepine 1,1-dioxide; 4-[6-methyl-4-(phenylsulfonyl)quinolin-2-yl]-2,3,4,5-tetrahydro-1,4-benzothiazepine 1,1-dioxide; N-(2-aminoethyl)-2-(1,1-dioxido-2,3-dihydro-1,4-benzothiazepin-4(5H)-yl)-6-methylquinoline-4-sulfonamide; methyl 4-({[3-(aminomethyl)oxetan-3-yl]methyl}amino)-2-(1,1-dioxido-2,3-dihydro-1,4-benzothiazepin-4(5H)-yl)quinoline-6-carboxylate; 4-({[3-(aminomethyl)oxetan-3-yl]methyl}amino)-2-(1,1-dioxido-2,3-dihydro-1,4-benzothiazepin-4(5H)-yl)quinoline-6-carboxylic acid; [4-({[3-(aminomethyl)oxetan-3-yl]methyl}amino)-2-(1,1-dioxido-2,3-dihydro-1,4-benzothiazepin-4(5H)-yl)quinolin-6-yl]methanol; N-{[3-(aminomethyl)oxetan-3-yl]methyl}-6-(~2~H_3_)methyl-2-(1-oxido-2,3-dihydro-1,4-benzothiazepin-4(5H)-yl)quinazolin-4-amine; 4-({[3-(aminomethyl)oxetan-3-yl]methyl}amino)-2-(1,1-dioxido-2,3-dihydro-1,4-benzothiazepin-4(5H)-yl)quinazoline-6-carboxylic acid; 4-({[3-(aminomethyl)oxetan-3-yl]methyl}amino)-2-(1-oxido-2,3-dihydro-1,4-benzothiazepin-4(5H)-yl)quinazoline-6-carboxylic acid; [4-({[3-(aminomethyl)oxetan-3-yl]methyl}amino)-2-(1-oxido-2,3-dihydro-1,4-benzothiazepin-4(5H)-yl)quinazolin-6-yl]methanol; [4-({[3-(aminomethyl)oxetan-3-yl]methyl}amino)-2-(1,1-dioxido-2,3-dihydro-1,4-benzothiazepin-4(5H)-yl)quinazolin-6-yl]methanol; N-[(1-aminocyclopropyl)methyl]-2-(1,1-dioxido-2,3-dihydro-1,4-benzothiazepin-4(5H)-yl)-6-methylquinazolin-4-amine; and 2-(1,1-dioxido-2,3-dihydro-1,4-benzothiazepin-4(5H)-yl)-6-methyl-N-(pyrrolidin-3-yl)quinazolin-4-amine.

46. The compound according to claim 1 or a pharmaceutically acceptable salt thereof, wherein
$R^1$ is hydrogen or halogen;
$R^2$ and $R^4$ are hydrogen;
$R^3$ is hydrogen or halogen;
$R^5$ is hydrogen or halogen;
$R^6$ is hydrogen, halogen, hydroxy, $C_{1-6}$alkoxy or carboxy;
$R^7$ is hydrogen, halogen, $C_{1-6}$alkoxy, $C_{1-6}$alkylaminocarbonyl, di$C_{1-6}$alkylaminocarbonyl or $C_{1-6}$alkylsulfonyl;
$R^8$ is hydrogen or halogen;
$R^9$ is hydrogen or =O;
$R^{10}$ is hydrogen or =O, provided that $R^9$ and $R^{10}$ are not =O simultaneously;
A is —C—$R^{11}$, wherein $R^{11}$ is hydrogen, halogen, $C_{1-6}$alkyl, $C_{1-6}$alkoxy, trifluoromethyl, trifluoromethoxy, pyridinyloxy, difluoromethoxy or $C_{1-6}$alkylsulfonyl;
X is —CH$_2$—, —O—, —NH—, —CF$_2$, —C(CH$_3$)(OH)—, C=O, or —C(=N—$C_{1-6}$alkoxy)-;
Y is —CH— or nitrogen;
Q is hydrogen; halogen; $C_{1-6}$alkyl, once or twice substituted by hydroxy provided that disubstitution of hydroxy is not on the same carbon; amino(CH$_2$)$_{2-6}$aminosulfonyl; 2-amino-4,5-dihydro-1,3-oxazol-4-ylethyl; or NR$^{12}$R$^{13}$, wherein one of $R^{12}$ and $R^{13}$ is hydrogen, $C_{1-6}$alkyl or hydroxy(CH$_2$)$_{2-}$, and the other one is guanidino(CH$_2$)$_{2-6}$; 3-aminomethyl-1,1-dioxidothietan-3-ylmethyl; 3-amino-1,1-dioxidothietan-3-ylmethyl; 3-(aminomethyl)thietan-3-ylmethyl; amino(CH$_2$)$_{2-6}$—O—(CH$_2$)$_{2-6}$; amino(CH$_2$)$_{2-10}$; amino(CH$_2$)$_{1-6}$carbonyl; amino(CH$_2$)$_{1-6}$difluoromethyl(CH$_2$)$_{1-6}$; amino(CH$_2$)$_{1-6}$oxetanyl(CH$_2$)$_{1-6}$; amino(CH$_2$)$_{2-6}$sulfonyl(CH$_2$)$_{2-6}$; 3-aminocyclohexyl; 4-aminocyclohexyl; 2-amino-4,5-dihydro-oxazol-5-yl(CH$_2$)$_{1-6}$; aminooxetanyl(CH$_2$)$_{1-6}$; $C_{1-6}$alkylamino(CH$_2$)$_{2-6}$; $C_{1-6}$alkylaminocarbonyl; di$C_{1-6}$alkylamino(CH$_2$)$_{2-6}$; hydroxy(CH$_2$)$_{2-6}$; piperazinyl(CH$_2$)$_{2-6}$; pyrrolidin-3-yl; or

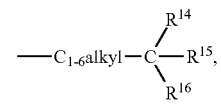

or wherein $R^{14}$ is hydrogen, $C_{1-6}$alkyl or hydroxy(CH$_2$)$_{1-6}$; $R^{15}$ is hydroxy, hydroxy(CH$_2$)$_{1-6}$ or amino; and $R^{16}$ is $C_{1-6}$alkyl, hydroxy(CH$_2$)$_{1-6}$ or amino(CH$_2$)$_{1-6}$; or
$R^{12}$ and $R^{13}$, with the nitrogen atom to which they are attached, may form a pyrrolidinyl, piperazinyl or diazepanyl ring; which may be unsubstituted, once or twice substituted by a group selected from $C_{1-6}$alkyl, amino or hydroxy.

47. The compound according to claim 46 or a pharmaceutically acceptable salt thereof, wherein
$R^1$ is hydrogen or chloro;
$R^2$ and $R^4$ are hydrogen;
$R^3$ is hydrogen or chloro;
$R^5$ is hydrogen or fluoro;
$R^6$ is hydrogen, fluoro, hydroxy, methoxy, ethoxy or carboxy;
$R^7$ is hydrogen, fluoro, bromo, methoxy, dimethylaminocarbonyl, methylsulfonyl or ethylsulfonyl;
$R^8$ is hydrogen or chloro;
A is CR$^{11}$, wherein $R^{11}$ is hydrogen, fluoro, chloro, bromo, methyl, methoxy, trifluoromethyl, trifluoromethoxy, pyridinyloxy, difluoromethoxy or methylsulfonyl;
Q is hydrogen; chloro; hydroxymethyl; hydroxymethyl(hydroxy)ethyl; aminoethylaminosulfonyl; 2-amino-4,5-dihydro-1,3-oxazol-4-ylethyl; or NR$^{12}$R$^{13}$, wherein one of $R^{12}$ and $R^{13}$ is hydrogen, methyl or hydroxyethyl; and the other one is aminobutyl; 3-aminocyclohexyl; 4-aminocyclohexyl; 2-amino-4,5-dihydro-oxazol-5-ylmethyl; 3-amino-1,1-dioxidothietan-3-ylmethyl; aminoethoxyethyl; aminoethyl; aminoethylsulfonylethyl; aminomethylcarbonyl; aminomethyldifluoromethylmethyl; 3-aminomethyl-1,1-dioxidothietan-3-ylmethyl; 3-(aminomethyl)thietan-3-ylmethyl; aminomethyloxetanylmethyl; aminooxetanylmethyl; aminopropyl; dimethylaminoethyl; ethylaminocarbonyl; guanidinoethyl; hydroxyethyl; hydroxypropyl; methylaminoethyl; piperazin-1-ylethyl; pyrrolidin-3-yl; or

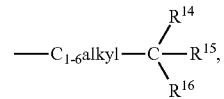

wherein $R^{14}$ is hydrogen, methyl or hydroxymethyl; $R^{15}$ is hydroxy, hydroxymethyl or amino; and $R^{16}$ is methyl, hydroxymethyl or aminomethyl; or $R^{12}$ and $R^{13}$, with the nitrogen atom to which they are attached, may form a pyrrolidinyl, piperazinyl or diazepanyl ring; which may be unsubstituted, once or twice substituted by a group selected from methyl, amino or hydroxy.

48. The compound according to claim 46 or a pharmaceutically acceptable salt thereof, selected from the group consisting of:

N-[(3-amino oxetan-3-yl)methyl]-2-(5,5-difluoro-1,3,4,5-tetrahydro-2H-2-benzazepin-2-yl)-6-methylquinolin-4-amine; N-[2-(2-aminoethoxy)ethyl]-2-(5,5-difluoro-1,3,4,5-tetrahydro-2H-2-benzazepin-2-yl)-6-methylquinolin-4-amine; N-[2-(5,5-difluoro-1,3,4,5-tetrahydro-2H-2-benzazepin-2-yl)-6-methylquinolin-4-yl]-N'-methylethane-1,2-diamine; 1-amino-3-{[2-(5,5-difluoro-1,3,4,5-tetrahydro-2H-2-benzazepin-2-yl)-6-methylquinolin-4-yl]amino}propan-2-ol; 3-{[2-(5,5-difluoro-1,3,4,5-tetrahydro-2H-2-benzazepin-2-yl)-6-methylquinolin-4-yl]amino}propane-1,2-diol; 3-{[2-(5,5-difluoro-1,3,4,5-tetrahydro-2H-2-benzazepin-2-yl)-6-methylquinolin-4-yl]amino}propan-1-ol; 2-(5,5-difluoro-1,3,4,5-tetrahydro-2H-2-benzazepin-2-yl)-6-methyl-N-[2-(piperazin-1-yl)ethyl]quinolin-4-amine; N~1~-[2-(5,5-difluoro-1,3,4,5-tetrahydro-2H-2-benzazepin-2-yl)-6-methylquinolin-4-yl]propane-1,2-diamine; cis-N-[2-(5,5-difluoro-1,3,4,5-tetrahydro-2H-2-benzazepin-2-yl)-6-methylquinolin-4-yl]cyclohexane-1,4-diamine; and 2-(9,9-difluoro-6,7,8,9-tetrahydro-5H-benzo[7]annulen-6-yl)-6-methyl-N-(pyrrolidin-3-yl)quinolin-4-amine.

49. The compound according to claim 46 or a pharmaceutically acceptable salt thereof, selected from the group consisting of:

2,2'-{[2-(5,5-difluoro-1,3,4,5-tetrahydro-2H-2-benzazepin-2-yl)-6-methylquinolin-4-yl]imino}diethanol; N~1~-[2-(5,5-difluoro-1,3,4,5-tetrahydro-2H-2-benzazepin-2-yl)-6-methylquinolin-4-yl]-2-methylpropane-1,2-diamine; 5,5-difluoro-2-[6-methyl-4-(4-methylpiperazin-1-yl)quinolin-2-yl]-2,3,4,5-tetrahydro-1H-2-benzazepine; 1-[2-(9,9-difluoro-6,7,8,9-tetrahydro-5H-benzo[7]annulen-6-yl)-6-methylquinolin-4-yl]-3-ethylurea; N-{[3-(aminomethyl)oxetan-3-yl]methyl}-2-(5,5-difluoro-1,3,4,5-tetrahydro-2H-2-benzazepin-2-yl)-6-methylquinolin-4-amine; 5,5-difluoro-2-[6-methyl-4-(piperazin-1-yl)quinolin-2-yl]-2,3,4,5-tetrahydro-1H-2-benzazepine; 2-[4-(1,4-diazepan-1-yl)-6-methylquinolin-2-yl]-5,5-difluoro-2,3,4,5-tetrahydro-1H-2-benzazepine; N-[2-(5,5-difluoro-1,3,4,5-tetrahydro-2H-2-benzazepin-2-yl)-6-methylquinolin-4-yl]-N-methylethane-1,2-diamine; 1-[2-(5,5-difluoro-1,3,4,5-tetrahydro-2H-2-benzazepin-2-yl)-6-methylquinolin-4-yl]pyrrolidin-3-amine; 2-{[2-(5,5-difluoro-1,3,4,5-tetrahydro-2H-2-benzazepin-2-yl)-6-methylquinolin-4-yl]amino}ethanol; and N-[2-(5,5-difluoro-1,3,4,5-tetrahydro-2H-2-benzazepin-2-yl)-6-methylquinolin-4-yl]ethane-1,2-diamine.

50. The compound according to claim 46 or a pharmaceutically acceptable salt thereof, selected from the group consisting of:

N-[2-(5,5-difluoro-1,3,4,5-tetrahydro-2H-2-benzazepin-2-yl)-6-methylquinolin-4-yl]cyclohexane-1,3-diamine; N'-[2-(5,5-difluoro-1,3,4,5-tetrahydro-2H-2-benzazepin-2-yl)-6-methylquinolin-4-yl]-N,N-dimethylethane-1,2-diamine; N-[2-(5,5-difluoro-1,3,4,5-tetrahydro-2H-2-benzazepin-2-yl)-6-methylquinolin-4-yl]propane-1,3-diamine; N-[2-(5,5-difluoro-1,3,4,5-tetrahydro-2H-2-benzazepin-2-yl)-6-methylquinolin-4-yl]butane-1,4-diamine; trans-4-amino-1-[2-(5,5-difluoro-1,3,4,5-tetrahydro-2H-2-benzazepin-2-yl)-6-methylquinolin-4-yl]pyrrolidin-3-ol; N-{[3-(aminomethyl)-1,1-dioxidothietan-3-yl]methyl}-2-(5,5-difluoro-1,3,4,5-tetrahydro-2H-2-benzazepin-2-yl)-6-methylquinolin-4-amine; N-{2-[(2-amino ethyl)sulfonyl]ethyl}-2-(5,5-difluoro-1,3,4,5-tetrahydro-2H-2-benzazepin-2-yl)-6-methylquinolin-4-amine; N-{[3-(aminomethyl)thietan-3-yl]methyl}-2-(5,5-difluoro-1,3,4,5-tetrahydro-2H-2-benzazepin-2-yl)-6-methylquinazolin-4-amine; N-{[3-(aminomethyl)oxetan-3-yl]methyl}-2-(5,5-difluoro-1,3,4,5-tetrahydro-2H-2-benzazepin-2-yl)-6-methylquinazolin-4-amine; and 2-(aminomethyl)-2-({[2-(5,5-diflouro-1,3,4,5-tetrahydro-2H-2-benzazepin-2-yl)-6-methylquinazolin-4-yl]amino}methyl)propane-1,3-diol.

51. The compound according to claim 46, or a pharmaceutically acceptable salt thereof, selected from the group consisting of:

2-(4-{[(3-aminooxetan-3-yl)methyl]amino}-6-methylquinazolin-2-yl)-5-methyl-2,3,4,5-tetrahydro-1H-2-benzazepin-5-ol; N-[(3-aminooxetan-3-yl)methyl]-2-(5,5-difluoro-1,3,4,5-tetrahydro-2H-2-benzazepin-2-yl)-6-methylquinazolin-4-amine; N-[(3-amino-1,1-dioxidothietan-3-yl)methyl]-2-(5,5-difluoro-1,3,4,5-tetrahydro-2H-2-benzazepin-2-yl)-6-methylquinazolin-4-amine; N-[2-(5,5-difluoro-1,3,4,5-tetrahydro-2H-2-benzazepin-2-yl)-6-methylquinazolin-4-yl]-2,2-difluoropropane-1,3-diamine; N-[2-(7-bromo-1,3,4,5-tetrahydro-2H-2-benzazepin-2-yl)-6-chloroquinolin-4-yl]ethane-1,2-diamine; 2-{4-[(2-amino ethyl)amino]quinolin-2-yl}-2,3,4,5-tetrahydro-1H-2-benzazepin-8-ol; N-[6-methyl-2-(1,3,4,5-tetrahydro-2H-2-benzazepin-2-yl)quinolin-4-yl]ethane-1,2-diamine; N-[2-(8-fluoro-1,3,4,5-tetrahydro-2H-2-benzazepin-2-yl)-6-methylquinolin-4-yl]ethane-1,2-diamine; N-[6-chloro-2-(1,3,4,5-tetrahydro-2H-2-benzazepin-2-yl)quinolin-4-yl]ethane-1,2-diamine; N-[6-chloro-2-(9-fluoro-1,3,4,5-tetrahydro-2H-2-benzazepin-2-yl)quinolin-4-yl]ethane-1,2-diamine; N-[2-(8-fluoro-1,3,4,5-tetrahydro-2H-2-benzazepin-2-yl)quinolin-4-yl]ethane-1,2-diamine; and 1-amino-3-{[2-(1,3,4,5-tetrahydro-2H-2-benzazepin-2-yl)quinolin-4-yl]amino}propan-2-ol trifluoroacetate.

52. The compound according to claim 46 or a pharmaceutically acceptable salt thereof, selected from the group consisting of:

N-[2-(1,3,4,5-tetrahydro-2H-2-benzazepin-2-yl)quinolin-4-yl]ethane-1,2-diamine; N-[6-bromo-2-(1,3,4,5-tetrahydro-2H-2-benzazepin-2-yl)quinolin-4-yl]ethane-1,2-diamine; N-[6-methoxy-2-(1,3,4,5-tetrahydro-2H-2-benzazepin-2-yl)quinolin-4-yl]ethane-1,2-diamine; N-[2-(6-chloro-1,3,4,5-tetrahydro-2H-2-benzazepin-2-yl)quinolin-4-yl]ethane-1,2-diamine; N-[2-(7-fluoro-1,3,4,5-tetrahydro-2H-2-benzazepin-2-yl)-6-methylquinolin-4-yl]ethane-1,2-diamine; N-methyl-N-[2-(1,3,4,5-tetrahydro-2H-2-benzazepin-2-yl)quinolin-4-yl]ethane-1,2-diamine; N-[2-(7-methoxy-1,3,4,5-tetrahydro-2H-2-benzazepin-2-yl)quinolin-4-yl]ethane-1,2-diamine; N-[2-(7-fluoro-1,3,4,5-tetrahydro-2H-2-benzazepin-2-yl)quinolin-4yl]ethane-1,2-diamine; N-[2-(8-methoxy-1,3,4,5-tetrahydro-2H-2-benzazepin-2-yl)quinolin-4-yl]ethane-1,2-diamine; N-[6-(difluoromethoxy)-2-(1,3,4,5-tetrahydro-2H-2-benzazepin-2-yl)quinolin-4-yl]ethane-1,2-diamine; N-[2-(1,3,4,5-tetrahydro-2H-2-benzazepin-2-yl)-6-(trifluoromethyl)quinolin-4-yl]ethane-1,2-diamine; and N-[8-chloro-2-(1,3,4,5-tetrahydro-2H-2-benzazepin-2-yl)quinolin-4-yl]ethane-1,2-diamine.

53. The compound according to claim 46 or a pharmaceutically acceptable salt thereof, selected from the group consisting of:

N-[6-fluoro-2-(1,3,4,5-tetrahydro-2H-2-benzazepin-2-yl)quinolin-4-yl]ethane-1,2-diamine; N,N-dimethyl-N'-[2-(1,3,4,5-tetrahydro-2H-2-benzazepin-2-yl)quinolin-4-yl]ethane-1,2-diamine; N-[2-(1,3,4,5-tetrahydro-2H-2-benzazepin-2-yl)-6-(trifluoromethoxy)quinolin-4-yl]ethane-1,2-diamine; N-[6-(methylsulfonyl)-2-(1,3,4,5-tetrahydro-2H-2-benzazepin-2-yl)quinolin-4-yl]ethane-1,2-diamine; 2-{4-[(2-amino ethyl)amino]quinolin-2-yl}-2,3,4,5-tetrahydro-1H-2-benzazepine-8-carboxylic acid; 2-(4-chloroquinolin-2-yl)-2,3,4,5-tetrahydro-1H-2-benzazepine; N-[5-chloro-2-(1,3,4,5-tetrahydro-2H-2-benzazepin-2-yl)quinolin-4-yl]ethane-1,2-diamine; N-{2-[7-(methylsulfonyl)-1,3,4,5-tetrahydro-2H-2-benzazepin-2-yl]quinolin-4yl}ethane-1,2-diamine; N-{2-[7-(ethylsulfonyl)-1,3,4,5-tetrahydro-2H-2-benzazepin-2-yl]quinolin-4-yl}ethane-1,2-diamine; N-[2-(8-ethoxy-1,3,4,5-tetrahydro-2H-2-benzazepin-2-yl)quinolin-4-yl]ethane-1,2-diamine; N-[6-(pyridin-2-yloxy)-2-(1,3,4,5-tetrahydro-2H-2-benzazepin-2-yl)quinolin-4-yl]ethane-1,2-diamine; 2-{4-[(2-amino ethyl)amino]-6-chloroquinolin-2-yl}-N,N-dimethyl-2,3,4,5-tetrahydro-1H-2-benzazepine-7-carboxamide; 2-{4-[(2-aminoethyl)amino]quinolin-2-yl}-7-bromo-1,2,4,5-tetrahydro-3H-2-benzazepin-3-one; and 1-(2-{[2-(1,3,4,5-tetrahydro-2H-2-benzazepin-2-yl)quinolin-4-yl]amino}ethyl)guanidine trifluoroacetate.

54. The compound according to claim 46 or a pharmaceutically acceptable salt thereof, selected from the group consisting of:

N-[(2-amino-4,5-dihydro-1,3-oxazol-5-yl)methyl]-2-(1,3,4,5-tetrahydro-2H-2-benzazepin-2-yl)quinolin-4-amine trifluoroacetate; N-[(2-amino-4,5-dihydro-1,3-oxazol-5-yl)methyl]-6-chloro-2-(1,3,4,5-tetrahydro-2H-2-benzazepin-2-yl)quinolin-4-amine; N-[2-(1,3,4,5-tetrahydro-2H-2-benzazepin-2-yl)quinolin-4-yl] glycinamide; 3-[2-(1,3,4,5-tetrahydro-2H-2-benzazepin-2-yl)quinolin-4-yl]propan-1-amine; [2-(1,3,4,5-tetrahydro-2H-2-benzazepin-2-yl)quinolin-4-yl]methanol; 2-(6-chloroquinolin-2-yl)-2,3,4,5-tetrahydro-1H-2-benzazepine; 3-[6-chloro-2-(1,3,4,5-tetrahydro-2H-2-benzazepin-2-yl)quinolin-4-yl]propane-1,2-diol; (4S)-4-{2-[2-(1,3,4,5-tetrahydro-2H-2-benzazepin-2-yl)quinolin-4-yl]ethyl}-4,5-dihydro-1,3-oxazol-2-amine; N-(2-aminoethyl)-2-(1,3,4,5-tetrahydro-2H-2-benzazepin-2-yl)quinoline-4-sulfonamide trifluoroacetate; 4-{4-[(2-aminoethyl)amino]-6-methylquinolin-2-yl}-1,3,4,5-tetrahydro-2H-1,4-benzodiazepin-2-one; N-[6-methyl-2-(1,2,3,5-tetrahydro-4H-1,4-benzodiazepin-4-yl)quinolin-4-yl]ethane-1,2-diamine; N-[2-(2,3-dihydro-1,4-benzoxazepin-4(5H)-yl)quinolin-4-yl]ethane-1,2-diamine; N-[(3-aminooxetan-3-yl)methyl]-2-[(5E)-5-(methoxyimino)-1,3,4,5-tetrahydro-2H-2-benzazepin-2-yl]-6-methylquinolin-4-amine and 2-(4-{[(3-aminooxetan-3-yl)methyl]amino}-6-methylquinazolin-2-yl)-1,2,3,4-tetrahydro-5H-2-benzazepin-5-one.

55. A pharmaceutical composition comprising a therapeutically effective amount of a compound in accordance with claim 1 and a pharmaceutically acceptable carrier.

56. A method for the treatment of respiratory syncytial virus infection, which method comprisis administering an effective amount of a compound of claim 1.

* * * * *

UNITED STATES PATENT AND TRADEMARK OFFICE
CERTIFICATE OF CORRECTION

PATENT NO. : 8,871,756 B2
APPLICATION NO. : 13/561366
DATED : October 28, 2014
INVENTOR(S) : Li Chen et al.

It is certified that error appears in the above-identified patent and that said Letters Patent is hereby corrected as shown below:

In the Claims

At Column 538, Line 6, "(3R,4R)-1-[21, 1-dioxido-2,3-" should be replaced with "(3R,4R)-1-[2-(1,1-dioxido-2,3-";

At Column 544, Line 48, "R11" should be replaced with "N- [(3-aminooxetan-3-yl)methyl]-2-(1,1-dioxido-2,3-dihydro-1,4-benzothiazepin-4(5H)-yl)quinazolin-4-amine;";

At Column 544, from the beginning of Line 63, --N-[(3-aminooxetan-3-yl)methyl]-2-(1,1-dioxido-2,3-dihydro-1,4-benzothiazepin-4(5H)-y1)-6-methylquinazolin-4-amine;-- should be inserted;

At Column 548, Line 19, "or" should be deleted; and

At Column 550, Line 13, "2-(5,5-diflouro-1,3,4,5" should be replaced with "2-(5,5-difluoro-1,3,4,5".

Signed and Sealed this
Twenty-second Day of September, 2020

Andrei Iancu
*Director of the United States Patent and Trademark Office*